United States Patent
Han et al.

(10) Patent No.: US 12,144,864 B2
(45) Date of Patent: *Nov. 19, 2024

(54) TUBULYSINS AND PROTEIN-TUBULYSIN CONJUGATES

(71) Applicant: Regeneron Pharmaceuticals, Inc., Tarrytown, NY (US)

(72) Inventors: Amy Han, Hockessin, DE (US); Marcus Kelly, New York, NY (US); William Olson, Yorktown Heights, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 750 days.

This patent is subject to a terminal disclaimer.

(21) Appl. No.: 16/724,164

(22) Filed: Dec. 20, 2019

(65) Prior Publication Data

US 2021/0260208 A1    Aug. 26, 2021

Related U.S. Application Data

(60) Provisional application No. 62/784,325, filed on Dec. 21, 2018.

(51) Int. Cl.
*A61K 47/65*    (2017.01)
*A61K 31/454*    (2006.01)
*A61K 47/54*    (2017.01)
*A61K 47/68*    (2017.01)

(52) U.S. Cl.
CPC ........ *A61K 47/6803* (2017.08); *A61K 31/454* (2013.01); *A61K 47/545* (2017.08); *A61K 47/65* (2017.08)

(58) Field of Classification Search
CPC ................................................ A61K 47/6803
See application file for complete search history.

(56) References Cited

U.S. PATENT DOCUMENTS

| | | | |
|---|---|---|---|
| 5,208,020 A | 5/1993 | Chari et al. | |
| 5,714,586 A | 2/1998 | Kunstmann et al. | |
| 7,750,116 B1 | 7/2010 | Doronina et al. | |
| 8,476,451 B2 | 7/2013 | Ellman et al. | |
| 8,580,820 B2* | 11/2013 | Zanda | A61P 35/00 548/200 |
| 8,980,833 B2* | 3/2015 | Richter | A61P 35/00 514/19.2 |
| 9,382,289 B2 | 7/2016 | Cong et al. | |
| 2007/0258987 A1 | 11/2007 | Francisco et al. | |
| 2008/0171040 A1 | 7/2008 | Ebens et al. | |
| 2008/0305044 A1 | 12/2008 | Mcdonagh et al. | |
| 2008/0305497 A1 | 12/2008 | Kosmeder et al. | |
| 2010/0129314 A1 | 5/2010 | Singh et al. | |
| 2010/0240701 A1 | 9/2010 | Vlahov et al. | |
| 2011/0245295 A1 | 10/2011 | Chal et al. | |
| 2011/0263650 A1 | 10/2011 | Ellman et al. | |
| 2013/0101546 A1 | 4/2013 | Yurkovetskiy et al. | |
| 2013/0217638 A1 | 8/2013 | Wessjohann et al. | |
| 2014/0227295 A1* | 8/2014 | Cong | A61K 38/05 424/179.1 |
| 2015/0202314 A1 | 7/2015 | Krantz | |
| 2015/0291657 A1 | 10/2015 | Gingipalli et al. | |
| 2016/0016993 A1 | 1/2016 | Vlahov et al. | |
| 2016/0022829 A1 | 1/2016 | Yurkovetskiy et al. | |
| 2016/0130299 A1 | 5/2016 | Perez et al. | |
| 2018/0125992 A1 | 5/2018 | Vlahov et al. | |
| 2020/0276261 A1 | 9/2020 | Zhao et al. | |

FOREIGN PATENT DOCUMENTS

| | | | |
|---|---|---|---|
| EP | 2409983 A1 | 1/2012 | |
| JP | WO 2017/054080 A1 | 4/2017 | |
| WO | WO 2005/089808 A2 | 9/2005 | |
| WO | WO 2008/122039 A2 | 10/2008 | |
| WO | WO 2008/138561 A1 | 11/2008 | |
| WO | WO2008138561 * | 11/2008 | ............... C07K 5/02 |
| WO | WO 2009/055562 A1 | 4/2009 | |
| WO | WO 2011/017249 A1 | 2/2011 | |
| WO | WO 2011/130598 A1 | 10/2011 | |
| WO | WO 2012/005982 A2 | 1/2012 | |
| WO | WO 2012/166559 A1 | 12/2012 | |
| WO | WO 2013/053872 A1 | 4/2013 | |
| WO | WO 2013/053873 A1 | 4/2013 | |
| WO | WO 2013/055990 A1 | 4/2013 | |
| WO | WO 2013/055993 A1 | 4/2013 | |
| WO | WO 2013/068874 A1 | 5/2013 | |
| WO | WO 2014/009774 A1 | 1/2014 | |
| WO | WO 2014/065661 A1 | 5/2014 | |
| WO | WO 2014/126836 A1 | 8/2014 | |
| WO | WO 2014/191578 A1 | 12/2014 | |
| WO | WO 2015/026907 A1 | 2/2015 | |
| WO | WO 2015/095755 | 6/2015 | |
| WO | WO 2015/113760 A1 | 8/2015 | |

(Continued)

OTHER PUBLICATIONS

Sundaresan, Protein Science (2002), 11:1330-1339.*
Venkatesh, J. Pharm. Sci. 89, 145-154 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Wolff, Burger's medicinal Chemistry and Drug Discovery, vol. 1, Principles and Practice, John Wiley & sons, New York, 1997.*

(Continued)

*Primary Examiner* — Nizal S Chandrakumar

(74) *Attorney, Agent, or Firm* — Squire Patton Boggs (US) LLP

(57) ABSTRACT

Provided herein are compounds, compositions, and methods for the treatment of diseases and disorders associated with cancer, including tubulysins and protein (e.g., antibody) drug conjugates thereof.

33 Claims, 26 Drawing Sheets

Specification includes a Sequence Listing.

(56) References Cited

FOREIGN PATENT DOCUMENTS

| WO | WO 2015/157594 A1 | | 10/2015 | |
|---|---|---|---|---|
| WO | WO 2016/040684 | | 3/2016 | |
| WO | WO 2016/049313 | | 3/2016 | |
| WO | WO 2016/059622 | | 4/2016 | |
| WO | WO 2016/077260 | * | 5/2016 | ............. C07K 5/062 |
| WO | WO 2016/077260 A1 | | 5/2016 | |
| WO | WO 2016/089879 | | 6/2016 | |
| WO | WO 2016/090050 | | 6/2016 | |
| WO | WO 2016/138288 A1 | | 9/2016 | |
| WO | WO 2016/140957 | | 9/2016 | |
| WO | WO 2016/168471 | | 10/2016 | |
| WO | WO 2017/031209 | | 2/2017 | |
| WO | WO 2017/083451 | | 5/2017 | |
| WO | WO 2017/134547 | | 8/2017 | |
| WO | WO 2017/147542 A2 | | 8/2017 | |
| WO | WO 2017/196598 A1 | | 11/2017 | |
| WO | WO 2018/031690 | | 2/2018 | |
| WO | WO 2018/058001 A1 | | 3/2018 | |
| WO | WO 2019/094395 A2 | | 5/2019 | |
| WO | WO 2020/132658 A2 | | 6/2020 | |
| WO | WO 2020/258893 A1 | | 12/2020 | |
| WO | WO 2021/174113 A1 | | 9/2021 | |
| WO | WO 2021/262910 A2 | | 12/2021 | |

OTHER PUBLICATIONS

Ahrens et al., "A cleavable cytolysin-neuropeptide Y bioconjugate enables specific drug delivery and demonstrates intracellular mode of action", Journal of Controlled Release, 2015, vol. 209, pp. 170-178.
Balasubramanian et al., "Total Synthesis and Biological Evaluation of Tubulysin U, Tubulysin V, and their Analogs", J. Med. Chem., Jan. 22, 2009, vol. 52(2), pp. 238-240.
Burke et al., "Development of Novel Quaternary Ammonium Linkers for Antibody-Drug Conjugates", Molecular Cancer Therapeutics (2016), 15(5), pp. 938-945.
Burkhart et al., "Syntheses and Evaluation of Simplified Pretubulysin Analogues", Eur. J. Org. Chem., 2011, pp. 3050-3059; DOI: 10.1002/ejoc.201100155.
Colombo et al., "Total Synthesis and Biological Evaluation of Tubulysin Analogues", J. Org. Chem, 2016, vol. 81, pp. 10302-10320.
Eirich et al., "Pretubulysin derived probes as novel tools for monitoring the microtubule network via activity-based protein profiling and fluorescence microscopy", Mol. BioSyst., 2012, 8, pp. 2067-2075.
Floyd III et al.," Chemotherapeutic Evaluation of a Novel Synthetic Tubulysin Analogue-Dendrimer Conjugate in C26 Tumor Bearing Mice", ChemMedChem., Jan. 3, 2011; 6(1): 49-53. doi:10.1002/cmdc.201000377.
Friestad et al., "Stereoselective Access to Tubuphenylalanine and Tubuvaline: Improved Mn—Mediated Radical Additions and Assembly of a Tubulysin Tetrapeptide Analog", Journal of Antibiotics, 2016, 69(4), pp. 294-298.
Hoffmann et al., "A Straightforward Approach towards Cyclic Photoactivatable Tubulysin Derivatives", Angew. Chem. Int. Ed., 2014, 53(42), pp. 11356-11360.
Hoffmann et al., "Synthesis of pretubulysin-derivatives via the TubUgi-approach", Organic & Biomolecular Chemistry, 2015, 13(21), pp. 6010-6020.
Lamidi et al. "The tubulysin analogue KEMTUB10 induces apoptosis in breast cancer cells via p53, Bim and Bcl-2", Journal of Cancer Research and Clinical Oncology (2015), 141(9), pp. 1575-1583.
Leamon et al., "Enhancing the therapeutic range of a targeted small-molecule tubulysin conjugate for folate receptor-based cancer therapy", Cancer Chemother Pharmacol (2017) vol. 79, pp. 1151-1160.
Leamon et al., "Folate Targeting Enables Durable and Specific Antitumor Responses from a Therapeutically Null Tubulysin B Analogue", Cancer Res., Dec. 1, 2008, 68 (23), pp. 9839-9844.
Leveret et al., "Design, Synthesis, and Cytotoxic Evaluation of Novel Tubulysin Analogues as ADC Payloads", ACS Med. Chem. Lett. 2016, vol. 7, pp. 999-1004.
Li et al., "A Biparatopic HER2-TargetingAntibody-DrugConjugate Induces Tumor Regression in Primary Models Refractory to or Ineligible for HER2-Targeted Therapy", Cancer Cell, vol. 29, Jan. 11, 2016, pp. 117-129.
Nicolaou et al., "Total Synthesis and Biological Evaluation of Natural and Designed Tubulysins", J. Am. Chem. Soc., 2016, 138(5), pp. 1698-1708.
Pando et al., "The Multiple Multicomponent Approach to Natural Product Mimics: Tubugis, N-Substituted Anticancer Peptides with Picomolar Activity", J. am. Chem. Soc., 2011, vol. 133, pp. 7692-7695.
Park et al., "A concise synthesis of tubuphenylalanine and epi-tubuphenylalanine via a diastereoselective Mukaiyama aldol reaction of silyl ketene acetal", Organic & Biomolecular Chemistry, 2016, 14(3), pp. 913-919.
Park et al., "Synthesis of stereochemically diverse cyclic analogs of tubulysins", Bioorganic and Medicinal Chem, 2015, 23(21), pp. 6827-6843.
Patterson et al., "Design, Synthesis, and Biological Properties of Highly Potent Tubulysin D Analogues", Chem. Eur. J., 2007, vol. 13, pp. 9534-9541.
Peng-Cheng LV et al., "Evaluation of Nonpeptidic Ligand Conjugates for the Treatment of Hypoxic and Carbonic Anhydrase IX-Expressing Cancers", Molecular Cancer Therapeutics, 2017, 16(3), pp. 453-460.
Raghavan et al., "Cytotoxic Simplified Tubulysin Analogues", J. Med. Chem., 2008, vol. 51, pp. 1530-1533.
Rao et al., "Development and validation of a UPLC-MS/MS method for the novel folate-targeted small molecule drug conjugate EC1456 and its metabolites in tumor homogenates from mice", Journal of Pharmaceutical and Biomedical Analysis (2016), vol. 122, pp. 148-156.
Rath et al., Anti-angiogenic effects of the tubulysin precursor pretubulysin and of simplified pretubulysin derivatives*, British Journal of Pharmacology, 2012, vol. 167(5), pp. 1048-1061.
Shankar et al., "Synthesis and cytotoxicity evaluation of diastereoisomers and N-terminal analogues of tubulysin-U", Tetrahedron Letters, 54, 2013, pp. 6137-6141.
Shankar P et al., "Total Synthesis and Cytotoxicity Evaluation of an Oxazole Analogue of Tubulysin U", Synlett, 2011, 12, pp. 1673-1676.
Shibue et al, "Synthesis and biological evaluation of tubulysin D analogs related to stereoisomers of tubuvaline", Bioorg Med Chem Lett., 2011, vol. 21, pp. 431-434.
Shibue et al., "Total Syntheses of Tubulysins", Chem, Eur. J., 2010, vol. 16, pp. 11678-11688.
Thompson et al., "Rational design, biophysical and biological characterization of site-specific antibody-tubulysin conjugates with improved stability, efficacy and pharmacokinetics", Journal of Controlled Release (2016), vol. 236, pp. 100-116.
Toader et al., "Structure-Cytotoxicity Relationships of Analogues of $N^{14}$-Desacetoxytubulysin H", J. Med. Chem. 2016, vol. 59, pp. 10781-10787.
Ullrich et al., "Synthesis and Biological Evaluation of Pretubulysin and Derivatives", Eur. J. Org. Chem. 2009, pp. 6367-6378.
Vlahov et al., "Acid mediated formation of an N-acyliminium ion from tubulysins: a new methodology for the synthesis of natural tubulysins and their analogs", Bioorg. Med. Chem. Lett., 2011, vol. 21, pp. 6778-6781.
Vlahov et al., "Design and regioselective synthesis of a new generation of targeted chemotherapeutics. Part II: Folic acid conjugates of tubulysins and their hydrazides", Bioorg Med. Chem Lett, 2008, vol. 18, pp. 4558-4561.
Wang et al., "Structure-activity and High-content Imaging Analyses of Novel Tubulysins", Chem Biol Drug Des, 2007, vol. 70, pp. 75-86.

(56) References Cited

OTHER PUBLICATIONS

Wayua et al, "Selective Tumor Targeting of Desacetyl Vinblastine Hydrazide and Tubulysin B via Conjugation to a Cholecystokinin 2 Receptor (CCK2R) Ligand", Molecular Pharmaceutics, 2015, 12(7), pp. 2477-2483.

Xinfa et al., "Synthesis and Anti-tumor Activity of Tubulysins Analogues", Chemical Journal Of Chinese Universities (2017), 38(1), pp. 47-55; English abstract.

Yang et al., "Design, synthesis, and biological activities of triazole tubulysin V analogue", Tetrahedron Letters 54, 2013, pp. 2986-2988.

Yang et al., "Total Synthesis of Tubulysin U and Its C-4 Epimer", Chem Asian J., 2013, vol. 8, pp. 1213-1222.

Andre H. St. Amant et al., "A Reactive Antibody Platform for One-Step Production of Antibody-Drug Conjugates through a Diels-Alder Reaction with Maleimide", Bioconjugate Chemistry, vol. 30, Aug. 5, 2019, pp. 2340-2348, XP055614773. DOI: 10.1021/acs.bioconjchem.9b00436.

Leanna R. Staben et al., "Stabilizing a Tubulysin Antibody-Drug Conjugate to Enable Activity Against Multidrug-Resistant Tumors", ACS Medicinal Chemistry Letters, vol. 8, No. 10, Sep. 5, 2017, pp. 1037-1041, XP055532485. DOI: 10.1021/acsmedchemlett.7b00243.

Agard et al., "A Strain-Promoted [3+2] Azide—Alkyne Cycloaddition for Covalent Modification of Biomolecules in Living Systems", J. Am. Chem. Soc., Nov. 24, 2004, vol. 126, No. 46, pp. 15046-15047.

Agarwal et al., "A Pictet-Spengler ligation for protein chemical modification", PNAS, Jan. 2, 2013, vol. 110, No. 1, pp. 46-51.

Angal et al., "A Single Amino Acid Substitution Abolishes the Heterogeneity of Chimeric Mouse/Human (IgG4) Antibody", Molecular Immunology, Jan. 1993, vol. 30, No. 1, pp. 105-108.

Balasubramanian et al., "Tubulysin analogs incorporating desmethyl and dimethyl tubuphenylalanine derivatives", Bioorganic & Medicinal Chemistry Letters, vol. 18, 2008, pp. 2996-2999.

Baskin et al., "Copper-free click chemistry for dynamic in vivo imaging", PNAS, Oct. 23, 2007, vol. 104, No. 43, pp. 16793-16797.

Boersma et al., "DARPins and other repeat protein scaffolds: advances in engineering and applications", 2011, Current Opinion in Biotechnology, 2011, vol. 22, pp. 849-857.

Burke et al., "Glucuronide-Linked Antibody-Tubulysin Conjugates Display Activity in MDRp and Heterogeneous Tumor Models", Mol Cancer Ther; 17(8), Aug. 2018, pp. 1752-1760. Published OnlineFirst Jun. 4, 2018; DOI:10.1158/1535-7163.MCT-18-0073.

Carrico et al., "Introducing genetically enclosed aldehydes into proteins", Nature Chemical Biology, Jun. 2007, vol. 3, No. 6, pp. 321-322.

Chai Y. et al., "Discovery of 23 Natural Tubulysins from Angiococcus disciformis an d48 and Cystobacter SBCb004", Chemistry And Biology, Current Biology, London, GB, vol. 17, No. 3, Mar. 26, 2010, pp. 296-309.

Cohen et al., "Development of Novel ADCs: Conjugation of Tubulysin Analogues to Trastuzumab Monitored by Dual Radiolabeling", Cancer Res; 74(20) Oct. 15, 2014, pp. 5700-5710; Published OnlineFirst Aug. 21, 2014.

Dennler et al., "Transglutaminase-Based Chemo-Enzymatic Conjugation Approach Yields Homogeneous Antibody-Drug Conjugates", Bioconjugate Chem., Feb. 3, 2014, vol. 25, pp. 569-578.

Doronina et al., "Development of potent monoclonal antibody auristatin conjugates for cancer therapy", Nature Biotechnology, Jul. 2003, vol. 21, No. 7, pp. 778-941.

Hofer et al., "An engineered selenocysteine defines a unique class of antibody derivatives", PNAS, Aug. 26, 2008, vol. 105, No. 34, pp. 12451-12456.

Hollander et al., "Selection of Reaction Additives Used in the Preparetion of Monomeric Antibody-Calicheamicin Conjugates", Bioconjugate Chem., 2008, vol. 19, pp. 358-361; published online Nov. 10, 2007.

Huisgen, "1,3-Dipolar Cycloadditions", Proceedings of the Chemical Society, Oct. 1961, pp. 357-369.

Jain R. A., "The manufacturing techniques of various drug loaded biodegradable poly(lactide-co-glycolide) (PLGA) devices", Biomaterials 21(23), 2000, pp. 2475-2490.

Kaur et al., "Biological evaluation of tubulysin A: a potential anticancer and antiangiogenic natural product", Biochem. J. (2006) 396, 235-242 (Printed in Great Britain); doi:10.1042/BJ20051735.

Lhospice et al. "Site-Specific Conjugation of Monomethyl Auristatin E to Anti-CD30 Antibodies Improves Their Pharmacokinetics and Therapeutic Index in Rodent Models", Mol. Pharmaceutics, 2015, vol. 12, pp. 1863-1871.

Murray et al., "Chemistry and biology of tubulysins: antimitotic tetrapeptides with activity against drug resistant cancer", Nat. Prod. Rep., 2015, vol. 32, pp. 654-662.

Pando et al., "First Total Synthesis of Tubulysin B", Organic Letters, 2009, vol. 11, No. 24, pp. 5567-5569; Published on Web Nov. 17, 2009 and supporting information, S-1 to S19.

Park T. G., "Degradation of poly(lactic-co-glycolic acid) microspheres: effect of copolymer composition", Biomaterials 16(15), 1995, pp. 1123-1130.

Patterson et al., "Expedient Synthesis of N-Methyl Tubulysin Analogues with High Cytotoxicity", J. Org. Chem. 2008, vol. 73, pp. 4362-4369.

Peltier et al., "The Total Synthesis of Tubulysin D", J. Am. Chem. Soc. 2006, vol. 128, pp. 16018-16019; and Supporting Information, 33 pages.

Rabuka et al., "Site-specific chemical protein conjugation using genetically encoded aldehyde tags", Nat Protoc., vol. 7, No. 6, pp. 1052-1067, Dec. 1, 2012, doi:10.1038/nprot.2012.04.

Ryan et al., "Polyclonal Antibody Production Against Chito-Oligosaccharides", Food and Agricultural Immunology, 2001, vol. 13, pp. 127-130.

Sani et al., "Synthesis and Superpotent Anticancer Activity of Tubulysins Carrying Non-hydrolysable N-Substituents on Tubuvaline", Chemistry—A European Journal, vol. 23, No. 24, Apr. 27, 2017, pp. 5842-5850.

Shankar et al., "Synthesis and structure—activity relationship studies of novel tubulysin U analogues—effect on cytotoxicity of structural variations in the tubuvaline fragment", Org. Biomol. Chem., 2013, vol. 11, pp. 2273-2287.

Steinmetz et al., "Isolation, Crystal and Solution Structure Determination, and Biosynthesis of Tubulysins—Powerful Inhibitors of Tubulin Polymerization from Myxobacteria", Angew. Chem. Int. Ed., 2004, vol. 43, 2004, pp. 4888-4892.

Taylor et al., "A transgenic mouse that expresses a diversity of human sequence heavy and light chain immunoglobulins", Nucleic Acids Research, 1992, vol. 20, No. 23, pp. 6287-6295.

Tumey et al., "Optimization of Tubulysin Antibody-Drug Conjugates: a Case Study in Addressing ADC Metabolism", ACS Medicinal Chemistry Letters, 2016, vol. 7, pp. 977-982.

Uhrich et al., "Polymeric Systems for Controlled Drug Release", Chemical Reviews, 1999, vol. 11, pp. 3181-3198.

Vert et al., "Something new in the field of PLA/GA bioresorbable polymers?" Journal of Controlled Release, 1998, vol. 53, pp. 85-92.

Wang et al., "Bioconjugation by Copper(I)-Catalyzed Azide-Alkyne [3+2] Cycloaddition", J. Am. Chem. Soc. 2003, vol. 125, pp. 3192-3193.

Xu et al., "A Versatile Chemo-Enzymatic Conjugation Approach Yields Homogeneous and Highly Potent Antibody-Drug Conjugates", Int. J. Mol. Sci., vol. 18, No. 11, Nov. 1, 2017, p. 2284, XP55709824.

Yusa et al., "Reversal Mechanism of Multidrug Resistance by Verapamil: Direct Binding of Verapamil to P-Glycoprotein on Specific Sites and Transport of Verapamil Outward across the Plasma Membrane of K562/ADM Cells", Cancer Research 49, Sep. 15, 1989, pp. 5002-5006.

\* cited by examiner

TUBULYSINS AND PROTEIN-TUBULYSIN CONJUGATES

FIELD

Provided herein are novel tubulysins and protein conjugates thereof, and methods for treating a variety of diseases, disorders, and conditions including administering the tubulysins, and protein conjugates thereof.

BACKGROUND

While antibody-drug conjugates (ADCs) find increasing application in cancer treatment regimens, de novo or treatment-emergent resistance mechanisms could impair clinical benefit. Two resistance mechanisms that emerge under continuous ADC exposure in vitro include upregulation of transporters that confer multidrug resistance (MDR) and loss of cognate antigen expression. New technologies that circumvent these resistance mechanisms may serve to extend the utility of next generation ADCs.

The tubulysins, first isolated from myxobacterial culture broth, are a group of extremely potent tubulin polymerization inhibitors that rapidly disintegrate the cytoskeleton of dividing cells and induce apoptosis. Tubulysins are comprised of N-methyl-D-pipecolinic acid (Mep), L-isoleucine (Ile), and tubuvaline (Tuv), which contains an unusual N,O-acetal and a secondary alcohol or acetoxy group. Tubulysins A, B, C, G, and I contain the C-terminal tubutyrosine (Tut) γ-amino acid, while D, E, F, and H instead have tubuphenylalanine (Tup) at this position (*Angew. Chem. Int. Ed. Engl.* 43, 4888-4892).

Tubulysins have emerged as promising anticancer leads due to their powerful activity in drug-resistant cells through a validated mechanism of action. The average cell growth inhibitory activity outperforms that of well-known epothilones, vinblastines, and taxols by 10-fold to more than 1000-fold, including activity against multi-drug resistant carcinoma (*Biochem. J* 2006, 396, 235-242; *Nat. Prod. Rep.* 2015, 32, 654-662). Tubulysins have extremely potent antiproliferative activity against cancer cells, including multi-drug resistant KB-V1 cervix carcinoma cells. (*Angew. Chem. Int. Ed.* 2004, 43, 4888-4892; and *Biochemical Journal* 2006, 396, 235-242).

SUMMARY

Provided herein are compounds useful, for example, in anti-cancer and anti-angiogenesis treatments.

In one embodiment, provided are compounds having the structure of Formula I.

or a pharmaceutically acceptable salt thereof, wherein $R^1$ is $C_1$-$C_{10}$ alkyl;

$R^3$ is —C(O)$C_1$-$C_5$ alkyl, —C(O)N(H)$C_1$-$C_{10}$ alkyl, or —($C_1$-$C_{10}$ alkylene)-$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted;

$R^4$ and $R^5$ are, independently in each instance, hydrogen or $C_1$-$C_5$ alkyl;

$R^6$ is —OH or —NHNH$_2$;

$R^7$ is, independently in each instance, hydrogen, —OH, halogen, or —$NR^{7a}R^{7b}$, wherein $R^{7a}$ and $R^{7b}$ are independently in each instance, hydrogen, alkyl, alkenyl, alkynyl, cycloalkyl, aryl, heteroaryl, acyl, and amino acid residue, wherein alkyl, alkenyl, alkynyl, cycloalkyl, aryl, heteroaryl, and acyl are optionally substituted;

$R^8$ is, independently in each instance, hydrogen, deuterium, —$NHR^9$, or halogen, wherein $R^9$ is hydrogen, —$C_1$-$C_5$ alkyl, or —C(O)$C_1$-$C_5$ alkyl; and m is 1 or 2;

Q is —CH$_2$— or —O— wherein when Q is —O—, then $R^2$ is $C_1$-$C_{10}$ alkyl, $C_1$-$C_{10}$ alkynyl, —$C_1$-$C_{10}$ alkylene-(5-membered heteroaryl), —$C_1$-$C_3$ alkylene-$Q^1$-(CH$_2$)$_n$aryl, or $C_1$-$C_3$ hydroxyalkyl; or when Q is —CH$_2$—, then $R^2$ is $C_5$-$C_{10}$ alkyl, $C_1$-$C_{10}$ alkynyl, —$C_1$-$C_{10}$ alkylene-(5-membered heteroaryl), —$C_1$-$C_3$ alkylene-$Q^1$-(CH$_2$)$_n$aryl, or $C_1$-$C_3$ hydroxyalkyl; and $Q^1$ is —CH$_2$— or —O—;

wherein said heteroaryl is unsubstituted or substituted with alkyl, aminoalkyl, hydroxylalkyl, carboxyalkyl, benzyl, or phenyl;

wherein said aryl is unsubstituted or substituted with nitro or amino; and wherein n is an integer from 1 to 5.

In one embodiment, provided are compounds having the structure of Formula I:

Formula I

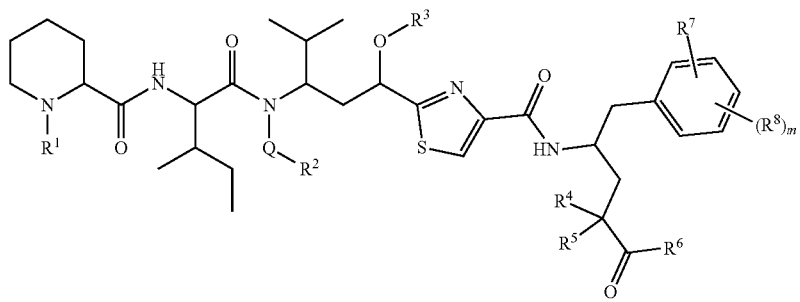

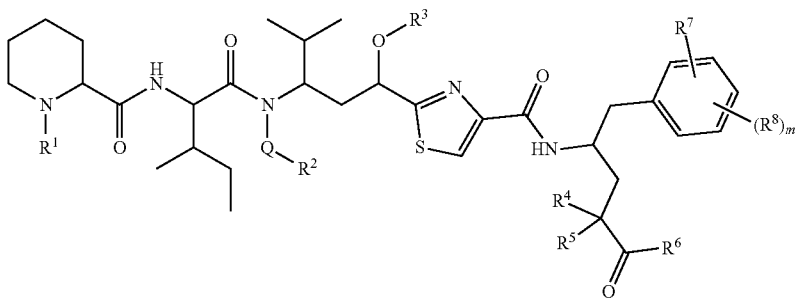

Formula I or a pharmaceutically acceptable salt thereof, wherein
$R^1$ is $C_1$-$C_{10}$ alkyl;
$R^3$ is —C(O)$C_1$-$C_5$ alkyl, —C(O)N(H)$C_1$-$C_{10}$ alkyl, or —($C_1$-$C_{10}$ alkylene)-N$R^{3a}R^{3b}$,
  wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted;
$R^4$ and $R^5$ are, independently in each instance, hydrogen or $C_1$-$C_5$ alkyl; or, in certain embodiments, $R^4$ and $R^5$, together with the carbon to which they are attached, form a 3-8 membered cycloalkyl, substituted cycloalkyl, heterocycloalkyl, or substituted heterocycloalkyl;
$R^6$ is —OH or —NHNH$_2$; or, in certain embodiments, $R^6$ is —NHSO$_2R^{60}$, wherein $R^{60}$ is alkyl, alkenyl, alkynyl, cycloalkyl, heterocycloalkyl, aryl, heteroaryl, substituted aryl, or substituted heteroaryl;
$R^7$ is, independently in each instance, hydrogen, —OH, halogen, or —N$R^{7a}R^{7b}$,
  wherein $R^{7a}$ and $R^{7b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted;
$R^8$ is, independently in each instance, hydrogen, deuterium, —NH$R^9$, or halogen,
  wherein $R^9$ is hydrogen, —$C_1$-$C_5$ alkyl, or —C(O)$C_1$-$C_5$ alkyl; and
m is 1 or 2;
Q is —CH$_2$— or —O— wherein
  when Q is —O—, then $R^2$ is $C_1$-$C_{10}$ alkyl, $C_1$-$C_{10}$ alkynyl, —$C_1$-$C_{10}$ alkylene-(5-membered heteroaryl), —$C_1$-$C_3$ alkylene-$Q^1$-(CH$_2$)$_n$aryl, or $C_1$-$C_3$ hydroxyalkyl; or
  when Q is —CH$_2$—, then $R^2$ is $C_5$-$C_{10}$ alkyl, $C_1$-$C_{10}$ alkynyl, —$C_1$-$C_{10}$ alkylene-(5-membered heteroaryl), —$C_1$-$C_3$ alkylene-$Q^1$-(CH$_2$)$_n$aryl, or $C_1$-$C_3$ hydroxyalkyl; and
$Q^1$ is —CH$_2$— or —O—;
wherein said heteroaryl is unsubstituted or substituted with alkyl, aminoalkyl, hydroxylalkyl, carboxyalkyl, benzyl, or phenyl;
wherein said aryl is unsubstituted or substituted with nitro or amino; and
wherein n is an integer from 1 to 5.

In another embodiment, provided is a compound of Formula A, B, C, or D:

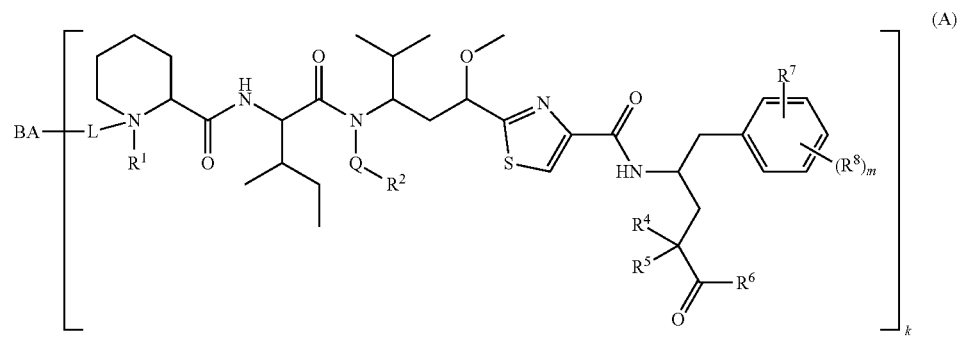

(A)

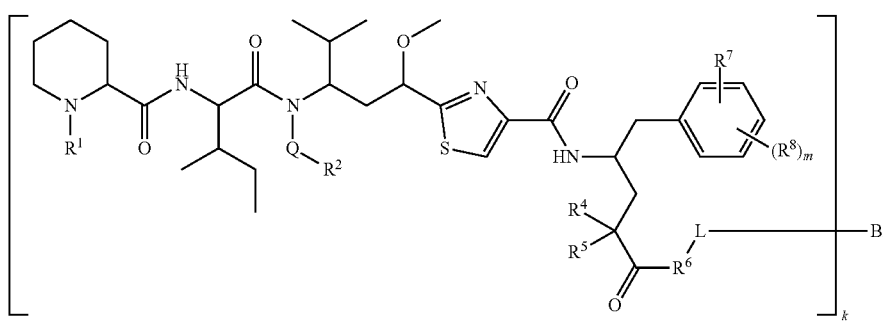
(B)

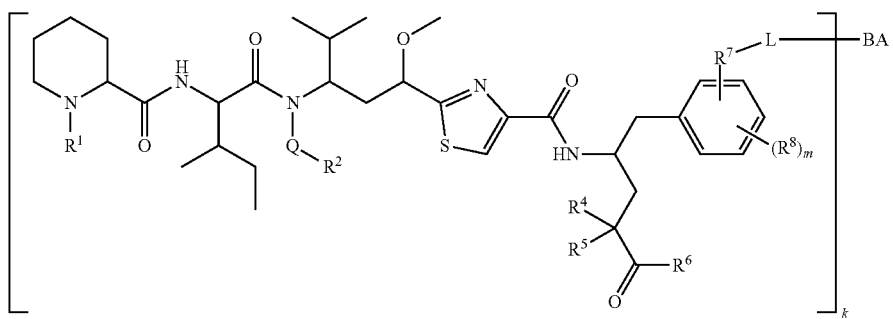
(C)

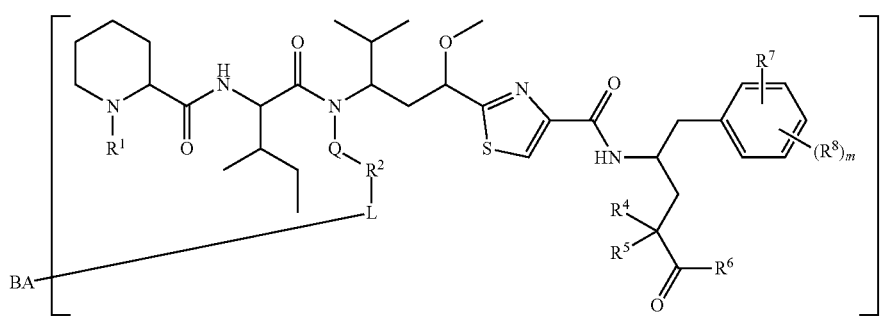
(D)

or a pharmaceutically acceptable salt thereof, wherein
L is a linker;
BA is a binding agent;
k is an integer from 1 to 30;
$R^1$ is $C_1$-$C_{10}$ alkyl;
$R^3$ is —C(O)$C_1$-$C_5$ alkyl, —C(O)N(H)$C_1$-$C_{10}$ alkyl, or —($C_1$-$C_{10}$ alkylene)-NR$^{3a}$R$^{3b}$,
  wherein R$^{3a}$ and R$^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted;
$R^4$ and $R^5$ are, independently in each instance, hydrogen or $C_1$-$C_5$ alkyl;
$R^6$ is —OH, —O—, —NHNH$_2$, or —NHNH—;
$R^7$ is, independently in each instance, hydrogen, —OH, —O—, halogen, or —NR$^{7a}$R$^{7b}$,
  wherein R$^{7a}$ and R$^{7b}$ are independently in each instance, a bond, hydrogen, alkyl, alkenyl, alkynyl, cycloalkyl, aryl, heteroaryl, acyl, and amino acid residue, wherein alkyl, alkenyl, alkynyl, cycloalkyl, aryl, heteroaryl, and acyl are optionally substituted;
$R^8$ is, independently in each instance, hydrogen, deuterium, —NHR$^9$, or halogen,
  wherein $R^9$ is hydrogen, —$C_1$-$C_5$ alkyl, or —C(O)$C_1$-$C_5$ alkyl; and m is 1 or 2;
Q is —CH$_2$— or —O— wherein
  when Q is —O—, then $R^2$ is $C_1$-$C_{10}$ alkyl, $C_1$-$C_{10}$ alkynyl, a regioisomeric $C_1$-$C_{10}$ triazolylene, —$C_1$-$C_{10}$ alkylene-(5-membered heteroaryl), a regioisomeric —$C_1$-$C_{10}$ alkylene-(5-membered heteroarylene), —$C_1$-$C_3$ alkylene-Q$^1$-(CH$_2$)$_n$aryl, $C_1$-$C_3$ hydroxyalkyl, or $C_1$-$C_{10}$ alkylether; or
  when Q is —CH$_2$—, then $R^2$ is $C_5$-$C_{10}$ alkyl, $C_1$-$C_{10}$ alkynyl, a regioisomeric $C_1$-$C_{10}$ triazolylene, —$C_1$-$C_{10}$ alkylene-(5-membered heteroaryl), a regioisomeric —$C_1$-$C_{10}$ alkylene-(5-membered heteroarylene), —$C_1$-$C_3$ alkylene-Q$^1$-(CH$_2$)$_n$aryl, $C_1$-$C_3$ hydroxyalkyl, or $C_1$-$C_{10}$ alkylether; and
$Q^1$ is —CH$_2$— or —O—;
wherein said regioisomeric triazolylene is unsubstituted or substituted with alkyl, alkenyl, alkynyl, cycloalkyl, aryl, heteroaryl, and acyl;
wherein said heteroaryl or regioisomeric heteroarylene is unsubstituted or substituted with alkyl, aminoalkyl, -alkylene-NH—, hydroxylalkyl, -alkylene-O—, carboxyalkyl, -alkylene-COO—, benzyl, or phenyl;
wherein said aryl is unsubstituted or substituted with nitro, amino, or —NH—; and
wherein n is an integer from 1 to 5.

In another embodiment, provided is a compound of Formula A, B, C, or D:

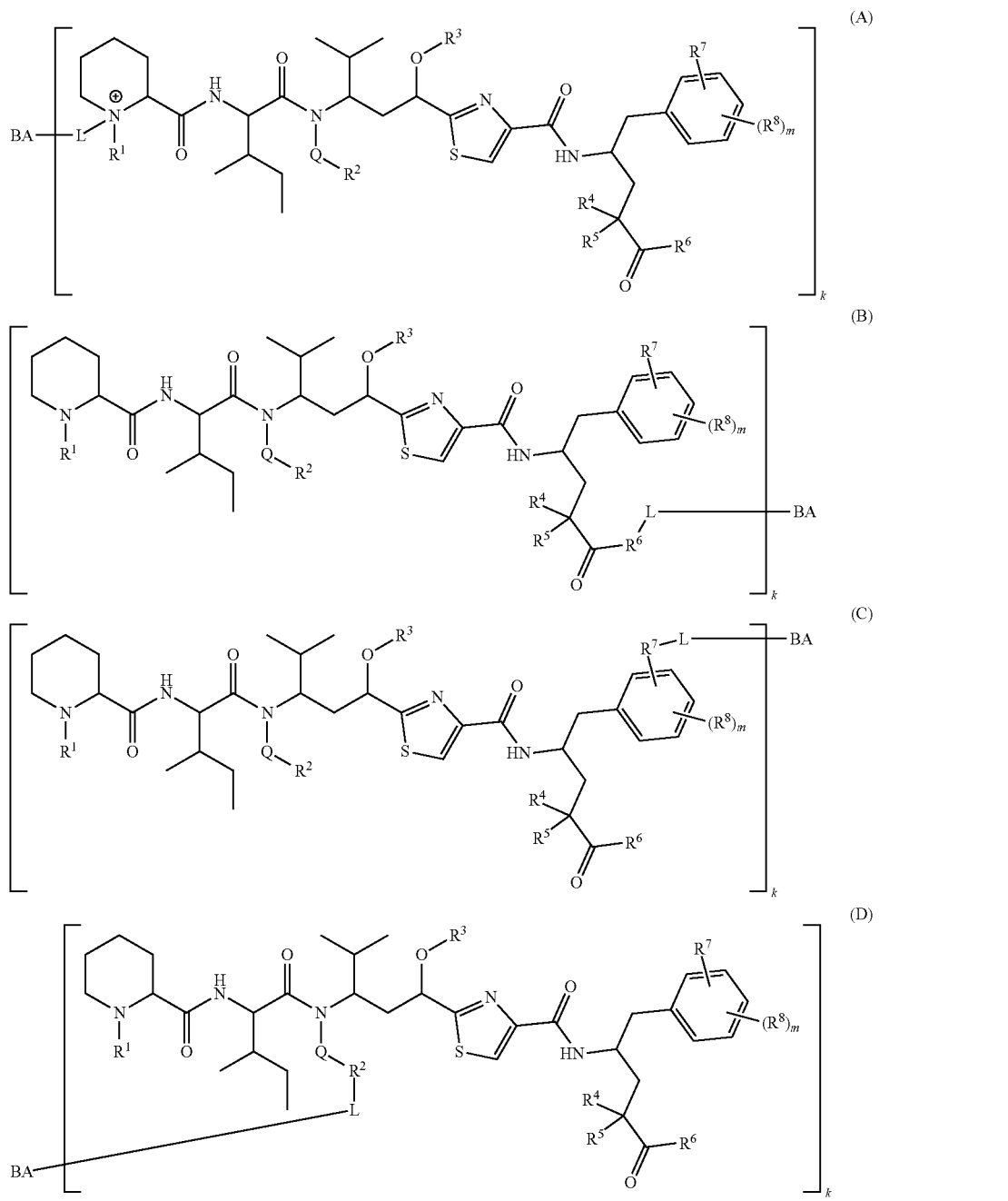

or a pharmaceutically acceptable salt thereof, wherein
L is a linker;
BA is a binding agent;
k is an integer from 1 to 30;
$R^1$ is $C_1$-$C_{10}$ alkyl;
$R^3$ is —C(O)$C_1$-$C_5$ alkyl, —C(O)N(H)$C_1$-$C_{10}$ alkyl, or —($C_1$-$C_{10}$ alkylene)-NR$^{3a}$R$^{3b}$,
    wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted;

$R^4$ and $R^5$ are, independently in each instance, hydrogen or $C_1$-$C_5$ alkyl;

$R^6$ is —OH, —O—, —NHNH$_2$, or —NHNH—; or, in certain embodiments, $R^6$ is —NHSO$_2$R$^{60}$, wherein $R^{60}$ is alkyl, alkenyl, alkynyl, cycloalkyl, heterocycloalkyl, aryl, heteroaryl, substituted aryl, substituted heteroaryl, or divalent -alkylene-, -alkenylene-, -alkynylene-, -cycloalkylene-, -heterocycloalkylene-, -arylene-, -heteroarylene-, substituted -arylene-, or substituted -heteroarylene- when bonded to -L-;

$R^7$ is, independently in each instance, hydrogen, —OH, —O—, halogen, or —NR$^{7a}$R$^{7b}$,
    wherein $R^{7a}$ and $R^{7b}$ are independently in each instance, a bond, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted, or divalent -alkylene-, -alkenylene-, -alkynylene-, -cycloalkylene-, -arylene-, -heteroarylene-, or -acylene- when bonded to -L-, wherein -alkylene-, -alkenylene-, -alkynylene-, -cycloalkylene-, -arylene-, -heteroarylene-, and -acylene- are optionally substituted;

$R^8$ is, independently in each instance, hydrogen, deuterium, —$NHR^9$, or halogen,
wherein $R^9$ is hydrogen, —$C_1$-$C_5$ alkyl, or —$C(O)C_1$-$C_5$ alkyl; and
m is 1 or 2;

Q is —$CH_2$— or —O— wherein
when Q is —O—, then $R^2$ is $C_1$-$C_{10}$ alkyl, divalent —$C_1$-$C_{10}$ alkylene-, $C_1$-$C_{10}$ alkynyl, divalent —$C_1$-$C_{10}$ alkynylene-, a regioisomeric $C_1$-$C_{10}$ alkyl triazolyl, a regioisomeric divalent —$C_1$-$C_{10}$ alkyl triazolylene-, —$C_1$-$C_{10}$ alkylene-(5-membered heteroaryl), a regioisomeric divalent —$C_1$-$C_{10}$ alkylene-(5-membered heteroarylene)-, —$C_1$-$C_3$ alkylene-$Q^1$-$(CH_2)_n$aryl, divalent —$C_1$-$C_3$ alkylene-$Q^1$-$(CH_2)_n$arylene-, $C_1$-$C_3$ hydroxyalkyl, divalent —$C_1$-$C_3$ hydroxyalkylene-, $C_1$-$C_{10}$ alkylether, or divalent —$C_1$-$C_{10}$ alkylether-; or when Q is —$CH_2$—, then $R^2$ is $C_5$-$C_{10}$ alkyl, divalent —$C_5$-$C_{10}$ alkylene-, $C_1$-$C_{10}$ alkynyl, divalent —$C_1$-$C_{10}$ alkynylene-, a regioisomeric $C_1$-$C_{10}$ alkyl triazolyl, a regioisomeric divalent —$C_1$-$C_{10}$ alkyl triazolylene-, —$C_1$-$C_{10}$ alkylene-(5-membered heteroaryl), a regioisomeric divalent —$C_1$-$C_{10}$ alkylene-(5-membered heteroarylene)-, —$C_1$-$C_3$ alkylene-$Q^1$-$(CH_2)_n$aryl, divalent —$C_1$-$C_3$ alkylene-$Q^1$-$(CH_2)_n$arylene-, $C_1$-$C_3$ hydroxyalkyl, divalent —$C_1$-$C_3$ hydroxyalkylene-, $C_1$-$C_{10}$ alkylether, or divalent —$C_1$-$C_{10}$ alkylether-; and $Q^1$ is —$CH_2$— or —O—;
wherein said regioisomeric triazolylene is unsubstituted or substituted with alkyl, alkenyl, alkynyl, cycloalkyl, aryl, heteroaryl, and acyl;
wherein said heteroaryl or regioisomeric heteroarylene is unsubstituted or substituted with alkyl, aminoalkyl, -alkylene-NH—, hydroxylalkyl, -alkylene-O—, carboxyalkyl, -alkylene-COO—, benzyl, or phenyl;
wherein said aryl is unsubstituted or substituted with nitro, amino, or —NH—; and
wherein n is an integer from 1 to 5.

In one embodiment, provided is a linker-payload of Formula LPa, LPb, LPc, or LPd:

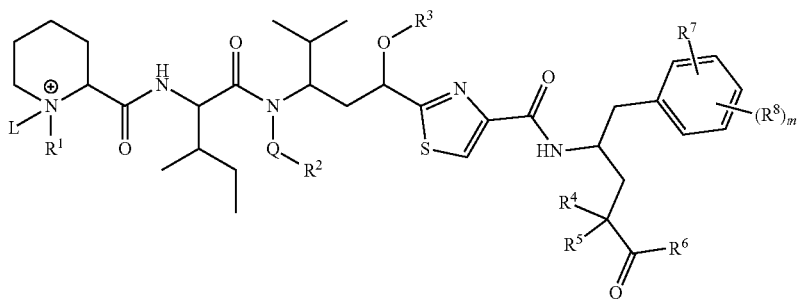

(LPa)

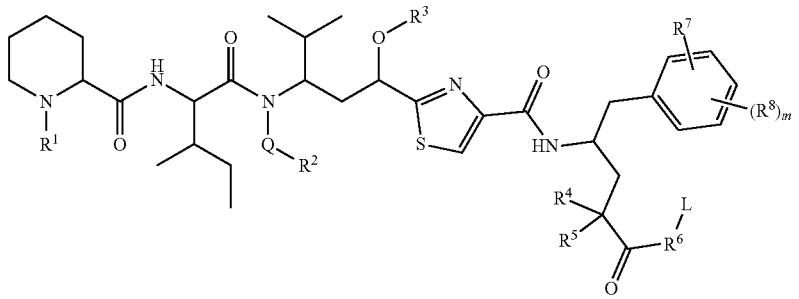

(LPb)

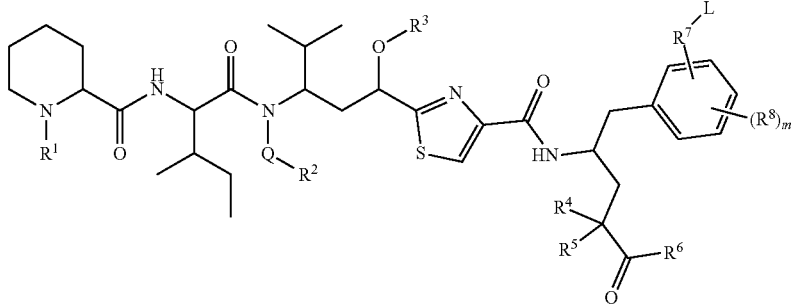

(LPc)

or

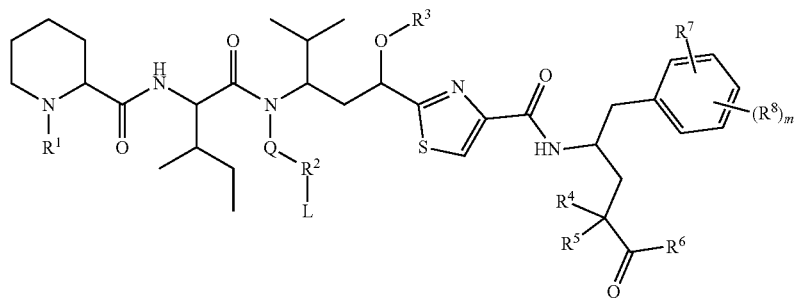

(LPd)

or a pharmaceutically acceptable salt thereof, wherein
L is a linker;
$R^1$ is $C_1$-$C_{10}$ alkyl;
$R^3$ is —C(O)$C_1$-$C_5$ alkyl, —C(O)N(H)$C_1$-$C_{10}$ alkyl, or —($C_1$-$C_{10}$ alkylene)-N$R^{3a}R^{3b}$,
  wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted;
$R^4$ and $R^5$ are, independently in each instance, hydrogen or $C_1$-$C_5$ alkyl;
$R^6$ is —OH, —O—, —NHNH$_2$, or —NHNH—;
$R^7$ is, independently in each instance, hydrogen, —OH, —O—, halogen, or —N$R^{7a}R^{7b}$,
  wherein $R^{7a}$ and $R^{7b}$ are independently in each instance, a bond, hydrogen, alkyl, alkenyl, alkynyl, cycloalkyl, aryl, heteroaryl, acyl, and amino acid residue, wherein alkyl, alkenyl, alkynyl, cycloalkyl, aryl, heteroaryl, and acyl are optionally substituted;
$R^8$ is, independently in each instance, hydrogen, deuterium, —NH$R^9$, or halogen,
wherein $R^9$ is hydrogen, —$C_1$-$C_5$ alkyl, or —C(O)$C_1$-$C_5$ alkyl; and m is 1 or 2;
Q is —CH$_2$— or —O— wherein
  when Q is —O—, then $R^2$ is $C_1$-$C_{10}$ alkyl, $C_1$-$C_{10}$ alkynyl, a regioisomeric $C_1$-$C_{10}$ triazolylene, —$C_1$-$C_{10}$ alkylene-(5-membered heteroaryl), a regioisomeric —$C_1$-$C_{10}$ alkylene-(5-membered heteroarylene), —$C_1$-$C_3$ alkylene-$Q^1$-(CH$_2$)$_n$aryl, $C_1$-$C_3$ hydroxyalkyl, or $C_1$-$C_{10}$ alkylether; or
  when Q is —CH$_2$—, then $R^2$ is $C_5$-$C_{10}$ alkyl, $C_1$-$C_{10}$ alkynyl, a regioisomeric $C_1$-$C_{10}$ triazolylene, —$C_1$-$C_{10}$ alkylene-(5-membered heteroaryl), a regioisomeric —$C_1$-$C_{10}$ alkylene-(5-membered heteroarylene), —$C_1$-$C_3$ alkylene-$Q^1$-(CH$_2$)$_n$aryl, $C_1$-$C_3$ hydroxyalkyl, or $C_1$-$C_{10}$ alkylether; and
$Q^1$ is —CH$_2$— or —O—;
wherein said regioisomeric triazolylene is unsubstituted or substituted with alkyl, alkenyl, alkynyl, cycloalkyl, aryl, heteroaryl, and acyl;
wherein said heteroaryl or regioisomeric heteroarylene is unsubstituted or substituted with alkyl, aminoalkyl, -alkylene-NH—, hydroxylalkyl, -alkylene-O—, carboxyalkyl, -alkylene-COO—, benzyl, or phenyl;
wherein said aryl is unsubstituted or substituted with nitro, amino, or —NH—; and
wherein n is an integer from 1 to 5.

In one embodiment, provided is a linker-payload of Formula LPa, LPb, LPc, or LPd:

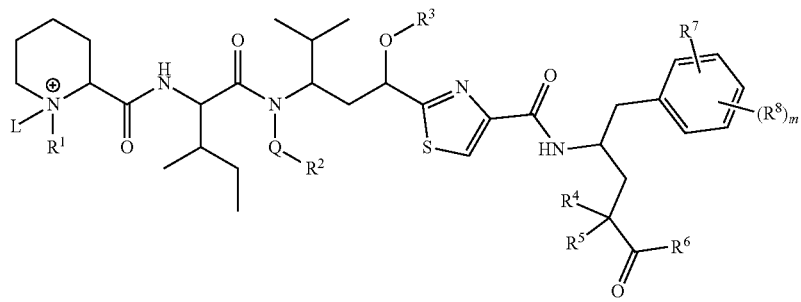

(LPa)

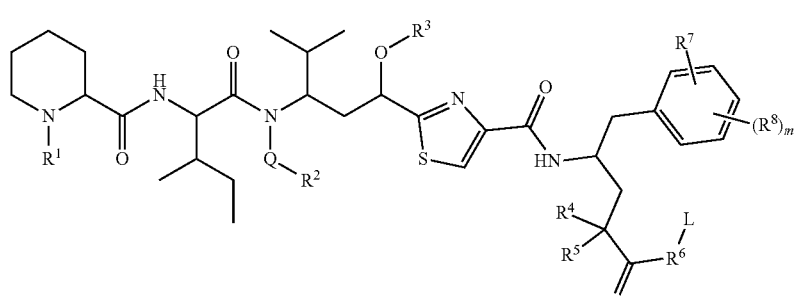
(LPb)

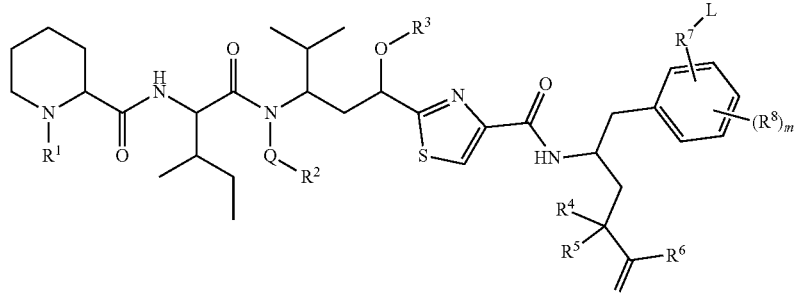
or
(LPc)

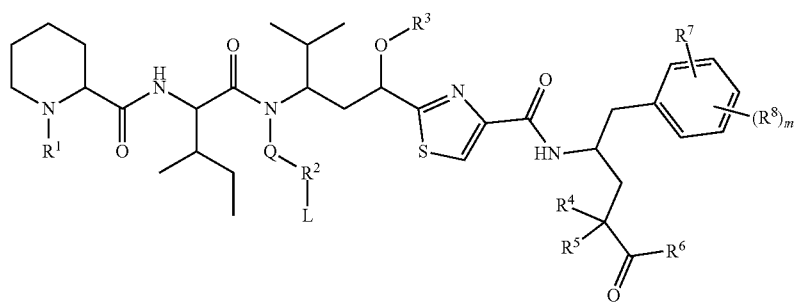
(LPd)

or a pharmaceutically acceptable salt thereof, wherein
L is a linker;
R$^1$ is C$_1$-C$_{10}$ alkyl;
R$^3$ is —C(O)C$_1$-C$_5$ alkyl, —C(O)N(H)C$_1$-C$_{10}$ alkyl, or —(C$_1$-C$_{10}$ alkylene)-NR$^{3a}$R$^{3b}$,
  wherein R$^{3a}$ and R$^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted;
R$^4$ and R$^5$ are, independently in each instance, hydrogen or C$_1$-C$_5$ alkyl;
R$^6$ is —OH, —O—, —NHNH$_2$, or —NHNH—; or, in certain embodiments, R$^6$ is —NHSO$_2$R$^{60}$, wherein R$^{60}$ is alkyl, alkenyl, alkynyl, cycloalkyl, heterocycloalkyl, aryl, heteroaryl, substituted aryl, substituted heteroaryl, or divalent -alkylene-, -alkenylene-, -alkynylene-, -cycloalkylene-, -heterocycloalkylene-, -arylene-, -heteroarylene-, substituted -arylene-, or substituted -heteroarylene- when bonded to -L-;
R$^7$ is, independently in each instance, hydrogen, —OH, —O—, halogen, or —NR$^{7a}$R$^{7b}$,
  wherein R$^{7a}$ and R$^{7b}$ are independently in each instance, a bond, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted, or divalent -alkylene-, -alkenylene-, -alkynylene-, -cycloalkylene-, -arylene-, -heteroarylene-, or -acylene- when bonded to -L-, wherein -alkylene-, -alkenylene-, -alkynylene-, -cycloalkylene-, -arylene-, -heteroarylene-, and -acylene- are optionally substituted;
R$^8$ is, independently in each instance, hydrogen, deuterium, —NHR$^9$, or halogen,
  wherein R$^9$ is hydrogen, —C$_1$-C$_5$ alkyl, or —C(O)C$_1$-C$_5$ alkyl; and
m is 1 or 2;
Q is —CH$_2$— or —O— wherein when Q is —O—, then R$^2$ is C$_1$-C$_{10}$ alkyl, divalent —C$_1$-C$_{10}$ alkylene-, C$_1$-C$_{10}$ alkynyl, divalent —C$_1$-C$_{10}$ alkynylene-, a regioisomeric C$_1$-C$_{10}$ alkyl triazolyl, a regioisomeric divalent —C$_1$-C$_{10}$ alkyl triazolylene-, C$_1$-C$_{10}$ alkylene-(5-membered heteroaryl), a regioisomeric divalent —C$_1$-C$_{10}$ alkylene-(5-membered heteroarylene)-, —C$_1$-C$_3$ alkylene-Q$^1$-(CH$_2$)$_n$aryl, divalent —C$_1$-C$_3$ alkylene-Q$^1$-(CH$_2$)$_n$arylene-, C$_1$-C$_3$ hydroxyalkyl, divalent —C$_1$-C$_3$ hydroxyalkylene-, C$_1$-C$_{10}$ alkylether, or divalent —C$_1$-C$_{10}$ alkylether-; or
when Q is —CH$_2$—, then R$^2$ is C$_5$-C$_{10}$ alkyl, divalent —C$_5$-C$_{10}$ alkylene-, C$_1$-C$_{10}$ alkynyl, divalent —C$_1$-C$_{10}$ alkynylene-, a regioisomeric C$_1$-C$_{10}$ alkyl triazolyl, a regioisomeric divalent —C$_1$-C$_{10}$ alkyl triazolylene-, —C$_1$-C$_{10}$ alkylene-(5-membered heteroaryl), a regioisomeric divalent —C$_1$-C$_{10}$ alkylene-(5-membered heteroarylene)-, —$C_1$-$C_3$ alkylene-$Q^1$-$(CH_2)_n$aryl, divalent —$C_1$-$C_3$ alkylene-$Q^1$-$(CH_2)_n$arylene-, $C_1$-$C_3$ hydroxyalkyl, divalent —$C_1$-$C_3$ hydroxyalkylene-, $C_1$-$C_{10}$ alkylether, or divalent —$C_1$-$C_{10}$ alkylether-; and $Q^1$ is —$CH_2$— or —O—;

wherein said regioisomeric triazolylene is unsubstituted or substituted with alkyl, alkenyl, alkynyl, cycloalkyl, aryl, heteroaryl, and acyl;

wherein said heteroaryl or regioisomeric heteroarylene is unsubstituted or substituted with alkyl, aminoalkyl, -alkylene-NH—, hydroxylalkyl, -alkylene-O—, carboxyalkyl, -alkylene-COO—, benzyl, or phenyl;

wherein said aryl is unsubstituted or substituted with nitro, amino, or —NH—; and wherein n is an integer from 1 to 5.

In another embodiment, set forth herein is an antibody-drug conjugate including an antibody, or antigen binding fragment thereof, wherein said antibody or antigen binding fragment thereof is conjugated to a compound as described herein.

In another embodiment, set forth herein are methods for making the compounds, linker-payloads, or antibody-drug conjugates, and compositions described herein.

BRIEF DESCRIPTIONS OF THE DRAWING

DESCRIPTION OF EXEMPLARY EMBODIMENTS

Figure 1:
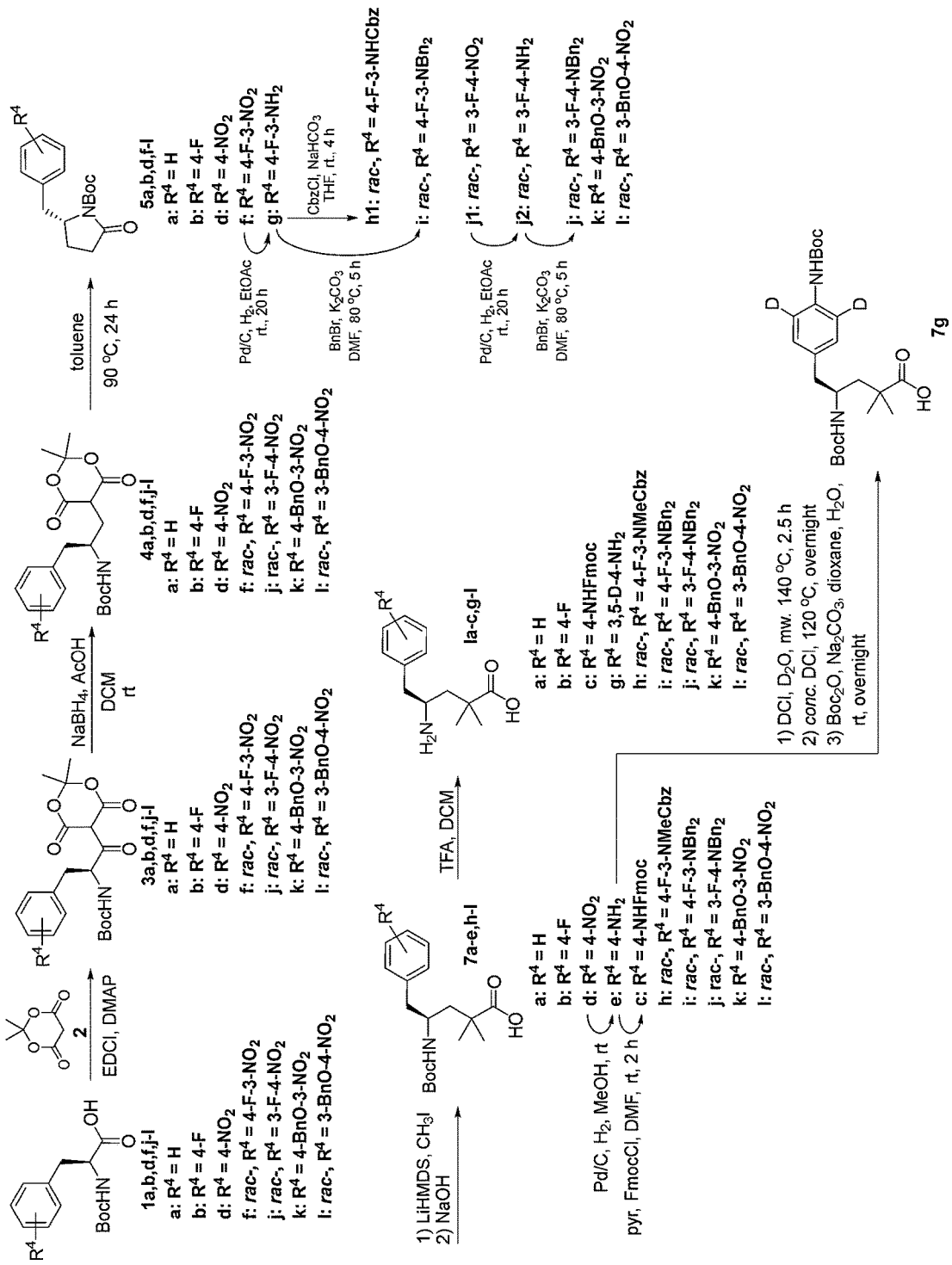
FIGS. 1-14 show synthetic chemistry schemes for tubulyisin payloads, tubulysin linker-payloads, and protein conjugates thereof.

Provided herein are compounds, compositions, and methods useful for treating for example, cancer in a subject.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term provided herein, these Definitions prevail unless stated otherwise.

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those radicals having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to, methyl, ethyl, n-propyl, i-propyl, n-butyl, β-butyl, t-butyl, i-butyl, a pentyl moiety, a hexyl moiety, cyclopropyl, cyclobutyl, cyclopentyl, and cyclohexyl. A pentyl moiety includes, but is not limited to, n-pentyl and i-pentyl. A hexyl moiety includes, but is not limited to, n-hexyl.

As used herein, "alkylene" refers to a divalent alkyl group. Unless specified otherwise, alkylene includes, but is not limited to, 1-20 carbon atoms. The alkylene group is optionally substituted as described herein for alkyl. In some embodiments, alkylene is unsubstituted.

Designation of an amino acid or amino acid residue without specifying its stereochemistry is intended to encompass the L-form of the amino acid, the D-form of the amino acid, or a racemic mixture thereof.

As used herein, "haloalkyl" refers to alkyl, as defined above, wherein the alkyl includes at least one substituent selected from a halogen, for example, fluorine (F), chlorine (Cl), bromine (Br), or iodine (I). Examples of haloalkyl include, but are not limited to, —$CF_3$, —$CH_2CF_3$, —$CCl_2F$, and —$CCl_3$.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those radicals having 2-20 carbon atoms, i.e., $C_{2-20}$ alkenyl; 2-12 carbon atoms, i.e., $C_{2-12}$ alkenyl; 2-8 carbon atoms, i.e., $C_2$-s alkenyl; 2-6 carbon atoms, i.e., $C_{2-6}$ alkenyl; and 2-4 carbon atoms, i.e., $C_{2}4$ alkenyl. Examples of alkenyl moieties include, but are not limited to, vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those radicals having 2-20 carbon atoms, i.e., $C_{2-20}$ alkynyl; 2-12 carbon atoms, i.e., $C_{2-12}$ alkynyl; 2-8 carbon atoms, i.e., $C_2$-s alkynyl; 2-6 carbon atoms, i.e., $C_{2-6}$ alkynyl; and 2-4 carbon atoms, i.e., $C_{2}4$ alkynyl. Examples of alkynyl moieties include, but are not limited to ethynyl, propynyl, and butynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2$—O for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to, methoxy, ethoxy, n-propoxy, i-propoxy, n-butoxy, β-butoxy, t-butoxy, i-butoxy, a pentoxy moiety, a hexoxy moiety, cyclopropoxy, cyclobutoxy, cyclopentoxy, and cyclohexoxy.

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to, those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are limited to, phenyl, naphthyl, fluorenyl, azulenyl, anthryl, phenanthryl, and pyrenyl.

As used herein, "arylalkyl" refers to a monovalent moiety that is a radical of an alkyl compound, wherein the alkyl compound is substituted with an aromatic substituent, i.e., the aromatic compound includes a single bond to an alkyl group and wherein the radical is localized on the alkyl group. An arylalkyl group bonds to the illustrated chemical structure via the alkyl group. An arylalkyl can be represented by the structure, e.g.,

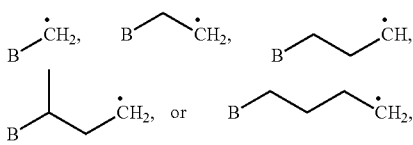

wherein B is an aromatic moiety, e.g., aryl or phenyl. Arylalkyl is optionally substituted, i.e., the aryl group and/or the alkyl group, can be substituted as disclosed herein. Examples of arylalkyl include, but are not limited to, benzyl.

As used herein, "alkylaryl" refers to a monovalent moiety that is a radical of an aryl compound, wherein the aryl compound is substituted with an alkyl substituent, i.e., the aryl compound includes a single bond to an alkyl group and wherein the radical is localized on the aryl group. An alkylaryl group bonds to the illustrated chemical structure via the aryl group. An alkylaryl can be represented by the structure, e.g.,

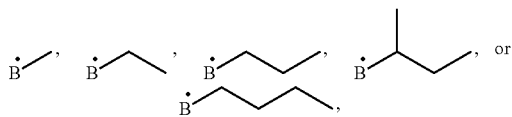

wherein B is an aromatic moiety, e.g., phenyl. Alkylaryl is optionally substituted, i.e., the aryl group and/or the alkyl group, can be substituted as disclosed herein. Examples of alkylaryl include, but are not limited to, toluyl.

As used herein, "aryloxy" refers to a monovalent moiety that is a radical of an aromatic compound wherein the ring atoms are carbon atoms and wherein the ring is substituted with an oxygen radical, i.e., the aromatic compound includes a single bond to an oxygen atom and wherein the radical is localized on the oxygen atom, e.g.,

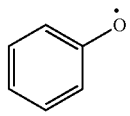

for phenoxy. Aryloxy substituents bond to the compound which they substitute through this oxygen atom. Aryloxy is optionally substituted. Aryloxy includes, but is not limited to, those radicals having 6 to 20 ring carbon atoms, i.e., $C_{6-20}$ aryloxy; 6 to 15 ring carbon atoms, i.e., $C_{6-15}$ aryloxy, and 6 to 10 ring carbon atoms, i.e., $C_{6-10}$ aryloxy. Examples of aryloxy moieties include, but are not limited to phenoxy, naphthoxy, and anthroxy.

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of arylene moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkynyl in which one or more carbon atoms are replaced by heteroatoms. Suitable heteroatoms include, but are not limited to, nitrogen, oxygen, and sulfur atoms. Heteroalkyl, heteroalkenyl, and heteroalkynyl are optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to a divalent heteroaryl in which one or more ring atoms of the aromatic ring are replaced with an oxygen, sulfur, nitrogen, or phosphorus atom. Heteroarylene is optionally substituted.

As used herein, "heterocycloalkyl" refers to a cycloalkyl in which one or more carbon atoms are replaced by heteroatoms. Suitable heteroatoms include, but are not limited to, nitrogen, oxygen, and sulfur atoms. Heterocycloalkyl is optionally substituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "Lewis acid" refers to a molecule or ion that accepts an electron lone pair. The Lewis acids used in the methods described herein are those other than protons. Lewis acids include, but are not limited to, non-metal acids, metal acids, hard Lewis acids, and soft Lewis acids. Lewis acids include, but are not limited to, Lewis acids of aluminum, boron, iron, tin, titanium, magnesium, copper, antimony, phosphorus, silver, ytterbium, scandium, nickel, and zinc. Illustrative Lewis acids include, but are not limited to, $AlBr_3$, $AlCl_3$, $BCl_3$, boron trichloride methyl sulfide, $BF_3$, boron trifluoride methyl etherate, boron trifluoride methyl sulfide, boron trifluoride tetrahydrofuran, dicyclohexylboron trifluoromethanesulfonate, iron (III) bromide, iron (III) chloride, tin (IV) chloride, titanium (IV) chloride, titanium (IV) isopropoxide, $Cu(OTf)_2$, $CuCl_2$, $CuBr_2$, zinc chloride, alkylaluminum halides ($R_nAlX_{3-n}$, wherein R is hydrocarbyl), $Zn(OTf)_2$, $ZnCl_2$, $Yb(OTf)_3$, $Sc(OTf)_3$, $MgBr_2$, $NiCl_2$, $Sn(OTf)_2$, $Ni(OTf)_2$, and $Mg(OTf)_2$.

As used herein, "N-containing heterocycloalkyl," refers to a cycloalkyl in which one or more carbon atoms are replaced by heteroatoms and wherein at least one replacing heteroatom is a nitrogen atom. Suitable heteroatoms in addition to nitrogen, include, but are not limited to, oxygen and sulfur atoms. N-containing heterocycloalkyl is optionally substituted. Examples of N-containing heterocycloalkyl moieties include, but are not limited to, morpholinyl, piperidinyl, pyrrolidinyl, imidazolidinyl, oxazolidinyl, or thiazolidinyl.

As used herein, "optionally substituted," when used to describe a radical moiety, for example, optionally substituted alkyl, means that such moiety is optionally bonded to one or more substituents. Examples of such substituents include, but are not limited to, halo, cyano, nitro, amino, hydroxyl, optionally substituted haloalkyl, aminoalkyl, hydroxyalkyl, azido, epoxy, optionally substituted heteroaryl, optionally substituted heterocycloalkyl,

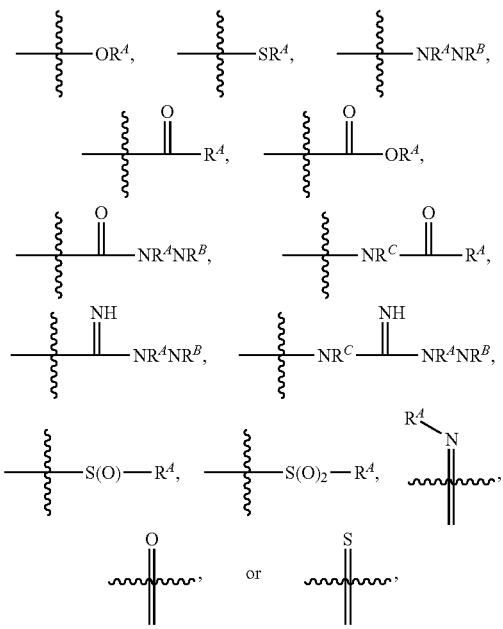

wherein $R^A$, $R^B$, and $R^C$ are, independently at each occurrence, a hydrogen atom, alkyl, alkenyl, alkynyl, aryl, alkylaryl, arylalkyl, heteroalkyl, heteroaryl, or heterocycloalkyl, or $R^A$ and $R^B$ together with the atoms to which they are bonded, form a saturated or unsaturated carbocyclic ring, wherein the ring is optionally substituted, and wherein one or more ring atoms is optionally replaced with a heteroatom. In certain embodiments, when a radical moiety is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents. In some embodiments, when a group described herein is optionally substituted, the substituent bonded to the group is unsubstituted unless otherwise specified.

As used herein, "binding agent" refers to any molecule, e.g., protein, antibody, or fragment thereof, capable of binding with specificity to a given binding partner, e.g., antigen.

As used herein, "linker" refers to a divalent, trivalent, or multivalent moiety that covalently links, or is capable of covalently linking (e.g., via a reactive group), the binding agent to one or more compounds described herein, for instance, payload compounds and enhancement agents.

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refers to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy)tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), 0-(benzotriazol-1-yl)-N,N,N',N'-tetramethyluronium tetrafluoroborate (TBTU), 1-[Bis(dimethylamino)methylene]-1H-1,2,3-triazolo[4,5-b]pyridinium 3-oxid hexafluorophosphate (HATU), N-ethoxycarbonyl-2-ethoxy-1,2-dihydroquinoline (EEDQ), N-ethyl-N'-(3-dimethylaminopropyl)carbodiimide (EDC), 2-chloro-1,3-dimethylimidazolidinium hexafluorophosphate (CIP), 2-chloro-4,6-dimethoxy-1,3,5-triazine (CDMT), and carbonyldiimidazole (CDI). In some examples, a carboxylic acid is first converted to an activated carboxylic ester before treating the activated carboxylic ester with an amine to form an amide bond. In certain embodiments, the carboxylic acid is treated with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. The activated carboxylic esters for certain carboxylic acids are subsequently more susceptible to nucleophilic attack by an amine than the carboxylic acid is before it is activated. This results in amide bond formation. As such, the carboxylic acid is described as activated. Exemplary reagents include DCC and DIC.

As used herein, "regioisomer," "regioisomers," or "mixture of regioisomers" refers to the product(s) of 1,3-cycloadditions or strain-promoted alkyne-azide cycloadditions (SPAACs)—otherwise known as click reactions—that derive from suitable azides (e.g., —N₃, or -PEG-N₃ derivitized antibodies) treated with suitable alkynes. In certain embodiments, for example, regioisomers and mixtures of regioisomers are characterized by the click reaction products shown below:

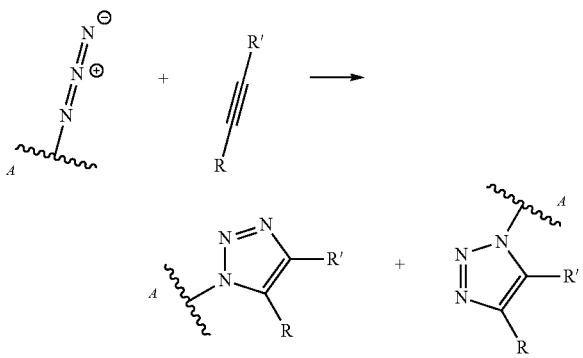

In certain embodiments, more than one suitable azide and more than one suitable alkyne can be utilized within a synthetic scheme en route to a product, where each pair of azide-alkyne can participate in one or more independent click reactions to generate a mixture of regioisomeric click reaction products. For example, a person of skill will recognize that a first suitable azide may independently react with a first suitable alkyne, and a second suitable azide may independently react with a second suitable alkyne, en route to a product, resulting in the generation of four possible click reaction regioisomers or a mixture of the four possible click reaction regioisomers.

As used herein, the term "residue" refers to the chemical moiety within a compound that remains after a chemical reaction. For example, the term "amino acid residue" or "N-alkyl amino acid residue" refers to the product of an amide coupling or peptide coupling of an amino acid or a N-alkyl amino acid to a suitable coupling partner; wherein, for example, a water molecule is expelled after the amide or peptide coupling of the amino acid or the N-alkylamino acid, resulting in the product having the amino acid residue or N-alkyl amino acid residue incorporated therein. The term "amino acid" refers to naturally occurring and synthetic α, β, γ, or δ amino acids, and includes, but is not limited to, amino acids found in proteins, viz., glycine, alanine, valine, leucine, isoleucine, methionine, phenylalanine, tryptophan, proline, serine, threonine, cysteine, tyrosine, asparagine, glutamine, aspartate, glutamate, lysine, arginine, and histidine. In certain embodiments, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In certain embodiments, an amino acid residue is

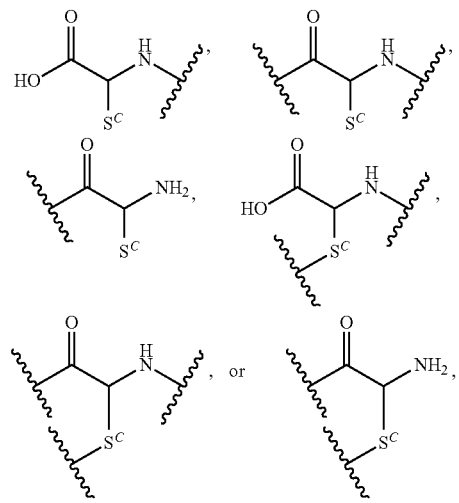

wherein $S^c$ is a side chain of a naturally occurring or non-naturally occurring amino acid or a bond (e.g., hydrogen, as in glycine; —$CH_2OH$ as in serine; —$CH_2SH$ as in cysteine; —$CH_2CH_2CH_2CH_2NH_2$ as in lysine; —$CH_2CH_2COOH$ as in glutamic acid; —$CH_2CH_2C(O)NH_2$ as in glutamine; or —$CH_2C_6H_5OH$ as in tyrosine; and the like); and ⸭ represents the bonding to another chemical entity. In certain embodiments, $S^c$ is selected from the group consisting of hydrogen, alkyl, heteroalkyl, arylalkyl, and heteroarylalkyl.

As used herein, "therapeutically effective amount" refers to an amount (e.g., of a compound) that is sufficient to provide a therapeutic benefit to a patient in the treatment or management of a disease or disorder, or to delay or minimize one or more symptoms associated with the disease or disorder.

As used herein, "constitutional isomers" refers to compounds that have the same molecular formula, but different chemical structures resulting from the way the atoms are arranged. Exemplary constitutional isomers include n-propyl and isopropyl; n-butyl, sec-butyl, and tert-butyl; and n-pentyl, isopentyl, and neopentyl, and the like.

Certain groups, moieties, substituents, and atoms are depicted with a wiggly line that intersects a bond or bonds to indicate the atom through which the groups, moieties, substituents, atoms are bonded. For example, a phenyl group that is substituted with a propyl group depicted as:

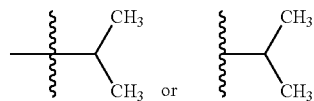

has the following structure:

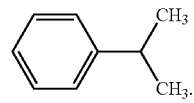

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

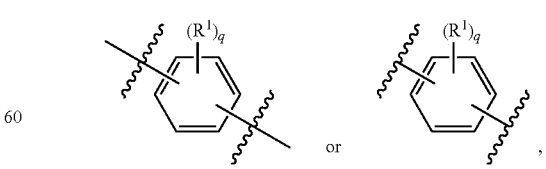

wherein subscript q is an integer from 0 to 4 and in which the positions of substituent $R^1$ are described generically, i.e., not directly attached to any vertex of the bond line structure, i.e., specific ring carbon atom, includes the following, non-limiting examples of groups in which the substituent R¹ is bonded to a specific ring carbon atom:
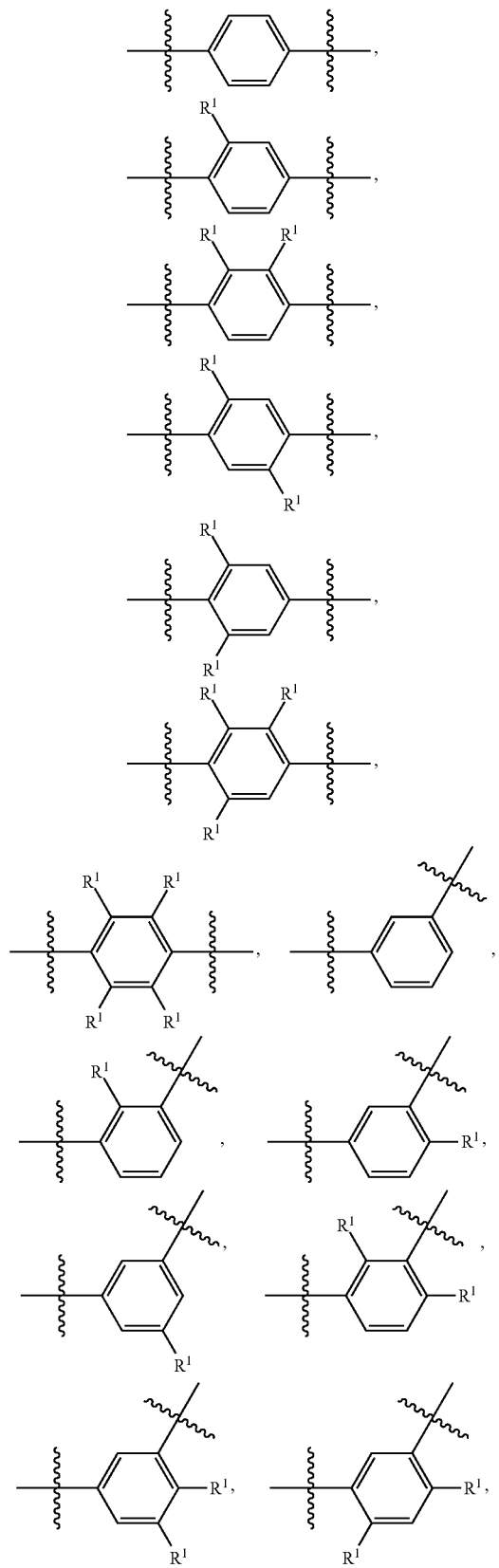
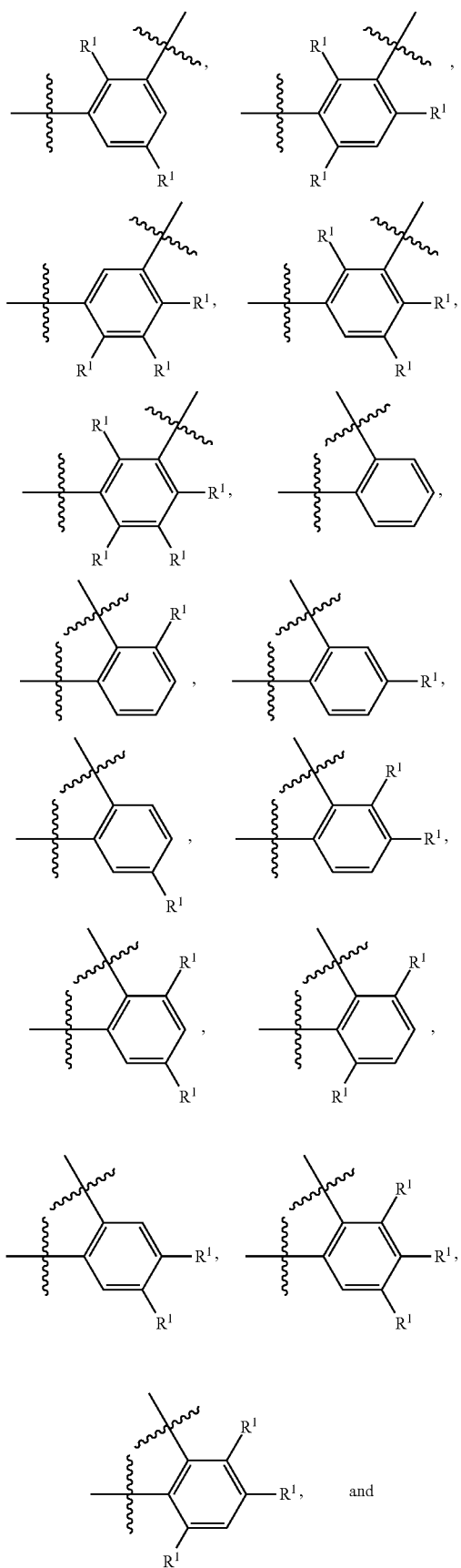

-continued

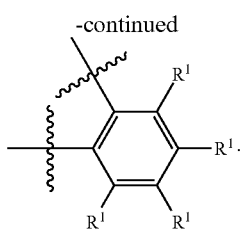

As used herein, the phrase "reactive linker," or the abbreviation "RL" refers to a monovalent group that includes a reactive group ("RG") and spacer group ("SP"), depicted, for example, as

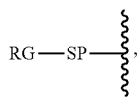

wherein RG is the reactive group and SP is the spacer group. As described herein, a reactive linker may include more than one reactive group and more than one spacer group. The spacer group is any divalent moiety that bridges the reactive group to another group, such as a payload. The reactive linkers (RLs), together with the payloads to which they are bonded, provide intermediates ("linker-payloads" or LPs) useful as synthetic precursors for the preparation of the antibody conjugates described herein. The reactive linker includes a reactive group, which is a functional group or moiety that is capable of reacting with a reactive portion of another group, for instance, an antibody, modified antibody, or antigen binding fragment thereof, or an enhancement group. The moiety resulting from the reaction of the reactive group with the antibody, modified antibody, or antigen binding fragment thereof, together with the linking group, include the "binding agent linker" ("BL") portion of the conjugate, described herein. In certain embodiments, the "reactive group" is a functional group or moiety (e.g., maleimide or N-hydroxysuccinimide (NHS) ester) that reacts with a cysteine or lysine residue of an antibody or antigen-binding fragment thereof. In certain embodiments, the "reactive group" is a functional group or moiety that is capable of undergoing a click chemistry reaction (see, e.g., click chemistry, Huisgen *Proc. Chem. Soc.* 1961, Wang et al. *J Am. Chem. Soc.* 2003, and Agard et al. *J Am. Chem. Soc.* 2004). In some embodiments of said click chemistry reaction, the reactive group is an alkyne that is capable of undergoing a 1,3-cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3-cycloaddition reactions with alkynes in the absence of copper catalysts. Suitable alkynes also include, but are not limited to, dibenzoazacyclooctyne or (DIBAC)

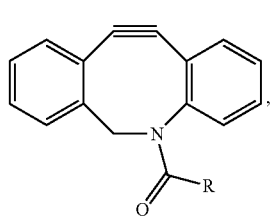

dibenzocyclooctyne or (DIBO)

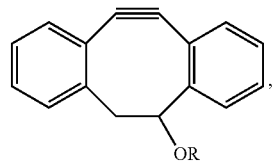

biarylazacyclooctynone or (BARAC)

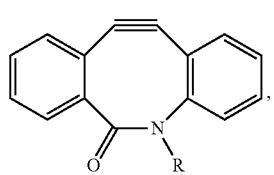

difluorinated cyclooctyne or

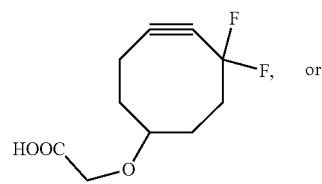

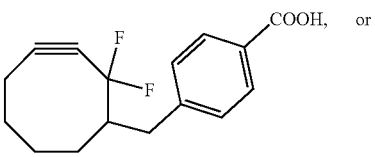

(DIFO)

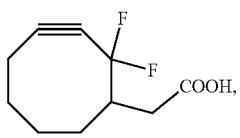

substituted, e.g., fluorinated alkynes, aza-cycloalkynes, bicycle[6.1.0]nonyne or (BCN

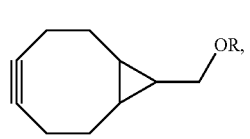

where R is alkyl, alkoxy, or acyl), and derivatives thereof. Particularly useful alkynes include

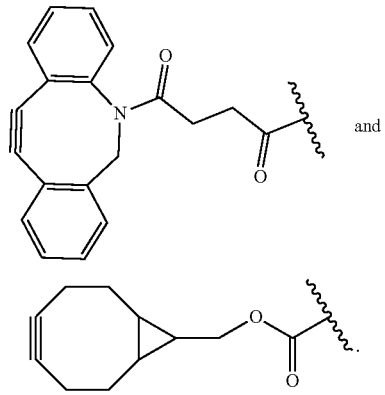

and

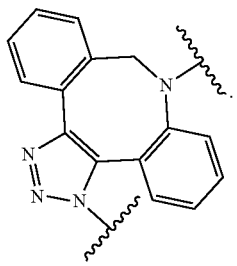

Linker-payloads including such reactive groups are useful for conjugating antibodies that have been functionalized with azido groups. Such functionalized antibodies include antibodies functionalized with azido-polyethylene glycol groups. In certain embodiments, such a functionalized antibody is derived by treating an antibody having at least one glutamine residue, e.g., heavy chain Gln295, with a compound bearing an an amino agroup and an azide group, in the presence of the enzyme transglutaminase.

In some examples, the reactive group is an alkyne, e.g.,

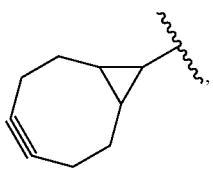 [SMILES: *C1C2CCC#CCCC12]

which can react via click chemistry with an azide, e.g.,

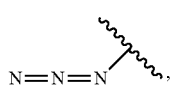

to form a click chemistry product, e.g.,

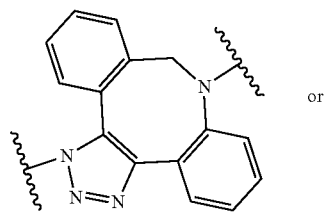

or

In some examples, the group reacts with an azide on a modified antibody or antigen binding fragment thereof. In some examples, the reactive group is an alkyne, e.g.,

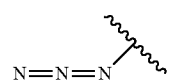

which can react via click chemistry with an azide, e.g.,

N=N=N to form a click chemistry product, e.g.,

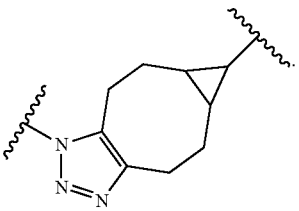 [SMILES: *C1C2CCc3nnn(*)c3CCC12]

In some examples, the reactive group is an alkyne, e.g.,

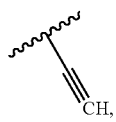

which can react via click chemistry with an azide, e.g.,

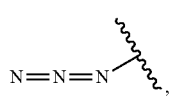

to form a click chemistry product, e.g.,

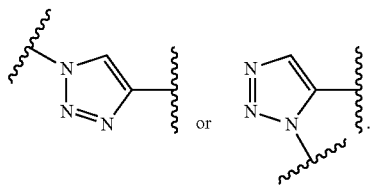 [SMILES: *c1cn(*)nn1 ; *c1cnnn1*]

In some examples, the reactive group is a functional group, e.g.,

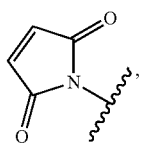

which reacts with a cysteine residue on an antibody or antigen-binding fragment thereof, to form a carbon-sulfur bond thereto, e.g.,

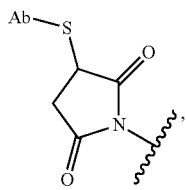

wherein Ab refers to an antibody or antigen-binding fragment thereof and S refers to the S atom on a cysteine residue through which the functional group bonds to the Ab. In some examples, the reactive group is a functional group, e.g.,

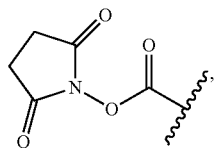 [SMILES: *C(=O)ON1C(=O)CCC1=O]

which reacts with a lysine residue on an antibody or antigen-binding fragment thereof, to form an amide bond thereto, e.g.,

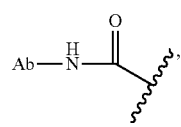

wherein Ab refers to an antibody or antigen-binding fragment thereof and NH refers to the NH atom on a lysine side chain residue through which the functional group bonds to the Ab.

As used herein, the phrase "biodegradable moiety" refers to a moiety that degrades in vivo to non-toxic, biocompatible components which can be cleared from the body by ordinary biological processes. In some embodiments, a biodegradable moiety completely or substantially degrades in vivo over the course of about 90 days or less, about 60 days or less, or about 30 days or less, where the extent of degradation is based on percent mass loss of the biodegradable moiety, and wherein complete degradation corresponds to 100% mass loss. Exemplary biodegradable moieties include, without limitation, aliphatic polyesters such as poly(s-caprolactone) (PCL), poly(3-hydroxybutyrate) (PHB), poly(glycolic acid) (PGA), poly(lactic acid) (PLA) and its copolymers with glycolic acid (i.e., poly(D,L-lactide-coglycolide) (PLGA) (Vert M, Schwach G, Engel R and Coudane J (1998) J Control Release 53(1-3):85-92; Jain R A (2000) Biomaterials 21(23):2475-2490; Uhrich K E, Cannizzaro S M, Langer R S and Shakesheff K M (1999) Chemical Reviews 99(11): 3181-3198; and Park T G (1995) Biomaterials 16(15):1123-1130, each of which are incorporated herein by reference in their entirety).

As used herein, the phrase "binding agent linker," or "BL" refers to any divalent, trivalent, or multi-valent group or moiety that links, connects, or bonds a binding agent (e.g., an antibody or an antigen-binding fragment thereof) with a payload compound set forth herein (e.g., tubulysins) and, optionally, with one or more side chain compounds. Generally, suitable binding agent linkers for the antibody conjugates described herein are those that are sufficiently stable to exploit the circulating half-life of the antibody conjugates and, at the same time, capable of releasing its payload after antigen-mediated internalization of the conjugate. Linkers can be cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolytically-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyloxycarbonyl (PABC), para-aminobenzyl (PAB) units. In some embodiments, the binding agent linker (BL) includes a moiety that is formed by the reaction of the reactive group (RG) of a reactive linker (RL) and reactive portion of the binding agent, e.g., antibody, modified antibody, or antigen binding fragment thereof.

In some examples, the BL includes the following moiety:

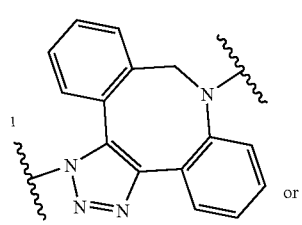

-continued

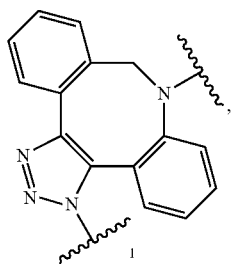

wherein $\overset{1}{\xi}$ is the bond to the binding agent. In some examples, the BL includes the following moiety:

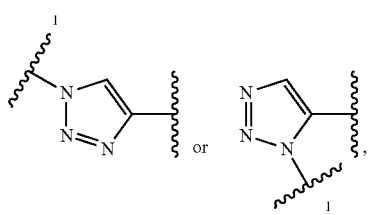

wherein $\overset{1}{\xi}$ is the bond to the binding agent. In some examples, the BL includes the following moiety:

wherein $\overset{1}{\xi}$ is the bond to the binding agent. In some examples, the BL includes the following moiety:

wherein $\overset{1}{\xi}$ is the bond to the cysteine of the antibody or antigen-binding fragment thereof. In some examples, the BL includes the following moiety:

wherein $\overset{1}{\xi}$ is the bond to the lysine of the antibody or antigen-binding fragment thereof.

As applied to polypeptides, the phrase "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Sequence similarity may also be determined using the BLAST algorithm, described in Altschul et al. J. Mol. Biol. 215: 403-10 (using the published default settings), or available at blast.ncbi.nlm.nih.gov/Blast.cgi. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Methods for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine, and isoleucine;

(2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate; and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Compounds or Payloads—Q is Carbon

Provided herein are compounds or payloads. Without being bound by any particular theory of operation, the compounds include tubulysins or tubulysin derivatives. In certain embodiments, the compounds can be delivered to cells as part of a conjugate. In certain embodiments, the compounds are capable of carrying out any activity of tubulysin or a tubulysin derivative at or in a target, for instance, a target cell. Certain compounds can have one or more additional activities. In certain embodiments, the compounds are capable of modulating the activity of a folate receptor, a somatostatin receptor, and/or a bombesin receptor.

In certain embodiments, set forth herein is a compound having the structure of Formula I:

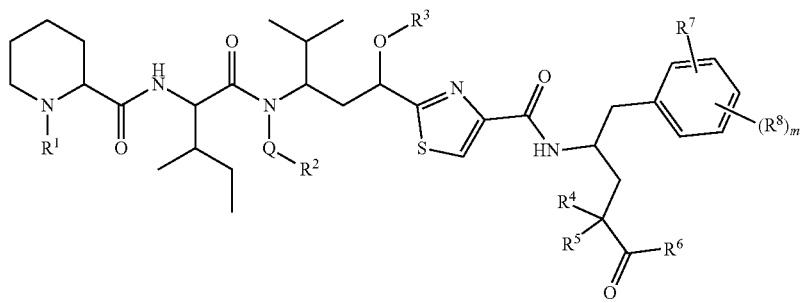

Formula I or a pharmaceutically acceptable salt or prodrug thereof, wherein Q is —CH$_2$—; R$^2$ is C$_5$-C$_{10}$ alkyl; R$^3$ is —C(O)C$_1$-C$_5$ alkyl; R$^4$ is hydrogen; R$^5$ is C$_1$-C$_5$ alkyl; and R$^7$ is halogen. In Formula I, in certain embodiments, useful R$^1$ groups include methyl and ethyl. In certain embodiments, useful R$^1$ groups include propyl, butyl, pentyl, hexyl, heptyl, octyl, nonyl, decyl, and constitutional isomers thereof. In one embodiment, R$^1$ is methyl. In one embodiment, R$^1$ is ethyl. In one embodiment, R$^1$ is propyl, and constitutional isomers thereof. In one embodiment, R$^1$ is butyl, and constitutional isomers thereof. In one embodiment, R$^1$ is pentyl, and constitutional isomers thereof. In one embodiment, R$^1$ is hexyl, and constitutional isomers thereof. In one embodiment, R$^1$ is heptyl, and constitutional isomers thereof. In one embodiment, R$^1$ is octyl, and constitutional isomers thereof. In one embodiment, R$^1$ is nonyl, and constitutional isomers thereof. In one embodiment, R$^1$ is decyl, and constitutional isomers thereof. In Formula I, in certain embodiments above, useful R$^2$ groups include n-pentyl, n-hexyl, n-heptyl, n-octyl, n-nonyl, and n-decyl. In one embodiment, R$^2$ is n-pentyl, or constitutional isomers thereof. In another embodiment, R$^2$ is n-hexyl, or constitutional isomers thereof. In another embodiment, R$^2$ is n-heptyl, or constitutional isomers thereof. In another embodiment, R$^2$ is n-octyl, or constitutional isomers thereof. In another embodiment, R$^2$ is n-nonyl, or constitutional isomers thereof. In another embodiment, R$^2$ is n-decyl, or constitutional isomers thereof. In one embodiment, Q-R$^2$ is n-hexyl. In certain embodiments of Formula I above, useful R$^3$ groups include —C(O)Me, —C(O)Et, —C(O)propyl, —C(O)butyl, and —C(O)pentyl. In one embodiment, R$^3$ is —C(O)Me. In another embodiment, R$^3$ is —C(O)Et. In another embodiment, R$^3$ is —C(O)propyl, and constitutional isomers thereof. In another embodiment, R$^3$ is —C(O)butyl, and constitutional isomers thereof. In another embodiment, R$^3$ is —C(O)pentyl, and constitutional isomers thereof. In certain embodiments of Formula I above, useful R$^5$ groups include methyl, ethyl, propyl, butyl, and pentyl. In one embodiment, R$^5$ is methyl. In another embodiment, R$^5$ is ethyl. In another embodiment, R$^5$ is propyl, and constitutional isomers thereof. In another embodiment, R$^5$ is butyl, and constitutional isomers thereof. In another embodiment, R$^5$ is pentyl, and constitutional isomers thereof. In certain embodiments of Formula I above, R$^6$ includes —OH or —NHNH$_2$. In one embodiment, R$^6$ is —OH. In another embodiment, R$^6$ is —NHNH$_2$. In Formula I, in certain embodiments above, each R$^7$ includes, independently, fluorine, chlorine, bromine, and iodine. In one embodiment, R$^7$ is fluorine. In another embodiment, R$^7$ is chlorine. In another embodiment, R$^7$ is bromine. In another embodiment, R$^7$ is iodine. In Formula I, in certain embodiments above, R$^8$ incudes hydrogen, deuterium, —NHR$^9$, or halogen. In certain embodiments of Formula I above, R$^9$ is hydrogen, —C$_1$-C$_5$ alkyl, or —C(O)C$_1$-C$_5$ alkyl. In certain embodiments of Formula I above, m is 1 or 2. In one embodiment, R$^8$ is hydrogen. In one embodiment, R$^8$ is deuterium. In certain embodiments, R$^8$ includes, independently, fluorine, chlorine, bromine, and iodine. In one embodiment, R$^8$ is fluorine. In another embodiment, R$^8$ is chlorine. In another embodiment, R$^8$ is bromine. In another embodiment, R$^8$ is iodine. In one embodiment, —NHR$^9$ is —NH$_2$. In one embodiment, —NHR$^9$ includes —NHMe, —NHEt, —NHCH$_2$CH$_2$CH$_3$, —NHCH$_2$CH$_2$CH$_3$, and —NHCH$_2$CH$_2$CH$_2$CH$_3$. In one embodiment, —NHR$^9$ is —NHMe. In one embodiment, —NHR$^9$ is —NHEt. In one embodiment, —NHR$^9$ is —NHCH$_2$CH$_2$CH$_3$. In one embodiment, —NHR$^9$ is —NHCH$_2$CH$_2$CH$_3$. In one embodiment, —NHR$^9$ is —NHCH$_2$CH$_2$CH$_2$CH$_3$. In one embodiment, —NHR$^9$ includes —NHC(O)Me, —NHC(O)Et, —NHC(O)CH$_2$CH$_2$CH$_3$, —NHC(O)CH$_2$CH$_2$CH$_2$CH$_3$, and —NHC(O)CH$_2$CH$_2$CH$_2$CH$_2$CH$_3$. In one embodiment, —NHR$^9$ is —NHC(O)Me. In one embodiment, —NHR⁹ is —NHC(O)Et. In one embodiment, —NHR⁹ is —NHC(O)CH₂CH₂CH₃. In one embodiment, —NHR⁹ is —NHC(O)CH₂CH₂CH₂CH₃. In one embodiment, —NHR⁹ is —NHC(O)CH₂CH₂CH₂CH₂CH₃. In one embodiment, m is 1. In one embodiment, m is 2.

In certain embodiments, set forth herein is a compound having the structure of Formula II:

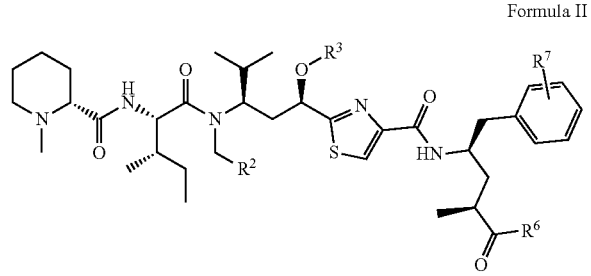

Formula II or a pharmaceutically acceptable salt or prodrug thereof. In certain embodiments, $R^2$, $R^3$, $R^6$, and $R^7$ are as described in the preceding paragraph.

In certain embodiments, set forth herein is a compound having the structure of Formula I, or a pharmaceutically acceptable salt or prodrug thereof, wherein Q is —CH₂—; $R^2$ is $C_5$-$C_{10}$ alkyl; $R^3$ is —C(O)$C_1$-$C_5$ alkyl; $R^4$ and $R^5$ are methyl; $R^7$ is —OH, halogen, or —NH₂; $R^8$ is, independently in each occurrence, hydrogen, deuterium, —NHR⁹, or halogen, wherein $R^9$ is hydrogen or —$C_1$-$C_5$ alkyl; and m is 1 or 2. In certain embodiments, $R^1$, $R^2$, $R^3$, and Q-$R^2$ are as described in Formula I above. In certain embodiments of Formula I above, $R^7$ includes fluorine, chlorine, bromine, and iodine. In one embodiment, $R^7$ is fluorine. In another embodiment, $R^7$ is chlorine. In another embodiment, $R^7$ is bromine. In another embodiment, $R^7$ is iodine. In one embodiment, $R^7$ is —OH. In one embodiment, $R^7$ is —NH₂. In one embodiment, $R^8$ is hydrogen. In one embodiment, $R^8$ is deuterium. In certain embodiments, $R^8$ includes, independently, fluorine, chlorine, bromine, and iodine. In one embodiment, $R^8$ is fluorine. In another embodiment, $R^8$ is chlorine. In another embodiment, $R^8$ is bromine. In another embodiment, $R^8$ is iodine. In one embodiment, $R^8$ is —NHR⁹. In one embodiment, —NHR⁹ is —NH₂. In one embodiment, —NHR⁹ includes —NHMe, —NHEt, —NHCH₂CH₂CH₃, —NHCH₂CH₂CH₂CH₃, and —NHCH₂CH₂CH₂CH₂CH₃. In one embodiment, —NHR⁹ is —NHMe. In one embodiment, —NHR⁹ is —NHEt. In one embodiment, —NHR⁹ is —NHCH₂CH₂CH₃. In one embodiment, —NHR⁹ is —NHCH₂CH₂CH₂CH₃. In one embodiment, —NHR⁹ is —NHCH₂CH₂CH₂CH₂CH₃. In one embodiment, m is 1. In one embodiment, m is 2.

In certain embodiments, set forth herein is a compound having the structure of Formula III:

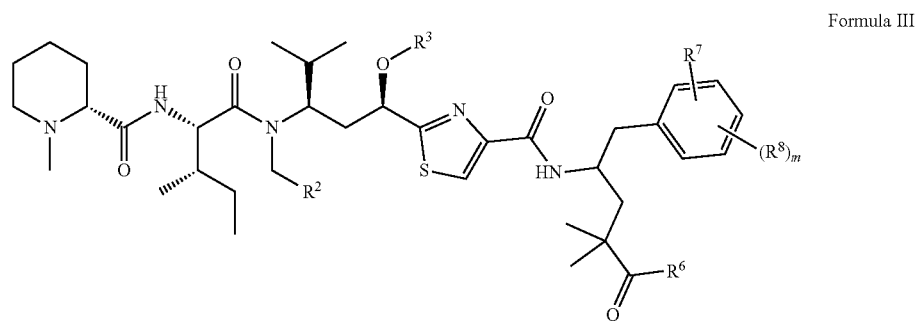

Formula III or a pharmaceutically acceptable salt thereof. In certain embodiments, Q, $R^2$, $R^3$, $R^7$, $R^8$, $R^9$, and $Q-R^2$ are as described in the preceding paragraph.

In certain embodiments, set forth herein is a compound having the structure of Formula I, or a pharmaceutically acceptable salt or prodrug thereof, wherein Q is —$CH_2$—; $R^2$ is $C_1$-$C_{10}$ alkynyl; and $R^6$ is —OH. In certain embodiments, $R^1$, $R^3$, $R^4$, $R^5$, $R^7$, and $R^8$ are as described above. In one embodiment of Formula I, $R^2$ is —$CH_2CCH$. In one embodiment of Formula I, $R^2$ is —$CH_2CH_2CCH$. In one embodiment of Formula I, $R^2$ is —$CH_2CH_2CH_2CCH$. In one embodiment of Formula I, $R^2$ is —$CH_2CH_2CH_2CH_2CCH$. In one embodiment of Formula I, $R^2$ is —$CH_2CH_2CH_2CH_2CH_2CCH$. In one embodiment of Formula I, $R^2$ is —$CH_2CH_2CH_2CH_2CH_2CH_2CCH$. In one embodiment of Formula I, $R^2$ is —$CH_2CH_2CH_2CH_2CH_2CH_2CH_2CCH$. In one embodiment of Formula I, $R^2$ is —$CH_2CH_2CH_2CH_2CH_2CH_2CH_2CH_2CCH$. In one embodiment of Formula I, $R^2$ is —$CH_2CH_2CH_2CH_2CH_2CH_2CH_2CH_2CH_2CCH$. In one embodiment of Formula I, $R^2$ is —$CH_2CH_2CH_2CH_2CH_2CH_2CH_2CH_2CH_2CH_2CCH$.

In certain embodiments, set for the herein is a compound having the structure of Formula IV:

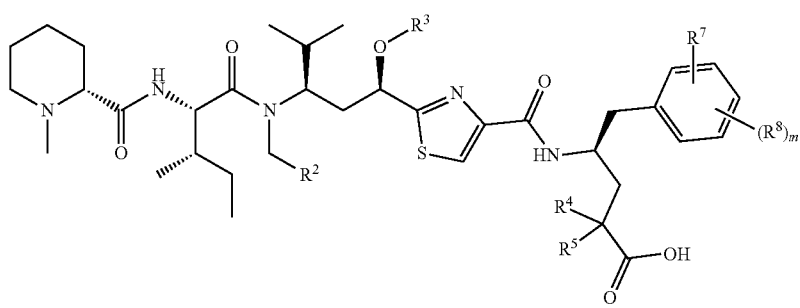

Formula IV or a pharmaceutically acceptable salt thereof. In certain embodiments, $R^2$, $R^3$, $R^4$, $R^5$, $R^7$, and $R^8$ are as described in the preceding paragraph.

In certain embodiments, set forth herein is a compound having the structure of Formula I, or a pharmaceutically acceptable salt or prodrug thereof, wherein Q is —$CH_2$—; $R^2$ is regioisomeric —$C_1$-$C_{10}$ alkylene-(5-membered heteroaryl), wherein said heteroaryl is unsubstituted or substituted with alkyl, aminoalkyl, hydroxylalkyl, carboxyalkyl, benzyl, or phenyl; $R^3$ is —$C(O)C_1$-$C_5$ alkyl; $R^4$ and $R_5$ are $C_1$-$C_5$ alkyl; $R^6$ is —OH; and $R^7$ is —$NH_2$. In certain embodiments, $R^1$, $R^8$, and $R^9$ are as described above. In certain embodiments of Formula I above, useful $R^2$ groups include regioisomeric —$C_1$-$C_{10}$ alkylene-(1,2,3-triazoles), wherein said regioisomeric 1,2,3-triazoles are unsubstituted or substituted with alkyl, aminoalkyl, hydroxylalkyl, carboxyalkyl, benzyl, or phenyl. In the following embodiments, the 1,2,3-triazoles derive from click-chemistry reactions between terminal alkynes and azides giving rise to regioisomeric products, as described elsewhere herein. In one embodiment, $R^2$ is In one embodiment, $R^2$ is

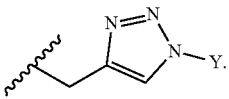

In one embodiment, $R^2$ is

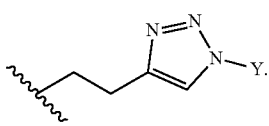

In one embodiment, $R^2$ is

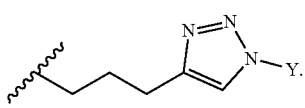

In one embodiment, $R^2$ is

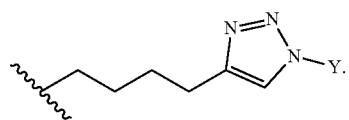

In one embodiment, $R^2$ is

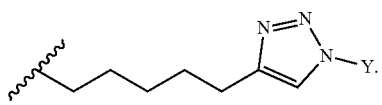

In one embodiment, $R^2$ is

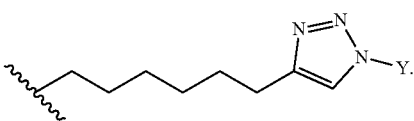

In one embodiment, R² is

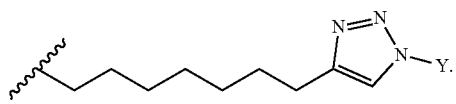

In one embodiment, R² is

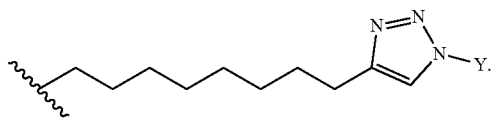

In one embodiment, R² is

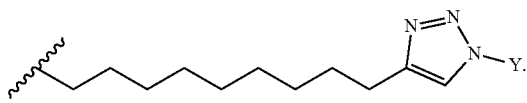

In one embodiment, R² is

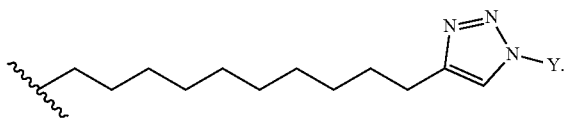

In any one or more of the embodiments in this paragraph, Y is hydrogen, alkyl, aminoalkyl, hydroxylalkyl, carboxyalkyl, benzyl, or phenyl. In one embodiment, Y is hydrogen. In one embodiment, Y is alkyl. In one embodiment, Y is aminoalkyl. In one embodiment, Y is hydroxylalkyl. In one embodiment, Y is carboxyalkyl. In one embodiment, Y is phenyl. In certain embodiments of Formula I above, useful R³ groups include —C(O)Me, —C(O)Et, —C(O)propyl, —C(O)butyl, and —C(O)pentyl. In one embodiment, R³ is —C(O)Me. In another embodiment, R³ is —C(O)Et. In another embodiment, R³ is —C(O)propyl, and constitutional isomers thereof. In another embodiment, R³ is —C(O)butyl, and constitutional isomers thereof. In another embodiment, R³ is —C(O)pentyl, and constitutional isomers thereof. In certain embodiments of Formula I above, useful R⁴ and R⁵ groups, independently, include methyl, ethyl, propyl, and constitutional isomers thereof, butyl and constitutional isomers thereof, and pentyl and constitutional isomers thereof, and combinations thereof. For example, in one embodiment, R⁴ and R⁵ is Me. By way of another example, in one embodiment, R⁴ and R⁵ is ethyl. By way of another example, R⁴ is methyl and R⁵ is ethyl. Other exemplary combinations or perturbations for R⁴ and R⁵ as embodiments within this paragraph are contemplated herein.

In certain embodiments, set forth herein is a compound having the structure of Formula V:

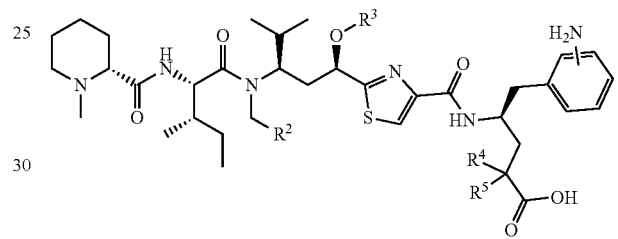

Formula V or a pharmaceutically acceptable salt thereof. In certain embodiments, R², R³, R⁴, and R⁵ are as described in the preceding paragraph.

In certain embodiments, set forth herein is a compound having the structure of Formula VI or Formula VII:

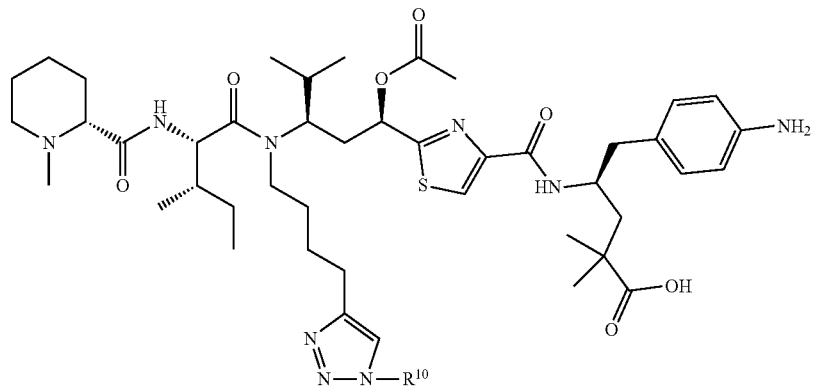

Formula VI

Formula VII

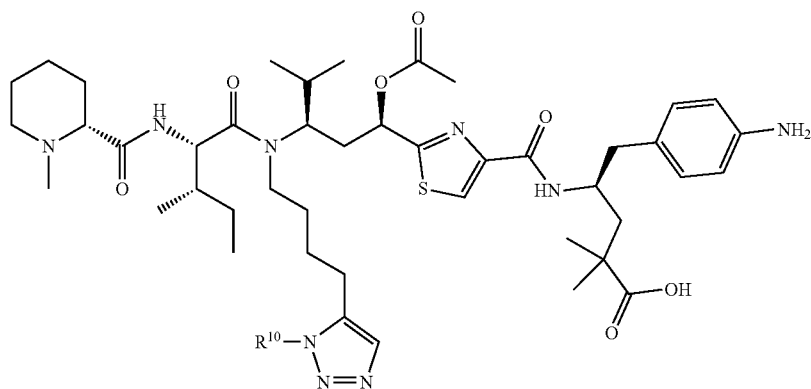

wherein R[10] is hydrogen, methyl, —CH₂CH₂NH₂, —CH₂CH₂OH, —CH₂COOH, —CH₂CH₂CH₂COOH, benzyl, or phenyl; or a pharmaceutically acceptable salt thereof. In one embodiment, R[10] is hydrogen. In one embodiment, R[10] is methyl. In one embodiment, R[10] is —CH₂CH₂NH₂. In one embodiment, R[10] is —CH₂CH₂OH. In one embodiment, R[10] is —CH₂COOH. In one embodiment, R[10] is —CH₂CH₂CH₂COOH. In one embodiment, R[10] is benzyl. In one embodiment, R[10] is phenyl.

In certain embodiments, provided herein are compounds according to any of Formulae I, II, III, IV, V, VI, or VII that may be selected from the group consisting of:

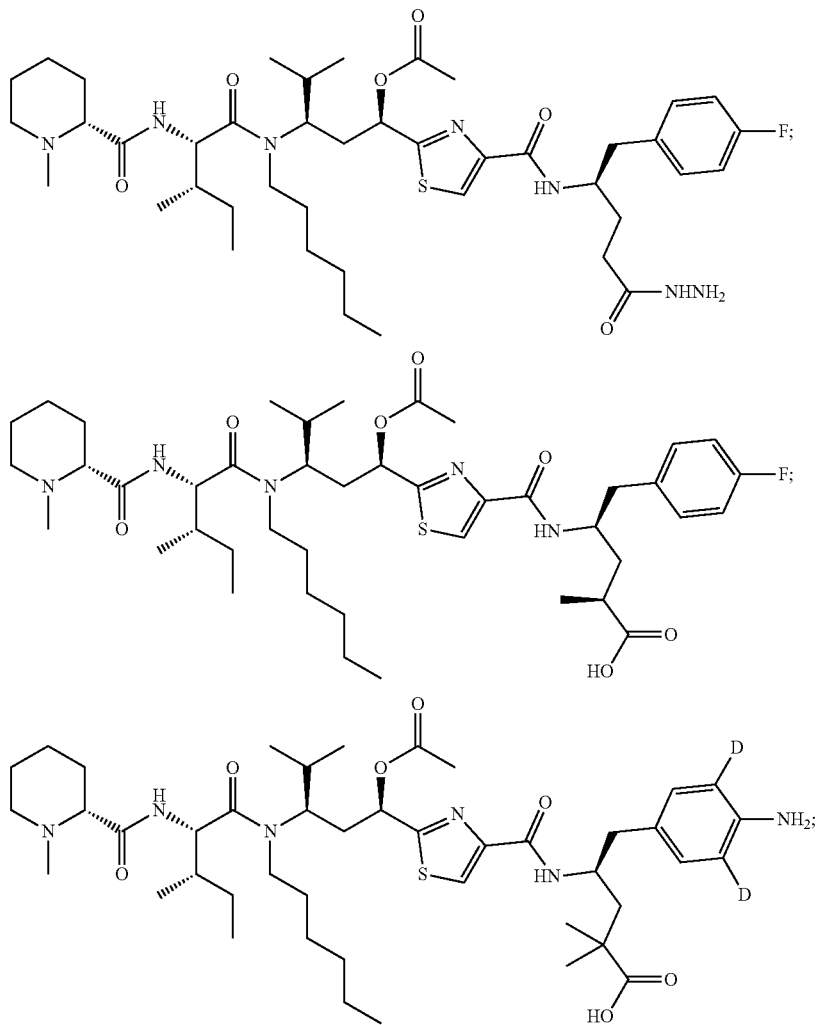

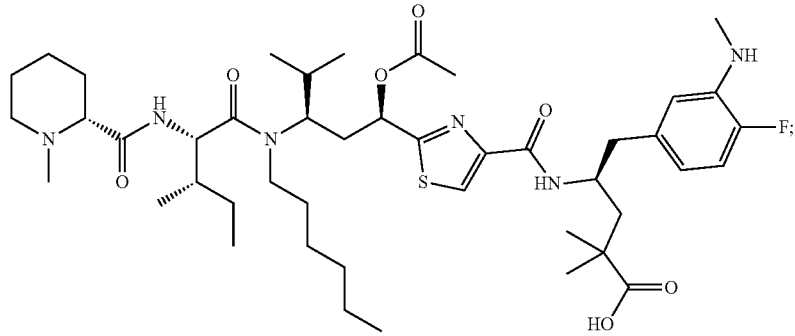
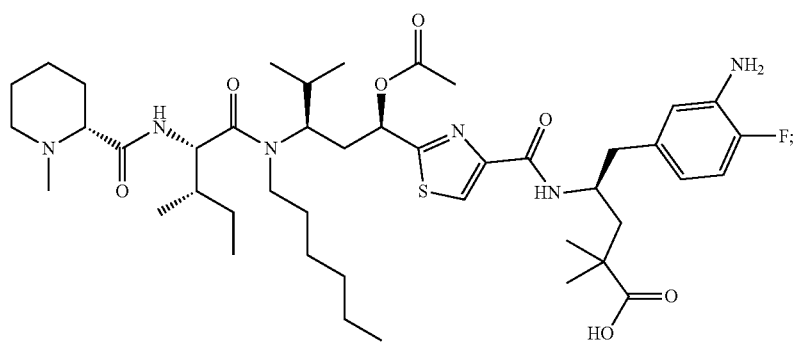
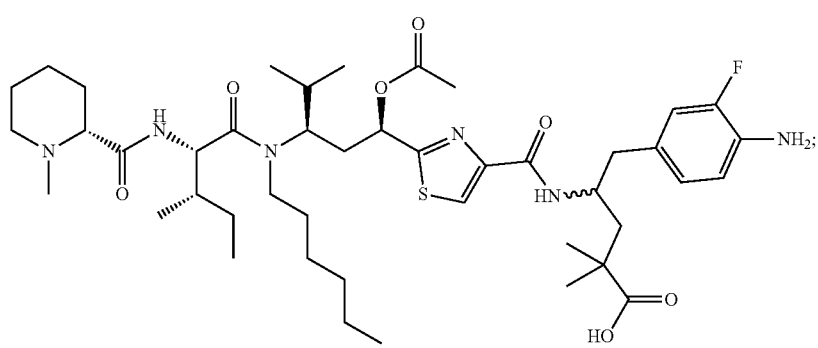
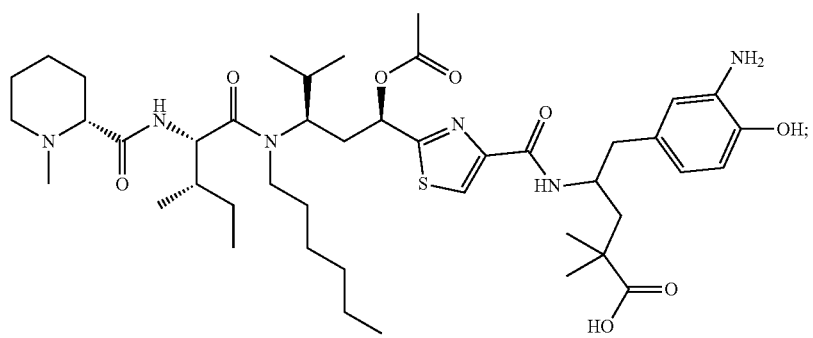
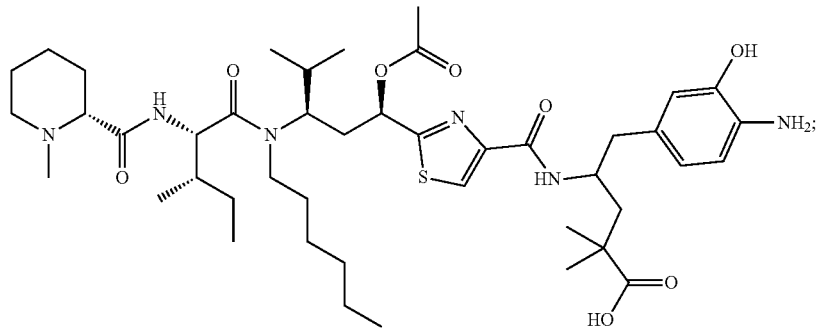

-continued
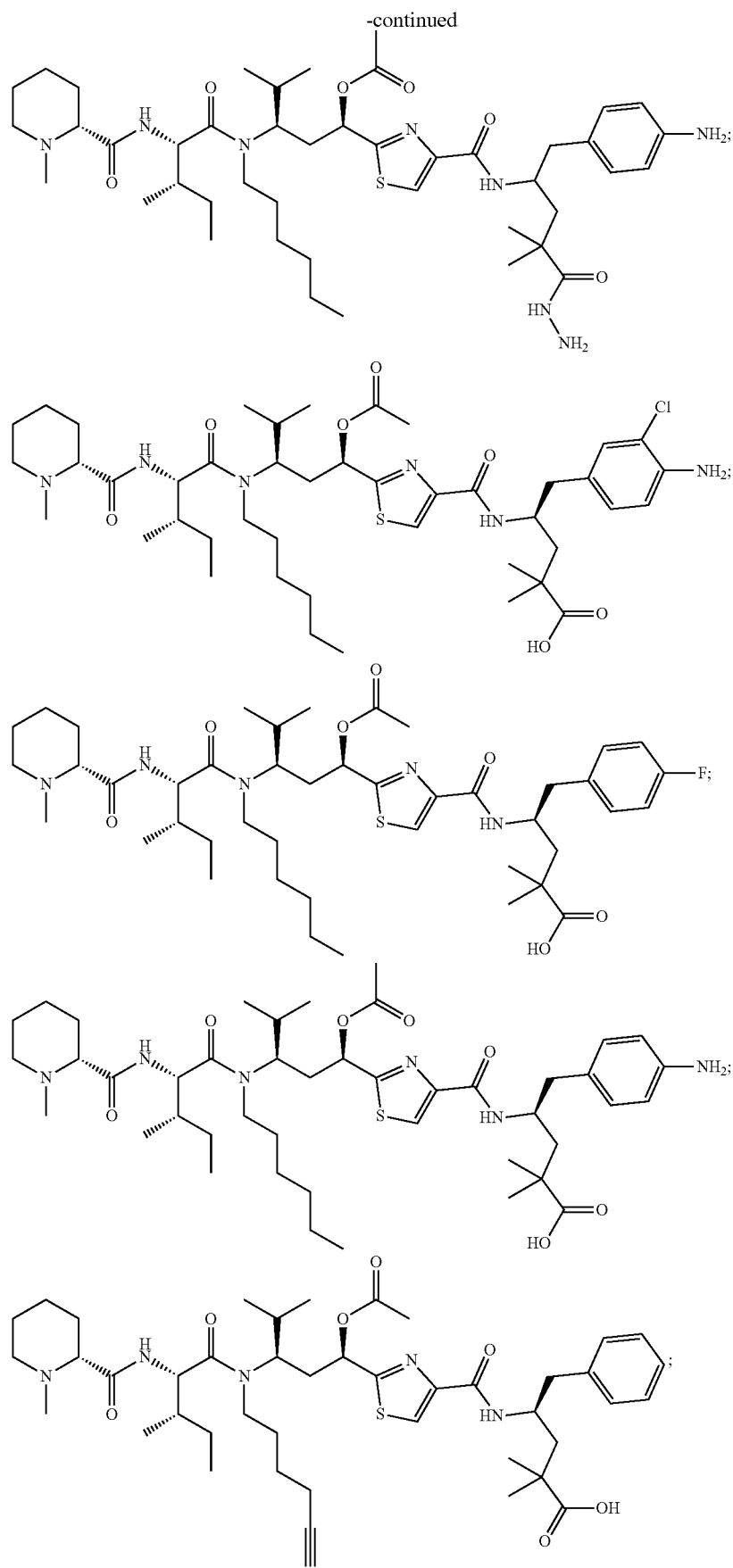

-continued
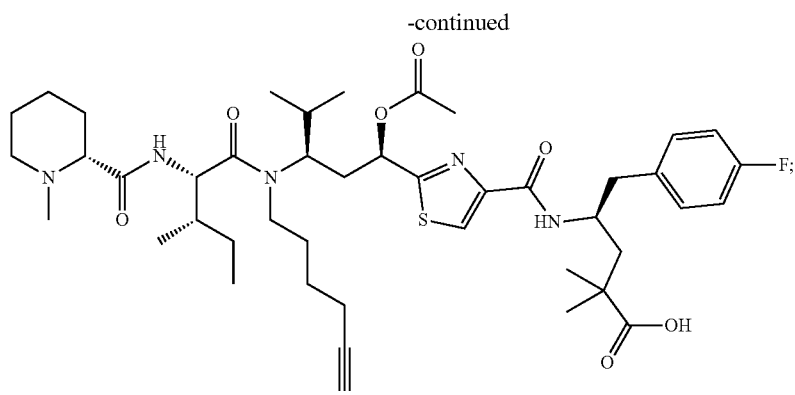
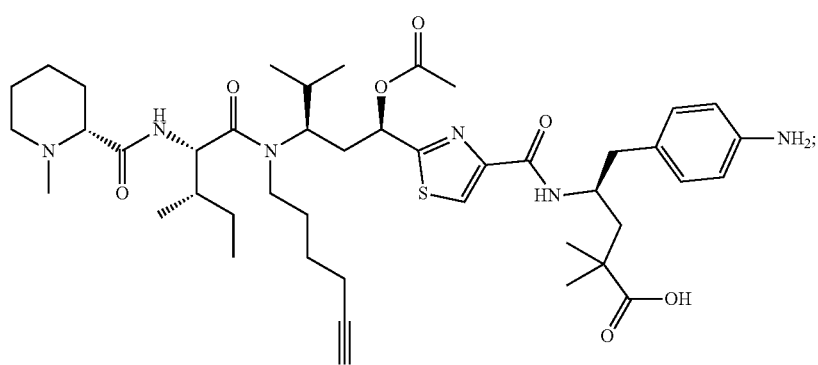
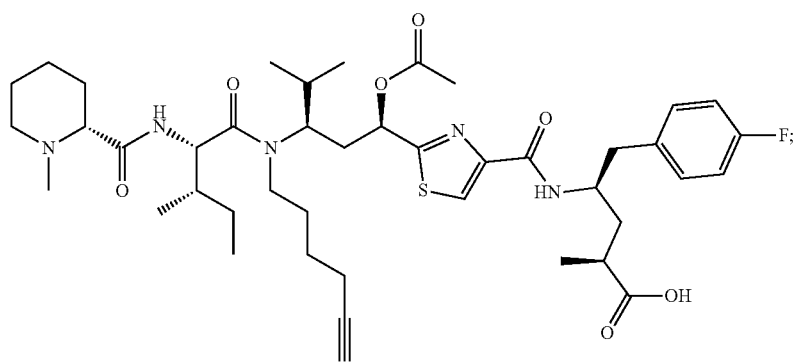
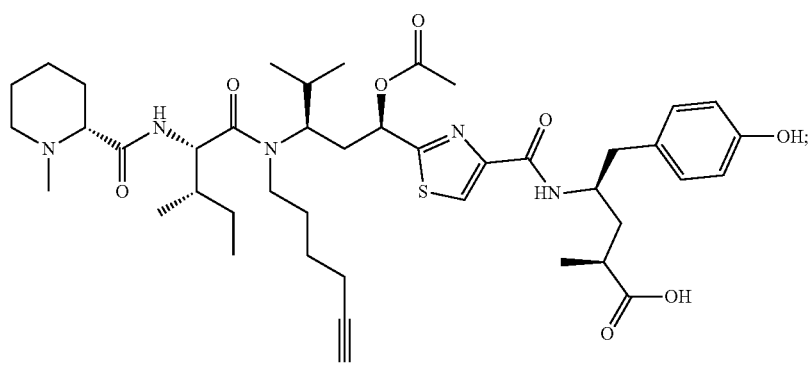

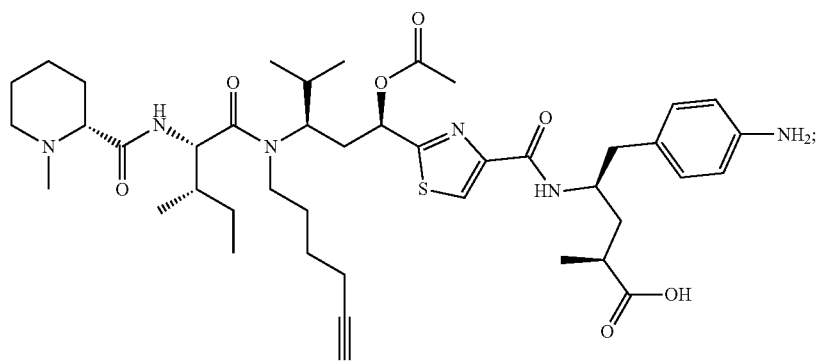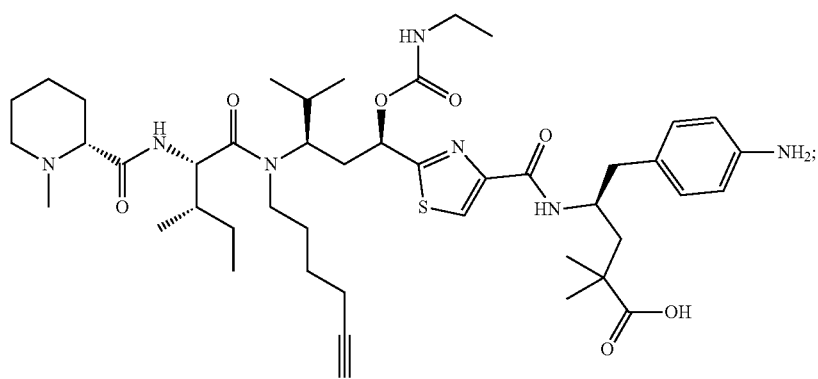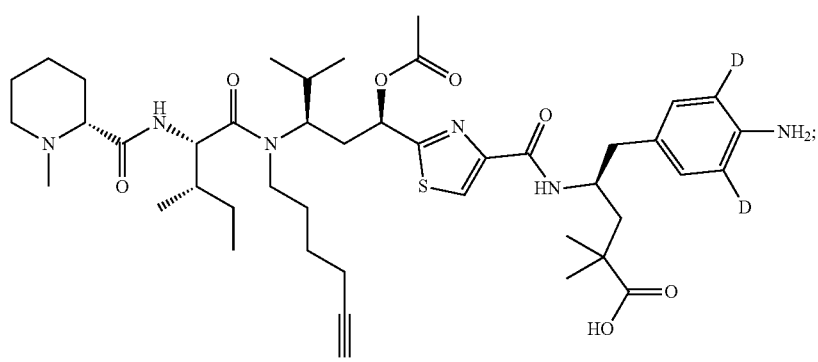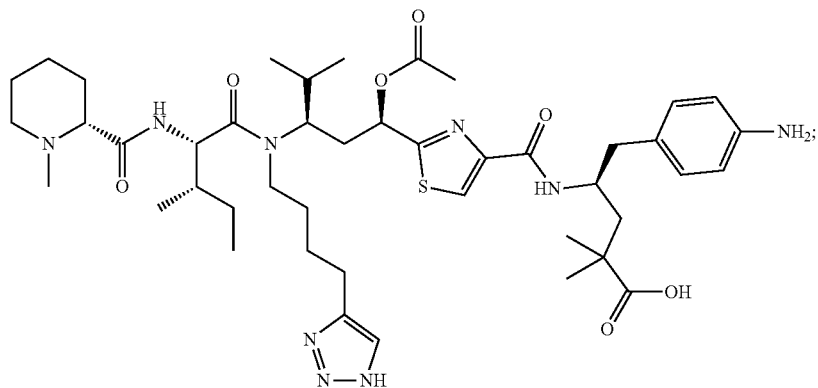

-continued
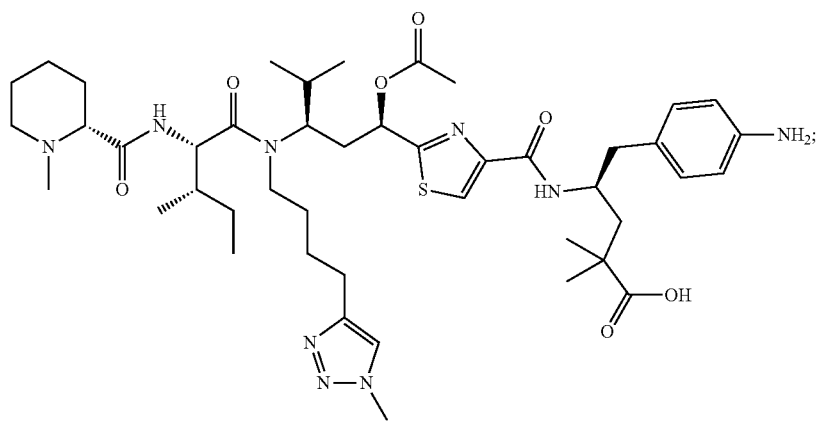
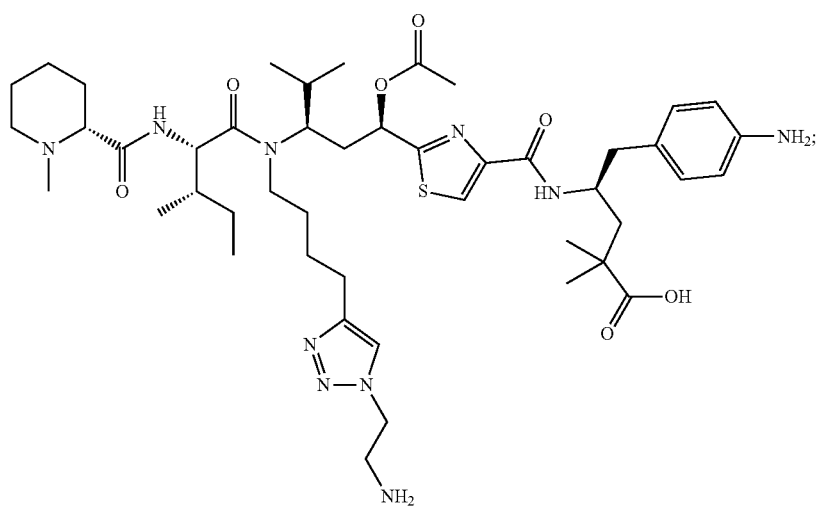
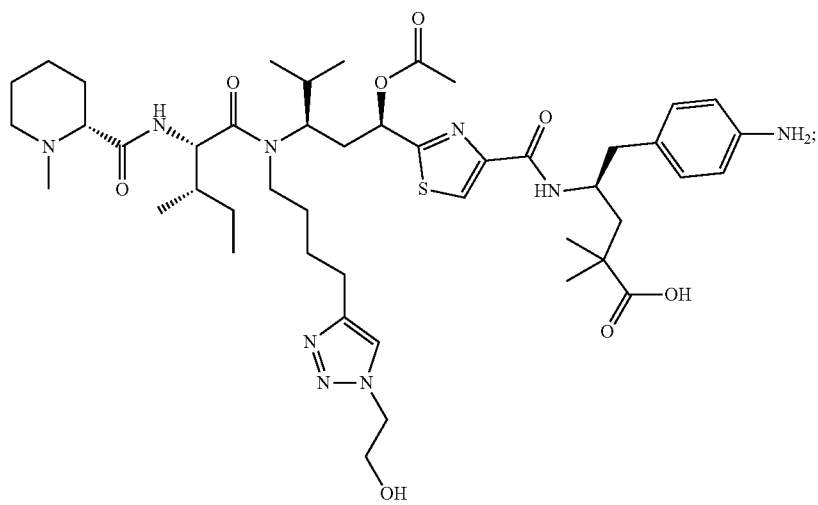

-continued
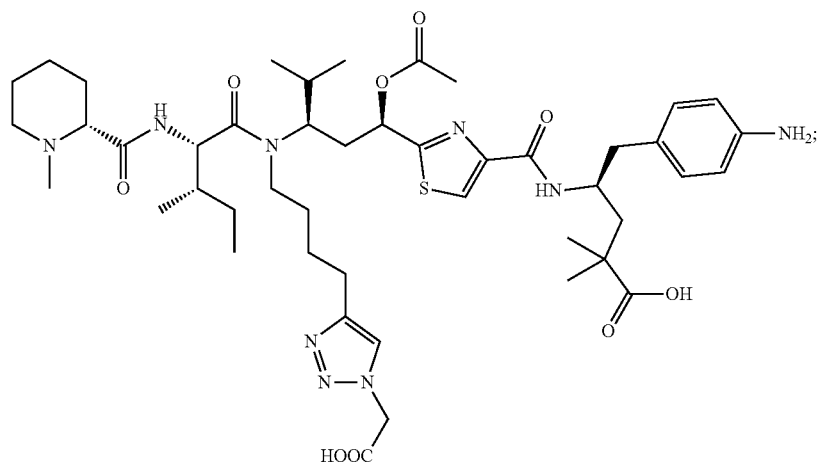
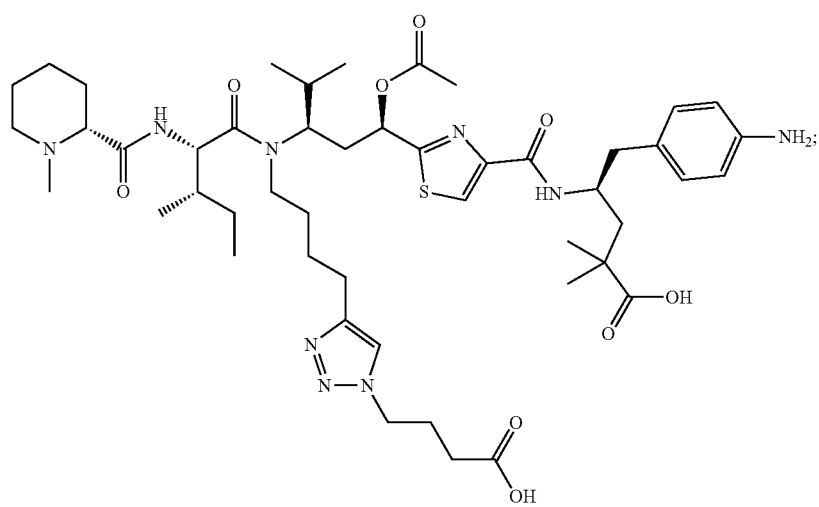
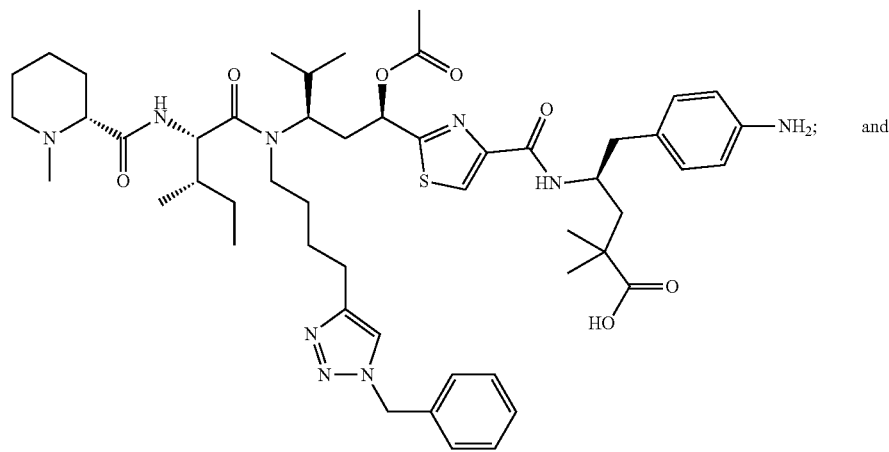
and

-continued

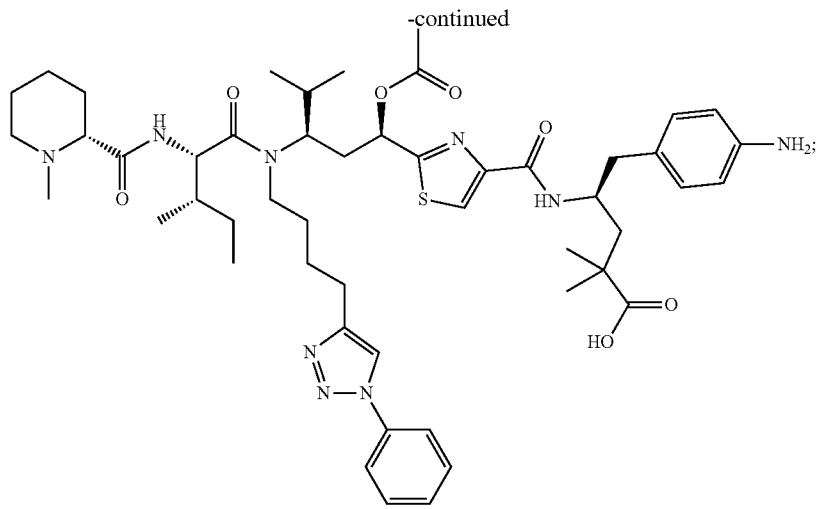

a regioisomer thereof; or a pharmaceutically acceptable salt thereof.

In certain embodiments, set forth herein is a compound having the structure of Formula XIII:

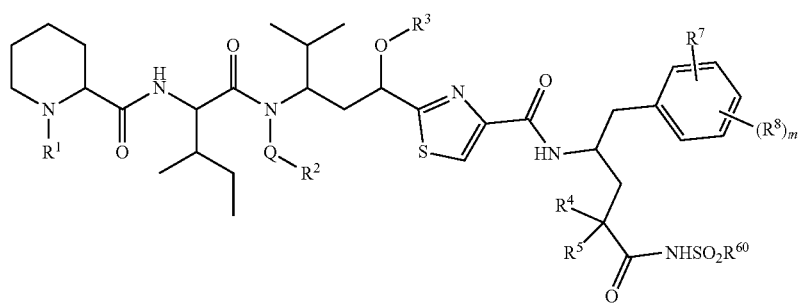

Formula XIII or a pharmaceutically acceptable salt or prodrug thereof, wherein Q is —$CH_2$—; $R^2$ is $C_5$-$C_{10}$ alkyl; $R^3$ is —C(O) $C_1$-$C_5$ alkyl; $R^4$ is hydrogen or $C_1$-$C_5$ alkyl; $R^5$ is $C_1$-$C_5$ alkyl; or $R^4$ and $R^5$, together with the carbon to which they are attached, form a 3-8 membered cycloalkyl, substituted cycloalkyl, heterocycloalkyl, or substituted heterocycloalkyl; and $R^7$ is halogen. In Formula XIII, in certain embodiments, useful $R^1$ groups include methyl and ethyl. In certain embodiments, useful $R^1$ groups include propyl, butyl, pentyl, hexyl, heptyl, octyl, nonyl, decyl, and constitutional isomers thereof. In one embodiment, $R^1$ is methyl. In one embodiment, $R^1$ is ethyl. In one embodiment, $R^1$ is propyl, and constitutional isomers thereof. In one embodiment, $R^1$ is butyl, and constitutional isomers thereof. In one embodiment, $R^1$ is pentyl, and constitutional isomers thereof. In one embodiment, $R^1$ is hexyl, and constitutional isomers thereof. In one embodiment, $R^1$ is heptyl, and constitutional isomers thereof. In one embodiment, $R^1$ is octyl, and constitutional isomers thereof. In one embodiment, $R^1$ is nonyl, and constitutional isomers thereof. In one embodiment, $R^1$ is decyl, and constitutional isomers thereof. In Formula XIII, in certain embodiments above, useful $R^2$ groups include n-pentyl, n-hexyl, n-heptyl, n-octyl, n-nonyl, and n-decyl. In one embodiment, $R^2$ is n-pentyl, or constitutional isomers thereof. In another embodiment, $R^2$ is n-hexyl, or constitutional isomers thereof. In another embodiment, $R^2$ is n-heptyl, or constitutional isomers thereof. In another embodiment, $R^2$ is n-octyl, or constitutional isomers thereof. In another embodiment, $R^2$ is n-nonyl, or constitutional isomers thereof. In another embodiment, $R^2$ is n-decyl, or constitutional isomers thereof. In one embodiment, Q-$R^2$ is n-hexyl. In certain embodiments of Formula XIII above, useful $R^3$ groups include —C(O)Me, —C(O)Et, —C(O) propyl, —C(O)butyl, and —C(O)pentyl. In one embodiment, $R^3$ is —C(O)Me. In another embodiment, $R^3$ is —C(O)Et. In another embodiment, $R^3$ is —C(O)propyl, and constitutional isomers thereof. In another embodiment, $R^3$ is —C(O)butyl, and constitutional isomers thereof. In another embodiment, $R^3$ is —C(O)pentyl, and constitutional isomers thereof. In one embodiment, $R^4$ is hydrogen. In certain embodiments of Formula XIII above, useful $R^4$ groups include methyl, ethyl, propyl, butyl, and pentyl. In one embodiment, $R^4$ is methyl. In another embodiment, $R^4$ is ethyl. In another embodiment, $R^4$ is propyl, and constitutional isomers thereof. In another embodiment, $R^4$ is butyl, and constitutional isomers thereof. In another embodiment, $R^4$ is pentyl, and constitutional isomers thereof. In certain embodiments of Formula XIII above, useful $R^5$ groups include methyl, ethyl, propyl, butyl, and pentyl. In one embodiment, $R^5$ is methyl. In another embodiment, $R^5$ is ethyl. In another embodiment, $R^5$ is propyl, and constitutional isomers thereof. In another embodiment, $R^5$ is butyl, and constitutional isomers thereof. In another embodiment, $R^5$ is pentyl, and constitutional isomers thereof. In one embodiment, $R^4$ and $R^5$ are methyl. In one embodiment, $R^4$ and $R^5$, together with the carbon to which they are attached, is cyclopropyl or substituted cyclopropyl. In one embodiment, $R^4$ and $R^5$, together with the carbon to which they are attached, is cyclobutyl or substituted cyclobutyl. In one embodiment, $R^4$ and $R^5$, together with the carbon to which they are attached, is cyclopentyl or substituted cyclopentyl. In one embodiment, $R^4$ and $R^5$, together with the carbon to which they are attached, is cyclohexyl or substituted cyclohexyl. In one embodiment, $R^4$ and $R^5$, together with the carbon to which they are attached, is cycloheptyl or substituted cycloheptyl. In one embodiment, $R^4$ and $R^5$, together with the carbon to which they are attached, is cyclooctyl or substituted cyclooctyl. In one embodiment, $R^4$ and $R^5$, together with the carbon to which they are attached, is cyclopropyl where one methylene carbon in the cyclopropyl is replaced with Z, where Z is oxygen, nitrogen, or sulfur. In one embodiment, $R^4$ and $R^5$, together with the carbon to which they are attached, is cyclobutyl where one methylene carbon in the cyclobutyl is replaced with Z, where Z is oxygen, nitrogen, or sulfur. In one embodiment, $R^4$ and $R^5$, together with the carbon to which they are attached, is cyclopentyl where one or more methylene carbons in the cyclopentyl is replaced with Z, where Z is oxygen, nitrogen, or sulfur. In one embodiment, $R^4$ and $R^5$, together with the carbon to which they are attached, is cyclohexyl where one or more methylene carbons in the cyclohexyl is replaced with Z, where Z is oxygen, nitrogen, or sulfur. In one embodiment, $R^4$ and $R^5$, together with the carbon to which they are attached, is cycloheptyl where one or more methylene carbons in the cycloheptyl is replaced with Z, where Z is oxygen, nitrogen, or sulfur. In one embodiment, $R^4$ and $R^5$, together with the carbon to which they are attached, is cyclooctyl where one or more methylene carbons in the cyclooctyl is replaced with Z, where Z is oxygen, nitrogen, or sulfur. In certain embodiments of Formula XIII above, $R^{60}$ is alkyl, alkenyl, alkynyl, cycloalkyl, heterocycloalkyl, aryl, heteroaryl, substituted aryl, or substituted heteroaryl. Suitable $R^{60}$ alkyl groups include those described in this paragraph for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in this paragraph. In Formula XIII, in certain embodiments above, each $R^7$ includes, independently, fluorine, chlorine, bromine, and iodine. In one embodiment, $R^7$ is fluorine. In another embodiment, $R^7$ is chlorine. In another embodiment, $R^7$ is bromine. In another embodiment, $R^7$ is iodine. In Formula XIII, in certain embodiments above, $R^8$ incudes hydrogen, deuterium, —$NHR^9$, or halogen. In certain embodiments of Formula XIII above, $R^9$ is hydrogen, —$C_1$-$C_5$ alkyl, or —$C(O)C_1$-$C_5$ alkyl. In certain embodiments of Formula XIII above, m is 1 or 2. In one embodiment, $R^8$ is hydrogen. In one embodiment, $R^8$ is deuterium. In certain embodiments, $R^8$ includes, independently, fluorine, chlorine, bromine, and iodine. In one embodiment, $R^8$ is fluorine. In another embodiment, $R^8$ is chlorine. In another embodiment, $R^8$ is bromine. In another embodiment, $R^8$ is iodine. In one embodiment, —$NHR^9$ is —$NH_2$. In one embodiment, —$NHR^9$ includes —NHMe, —NHEt, —$NHCH_2CH_2CH_3$, —$NHCH_2CH_2CH_2CH_3$, and —$NHCH_2CH_2CH_2CH_2CH_3$. In one embodiment, —$NHR^9$ is —NHMe. In one embodiment, —$NHR^9$ is —NHEt. In one embodiment, —$NHR^9$ is —$NHCH_2CH_2CH_3$. In one embodiment, —$NHR^9$ is —$NHCH_2CH_2CH_2CH_3$. In one embodiment, —$NHR^9$ is —$NHCH_2CH_2CH_2CH_2CH_3$. In one embodiment, —$NHR^9$ includes —NHC(O)Me, —NHC(O)Et, —$NHC(O)CH_2CH_2CH_3$, —$NHC(O)CH_2CH_2CH_2CH_3$, and —$NHC(O)CH_2CH_2CH_2CH_2CH_3$. In one embodiment, —$NHR^9$ is —NHC(O)Me. In one embodiment, —$NHR^9$ is —NHC(O)Et. In one embodiment, —$NHR^9$ is —$NHC(O)CH_2CH_2CH_3$. In one embodiment, —$NHR^9$ is —$NHC(O)CH_2CH_2CH_2CH_3$. In one embodiment, —$NHR^9$ is —$NHC(O)CH_2CH_2CH_2CH_2CH_3$. In one embodiment, m is 1. In one embodiment, m is 2.

In certain embodiments, set forth herein is a compound having the structure of Formula XIV:

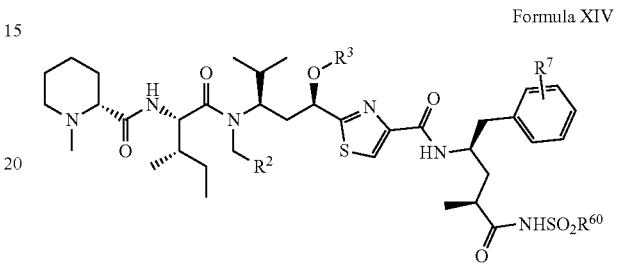

Formula XIV or a pharmaceutically acceptable salt or prodrug thereof. In certain embodiments, $R^2$, $R^3$, $R^7$, and $R^{60}$ are as described in the preceding paragraph.

In certain embodiments, set forth herein is a compound having the structure of Formula XIII, or a pharmaceutically acceptable salt or prodrug thereof, wherein Q is —$CH_2$—; $R^2$ is $C_5$-$C_{10}$ alkyl; $R^3$ is —$C(O)C_1$-$C_5$ alkyl; $R^4$ and $R^5$ are methyl; $R^7$ is —OH, halogen, or —$NH_2$; $R^8$ is, independently in each occurrence, hydrogen, deuterium, —$NHR^9$, or halogen, wherein $R^9$ is hydrogen or —$C_1$-$C_5$ alkyl; and m is 1 or 2. In certain embodiments, $R^1$, $R^2$, $R^3$, and Q-$R^2$ are as described in Formula XIII above. In certain embodiments of Formula XIII above, $R^7$ includes fluorine, chlorine, bromine, and iodine. In one embodiment, $R^7$ is fluorine. In another embodiment, $R^7$ is chlorine. In another embodiment, $R^7$ is bromine. In another embodiment, $R^7$ is iodine. In one embodiment, $R^7$ is —OH. In one embodiment, $R^7$ is —$NH_2$. In one embodiment, $R^8$ is hydrogen. In one embodiment, $R^8$ is deuterium. In certain embodiments, $R^8$ includes, independently, fluorine, chlorine, bromine, and iodine. In one embodiment, $R^8$ is fluorine. In another embodiment, $R^8$ is chlorine. In another embodiment, $R^8$ is bromine. In another embodiment, $R^8$ is iodine. In another embodiment, $R^8$ is —$NHR^9$. In one embodiment, —$NHR^9$ is —$NH_2$. In one embodiment, —$NHR^9$ includes —NHMe, —NHEt, —$NHCH_2CH_2CH_3$, —$NHCH_2CH_2CH_2CH_3$, and —$NHCH_2CH_2CH_2CH_2CH_3$. In one embodiment, —$NHR^9$ is —NHMe. In one embodiment, —$NHR^9$ is —NHEt. In one embodiment, —$NHR^9$ is —$NHCH_2CH_2CH_3$. In one embodiment, —$NHR^9$ is —$NHCH_2CH_2CH_2CH_3$. In one embodiment, —$NHR^9$ is —$NHCH_2CH_2CH_2CH_2CH_3$. In certain embodiments of Formula XIII above, $R^{60}$ is alkyl, alkenyl, alkynyl, cycloalkyl, heterocycloalkyl, aryl, heteroaryl, substituted aryl, or substituted heteroaryl. Suitable $R^{60}$ alkyl groups include those described in the context of Formula XIII for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in the context of Formula XIII. In one embodiment, m is 1. In one embodiment, m is 2.

In certain embodiments, set forth herein is a compound having the structure of Formula XV:

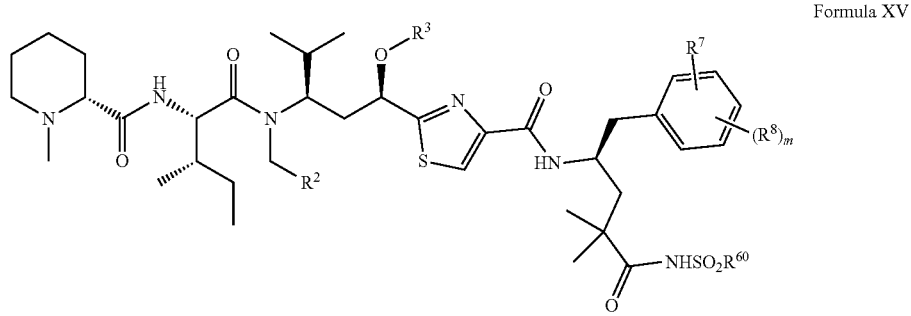

Formula XV or a pharmaceutically acceptable salt thereof. In certain embodiments, Q, $R^2$, $R^3$, $R^7$, $R^8$, $R^9$, Q-$R^2$, and $R^{60}$ are as described in the preceding paragraph.

In certain embodiments, set forth herein is a compound having the structure of Formula XIII, or a pharmaceutically acceptable salt or prodrug thereof, wherein Q is —$CH_2$—; $R^2$ is $C_1$-$C_{10}$ alkynyl; and $R^{60}$ is alkyl, alkenyl, alkynyl, cycloalkyl, heterocycloalkyl, aryl, heteroaryl, substituted aryl, or substituted heteroaryl. Suitable $R^{60}$ alkyl groups include those described in the context of Formula XIII for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in the context of Formula XIII. In certain embodiments, $R^1$, $R^3$, $R^4$, $R^5$, $R^7$, and $R^8$ are as described above. In one embodiment of Formula XIII, $R^2$ is —$CH_2$CCH. In one embodiment of Formula XIII, $R^2$ is —$CH_2CH_2$CCH. In one embodiment of Formula XIII, $R^2$ is —$CH_2CH_2CH_2$CCH. In one embodiment of Formula XIII, $R^2$ is —$CH_2CH_2CH_2CH_2$CCH. In one embodiment of Formula XIII, $R^2$ is —$CH_2CH_2CH_2CH_2CH_2$CCH. In one embodiment of Formula XIII, $R^2$ is —$CH_2CH_2CH_2CH_2CH_2CH_2$CCH. In one embodiment of Formula XIII, $R^2$ is —$CH_2CH_2CH_2CH_2CH_2CH_2CH_2$CCH. In one embodiment of Formula XIII, $R^2$ is —$CH_2CH_2CH_2CH_2CH_2CH_2CH_2CH_2$CCH. In one embodiment of Formula XIII, $R^2$ is —$CH_2CH_2CH_2CH_2CH_2CH_2CH_2CH_2CH_2$CCH. In one embodiment of Formula XIII, $R^2$ is —$CH_2CH_2CH_2CH_2CH_2CH_2CH_2CH_2CH_2CH_2$CCH.

In certain embodiments, set forth the herein is a compound having the structure of Formula XVI:

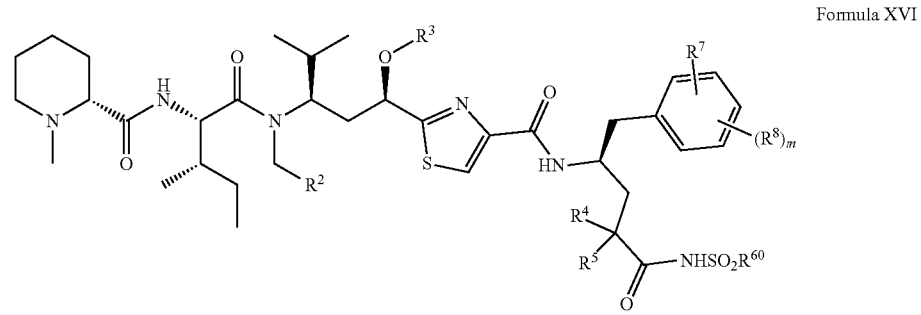

Formula XVI or a pharmaceutically acceptable salt thereof. In certain embodiments, $R^2$, $R^3$, $R^4$, $R^5$, $R^7$, $R^8$, and $R^{60}$ are as described in the preceding paragraph.

In certain embodiments, set forth herein is a compound having the structure of Formula XIII, or a pharmaceutically acceptable salt or prodrug thereof, wherein Q is —$CH_2$—; $R^2$ is regioisomeric —$C_1$-$C_{10}$ alkylene-(5-membered heteroaryl), wherein said heteroaryl is unsubstituted or substituted with alkyl, aminoalkyl, hydroxylalkyl, carboxyalkyl, benzyl, or phenyl; $R^3$ is —C(O)$C_1$-$C_5$ alkyl; $R^4$ and $R_5$ are $C_1$-$C_5$ alkyl; $R^7$ is —$NH_2$; and $R^{60}$ is alkyl, alkenyl, alkynyl, cycloalkyl, heterocycloalkyl, aryl, heteroaryl, substituted aryl, or substituted heteroaryl. Suitable $R^{60}$ alkyl groups include those described in the context of Formula XIII for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in the context of Formula XIII. In certain embodiments, $R^1$, $R^8$, and $R^9$ are as described above. In certain embodiments of Formula XIII above, useful $R^2$ groups include regioisomeric —$C_1$-$C_{10}$ alkylene-(1,2,3-triazoles), wherein said regioisomeric 1,2,3-triazoles are unsubstituted or substituted with alkyl, aminoalkyl, hydroxylalkyl, carboxyalkyl, benzyl, or phenyl. In the following embodiments, the 1,2,3-triazoles derive from click-chemistry reactions between terminal alkynes and azides giving rise to regioisomeric products, as described elsewhere herein. In one embodiment, $R^2$ is

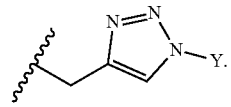

In one embodiment, $R^2$ is

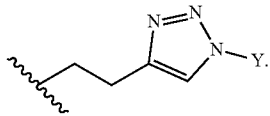

In one embodiment, $R^2$ is

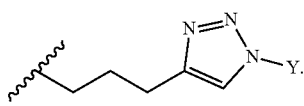

In one embodiment, $R^2$ is

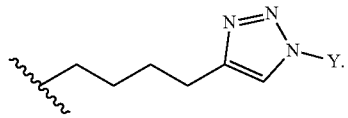

In one embodiment, $R^2$ is

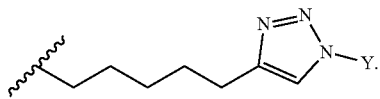

In one embodiment, $R^2$ is

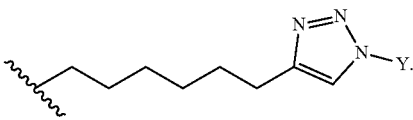

In one embodiment, $R^2$ is

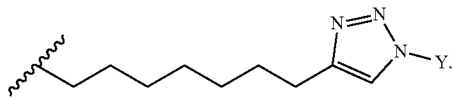

In one embodiment, $R^2$ is

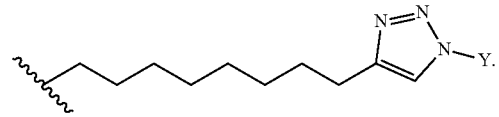

In one embodiment, $R^2$ is

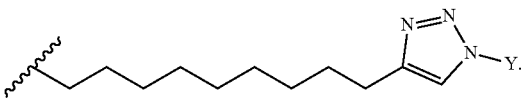

In one embodiment, $R^2$ is

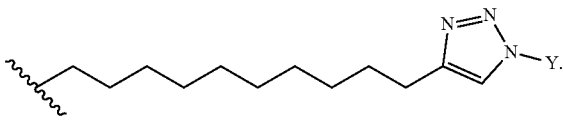

In any one or more of the embodiments in this paragraph, Y is hydrogen, alkyl, aminoalkyl, hydroxylalkyl, carboxyalkyl, benzyl, or phenyl. In one embodiment, Y is hydrogen. In one embodiment, Y is alkyl. In one embodiment, Y is aminoalkyl. In one embodiment, Y is hydroxylalkyl. In one embodiment, Y is carboxyalkyl. In one embodiment, Y is phenyl. In certain embodiments of Formula XIII above, useful $R^3$ groups include —C(O)Me, —C(O)Et, —C(O)propyl, —C(O)butyl, and —C(O)pentyl. In one embodiment, $R^3$ is —C(O)Me. In another embodiment, $R^3$ is —C(O)Et. In another embodiment, $R^3$ is —C(O)propyl, and constitutional isomers thereof. In another embodiment, $R^3$ is —C(O)butyl, and constitutional isomers thereof. In another embodiment, $R^3$ is —C(O)pentyl, and constitutional isomers thereof. In certain embodiments of Formula XIII above, useful $R^4$ and $R^5$ groups, independently, include methyl, ethyl, propyl and constitutional isomers thereof, butyl and constitutional isomers thereof, and pentyl and constitutional isomers thereof, and combinations thereof. For example, in one embodiment, $R^4$ and $R^5$ is methyl. By way of another example, in one embodiment, $R^4$ and $R^5$ is ethyl. By way of another example, $R^4$ is methyl and $R^5$ is ethyl. Other exemplary combinations or perturbations for $R^4$ and $R^5$ as embodiments within this paragraph are contemplated herein.

In certain embodiments, set forth herein is a compound having the structure of Formula XVII:

Formula XVII

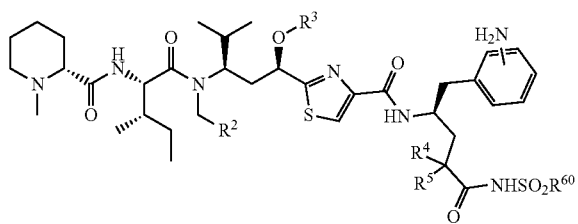

or a pharmaceutically acceptable salt thereof. In certain embodiments, $R^2$, $R^3$, $R^4$, $R^5$, and $R^{60}$ are as described preceding paragraph.

In certain embodiments, set forth herein is a compound having the structure of Formula XVIII or Formula XIX:

wherein $R^{60}$ is alkyl, alkenyl, alkynyl, cycloalkyl, heterocycloalkyl, aryl, heteroaryl, substituted aryl, or substituted heteroaryl. Suitable $R^{60}$ alkyl groups include those described in the context of Formula XIII for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in the context of Formula XIII. In certain embodiments, $R^{10}$ is hydrogen, methyl, $-CH_2CH_2NH_2$, $-CH_2CH_2OH$, $-CH_2COOH$, $-CH_2CH_2CH_2COOH$, benzyl, or phenyl; or a pharmaceutically acceptable salt thereof. In one embodiment, $R^{10}$ is hydrogen. In one embodiment, $R^{10}$ is methyl. In one embodiment, $R^{10}$ is $-CH_2CH_2NH_2$. In one embodiment, $R^{10}$ is $-CH_2CH_2OH$. In one embodiment, $R^{10}$ is $-CH_2COOH$. In one embodiment, $R^{10}$ is $-CH_2CH_2CH_2COOH$. In one embodiment, $R^{10}$ is benzyl. In one embodiment, $R^{10}$ is phenyl.

In any preceding embodiment in this section, $R^7$ is $-NR^{7a}R^{7b}$, wherein $R^{7a}$ and $R^{7b}$ are independently in each instance, hydrogen, alkyl, alkenyl, alkynyl, cycloalkyl, aryl, heteroaryl, acyl, and amino acid residue, wherein alkyl, alkenyl, alkynyl, cycloalkyl, aryl, heteroaryl, and acyl are optionally substituted. In certain embodiments $R^{7a}$ is hydrogen and $R^{7b}$ is an amino acid residue.

Formula XVIII

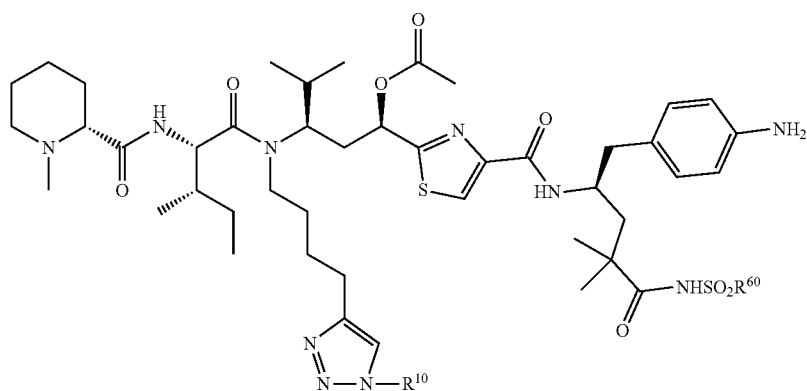

Formula XIX

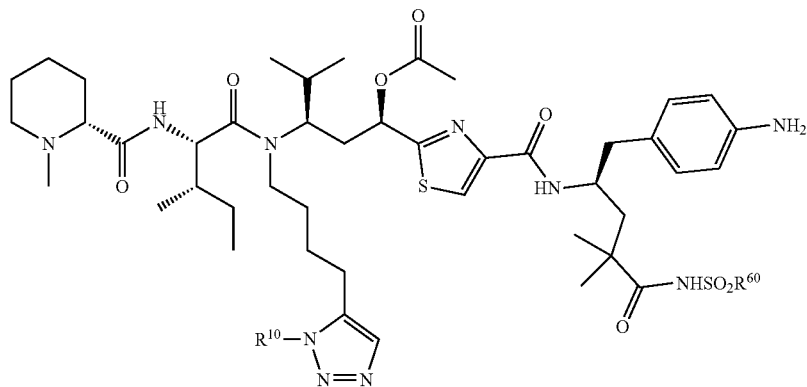

Compounds or Payloads—Q is Oxygen

In certain embodiments, set forth herein is a compound having the structure of Formula I:

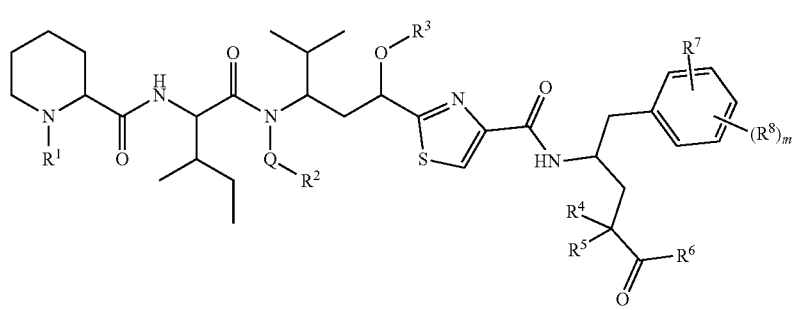

Formula I or a pharmaceutically acceptable salt or prodrug thereof, wherein Q is —O—; $R^2$ is $C_1$-$C_{10}$ alkyl; and $R^7$ is —OH or —$NH_2$. In Formula I, in certain embodiments, useful $R^1$ groups include methyl and ethyl. In certain embodiments, useful $R^1$ groups include propyl, butyl, pentyl, hexyl, heptyl, octyl, nonyl, decyl, and constitutional isomers thereof. In one embodiment, $R^1$ is methyl. In one embodiment, $R^1$ is ethyl. In one embodiment, $R^1$ is propyl, and constitutional isomers thereof. In one embodiment, $R^1$ is butyl, and constitutional isomers thereof. In one embodiment, $R^1$ is pentyl, and constitutional isomers thereof. In one embodiment, $R^1$ is hexyl, and constitutional isomers thereof. In one embodiment, $R^1$ is heptyl, and constitutional isomers thereof. In one embodiment, $R^1$ is octyl, and constitutional isomers thereof. In one embodiment, $R^1$ is nonyl, and constitutional isomers thereof. In one embodiment, $R^1$ is decyl, and constitutional isomers thereof. In Formula I, in certain embodiments above, useful $R^2$ groups include methyl, ethyl, n-propyl, n-butyl, n-pentyl, n-hexyl, n-heptyl, n-octyl, n-nonyl, and n-decyl. In one embodiment, $R^2$ is methyl. In one embodiment, $R^2$ is ethyl. In one embodiment, $R^2$ is n-propyl, or constitutional isomers thereof. In one embodiment, $R^2$ is n-butyl, or constitutional isomers thereof. In one embodiment, $R^2$ is n-pentyl, or constitutional isomers thereof. In another embodiment, $R^2$ is n-hexyl, or constitutional isomers thereof. In another embodiment, $R^2$ is n-heptyl, or constitutional isomers thereof. In another embodiment, $R^2$ is n-octyl, or constitutional isomers thereof. In another embodiment, $R^2$ is n-nonyl, or constitutional isomers thereof. In another embodiment, $R^2$ is n-decyl, or constitutional isomers thereof. In certain embodiments, $R^3$ is —C(O)$C_1$-$C_5$ alkyl, —C(O)N(H)$C_1$-$C_{10}$ alkyl, or —($C_1$-$C_{10}$ alkylene)-N$R^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In certain embodiments of Formula I above, useful $R^3$ groups include —C(O)Me, —C(O)Et, —C(O)propyl, —C(O)butyl, and —C(O)pentyl, and constitutional isomers thereof. In one embodiment, $R^3$ is —C(O)Me. In another embodiment, $R^3$ is —C(O)Et. In another embodiment, $R^3$ is —C(O)propyl, and constitutional isomers thereof. In another embodiment, $R^3$ is —C(O)butyl, and constitutional isomers thereof. In another embodiment, $R^3$ is —C(O)pentyl, and constitutional isomers thereof. In certain embodiments of Formula I above, useful $R^3$ groups include —C(O)N(H)Me, —C(O)N(H)Et, —C(O)N(H)propyl and constitutional isomers thereof, —C(O)N(H)butyl and constitutional isomers thereof, —C(O)N(H)pentyl and constitutional isomers thereof, —C(O)N(H)hexyl and constitutional isomers thereof, —C(O)N(H)heptyl and constitutional isomers thereof, —C(O)N(H)octyl and constitutional isomers thereof, —C(O)N(H)nonyl and constitutional isomers thereof, —C(O)N(H)decyl and constitutional isomers thereof. In one embodiment of Formula I above, $R^3$ is —C(O)N(H)Me. In one embodiment of Formula I above, $R^3$ is —C(O)N(H)Et. In one embodiment of Formula I above, $R^3$ is —C(O)N(H)propyl, and constitutional isomers thereof. In one embodiment of Formula I above, $R^3$ is —C(O)N(H)butyl, and constitutional isomers thereof. In one embodiment of Formula I above, $R^3$ is —C(O)N(H)pentyl, and constitutional isomers thereof. In one embodiment of Formula I above, $R^3$ is —C(O)N(H)hexyl, and constitutional isomers thereof. In one embodiment of Formula I above, $R^3$ is —C(O)N(H)heptyl, and constitutional isomers thereof. In one embodiment of Formula I above, $R^3$ is —C(O)N(H)octyl, and constitutional isomers thereof. In one embodiment of Formula I above, $R^3$ is —C(O)N(H)nonyl, and constitutional isomers thereof. In one embodiment of Formula I above, $R^3$ is —C(O)N(H)decyl, and constitutional isomers thereof. In certain embodiments of Formula I above, useful $R^3$ groups include —$CH_2$—N$R^{3a}R^{3b}$, —$CH_2CH_2$—N$R^{3a}R^{3b}$, —$CH_2CH_2CH_2$—N$R^{3a}R^{3b}$, —$CH_2CH_2CH_2CH_2$—N$R^{3a}R^{3b}$, —$CH_2CH_2CH_2CH_2CH_2$—N$R^{3a}R^{3b}$, —$CH_2CH_2CH_2CH_2CH_2CH_2$—N$R^{3a}R^{3b}$, —$CH_2CH_2CH_2CH_2CH_2CH_2CH_2$—N$R^{3a}R^{3b}$, —$CH_2CH_2CH_2CH_2CH_2CH_2CH_2CH_2$—N$R^{3a}R^{3n}$, —$CH_2CH_2CH_2CH_2CH_2CH_2CH_2CH_2CH_2$—N$R^{3a}R^{3b}$, and —$CH_2CH_2CH_2CH_2CH_2CH_2CH_2CH_2CH_2CH_2$—N$R^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula I above, $R^3$ is —$CH_2$—N$R^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula I above, $R^3$ is —$CH_2CH_2$—N$R^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula I above, $R^3$ is —$CH_2CH_2$—N$R^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula I above, $R^3$ is —$CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula I above, $R^3$ is —$CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula I above, $R^3$ is —$CH_2CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula I above, $R^3$ is —$CH_2CH_2CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula I above, $R^3$ is —$CH_2CH_2CH_2CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula I above, $R^3$ is —$CH_2CH_2CH_2CH_2CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In certain embodiments of Formula I above, useful $R^4$ groups include hydrogen, methyl, ethyl, propyl, butyl, and pentyl, and constitutional isomers thereof. In one embodiment, $R^4$ is hydrogen. In one embodiment, $R^4$ is methyl. In another embodiment, $R^4$ is ethyl. In another embodiment, $R^4$ is propyl, and constitutional isomers thereof. In another embodiment, $R^4$ is butyl, and constitutional isomers thereof. In another embodiment, $R^4$ is pentyl, and constitutional isomers thereof. In certain embodiments of Formula I above, useful $R^5$ groups include hydrogen, methyl, ethyl, propyl, butyl, and pentyl, and constitutional isomers thereof. In one embodiment, $R^5$ is hydrogen. In one embodiment, $R^5$ is methyl. In another embodiment, $R^5$ is ethyl. In another embodiment, $R^5$ is propyl, and constitutional isomers thereof. In another embodiment, $R^5$ is butyl, and constitutional isomers thereof. In another embodiment, $R^5$ is pentyl, and constitutional isomers thereof. In certain embodiments, $R^4$ and $R^5$, together with the carbon to which they are attached, form a 3-8 membered cycloalkyl, substituted cycloalkyl, heterocycloalkyl, or substituted heterocycloalkyl. Other exemplary combinations or perturbations for $R^4$ and $R^5$ as embodiments within this paragraph are contemplated herein. In certain embodiments of Formula I above, $R^6$ includes —OH or —$NHNH_2$. In one embodiment, $R^6$ is —OH. In another embodiment, $R^6$ is —$NHNH_2$. In certain embodiments, $R^6$ is —$NHSO_2R^{60}$, wherein $R^{60}$ is alkyl, alkenyl, alkynyl, cycloalkyl, heterocycloalkyl, aryl, heteroaryl, substituted aryl, or substituted heteroaryl. In Formula I above, in one embodiment, $R^7$ is —OH. In Formula I above, in one embodiment, $R^7$ is —$NH_2$. In Formula I, in certain embodiments above, $R^8$ incudes hydrogen, deuterium, —$NHR^9$, or halogen. In certain embodiments of Formula I above, $R^9$ is hydrogen, —$C_1$-$C_5$ alkyl, or —$C(O)$ $C_1$-$C_5$ alkyl. In certain embodiments of Formula I above, m is 1 or 2. In one embodiment, $R^8$ is hydrogen. In one embodiment, $R^8$ is deuterium. In certain embodiments, $R^8$ includes, independently, fluorine, chlorine, bromine, and iodine. In one embodiment, $R^8$ is fluorine. In another embodiment, $R^8$ is chlorine. In another embodiment, $R^8$ is bromine. In another embodiment, $R^8$ is iodine. In one embodiment, —$NHR^9$ is —$NH_2$. In one embodiment, —$NHR^9$ includes —NHMe, —NHEt, —$NHCH_2CH_2CH_3$, —$NHCH_2CH_2CH_2CH_3$, and —$NHCH_2CH_2CH_2CH_2CH_3$. In one embodiment, —$NHR^9$ is —NHMe. In one embodiment, —$NHR^9$ is —NHEt. In one embodiment, —$NHR^9$ is —$NHCH_2CH_2CH_3$. In one embodiment, —$NHR^9$ is —$NHCH_2CH_2CH_2CH_3$. In one embodiment, —$NHR^9$ is —$NHCH_2CH_2CH_2CH_2CH_3$. In one embodiment, —$NHR^9$ includes —NHC(O)Me, —NHC(O)Et, —$NHC(O)CH_2CH_2CH_3$, —$NHC(O)CH_2CH_2CH_2CH_3$, and —$NHC(O)CH_2CH_2CH_2CH_2CH_3$. In one embodiment, —$NHR^9$ is —NHC(O)Me. In one embodiment, —$NHR^9$ is —NHC(O)Et. In one embodiment, —$NHR^9$ is —$NHC(O)CH_2CH_2CH_3$. In one embodiment, —$NHR^9$ is —$NHC(O)CH_2CH_2CH_2CH_3$. In one embodiment, —$NHR^9$ is —$NHC(O)CH_2CH_2CH_2CH_2CH_3$. In one embodiment, m is 1. In one embodiment, m is 2.

In certain embodiments, set forth herein is a compound having the structure of Formula VIII:

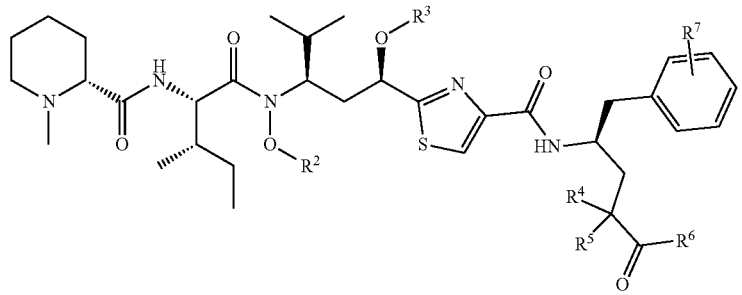

Formula VIII or a pharmaceutically acceptable salt thereof. In certain embodiments, $R^2$, $R^3$, $R^4$, $R^5$, $R^6$, and $R^7$, are as described in the preceding paragraph. In one embodiment of Formula VIII, $R^3$ is —C(O)Me, and $R^2$, $R^4$, $R^5$, $R^6$, and $R^7$, are as described in the preceding paragraph. In one embodiment of Formula VIII, $R_3$ is —C(O)N(H)$C_1$-$C_{10}$ alkyl, and $R^2$, $R^4$, $R^5$, $R^6$, and $R^7$, are as described in the preceding paragraph.

In certain embodiments, set forth herein is a compound having the structure of Formula I, or a pharmaceutically acceptable salt or prodrug thereof, wherein $R^3$ is —C(O)N(H)$C_1$-$C_{10}$ alkyl; $R^4$ is hydrogen; $R^5$ is $C_1$-$C_5$ alkyl; and $R^6$ and $R^7$ are —OH. In certain embodiments, $R^2$ is as described in Formula I above. In certain embodiments of Formula I above, useful $R^3$ groups include —C(O)N(H)Me, —C(O)N(H)Ft, —C(O)N(H)propyl and constitutional isomers thereof, —C(O)N(H)butyl and constitutional isomers thereof, —C(O)N(H)pentyl and constitutional isomers thereof, —C(O)N(H)hexyl and constitutional isomers thereof, —C(O)N(H)heptyl and constitutional isomers thereof, —C(O)N(H)octyl and constitutional isomers thereof, —C(O)N(H)nonyl and constitutional isomers thereof, —C(O)N(H)decyl and constitutional isomers thereof. In one embodiment of Formula I above, $R^3$ is —C(O)N(H)Me. In one embodiment of Formula I above, $R^3$ is —C(O)N(H)Ft. In one embodiment of Formula I above, $R^3$ is —C(O)N(H)propyl, and constitutional isomers thereof. In one embodiment of Formula I above, $R^3$ is —C(O)N(H)butyl, and constitutional isomers thereof. In one embodiment of Formula I above, $R^3$ is —C(O)N(H)pentyl, and constitutional isomers thereof. In one embodiment of Formula I above, $R^3$ is —C(O)N(H)hexyl, and constitutional isomers thereof. In one embodiment of Formula I above, $R^3$ is —C(O)N(H)heptyl, and constitutional isomers thereof. In one embodiment of Formula I above, $R^3$ is —C(O)N(H)octyl, and constitutional isomers thereof. In one embodiment of Formula I above, $R^3$ is —C(O)N(H)nonyl, and constitutional isomers thereof. In one embodiment of Formula I above, $R^3$ is —C(O)N(H)decyl, and constitutional isomers thereof. In one embodiment, $R^5$ is methyl. In another embodiment, $R^5$ is ethyl. In another embodiment, $R^5$ is propyl, and constitutional isomers thereof. In another embodiment, $R^5$ is butyl, and constitutional isomers thereof. In another embodiment, $R^5$ is pentyl, and constitutional isomers thereof.

In certain embodiments, set forth herein is a compound having the structure of Formula IX:

wherein $R^{11}$ is $C_1$-$C_{10}$ alkyl; or a pharmaceutically acceptable salt thereof. In one embodiment, $R^{11}$ is methyl. In one embodiment, $R^{11}$ is ethyl. In one embodiment, $R^{11}$ is propyl, and constitutional isomers thereof. In one embodiment, $R^{11}$ is butyl, and constitutional isomers thereof. In one embodiment, $R^{11}$ is pentyl, and constitutional isomers thereof. In one embodiment, $R^{11}$ is hexyl, and constitutional isomers thereof. In one embodiment, $R^{11}$ is heptyl, and constitutional isomers thereof. In one embodiment, $R^{11}$ is octyl, and constitutional isomers thereof. In one embodiment, $R^{11}$ is nonyl, and constitutional isomers thereof. In one embodiment, $R^{11}$ is decyl, and constitutional isomers thereof.

In certain embodiments, set forth herein is a compound having the structure of Formula I, or a pharmaceutically acceptable salt or prodrug thereof, wherein Q is —O—; $R^2$ is $C_1$-$C_{10}$ alkynyl; $R^3$ is —C(O)$C_1$-$C_5$ alkyl; and $R^6$ is —OH. In certain embodiments, $R^1$, $R^4$, $R^5$, $R^7$, and $R^8$, are as described in Formula I above. In one embodiment of Formula I, $R^2$ is —$CH_2$CCH. In one embodiment of Formula I, $R^2$ is —$CH_2CH_2$CCH. In one embodiment of Formula I, $R^2$ is —$CH_2CH_2CH_2$CCH. In one embodiment of Formula I, $R^2$ is —$CH_2CH_2CH_2CH_2$CCH. In one embodiment of Formula I, $R^2$ is —$CH_2CH_2CH_2CH_2CH_2$CCH. In one embodiment of Formula I, $R^2$ is —$CH_2CH_2CH_2CH_2CH_2CH_2$CCH. In one embodiment of Formula I, $R^2$ is —$CH_2CH_2CH_2CH_2CH_2CH_2CH_2$CCH. In one embodiment of Formula I, $R^2$ is —$CH_2CH_2CH_2CH_2CH_2CH_2CH_2CH_2$CCH. In one embodiment of Formula I, $R^2$ is —$CH_2CH_2CH_2CH_2CH_2CH_2CH_2CH_2CH_2$CCH. In one embodiment of Formula I, $R^2$ is —$CH_2CH_2CH_2CH_2CH_2CH_2CH_2CH_2CH_2CH_2$CCH. In one embodiment, $R^3$ is —C(O)Me. In another embodiment, $R^3$ is —C(O)Et. In another embodiment, $R^3$ is —C(O)propyl, and constitutional isomers thereof. In another embodiment, $R^3$ is —C(O)butyl, and constitutional isomers thereof. In another embodiment, $R^3$ is —C(O)pentyl, and constitutional isomers thereof.

In certain embodiments, set forth herein is a compound having the structure of Formula X.

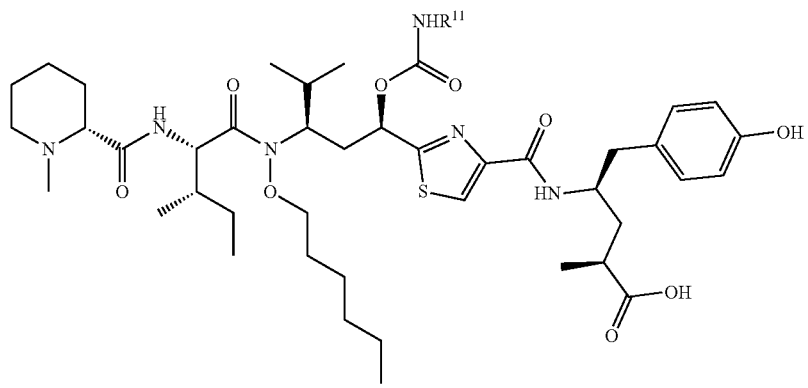

Formula IX

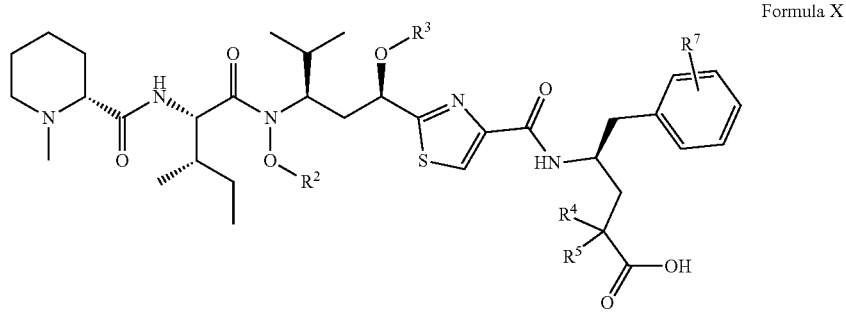

Formula X or a pharmaceutically acceptable salt thereof. In certain embodiments, $R^2$, $R^3$, $R^4$, $R^5$, and $R^7$ are as described in the preceding paragraph.

In certain embodiments, set forth herein is a compound having the structure of Formula I, or a pharmaceutically acceptable salt or prodrug thereof, wherein Q is —O—; $R^2$ is $C_1$-$C_{10}$ alkynyl; $R^3$ is —C(O)N(H)$C_1$-$C_{10}$ alkyl; and $R^6$ is —OH. In certain embodiments, $R^1$, $R^4$, $R^5$, $R^7$, and $R^8$, are as described in Formula I above. In one embodiment of Formula I, $R^2$ is —CH$_2$CCH. In one embodiment of Formula I, $R^2$ is —CH$_2$CH$_2$CCH. In one embodiment of Formula I, $R^2$ is —CH$_2$CH$_2$CH$_2$CCH. In one embodiment of Formula I, $R^2$ is —CH$_2$CH$_2$CH$_2$CH$_2$CCH. In one embodiment of Formula I, $R^2$ is —CH$_2$CH$_2$CH$_2$CH$_2$CH$_2$CCH. In one embodiment of Formula I, $R^2$ is —CH$_2$CH$_2$CH$_2$CH$_2$CH$_2$CH$_2$CCH. In one embodiment of Formula I, $R^2$ is —CH$_2$CH$_2$CH$_2$CH$_2$CH$_2$CH$_2$CH$_2$CCH. In one embodiment of Formula I, $R^2$ is —CH$_2$CH$_2$CH$_2$CH$_2$CH$_2$CH$_2$CH$_2$CH$_2$CCH. In one embodiment of Formula I, $R^2$ is —CH$_2$CH$_2$CH$_2$CH$_2$CH$_2$CH$_2$CH$_2$CH$_2$CH$_2$CCH. In one embodiment of Formula I, $R^2$ is —CH$_2$CH$_2$CH$_2$CH$_2$CH$_2$CH$_2$CH$_2$CH$_2$CH$_2$CH$_2$CCH. In one embodiment of Formula I above, $R^3$ is —C(O)N(H)Me. In one embodiment of Formula I above, $R^3$ is —C(O)N(H)Et. In one embodiment of Formula I above, $R^3$ is —C(O)N(H)propyl, and constitutional isomers thereof. In one embodiment of Formula I above, $R^3$ is —C(O)N(H)butyl, and constitutional isomers thereof. In one embodiment of Formula I above, $R^3$ is —C(O)N(H)pentyl, and constitutional isomers thereof. In one embodiment of Formula I above, $R^3$ is —C(O)N(H)hexyl, and constitutional isomers thereof. In one embodiment of Formula I above, $R^3$ is —C(O)N(H)heptyl, and constitutional isomers thereof. In one embodiment of Formula I above, $R^3$ is —C(O)N(H)octyl, and constitutional isomers thereof. In one embodiment of Formula I above, $R^3$ is —C(O)N(H)nonyl, and constitutional isomers thereof. In one embodiment of Formula I above, $R^3$ is —C(O)N(H)decyl, and constitutional isomers thereof.

In certain embodiments, set forth herein is a compound having the structure of Formula XI:

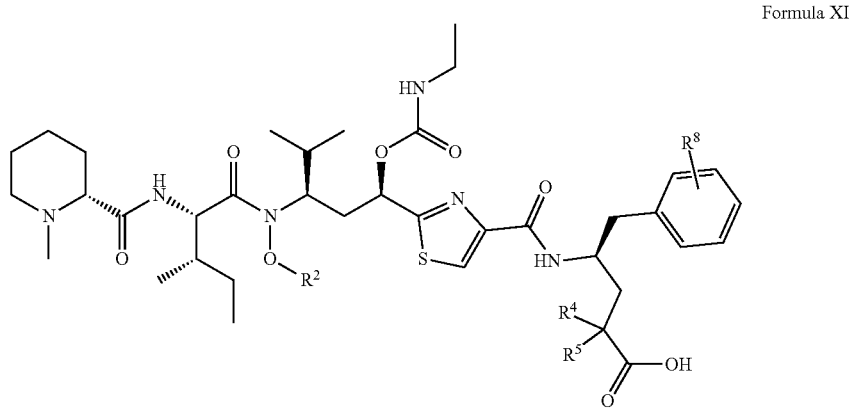

Formula XI or a pharmaceutically acceptable salt thereof. In certain embodiments, $R^2$, $R^4$, $R^5$, and $R^8$ are as described in the preceding paragraph.

In certain embodiments, set forth herein is a compound having the structure of Formula I, or a pharmaceutically acceptable salt or prodrug thereof, wherein Q is —O—; $R^2$ is $C_1$-$C_3$ alkylene-$Q^1$-$(CH_2)_n$aryl; or $C_1$-$C_3$ hydroxyalkyl; $R^3$ is —C(O)$C_1$-$C_5$ alkyl; $R^4$ is hydrogen; $R^5$ is $C_1$-$C_5$ alkyl; and $R^6$ and $R^7$ is —OH. In certain embodiments, $R^1$ and $R^8$, are as described in Formula I above. In certain embodiments, $R^2$ is $C_1$-$C_3$ alkylene-$Q^1$-$(CH_2)_n$aryl, and $Q^1$ is —$CH_2$—. Accordingly, in one embodiment, $R^2$ is —$CH_2CH_2$$(CH_2)_n$aryl, wherein aryl is unsubstituted or substituted with nitro or amino, and n is an integer from 1 to 5. In one embodiment, $R^2$ is —$CH_2CH_2(CH_2)_n$phenyl, and n is 1, 2, 3, 4, or 5. In one embodiment, $R^2$ is —$CH_2CH_2(CH_2)_n$p-nitrophenyl, and n is 1, 2, 3, 4, or 5. In one embodiment, $R^2$ is —$CH_2CH_2(CH_2)_n$p-aminophenyl, and n is 1, 2, 3, 4, or 5. In one embodiment, $R^2$ is —$CH_2CH_2CH_2(CH_2)_n$aryl, wherein aryl is unsubstituted or substituted with nitro or amino, and n is an integer from 1 to 5. In one embodiment, $R^2$ is —$CH_2CH_2CH_2(CH_2)_n$phenyl, and n is 1, 2, 3, 4, or 5. In one embodiment, $R^2$ is —$CH_2CH_2CH_2(CH_2)_n$p-nitrophenyl, and n is 1, 2, 3, 4, or 5. In one embodiment, $R^2$ is —$CH_2CH_2CH_2(CH_2)_n$p-aminophenyl, and n is 1, 2, 3, 4, or 5. In one embodiment, $R^2$ is —$CH_2CH_2CH_2CH_2(CH_2)_n$aryl, wherein aryl is unsubstituted or substituted with nitro or amino, and n is an integer from 1 to 5. In one embodiment, $R^2$ is —$CH_2CH_2CH_2CH_2(CH_2)_n$phenyl, and n is 1, 2, 3, 4, or 5. In one embodiment, $R^2$ is —$CH_2CH_2CH_2CH_2(CH_2)_n$p-nitrophenyl, and n is 1, 2, 3, 4, or 5. In one embodiment, $R^2$ is —$CH_2CH_2CH_2CH_2(CH_2)_n$p-aminophenyl, and n is 1, 2, 3, 4, or 5. In certain embodiments, $R^2$ is $C_1$-$C_3$ alkylene-$Q^1$-$(CH_2)_n$aryl, and $Q^1$ is —O—. Accordingly, in one embodiment, $R^2$ is —$CH_2O$—$(CH_2)_n$aryl, wherein aryl is unsubstituted or substituted with nitro or amino, and n is an integer from 1 to 5. In one embodiment, $R^2$ is —$CH_2O$—$(CH_2)_n$phenyl, and n is 1, 2, 3, 4, or 5. In one embodiment, $R^2$ is —$CH_2O$—$(CH_2)_n$p-nitrophenyl, and n is 1, 2, 3, 4, or 5. In one embodiment, $R^2$ is —$CH_2O$—$(CH_2)_n$p-aminophenyl, and n is 1, 2, 3, 4, or 5. In one embodiment, $R^2$ is —$CH_2CH_2O$—$(CH_2)_n$aryl, wherein aryl is unsubstituted or substituted with nitro or amino, and n is an integer from 1 to 5. In one embodiment, $R^2$ is —$CH_2CH_2O$—$(CH_2)_n$phenyl, and n is 1, 2, 3, 4, or 5. In one embodiment, $R^2$ is —$CH_2CH_2O$—$(CH_2)_n$p-nitrophenyl, and n is 1, 2, 3, 4, or 5. In one embodiment, $R^2$ is —$CH_2CH_2O$—$(CH_2)_n$p-aminophenyl, and n is 1, 2, 3, 4, or 5. In one embodiment, $R^2$ is —$CH_2CH_2CH_2O$—$(CH_2)_n$aryl, wherein aryl is unsubstituted or substituted with nitro or amino, and n is an integer from 1 to 5. In one embodiment, $R^2$ is —$CH_2CH_2CH_2O$—$(CH_2)_n$phenyl, and n is 1, 2, 3, 4, or 5. In one embodiment, $R^2$ is —$CH_2CH_2CH_2O$—$(CH_2)_n$p-nitrophenyl, and n is 1, 2, 3, 4, or 5. In one embodiment, $R^2$ is —$CH_2CH_2CH_2O$—$(CH_2)_n$p-aminophenyl, and n is 1, 2, 3, 4, or 5. In one embodiment, $R^2$ is —$CH_2OH$. In one embodiment, $R^2$ is —$CH_2CH_2OH$. In one embodiment, $R^2$ is —$CH_2CH_2CH_2OH$. In certain embodiments of Formula I above, useful $R^3$ groups include —C(O)Me, —C(O)Et, —C(O)propyl, —C(O)butyl, and —C(O)pentyl, and constitutional isomers thereof. In one embodiment, $R^3$ is —C(O)Me. In another embodiment, $R^3$ is —C(O)Et. In another embodiment, $R^3$ is —C(O)propyl, and constitutional isomers thereof. In another embodiment, $R^3$ is —C(O)butyl, and constitutional isomers thereof. In another embodiment, $R^3$ is —C(O)pentyl, and constitutional isomers thereof. In certain embodiments of Formula I above, useful $R^5$ groups include methyl, ethyl, propyl, butyl, and pentyl, and constitutional isomers thereof. In one embodiment, $R^5$ is methyl. In another embodiment, $R^5$ is ethyl. In another embodiment, $R^5$ is propyl, and constitutional isomers thereof. In another embodiment, $R^5$ is butyl, and constitutional isomers thereof. In another embodiment, $R^5$ is pentyl, and constitutional isomers thereof.

In certain embodiments, set forth herein is a compound having the structure of Formula XII:

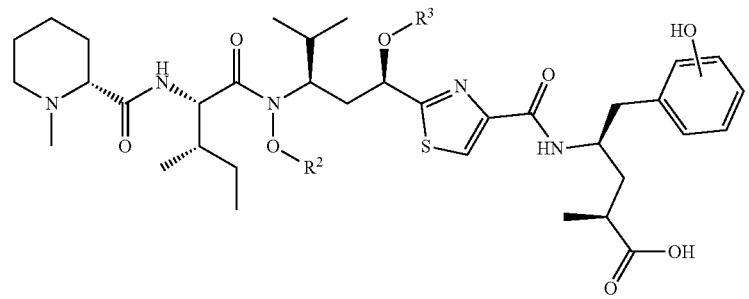

Formula XII or a pharmaceutically acceptable salt thereof. In certain embodiments, R² and R³ are as described in the preceding paragraph. In one embodiment of Formula XII, R² is C₁-C₃ alkylene-O—(CH₂)ₙaryl, as described in the preceding paragraph. In one embodiment of Formula XII, R² is C₁-C₃ hydroxyalkyl, as described in the preceding paragraph.

In certain embodiments, provided herein are compounds according to any of Formulae I, VIII, IX, X, XI, or XII that may be selected from the group consisting of:

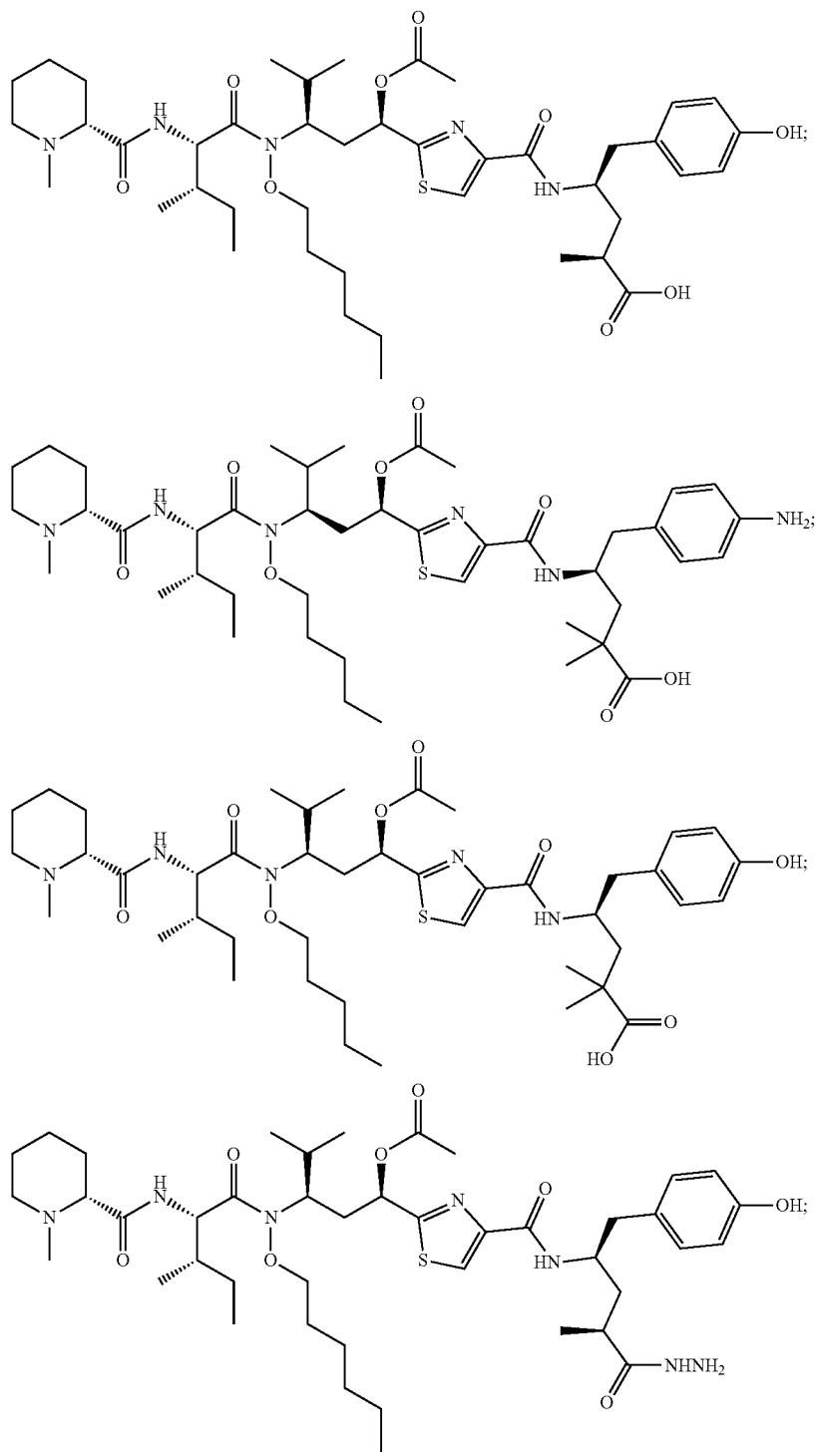

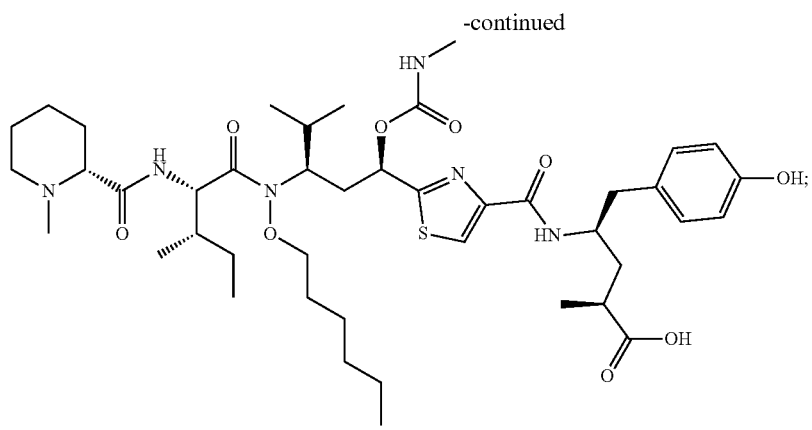
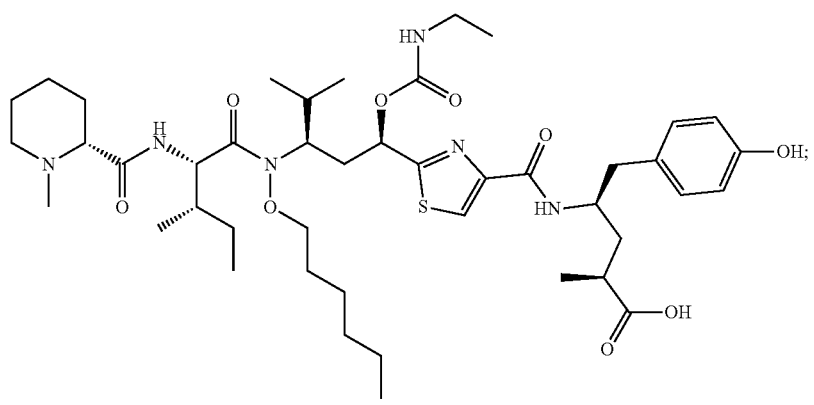
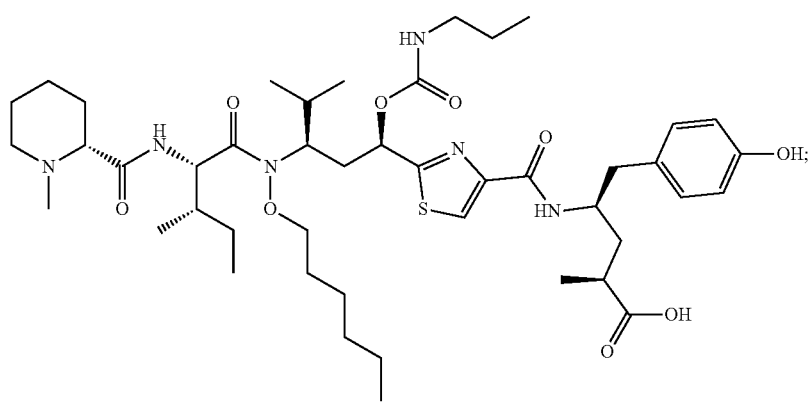
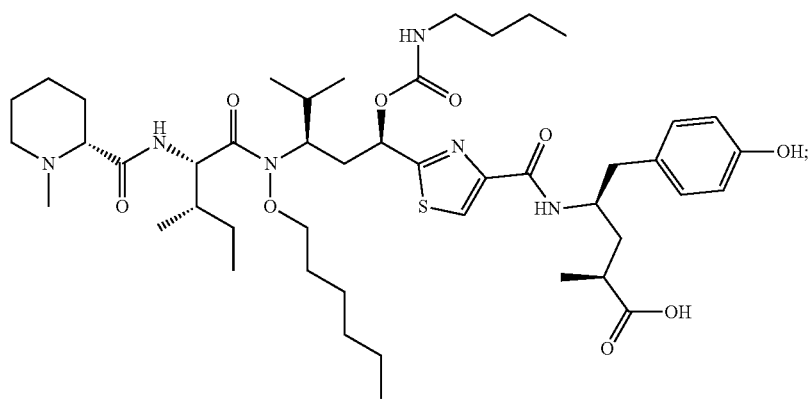

-continued
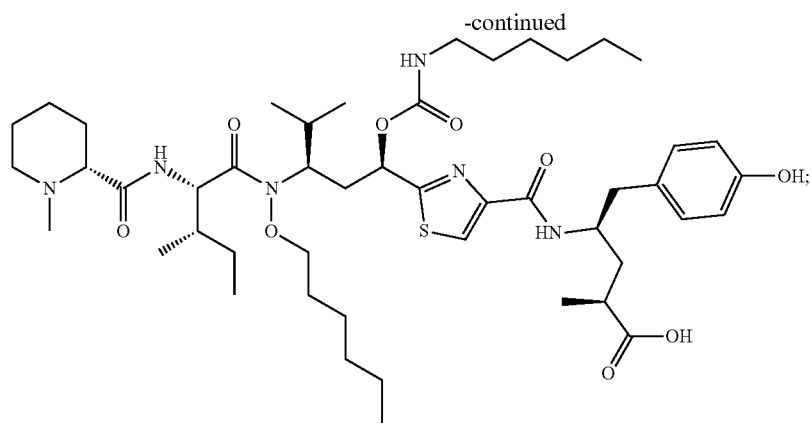
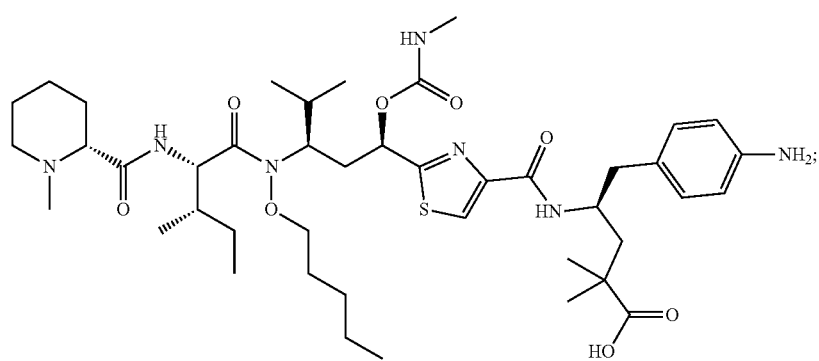
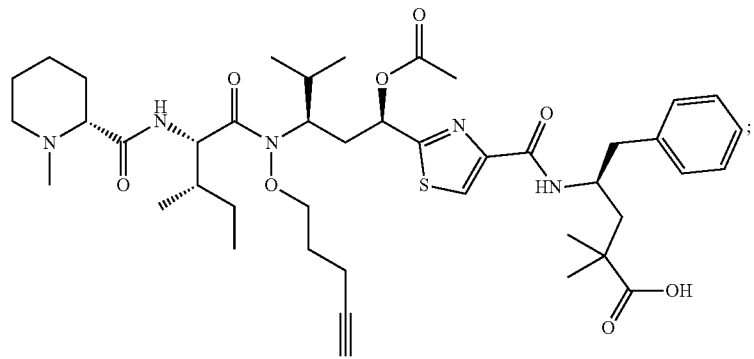
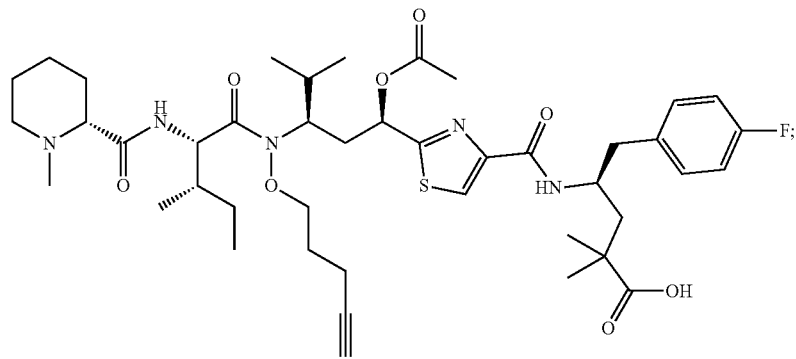

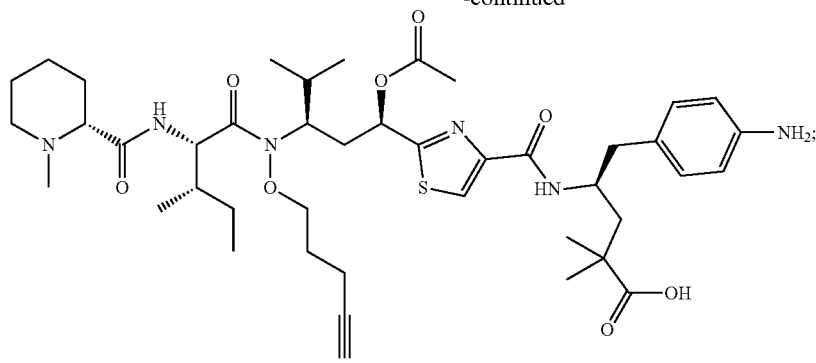
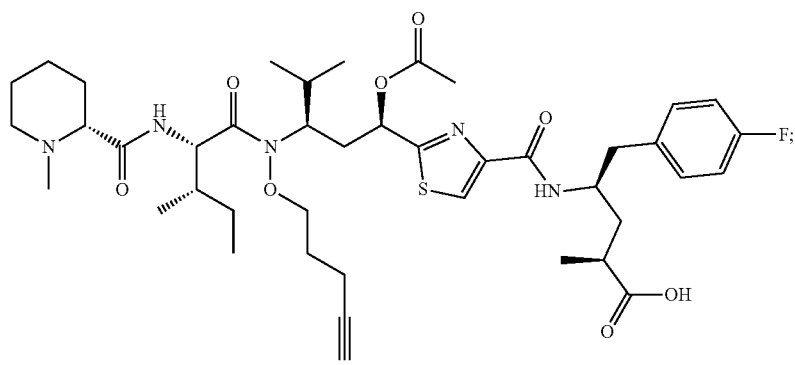
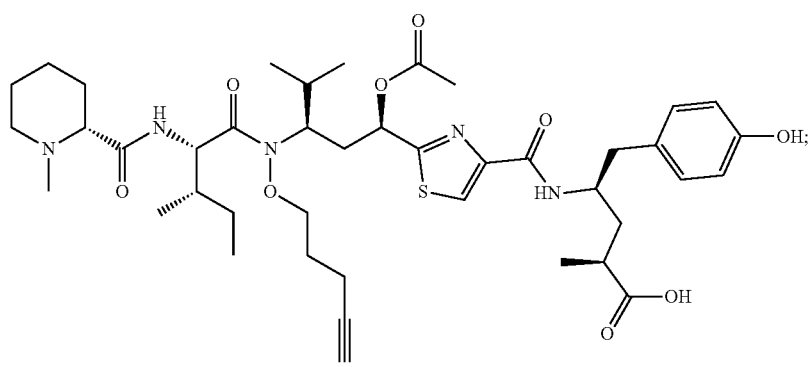
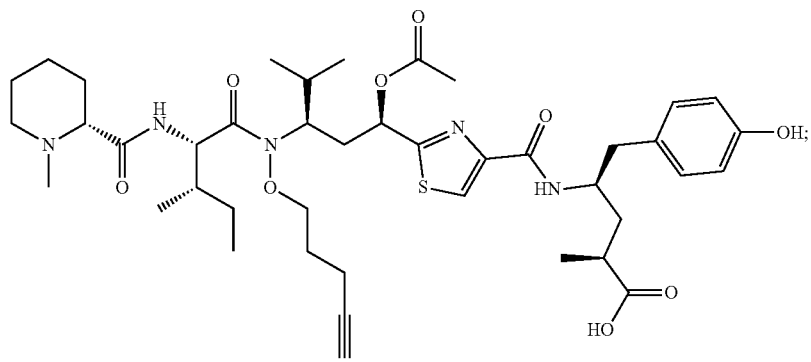

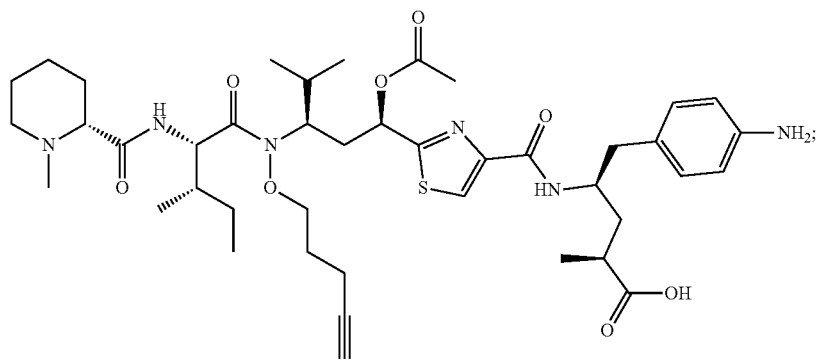
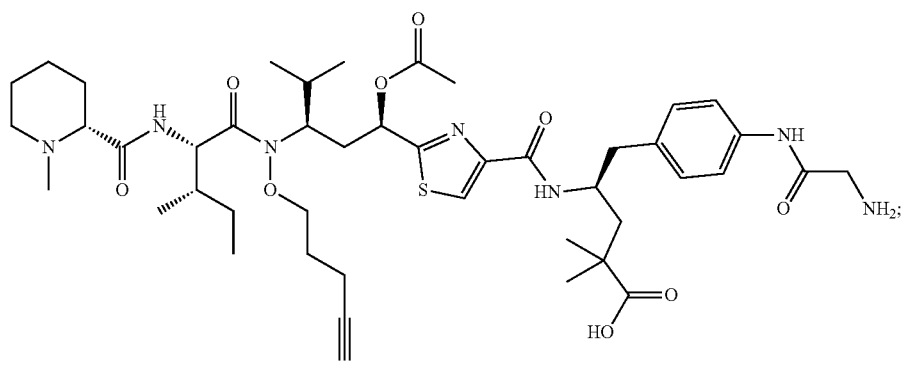
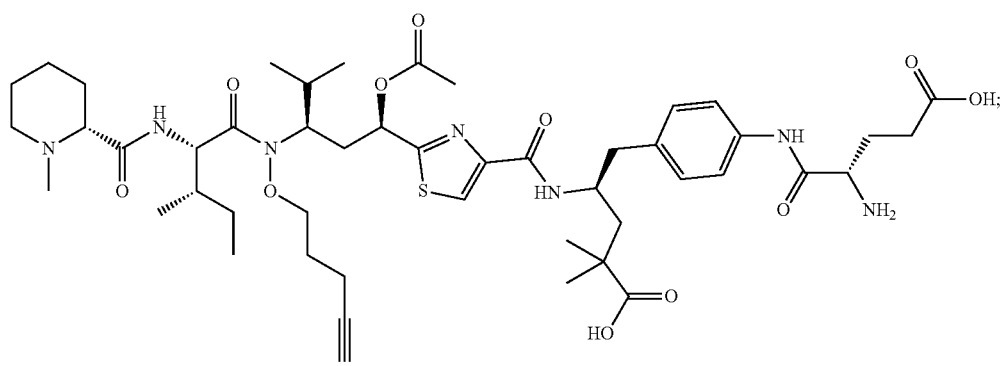
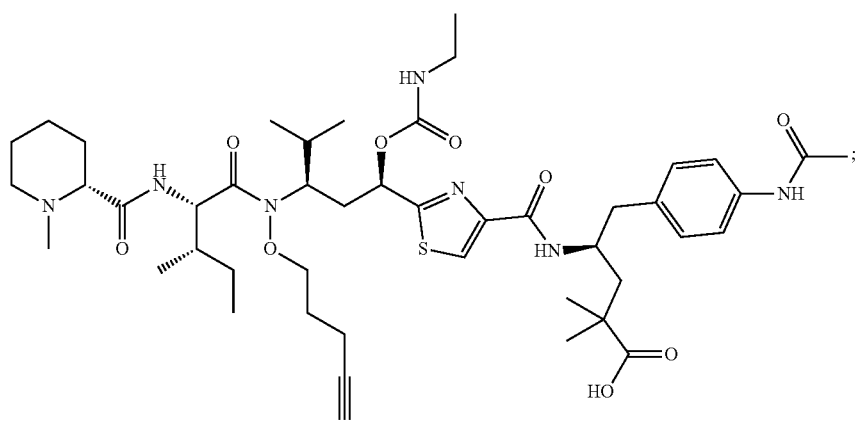

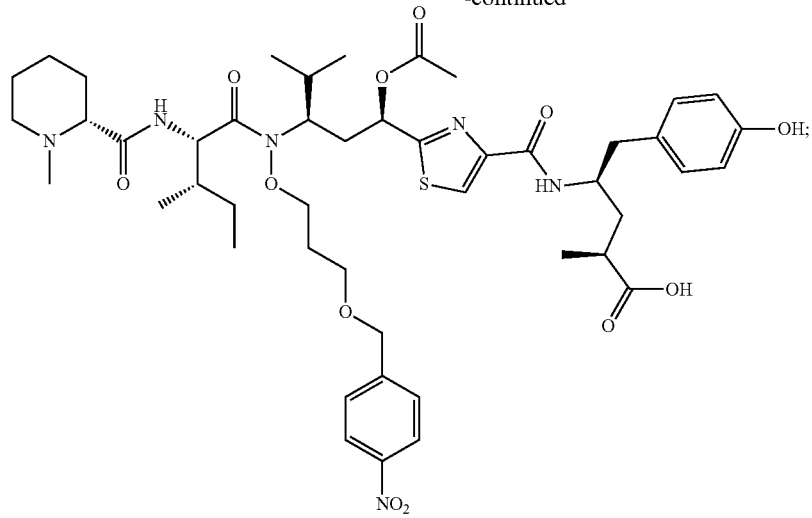
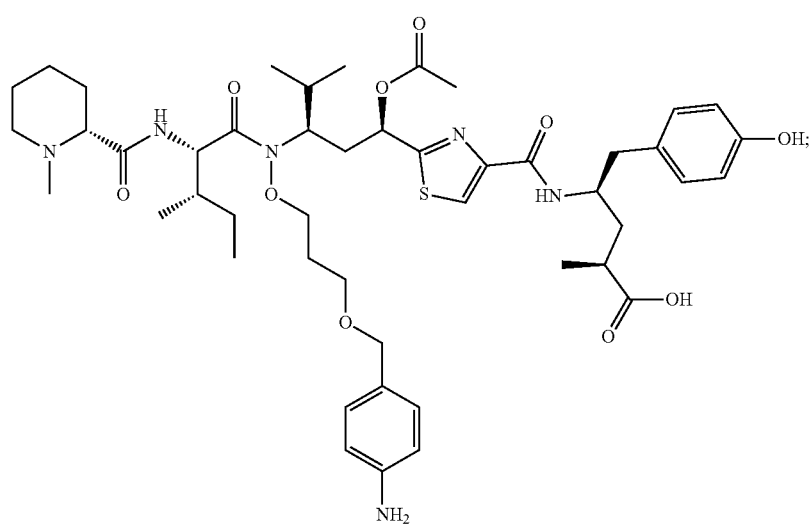
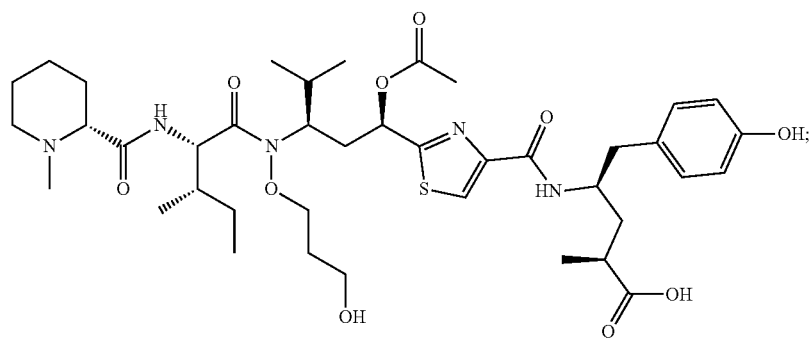
a pharmaceutically acceptable salt thereof.

In certain embodiments, set forth herein is a compound having the structure of Formula XIII:

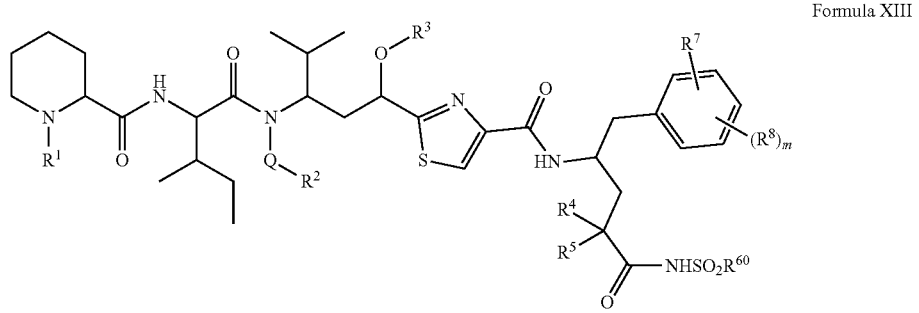

Formula XIII or a pharmaceutically acceptable salt or prodrug thereof, wherein Q is —O—; $R^2$ is $C_1$-$C_{10}$ alkyl; and $R^7$ is —OH or —$NH_2$. In Formula XIII, in certain embodiments, useful $R^1$ groups include methyl and ethyl. In certain embodiments, useful $R^1$ groups include propyl, butyl, pentyl, hexyl, heptyl, octyl, nonyl, decyl, and constitutional isomers thereof. In one embodiment, $R^1$ is methyl. In one embodiment, $R^1$ is ethyl. In one embodiment, $R^1$ is propyl, and constitutional isomers thereof. In one embodiment, $R^1$ is butyl, and constitutional isomers thereof. In one embodiment, $R^1$ is pentyl, and constitutional isomers thereof. In one embodiment, $R^1$ is hexyl, and constitutional isomers thereof. In one embodiment, $R^1$ is heptyl, and constitutional isomers thereof. In one embodiment, $R^1$ is octyl, and constitutional isomers thereof. In one embodiment, $R^1$ is nonyl, and constitutional isomers thereof. In one embodiment, $R^1$ is decyl, and constitutional isomers thereof. In Formula XIII, in certain embodiments above, useful $R^2$ groups include methyl, ethyl, n-propyl, n-butyl, n-pentyl, n-hexyl, n-heptyl, n-octyl, n-nonyl, and n-decyl. In one embodiment, $R^2$ is methyl. In one embodiment, $R^2$ is ethyl. In one embodiment, $R^2$ is n-propyl, or constitutional isomers thereof. In one embodiment, $R^2$ is n-butyl, or constitutional isomers thereof. In one embodiment, $R^2$ is n-pentyl, or constitutional isomers thereof. In another embodiment, $R^2$ is n-hexyl, or constitutional isomers thereof. In another embodiment, $R^2$ is n-heptyl, or constitutional isomers thereof. In another embodiment, $R^2$ is n-octyl, or constitutional isomers thereof. In another embodiment, $R^2$ is n-nonyl, or constitutional isomers thereof. In another embodiment, $R^2$ is n-decyl, or constitutional isomers thereof. In certain embodiments, $R^3$ is —C(O)$C_1$-$C_5$ alkyl, —C(O)N(H)$C_1$-$C_{10}$ alkyl, or —($C_1$-$C_{10}$ alkylene)-$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In certain embodiments of Formula XIII above, useful $R^3$ groups include —C(O)Me, —C(O)Et, —C(O)propyl, —C(O)butyl, and —C(O)pentyl, and constitutional isomers thereof. In one embodiment, $R^3$ is —C(O)Me. In another embodiment, $R^3$ is —C(O)Et. In another embodiment, $R^3$ is —C(O)propyl, and constitutional isomers thereof. In another embodiment, $R^3$ is —C(O)butyl, and constitutional isomers thereof. In another embodiment, $R^3$ is —C(O)pentyl, and constitutional isomers thereof. In certain embodiments of Formula I above, useful $R^3$ groups include —C(O)N(H)Me, —C(O)N(H)Et, —C(O)N(H)propyl and constitutional isomers thereof, —C(O)N(H)butyl and constitutional isomers thereof, —C(O)N(H)pentyl and constitutional isomers thereof, —C(O)N(H)hexyl and constitutional isomers thereof, —C(O)N(H)heptyl and constitutional isomers thereof, —C(O)N(H)octyl and constitutional isomers thereof, —C(O)N(H)nonyl and constitutional isomers thereof, —C(O)N(H)decyl and constitutional isomers thereof. In one embodiment of Formula XIII above, $R^3$ is —C(O)N(H)Me. In one embodiment of Formula XIII above, $R^3$ is —C(O)N(H)Et. In one embodiment of Formula XIII above, $R^3$ is —C(O)N(H)propyl, and constitutional isomers thereof. In one embodiment of Formula XIII above, $R^3$ is —C(O)N(H)butyl, and constitutional isomers thereof. In one embodiment of Formula XIII above, $R^3$ is —C(O)N(H)pentyl, and constitutional isomers thereof. In one embodiment of Formula XIII above, $R^3$ is —C(O)N(H)hexyl, and constitutional isomers thereof. In one embodiment of Formula XIII above, $R^3$ is —C(O)N(H)heptyl, and constitutional isomers thereof. In one embodiment of Formula XIII above, $R^3$ is —C(O)N(H)octyl, and constitutional isomers thereof. In one embodiment of Formula XIII above, $R^3$ is —C(O)N(H)nonyl, and constitutional isomers thereof. In one embodiment of Formula XIII above, $R^3$ is —C(O)N(H)decyl, and constitutional isomers thereof. In certain embodiments of Formula XIII above, useful $R^3$ groups include —$CH_2$—$NR^{3a}R^{3b}$, —$CH_2CH_2$—$NR^{3a}R^{3b}$, —$CH_2CH_2CH_2$—$NR^{3a}R^{3b}$, —$CH_2CH_2CH_2CH_2$—$NR^{3a}R^{3b}$, —$CH_2CH_2CH_2CH_2CH_2$—$NR^{3a}R^{3b}$, —$CH_2CH_2CH_2CH_2CH_2CH_2$—$NR^{3a}R^{3b}$, —$CH_2CH_2CH_2CH_2CH_2CH_2CH_2$—$NR^{3a}R^{3b}$, —$CH_2CH_2CH_2CH_2CH_2CH_2CH_2CH_2$—$NR^{3a}R^{3b}$, —$CH_2CH_2CH_2CH_2CH_2CH_2CH_2CH_2CH_2$—$NR^{3a}R^{3b}$, and —$CH_2CH_2CH_2CH_2CH_2CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula XIII above, $R^3$ is —$CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula XIII above, $R^3$ is —$CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula XIII above, $R^3$ is —$CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula XIII above, $R^3$ is —$CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula XIII above, $R^3$ is —$CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula XIII above, $R^3$ is —$CH_2CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula XIII above, $R^3$ is —$CH_2CH_2CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula XIII above, $R^3$ is —$CH_2CH_2CH_2CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In one embodiment of Formula XIII above, $R^3$ is —$CH_2CH_2CH_2CH_2CH_2CH_2CH_2CH_2CH_2$—$NR^{3a}R^{3b}$, wherein $R^{3a}$ and $R^{3b}$ are independently in each instance, hydrogen, alkyl, alkenyl, alkynyl, cycloalkyl, aryl, heteroaryl, and acyl, wherein alkyl, alkenyl, alkynyl, cycloalkyl, aryl, heteroaryl, and acyl are optionally substituted. In certain embodiments of Formula XIII above, useful $R^4$ groups include hydrogen, methyl, ethyl, propyl, butyl, and pentyl, and constitutional isomers thereof. In one embodiment, $R^4$ is hydrogen. In one embodiment, $R^4$ is methyl. In another embodiment, $R^4$ is ethyl. In another embodiment, $R^4$ is propyl, and constitutional isomers thereof. In another embodiment, $R^4$ is butyl, and constitutional isomers thereof. In another embodiment, $R^4$ is pentyl, and constitutional isomers thereof. In certain embodiments of Formula XIII above, useful $R^5$ groups include hydrogen, methyl, ethyl, propyl, butyl, and pentyl, and constitutional isomers thereof. In one embodiment, $R^5$ is hydrogen. In one embodiment, $R^5$ is methyl. In another embodiment, $R^5$ is ethyl. In another embodiment, $R^5$ is propyl, and constitutional isomers thereof. In another embodiment, $R^5$ is butyl, and constitutional isomers thereof. In another embodiment, $R^5$ is pentyl, and constitutional isomers thereof. In one embodiment, $R^4$ and $R^5$ are methyl. In certain embodiments, $R^4$ and $R^5$, together with the carbon to which they are attached, form a 3-8 membered cycloalkyl, substituted cycloalkyl, heterocycloalkyl, or substituted heterocycloalkyl. Other exemplary combinations or perturbations for $R^4$ and $R^5$ as embodiments within this paragraph are contemplated herein. In one embodiment, $R^4$ and $R^5$, together with the carbon to which they are attached, is cyclopropyl or substituted cyclopropyl. In one embodiment, $R^4$ and $R^5$, together with the carbon to which they are attached, is cyclobutyl or substituted cyclobutyl. In one embodiment, $R^4$ and $R^5$, together with the carbon to which they are attached, is cyclopentyl or substituted cyclopentyl. In one embodiment, $R^4$ and $R^5$, together with the carbon to which they are attached, is cyclohexyl or substituted cyclohexyl. In one embodiment, $R^4$ and $R^5$, together with the carbon to which they are attached, is cycloheptyl or substituted cycloheptyl. In one embodiment, $R^4$ and $R^5$, together with the carbon to which they are attached, is cyclooctyl or substituted cyclooctyl. In one embodiment, $R^4$ and $R^5$, together with the carbon to which they are attached, is cyclopropyl where one methylene carbon in the cyclopropyl is replaced with Z, where Z is oxygen, nitrogen, or sulfur. In one embodiment, $R^4$ and $R^5$, together with the carbon to which they are attached, is cyclobutyl where one methylene carbon in the cyclobutyl is replaced with Z, where Z is oxygen, nitrogen, or sulfur. In one embodiment, $R^4$ and $R^5$, together with the carbon to which they are attached, is cyclopentyl where one or more methylene carbons in the cyclopentyl is replaced with Z, where Z is oxygen, nitrogen, or sulfur. In one embodiment, $R^4$ and $R^5$, together with the carbon to which they are attached, is cyclohexyl where one or more methylene carbons in the cyclohexyl is replaced with Z, where Z is oxygen, nitrogen, or sulfur. In one embodiment, $R^4$ and $R^5$, together with the carbon to which they are attached, is cycloheptyl where one or more methylene carbons in the cycloheptyl is replaced with Z, where Z is oxygen, nitrogen, or sulfur. In one embodiment, $R^4$ and $R^5$, together with the carbon to which they are attached, is cyclooctyl where one or more methylene carbons in the cyclooctyl is replaced with Z, where Z is oxygen, nitrogen, or sulfur. In certain embodiments of Formula XIII above, $R^{60}$ is alkyl, alkenyl, alkynyl, cycloalkyl, heterocycloalkyl, aryl, heteroaryl, substituted aryl, or substituted heteroaryl. Suitable $R^{60}$ alkyl groups include those described in this paragraph for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in this paragraph. In Formula XIII above, in one embodiment, $R^7$ is —OH. In Formula XIII above, in one embodiment, $R^7$ is —$NH_2$. In Formula XIII, in certain embodiments above, $R^8$ incudes hydrogen, deuterium, —$NHR^9$, or halogen. In certain embodiments of Formula XIII above, $R^9$ is hydrogen, —$C_1$-$C_5$ alkyl, or —$C(O)C_1$-$C_5$ alkyl. In certain embodiments of Formula XIII above, m is 1 or 2. In one embodiment, $R^8$ is hydrogen. In one embodiment, $R^8$ is deuterium. In certain embodiments, $R^8$ includes, independently, fluorine, chlorine, bromine, and iodine. In one embodiment, $R^8$ is fluorine. In another embodiment, $R^8$ is chlorine. In another embodiment, $R^8$ is bromine. In another embodiment, $R^8$ is iodine. In one embodiment, —$NHR^9$ is —$NH_2$. In one embodiment, —$NHR^9$ includes —NHMe, —NHEt, —$NHCH_2CH_2CH_3$, —$NHCH_2CH_2CH_2CH_3$, and —$NHCH_2CH_2CH_2CH_2CH_3$. In one embodiment, —$NHR^9$ is —NHMe. In one embodiment, —$NHR^9$ is —NHEt. In one embodiment, —$NHR^9$ is —$NHCH_2CH_2CH_3$. In one embodiment, —$NHR^9$ is —$NHCH_2CH_2CH_2CH_3$. In one embodiment, —$NHR^9$ is —$NHCH_2CH_2CH_2CH_2CH_3$. In one embodiment, —$NHR^9$ includes —NHC(O)Me, —NHC(O)Et, —NHC(O)$CH_2CH_2CH_3$, —NHC(O)$CH_2CH_2CH_2CH_3$, and —NHC(O)$CH_2CH_2CH_2CH_2CH_3$. In one embodiment, —$NHR^9$ is —NHC(O)Me. In one embodiment, —$NHR^9$ is —NHC(O)Et. In one embodiment, —$NHR^9$ is —NHC(O)$CH_2CH_2CH_3$. In one embodiment, —$NHR^9$ is —NHC(O)$CH_2CH_2CH_2CH_3$. In one embodiment, —$NHR^9$ is —NHC(O)$CH_2CH_2CH_2CH_2CH_3$. In one embodiment, m is 1. In one embodiment, m is 2.

In certain embodiments, set forth herein is a compound having the structure of Formula XX:

Formula XX

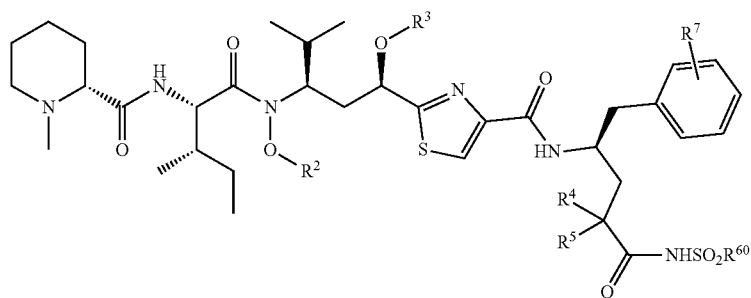

or a pharmaceutically acceptable salt thereof. In certain embodiments, $R^2$, $R^3$, $R^4$, $R^5$, $R^7$, and $R^{60}$ are as described in the preceding paragraph. In one embodiment of Formula VIII, $R^3$ is —C(O)Me, and $R^2$, $R^4$, $R^5$, $R^7$, and $R^{60}$ are as described in the preceding paragraph. In one embodiment of Formula VIII, $R_3$ is —C(O)N(H)$C_1$-$C_{10}$ alkyl, and $R^2$, $R^4$, $R^5$, $R^7$, and $R^{60}$ are as described in the preceding paragraph.

In certain embodiments, set forth herein is a compound having the structure of Formula XIII, or a pharmaceutically acceptable salt or prodrug thereof, wherein $R^3$ is —C(O)N(H)$C_1$-$C_{10}$ alkyl; $R^4$ is hydrogen or $C_1$-$C_5$ alkyl; $R^5$ is $C_1$-$C_5$ alkyl; $R^7$ is —OH; and $R^{60}$ is as described in the context of Formula XIII. In certain embodiments, $R^2$ is as described in Formula XIII above. In certain embodiments of Formula XIII above, useful $R^3$ groups include —C(O)N(H)Me, —C(O)N(H)Et, —C(O)N(H)propyl and constitutional isomers thereof, —C(O)N(H)butyl and constitutional isomers thereof, —C(O)N(H)pentyl and constitutional isomers thereof, —C(O)N(H)hexyl and constitutional isomers thereof, —C(O)N(H)heptyl and constitutional isomers thereof, —C(O)N(H)octyl and constitutional isomers thereof, —C(O)N(H)nonyl and constitutional isomers thereof, —C(O)N(H)decyl and constitutional isomers thereof. In one embodiment of Formula XIII above, $R^3$ is —C(O)N(H)Me. In one embodiment of Formula XIII above, $R^3$ is —C(O)N(H)Et. In one embodiment of Formula XIII above, $R^3$ is —C(O)N(H)propyl, and constitutional isomers thereof. In one embodiment of Formula XIII above, $R^3$ is —C(O)N(H)butyl, and constitutional isomers thereof. In one embodiment of Formula XIII above, $R^3$ is —C(O)N(H)pentyl, and constitutional isomers thereof. In one embodiment of Formula XIII above, $R^3$ is —C(O)N(H)hexyl, and constitutional isomers thereof. In one embodiment of Formula XIII above, $R^3$ is —C(O)N(H)heptyl, and constitutional isomers thereof. In one embodiment of Formula XIII above, $R^3$ is —C(O)N(H)octyl, and constitutional isomers thereof. In one embodiment of Formula XIII above, $R^3$ is —C(O)N(H)nonyl, and constitutional isomers thereof. In one embodiment of Formula XIII above, $R^3$ is —C(O)N(H)decyl, and constitutional isomers thereof. In one embodiment, $R^4$ is hydrogen. In one embodiment, $R^4$ is methyl. In another embodiment, $R^4$ is ethyl. In another embodiment, $R^4$ is propyl, and constitutional isomers thereof. In another embodiment, $R^4$ is butyl, and constitutional isomers thereof. In another embodiment, $R^4$ is pentyl, and constitutional isomers thereof. In one embodiment, $R^5$ is methyl. In another embodiment, $R^5$ is ethyl. In another embodiment, $R^5$ is propyl, and constitutional isomers thereof. In another embodiment, $R^5$ is butyl, and constitutional isomers thereof. In another embodiment, $R^5$ is pentyl, and constitutional isomers thereof. In one embodiment, $R^4$ and $R^5$ are methyl.

In certain embodiments, set forth herein is a compound having the structure of Formula XXI:

Formula XXI

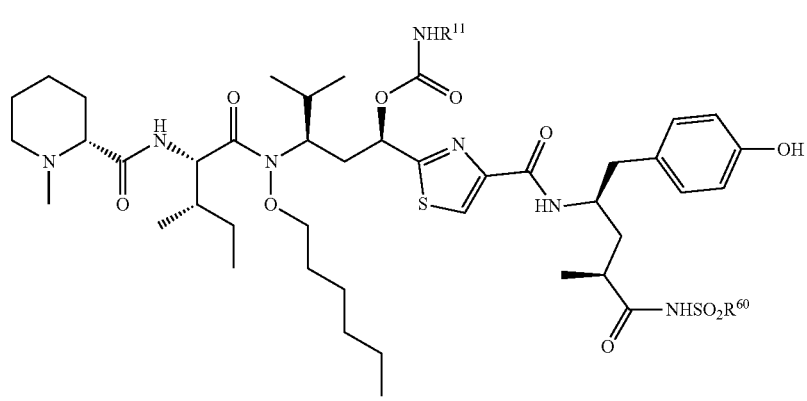

wherein $R^{60}$ is alkyl, alkenyl, alkynyl, cycloalkyl, heterocycloalkyl, aryl, heteroaryl, substituted aryl, or substituted heteroaryl. Suitable $R^{60}$ alkyl groups include those described in the context of Formula XIII for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in the context of Formula XIII. In certain embodiments, $R^{11}$ is $C_1$-$C_{10}$ alkyl; or a pharmaceutically acceptable salt thereof. In one embodiment, $R^{11}$ is methyl. In one embodiment, $R^{11}$ is ethyl. In one embodiment, $R^{11}$ is propyl, and constitutional isomers thereof. In one embodiment, $R^{11}$ is butyl, and constitutional isomers thereof. In one embodiment, $R^{11}$ is pentyl, and constitutional isomers thereof. In one embodiment, $R^{11}$ is hexyl, and constitutional isomers thereof. In one embodiment, $R^{11}$ is heptyl, and constitutional isomers thereof. In one embodiment, $R^{11}$ is octyl, and constitutional isomers thereof. In one embodiment, $R^{11}$ is nonyl, and constitutional isomers thereof. In one embodiment, $R^{11}$ is decyl, and constitutional isomers thereof.

In certain embodiments, set forth herein is a compound having the structure of Formula XIII, or a pharmaceutically acceptable salt or prodrug thereof, wherein Q is —O—; $R^2$ is $C_1$-$C_{10}$ alkynyl; $R^3$ is —C(O)$C_1$-$C_5$ alkyl; and $R^{60}$ is alkyl, alkenyl, alkynyl, cycloalkyl, heterocycloalkyl, aryl, heteroaryl, substituted aryl, or substituted heteroaryl. Suitable $R^{60}$ alkyl groups include those described in the context of Formula XIII for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in the context of Formula XIII. In certain embodiments, $R^1$, $R^4$, $R^5$, $R^7$, and $R^8$, are as described in Formula XIII above. In one embodiment of Formula XIII, $R^2$ is —CH$_2$CCH. In one embodiment of Formula XIII, $R^2$ is —CH$_2$CH$_2$CCH. In one embodiment of Formula XIII, $R^2$ is —CH$_2$CH$_2$CH$_2$CCH. In one embodiment of Formula XIII, $R^2$ is —CH$_2$CH$_2$CH$_2$CH$_2$CCH. In one embodiment of Formula XIII, $R^2$ is —CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CH$_2$CH$_2$CH$_2$CH$_2$CCH. In one embodiment of Formula XIII above, $R^3$ is —C(O)Me. In another embodiment, $R^3$ is —C(O)Et. In another embodiment, $R^3$ is —C(O)propyl, and constitutional isomers thereof. In another embodiment, $R^3$ is —C(O)butyl, and constitutional isomers thereof. In another embodiment, $R^3$ is —C(O)pentyl, and constitutional isomers thereof.

In certain embodiments, set forth herein is a compound having the structure of Formula XXII:

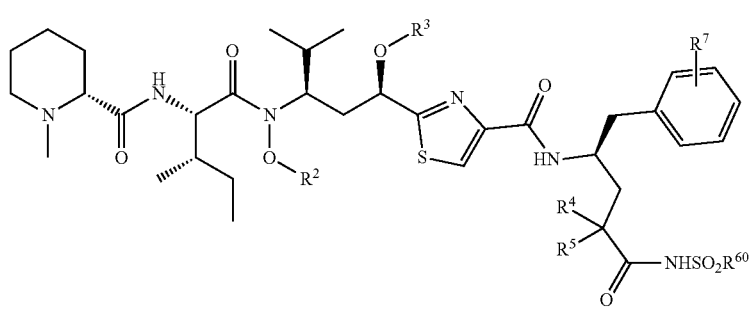

Formula XXII or a pharmaceutically acceptable salt thereof. In certain embodiments, $R^2$, $R^3$, $R^4$, $R^5$, $R^7$, and $R^{60}$ are as described in the preceding paragraph.

In certain embodiments, set forth herein is a compound having the structure of Formula XIII, or a pharmaceutically acceptable salt or prodrug thereof, wherein Q is —O—; $R^2$ is $C_1$-$C_{10}$ alkynyl; $R^3$ is —C(O)N(H)$C_1$-$C_{10}$ alkyl; and $R^{60}$ is alkyl, alkenyl, alkynyl, cycloalkyl, heterocycloalkyl, aryl, heteroaryl, substituted aryl, or substituted heteroaryl. Suitable $R^{60}$ alky groups include those described in the context of Formula XIII for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in the context of Formula XIII. In certain embodiments, $R^1$, $R^4$, $R^5$, $R^7$, and $R^8$, are as described in Formula XIII above. In one embodiment of Formula XIII, $R^2$ is —CH$_2$CCH. In one embodiment of Formula XIII, $R^2$ is —CH$_2$CH$_2$CCH. In one embodiment of Formula XIII, $R^2$ is —CH$_2$CH$_2$CH$_2$CCH. In one embodiment of Formula XIII, $R^2$ is —CH$_2$CH$_2$CH$_2$CH$_2$CCH. In one embodiment of Formula XIII, $R^2$ is —CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CH$_2$CH$_2$CH$_2$CCH. In one embodiment of Formula XIII, $R^2$ is —CH$_2$CH$_2$CH$_2$CH$_2$CH$_2$CH$_2$CH$_2$CH$_2$CH$_2$CH$_2$CCH. In one embodiment of Formula XIII above, $R^3$ is —C(O)N(H)Me. In one embodiment of Formula XIII above, $R^3$ is —C(O)N(H)Et. In one embodiment of Formula XIII above, $R^3$ is —C(O)N(H)propyl, and constitutional isomers thereof. In one embodiment of Formula XIII above, $R^3$ is —C(O)N(H)butyl, and constitutional isomers thereof. In one embodiment of Formula XIII above, $R^3$ is —C(O)N(H)pentyl, and constitutional isomers thereof. In one embodiment of Formula XIII above, $R^3$ is —C(O)N(H)hexyl, and constitutional isomers thereof. In one embodiment of Formula XIII above, $R^3$ is —C(O)N(H)heptyl, and constitutional isomers thereof.

In one embodiment of Formula XIII above, $R^3$ is —C(O)N(H)octyl, and constitutional isomers thereof. In one embodiment of Formula XIII above, $R^3$ is —C(O)N(H)nonyl, and constitutional isomers thereof. In one embodiment of Formula XIII above, $R^3$ is —C(O)N(H)decyl, and constitutional isomers thereof.

In certain embodiments, set forth herein is a compound having the structure of Formula XXIII:

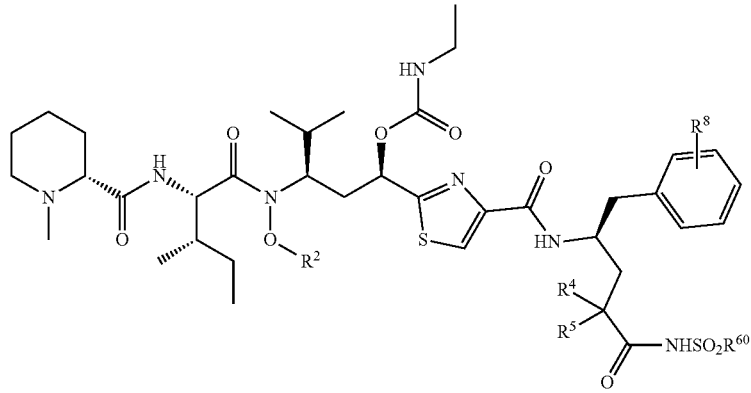

Formula XXIII or a pharmaceutically acceptable salt thereof. In certain embodiments, $R^2$, $R^4$, $R^5$, $R^8$, and $R^{60}$ are as described in the preceding paragraph.

In certain embodiments, set forth herein is a compound having the structure of Formula XIII, or a pharmaceutically acceptable salt or prodrug thereof, wherein Q is —O—; $R^2$ is $C_1$-$C_3$ alkylene-$Q^1$-$(CH_2)_n$aryl; or $C_1$-$C_3$ hydroxyalkyl; $R^3$ is —C(O)$C_1$-$C_5$ alkyl; $R^4$ is hydrogen or $C_1$-$C_5$ alkyl; $R^1$ is $C_1$-$C_5$ alkyl; $R^7$ is —OH; and $R^{60}$ is alkyl, alkenyl, alkynyl, cycloalkyl, heterocycloalkyl, aryl, heteroaryl, substituted aryl, or substituted heteroaryl. Suitable $R^{60}$ alkyl groups include those described in the context of Formula XIII for $R^1$, for example, methyl, ethyl, and the like. Suitable $R^{60}$ alkenyl, alkynyl, aryl, and heteroaryl are described elsewhere herein. Suitable $R^{60}$ cycloalkyl and heterocycloalkyl include those described for $R^4$ and $R^5$, together with the carbon to which they are attached, as described in the context of Formula XIII. In certain embodiments, $R^1$ and $R^8$, are as described in Formula XIII above. In certain embodiments, $R^2$ is $C_1$-$C_3$ alkylene-$Q^1$-$(CH_2)_n$aryl, and $Q^1$ is —$CH_2$—. Accordingly, in one embodiment, $R^2$ is —$CH_2CH_2(CH_2)_n$aryl, wherein aryl is unsubstituted or substituted with nitro or amino, and n is an integer from 1 to 5. In one embodiment, $R^2$ is —$CH_2CH_2(CH_2)_n$phenyl, and n is 1, 2, 3, 4, or 5. In one embodiment, $R^2$ is —$CH_2CH_2(CH_2)_n$p-nitrophenyl, and n is 1, 2, 3, 4, or 5. In one embodiment, $R^2$ is —$CH_2CH_2(CH_2)_n$p-aminophenyl, and n is 1, 2, 3, 4, or 5. In one embodiment, $R^2$ is —$CH_2CH_2CH_2(CH_2)_n$aryl, wherein aryl is unsubstituted or substituted with nitro or amino, and n is an integer from 1 to 5. In one embodiment, $R^2$ is —$CH_2CH_2CH_2CH_2(CH_2)_n$phenyl, and n is 1, 2, 3, 4, or 5. In one embodiment, $R^2$ is —$CH_2CH_2CH_2CH_2(CH_2)_n$p-nitrophenyl, and n is 1, 2, 3, 4, or 5. In one embodiment, $R^2$ is —$CH_2CH_2CH_2CH_2(CH_2)_n$p-aminophenyl, and n is 1, 2, 3, 4, or 5. In certain embodiments, $R^2$ is $C_1$-$C_3$ alkylene-$Q^1$-$(CH_2)_n$aryl, and $Q^1$ is —O—. Accordingly, in one embodiment, $R^2$ is —$CH_2O$—$(CH_2)_n$aryl, wherein aryl is unsubstituted or substituted with nitro or amino, and n is an integer from 1 to 5. In one embodiment, $R^2$ is —$CH_2O$—$(CH_2)_n$phenyl, and n is 1, 2, 3, 4, or 5. In one embodiment, $R^2$ is —$CH_2O$—$(CH_2)_n$p-nitrophenyl, and n is 1, 2, 3, 4, or 5. In one embodiment, $R^2$ is —$CH_2O$—$(CH_2)_n$p-aminophenyl, and n is 1, 2, 3, 4, or 5. In one embodiment, $R^2$ is —$CH_2CH_2O$—$(CH_2)_n$aryl, wherein aryl is unsubstituted or substituted with nitro or amino, and n is an integer from 1 to 5. In one embodiment, $R^2$ is —$CH_2CH_2O$—$(CH_2)_n$phenyl, and n is 1, 2, 3, 4, or 5. In one embodiment, $R^2$ is —$CH_2CH_2O$—$(CH_2)_n$p-nitrophenyl, and n is 1, 2, 3, 4, or 5. In one embodiment, $R^2$ is —$CH_2CH_2O$—$(CH_2)_n$p-aminophenyl, and n is 1, 2, 3, 4, or 5. In one embodiment, $R^2$ is —$CH_2CH_2CH_2O$—$(CH_2)_n$aryl, wherein aryl is unsubstituted or substituted with nitro or amino, and n is an integer from 1 to 5. In one embodiment, $R^2$ is —$CH_2CH_2CH_2O$—$(CH_2)_n$phenyl, and n is 1, 2, 3, 4, or 5. In one embodiment, $R^2$ is —$CH_2CH_2CH_2O$—$(CH_2)_n$p-nitrophenyl, and n is 1, 2, 3, 4, or 5. In one embodiment, $R^2$ is —$CH_2CH_2CH_2O$—$(CH_2)_n$p-aminophenyl, and n is 1, 2, 3, 4, or 5. In one embodiment, $R^2$ is —$CH_2OH$. In one embodiment, $R^2$ is —$CH_2CH_2OH$. In one embodiment, $R^2$ is —$CH_2CH_2CH_2OH$. In certain embodiments of Formula XIII above, useful $R^3$ groups include —C(O)Me, —C(O)Et, —C(O)propyl, —C(O)butyl, and —C(O)pentyl, and constitutional isomers thereof. In one embodiment, $R^3$ is —C(O)Me. In another embodiment, $R^3$ is —C(O)Et. In another embodiment, $R^3$ is —C(O)propyl, and constitutional isomers thereof. In another embodiment, $R^3$ is —C(O)butyl, and constitutional isomers thereof. In another embodiment, $R^3$ is —C(O)pentyl, and constitutional isomers thereof. In one embodiment, $R^4$ is hydrogen. In certain embodiments of Formula I above, useful $R^4$ groups include methyl, ethyl, propyl, butyl, and pentyl, and constitutional isomers thereof. In one embodiment, $R^4$ is methyl. In another embodiment, $R^4$ is ethyl. In another embodiment, $R^4$ is propyl, and constitutional isomers thereof. In another embodiment, $R^4$ is butyl, and constitutional isomers thereof. In another embodiment, $R^4$ is pentyl, and constitutional isomers thereof. In certain embodiments of Formula I above, useful $R^5$ groups include methyl, ethyl, propyl, butyl, and pentyl, and constitutional isomers thereof. In one embodiment, $R^5$ is methyl.

In another embodiment, $R^5$ is ethyl. In another embodiment, $R^5$ is propyl, and constitutional isomers thereof. In another embodiment, $R^5$ is butyl, and constitutional isomers thereof. In another embodiment, $R^5$ is pentyl, and constitutional isomers thereof. In one embodiment, $R^4$ and $R^5$ are methyl.

In certain embodiments, set forth herein is a compound having the structure of Formula XXIV:

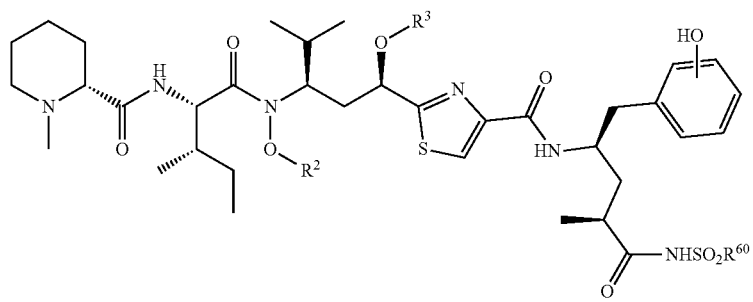

Formula XXIV or a pharmaceutically acceptable salt thereof. In certain embodiments, $R^2$, $R^3$, and $R^{60}$ are as described in the preceding paragraph. In one embodiment of Formula XXIV, $R^2$ is $C_1$-$C_3$ alkylene-O—$(CH_2)_n$aryl, as described in the preceding paragraph. In one embodiment of Formula XXIV, $R^2$ is $C_1$-$C_3$ hydroxyalkyl, as described in the preceding paragraph.

In any preceding embodiment in this section, $R^7$ is —$NR^{7a}R^{7b}$, wherein $R^{7a}$ and $R^{7b}$ are independently in each instance, hydrogen, alkyl, alkenyl, alkynyl, cycloalkyl, aryl, heteroaryl, acyl, and amino acid residue, wherein alkyl, alkenyl, alkynyl, cycloalkyl, aryl, heteroaryl, and acyl are optionally substituted. In certain embodiments $R^{7a}$ is hydrogen and $R^{7b}$ is an amino acid residue.

Binding Agents

Suitable binding agents for any of the conjugates provided in the instant disclosure include, but are not limited to, antibodies, lymphokines (e.g., IL-2 or IL-3), hormones (e.g., insulin and glucocorticoids), growth factors (e.g., EGF, transferrin, and fibronectin type III), viral receptors, interleukins, or any other cell binding or peptide binding molecules or substances. Binding agents also include, but are not limited to, ankyrin repeat proteins and interferons.

In some embodiments, the binding agent is an antibody or an antigen-binding fragment thereof. The antibody can be in any form known to those of skill in the art. The term "antibody," as used herein, refers to any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of disclosed herein, the FRs of the antibodies (or antigen-binding portion thereof) suitable for the compounds herein may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable, standard technique(s) such as proteolytic digestion or recombinant genetic engineering technique(s) involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add, or delete amino acids, etc. Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated CDR such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$, or $V_L$-$V_L$ dimers. Alternatively, the antigen-binding fragment of an antibody may contain a monomeric $V_H$ or $V_L$ domain. In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$CH_3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60, or more) amino acids which result in a flexible or semi-flexible linkage between adjacent variable and/or constant domains in a single polypeptide molecule. As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art. In certain embodiments described herein, antibodies described herein are human antibodies. The term "human antibody," as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example, in the CDRs and in particular CDR3. However, the term "human antibody," as used herein, is not intended to include antibodies in which CDR sequences derived from the germline of another mammalian species, such as a mouse, have been grafted onto human framework sequences. The term "human antibody" does not include naturally occurring molecules that normally exist without modification or human intervention/manipulation, in a naturally occurring, unmodified living organism. The antibodies disclosed herein may, in some embodiments, be recombinant human antibodies. The term "recombinant human antibody," as used herein, is intended to include all human antibodies that are prepared, expressed, created, or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created, or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge, $C_H2$, or $C_H3$ region which may be desirable, for example, in production, to improve the yield of the desired antibody form. The antibodies described herein may be isolated antibodies. An "isolated antibody," as used herein, refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the instant disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals. The antibodies used herein can comprise one or more amino acid substitutions, insertions, and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. This disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2, or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure. Antibodies useful for the compounds herein also include antibodies comprising variants of any of the HCVR, LCVR, and/or CDR amino acid sequences disclosed herein having one or more conservative substitutions. The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

In certain embodiments, the antibody comprises a light chain. In certain embodiments, the light chain is a kappa light chain. In certain embodiments, the light chain is a lambda light chain. In certain embodiments, the antibody comprises a heavy chain. In some embodiments, the heavy chain is an IgA. In some embodiments, the heavy chain is an IgD. In some embodiments, the heavy chain is an IgE. In some embodiments, the heavy chain is an IgG. In some embodiments, the heavy chain is an IgM. In some embodiments, the heavy chain is an IgG1. In some embodiments, the heavy chain is an IgG2. In some embodiments, the heavy chain is an IgG3. In some embodiments, the heavy chain is an IgG4. In some embodiments, the heavy chain is an IgA1. In some embodiments, the heavy chain is an IgA2.

In some embodiments, the antibody is an antibody fragment. In some embodiments, the antibody fragment is an Fv fragment. In some embodiments, the antibody fragment is a Fab fragment. In some embodiments, the antibody fragment is a F(ab')$_2$ fragment. In some embodiments, the antibody fragment is a Fab' fragment. In some embodiments, the antibody fragment is an scFv (sFv) fragment. In some embodiments, the antibody fragment is an scFv-Fc fragment.

In some embodiments, the antibody is a monoclonal antibody. In some embodiments, the antibody is a polyclonal antibody. In some embodiments, the antibody is a bispecific antibody including a first antigen-binding domain (also referred to herein as "D1"), and a second antigen-binding domain (also referred to herein as "D2").

As used herein, the expression "antigen-binding domain" means any peptide, polypeptide, nucleic acid molecule, scaffold-type molecule, peptide display molecule, or polypeptide-containing construct that is capable of specifically binding a particular antigen of interest (e.g., PRLR or STEAP2). The term "specifically binds" or the like, as used herein, means that the antigen-binding domain forms a complex with a particular antigen characterized by a dissociation constant ($K_D$) of 1 μM or less, and does not bind other unrelated antigens under ordinary test conditions. "Unrelated antigens" are proteins, peptides, or polypeptides that have less than 95% amino acid identity to one another.

Exemplary categories of antigen-binding domains that can be used in the context of the present disclosure include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

Methods for determining whether two molecules specifically bind one another are well known in the art and include, for example, equilibrium dialysis, surface plasmon resonance, and the like. For example, an antigen-binding domain, as used in the context of the present disclosure, includes polypeptides that bind a particular antigen (e.g., a target molecule [T] or an internalizing effector protein [E]) or a portion thereof with a $K_D$ of less than about 1 μM, less than about 500 nM, less than about 250 nM, less than about 125 nM, less than about 60 nM, less than about 30 nM, less than about 10 nM, less than about 5 nM, less than about 2 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

In some embodiments, the antibody is a chimeric antibody. In some embodiments, the antibody is a humanized antibody. In some embodiments, the antibody is a human antibody.

In some embodiments, the antibody is an anti-PSMA, anti-PRLR, anti-MUC16, anti-HER2, or anti-EGFRvIII, or anti-STEAP2 antibody. In some embodiments, the antibody is an anti-PRLR or anti HER2 antibody. In some embodiments, the antibody, or antigen-binding fragment thereof, is anti-STEAP2. In some embodiments, the antibody, or antigen-binding fragment thereof, is anti-PRLR The antibody can have binding specificity for any antigen deemed suitable to those of skill in the art. In certain embodiments, the antigen is a transmembrane molecule (e.g., receptor). In one embodiment, the antigen is expressed on a tumor. In some embodiments, the binding agents interact with or bind to tumor antigens, including antigens specific for a type of tumor or antigens that are shared, overexpressed, or modified on a particular type of tumor. In one embodiment, the antigen is expressed on solid tumors. Exemplary antigens include, but are not limited to, lipoproteins; alpha1-antitrypsin; a cytotoxic T-lymphocyte associated antigen (CTLA), such as CTLA-4; vascular endothelial growth factor (VEGF); receptors for hormones or growth factors; protein A or D; fibroblast growth factor receptor 2 (FGFR2), EpCAM, GD3, FLT3, PSMA, PSCA, MUC1, MUC16, STEAP, STEAP2, CEA, TENB2, EphA receptors, EphB receptors, folate receptor, FOLRI, mesothelin, cripto, alphavbeta6, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152, or an antibody which binds to one or more tumor-associated antigens or cell-surface receptors disclosed in US Publication No. 2008/0171040 or US Publication No. 2008/0305044 each incorporated in their entirety by reference; erythropoietin; osteoinductive factors; immunotoxins; a bone morphogenetic protein (BMP); T-cell receptors; surface membrane proteins; integrins, such as CD11a, CD11b, CD11c, CD18, an ICAM, VLA-4 and VCAM; a tumor associated antigen such as AFP, ALK, B7H4, BAGE proteins, 0-catenin, brc-abl, BRCA1, BORIS, CA9 (carbonic anhydrase IX), caspase-8, CD20, CD40, CD123, CDK4, CEA, CLEC12A, c-kit, cMET, CTLA4, cyclin-B1, CYP1B1, EGFR, EGFRvIII, endoglin, Epcam, EphA2, ErbB2/Her2, ErbB3/Her3, ErbB4/Her4, ETV6-AML, Fra-1, FOLR1, GAGE proteins, GD2, GD3, GloboH, glypican-3, GM3, gp100, Her2, HLA/B-raf, HLA/EBNA1, HLA/k-ras, HLA/MAGE-A3, hTERT, IGF1R, LGR5, LMP2, MAGE proteins, MART-1, mesothelin, ML-IAP, Muc1, Muc16, CA-125, MUM1, NA17, NGEP, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSCA, PSGR, PSMA (FOLH1), RAGE proteins, Ras, RGS5, Rho, SART-1, SART-3, Steap-1, Steap-2, STn, survivin, TAG-72, TGF-β, TMPRSS2, Tn, TNFRSF17, TRP-1, TRP-2, tyrosinase, and uroplakin-3, and fragments of any of the above-listed polypeptides; cell-surface expressed antigens; MUC16; c-MET; molecules such as class A scavenger receptors including scavenger receptor A (SR-A), and other membrane proteins such as B7 family-related member including V-set and Ig domain-containing 4 (VSIG4), Colony stimulating factor 1 receptor (CSF1R), asialoglycoprotein receptor (ASGPR), and Amyloid beta precursor-like protein 2 (APLP-2). In some embodiments, the antigen is PRLR or HER2. In some embodiments, the antigen is STEAP2. In some embodiments the antigen is human STEAP2. In some examples, the MAGE proteins are selected from MAGE-1, -2, -3, -4, -6, and -12. In some examples, the GAGE proteins are selected from GAGE-1 and GAGE-2.

Exemplary antigens also include, but are not limited to, BCMA, SLAMF7, GPNMB, and UPK3A. Exemplary antigens also include, but are not limited to, MUC16, STEAP2, and HER2.

In some embodiments, the antigens include MUC16. In some embodiments, the antigens include STEAP2. In some embodiments, the antigens include PSMA. In some embodiments, the antigens include HER2. In some embodiments, the antigen is prolactin receptor (PRLR) or prostate-specific membrane antigen (PSMA). In some embodiments, the antigen is MUC16. In some embodiments, the antigens include PSMA. In some embodiments, the antigen is HER2. In some embodiments, the antigen is STEAP2.

In certain embodiments, the antibody comprises a glutamine residue at one or more heavy chain positions numbered 295 in the EU numbering system. In the present disclosure, this position is referred to as glutamine 295, or as Gln295, or as Q295. Those of skill will recognize that this is a conserved glutamine residue in the wild type sequence of many antibodies. In other useful embodiments, the antibody can be engineered to comprise a glutamine residue. In certain embodiments, the antibody comprises one or more N297Q mutations. Techniques for modifying an antibody sequence to include a glutamine residue are within the skill of those in the art (see, e.g., Ausubel et al. *Current Protoc. Mol. Biol.*).

In some embodiments, the antibody, or antigen-binding fragment thereof, conjugated to the linker-payload or payload can be an antibody that targets STEAP2. Suitable anti-STEAP2 antibodies or antigen binding fragments thereof include those, for example, in International Publication No. WO 2018/058001 A1, including those comprising amino acid sequences disclosed in Table 1, on page 75 therein. In some embodiments, an anti-STEAP2 antibody is H1H7814N of WO 2018/058001 A1, comprising the CDRs of H1M7814N in the same publication. In some embodiments, an anti-STEAP2 antibody comprises a heavy chain complementarity determining region (HCDR)-1 comprising SEQ ID NO: 2; an HCDR2 comprising SEQ ID NO: 3; an HCDR3 comprising SEQ ID NO: 4; a light chain complementarity determining region (LCDR)-1 comprising SEQ ID NO: 6; an LCDR2 comprising SEQ ID NO: 7; and an LCDR3 comprising SEQ ID NO: 8. In some embodiments, an anti-STEAP2 antibody comprises a heavy chain variable region (HCVR) comprising SEQ ID NO: 1 and a light chain variable region (LCVR) comprising SEQ ID NO: 5. In any of the foregoing embodiments, the anti-STEAP2 antibody can be prepared by site-directed mutagenesis to insert a glutamine residue at a site without resulting in disabled antibody function or binding. For example, in any of the foregoing embodiments, the anti-STEAP2 antibody can comprise an Asn297Gln (N297Q) mutation. Such antibodies having an N297Q mutation can also contain one or more additional naturally occurring glutamine residues in their variable regions, which can be accessible to transglutaminase and therefore capable of conjugation to a payload or a linker-payload (Table A). In certain embodiments, the antibody or antigen-binding fragment thereof comprises three heavy chain complementarity determining regions (HCDR1, HCDR2, and HCDR3) within a heavy chain variable region (HCVR) amino acid sequence of SEQ ID NO: 1; and three light chain complementarity determining regions (LCDR1, LCDR2, and LCDR3) within a light chain variable region (LCVR) amino acid sequence of SEQ ID NO:5. In certain embodiments, the antibody or antigen-binding fragment thereof comprises an HCVR amino acid sequence of SEQ ID NO: 1; and an LCVR amino acid sequence of SEQ ID NO:5. International Publication No. WO 2018/058001 A1 is hereby incorporated herein by reference in its entirety.

In some embodiments, the antibody, or antigen-binding fragment thereof, conjugated to the linker-payload or payload can be an antibody that targets human prolactin receptor (PRLR). Suitable anti-PRLR antibodies or antigen-binding fragments thereof include those, for example, in International Publication No. WO 2015/026907 A1, including those comprising amino acid sequences disclosed in Table 1, on page 36 therein. In some embodiments, an anti-PRLR antibody is H1H6958N2 of WO 2015/026907 A1, comprising the CDRs of H2M6958N2 in the same publication. In some embodiments, an anti-PRLR antibody comprises a heavy chain complementarity determining region (HCDR)-1 comprising SEQ ID NO: 10; an HCDR2 comprising SEQ ID NO: 11; an HCDR3 comprising SEQ ID NO: 12; a light chain complementarity determining region (LCDR)-1 comprising SEQ ID NO: 14; an LCDR2 comprising SEQ ID NO: 15; and an LCDR3 comprising SEQ ID NO: 16. In some embodiments, an anti-PRLR antibody comprises a heavy chain variable region (HCVR) comprising SEQ ID NO: 9 and a light chain variable region (LCVR) comprising SEQ ID NO: 13. In any of the foregoing embodiments, the anti-PRLR antibody can be prepared by site-directed mutagenesis to insert a glutamine residue at a site without resulting in disabled antibody function or binding. For example, in any of the foregoing embodiments, the anti-PRLR antibody can comprise an Asn297Gln (N297Q) mutation. Such antibodies having an N297Q mutation can also contain one or more additional naturally occurring glutamine residues in their variable regions, which can be accessible to transglutaminase and therefore capable of conjugation to a payload or a linker-payload (Table A). In certain embodiments, the antibody or antigen-binding fragment thereof comprises three heavy chain complementarity determining regions (HCDR1, HCDR2, and HCDR3) within a heavy chain variable region (HCVR) amino acid sequence of SEQ ID NO:9; and three light chain complementarity determining regions (LCDR1, LCDR2, and LCDR3) within a light chain variable region (LCVR) amino acid sequence of SEQ ID NO:13. In certain embodiments, the antibody or antigen-binding fragment thereof comprises an HCVR amino acid sequence of SEQ ID NO:9; and an LCVR amino acid sequence of SEQ ID NO:13. International Publication No. WO 2015/026907 A1 is hereby incorporated herein by reference in its entirety.

TABLE A

Sequences of Exemplary Antibodies H1H7814N (anti-STEAP2) and H1H6958N2 (anti-PRLR)

| SEQ ID NO: | Molecule Antibody | Region | Sequence |
|---|---|---|---|
| 1 | H1H7814N | HCVR | QVQLVESGGGVVQPGRSLRLSCVASGFTISSYGMNWVRQAPG KGLEWVAVISYDGGNKYSVDSVKGRFTISRDNSKNTLYLQMN SLRAEDSAVYYCARGRYFDLWGRGTLVTVSS |
| 2 | H1H7814N | HCDR1 | GFTISSYG |
| 3 | H1H7814N | HCDR2 | ISYDGGNK |
| 4 | H1H7814N | HCDR3 | ARGRYFDL |
| 5 | H1H7814N | LCVR | DIQMTQSPSTLSASVGDRVTITCRASQSISSWLAWYQQKPGR APNLLISKASSLKSGVPSRFSGSGSGTEFTLTVSSLQPDDFA TYYCQQYYSYSYTFGQGTKLEIK |
| 6 | H1H7814N | LCDR1 | QSISSW |
| 7 | H1H7814N | LCDR2 | KAS |
| 8 | H1H7814N | LCDR3 | QQYYSYSYT |
| 9 | H1H6958N2 | HCVR | QVQLVESGGGVVQPGRSLRLSCGASGFTFRNYGMQWVRQGPG KGLEWVTLISFDGNDKYYADSVKGRFTISRDNSKNTLFLQMN SLRTEDTAVYYCARGGDFDYWGQGTLVTVSS |
| 10 | H1H6958N2 | HCDR1 | GFTFRNYG |
| 11 | H1H6958N2 | HCDR2 | ISFDGNDK |
| 12 | H1H6958N2 | HCDR3 | ARGGDFDY |
| 13 | H1H6958N2 | LCVR | DIQMTQSPSSLSASVGDRVTITCRASQDIRKDLGWYQQKPGK APKRLIYAASSLHSGVPSRFSGSGSGTEFTLTISSLQPEDFA TYYCLQHNSYPMYTFGQGTKLEIK |
| 14 | H1H6958N2 | LCDR1 | QDIRKD |
| 15 | H1H6958N2 | LCDR2 | AAS |
| 16 | H1H6958N2 | LCDR3 | LQHNSYPMYT |

TABLE A-continued

Sequences of Exemplary Antibodies H1H7814N (anti-STEAP2)
and H1H6958N2 (anti-PRLR)

| SEQ ID NO: | Molecule Antibody Region | Sequence |
|---|---|---|
| 17 | hPRLR ecto-MMH | MHRPRRRGTRPPPLALLAALLLAARGADAQLPPGKPEIFKCR SPNKETFTCWWRPGTDGGLPTNYSLTYHREGETLMHECPDYI TGGPNSCHFGKQYTSMWRTYIMMVNATNQMGSSFSDELYVDV TYIVQPDPPLELAVEVKQPEDRKPYLWIKWSPPTLIDLKTGW FTLLYEIRLKPEKAAEWEIHFAGQQTEFKILSLHPGQKYLVQ VRCKPDHGYWSAWSPATFIQIPSDFTMNDEQKLISEEDLGGE QKLISEEDLHHHHHH |

This disclosure provides antibodies or antigen-binding fragments thereof that specifically bind STEAP2, comprising an HCVR comprising an amino acid sequence selected from any of the HCVR amino acid sequences listed in Table A, or a substantially similar sequence thereof having at least 90%, at least 95%, at least 98%, or at least 99% sequence identity thereto.

This disclosure also provides antibodies or antigen-binding fragments thereof that specifically bind STEAP2, comprising an LCVR comprising an amino acid sequence selected from any of the LCVR amino acid sequences listed in Table A, or a substantially similar sequence thereof having at least 90%, at least 95%, at least 98%, or at least 99% sequence identity thereto.

This disclosure also provides antibodies or antigen-binding fragments thereof that specifically bind STEAP2, comprising an HCVR and an LCVR amino acid sequence pair (HCVR/LCVR) comprising any of the HCVR amino acid sequences listed in Table A paired with any of the LCVR amino acid sequences listed in Table A. According to certain embodiments, this disclosure provides antibodies, or antigen-binding fragments thereof, comprising an HCVR/LCVR amino acid sequence pair contained within any of the exemplary anti-STEAP2 antibodies listed in Table A. In certain embodiments, the HCVR/LCVR amino acid sequence pair is selected from the group consisting of: 250/258; as described in International Publication No. WO 2018/058001 A1, the contents of which are incorporated herein by reference in its entirety.

This disclosure also provides antibodies or antigen-binding fragments thereof that specifically bind STEAP2, comprising a heavy chain CDR1 (HCDR1) comprising an amino acid sequence selected from any of the HCDR1 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind STEAP2, comprising a heavy chain CDR2 (HCDR2) comprising an amino acid sequence selected from any of the HCDR2 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind STEAP2, comprising a heavy chain CDR3 (HCDR3) comprising an amino acid sequence selected from any of the HCDR3 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind STEAP2, comprising a light chain CDR1 (LCDR1) comprising an amino acid sequence selected from any of the LCDR1 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind STEAP2, comprising a light chain CDR2 (LCDR2) comprising an amino acid sequence selected from any of the LCDR2 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind STEAP2, comprising a light chain CDR3 (LCDR3) comprising an amino acid sequence selected from any of the LCDR3 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind STEAP2, comprising an HCDR3 and an LCDR3 amino acid sequence pair (HCDR3/LCDR3) comprising any of the HCDR3 amino acid sequences listed in Table A paired with any of the LCDR3 amino acid sequences listed in Table A. According to certain embodiments, this disclosure provides antibodies, or antigen-binding fragments thereof, comprising an HCDR3/LCDR3 amino acid sequence pair contained within any of the exemplary anti-STEAP2 antibodies listed in Table A. In certain embodiments, the HCDR3/LCDR3 amino acid sequence pair is selected from the group consisting of: 256/254; as described in International Publication No. WO 2018/058001 A1, the contents of which are incorporated herein by reference in its entirety.

This disclosure also provides antibodies or antigen-binding fragments thereof that specifically bind STEAP2, comprising a set of six CDRs (i.e., HCDR1-HCDR2-HCDR3-LCDR1-LCDR2-LCDR3) contained within any of the exemplary anti-STEAP2 antibodies listed in Table A. In certain embodiments, the HCDR1-HCDR2-HCDR3-LCDR1-LCDR2-LCDR3 amino acid sequence set is selected from the group consisting of: 252-254-256-260-262-264; as described in International Publication No. WO 2018/058001 A1, the contents of which are incorporated herein by reference in its entirety.

In a related embodiment, this disclosure provides antibodies, or antigen-binding fragments thereof that specifically bind STEAP2, comprising a set of six CDRs (i.e., HCDR1-HCDR2-HCDR3-LCDR1-LCDR2-LCDR3) contained within an HCVR/LCVR amino acid sequence pair as defined by any of the exemplary anti-STEAP2 antibodies listed in Table A. For example, this disclosure includes antibodies or antigen-binding fragments thereof that specifically bind STEAP2, comprising the HCDR1-HCDR2-HCDR3-LCDR1-LCDR2-LCDR3 amino acid sequence set contained within an HCVR/LCVR amino acid sequence pair selected from the group consisting of: 250/258; as described in International Publication No. WO 2018/058001 A1, the contents of which are incorporated herein by reference in its entirety. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

This disclosure provides antibodies or antigen-binding fragments thereof that specifically bind PRLR, comprising an HCVR comprising an amino acid sequence selected from any of the HCVR amino acid sequences listed in Table A, or a substantially similar sequence thereof having at least 90%, at least 95%, at least 98%, or at least 99% sequence identity thereto.

This disclosure also provides antibodies or antigen-binding fragments thereof that specifically bind PRLR, comprising an LCVR comprising an amino acid sequence selected from any of the LCVR amino acid sequences listed in Table A, or a substantially similar sequence thereof having at least 90%, at least 95%, at least 98%, or at least 99% sequence identity thereto.

This disclosure also provides antibodies or antigen-binding fragments thereof that specifically bind PRLR, comprising an HCVR and an LCVR amino acid sequence pair (HCVR/LCVR) comprising any of the HCVR amino acid sequences listed in Table A paired with any of the LCVR amino acid sequences listed in Table A. According to certain embodiments, this disclosure provides antibodies, or antigen-binding fragments thereof, comprising an HCVR/LCVR amino acid sequence pair contained within any of the exemplary anti-PRLR antibodies listed in Table A. In certain embodiments, the HCVR/LCVR amino acid sequence pair is selected from the group consisting of: 18/26; 66/74; 274/282; 290/298; and 370/378; as described in International Publication No. WO 2015/026907 A1, the contents of which are incorporated herein by reference in its entirety.

This disclosure also provides antibodies or antigen-binding fragments thereof that specifically bind PRLR, comprising a heavy chain CDR1 (HCDR1) comprising an amino acid sequence selected from any of the HCDR1 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind PRLR, comprising a heavy chain CDR2 (HCDR2) comprising an amino acid sequence selected from any of the HCDR2 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind PRLR, comprising a heavy chain CDR3 (HCDR3) comprising an amino acid sequence selected from any of the HCDR3 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind PRLR, comprising a light chain CDR1 (LCDR1) comprising an amino acid sequence selected from any of the LCDR1 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind PRLR, comprising a light chain CDR2 (LCDR2) comprising an amino acid sequence selected from any of the LCDR2 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind PRLR, comprising a light chain CDR3 (LCDR3) comprising an amino acid sequence selected from any of the LCDR3 amino acid sequences listed in Table A or a substantially similar sequence thereof having at least 90%, at least 95%, at least 98%, or at least 99% sequence identity.

This disclosure also provides antibodies or antigen-binding fragments thereof that specifically bind PRLR, comprising an HCDR3 and an LCDR3 amino acid sequence pair (HCDR3/LCDR3) comprising any of the HCDR3 amino acid sequences listed in Table A paired with any of the LCDR3 amino acid sequences listed in Table A. According to certain embodiments, this disclosure provides antibodies, or antigen-binding fragments thereof, comprising an HCDR3/LCDR3 amino acid sequence pair contained within any of the exemplary anti-PRLR antibodies listed in Table A. In certain embodiments, the HCDR3/LCDR3 amino acid sequence pair is selected from the group consisting of: 24/32; 72/80; 280/288; 296/304; and 376/384; as described in International Publication No. WO 2015/026907 A1, the contents of which are incorporated herein by reference in its entirety.

This disclosure also provides antibodies or antigen-binding fragments thereof that specifically bind PRLR, comprising a set of six CDRs (i.e., HCDR1-HCDR2-HCDR3-LCDR1-LCDR2-LCDR3) contained within any of the exemplary anti-PRLR antibodies listed in Table A. In certain embodiments, the HCDR1-HCDR2-HCDR3-LCDR1-LCDR2-LCDR3 amino acid sequence set is selected from the group consisting of: 20-22-24-28-30-32; 68-70-72-76-78-80; 276-278-280-284-286-288; 292-294-296-300-302-304; and 372-374-376-380-382-384; as described in International Publication No. WO 2015/026907 A1, the contents of which are incorporated herein by reference in its entirety.

In a related embodiment, this disclosure provides antibodies, or antigen-binding fragments thereof that specifically bind PRLR, comprising a set of six CDRs (i.e., HCDR1-HCDR2-HCDR3-LCDR1-LCDR2-LCDR3) contained within an HCVR/LCVR amino acid sequence pair as defined by any of the exemplary anti-PRLR antibodies listed in Table A. For example, this disclosure includes antibodies or antigen-binding fragments thereof that specifically bind PRLR, comprising the HCDR1-HCDR2-HCDR3-LCDR1-LCDR2-LCDR3 amino acid sequence set contained within an HCVR/LCVR amino acid sequence pair selected from the group consisting of: 18/26; 66/74; 274/282; 290/298; and 370/378; as described in International Publication No. WO 2015/026907 A1, the contents of which are incorporated herein by reference in its entirety. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

The binding agent linkers can be bonded to the binding agent, e.g., antibody or antigen-binding molecule, through an attachment at a particular amino acid within the antibody or antigen-binding molecule. Exemplary amino acid attachments that can be used in the context of this embodiment of the disclosure include, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.,* 2007, 3:321-322; Agarwal et al., *Proc. Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130).

In some examples, the binding agent is an antibody or antigen binding molecule, and the antibody is bonded to the linker through a lysine residue. In some embodiments, the antibody or antigen binding molecule is bonded to the linker through a cysteine residue.

Linkers can also be conjugated to one or more glutamine residues via transglutaminase-based chemo-enzymatic conjugation (see, e.g., Dennler et al., *Bioconjugate Chem.* 2014, 25, 569-578). For example, in the presence of transglutaminase, one or more glutamine residues of an antibody can be coupled to a primary amine compound. Primary amine compounds include, e.g., payloads or linker-payloads, which directly provide antibody drug conjugates via transglutaminase-mediated coupling. Primary amine compounds also include linkers and spacers that are functionalized with reactive groups that can be subsequently reacted with further compounds towards the synthesis of antibody drug conjugates. Antibodies comprising glutamine residues can be isolated from natural sources or engineered to comprise one or more glutamine residues. Techniques for engineering glutamine residues into an antibody polypeptide chain (glutaminyl-modified antibodies or antigen binding molecules) are within the skill of the practitioners in the art. In certain embodiments, the antibody is aglycosylated.

In certain embodiments, the antibody or a glutaminyl-modified antibody or antigen binding molecule comprises at least one glutamine residue in at least one polypeptide chain sequence. In certain embodiments, the antibody or a glutaminyl-modified antibody or antigen binding molecule comprises two heavy chain polypeptides, each with one Gln295 or Q295 residue. In further embodiments, the antibody or a glutaminyl-modified antibody or antigen binding molecule comprises one or more glutamine residues at a site other than a heavy chain 295. Included herein are antibodies of this section bearing N297Q mutation(s) described herein.

Primary Amine Compounds

In certain embodiments, primary amine compounds useful for the transglutaminase mediated coupling of an antibody (or antigen binding compound) comprising a glutamine can be any primary amine compound deemed useful by the practitioner of ordinary skill. Generally, the primary amine compound has the formula $H_2N-R$, where R can be any group compatible with the antibody and reaction conditions. In certain embodiments, R is alkyl, substituted alkyl, heteroalkyl, or substituted heteroalkyl.

In some embodiments, the primary amine compound comprises a reactive group or protected reactive group. Useful reactive groups include azides, alkynes, cycloalkynes, thiols, alcohols, ketones, aldehydes, carboxylic acids, esters, amides, hydrazides, anilines, and amines. In certain embodiments, the reactive group is selected from the group consisting of azide, alkyne, sulfhydryl, cycloalkyne, aldehyde, and carboxyl.

In certain embodiments, the primary amine compound is according to the formula $H_2N$-LL-X, where LL is a divalent spacer and X is a reactive group or protected reactive group. In particular embodiments, LL is a divalent polyethylene glycol (PEG) group. In certain embodiments, X is selected from the group consisting of —SH, —$N_3$, alkyne, aldehyde, and tetrazole. In particular embodiments, X is —$N_3$.

In certain embodiments, the primary amine compound is according to one of the following formulas:

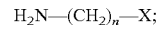

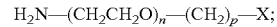

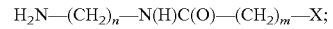

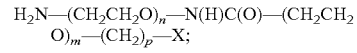

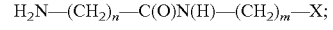

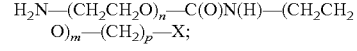

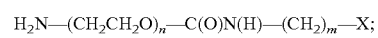

where n is an integer selected from 1 to 12;
m is an integer selected from 0 to 12;
p is an integer selected from 0 to 2;
and X is selected from the group consisting of —SH, —N$_3$, —C≡CH, —C(O)H, tetrazole, and any of

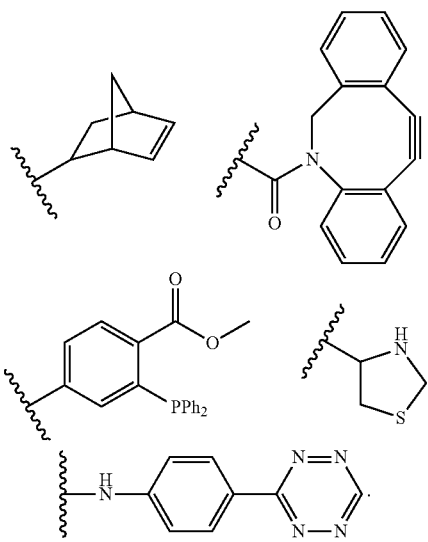

In the above, any of the alkyl or alkylene (i.e., —CH$_2$—) groups can optionally be substituted, for example, with C$_{1-8}$ alkyl, methylformyl, or —SO$_3$H. In certain embodiments, the alkyl groups are unsubstituted.

In certain embodiments, the primary amine compound is selected from the group consisting of:

In particular embodiments, the primary amine compound is

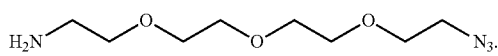 [SMILES: [N-]=[N+]=NCCOCCOCCOCCN]

Exemplary conditions for the above reactions are provided in the Examples below.

Linkers

In certain embodiments, the linker L portion of the conjugates described herein is a moiety, for instance a divalent moiety, that covalently links a binding agent to a payload compound described herein. In other instances, the linker L is a trivalent or multivalent moiety that covalently links a binding agent to a payload compound described herein. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. In certain embodiments, the linker L portion of the linker-payloads described herein is a moiety covalently linked to a payload compound described herein, capable of divalently and covalently linking a binding agent to a payload compound described herein. In other instances, the linker L portion of the linker-payloads described herein is a moiety covalently linked to a payload compound described herein, capable of covalently linking, as a trivalent or multivalent moiety, a binding agent to a payload compound described herein. Payload compounds include compounds of Formulae I, II, III, IV, V, VI, VII, VIII IX, X, XI, and XII above, and their residues following bonding or incorporation with linker L are linker-payloads. The linker-payloads can be further bonded to binding agents such as antibodies or antigen binding fragments thereof to form antibody-drug conjugates. Those of skill in the art will recognize that certain functional groups of payload moieties are convenient for linking to linkers and/or binding agents. For example, in certain embodiments, the linker is absent and payloads are directly bonded to binding agents. In one embodiment, payloads include terminal alkynes and binding agents include azides, where each alkyne and azide participate in regioisomeric click chemistry to bind payload residues directly to binding agent residues. In another embodiment, payloads include carboxylic acids and binding agents include lysines, where each carboxylic acid and lysine participate in amide bond formation to bind payload residues directly to binding agent residues. Payload functional groups further include amines (e.g., Formulae C, D, LPc, and LPd), quaternary ammonium ions (e.g., Formulae A and LPa), hydroxyls (e.g., Formulae C, D, LPc, and LPd), phosphates, carboxylic acids (e.g., in the form of esters upon linking to L, as in Formulae B, D, LPb, and LPd), hydrazides (e.g., Formulae B and LPb), amides (e.g., derived from anilines of Formula C and LPc, or amines of Formulae D and LPd), and sugars.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, β-glucuronide linkages, and disulfide linkages. In some embodiments, the linker comprises a cathepsin-cleavable linker. In some embodiments, the linker comprises a β-glucuronidase (GUSB)-cleavable linker (see, e.g., GUSB linkers from Creative Biolabs, creative-biolabs.com/adc/beta-glucuronide-linker.htm, or *ACS Med. Chem. Lett.* 2010, 1: 277-280).

In some embodiments, the linker comprises a non-cleavable moiety. In some embodiments, the non-cleavable linker is derived from

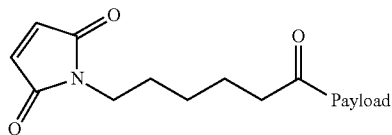

or a residue thereof. In some embodiments, the non-cleavable linker-payload residue is

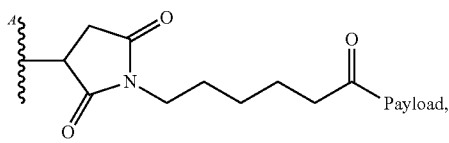

or a regioisomer thereof. In some embodiments, the non-cleavable linker is derived from

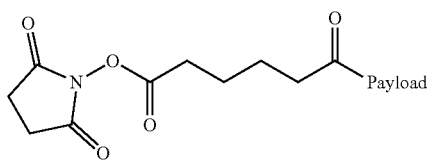

or a residue thereof. In some embodiments, the non-cleavable linker-payload residue is

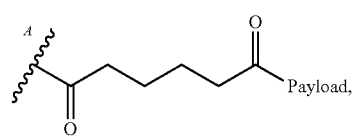

or a regioisomer thereof. In one embodiment, the linker is maleimide cyclohexane carboxylate or 4-(N-maleimidomethyl)cyclohexanecarboxylic acid (MCC). In the structures,

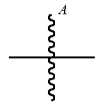

indicates a bond to a binding agent. In the structures, in some examples,

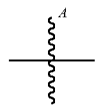

indicates a click chemistry residue which results from the reaction of, for example, a binding agent having an azide or alkyne functionality and a linker-payload having a complementary alkyne or azide functionality. In the structures, in other examples,

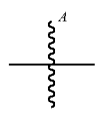

indicates a divalent sulfide which results from the reaction of, for example, one or more binding agent cysteines with one or more linkers or linker-payloads having maleimide functionality via Michael addition reactions. In the structures, in other examples,

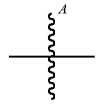

indicates an amide bond which results from the reaction of, for example, one or more binding agent lysines with one or more linkers or linker-payloads having activated or unactivated carboxyl functionality, as would be appreciated by a person of skill in the art. In one embodiment,

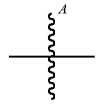

indicates an amide bond which results from the reaction of, for example, one or more binding agent lysines with one or more linkers or linker-payloads having activated carboxyl functionality, as would be appreciated by a person of skill in the art.

In some embodiments, suitable linkers include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L- or D-α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or any combination thereof (e.g., dipeptides, tripeptides, oligopeptides, polypeptides, and the like). In certain embodiments, one or more side chains of the amino acids are linked to a side chain group, described below. In some embodiments, the linker is a peptide comprising or consisting of the amino acids valine and citrulline (e.g., divalent -Val-Cit- or divalent -VCit-). In some embodiments, the linker is a peptide comprising or consisting of the amino acids alanine and alanine, or divalent -AA-. In some embodiments, the linker is a peptide comprising or consisting of the amino acids glutamic acid and alanine, or -EA-. In some embodiments, the linker is a peptide comprising or consisting of the amino acids glutamic acid and glycine, or -EG-. In some embodiments, the linker is a peptide comprising or consisting of the amino acids glycine and glycine, or -GG-. In some embodiments, the linker is a peptide comprising or consisting of the amino acids glutamine, valine, and citrulline, or -Q-V-Cit- or -QVCit-. In some embodiments, the linker is a peptide comprising or consisting of the amino acids glutamic acid, valine, and citrulline, or -E-V-Cit- or -EVCit-. In some embodiments, the linker is a peptide comprising or consisting of the amino acids -GGGGS-. In some embodiments, the linker is a peptide comprising or consisting of the amino acids -GGGGG-. In some embodiments, the linker is a peptide comprising or consisting of the amino acids -GGGGK-. In some embodiments, the linker is a peptide comprising or consisting of the amino acids -GFGG-. In some embodiments, the linker is a peptide comprising or consisting of the amino acids lysine, valine, and citrulline, or -KVCit-. In some embodiments, the linker is a peptide comprising or consisting of the amino acids -KVA-. In some embodiments, the linker is a peptide comprising or consisting of the amino acids -VA-. In any of the embodiments in this paragraph, and throughout this disclosure, the standard three-letter or one-letter amino acid designations are used, as would be appreciated by a person of skill in the art. Exemplary single-letter amino acid designations include, G for glycine, K for lysine, S for serine, V for valine, A for alanine, and F for phenylalanine.

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker is:

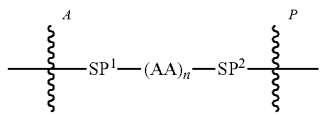

wherein:
SP$^1$ is a spacer;
SP$^2$ is a spacer;

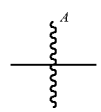

is one or more bonds to the binding agent;

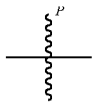

is one or more bonds to the payload;
each AA is an amino acid residue; and
n is an integer from 1 to 10.

The SP$^1$ spacer is a moiety that connects the (AA)$_n$ moiety or residue to the binding agent (BA) or to a reactive group residue which is bonded to BA. Suitable SP$^1$ spacers include, but are not limited to, those comprising alkylene or polyether, or both. The ends of the spacers, for example, the portion of the spacer bonded to the BA or an AA, can be moieties derived from reactive moieties that are used for purposes of coupling the antibody or an AA to the spacer during chemical synthesis of the conjugate. In certain embodiments, n is 1, 2, 3, or 4. In particular embodiments, n is 2. In particular embodiments, n is 3. In particular embodiments, n is 4.

In some embodiments, the SP$^1$ spacer comprises an alkylene. In some embodiments, the SP$^1$ spacer comprises a C$_{57}$ alkylene. In some embodiments, the SP$^1$ spacer comprises a polyether. In some embodiments, the SP$^1$ spacer comprises a polymer of ethylene oxide such as polyethylene glycol.

In some embodiments, the SP$^1$ spacer is:

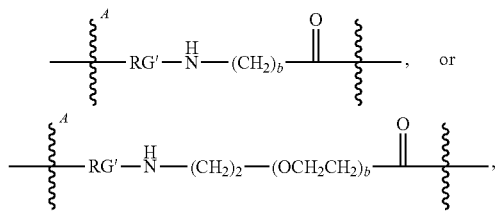

wherein:
RG' is a reactive group residue following reaction of a reactive group RG with a binding agent;

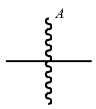

is a bond to the binding agent;

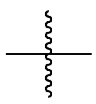

is a bond to (AA)$_n$ where n is an integer from 1 to 10; and
b is an integer from 2 to 8.

The reactive group RG can be any reactive group known to those of skill in the art to be capable of forming one or more bonds to the binding agent. The reactive group RG is a moiety comprising a portion in its structure that is capable of reacting with the binding agent (e.g., reacting with an antibody at its cysteine or lysine residues, or at an azide moiety, for example, a PEG-N$_3$ functionalized antibody at one or more glutamine residues) to form a compound of Formula A, A', B, B', C, C', D, or D'. Following conjugation to the binding agent, the reactive group becomes the reactive group residue (RG'). Illustrative reactive groups include, but are not limited to, those that comprise haloacetyl, isothiocyanate, succinimide, N-hydroxysuccinimide, or maleimide portions that are capable of reacting with the binding agent.

In certain embodiments, reactive groups include, but are not limited to, alkynes. In certain embodiments, the alkynes are alkynes capable of undergoing 1,3-cycloaddition reactions with azides in the absence of copper catalysts, such as strained alkynes. Strained alkynes are suitable for strain-promoted alkyne-azide cycloadditions (SPAAC), and include cycloalkynes, for example, cyclooctynes and benzannulated alkynes. Suitable alkynes include, but are not limited to, dibenzoazacyclooctyne or

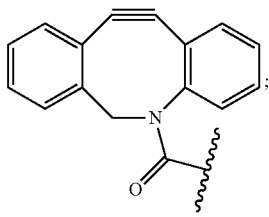

(DIBAC)

dibenzocyclooctyne or

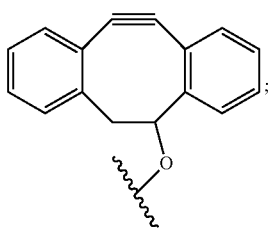

(DIBO)

biarylazacyclooctynone or

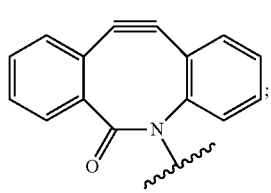

(BARAC)

difluorinated cyclooctyne or

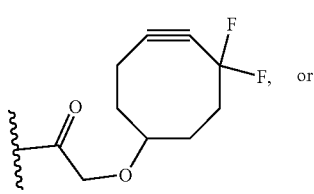

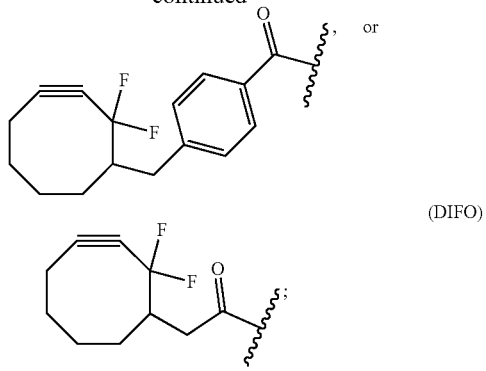

(DIFO)

substituted, for example, fluorinated alkynes, aza-cycloalkynes, bicycle[6.1.0]nonyne or

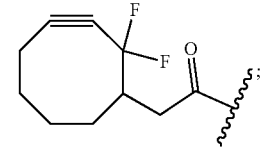

(BCN)

and derivatives thereof. Particularly useful alkynes include

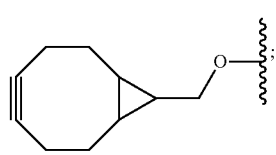

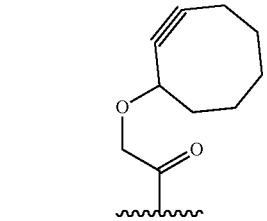

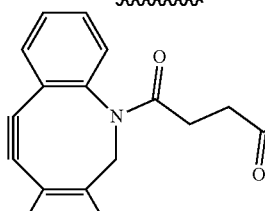

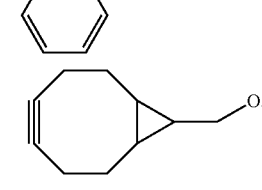

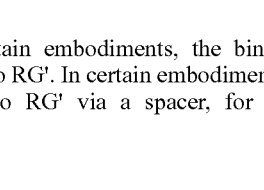

In certain embodiments, the binding agent is bonded directly to RG'. In certain embodiments, the binding agent is bonded to RG' via a spacer, for instance SP$^4$, located between

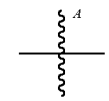

and RG'. In particular embodiments, the binding agent is bonded indirectly to RG' via SP$^4$, for example, a PEG spacer. As discussed in detail below, in certain embodiments, the binding agent is prepared by functionalizing with one or more azido groups. Each azido group is capable of reacting with RG to form RG'. In particular embodiments, the binding agent is derivatized with -PEG-N$_3$ linked to a glutamine residue. Exemplary —N$_3$ derivatized binding agents, methods for their preparation, and methods for their use in reacting with RG are provided herein. In certain embodiments, RG is an alkyne suitable for participation in 1,3-cycloadditions, and RG' is a regioisomeric 1,2,3-triazolyl moiety formed from the reaction of RG with an azido-functionalized binding agent. By way of further example, in certain embodiments, RG' is linked to the binding agent as shown in

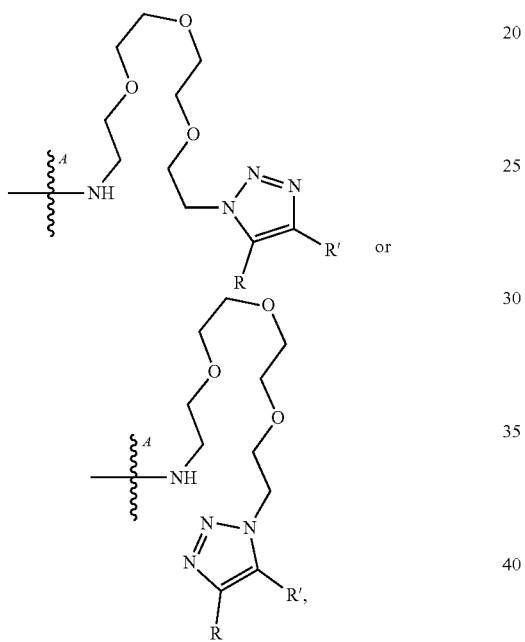

or a mixture of each regioisomer. Each R and R' is as described or exemplified herein.

The SP$^2$ spacer, when present, is a moiety that connects the (AA)$_n$ moiety to the payload. Suitable spacers include, but are not limited to, those described above as SP' spacers. Further suitable SP$^2$ spacers include, but are not limited to, those comprising alkylene or polyether, or both. The ends of the SP$^2$ spacers, for example, the portion of the spacer directly bonded to the payload or an AA, can be moieties derived from reactive moieties that are used for purposes of coupling the payload or AA to the SP$^2$ spacer during the chemical synthesis of the conjugate. In some examples, the ends of the SP$^2$ spacers, for example, the portion of the SP$^2$ spacer directly bonded to the payload or an AA, can be residues of reactive moieties that are used for purposes of coupling the payload or an AA to the spacer during the chemical synthesis of the conjugate.

In some embodiments, the SP$^2$ spacer, when present, is selected from the group consisting of —NH-(p-C$_6$H$_4$)—CH$_2$—, —NH-(p-C$_6$H$_4$)—CH$_2$OC(O)—, an amino acid, a dipeptide, a tripeptide, an oligopeptide, —O—, —N(H)—,

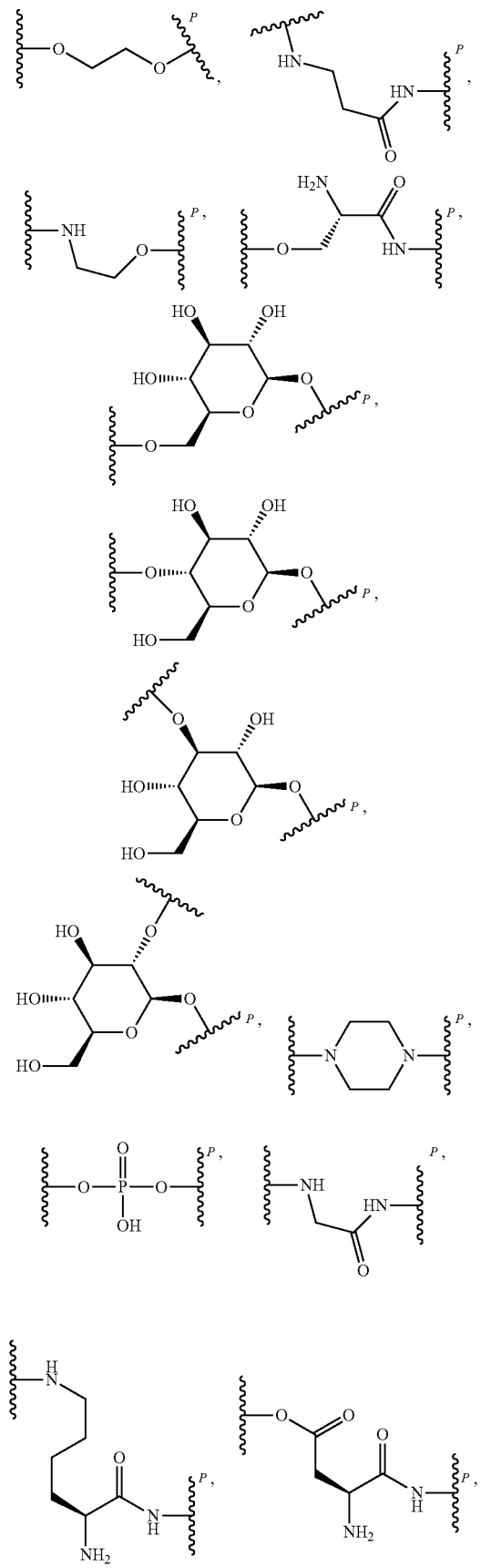

123

-continued

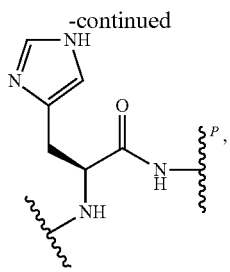

and any combinations thereof. In certain embodiments, each

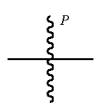

is a bond to the payload, and each

is a bond to $(AA)_n$.

In the above formulas, each $(AA)_n$ is an amino acid or, optionally, a p-aminobenzyloxycarbonyl residue (PABC),

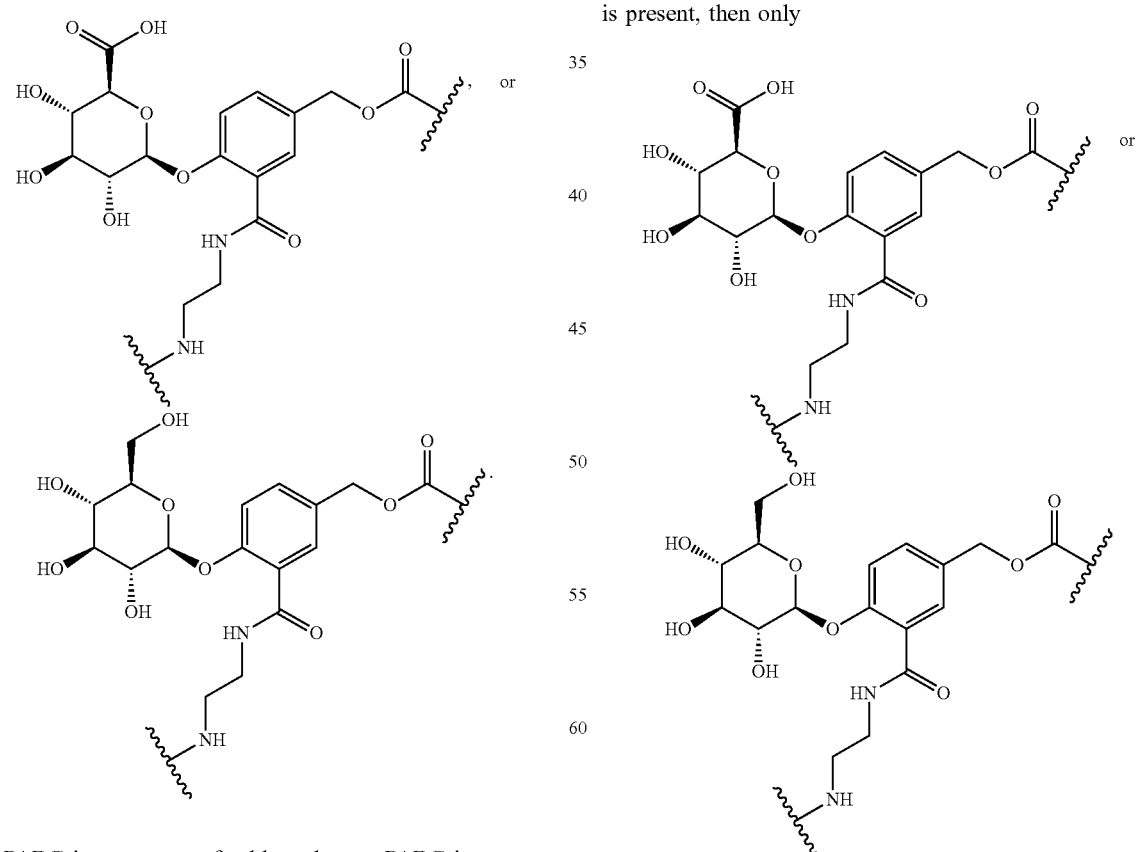

124

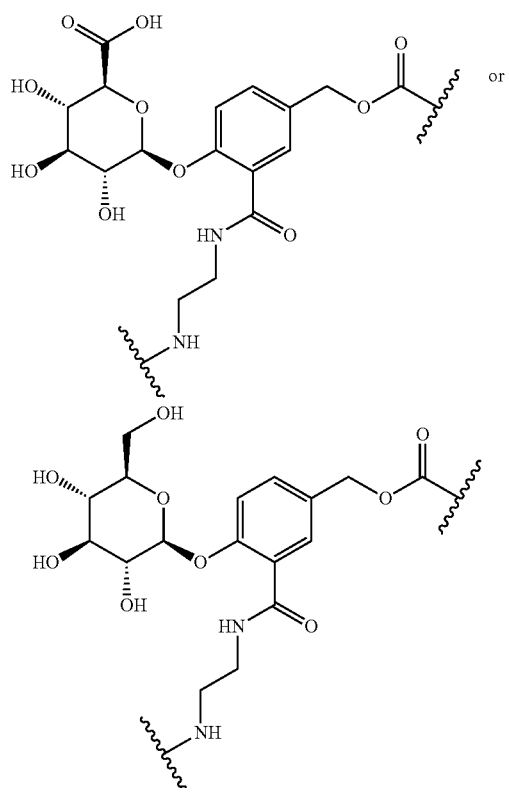

is present, then only

If PABC is present, preferably only one PABC is present. Preferably, the PABC residue, if present, is bonded to a terminal AA in the $(AA)_n$ group, proximal to the payload. If is present. Preferably, the

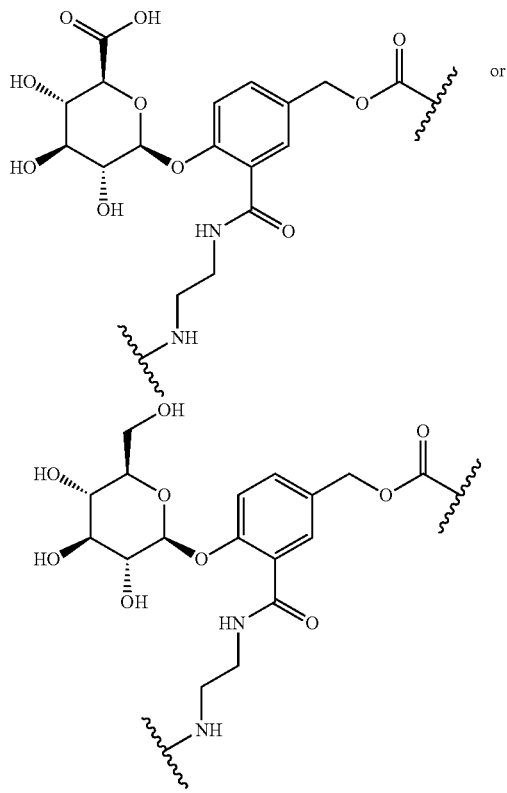

residue, if present, is bonded to the payload via the benzyloxycarbonyl moiety, and no AA is present. Suitable amino acids for each AA include natural, non-natural, standard, non-standard, proteinogenic, non-proteinogenic, and L- or D-ax-amino acids. In some embodiments, the AA comprises alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or any combinations thereof (e.g., dipeptides, tripeptides, and oligopeptides, and the like). In certain embodiments, one or more side chains of the amino acids is linked to a side chain group, described below. In some embodiments, n is two. In some embodiments, the $(AA)_n$ is valine-citrulline. In some embodiments, $(AA)_n$ is citrulline-valine. In some embodiments, $(AA)_n$ is valine-alanine. In some embodiments, $(AA)_n$ is alanine-valine. In some embodiments, $(AA)_n$ is valine-glycine. In some embodiments, $(AA)_n$ is glycine-valine. In some embodiments, n is three. In some embodiments, the $(AA)_n$ is valine-citrulline-PABC. In some embodiments, $(AA)_n$ is citrulline-valine-PABC. In some embodiments, $(AA)_n$ is glutamate-valine-citrulline. In some embodiments, $(AA)_n$ is glutamine-valine-citrulline. In some embodiments, $(AA)_n$ is lysine-valine-alanine. In some embodiments, $(AA)_n$ is lysine-valine-citrulline. In some embodiments, n is four. In some embodiments, $(AA)_n$ is glutamate-valine-citrulline-PAB. In some embodiments, $(AA)_n$ is glutamine-valine-citrulline-PABC. Those of skill will recognize PABC as a residue of p-aminobenzyloxycarbonyl with the following structure:

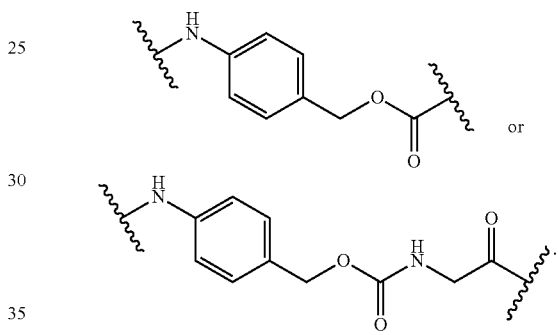

The PABC residue has been shown to facilitate cleavage of certain linkers in vitro and in vivo. Those of skill will recognize PAB as a divalent residue of p-aminobenzyl or $-NH-(p-C_6H_4)-CH_2-$.

In some embodiments, the linker is:

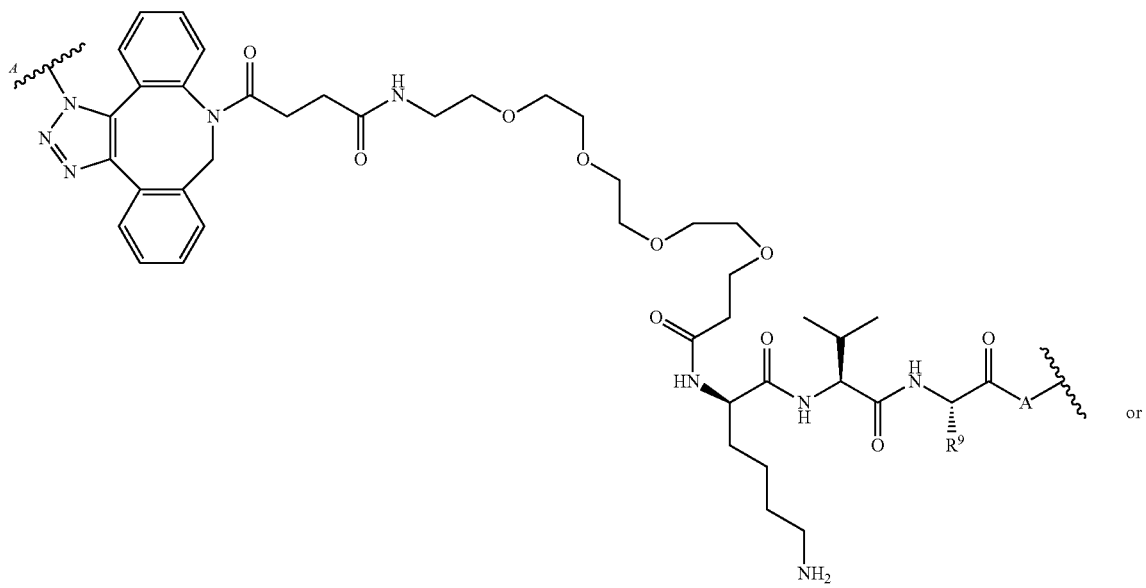

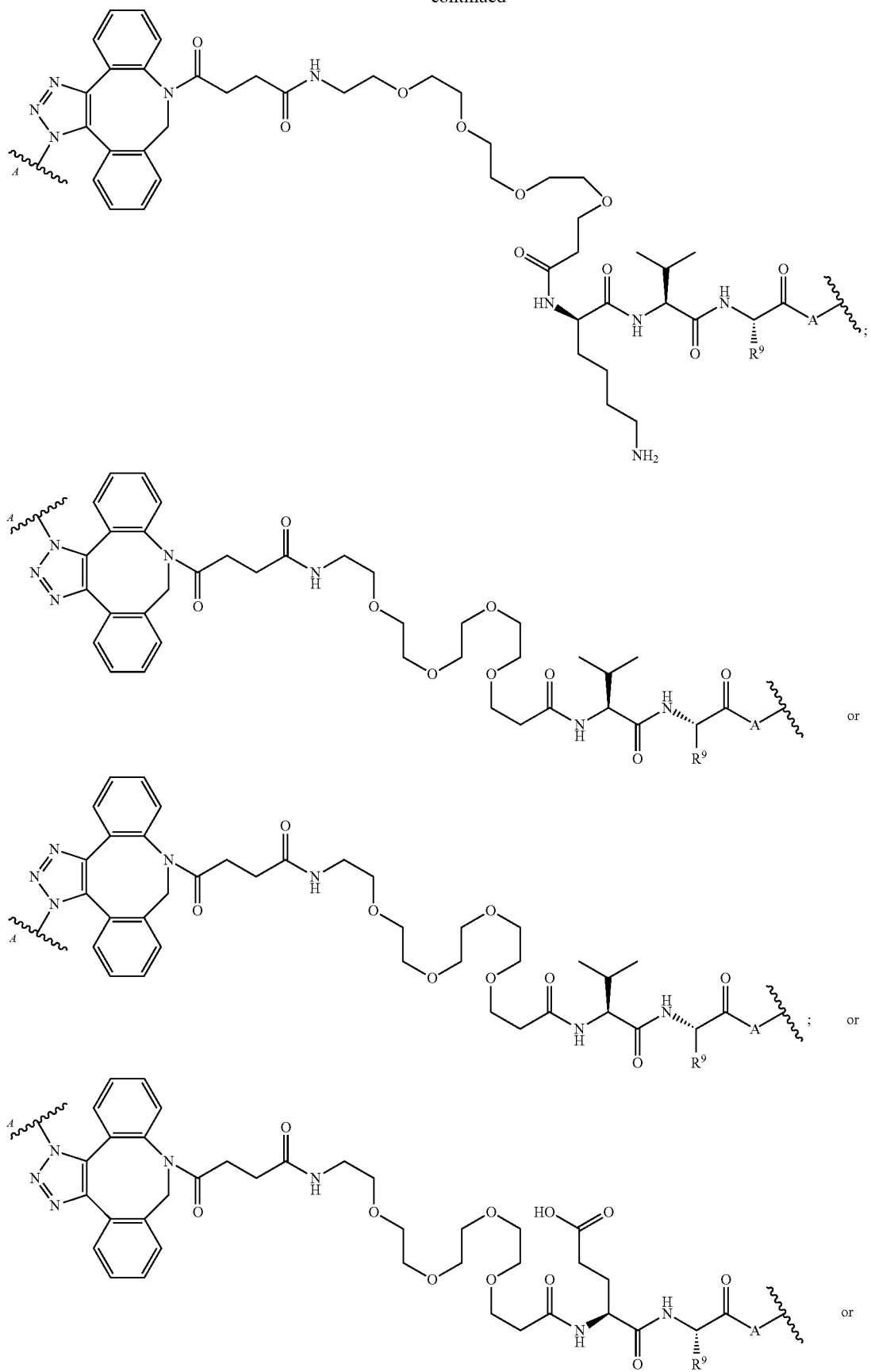

-continued

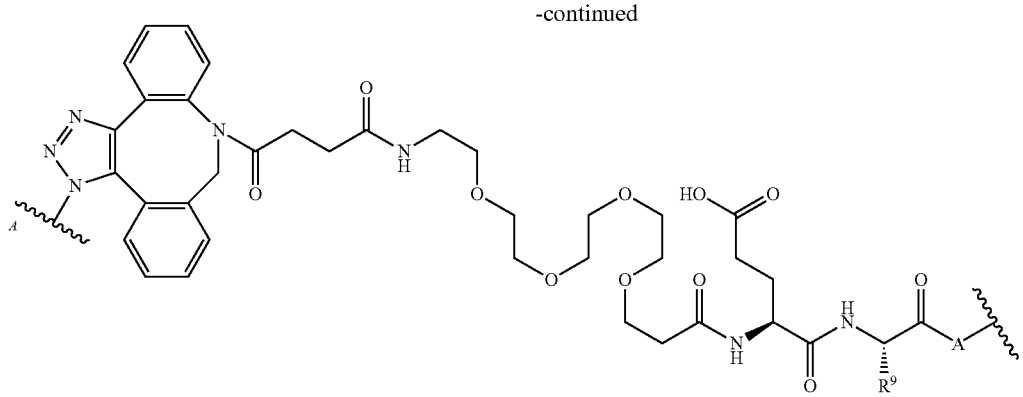

wherein:
each

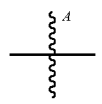

is a bond to the binding agent;
each

is a bond to the payload;
each $R^9$ is —CH$_3$ or —(CH$_2$)$_3$N(H)C(O)NH$_2$; and
each A is —O—, —NH—,

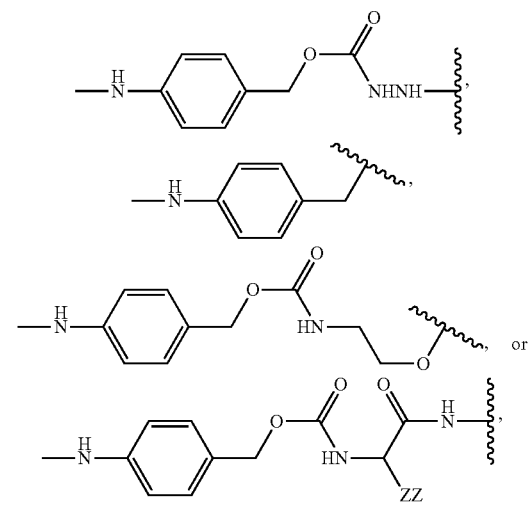

where ZZ is hydrogen, or a side chain for an amino acid as discussed elsewhere herein. By way of further example, in one embodiment, ZZ is C$_{1-6}$ alkyl. By way of further example, in one embodiment, ZZ is C$_{1-6}$ heteroalkyl. In particular embodiments of this paragraph, A may be derived from a primary amine compound or a residue thereof where X is —N$_3$, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

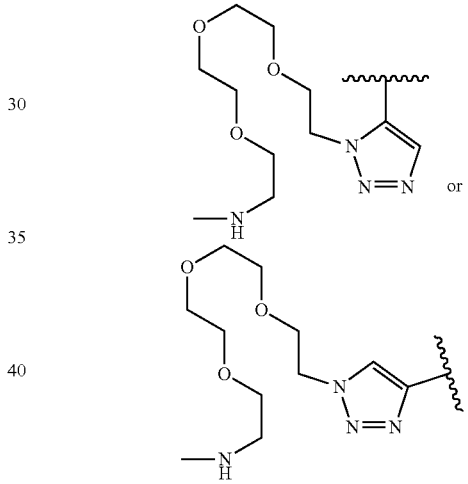

or a mixture thereof. Alternatively, in another embodiment, A is

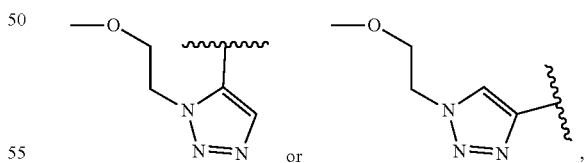

or a mixture thereof. In another embodiment, A is

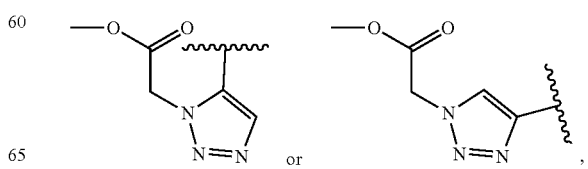

131
or a mixture thereof. In another embodiment, A is
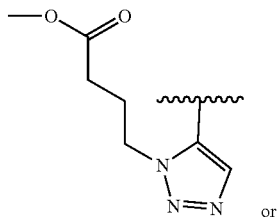
or
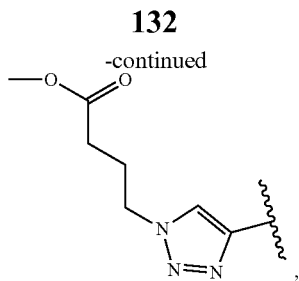
or a mixture thereof. As discussed above, the bond to the binding agent can be direct, or via a spacer. In certain embodiments, the bond to the binding agent is via a PEG spacer to a glutamine residue of the binding agent.
In some embodiments, the linker is:
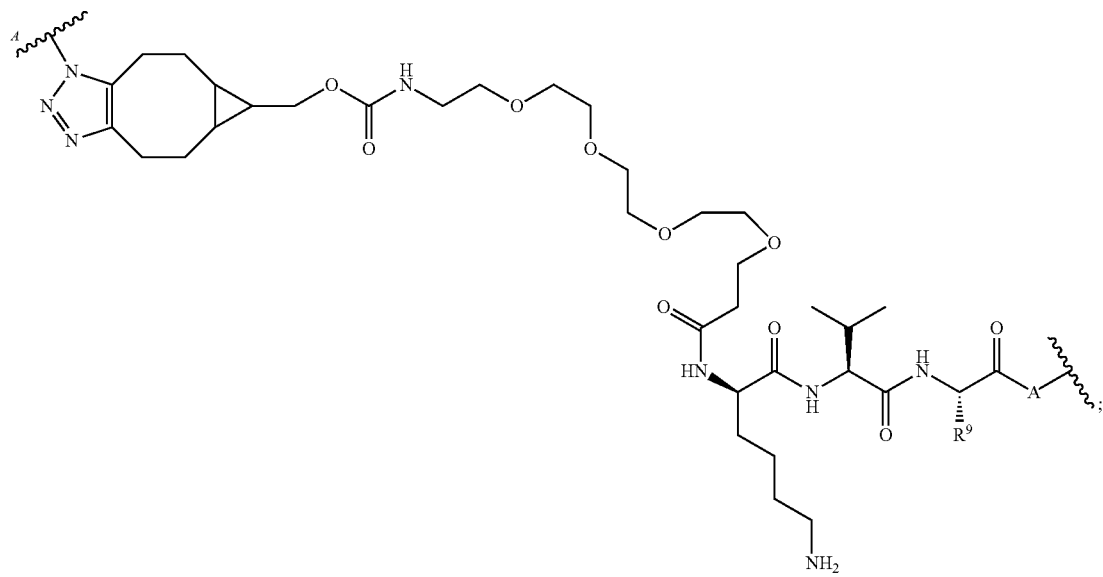
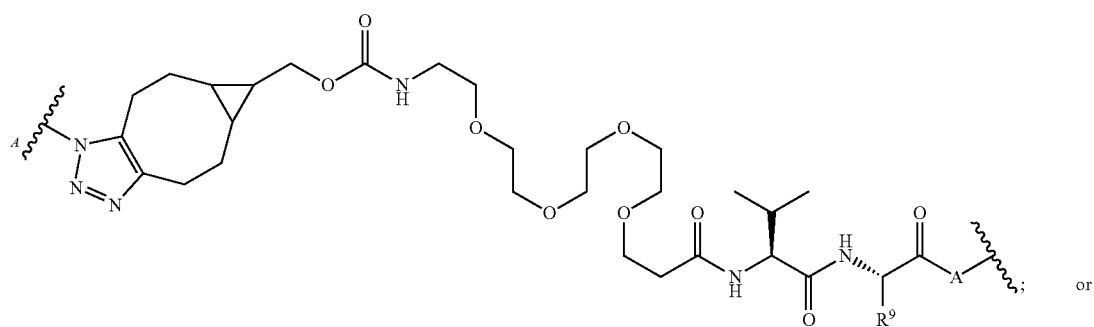
or

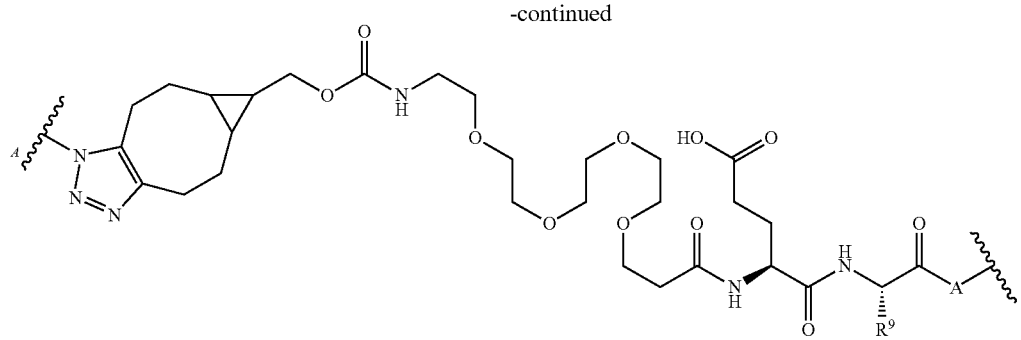

wherein:

each

is a bond to the binding agent;
each

is a bond to the payload;
each $R^9$ is —CH$_3$ or —(CH$_2$)$_3$N(H)C(O)NH$_2$; and
each A is —O—, —N(H)—,

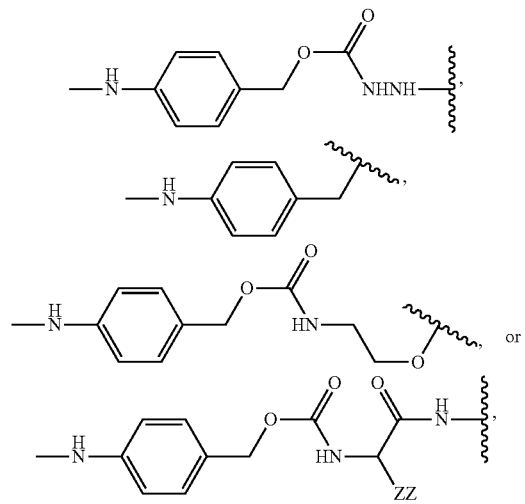

where ZZ is hydrogen, or a side chain for an amino acid as discussed elsewhere herein. For example, in one embodiment, ZZ is C$_{1-6}$ alkyl. By way of further example, in one embodiment, ZZ is C$_{1-6}$ heteroalkyl. In particular embodiments of this paragraph, A may be derived from a primary amine compound or a residue thereof where X is —N$_3$, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

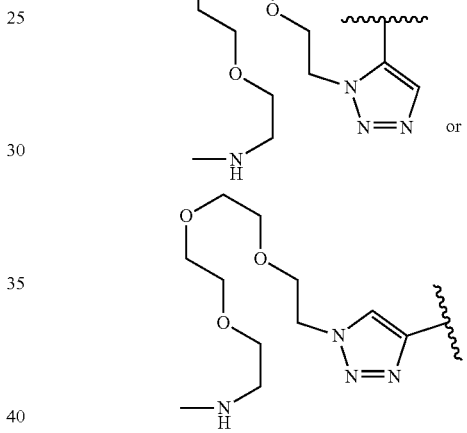

or a mixture thereof. Alternatively, in another embodiment, A is

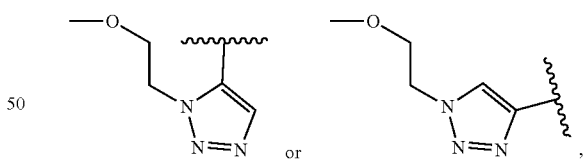

or a mixture thereof. In another embodiment, A is

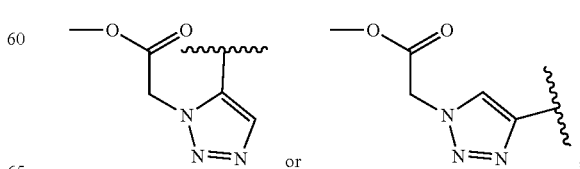

or a mixture thereof. In another embodiment, A is

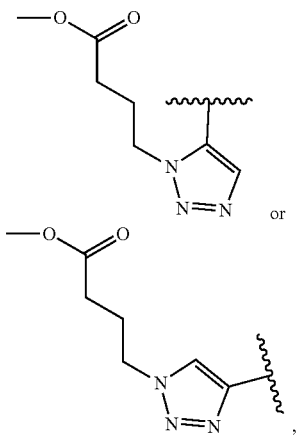

or a mixture thereof. As discussed above, the bond to the binding agent can be direct, or via a spacer. In certain embodiments, the bond to the binding agent is via a PEG spacer to a glutamine residue of the binding agent.

In any of the above embodiments, the $(AA)_n$ group can be modified with one or more enhancement groups. Advantageously, the enhancement group can be linked to the side chain of any amino acid in $(AA)_n$. Useful amino acids for linking enhancement groups include lysine, asparagine, aspartate, glutamine, glutamate, and citrulline. The link to the enhancement group can be a direct bond to the amino acid side chain, or the link can be indirect via a spacer and/or reactive group. Useful spacers and reactive groups include any described above. The enhancement group can be any group deemed useful by those of skill in the art. For example, the enhancement group can be any group that imparts a beneficial effect to the compound, payload, linker payload, or antibody conjugate including, but not limited to, biological, biochemical, synthetic, solubilizing, imaging, detecting, and reactivity effects, and the like. In certain embodiments, the enhancement group is a hydrophilic group. In certain embodiments, the enhancement group is a cyclodextrin. In certain embodiments, the enhancement group is an alkyl, heteroalkyl, alkylenyl, heteroalkylenyl sulfonic acid, heteroalkylenyl taurine, heteroalkylenyl phosphoric acid or phosphate, heteroalkylenyl amine (e.g., quaternary amine), or heteroalkylenyl sugar. In certain embodiments, sugars include, without limitation, monosaccharides, disaccharides, and polysaccharides. Exemplary monosaccharides include glucose, ribose, deoxyribose, xylose, arabinose, mannose, galactose, fructose, and the like. In certain embodiments, sugars include sugar acids such as glucuronic acid, further including conjugated forms such as glucuronides (i.e., via glucuronidation). Exemplary disaccharides include maltose, sucrose, lactose, lactulose, trehalose, and the like. Exemplary polysaccharides include amylose, amylopectin, glycogen, inulin, cellulose, and the like. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the enhancement group is capable of improving solubility of the remainder of the conjugate. In certain embodiments, the alkyl, heteroalkyl, alkylenyl, or heteroalkylenyl sulfonic acid is substituted or non-substituted. In certain embodiments, the alkyl, heteroalkyl, alkylenyl, or heteroalkylenyl sulfonic acid is $-(CH_2)_{1-5}SO_3H$, $-(CH_2)_n-NH-(CH_2)_{1-5}SO_3H$, $-(CH_2)_n-C(O)NH-(CH_2)_{1-5}SO_3H$, $-(CH_2CH_2O)_m-C(O)NH-(CH_2)_{1-5}SO_3H$, $-(CH_2)_n-N((CH_2)_{1-5}C(O)NH(CH_2)_{1-5}SO_3H)_2$, $-(CH_2)_n-C(O)N((CH_2)_{1-5}C(O)NH(CH_2)_{1-5}SO_3H)_2$, or $-(CH_2CH_2O)_m-C(O)N((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl or alkylenyl sulfonic acid is $-(CH_2)_{1-5}SO_3H$. In another embodiment, the heteroalkyl or heteroalkylenyl sulfonic acid is $-(CH_2)_n-NH-(CH_2)_{1-5}SO_3H$, wherein n is 1, 2, 3, 4, or 5. In another embodiment, the alkyl, heteroalkyl, alkylenyl, or heteroalkylenyl sulfonic acid is $-(CH_2)_n-C(O)NH-(CH_2)_{1-5}SO_3H$, wherein n is 1, 2, 3, 4, or 5. In another embodiment, the alkyl, heteroalkyl, alkylenyl, or heteroalkylenyl sulfonic acid is $-(CH_2CH_2O)_m-C(O)NH-(CH_2)_{1-5}SO_3H$, wherein m is 1, 2, 3, 4, or 5. In another embodiment, the alkyl, heteroalkyl, alkylenyl, or heteroalkylenyl sulfonic acid is $-(CH_2)_n-N((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is $-(CH_2)_n-C(O)N((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is $-(CH_2CH_2O)_m-C(O)N((CH_2)_{1-5}C(O)NH(CH_2)_{1-5}SO_3H)_2$, wherein m is 1, 2, 3, 4, or 5. In some embodiments, the linker is:

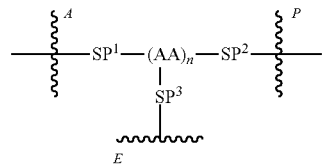

wherein:
SP$^1$ is a spacer;
SP$^2$ is a spacer;
SP$^3$ is a spacer, linked to one AA of $(AA)_n$;

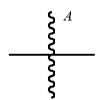

is one or more bonds to the binding agent;

is one or more bonds to the payload;

is one or more bonds to the enhancement group EG;
each AA is an amino acid; and
n is an integer from 1 to 10.

As discussed above, the bond to the binding agent can be direct, or via a spacer. In certain embodiments, the bond to the binding agent is via a PEG spacer to a glutamine residue of the binding agent.

The $SP^1$ spacer group is as described above. The $SP^2$ spacer group is as described above. Each $(AA)_n$ group is as described above.

The $SP^3$ spacer is a moiety that connects the $(AA)_n$ moiety to the enhancement group (EG). Suitable $SP^3$ spacers include, but are not limited to, those comprising alkylene or polyether, or both. The ends of the $SP^3$ spacers, i.e., the portion of the $SP^3$ spacer directly bonded to the enhancement group or an AA, can be moieties derived from reactive moieties that are used for purposes of coupling the enhancement group or an AA to the $SP^3$ spacer during the chemical synthesis of the conjugate. In some examples, the ends of the $SP^3$ spacers, i.e., the portion of the spacer directly bonded to the enhancement group or an AA, can be residues of reactive moieties that are used for purposes of coupling the enhancement group or an AA to the spacer during the chemical synthesis of the conjugate. In certain embodiments, $SP^3$ is a spacer, linked to one and only one AA of $(AA)_n$. In certain embodiments, the $SP^3$ spacer is linked to the side chain of a lysine residue of $(AA)_n$.

In some embodiments, the $SP^3$ spacer is:

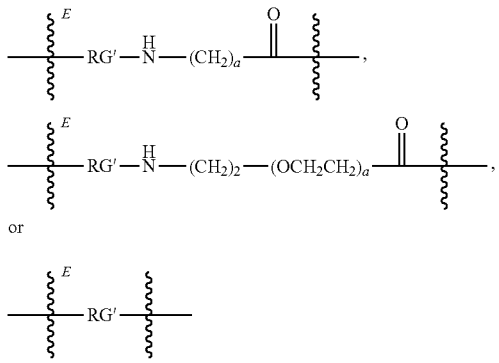

wherein:
RG' is a reactive group residue following reaction of a reactive group RG with an enhancement agent EG;

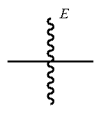

is a bond to the enhancement agent;

is a bond to $(AA)_n$;
a is an integer from 2 to 8; and
n is an integer from 1 to 4.

The reactive group RG can be any reactive group known to those of skill in the art to be capable of forming one or more bonds to the enhancement agent. The reactive group RG is a moiety comprising a portion in its structure that is capable of reacting with the enhancement group to form a compound of Formula LPa, LPb, LPc, LPd, LPa', LPb', LPc', LPd', A, B, C, D, A', B', C', D', or A". Following conjugation to the enhancement group, the reactive group becomes the reactive group residue (RG'). The reactive group RG can be any reactive group described above. Illustrative reactive groups include, but are not limited to, those that comprise haloacetyl, isothiocyanate, succinimide, N-hydroxysuccinimide, or maleimide portions that are capable of reacting with the binding agent.

In certain embodiments, reactive groups include, but are not limited to, alkynes. In certain embodiments, the alkynes are alkynes capable of undergoing 1,3-cycloaddition reactions with azides in the absence of copper catalysts such as strained alkynes. Strained alkynes are suitable for strain-promoted alkyne-azide cycloadditions (SPAAC), cycloalkynes, e.g., cyclooctynes, and benzannulated alkynes. Suitable alkynes include, but are not limited to, dibenzoazacyclooctyne or

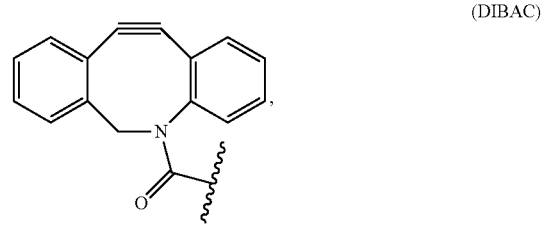 [SMILES: *C(=O)N1Cc2ccccc2C#Cc2ccccc21]

(DIBAC)

dibenzocyclooctyne or

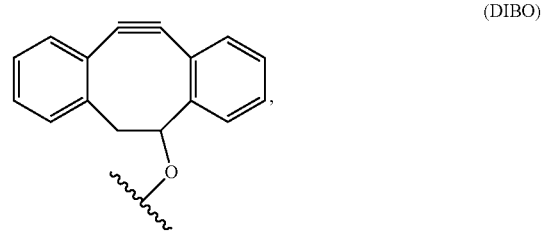 [SMILES: *OC1Cc2ccccc2C#Cc2ccccc21]

(DIBO)

biarylazacyclooctynone or

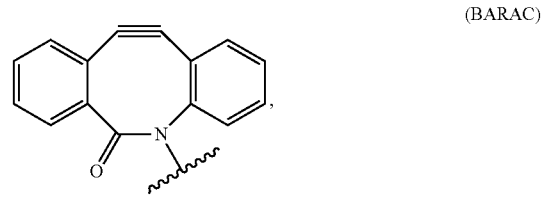 [SMILES: *N1C(=O)c2ccccc2C#Cc2ccccc21]

(BARAC)

difluorinated cyclooctyne or

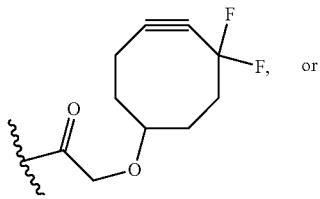 (DIFO)

or

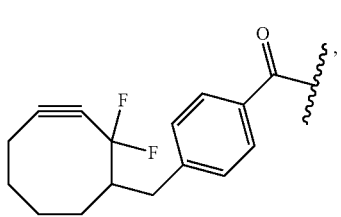

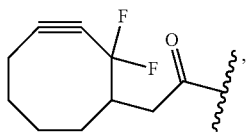

substituted, e.g., fluorinated alkynes, aza-cycloalkynes, bicycle[6.1.0]nonyne or

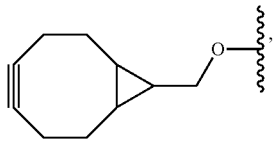 (BCN)

and derivatives thereof. Particularly useful alkynes include

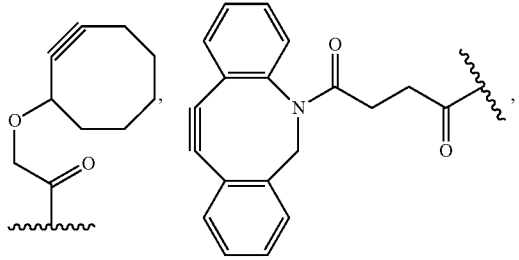

and

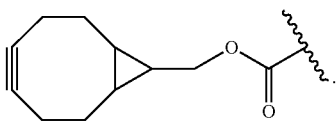

In some embodiments, the linker is:

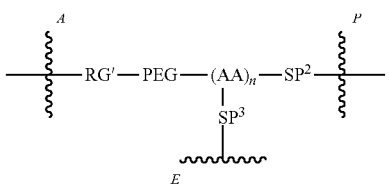

wherein:

RG' is a reactive group residue following reaction of a reactive group RG with a binding agent;

PEG is —NH-PEG4-C(O)—;

$SP^2$ is a spacer;

$SP^3$ is a spacer, linked to one AA residue of $(AA)_n$;

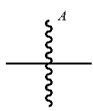

is one or more bonds to the binding agent;

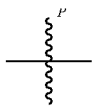

is one or more bonds to the payload;

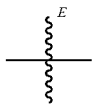

is one or more bonds to the enhancement group EG;

each AA is an amino acid residue; and n is an integer from 1 to 10.

As discussed above, the bond to the binding agent can be direct, or via a spacer. In certain embodiments, the bond to the binding agent is via a PEG spacer to a glutamine residue of the binding agent.

In certain embodiments, the linker is:

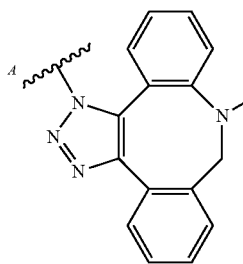
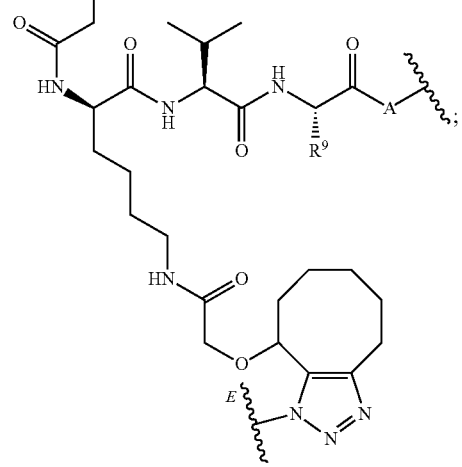

or a pharmaceutically acceptable salt, solvate, or stereoisomeric form thereof, or a regioisomer thereof, or a mixture of regioisomers thereof, wherein:
each

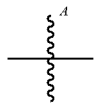

is a bond to the binding agent;
each

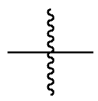

is a bond to the payload;
each

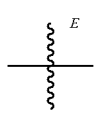

is a bond to the enhancement agent;
each $R^9$ is —CH$_3$ or —(CH$_2$)$_3$N(H)C(O)NH$_2$; and
each A is —O—, —N(H)—,

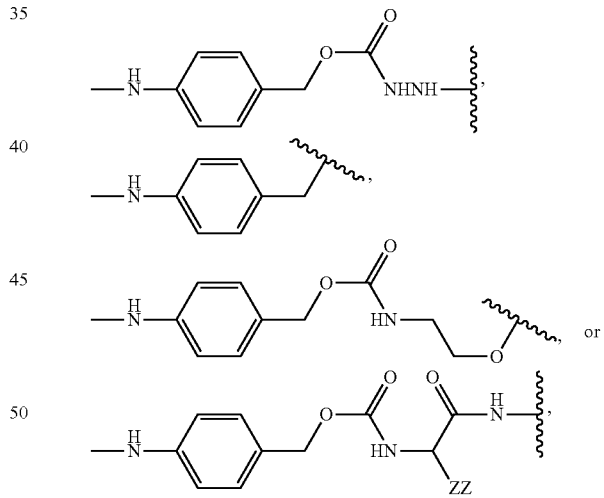

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In particular embodiments of this paragraph, A may be derived from a primary amine compound or a residue thereof where X is —N$_3$, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

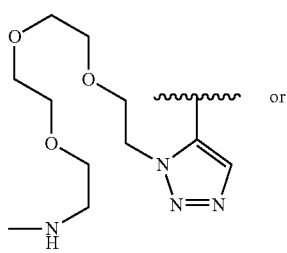 or

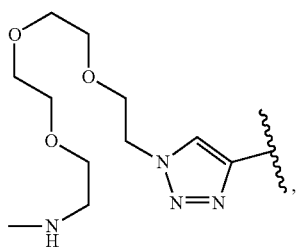

or a mixture thereof. Alternatively, in another embodiment, A is

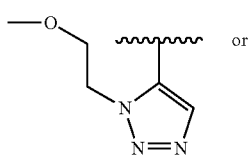 or

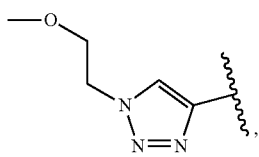, or a mixture thereof. In another embodiment, A is

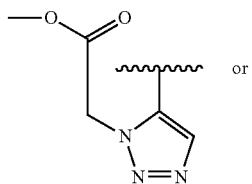 or

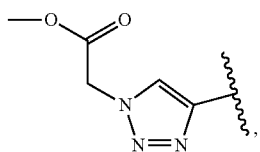, or a mixture thereof. In another embodiment, A is

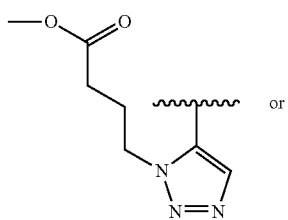 or

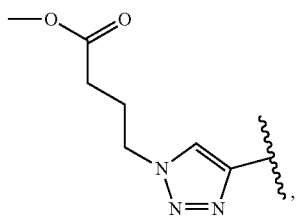, or a mixture thereof. In certain embodiments, 1,3-cycloaddition or SPAAC regioisomers, or mixture of regioisomers, are derived from PEG-$N_3$ derivitized antibodies treated with suitable alkynes. For example, in one embodiment, the linker is:

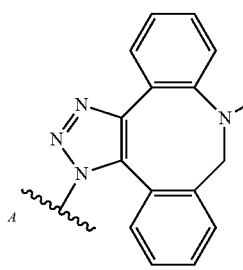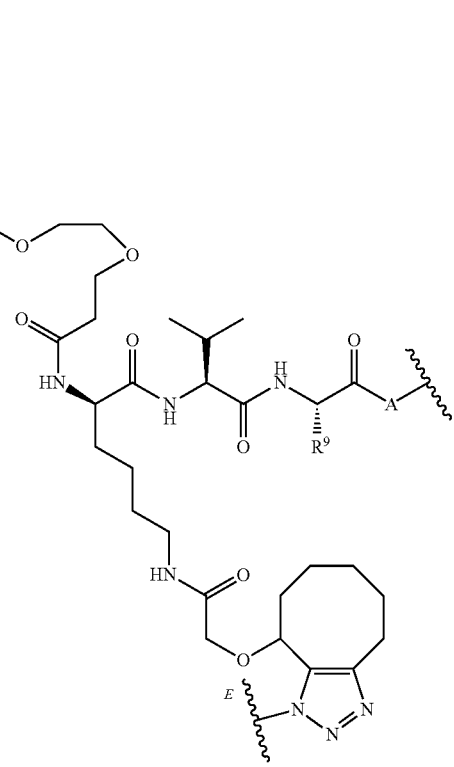
or a pharmaceutically acceptable salt, solvate, or stereoisomeric form thereof, or a regioisomer thereof, or a mixture of regioisomers thereof. By way of further example, in one embodiment, the linker is:
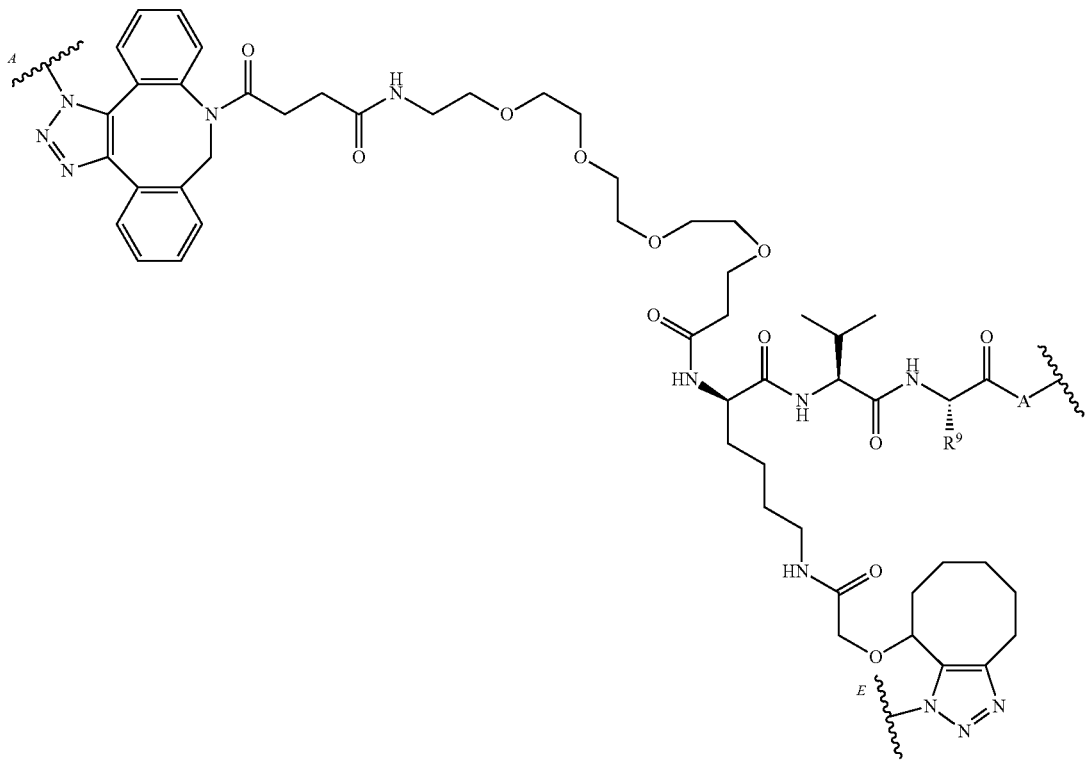

or a pharmaceutically acceptable salt, solvate, or stereoisomeric form thereof, or a regioisomer thereof, or a mixture of regioisomers thereof. By way of further example, the linker is:

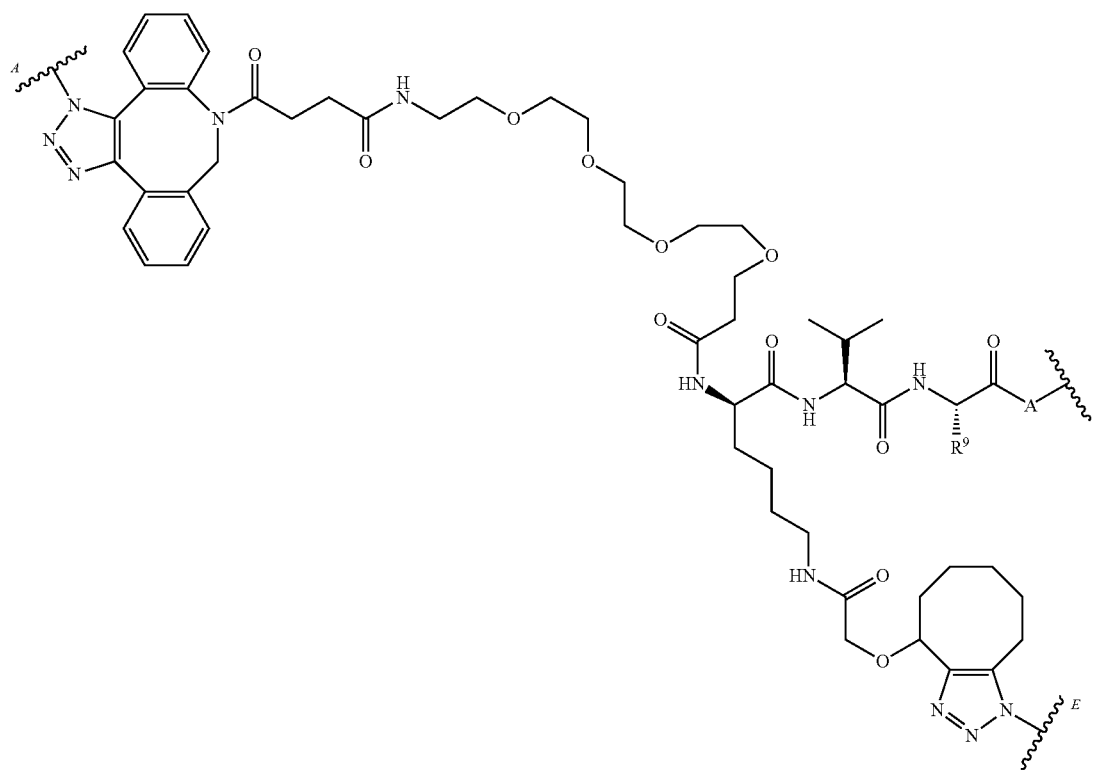

or a pharmaceutically acceptable salt, solvate, or stereoisomeric form thereof, or a regioisomer thereof, or a mixture of regioisomers thereof. By way of further example, in one embodiment, the linker is:

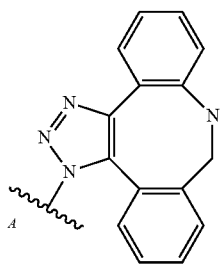
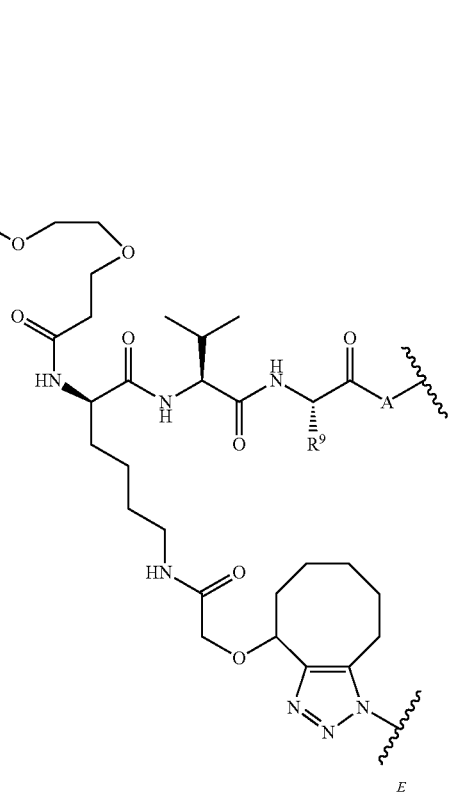

or a pharmaceutically acceptable salt, solvate, or stereoisomeric form thereof, or a regioisomer thereof, or a mixture of regioisomers thereof. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, heteroalkylenyl sulfonic acid, heteroalkylenyl taurine, heteroalkylenyl phosphoric acid or phosphate, heteroalkylenyl amine (e.g., quaternary amine), or heteroalkylenyl sugar. In certain embodiments, sugars include, without limitation, monosaccharides, disaccharides, and polysaccharides. Exemplary monosaccharides include glucose, ribose, deoxyribose, xylose, arabinose, mannose, galactose, fructose, and the like. In certain embodiments, sugars include sugar acids such as glucuronic acid, further including conjugated forms such as glucuronides (i.e., via glucuronidation). Exemplary disaccharides include maltose, sucrose, lactose, lactulose, trehalose, and the like. Exemplary polysaccharides include amylose, amylopectin, glycogen, inulin, cellulose, and the like. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_n$—NH—$(CH_2)_{1-5}SO_3H$, —$(CH_2)_n$—C(O)NH—$(CH_2)_{1-5}SO_3H$, —$(CH_2CH_2O)_m$—C(O)NH—$(CH_2)_{1-5}SO_3H$, —$(CH_2)_n$—N(($CH_2)_{1-5}$C(O)NH($CH_2)_{1-5}SO_3H)_2$, —$(CH_2)_n$—C(O)N(($CH_2)_{1-5}$C(O)NH($CH_2)_{1-5}SO_3H)_2$, or —$(CH_2CH_2O)_m$—C(O)N(($CH_2)_{1-5}$C(O)NH($CH_2)_{1-5}SO_3H)_2$, wherein n is 1, 2, 3, 4, or 5, and m is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_n$—NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2)_n$—C(O)NH—$(CH_2)_{1-5}SO_3H$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)NH—$(CH_2)_{1-5}SO_3H$, wherein m is 1, 2, 3, 4, or 5. In another embodiment, the alkyl, heteroalkyl, alkylenyl, or heteroalkylenyl sulfonic acid is —$(CH_2)_n$—N(($CH_2)_{1-5}$C(O)NH($CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2)_n$—C(O)N(($CH_2)_{1-5}$C(O)NH($CH_2)_{1-5}SO_3H)_2$, wherein n is 1, 2, 3, 4, or 5. In another embodiment, the alkyl, heteroalkyl, alkylenyl, or heteroalkylenyl sulfonic acid is —$(CH_2CH_2O)_m$—C(O)N(($CH_2)_{1-5}$C(O)NH($CH_2)_{1-5}SO_3H)_2$, wherein m is 1, 2, 3, 4, or 5.

In some embodiments, the linker is:

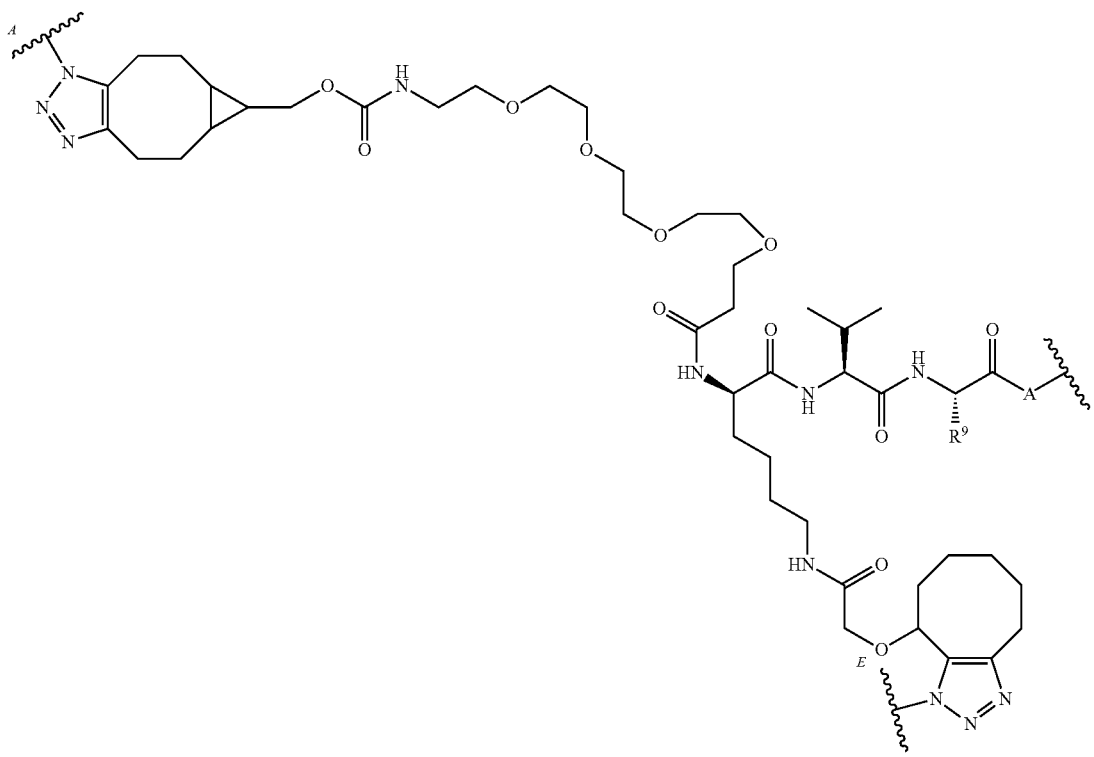

or a pharmaceutically acceptable salt, solvate, or stereoisomeric form thereof, or a regioisomer thereof, or mixture of regioisomers thereof, wherein:

each

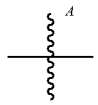

is a bond to the binding agent;
each

is a bond to the enhancement agent;
each

is a bond to the payload;
each $R^9$ is —CH$_3$ or —(CH$_2$)$_3$N(H)C(O)NH$_2$; and
each A is —O—, —N(H)—,

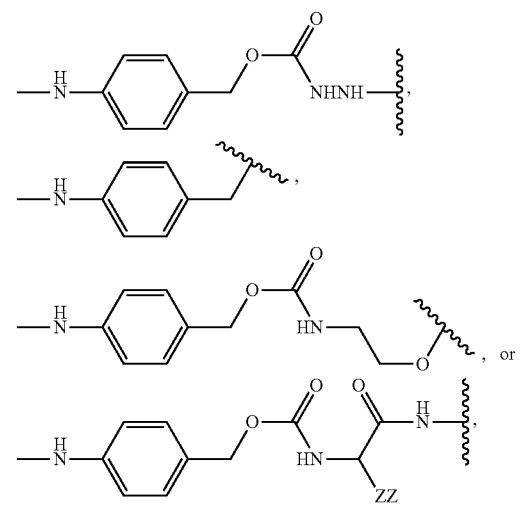

where ZZ is hydrogen, or a side chain for an amino acid as discussed elsewhere herein. For example, in one embodiment, ZZ is C$_{1-6}$ alkyl. By way of further example, in one embodiment, ZZ is C$_{1-6}$ heteroalkyl. In particular embodiments of this paragraph, A may be derived from a primary amine compound or a residue thereof where X is —N$_3$, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

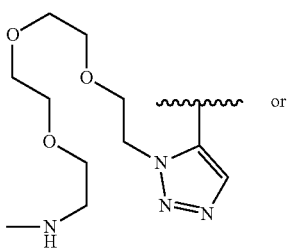

or

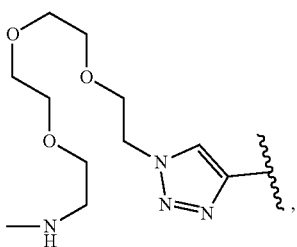

or a mixture thereof. Alternatively, in another embodiment, A is

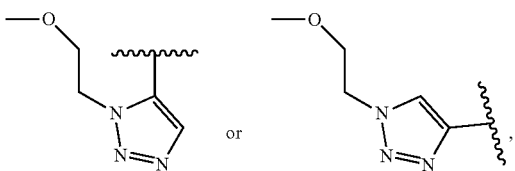

or a mixture thereof. In another embodiment, A is

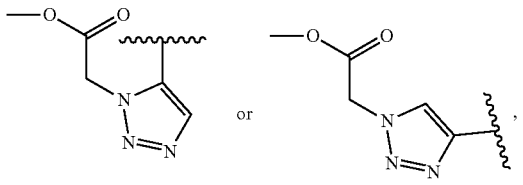 [SMILES: *c1cnnn1CC(=O)OC ; *c1cn(CC(=O)OC)nn1]

or a mixture thereof. In another embodiment, A is

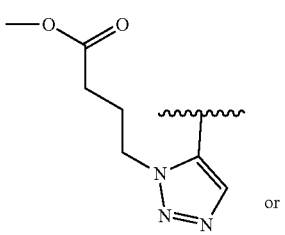

or

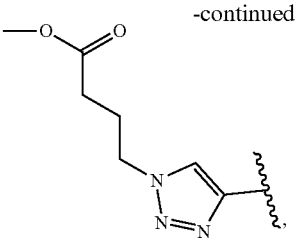

or a mixture thereof. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, heteroalkylenyl sulfonic acid, heteroalkylenyl taurine, heteroalkylenyl phosphoric acid or phosphate, heteroalkylenyl amine (e.g., quaternary amine), or heteroalkylenyl sugar. In certain embodiments, sugars include, without limitation, monosaccharides, disaccharides, and polysaccharides. Exemplary monosaccharides include glucose, ribose, deoxyribose, xylose, arabinose, mannose, galactose, fructose, and the like. In certain embodiments, sugars include sugar acids such as glucuronic acid, further including conjugated forms such as glucuronides (i.e., via glucuronidation). Exemplary disaccharides include maltose, sucrose, lactose, lactulose, trehalose, and the like. Exemplary polysaccharides include amylose, amylopectin, glycogen, inulin, cellulose, and the like. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is $-(CH_2)_{1-5}SO_3H$, $-(CH_2)_n-NH-(CH_2)_{1-5}SO_3H$, $-(CH_2)_n-C(O)NH-(CH_2)_{1-5}SO_3H$, $-(CH_2CH_2O)_m-C(O)NH-(CH_2)_{1-5}SO_3H$, $-(CH_2)_n-N((CH_2)_{1-5}C(O)NH(CH_2)_{1-5}SO_3H)_2$, $-(CH_2)_n-C(O)N((CH_2)_{1-5}C(O)NH(CH_2)_{1-5}SO_3H)_2$, or $-(CH_2CH_2O)_m-C(O)N((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl or alkylenyl sulfonic acid is $-(CH_2)_{1-5}SO_3H$. In another embodiment, the heteroalkyl or heteroalkylenyl sulfonic acid is $-(CH_2)_n-NH-(CH_2)_{1-5}SO_3H$, wherein n is 1, 2, 3, 4, or 5. In another embodiment, the alkyl, heteroalkyl, alkylenyl, or heteroalkylenyl sulfonic acid is $-(CH_2)_n-C(O)NH-(CH_2)_{1-5}SO_3H$, wherein n is 1, 2, 3, 4, or 5. In another embodiment, the alkyl, heteroalkyl, alkylenyl, or heteroalkylenyl sulfonic acid is $-(CH_2CH_2O)_m-C(O)NH-(CH_2)_{1-5}SO_3H$, wherein m is 1, 2, 3, 4, or 5. In another embodiment, the alkyl, heteroalkyl, alkylenyl, or heteroalkylenyl sulfonic acid is $-(CH_2)_n-N((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is $-(CH_2)_n-C(O)N((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is $-(CH_2CH_2O)_m-C(O)N((CH_2)_{1-5}C(O)NH(CH_2)_{1-5}SO_3H)_2$, wherein m is 1, 2, 3, 4, or 5.

In some embodiments, the linker is:
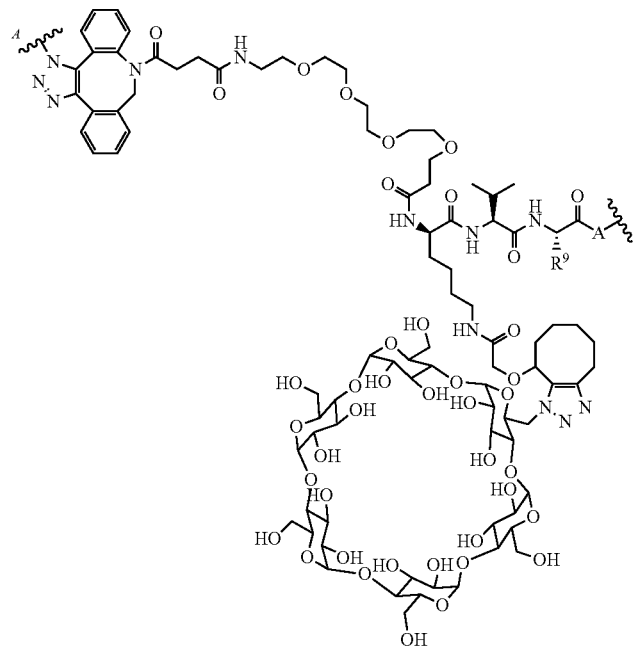
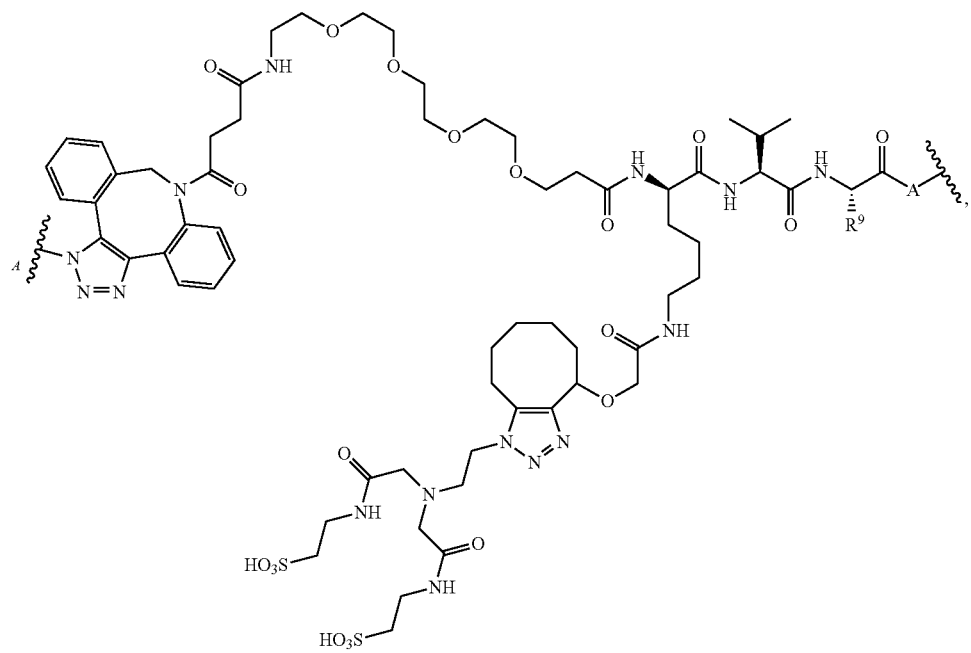

-continued

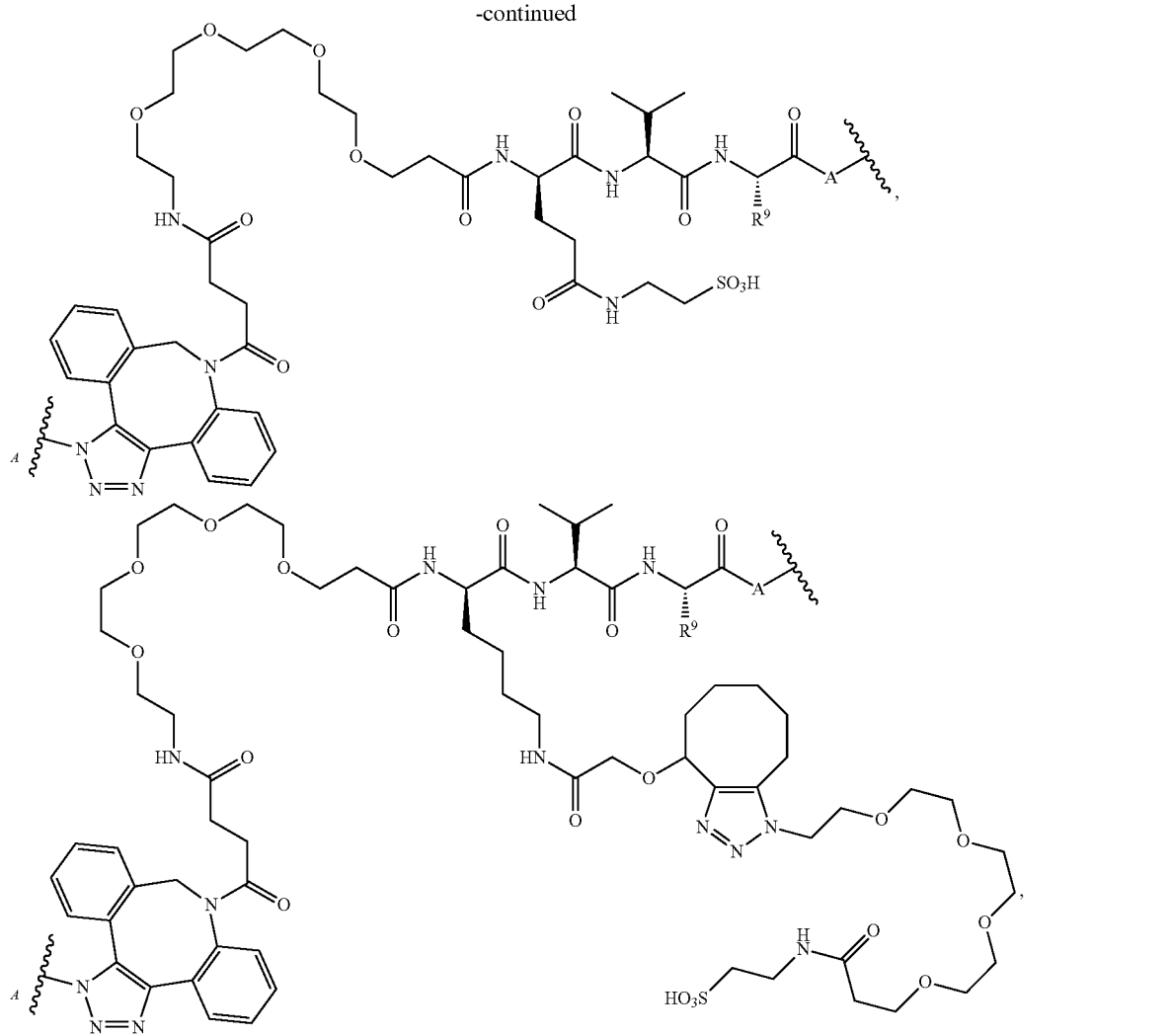

or a pharmaceutically acceptable salt, solvate, or stereoisomeric form thereof, or a regioisomer thereof, or mixture of regioisomers thereof, wherein:

each

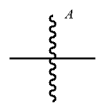

is a bond to the binding agent;
each

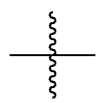

is a bond to the payload;
$R^9$ is —CH$_3$ or —(CH$_2$)$_3$N(H)C(O)NH$_2$; and
A is —O—, —N(H)—,

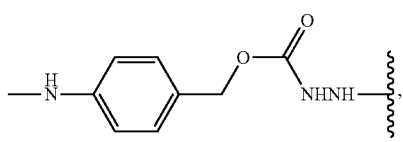

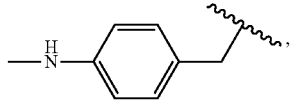

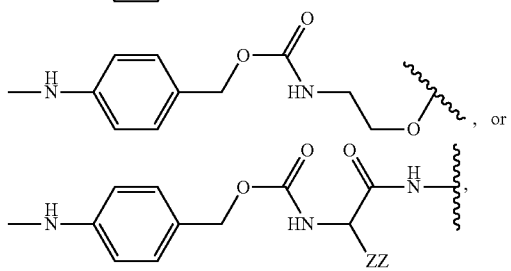

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In particular embodiments of this paragraph, A may be derived from a primary amine compound or a residue thereof where X is —N$_3$, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

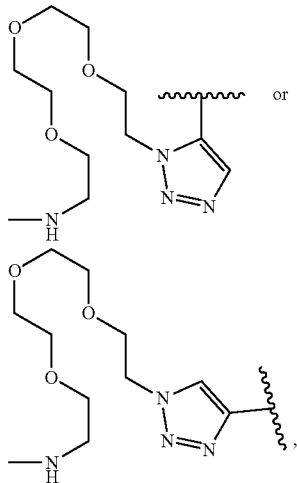

or a mixture thereof. Alternatively, in another embodiment, A is

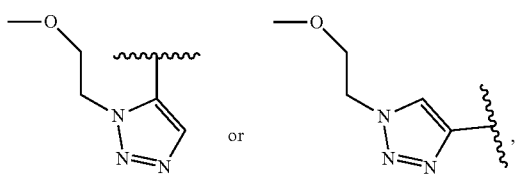

or a mixture thereof. In another embodiment, A is

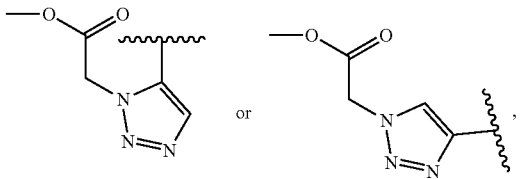 [SMILES: *c1cnnn1CC(=O)OC ; *c1cn(CC(=O)OC)nn1]

or a mixture thereof. In another embodiment, A is

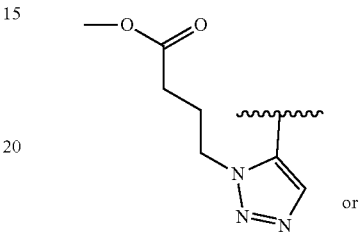

or

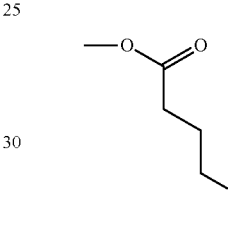

or a mixture thereof. As discussed above, the bond to the binding agent can be direct, or via a spacer. In certain embodiments, the bond to the binding agent is via a PEG spacer to a glutamine residue of the binding agent.

In some embodiments, the linker is:

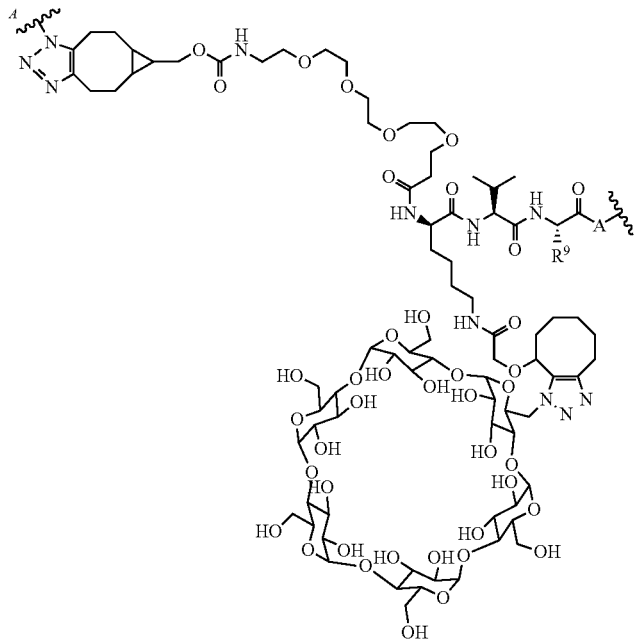

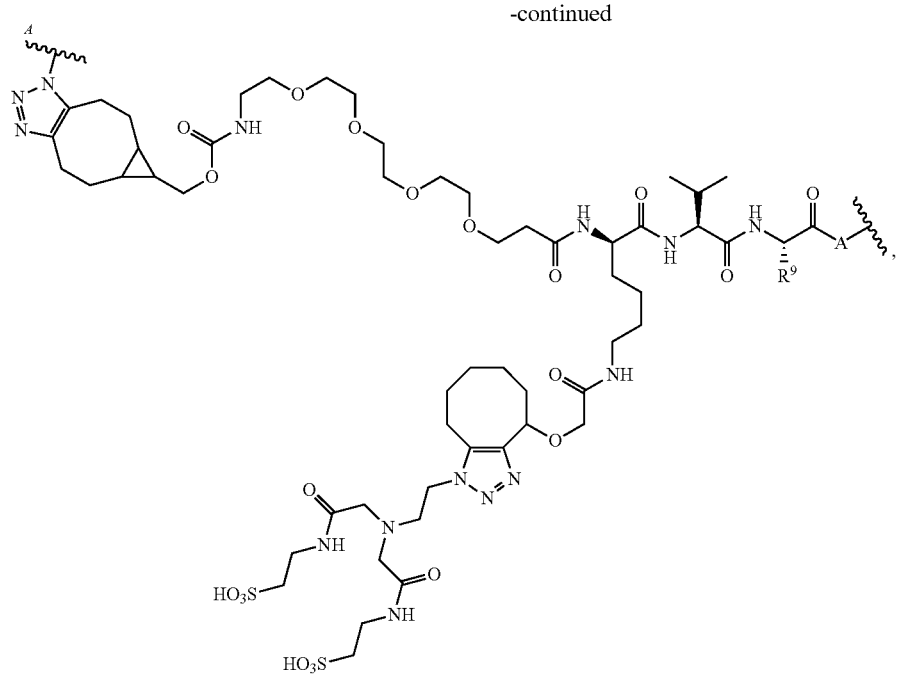
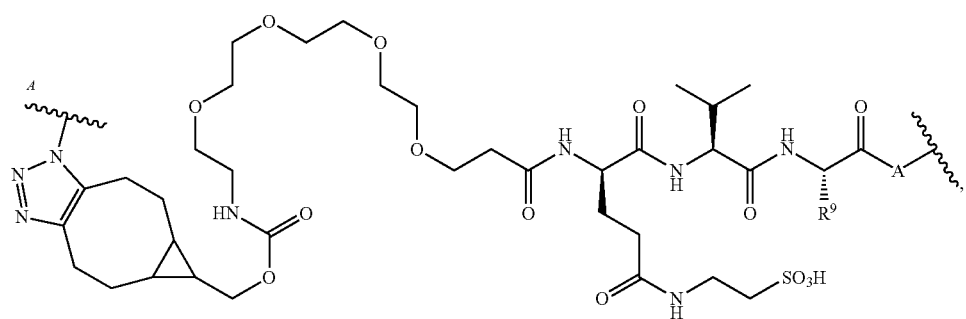
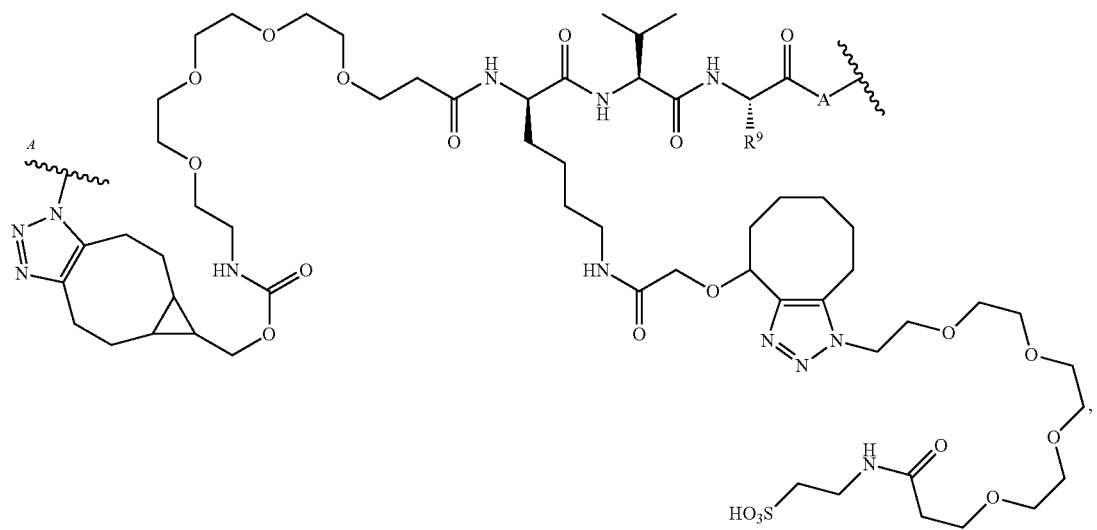

or a pharmaceutically acceptable salt, solvate, or stereoisomeric form thereof, or a regioisomer thereof, or mixture of regioisomers thereof, wherein:

each

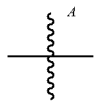

is a bond to the binding agent;
each

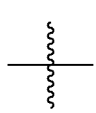

H is a bond to the payload;
R⁹ is —CH₃ or —(CH₂)₃N(H)C(O)NH₂; and
A is —O—, —N(H)—,

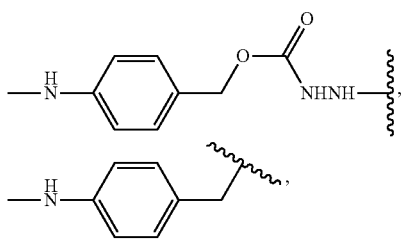

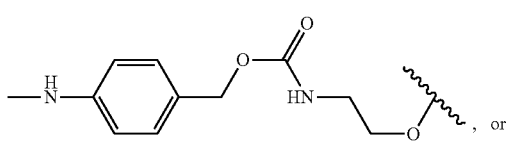

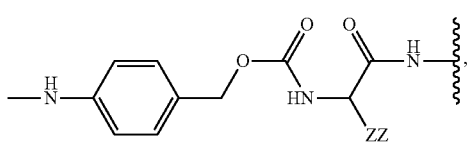

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In particular embodiments of this paragraph, A may be derived from a primary amine compound or a residue thereof where X is —N₃, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

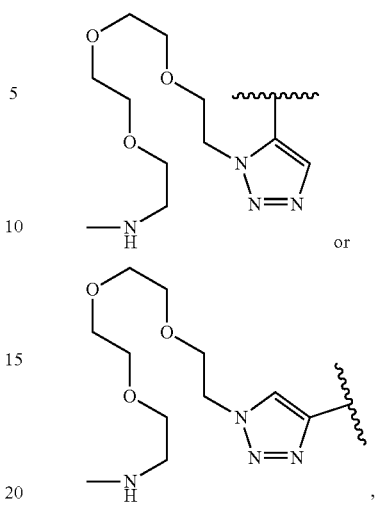

or a mixture thereof. Alternatively, in another embodiment, A is

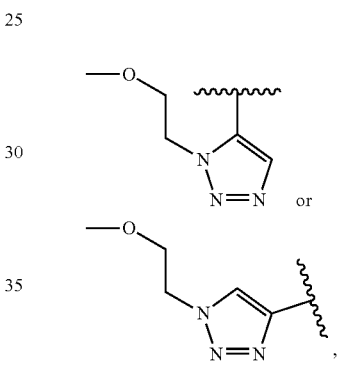

or a mixture thereof. In another embodiment, A is

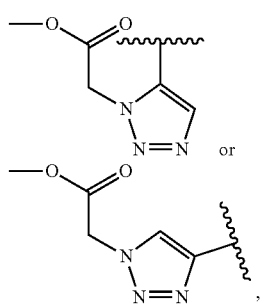

or a mixture thereof. In another embodiment, A is

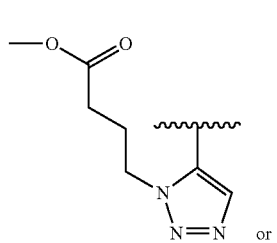

or

-continued

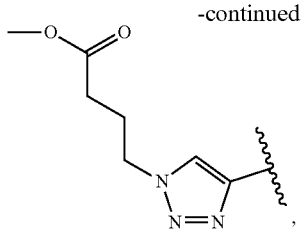

or a mixture thereof. As discussed above, the bond to the binding agent can be direct, or via a spacer. In certain embodiments, the bond to the binding agent is via a PEG spacer to a glutamine residue of the binding agent.

In some embodiments, the linker is:

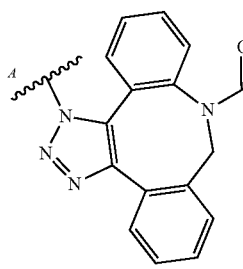

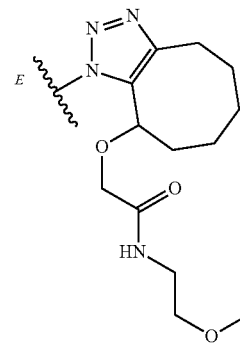

or a pharmaceutically acceptable salt, solvate, or stereoisomeric form thereof, or a regioisomer thereof, or mixture of regioisomers thereof, wherein:

each

is a bond to the binding agent;

each

is a bond to the payload;

each

is a bond to the enhancement group;

each $R^9$ is —$CH_3$ or —$(CH_2)_3N(H)C(O)NH_2$; and each A is —O—, —N(H)—,

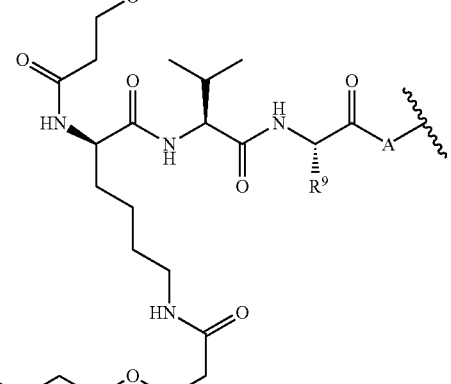

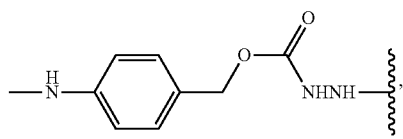

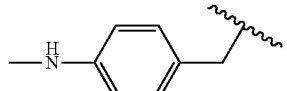

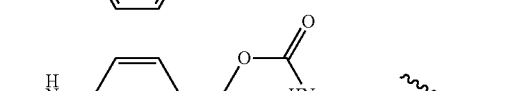

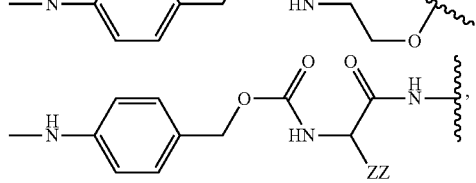

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In particular embodiments of this paragraph, A may be derived from a primary amine compound or a residue thereof where X is $-N_3$, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

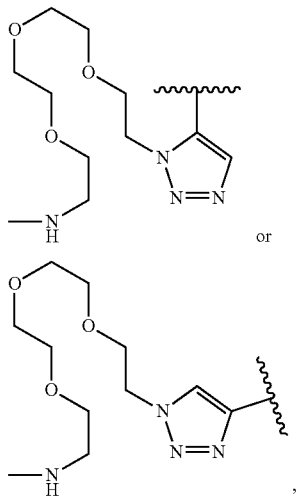

or a mixture thereof. Alternatively, in another embodiment, A is

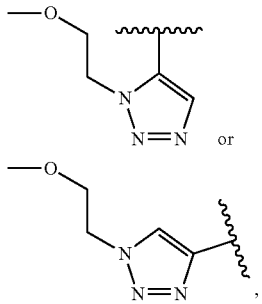

or a mixture thereof. In another embodiment, A is

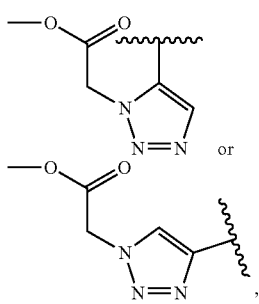

or a mixture thereof. In another embodiment, A is

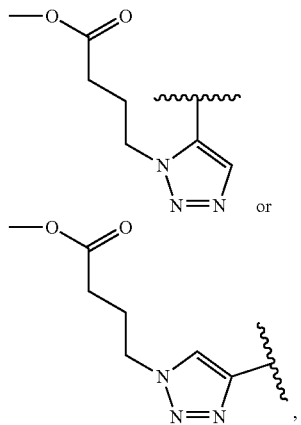

or a mixture thereof. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, heteroalkylenyl sulfonic acid, heteroalkylenyl taurine, heteroalkylenyl phosphoric acid or phosphate, heteroalkylenyl amine (e.g., quaternary amine), or heteroalkylenyl sugar. In certain embodiments, sugars include, without limitation, monosaccharides, disaccharides, and polysaccharides. Exemplary monosaccharides include glucose, ribose, deoxyribose, xylose, arabinose, mannose, galactose, fructose, and the like. In certain embodiments, sugars include sugar acids such as glucuronic acid, further including conjugated forms such as glucuronides (i.e., via glucuronidation). Exemplary disaccharides include maltose, sucrose, lactose, lactulose, trehalose, and the like. Exemplary polysaccharides include amylose, amylopectin, glycogen, inulin, cellulose, and the like. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is $-(CH_2)_{1-5}SO_3H$, $-(CH_2)_n-NH-(CH_2)_{1-5}SO_3H$, $-(CH_2)_n-C(O)NH-(CH_2)_{1-5}SO_3H$, $-(CH_2CH_2O)_m-C(O)NH-(CH_2)_{1-5}SO_3H$, $-(CH_2)_n-N((CH_2)_{1-5}C(O)NH(CH_2)_{1-5}SO_3H)_2$, $-(CH_2)_n-C(O)N((CH_2)_{1-5}C(O)NH(CH_2)_{1-5}SO_3H)_2$, or $-(CH_2CH_2O)_m-C(O)N((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl or alkylenyl sulfonic acid is $-(CH_2)_{1-5}SO_3H$. In another embodiment, the heteroalkyl or heteroalkylenyl sulfonic acid is $-(CH_2)_n-NH-(CH_2)_{1-5}SO_3H$, wherein n is 1, 2, 3, 4, or 5. In another embodiment, the alkyl, heteroalkyl, alkylenyl, or heteroalkylenyl sulfonic acid is $-(CH_2)_n-C(O)NH-(CH_2)_{1-5}SO_3H$, wherein n is 1, 2, 3, 4, or 5. In another embodiment, the alkyl, heteroalkyl, alkylenyl, or heteroalkylenyl sulfonic acid is $-(CH_2CH_2O)_m-C(O)NH-(CH_2)_{1-5}SO_3H$, wherein m is 1, 2, 3, 4, or 5. In another embodiment, the alkyl, heteroalkyl, alkylenyl, or heteroalkylenyl sulfonic acid is —(CH$_2$)$_n$—N((CH$_2$)$_{1-5}$C(O)NH(CH$_2$)$_{1-5}$SO$_3$H)$_2$, wherein n is 1, 2, 3, 4, or 5. In another embodiment, the alkyl, heteroalkyl, alkylenyl, or heteroalkylenyl sulfonic acid is —(CH$_2$)$_n$—C(O)N((CH$_2$)$_{1-5}$C(O)NH(CH$_2$)$_{1-5}$SO$_3$H)$_2$, wherein n is 1, 2, 3, 4, or 5. In another embodiment, the alkyl, heteroalkyl, alkylenyl, or heteroalkylenyl sulfonic acid is —(CH$_2$CH$_2$O)$_m$—C(O)N((CH$_2$)$_{1-5}$C(O)NH(CH$_2$)$_{1-5}$SO$_3$H)$_2$, wherein m is 1, 2, 3, 4, or 5.

In some embodiments, the linker is:

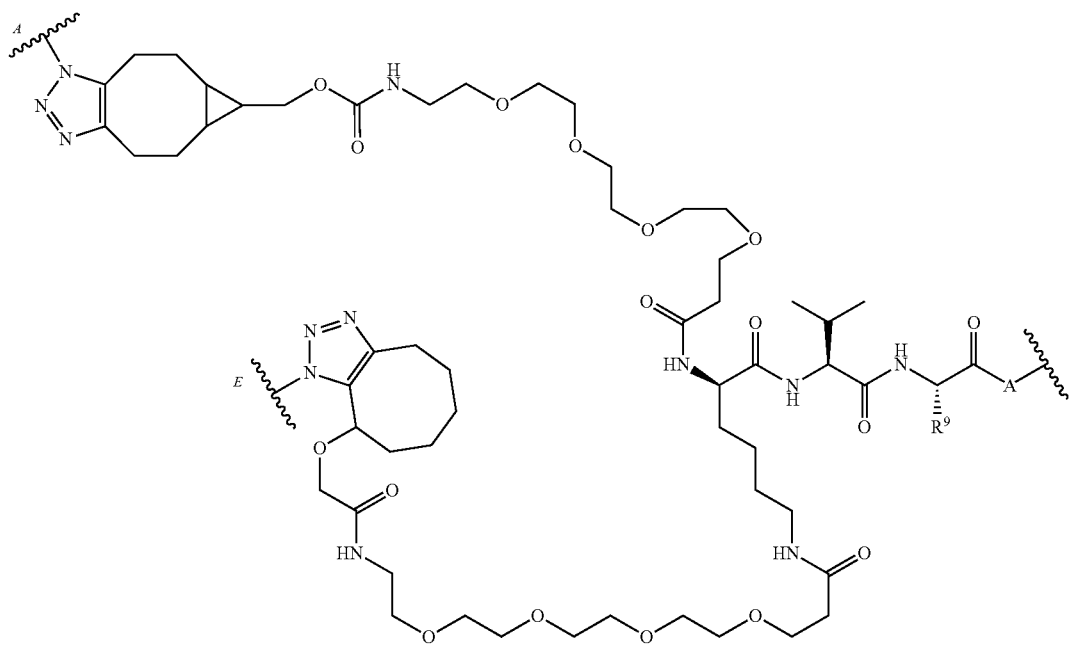

or a pharmaceutically acceptable salt, solvate, or stereoisomeric form thereof, or a regioisomer thereof, or mixture of regioisomers thereof, wherein:

each

is a bond to the binding agent;

each

is a bond to the payload;

each R$^9$ is —CH$_3$ or —(CH$_2$)$_3$N(H)C(O)NH$_2$; and each A is —O—, —N(H)—,

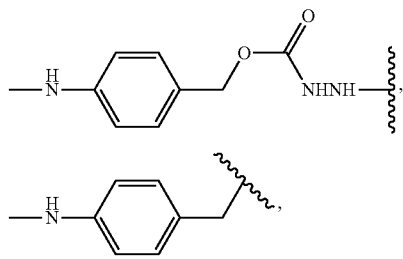

-continued

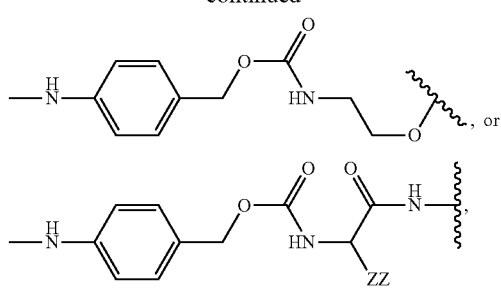

where ZZ is hydrogen, or a side chain for an amino acid as discussed elsewhere herein. For example, in one embodiment, ZZ is C$_{1-6}$ alkyl. By way of further example, in one embodiment, ZZ is C$_{1-6}$ heteroalkyl. In particular embodiments of this paragraph, A may be derived from a primary amine compound or a residue thereof where X is —N$_3$, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

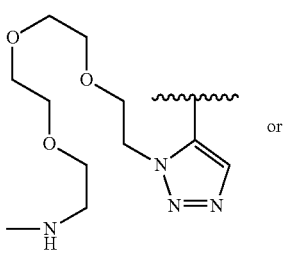

or

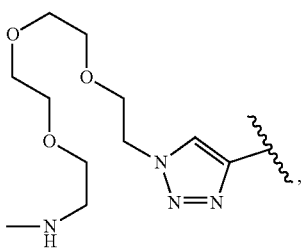

or a mixture thereof. Alternatively, in another embodiment, A is

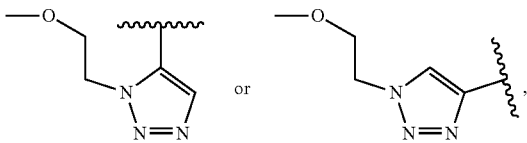

or a mixture thereof. In another embodiment, A is

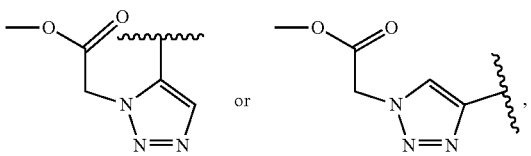 [SMILES: *c1cnnn1CC(=O)OC ; *c1cn(CC(=O)OC)nn1]

or a mixture thereof. In another embodiment, A is

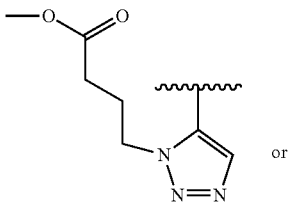

or

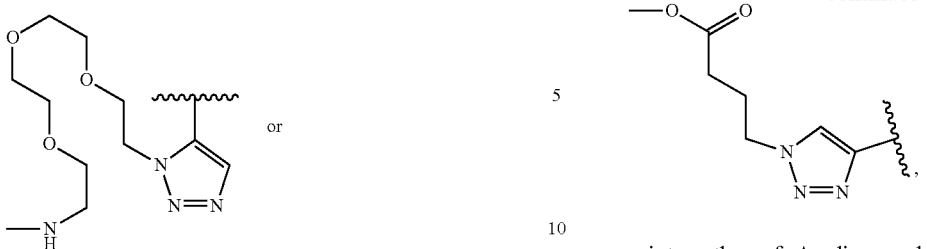

or a mixture thereof. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, heteroalkylenyl sulfonic acid, heteroalkylenyl taurine, heteroalkylenyl phosphoric acid or phosphate, heteroalkylenyl amine (e.g., quaternary amine), or heteroalkylenyl sugar. In certain embodiments, sugars include, without limitation, monosaccharides, disaccharides, and polysaccharides. Exemplary monosaccharides include glucose, ribose, deoxyribose, xylose, arabinose, mannose, galactose, fructose, and the like. In certain embodiments, sugars include sugar acids such as glucuronic acid, further including conjugated forms such as glucuronides (i.e., via glucuronidation). Exemplary disaccharides include maltose, sucrose, lactose, lactulose, trehalose, and the like. Exemplary polysaccharides include amylose, amylopectin, glycogen, inulin, cellulose, and the like. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is $-(CH_2)_{1-5}SO_3H$, $-(CH_2)_n-NH-(CH_2)_{1-5}SO_3H$, $-(CH_2)_n-C(O)NH-(CH_2)_{1-5}SO_3H$, $-(CH_2CH_2O)_m-C(O)NH-(CH_2)_{1-5}SO_3H$, $-(CH_2)_n-N((CH_2)_{1-5}C(O)NH(CH_2)_{1-5}SO_3H)_2$, $-(CH_2)_n-C(O)N((CH_2)_{1-5}C(O)NH(CH_2)_{1-5}SO_3H)_2$, or $-(CH_2CH_2O)_m-C(O)N((CH_2)_{1-5}C(O)NH(CH_2)_{1-5}SO_3H)_2$, wherein n is 1, 2, 3, 4, or 5, and m is 1, 2, 3, 4, or 5. In one embodiment, the alkyl or alkylenyl sulfonic acid is $-(CH_2)_{1-5}SO_3H$. In another embodiment, the heteroalkyl or heteroalkylenyl sulfonic acid is $-(CH_2)_n-NH-(CH_2)_{1-5}SO_3H$, wherein n is 1, 2, 3, 4, or 5. In another embodiment, the alkyl, heteroalkyl, alkylenyl, or heteroalkylenyl sulfonic acid is $-(CH_2)_n-C(O)NH-(CH_2)_{1-5}SO_3H$, wherein n is 1, 2, 3, 4, or 5. In another embodiment, the alkyl, heteroalkyl, alkylenyl, or heteroalkylenyl sulfonic acid is $-(CH_2CH_2O)_m-C(O)NH-(CH_2)_{1-5}SO_3H$, wherein m is 1, 2, 3, 4, or 5. In another embodiment, the alkyl, heteroalkyl, alkylenyl, or heteroalkylenyl sulfonic acid is $-(CH_2)_n-N((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is $-(CH_2)_n-C(O)N((CH_2)_{1-5}C(O)NH(CH_2)_{1-5}SO_3H)_2$, wherein n is 1, 2, 3, 4, or 5. In another embodiment, the alkyl, heteroalkyl, alkylenyl, or heteroalkylenyl sulfonic acid is $-(CH_2CH_2O)_m-C(O)N((CH_2)_{1-5}C(O)NH(CH_2)_{1-5}SO_3H)_2$, wherein m is 1, 2, 3, 4, or 5.

In some embodiments, the linker is:
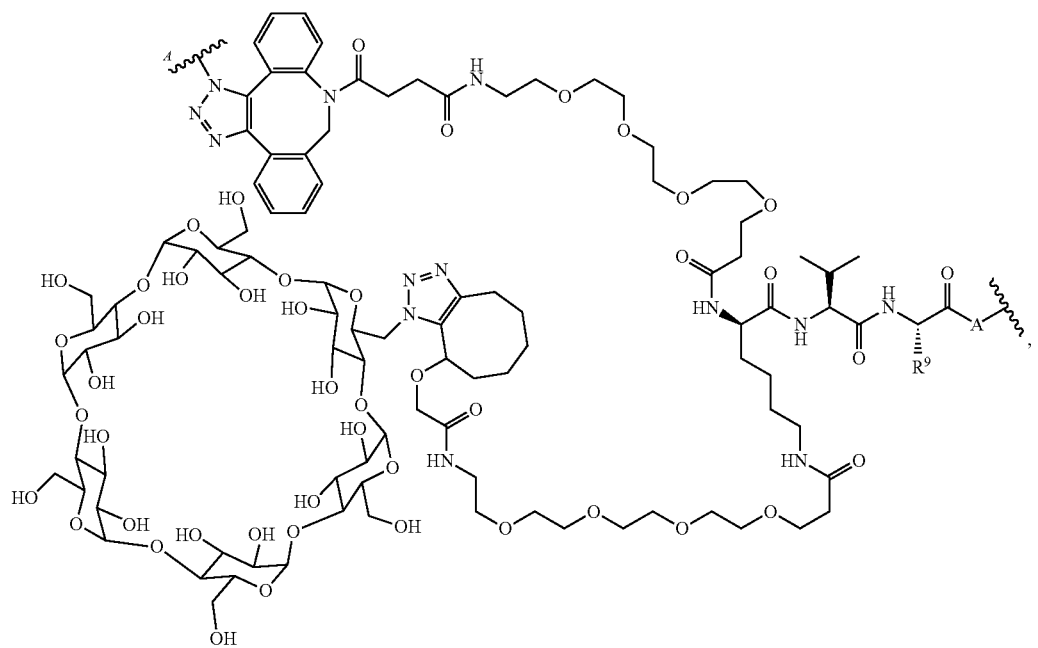
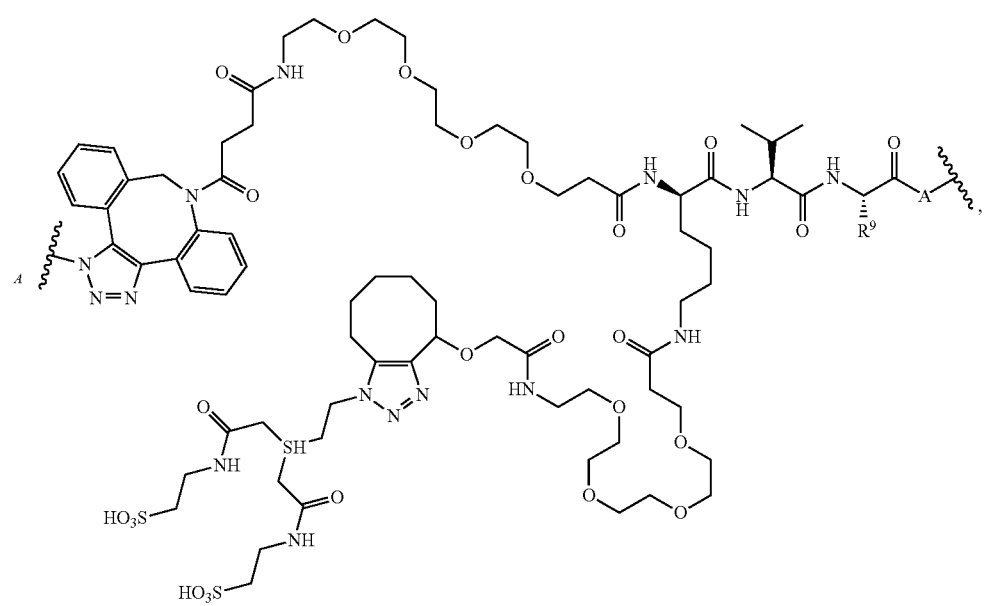

-continued

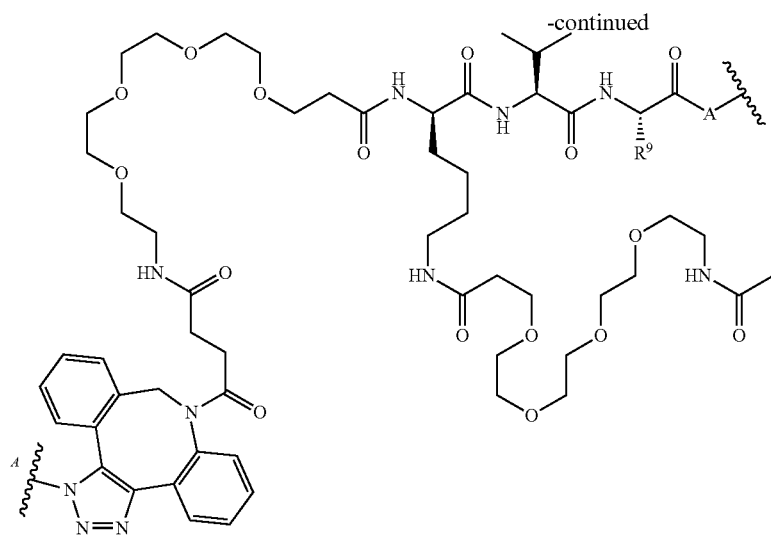
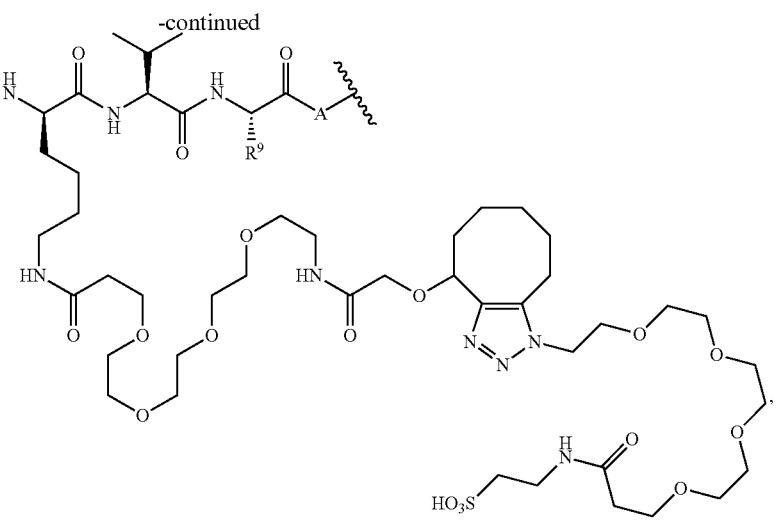

or a pharmaceutically acceptable salt, solvate, or stereoisomeric form thereof, or a regioisomer thereof, or mixture of regioisomers thereof, wherein:

each

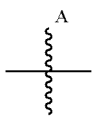

is a bond to the binding agent;
each

is a bond to the payload;
$R^9$ is —CH$_3$ or —(CH$_2$)$_3$N(H)C(O)NH$_2$; and
A is —O—, —N(H)—,

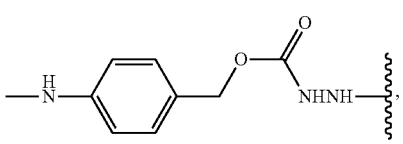

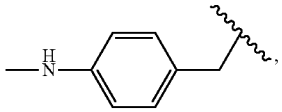

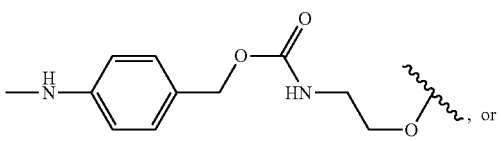

-continued

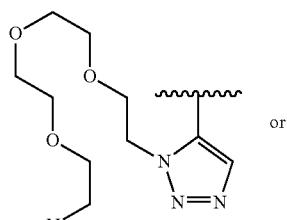

where ZZ is hydrogen, or a side chain for an amino acid as discussed elsewhere herein. For example, in one embodiment, ZZ is C$_{1-6}$ alkyl. By way of further example, in one embodiment, ZZ is C$_{1-6}$ heteroalkyl. In particular embodiments of this paragraph, A may be derived from a primary amine compound or a residue thereof where X is —N$_3$, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

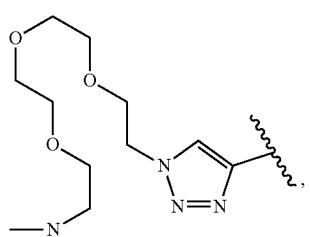

or a mixture thereof. Alternatively, in another embodiment, A is

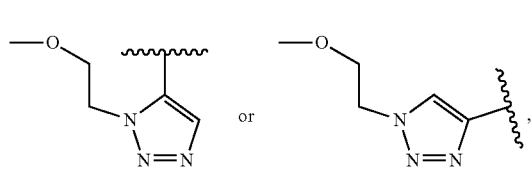

or a mixture thereof. In another embodiment, A is

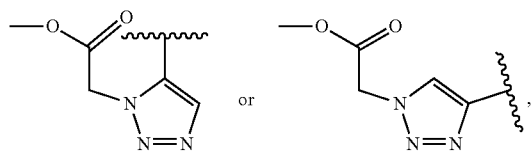 [SMILES: *c1cnnn1CC(=O)OC ; *c1cn(CC(=O)OC)nn1]

or a mixture thereof. In another embodiment, A is

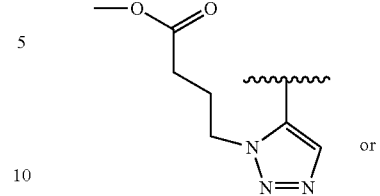

or

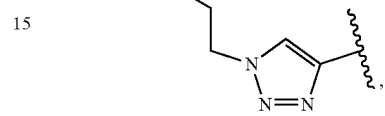

or a mixture thereof. As discussed above, the bond to the binding agent can be direct, or via a spacer. In certain embodiments, the bond to the binding agent is via a PEG spacer to a glutamine residue of the binding agent.

In some embodiments, the linker is:

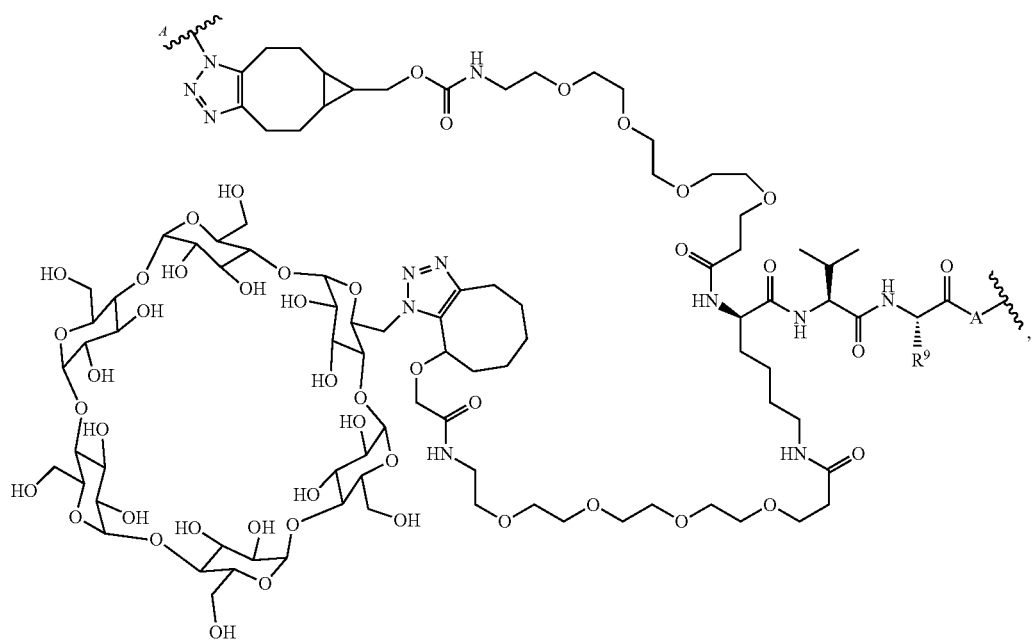

-continued
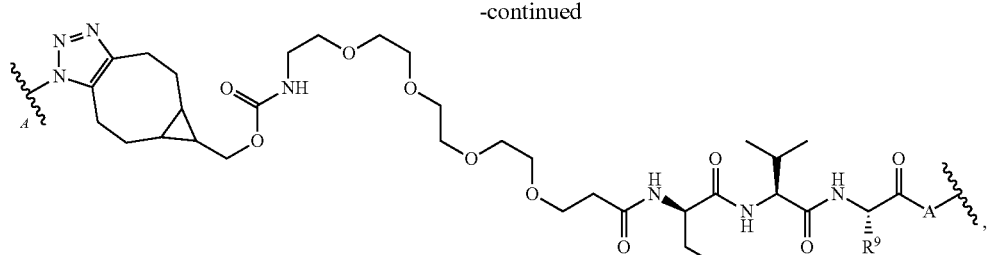
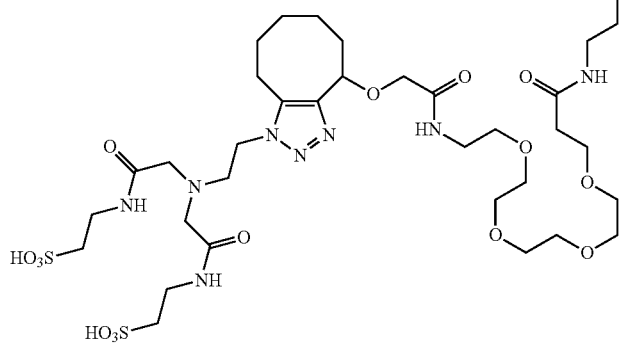
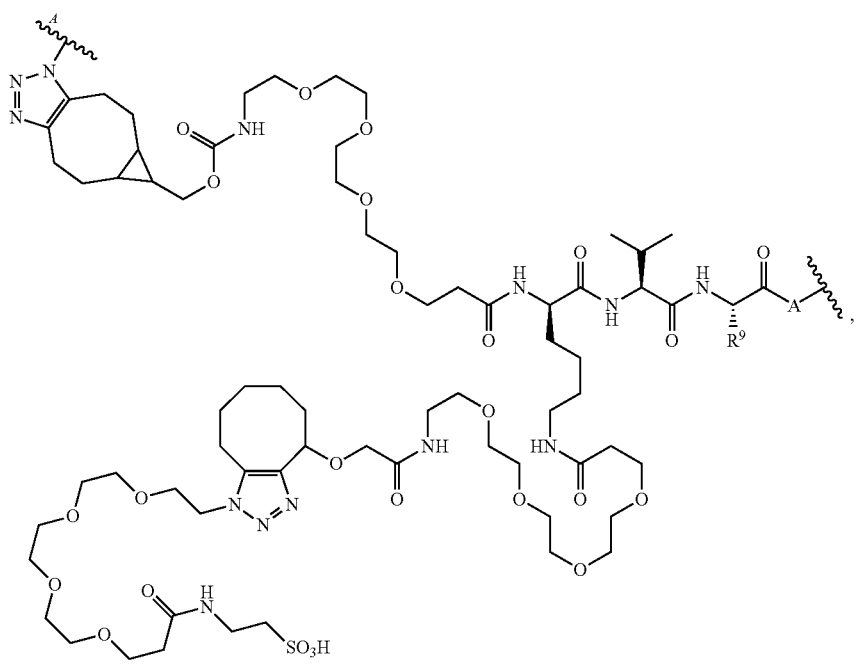
or a pharmaceutically acceptable salt, solvate, or stereoisomeric form thereof, or a regioisomer thereof, or mixture of regioisomers thereof, wherein:
each
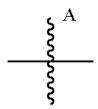
is a bond to the binding agent;
each
is a bond to the payload;
$R^9$ is —CH$_3$ or —(CH$_2$)$_3$N(H)C(O)NH$_2$; and
A is —O—, —N(H)—,

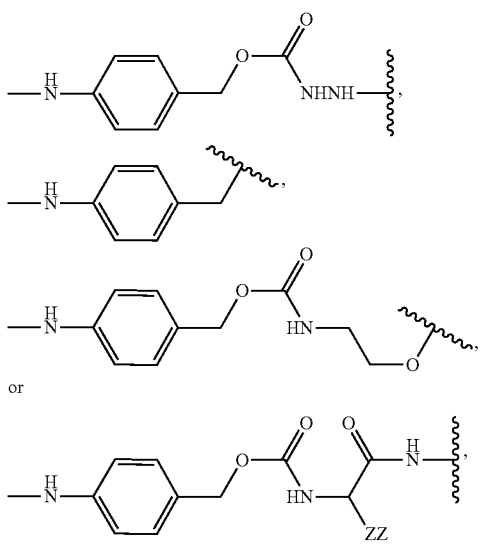

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In particular embodiments of this paragraph, A may be derived from a primary amine compound or a residue thereof where X is $-N_3$, as described elsewhere herein. In these embodiments, a 1,2,3-triazole residue is derived from the azide following participation in a click chemistry reaction, as described elsewhere herein, with an alkyne or terminal acetylene of a compound or payload described herein. Accordingly, in one non-limiting example, A is

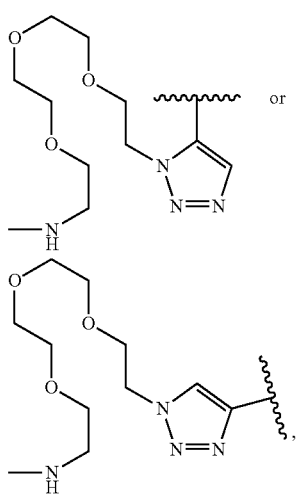

or a mixture thereof. Alternatively, in another embodiment, A is

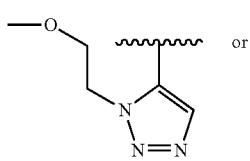

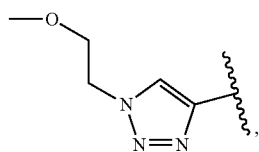

or a mixture thereof. In another embodiment, A is

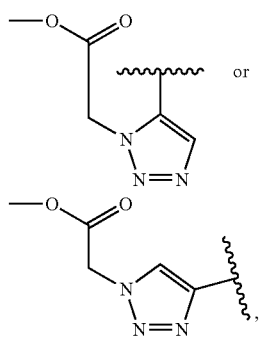

or a mixture thereof. In another embodiment, A is

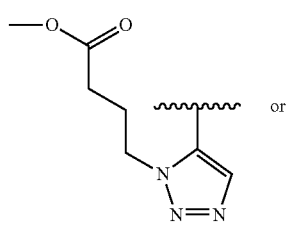

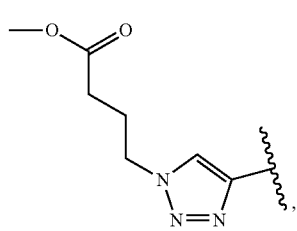

or a mixture thereof. As discussed above, the bond to the binding agent can be direct, or via a spacer. In certain embodiments, the bond to the binding agent is via a PEG spacer to a glutamine residue of the binding agent.

In particular embodiments, disclosed compounds or payloads with an alkyne or terminal acetylene may be linked to a binding agent derivatized with -PEG-$N_3$ linked to a glutamine residue. Exemplary $-N_3$ derivatized binding agents, methods for their preparation, and methods for their use are provided herein. In certain embodiments, a compound or payload with an alkyne described herein suitable for participation in 1,3-cycloadditions with binding agents derivatized with -PEG-$N_3$ provide regioisomeric 1,2,3-triazolyl linked moieties. For example, in certain embodiments, compounds or payloads linked to the binding agent may be

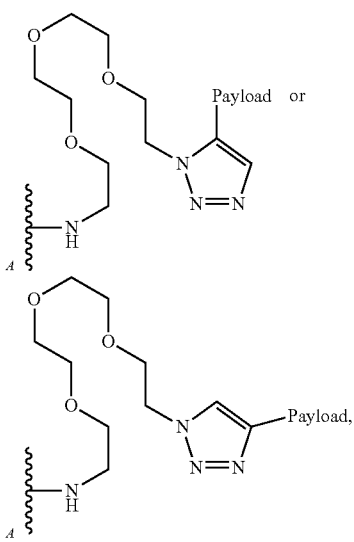

or a mixture thereof, where each

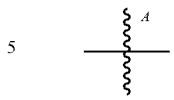

is a bond to the binding agent.

Linker-Payloads

In certain embodiments, linker-payloads include any specific compound embraced by any one or more of Formulae I, II, III, IV, V, VI, VII, VIII, IX, X, XI, or XII above, bonded to a linker, wherein the linker(s) described herein include a moiety that is reactive with an antibody or antigen binding fragment thereof described herein. In particular embodiments, the linker is bonded to the piperdine nitrogen, $R^2$, $R^6$, or $R^7$ in any one or more of Formulae I, II, III, IV, V, VI, VII, VIII, IX, X, XI, or XII above. In one embodiment, the linker-payload has a structure of Formula LPa':

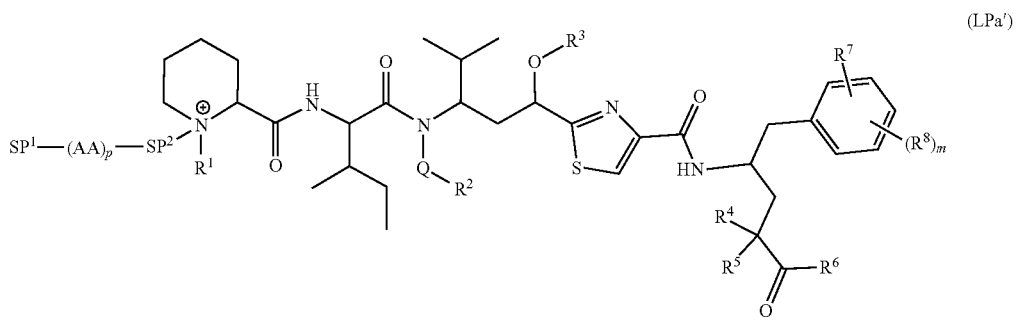

wherein $SP^1$, $(AA)_p$, $SP^2$, $R^1$, Q, $Q^1$, $R^2$, $R^3$, $R^4$, $R^5$, $R^6$, $R^7$, and $R^8$ are as described in any of the embodiments disclosed herein. In one embodiment, the linker-payload has a structure of Formula LPb':

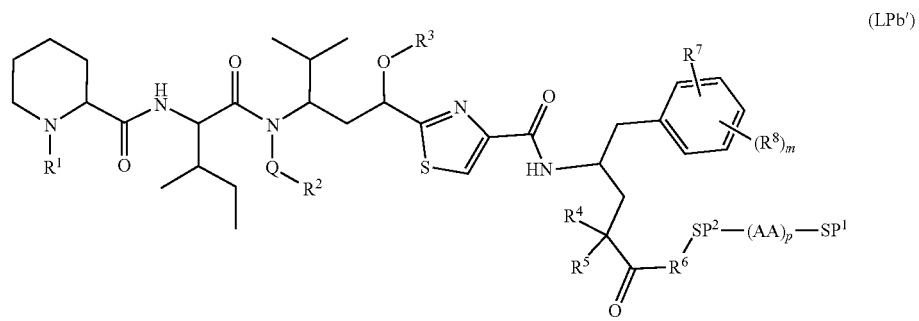

wherein $SP^1$, $(AA)_p$, $SP^2$, $R^1$, Q, $Q^1$, $R^2$, $R^3$, $R^4$, $R^5$, $R^6$, $R^7$, and $R^8$ are as described in any of the embodiments disclosed herein. In one embodiments, the linker-payload has a structure of Formula LPc':

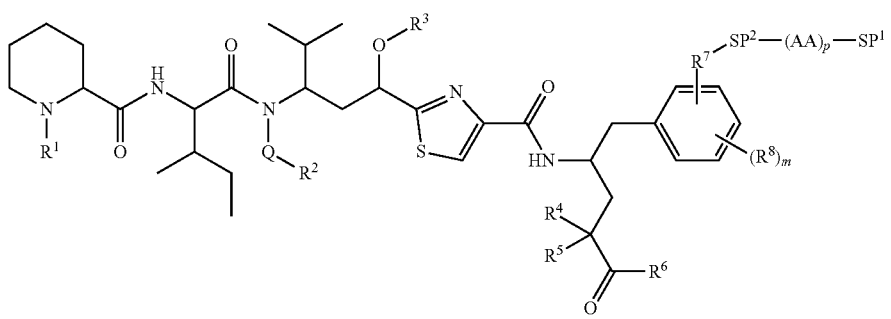

(LPc')

wherein $SP^1$, $(AA)_p$, $SP^2$, $R^1$, Q, $Q^1$, $R^2$, $R^3$, $R^4$, $R^5$, $R^6$, $R^7$, and $R^8$ are as described in any of the embodiments disclosed herein. In one embodiments, the linker-payload has a structure of Formula LPd':

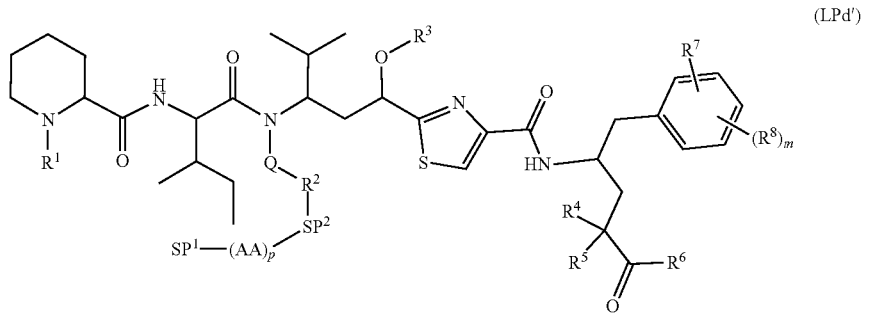

(LPd')

wherein $SP^1$, $(AA)_p$, $SP^2$, $R^1$, Q, $Q^1$, $R^2$, $R^3$, $R^4$, $R^5$, $R^6$, $R^7$, and $R^8$ are as described in any of the embodiments disclosed herein. In any of the embodiments in this paragraph, Formulae LPa', LPb', LPc', or LPd' may be a pharmaceutically acceptable salt thereof. In any of the embodiments in this paragraph, p is 1, 2, 3, 4, 5, 6, 7, 8, 9, or 10.

In any of the foregoing embodiments, aryl includes phenyl, naphthyl, fluorenyl, azulenyl, anthryl, phenanthryl, and pyrenyl; heteroaryl includes furanyl, thiophenyl, pyrrolyl, oxazolyl, thiazolyl, imidazolyl, pyrazolyl, isoxazolyl, isothiazolyl, pyridyl, pyrazinyl, pyrimidinyl, pyridazinyl, quinolinyl, isoquinolinyl, cinnolinyl, quinazolinyl, quinoxalinyl, phthalazinyl, pteridinyl, benzofuranyl, dibenzofuranyl, benzothiophenyl, benzoxazolyl, benzthiazoyl, dibenzothiophenyl, indolyl, indolinyl, benzimidazolyl, indazolyl, and benztriazolyl; and acyl includes —C(O)$R^{3c}$, wherein $R^{3c}$ comprises alkyl, alkenyl, alkynyl, cycloalkyl, aryl, and heteroaryl. In one embodiment, aryl is phenyl. In one embodiment, aryl is naphthyl. In one embodiment, aryl is fluorenyl. In one embodiment, aryl is azulenyl. In one embodiment, aryl is anthryl. In one embodiment, aryl is phenanthryl. In one embodiment, aryl is pyrenyl. In one embodiment, heteroaryl is furanyl. In one embodiment, heteroaryl is thiophenyl. In one embodiment, heteroaryl is pyrrolyl. In one embodiment, heteroaryl is oxazolyl. In one embodiment, heteroaryl is thiazolyl. In one embodiment, heteroaryl is imidazolyl. In one embodiment, heteroaryl is pyrazolyl. In one embodiment, heteroaryl is isoxazolyl. In one embodiment, heteroaryl is isothiazolyl. In one embodiment, heteroaryl is pyridyl. In one embodiment, heteroaryl is pyrazinyl. In one embodiment, heteroaryl is pyrimidinyl. In one embodiment, heteroaryl is pyridazinyl. In one embodiment, heteroaryl is quinolinyl. In one embodiment, heteroaryl is isoquinolinyl. In one embodiment, heteroaryl is cinnolinyl. In one embodiment, heteroaryl is quinazolinyl. In one embodiment, heteroaryl is quinoxalinyl. In one embodiment, heteroaryl is phthalazinyl. In one embodiment, heteroaryl is pteridinyl. In one embodiment, heteroaryl is benzofuranyl. In one embodiment, heteroaryl is dibenzofuranyl. In one embodiment, heteroaryl is benzothiophenyl. In one embodiment, heteroaryl is benzoxazolyl. In one embodiment, heteroaryl is benzthiazoyl. In one embodiment, heteroaryl is dibenzothiophenyl. In one embodiment, heteroaryl is indolyl. In one embodiment, heteroaryl is indolinyl. In one embodiment, heteroaryl is benzimidazolyl. In one embodiment, heteroaryl is indazolyl. In one embodiment, heteroaryl is benztriazolyl. In one embodiment, acyl is —C(O)$R^{3c}$, and $R^{3c}$ is alkyl. In one embodiment, acyl is —C(O)$R^{3c}$, and $R^{3c}$ is alkenyl. In one embodiment, acyl is —C(O)$R^{3c}$, and $R^{3c}$ is alkynyl. In one embodiment, acyl is —C(O)$R^{3c}$, and $R^{3c}$ is cycloalkyl. In one embodiment, acyl is —C(O)$R^{3c}$, and $R^{3c}$ is aryl. In one embodiment, acyl is —C(O)$R^{3c}$, and $R^{3c}$ is heteroaryl.

In any preceding embodiment in this section, $R^7$ is —$NR^{7a}R^{7b}$, wherein $R^{7a}$ and $R^{7b}$ are independently in each instance, hydrogen, alkyl, alkenyl, alkynyl, cycloalkyl, aryl, heteroaryl, acyl, and amino acid residue, wherein alkyl, alkenyl, alkynyl, cycloalkyl, aryl, heteroaryl, and acyl are optionally substituted. In certain embodiments $R^{7a}$ is hydrogen and $R^{7b}$ is an amino acid residue.

Conjugates/Antibody Drug Conjugates (ADCs)

Provided herein are antibodies, or an antigen binding fragment thereof, wherein said antibody is conjugated to one or more compounds of Formula I, II, III, IV, V, VI, VII, VIII, IX, X, XI, and/or XII as described herein.

Provided herein are conjugates of Formula A:

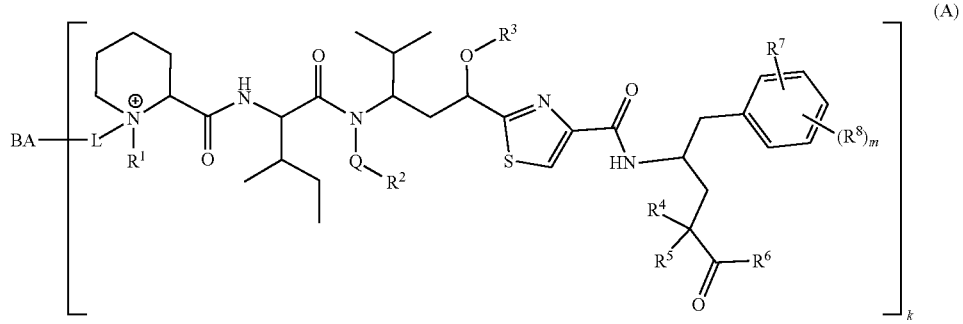

(A)

or a pharmaceutically acceptable salt, solvate, regioisomeric, or stereoisomeric form thereof, wherein $R^1$, Q, $Q^1$, $R^2$, $R^3$, $R^4$, $R^5$, $R^6$, $R^7$, $R^8$, $R^9$, and m, are as described above in the context of Formula I, BA is a binding agent, L is a linker, and k is 1, 2, 3, 4, 5, 6, 7, 8, 9, or 10. In certain embodiments, k is a range from 1-2, 1-3, 2-3, 2-4, 3-4, or 1-4. In certain embodiments, compounds conjugated to -L-BA in Formula A include one or more compounds of Formulae II, III, IV, V, VI, VII, VIII, IX, X, XI, and/or XII, as described above, wherein BA is a binding agent; L is a linker; and k is 1, 2, 3, 4, 5, 6, 7, 8, 9, or 10. In certain embodiments, k is a range from 1-2, 1-3, 2-3, 2-4, 3-4, or 1-4. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any embodiment in this paragraph, BA is antibody, or antigen binding fragment thereof, wherein the antibody is conjugated to a compound of Formula IV, as described above. In any embodiment in this paragraph, BA is antibody, or antigen binding fragment thereof, wherein the antibody is conjugated to a compound of Formula V, as described above. In any embodiment in this paragraph, BA is antibody, or antigen binding fragment thereof, wherein the antibody is conjugated to a compound of Formula VI, as described above. In any embodiment in this paragraph, BA is antibody, or antigen binding fragment thereof, wherein the antibody is conjugated to a compound of Formula VII, as described above. In any embodiment in this paragraph, BA is antibody, or antigen binding fragment thereof, wherein the antibody is conjugated to a compound of Formula VIII, as described above. In any embodiment in this paragraph, BA is antibody, or antigen binding fragment thereof, wherein the antibody is conjugated to a compound of Formula IX, as described above. In any embodiment in this paragraph, BA is antibody, or antigen binding fragment thereof, wherein the antibody is conjugated to a compound of Formula X, as described above. In any embodiment in this paragraph, BA is antibody, or antigen binding fragment thereof, wherein the antibody is conjugated to a compound of Formula XI, as described above. In any embodiment in this paragraph, BA is antibody, or antigen binding fragment thereof, wherein the antibody is conjugated to a compound of Formula XII, as described above. In any of the embodiments in this paragraph, any one or more compounds of Formulae I, II, III, IV, V, VI, VII, VIII, IX, X, XI, and/or XII conjugated to -L-BA in Formula A are conjugated via the piperidine nitrogen.

Provided herein are conjugates of Formula B:

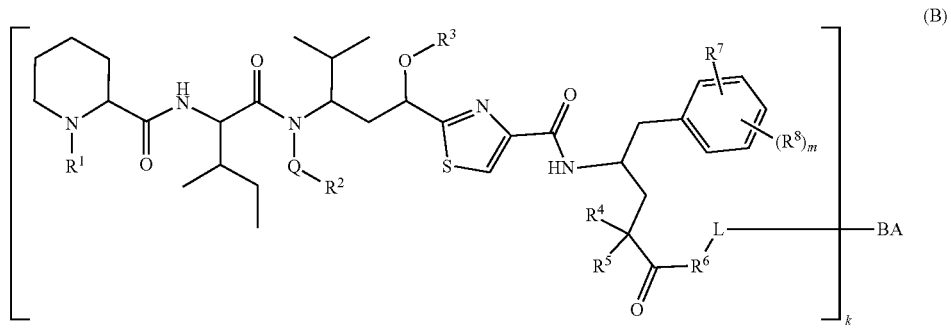

(B)

or a pharmaceutically acceptable salt, solvate, regioisomeric, or stereoisomeric form thereof, wherein $R^1$, Q, $Q^1$, $R^2$, $R^3$, $R^4$, $R^5$, $R^6$, $R^7$, $R^8$, $R^9$, and m, are as described above in the context of Formula I, BA is a binding agent, L is a linker, and k is 1, 2, 3, 4, 5, 6, 7, 8, 9, or 10. In certain embodiments, k is a range from 1-2, 1-3, 2-3, 2-4, 3-4, or 1-4. In certain embodiments, compounds conjugated to -L-BA in Formula B include one or more compounds of Formulae II, III, IV, V, VI, VII, VIII, IX, X, XI, and/or XII, as described above, wherein BA is a binding agent; L is a linker; and k is 1, 2, 3, 4, 5, 6, 7, 8, 9, or 10. In certain embodiments, k is a range from 1-2, 1-3, 2-3, 2-4, 3-4, or 1-4. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any embodiment in this paragraph, BA is antibody, or antigen binding fragment thereof, wherein the antibody is conjugated to a compound of Formula IV, as described above. In any embodiment in this paragraph, BA is antibody, or antigen binding fragment thereof, wherein the antibody is conjugated to a compound of Formula V, as described above. In any embodiment in this paragraph, BA is antibody, or antigen binding fragment thereof, wherein the antibody is conjugated to a compound of Formula VI, as described above. In any embodiment in this paragraph, BA is antibody, or antigen binding fragment thereof, wherein the antibody is conjugated to a compound of Formula VII, as described above. In any embodiment in this paragraph, BA is antibody, or antigen binding fragment thereof, wherein the antibody is conjugated to a compound of Formula VIII, as described above. In any embodiment in this paragraph, BA is antibody, or antigen binding fragment thereof, wherein the antibody is conjugated to a compound of Formula IX, as described above. In any embodiment in this paragraph, BA is antibody, or antigen binding fragment thereof, wherein the antibody is conjugated to a compound of Formula X, as described above. In any embodiment in this paragraph, BA is antibody, or antigen binding fragment thereof, wherein the antibody is conjugated to a compound of Formula XI, as described above. In any embodiment in this paragraph, BA is antibody, or antigen binding fragment thereof, wherein the antibody is conjugated to a compound of Formula XII, as described above. In any of the embodiments in this paragraph, any one or more compounds of Formulae I, II, III, IV, V, VI, VII, VIII, IX, X, XI, and/or XII conjugated to -L-BA in Formula B are conjugated via divalent $R^6$.

Provided herein are conjugates of Formula C:

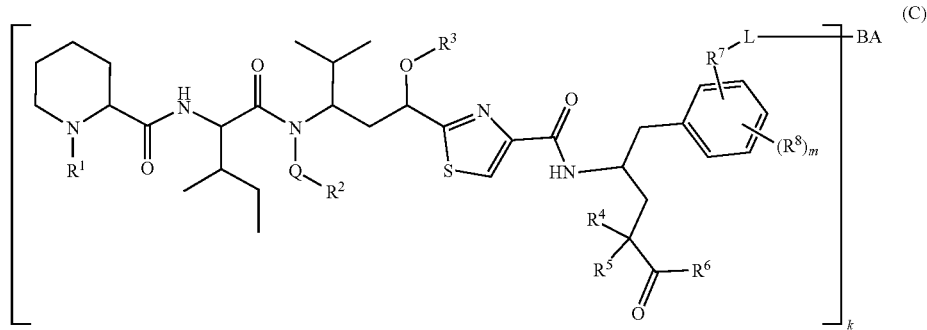

or a pharmaceutically acceptable salt, solvate, regioisomeric, or stereoisomeric form thereof, wherein $R^1$, Q, $Q^1$, $R^2$, $R^3$, $R^4$, $R^5$, $R^6$, $R^7$, $R^8$, $R^9$, and m, are as described above in the context of Formula I, BA is a binding agent, L is a linker, and k is 1, 2, 3, 4, 5, 6, 7, 8, 9, or 10. In certain embodiments, k is a range from 1-2, 1-3, 2-3, 2-4, 3-4, or 1-4. In certain embodiments, compounds conjugated to -L-BA in Formula C include one or more compounds of Formulae II, III, IV, V, VI, VII, VIII, IX, X, XI, and/or XII, as described above, wherein BA is a binding agent; L is a linker; and k is 1, 2, 3, 4, 5, 6, 7, 8, 9, or 10. In certain embodiments, k is a range from 1-2, 1-3, 2-3, 2-4, 3-4, or 1-4. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any embodiment in this paragraph, BA is antibody, or antigen binding fragment thereof, wherein the antibody is conjugated to a compound of Formula IV, as described above. In any embodiment in this paragraph, BA is antibody, or antigen binding fragment thereof, wherein the antibody is conjugated to a compound of Formula V, as described above. In any embodiment in this paragraph, BA is antibody, or antigen binding fragment thereof, wherein the antibody is conjugated to a compound of Formula VI, as described above. In any embodiment in this paragraph, BA is antibody, or antigen binding fragment thereof, wherein the antibody is conjugated to a compound of Formula VII, as described above. In any embodiment in this paragraph, BA is antibody, or antigen binding fragment thereof, wherein the antibody is conjugated to a compound of Formula VIII, as described above. In any embodiment in this paragraph, BA is antibody, or antigen binding fragment thereof, wherein the antibody is conjugated to a compound of Formula IX, as described above. In any embodiment in this paragraph, BA is antibody, or antigen binding fragment thereof, wherein the antibody is conjugated to a compound of Formula X, as described above. In any embodiment in this paragraph, BA is antibody, or antigen binding fragment thereof, wherein the antibody is conjugated to a compound of Formula XI, as described above. In any embodiment in this paragraph, BA is antibody, or antigen binding fragment thereof, wherein the antibody is conjugated to a compound of Formula XII, as described above. In any of the embodiments in this paragraph, any one or more compounds of Formulae I, II, III, IV, V, VI, VII, VIII, IX, X, XI, and/or XII conjugated to -L-BA in Formula C are conjugated via divalent $R^7$.

Provided herein are conjugates of Formula D:

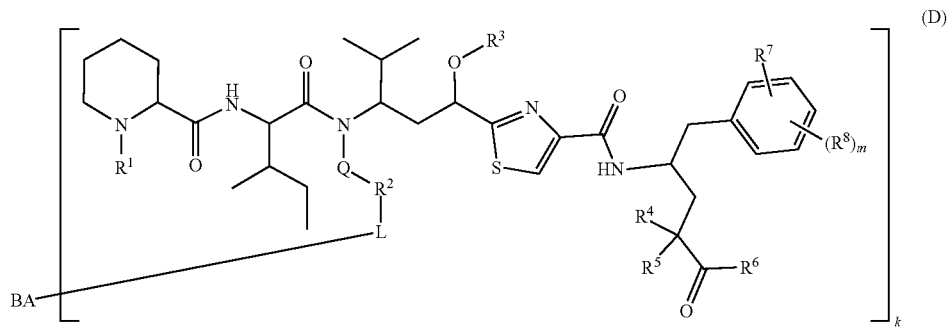

(D)

or a pharmaceutically acceptable salt, solvate, regioisomeric, or stereoisomeric form thereof, wherein $R^1$, Q, $Q^1$, $R^2$, $R^3$, $R^4$, $R^5$, $R^6$, $R^7$, $R^8$, $R^9$, and m, are as described above in the context of Formula I, BA is a binding agent, L is a linker, and k is 1, 2, 3, 4, 5, 6, 7, 8, 9, or 10. In certain embodiments, k is a range from 1-2, 1-3, 2-3, 2-4, 3-4, or 1-4. In certain embodiments, compounds conjugated to -L-BA in Formula D include one or more compounds of Formulae II, III, IV, V, VI, VII, VIII, IX, X, XI, and/or XII, as described above, wherein BA is a binding agent; L is a linker; and k is 1, 2, 3, 4, 5, 6, 7, 8, 9, or 10. In certain embodiments, k is a range from 1-2, 1-3, 2-3, 2-4, 3-4, or 1-4. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any embodiment in this paragraph, BA is antibody, or antigen binding fragment thereof, wherein the antibody is conjugated to a compound of Formula IV, as described above. In any embodiment in this paragraph, BA is antibody, or antigen binding fragment thereof, wherein the antibody is conjugated to a compound of Formula V, as described above. In any embodiment in this paragraph, BA is antibody, or antigen binding fragment thereof, wherein the antibody is conjugated to a compound of Formula VI, as described above. In any embodiment in this paragraph, BA is antibody, or antigen binding fragment thereof, wherein the antibody is conjugated to a compound of Formula VII, as described above. In any embodiment in this paragraph, BA is antibody, or antigen binding fragment thereof, wherein the antibody is conjugated to a compound of Formula VIII, as described above. In any embodiment in this paragraph, BA is antibody, or antigen binding fragment thereof, wherein the antibody is conjugated to a compound of Formula IX, as described above. In any embodiment in this paragraph, BA is antibody, or antigen binding fragment thereof, wherein the antibody is conjugated to a compound of Formula X, as described above. In any embodiment in this paragraph, BA is antibody, or antigen binding fragment thereof, wherein the antibody is conjugated to a compound of Formula XI, as described above. In any embodiment in this paragraph, BA is antibody, or antigen binding fragment thereof, wherein the antibody is conjugated to a compound of Formula XII, as described above. In any of the embodiments in this paragraph, any one or more compounds of Formulae I, II, III, IV, V, VI, VII, VIII, IX, X, XI, and/or XII conjugated to -L-BA in Formula D are conjugated via divalent $R^2$.

In one embodiment of Formula B, BA is a binding agent; L is a linker; Q is —$CH_2$—; $R^1$ is $C_1$-$C_{10}$ alkyl; $R^2$ is $C_5$-$C_{10}$ alkyl; $R^3$ is —$C(O)C_1$-$C_5$ alkyl; $R^4$ is hydrogen; $R^5$ is $C_1$-$C_5$ alkyl; $R^6$ is —NHNH—; $R^7$ is halogen; $R^8$ is hydrogen; m is one; and k is 1, 2, 3, 4, 5, 6, 7, 8, 9, or 10. In one embodiment of Formula B, BA is a binding agent; L is a linker; Q is —$CH_2$—; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl, and constitutional isomers thereof, $R^3$ is —$C(O)CH_3$, —$C(O)CH_2CH_3$, —$C(O)CH_2CH_2CH_3$, —$C(O)CH_2CH_2CH_2CH_3$, or —$C(O)CH_2CH_2CH_2CH_2CH_3$; $R^4$ is hydrogen; $R^5$ is methyl, ethyl, propyl, butyl, or pentyl, and constitutional isomers thereof; $R^6$ is —NHNH—; $R^7$ is fluoro, chloro, bromo, or iodo; $R^8$ is hydrogen; m is one; and k is 1, 2, 3, 4, 5, 6, 7, 8, 9, or 10. In one embodiment, conjugates of Formula B include Formula Bi:

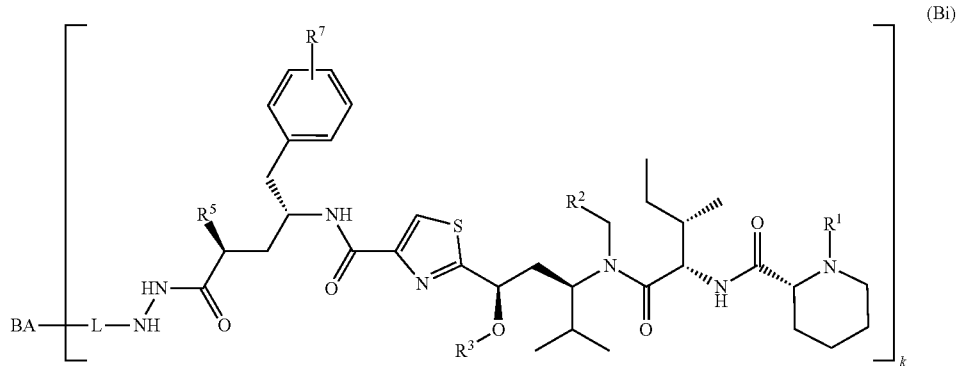

wherein BA is a binding agent; L is a linker; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl, and constitutional isomers thereof; $R^3$ is —C(O)CH$_3$, —C(O)CH$_2$CH$_3$, —C(O)CH$_2$CH$_2$CH$_3$, —C(O)CH$_2$CH$_2$CH$_2$CH$_3$, or —C(O)CH$_2$CH$_2$CH$_2$CH$_2$CH$_3$; $R^5$ is methyl, ethyl, propyl, butyl, or pentyl, and constitutional isomers thereof; $R^7$ is fluoro, chloro, bromo, or iodo; and k is 1, 2, 3, or 4. In one embodiment of Formula Bi, BA is a binding agent; L is a linker; $R^1$ is methyl; $R^2$ is pentyl, and constitutional isomers thereof; $R^3$ is —C(O)CH$_3$; $R^5$ is methyl; $R^7$ is fluoro, chloro, bromo, or iodo; and k is 1, 2, 3, or 4. In one embodiment, conjugates of Formula B include the following conjugate:

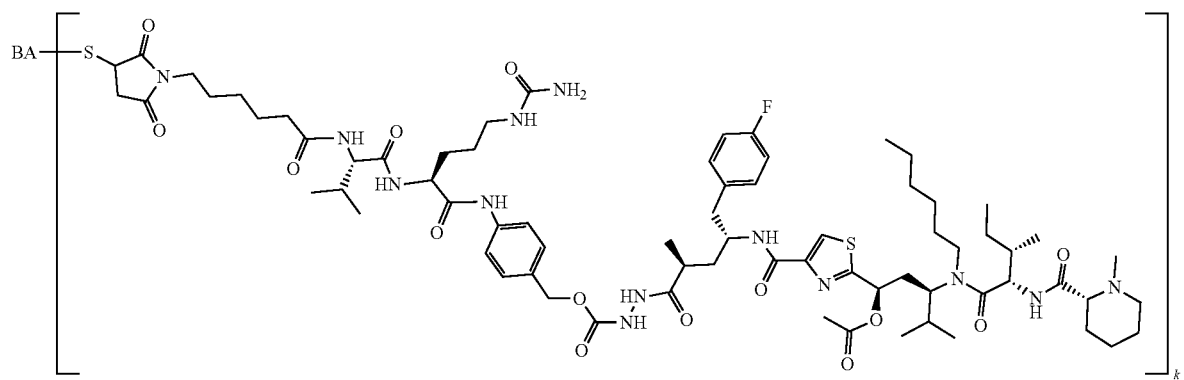

wherein BA is a binding agent; and k is 1, 2, 3, or 4. In any of the embodiments in this paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In one embodiment of Formula B, BA is a binding agent; L is a linker; Q is —O—; $R^1$ is $C_1$-$C_{10}$ alkyl; $R^2$ is $C_5$-$C_{10}$ alkyl; $R^3$ is —C(O)$C_1$-$C_5$ alkyl; $R^4$ is hydrogen; $R^5$ is $C_1$-$C_5$ alkyl; $R^6$ is —NHNH—; $R^7$ is —OH; $R^8$ is hydrogen; m is one; and k is 1, 2, 3, 4, 5, 6, 7, 8, 9, or 10. In one embodiment of Formula B, BA is a binding agent; L is a linker; Q is —O—; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl, and constitutional isomers thereof, $R^3$ is —C(O)$CH_3$, —C(O)$CH_2CH_3$, —C(O)$CH_2CH_2CH_3$, —C(O)$CH_2CH_2CH_2CH_3$, or —C(O)$CH_2CH_2CH_2CH_2CH_3$; $R^4$ is hydrogen; $R^5$ is methyl, ethyl, propyl, butyl, or pentyl, and constitutional isomers thereof; $R^6$ is —NHNH—; $R^7$ is —OH; $R^8$ is hydrogen; m is one; and k is 1, 2, 3, 4, 5, 6, 7, 8, 9, or 10. In one embodiment, conjugates of Formula B include Formula Bii.

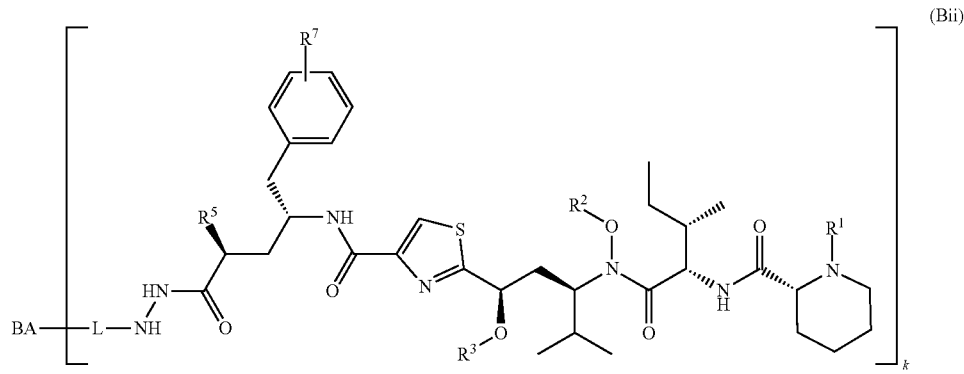

(Bii)

wherein BA is a binding agent; L is a linker; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl, and constitutional isomers thereof; $R^3$ is —C(O)$CH_3$, —C(O)$CH_2CH_3$, —C(O)$CH_2CH_2CH_3$, —C(O)$CH_2CH_2CH_2CH_3$, or —C(O)$CH_2CH_2CH_2CH_2CH_3$; $R^5$ is methyl, ethyl, propyl, butyl, or pentyl, and constitutional isomers thereof; $R^7$ is —OH; and k is 1, 2, 3, or 4. In one embodiment of Formula Bii, BA is a binding agent; L is a linker; $R^1$ is methyl; $R^2$ is pentyl, and constitutional isomers thereof; $R^3$ is —C(O)$CH_3$; $R^5$ is methyl; $R^7$ is —OH; and k is 1, 2, 3, or 4. In one embodiment, conjugates of Formula B include a compound selected from the group consisting of:

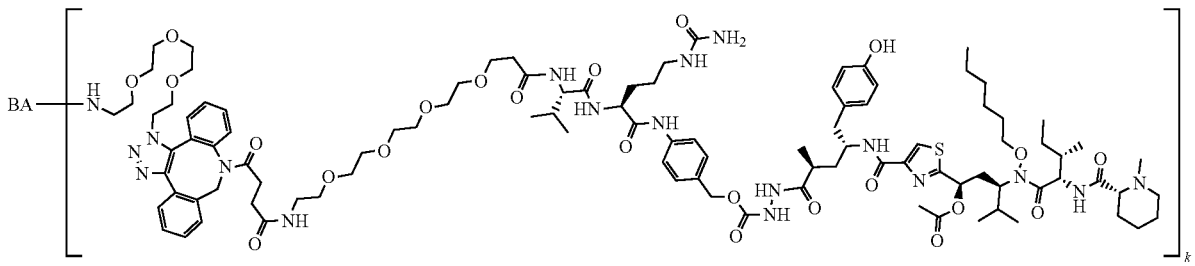

-continued and

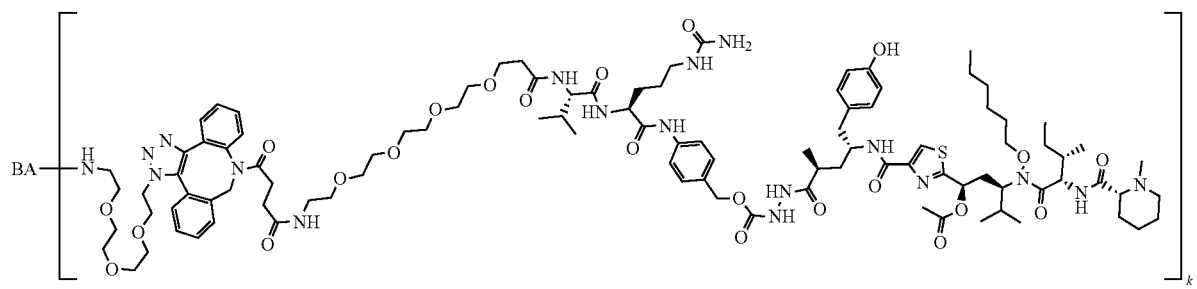

wherein BA is a binding agent; and k is 1, 2, 3, or 4. In any of the embodiments in this paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In one embodiment of Formula C, BA is a binding agent; L is a linker; Q is —$CH_2$—; $R^1$ is $C_1$-$C_{10}$ alkyl; $R^2$ is $C_5$-$C_{10}$ alkynyl; $R^3$ is —$C(O)C_1$-$C_5$ alkyl; $R^4$ and $R^5$ are, independently, $C_1$-$C_5$ alkyl; $R^6$ is —OH; $R^7$ is —NH—; $R^8$ is hydrogen; m is one; and k is 1, 2, 3, 4, 5, 6, 7, 8, 9, or 10. In one embodiment of Formula C, BA is a binding agent; L is a linker; Q is —$CH_2$—; $R^1$ is methyl, ethyl, propyl, butyl, pentyl, hexyl, heptyl, octyl, nonyl, or decyl, and constitutional isomers thereof; $R^2$ is pentynyl, hexynyl, heptynyl, octynyl, nonynyl, or decynyl; $R^3$ is —$C(O)CH_3$, —$C(O)CH_2CH_3$, —$C(O)CH_2CH_2CH_3$, —$C(O)CH_2CH_2CH_2CH_3$, or —$C(O)CH_2CH_2CH_2CH_2CH_3$; $R^4$ and $R^5$ are, independently, methyl, ethyl, propyl, butyl, or pentyl, and constitutional isomers thereof; $R^6$ is —OH; $R^7$ is —NH—; $R^8$ is hydrogen; m is one; and k is 1, 2, 3, 4, 5, 6, 7, 8, 9, or 10. In one embodiment, conjugates of Formula C include Formula Ci:

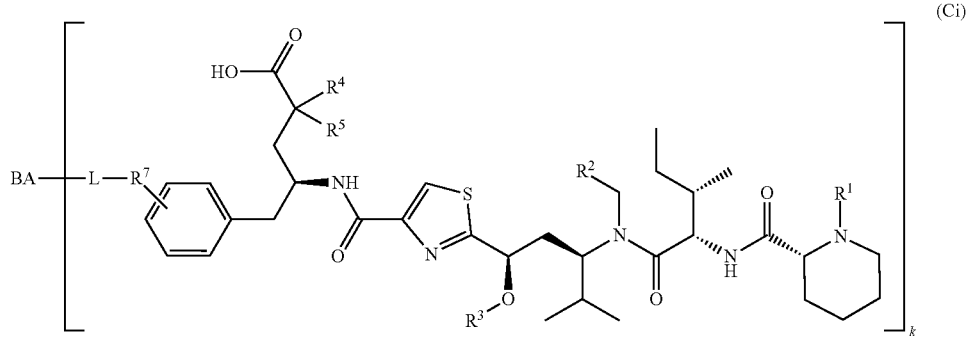

(Ci)

wherein BA is a binding agent; L is a linker; $R^1$ is methyl, ethyl, propyl, butyl, pentyl, hexyl, heptyl, octyl, nonyl, or decyl, and constitutional isomers thereof; $R^2$ is pentynyl, hexynyl, heptynyl, octynyl, nonynyl, or decynyl; $R^3$ is —$C(O)CH_3$, —$C(O)CH_2CH_3$, —$C(O)CH_2CH_2CH_3$, —$C(O)CH_2CH_2CH_2CH_3$, or —$C(O)CH_2CH_2CH_2CH_2CH_3$; $R^4$ and $R^5$ are, independently, methyl, ethyl, propyl, butyl, or pentyl, and constitutional isomers thereof; $R^7$ is —NH—; and k is 1, 2, 3, or 4. In one embodiment of Formula Ci, BA is a binding agent; L is a linker; $R^1$ is methyl; $R^2$ is pentynyl; $R^3$ is —$C(O)CH_3$; $R^4$ and $R^5$ are methyl; $R^7$ is —NH—; and k is 1, 2, 3, or 4. In one embodiment, conjugates of Formula C include a compound selected from the group consisting of:

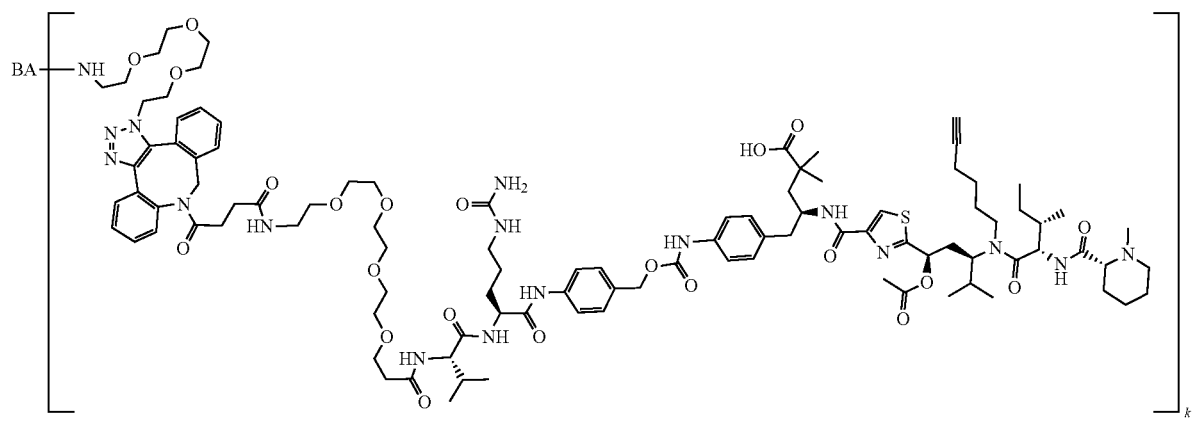

and

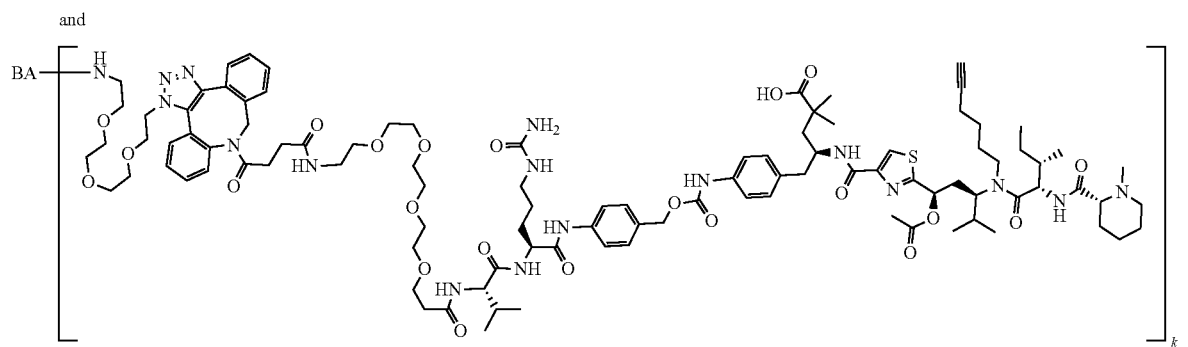

wherein BA is a binding agent; and k is 1, 2, 3, or 4. In any of the embodiments in ti paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In one embodiment of Formula C, BA is a binding agent; L is a linker; Q is —O—; $R^1$ is $C_1$-$C_{10}$ alkyl; $R^2$ is $C_5$-$C_{10}$ alkynyl; $R^3$ is —C(O)$C_1$-$C_5$ alkyl; $R^4$ and $R^5$ are, independently, $C_1$-$C_5$ alkyl; $R^6$ is —OH; $R^7$ is —NH—; $R^1$ is hydrogen; m is one; and k is 1, 2, 3, 4, 5, 6, 7, 8, 9, or 10.

In one embodiment of Formula C, BA is a binding agent; L is a linker; Q is —O—; $R^1$ is methyl, ethyl, propyl, butyl, pentyl, hexyl, heptyl, octyl, nonyl, or decyl, and constitutional isomers thereof; $R^2$ is pentynyl, hexynyl, heptynyl, octynyl, nonynyl, or decynyl; $R^3$ is —C(O)$CH_3$, —C(O)$CH_2CH_3$, —C(O)$CH_2CH_2CH_3$, —C(O)$CH_2CH_2CH_2CH_3$, or —C(O)$CH_2CH_2CH_2CH_2CH_3$; $R^4$ and $R^5$ are, independently, methyl, ethyl, propyl, butyl, or pentyl, and constitutional isomers thereof; $R^6$ is —OH; $R^7$ is —NH—; $R^1$ is hydrogen; m is one; and k is 1, 2, 3, 4, 5, 6, 7, 8, 9, or 10. In one embodiment, conjugates of Formula C include Formula Cii:

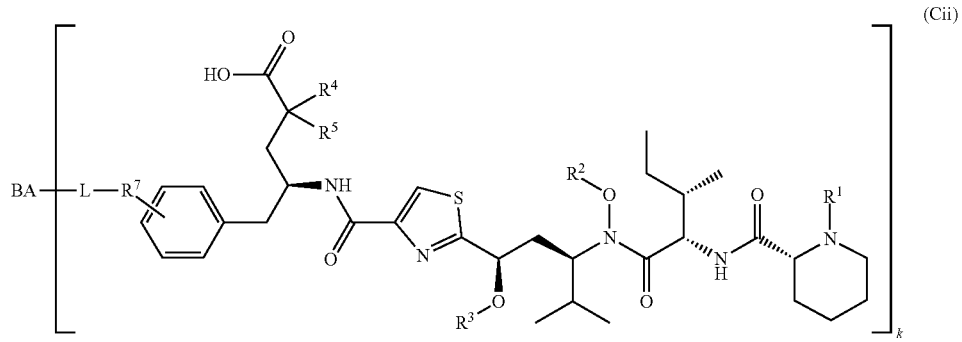

(Cii)

wherein BA is a binding agent; L is a linker; $R^1$ is methyl, ethyl, propyl, butyl, pentyl, hexyl, heptyl, octyl, nonyl, or decyl, and constitutional isomers thereof; $R^2$ is pentynyl, hexynyl, heptynyl, octynyl, nonynyl, or decynyl; $R^3$ is —C(O)CH$_3$, —C(O)CH$_2$CH$_3$, —C(O)CH$_2$CH$_2$CH$_3$, —C(O)CH$_2$CH$_2$CH$_2$CH$_3$, or —C(O)CH$_2$CH$_2$CH$_2$CH$_2$CH$_3$; $R^4$ and $R^5$ are, independently, methyl, ethyl, propyl, butyl, or pentyl, and constitutional isomers thereof; $R^7$ is —NH—; and k is 1, 2, 3, or 4. In one embodiment of Formula Cii, BA is a binding agent; L is a linker; $R^1$ is methyl; $R^2$ is pentynyl; $R^3$ is —C(O)CH$_3$; $R^4$ and $R^5$ are methyl; $R^7$ is —NH—; and k is 1, 2, 3, or 4. In one embodiment, conjugates of Formula C include a compound selected from the group consisting of:

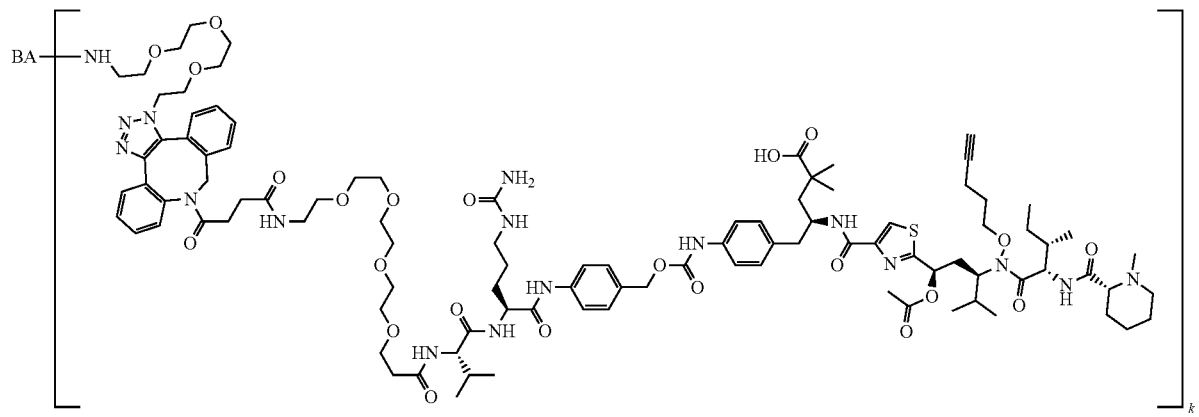

and

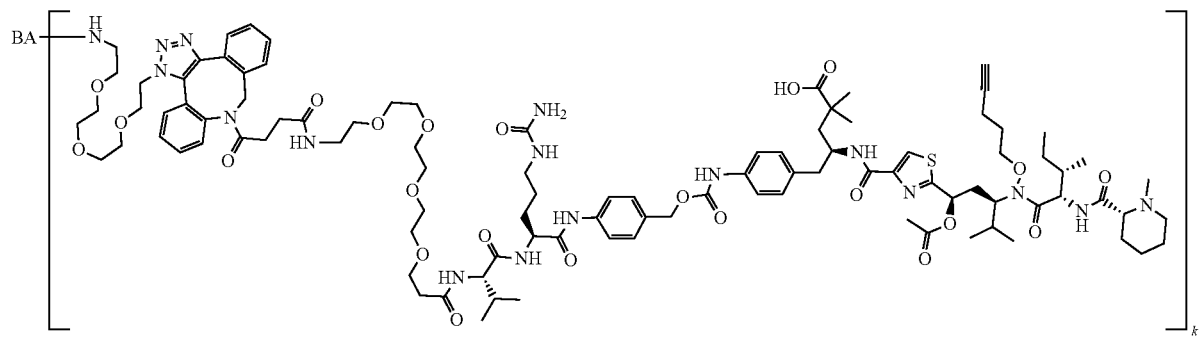

wherein BA is a binding agent; and k is 1, 2, 3, or 4. In one embodiment, conjugates of Formula C include a compound selected from the group consisting of:

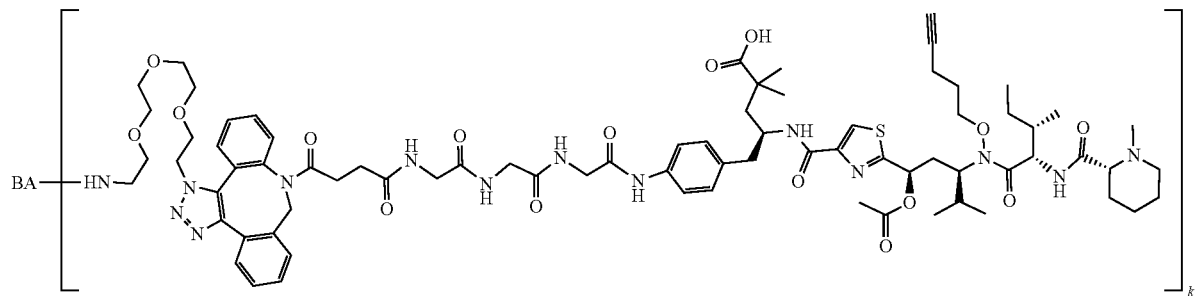

and
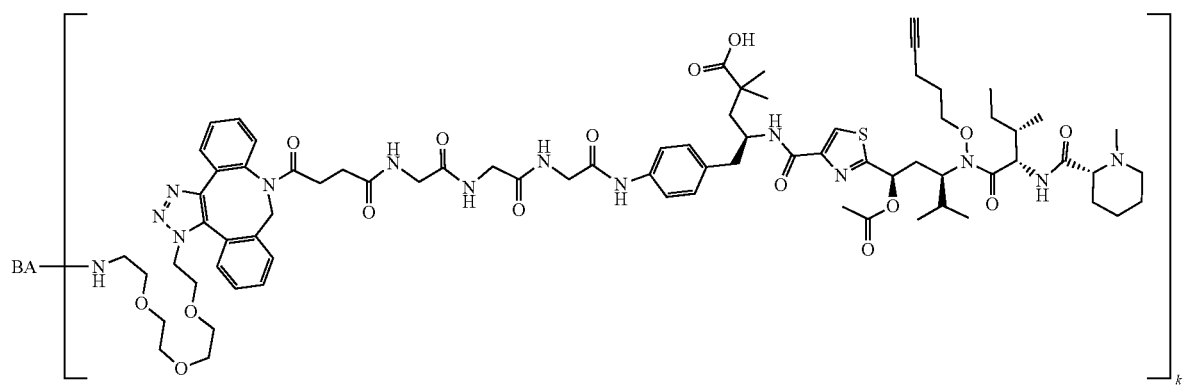
wherein BA is a binding agent; and k is 1, 2, 3, or 4. In one embodiment, conjugates of Formula C include a compound selected from the group consisting of:
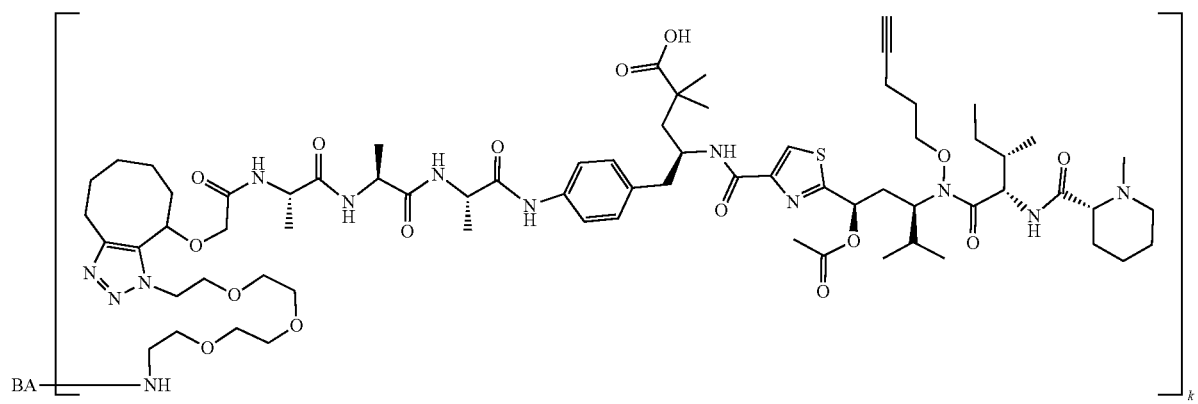
and
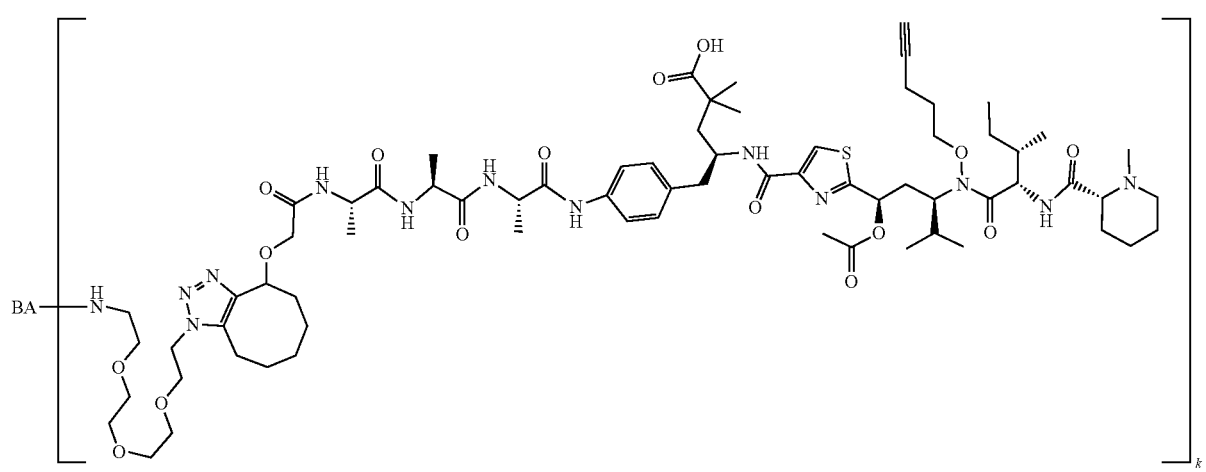

wherein BA is a binding agent; and k is 1, 2, 3, or 4. In one embodiment, conjugates of Formula C include a compound selected from the group consisting of:
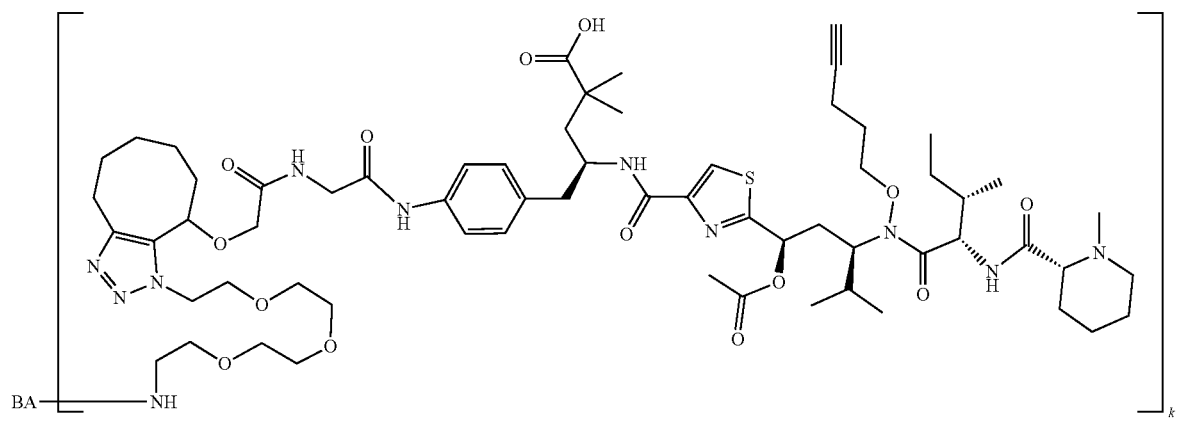
and
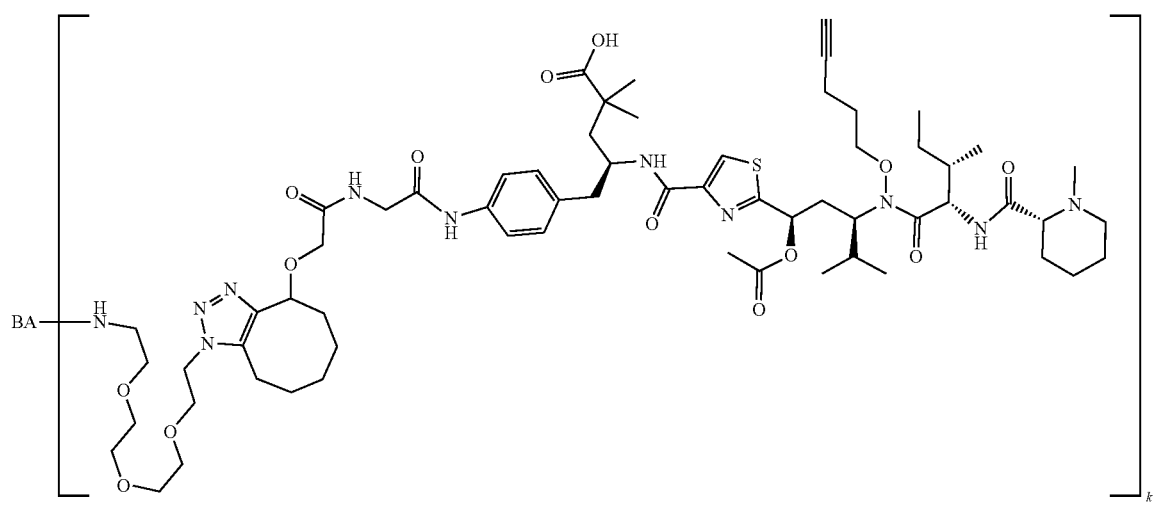
wherein BA is a binding agent; and k is 1, 2, 3, or 4. In one embodiment, conjugates of Formula C include a compound selected from the group consisting of:
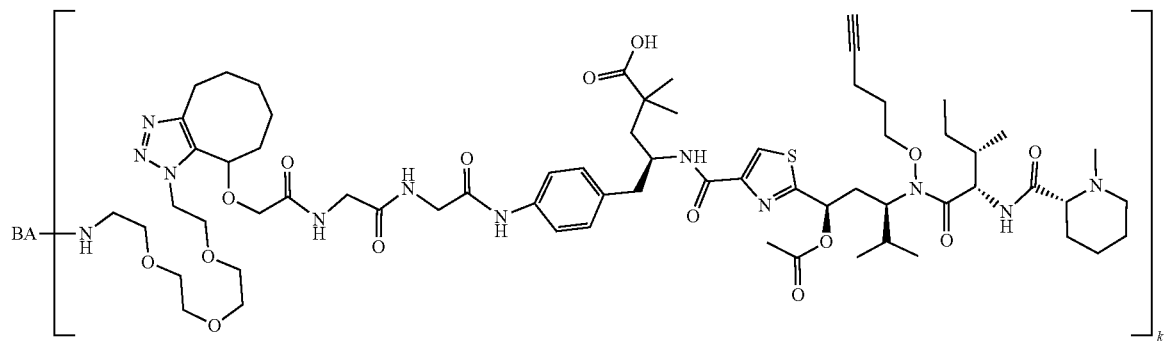

and
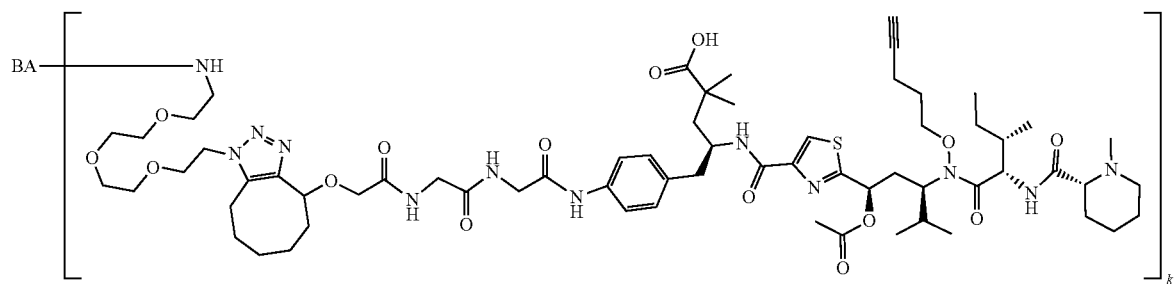
wherein BA is a binding agent; and k is 1, 2, 3, or 4. In one embodiment, conjugates of Formula C include a compound selected from the group consisting of:
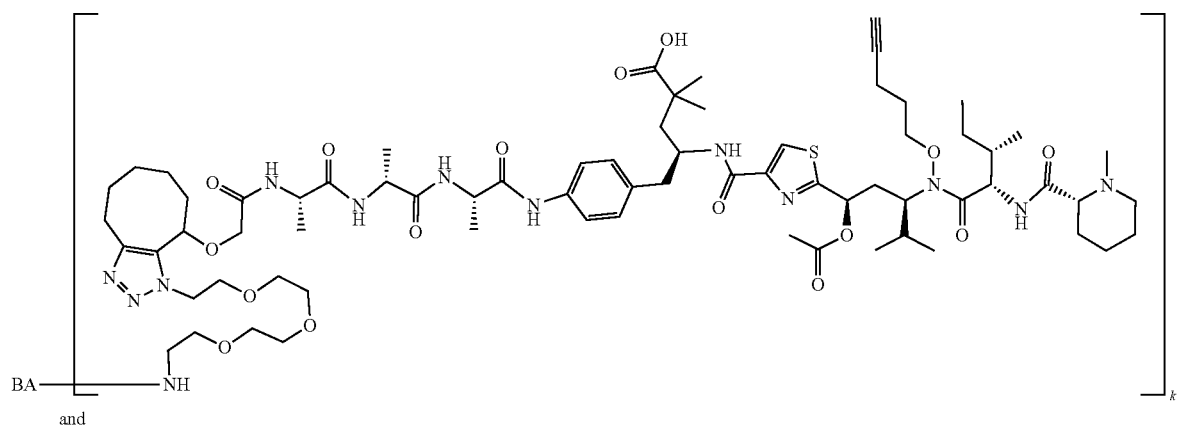
and
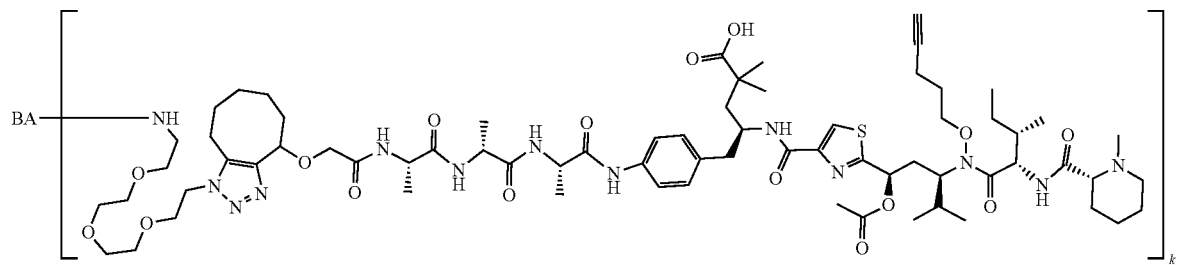
wherein BA is a binding agent; and k is 1, 2, 3, or 4. In one embodiment, conjugates of Formula C include a compound selected from the group consisting of:
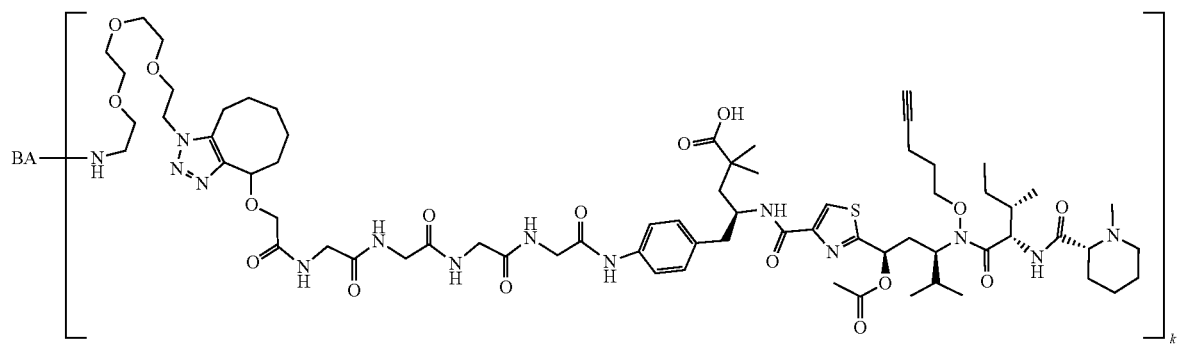

and
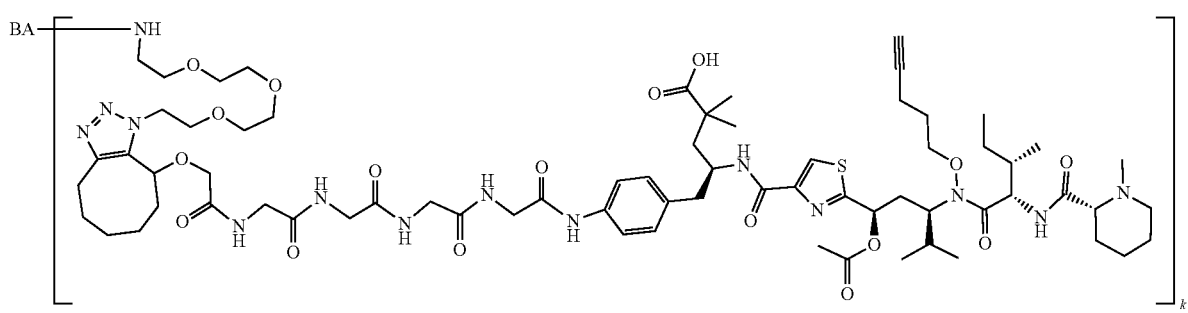
wherein BA is a binding agent; and k is 1, 2, 3, or 4. In one embodiment, conjugates of Formula C include a compound selected from the group consisting of:
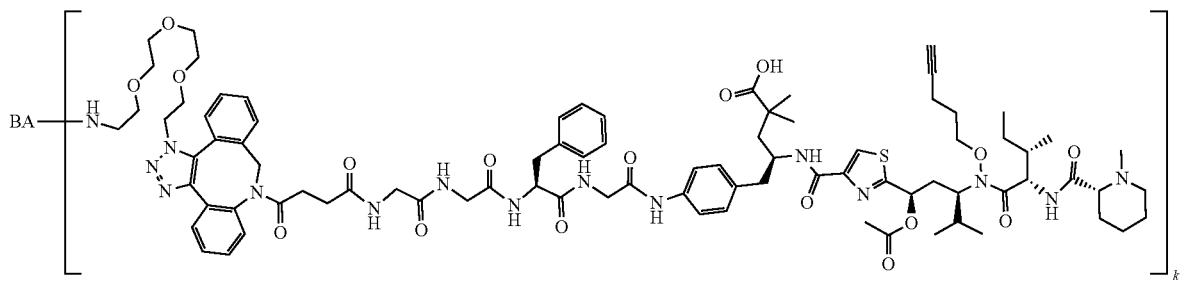
and
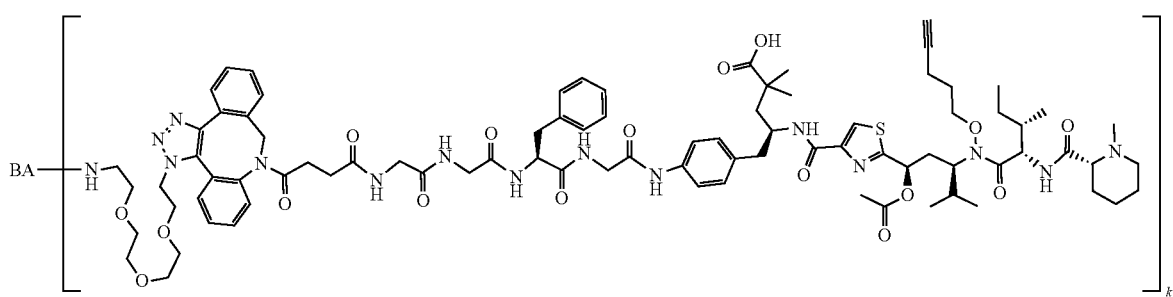
wherein BA is a binding agent; and k is 1, 2, 3, or 4. In one embodiment, conjugates of Formula C include a compound selected from the group consisting of:
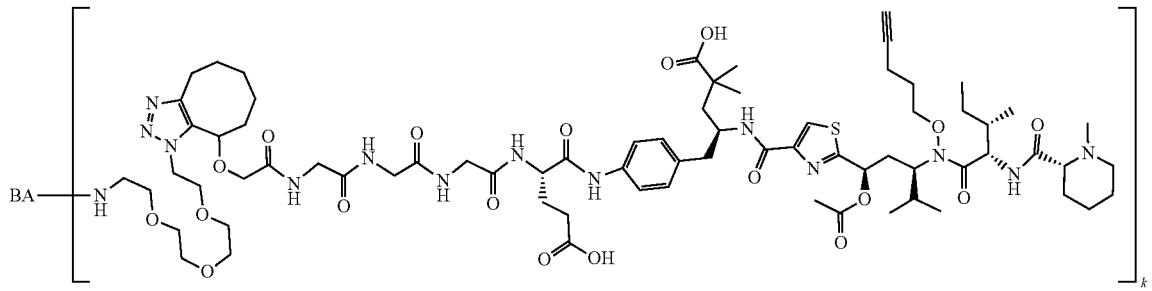

and
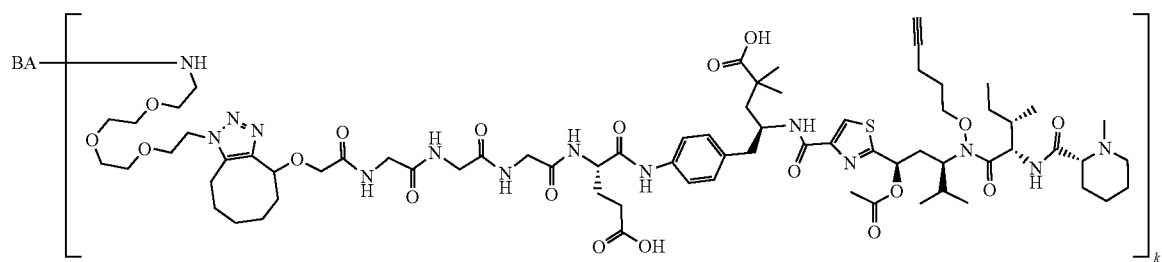
wherein BA is a binding agent; and k is 1, 2, 3, or 4. In one embodiment, conjugates of Formula C include a compound selected from the group consisting of:
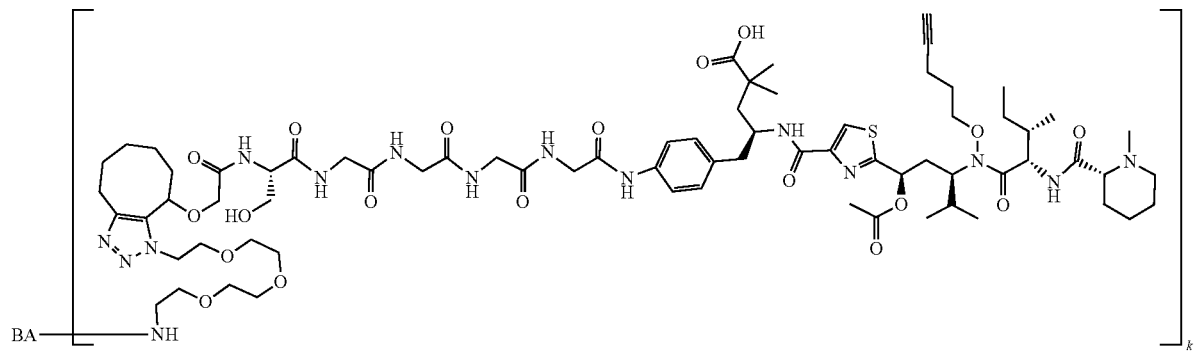
and
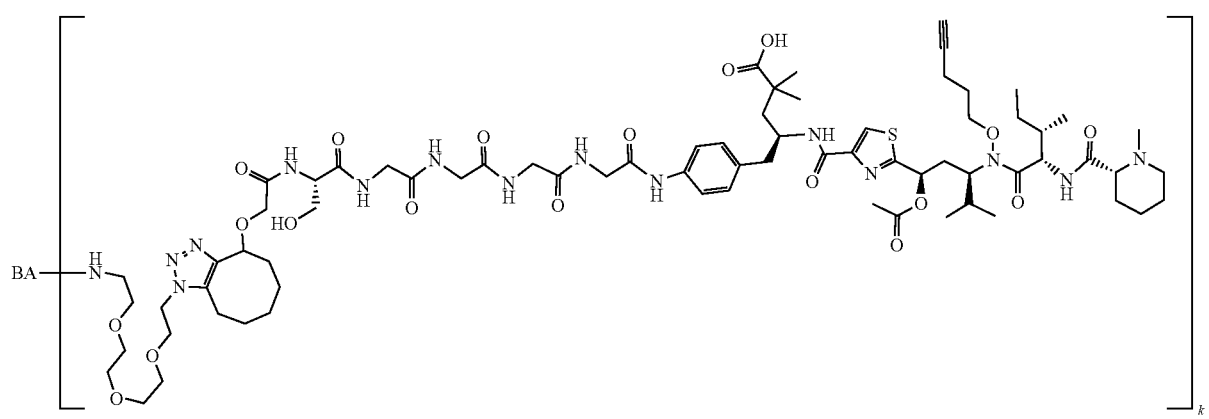

wherein BA is a binding agent; and k is 1, 2, 3, or 4. In one embodiment, conjugates of Formula C include a compound selected from the group consisting of:
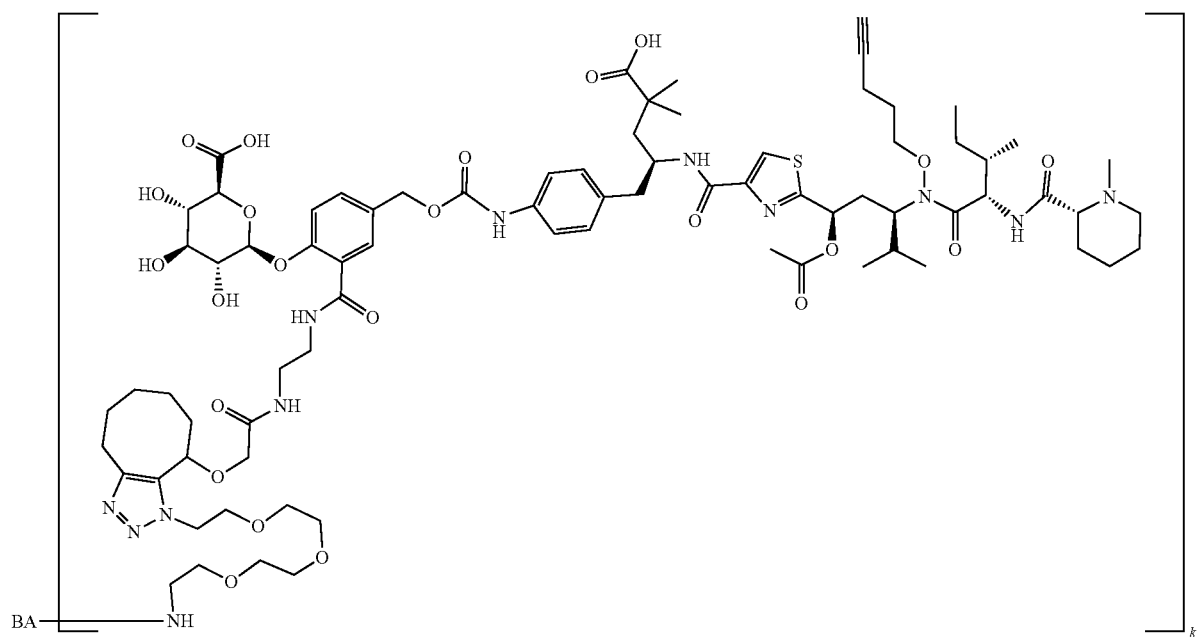
and
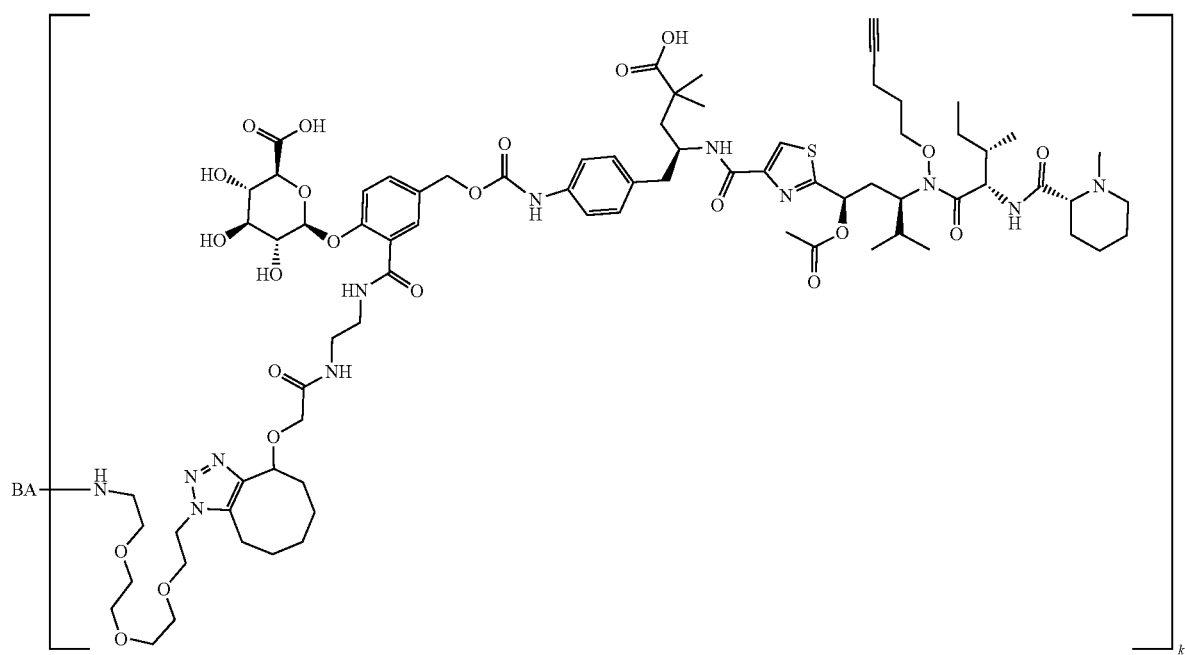

wherein BA is a binding agent; and k is 1, 2, 3, or 4. In one embodiment, conjugates of Formula C include a compound selected from the group consisting of:

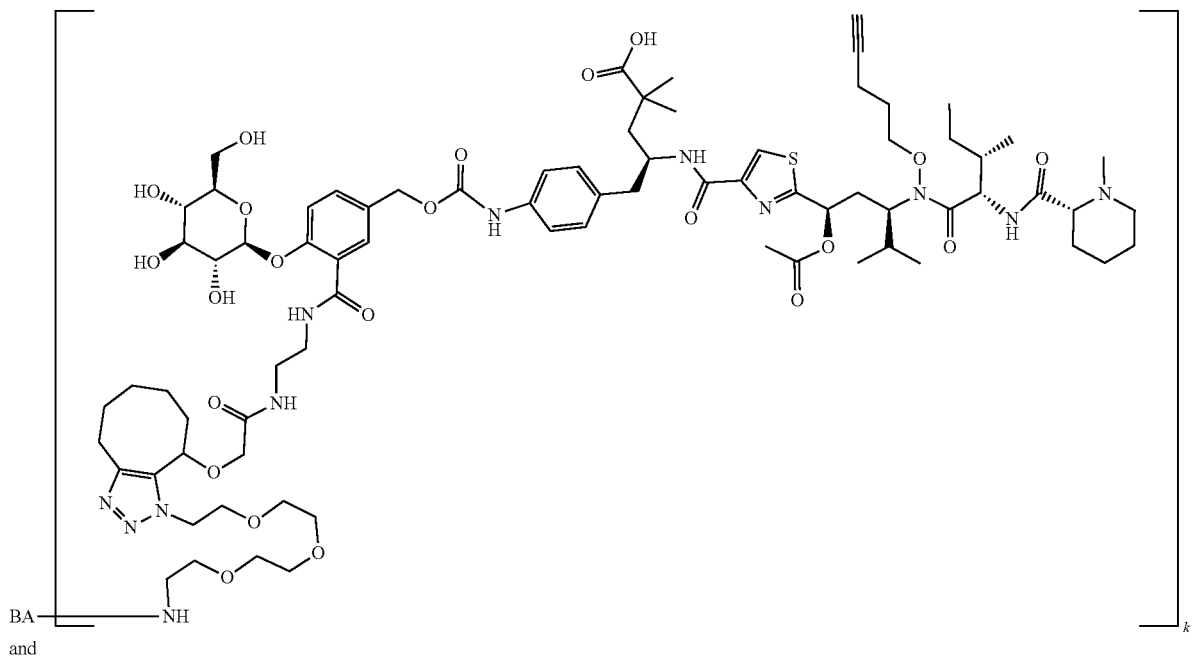

and

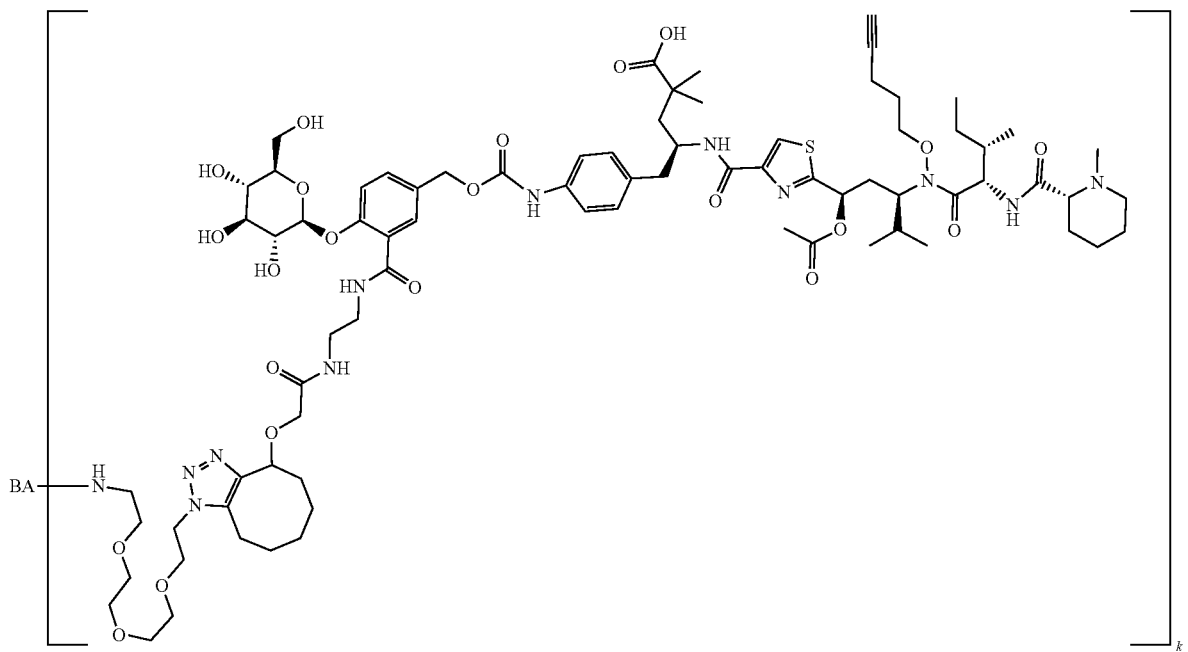

wherein BA is a binding agent; and k is 1, 2, 3, or 4. In any of the embodiments in this paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In one embodiment of Formula C, BA is a binding agent; L is a linker; Q is —CH$_2$—; R$^1$ is C$_1$-C$_{10}$ alkyl; R$^2$ is C$_5$-C$_{10}$ alkynyl; R$^3$ is —C(O)C$_1$-C$_5$ alkyl; R$^4$ and R$^5$ are, independently, C$_1$-C$_5$ alkyl; R$^6$ is —OH; R$^7$ is —NH—; R$^8$ is hydrogen; m is one; and k is 1, 2, 3, 4, 5, 6, 7, 8, 9, or 10.

In one embodiment of Formula C, BA is a binding agent; L is a linker; Q is —CH$_2$—; R$^1$ is methyl, ethyl, propyl, butyl, pentyl, hexyl, heptyl, octyl, nonyl, or decyl, and constitutional isomers thereof; R$^2$ is pentynyl, hexynyl, heptynyl, octynyl, nonynyl, or decynyl; R$^3$ is —C(O)CH$_3$, —C(O)CH$_2$CH$_3$, —C(O)CH$_2$CH$_2$CH$_3$, —C(O)CH$_2$CH$_2$CH$_2$CH$_3$, or —C(O)CH$_2$CH$_2$CH$_2$CH$_2$CH$_3$; R$^4$ and R$^5$ are, independently, methyl, ethyl, propyl, butyl, or pentyl, and constitutional isomers thereof; R$^6$ is —OH; R$^7$ is —NH—; R$^8$ is hydrogen; m is one; and k is 1, 2, 3, 4, 5, 6, 7, 8, 9, or 10. In one embodiment, conjugates of Formula C include Formula Ci:

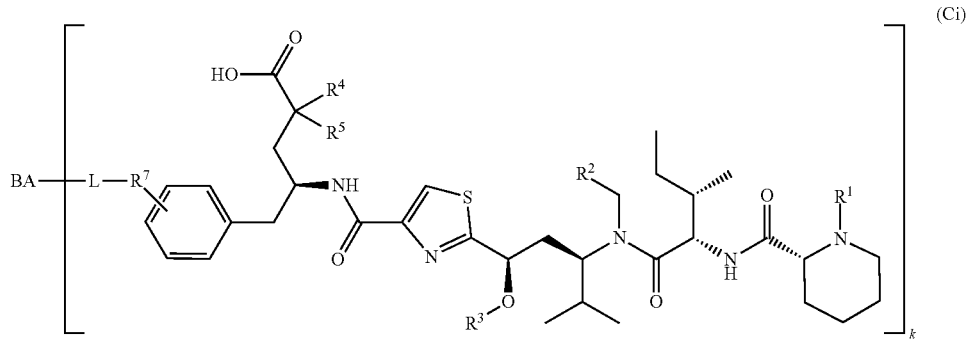

(Ci)

wherein BA is a binding agent; L is a linker; $R^1$ is methyl, ethyl, propyl, butyl, pentyl, hexyl, heptyl, octyl, nonyl, or decyl, and constitutional isomers thereof; $R^2$ is pentynyl, hexynyl, heptynyl, octynyl, nonynyl, or decynyl; $R^3$ is —C(O)CH₃, —C(O)CH₂CH₃, —C(O)CH₂CH₂CH₃, —C(O)CH₂CH₂CH₂CH₃, or —C(O)CH₂CH₂CH₂CH₂CH₃; $R^4$ and $R^5$ are, independently, methyl, ethyl, propyl, butyl, or pentyl, and constitutional isomers thereof; $R^7$ is —NH—; and k is 1, 2, 3, or 4. In one embodiment of Formula Ci, BA is a binding agent; L is a linker; $R^1$ is methyl; $R^2$ is pentynyl; $R^3$ is —C(O)CH₃; $R^4$ and $R^5$ are methyl; $R^7$ is —NH—; and k is 1, 2, 3, or 4. In one embodiment, conjugates of Formula C include a compound selected from the group consisting of:

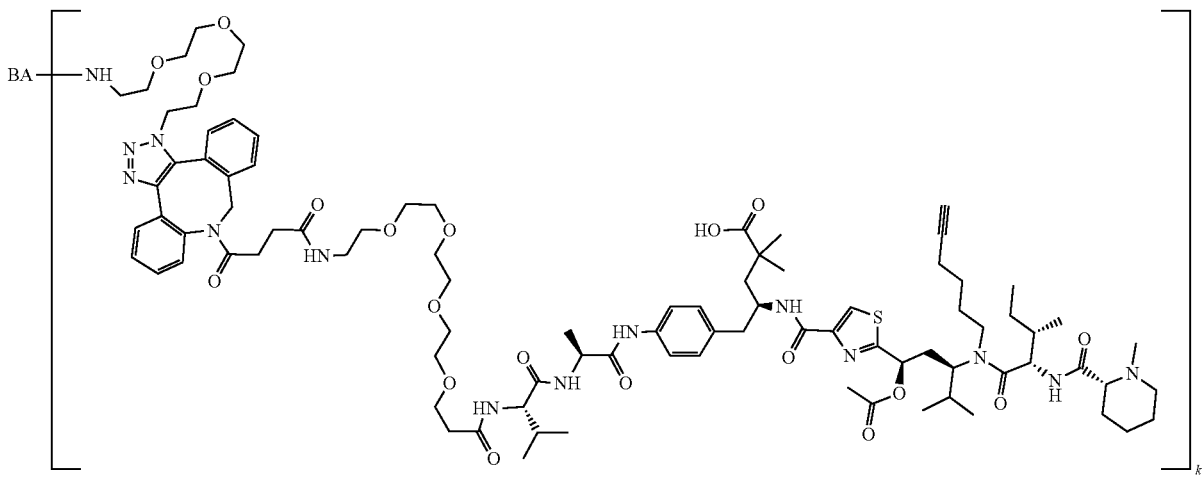

and

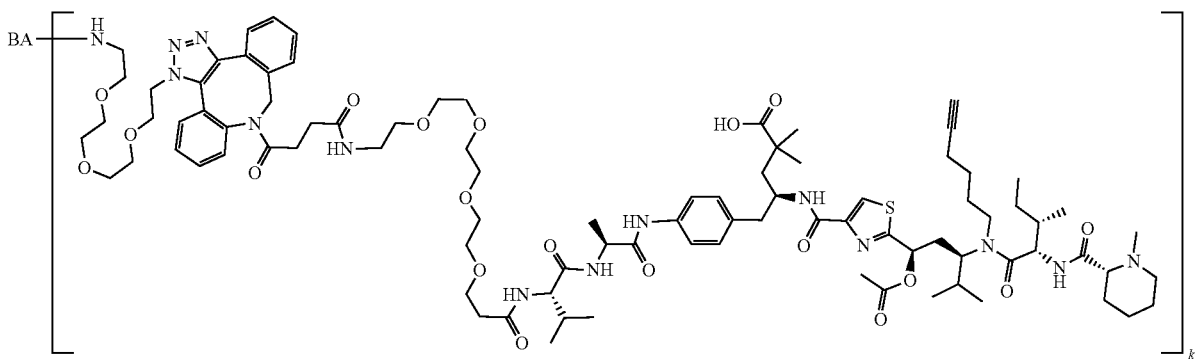

wherein BA is a binding agent; and k is 1, 2, 3, or 4. In any of the embodiments in this paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In one embodiment of Formula C, BA is a binding agent; L is a linker; Q is —O—; $R^1$ is $C_1$-$C_{10}$ alkyl; $R^2$ is $C_5$-$C_{10}$ alkyl; $R^3$ is —C(O)$C_1$-$C_5$ alkyl; $R^4$ and $R^5$ are, independently, $C_1$-$C_5$ alkyl; $R^6$ is —OH; $R^7$ is —NH—; $R^8$ is hydrogen; m is one; and k is 1, 2, 3, 4, 5, 6, 7, 8, 9, or 10. In one embodiment of Formula C, BA is a binding agent; L is a linker; Q is —O—; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl, and constitutional isomers thereof; $R^3$ is —C(O)$CH_3$, —C(O)$CH_2CH_3$, —C(O)$CH_2CH_2CH_3$, —C(O)$CH_2CH_2CH_2CH_3$, or —C(O)$CH_2CH_2CH_2CH_2CH_3$; $R^4$ and $R^5$ are, independently, methyl, ethyl, propyl, butyl, or pentyl, and constitutional isomers thereof; $R^6$ is —OH; $R^7$ is —NH—; $R^8$ is hydrogen; m is one; and k is 1, 2, 3, 4, 5, 6, 7, 8, 9, or 10. In one embodiment, conjugates of Formula C include Formula Cii:

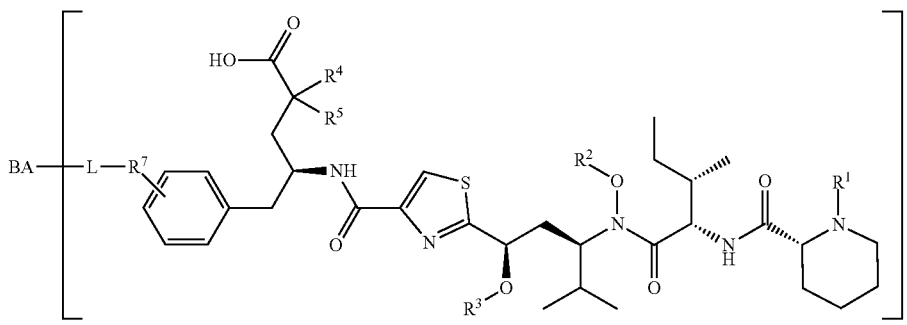

wherein BA is a binding agent; L is a linker; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl, and constitutional isomers thereof; $R^3$ is —C(O)$CH_3$, —C(O)$CH_2CH_3$, —C(O)$CH_2CH_2CH_3$, —C(O)$CH_2CH_2CH_2CH_3$, or —C(O)$CH_2CH_2CH_2CH_2CH_3$; $R^4$ and $R^5$ are, independently, methyl, ethyl, propyl, butyl, or pentyl, and constitutional isomers thereof; $R^7$ is —NH—; and k is 1, 2, 3, or 4. In one embodiment of Formula Cii, BA is a binding agent; L is a linker; $R^1$ is methyl; $R^2$ is pentyl; $R^3$ is —C(O)$CH_3$; $R^4$ and $R^5$ are methyl; $R^7$ is —NH—; and k is 1, 2, 3, or 4. In one embodiment, conjugates of Formula C include a compound selected from the group consisting of:

221
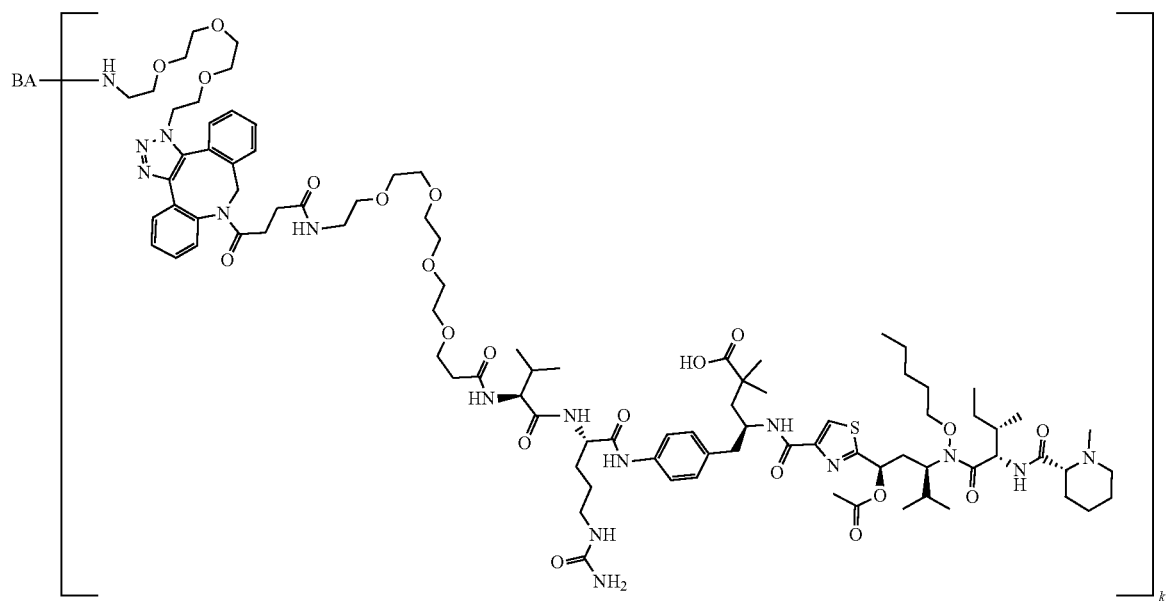
222
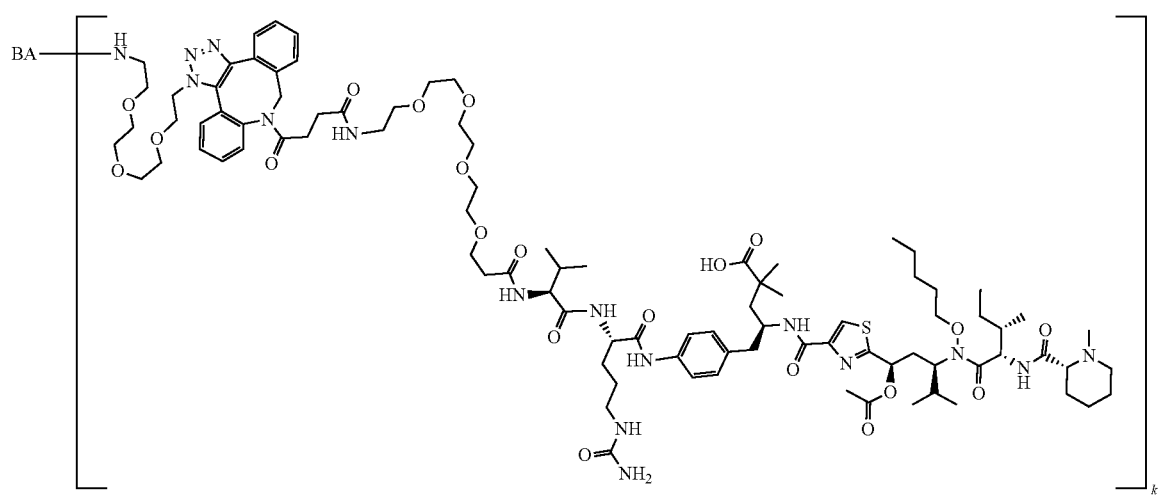
wherein BA is a binding agent; and k is 1, 2, 3, or 4. In one embodiment, conjugates of Formula C include a compound selected from the group consisting of:
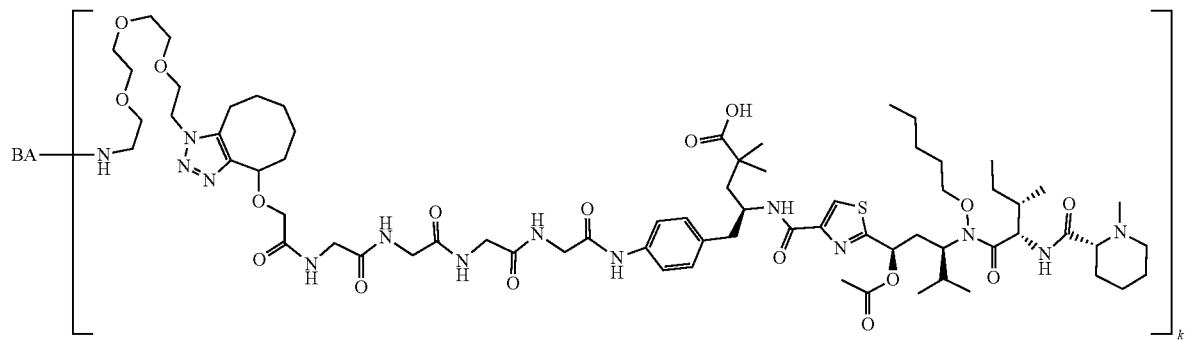

and

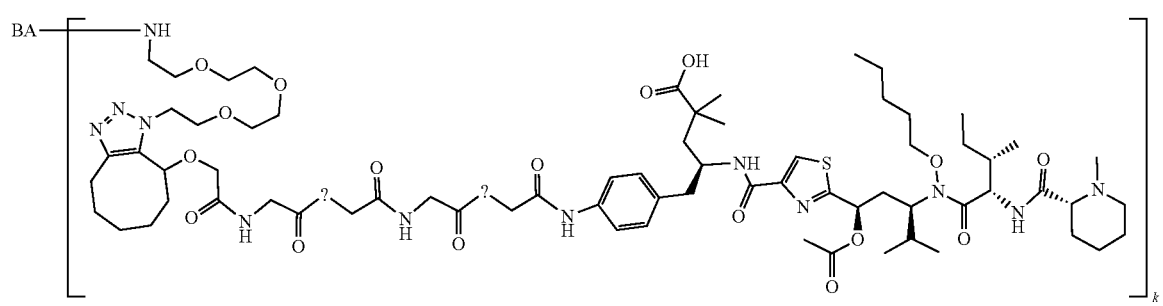

wherein BA is a binding agent; and k is 1, 2, 3, or 4. In one embodiment, conjugates of Formula C include a compound selected from the group consisting of:

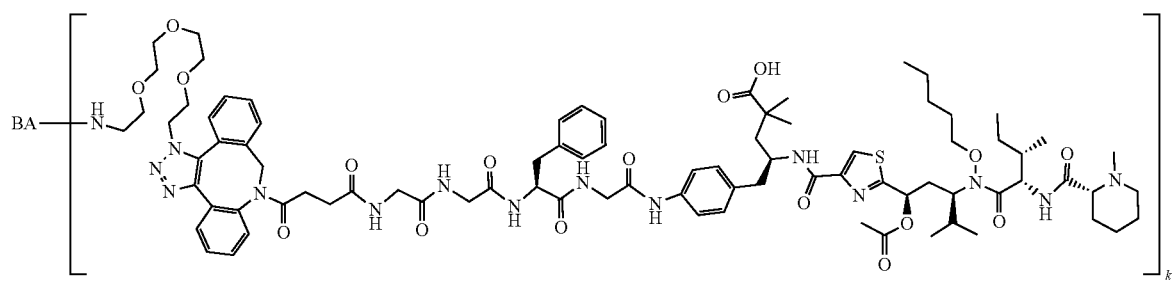

and

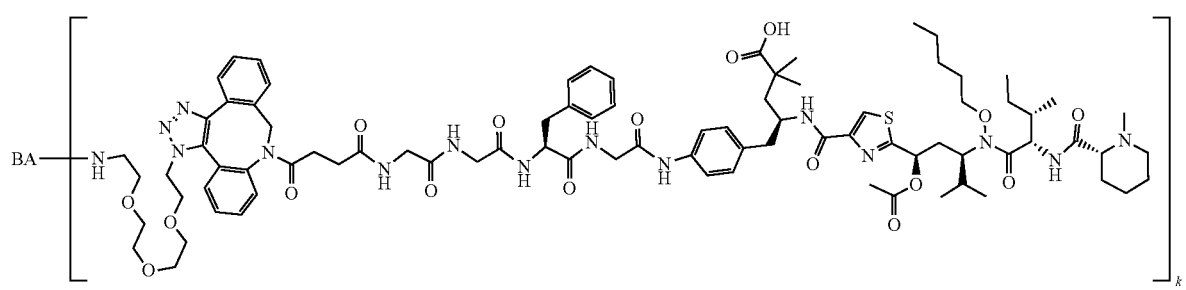

wherein BA is a binding agent; and k is 1, 2, 3, or 4. In any of the embodiments in this paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In one embodiment of Formula C, BA is a binding agent; L is a linker; Q is —$CH_2$—; $R^1$ is $C_1$-$C_{10}$ alkyl; $R^2$ is $C_5$-$C_{10}$ alkynyl; $R^3$ is —$C(O)C_1$-$C_5$ alkyl; $R^4$ and $R^5$ are, independently, $C_1$-$C_5$ alkyl; $R^6$ is —OH; $R^7$ is —NH—; $R^8$ is hydrogen; m is one; and k is 1, 2, 3, 4, 5, 6, 7, 8, 9, or 10.

In one embodiment of Formula C, BA is a binding agent; L is a linker; Q is —$CH_2$—; $R^1$ is methyl, ethyl, propyl, butyl, pentyl, hexyl, heptyl, octyl, nonyl, or decyl, and constitutional isomers thereof; $R^2$ is pentynyl, hexynyl, heptynyl, octynyl, nonynyl, or decynyl; $R^3$ is —$C(O)CH_3$, —$C(O)CH_2CH_3$, —$C(O)CH_2CH_2CH_3$, —$C(O)CH_2CH_2CH_2CH_3$, or —$C(O)CH_2CH_2CH_2CH_2CH_3$; $R^4$ and $R^5$ are, independently, methyl, ethyl, propyl, butyl, or pentyl, and constitutional isomers thereof; $R^6$ is —OH; $R^7$ is —NH—; $R^8$ is hydrogen; m is one; and k is 1, 2, 3, 4, 5, 6, 7, 8, 9, or 10. In one embodiment, conjugates of Formula C include Formula Ci:

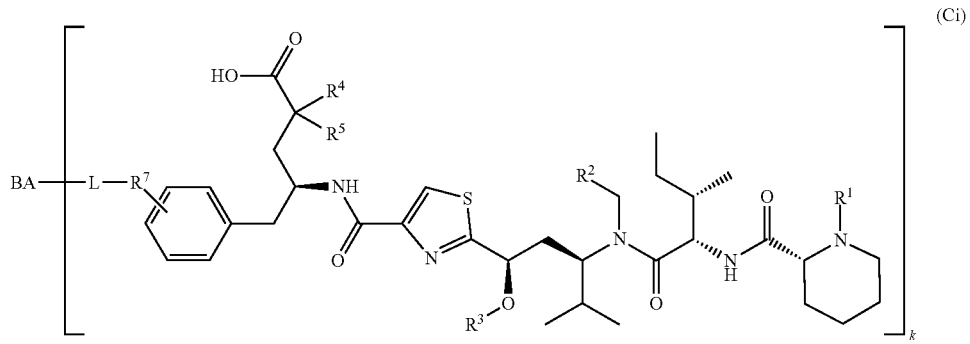

wherein BA is a binding agent; L is a linker; $R^1$ is methyl, ethyl, propyl, butyl, pentyl, hexyl, heptyl, octyl, nonyl, or decyl, and constitutional isomers thereof; $R^2$ is pentynyl, hexynyl, heptynyl, octynyl, nonynyl, or decynyl; $R^3$ is —C(O)CH$_3$, —C(O)CH$_2$CH$_3$, —C(O)CH$_2$CH$_2$CH$_3$, —C(O)CH$_2$CH$_2$CH$_2$CH$_3$, or —C(O)CH$_2$CH$_2$CH$_2$CH$_2$CH$_3$; $R^4$ and $R^5$ are, independently, methyl, ethyl, propyl, butyl, or pentyl, and constitutional isomers thereof; $R^7$ is —NH—; and k is 1, 2, 3, or 4. In one embodiment of Formula Ci, BA is a binding agent; L is a linker; $R^1$ is methyl; $R^2$ is pentynyl; $R^3$ is —C(O)CH$_3$; $R^4$ and $R^5$ are methyl; $R^7$ is —NH—; and k is 1, 2, 3, or 4. In one embodiment, conjugates of Formula C include a compound selected from the group consisting of:

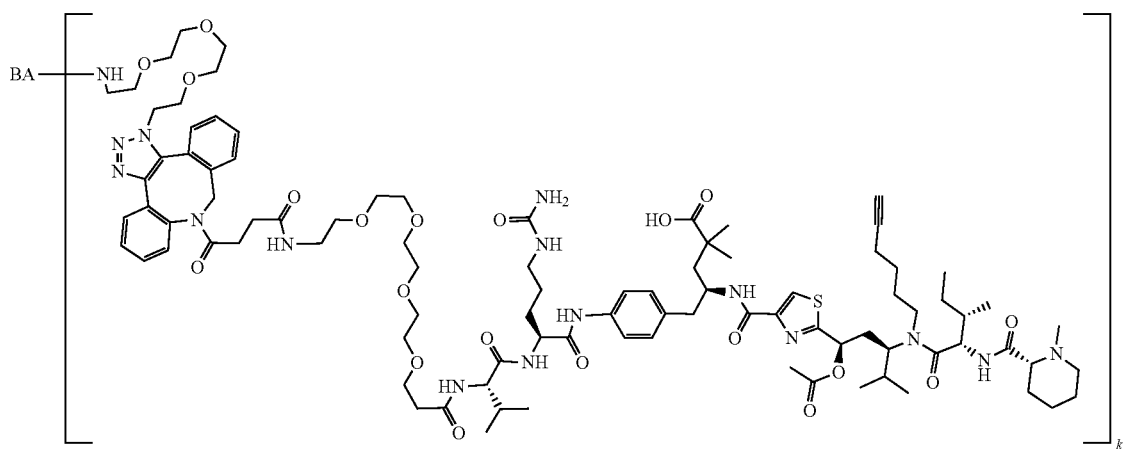

and

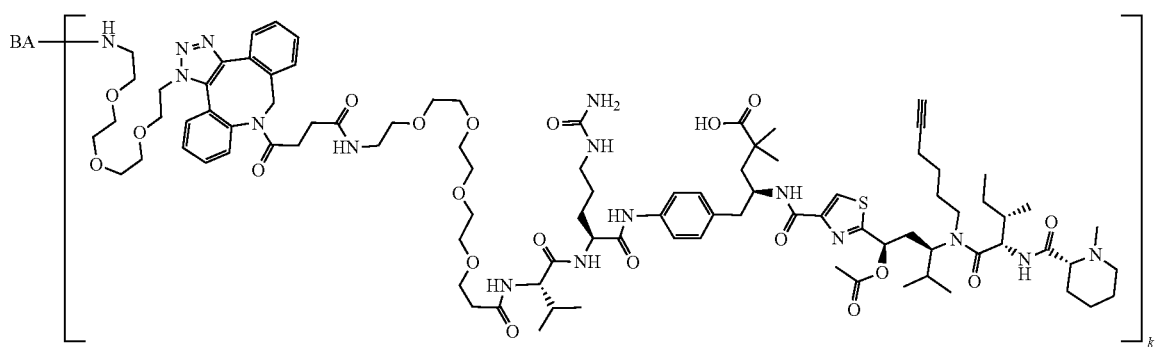

wherein BA is a binding agent; and k is 1, 2, 3, or 4. In any of the embodiments in this paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In one embodiment of Formula C, BA is a binding agent; L is a linker; Q is —$CH_2$—; $R^1$ is $C_1$-$C_{10}$ alkyl; $R^2$ is $C_5$-$C_{10}$ alkyl; $R^3$ is —$C(O)C_1$-$C_5$ alkyl; $R^4$ and $R^5$ are, independently, $C_1$-$C_5$ alkyl; $R^6$ is —OH; $R^7$ is —NH—; $R^1$ is halogen; m is one; and k is 1, 2, 3, 4, 5, 6, 7, 8, 9, or 10. In one embodiment of Formula C, BA is a binding agent; L is a linker; Q is —$CH_2$—; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl; $R^3$ is —$C(O)CH_3$, —$C(O)CH_2CH_3$, —$C(O)CH_2CH_2CH_3$, —$C(O)CH_2CH_2CH_2CH_3$, or —$C(O)CH_2CH_2CH_2CH_2CH_3$; $R^4$ and $R^5$ are, independently, methyl, ethyl, propyl, butyl, or pentyl, and constitutional isomers thereof; $R^6$ is —OH; $R^7$ is —NH—; $R^8$ is halogen; m is one; and k is 1, 2, 3, 4, 5, 6, 7, 8, 9, or 10. In one embodiment, conjugates of Formula C include Formula Ciii:

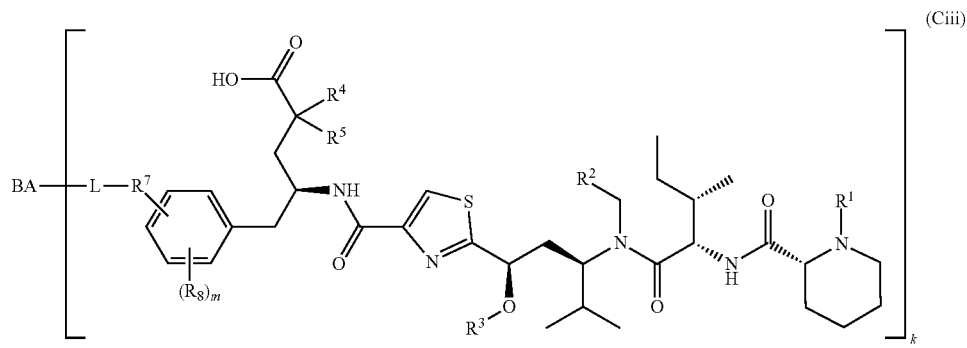

wherein BA is a binding agent; L is a linker; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl; $R^3$ is —$C(O)CH_3$, —$C(O)CH_2CH_3$, —$C(O)CH_2CH_2CH_3$, —$C(O)CH_2CH_2CH_2CH_3$, or —$C(O)CH_2CH_2CH_2CH_2CH_3$; $R^4$ and $R^5$ are, independently, methyl, ethyl, propyl, butyl, or pentyl, and constitutional isomers thereof; $R^7$ is —NH—; $R^8$ is halogen; m is one; and k is 1, 2, 3, or 4. In one embodiment of Formula Ciii, BA is a binding agent; L is a linker; $R^1$ is methyl; $R^2$ is pentyl; $R^3$ is —$C(O)CH_3$; $R^4$ and $R^5$ are methyl; $R^7$ is —NH—; $R^8$ is halogen; m is one; and k is 1, 2, 3, or 4. In one embodiment, conjugates of Formula C include a compound selected from the group consisting of:

229
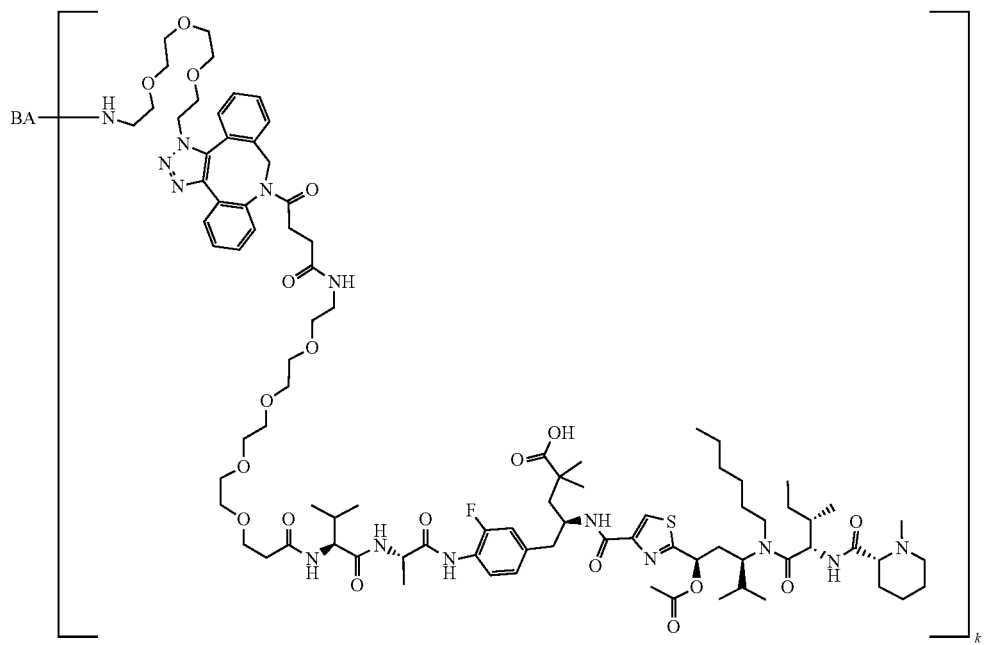
and
230
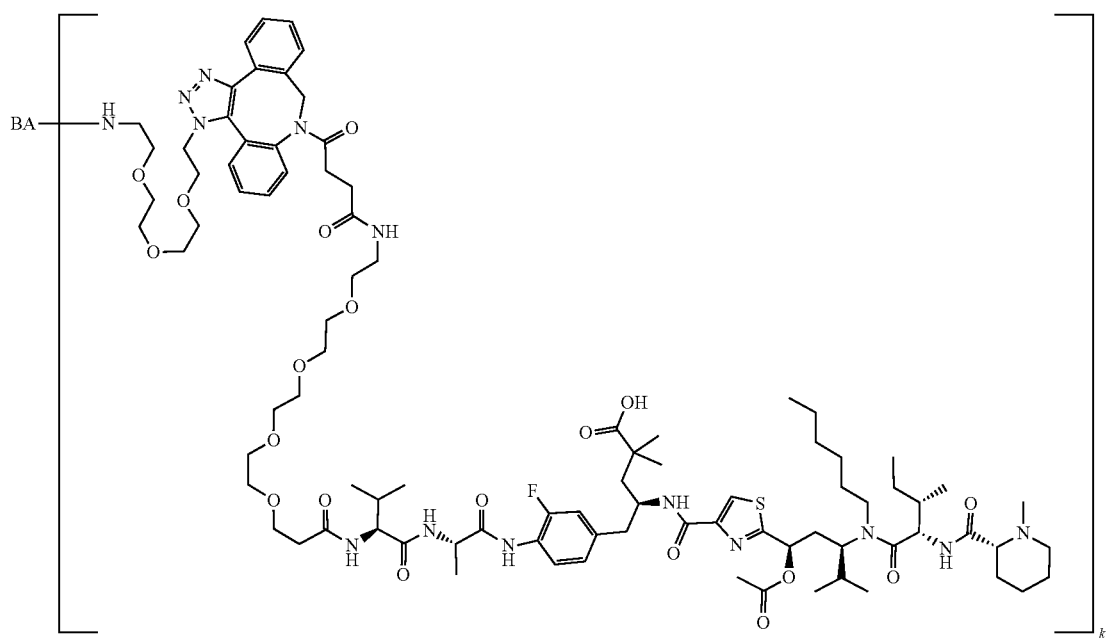

wherein BA is a binding agent; and k is 1, 2, 3, or 4. In one embodiment, conjugates of Formula C include

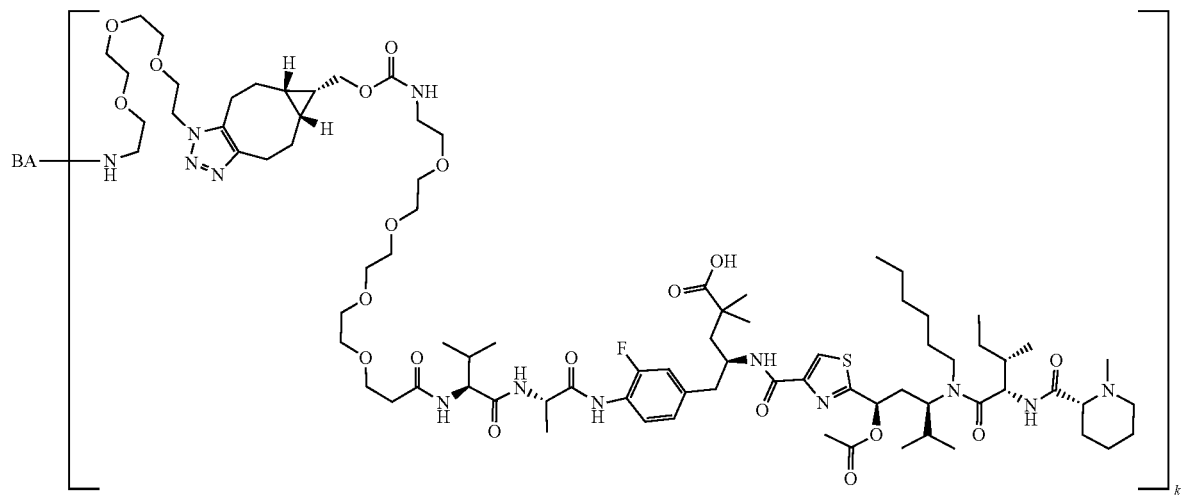

wherein BA is a binding agent; and k is 1, 2, 3, or 4. In any of the embodiments in this paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In one embodiment of Formula C, BA is a binding agent; L is a linker; Q is —O—; $R^1$ is $C_1$-$C_{10}$ alkyl; $R^2$ is $C_5$-$C_{10}$ alkyl; $R^3$ is —C(O)N(H)$C_1$-$C_{10}$ alkyl; $R^4$ and $R^5$ are, independently, $C_1$-$C_5$ alkyl; $R^6$ is —OH; $R^7$ is —NH—; $R^8$ is hydrogen; m is one; and k is 1, 2, 3, 4, 5, 6, 7, 8, 9, or 10.

In one embodiment of Formula C, BA is a binding agent; L is a linker; Q is —O—; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl, and constitutional isomers thereof; $R^3$ is —C(O)N(H)$CH_3$, —C(O)N(H)$CH_2CH_3$, —C(O)N(H)$CH_2CH_2CH_3$, —C(O)N(H)$CH_2CH_2CH_2CH_3$, or —C(O)N(H)$CH_2CH_2CH_2CH_2CH_3$; $R^4$ and $R^5$ are, independently, methyl, ethyl, propyl, butyl, or pentyl, and constitutional isomers thereof; $R^6$ is —OH; $R^7$ is —NH—; $R^8$ is hydrogen; m is one; and k is 1, 2, 3, 4, 5, 6, 7, 8, 9, or 10. In one embodiment, conjugates of Formula C include Formula Cii:

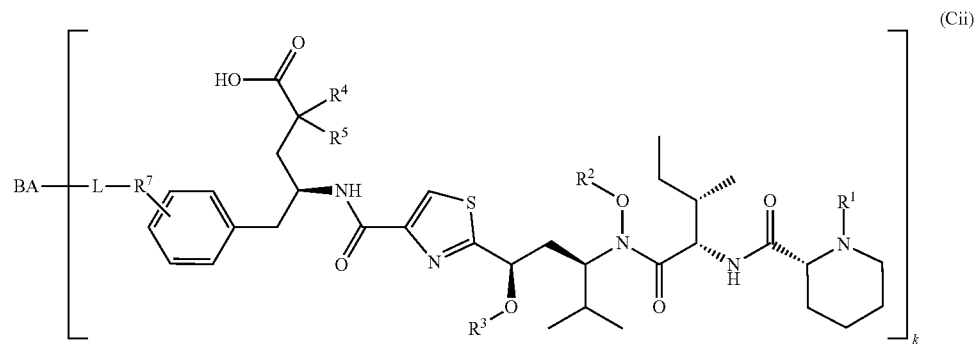

(Cii)

wherein BA is a binding agent; L is a linker; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl, and constitutional isomers thereof; $R^3$ is —C(O)N(H)CH$_3$, —C(O)N(H)CH$_2$CH$_3$, —C(O)N(H)CH$_2$CH$_2$CH$_3$, —C(O)N(H)CH$_2$CH$_2$CH$_2$CH$_3$, or —C(O)N(H)CH$_2$CH$_2$CH$_2$CH$_2$CH$_3$; $R^4$ and $R^5$ are, independently, methyl, ethyl, propyl, butyl, or pentyl, and constitutional isomers thereof; $R^7$ is —NH—; and k is 1, 2, 3, or 4. In one embodiment of Formula Cii, BA is a binding agent; L is a linker; $R^1$ is methyl; $R^2$ is pentyl; $R^3$ is —C(O)N(H)CH$_3$; $R^4$ and $R^5$ are methyl; $R^7$ is —NH—; and k is 1, 2, 3, or 4. In one embodiment, conjugates of Formula C include a compound selected from the group consisting of:

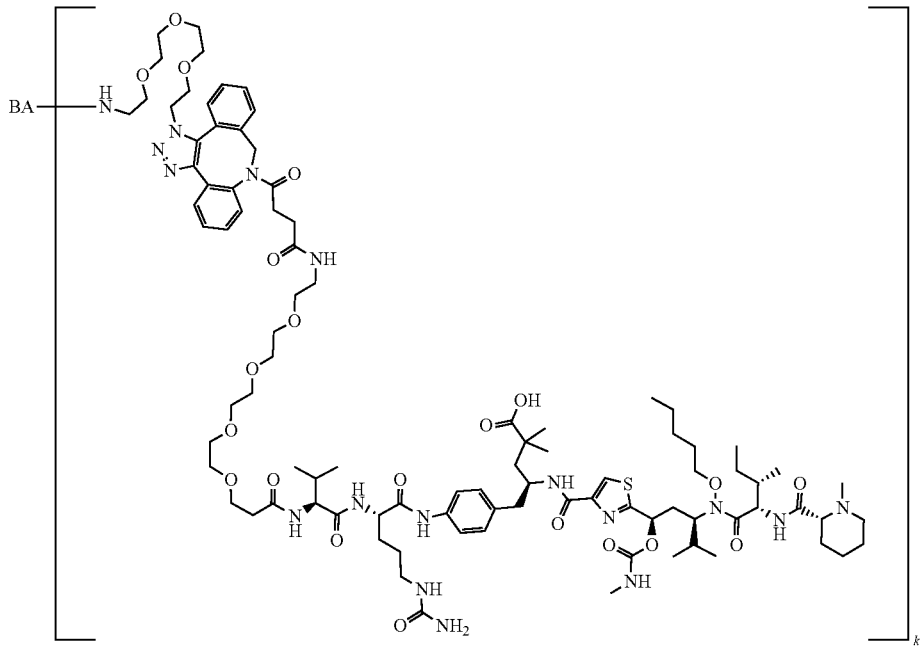

and

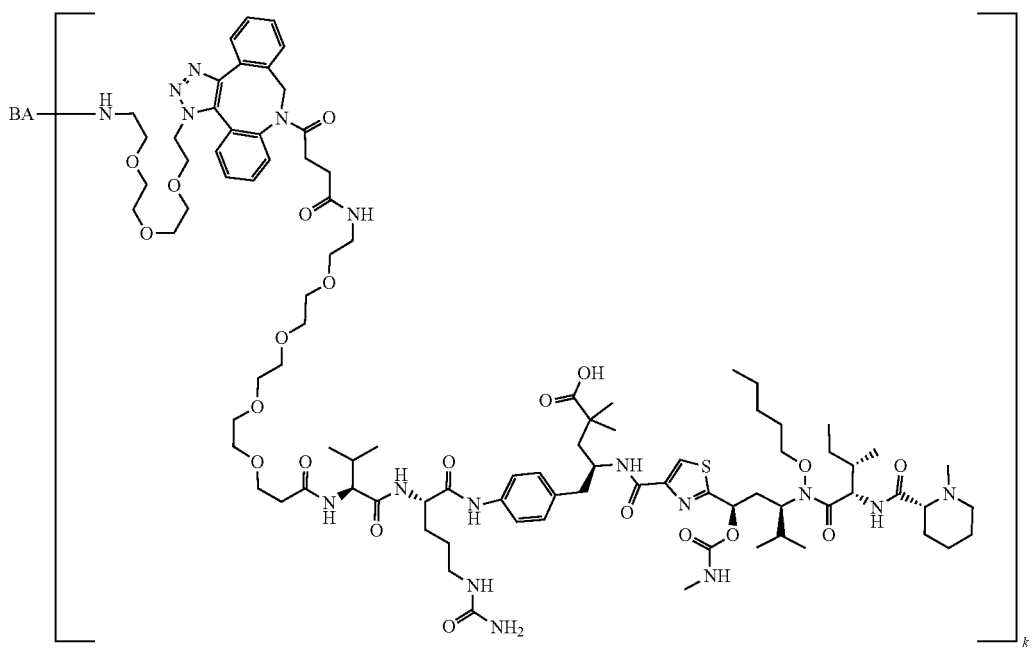

wherein BA is a binding agent; and k is 1, 2, 3, or 4. In one embodiment, conjugates of Formula C include a compound selected from the group consisting of:

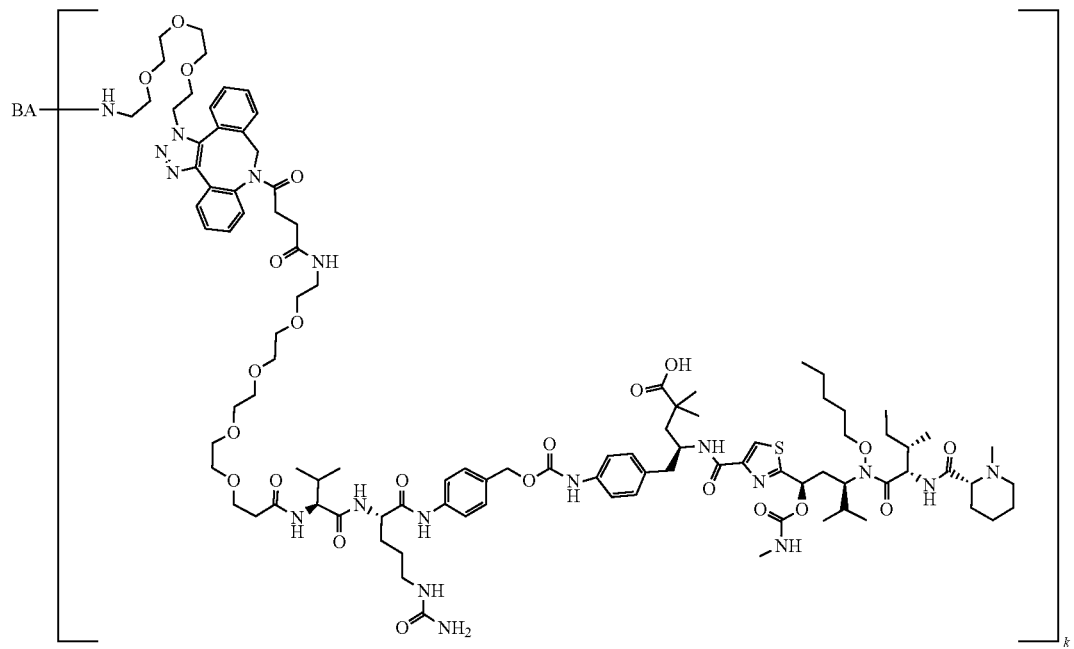

and

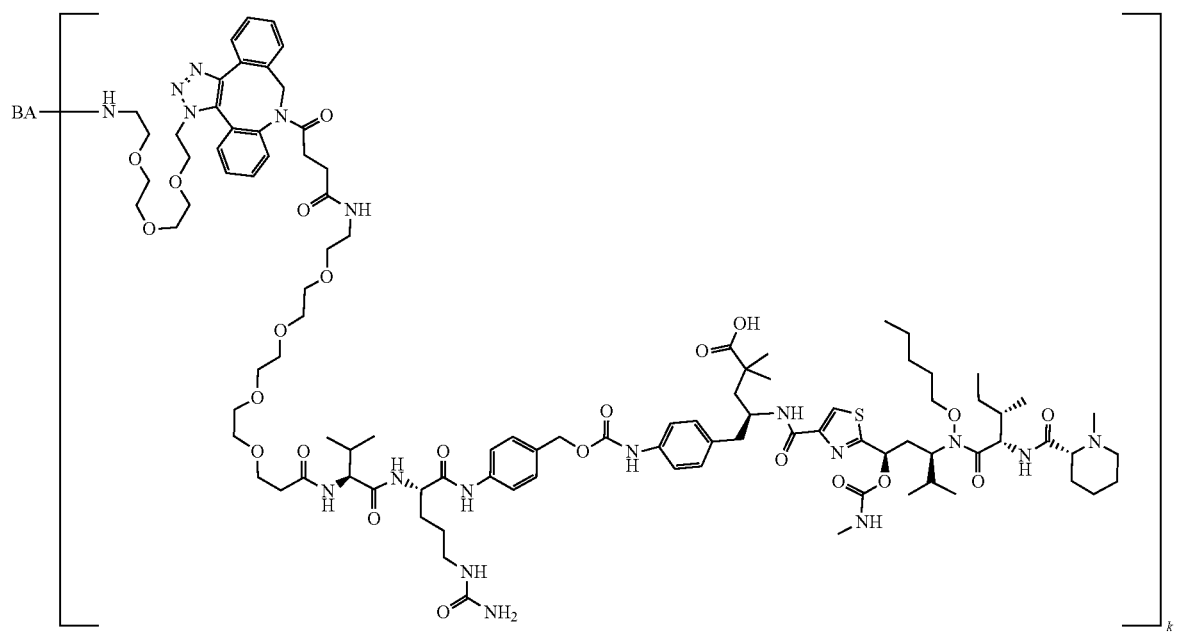

wherein BA is a binding agent; and k is 1, 2, 3, or 4. In any of the embodiments in this paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In one embodiment of Formula C, BA is a binding agent; L is a linker; Q is —$CH_2$—; $R^1$ is $C_1$-$C_{10}$ alkyl; $R^2$ is $C_5$-$C_{10}$ alkyl; $R^3$ is —C(O)N(H)$C_1$-$C_5$ alkyl; $R^4$ and $R^5$ are, independently, $C_1$-$C_5$ alkyl; $R^6$ is —OH; $R^7$ is —NH—; $R^8$ is halogen; m is one; and k is 1, 2, 3, 4, 5, 6, 7, 8, 9, or 10. In one embodiment of Formula C, BA is a binding agent; L is a linker; Q is —$CH_2$—; $R^1$ is methyl, ethyl, propyl, butyl, pentyl, hexyl, heptyl, octyl, nonyl, or decyl, and constitutional isomers thereof; $R^2$ is pentyl, hexyl, heptyl, octyl, nonyl, or decyl; $R^3$ is —C(O)N(H)$CH_3$, —C(O)N(H)$CH_2CH_3$, —C(O)N(H)$CH_2CH_2CH_3$, —C(O)N(H)$CH_2CH_2CH_2CH_3$, or —C(O)N(H)$CH_2CH_2CH_2CH_2CH_3$; $R^4$ and $R^5$ are, independently, methyl, ethyl, propyl, butyl, or pentyl, and constitutional isomers thereof; $R^6$ is —OH; $R^7$ is —NH—; $R^8$ is halogen; m is one; and k is 1, 2, 3, 4, 5, 6, 7, 8, 9, or 10. In one embodiment, conjugates of Formula C include Formula Ciii:

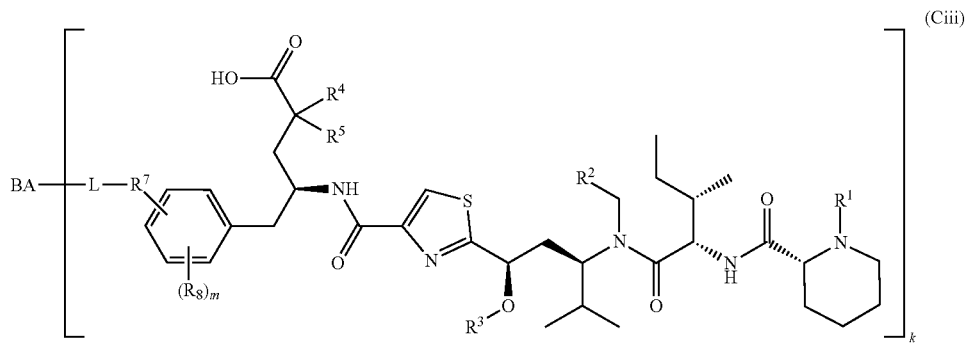

wherein BA is a binding agent; L is a linker; R¹ is methyl, ethyl, propyl, butyl, pentyl, hexyl, heptyl, octyl, nonyl, or decyl, and constitutional isomers thereof; R² is pentyl, hexyl, heptyl, octyl, nonyl, or decyl; R³ is —C(O)N(H)CH₃, —C(O)N(H)CH₂CH₃, —C(O)N(H)CH₂CH₂CH₃, —C(O)N(H)CH₂CH₂CH₂CH₃, or —C(O)N(H)CH₂CH₂CH₂CH₂CH₃; R⁴ and R⁵ are, independently, methyl, ethyl, propyl, butyl, or pentyl, and constitutional isomers thereof; R⁷ is —NH—; R⁸ is halogen; m is one; and k is 1, 2, 3, or 4. In one embodiment of Formula Ciii, BA is a binding agent; L is a linker; R¹ is methyl; R² is pentyl; R³ is —C(O)N(H)CH₃; R⁴ and R⁵ are methyl; R⁷ is —NH—; R⁸ is halogen; m is one; and k is 1, 2, 3, or 4. In one embodiment, conjugates of Formula C include a compound selected from the group consisting of:

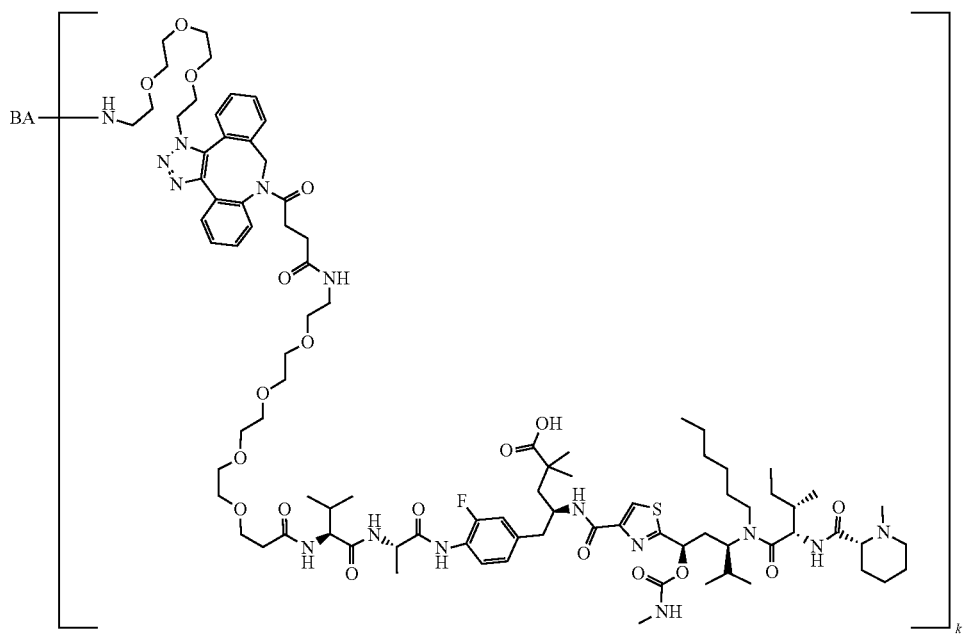

and

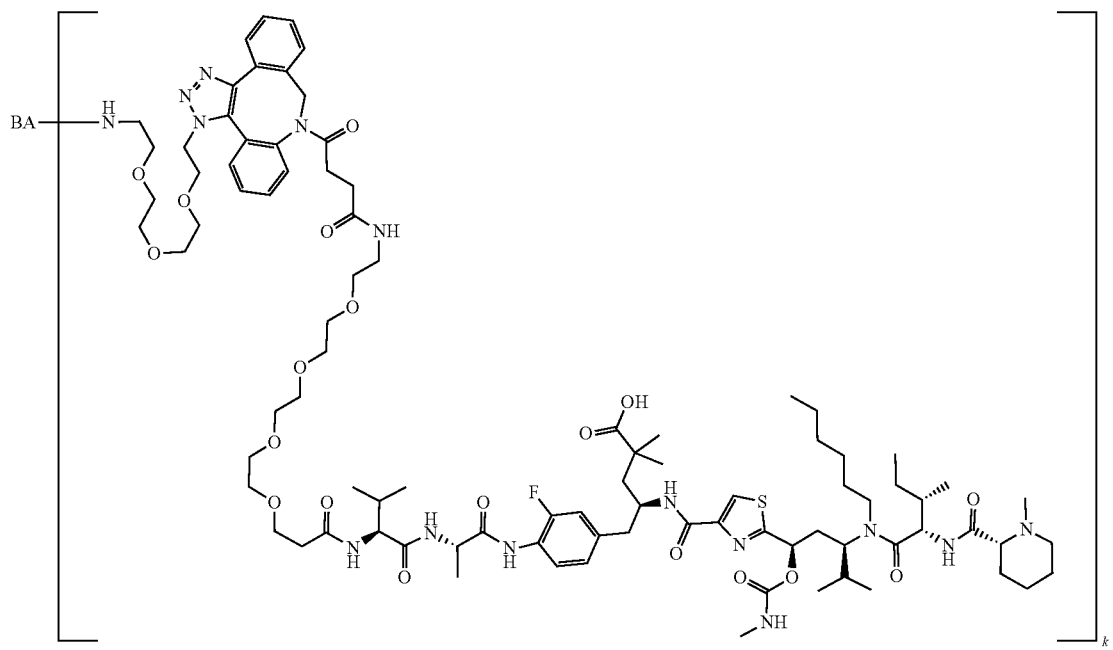

wherein BA is a binding agent; and k is 1, 2, 3, or 4. In any of the embodiments in this paragraph, BA is an antibody or antigen binding fragment thereof. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In certain embodiments, an antibody or antigen-binding fragment thereof can be conjugated directly to any one or more of Formulae I, II, III, IV, V, VI, VII, VIII, IX, X, XI, and/or XII, as described herein. In one embodiment, an antibody-drug conjugate includes an antibody or antigen binding fragment thereof conjugated to any one or more of Formulae I, II, III, IV, V, VI, VII, VIII, IX, X, XI, and/or XII, as described herein, selected from the group consisting of

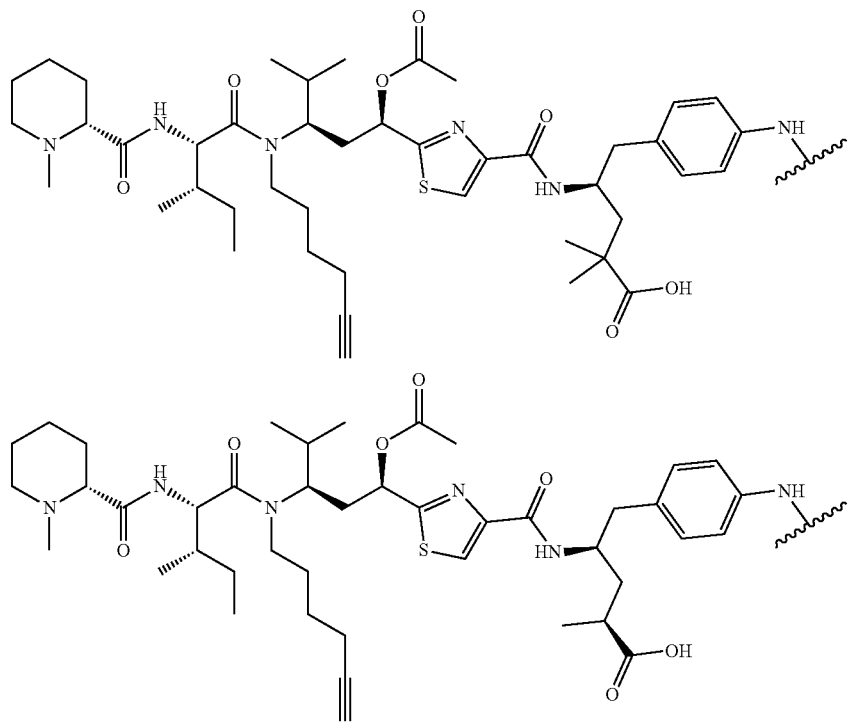

-continued
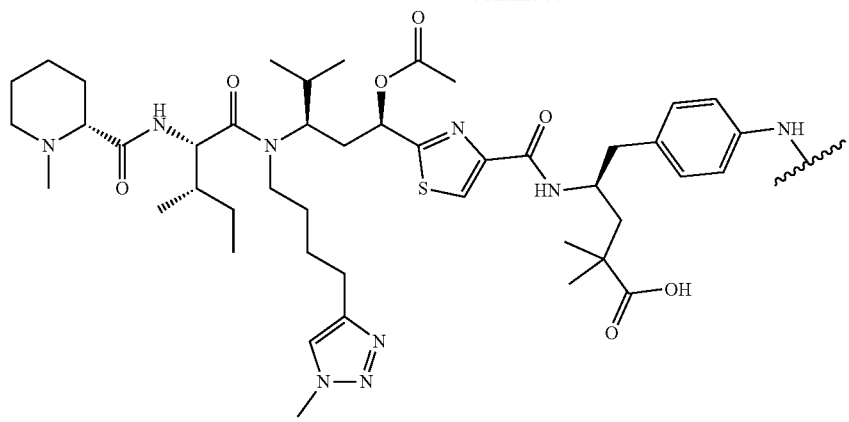
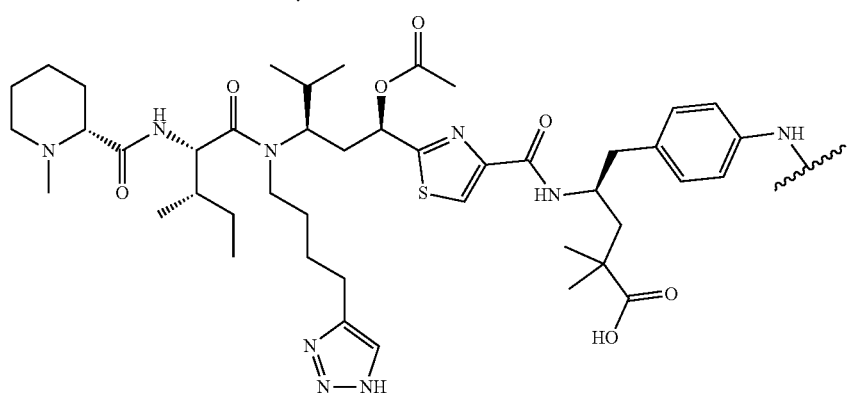
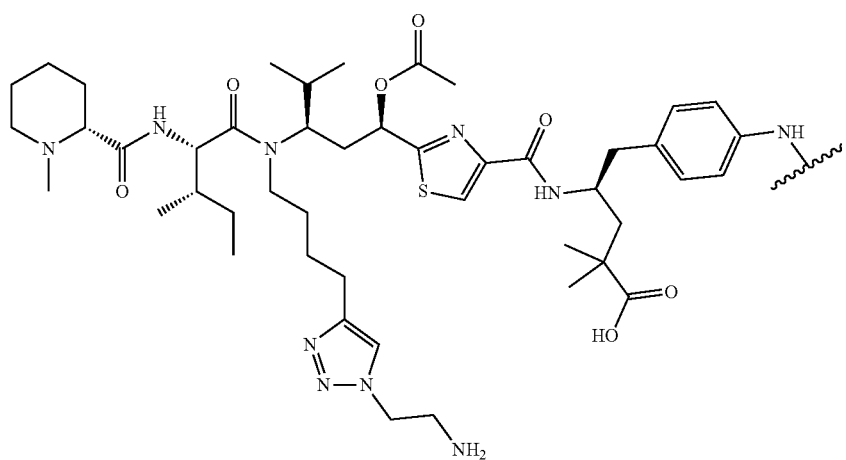
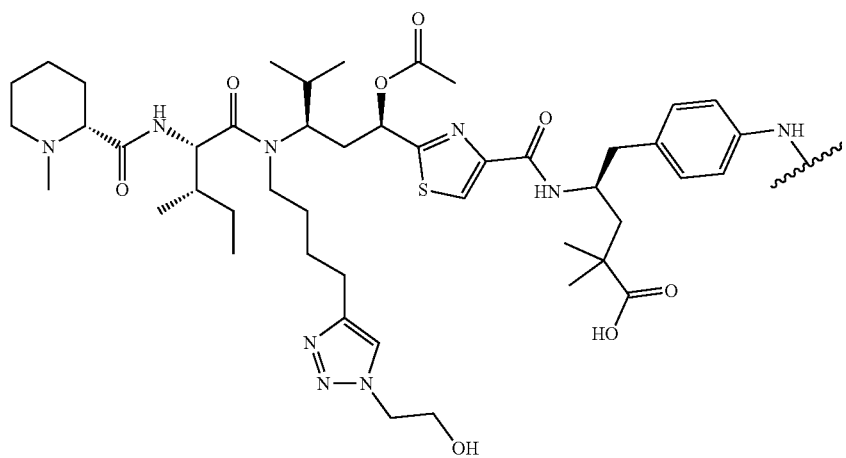

-continued
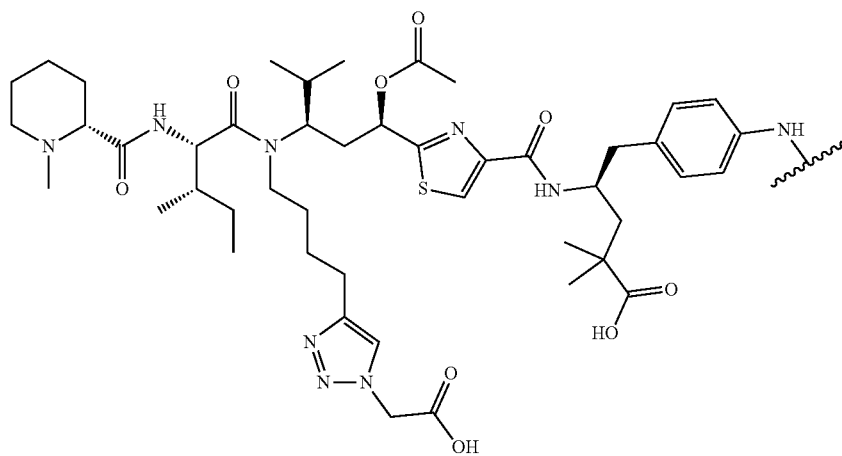
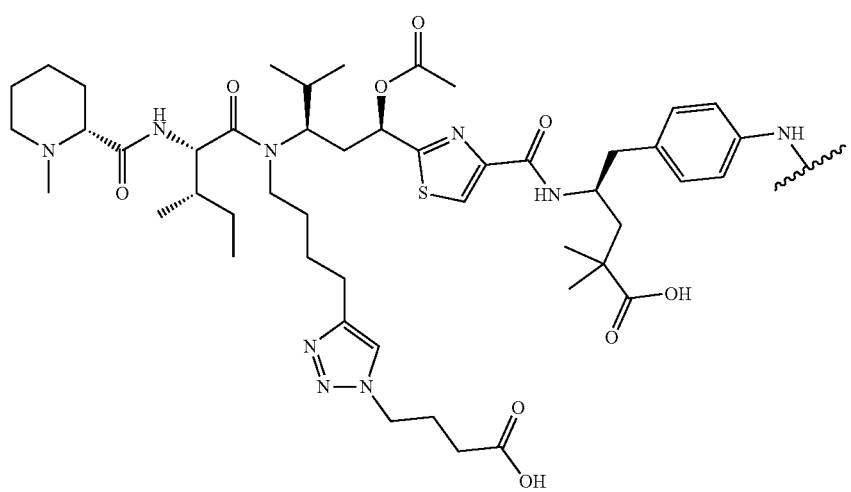
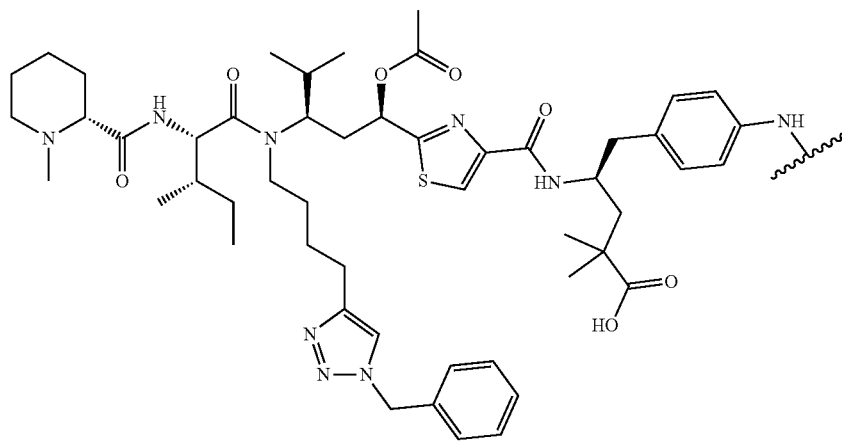

-continued
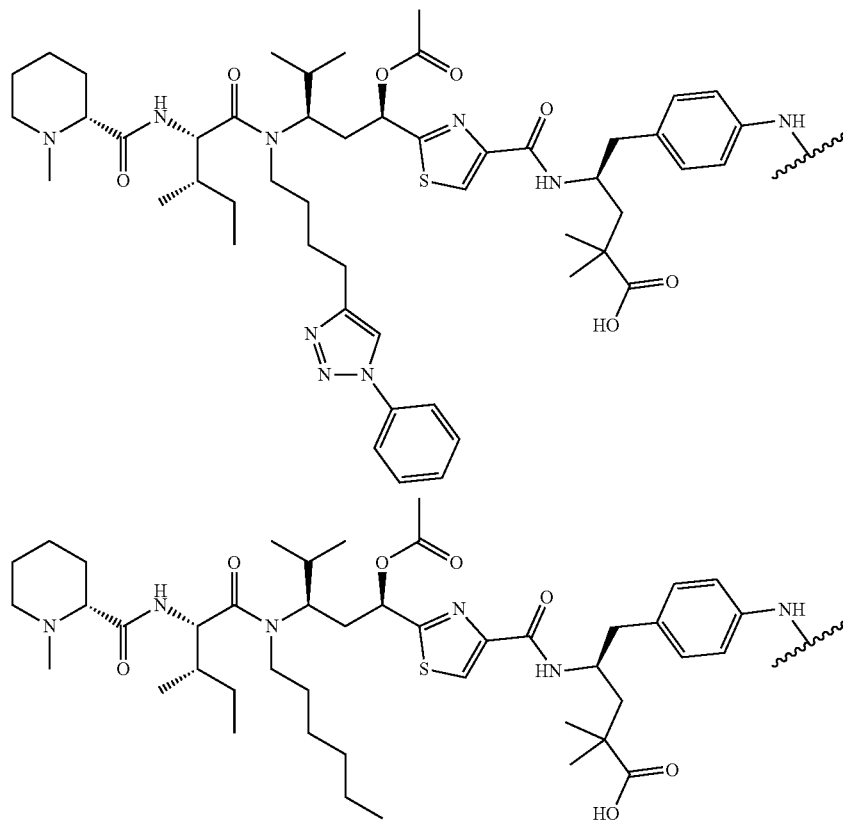
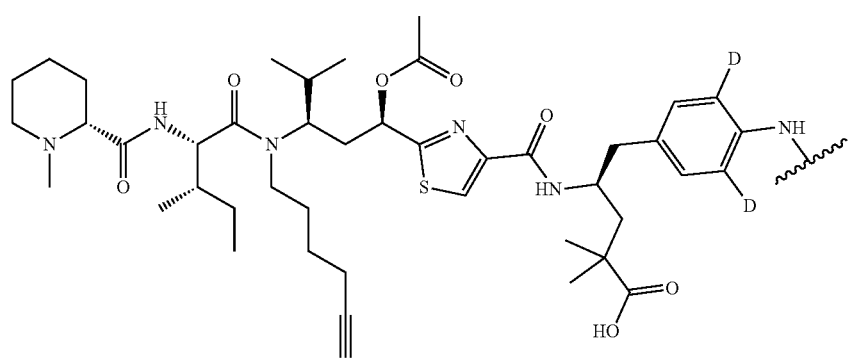
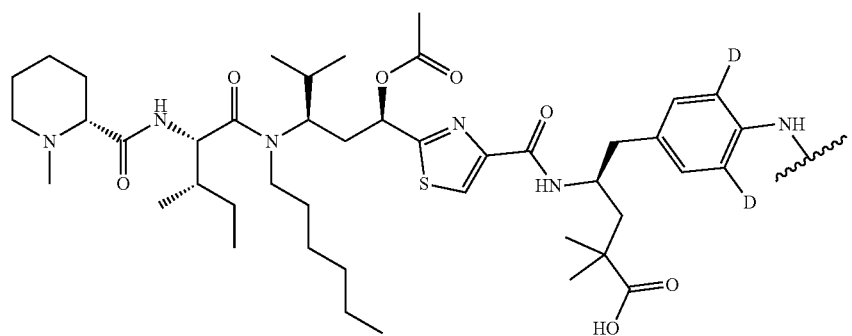

-continued
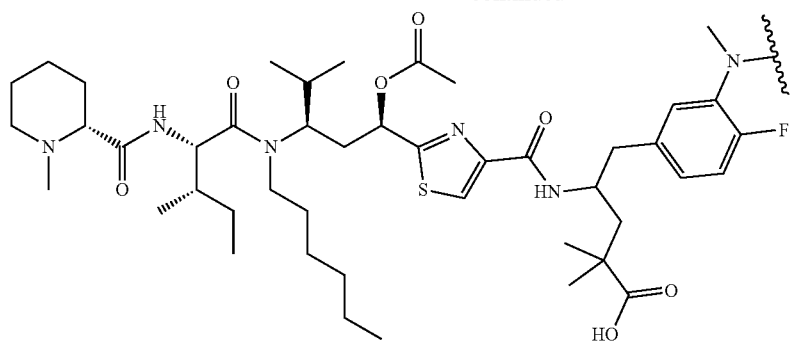
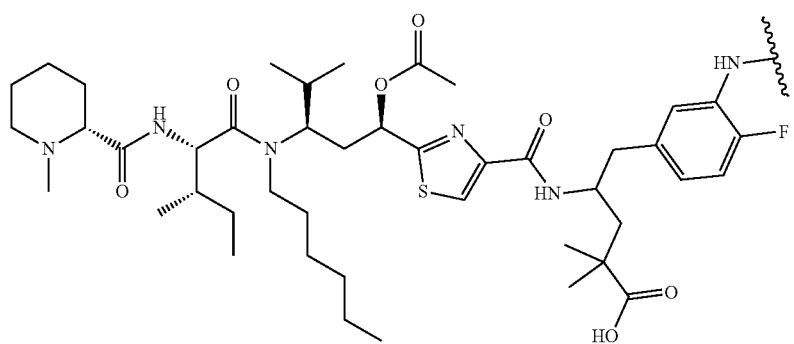
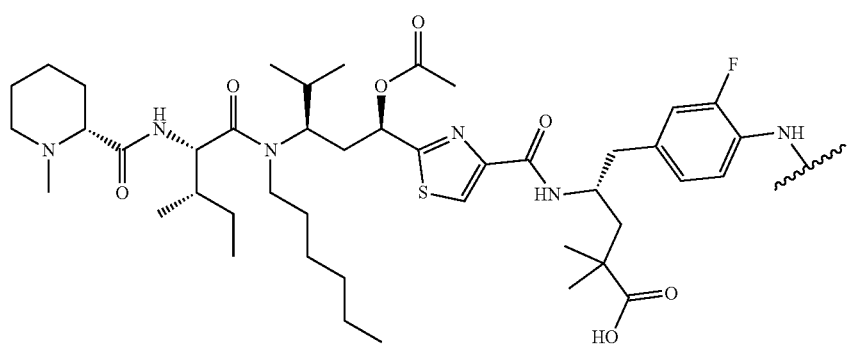
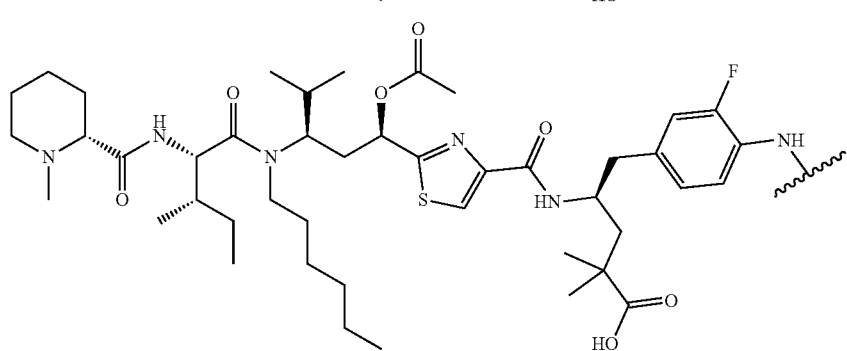
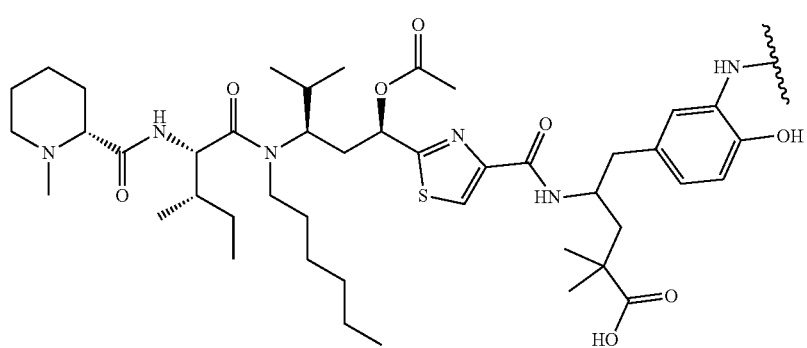

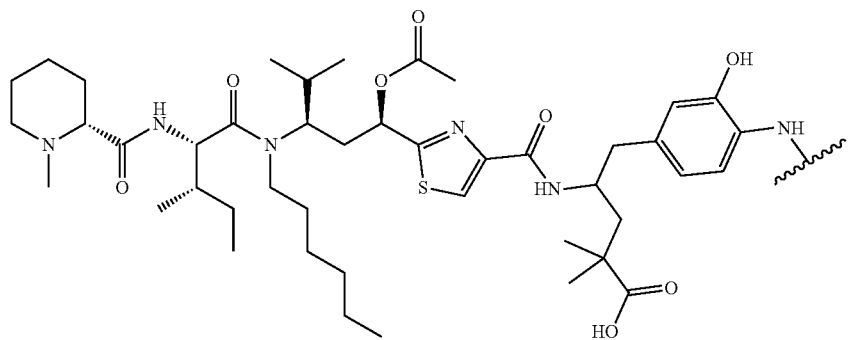
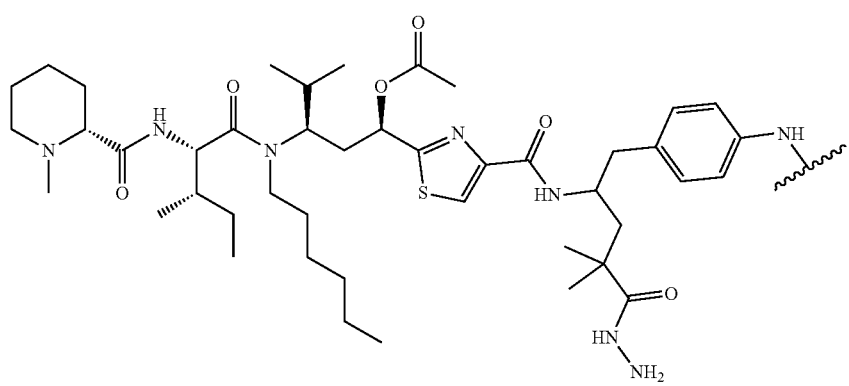
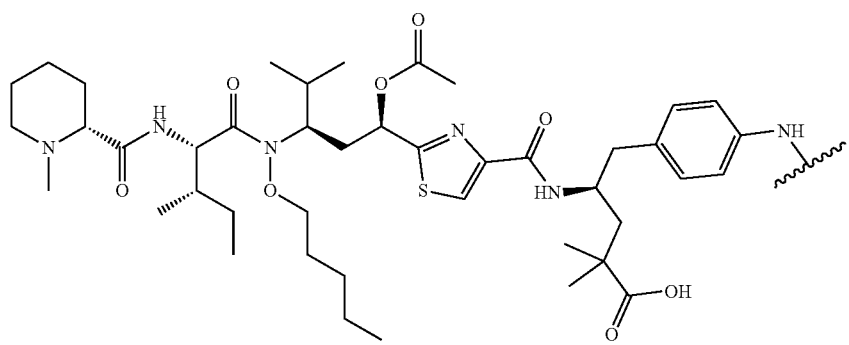
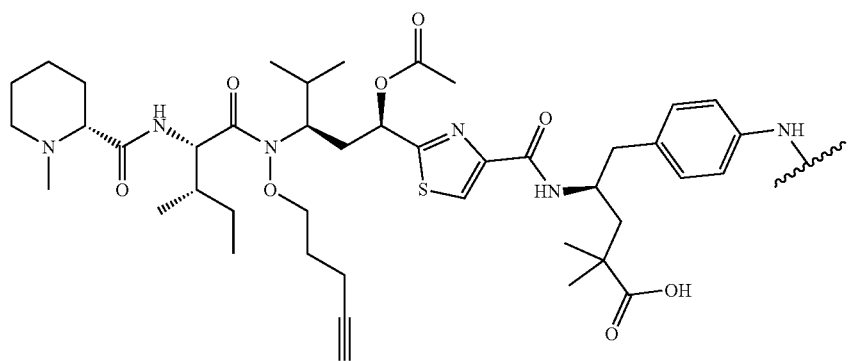

-continued
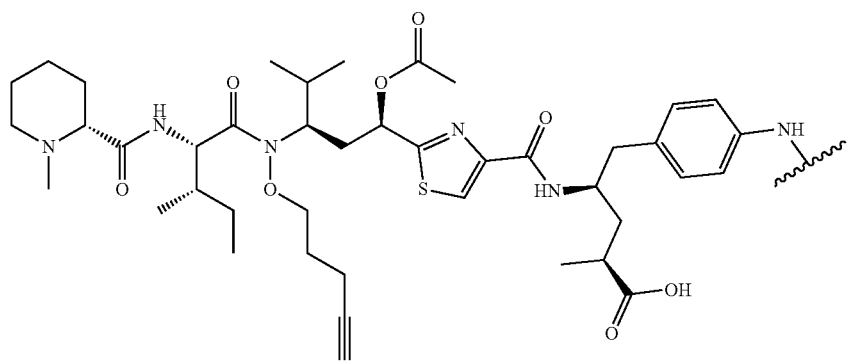
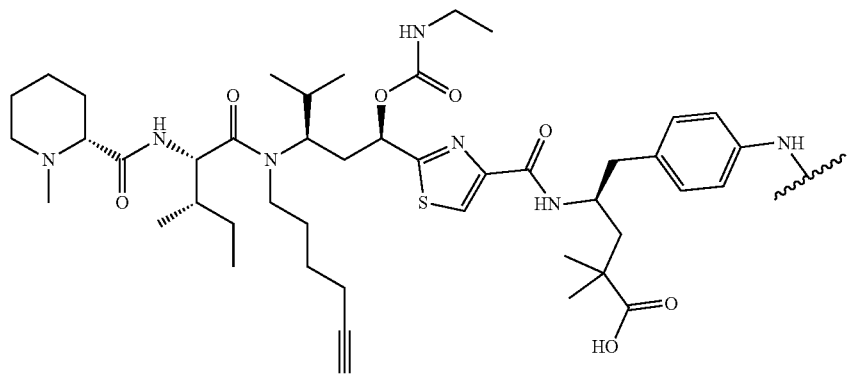
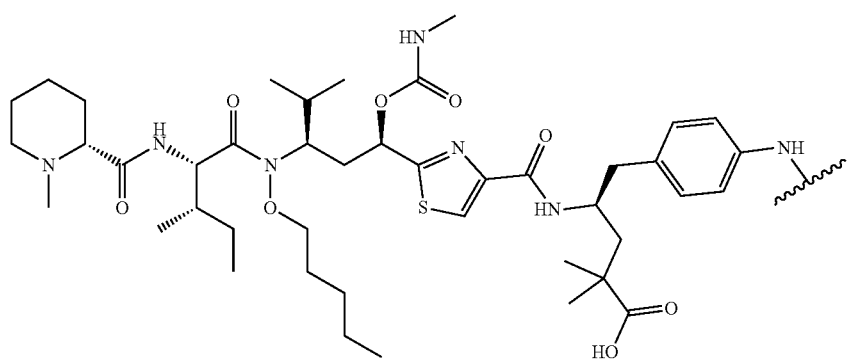
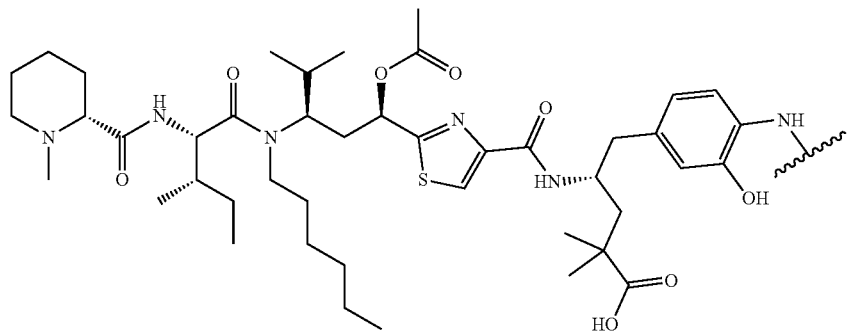

-continued
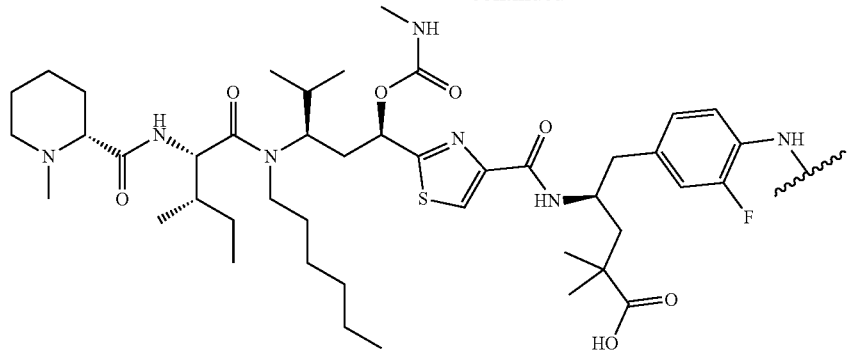
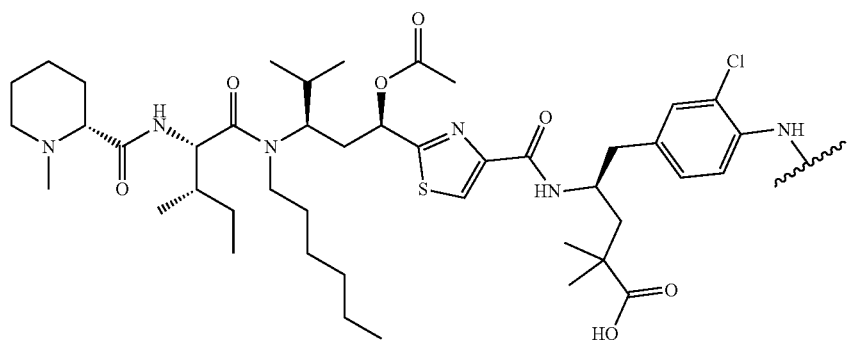
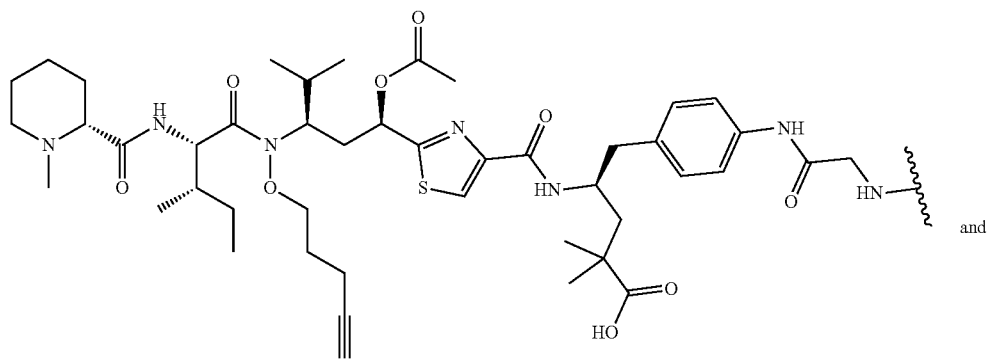
and
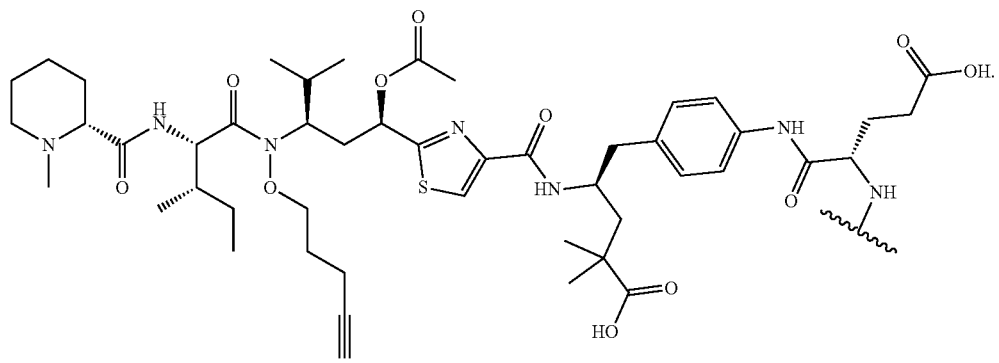

In one embodiment, an antibody-drug conjugate includes an antibody or antigen binding fragment thereof conjugated to
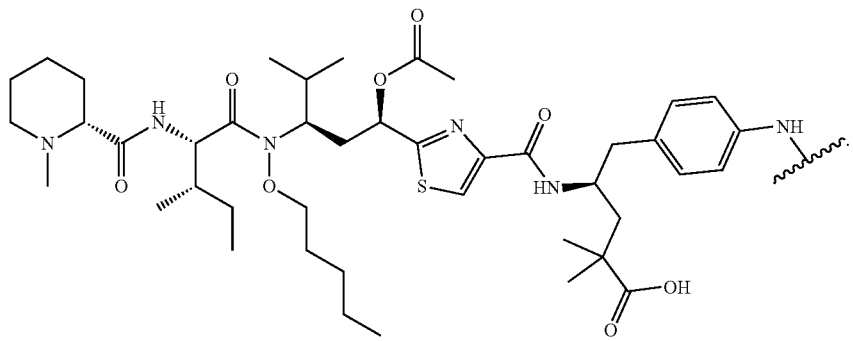 [SMILES: *Nc1ccc(C[C@@H](CC(C)(C)C(=O)O)NC(=O)c2csc([C@@H](C[C@H](C(C)C)N(OCCCCC)C(=O)[C@@H](NC(=O)[C@H]3CCCCN3C)[C@@H](C)CC)OC(C)=O)n2)cc1]
In one embodiment, an antibody-drug conjugate includes an antibody or antigen binding fragment thereof conjugated to
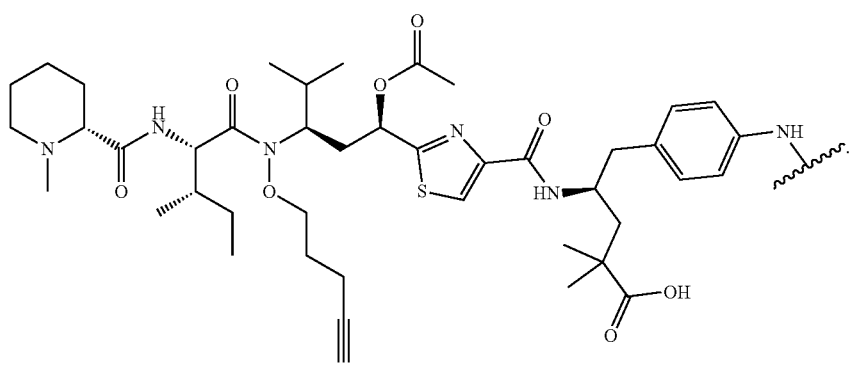 [SMILES: *Nc1ccc(C[C@@H](CC(C)(C)C(=O)O)NC(=O)c2csc([C@@H](C[C@H](C(C)C)N(OCCCC#C)C(=O)[C@@H](NC(=O)[C@H]3CCCCN3C)[C@@H](C)CC)OC(C)=O)n2)cc1]
In one embodiment, an antibody-drug conjugate includes an antibody or antigen binding fragment thereof conjugated to
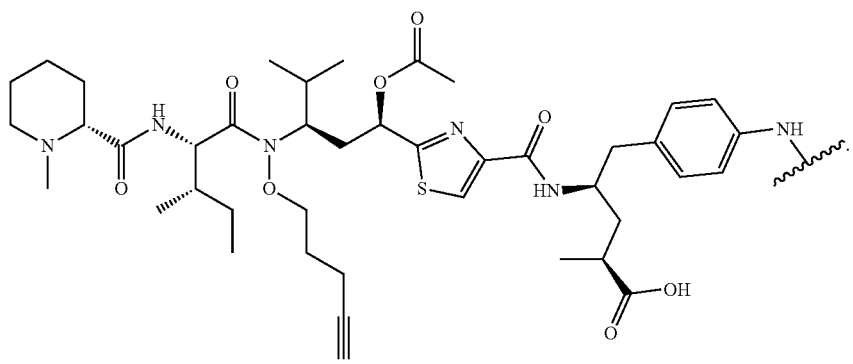 [SMILES: *Nc1ccc(C[C@@H](C[C@H](C)C(=O)O)NC(=O)c2csc([C@@H](C[C@H](C(C)C)N(OCCCC#C)C(=O)[C@@H](NC(=O)[C@H]3CCCCN3C)[C@@H](C)CC)OC(C)=O)n2)cc1]

In one embodiment, an antibody-drug conjugate includes an antibody or antigen binding fragment thereof conjugated to
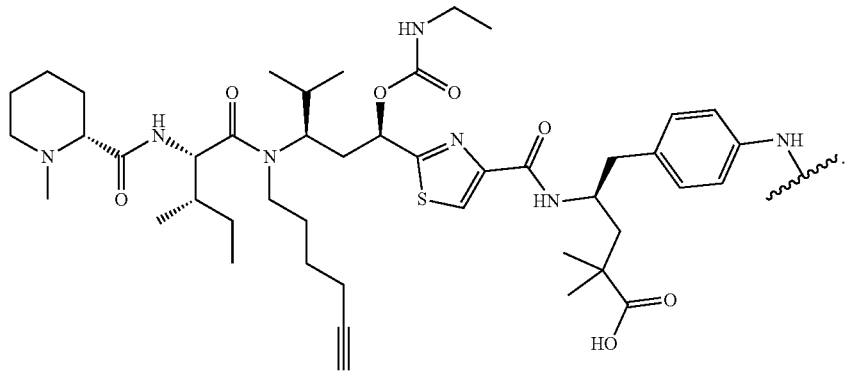 [SMILES: *Nc1ccc(C[C@@H](CC(C)(C)C(=O)O)NC(=O)c2csc([C@@H](C[C@H](C(C)C)N(CCCCC#C)C(=O)[C@@H](NC(=O)[C@H]3CCCCN3C)[C@@H](C)CC)OC(=O)NCC)n2)cc1]
In one embodiment, an antibody-drug conjugate includes an antibody or antigen binding fragment thereof conjugated to
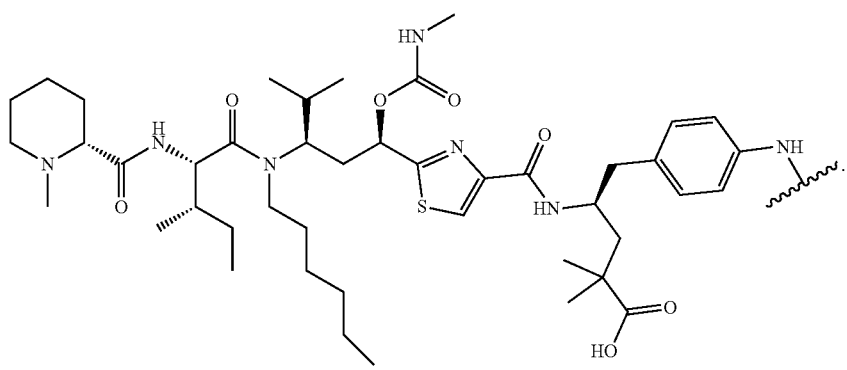 [SMILES: *Nc1ccc(C[C@@H](CC(C)(C)C(=O)O)NC(=O)c2csc([C@@H](C[C@H](C(C)C)N(CCCCCC)C(=O)[C@@H](NC(=O)[C@H]3CCCCN3C)[C@@H](C)CC)OC(=O)NC)n2)cc1]
In one embodiment, an antibody-drug conjugate includes an antibody or antigen binding fragment thereof conjugated to
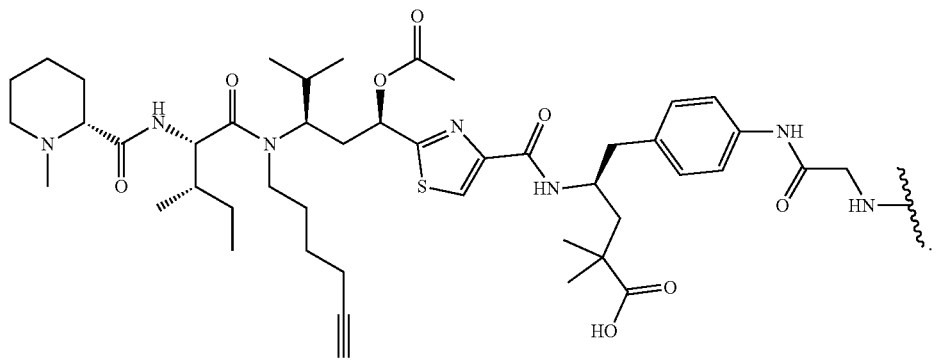 [SMILES: *NCC(=O)Nc1ccc(C[C@@H](CC(C)(C)C(=O)O)NC(=O)c2csc([C@@H](C[C@H](C(C)C)N(CCCCC#C)C(=O)[C@@H](NC(=O)[C@H]3CCCCN3C)[C@@H](C)CC)OC(C)=O)n2)cc1]

In one embodiment, an antibody-drug conjugate includes an antibody or antigen binding fragment thereof conjugated to paragraph, k is from 1 to 4. In certain embodiments, k is 1, 2, 3, or 4. In certain embodiments, k is 4.

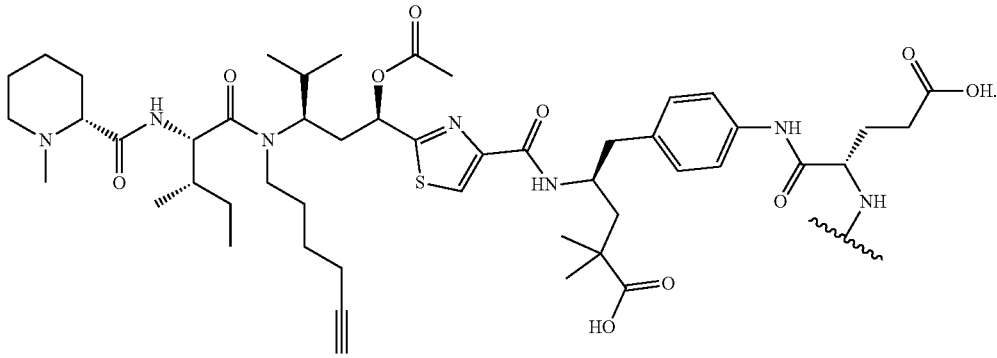 [SMILES: *N[C@@H](CCC(=O)O)C(=O)Nc1ccc(C[C@@H](CC(C)(C)C(=O)O)NC(=O)c2csc([C@@H](C[C@H](C(C)C)N(CCCCC#C)C(=O)[C@@H](NC(=O)[C@H]3CCCCN3C)[C@@H](C)CC)OC(C)=O)n2)cc1]

In any of the compound or conjugate embodiments provided, BA is an antibody, or antigen binding fragment thereof, that binds PRLR. In any of the compound or conjugate embodiments provided, BA is an antibody, or antigen binding fragment thereof, that binds STEAP2. In any of the compound or conjugate embodiments provided, BA is an antibody or antigen-binding fragment thereof, and conjugation is through at least one Q295 residue. In any of the compound or conjugate embodiments provided, BA is an antibody or antigen-binding fragment thereof, and conjugation is through two Q295 residues. In any of the compound or conjugate embodiments provided, BA is a N297Q antibody or antigen-binding fragment thereof. In any of the compound or conjugate embodiments provided, BA is a N297Q antibody or antigen-binding fragment thereof, and conjugation is through at least one Q295 and at least one Q297 residue. In any of the compound or conjugate embodiments provided, BA is a N297Q antibody or antigen-binding fragment thereof, and conjugation is through two Q295 residues and two Q297 residues. In particular embodiments, numbering is according to the EU numbering system.

In any of the embodiments above, BA is an anti-STEAP2 antibody. In certain embodiments, BA is the anti-STEAP2 antibody H1H7814N described in the Examples below. In certain embodiments, BA is the anti-STEAP2 antibody H1H7814N N297Q described in the Examples below. In certain embodiments, BA is an anti-STEAP2 antibody comprising an HCVR according to SEQ ID NO:1 and an LCVR according to SEQ ID NO:5. In certain embodiments, BA is an N297Q antibody comprising an HCVR according to SEQ ID NO:1 and an LCVR according to SEQ ID NO:5. In certain embodiments, BA is an anti-STEAP2 antibody comprising one, two, three, four, five, or six of HCDR1, HCDR2, HCDR3, LCDR1, LCDR2, and LCDR3 according to SEQ ID NOS:2, 3, 4, 6, 7, and 8, respectively. In certain embodiments, BA is an N297Q antibody comprising one, two, three, four, five, or six of HCDR1, HCDR2, HCDR3, LCDR1, LCDR2, and LCDR3 according to SEQ ID NOS:2, 3, 4, 6, 7, and 8, respectively. N297Q indicates that one or more residues 297 are mutated from asparagine (N) to glutamine (Q). Preferably, each residue 297 is mutated to Q. In preferred embodiments, numbering is according to the EU numbering system. In certain embodiments of this paragraph, k is from 1 to 4. In certain embodiments, k is 1, 2, 3, or 4. In certain embodiments, k is 4.

In any of the embodiments above, BA is an anti-PRLR antibody. In certain embodiments, BA is the anti-PRLR antibody H1H6958N2 described in the Examples below. In certain embodiments, BA is the anti-PRLR antibody H1H6958N2 N297Q described in the Examples below. In certain embodiments, BA is an anti-PRLR antibody comprising an HCVR according to SEQ ID NO:9 and an LCVR according to SEQ ID NO: 13. In certain embodiments, BA is an N297Q antibody comprising an HCVR according to SEQ ID NO:9 and an LCVR according to SEQ ID NO:13. In certain embodiments, BA is an anti-PRLR antibody comprising one, two, three, four, five, or six of HCDR1, HCDR2, HCDR3, LCDR1, LCDR2, and LCDR3 according to SEQ ID NOS:10, 11, 12, 14, 15, and 16, respectively. In certain embodiments, BA is an N297Q antibody comprising one, two, three, four, five, or six of HCDR1, HCDR2, HCDR3, LCDR1, LCDR2, and LCDR3 according to SEQ ID NOS:10, 11, 12, 14, 15, and 16, respectively. N297Q indicates that one or more residues 297 are mutated from asparagine (N) to glutamine (Q). Preferably, each residue 297 is mutated to Q. In preferred embodiments, numbering is according to the EU numbering system. In certain embodiments of this paragraph, k is from 1 to 4. In certain embodiments, k is 1, 2, 3, or 4. In certain embodiments, k is 4.

In any preceding embodiment in this section, $R^7$ is $-NR^{7a}R^{7b}$, wherein $R^{7a}$ and $R^{7b}$ are independently in each instance, hydrogen, alkyl, alkenyl, alkynyl, cycloalkyl, aryl, heteroaryl, acyl, and amino acid residue, wherein alkyl, alkenyl, alkynyl, cycloalkyl, aryl, heteroaryl, and acyl are optionally substituted. In certain embodiments $R^{7a}$ is hydrogen and $R^{7b}$ is an amino acid residue.

Methods of Preparing Compounds or Payloads, and Linker—Payloads

The compounds provided herein can be prepared, isolated, or obtained by any method apparent to those of skill in the art. Exemplary methods of preparation are described in detail in the Examples below. In certain embodiments, compounds provided herein can generally be prepared according to Schemes A-D:

Scheme A. Exemplary Preparation Scheme
Scheme C. Exemplary Preparation Scheme
Scheme B. Exemplary Preparation Scheme
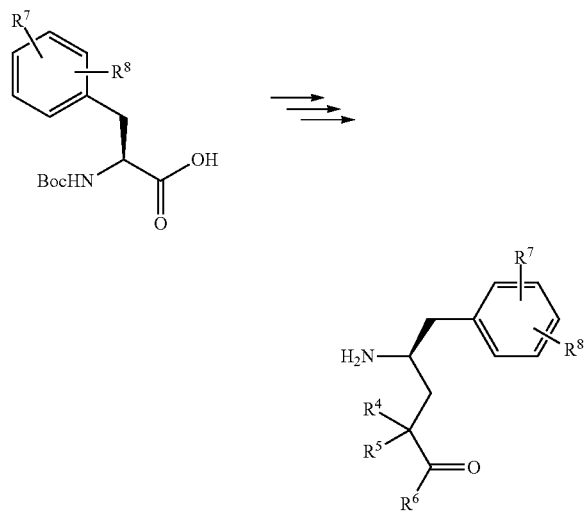
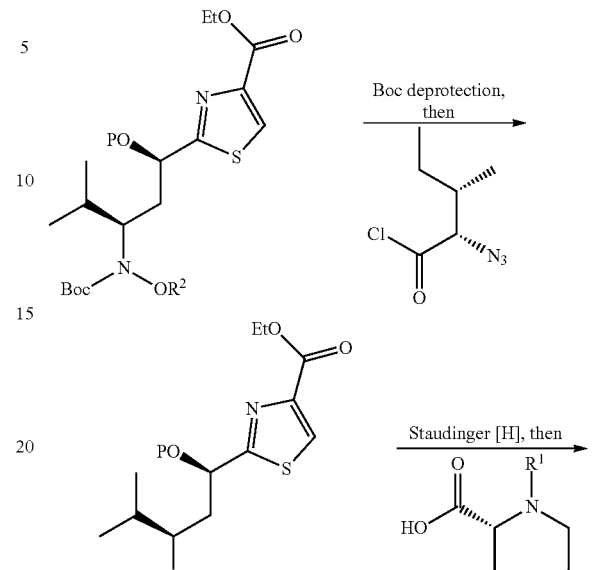
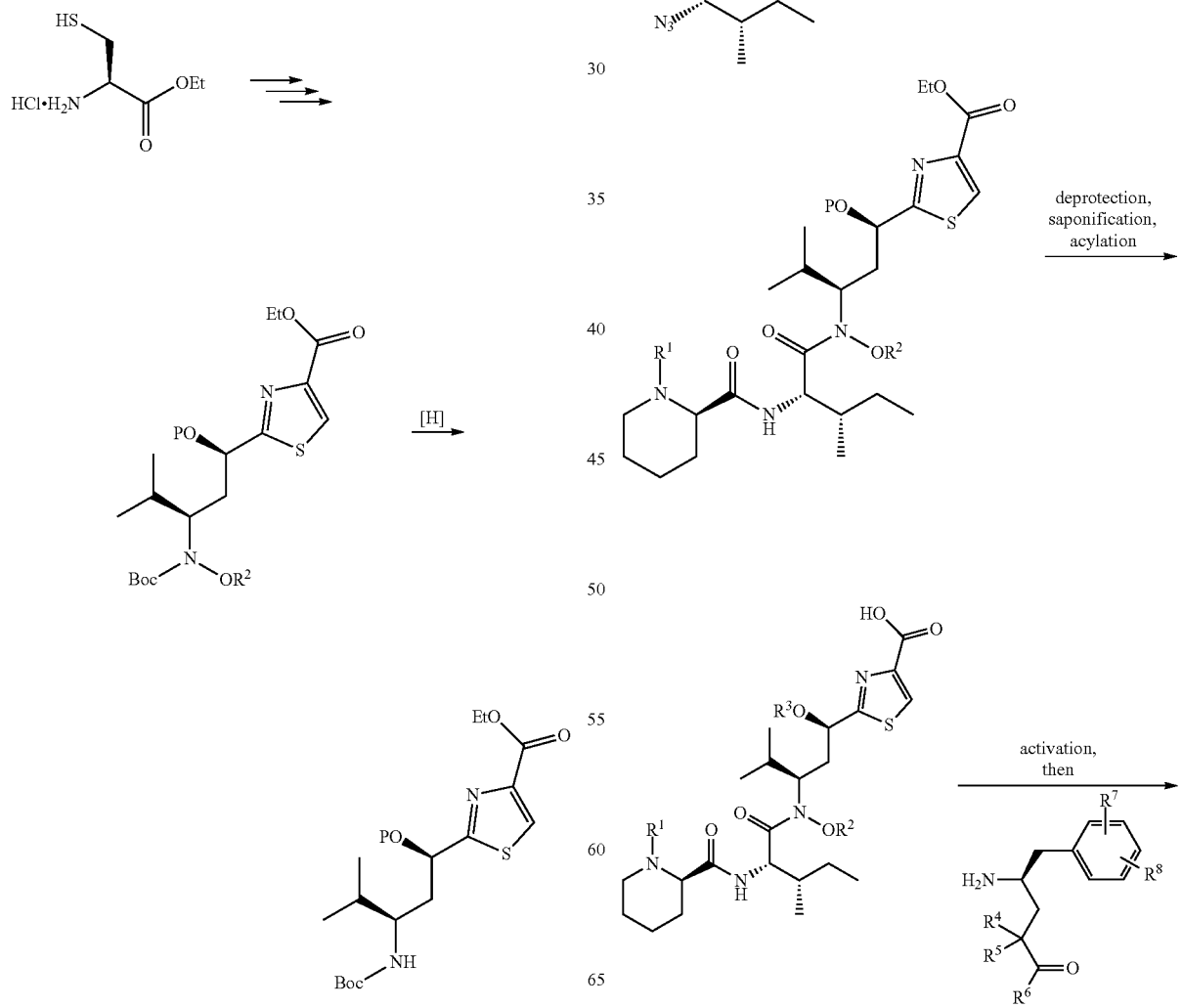

-continued

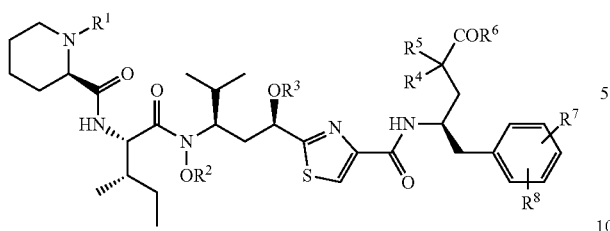

Scheme D. Exemplary Preparation Scheme

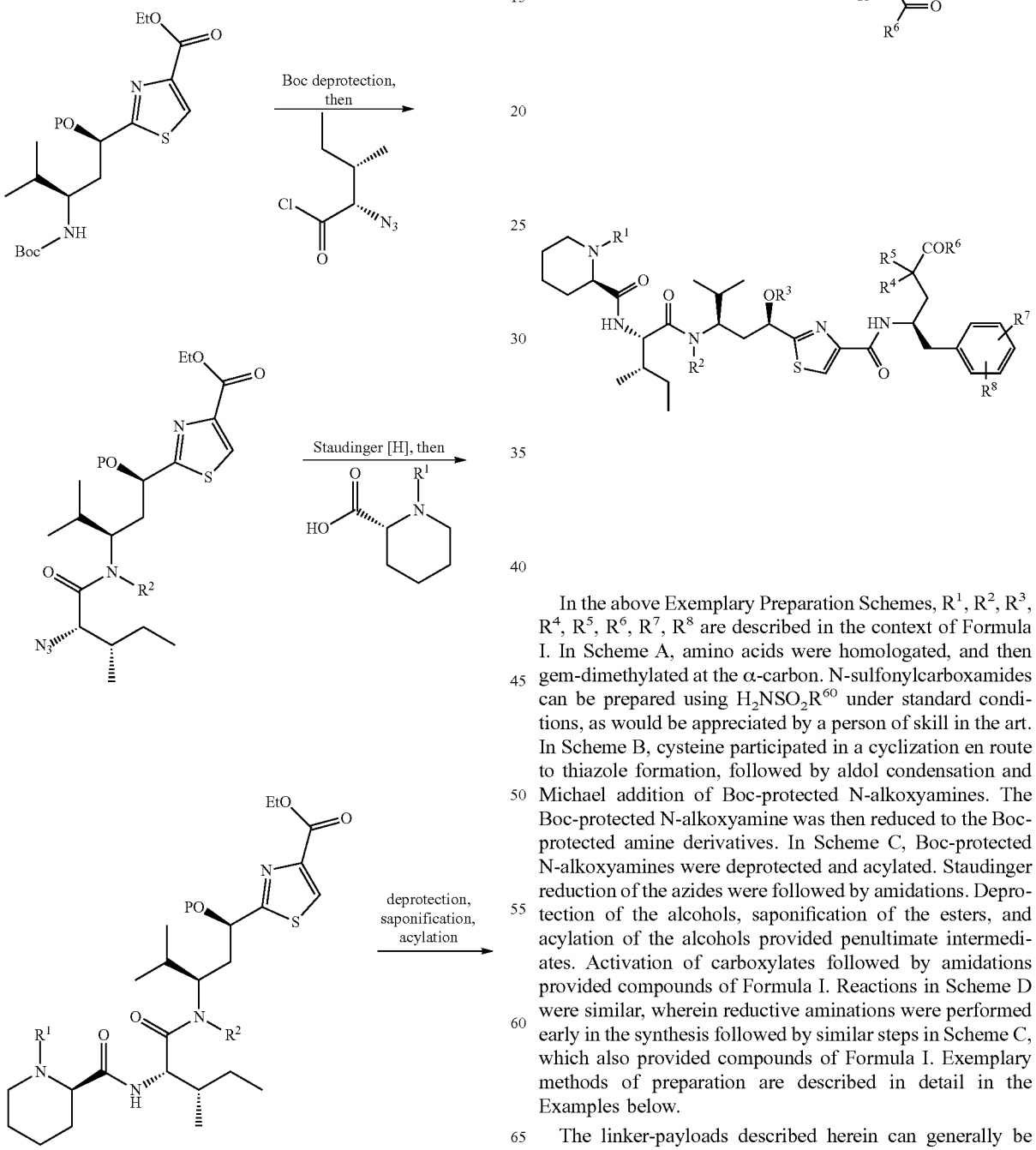

-continued

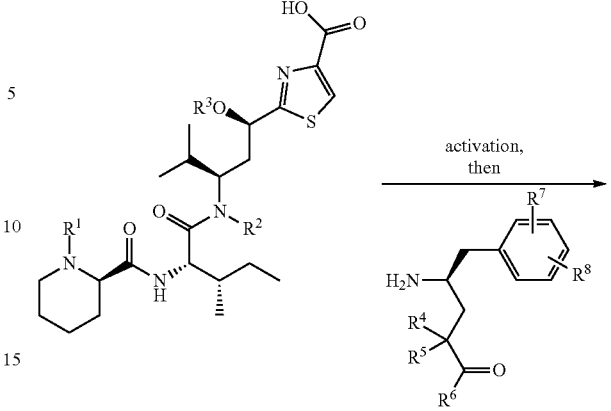

In the above Exemplary Preparation Schemes, $R^1$, $R^2$, $R^3$, $R^4$, $R^5$, $R^6$, $R^7$, $R^8$ are described in the context of Formula I. In Scheme A, amino acids were homologated, and then gem-dimethylated at the α-carbon. N-sulfonylcarboxamides can be prepared using $H_2NSO_2R^{60}$ under standard conditions, as would be appreciated by a person of skill in the art. In Scheme B, cysteine participated in a cyclization en route to thiazole formation, followed by aldol condensation and Michael addition of Boc-protected N-alkoxyamines. The Boc-protected N-alkoxyamine was then reduced to the Boc-protected amine derivatives. In Scheme C, Boc-protected N-alkoxyamines were deprotected and acylated. Staudinger reduction of the azides were followed by amidations. Deprotection of the alcohols, saponification of the esters, and acylation of the alcohols provided penultimate intermediates. Activation of carboxylates followed by amidations provided compounds of Formula I. Reactions in Scheme D were similar, wherein reductive aminations were performed early in the synthesis followed by similar steps in Scheme C, which also provided compounds of Formula I. Exemplary methods of preparation are described in detail in the Examples below.

The linker-payloads described herein can generally be synthesized by a series of coupling steps as shown in Schemes E-H, J, K, M, and N:

Scheme E. Exemplary Preparation Scheme
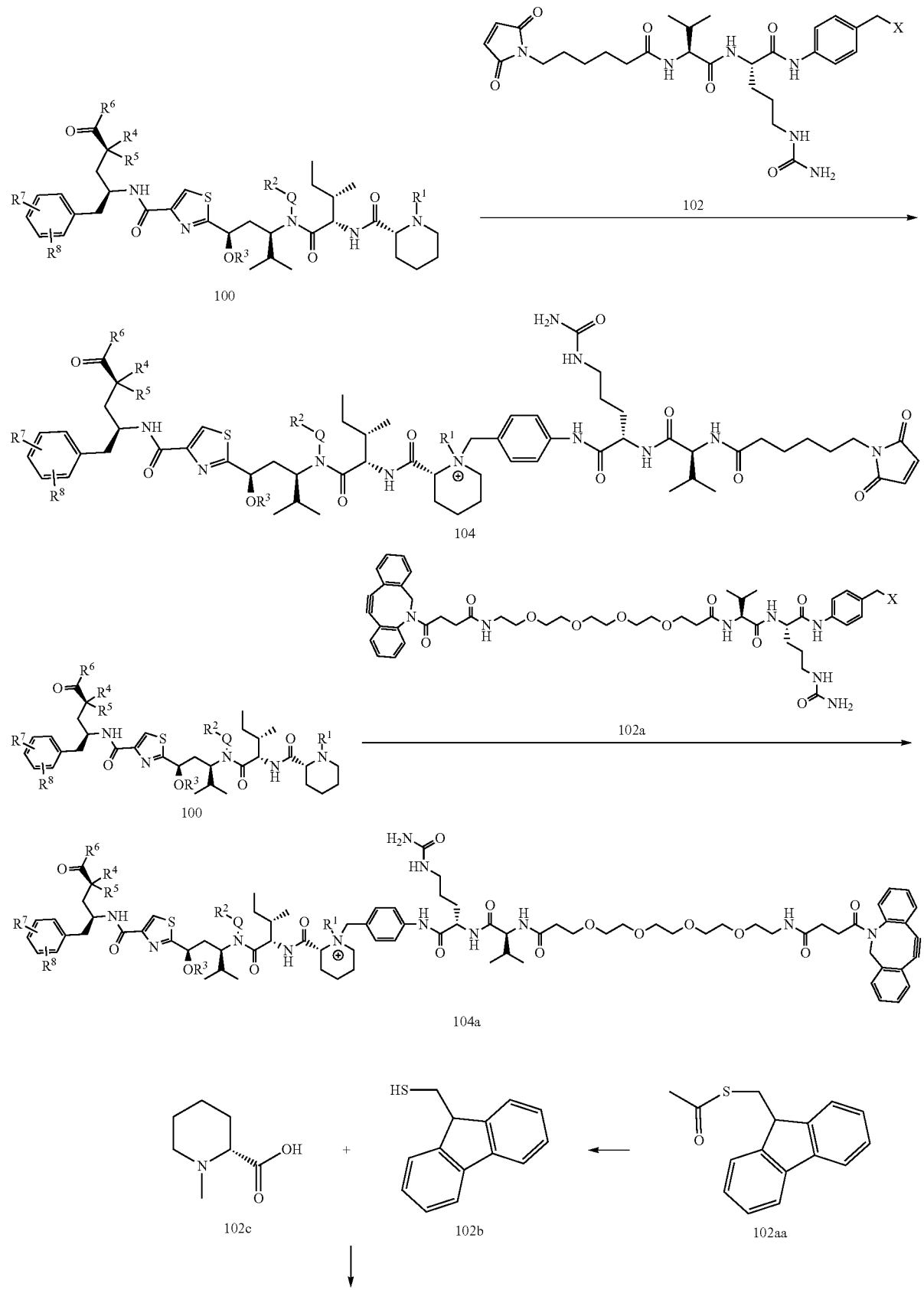

-continued
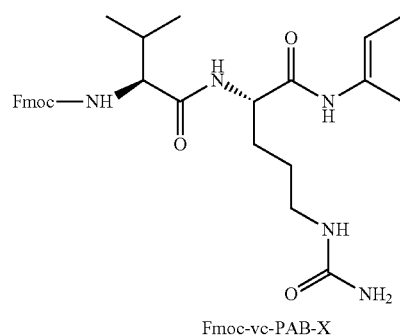
Fmoc-vc-PAB-X
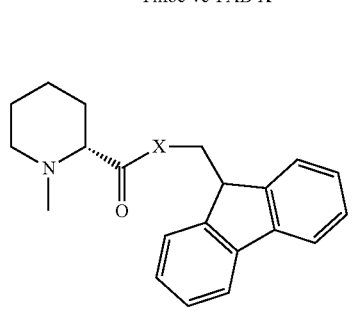
102d, X = O known compound
102dd, X = S from reaction of 102c and 102b
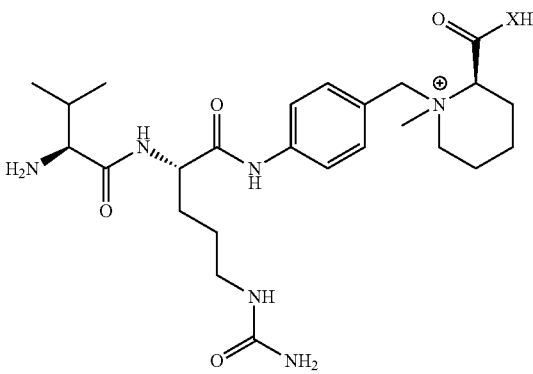
102f
X = O or S
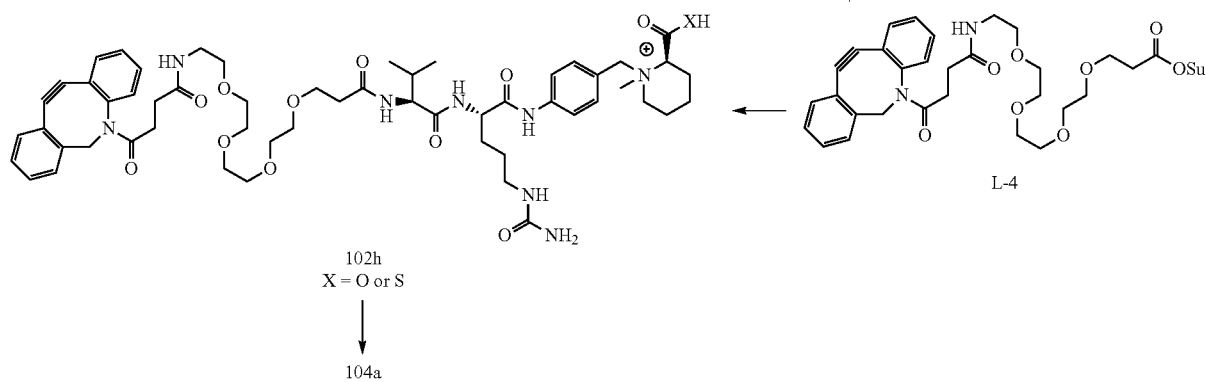
102h
X = O or S
↓
104a
L-4

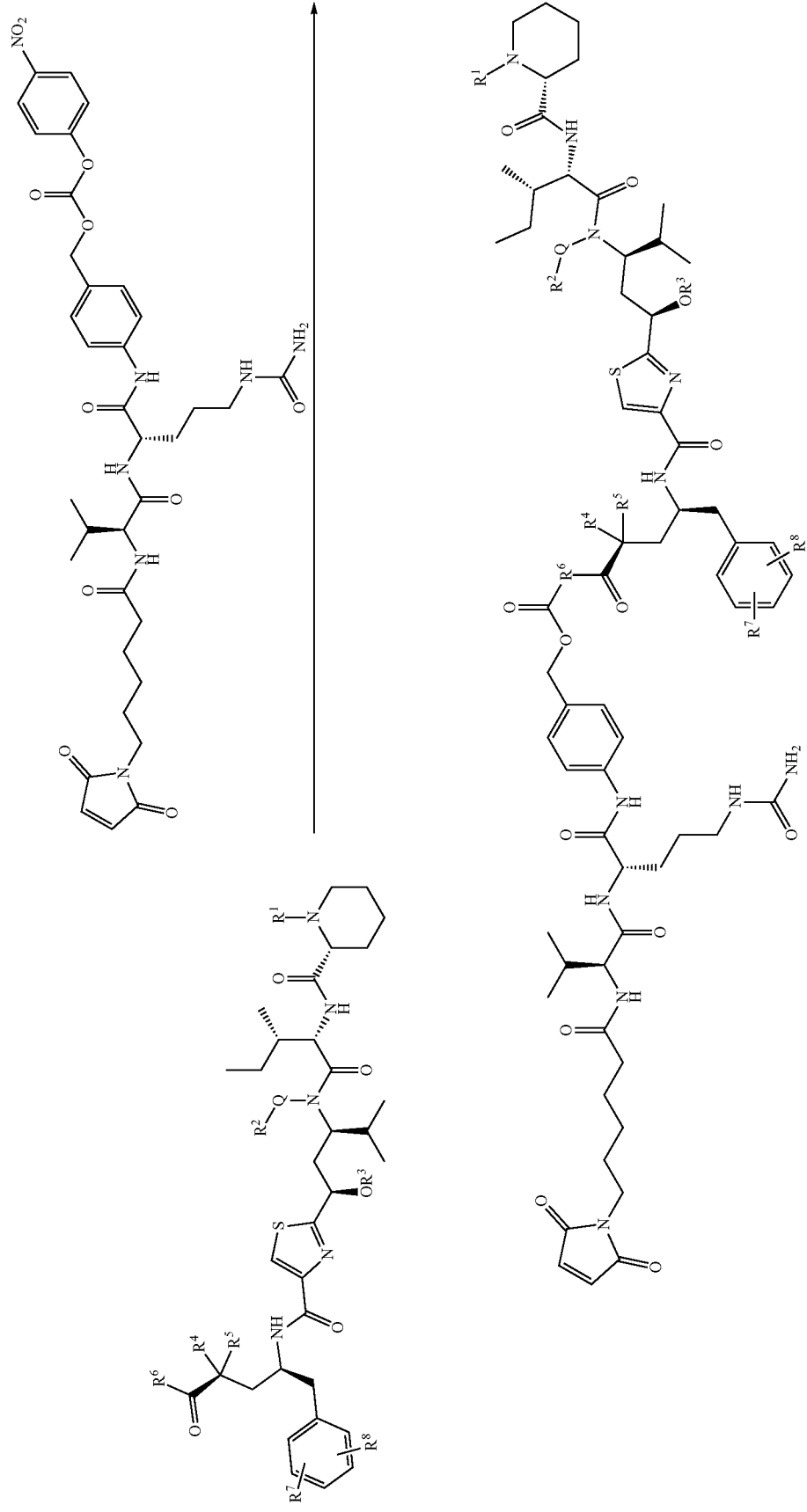
Scheme F. Exemplary Preparation Scheme

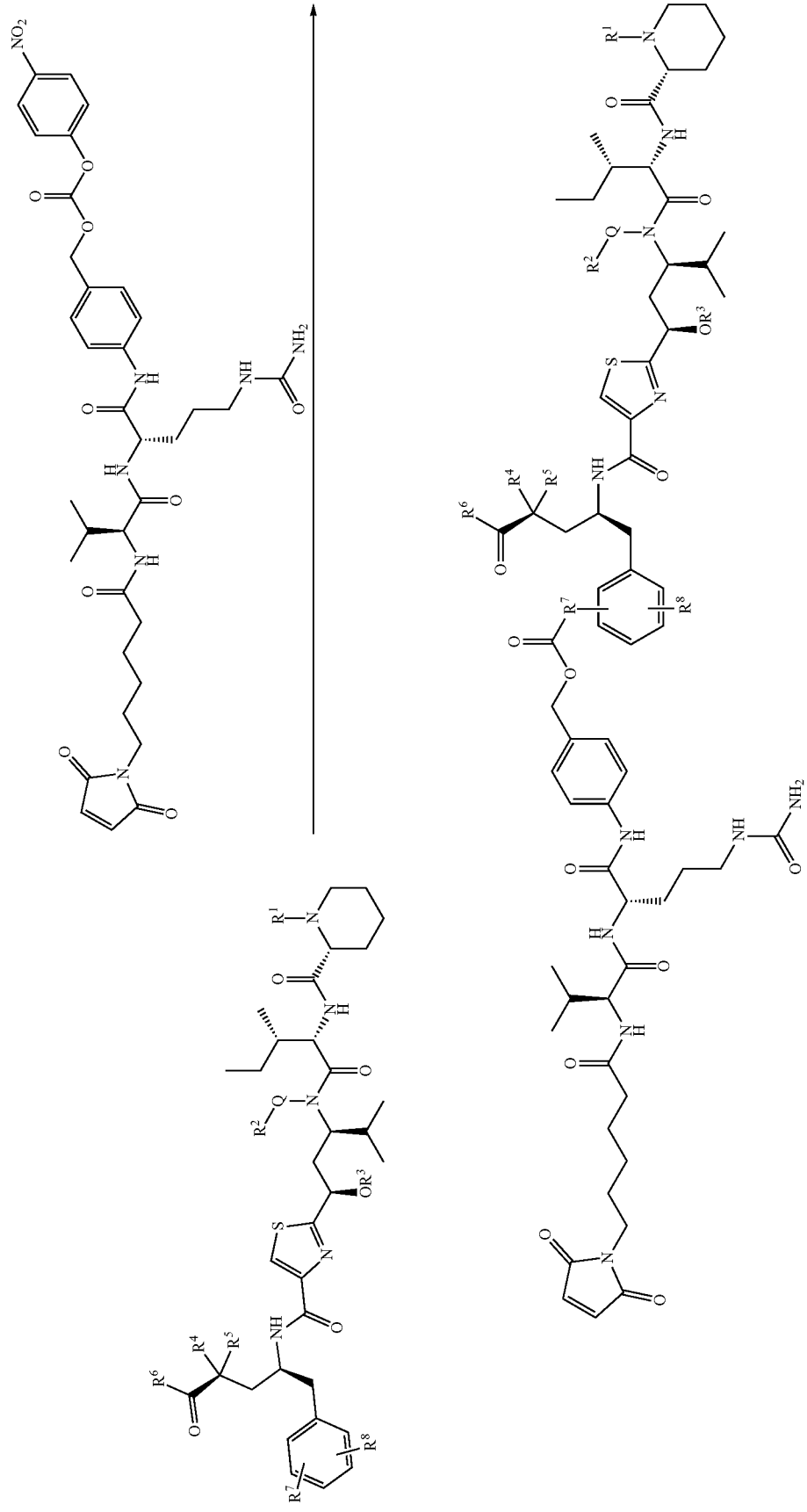
Scheme G. Exemplary Preparation Scheme

Scheme H. Exemplary Preparation Scheme
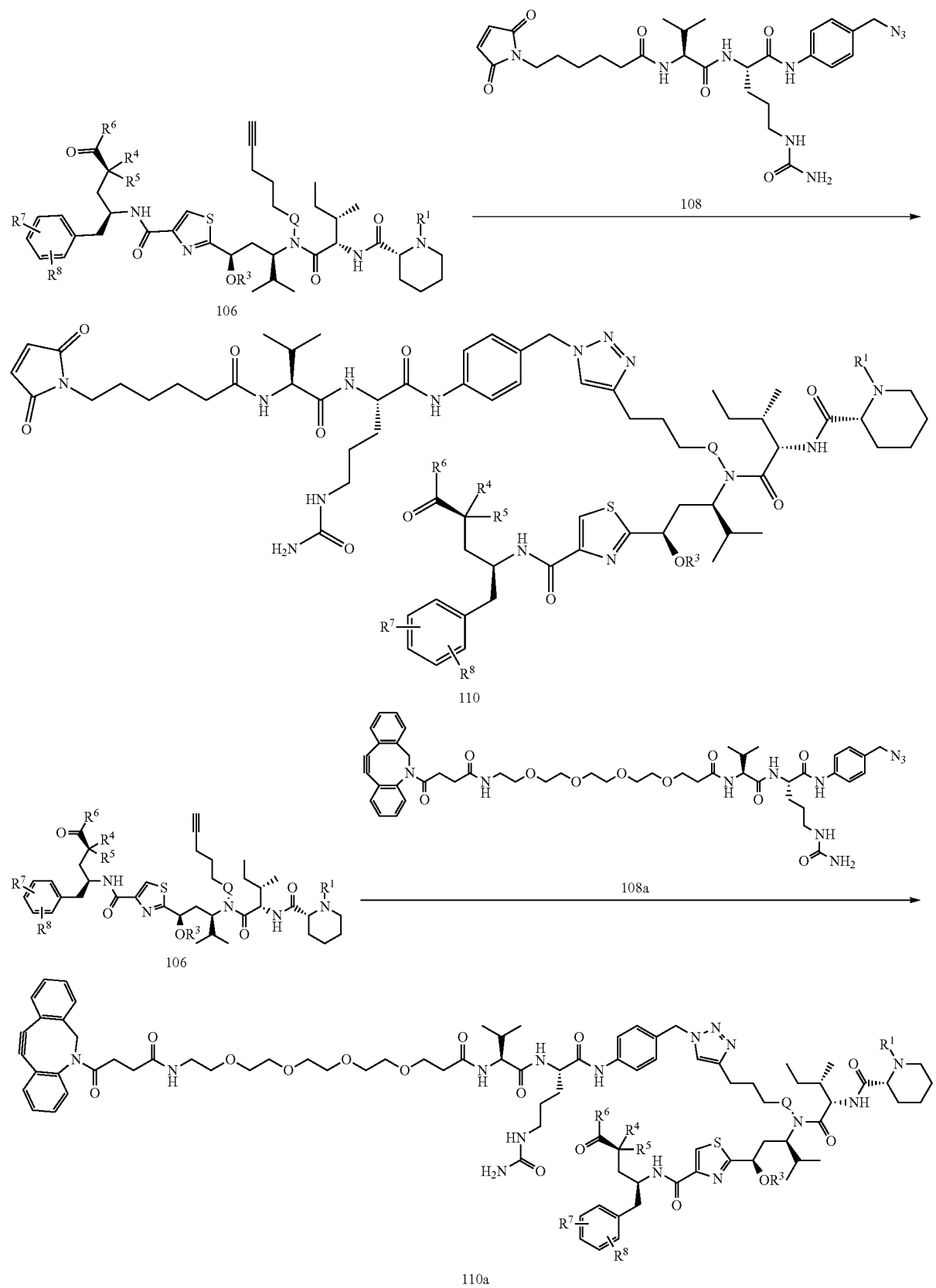

Scheme J. Exemplary Preparation Scheme
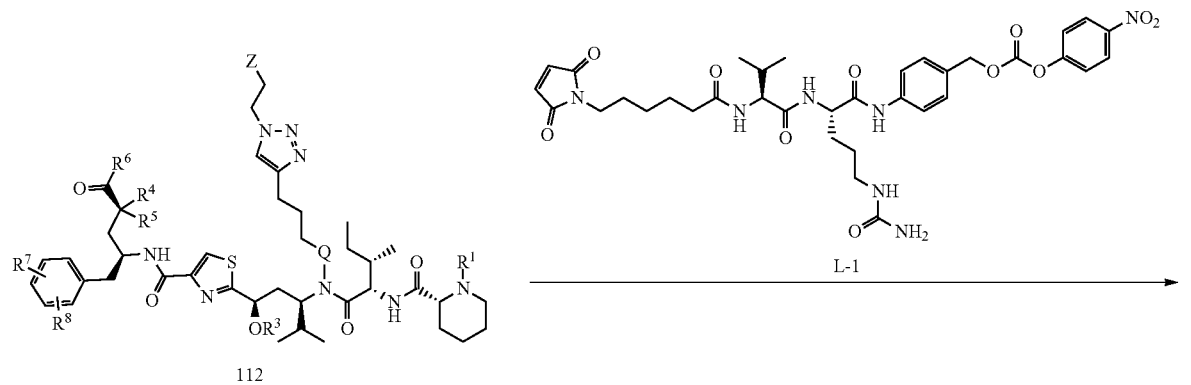
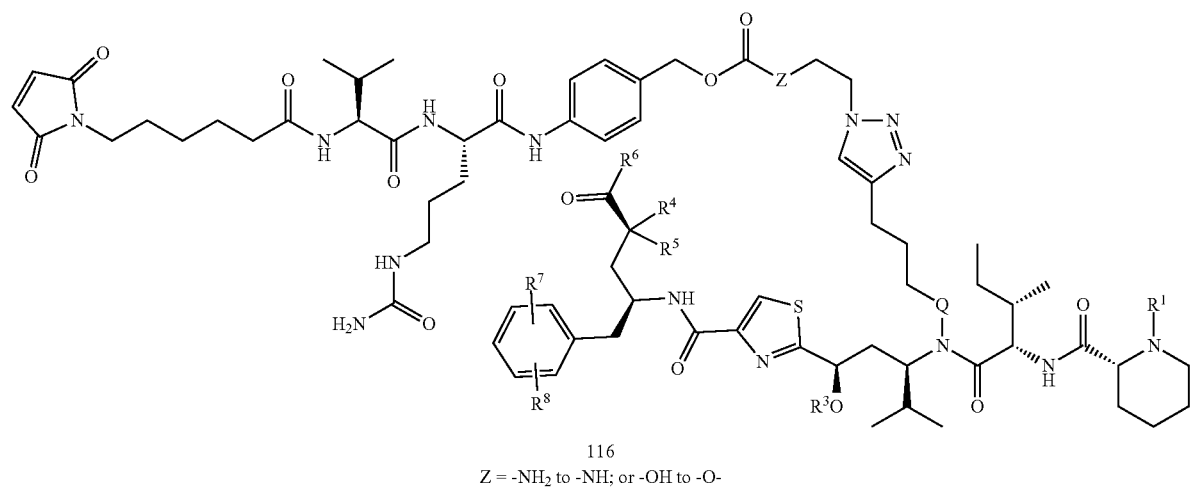
116
Z = -NH$_2$ to -NH; or -OH to -O-
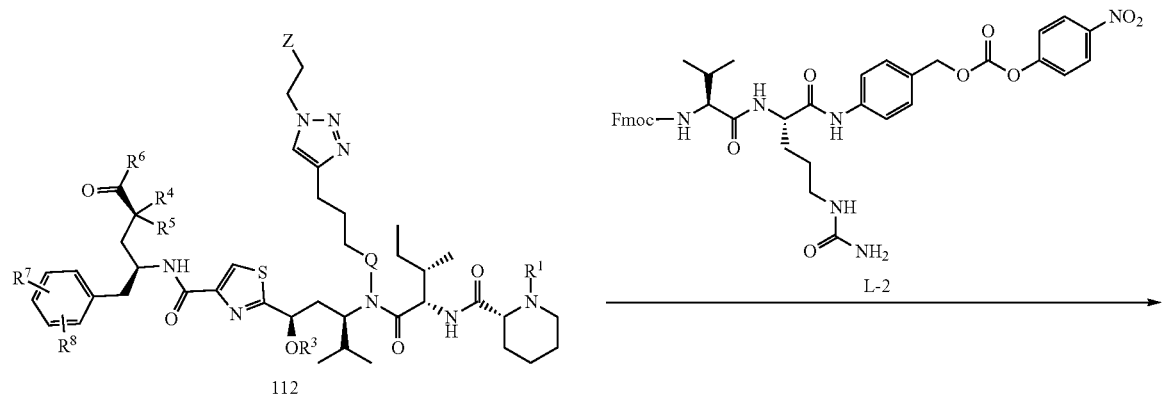

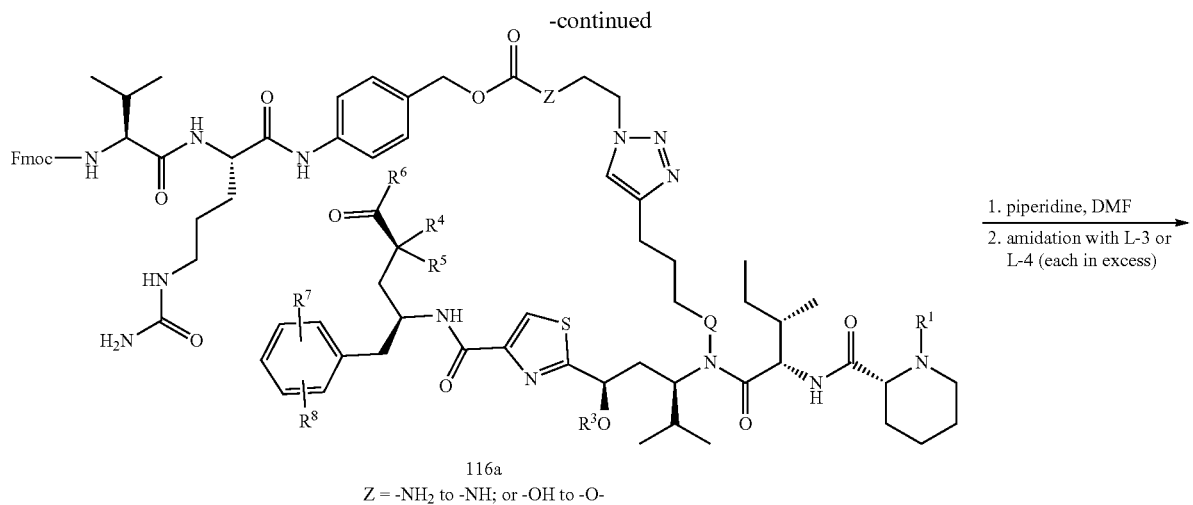
116a
Z = -NH₂ to -NH; or -OH to -O-
1. piperidine, DMF
2. amidation with L-3 or L-4 (each in excess) →
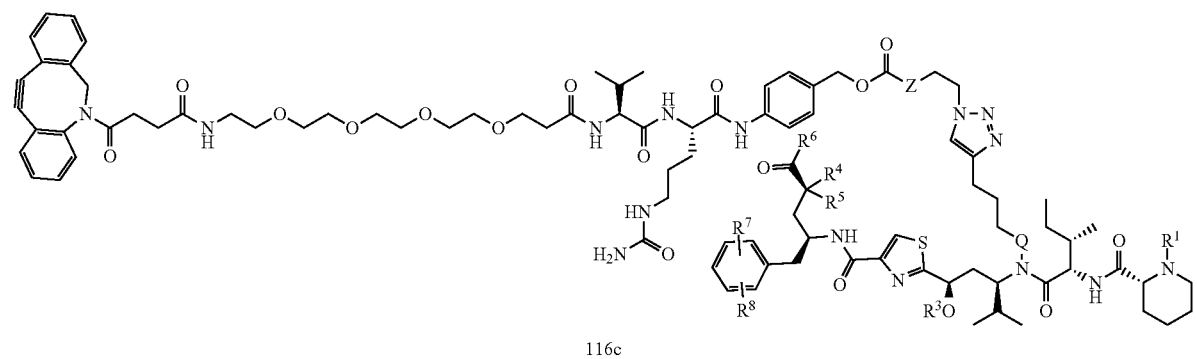
116c
Scheme K. Exemplary Preparation Scheme
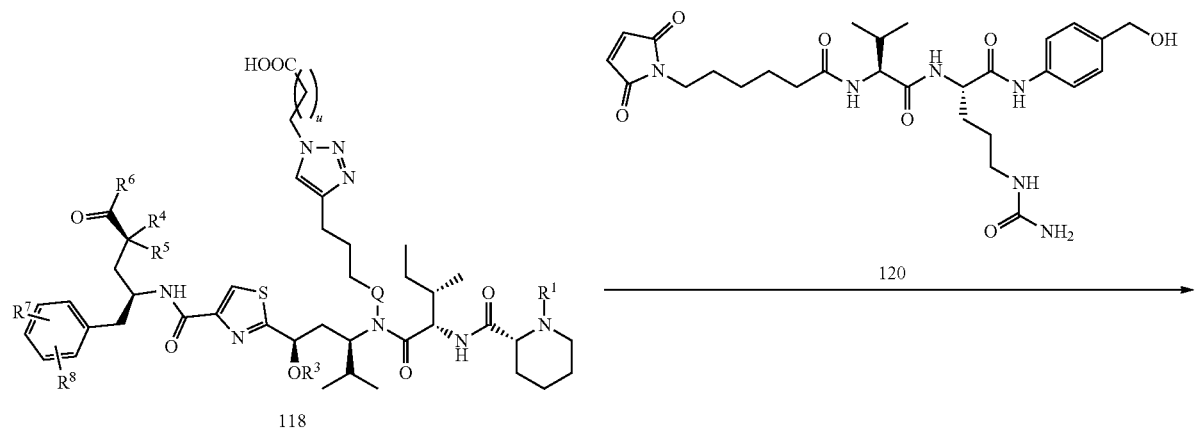
118    120

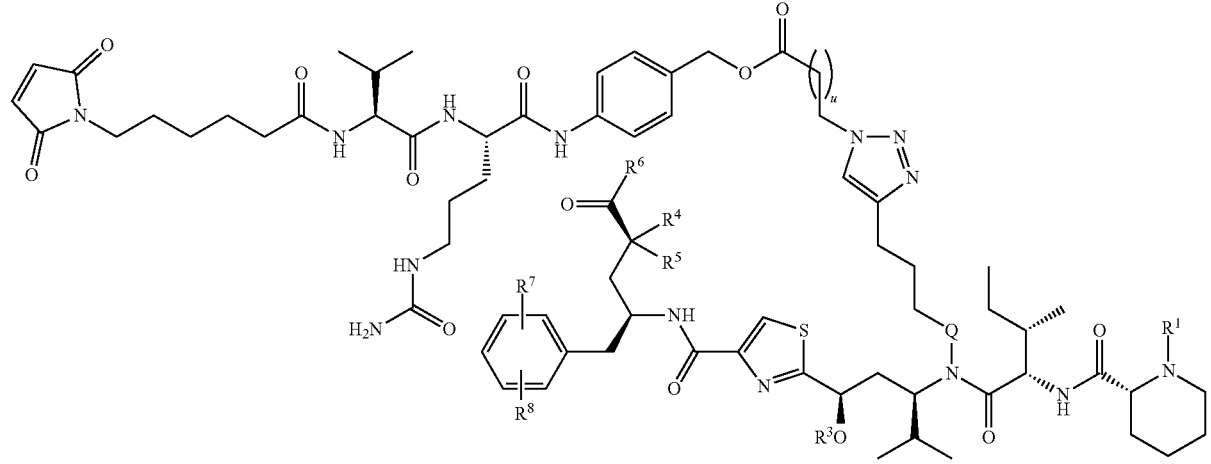
122
u = zero or 2
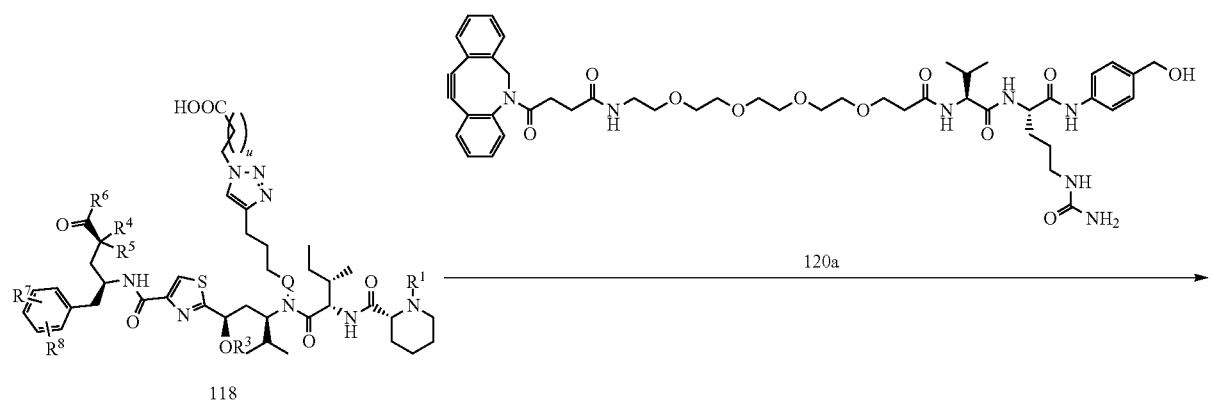
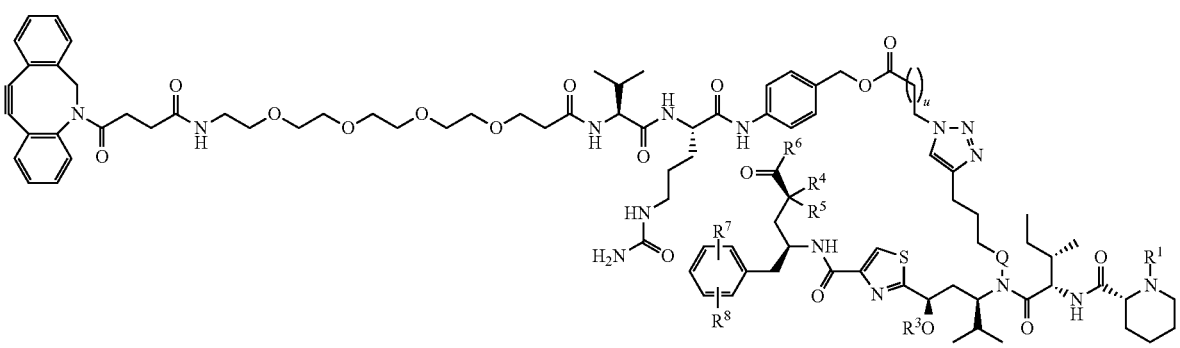
122a
u = zero or 2

Scheme M. Exemplary Preparation Scheme
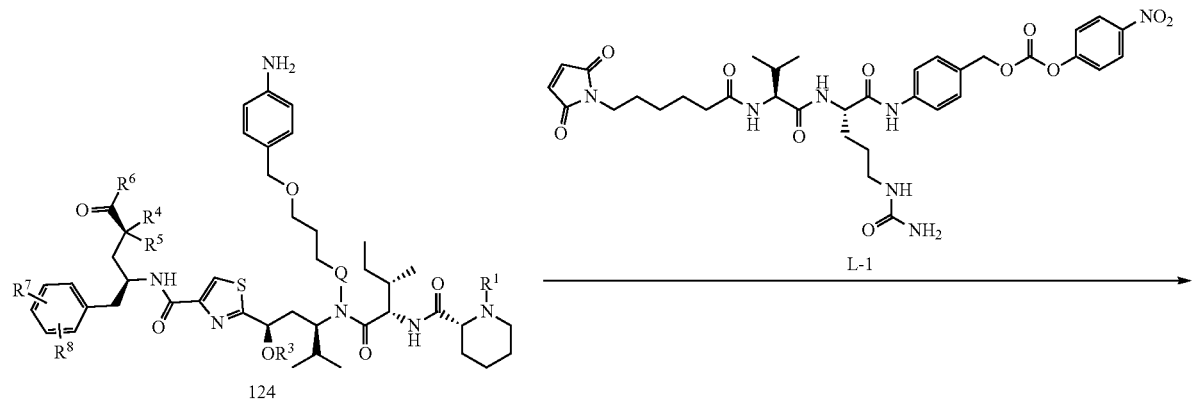
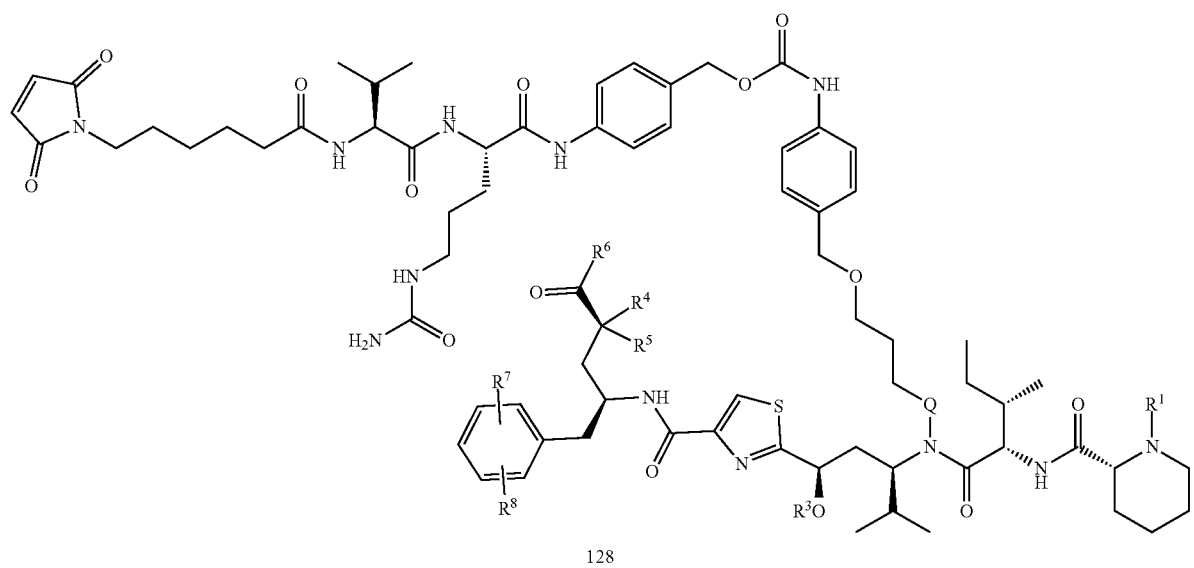
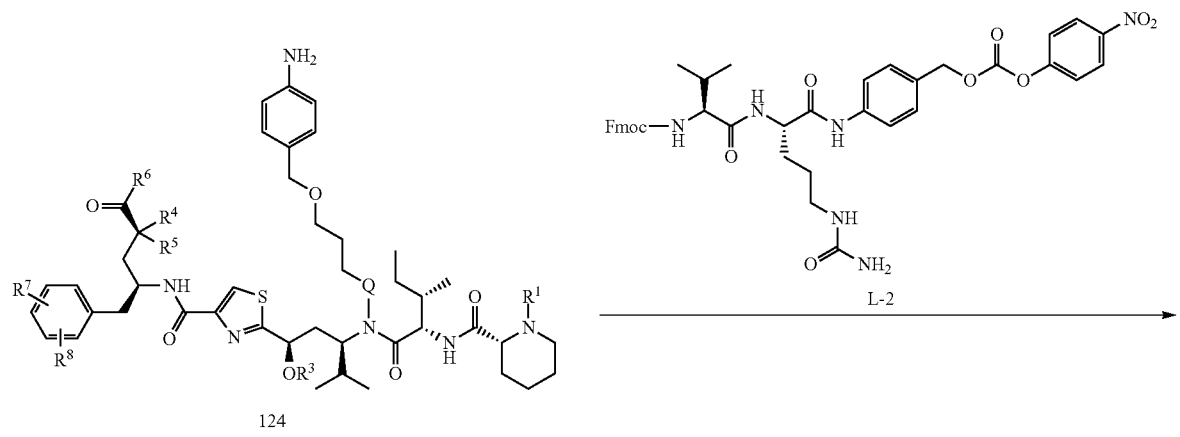

-continued
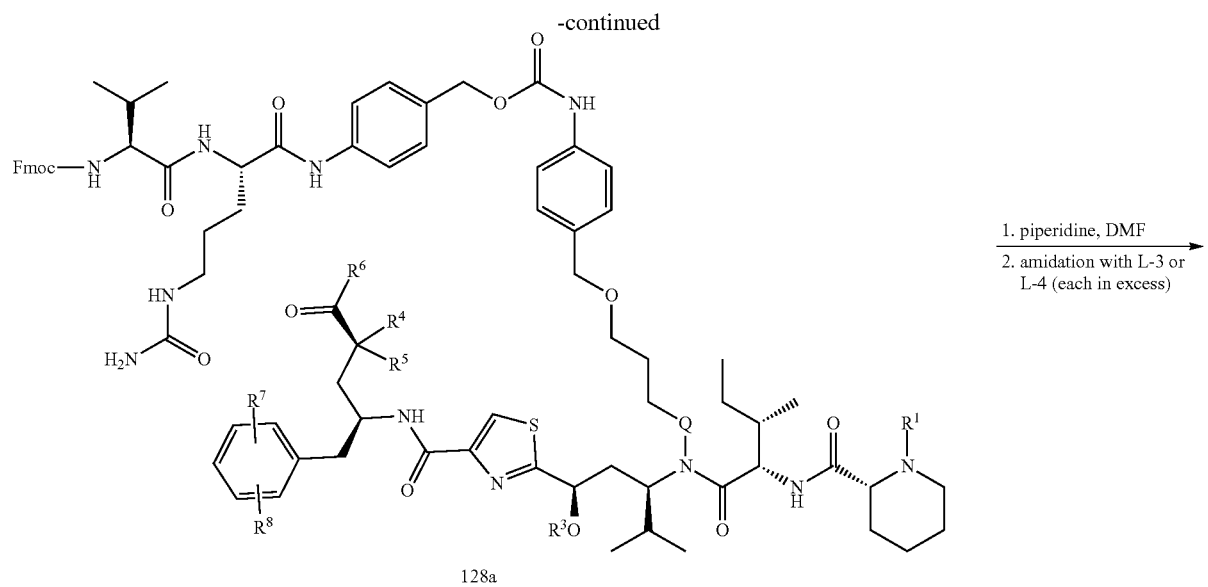
128a
1. piperidine, DMF
2. amidation with L-3 or L-4 (each in excess)
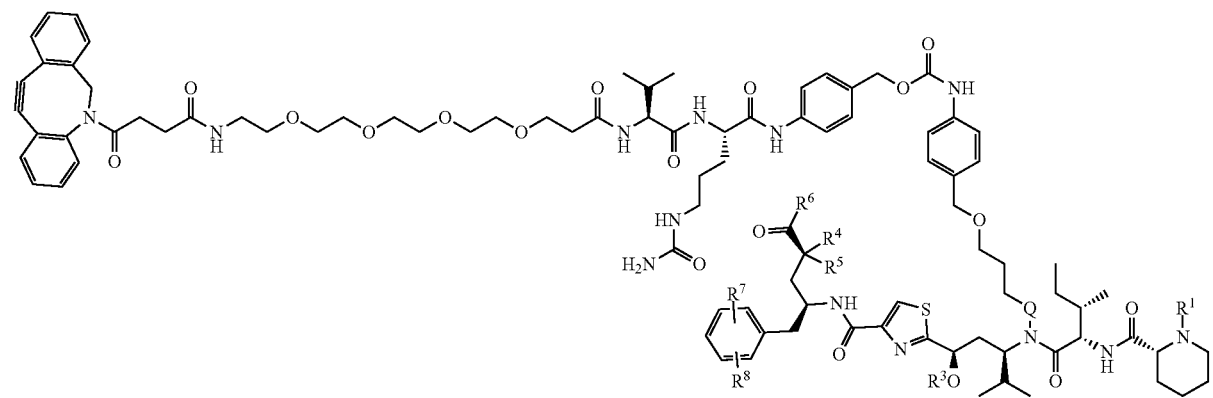
128c
Scheme N. Exemplary Preparation Scheme
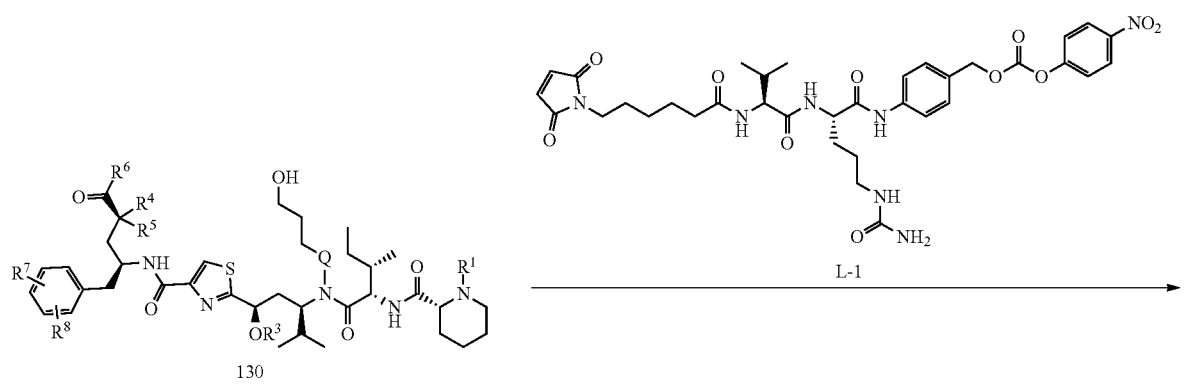
130
L-1

-continued
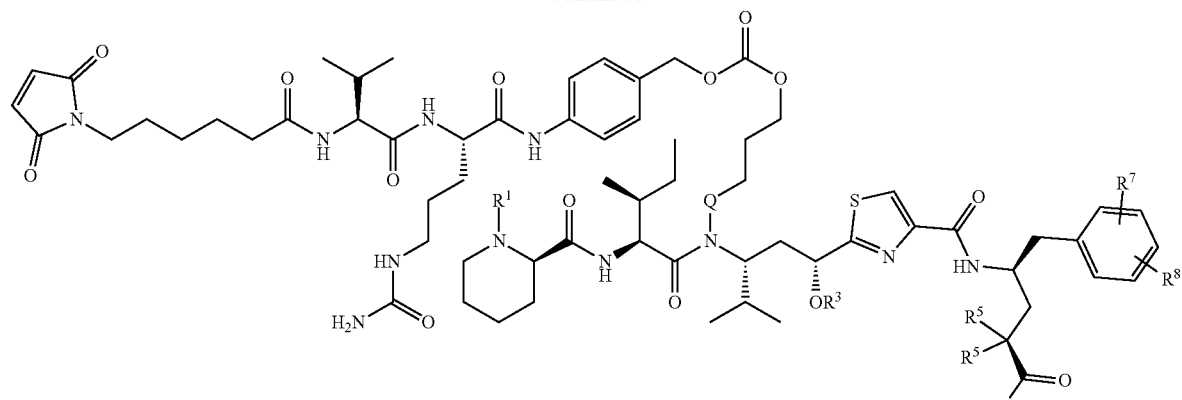
134
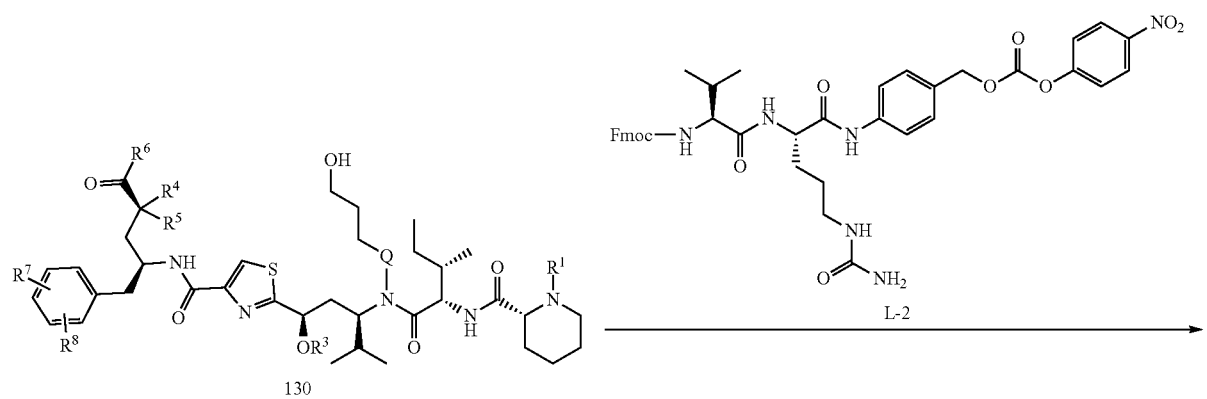
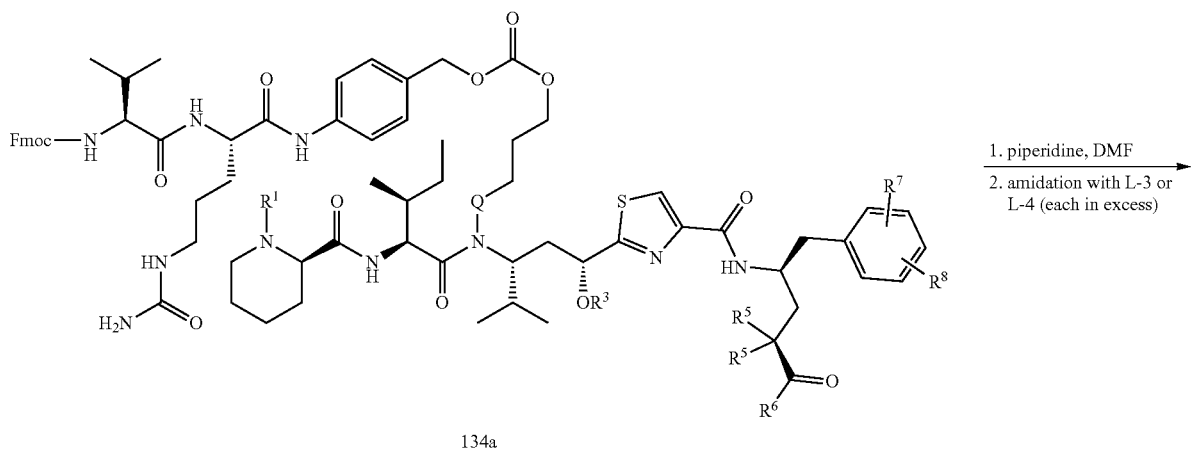
134a
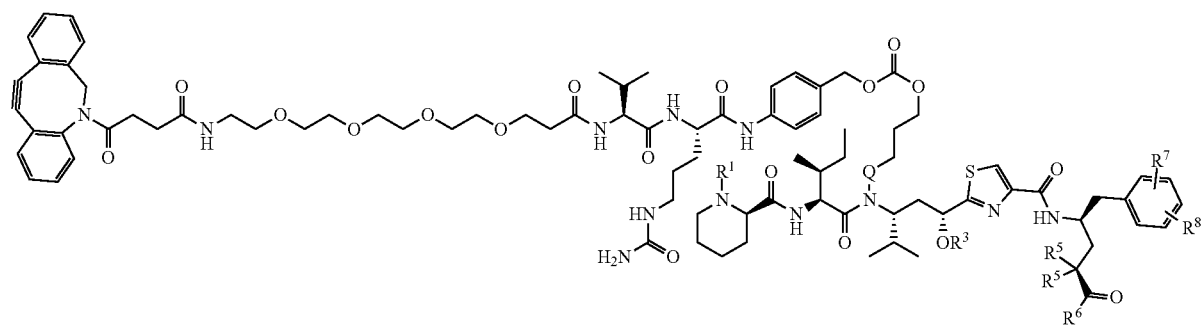
134c

In the above Exemplary Preparation Schemes, $R^1$, $R^2$, $R^3$, $R^4$, $R^5$, $R^6$, $R^7$, $R^8$ are described in the context of Formula I. In Scheme E, a payload is treated with a benzyl halide to form a quaternary ammonium linker-payload. In Schemes F, G, J, M, and N a payload is treated with a carbonate to form linker-payloads. In Scheme H, a payload is treated with a benzyl azide to form a triazolyl linker-payload. In Scheme K, a payload is esterified with a benzyl alcohol to form a linker-payload.

In certain embodiments, provided herein are compounds (e.g., linker-payloads) selected from the group consisting of:

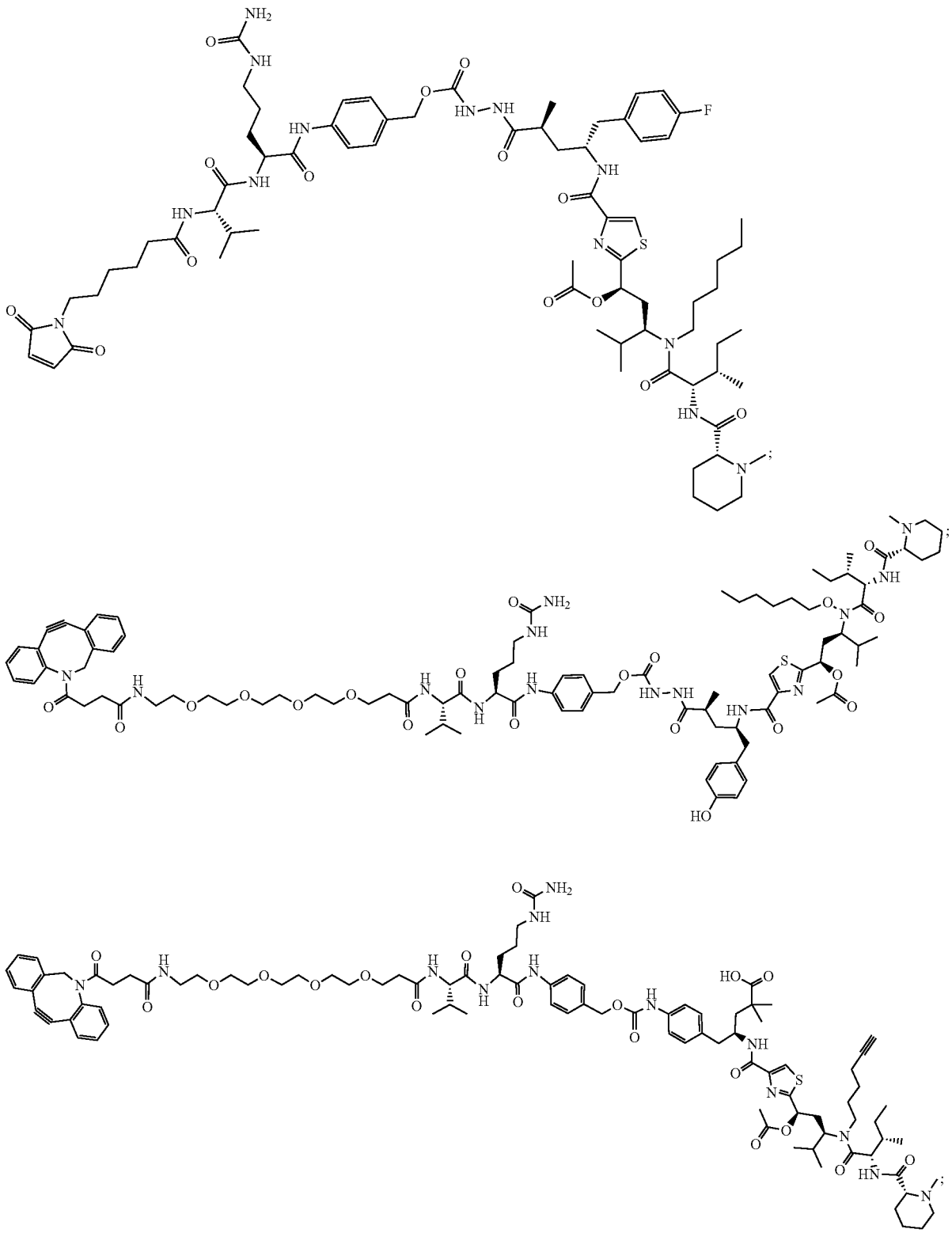

-continued
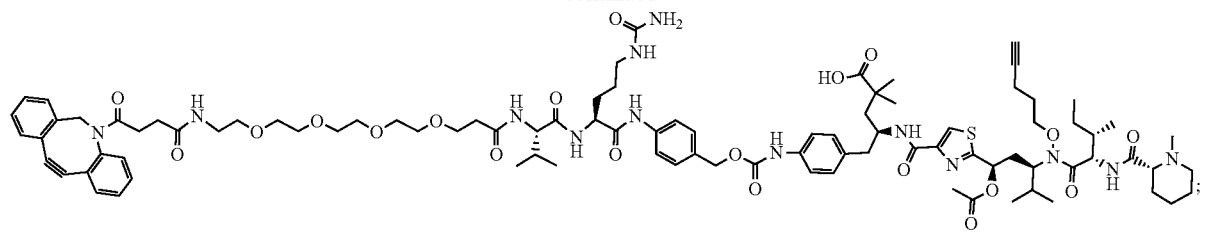
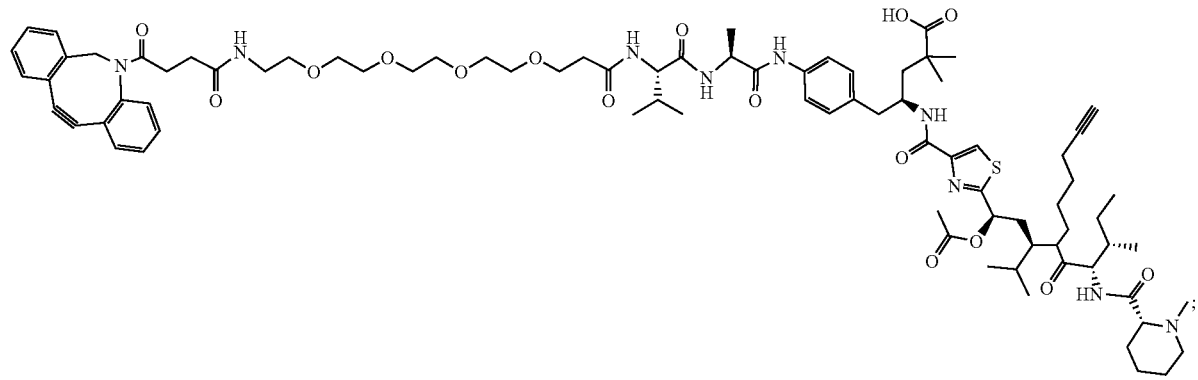
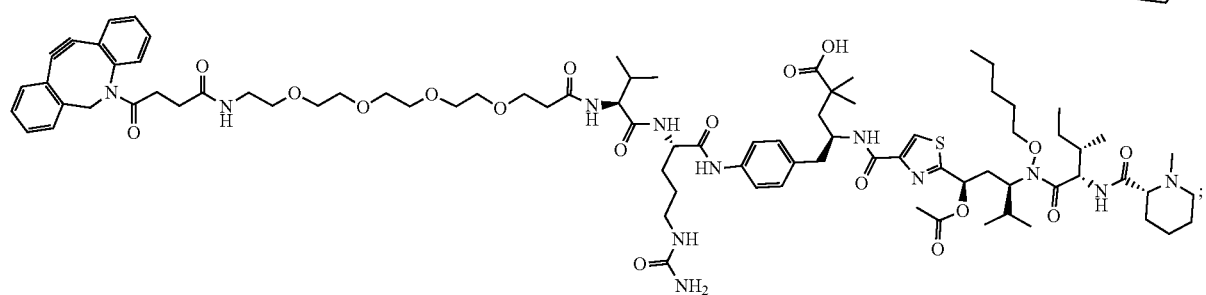
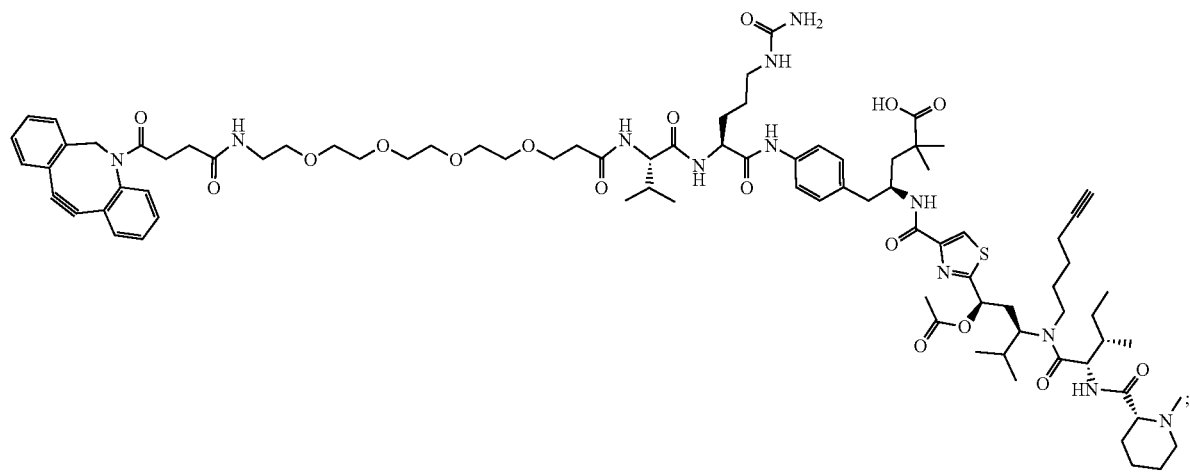
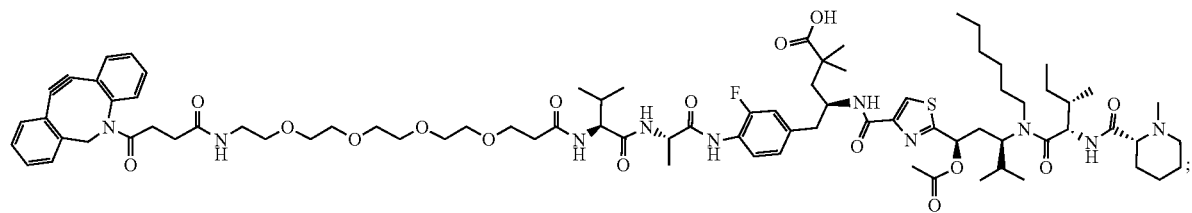

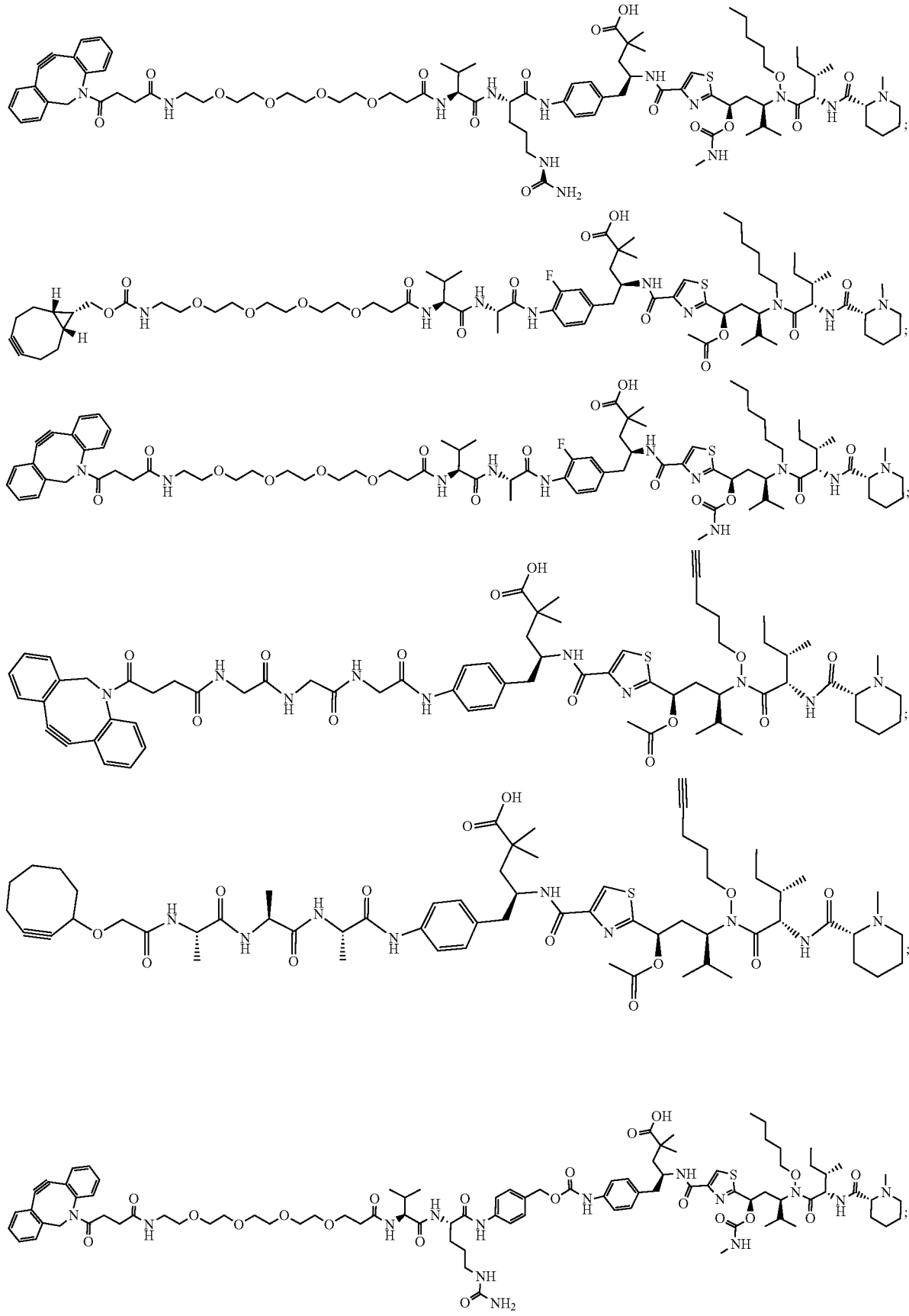

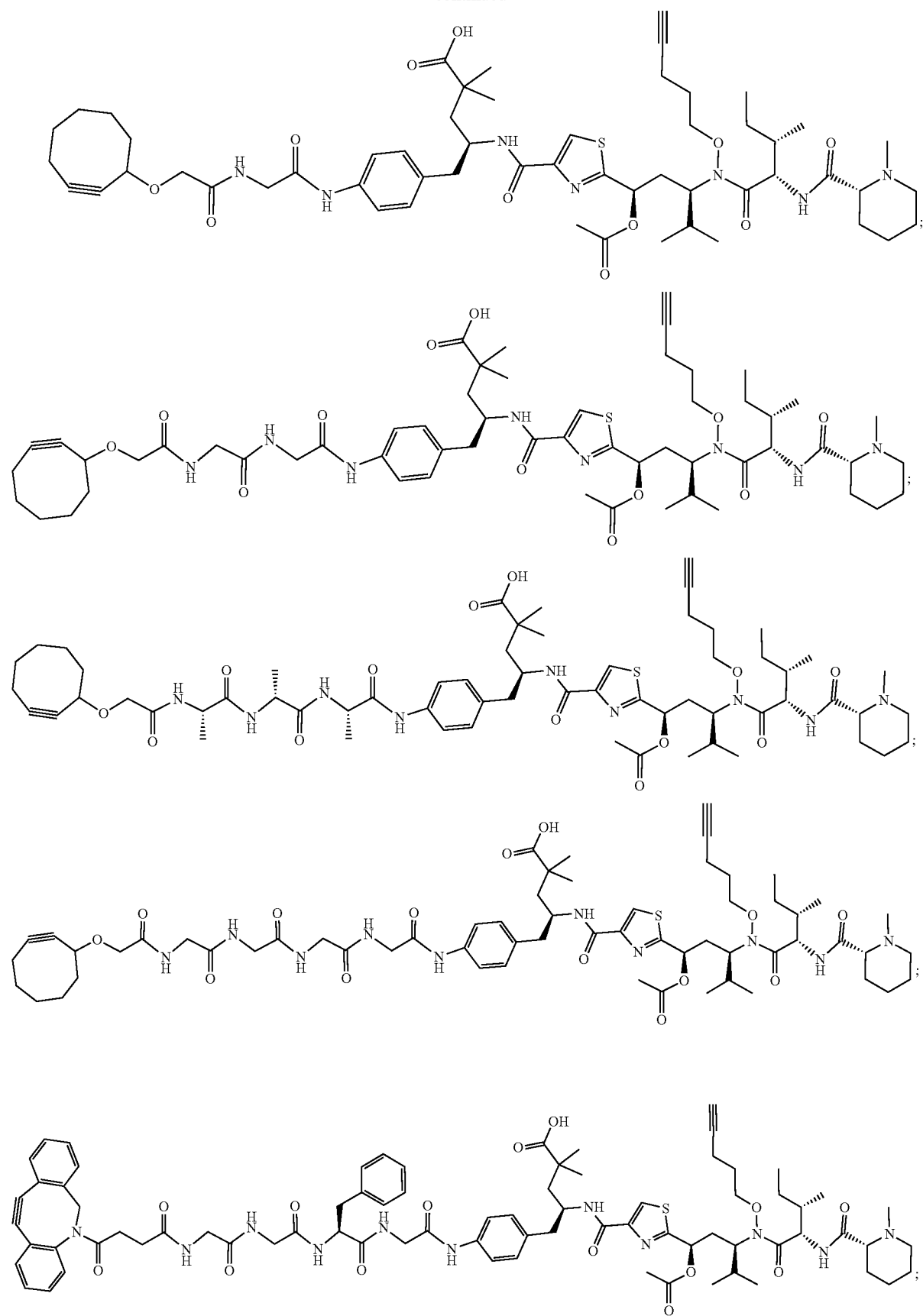

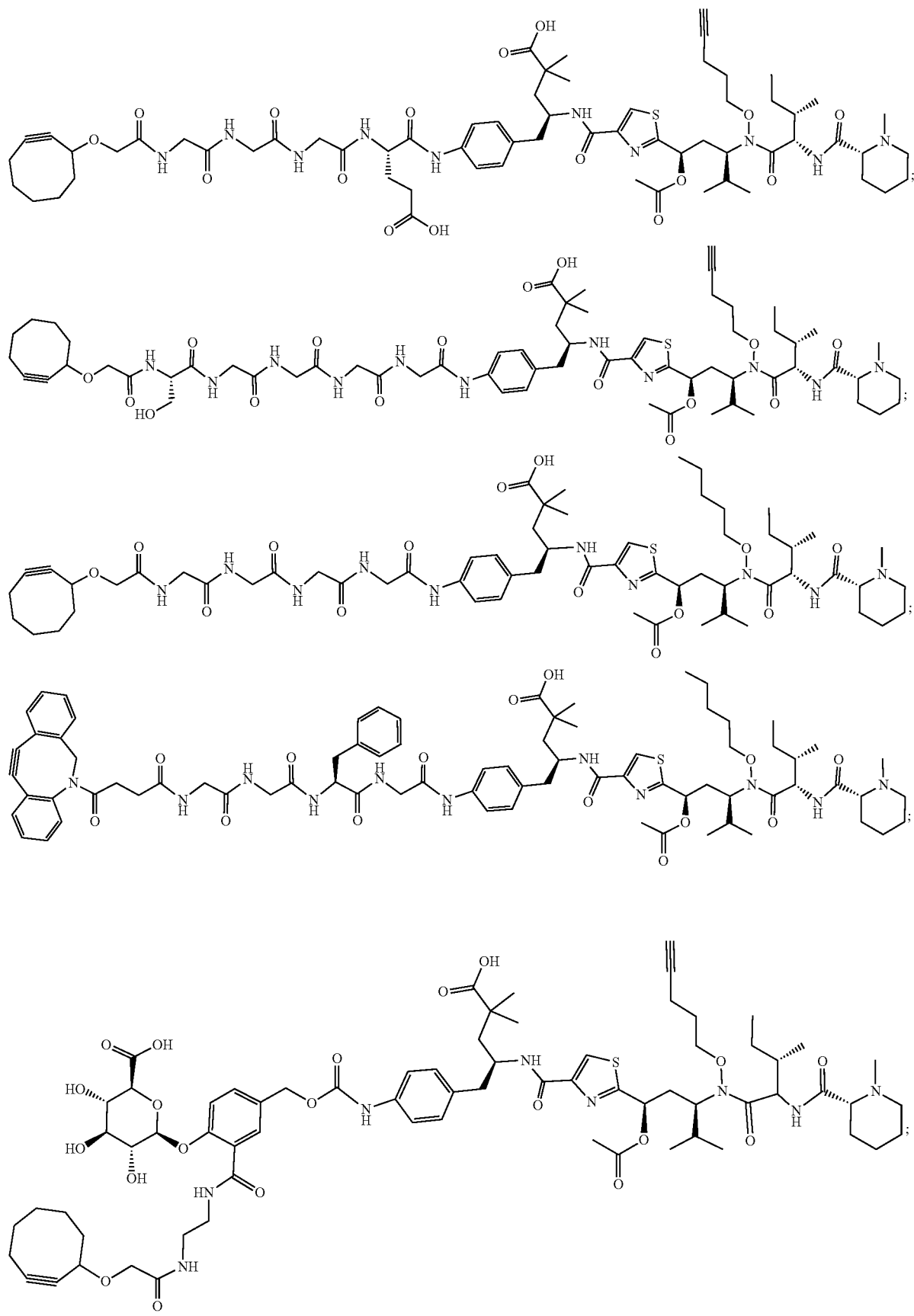

297
298
-continued
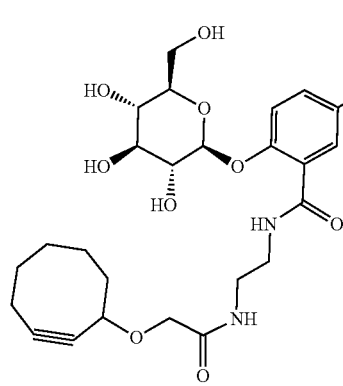
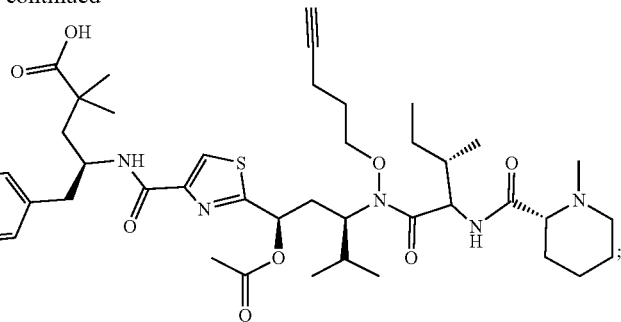
and
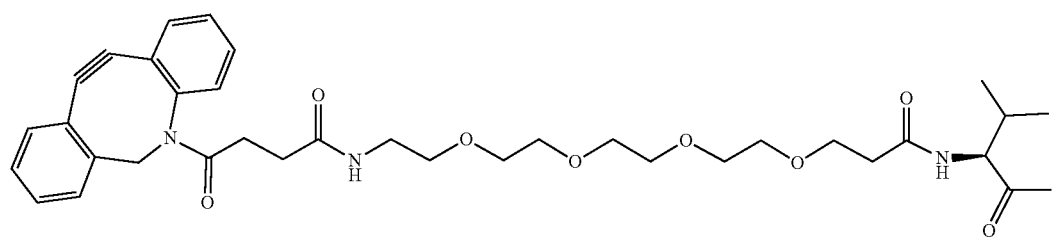
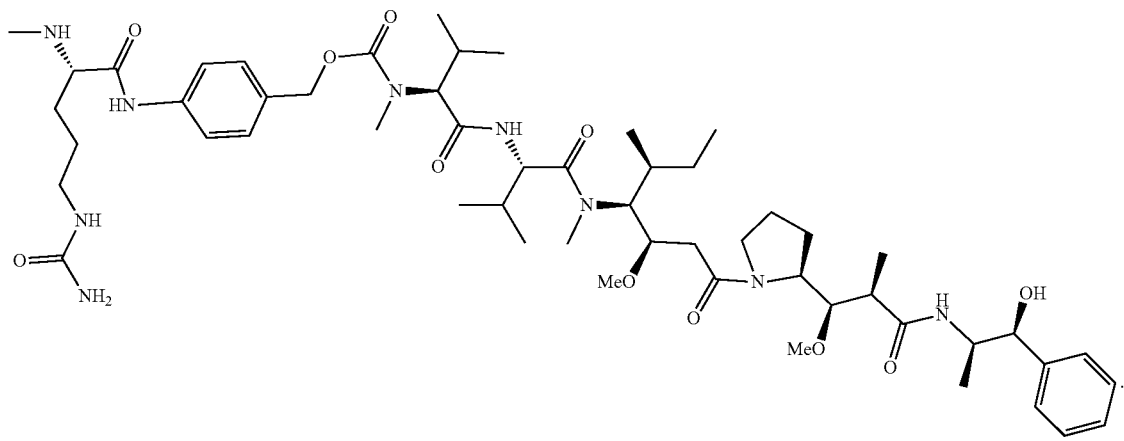
In certain embodiments within this paragraph, all diastereomers are contemplated. For example, in one embodiment, the stereochemistry within
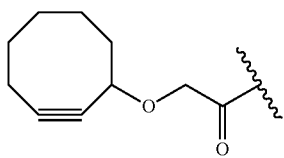 [SMILES: *C(=O)COC1C#CCCCCC1]
is undefined or racemic. By way of further example, in one embodiment, the stereochemistry within
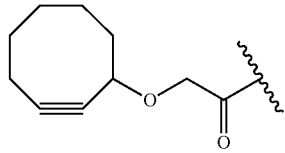 [SMILES: *C(=O)COC1C#CCCCCC1]

is (R)-. By way of further example, in one embodiment, the stereochemistry within

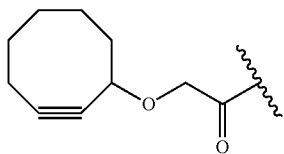 [SMILES: *C(=O)COC1C#CCCCCC1]

(S)-. By way of further example, in one embodiment, the stereochemistry within

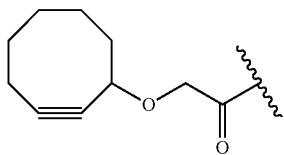 [SMILES: *C(=O)COC1C#CCCCCC1]

is (R)- in excess of (S)-. By way of further example, in one embodiment, the stereochemistry within

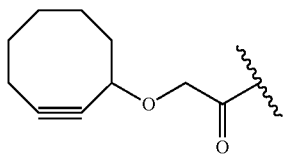 [SMILES: *C(=O)COC1C#CCCCCC1]

is (S)-in excess of (R)-.

The conjugates described herein can be synthesized by coupling the linker-payloads described herein with a binding agent, for example, an antibody under standard conjugation conditions (see, e.g., Doronina et al. *Nature Biotechnology* 2003, 21, 778, which is incorporated herein by reference in its entirety). When the binding agent is an antibody, the antibody may be coupled to a linker-payload via one or more cysteine or lysine residues of the antibody. Linker-payloads can be coupled to cysteine residues, for example, by subjecting the antibody to a reducing agent, for example, dithiotheritol, to cleave the disulfide bonds of the antibody, purifying the reduced antibody, for example, by gel filtration, and subsequently treating the antibody with a linker-payload containing a suitable reactive moiety, for example, a maleimido group. Suitable solvents include, but are not limited to water, DMA, DMF, and DMSO. Linker-payloads containing a reactive group, for example, an activated ester or acid halide group, can be coupled to lysine residues of the antibody. Suitable solvents include, but are not limited to, water, DMA, DMF, and DMSO. Conjugates can be purified using known protein techniques, including, for example, size exclusion chromatography, dialysis, and ultrafiltration/diafiltration.

Binding agents, for example antibodies, can also be conjugated via click chemistry reactions. In some embodiments of said click chemistry reactions, the linker-payload includes a reactive group, for example an alkyne, that is capable of undergoing a regioisomeric 1,3-cycloaddition reaction with an azide. Such suitable reactive groups are described above. The antibody includes one or more azide groups. Such antibodies include antibodies functionalized with, for example, azido-polyethylene glycol groups. In certain embodiments, such functionalized antibody is derived by treating an antibody having at least one glutamine residue, for example, heavy chain Gln295, with a primary amine compound in the presence of the enzyme transglutaminase. In certain embodiments, such functionalized antibody is derived by treating an antibody having at least one glutamine residue, for example, heavy chain Gln297, with a primary amine compound in the presence of the enzyme transglutaminase. Such antibodies include Asn297Gln (N297Q) mutants. In certain embodiments, such functionalized antibody is derived by treating an antibody having at least two glutamine residues, for example, heavy chain Gln295 and heavy chain Gln297, with a primary amine compound in the presence of the enzyme transglutaminase. Such antibodies include Asn297Gln (N297Q) mutants. In certain embodiments, the antibody has two heavy chains as described in this paragraph for a total of two or a total of four glutamine residues.

In certain embodiments, the antibody comprises two glutamine residues, one in each heavy chain. In particular embodiments, the antibody comprises a Q295 residue in each heavy chain. In further embodiments, the antibody comprises one, two, three, four, five, six, seven, eight, or more glutamine residues. These glutamine residues can be in heavy chains, light chains, or in both heavy chains and light chains. These glutamine residues can be wild-type residues, or engineered residues. The antibodies can be prepared according to standard techniques.

Those of skill will recognize that antibodies are often glycosylated at residue N297, near residue Q295 in a heavy chain sequence. Glycosylation at residue N297 can interfere with a transglutaminase at residue Q295 (Dennler et al., supra). Accordingly, in advantageous embodiments, the antibody is not glycosylated. In certain embodiments, the antibody is deglycoslated or aglycosylated. In particular embodiments, an antibody heavy chain has an N297 mutation. Alternatively stated, the antibody is mutated to no longer have an asparagine residue at position 297. In particular embodiments, an antibody heavy chain has an N297Q mutation. Such an antibody can be prepared by site-directed mutagenesis to remove or disable a glycosylation sequence or by site-directed mutagenesis to insert a glutamine residue at a site apart from any interfering glycosylation site or any other interfering structure. Such an antibody also can be isolated from natural or artificial sources.

The antibody without interfering glycosylation is then reacted or treated with a primary amine compound. In certain embodiments, an aglycosylated antibody is reacted or treated with a primary amine compound to produce a glutaminyl-modified antibody. In certain embodiments, a deglycosylated antibody is reacted or treated with a primary amine compound to produce a glutaminyl-modified antibody.

The primary amine can be any primary amine that is capable of forming a covalent bond with a glutamine residue in the presence of a transglutaminase. Useful primary amines are described herein. The transglutaminase can be any transglutaminase deemed suitable by those of skill in the art. In certain embodiments, the transglutaminase is an enzyme that catalyzes the formation of an isopeptide bond between a free amine group on the primary amine compound and the acyl group on the side chain of a glutamine residue. Transglutaminase is also known as protein-glutamine-γ-glutamyltransferase. In particular embodiments, the transglutaminase is classified as EC 2.3.2.13. The transglutaminase can be from any source deemed suitable. In certain embodiments, the transglutaminase is microbial. Useful transglutaminases have been isolated from *Streptomyces mobaraense, Streptomyces cinnamoneum, Streptomyces griseo-carneum, Streptomyces lavendulae,* and *Bacillus subtilis*. Non-microbial transglutaminases, including mammalian transglutaminases, can also be used. In certain embodiments, the transglutaminase can be produced by any technique or obtained from any source deemed suitable by the practitioner of skill. In particular embodiments, the transglutaminase is obtained from a commercial source.

In particular embodiments, the primary amine compound comprises a reactive group capable of further reaction after transglutamination. In these embodiments, the glutaminyl-modified antibody can be reacted or treated with a reactive payload compound or a reactive linker-payload compound to form an antibody-payload conjugate or an antibody-linker-payload conjugate. In certain embodiments, the primary amine compound comprises an azide.

In certain embodiments, the glutaminyl-modified antibody is reacted or treated with a reactive linker-payload to form an antibody-linker-payload conjugate. The reaction can proceed under conditions deemed suitable by those of skill in the art. In certain embodiments, the glutaminyl-modified antibody is contacted with the reactive linker-payload compound under conditions suitable for forming a bond between the glutaminyl-modified antibody and the linker-payload compound. Suitable reaction conditions are well known to those in the art. Exemplary reactions are provided in the Examples below.

Pharmaceutical Compositions and Methods of Treatment

Provided herein are methods of treating and preventing diseases, conditions, or disorders comprising administering a therapeutically or prophylactically effective amount or one or more of the compounds disclosed herein, for example, one or more of the compounds of a formula provided herein. Diseases, disorders, and/or conditions include, but are not limited to, those associated with the antigens listed herein.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: a second tubulysin, an autoimmune therapeutic agent, a hormone, a biologic, or a monoclonal antibody. Suitable therapeutic agents also include, but are not limited to any pharmaceutically acceptable salts, acids, or derivatives of a compound set forth herein.

In some embodiments of the methods described herein, multiple doses of a compound described herein (or a pharmaceutical composition comprising a combination of a compound described herein and any of the additional therapeutic agents mentioned herein) may be administered to a subject over a defined time course. The methods according to this embodiment of the disclosure comprise sequentially administering to a subject multiple doses of a compound described herein. As used herein, "sequentially administering" means that each dose of the compound is administered to the subject at a different point in time, e.g., on different days separated by a predetermined interval (e.g., hours, days, weeks, or months). The present disclosure includes methods which comprise sequentially administering to the patient a single initial dose of a compound described herein, followed by one or more secondary doses of the compound, and optionally followed by one or more tertiary doses of the compound.

The terms "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all include the same amount the compound described herein, but generally can differ from one another in terms of frequency of administration. In certain embodiments, the amount of the compound included in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose the compound which is administered to a patient prior to the administration of the very next dose in the sequence with no intervening doses.

The methods according to this embodiment of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this embodiment of the disclosure, if the loading doses are administered at a frequency of once a month, then the maintenance doses may be administered to the patient once every six weeks, once every two months, once every three months, etc.

The present disclosure includes pharmaceutical compositions of the compounds and/or conjugates described herein, e.g., the compounds Formulae I, II, III, IV, V, VI, VII, VIII IX, X, XI, and XII, e.g., compositions comprising a compound described herein, a salt, stereoisomer, regioisomer, polymorph thereof, and a pharmaceutically acceptable carrier, diluent, and/or excipient. Examples of suitable carriers, diluents and excipients include, but are not limited to, buffers for maintenance of proper composition pH (e.g., citrate buffers, succinate buffers, acetate buffers, phosphate buffers, lactate buffers, oxalate buffers, and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants.

In some examples, set forth herein is a method of treating cancer comprising administering to a patient having said cancer a therapeutically effective amount of a compound of Formulae I, II, III, IV, V, VI, VII, VIII IX, X, XI, and XII, or a pharmaceutical composition thereof. In some embodiments, provided herein is a method of treating cancer comprising administering to a patient having said cancer a therapeutically effective amount of a an antibody-tubulysin conjugate described herein, or a pharmaceutical composition thereof. In some embodiments, the binding agent, e.g., antibody, of the conjugates, e.g., antibody-drug conjugates described herein interact with or bind to tumor antigens, including antigens specific for a type of tumor or antigens that are shared, overexpressed, or modified on a particular type of tumor. Examples include, but are not limited to, alpha-actinin-4 with lung cancer, ARTC1 with melanoma, BCR-ABL fusion protein with chronic myeloid leukemia, B-RAF, CLPP or Cdc27 with melanoma, CASP-8 with squamous cell carcinoma, and hsp70-2 with renal cell carcinoma as well as the following shared tumor-specific antigens, for example, BAGE-1, GAGE, GnTV, KK-LC-1, MAGE-A2, NA88-A, TRP2-INT2. Further examples of tumor antigens include, but are not limited to, PSMA, PRLR, MUC16, HER2, EGFRvIII, and anti-STEAP2, and MET.

The compounds disclosed herein can be used for treating primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the compounds provided herein are used to treat one or more of the following cancers: renal cell carcinoma, pancreatic carcinoma, head and neck cancer (e.g., head and neck squamous cell carcinoma [HNSCC]), prostate cancer, castrate-resistant prostrate cancer, malignant gliomas, osteosarcoma, colorectal cancer, gastric cancer (e.g., gastric cancer with MET amplification), mesothelioma, malignant mesothelioma, multiple myeloma, ovarian cancer, lung cancer, small cell lung cancer, non-small cell lung cancer, synovial sarcoma, thyroid cancer, breast cancer, PRLR positive (PRLR+) breast cancer, melanoma, acute myelogenous leukemia, adult T-cell leukemia, astrocytomas, bladder cancer, cervical cancer, cholangiocarcinoma, endometrial cancer, esophageal cancer, glioblastomata, Kaposi's sarcoma, kidney cancer, leiomyosarcomas, liver cancer, lymphomas, MFH/fibrosarcoma, nasopharyngeal cancer, rhabdomyosarcoma, colon cancer, stomach cancer, uterine cancer, residual cancer wherein "residual cancer" means the existence or persistence of one or more cancerous cells in a subject following treatment with an anti-cancer therapy, and Wilms' tumor. In some embodiments, the cancer is breast cancer. In some embodiments, the cancer is prostate cancer.

In some examples, set forth herein is a method of preventing prostate cancer comprising administering to a patient having said disorder a prophylactically effective amount of a compound of Formulae I, II, III, IV, V, VI, VII, VIII IX, X, XI, and XII, or a pharmaceutical composition thereof.

EXAMPLES

Provided herein are novel tubulysins, protein conjugates thereof, and methods for treating diseases, disorders, and conditions including administering the tubulysins and conjugates.

TABLE 1

Tubulysin Payloads

| # in Scheme(s) | Structure |
|---|---|
| Tub A | 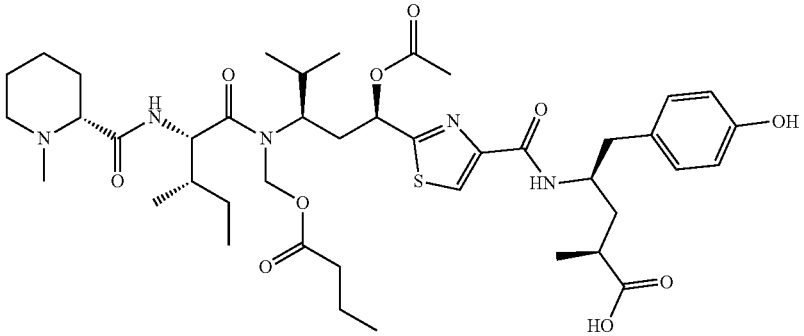 [SMILES: CCCC(=O)OCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)cc2)C[C@H](C)C(=O)O)cs1)C(C)C] |

TABLE 1-continued
Tubulysin Payloads
| # in Scheme(s) | Structure |
|---|---|
| IVa | 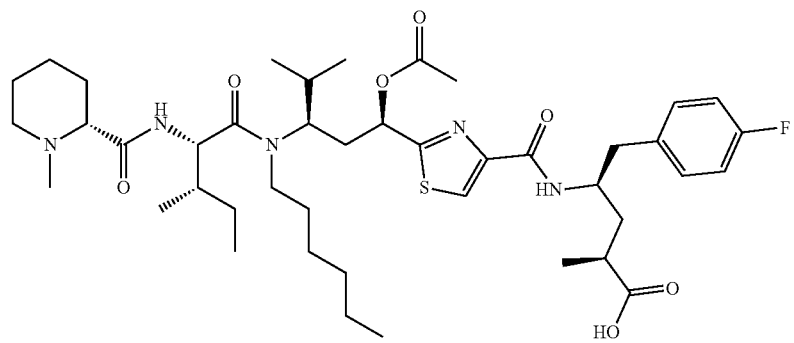 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(F)cc2)C[C@H](C)C(=O)O)cs1)C(C)C] |
| IVa' | 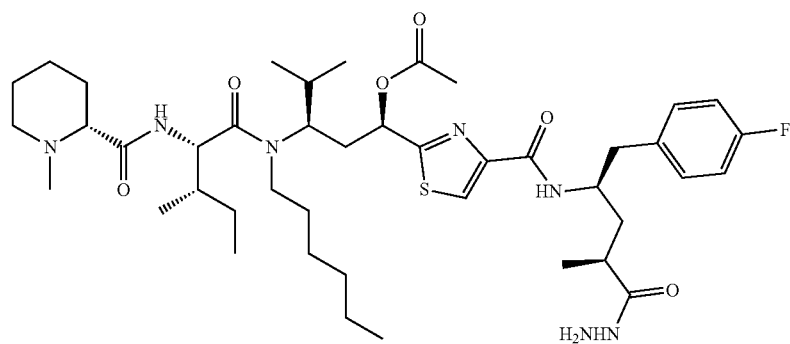 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(F)cc2)C[C@H](C)C(=O)NN)cs1)C(C)C] |
| IVb | 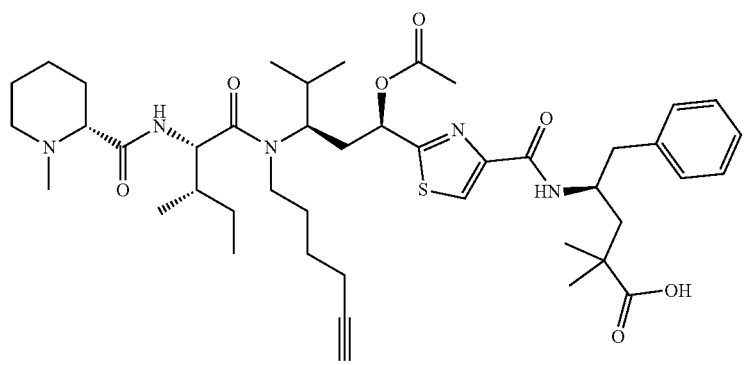 [SMILES: C#CCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccccc2)CC(C)(C)C(=O)O)cs1)C(C)C] |
| IVc | 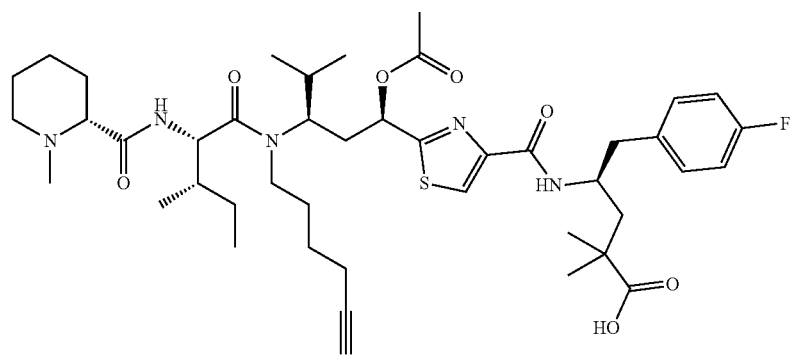 [SMILES: C#CCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(F)cc2)CC(C)(C)C(=O)O)cs1)C(C)C] |

TABLE 1-continued
Tubulysin Payloads
| # in Scheme(s) | Structure |
|---|---|
| IVd | 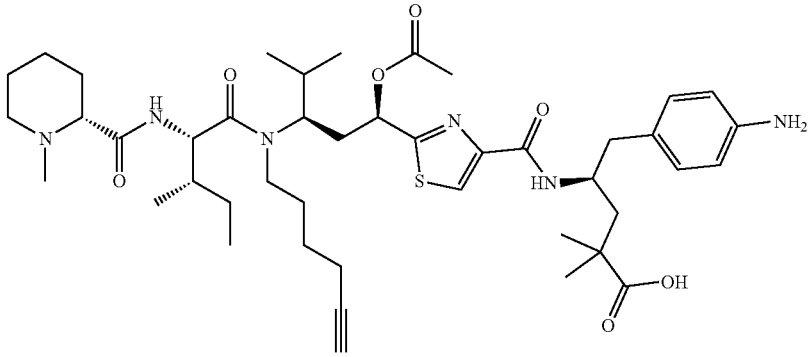 |
| IVe | 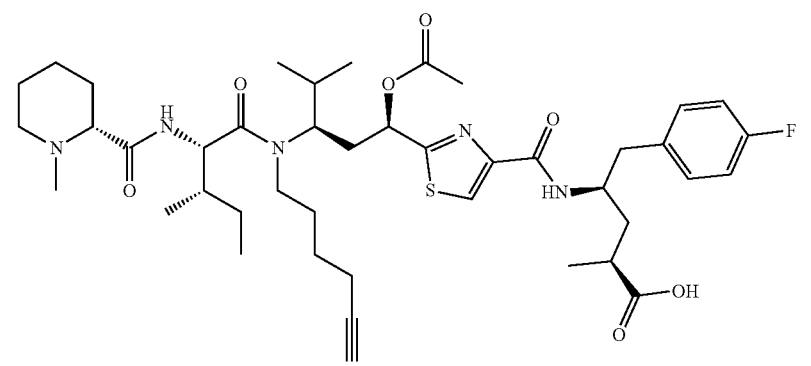 [SMILES: C#CCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(F)cc2)C[C@H](C)C(=O)O)cs1)C(C)C] |
| IVf | 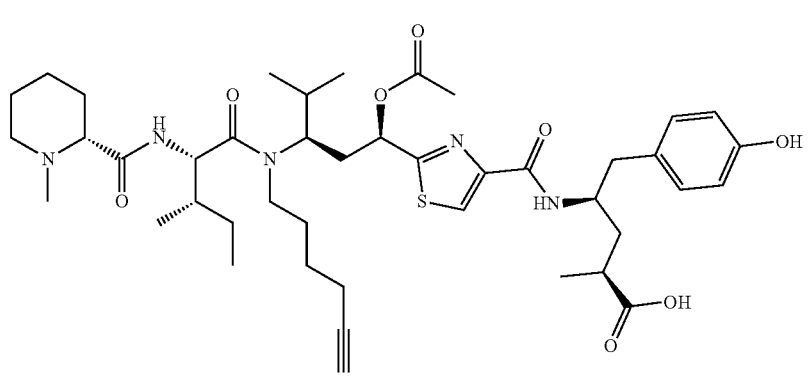 |
| IVg | 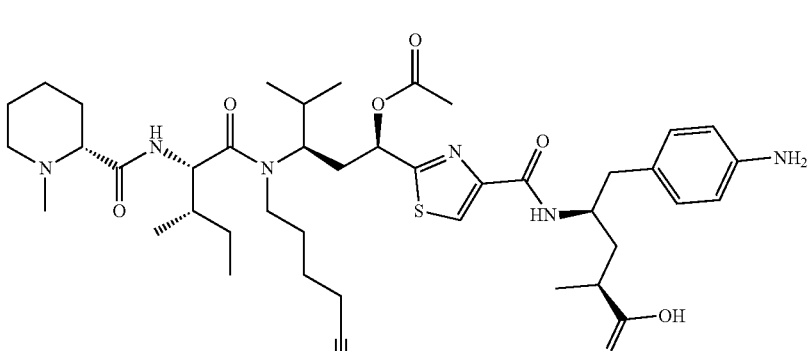 |

TABLE 1-continued

Tubulysin Payloads

| # in Scheme(s) | Structure |
|---|---|
| IVh | 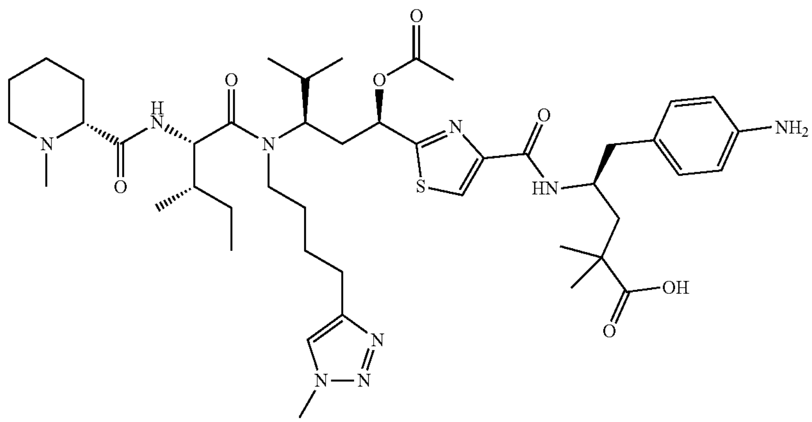 [SMILES: CC[C@H](C)[C@H](NC(=O)[C@H]1CCCCN1C)C(=O)N(CCCCc1cn(C)nn1)[C@H](C[C@@H](OC(C)=O)c1nc(C(=O)N[C@@H](Cc2ccc(N)cc2)CC(C)(C)C(=O)O)cs1)C(C)C] |
| IVj | 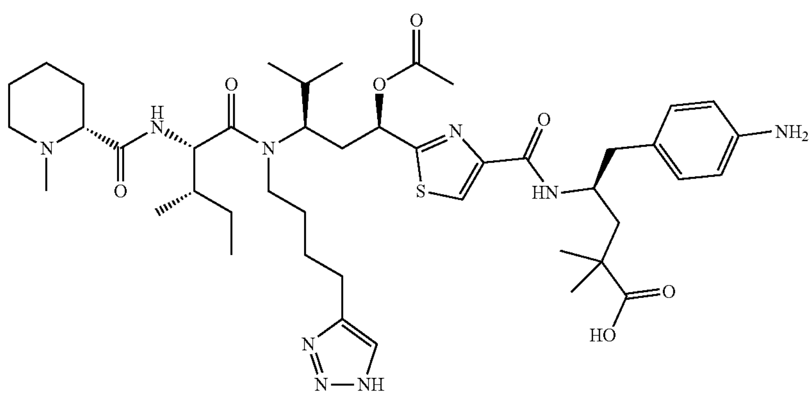 [SMILES: CC[C@H](C)[C@H](NC(=O)[C@H]1CCCCN1C)C(=O)N(CCCCc1c[nH]nn1)[C@H](C[C@@H](OC(C)=O)c1nc(C(=O)N[C@@H](Cc2ccc(N)cc2)CC(C)(C)C(=O)O)cs1)C(C)C] |
| IVk | 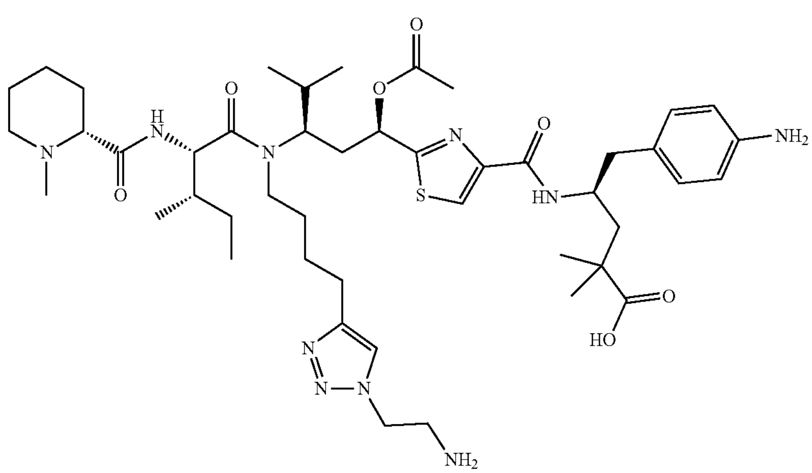 [SMILES: CC[C@H](C)[C@H](NC(=O)[C@H]1CCCCN1C)C(=O)N(CCCCc1cn(CCN)nn1)[C@H](C[C@@H](OC(C)=O)c1nc(C(=O)N[C@@H](Cc2ccc(N)cc2)CC(C)(C)C(=O)O)cs1)C(C)C] |

TABLE 1-continued
Tubulysin Payloads
| # in Scheme(s) | Structure |
|---|---|
| IVl | 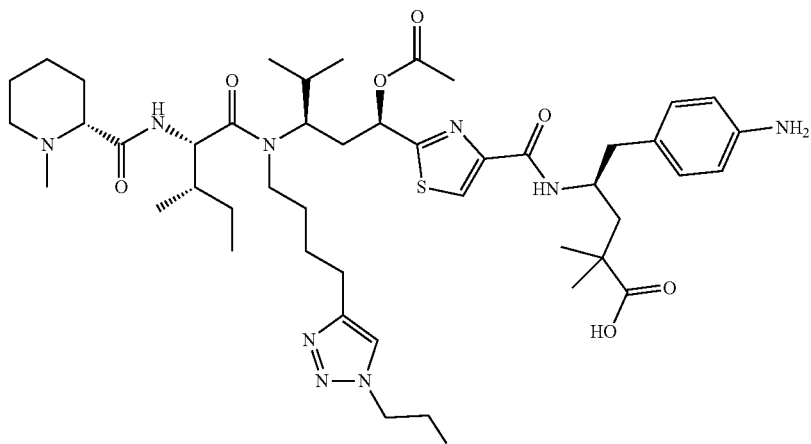 |
| IVm | 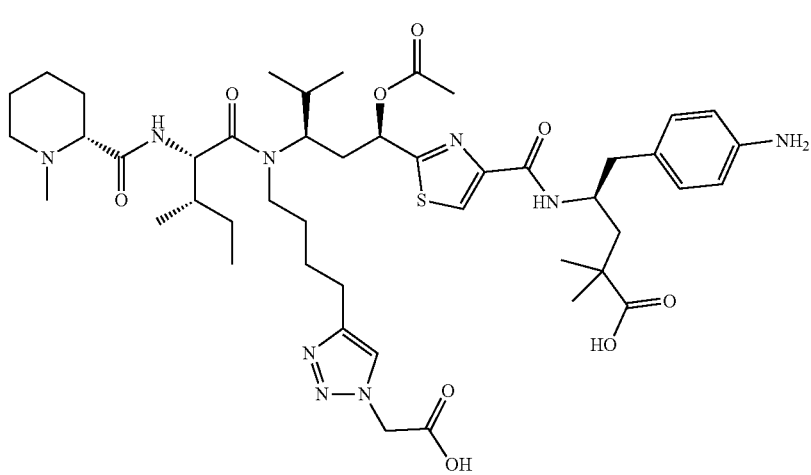 [SMILES: CC[C@H](C)[C@H](NC(=O)[C@H]1CCCCN1C)C(=O)N(CCCCc1cn(CC(=O)O)nn1)[C@H](C[C@@H](OC(C)=O)c1nc(C(=O)N[C@@H](Cc2ccc(N)cc2)CC(C)(C)C(=O)O)cs1)C(C)C] |
| IVn | 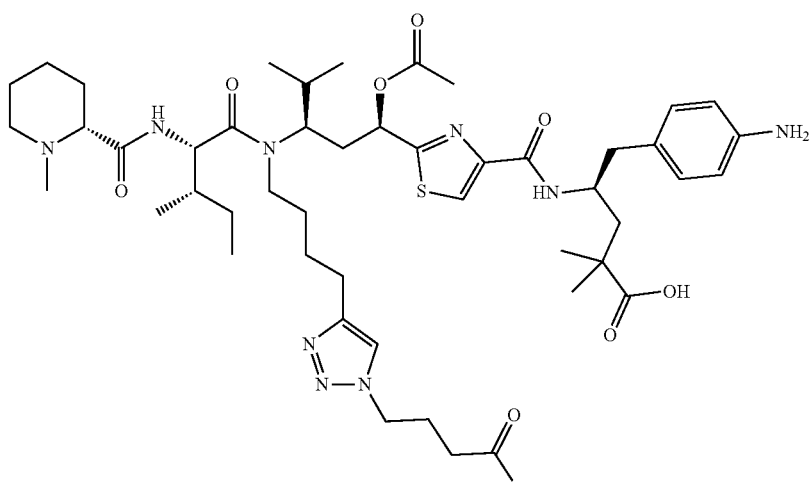 |

TABLE 1-continued
Tubulysin Payloads
| # in Scheme(s) | Structure |
|---|---|
| IVo | 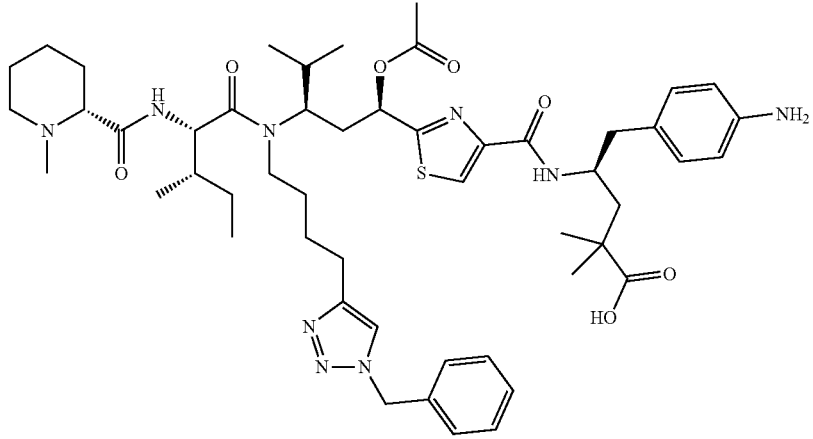 [SMILES: CC[C@H](C)[C@H](NC(=O)[C@H]1CCCCN1C)C(=O)N(CCCCc1cn(Cc2ccccc2)nn1)[C@H](C[C@@H](OC(C)=O)c1nc(C(=O)N[C@@H](Cc2ccc(N)cc2)CC(C)(C)C(=O)O)cs1)C(C)C] |
| IVp | 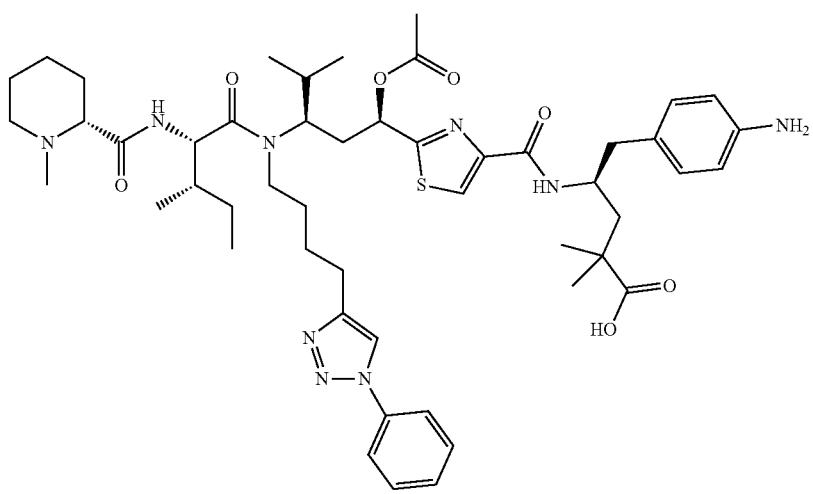 [SMILES: CC[C@H](C)[C@H](NC(=O)[C@H]1CCCCN1C)C(=O)N(CCCCc1cn(-c2ccccc2)nn1)[C@H](C[C@@H](OC(C)=O)c1nc(C(=O)N[C@@H](Cc2ccc(N)cc2)CC(C)(C)C(=O)O)cs1)C(C)C] |
| IVq | 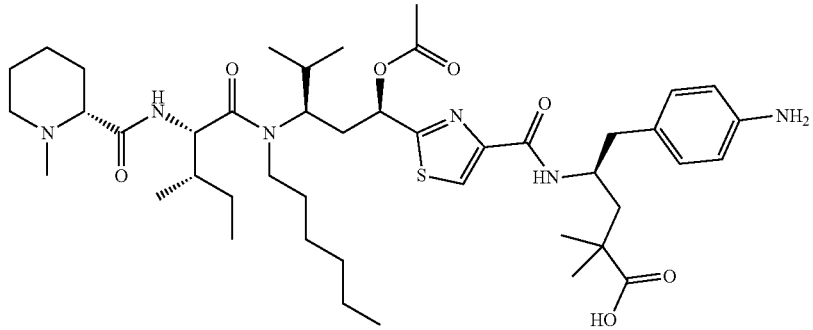 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(N)cc2)CC(C)(C)C(=O)O)cs1)C(C)C] |

TABLE 1-continued
Tubulysin Payloads
| # in Scheme(s) | Structure |
|---|---|
| IVr | 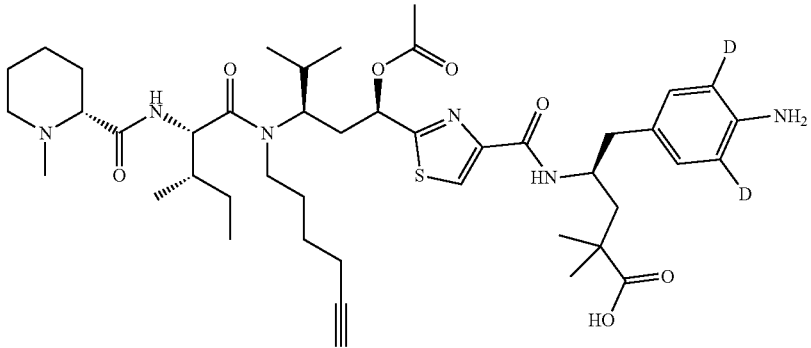 [SMILES: [2H]c1cc(C[C@@H](CC(C)(C)C(=O)O)NC(=O)c2csc([C@@H](C[C@H](C(C)C)N(CCCCC#C)C(=O)[C@@H](NC(=O)[C@H]3CCCCN3C)[C@@H](C)CC)OC(C)=O)n2)cc([2H])c1N] |
| IVs | 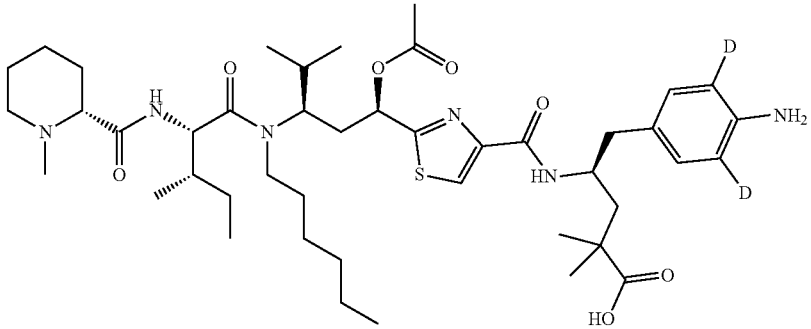 [SMILES: [2H]c1cc(C[C@@H](CC(C)(C)C(=O)O)NC(=O)c2csc([C@@H](C[C@H](C(C)C)N(CCCCCC)C(=O)[C@@H](NC(=O)[C@H]3CCCCN3C)[C@@H](C)CC)OC(C)=O)n2)cc([2H])c1N] |
| IVt | 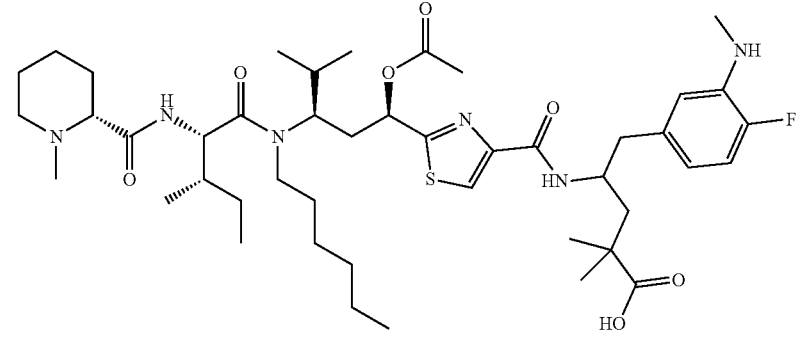 [SMILES: CCCCCCN(C(=O)[C@@H](NC(=O)[C@H]1CCCCN1C)[C@@H](C)CC)[C@H](C[C@@H](OC(C)=O)c1nc(C(=O)NC(Cc2ccc(F)c(NC)c2)CC(C)(C)C(=O)O)cs1)C(C)C] |
| IVu | 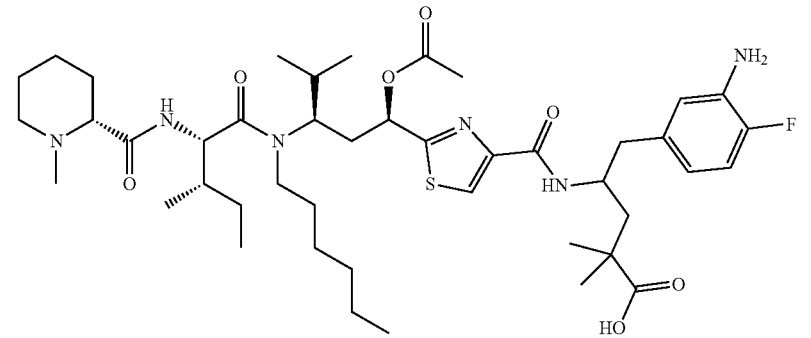 [SMILES: CCCCCCN(C(=O)[C@@H](NC(=O)[C@H]1CCCCN1C)[C@@H](C)CC)[C@H](C[C@@H](OC(C)=O)c1nc(C(=O)NC(Cc2ccc(F)c(N)c2)CC(C)(C)C(=O)O)cs1)C(C)C] |

TABLE 1-continued
Tubulysin Payloads
| # in Scheme(s) | Structure |
|---|---|
| IVvA | 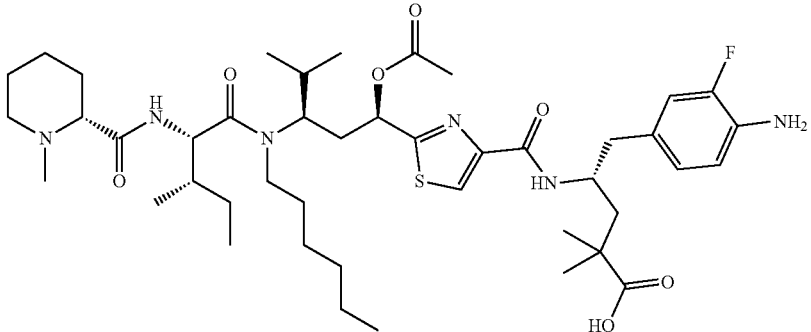 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@H](Cc2ccc(N)c(F)c2)CC(C)(C)C(=O)O)cs1)C(C)C] |
| IVvB | 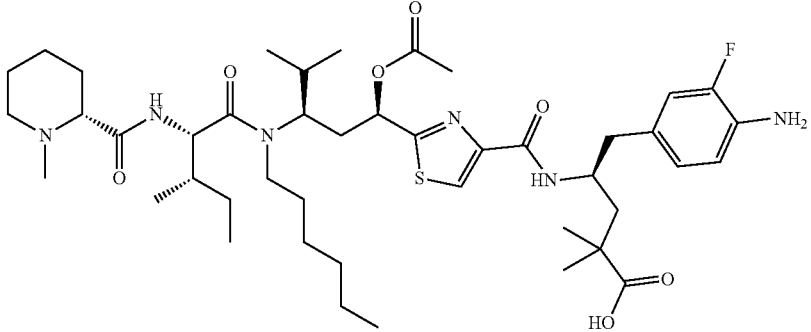 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(N)c(F)c2)CC(C)(C)C(=O)O)cs1)C(C)C] |
| IVw | 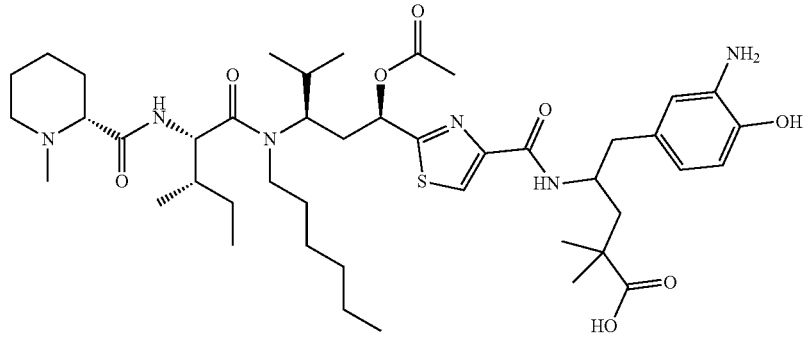 [SMILES: CCCCCCN(C(=O)[C@@H](NC(=O)[C@H]1CCCCN1C)[C@@H](C)CC)[C@H](C[C@@H](OC(C)=O)c1nc(C(=O)NC(Cc2ccc(O)c(N)c2)CC(C)(C)C(=O)O)cs1)C(C)C] |
| IVx | 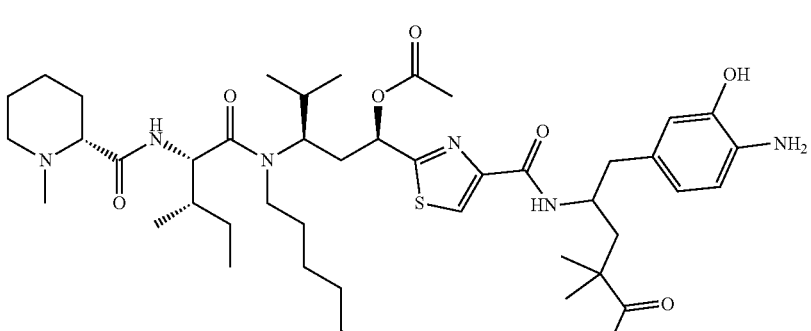 |

TABLE 1-continued
Tubulysin Payloads
| # in Scheme(s) | Structure |
|---|---|
| IVy | 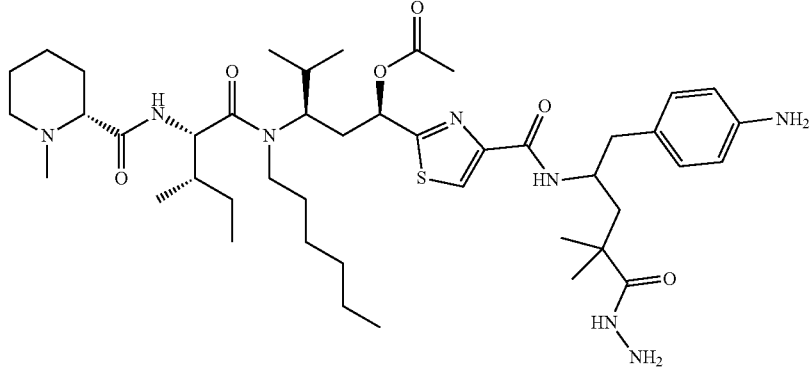 [SMILES: CCCCCCN(C(=O)[C@@H](NC(=O)[C@H]1CCCCN1C)[C@@H](C)CC)[C@H](C[C@@H](OC(C)=O)c1nc(C(=O)NC(Cc2ccc(N)cc2)CC(C)(C)C(=O)NN)cs1)C(C)C] |
| Va | 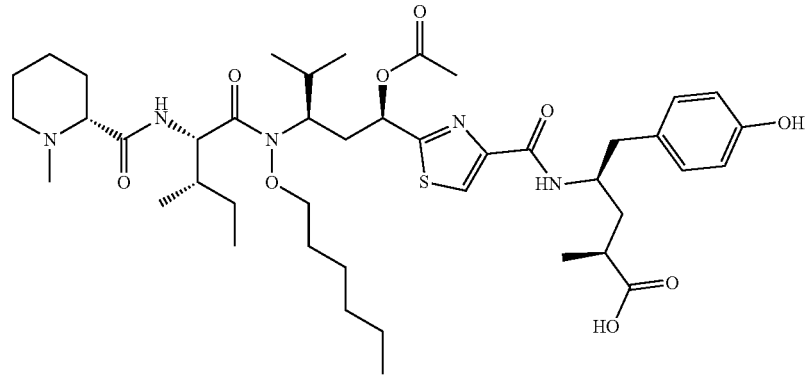 [SMILES: CCCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)cc2)C[C@H](C)C(=O)O)cs1)C(C)C] |
| Va' | 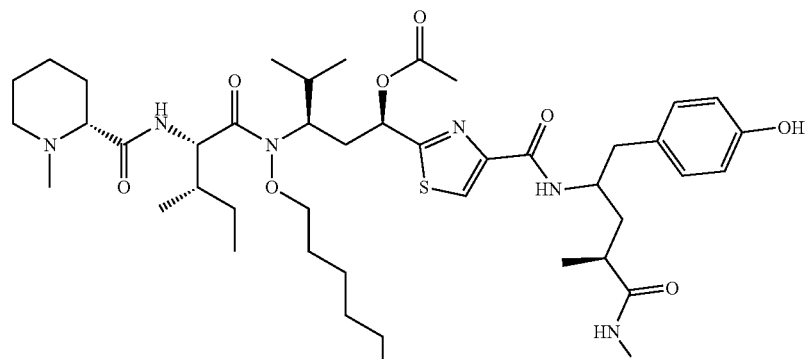 |
| Vb | 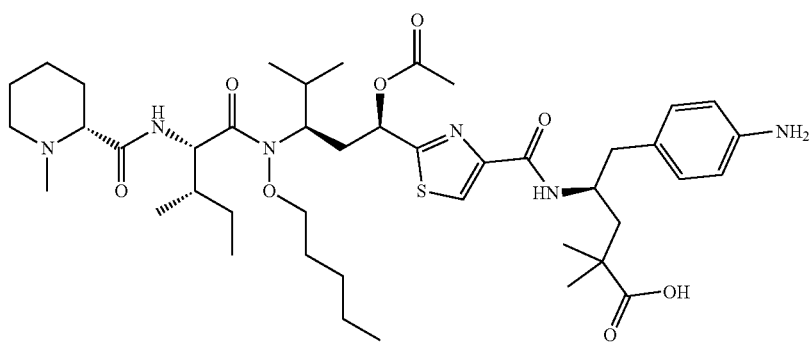 [SMILES: CCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(N)cc2)CC(C)(C)C(=O)O)cs1)C(C)C] |

TABLE 1-continued
Tubulysin Payloads
| # in Scheme(s) | Structure |
|---|---|
| Vc | 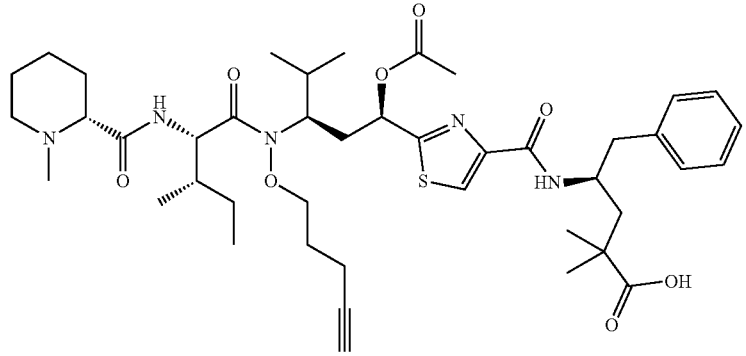 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccccc2)CC(C)(C)C(=O)O)cs1)C(C)C] |
| Vd | 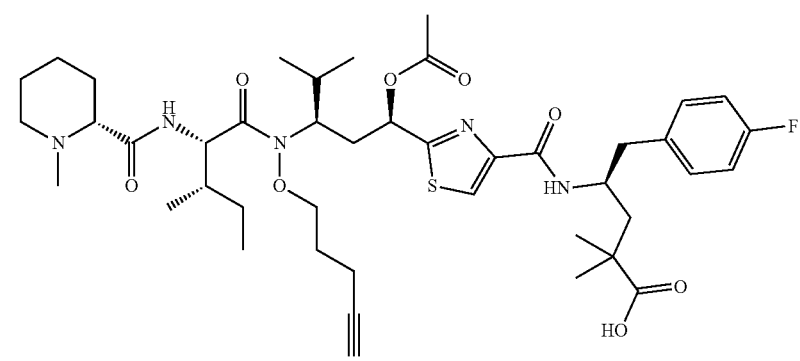 |
| Ve | 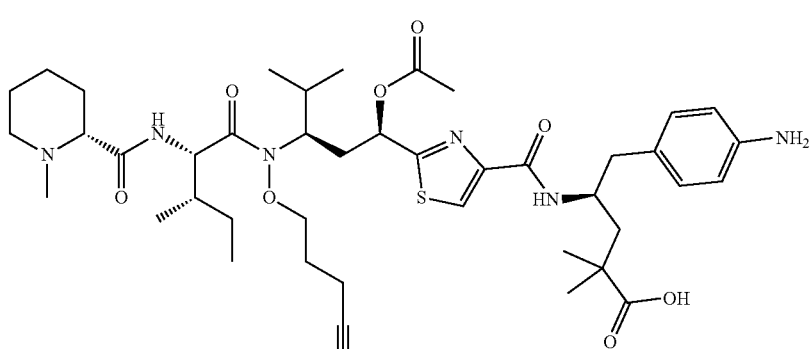 |
| Vf | 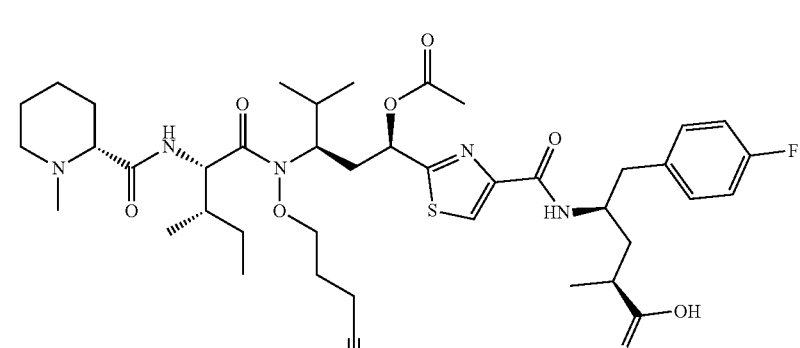 |

TABLE 1-continued
Tubulysin Payloads
| # in Scheme(s) | Structure |
|---|---|
| Vg | 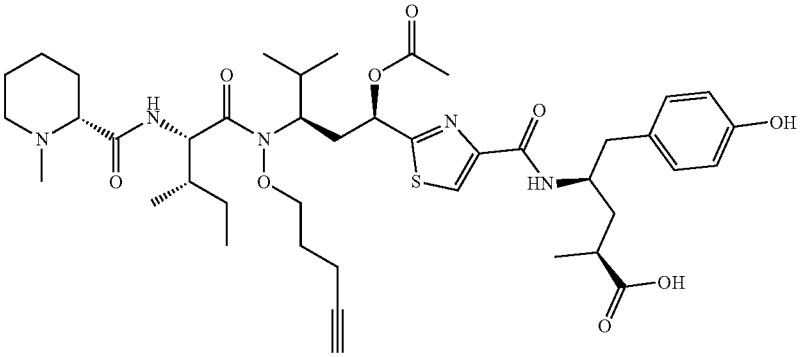 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)cc2)C[C@H](C)C(=O)O)cs1)C(C)C] |
| Vh | 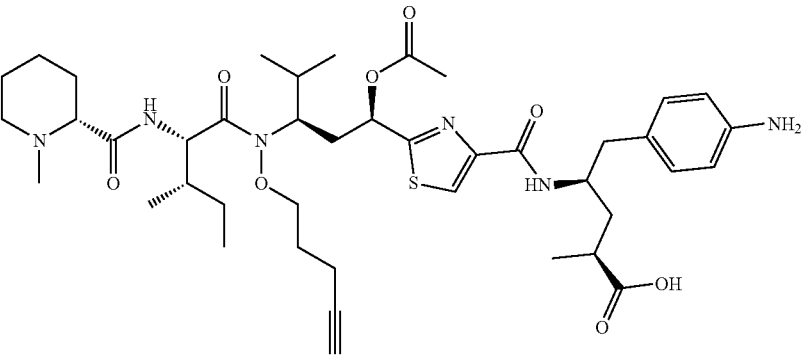 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(N)cc2)C[C@H](C)C(=O)O)cs1)C(C)C] |
| Vi | 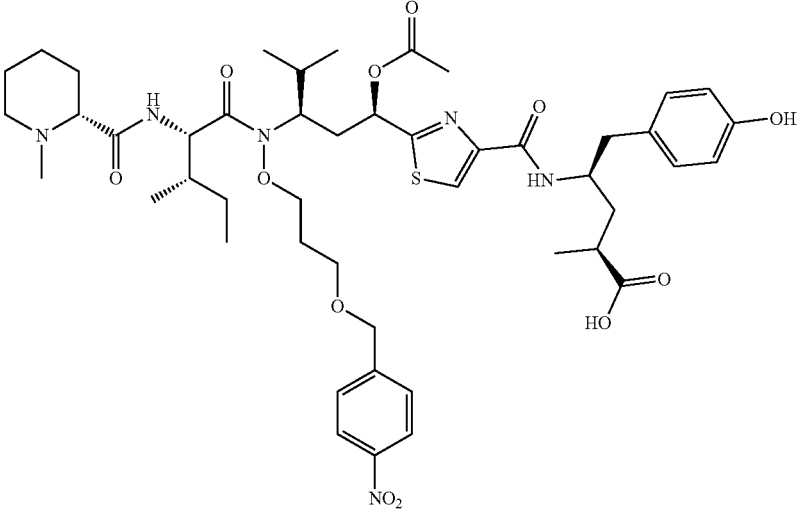 |

TABLE 1-continued
Tubulysin Payloads
| # in Scheme(s) | Structure |
|---|---|
| Vj | 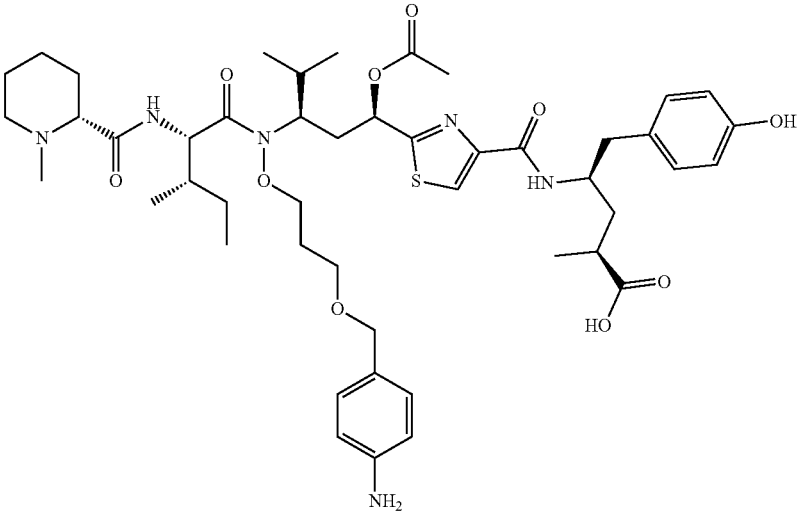 [SMILES: CC[C@H](C)[C@H](NC(=O)[C@H]1CCCCN1C)C(=O)N(OCCCOCc1ccc([N+](=O)[O-])cc1)[C@H](C[C@@H](OC(C)=O)c1nc(C(=O)N[C@@H](Cc2ccc(O)cc2)C[C@H](C)C(=O)O)cs1)C(C)C] |
| Vk | 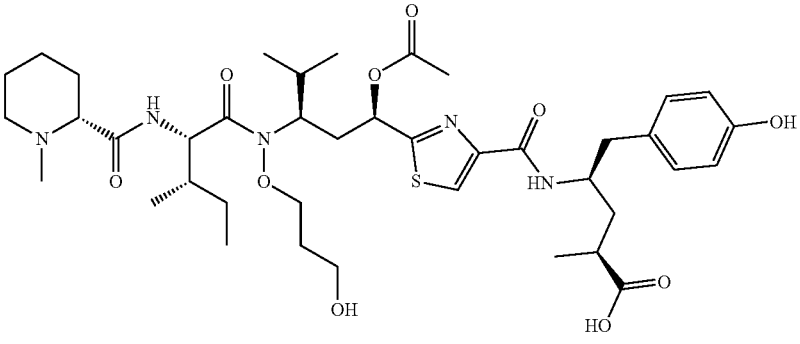 [SMILES: CC[C@H](C)[C@H](NC(=O)[C@H]1CCCCN1C)C(=O)N(OCCCO)[C@H](C[C@@H](OC(C)=O)c1nc(C(=O)N[C@@H](Cc2ccc(O)cc2)C[C@H](C)C(=O)O)cs1)C(C)C] |
| VIa | 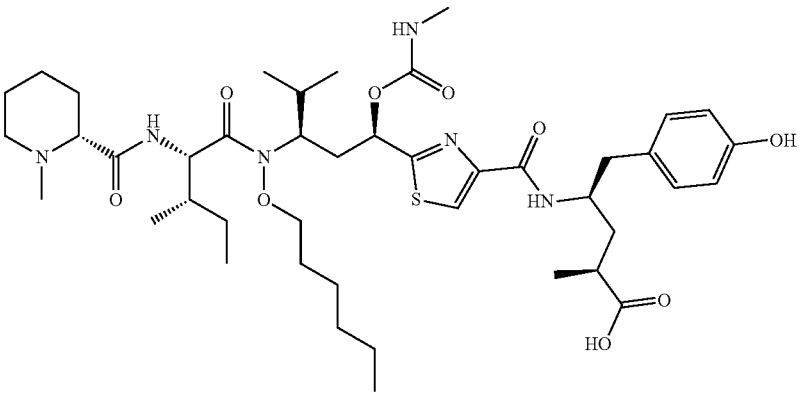 [SMILES: CCCCCCON(C(=O)[C@@H](NC(=O)[C@H]1CCCCN1C)[C@@H](C)CC)[C@H](C[C@@H](OC(=O)NC)c1nc(C(=O)N[C@@H](Cc2ccc(O)cc2)C[C@H](C)C(=O)O)cs1)C(C)C] |

TABLE 1-continued
Tubulysin Payloads
| # in Scheme(s) | Structure |
|---|---|
| IVb | 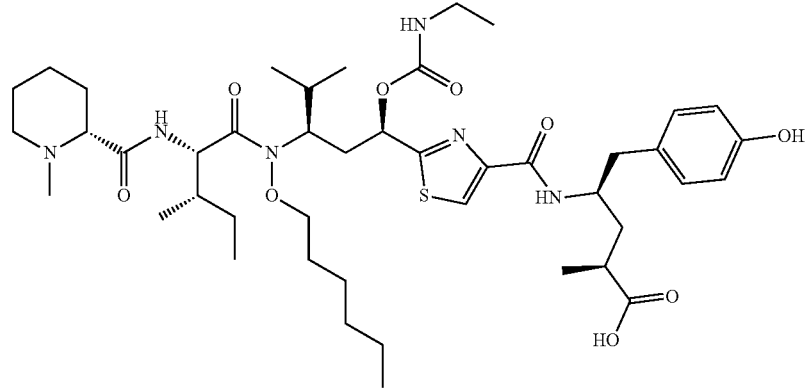 [SMILES: CCCCCCON(C(=O)[C@@H](NC(=O)[C@H]1CCCCN1C)[C@@H](C)CC)[C@H](C[C@@H](OC(=O)NCC)c1nc(C(=O)N[C@@H](Cc2ccc(O)cc2)C[C@H](C)C(=O)O)cs1)C(C)C] |
| VIc | 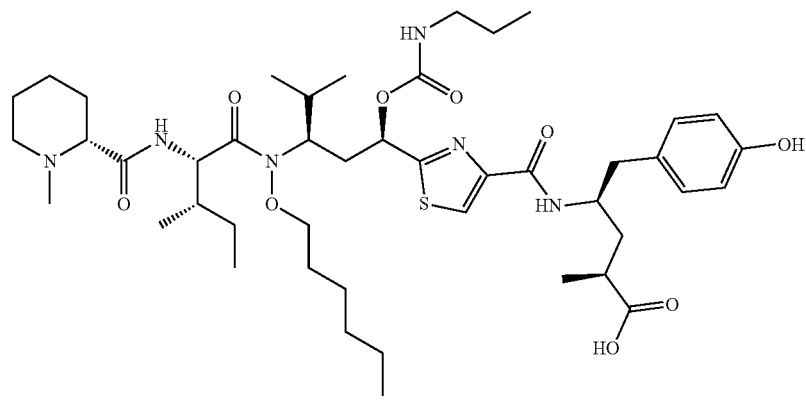 [SMILES: CCCCCCON(C(=O)[C@@H](NC(=O)[C@H]1CCCCN1C)[C@@H](C)CC)[C@H](C[C@@H](OC(=O)NCCC)c1nc(C(=O)N[C@@H](Cc2ccc(O)cc2)C[C@H](C)C(=O)O)cs1)C(C)C] |
| VId | 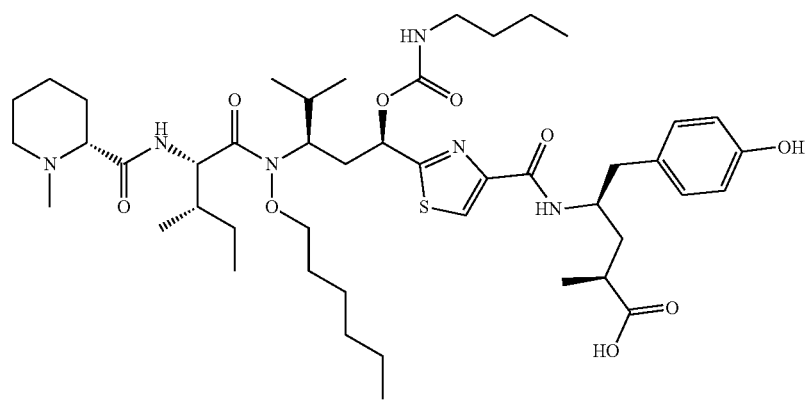 [SMILES: CCCCCCON(C(=O)[C@@H](NC(=O)[C@H]1CCCCN1C)[C@@H](C)CC)[C@H](C[C@@H](OC(=O)NCCCC)c1nc(C(=O)N[C@@H](Cc2ccc(O)cc2)C[C@H](C)C(=O)O)cs1)C(C)C] |

TABLE 1-continued

Tubulysin Payloads

| # in Scheme(s) | Structure |
|---|---|
| VIe | 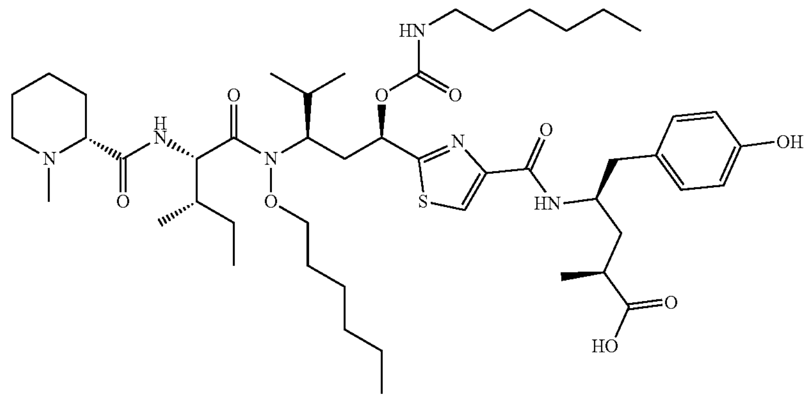 [SMILES: CCCCCCNC(=O)O[C@H](C[C@H](C(C)C)N(OCCCCCC)C(=O)[C@@H](NC(=O)[C@H]1CCCCN1C)[C@@H](C)CC)c1nc(C(=O)N[C@@H](Cc2ccc(O)cc2)C[C@H](C)C(=O)O)cs1] |
| VIf | 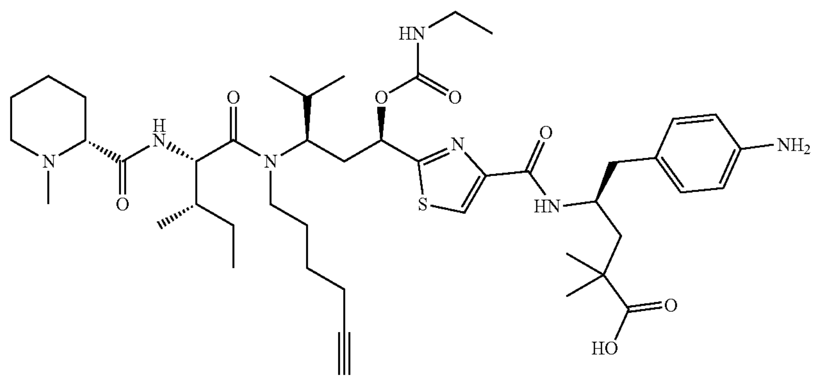 [SMILES: C#CCCCCN(C(=O)[C@@H](NC(=O)[C@H]1CCCCN1C)[C@@H](C)CC)[C@H](C[C@@H](OC(=O)NCC)c1nc(C(=O)N[C@@H](Cc2ccc(N)cc2)CC(C)(C)C(=O)O)cs1)C(C)C] |
| VIg | 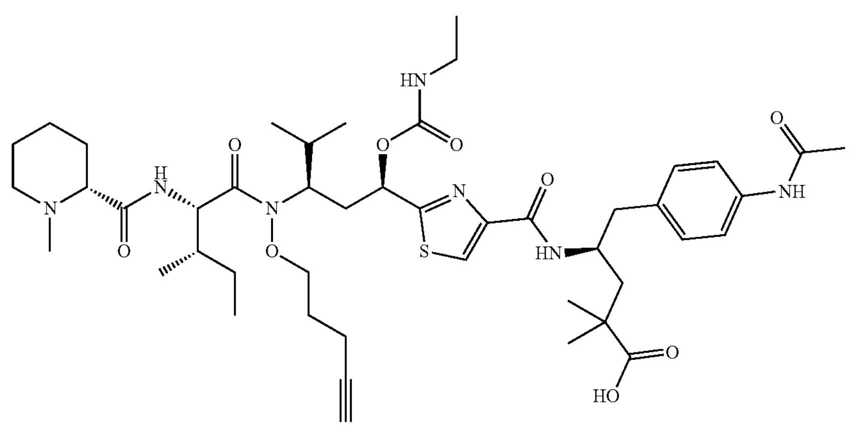 [SMILES: C#CCCCON(C(=O)[C@@H](NC(=O)[C@H]1CCCCN1C)[C@@H](C)CC)[C@H](C[C@@H](OC(=O)NCC)c1nc(C(=O)N[C@@H](Cc2ccc(NC(C)=O)cc2)CC(C)(C)C(=O)O)cs1)C(C)C] |
| VIh | 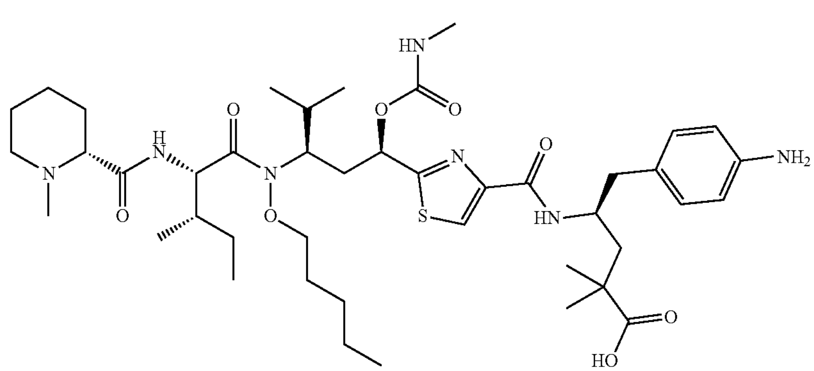 [SMILES: CCCCCON(C(=O)[C@@H](NC(=O)[C@H]1CCCCN1C)[C@@H](C)CC)[C@H](C[C@@H](OC(=O)NC)c1nc(C(=O)N[C@@H](Cc2ccc(N)cc2)CC(C)(C)C(=O)O)cs1)C(C)C] |

TABLE 1-continued
Tubulysin Payloads
| # in Scheme(s) | Structure |
|---|---|
| VI | 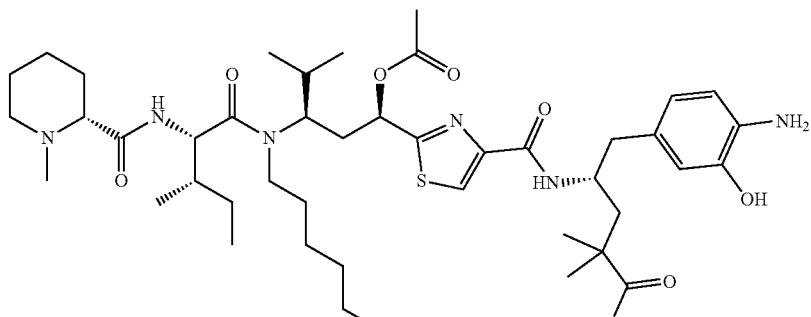 |
| VIi | 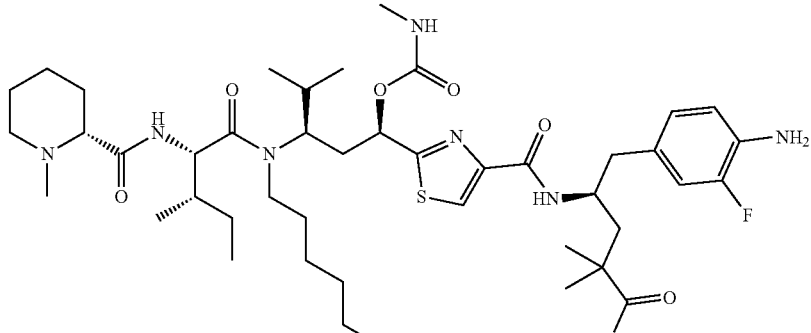 |
| VII | 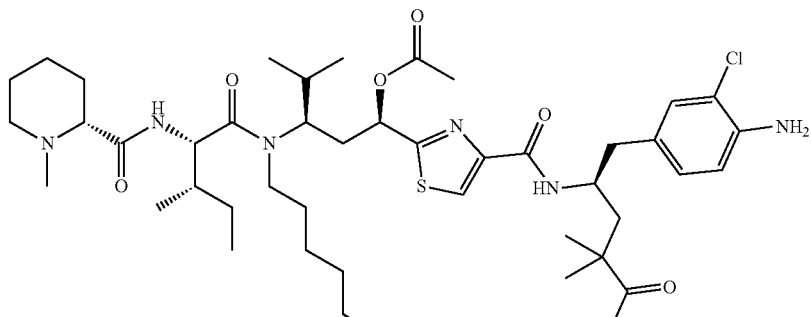 |
| VIII | 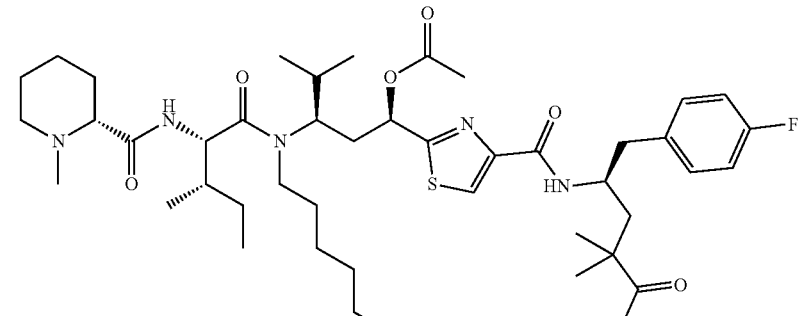 |

TABLE 1-continued
Tubulysin Payloads
| # in Scheme(s) | Structure |
|---|---|
| IX | 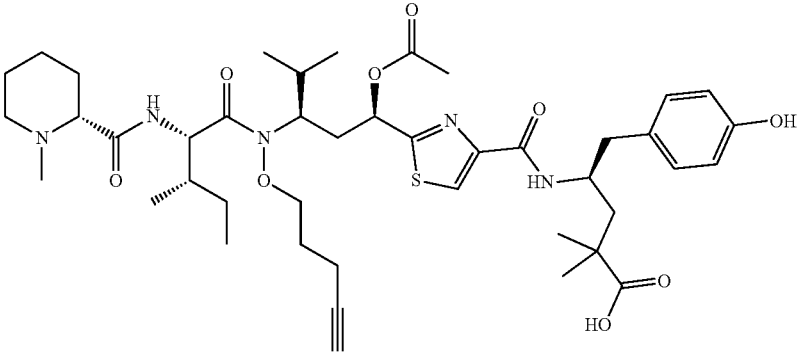 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)cc2)CC(C)(C)C(=O)O)cs1)C(C)C] |
| X | 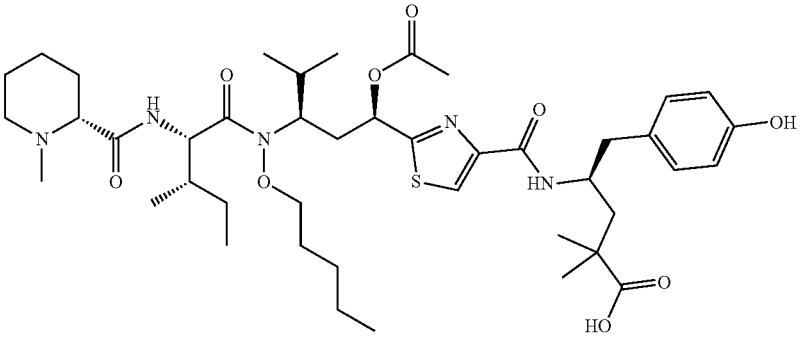 [SMILES: CCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)cc2)CC(C)(C)C(=O)O)cs1)C(C)C] |
| D-5a | 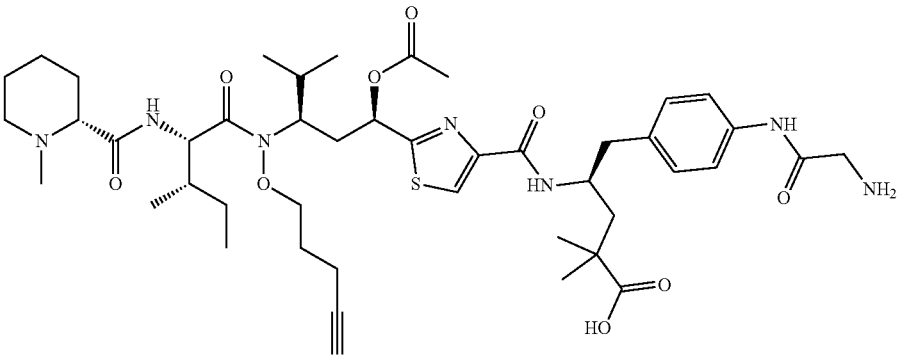 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CN)cc2)CC(C)(C)C(=O)O)cs1)C(C)C] |
| D-5c | 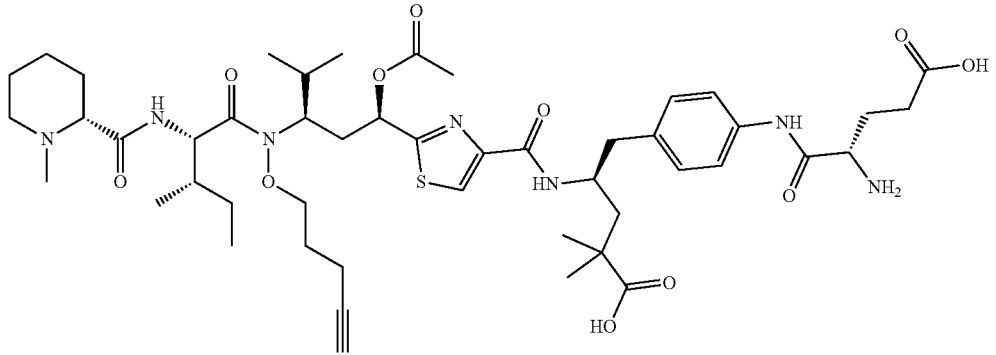 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@@H](N)CCC(=O)O)cc2)CC(C)(C)C(=O)O)cs1)C(C)C] |

TABLE 1-continued

Tubulysin Payloads

| # in Scheme(s) | cLogP | MF | MW | MS (M + H) or m/z 100% | HPLC purity |
|---|---|---|---|---|---|
| Tub A | | $C_{42}H_{63}N_5O_{10}S$ | | | |
| IVa | 4.75 | $C_{43}H_{66}FN_5O_7S$ | 816.08 | 816.4 | 96 |
| IVa' | 6.28 | $C_{43}H_{68}FN_7O_6S$ | 830.11 | 830.3 | > 95 |
| IVb | 4.37 | $C_{44}H_{65}N_5O_7S$ | 808.08 | 808.3 | 100 |
| IVc | 4.51 | $C_{44}H_{64}FN_5O_7S$ | 826.07 | 826.2 | 100 |
| IVd | 3.54 | $C_{44}H_{66}N_6O_7S$ | 823.10 | 412.3 [M/2 + H] | 100 |
| IVe | 3.94 | $C_{43}H_{62}FN_5O_7S$ | 812.05 | 812.4 | 100 |
| IVf | 3.47 | $C_{43}H_{63}N_5O_8S$ | 810.05 | 810.3 | 100 |
| IVg | 2.97 | $C_{43}H_{64}N_6O_7S$ | 809.07 | 809.2 | 100 |
| IVh | 2.95 | $C_{45}H_{69}N_9O_7S$ | 880.15 | 880.4 | 99 |
| IVj | 2.83 | $C_{44}H_{67}N_9O_7S$ | 866.12 | 433.8 [M/2 + H] | 100 |
| IVk | 2.46 | $C_{46}H_{72}N_{10}O_7S$ | 909.19 | 455.3 | 96 |
| IVl | 2.26 | $C_{46}H_{71}N_9O_8S$ | 910.18 | 910.4 | 94 |
| IVm | 1.51 | $C_{46}H_{69}N_9O_9S$ | 924.16 | 924.4 | 97 |
| IVn | 2.07 | $C_{48}H_{73}N_9O_9S$ | 952.21 | 476.8 [M/2 + H] | 95.6 |
| IVo | 4.68 | $C_{51}H_{73}N_9O_7S$ | 956.25 | 956.4 | 100 |
| IVp | 4.61 | $C_{50}H_{71}N_9O_7S$ | 942.22 | 942.4 | 100 |
| IVq | 4.34 | $C_{44}H_{70}N_6O_7S$ | 827.13 | 414.3 [M/2 + H] | 97.2 |
| IVr | 3.54 | $C_{44}H_{64}D_2N_6O_7S$ | 825.12 | 825.5 | 98.9 |
| IVs | 4.34 | $C_{44}H_{68}D_2N_6O_7S$ | 829.14 | 829.5 | 100 |
| IVt | 4.79 | $C_{45}H_{71}FN_6O_7S$ | 859.15 | 859.5 | 100 |
| IVu | 4.51 | $C_{44}H_{69}FN_6O_7S$ | 845.12 | 423.3 [M/2 + H] | 100 |
| IVvA | 4.48 | $C_{44}H_{69}FN_6O_7S$ | 845.12 | 846.5 | 95 |
| IVvB | 4.48 | $C_{44}H_{69}FN_6O_7S$ | 845.1 | 845.5 | >99 |
| IVw | 4.01 | $C_{44}H_{70}N_6O_8S$ | 843.13 | 422.3 [M/2 + H] | 100 |
| IVx | 4.01 | $C_{44}H_{70}N_6O_8S$ | 843.13 | 422.4 [M/2 + H] | 100 |
| IVy | 5.87 | $C_{44}H_{72}N_8O_6S$ | 841.16 | 841.5 | 95 |
| Va | 4.42 | $C_{43}H_{67}N_5O_9S$ | 830.09 | 830.1 | 97 |
| Va' | 5.99 | $C_{43}H_{69}N_7O_8S$ | 844.12 | 844.2 | 97 |
| Vb | 4.05 | $C_{43}H_{68}N_6O_8S$ | 829.1 | 829.4 | >99 |
| Vc | 4.08 | $C_{43}H_{63}N_5O_8S$ | 810.05 | 810.0 | 100 |
| Vd | 4.21 | $C_{43}H_{62}FN_5O_8S$ | 828.04 | 828.4 | 100 |
| Ve | 3.24 | $C_{43}H_{64}N_6O_8S$ | 825.1 | 825.4 | 98 |
| Vf | 3.65 | $C_{42}H_{60}FN_5O_8S$ | 814.02 | 814.3 | 98 |
| Vg | 3.17 | $C_{42}H_{61}N_5O_9S$ | 812.03 | 812.3 | 100 |
| Vh | 2.68 | $C_{42}H_{62}N_6O_8S$ | 811.04 | 406.2 [M/2 + H] | 100 |
| Vi | 3.89 | $C_{47}H_{66}N_6O_{12}S$ | 939.13 | 939.2 | 98 |
| Vj | 3.11 | $C_{47}H_{68}N_6O_{10}S$ | 909.14 | 909.1 | 100 |
| Vk | 1.58 | $C_{40}H_{61}N_5O_{10}S$ | 804.01 | 804.2 | 100 |
| VIa | 4.31 | $C_{43}H_{68}N_6O_9S$ | 845.10 | 845 | 99 |
| IVb | 4.67 | $C_{44}H_{70}N_6O_9S$ | 859.13 | 859.2 | 95 |
| VIc | 5.19 | $C_{45}H_{72}N_6O_9S$ | 873.15 | 873.5 | 95 |
| VId | 5.64 | $C_{46}H_{74}N_6O_9S$ | 887.18 | 887.5 | 95 |
| VIe | 6.53 | $C_{48}H_{78}N_6O_9S$ | 915.23 | 915.5 | 95 |
| VIf | 3.49 | $C_{44}H_{67}N_7O_8S$ | 854.11 | 854.5 | 99 |
| VIg | 3.53 | $C_{46}H_{69}N_7O_9S$ | 896.15 | 896.5 | 100 |
| VIh | 3.94 | $C_{43}H_{69}N_7O_8S$ | 844.1 | 844.2 | >99 |
| VI | 4.01 | $C_{44}H_{70}N_6O_8S$ | 843 | 844 | 100 |
| VIi | 4.37 | $C_{44}H_{70}FN_7O_7S$ | 860.1 | 860.5 | >99 |
| VII | 4.95 | $C_{44}H_{69}ClN_6O_7S$ | 861.6 | 861.3 | >99 |
| VIII | 5.31 | $C_{44}H_{68}FN_5O_7S$ | 830.1 | 830.5 | >99 |
| IX | 3.73 | $C_{43}H_{63}N_5O_9S$ | 826.1 | 826.5 | 95 |
| X | 4.54 | $C_{43}H_{67}N_5O_9S$ | 830.1 | 830.1 | >99 |
| D-5a | | $C_{45}H_{67}N_7O_9S$ | 882.13 | 882.4 | |
| D-5c | | $C_{48}H_{71}N_7O_{11}S$ | 954.19 | 478.0 [M/2 + H] | |

TABLE 2

| Tubulysin Linker-payloads | | | | | | | |
|---|---|---|---|---|---|---|---|
| | | | MS | HPLC | | | |
| # | MF | MW | (m/z) 100% | purity (%) | $R_t$ (min) | CLogP | Payload |
| LP1 | $C_{72}H_{106}FN_{13}O_{14}S$ | 1428.8 | 715.0 [M/2 + H] | 85 | 9.51 (B) | 7.00 | IVa |
| LP2 | $C_{92}H_{130}N_{14}O_{20}S$ | 1784.2 | 892.5 [M/2 + H] | 95 | 9.32 (B) | 7.94 | Va |
| LP3 | $C_{93}H_{127}N_{13}O_{19}S$ | 1763.1 | 882.0 [M/2 + H] | 95 | 7.98 (B) | 5.82 | IVd |
| LP4 | $C_{92}H_{125}N_{13}O_{20}S$ | 1765.1 | 883.0 [M/2 + H] | 90 | 8.05 (B) | 5.53 | Ve |
| LP5 | $C_{82}H_{114}N_{10}O_{16}S$ | 1527.9 | 764.5 [M/2 + H] | 100 | 8.17 (B) | 5.33 | IVd |
| LP6 | $C_{84}H_{122}N_{12}O_{18}S$ | 1620.0 | 810.5 [M/2 + H] | 100 | 8.52 (B) | 4.75 | Vb |
| LP7 | $C_{85}H_{120}N_{12}O_{17}S$ | 1614.0 | 807.5 [M/2 + H] | 97.2 | 7.73 (B) | 4.24 | IVd |
| LP9 | $C_{82}H_{117}FN_{10}O_{16}S$ | 1549.9 | 775.3 (M/2 + H) | 99 | | 6.28 | IVvB |
| LP10 | $C_{84}H_{123}N_{13}O_{18}S$ | 1635.0 | 818.0 (M/2 + H) | >99 | | 4.64 | VIh |
| LP11 | $C_{74}H_{116}FN_{9}O_{16}S$ | 1438.8 | 719.7 (M/2 + H) | >99 | | 6.16 | IVvB |
| LP12 | $C_{82}H_{118}FN_{11}O_{16}S$ | 1564.9 | 782.7 (M/2 + H) | >99 | | 6.17 | VIi |
| LP13 | $C_{68}H_{86}N_{10}O_{13}S$ | 1283.5 | 642.5 (M/2 + H) | 99 | | 2.96 | Ve |
| LP14 | $C_{62}H_{91}N_{9}O_{13}S$ | 1202.5 | | | | | Ve |
| LP15 | $C_{92}H_{130}N_{14}O_{20}S$ | 1784.2 | 892.2 (M/2 + H) | 99 | | 6.22 | VIh |
| LP16 | $C_{55}H_{79}N_{7}O_{11}S$ | 1046.3 | 523.8 (M/2 + H) | >95 | | 4.43 | Ve |
| LP17 | $C_{57}H_{82}N_{8}O_{12}S$ | 1103.4 | 552.3 (M/2 + H) | >95 | | 3.33 | Ve |
| LP18 | $C_{62}H_{91}N_{9}O_{13}S$ | 1202.5 | 601.8 | 95 | | 3.93 | Ve |

TABLE 2-continued
| | Tubulysin Linker-payloads | | | | |
|---|---|---|---|---|---|
| LP19 | $C_{61}H_{88}N_{10}O_{14}S$ | 1217.5 | (M/2 + H) 609.3 | 95 | 1.12 | Ve |
| LP20 | $C_{77}H_{95}N_{11}O_{14}S$ | 1430.7 | (M/2 + H) 716.0 | 95 | 4.08 | Ve |
| LP21 | $C_{64}H_{92}N_{10}O_{16}S$ | 1289.6 | (M/2 + H) 645.4 | 95 | 0.98 | Ve |
| LP22 | $C_{64}H_{93}N_{11}O_{16}S$ | 1304.6 | (M/2 + H) 653.0 | >95 | −0.47 | Ve |
| LP23 | $C_{61}H_{92}N_{10}O_{14}S$ | 1221.5 | (M/2 + H) 611.3 | >99 | 1.93 | Vb |
| LP24 | $C_{77}H_{99}N_{11}O_{14}S$ | 1434.7 | (M/2 + H) 718.0 | >99 | 4.89 | Vb |
| LP25 | $C_{70}H_{96}N_8O_{20}S$ | 1401.6 | (M/2 + H) 701.3 | >95 | 3.49 | Ve |
| LP26 | $C_{70}H_{98}N_8O_{19}S$ | 1387.7 | (M/2 + H) 694.3 | >95 | 3.41 | Ve |
Structures
LP1
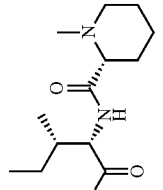

TABLE 2-continued
Tubulysin Linker-payloads
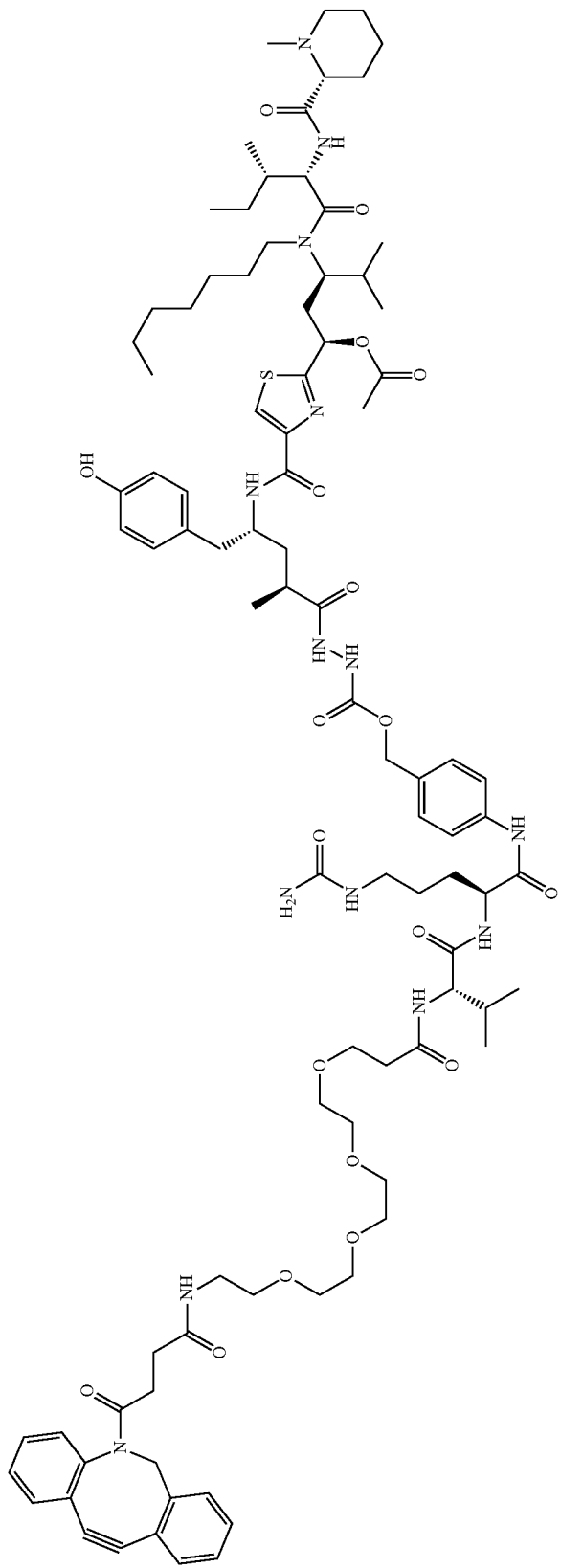
LP2

TABLE 2-continued
Tubulysin Linker-payloads
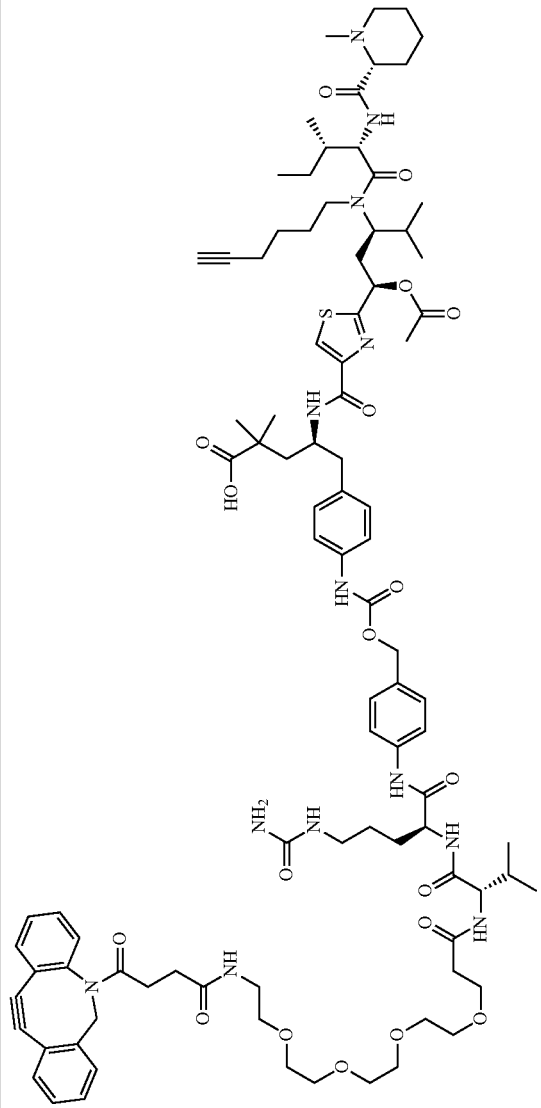
LP3
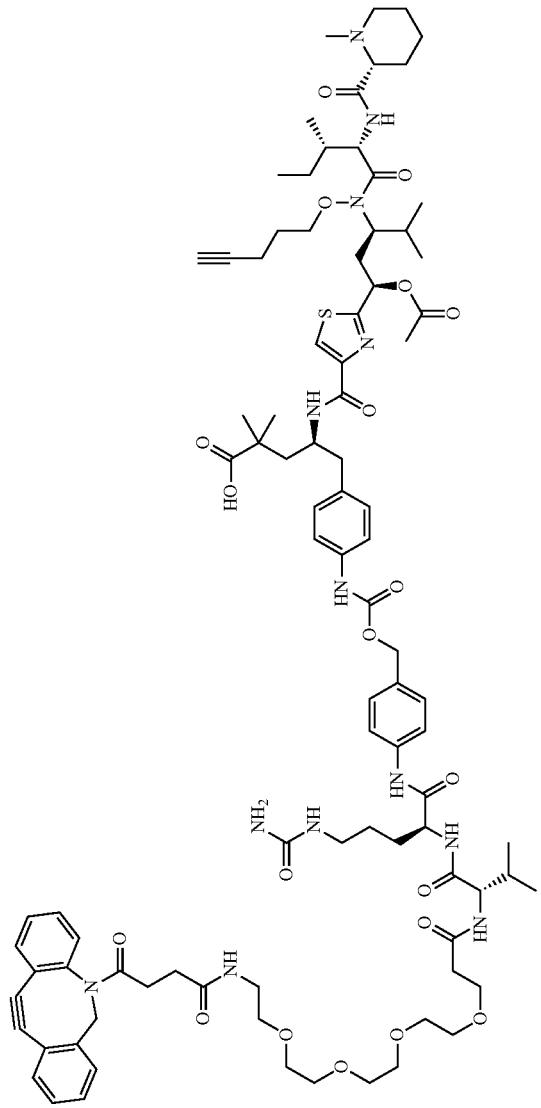
LP4

TABLE 2-continued
Tubulysin Linker-payloads
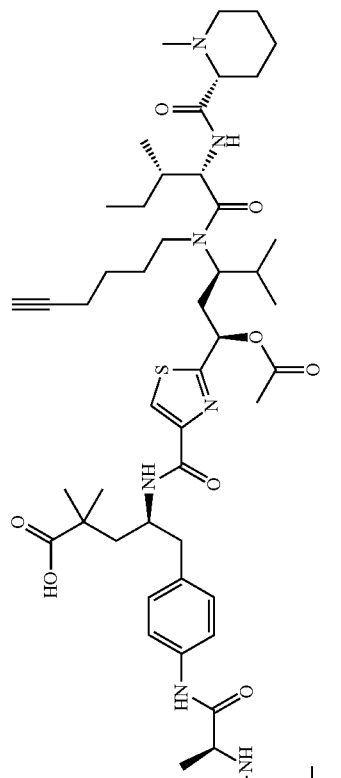
LP5

TABLE 2-continued
Tubulysin Linker-payloads
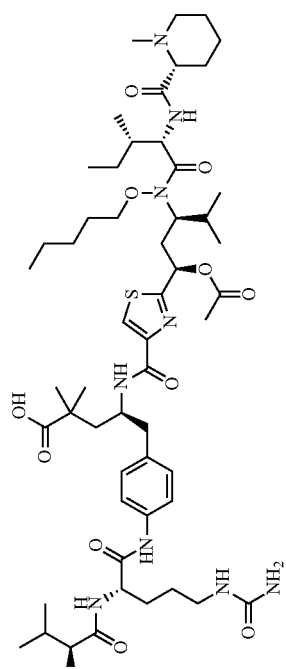
LP6

TABLE 2-continued
Tubulysin Linker-payloads
LP7
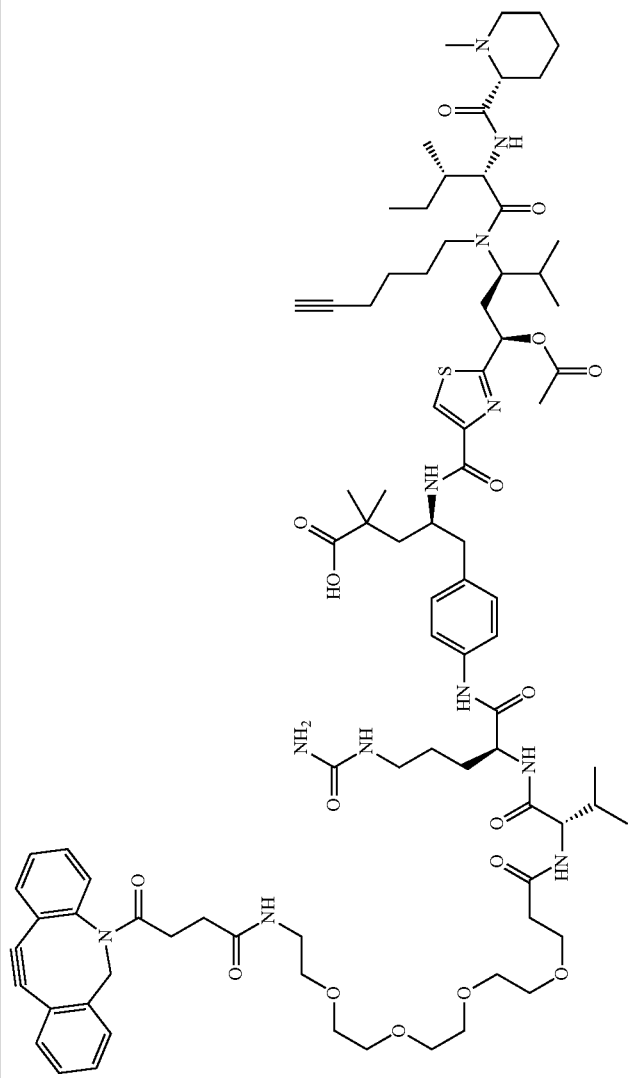

TABLE 2-continued
Tubulysin Linker-payloads
LP8 ref
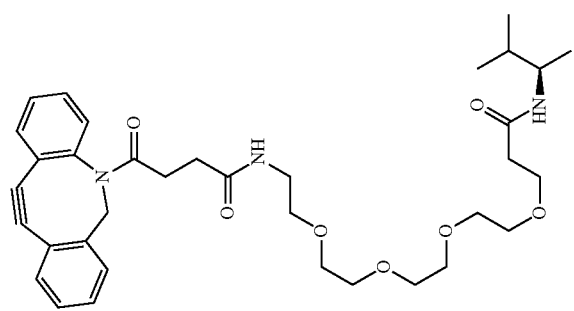

TABLE 2-continued
Tubulysin Linker-payloads
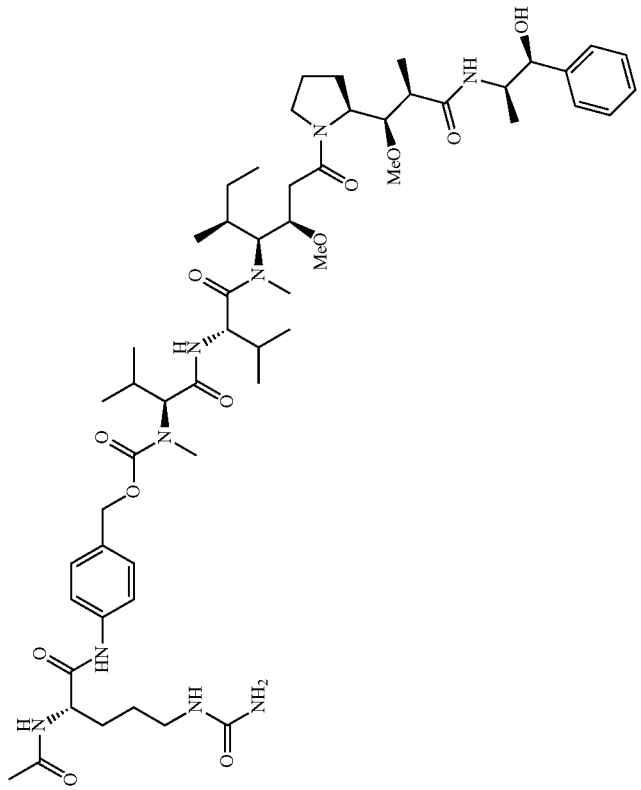
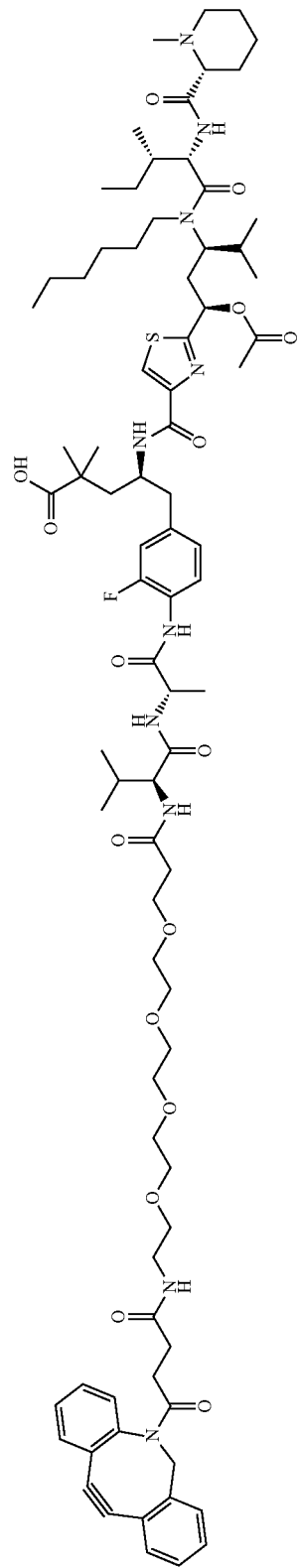
LP9

TABLE 2-continued
Tubulysin Linker-payloads
| LP10 | 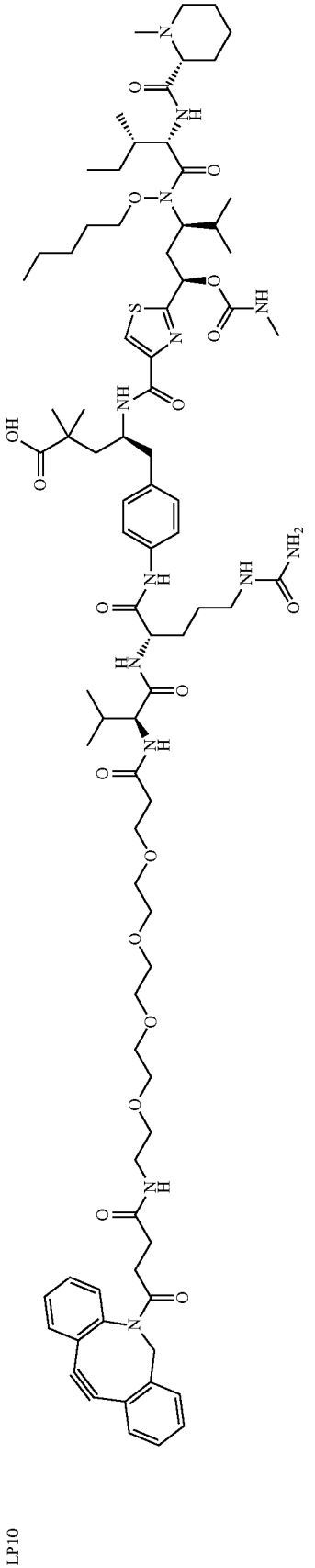 |
| LP11 | 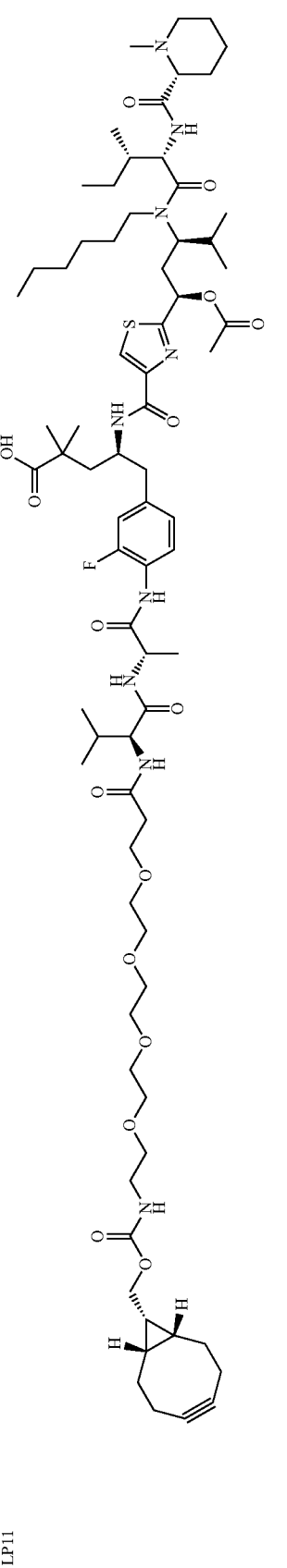 |
| LP12 | 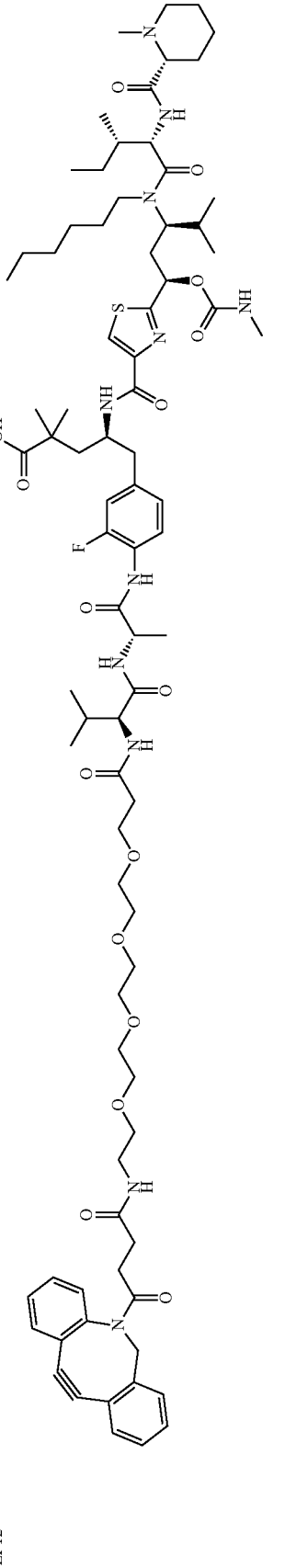 |

TABLE 2-continued
Tubulysin Linker-payloads
| | |
|---|---|
| LP13 | 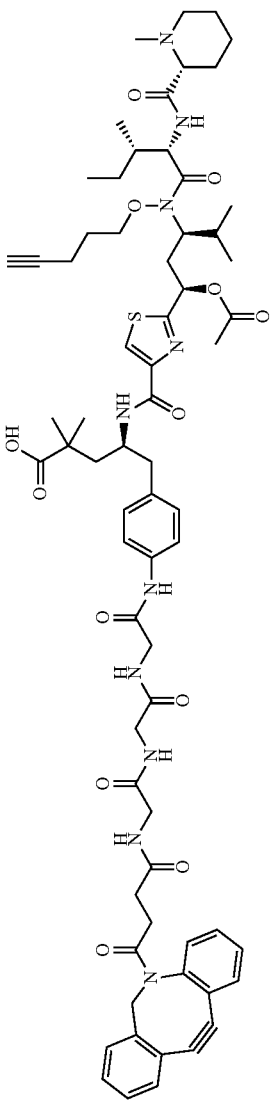 |
| LP14 | 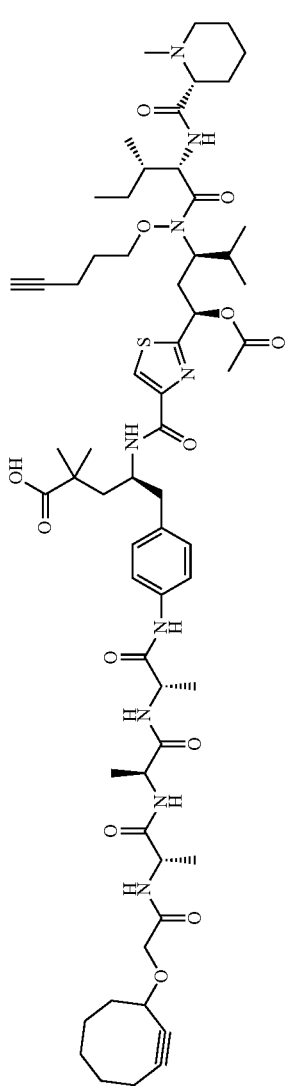 |
| LP15 | 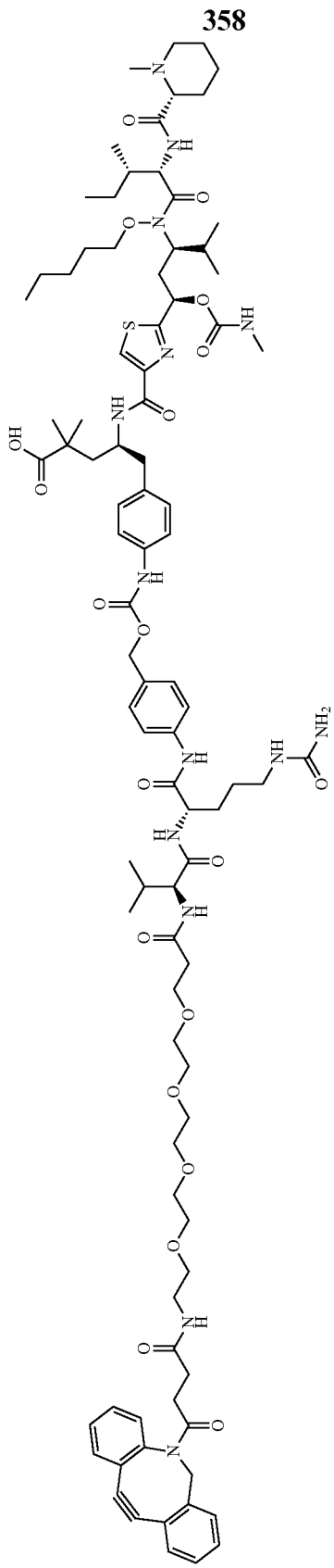 |

TABLE 2-continued
Tubulysin Linker-payloads
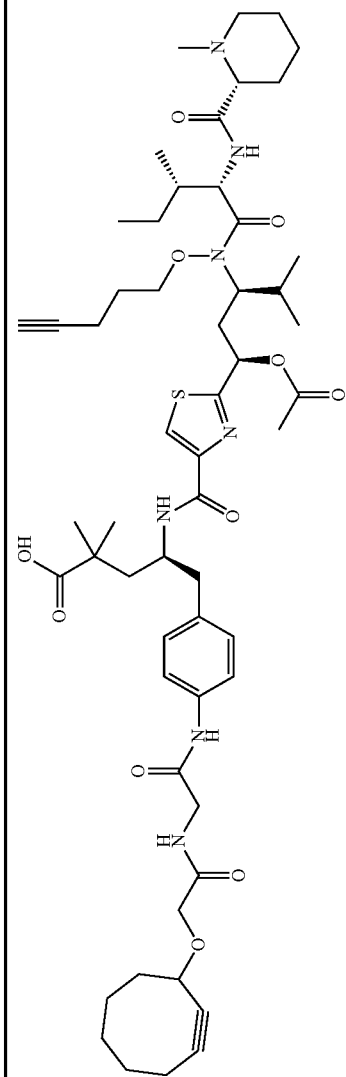
LP16
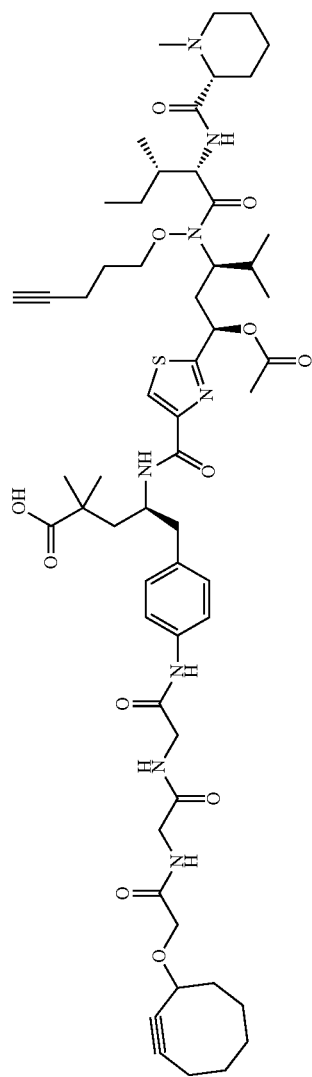
LP17
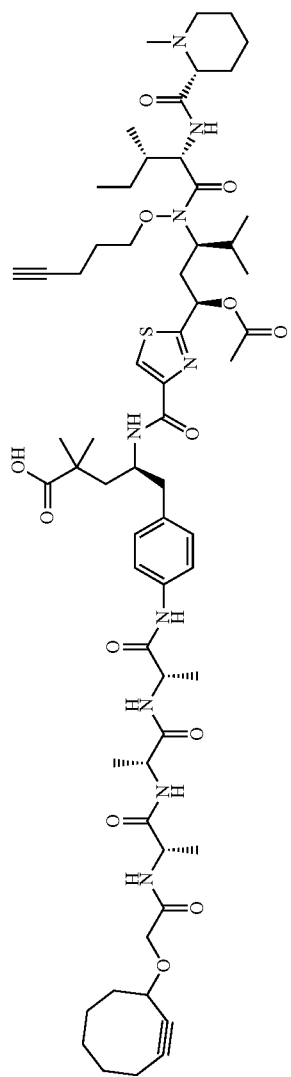
LP18

TABLE 2-continued

Tubulysin Linker-payloads

LP19

LP20

LP21

TABLE 2-continued
Tubulysin Linker-payloads
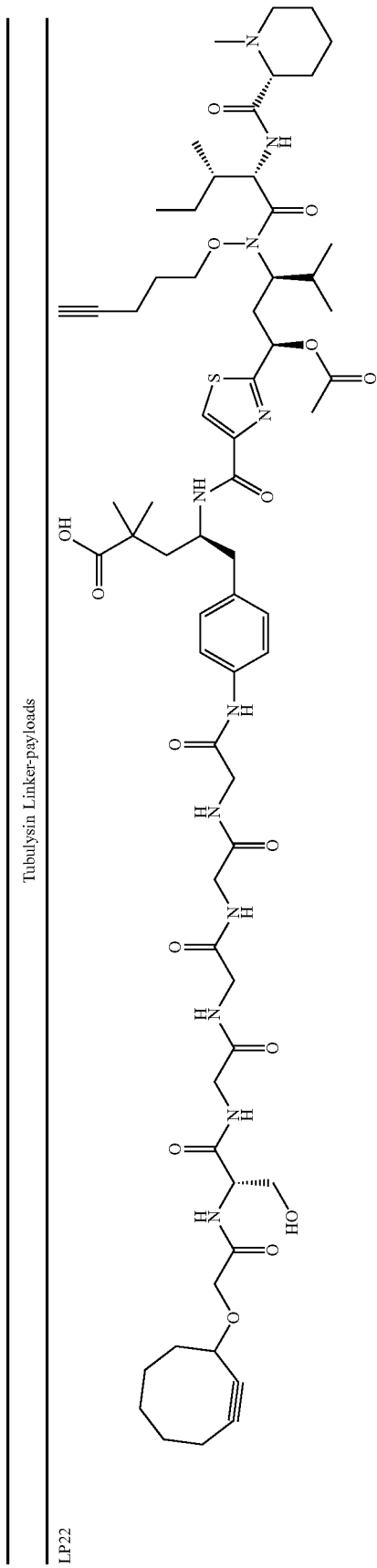
LP22
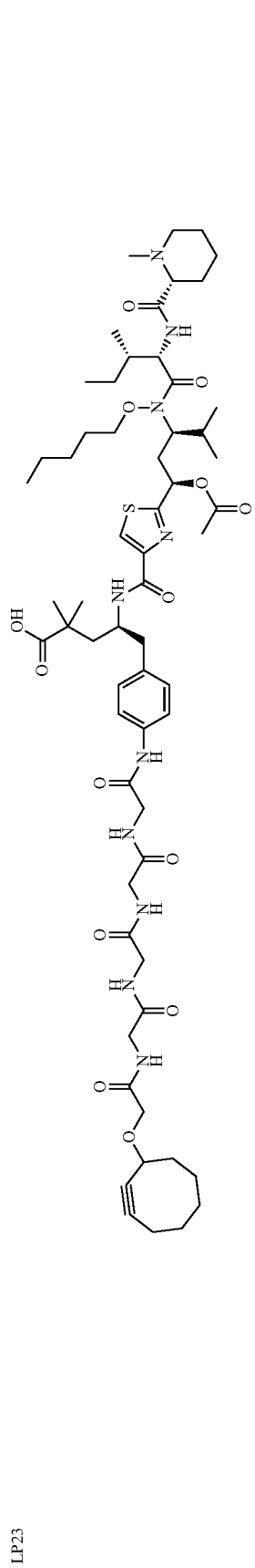
LP23
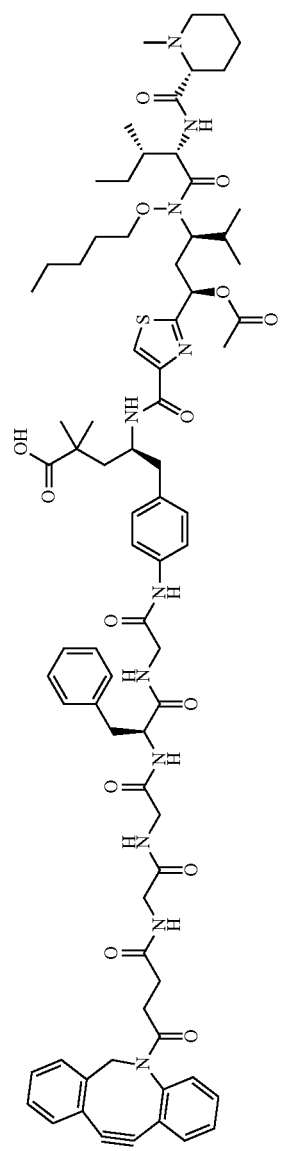
LP24

TABLE 2-continued
Tubulysin Linker-payloads
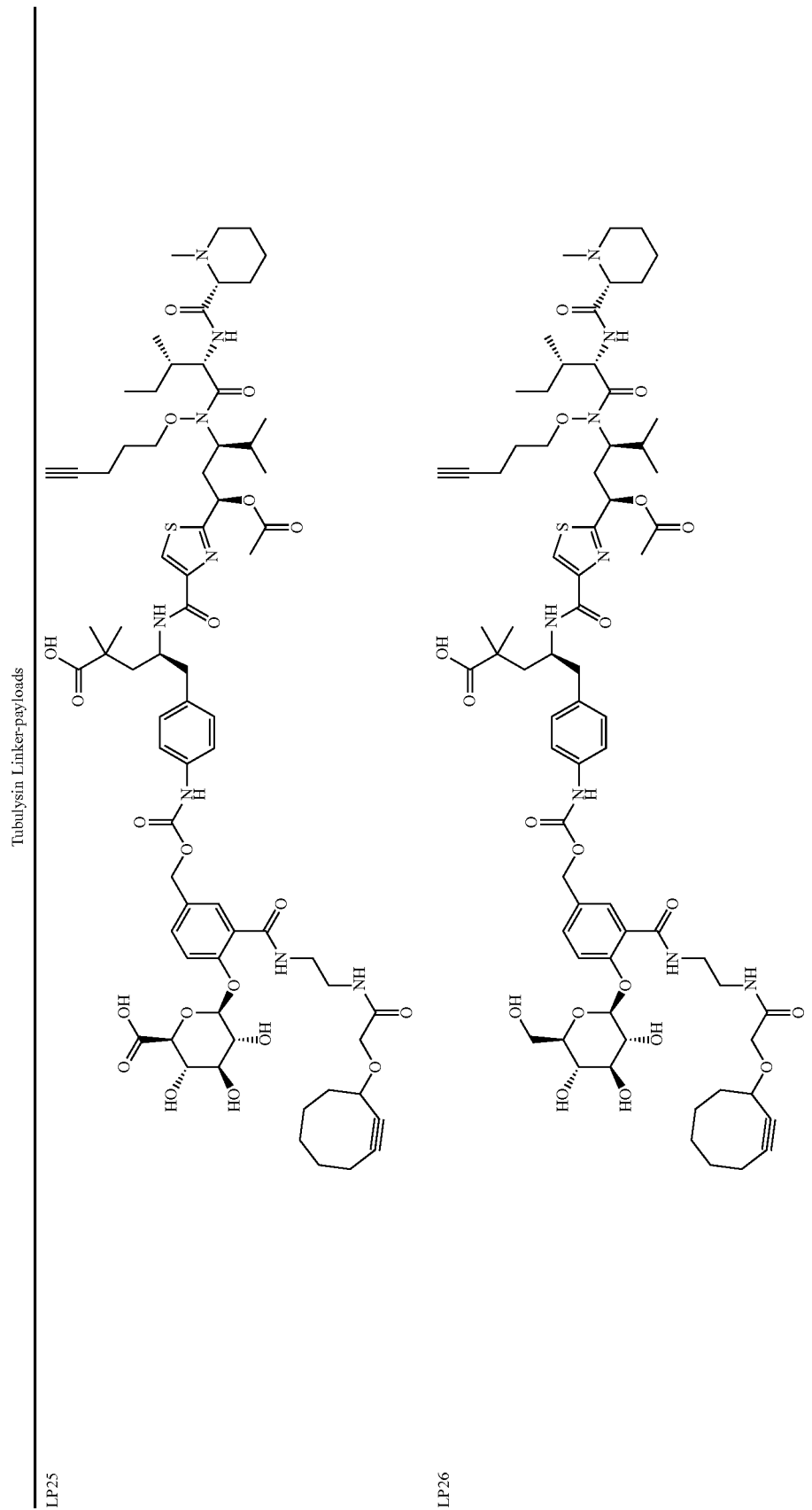
LP25
LP26

Certain embodiments of the invention are illustrated by the following non-limiting examples. As used herein, the symbols and conventions used in these processes, schemes, and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the Examples, and throughout the specification:

| Abbreviation | Term or Phrase |
| --- | --- |
| ADC | Antibody-drug conjugate |
| Aglycosylated antibody | Antibody does not have any glycan |
| API | Atmospheric pressure ionization |
| aq | Aqueous |
| Boc | N-tert-butoxycarbonyl |
| BupH ™ | Thermo Scientific Prod# 28372, containing 100 mM sodium phosphate and 150 mM sodium chloride, potassium free, pH was adjusted from 7.2 to 7.6-7.8 MQ, unless otherwise noted. |
| CD | Cyclodextrin |
| COT | Cyclooctynol |
| Da | Dalton |
| DAD | Diode array detector |
| DAR | Drug to antibody ratio |
| DCM | Dichloromethane |
| DIBAC | 11,12-didehydro-5,6-dihydro-Dibenz[b,f]azocine |
| DIBAC-Suc | 11,12-didehydro-5,6-dihydro-Dibenz[b,f]azocine succinamic acid |
| DIBAC-Suc-PEG4-VC-pAB-PNP | {4-[(2S)-2-[(2S)-2-[1-(4-{2-azatri-cyclo[10.4.0.0$^{4,9}$]hexadeca-1(12),4(9),5,7,13,15-hexaen-10-yn-2-yl]-4-oxobutanamido)-3,6,9,12-tetraoxapentadecan-15-amido]-3-methylbutanamido]-5-(carbamoylamino)pentana-mido]phenyl}methyl 4-nitrophenyl carbonate |
| DIBACT | 3H-Benzo[c]-1,2,3-triazolo[4,5-e][1]benzazocine, 8,9-dihydro- |
| DIPEA | Diisopropylethylamine |
| DMF | N,N-dimethylformamide |
| DMSO | Dimethylsulfoxide |
| EC | Enzyme commission |
| ELSD | Evaporative light scattering detector |
| ESI | Electrospray ionization |
| Fmoc | N-(9-fluorenylmethyloxycarbonyl) |
| Fmoc-vcPAB-PNP | N-Fmoc-L-valine-L-citrulline-p-aminobenzyl alcohol p-nitrophenyl carbonate |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney (cells) |
| HPLC | High performance liquid chromatography |
| hr, h, or hrs | Hours |
| LC | Light chain of immunoglobulin |
| LCh | Liquid chromatography |
| MALDI | Matrix-assisted laser desorption/ionization |
| MC | Maleimidocaproyl |
| mg | milligrams |
| min | minutes |
| mL | milliliters |
| mmh | myc-myc-hexahistidine tag |
| µL | microliters |
| mM | millimolar |
| µM | micromolar |
| MMAE | Monomethyl auristatin E |
| MS | Mass spectrometry |
| MsCl | Methanesulfonyl chloride |
| MSD | Mass-selective detector |
| MTG | Microbial transglutaminase (MTG EC 2.3.2.13, Zedira, Darmstadt, Germany) |
| MW | Molecular weight |
| ncADC | Non-Cytotoxic antibody drug conjugate |
| NHS | N-hydroxy succinimide |
| nM | nanomolar |
| NMR | Nuclear magnetic resonance |
| NOESY | Nuclear Overhauser effect spectroscopy |
| PAB | Para-aminobenzyloxy(carbonyl) |
| PBS | 10 mM sodium phosphate buffer and 150 mM sodium chloride |
| PBSg | 10 mM phosphate, 150 mM sodium chloride, 5% glycerol |
| PEG | Polyethyleneglycol |
| PNP | p-nitrophenyl |
| MC-VC-PAB-PNP | Maleimidocaproyl-L-valine-L-citrulline-p-aminobenzyl alcohol p-nitrophenyl carbonate |
| ppm | Parts per million (chemical shift, δ) |
| RP | Reversed phase |
| rt or RT | room temperature |
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TMS | tetramethylsilane |
| TFA | Trifluoroacetic acid |
| TG | Transglutaminase |
| THF | Tetrahydrofuran |
| TOF | Time-of-flight |
| UPLC | Ultra Performance Liquid Chromatography |
| UV | Ultraviolet |
| VA | Valine-alanine |
| VC | Valine-citrulline |
| VC-PAB | Valine-citrulline-para-aminobenzyloxy(carbonyl) |

Reagents and solvents were obtained from commercial sources such as Sinopharm Chemical Reagent Co. (SCRC), Sigma-Aldrich, Alfa, or other vendors, unless explicitly stated otherwise. $^1$H NMR and other NMR spectra were recorded on a Bruker AVIII 400 or Bruker AVIII 500. The data were processed with Nuts software or MestReNova software, measuring proton shifts in parts per million (ppm) downfield from an internal standard tetramethylsilane (TMS).

HPLC-MS measurements were run on an Agilent 1200 HPLC/6100 SQ System using the follow conditions: Method A for HPLC-MS measurements included, as the Mobile Phase: A: Water (0.01% trifluoroacetic acid (TFA)), B: acetonitrile (0.01% TFA); Gradient Phase: 5% of B increased to 95% of B within 15 min; Flow Rate: 1.0 mL/min; Column: SunFire C18, 4.6×50 mm, 3.5 µm; Column Temperature: 50° C. Detectors: Analog to Digital Converter (ADC) Evaporative Light-scattering Detector (ELSD), Diode array detector (DAD) (214 nm and 254 nm), electrospray ionization-atmospheric ionization (ES-API). Method B for HPLC-MS measurements included, as the Mobile Phase: A: Water (10 mM NH$_4$HCO$_3$), B: acetonitrile; Gradient Phase: 5% to 95% of B within 15 min; Flow Rate: 1.0 mL/min; Column: XBridge C18, 4.6×50 mm, 3.5 µm; Column Temperature: 50° C. Detectors: ADC ELSD, DAD (214 nm and 254 nm), mass selective detector (MSD) (ES-API).

LC-MS measurements were run on an Agilent 1200 HPLC/6100 SQ System using the following conditions: Method A for LC-MS measurements included, as the Instrument: WATERS 2767; column: Shimadzu Shim-Pack, PRC-ODS, 20×250 mm, 15 µm, two connected in series; Mobile Phase: A: Water (0.01% TFA), B: acetonitrile (0.01% TFA); Gradient Phase: 5% of B increased to 95% of B within 3 min; Flow Rate: 1.8-2.3 mL/min; Column: SunFire C18, 4.6×50 mm, 3.5 µm; Column Temperature: 50° C. Detectors: ADC ELSD, DAD (214 nm and 254 nm), ES-API. Method B for LC-MS measurement included, as the Instrument: Gilson GX-281; column: Xbridge Prep C18 10 µm OBD, 19×250 mm; Mobile Phase: A: Water (10 mM $NH_4HCO_3$), B: Acetonitrile; Gradient Phase: 5% to 95% of B within 3 min; Flow Rate: 1.8-2.3 mL/min; Column: XBridge C18, 4.6×50 mm, 3.5 µm; Column Temperature: 50° C. Detectors: ADC ELSD, DAD (214 nm and 254 nm), MSD (ES-API).

Preparative high-pressure liquid chromatography (Prep-HPLC) in an acidic or basic solvent system was utilized on a Gilson GX-281 instrument. The acidic solvent system used a Waters SunFire 10 µm C18 column (100 Å, 250×19 mm), and solvent A for prep-HPLC was water/0.05% TFA and solvent B was acetonitrile. The elution conditions were a linear gradient increase of solvent B from 5% to 100% over a time period of 20 min at a flow rate of 30 mL/min. The basic solvent system included a Waters Xbridge 10 µm C18 column (100 Å, 250×19 mm), and solvent A used for prep-HPLC was water/10 mM ammonium bicarbonate ($NH_4HCO_3$) and solvent B was acetonitrile. The elution conditions were a linear gradient increase of solvent B from 5% to 100% over a time period of 20 min at a flow rate of 30 mL/min.

Flash chromatography was performed on a Biotage instrument, with Agela Flash Column silica-CS cartridges; Reversed phase flash chromatography was performed on Biotage instrument, with Boston ODS or Agela C18 cartridges.

Analytical chiral HPLC method—SFC conditions
a) Instrument: SFC Method Station (Thar, Waters)
b) Column: CHIRALPAK AD-H/AS-H/OJ-H/OD-H 4.6×100 mm, 5 µm (Daicel)
c) Column temperature: 40° C.
d) Mobile phase: $CO_2$/TPA (0.1% DEA)=55/45
e) Flow: 4.0 mL/min
f) Back Pressure: 120 Bar
g) Injection volume: 2 µL Preparative Chiral HPLC Method—SFC Conditions
a) Instrument: SFC-80 (Thar, Waters)
b) Column: CHIRALPAK AD-H/AS-H/OJ-H/OD-H 20×250 mm, 10 µm (Daicel)
c) Column temperature: 35° C.
d) Mobile phase: $CO_2$/TPA (0.2% Methanol Ammonia)=30/70
e) Flow rate: 80 g/min
f) Back pressure: 100 bar
g) Detection wavelength: 214 nm
h) Cycle time: 6.0 min
i) Sample solution: 1500 mg dissolved in 70 mL Methanol
j) Injection volume: 2 mL (loading: 42.86 mg/injection)

PREPARATION METHODS

Figure 4:
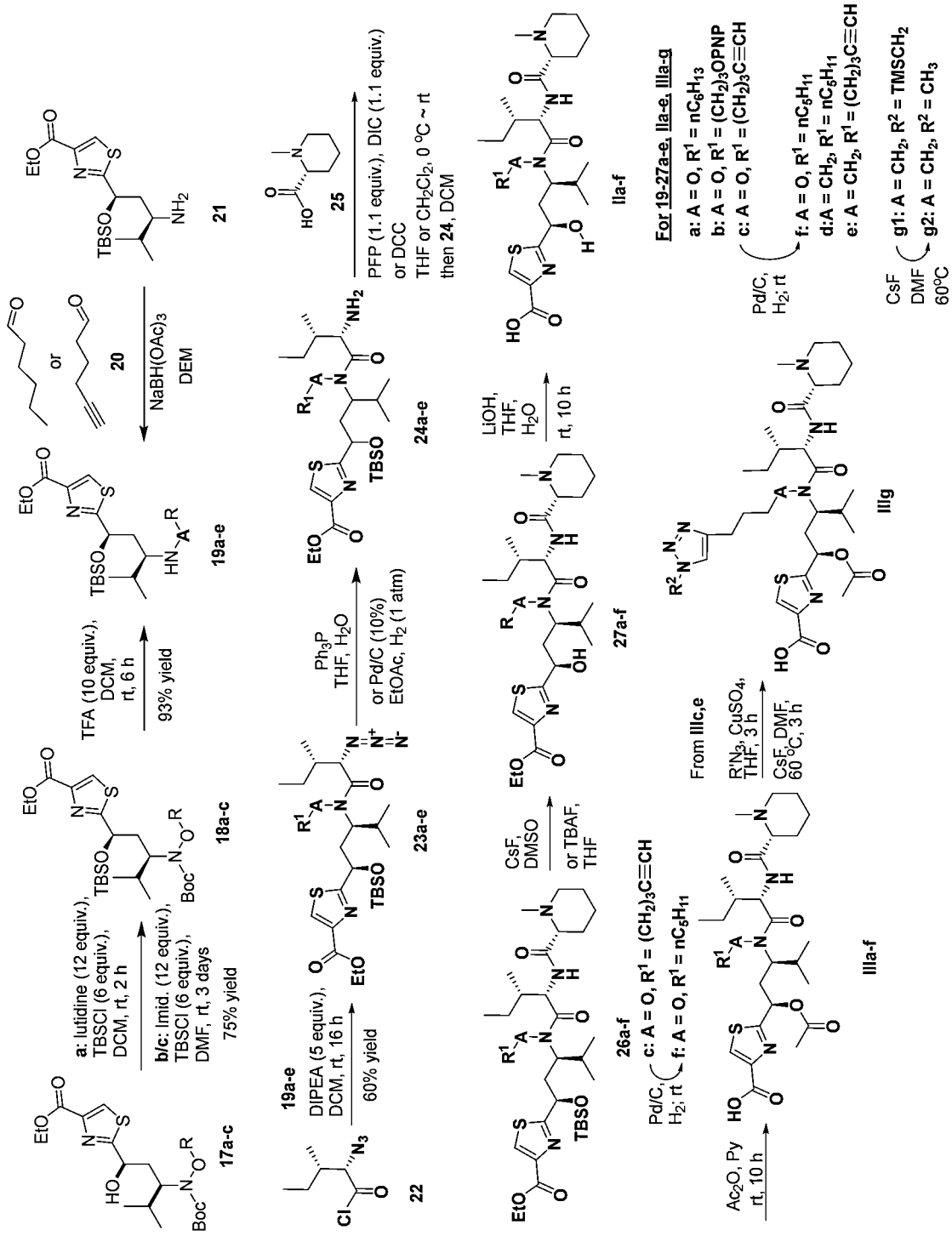
Figure 5:
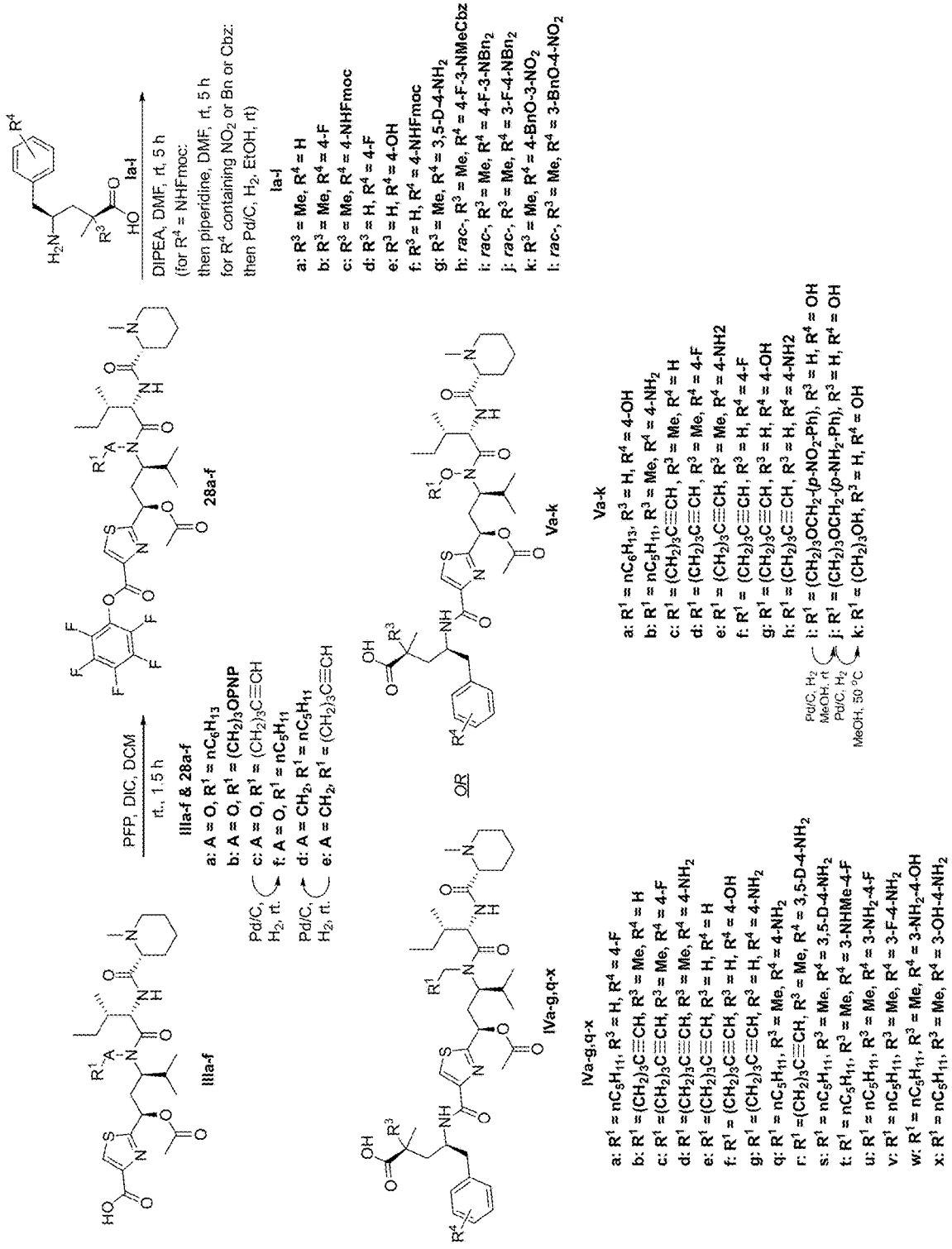

The tubulysin payloads (IV, V, VI) in Table 1 were synthesized from intermediate I (FIG. 1), II, and III (FIGS. 4-6). The tubulysin-linker-payloads in Table 2 were synthesized from tubulysin payloads with known linkers L-1 (FIG. 8), L-2, L-3 (FIG. 9), and L-4 (FIG. 10A) that are commercially available or were synthesized according to the literature (See, e.g., US 2014/227295; and WO2014/191578 A1).

The synthesis of intermediates Ia-c and Ig-1 are shown in FIG. 1. The Boc-aminoacid 1 was condensed with 2,2-dimethyl-1,3-dioxane-4,6-dione 2, followed by a reduction of ketone 3 with $NaBH_4$ to provide compound 4. Compound 4 was converted to the lactam 5 via de-carboxylation of 4 under heated conditions for ring-opening and subsequent ring-closure in one step. Methylation at the α-position of 5, followed by basic hydrolysis to convert lactam 5 to acid 7, and finally Boc deprotection provided intermediates Ia-c and Ig-1.

The synthesis of intermediates Id-f followed the procedures described in: WO2016/138288 A1 for Id ($R^4$=F); Org. Lett. 2009, 11(24), 5567-5569 for Ie ($R^4$=OH); and U.S. Pat. No. 9,382,289 B2 for If ($R^4$=$NH_2$).

Figure 2:
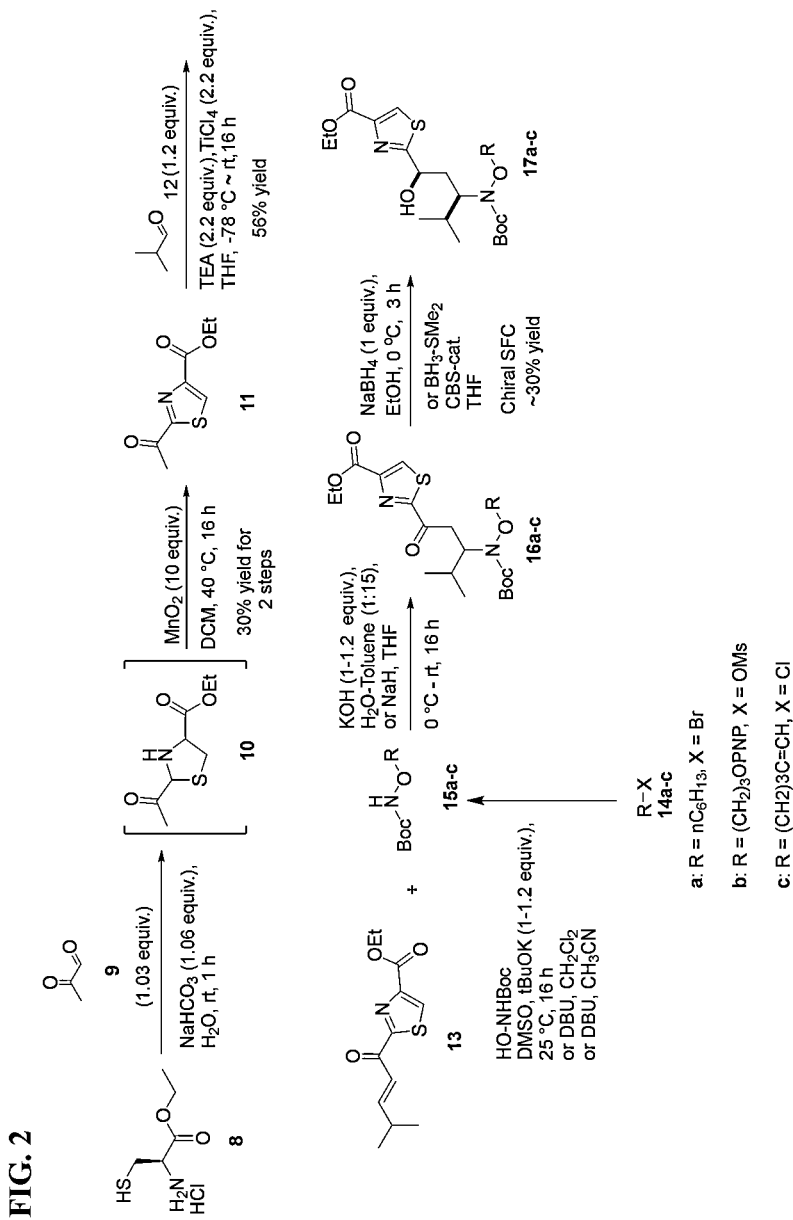

The synthesis of intermediates 17a-c is shown in FIG. 2. Thiazole 11 was obtained from cysteine ethyl ester 8 via cyclization with 2-oxo-propanal 9, followed by $MnO_2$ oxidation. The α,β-unsaturated ketone 13 was obtained from an aldol condensation of 11 with 2-methyl propanal 12. The Michael addition of hydroxylamine derivative 15 to α,β-unsaturated ketone 13, followed by CBS catalyzed reduction, provided a mixture of cis-17 and trans-17, which were separated by column chromatography and further purified by chiral HPLC or SFC to provide the desired chiral 17a-c.

The Corey-Bakshi-Shibata Reduction (aka CBS reduction) or the Itsuno-Corey Reduction is a well-established and highly enantioselective ketone-reduction reaction. It was reported that the oxazaborolidine reagent mediates the reduction of ketone 16A to provide alcohol 17A in a high ee, where 17A and stereo-isomer 17B were fully characterized (Angew. Chem. Int. Ed. 2007, 46, 3526-3529; see FIG. 3). We reduced 16a and 16b using $CBS-BH_3$ SMe and obtained cis-17a or cis-17b (de >90%) and trans-17a or trans-17b (de ~80%) from the reaction crudes, separately. Those mixed enantiomers were further purified by Chiral SFC to provide pure enantiomers (de >95%). We also tried alternative reduction conditions and reduced 16c using sodium borohydride to obtain cis-17c and trans-17c, after silica gel column chromatography. Each pair of separated isomers were further isolated by Chiral HPLC, respectively, to give 17c-P1, 17c-P2, 17c-P3, and 17c-P4 (all ee >99%). To determine the chiral centers for all four isomers, the N—O bond of each compound was cleaved using $Mo(CO)_6$ to provide 17A or 17B, and their diastereoisomers 17A' or 17B', respectively. The chiral centers of compounds 17a-c were determined by comparing the $^1H$ NMR data and optical rotation data for both 17A and 17B with the published data for the same compounds.

The synthesis of the 0-intermediate and C-intermediate (II and III) are shown in FIG. 4. Compounds 19a-c were obtained from O-TBS protections of 17a-c, followed by Boc deprotections of 18a-c. Compounds 19d-e were obtained from a reductive amination of caproaldehyde or 5-hexynaldehyde 20 with a known compound 21 (Eur. Pat. Appl., 2409983, 25 Jan. 2012), respectively. The triple bond in 19c can be reduced with palladium-carbon to provide 19f. Compounds 19a-e were treated with (2S,3S)-2-azido-3-methylpentanoyl chloride 22 to provide amides 23a-e, which then underwent Staudinger reductions in the presence of triphenyl phosphine, followed by amidations with N-methyl-2R-piperidinecarboxylic acid 25 to provide amides 26a-e. Compounds 26a-e were converted to intermediates IIa-e via TBS deprotections with cesium fluoride and subsequent basic hydrolyses. The triple bond in IIc can be reduced with palladium-carbon to provide IIf. Intermediates IIIa-f were obtained from acetylation of intermediates IIa-f. Intermediate IIIg was obtained from IIIe via a [3+2] cyclization with TMS-CH$_2$N$_3$, followed by TBS deprotection with cesium fluoride.

The synthesis for making C-tubulysin derivatives (IV) and O-tubulysin derivatives (V) are shown in FIG. 5. The C-tubulysin derivatives (IV) were synthesized according to the procedures reported in *J. Org. Chem.* 2008, 73 (12), 4362-4369. Shown in FIG. 5, the esterification of intermediates IIId-e with pentafluorophenol (PFP) in the presence of N,N'-diisopropylcarbodiimide (DIC) provided pentafluorophenyl esters 28a-e, which were treated with amines Ia-1 in amidations to give C-tubulysin payloads IVa-g and IVq-x, respectively, after additional deprotection of Fmoc or TMS (for TMS deprotection, see FIG. 6A). The O-tubulysin derivatives (V) were synthesized using the methods described above from IIIa-c and f, via an esterification with PFP in the presence of DIC, followed by an amidation with Ia-1. The O-tubulysin derivatives Vb, Ve, and Vh were obtained after additional deprotections of Fmoc. Hydrogenation of O-tubulysin derivative Vi with palladium-carbon provided aniline derivative Vj, which was further hydrogenated with heat to provide Vk.

Figure 6A:
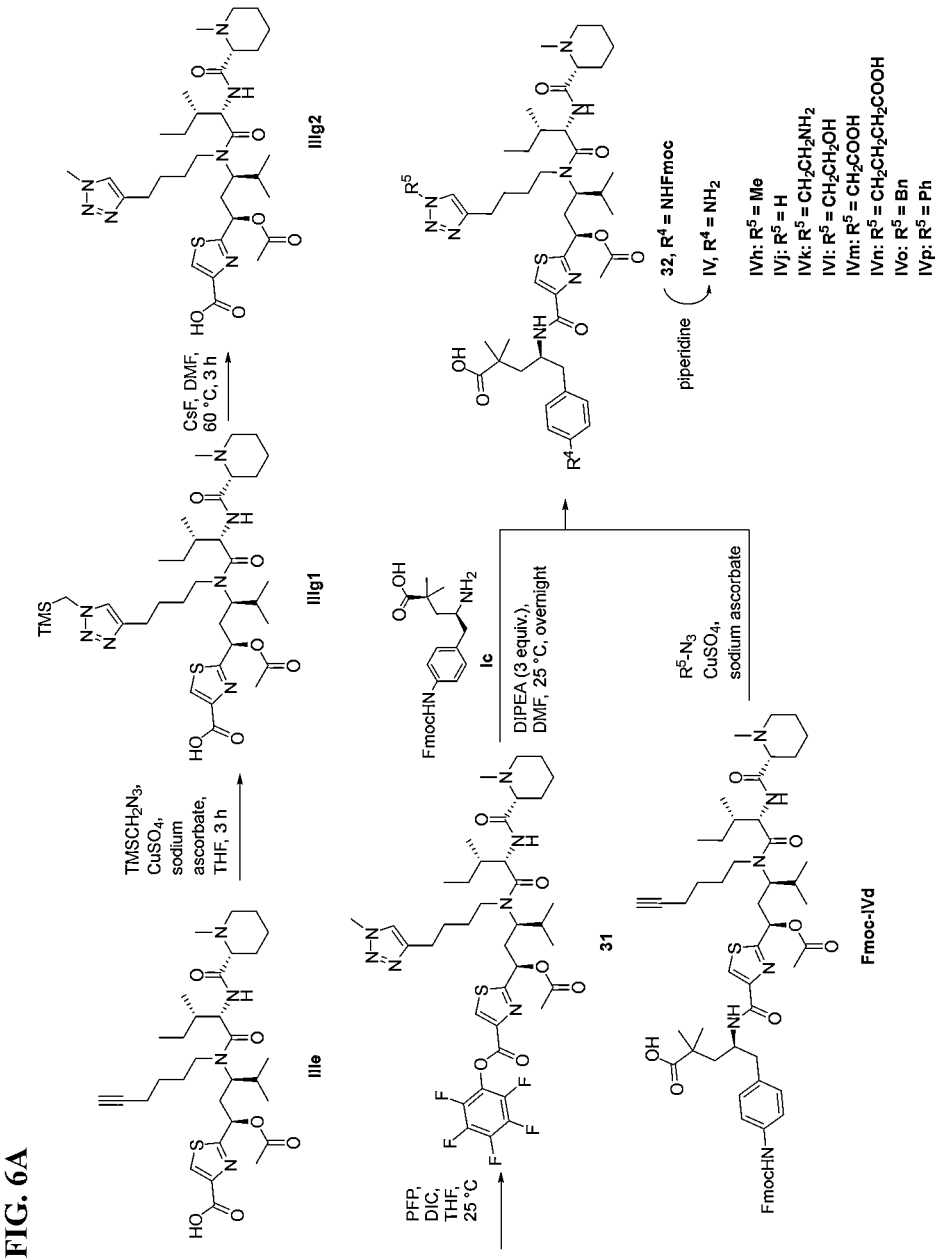

The C-triazole tubulysin analogs (IVh and j-p) were prepared via two approaches shown in FIG. 6A. In the first approach, the intermediate IIIe was treated with TMS-methyl azide in a [3+2] click reaction to form IIIg1, followed by TMS deprotection with cesium fluoride to provide IIIg2. Conversion of IIIg2 to the pentafluorophenyl ester 31 and subsequent amide coupling afforded IVh after Fmoc deprotection. In the second approach, the triazole tubulysin analogs IVj-p were made via [3+2] click reactions with intermediate Fmoc-IVd and different azido reagents (R$^5$—N$_3$), followed by Fmoc deprotections.

Figure 7A:
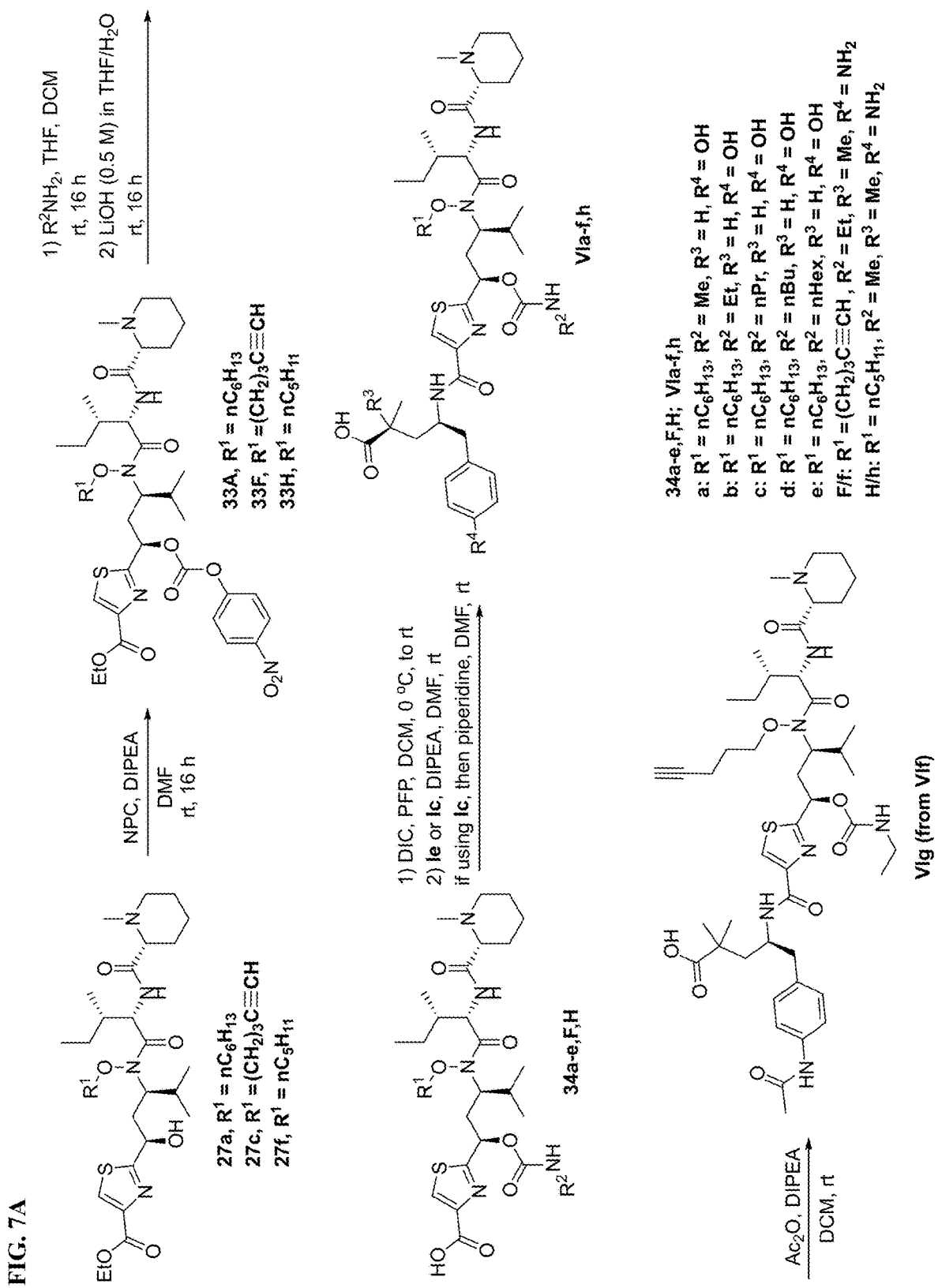
Figure 7B:
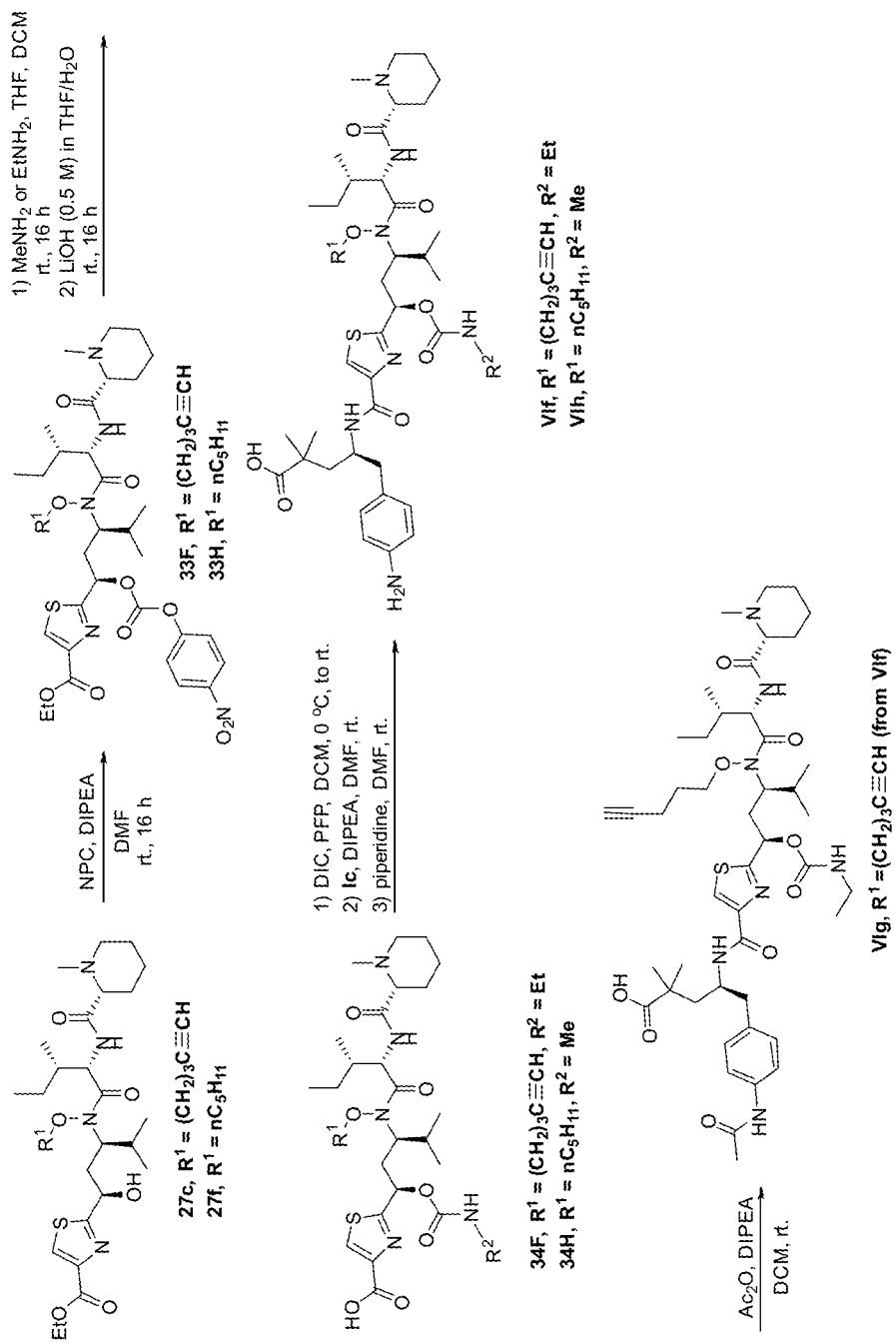

The synthesis for making O-tubulysin derivatives VIa-f,h is shown in FIGS. 7A and 7B. Compound 27a was treated with bis(4-nitrophenyl) carbonate (NPC) to form an activated carbonate 33, which was then treated with primary amines to provide compounds 34a-e,F,H respectively. The carbamates VIa-f,h were obtained from amidation of compounds 34a-e,F,H with, for example, intermediate Ie, respectively.

Figure 8:
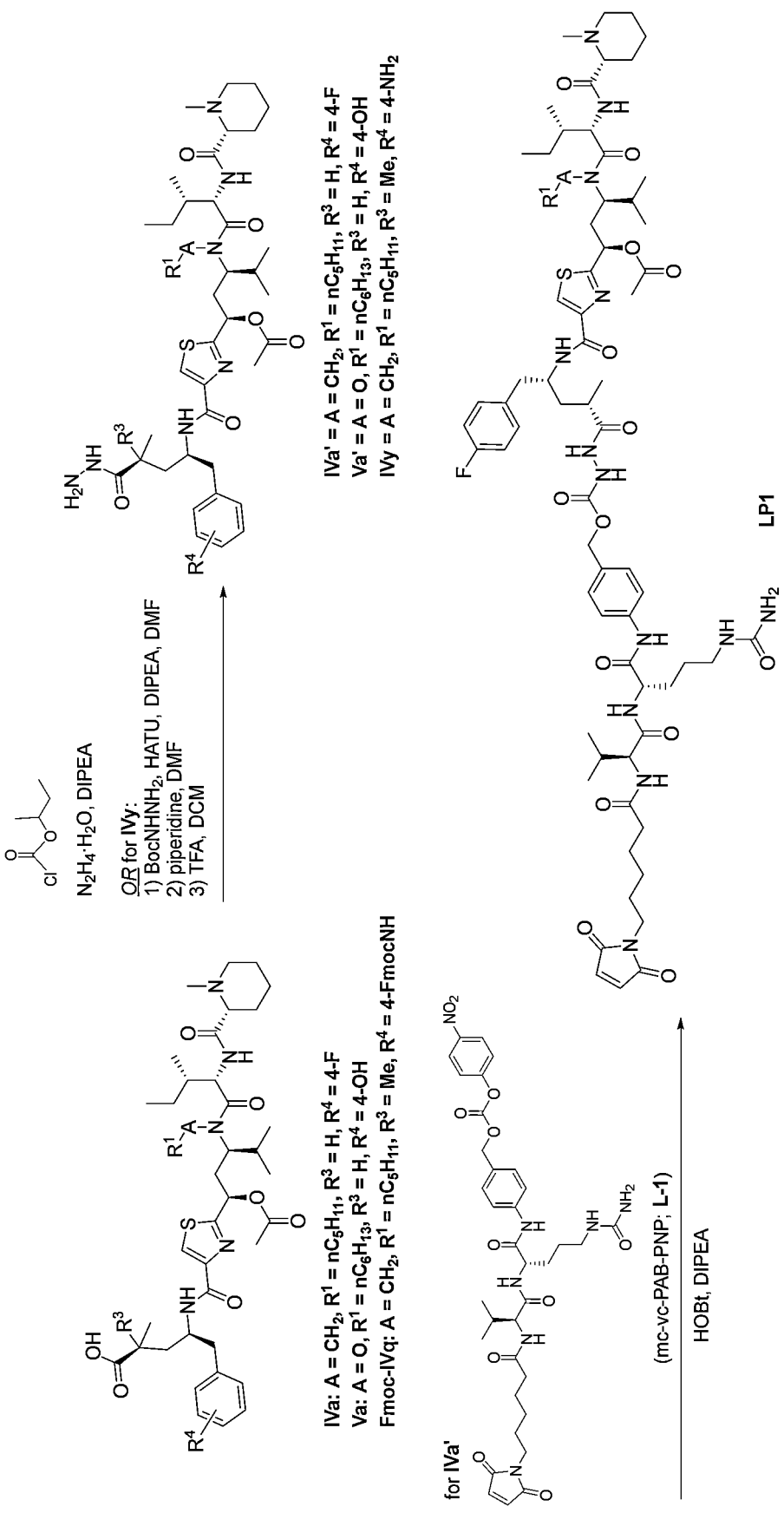
Figure 9:
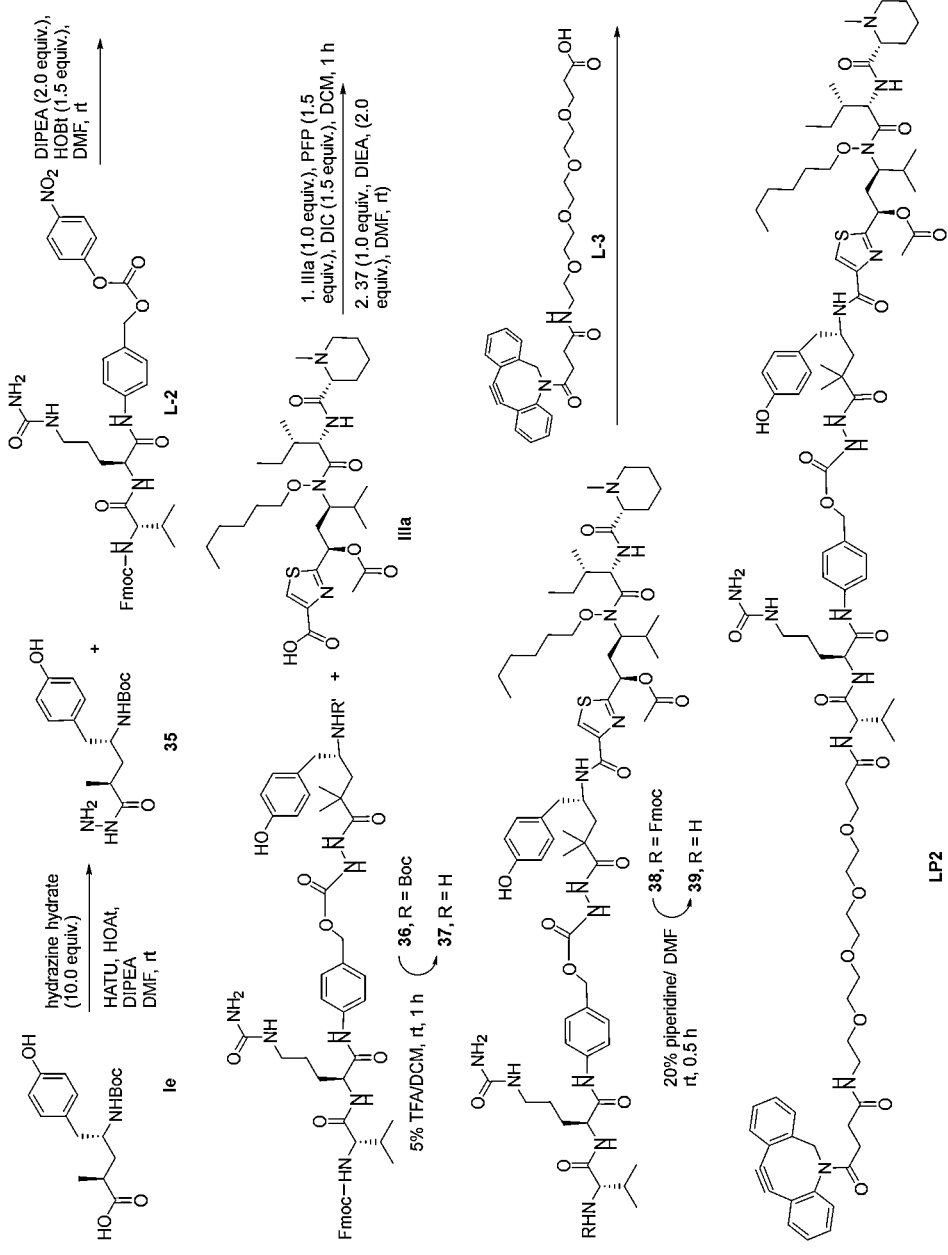
Figure 10A:
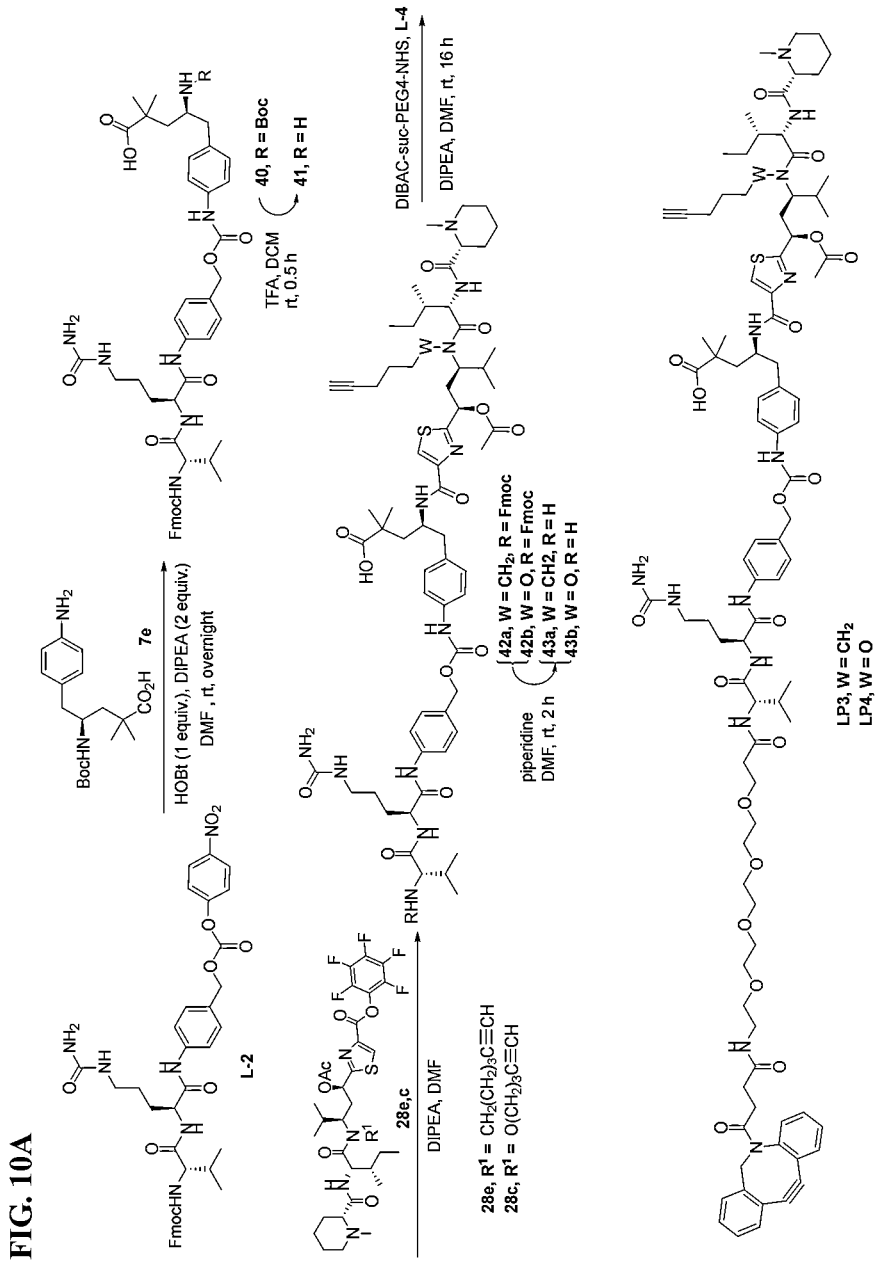
Figure 10B:
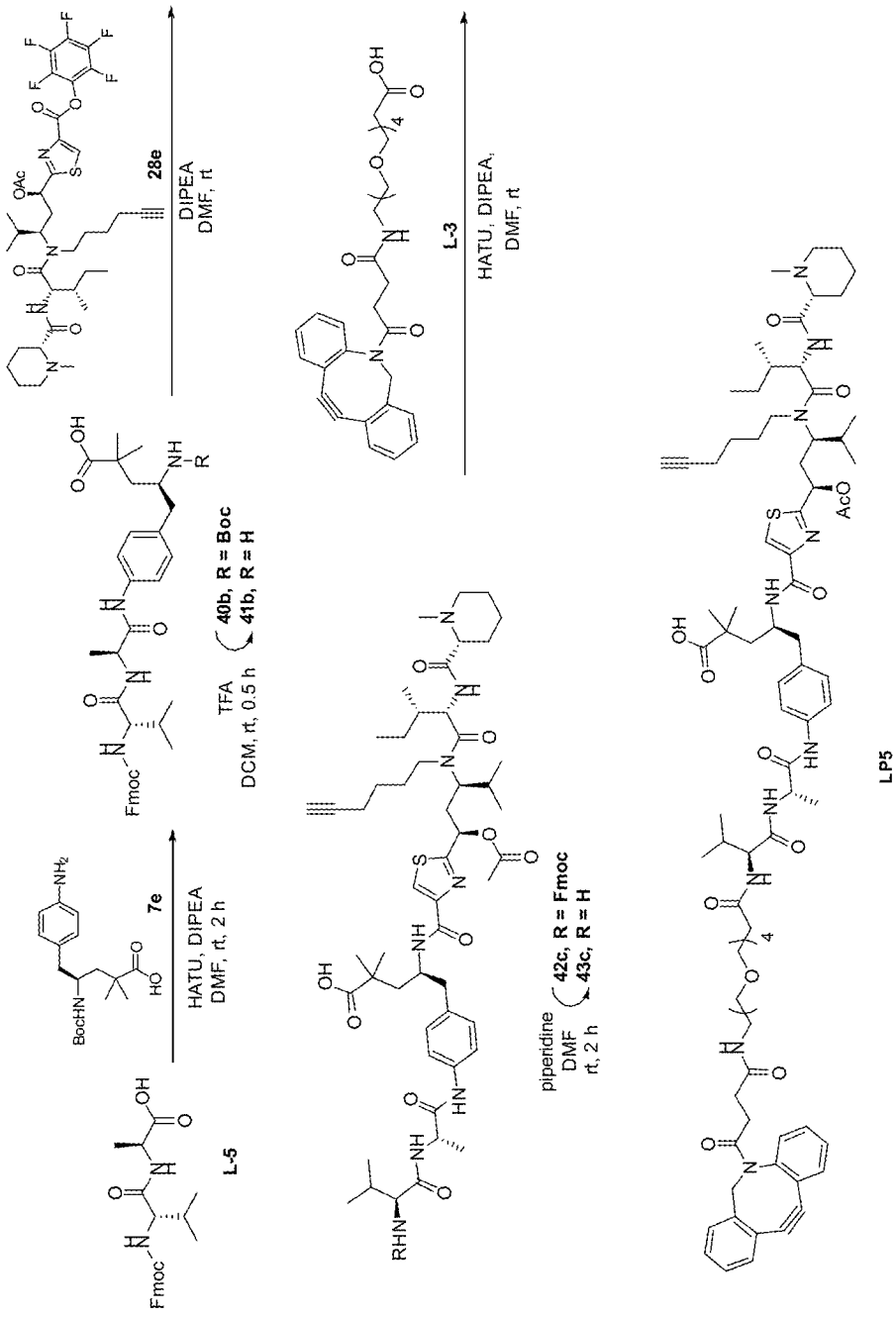

The synthesis for making linker-tubulysin-payloads (LPs) is shown in FIG. 8 for LP1, FIG. 9 for LP2, and FIG. 10A for LP3 and LP4, FIG. 10B for LP5. There are two approaches to make the linker-payloads. One way is to conjugate a linker with a payload exemplified in the synthesis of LP1 (FIG. 8); another way is to link a linker with a fragment of the payload, followed by an amide coupling to make a linker-payload exemplified in the synthesis of LP2 (FIG. 9).

Shown in FIG. 8, LP1 was synthesized from the reaction of IVa with hydrazine hydrate to give IVa', followed by treating with MC-VC-PAB-PNP (L-1).

Shown in FIG. 9, LP2 was synthesized by first coupling VC-PAB with the hydrazide of intermediate Ie. In other words, the intermediate Ie was treated with hydrazine hydrate to form hydrazide 35, which was treated with N-Fmoc-VC-PAB-PNP (L-2) to afford compound 37 after Boc deprotection using TFA. Amidation of 37 with intermediate IIa provided compound 39 after deprotection of Fmoc; amidation of 39 with DIBAC-suc-PEG4-COOH (L-3) afforded LP2.

The key intermediates were analyzed on Chiral SFC under different column conditions where they all showed >99% ee and the detailed retention times (R$_t$) are summarized as follows in Table 3.

TABLE 3

Chiral SFC R$_t$ to determine ee of intermediates

| Compd. | Chiral SFC R$_t$ (min) | | | |
|---|---|---|---|---|
| | AD-H | AS-H | OJ-H | OD-H |
| 37 | 2.14 | 3.89 | 1.99 | 4.97 |
| 38 | 2.19 | 3.99 | 2.06 | 6.24 |
| 39 | 2.37 | 2.11 | 5.73 | |

Shown in FIG. 10A, linker L-2 was treated with intermediate 7e to afford compound 41 after Boc deprotection. An amide coupling reaction of compound 41 with 28e or 28c afforded 43a or 43b, respectively, after Fmoc deprotection. Compound 43a or 43b was coupled with DIBAC-suc-PEG4-NHS (L-4) to afford LP3 or LP4, respectively.

EXPERIMENTAL PROCEDURES

Synthesis of Intermediate I in FIG. 1

General Procedure for Compound 3

To a mixture of compound 1 (5 g, 1.0 equiv.) in DCM (20 mL) were added compound 2 (1.1 equiv.) and DMAP (1.5 equiv.) at 0° C., and the mixture was stirred at 0° C. for 30 minutes before EDCI (1.1 equiv.) was added into the reaction mixture. The resulting mixture was stirred at rt overnight. LCMS showed the reaction was completed. The mixture was washed with aq. potassium bisulfate (5%, 4×) and brine. The organic layer was separated and dried over sodium sulfate and concentrated in vacuo. The residue was triturated from methanol to give compound 3 (50-60% yield) as a white solid.

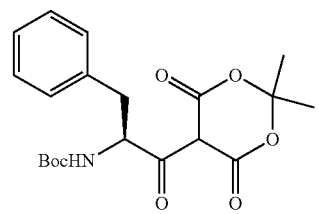 [SMILES: CC(C)(C)OC(=O)N[C@@H](Cc1ccccc1)C(=O)C1C(=O)OC(C)(C)OC1=O]

tert-Butyl N-[(2S)-1-(2,2-dimethyl-4,6-dioxo-1,3-dioxan-5-yl)-1-oxo-3-phenylpropan-2-yl] carbamate (3a)

Following the general procedure for Compound 3, compound 3a (4.2 g, 57% yield) was obtained as a white solid. ESI m/z: 805 (2M+Na)$^+$. $^1$H NMR (500 MHz, CDCl$_3$) δ 15.57 (s, 1H), 7.34-7.27 (m, 4H), 7.26-7.23 (m, 1H), 5.89 (s, 1H), 5.09-4.79 (m, 1H), 3.25-3.05 (m, 1H), 2.94-2.79 (m, 1H), 1.75 (s, 3H), 1.65 (s, 3H), 1.36 (s, 9H) ppm.

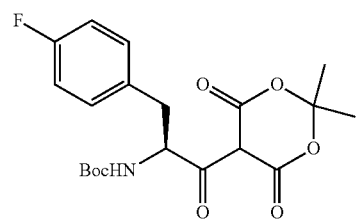 [SMILES: CC(C)(C)OC(=O)N[C@@H](Cc1ccc(F)cc1)C(=O)C1C(=O)OC(C)(C)OC1=O]

tert-Butyl N-[(2S)-1-(2,2-dimethyl-4,6-dioxo-1,3-dioxan-5-yl)-3-(4-fluorophenyl)-1-oxopropan-2-yl]carbamate (3b)

Following the general procedure for Compound 3, compound 3b (4.2 g, 58% yield) was obtained as a white solid. ESI m/z: 841 (2M+Na)⁺. ¹H NMR (500 MHz, CDCl₃) δ 7.30-7.24 (m, 2H), 7.03-6.97 (m, 2H), 5.93-5.78 (m, 1H), 5.08-4.96 (m, 1H), 3.23-3.09 (m, 1H), 2.86-2.74 (m, 1H), 2.06-1.82 (m, 1H), 1.76 (s, 3H), 1.68 (s, 3H), 1.36 (s, 9H) ppm.

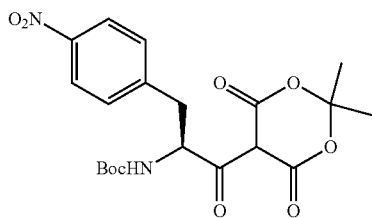 [SMILES: CC(C)(C)OC(=O)N[C@@H](Cc1ccc([N+](=O)[O-])cc1)C(=O)C1C(=O)OC(C)(C)OC1=O]

(S)-tert-Butyl 1-(2,2-dimethyl-4,6-dioxo-1,3-dioxan-5-yl)-3-(4-nitrophenyl)-1-oxopropan-2-ylcarbamate (3d)

Following the general procedure for Compound 3, compound 3c (3.3 g, 47% yield) was obtained as a white solid. ESI m/z: 459 (M+Na)⁺. ¹H NMR (500 MHz, CDCl₃) δ 15.7 (s, 1H), 8.19 (d, J=9.0 Hz, 2H), 7.53 (d, J=9.0 Hz, 2H), 5.87 (s, 1H), 5.09-5.08 (m, 1H), 3.33-3.31 (m, 1H), 2.90-2.86 (m, 1H), 1.73 (s, 6H), 1.33 (s, 9H) ppm.

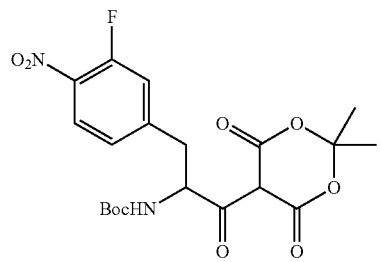

tert-Butyl 1-(2,2-dimethyl-4,6-dioxo-1,3-dioxan-5-yl)-3-(3-fluoro-4-nitrophenyl)-1-oxopropan-2-ylcarbamate (3j)

To a solution of 2-amino-3-(3-fluoro-4-nitrophenyl)propanoic acid (3.5 g, 15 mmol; synthesized according to Medicinal Chemistry Letters 2016, 7(3), 250-255) in dioxane (140 mL) and water (70 mL) were added sodium carbonate (4.8 g, 46 mmol) and Boc₂O (3.6 g, 17 mmol) at 0° C. The mixture was stirred at RT for 4 hours until the reaction was completed, which was monitored by LCMS. The reaction mixture was diluted with water and acidified with conc. HCl to pH 2-3. The aqueous mixture was extracted with ethyl acetate and the combined organic solution was washed with brine. The volatiles were removed in vacuo and the residual crude product was recrystallized from 25% ethyl acetate in petroleum ether to give compound 1j (4.7 g, 87% yield) as a pale yellow solid. ESI m/z: 351.1 (M+Na)⁺. Following the general procedure for Compound 3 using compound 1j, compound 3j (4.0 g, 96% crude yield) was obtained as a brown solid, which was used for the next step without further purification. ESI m/z: 477.1 (M+Na)⁺.

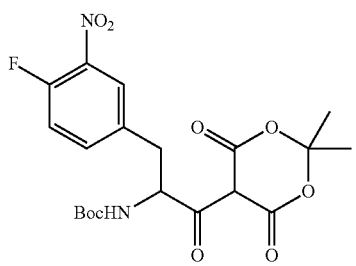 [SMILES: CC(C)(C)OC(=O)NC(Cc1ccc(F)c([N+](=O)[O-])c1)C(=O)C1C(=O)OC(C)(C)OC1=O]

tert-Butyl 1-(2,2-dimethyl-4,6-dioxo-1,3-dioxan-5-yl)-3-(4-fluoro-3-nitrophenyl)-1-oxopropan-2-ylcarbamate (3f)

Following the general procedure for Compound 3, compound 3f (62 g, crude) was obtained as a yellow solid, which was used for the next step without further purification. ESI m/z: 477 (M+Na)⁺. (Note: compound if was synthesized according to Ref: *J Am. Chem. Soc.*, 2010, 132(22), 7776-7783).

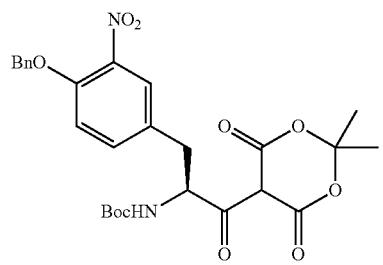

tert-Butyl (S)-(3-(4-(benzyloxy)-3-nitrophenyl)-1-(2,2-dimethyl-4,6-dioxo-1,3-dioxan-5-yl)-1-oxopropan-2-yl)carbamate (3k)

Following the general procedure for Compound 3 using compound 1k (synthesized according to *J. Am. Chem. Soc.* 1980, 102, 7156-7157), compound 3k (4.8 g, 97% crude yield) was obtained as a pale-green solid, which was used in the next step without further purification. ESI m/z: 565.1 (M+Na)⁺.

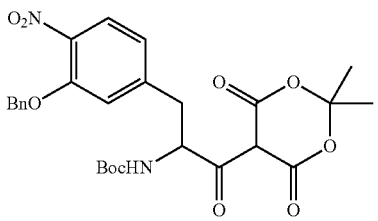 [SMILES: CC(C)(C)OC(=O)NC(Cc1ccc([N+](=O)[O-])c(OCc2ccccc2)c1)C(=O)C1C(=O)OC(C)(C)OC1=O]

tert-Butyl (3-(3-(benzyloxy)-4-nitrophenyl)-1-(2,2-dimethyl-4,6-dioxo-1,3-dioxan-5-yl)-1-oxopropan-2-yl)carbamate (31)

Following the general procedure for Compound 3 using compound 11 (synthesized using a similar procedure as in 1k, except starting from 2-amino-3-(3-hydroxy-4-nitrophenyl)propanoic acid, which was synthesized according to *J. Med. Chem.* 1997, 40, 3182-3191), compound 31 (4.6 g, 95% crude yield) was obtained as a pale solid, which was used in the next step without further purification. ESI m/z: 565.1 (M+Na)$^+$.

General Procedure for Compound 4

To a solution of compound 3 (1.0 equiv.) in DCM (20 mL) were successively added at 0° C. acetic acid (11 equiv.) by syringe and sodium borohydride (2.5 equiv.) in several portions. The reaction mixture was stirred at 0° C. for 2 hours until compound 3 was totally consumed, which was monitored by LCMS. The mixture was then quenched with brine at 0° C. and extracted with DCM (3 times). The combined organic layers were dried over sodium sulfate and concentrated in vacuo. The residue was purified by silica gel column chromatography (eluted by ethyl acetate/DCM) to give compound 4 (83-96% yield).

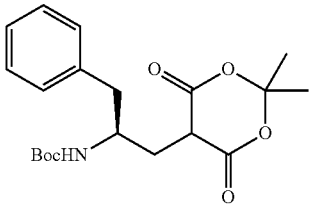 [SMILES: CC(C)(C)OC(=O)N[C@@H](Cc1ccccc1)CC1C(=O)OC(C)(C)OC1=O]

tert-Butyl N-[(2R)-1-(2,2-dimethyl-4,6-dioxo-1,3-dioxan-5-yl)-3-phenylpropan-2-yl]carbamate (4a)

Following the general procedure for Compound 4, compound 4a (3.8 g, 95% yield) was obtained as a colorless oil after purification by silica gel column chromatography (eluted by ethyl acetate/DCM, v/v=1/10). ESI m/z: 777 (2M+Na)$^+$. $^1$H NMR (500 MHz, CDCl$_3$) δ 7.33-7.28 (m, 2H), 7.25-7.28 (m, 3H), 4.55-4.40 (m, 1H), 4.28-4.18 (m, 1H), 3.98-3.84 (s, 1H), 2.86 (d, J=6.3 Hz, 2H), 2.36-2.12 (m, 2H), 1.78 (s, 3H), 1.74 (s, 3H), 1.36 (s, 9H) ppm.

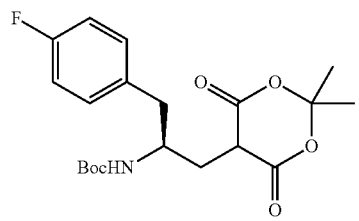 [SMILES: CC(C)(C)OC(=O)N[C@@H](Cc1ccc(F)cc1)CC1C(=O)OC(C)(C)OC1=O]

tert-Butyl N-[(2R)-1-(2,2-dimethyl-4,6-dioxo-1,3-dioxan-5-yl)-3-(4-fluorophenyl)propan-2-yl] carbamate (4b)

Following the general procedure for Compound 4, compound 4b (3.8 g, 95% yield) was obtained as a colorless oil after purification by silica gel column chromatography (eluted by ethyl acetate/DCM, v/v=1/1). ESI m/z: 813 (2M+Na)$^+$. $^1$H NMR (400 MHz, CDCl$_3$) δ 7.20-7.12 (m, 2H), 7.03-6.94 (m, 2H), 4.50-4.40 (m, 1H), 4.25-4.13 (m, 1H), 3.92-3.84 (m, 1H), 2.87-2.74 (m, 2H), 2.34-2.06 (m, 2H), 1.78 (s, 3H), 1.73 (s, 3H), 1.35 (s, 9H) ppm.

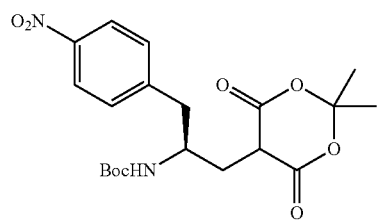 [SMILES: CC(C)(C)OC(=O)N[C@@H](Cc1ccc([N+](=O)[O-])cc1)CC1C(=O)OC(C)(C)OC1=O]

tert-Butyl N-[(2R)-1-(2,2-dimethyl-4,6-dioxo-1,3-dioxan-5-yl)-3-(4-nitrophenyl)propan-2-yl] carbamate (4d)

Following the general procedure for Compound 4, compound 4d (11 g, 83% yield) was obtained as a colorless oil after purification by silica gel column chromatography (eluted by ethyl acetate/DCM, v/v=3/2). ESI m/z: 867 (2M+Na)$^+$. $^1$H NMR (500 MHz, CDCl$_3$) δ 8.18 (d, J=8.6 Hz, 2H), 7.40 (d, J=8.6 Hz, 2H), 4.52 (d, J=8.4 Hz, 1H), 4.39-4.18 (m, 1H), 3.84 (s, 1H), 3.05-2.87 (m, 2H), 2.39-2.14 (m, 2H), 1.80 (s, 3H), 1.75 (s, 3H), 1.35 (s, 9H) ppm.

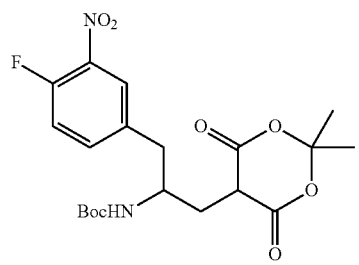 [SMILES: CC(C)(C)OC(=O)NC(Cc1ccc(F)c([N+](=O)[O-])c1)CC1C(=O)OC(C)(C)OC1=O]

tert-Butyl 1-(2,2-dimethyl-4,6-dioxo-1,3-dioxan-5-yl)-3-(4-fluoro-3-nitrophenyl)propan-2-ylcarbamate (4f)

Following the general procedure for Compound 4, compound 4f (35 g, 79% yield in 2 steps) was obtained as a yellow solid. ESI m/z: 463 (M+Na)$^+$.

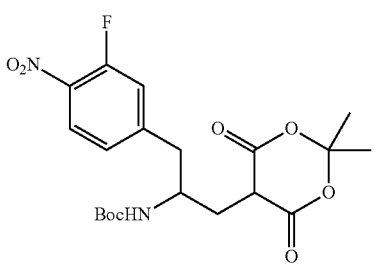 [SMILES: CC(C)(C)OC(=O)NC(Cc1ccc([N+](=O)[O-])c(F)c1)CC1C(=O)OC(C)(C)OC1=O]

tert-Butyl 1-(2,2-dimethyl-4,6-dioxo-1,3-dioxan-5-yl)-3-(3-fluoro-4-nitrophenyl)propan-2-ylcarbamate (4j)

Following the general procedure for Compound 4 using compound 3j, compound 4j (3.4 g, 77% yield in 2 steps) was obtained as a yellow solid. ESI m/z: 463.1 (M+Na)+.

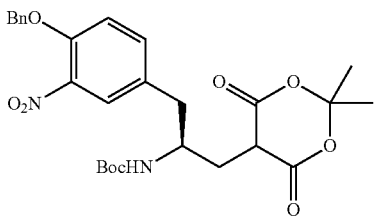 [SMILES: CC(C)(C)OC(=O)N[C@@H](Cc1ccc(OCc2ccccc2)c([N+](=O)[O-])c1)CC1C(=O)OC(C)(C)OC1=O]

tert-Butyl (S)-(1-(4-(benzyloxy)-3-nitrophenyl)-3-(2,2-dimethyl-4,6-dioxo-1,3-dioxan-5-yl)propan-2-yl)carbamate (4k)

Following the general procedure for Compound 4, compound 4k (2.0 g, 46% yield) was obtained as a white solid after purification by silica gel column chromatography (eluted by ethyl acetate/petroleum ether, v/v=1/1). ESI m/z: 552.1 (M+Na)+.

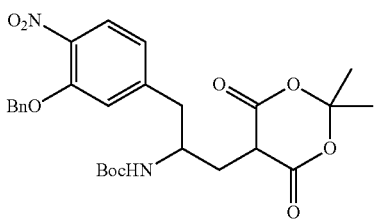 [SMILES: CC(C)(C)OC(=O)NC(Cc1ccc([N+](=O)[O-])c(OCc2ccccc2)c1)CC1C(=O)OC(C)(C)OC1=O]

tert-Butyl (1-(3-(benzyloxy)-4-nitrophenyl)-3-(2,2-dimethyl-4,6-dioxo-1,3-dioxan-5-yl)propan-2-yl)carbamate (4l)

Following the general procedure for Compound 4, compound 4l (2.0 g, 48% yield) was obtained as a white solid after purification by silica gel column chromatography (eluted by ethyl acetate/petroleum ether, v/v=1/1). ESI m/z: 552.1 (M+Na)+.

General Procedure for Compound 5

A solution of compound 4 in toluene (0.2-0.5 g/mL) was stirred at 90° C. for 3 hours, where conversion of compound 4 to compound 5 was monitored by LCMS. The volatiles were then removed in vacuo. The residue was purified by silica gel column chromatography (eluted by ethyl acetate/petroleum ether) to give compound 5 (82-91% yield) as an oil.

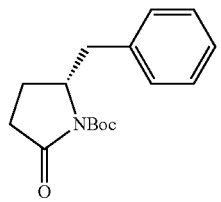

tert-Butyl (2R)-2-benzyl-5-oxopyrrolidine-1-carboxylate (5a)

Following the general procedure for Compound 5, compound 5a (2.3 g, 82% yield) was obtained as a colorless oil after purification by silica gel column chromatography (eluted by ethyl acetate/petroleum ether, v/v=1/9). ESI m/z: 220 (M−55)+. $^1$H NMR (500 MHz, CDCl$_3$) δ 7.35-7.29 (m, 2H), 7.28-7.24 (m, 1H), 7.21-7.17 (m, 2H), 4.40-4.34 (m, 1H), 3.18-3.10 (m, 1H), 2.77-2.70 (m, 1H), 2.35-2.29 (m, 2H), 2.01-1.91 (m, 1H), 1.85-1.77 (m, 1H), 1.59 (s, 9H) ppm.

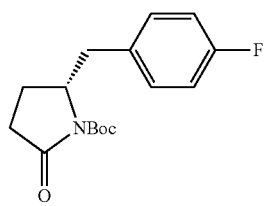 [SMILES: CC(C)(C)OC(=O)N1C(=O)CC[C@@H]1Cc1ccc(F)cc1]

tert-Butyl (2R)-2-[(4-fluorophenyl)methyl]-5-oxopyrrolidine-1-carboxylate (5b)

Following the general procedure for Compound 5, compound 5b (5.1 g, 91% yield) was obtained as a yellow oil after purification by silica gel column chromatography (eluted by ethyl acetate/petroleum ether, v/v=1/5). ESI m/z: 609 (2M+Na)+. $^1$H NMR (500 MHz, CDCl$_3$) δ 7.18-7.13 (m, 2H), 7.04-6.99 (m, 2H), 4.37-4.31 (m, 1H), 3.13-3.07 (m, 1H), 2.76-2.69 (m, 1H), 2.40-2.26 (m, 2H), 2.04-1.91 (m, 1H), 1.81-1.75 (m, 1H), 1.58 (s, 9H) ppm.

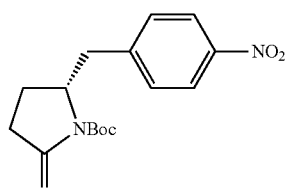

tert-Butyl (2R)-2-[(4-nitrophenyl)methyl]-5-oxopyrrolidine-1-carboxylate (5d)

Following the general procedure for Compound 5, compound 5d (7.9 g, 90% yield) was obtained as a yellow oil after purification by silica gel column chromatography (eluted by ethyl acetate/petroleum ether, v/v=1/9). ESI m/z: 663 (2M+Na)⁺. ¹H NMR (500 MHz, CDCl₃) δ 8.20 (d, J=8.6 Hz, 2H), 7.39 (d, J=8.6 Hz, 2H), 4.46-4.36 (m, 1H), 3.32-3.24 (m, 1H), 2.88-2.80 (m, 1H), 2.48-2.37 (m, 2H), 2.08-1.97 (m, 1H), 1.80-1.71 (m, 1H), 1.58 (s, 9H) ppm.

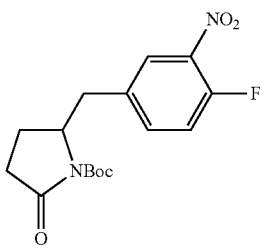 [SMILES: CC(C)(C)OC(=O)N1C(=O)CCC1Cc1ccc(F)c([N+](=O)[O-])c1]

tert-Butyl 2-(4-fluoro-3-nitrobenzyl)-5-oxopyrrolidine-1-carboxylate (5f)

Following the general procedure for Compound 5, compound 5f (15 g, 78% yield) was obtained as a yellow oil after purification by silica gel column chromatography (eluted by DCM). ESI m/z: 361 (M+Na)⁺.

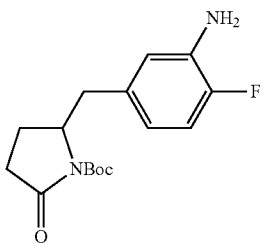

tert-Butyl 2-(3-amino-4-fluorobenzyl)-5-oxopyrrolidine-1-carboxylate (5g)

To a solution of compound 5f (15 g, 44 mmol) in ethyl acetate (100 mL) was added wet 10% Pd/C (1.5 g). The mixture was degassed and exchanged with hydrogen 3 times, and the resulting mixture was stirred at room temperature under a hydrogen balloon for 3 hours until the reaction was completed according to LCMS. The resulting mixture was filtered through Celite, and the filtrate was concentrated in vacuo to provide crude compound 5g (14 g, crude) as a yellow solid, which was used directly for the next step. ESI m/z: 209.1 (M−Boc+H)⁺.

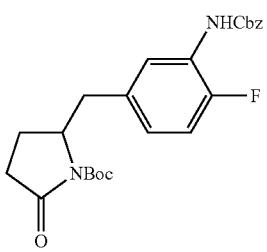 [SMILES: CC(C)(C)OC(=O)N1C(=O)CCC1Cc1ccc(F)c(NC(=O)OCc2ccccc2)c1]

tert-Butyl 2-(3-(benzyloxycarbonylamino)-4-fluorobenzyl)-5-oxopyrrolidine-1-carboxylate (5h1)

To a solution of compound 5g (0.74 g, 2.4 mmol) in THF (10 mL) were added sodium bicarbonate (0.30 g, 3.6 mmol) and CbzCl (0.38 mL, 2.64 mmol) at 0° C. The mixture was stirred at rt for 4 hours which was monitored by LCMS. The resulting mixture was concentrated and the residue was purified by silica gel column chromatography (0-35% ethyl acetate in petroleum ether) to afford the compound 5h1 (0.85 g, 80% yield) as pale yellow oil. ESI m/z: 343.1 (M−Boc+H)⁺.

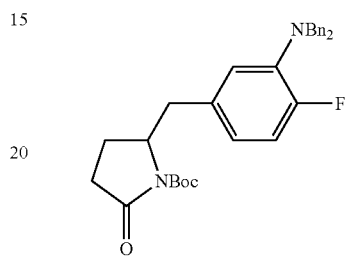

tert-Butyl 2-(3-(dibenzylamino)-4-fluorobenzyl)-5-oxopyrrolidine-1-carboxylate (5i)

To a solution of compound 5g (14 g, 44 mmol) in DMF (200 mL) were added potassium carbonate (18 g, 0.13 mol) and benzylbromide (13 mL, 0.11 mol) at room temperature. The resulting mixture was stirred at 80° C. overnight until no more 5i was formed according to LCMS. After cooling to room temperature, the resulting mixture was poured into water (500 mL) and extracted with DCM (200 mL×2). The combined organic solution was washed with water (100 mL×2) and brine (200 mL×1), dried over sodium sulfate, and concentrated in vacuo to afford compound 5i (24 g, crude) as yellow oil. ESI m/z: 489.2 (M+H)⁺.

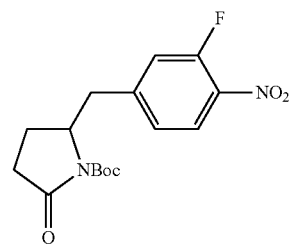 [SMILES: CC(C)(C)OC(=O)N1C(=O)CCC1Cc1ccc([N+](=O)[O-])c(F)c1]

tert-Butyl 2-(3-fluoro-4-nitrobenzyl)-5-oxopyrrolidine-1-carboxylate (5j1)

Following the general procedure for Compound 5 using compound 4j, compound 5j1 (1.7 g, 63% yield) was obtained as yellow oil after purification by silica gel column chromatography (eluted by DCM). ESI m/z: 361.1 (M+Na)⁺. ¹H NMR (500 MHz, DMSO$_{d6}$) δ 8.15 (t, J=8.2 Hz, 1H), 7.48 (dd, J=12.3, 1.4 Hz, 1H), 7.30 (dd, J=8.5, 1.2 Hz, 1H), 4.38-4.31 (m, 1H), 3.13 (dd, J=13.1, 4.4 Hz, 1H), 2.97 (dd, J=13.1, 8.8 Hz, 1H), 2.59-2.52 (m, 1H), 2.29-2.21 (m, 1H), 1.99 (m, 1H), 1.71-1.62 (m, 1H), 1.44 (s, 9H) ppm.

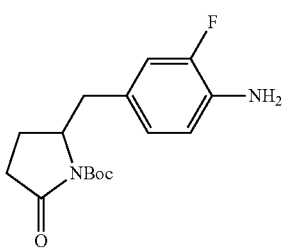 [SMILES: CC(C)(C)OC(=O)N1C(=O)CCC1Cc1ccc(N)c(F)c1]

tert-Butyl 2-(4-amino-3-fluorobenzyl)-5-oxopyrrolidine-1-carboxylate (5j2)

To a solution of compound 5j1 (1.5 g, 4.4 mmol) in ethyl acetate (30 mL) was added wet 10% Pd/C (0.30 g). The mixture was degassed and exchanged with hydrogen 3 times, and the resulting mixture was stirred at rt under a hydrogen balloon for 3 hours until the reaction was completed according to LCMS. The resulting mixture was filtered through Celite, and the filtrate was concentrated in vacuo to provide crude compound 5j2 (1.4 g, crude) as a yellow solid, which was used directly for the next step. ESI m/z: 209.1 (M−Boc+H)$^+$.

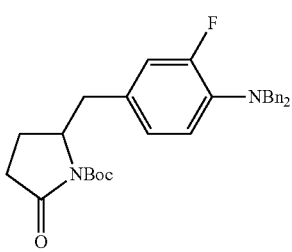

tert-Butyl 2-(4-(dibenzylamino)-3-fluorobenzyl)-5-oxopyrrolidine-1-carboxylate (5j)

To a solution of compound 5j2 (0.22 g, 0.71 mmol) in DMF (3 mL) were added potassium carbonate (0.35 g, 2.5 mmol) and benzylbromide (0.25 mL, 2.1 mmol) at room temperature. The resulting mixture was stirred at 80° C. overnight until no more 5j was present according to LCMS. After cooling to room temperature, the resulting mixture was poured into water (50 mL) and extracted with DCM (25 mL×2). The combined organic solution was washed with water (25 mL×2) and brine (50 mL×1), dried over sodium sulfate, and concentrated in vacuo to afford compound 5j (0.33 g, 95% crude yield) as yellow oil. ESI m/z: 489.3 (M+H)$^+$.

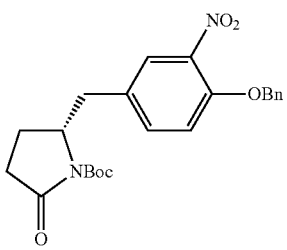 [SMILES: CC(C)(C)OC(=O)N1C(=O)CC[C@@H]1Cc1ccc(OCc2ccccc2)c([N+](=O)[O-])c1]

tert-Butyl (R)-2-(4-(benzyloxy)-3-nitrobenzyl)-5-oxopyrrolidine-1-carboxylate (5k)

Following the general procedure for Compound 5, compound 5k (0.5 g, 62% yield) was obtained as a white solid after purification by silica gel column chromatography (eluted by ethyl acetate/petroleum ether, v/v=1/1). ESI m/z: 327.1 (M−Boc+H)$^+$.

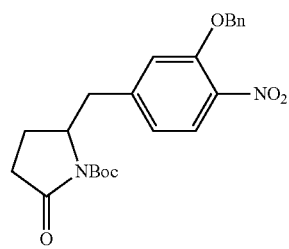 [SMILES: CC(C)(C)OC(=O)N1C(=O)CCC1Cc1ccc([N+](=O)[O-])c(OCc2ccccc2)c1]

tert-Butyl 2-(3-(benzyloxy)-4-nitrobenzyl)-5-oxopyrrolidine-1-carboxylate (5l)

Following the general procedure for Compound 5, compound 5l (0.6 g, 74% yield) was obtained as a white solid after purification by silica gel column chromatography (eluted by ethyl acetate/petroleum ether, v/v=1/1). ESI m/z: 327.1 (M−Boc+H)$^+$.

General Procedure for Compounds 7(a,b,d,h-j)

To a solution of compound 5 (1.0 equiv.) in THF (0.1 g/mL) was added lithium bis(trimethylsilyl)amide in hexane (1 M, 2.5 equiv.) at −78° C., and the mixture was stirred at −78° C. for 30 minutes before iodomethane (4 equiv.) was added in one portion at −78° C. The resulting mixture was stirred at −78° C. for 2 hours until compound 5 was totally consumed, as monitored by LCMS. The reaction mixture was allowed to warm up to rt and to the mixture was added aq. sodium hydroxide (2 M, 2-3 equiv.). The resulting mixture was stirred at rt for 2 hours, which was monitored by LCMS. After the reaction was completed, the reaction was cooled to 0° C. and acidified by aq. hydrochloride (1 M) to pH 3. The mixture was diluted with brine until the mixture separated into two layers. The aqueous layer was extracted with ethyl acetate (3 times) and the combined organic solution was dried over sodium sulfate, and concentrated in vacuo. The residue was purified by reversed phase flash chromatography (5-95% acetonitrile in water) to give compound 7 (15-46% yield) as a light yellow solid.

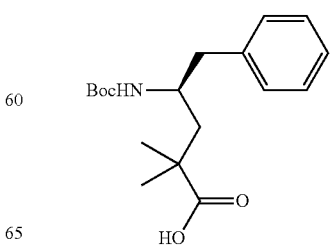

(4S)-4-{[(tert-Butoxy)carbonyl]amino}-2,2-dimethyl-5-phenylpentanoic acid (7a)

Following the general procedure for Compound 7, compound 7a (0.31 g, 46% yield) was obtained as a light yellow oil. ESI m/z: 665 (2M+Na)+.

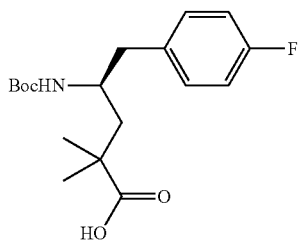 [SMILES: CC(C)(C)OC(=O)N[C@@H](Cc1ccc(F)cc1)CC(C)(C)C(=O)O]

(4S)-4-{[(tert-Butoxy)carbonyl]amino}-5-(4-fluorophenyl)-2,2-dimethylpentanoic acid (7b)

Following the general procedure for Compound 7, compound 7b (0.44 g, 15% yield) was obtained as a light yellow oil. ESI m/z: 701 (2M+Na)+.

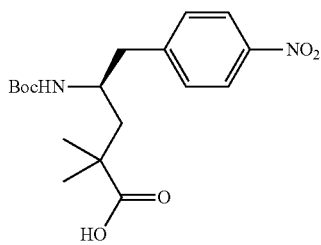 [SMILES: CC(C)(C)OC(=O)N[C@@H](Cc1ccc([N+](=O)[O-])cc1)CC(C)(C)C(=O)O]

(4S)-4-{[(tert-Butoxy)carbonyl]amino}-2,2-dimethyl-5-(4-nitrophenyl)pentanoic acid (7d)

Following the general procedure for Compound 7, compound 7d (1.2 g, 26% yield) was obtained as a light yellow oil. ESI m/z: 311 (M−55)+. 1H NMR (500 MHz, CDCl3) δ 8.18-8.13 (m, 2H), 7.38-7.31 (m, 2H), 6.98-6.91 (m, 1H), 4.00-3.88 (m, 1H), 2.87-2.68 (m, 2H), 2.26-2.14 (m, 1H), 1.46-1.39 (m, 1H), 1.35 (s, 1H), 1.25-1.13 (m, 15H) ppm.

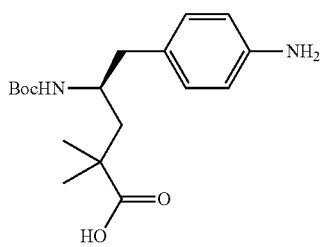 [SMILES: CC(C)(C)OC(=O)N[C@@H](Cc1ccc(N)cc1)CC(C)(C)C(=O)O]

(4S)-5-(4-Aminophenyl)-4-{[(tert-butoxy)carbonyl]amino}-2,2-dimethylpentanoic acid (7e)

To a solution of compound 7d (0.50 g, 1.4 mmol) in methanol (10 mL) and ethyl acetate (3 mL) was added Pd/C (10% Pd, 0.10 g) under a nitrogen atmosphere at rt. The mixture was stirred under a hydrogen atmosphere at rt for 2 hours, which was monitored by LCMS. The reaction mixture was filtered through celite and the celite was washed with methanol (3 times). The combined filtrate was concentrated in vacuo to give compound 7e (0.46 g, 99% yield) as a light yellow solid, which was used without purification in the next step. ESI m/z: 281 (M−tBu+H)+.

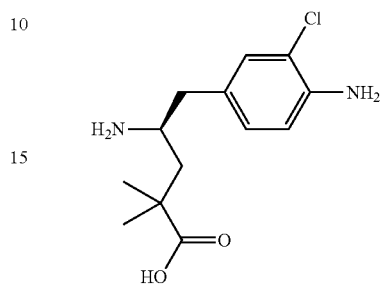

Figure 5A:
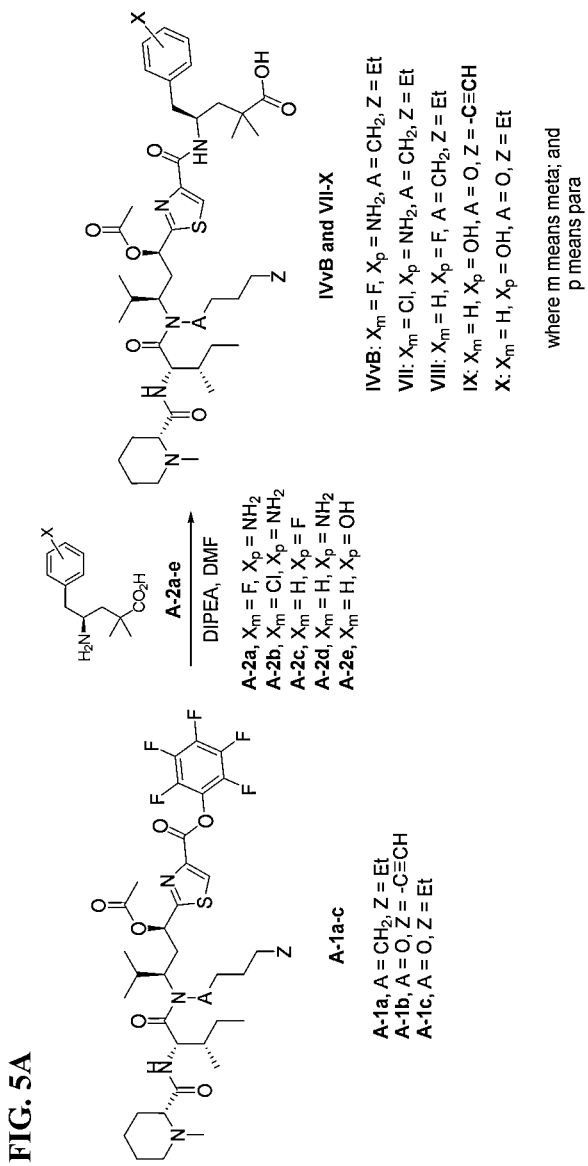

(4S)-4-Amino-5-(4-amino-3-chlorophenyl)-2,2-dimethylpentanoic acid, TFA salt (A-2b) (FIG. 5A)

To a solution of intermediate Boc-A-2d (or 7e) (0.55 g, 1.6 mmol,) in DMF (10 mL) was added N-chlorosuccinimide (NCS) (0.24 g, 1.8 mmol), and the mixture was stirred at RT overnight, which was monitored by LCMS. The resulting mixture was diluted with ethyl acetate (150 mL), washed with water and brine, dried over sodium sulfate and concentrated. The residue was purified by silica gel column chromatography (50% ethyl acetate in petroleum ether) to give Boc-A-2b (0.48 g, ESI m/z 315.0 (M−tBu+H)+) as a light yellow solid, which was dissolved in TFA (2 mL). The mixture was stirred at RT for 15 minutes until Boc was totally removed according to LCMS. The volatiles were removed in vacuo to give crude compound A-2b (0.64 g, TFA salt, 80% yield from Boc-A-2d) as a light yellow solid, which was used directly without further purification. ESI m/z 271.1 (M+H)+.

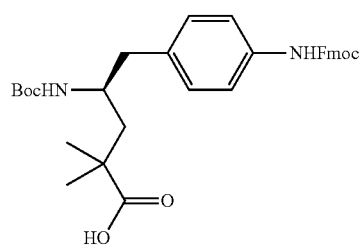

(4S)-4-{[(tert-Butoxy)carbonyl]amino}-5-(4-{[(9H-fluoren-9-ylmethoxy)carbonyl]amino}phenyl)-2,2-dimethylpentanoic acid (7c)

To a mixture of compound 7e (0.46 g, 1.4 mmol) in DCM (10 mL) was added pyridine (0.22 g, 2.7 mmol) at rt and the mixture was stirred for 3 minutes before 9-fluorenylmethyl chloroformate (Fmoc-Cl, 0.53 g, 2.1 mmol) was added. The mixture was then stirred at rt for 2 hours, and monitored by LCMS. The mixture was purified by Prep-HPLC (trifluoroacetic acid system) to give compound 7c (0.20 g, 26% yield) as a white solid. ESI m/z: 581 (M+Na)+. 1H NMR (500 MHz, methanol-d4) δ 7.83 (d, J=7.5 Hz, 2H), 7.72 (d, J=7.2

Hz, 2H), 7.50-7.28 (m, 6H), 7.20-7.05 (m, 2H), 4.55-4.38 (m, 2H), 4.30 (t, J=6.7 Hz, 1H), 3.90-3.80 (m, 1H), 2.75-2.50 (m, 2H), 1.90-1.80 (m, 1H), 1.70-1.60 (m, 1H), 1.38-1.10 (m, 15H) ppm.

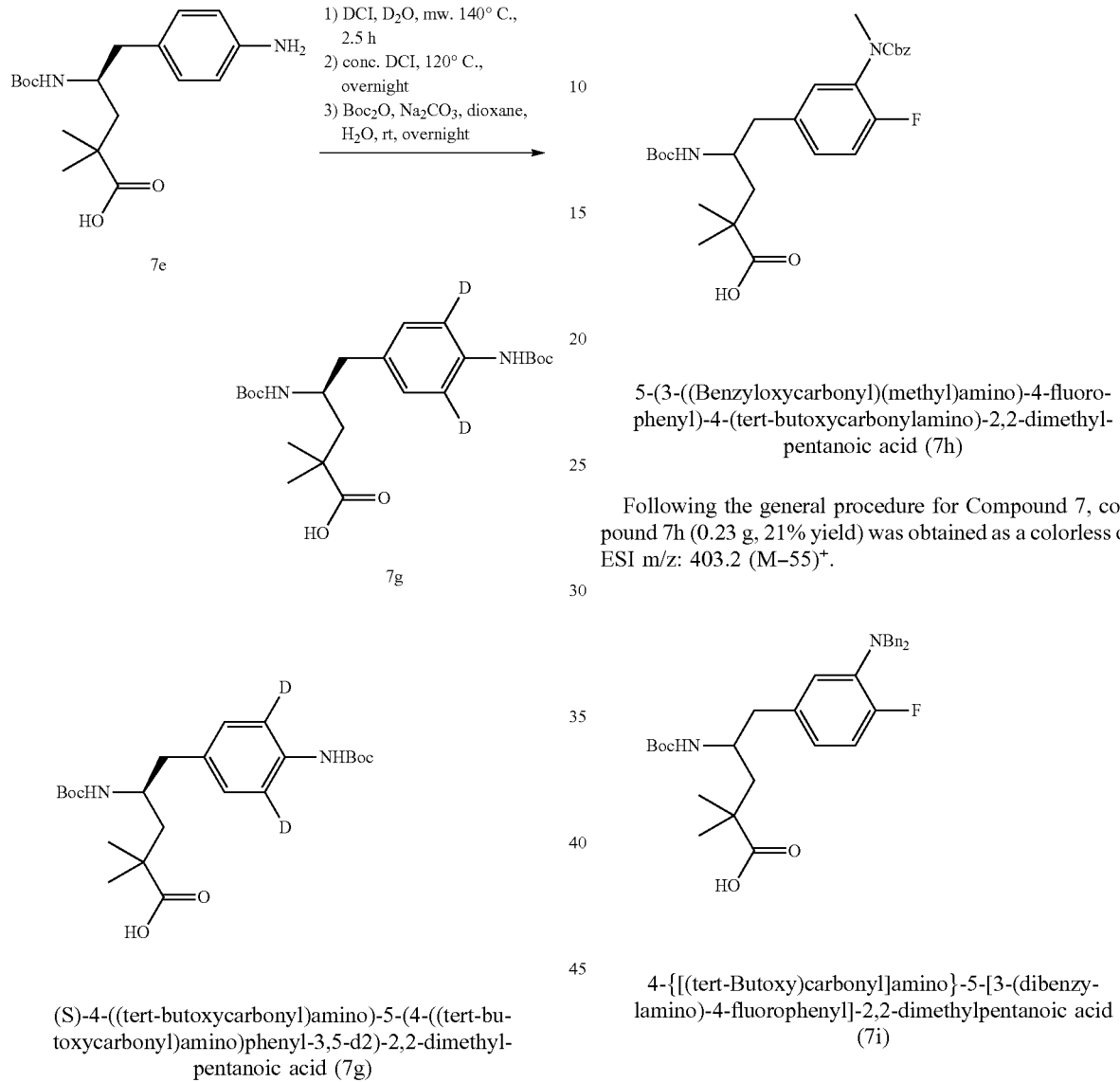

(S)-4-((tert-butoxycarbonyl)amino)-5-(4-((tert-butoxycarbonyl)amino)phenyl-3,5-d2)-2,2-dimethylpentanoic acid (7g)

To a mixture of compound 7e (0.10 g, 0.30 mmol) in D$_2$O (1 mL) was added conc. DCl (0.05 mL), where compound 7e dissolved. The solution was sealed and irradiated at 140° C. with microwave for 2.5 hours. After cooling to rt., to the mixture was added conc. DCl (2 mL) by syringe. The sealed tube was then heated to 120° C. by oil bath. The reaction mixture was stirred at this temperature overnight, which was monitored by LCMS. After cooling to rt., the mixture was neutralized with sat. sodium bicarbonate to pH 8. The aqueous solution was concentrated in vacuo and the residue was separated with ethyl acetate and water. The aqueous layer was lyophilized and the residue (50 mg with inorganic salts) was dissolved into a mixture of dioxane-water (3 mL, v/v=2/1). To the solution were added sodium carbonate (66 mg, 0.63 mmol) and Boc$_2$O (50 mg, 0.23 mmol) at rt. The mixture was stirred at rt overnight which was monitored by LCMS. The volatiles were removed in vacuo and the residue was purified by reversed phase flash chromatography (5-95% acetonitrile in water (with 10 mM ammonium bicarbonate)) to give compound 7g (15 mg, 11% yield) as a white solid. ESI m/z: 461 (M+Na)$^+$.

5-(3-((Benzyloxycarbonyl)(methyl)amino)-4-fluorophenyl)-4-(tert-butoxycarbonylamino)-2,2-dimethylpentanoic acid (7h)

Following the general procedure for Compound 7, compound 7h (0.23 g, 21% yield) was obtained as a colorless oil. ESI m/z: 403.2 (M−55)$^+$.

4-{[(tert-Butoxy)carbonyl]amino}-5-[3-(dibenzylamino)-4-fluorophenyl]-2,2-dimethylpentanoic acid (7i)

Following the general procedure for Compound 7 using compound 5i, compound 7i (2.1 g, 24% yield) was obtained as a yellow oil. ESI m/z: 535.2 (M+H)$^+$.

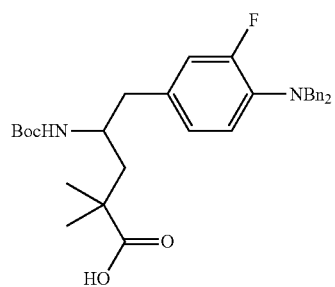

4-{[(tert-Butoxy)carbonyl]amino}-5-[4-(dibenzylamino)-3-fluorophenyl]-2,2-dimethylpentanoic acid (7j)

Following the general procedure for Compound 7 using compound 5j, compound 7j (60 mg, 17% yield) was obtained as a yellow oil. ESI m/z: 535.2 (M+H)$^+$.

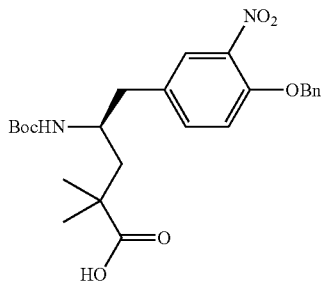 [SMILES: CC(C)(C)OC(=O)N[C@@H](Cc1ccc(OCc2ccccc2)c([N+](=O)[O-])c1)CC(C)(C)C(=O)O]

(S)-5-(4-(Benzyloxy)-3-nitrophenyl)-4-((tert-butoxycarbonyl)amino)-2,2-dimethylpentanoic acid (7k)

Following the general procedure for Compound 7, compound 7k (0.1 g, 24% yield) was obtained as a white solid. ESI m/z: 373.1 (M−Boc+H)$^+$.

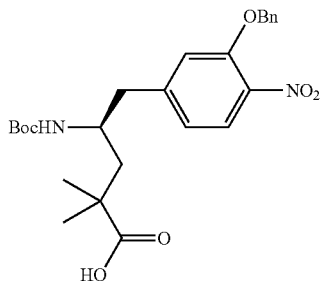 [SMILES: CC(C)(C)OC(=O)N[C@@H](Cc1ccc([N+](=O)[O-])c(OCc2ccccc2)c1)CC(C)(C)C(=O)O]

5-(3-(Benzyloxy)-4-nitrophenyl)-4-((tert-butoxycarbonyl)amino)-2,2-dimethylpentanoic acid (7l)

Following the general procedure for Compound 7, compound 7k (0.2 g, 36% yield) was obtained as a white solid. ESI m/z: 373.1 (M−Boc+H)$^+$.

General Procedure for Intermediate I

To a solution of compound 7 in DCM (50 mg/mL) was added trifluoroacetic acid ($V_{TFA}/V_{DCM}$=1/3) by syringe at rt. The mixture was stirred at rt for 2 hours until Boc was totally removed according to LCMS. The volatiles were removed in vacuo and the residue was purified by Prep-HPLC (trifluoroacetic acid system) to give intermediates Ia-c (80-94% yield) as a white solid.

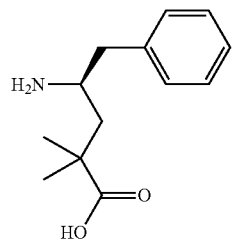 [SMILES: CC(C)(C[C@@H](N)Cc1ccccc1)C(=O)O]

(S)-4-Amino-2,2-dimethyl-5-phenylpentanoic acid (Ia)

Following the general procedure for Intermediate I, Ia (0.20 g, 94% yield) was obtained as a white solid. ESI m/z: 222 (M+H)$^+$. $^1$H NMR (500 MHz, DMSO$_{d6}$) δ 12.64 (s, 1H), 7.77 (s, 2H), 7.38-7.33 (m, 2H), 7.30-7.23 (m, 3H), 3.45-3.37 (m, 1H), 2.90-2.74 (m, 2H), 1.83-1.68 (m, 2H), 1.07 (s, 3H), 1.03 (s, 3H) ppm.

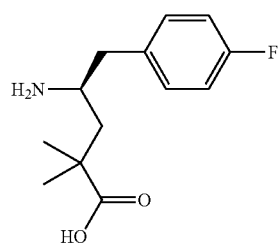 [SMILES: CC(C)(C[C@@H](N)Cc1ccc(F)cc1)C(=O)O]

(4S)-4-Amino-5-(4-fluorophenyl)-2,2-dimethylpentanoic acid (Ib)

Following the general procedure for Intermediate I, Ib (85 mg, 80% yield) was obtained as a white solid. ESI m/z: 240 (M+H)$^+$. $^1$H NMR (400 MHz, methanol-$d_4$) δ 7.36-7.25 (m, 2H), 7.12 (t, J=8.7 Hz, 2H), 3.56-3.44 (m, 1H), 3.03-2.81 (m, 2H), 1.97-1.89 (m, 1H), 1.78-1.70 (m, 1H), 1.23 (s, 3H), 1.07 (s, 3H) ppm.

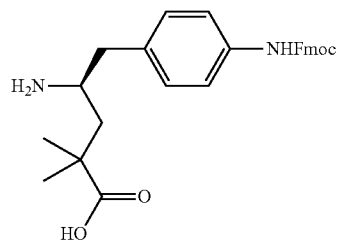

(4S)-4-Amino-5-(4-{[(9H-fluoren-9-ylmethoxy)carbonyl]amino}phenyl)-2,2-dimethylpentanoic acid (Ic)

Following the general procedure for Intermediate I, Ic (60 mg, 92% yield) was obtained as a white solid. ESI m/z: 459 (M+H)$^+$. $^1$H NMR (500 MHz, methanol-$d_4$) δ 7.84 (d, J=7.5 Hz, 2H), 7.72 (d, J=7.5 Hz, 2H), 7.52-7.40 (m, 4H), 7.35 (t, J=7.4 Hz, 2H), 7.20 (d, J=7.8 Hz, 2H), 4.52 (d, J=5.6 Hz, 2H), 4.30 (t, J=6.6 Hz, 1H), 3.51-3.44 (m, 1H), 2.94-2.84 (m, 2H), 1.96-1.87 (m, 1H), 1.78-1.72 (m, 1H), 1.23 (s, 3H), 1.09 (s, 3H) ppm.

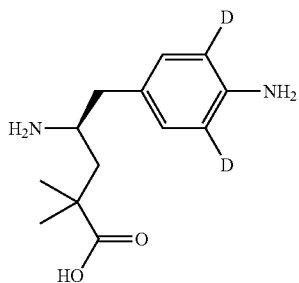 [SMILES: [2H]c1cc(C[C@H](N)CC(C)(C)C(=O)O)cc([2H])c1N]

(S)-4-Amino-5-(4-aminophenyl-3,5-d2)-2,2-dimethylpentanoic acid (Ig)

Following the general procedure for Intermediate I, Intermediate Ig (10 mg, 80% yield) was obtained as a brown oil. ESI m/z: 239 (M+H)⁺.

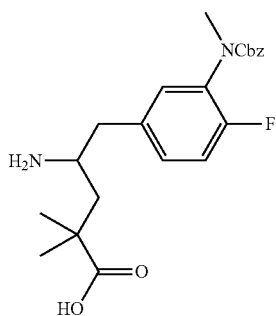 [SMILES: CN(C(=O)OCc1ccccc1)c1cc(CC(N)CC(C)(C)C(=O)O)ccc1F]

4-Amino-5-(3-(((benzyloxy)carbonyl)(methyl) amino)-4-fluorophenyl)-2,2-dimethylpentanoic acid (Ih)

Following the general procedure for Intermediate I, Intermediate Ih (0.18 g, 97% yield) was obtained as a brown oil. ESI m/z: 403 (M+H)⁺.

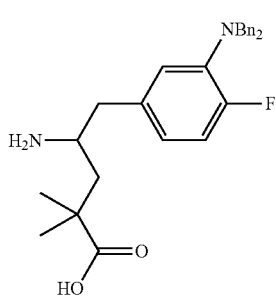

4-Amino-5-[3-(dibenzylamino)-4-fluorophenyl]-2,2-dimethylpentanoic acid (Ii)

Following the general procedure for Intermediate I, Intermediate Ii (50 mg, 99% yield) was obtained as brown oil. ESI m/z: 435 (M+H)⁺.

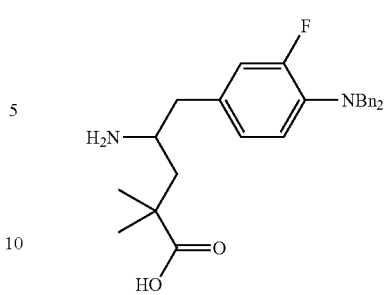

4-Amino-5-[4-(dibenzylamino)-3-fluorophenyl]-2,2-dimethylpentanoic acid (Ij)

Following the general procedure for Intermediate I, Intermediate Ij (40 mg, 99% yield) was obtained as a brown oil. ESI m/z: 435 (M+H)⁺.

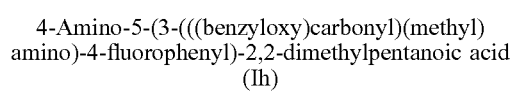

(S)-4-Amino-5-(4-(benzyloxy)-3-nitrophenyl)-2,2-dimethylpentanoic acid (Ik)

Following the general procedure for Intermediate I, Intermediate Ik (78 mg, 99% yield) was obtained as a white solid. ESI m/z: 373.1 (M+H)⁺.

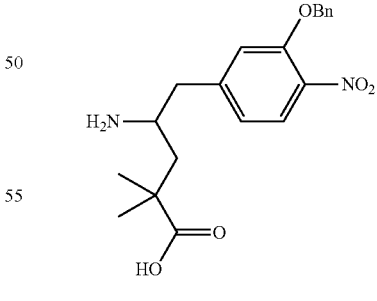

4-Amino-5-(3-(benzyloxy)-4-nitrophenyl)-2,2-dimethylpentanoic acid (Il)

Following the general procedure for Intermediate I, Intermediate Il (0.1 g, 99% yield) was obtained as a white solid. ESI m/z: 373.1 (M+H)⁺.

Synthesis of Intermediates II and III in FIG. 4

Synthesis of Intermediates IIa-c

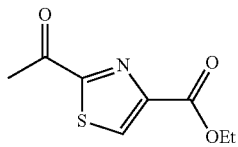

Ethyl 2-acetylthiazole-4-carboxylate (11) (FIG. 2)

To a solution of cysteine hydrochloride ethyl ester 8 (15 g, 81 mmol) in a mixture of ethanol and water (1.5 L, v/v=1) were added sodium bicarbonate (6.8 g, 81 mmol) and aq. pyruvic aldehyde 9 (35%, 18 mL, 0.11 mol) successively. The reaction mixture was stirred at RT for 18 hours and was then concentrated to half of its original volume with a <25° C. water bath. To the residual aqueous solution was added solid sodium chloride until saturation and the aqueous solution was extracted with DCM (twice). The combined organic solution was dried over sodium sulfate and concentrated in vacuo to give crude compound 10, which was used directly without any further purification.

To a solution of compound 10 (16 g, 81 mmol) in DCM (0.50 L) was added activated manganese dioxide (0.14 kg, 1.6 mol). The reaction mixture was stirred at 65° C. overnight, which was monitored by LCMS. After the reaction was cooled to rt, the suspension was filtered through a celite pad and the celite/residue was washed with ethyl acetate (2×200 mL). The combined filtrate was concentrated in vacuo. The crude product was purified by flash chromatography (eluted by ethyl acetate/hexane, v/v=1:3) to give compound 11 (5.9 g, 37% yield in two steps) as a yellow solid. ESI m/z: 199.9 (M+H)$^+$. $^1$H NMR (400 MHz, CDCl$_3$) δ 8.44 (s, 1H), 4.49 (q, J=7.1 Hz, 2H), 2.79 (s, 3H), 1.43 (t, J=7.1 Hz, 3H) ppm.

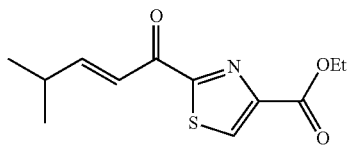 [SMILES: CCOC(=O)c1csc(C(=O)/C=C/C(C)C)n1]

Ethyl 2-(4-methylpent-2-enoyl)thiazole-4-carboxylate (13) (FIG. 2)

A solution of 11 (2.9 g, 15 mmol) in dry THF (50 mL) was cooled to 0° C. under nitrogen atmosphere. To this solution was added a solution of titanium tetrachloride in toluene (1 M, 32 mL, 32 mmol) via syringe. The resulting mixture was stirred at 0° C. for 30 min and was then cooled to −78° C. At −78° C., TEA (4.5 mL, 32 mmol) was added to the mixture. The reaction mixture was stirred at −78° C. for 10 min and then neat isobutyraldehyde (1.6 mL, 17 mmol) was added dropwise. The reaction was stirred at −78° C. for one hour until the reaction was completed according to LCMS. After the reaction was warmed to rt, the reaction was quenched with sat. aq. ammonium chloride (50 mL) and was extracted with ethyl acetate. The combined organic solution was dried over anhydrous sodium sulfate, filtered, and concentrated in vacuo. The residue was purified by flash chromatography (eluted by 10% ethyl acetate in hexane) to give compound 13 (1.5 g, 41% yield) as a colorless oil. ESI m/z: 253.9 (M+H)$^+$. $^1$H NMR (400 MHz, CDCl$_3$) δ 8.44 (s, 1H), 7.34-7.34 (m, 2H), 4.49 (q, J=7.0 Hz, 2H), 2.64 (m, 1H), 1.45 (t, J=7.0 Hz, 3H), 1.18 (d, J=7.0 Hz, 6H) ppm.

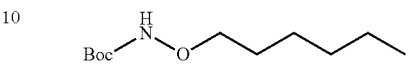

tert-Butyl N-(hexyloxy)carbamate (15a) (FIG. 2)

To a solution of tert-Butyl hydroxycarbamate (2.1 g, 16 mmol) in acetonitrile (50 mL) were added 1-bromohexane (2.7 g, 18 mmol) and DBU (2.5 g, 17 mmol) in DCM or MeCN, successively. The reaction was stirred at rt for 12 hours, and monitored by TLC and LCMS. The reaction mixture was quenched with aq. HCl (0.1 N) and was extracted with ethyl acetate. The combined organic layers were dried over sodium sulfate and concentrated in vacuo. The residue was purified by flash chromatography (eluted by 0-100% ethyl acetate in petroleum ether) to give compound 15a (1.7 g, 50% yield) as a colorless oil. $^1$H NMR (400 MHz, CDCl$_3$) δ 7.17 (br s, 1H), 3.84 (t, J=6.7 Hz, 2H), 1.65-1.58 (m, 2H), 1.49 (s, 9H), 1.40-1.26 (m, 6H), 0.89 (t, J=6.8 Hz, 3H) ppm.

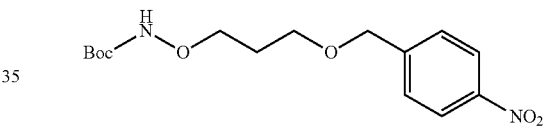

tert-Butyl 3-(4-nitrobenzyloxy)propoxycarbamate (15b) (FIG. 2)

A mixture of 1-(bromomethyl)-4-nitrobenzene (0.10 kg, 0.46 mol), 1,3-propanediol (0.39 L, 5.1 mol), and potassium hydroxide (27 g, 0.49 mol) was stirred at 80° C. overnight. After the reaction was cooled, the mixture was poured into water (500 mL) and filtered. The filtrate was extracted with DCM (2×400 mL). The combined organic layers were washed with water and dried over sodium sulfate and concentrated in vacuo to give 3-[(4-nitrophenyl)methoxy]propan-1-ol (95 g, 97%) as a brown oil [ESI m/z: 212 (M+H)$^+$. $^1$H NMR (500 MHz, CDCl$_3$) δ 8.23 (d, J=8 Hz, 2H), 7.52 (d, J=8 Hz, 2H), 4.65 (s, 2H), 3.83 (t, J=6 Hz, 2H), 3.73 (t, J=6 Hz, 2H), 2.04 (br s, 1H), 1.96-1.91 (m, 2H) ppm], where the purity was confirmed by LCMS and the material was used in the next step without further purification. The crude 3-[(4-nitrophenyl)methoxy]propan-1-ol (89 g, 0.42 mol) was dissolved in DCM (0.90 L) and to the solution was added TEA (85 g, 0.84 mol). The solution was cooled to 0° C. before methanesulfonyl chloride (72 g, 0.63 mol) was added dropwise. The reaction mixture was stirred at 0° C. for 30 minutes, monitored by LCMS, and was then washed with sat. aq. ammonium chloride (3 times). The organic layer was dried over sodium sulfate and filtered. To the filtrate were added tert-butyl hydroxycarbamate (90 g, 0.68 mol) and DBU (90 g, 0.59 mol) in DCM or MeCN, successively. The resulting mixture was stirred at rt overnight, and then tert-butyl hydroxycarbamate (30 g, 0.23 mol) and DBU (50 g, 0.33 mol) in DCM or MeCN were added again. The mixture was stirred at rt for another 2 days. LCMS showed most of the starting material was consumed. The reaction mixture was washed with sat. aq. ammonium chloride (3 times), dried over sodium sulfate and concentrated in vacuo. The residue was purified by flash chromatography (eluted by 0-15% ethyl acetate in petroleum ether) to afford compound 15b (90 g, 65% yield) as a yellow oil. ESI m/z: 349 (M+Na)$^+$. $^1$H NMR (500 MHz, CDCl$_3$) δ 8.23 (d, J=8.7 Hz, 2H), 7.53 (d, J=8.6 Hz, 2H), 7.18 (s, 1H), 4.64 (s, 2H), 4.01 (t, J=6.2 Hz, 2H), 3.68 (t, J=6.2 Hz, 2H), 2.00 (q, J=6.2 Hz, 2H), 1.50 (s, 9H) ppm.

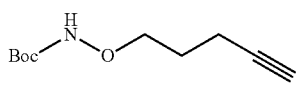

tert-Butyl N-(pent-4-yn-1-yloxy)carbamate (15c) (FIG. 2)

To a solution of tert-Butyl hydroxycarbamate (20 g, 15 mmol) in DMSO (0.50 L) were added potassium tert-butoxide (13 g, 12 mmol) and 5-chloro-1-pentyne (10 g, 10 mmol) successively. The reaction mixture was stirred at rt under nitrogen for 16 hours, which was monitored by LCMS. The mixture was then quenched with sat. aq. ammonium chloride. The aqueous solution was extracted with ethyl acetate (twice). The combined organic solution was washed with water (3 times), dried over sodium sulfate and concentrated. The crude product was purified by silica gel column chromatography (eluted by 5-20% ethyl acetate in petroleum ether) to give compound 15c (7.2 g, 36% yield) as a colorless oil. $^1$H NMR (400 MHz, CDCl$_3$) δ 7.18 (s, 1H), 3.95 (t, J=6.2 Hz, 2H), 2.33 (d, J=2.6 Hz, 2H), 1.96 (s, 1H), 1.89-1.81 (m, 2H), 1.49 (s, 9H) ppm.

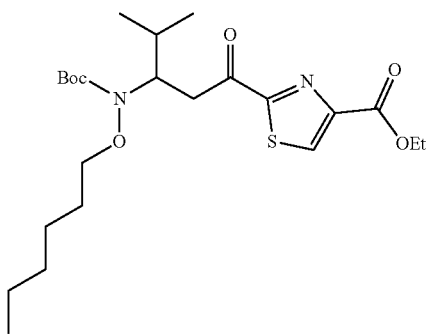 [SMILES: CCCCCCON(C(=O)OC(C)(C)C)C(CC(=O)c1nc(C(=O)OCC)cs1)C(C)C]

Ethyl 2-(3-{[(tert-butoxy)carbonyl](hexyloxy)amino}-4-methylpentanoyl)-1,3-thiazole-4-carboxylate (16a) (FIG. 2)

To a solution of compound 15a (2.6 g, 12 mmol) in THF (45 mL) was added sodium hydride (60% in mineral oil, 0.60 g, 12 mmol) at 0° C. in several portions under nitrogen. The mixture was stirred at rt for 20 minutes before a solution of compound 13 (1.5 g, 4.0 mmol) in THF (15 mL) was added dropwise. The resulting mixture was stirred at rt for an hour until 13 was consumed according to TLC (10% ethyl acetate in hexane). The reaction mixture was diluted with ethyl acetate and brine. The aqueous layer was extracted with ethyl acetate and the combined organic solution was dried over sodium sulfate and concentrated in vacuo. The residue was purified by silica gel column chromatography (eluted by 10% ethyl acetate in hexane) to give compound 16a (0.25 g, 60% yield) as a yellow oil. $^1$H NMR (400 MHz, CDCl$_3$) δ 8.42 (s, 1H), 4.45 (q, J=7.2 Hz, 2H), 4.38-4.30 (m, 1H), 3.87-3.76 (m, 2H), 3.61-3.53 (m, 1H), 3.43-3.37 (m, 1H), 2.09-1.99 (m, 1H), 1.56-1.43 (m, 2H), 1.46 (s, 9H), 1.43 (t, J=7.2 Hz, 3H), 1.33-1.21 (m, 6H), 1.02 (t, J=6.7 Hz, 6H), 0.86 (t, J=7.1 Hz, 3H) ppm.

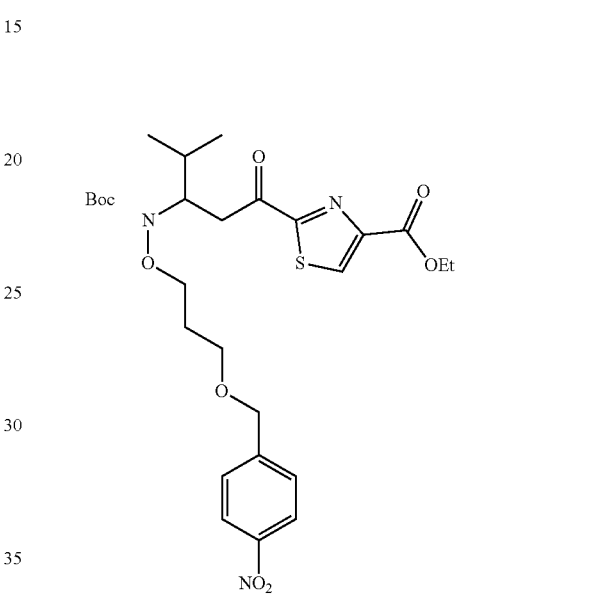

Ethyl 2-{3-[10,10-dimethyl-1-(4-nitrophenyl)-8-oxo-2,6,9-trioxa-7-azaundecan-7-yl]-4-methylpentanoyl}-1,3-thiazole-4-carboxylate (16b) (FIG. 2)

A mixture of compound 15b (5.2 g, 16 mmol) and compound 13 (2.7 g, 11 mmol) in toluene (50 mL) was cooled to 5° C. with an ice-water bath, and to the solution were added tetrabutylammonium bromide (0.34 g, 1.1 mmol) and aq. potassium hydroxide (50%, 1.4 g, 13 mmol) successively. The mixture was stirred at rt for 16 h. The mixture was poured into sat. aq. ammonium chloride (200 mL) and the suspension was extracted with ethyl acetate (3 times). The combined organic layers were washed with brine, dried over sodium sulfate, and concentrated in vacuo. The residue was purified by flash chromatography (eluted by 0-30% ethyl acetate in petroleum ether) to give crude 16b, which was purified again by reversed phase flash chromatography (ODS column, 50-100% acetonitrile in water (with 10 mM ammonium bicarbonate)) to give compound 16b (3.2 g, 52% yield) as a yellow oil. ESI m/z: 602 (M+Na)$^+$. $^1$H NMR (500 MHz, CDCl$_3$) δ 8.42 (s, 1H), 8.21 (d, J=8.6 Hz, 2H), 7.53 (d, J=8.4 Hz, 2H), 4.63 (s, 2H), 4.44 (q, J=6.8 Hz, 2H), 4.38-4.33 (m, 1H), 4.04-3.96 (m, 2H), 3.64-3.55 (m, 4H), 3.50-3.30 (m, 1H), 2.05-1.90 (m, 2H), 1.47-1.41 (m, 12H), 1.01 (d, J=6.7 Hz, 6H) ppm.

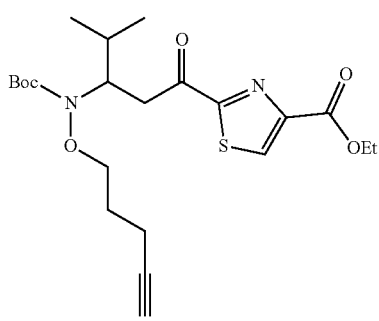 [SMILES: C#CCCCONC(CC(=O)c1nc(C(=O)OCC)cs1)C(C)C ; "Boc"]

Ethyl 2-(3-{[(tert-butoxy)carbonyl](pent-4-yn-1-yloxy)amino}-4-methylpentanoyl)-1,3-thiazole-4-carboxylate (16c) (FIG. 2)

Following the procedure for making 16b, 16c (38 g, 84% yield) was obtained as an oil. ESI m/z: 475 (M+Na)⁺. ¹H NMR (400 MHz, CDCl₃) δ 8.42 (s, 1H), 4.44 (q, J=6.9 Hz, 2H), 4.36 (td, J=9.5, 3.8 Hz, 1H), 3.99-3.87 (m, 3H), 3.65-3.67 (m, 1H), 3.45-3.30 (m, 1H), 2.43-2.15 (m, 3H), 1.83-1.70 (m, 2H), 1.46 (s, 9H), 1.43 (t, J=7.1 Hz, 3H), 1.01 (d, J=6.5 Hz, 6H) ppm.

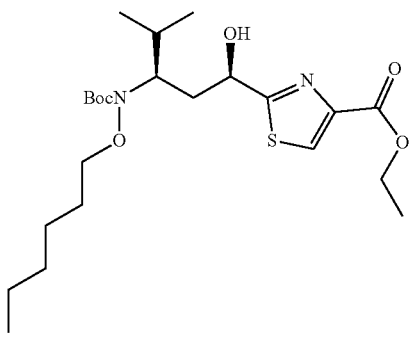 [SMILES: CCCCCCON(C(=O)OC(C)(C)C)[C@H](C[C@@H](O)c1nc(C(=O)OCC)cs1)C(C)C]

Figure 3:
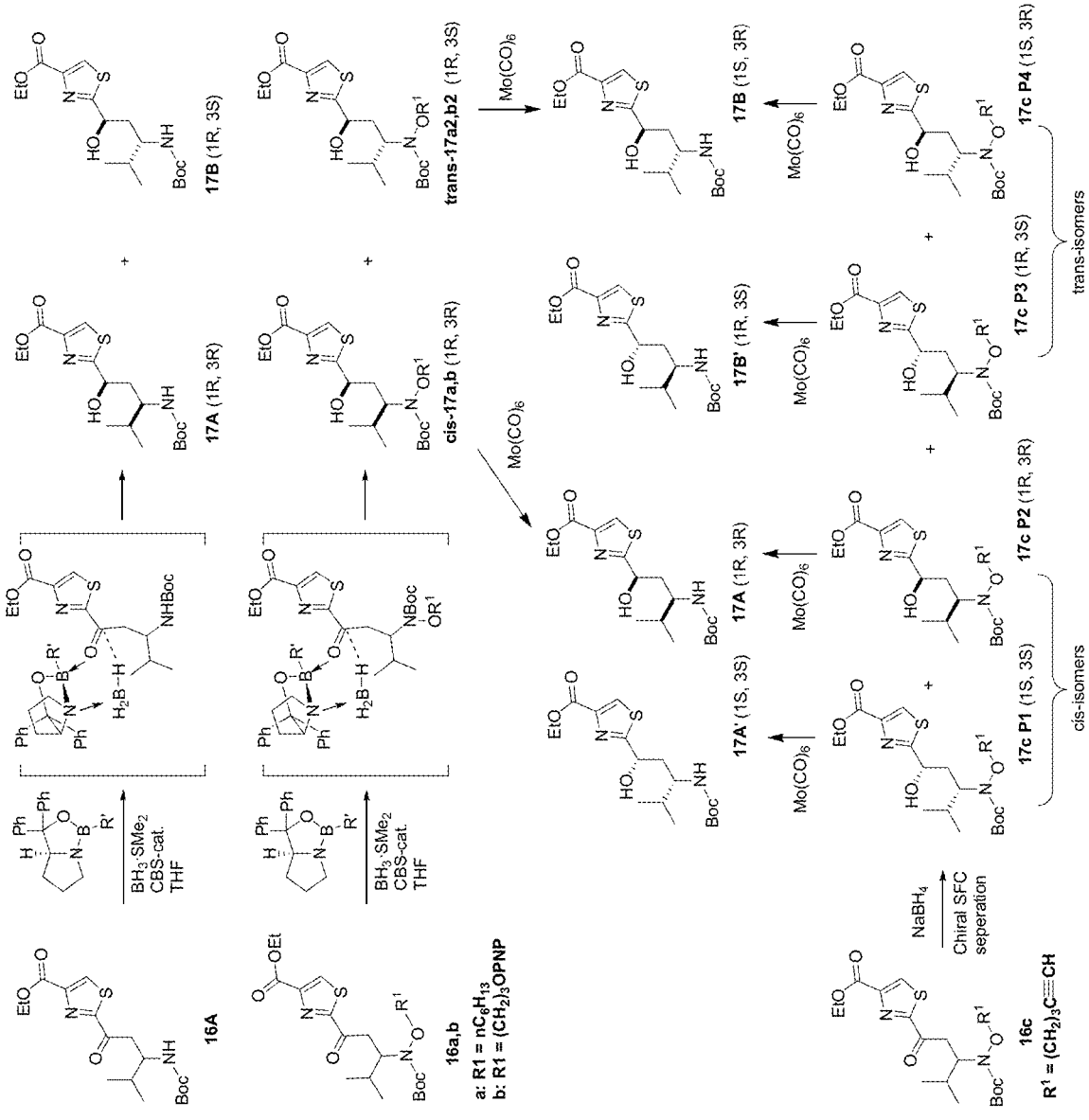

Ethyl 2-((1R,3R)-3-(tert-butoxycarbonyl(hexyloxy)amino)-1-hydroxy-4-methylpentyl) thiazole-4-carboxylate (17a); and ethyl 2-((1R,3S)-3-(tert-butoxycarbonyl(hexyloxy)amino)-1-hydroxy-4-methylpentyl) thiazole-4-carboxylate (17a2) (FIG. 3)

A commercial solution of (S)-2-methyl-CBS-oxazaborolidine in toluene (1 M, 64 μL, 64 μmol) was diluted with dry THF (3 mL) and was cooled to 0° C. To the solution was added a solution of BH₃·Me₂S in THF (2 M, 0.38 mL, 0.38 mmol) by syringe at 0° C. The solution was stirred for 10 min at 0° C. before a solution of 16a (0.15 g, 0.32 mmol) in dry THF (2 mL) was added dropwise. The reaction was warmed to rt and stirred overnight. The reaction was quenched with methanol (1 mL) and the volatiles were removed in vacuo. The residue was purified by flash chromatography (eluted by 20% ethyl acetate in hexane) to give 17a (70 mg, $R_f$=0.3, 20% ethyl acetate in hexane) and diastereoisomer 17a2 (61 mg, $R_f$=0.25, 20% ethyl acetate in hexane) (86% overall yield).

17a: $[a]_D^{23}$=+7.296 (c=1.82, CHCl₃, after chiral separation). ESI m/z: 473 (M+H)⁺. ¹H NMR (500 MHz, CDCl₃) δ 8.14 (s, 1H), 4.99 (d, J=10.2 Hz, 1H), 4.42 (q, J=7.1 Hz, 2H), 4.00 (dd, J=14.2, 6.8 Hz, 1H), 3.92 (dd, J=13.7, 7.0 Hz, 2H), 2.41 (m, 1H), 2.00 (m, 1H), 1.92 (t, J=11.2 Hz, 1H), 1.62 (m, 2H), 1.53 (s, 9H), 1.41 (m, 5H), 1.32 (m, 5H), 1.03 (d, J=6.6 Hz, 3H), 0.97 (d, J=6.7 Hz, 3H), 0.91 (t, J=6.8 Hz, 3H) ppm.

17a2: $[a]_D^{23}$=+28.81 (c=1.24, CHCl₃). ESI m/z: 473 (M+H)⁺. ¹H NMR (500 MHz, CDCl₃) δ 8.12 (s, 1H), 5.12 (d, J=6.6 Hz, 1H), 4.42 (q, J=7.1 Hz, 2H), 4.09 (s, 1H), 3.99 (dd, J=14.3, 6.9 Hz, 1H), 3.88-3.78 (m, 2H), 2.42 (dt, J=14.8, 3.3 Hz, 1H), 2.12-2.06 (m, 1H), 1.91 (tt, J=13.3, 6.6 Hz, 1H), 1.63-1.57 (m, 2H), 1.49 (s, 9H), 1.42-1.33 (m, 5H), 1.31-1.25 (m, 5H), 0.98 (dd, J=6.6, 4.3 Hz, 6H), 0.88 (t, J=6.8 Hz, 3H) ppm.

Determination of Chiral Centers of O-Tubulysins in FIGS. 3 and 4

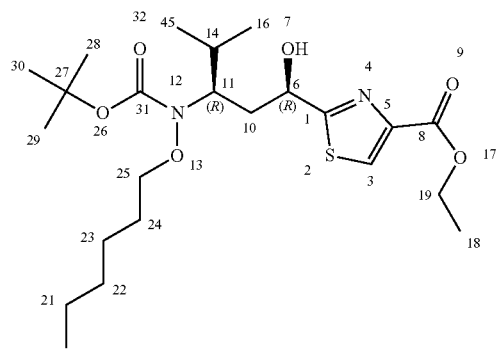

Ethyl 2-((1R,3R)-3-(tert-butoxycarbonylamino)-1-hydroxy-4-methylpentyl)thiazole-4-carboxylate (17A)

A mixture of compound 17a (500 mg, 1.06 mmol), Mo(CO)₆ (1 g, 3.79 mmol), CH₃CN (15 mL), and H₂O (5 mL) was stirred at 120° C. in a microwave reactor for 8 h. The mixture was then cooled, filtered, and concentrated. To the crude mixture were added MeOH (10 mL) and Boc₂O (500 mg, 2.29 mmol), and the resulting mixture was stirred at rt for 3 h. The mixture was concentrated, suspended in CH₂Cl₂ (10 mL) and filtered. The filtrate was concentrated and purified by flash chromatography (silica gel, PE to PE/EA=60/40), and then purified by prep-HPLC (NH₄HCO₃/H₂O/CH₃CN) to provide 17A as a white solid (25 mg, 6.3%). $[a]_D^{23}$=+13.571 (c=0.56, CHCl₃). ESI m/z: 373 (M+H)⁺. ¹H NMR (500 MHz, CDCl₃) δ 8.14 (s, 1H), 5.22 (d, J=3.8 Hz, 1H), 5.02 (d, J=11.2 Hz, 1H), 4.58 (d, J=9.6 Hz, 1H), 4.42 (q, J=7.1 Hz, 2H), 3.77-3.69 (m, 1H), 2.13-2.03 (m, 1H), 1.85-1.68 (m, 2H), 1.44-1.41 (s, 9H), 1.40 (t, J=7.1 Hz, 3H), 0.96 (d, J=6.8, 3.0 Hz, 3H), 0.95 (d, J=6.8 Hz, 3H) ppm.

Ethyl 2-((1R,3S)-3-(tert-butoxycarbonylamino)-1-hydroxy-4-methylpentyl)thiazole-4-carboxylate (17B)

A mixture of compound 17a2 (600 mg, 1.27 mmol), Mo(CO)₆ (1.2 g, 4.55 mmol), CH₃CN (12 mL), and H₂O (4 mL) was stirred in a microwave reactor at 100° C. for 2 h and at 120° C. for 6 h. The mixture was filtered and concentrated. The mixture was dissolved in MeOH (10 mL) and Boc$_2$O (600 mg, 2.75 mmol) was added. The mixture was stirred at rt overnight. The mixture was concentrated, suspended in CH$_2$Cl$_2$, dried over Na$_2$SO$_4$, and filtered. The filtrate was concentrated and purified by flash chromatography (silica gel, PE to PE/EA=50/50), and then by prep-HPLC (NH$_4$HCO$_3$/H$_2$O/CH$_3$CN). The resultant pooled fractions were concentrated and lyophilized to obtain 17B as a white solid (85 mg, 18%). [a]$_D^{23}$=+82.957 (c=1.6, CHCl$_3$). ESI m/z: 373 (M+H)$^+$. $^1$H NMR (500 MHz, CDCl$_3$) δ 8.04 (s, 1H), 4.90 (s, 1H), 5.07 (s, 1H), 4.53 (d, J=8.9 Hz, 1H), 4.35 (q, J=7.1 Hz, 2H), 3.58 (m, 1H), 2.30 (d, J=14.8 Hz, 1H), 2.00-1.85 (m, 2H), 1.34 (s, 9H), 1.32 (t, J=Hz, 3H), 0.9 (d, J=6.8 Hz, 3H), 0.86 (d, J=6.8 Hz, 3H).

The $^1$H NMR chemical shifts of 17A from 17a and 17B from 17a2 in chloroform-d are summarized in Table 4, along with the published $^1$H NMR data for (1R,3R)-17A and (1R,3S)-17B (*Organic and Biomolecular Chemistry* 2013, 11(14), 2273-2287). Upon review of all analytical data, the conclusion was 17a is (1R,3R)-17a that can be converted to (1R,3R)-17A, and 17a2 is (1R,3S)-17a that can be converted to (1R,3S)-17B.

TABLE 4

NMR data of (1R,3R)-17A, (1R,3R)-17A, (1R,3S)-17B, and (1R,3S)-17B

|  | (1R,3R)-17A (reference data) | (1R,3R)-17A (from 17a) |
|---|---|---|
| 1 | 8.08 (s, 1H) | 8.14 (s, 1H) |
| (NH) | 5.14 (br s, 1H) | 5.22 (d, J = 3.8 Hz, 1H) |
| 3 | 4.98 (br d, J = 11 Hz, 1H) | 5.02 (d, J = 11 Hz, 1H) |
| 4 | 4.58 (d, J = 9.4 Hz, 1H) | 4.58 (d, J = 9.6 Hz, 1H) |
| 5 | 4.36 (q, J = 7.3 Hz, 2H) | 4.42 (q, J = 7.1 Hz, 2H) |
| 6 | 3.75-3.64 (m, 1H) | 3.77-3.69 (m, 1H) |
| 7 | 2.04 (dt, J = 12, 2.2 Hz, 1H) | 2.13-2.03 (m, 1H) |
| 8 | 1.81-1.63 (m, 2H) | 1.85-1.68 (m, 2H) |
| 9 | 1.40 (s, 9H), | 1.44 (s, 9H) |
| 10 | 1.37 (t, J = 7.3 Hz, 3H) | 1.40 (t, J-7.1 Hz, 3H) |
| 11 | 0.93 (d, J = 7.0 Hz, 3H) | 0.96 (dd, J = 6.8, 3.0 Hz, 3H). |
| 12 | 0.91 (d, J = 6.8 Hz, 3H) | 0.95, (d, J = 6.8 Hz, 3H) |
|  | [a]$_D^{23}$ = +4.5 (c = 1.74 g/100 mL in CHCl$_3$) | [a]$_D^{23}$ = +13.571 (c = 0.56 g/100 mL in CHCl$_3$) R$_f$ = 0.51 (n-Hex/AcOEt = 6:4) on TLC |
|  | (1R,3S)-17B (reference data) | (1R,3S)-17B (from 17a2) |
| 1 | 8.07 (s, 1H) | 8.04 (s, 1H) |
| (NH) | 4.82 (br s, 1H), | 4.90 (s, 1H) |
| 3 | 5.18-5.04 (m, 1H) | 5.07 (s, 1H) |
| 4 | 4.56 (br d, J = 8.6 Hz, 1H) | 4.53 (d, J = 8.9 Hz, 1H) |
| 5 | 4.38 (q, J = 6.9 Hz, 2H) | 4.35 (q, J = 7.1 Hz, 2H) |
| 6 | 3.68-3.56 (m, 1H) | 3.584 (m, 1H) |
| 7 | 2.39-2.26 (m, 1H) | 2.30 (d, J = 14.8 Hz, 1H) |
| 8 | 1.98-1.77 (m, 2H) | 2.00-1.85 (m, 2H) |
| 9 | 1.39 (s, 9H), | 1.34 (s, 9H) |
| 10 | 1.37 (t, J = 6.9 Hz, 3H) | 1.32, (t, J = 7 Hz, 3H) |
| 11 | 0.94 (d, J = 6.8 Hz, 3H) | 0.90 (d, J = 6.8 Hz, 3H) |
| 12 | 0.90 (d, J = 6.7 Hz, 3H) | 0.86 (d, J = 6.8 Hz, 3H) |
|  | [a]$_D^{23}$ = +57.7 (c = 1.2 g/100 mL in CHCl$_3$) | [a]$_D^{23}$ = +82.957 (c = 1.6 g/100 mL in CHCl$_3$) R$_f$ = 0.27 (n-Hex/AcOEt = 6:4) on TLC |

Ethyl 2-((1R,3R)-3-(tert-butoxycarbonyl(3-(4-nitrobenzyloxy)propoxy)amino)-1-hydroxy-4-methylpentyl)thiazole-4-carboxylate (17b)

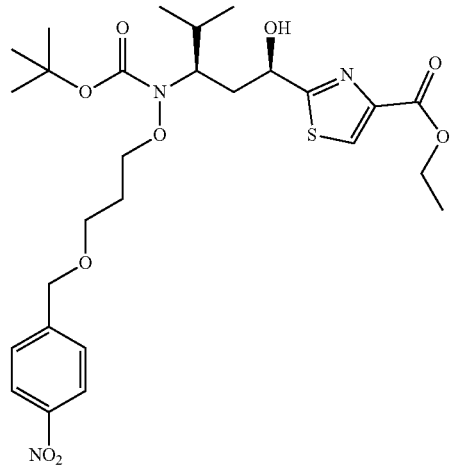 [SMILES: CCOC(=O)c1csc([C@H](O)C[C@H](C(C)C)N(OCCCOCc2ccc([N+](=O)[O-])cc2)C(=O)OC(C)(C)C)n1]

Using similar reaction conditions as described above for preparing (1R,3R)-17a, a crude (1R,3R)-17b (2.7 g, with 8000 ee, 4300 yield) and diastereomer (1R,3S)-17b (2.5 g, 3900 yield) were obtained separately. Compound 17b (crude) was further purified by chiral SFC to give enantiopure (1R,3R)-17b (1.7 g, 63% yield) as a yellow oil. The chirality of (1R,3R)-17b was identified using the same method described for 17a.

For (1R,3R)-17b: ESI m/z: 604 (M+Na)$^+$. $^1$H NMR (400 MHz, CDCl$_3$) δ 8.20 (d, J=8.7 Hz, 2H), 8.13 (s, 1H), 7.52 (d, J=8.7 Hz, 2H), 4.97 (d, J=10.0 Hz, 1H), 4.64 (s, 2H), 4.42 (q, J=7.1 Hz, 2H), 4.15-4.03 (m, 3H), 3.91 (t, J=9.7 Hz, 1H), 3.69 (t, J=6.4 Hz, 2H), 2.43-2.36 (m, 1H), 2.03-1.86 (m, 4H), 1.52 (s, 9H), 1.41 (t, J=7.1 Hz, 3H), 1.02 (d, J=6.6 Hz, 3H), 0.94 (d, J=6.7 Hz, 3H) ppm. Chiral SFC column OD-H, CO$_2$/MeOH (0.2% methanol ammonia). Retention time: 5.58 min, Area %: >99%.

For (1S,3S)-17b: ESI m/z: 604 (M+Na)$^+$. $^1$H NMR (500 MHz, CDCl$_3$) δ 8.21 (d, J=8.7 Hz, 2H), 8.13 (s, J=4.0 Hz, 1H), 7.51 (d, J=8.6 Hz, 2H), 5.15-5.12 (m, 1H), 4.62 (s, 2H), 4.45-4.41 (m, 2H), 4.15 (dd, J=14.4, 6.3 Hz, 1H), 4.05 (dd, J=14.2, 6.1 Hz, 1H), 3.95 (s, 1H), 3.80 (t, J=8.1 Hz, 1H), 3.66 (t, J=6.3 Hz, 2H), 2.43 (dt, J=14.8, 3.5 Hz, 1H), 2.13-1.89 (m, 4H), 1.50 (s, 9H), 1.42 (t, J=7.1 Hz, 3H), 1.00-0.98 (m, 6H) ppm. Chiral SFC column OD-H, CO$_2$/MeOH (0.2% methanol ammonia). Retention time: 4.37 min, Area %: >99%.

Ethyl 2-((1R,3R)-3-(tert-butoxycarbonyl (pent-4-ynyloxy) amino)-1-hydroxy-4-methylpentyl) thiazole-4-carboxylate (17c-P2); and ethyl 2-((1S, 3S)-3-(tert-butoxycarbonyl (pent-4-ynyloxy) amino)-1-hydroxy-4-methylpentyl)thiazole-4-carboxylate (17c-P1); Ethyl 2-((1R,3S)-3-(tert-butoxycarbonyl (pent-4-ynyloxy)amino)-1-hydroxy-4-methylpentyl) thiazole-4-carboxylate (17c-P3); and ethyl 2-((1S, 3R)-3-(tert-butoxycarbonyl(pent-4-ynyloxy)amino)-1-hydroxy-4-methylpentyl)thiazole-4-carboxylate (17c-P4)

To a solution of compound 16c (93 g, 0.21 mol) in ethanol (0.30 L) was added sodium borohydride (7.8 g, 0.21 mol) at 0° C. portionwise. The solution was stirred at 0° C. for 3 hours until the reaction was completed according to LCMS. The reaction was quenched with water (1 L) at 0° C. and the aqueous solution was extracted with DCM (1.5 L). The combined organic layers were concentrated in vacuo. The crude product was purified by silica gel column chromatography (eluted with 5-20% ethyl acetate in petroleum ether) to afford cis-17c (crude) (29 g, 31% yield) and trans-17c (26 g, 27% yield). The cis isomer was further purified by chiral SFC to give (1S,3S)-17c (peak 1) (6 g, 21% yield), and pure (1R,3R)-17c (peak 2) (8.2 g, 28% yield, 99% ee). The trans-17c (2 g) was separated by SFC to give (1R,3S)-17c-P3 (0.52 g, 26% yield) and (1S,3R)-17c-P4 (0.55 g, 27% yield).

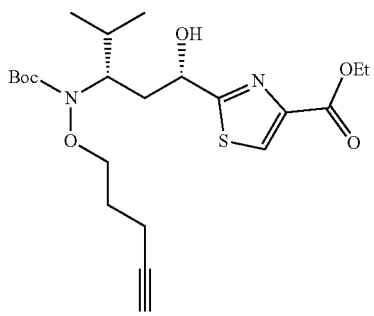 [SMILES: C#CCCCON(C(=O)OC(C)(C)C)[C@@H](C[C@H](O)c1nc(C(=O)OCC)cs1)C(C)C]

For (1S,3S)-17c (peak 1): ESI m/z: 477 (M+Na)+. 1H NMR (500 MHz, CDCl3) δ 8.13 (s, 1H), 4.98 (d, J=9.5 Hz, 1H), 4.41 (q, J=7.1 Hz, 2H), 4.10 (dd, J=14.0, 6.2 Hz, 1H), 4.03 (dd, J=13.6, 6.3 Hz, 1H), 3.92 (t, J=9.8 Hz, 1H), 2.48-2.39 (m, 1H), 2.36 (td, J=6.9, 2.5 Hz, 2H), 2.08 (t, J=2.4 Hz, 1H), 2.06-1.95 (m, 1H), 1.87 (dt, J=13.0, 8.9 Hz, 3H), 1.52 (s, 9H), 1.40 (t, J=7.1 Hz, 3H), 1.02 (d, J=6.5 Hz, 3H), 0.95 (d, J=6.7 Hz, 3H) ppm.

The (1R,3R)-17c (peak 2): ESI m/z: 477 (M+Na)+. 1H NMR (500 MHz, CDCl3) δ 8.13 (s, 1H), 4.98 (d, J=9.5 Hz, 1H), 4.41 (q, J=7.1 Hz, 2H), 4.10 (dd, J=14.0, 6.2 Hz, 1H), 4.03 (dd, J=13.6, 6.3 Hz, 1H), 3.92 (t, J=9.8 Hz, 1H), 2.48-2.39 (m, 1H), 2.36 (td, J=6.9, 2.5 Hz, 2H), 2.08 (t, J=2.4 Hz, 1H), 2.06-1.95 (m, 1H), 1.87 (dt, J=13.0, 8.9 Hz, 3H), 1.52 (s, 9H), 1.40 (t, J=7.1 Hz, 3H), 1.02 (d, J=6.5 Hz, 3H), 0.95 (d, J=6.7 Hz, 3H). Chiral SFC column EnantioPak OZ-H, CO2/EtOH (0.2% methanol ammonia). Retention time: 0.71, Area %: 100%.

For (1R,3S)-17c-P3: ESI m/z: 477 (M+Na)+. 1H NMR (500 MHz, CDCl3) δ 8.12 (s, 1H), 5.19-5.06 (m, 1H), 4.42 (q, J=7.1 Hz, 2H), 4.09 (dd, J=14.3, 6.1 Hz, 1H), 3.98 (dd, J=14.3, 6.1 Hz, 1H), 3.91 (s, 1H), 3.80 (t, J=8.4 Hz, 1H), 2.42 (dt, J=14.9,3.4 Hz, 1H), 2.32 (td, J=7.0, 2.6 Hz, 2H), 2.12 (ddd, J=14.9, 10.4, 8.9 Hz, 1H), 1.94 (dt, J=16.4, 4.7 Hz, 2H), 1.83 (p, J=6.7 Hz, 2H), 1.50 (s, 9H), 1.40 (t, J=7.1 Hz, 3H), 0.99 (s, 3H), 0.98 (d, J=0.8 Hz, 3H).

For (1S,3R)-17c-P4: ESI m/z: 477 (M+Na)+. 1H NMR (500 MHz, CDCl3) δ 8.12 (s, 1H), 5.16-5.10 (i, 1H), 4.44-4.39 (, 2H), 4.13-4.05 (i, 1H), 3.98 (dd, J=14.2, 6.2 Hz, 1H), 3.91 (s, 1H), 3.80 (t, J 8.2 Hz, 1H), 2.42 (dt, J 14.9, 3.4 Hz, 1H), 2.32 (td, J 7.0, 2.6 Hz, 2H), 2.18-2.07 (m, 1H), 1.94 (dt, J=16.5, 4.6 Hz, 2H), 1.83 (p, J=6.6 Hz, 2H), 1.50 (s, 9H), 1.40 (t, J=7.1 Hz, 3H), 0.99 (s, 3H), 0.98 (s, 3H).

The chirality of the 17c isomers was identified using the same method for 17a. For the two 17c cis isomers: 17c-P2 was converted to (1R,3R)-17A, and 17c-P1 was converted to (1S,3S)-17A. For the two 17c trans isomers: 17c-P3 was converted to (1R,3S)-17B, and 17c-P4 was converted to (1S,3R)-17B. The (H NMR chemical shifts of the 17A and 17B isomers from 17c (P1, P2, P3, P4) in chloroform-d are summarized in the following Table 5. Upon review of all analytical data, the conclusion was 17c-P2 is (1R,3R)-17c that can be converted to (1R,3R)-17A (reported), and 17c-P4 is (1S,3R)-17c that can be converted to (1S,3R)-17B (reported).

TABLE 5

NMR data of (1R,3R)-17A, (1R,3R)-17A, (1S,3S)-17A, (1R,3S)-17B, (1S,3R)-17B and (1R,3S)-17B

| | (1R,3R)-17A (reference) | (1R,3R)-17A from (1R,3R)-17c; cis-P2 | (1S,3S)-17A from (1S,3S)-17c; cis-P1 |
|---|---|---|---|
| 1 | 8.08 (s, 1H) | 8.13 (s, 1H) | 8.12 (s, 1H) |
| 2 (NH) | 5.14 (br s, 1H) | 3.84 (br s, 1H) | NA |
| 3 | 4.98 (br d, J = 11 Hz, 1H) | 5.02 (d, J = 11 Hz, 1H) | 5.02 (d, J = 11 Hz, 1H) |
| 4 | 4.58 (d, J = 9.4 Hz, 1H) | 4.59 (d, J = 9.6 Hz, 1H) | 4.56 (d, J = 9.6 Hz, 1H) |
| 5 | 4.36 (q, J = 7.3 Hz, 2H) | 4.42 (q, J = 7.1 Hz, 2H) | 4.42 (q, J = 7.1 Hz, 2H) |
| 6 | 3.75-3.64 (m, 1H), | 3.77-3.69 (m, 1H) | 3.77-3.67 (m, 1H) |
| 7 | 2.04 (dt, J =12, 2.2 Hz, 1H) | 2.12-2.03 (m, 1H) | 2.13-2.04 (m, 1H) |
| 8 | 1.81-1.63 (m, 2H) | 1.85-1.68 (m, 2H) | 1.82-1.70 (m, 2H) |
| 9 | 1.40 (s, 9H), | 1.44 (s, 9H) | 1.45 (s, 9H) |
| 10 | 1.37 (t, J = 7.3 Hz, 3H) | 1.40 (t, J = 7.1 Hz, 3H) | 1.40 (t, J = 7.1 Hz, 3H) |

TABLE 5-continued

NMR data of (1R,3R)-17A, (1R,3R)-17A, (1S,3S)-17A, (1R,3S)-17B, (1S,3R)-17B and (1R,3S)-17B

| 11 | 0.93 (d, J = 7.0 Hz, 3H) | 0.96 (d, J = 6.8 Hz, 3H) | 0.97 (d, J = 6.8 Hz, 3H) |
|---|---|---|---|
| 12 | 0.91 (d, J = 6.8 Hz, 3H) | 0.95 (d, J = 6.8 Hz, 3H) | 0.95 (d, J = 6.8 Hz, 3H) |
|  | $[\alpha]_D^{23} = +4.5$ | $[\alpha]_D^{23} = +10.244$ | $[\alpha]_D^{23} = -12.045$ |
|  | (c = 1.74 g/100 mL in CHCl$_3$) | (c = 2.46 g/100 mL in CHCl$_3$) | (c = 0.88 g/100 mL in CHCl$_3$) |

|  | (1R,3S)-17B (reference) | (1S,3R)-17B from (1S,3R)-17c; trans-P4 | (1R,3S)-17B from (1R,3S)-17c; trans-P3 |
|---|---|---|---|
| 1 | 8.07 (s, 1H) | 8.11 (s, 1H) | 8.11 (s, 1H) |
| 2 (NH) | 4.82 (br s, 1H), | NA | 1.86 (br s, 1H) |
| 3 | 5.18-5.04 (m, 1H) | 5.13 (d, J = 4.4 Hz, 1H) | 5.13 (d, J = 4.5 Hz, 1H) |
| 4 | 4.56 (br d, J = 8.6 Hz, 1H) | 4.59 (d, J = 8.5 Hz, 1H) | 4.58 (d, J = 8.2 Hz, 1H) |
| 5 | 4.38 (q, J = 6.9 Hz, 2H) | 4.41 (q, J = 7.1 Hz, 2H) | 4.41 (q, J = 7.1 Hz, 2H) |
| 6 | 3.68-3.56 (m, 1H) | 3.67-3.63 (m, 1H) | 3.71-3.58 (m, 1H) |
| 7 | 2.39-2.26 (m, 1H) | 2.40-2.33 (m, 1H) | 2.41-2.31 (m, 1H) |
| 8 | 1.98-1.77 (m, 2H) | 1.99-1.91 (m, 2H) | 1.98-1.89 (m, 2H) |
| 9 | 1.39 (s, 9H), | 1.41 (s, 9H) | 1.42 (s, 9H) |
| 10 | 1.37 (t, J = 6.9 Hz, 3H) | 1.40 (t, J = 7.0 Hz, 3H) | 1.40 (t, J = 6.7 Hz, 3H) |
| 11 | 0.94 (d, J = 6.8 Hz, 3H) | 0.97 (d, J = 6.8 Hz, 3H) | 0.97 (d, J = 6.7 Hz, 3H) |
| 12 | 0.90 (d, J = 6.7 Hz, 3H) | 0.93 (d, J = 6.8 Hz, 3H) | 0.93 (d, J = 6.8 Hz, 3H) |
|  | $[\alpha]_D^{23} = +57.7$ | $[\alpha]_D^{23} = -73.140$ | $[\alpha]_D^{23} = +61.579$ |
|  | (c = 1.2 g/100 mL in CHCl$_3$) | (c = 0.86 g/100 mL in CHCl$_3$) | (c = 1.52 g/100 mL in CHCl$_3$) |

The chiral SFC separation conditions for cis-17c and trans-17c were summarized in the following Table 6.

TABLE 6

| Compound | Cis 17c | Trans 17c |
|---|---|---|
| Instrument | SFC-200 (Thar, Waters) | SFC-200 (Thar, Waters) |
| Column | OZ 30*250 mm, 5 um (Decial) | AD 20*250 mm, 5 um (Dacel) |
| Column temperature | 35° C. | 35° C. |
| Mobile phase | CO$_2$/Methanol (0.1% NH$_4$OH) = 90/10 | CO$_2$/MeOH 0.2% NH$_4$OH (7M methanol) = 85/15 |
| Flow rate | 70 g/min | 120 g/min |
| Back pressure | 100 bar | 100 bar |
| Detection wavelength | 214 nm | 214 nm |
| Cycle time | 2.0 min | 3.6 min |
| Sample solution | 1.8 g dissolved in 20 ml Methanol | 1.8 g dissolved in 35 ml Methanol |
| Injection volume | 0.35 mL | 1.0 mL |

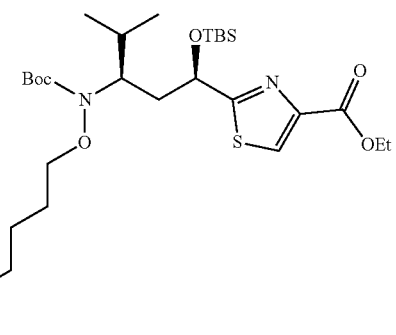

Ethyl 2-[(1R,3R)-3-{[(tert-butoxy)carbonyl](hexyloxy)amino}-1-[(tert-butyldimethylsilyl)oxy]-4-methylpentyl]-1,3-thiazole-4-carboxylate (18a)

To a solution of compound 17a (3.2 mmol) in DCM (16 mL) were added 2,6-lutidine (1.8 mL, 38.4 mmol) and tert-butyldimethylsilyl chloride (TBSCl, 1.7 mL, 19.2 mmol) successively at 4° C. The mixture was stirred at 4° C. for 30 minutes. The resulting mixture was allowed to warm to rt and stirred for 2 hours until the reaction was completed according to LCMS. The reaction mixture was then poured into brine. The aqueous layer was extracted with ethyl acetate. And the combined organic layers were washed with brine, dried over sodium sulfate and concentrated in vacuo. The residue was purified by flash chromatography (eluted by 25% ethyl acetate in hexane) to give compound 18a (1.8 g, 95% yield) as a colorless oil. $^1$H NMR (400 MHz, CDCl$_3$): δ 9.92 (s, 1H), 5.24 (d, J=2.5 Hz, 1H), 4.43-4.36 (m, 2H), 4.13-4.10 (m, 1H), 4.02-3.99 (m, 1H), 3.86 (m, 1H), 2.15-2.09 (m, 1H), 1.89-1.83 (m, 2H), 1.67-1.56 (m, 2H), 1.40 (s, 9H), 1.41-1.25 (m, 9H), 0.95-0.83 (m, 18H), 0.15 (s, 3H), 0.0 (s, 3H) ppm.

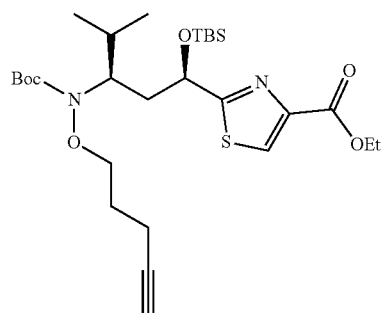

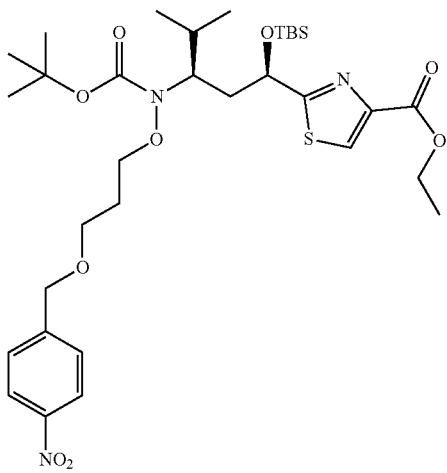 [SMILES: CCOC(=O)c1csc([C@@H](C[C@H](C(C)C)N(OCCCOCc2ccc([N+](=O)[O-])cc2)C(=O)OC(C)(C)C)O[Si](C)(C)C(C)(C)C)n1]

Ethyl 2-[(1R,3R)-1-[(tert-butyldimethylsilyl)oxy]-3-[10,10-dimethyl-1-(4-nitrophenyl)-8-oxo-2,6,9-trioxa-7-azaundecan-7-yl]-4-methylpentyl]-1,3-thiazole-4-carboxylate (18b)

To a mixture of compound 17b (1.7 g, 2.9 mmol) in DMF (50 mL) were added imidazole (2.37 g, 34.8 mmol) and TBSCl (2.69 g, 17.4 mmol) and the mixture was stirred at rt for 3 days. The mixture was poured into water (140 mL) and extracted with ethyl acetate (twice). The combined organic layers were washed with brine, dried over sodium sulfate, and concentrated in vacuo. The residue was purified by flash chromatography (eluted by 0-15% ethyl acetate in petroleum ether) to give compound 18b (1.8 g, 88% yield) as a colorless oil. ESI m/z: 696 (M+H)$^+$. $^1$H NMR (500 MHz, CDCl$_3$) δ 8.17 (d, J=8.6 Hz, 2H), 8.09 (s, 1H), 7.47 (d, J=8.5 Hz, 2H), 5.24 (d, J=8.6 Hz, 1H), 4.60 (s, 2H), 4.39 (m, 2H), 4.19 (m, 2H), 3.90 (s, 1H), 3.70 (m, 2H), 2.14 (m, 1H), 2.01 (m, 2H), 1.84 (m, 2H), 1.52 (s, 9H), 1.39 (t, J=7.1 Hz, 3H), 0.92 (m, 15H), 0.16 (s, 3H), −0.08 (s, 3H) ppm.

Ethyl 2-[(1R,3R)-3-{[(tert-butoxy)carbonyl](pent-4-yn-1-yloxy)amino}-1-[(tert-butyldimethylsilyl)oxy]-4-methylpentyl]-1,3-thiazole-4-carboxylate (18c)

Using the same procedure for making 18b, compound 18c (4.4 g, 70% yield) was obtained as an oil. ESI m/z: 569 (M+H)$^+$. $^1$H NMR (500 MHz, CDCl$_3$) δ 7.96 (s, 1H), 5.08 (d, J=8.5 Hz, 1H), 4.33-4.18 (m, 2H), 4.02 (dd, J=12.8, 7.1 Hz, 1H), 3.99-3.92 (m, 1H), 3.74 (br s, 1H), 2.23-2.17 (m, 2H), 2.04-1.95 (m, 1H), 1.78-1.65 (m, 5H), 1.36 (s, 9H), 1.25 (s, 3H), 0.80-0.76 (m, 15H), 0.00 (s, 3H), −0.25 (s, 3H) ppm.

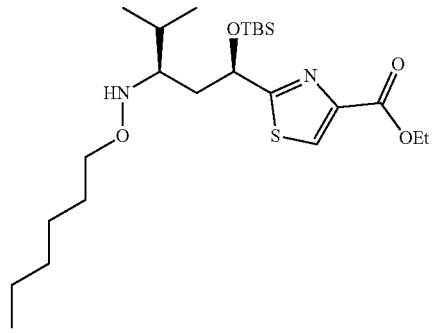 [SMILES: CCCCCCON[C@H](C[C@@H](O[Si](C)(C)C(C)(C)C)c1nc(C(=O)OCC)cs1)C(C)C]

Ethyl 2-[(5R,7R)-2,2,3,3-tetramethyl-7-(propan-2-yl)-4,9-dioxa-8-aza-3-silapentadecan-5-yl]-1,3-thiazole-4-carboxylate (19a)

A mixture of 18a (1.8 g, 3.1 mmol) in 10% TFA in DCM (10 mL) was stirred at rt for 24 hours, and was then concentrated in vacuo to give crude compound 19a (1.7 g, 80% yield), which was used in the next step without further purification.

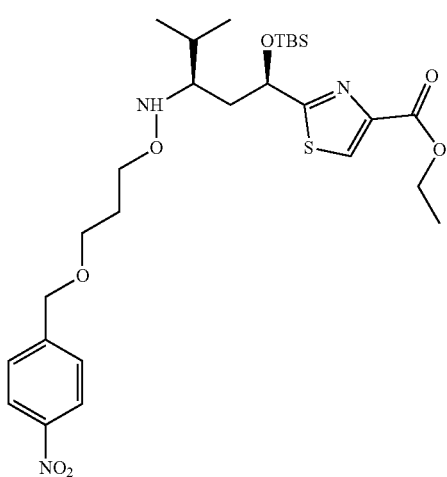 [SMILES: CCOC(=O)c1csc([C@@H](C[C@@H](NOCCCOCc2ccc([N+](=O)[O-])cc2)C(C)C)O[Si](C)(C)C(C)(C)C)n1]

Ethyl 2-[(8R,10R)-12,12,13,13-tetramethyl-1-(4-nitrophenyl)-8-(propan-2-yl)-2,6,11-trioxa-7-aza-12-silatetradecan-10-yl]-1,3-thiazole-4-carboxylate (19b)

To a mixture of compound 18b (1.4 g, 2.0 mmol) in DCM (50 mL) was added TFA (5.0 mL), the reaction mixture was stirred at rt for 4 hours until the Boc protecting group was totally removed according to LCMS. The mixture was then poured into sat. aq. sodium bicarbonate (100 mL) and extracted with DCM (3 times). The combined organic layers were dried over sodium sulfate and concentrated in vacuo to give compound 19b (1.2 g, crude, as TFA salt) as a light yellow oil. ESI m/z: 596 (M+H)$^+$. $^1$H NMR (400 MHz, CDCl$_3$) δ 8.22 (d, J=8.8 Hz, 2H), 8.11 (s, 1H), 7.52 (d, J=8.8 Hz, 2H), 5.33 (dd, J=6.8, 3.8 Hz, 1H), 4.62 (s, 2H), 4.50-4.35 (m, 2H), 3.81 (t, J=6.3 Hz, 2H), 3.62 (t, J=6.4 Hz, 2H), 2.89-2.85 (m, 1H), 2.04-1.98 (m, 1H), 1.97-1.84 (m, 3H), 1.73-1.66 (m, 1H), 1.42 (t, J=7.2 Hz, 3H), 0.96 (s, 9H), 0.83 (d, J=6.9 Hz, 6H), 0.17 (s, 3H), 0.00 (s, 3H) ppm.

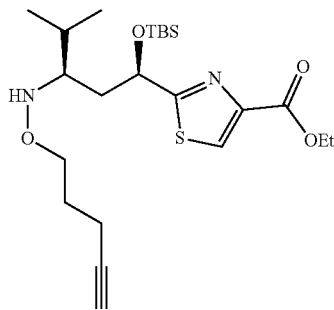 [SMILES: C#CCCCON[C@H](C[C@@H](O[Si](C)(C)C(C)(C)C)c1nc(C(=O)OCC)cs1)C(C)C]

Ethyl 2-[(5R,7R)-2,2,3,3-tetramethyl-7-(propan-2-yl)-4,9-dioxa-8-aza-3-silatetradec-13-yn-5-yl]-1,3-thiazole-4-carboxylate (19c)

Using the same procedure for making 19b, compound 19c (3.4 g, 94% crude yield, as TFA salt) was obtained. ESI m/z: 469 (M+H)$^+$. $^1$H NMR (500 MHz, CDCl$_3$) δ 8.11 (s, 1H), 5.80 (s, 1H), 5.33 (dd, J=7.1, 3.5 Hz, 1H), 4.49-4.36 (m, 2H), 3.75 (t, J=6.2 Hz, 2H), 2.84 (ddd, J=10.0, 4.0, 1.7 Hz, 1H), 2.27 (td, J=7.2, 2.6 Hz, 2H), 2.05-1.98 (m, 1H), 1.96 (t, J=2.6 Hz, 1H), 1.86 (ddd, J=14.6, 7.1, 1.8 Hz, 1H), 1.82-1.76 (m, 2H), 1.72-1.65 (m, 1H), 1.41 (t, J=7.1 Hz, 3H), 0.97 (s, 9H), 0.82 (dd, J=6.9, 2.3 Hz, 6H), 0.16 (s, 3H), 0.00 (s, 3H) ppm.

Figure 11:
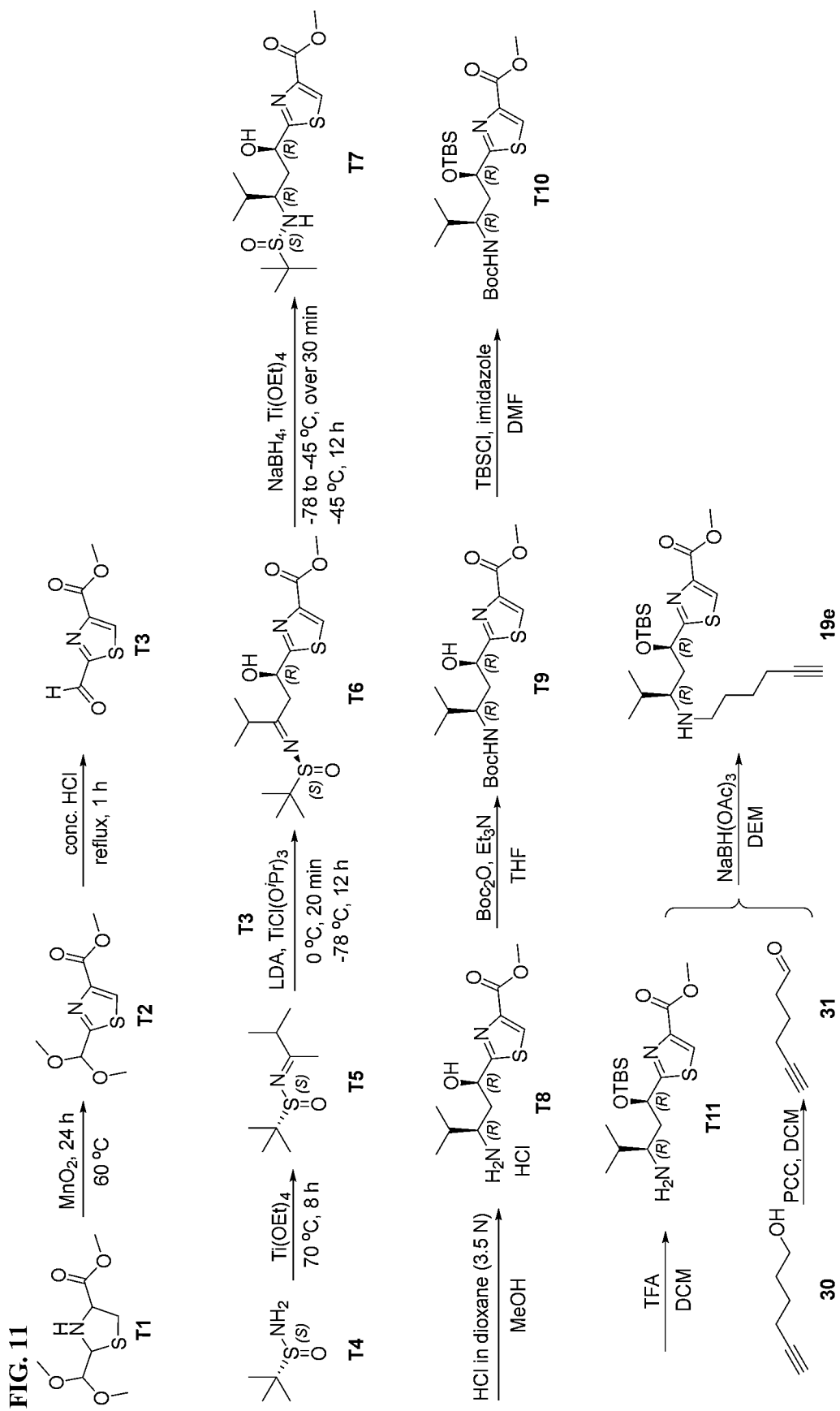

The synthesis of 19e was shown in FIG. 11.

Methyl 2-(dimethoxymethyl)thiazole-4-carboxylate (T2) (FIG. 11)

To the solution of compound T1 (0.57 kg, 2.7 mol, R$_f$=0.5 and 0.6, PE:EA=2:1, 20% PMA) in acetonitrile (15 L) was added manganese dioxide (2.5 kg) at room temperature, and the mixture was warmed to 60° C. and stirred for 6 hours. The mixture was then filtered through a celite pad and concentrated. Compound T2 (0.65 kg, R$_f$=0.55 and 0.65, PE:EA=2:1, UV) was obtained as a yellow solid and used without further purification.

Methyl 2-formylthiazole-4-carboxylate (T3)

To the solution of compound T2 (0.65 kg, 3.0 mol, R$_f$=0.55 and 0.65, PE:EA=2:1, UV) in acetone (15 L) was added conc. hydrochloride (2.0 L, 6 N) at room temperature, and the mixture was warmed to reflux and stirred for 1 h. The mixture was then cooled to rt and concentrated under reduced pressure. The crude was dissolved in ethyl acetate and the organic phase was washed with sat. aq. sodium bicarbonate and brine, dried over magnesium sulfate, filtered, and concentrated. The residue was recrystallized from 50% ethyl acetate in petroleum ether to provide compound T3 (66 g, 14% total yield over three steps, R$_f$=0.7, PE:EA=2:1, UV) as a yellow solid.

Methyl 2-((R)-3-((S)-tert-butylsulfinylimino)-1-hydroxy-4-methylpentyl)thiazole-4-carboxylate (T6)

(S)-2-Methylpropane-2-sulfinamide T4 (7.3 mL, 68 mmol) was dissolved in 100 mL tetrahydrofuran (THF), to which was added Ti(OEt)$_4$ (27 mL, 130 mmol) and 3-methyl-2-butanone (8 g, 41 mmol) at rt. The reaction mixture was refluxed overnight, then cooled and added to a brine solution. The resultant mixture was filtered and the cake was washed with EtOAc. The organic phase was concentrated to give a residue which was subjected silica gel column chromatography (DCM:EtOAc, 4:1) to give sulfinimine T5 (9.5 g, 37 mmol, 75%) as oil. (ref. U.S. Pat. No. 9,226,974, 2016)

A 0.5 M solution of diisopropylamine (27 mL, 0.27 mol) in ethyl ether (0.63 L) was cooled to 0° C. and to the solution was added n-butyllithium (0.12 L, 0.29 mol, 2.5 M solution in hexanes). The solution was stirred at 0° C. for 20 min and then cooled to −78° C. A solution of sulfinamide T5 (50 g, 0.27 mol) in ethyl ether (0.55 L) was added in slowly, and the reaction mixture was stirred at −78° C. for an additional 30 min, to which was added a solution of chlorotitanium triisopropoxide (0.14 kg, 0.53 mol) in ethyl ether (150 mL), and the reaction mixture was stirred at −78° C. for an additional 20 min. To the mixture was then added aldehyde T3 (29 g, 0.17 mol) in one portion, and the mixed solution was stirred at −78° C. for 12 h. The solution was then neutralized with a solution of THF/AcOH (150 mL, v/v=4:1) at −78° C., and then allowed to warm to rt. After dilution with water (250 mL), the resulting mixture was filtered through celite, and the filter cake was washed thoroughly with ethyl acetate. The combined filtrate was washed with brine, dried over magnesium sulfate, filtered, and concentrated under reduced pressure. The residue was purified by silica gel column chromatography which provided compound T6 (50 g, 79%; R$_f$=0.6, PE:EA=1:1, UV) as a yellow oil.

Methyl 2-((1R,3R)-3-((S)-1,1-dimethylethylsulfinamido)-1-hydroxy-4-methylpentyl)thiazole-4-carboxylate (T7)

To a 0.4 M solution of imine T6 (62 g, 0.17 mol) in THF (0.52 L) at −78° C. was added titanium ethoxide (76 mL, 0.33 mol), followed by sodium borohydride (26 g, 0.69 mol), and the solution was allowed to slowly warm to −45° C. over 30 min. The reaction mixture was stirred at −45° C. for 12 h, and then diluted with methanol (125 mL) slowly, keeping the internal temperature of the reaction below −30° C. until gas evolution ceased. The solution was warmed to rt and further quenched with water (1.4 L). The resulting suspension was filtered through a pad of celite, and the filter cake was washed thoroughly with ethyl acetate. The combined filtrate was washed once with brine, dried, filtered, and concentrated. The residue was purified by silica gel column chromatography to provide T7 (31 g, 50% yield, R$_f$=0.4, PE:EA=1:1, UV) as a yellow oil.

Methyl 2-((1R,3R)-3-amino-1-hydroxy-4-methylpentyl)thiazole-4-carboxylate hydrochloride (T8)

To a solution of compound T7 (31 g, 86 mmol) in methanol (0.50 L) was added hydrochloride in dioxane (1.0 L, 4.0 N). The reaction mixture was stirred at rt for 3 hours and the volatiles were then removed in vacuo to give the crude product T8 as a yellow solid, which was used in the next step without purification (see J. Am. Chem. Soc. 2006, 128, 16018-16019).

Methyl 2-((1R,3R)-3-(tert-butoxycarbonylamino)-1-hydroxy-4-methylpentyl)thiazole-4-carboxylate (T9)

To a solution of amino alcohol T8 (39 g, 86 mmol) in THF (1.5 L) at 0° C. were added triethylamine (21 g, 0.21 mol) and di-tert-butyl dicarbonate (21 g, 98 mmol). The reaction mixture was allowed to warm to rt and stirred overnight. The reaction mixture was filtered and the filtrate was concentrated to provide compound T9 (34 g, R$_f$=0.6, PE:EA=2:1, UV) as a white solid, which was used in the next step without purification.

Methyl 2-((5R,7R)-7-isopropyl-2,2,3,3,11,11-hexamethyl-9-oxo-4,10-dioxa-8-aza-3-siladodecan-5-yl)thiazole-4-carboxylate (T10)

A solution of T9 (34 g, 86 mmol, R$_f$=0.3, PE:EA=3:1, UV) in DMF (450 mL) was cooled to 0° C., to which were added imidazole (15 g, 0.22 mol) and tert-butyldimethylsilyl chloride (32 g, 0.22 mol). The reaction mixture was then allowed to warm to rt and stirred overnight. The resulting mixture was quenched with brine (1.0 L) and the aqueous layer was extracted with ethyl acetate. The combined organic solution was washed with brine, dried over magnesium sulfate, filtered, and concentrated under reduced pressure. The residue was purified by silica gel column chromatography to provide compound T10 (32 g, 78% yield over three steps, R$_f$=0.7, PE:EA=3:1, UV) as a colorless oil.

Methyl 2-((1R,3R)-3-amino-1-(tert-butyldimethylsilyloxy)-4-methylpentyl)thiazole-4-carboxylate (T11)

To a solution of T10 (32 g, 68 mmol) in DCM (800 mL) at 0° C. was added TFA (160 mL) dropwise. The resulting mixture was stirred at 0° C. for 5 hours, and then the volatiles were removed under reduced pressure. The residue was dissolved in DCM and washed with sodium bicarbonate. The organic solution was dried over sodium sulfate, filtered, and concentrated. The residue T11 (26 g, R$_f$=0.3, PE:EA=3:1, UV) was used in the next step without purification.

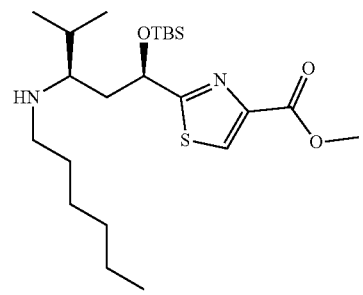 [SMILES: CCCCCCN[C@H](C[C@@H](O[Si](C)(C)C(C)(C)C)c1nc(C(=O)OC)cs1)C(C)C]

Methyl 2-((1R,3R)-1-(tert-butyldimethylsilyloxy)-3-(hexylamino)-4-methylpentyl)thiazole-4-carboxylate (19d)

Following a similar procedure for 19e below, compound 111a (4.2 g, 9.9 mmol) and caproaldehyde were used to provide compound 19d (3.0 g, 66% yield) as a yellow oil.

Methyl 2-((1R,3R)-1-(tert-butyldimethylsilyloxy)-3-(hex-5-ynylamino)-4-methylpentyl)thiazole-4-carboxylate (19e)

To a solution of hex-5-yn-1-ol 30 (23 g, 0.23 mol) in DCM (0.75 L) was added pyridinium chlorochromate (PCC, 0.10 kg, 0.47 mol) portion wise and the reaction mixture was stirred at rt overnight. The reaction mixture was then diluted with diethyl ether and filtered through celite. The filtrate was concentrated and distilled to afford the desired hex-5-ynal 31 (12 g, 52% yield). To a solution of compound T11 (26 g, 67 mmol, R$_f$=0.3-0.5, PE:EA=1:1, UV) in DEM (0.30 L) were added at 0° C. hex-5-ynal (6.5 g, 67 mmol) and sodium triacetoxyborohydride (43 g, 0.20 mol). The reaction mixture stirred at rt for 6 hours, and then was quenched with sodium bicarbonate. The mixture was extracted with DCM and the organic solution was dried over sodium sulfate, filtered, and concentrated in vacuo. The crude product was purified by silica gel column chromatography to give compound 19e (24 g, 78% yield over three steps, R$_f$=0.3-0.5, PE:EA=1:1, UV) as a yellow oil.

Figure 12:
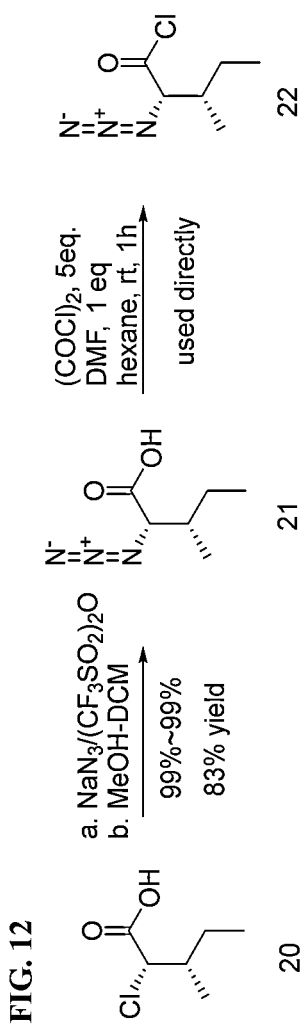

(2S,3S)-2-Azido-3-methylpentanoic acid (21) (FIG. 12)

A solution of sodium azide (1.78 g, 27.45 mmol) in distilled H$_2$O (4.5 mL) and CH$_2$Cl$_2$ (7.5 mL) was cooled in an ice bath. Triflic anhydride (0.93 mL, 5.55 mmol) was added slowly over 5 min with stirring and the resulting solution was stirred for 2 h. The CH$_2$Cl$_2$ phase was separated and the aqueous portion was extracted with CH$_2$Cl$_2$ (2×3.75 mL). The organic fractions, containing the triflyl azide, were pooled and washed once with saturated Na$_2$CO$_3$ and used in the next step without further purification. (2S,3S)-2-Chloro-3-methyl-N-valeric acid (20, 366 mg, 2.79 mmol) was mixed with K$_2$CO$_3$ (577.5 mg, 4.19 mmol) and CuSO$_4$ pentahydrate (6.98 mg, 27.9 μmol) in distilled H$_2$O (9 mL)

and CH$_3$OH (18 mL). To the mixture was added triflic azide in CH$_2$Cl$_2$ (15 mL), and the resulting mixture was stirred at ambient temperature overnight. The organic solvents were removed in vacuo and the aqueous slurry was diluted with H$_2$O (50 mL), subsequently acidified to pH 6 with conc. HCl, then diluted with pH 6.2 phosphate buffer (0.25 M, 50 mL), and extracted with EtOAc (4 times) to remove the sulfonamide by-product. The aqueous phase was then acidified to pH 2 with conc. HCl and then extracted with EtOAc (3 times). The EtOAc extracts were combined, dried with MgSO$_4$, and then evaporated to dryness to give crude compound 21 as a pale oil (390 mg, 89% yield). 21 was used without further purification. For 21: $^1$H NMR (300 MHz, CDCl$_3$) δ 3.84 (d, J=5.8 Hz, 1H), 2.15-1.95 (m, 2H), 1.70-1.55 (m, 1H), 1.45-1.25 (m, 1H), 1.04 (d, J=6.8 Hz, 3H), 0.94 (t, J=7.4 Hz, 3H) ppm.

(2S,3S)-2-Azido-3-methylpentanoyl chloride (22) (FIG. 12)

Oxalyl chloride (2.44 mL, 28.0 mmol) and DMF (0.464 mL, 5.97 mmol) were added to a 0.024 M solution of azido isoleucine 21 (0.938 g, 5.97 mmol) in hexane. The reaction mixture was stirred at rt for 1 h, filtered, and concentrated in vacuo. Acid chloride 22 was isolated and used immediately without further purification.

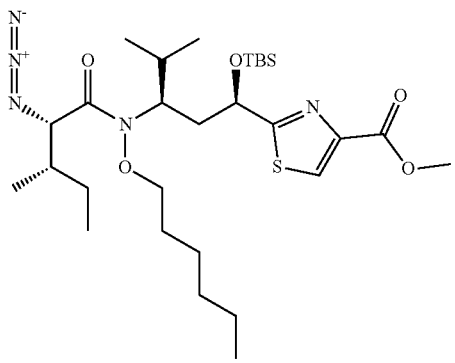 [SMILES: CCCCCCON(C(=O)[C@@H](N=[N+]=[N-])[C@@H](C)CC)[C@H](C[C@@H](O[Si](C)(C)C(C)(C)C)c1nc(C(=O)OC)cs1)C(C)C]

Ethyl 2-[(1R,3R)-3-[(2S,3S)-2-azido-N-(hexyloxy)-3-methylpentanamido]-1-[(tert-butyldimethylsilyl)oxy]-4-methylpentyl]-1,3-thiazole-4-carboxylate (23a)

A 0.10 M solution of 19a (1.46 g, 3.0 mmol, 1.0 equiv) in CH$_2$Cl$_2$ (37.3 mL) was cooled to 0° C. To the solution was added diisopropylethylamine (3.25 mL, 5.0 equiv) and acid chloride 22 (1.6 equiv). The reaction mixture was allowed to warm to rt and stirred for 18 h. Brine (50 mL) was then added to the reaction mixture, and the aqueous layer was extracted with EtOAc (2×75 mL). The combined organic portions were dried, filtered, and concentrated in vacuo. The residue was purified by column chromatography (1:1 hexanes/EtOAc) to give 23a (1.31 g, 70%) as a colorless oil. ESI m/z: 626 (M+H)$^+$. $^1$H NMR (400 MHz, CDCl$_3$): 8.08 (s, 1H), 4.35 (q, 2H, J=7.2 Hz), 4.23 (t, 2H, J=7.2 Hz), 3.83 (q, 1H, J=6.4 Hz), 3.68 (d, 1H, J=9 Hz), 2.24 (m, 1H), 2.09 (m, 1H), 1.89 (m, 2H), 1.75 (m, 1H), 1.58 (m, 2H), 1.35 (m, 5H), 1.26 (m, 6H), 0.95 (m, 24H), 0.09 (s, 3H), −0.15 (s 3H) ppm.

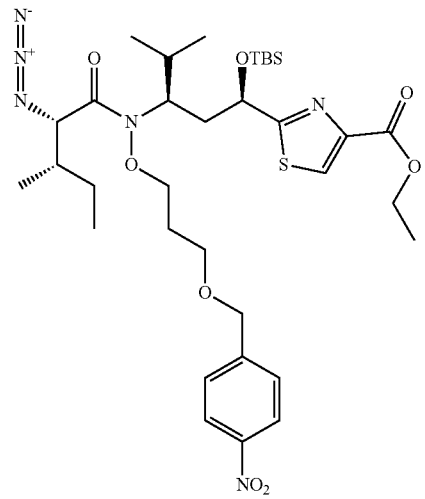 [SMILES: CCOC(=O)c1csc([C@@H](C[C@H](C(C)C)N(OCCCOCc2ccc([N+](=O)[O-])cc2)C(=O)[C@@H](N=[N+]=[N-])[C@@H](C)CC)O[Si](C)(C)C(C)(C)C)n1]

Ethyl 2-((8R,10R)-7-((2S,3S)-2-azido-3-methylpentanoyl)-8-isopropyl-12,12,13,13-tetramethyl-1-(4-nitrophenyl)-2,6,11-trioxa-7-aza-12-silatetradecan-10-yl)thiazole-4-carboxylate (23b)

Using similar reaction conditions for making 23a, compound 23b (310 mg, 63%) was obtained from 400 mg of compound 19b. ESI m/z: 735 (M+H)$^+$.

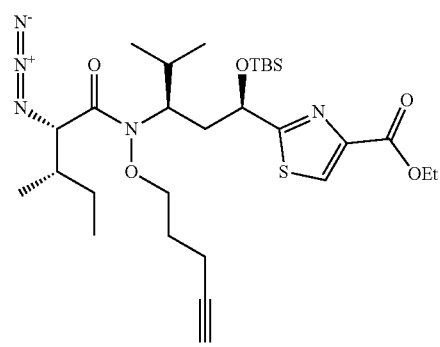 [SMILES: C#CCCCON(C(=O)[C@@H](N=[N+]=[N-])[C@@H](C)CC)[C@H](C[C@@H](O[Si](C)(C)C(C)(C)C)c1nc(C(=O)OCC)cs1)C(C)C]

Ethyl 2-[(1R,3R)-3-[(2S,3S)-2-azido-3-methyl-N-(pent-4-yn-1-yloxy)pentanamido]-1-[(tert-butyl dimethylsilyl)oxy]-4-methylpentyl]-1,3-thiazole-4-carboxylate (23c)

Using similar reaction conditions for making 23b, compound 23c (2.3 g, 60%) was obtained from 3 g of 19c. $^1$H NMR (500 MHz, CDCl$_3$) δ 8.04 (s, 1H), 5.05 (dd, J=25.8, 7.8 Hz, 1H), 4.40-4.22 (m, 4H), 4.09-4.03 (m, 1H), 3.69 (t, J=10.0 Hz, 1H), 2.33-2.28 (m, 2H), 2.27-2.20 (m, 1H), 2.10-2.01 (m, 1H), 1.97-1.86 (m, 3H), 1.81 (dd, J=12.1, 6.2 Hz, 2H), 1.76-1.64 (m, 1H), 1.33 (t, J=7.1 Hz, 3H), 1.27-1.23 (m, 1H), 0.93-0.86 (m, 21H), 0.00 (s, 3H), −0.07 (s, 3H) ppm.

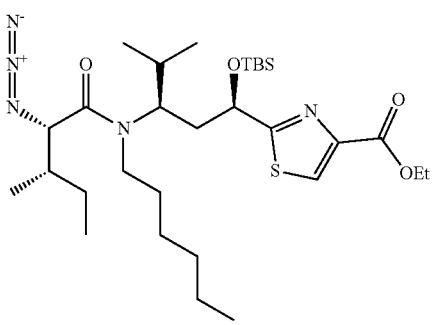 [SMILES: CCCCCCN(C(=O)[C@@H](N=[N+]=[N-])[C@@H](C)CC)[C@H](C[C@@H](O[Si](C)(C)C(C)(C)C)c1nc(C(=O)OCC)cs1)C(C)C]

Methyl 2-((1R,3R)-3-((2S,3S)-2-azido-N-hexyl-3-methylpentanamido)-1-(tert-butyldimethylsilyloxy)-4-methylpentyl)thiazole-4-carboxylate (23d)

Using similar reaction conditions for making compound 23a, compound 23d (4.1 g, yield 92%) was obtained as a colorless oil from 3.3 g of compound 19d.

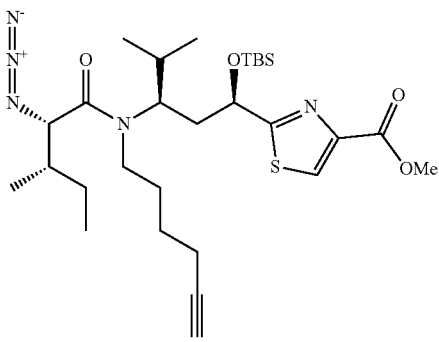 [SMILES: C#CCCCCN(C(=O)[C@@H](N=[N+]=[N-])[C@@H](C)CC)[C@H](C[C@@H](O[Si](C)(C)C(C)(C)C)c1nc(C(=O)OC)cs1)C(C)C]

Methyl 2-((1R,3R)-3-((2S,3S)-2-azido-N-(hex-5-ynyl)-3-methylpentanamido)-1-(tert-butyldimethylsilyloxy)-4-methylpentyl)thiazole-4-carboxylate (23e)

Using similar reaction conditions for making compound 23a, compound 23e (33 g, yield 92%, $R_f$=0.95, PE:EA=3:1, UV) was obtained as a colorless oil from 27 g of compound 19e.

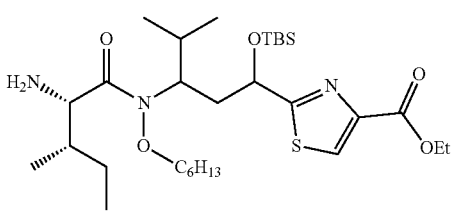

Ethyl 2-((5R,7R)-7-isopropyl-2,2,3,3-tetramethyl-8-((2R,3S)-3-methyl-2-((S)-1-methylpiperidin-2-yl)pentanoyl)-4,9-dioxa-8-aza-3-silapentadecan-5-yl)thiazole-4-carboxylate (24a)

To a solution of azide 23a (2.50 g, 3.99 mmol) in EtOAc (50 mL) were added 10% Pd/C (1.38 mg). The reaction mixture was then stirred under a hydrogen atmosphere for 27 h. The reaction mixture was filtered through a plug of celite, and the filter pad was washed with EtOAc. The combined filtrate was used directly in the next step without purification. ESI m/z 600.4 (M+H)$^+$.

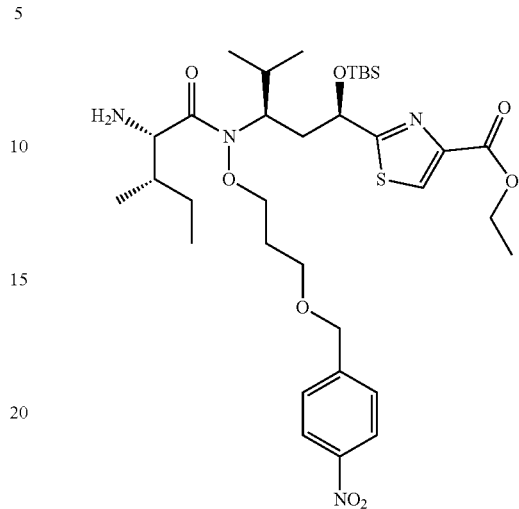

Ethyl 2-((8R,10R)-7-((2S,3S)-2-azido-3-methylpentanoyl)-8-isopropyl-12,12,13,13-tetramethyl-1-(4-nitrophenyl)-2,6,11-trioxa-7-aza-12-silatetradecan-10-yl)thiazole-4-carboxylate (24b)

A mixture of compound 23b (300 mg, 0.41 mmol) and Ph$_3$P (300 mg, 1.15 mmol) in THF (10 mL) and water (5 mL) was stirred at rt overnight. The mixture was diluted with DCM (100 mL), dried over Na$_2$SO$_4$, and filtered. The filtrate was concentrated in vacuo and purified by flash column chromatography (20 g of silica gel, DCM to DCM/MeOH=95/5) to give compound 24b as a colorless oil (210 mg, 72%). ESI m/z: 709 (M+H)$^+$. $^1$H NMR (400 MHz, CDCl$_3$) δ 8.17 (d, J=8.6 Hz, 2H), 8.09 (s, 1H), 7.46 (d, J=8.6 Hz, 2H), 5.11-5.09 (m, 1H), 4.60 (s, 2H), 4.35 (m, 4H), 4.11 (dd, J=14.6, 6.3 Hz, 1H), 3.68 (t, J=6.2 Hz, 2H), 3.53 (d, J=6.6 Hz, 1H), 2.35-2.29 (m, 1H), 2.06-1.94 (m, 4H), 1.77-1.71 (m, 2H), 1.39 (t, J=7.1 Hz, 3H), 1.16-1.07 (m, 1H), 0.93 (m, 23H), 0.13 (s, 3H), −0.10 (s, 3H) ppm.

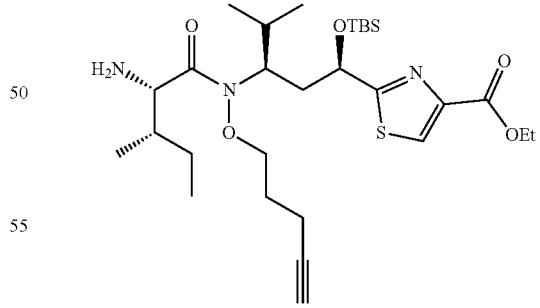

Ethyl 2-[(1R,3R)-3-[(2S,3S)-2-amino-3-methyl-N-(pent-4-yn-1-yloxy)pentanamido]-1-[(tert-butyl dimethylsilyl)oxy]-4-methylpentyl]-1,3-thiazole-4-carboxylate (24c)

Using similar reaction conditions for making 24b, compound 24c (1.2 g, 57%) was obtained from 2.2 g of compound 23c. ESI m/z: 582 (M+H)⁺. ¹H NMR (500 MHz, CDCl₃) δ 8.11 (s, 1H), 5.10 (d, J=7.1 Hz, 1H), 4.50-4.00 (m, 5H), 3.54 (d, J=6.6 Hz, 1H), 2.35-2.20 (m, 3H), 2.05-1.90 (m, 5H), 1.90-1.83 (m, 2H), 1.80-1.70 (m, 2H), 1.40 (t, J=7.1 Hz, 3H), 1.40-0.91 (m, 23H), 0.13 (s, 3H), −0.10 (s, 3H) ppm.

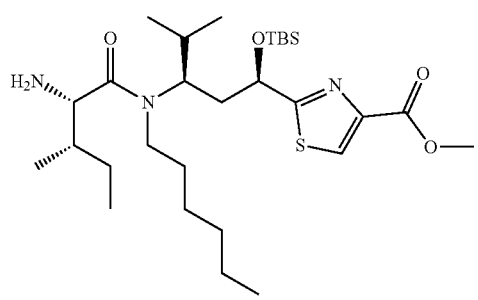 [SMILES: CCCCCCN(C(=O)[C@@H](N)[C@@H](C)CC)[C@H](C[C@@H](O[Si](C)(C)C(C)(C)C)c1nc(C(=O)OC)cs1)C(C)C]

Methyl 2-((1R,3R)-3-((2S,3S)-2-amino-N-hexyl-3-methylpentanamido)-1-(tert-butyldimethylsilyloxy)-4-methylpentyl)thiazole-4-carboxylate (24d)

Using similar reaction conditions for making compound 24a, crude compound 24d was obtained from 1.6 g of compound 23d. The crude product 24d was used in the next step without purification.

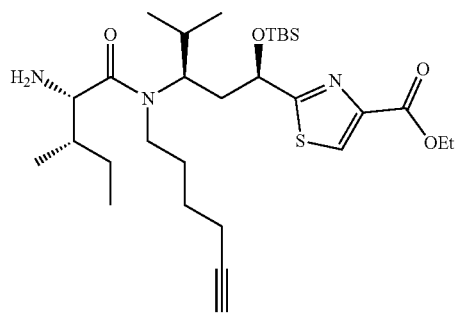 [SMILES: C#CCCCCN(C(=O)[C@@H](N)[C@@H](C)CC)[C@H](C[C@@H](O[Si](C)(C)C(C)(C)C)c1nc(C(=O)OCC)cs1)C(C)C]

Ethyl 2-((1R,3R)-3-((2S,3S)-2-amino-N-(hex-5-ynyl)-3-methylpentanamido)-1-(tert-butyldimethylsilyloxy)-4-methylpentyl)thiazole-4-carboxylate (24e)

Using similar reaction conditions for making compound 24a, crude compound 24e was obtained from 24 g of compound 23e. The crude product 24e was used in the next step without purification.

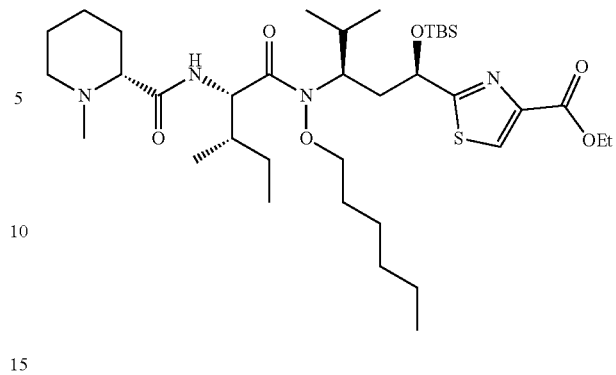

Ethyl 2-[(1R,3R)-1-[(tert-butyldimethylsilyl)oxy]-3-[(2S,3S)—N-(hexyloxy)-3-methyl-2-{[(2R)-1-methylpiperidin-2-yl]formamido}pentanamido]-4-methylpentyl]-1,3-thiazole-4-carboxylate (26a)

To a 0.4 M solution of compound 25 (1.72 g, 12 mmol) in EtOAc (30 mL, filtered through a plug of activated alumina) were added pentafluorophenol (2.43 g, 13.2 mmol, 1.1 equiv) and DCC (2.72 g, 13.2 mmol, 1.1 equiv). The reaction mixture was stirred for 21 h at rt and then filtered, and the residue was washed with EtOAc (10 mL). The activated ester was used immediately without purification or concentration. The solution of the activated ester (0.3 M, 40 mL) was added into a solution of 24a in EtOAc (50 mL, 4.0 mmol) obtained above. The resulting mixture was stirred at rt overnight. The volatiles were removed in vacuo and the residue was purified by flash chromatography (0-10% methanol in EtOAc) to give compound 26a (2.0 g, 69% yield) as a colorless oil. ESI m/z: 725 (M+H)⁺.

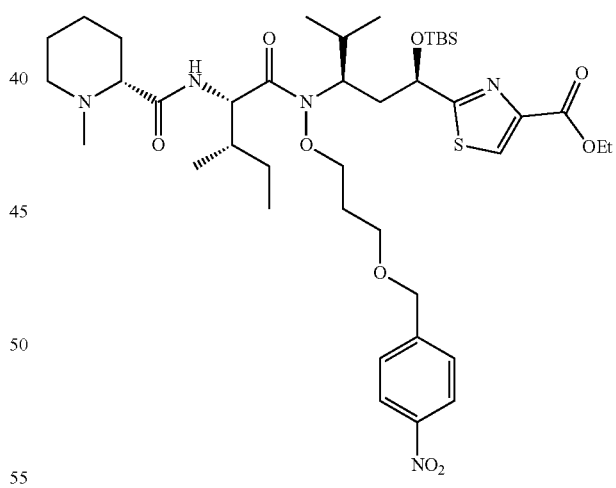

Ethyl 2-((8R,10R)-8-isopropyl-12,12,13,13-tetramethyl-7-((2S,3S)-3-methyl-2-((R)-1-methyl piperidine-2-carboxamido)pentanoyl)-1-(4-nitrophenyl)-2,6,11-trioxa-7-aza-12-silatetradecan-10-yl)thiazole-4-carboxylate (26b)

A solution of compound 25 (185 mg, 1.3 mmol) and pentafluorophenol (357 mg, 1.9 mmol) in dry methylene chloride (25 mL) was added dropwise a solution of DIC (245 mg, 1.9 mmol) in methylene chloride (1.0 mL) at 0° C. by syringe. The resulting solution was stirred for another 1 hour. Then the solution was filtered and the filtrate was concentrated to give crude pentafluorophenyl ester (400 mg). ESI m/z: 310.0 (M+H)⁺. The crude pentafluorophenyl ester was dissolved in dry DCM (11 mL). To the solution were added 24b (400 mg, 565 μmol) and DIPEA (275 mg, 889 μmol). The resulting solution was stirred at rt overnight. The reaction solution was concentrated to dryness and the residue was purified by flash column chromatography (eluting with EtOAc/PE=1/2 then 2/1) to give 26b (320 mg, 68% for two steps) as a pale yellow solid. ESI m/z: 834.4 (M+H)⁺. ¹H NMR (DMSO$_{d6}$, 500 MHz) δ 8.99 (d, J=9.0 Hz, 1H), 8.48 (s, 1H), 8.17 (d, J=8.5 Hz, 2H), 7.51 (d, J=8.5 Hz, 2H), 4.90 (d, J=9.5 Hz, 1H), 4.75 (t, J=9.0 Hz, 1H), 4.58 (s, 2H), 4.38-4.34 (m, 1H), 4.28 (q, J=7.5 Hz, 2H), 4.16-4.06 (m, 3H), 3.82-3.77 (m, 1H), 3.72-3.67 (m, 1H), 3.64-3.60 (m, 1H), 3.36-3.34 (m, 1H), 3.13-3.06 (m, 1H), 2.66 (d, J=4.0 Hz, 3H), 2.29-2.23 (m, 1H), 2.07-1.96 (m, 3H), 1.94-1.87 (m, 3H), 1.81-1.78 (m, 2H), 1.68-1.57 (m, 2H), 1.47-1.39 (m, 2H), 1.29 (t, J=7.0 Hz, 3H), 1.10-1.05 (m, 1H), 0.93-0.89 (m, 14H), 0.85 (d, J=6.0 Hz, 3H), 0.81 (t, J=7.5 Hz, 3H), 0.08 (s, 3H), −0.16 (s, 3H) ppm.

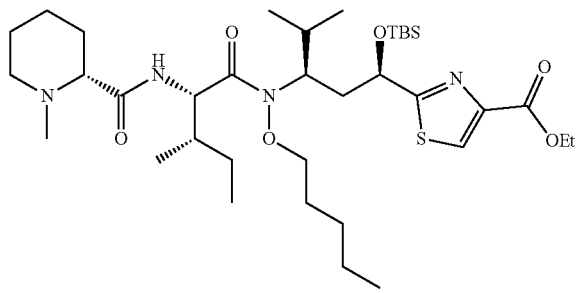

Ethyl 2-[(1R,3R)-1-[(tert-butyldimethylsilyl)oxy]-4-methyl-3-[(2S,3S)-3-methyl-2-{[(2R)-1-methyl piperidin-2-yl]formamido}-N-(pent-4-yn-1-yloxy)pentanamido]pentyl]-1,3-thiazole-4-carboxylate (26c)

Using similar reaction conditions for making 26b, compound 26c (1.7 g, 78%) was obtained from 1.8 g of compound 24c. ESI m/z: 707 (M+H)⁺. ¹H NMR (500 MHz, methanol$_{d4}$) δ 8.38 (s, 1H), 5.03 (d, J=8.1 Hz, 1H), 4.85 (t, J=6.3 Hz, 1H), 4.40 (q, J=7.5 Hz, 3H), 4.13-4.07 (m, 1H), 4.03-3.86 (m, 2H), 3.52-3.45 (m, 1H), 3.35-3.29 (m, 1H), 2.87 (s, 3H), 2.51-2.35 (m, 3H), 2.25 (t, J=2.4 Hz, 1H), 2.23-2.15 (m, 1H), 2.10-1.53 (m, 11H), 1.40 (t, J=7.1 Hz, 3H), 1.27-1.19 (m, 1H), 1.08-0.94 (m, 12H), 0.94 (s, 9H), 0.13 (s, 3H), −0.16 (s, 3H) ppm.

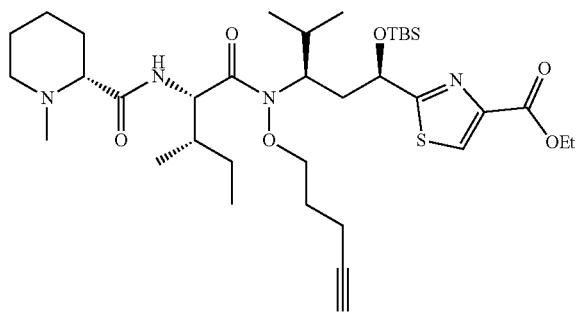 [SMILES: C#CCCCON(C(=O)[C@@H](NC(=O)[C@H]1CCCCN1C)[C@@H](C)CC)[C@H](C[C@@H](O[Si](C)(C)C(C)(C)C)c1nc(C(=O)OCC)cs1)C(C)C]

Ethyl 2-((5R,7R)-7-isopropyl-2,2,3,3-tetramethyl-8-((2S,3S)-3-methyl-2-((R)-1-methylpiperidine-2-carboxamido)pentanoyl)-4,9-dioxa-8-aza-3-silatetradecan-5-yl)thiazole-4-carboxylate (26f)

To a solution of compound 26c (20 mg, 28 μmol) in methanol (5 mL) was added 5% palladium on charcoal (5 mg) and the mixture was degassed and backfilled with hydrogen 3 times. The resulting mixture was stirred under hydrogen atmosphere at rt for 6 hours until the triple bond was totally reduced, as monitored by LCMS. The mixture was filtered through Celite and the Celite was washed with methanol (3 times). The combined filtrate was concentrated in vacuo to give compound 26f (18 mg, 90% crude yield) as a white solid, which was used in the next step without purification. ESI m/z: 712 (M+H)⁺.

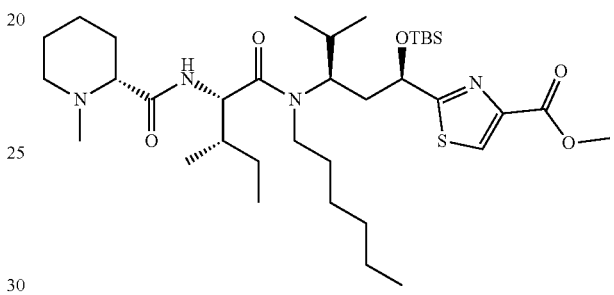

Methyl 2-((3S,6R,8R)-3-sec-butyl-5-hexyl-6-isopropyl-10,10,11,11-tetramethyl-1-((R)-1-methylpiperidin-2-yl)-1,4-dioxo-9-oxa-2,5-diaza-10-siladodecan-8-yl)thiazole-4-carboxylate (26d)

Crude 24d obtained above was dissolved in DCM (27 mL). To the solution were added HOBt (0.40 g, 3.0 mmol) and compound 25 (0.42 g, 2.34 mmol). After the reaction mixture was cooled to 0° C., EDCI (0.56 g, 2.92 mmol) and DIPEA (0.49 mL, 2.813 mmol) were added successively. The resulting mixture was stirred at rt overnight. The volatiles were removed and the residue was separated by ethyl acetate and aq. sodium bicarbonate. The aqueous solution was extracted with ethyl acetate and the combined organic solution was dried over sodium sulfate, filtered, and concentrated to give crude 26d (1.7 g, 89% yield from 23d), which was used in the next step without purification.

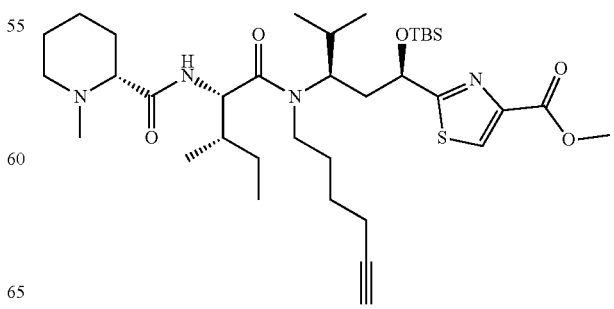

Methyl 2-((3S,6R,8R)-3-sec-butyl-5-(hex-5-ynyl)-6-isopropyl-10,10,11,11-tetramethyl-1-((R)-1-methylpiperidin-2-yl)-1,4-dioxo-9-oxa-2,5-diaza-10-siladodecan-8-yl)thiazole-4-carboxylate (26e)

Using similar reaction conditions for making compound 26d, compound 26e (39 g, yield, $R_f$=0.6, DCM:methanol=10:1, UV) was obtained from 53 g of compound 24e.

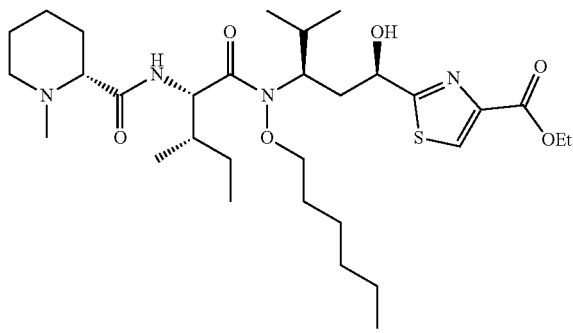 [SMILES: CCCCCCON(C(=O)[C@@H](NC(=O)[C@H]1CCCCN1C)[C@@H](C)CC)[C@H](C[C@@H](O)c1nc(C(=O)OCC)cs1)C(C)C]

Ethyl 2-[(1R,3R)-3-[(2S,3S)—N-(hexyloxy)-3-methyl-2-{[(2R)-1-methylpiperidin-2-yl]formamido} pentanamido]-1-hydroxy-4-methylpentyl]-1,3-thiazole-4-carboxylate (27a)

To a solution of 26a (2.0) in THF (40 mL) was added TBAF (10 mL, 1 M in THF) and the resulting solution was stirred at rt for 16 h, and was then concentrated. The residue was purified by HPFC purification (0-5% methanol in ethyl acetate) to provide 27a (1.5 g, 75% yield). ESI m/z: 611 (M+H)$^+$. $^1$H NMR (400 MHz, methanol$_{d4}$) δ 8.33 (s, 1H), 4.88 (m, 2H), 4.40 (q, J=7 Hz, 2H), 4.33 (t, J=7.6 Hz, 1H), 4.20 (m, 1H), 4.02 (m, 1H), 3.0 (m, 2H), 2.65 (m, 1H), 2.36 (s, 3H), 2.32 (m, 1H), 2.12, (m, 1H), 2.0 (m, 2H), 1.90 (m, 2H), 1.62-1.70 (m, 6H), 1.5 (m, 2H), 1.40 (t, J=7 Hz, 3H), 1.30-1.38 (m, 8H), 1.0 (m, 9H), 0.95 (m, 6H) ppm.

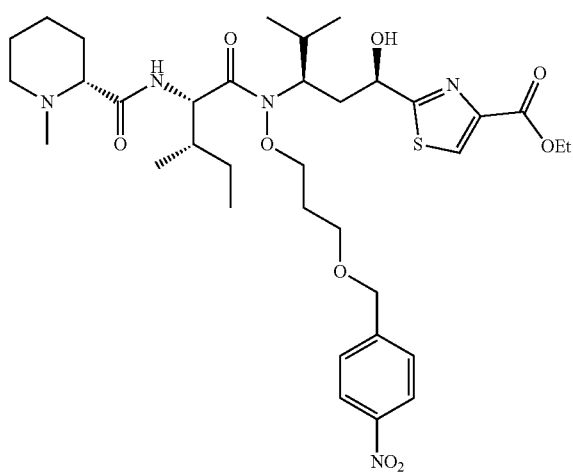 [SMILES: CCOC(=O)c1csc([C@H](O)C[C@H](C(C)C)N(OCCCOCc2ccc([N+](=O)[O-])cc2)C(=O)[C@@H](NC(=O)[C@H]2CCCCN2C)[C@@H](C)CC)n1]

Ethyl 2-((1R,3R)-1-hydroxy-4-methyl-3-((2S,3S)-3-methyl-2-((R)-1-methylpiperidine-2-carboxamido)-N-(3-(4-nitrobenzyloxy)propoxy)pentanamido)pentyl)thiazole-4-carboxylate (27b)

A mixture of compound 26b (130 mg, 240 μmol) and cesium fluoride (109 mg, 720 mmol) in DMSO (2.5 mL) was stirred at rt for 2 hrs. Then the solution was purified by RP column chromatography (0-100% acetonitrile in water) to give compound 27b (140 mg, yield 81%) as a pale yellow solid. ESI m/z: 720.3 (M+H)$^+$. $^1$H NMR (500 MHz, DMSO$_{d6}$) δ 8.42 (s, 1H), 8.16 (d, J=8.5 Hz, 2H), 7.59 (d, J=8.5 Hz, 2H), 7.52 (d, J=9.0 Hz, 1H), 6.37 (br s, 1H), 4.74 (t, J=9.0 Hz, 1H), 4.66 (s, 2H), 4.63 (d, J=11.0 Hz, 1H), 4.31-4.26 (m, 3H), 4.20-4.15 (m, 1H), 4.01 (br s, 1H), 3.74-3.62 (m, 2H), 2.83-2.80 (m, 1H), 2.47-2.44 (m, 2H), 2.07 (s, 3H), 1.98-1.92 (m, 4H), 1.82-1.77 (m, 2H), 1.59-1.33 (m, 6H), 1.29 (t, J=7.0 Hz, 3H), 1.14-1.04 (m, 2H), 0.86 (d, J=6.5 Hz, 9H), 0.79 (t, J=7.5 Hz, 3H) ppm. Chiral SFC >99% (AD-H, AS-H, OJ-H, and OD-H), $R_t$: 2.04 min (AD-H), 4.39 min (AS-H), 3.56 min (OD-H), and 3.72 min (OJ-H).

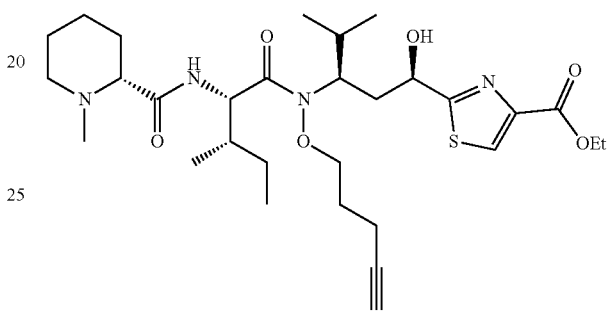

Ethyl 2-((1R,3R)-1-hydroxy-4-methyl-3-((2S,3S)-3-methyl-2-((R)-1-methylpiperidine-2-carboxamido)-N-(pent-4-ynyloxy)pentanamido)pentyl)thiazole-4-carboxylate (27c)

Using the similar procedure for making 27b, compound 27c (43 mg, 86% yield) as a white solid was obtained. ESI m/z: 593 (M+H)$^+$.

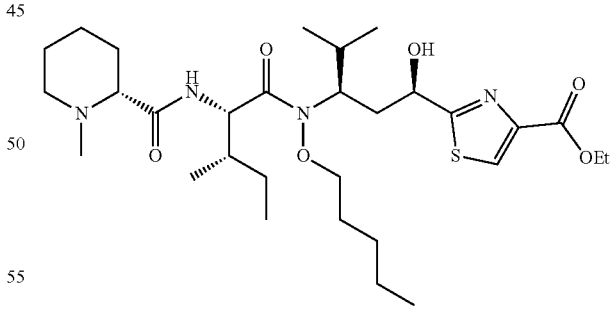

Ethyl 2-((1R,3R)-1-hydroxy-4-methyl-3-((2S,3S)-3-methyl-2-((R)-1-methylpiperidine-2-carboxamido)-N-(pentyloxy)pentanamido)pentyl)thiazole-4-carboxylate (27f)

Using a similar procedure for making 27a, compound 27f (13 mg, 86% yield) as a white solid was obtained. ESI m/z: 597 (M+H)$^+$.

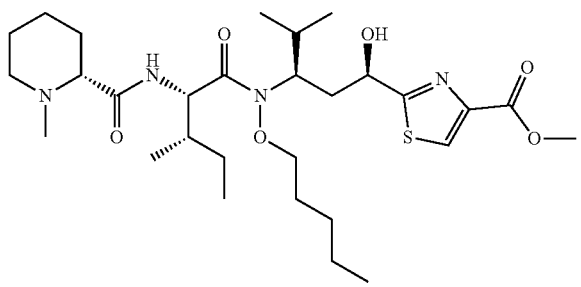 [SMILES: CCCCCON(C(=O)[C@@H](NC(=O)[C@H]1CCCCN1C)[C@@H](C)CC)[C@H](C[C@@H](O)c1nc(C(=O)OC)cs1)C(C)C]

Methyl 2-((1R,3R)-3-((2S,3S)—N-hexyl-3-methyl-2-((R)-1-methylpiperidine-2-carboxamido)pentanamido)-1-hydroxy-4-methylpentyl)thiazole-4-carboxylate (27d)

Using a similar procedure for making 27a, crude 27d (1.8 g) was obtained as a viscous yellow oil, which was used in the next step without purification.

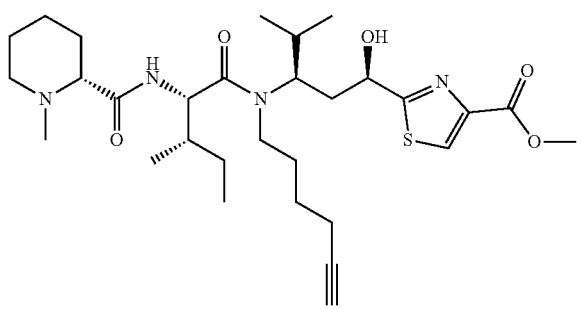 [SMILES: C#CCCCCN(C(=O)[C@@H](NC(=O)[C@H]1CCCCN1C)[C@@H](C)CC)[C@H](C[C@@H](O)c1nc(C(=O)OC)cs1)C(C)C]

Methyl 2-((1R,3R)-3-((2S,3S)—N-(hex-5-ynyl)-3-methyl-2-((R)-1-methylpiperidine-2-carboxamido)pentanamido)-1-hydroxy-4-methylpentyl)thiazole-4-carboxylate (27e)

Using a similar procedure for making 27a, crude compound 27e (44 g, $R_f$=0.55 and 0.5, DCM:methanol=10:1, UV) was obtained and used without further purification.

General Procedure for Intermediate II

To a solution of 27 (1.0 equiv) in THF (15-20 mg/mL) was added aq. lithium hydroxide (0.5 M, $V_{H2O}/V_{THF}$=1) and the mixture was stirred at rt for 10 hours until the hydrolysis was completed, as monitored by LCMS. The reaction mixture was then acidified with acetic acid to pH 3 and concentrated to 1/3 volume. The residual aqueous solution was purified directly by Prep-HPLC (ammonium bicarbonate system) to give intermediate IIa,b,c,e (66-90% yield) as a white solid.

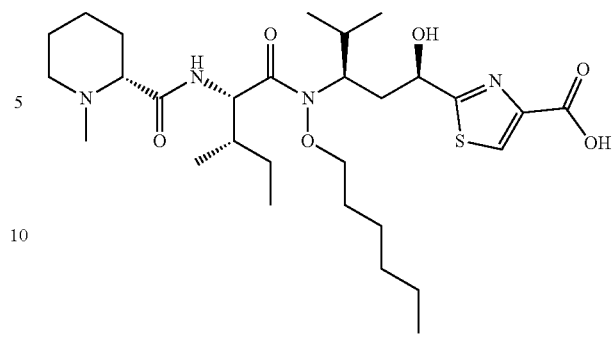

2-((1R,3R)-3-((2S,3S)—N-(Hexyloxy)-3-methyl-2-((R)-1-methylpiperidine-2-carboxamido)pentanamido)-1-hydroxy-4-methylpentyl)thiazole-4-carboxylic acid (IIa)

Following the general procedure for Intermediate II, IIa (0.25 g, 66% yield) was obtained as a white solid. ESI m/z: 583 (M+H)+. $^1$H NMR (400 MHz, methanol$_{d4}$) δ 8.05 (s, 1H), 4.77 (d, J=6.9 Hz, 1H), 4.34-4.11 (m, 2H), 3.88 (d, J=10.1 Hz, 1H), 3.73 (t, J=9.8 Hz, 1H), 3.46 (d, J=12.9 Hz, 1H), 2.99 (t, J=11.9 Hz, 1H), 2.74 (s, 3H), 2.74-2.62 (m, 1H), 2.24-2.15 (m, 2H), 2.02-1.86 (m, 4H), 1.83-1.71 (m, 6H), 1.40-1.50 (m, 2H), 1.23-1.4 (m, 6H), 1.06-0.90 (m, 17H) ppm.

2-((1R,3R)-1-Hydroxy-4-methyl-3-((2S,3S)-3-methyl-2-((R)-1-methylpiperidine-2-carboxamido)-N-(3-(4-nitrobenzyloxy)propoxy)pentanamido)pentyl)thiazole-4-carboxylic acid (Ib)

Following the general procedure for Intermediate II, Ib (0.10 g, 81% yield) was obtained as a white solid. ESI m/z: 692 (M+H)+. $^1$H NMR (500 MHz, DMSO$_{d6}$) δ 8.26 (s, 1H), 8.17 (d, J=8.5 Hz, 2H), 7.60 (d, J=8.5 Hz, 3H), 6.27 (brs, 1H), 4.74 (t, J=8.5 Hz, 1H), 4.66 (s, 2H), 4.63 (d, J=8.0 Hz, 1H), 4.32-4.28 (m, 1H), 4.20-4.15 (m, 1H), 4.02 (brs, 1H), 3.73-3.62 (m, 3H), 2.86-2.83 (m, 1H), 2.55-2.53 (m, 1H), 2.47-2.41 (m, 1H), 2.10 (s, 3H), 2.01-1.94 (m, 4H), 1.83-1.78 (m, 2H), 1.61-1.52 (m, 3H), 1.47-1.35 (m, 3H), 1.16-1.04 (m, 2H), 0.86 (d, J=6.5 Hz, 9H), 0.79 (t, J=7.5 Hz, 3H)

ppm. Chiral SFC >95% (AD-H, AS-H, and OJ-H), R$_t$: 2.05 min (AD-H), 2.66 min (AS-H), and 1.77 min (OJ-H).

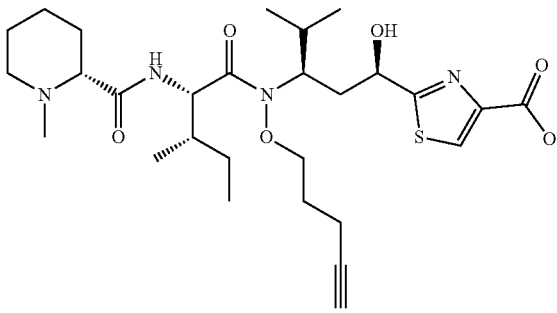

2-((1R,3R)-1-Hydroxy-4-methyl-3-((2S,3S)-3-methyl-2-((R)-1-methylpiperidine-2-carboxamido)-N-(pent-4-ynyloxy)pentanamido)pentyl)thiazole-4-carboxylic acid (Ic)

Following the general procedure for Intermediate II, IIc (37 mg, 90% yield) was obtained as a white solid. ESI m/z: 565 (M+H)$^+$.

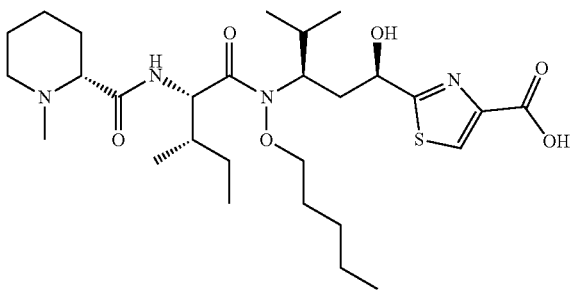 [SMILES: CCCCCON(C(=O)[C@@H](NC(=O)[C@H]1CCCCN1C)[C@@H](C)CC)[C@H](C[C@@H](O)c1nc(C(=O)O)cs1)C(C)C]

2-((1R,3R)-1-Hydroxy-4-methyl-3-((2S,3S)-3-methyl-2-((R)-1-methylpiperidine-2-carboxamido)-N-(pentyloxy)pentanamido)pentyl)thiazole-4-carboxylic acid (If)

Following the general procedure for Intermediate II, IIf (20 mg, 88% yield) was obtained as a white solid. ESI m/z: 569 (M+H)$^+$.

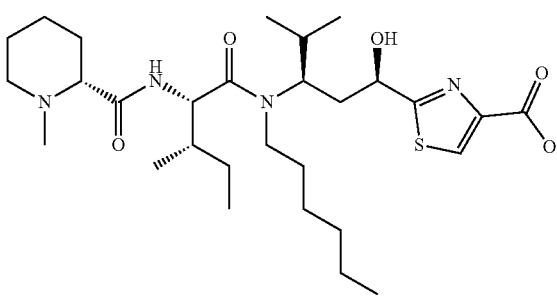

2-((1R,3R)-3-((2S,3S)—N-Hexyl-3-methyl-2-((R)-1-methylpiperidine-2-carboxamido)pentanamido)-1-hydroxy-4-methylpentyl)thiazole-4-carboxylic acid (Id)

Following the general procedure for Intermediate II, crude compound IId was obtained and used in the next step without purification.

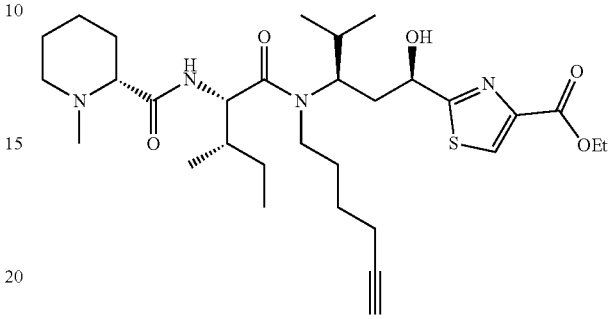

2-((1R,3R)-3-((2S,3S)—N-(Hex-5-ynyl)-3-methyl-2-((R)-1-methylpiperidine-2-carboxamido)pentanamido)-1-hydroxy-4-methylpentyl)thiazole-4-carboxylic acid (Ie)

Following the general procedure for Intermediate II, crude compound Ie (R$_f$=0.05, DCM:methanol=10:1, UV) was obtained and used in the next step without purification.

General Procedure for Intermediate III

To a solution of compound II (1.0 equiv.) in pyridine (15 mg/mL) was added acetic anhydride (3.0 equiv) by syringe at 0° C. The reaction mixture was stirred at rt for 10 hours, which was monitored by LCMS. The reaction mixture was quenched at rt with methanol (20 mL) and was then stirred at this temperature overnight. The volatiles were removed in vacuo and the residue was purified by prep-HPLC to give Intermediate III (88-99% yield) as a white solid.

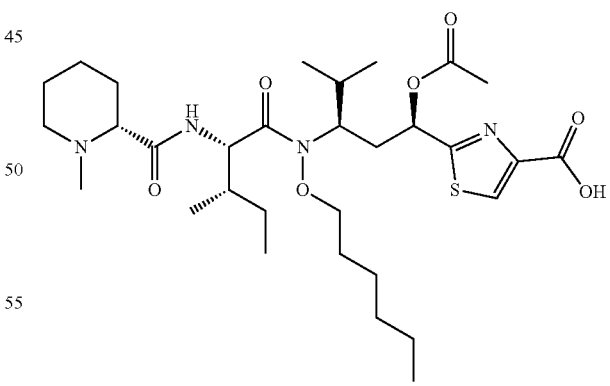

2-((1R,3R)-1-Acetoxy-3-((2S,3S)—N-(hexyloxy)-3-methyl-2-((R)-1-methylpiperidine-2-carboxamido)pentanamido)-4-methylpentyl)thiazole-4-carboxylic acid (IIIa)

Following the general procedure for Intermediate III, crude IIIa (40 mg, >99% yield) was obtained as a white solid. ESI m/z: 625.3 (M+H)⁺. ¹H NMR (400 MHz, methanol$_{d4}$) δ 8.38 (s, 1H), 7.60 (m, 1H), 4.81 (d, J=6.8 Hz, 1H), 4.01-3.95 (m, 2H), 3.67-3.63 (m, 1H), 3.49-3.46 (m, 1H), 3.33-3.25 (m, 1H), 3.21-3.12 (m, 1H), 2.91 (s, 3H), 2.66-2.60 (m, 1H), 2.38-2.19 (m, 3H), 2.15 (s, 3H), 1.99-1.19 (m, 15H), 1.06-0.92 (m, 17H) ppm.

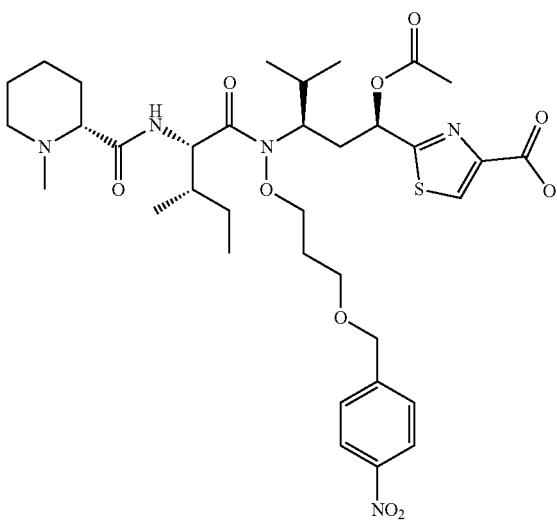

2-((8R,10R)-8-Isopropyl-7-((2S,3S)-3-methyl-2-((R)-1-methylpiperidine-2-carboxamido)pentanoyl)-1-(4-nitrophenyl)-12-oxo-2,6,11-trioxa-7-azatridecan-10-yl)thiazole-4-carboxylic acid (IIIb)

Following the general procedure for Intermediate III, IIIb (94 mg, 88% yield) was obtained as a white solid. ESI m/z: 734 (M+H)⁺. ¹H NMR (DMSO$_{d6}$, 500 MHz) δ 8.34 (s, 1H), 8.18 (d, J=8.5 Hz, 2H), 7.67-7.66 (m, 1H), 7.59 (d, J=8.5 Hz, 2H), 5.74 (d, J=11.5 Hz, 1H), 4.76 (t, J=8.5 Hz, 1H), 4.64 (s, 2H), 4.28-4.24 (m, 1H), 4.09-4.05 (m, 1H), 3.99 (brs, 1H), 3.68-3.58 (m, 3H), 2.88-2.85 (m, 1H), 2.63-2.59 (m, 1H), 2.40-2.36 (m, 1H), 2.29-2.25 (m, 1H), 2.14-2.08 (m, 7H), 1.98-1.94 (m, 3H), 1.78-1.76 (m, 1H), 1.67-1.55 (m, 3H), 1.46-1.37 (m, 3H), 1.24-1.15 (m, 1H), 1.05-0.98 (m, 1H), 0.91 (d, J=6.5 Hz, 3H), 0.86-0.84 (m, 6H), 0.80 (t, J=7.0 Hz, 3H) ppm. Chiral SFC >95% (AD-H, AS-H, OJ-H, and OD-H), R$_t$: 1.92 min (AD-H), 2.06 min (AS-H), 2.33 min(OD-H), and 1.60 min (OJ-H).

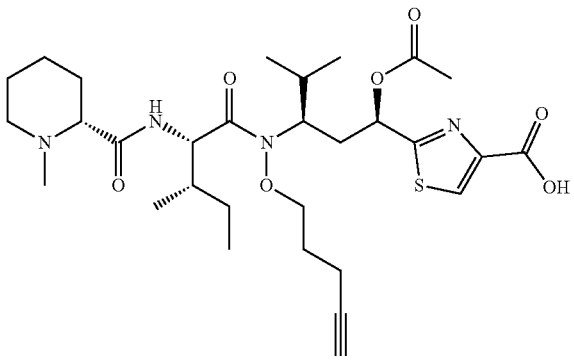 [SMILES: C#CCCCON(C(=O)[C@@H](NC(=O)[C@H]1CCCCN1C)[C@@H](C)CC)[C@H](C[C@@H](OC(C)=O)c1nc(C(=O)O)cs1)C(C)C]

2-((1R,3R)-1-Acetoxy-4-methyl-3-((2S,3S)-3-methyl-2-((R)-1-methylpiperidine-2-carboxamido)-N-(pent-4-ynyloxy)pentanamido)pentyl)thiazole-4-carboxylic acid (IIIc)

Following the general procedure for Intermediate III, IIIc (18 mg, 93% yield) was obtained as a white solid. ESI m/z: 607 (M+H)⁺.

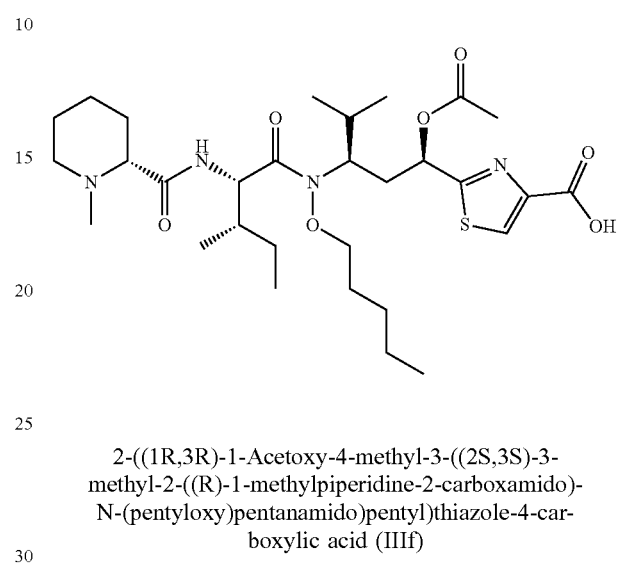

2-((1R,3R)-1-Acetoxy-4-methyl-3-((2S,3S)-3-methyl-2-((R)-1-methylpiperidine-2-carboxamido)-N-(pentyloxy)pentanamido)pentyl)thiazole-4-carboxylic acid (IIIf)

Following the general procedure for Intermediate III, IIIf (20 mg, 89% yield) was obtained as a white solid. ESI m/z: 611 (M+H)⁺.

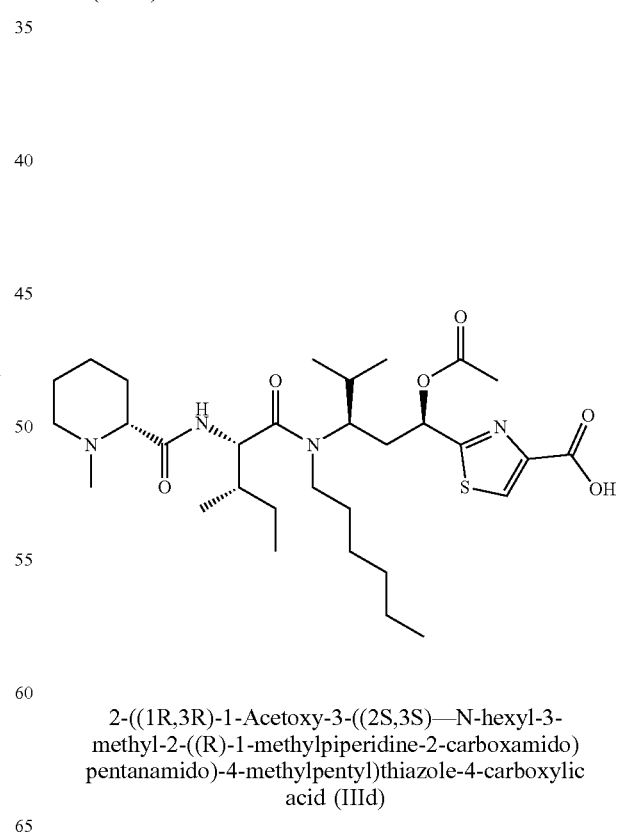

2-((1R,3R)-1-Acetoxy-3-((2S,3S)—N-hexyl-3-methyl-2-((R)-1-methylpiperidine-2-carboxamido)pentanamido)-4-methylpentyl)thiazole-4-carboxylic acid (IIId)

Following the general procedure for Intermediate III, IIId (0.81 g, 49% yield in 5 steps from 19d) was obtained.

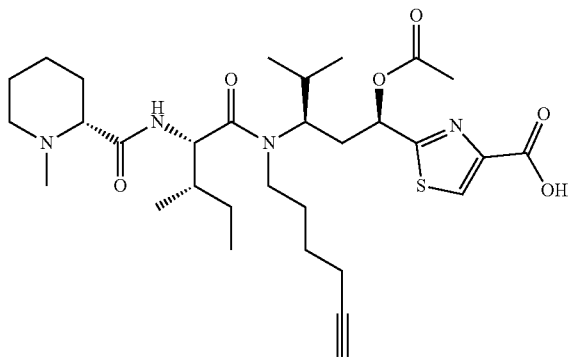 [SMILES: C#CCCCCN(C(=O)[C@@H](NC(=O)[C@H]1CCCCN1C)[C@@H](C)CC)[C@H](C[C@@H](OC(C)=O)c1nc(C(=O)O)cs1)C(C)C]

2-((1R,3R)-1-Acetoxy-3-((2S,3S)—N-(hex-5-yn-1-yl)-3-methyl-2-((R)-1-methylpiperidine-2-carboxamido)pentanamido)-4-methylpentyl)thiazole-4-carboxylic acid (IIIe)

Following the general procedure for Intermediate III, crude compound IIIe (12 g, 50% yield in 5 steps, $R_f$=0.1, DCM:methanol=10:1, UV) was obtained. ESI m/z: 603 (M−H)⁻. ¹H NMR (400 MHz, DMSO$_{d6}$) δ 8.11 (s, 1H), 7.75 (br s, 1H), 5.61 (d, 1H), 4.45 (t, 1H), 3.71 (t, 1H), 3.68-2.50 (m, 5H), 2.40-1.90 (m, 11H), 1.90-1.30 (m, 12H), 1.27-0.60 (m, 14H) ppm.

Synthesis of C-Tubulysin IV (FIG. 5)

General Procedure for IV

To a mixture of intermediate III (1.0 equiv.) and PFP (1.5 equiv.) in dry DCM (10-15 mg/mL) was added a solution of N,N'-diisopropylcarbodiimide (DIC, 1.5 equiv.) in DCM (7 mg/mL) dropwise at 0° C. by syringe. The resulting mixture was allowed to warm to rt and stirred for 16 hours, which was monitored by LCMS. The volatiles were removed in vacuo and the residue was suspended in ethyl acetate (III/ethyl acetate: 1 mg/mL). The suspension was stirred for 20 minutes and the solids were filtered off. The filtrate was concentrated in vauo to give crude pentafluorophenyl ester 28 as a pale yellow oil, which was dissolved in dry DMF (20 mg/mL). To the solution were added DIPEA (2.5 equiv.) and intermediate I (0.9-1.2 equiv.) subsequently at rt. The reaction mixture was stirred at rt overnight and deemed complete according to LCMS. For $R^4$=NHFmoc, to the reaction mixture was then added piperidine (0.5-1.0 mL) by syringe and the reaction mixture was stirred at rt for 2 hours until Fmoc was removed according to LCMS. The mixture was then directly purified by Prep-HPLC (ammonium bicarbonate system) to give IV (10-60% yield) as a white solid.

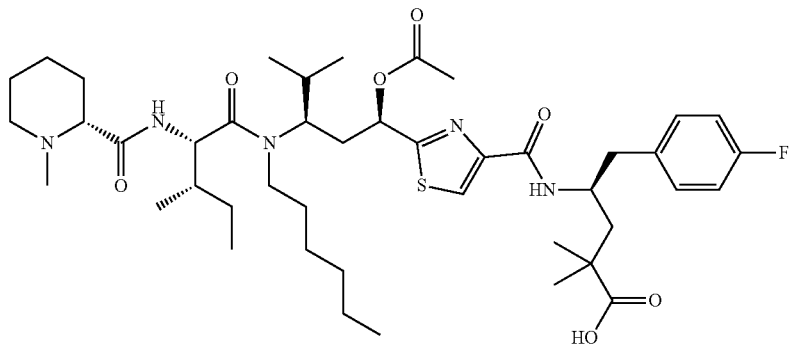

(IVa)

(2S,4R)-4-(2-((1R,3R)-1-Acetoxy-3-((2S,3S)—N-hexyl-3-methyl-2-((R)-1-methylpiperidine-2-carboxamido)pentanamido)-4-methylpentyl)thiazole-4-carboxamido)-5-(4-fluorophenyl)-2-methylpentanoic acid (IVa)

Following the general procedure for IV, IVa (17 mg, 3% yield) was obtained as a white solid. ESI m/z 816.5 (M+H)$^+$. $^1$H NMR (400 MHz, DMSO$_{d6}$) δ 8.18 (s, 1H), 7.90-7.80 (m, 1H), 7.72-7.61 (m, 1H), 7.25-7.17 (m, 2H), 7.10-7.00 (m, 2H), 5.64 (d, J=13.2 Hz, 1H), 4.48 (t, J=9.2 Hz, 1H), 4.22-4.10 (m, 1H), 3.75-3.60 (m, 1H), 3.11-2.73 (m, 4H), 2.45-2.24 (m, 3H), 2.11 (s, 3H), 2.06 (s, 3H), 2.00-1.78 (m, 5H), 1.65-1.43 (m, 7H), 1.41-1.20 (m, 9H), 1.10-0.91 (m, 8H), 0.90-0.76 (m, 10H), 0.72-0.62 (m, 3H) ppm. Anal. HPLC: >99%, R$_t$: 8.51 min (Method A).

(IVb) (4S)-4-({2-[(1R,3R)-1-(Acetyloxy)-3-[(2S, 3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-2,2-dimethyl-5-phenylpentanoic acid (IVb)

Following the general procedure for IV, IVb (2.0 mg, 10% yield) was obtained as a white solid. ESI m/z 808.3 (M+H)$^+$. $^1$H NMR (500 MHz, DMSO$_{d6}$) δ 8.15 (s, 1H), 7.72 (s, 2H), 7.28-7.21 (m, 2H), 7.19-7.16 (d, J=5.9 Hz, 2H), 5.65 (d, J=13.2 Hz, 1H), 4.46 (t, J=9.4 Hz, 1H), 4.34-4.24 (m, 1H), 3.76-3.70 (m, 1H), 3.03-2.97 (m, 1H), 2.85-2.81 (m, 2H), 2.76-2.72 (m, 2H), 2.29-2.17 (m, 4H), 2.13 (s, 3H), 2.07 (s, 3H), 1.97-1.84 (m, 4H), 1.84-1.80 (m, 3H), 1.61 (d, J=10.3 Hz, 2H), 1.54-1.32 (m, 7H), 1.19-1.06 (m, 10H), 0.95 (d, J=6.0 Hz, 3H), 0.86-0.80 (m, 6H), 0.69 (d, J=6.0 Hz, 3H) ppm. Anal. HPLC: >99%, R$_t$: 8.51 min (Method A).

(IVc) (4S)-4-({2-[(1R,3R)-1-(Acetyloxy)-3-[(2S, 3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-(4-fluorophenyl)-2,2-dimethylpentanoic acid (IVc)

Following the general procedure for IV, IVc (3.1 mg, 16% yield) was obtained as a white solid. ESI m/z 826.2 (M+H)$^+$. $^1$H NMR (500 MHz, DMSO$_{d6}$) δ 8.14 (s, 1H), 7.72-7.68 (m, 2H), 7.21-7.18 (m, 2H), 7.07-7.03 (m, 2H), 5.65 (d, J=13.0 Hz, 1H), 4.46 (t, J=9.5 Hz, 1H), 4.26-4.23 (m, 1H), 3.75-3.69 (m, 1H), 3.03-2.97 (m, 1H), 2.87-2.79 (m, 2H), 2.76-2.72 (m, 2H), 2.29-2.18 (m, 4H), 2.13 (s, 3H), 2.09 (s, 3H), 1.97-1.84 (m, 4H), 1.77-1.68 (m, 3H), 1.62-1.61 (m, 2H), 1.54-1.37 (m, 6H), 1.27-1.21 (m, 1H), 1.19-1.11 (m, 2H), 1.08-1.06 (m, 6H), 0.96-0.94 (m, 4H), 0.84-0.80 (m, 6H), 0.70-0.68 (m, 3H) ppm. Anal. HPLC: >99%, R$_t$: 8.44 min (Method B).

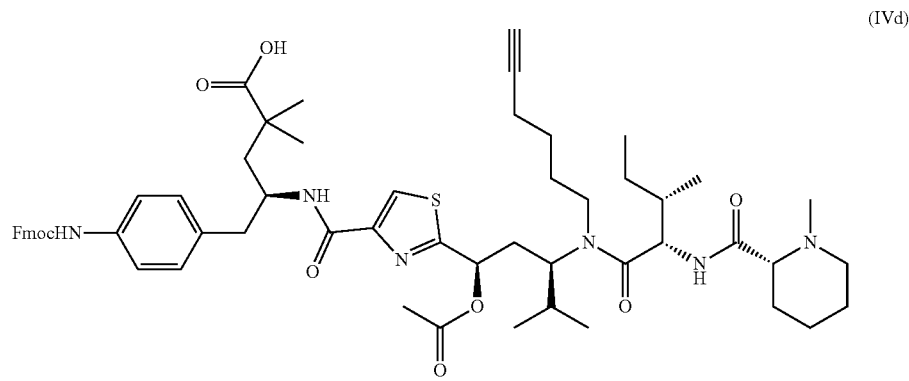

(IVd)

(4S)-4-({2-[(1R,3R)-1-(Acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-(4-aminophenyl)-2,2-dimethylpentanoic acid (IVd)

Following the general procedure for IV, IVd (5.8 mg, 14% yield) was obtained as a white solid. ESI m/z 412.3 (M/2+H)$^+$, 823.3 (M+H)$^+$(10%). $^1$H NMR (500 MHz, DMSO$_{d6}$) δ 8.16 (s, 1H), 7.77-7.61 (m, 2H), 6.82 (d, J=8.5 Hz, 2H), 6.45 (d, J=8.0 Hz, 2H), 5.66 (d, J=13.5 Hz, 1H), 4.84 (s, 2H), 4.47 (t, J=9.5 Hz, 1H), 4.19-4.16 (m, 1H), 3.76-3.71 (m, 1H), 3.05-2.99 (m, 1H), 2.85-2.82 (m, 1H), 2.74 (t, J=2.5 Hz, 1H), 2.64 (dd, J=13.5, 6.0 Hz, 1H), 2.58-2.53 (m, 1H), 2.31-2.14 (m, 7H), 2.07 (s, 3H), 1.87-1.72 (m, 7H), 1.69-1.52 (m, 10H), 1.19-1.08 (m, 2H), 1.05 (d, J=7.5 Hz, 6H), 0.96 (d, J=7.5 Hz, 3H), 0.85-0.81 (m, 6H), 0.69 (d, J=6.0 Hz, 3H) ppm. Anal. HPLC: >99%, R$_t$: 6.92 min (Method A).

(IVe) (2S,4R)-4-({2-[(1R,3R)-1-(Acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-(4-fluorophenyl)-2-methylpentanoic acid (IVe)

Following the general procedure for IV, IVe (9.0 mg, 45% yield) was obtained as a white solid. ESI m/z 812.4 (M+H)$^+$. $^1$H NMR (500 MHz, methanol$_{d4}$) δ 8.11 (s, 1H), 7.26 (dd, J=8.4, 5.5 Hz, 2H), 6.98 (s, 2H), 5.80 (d, J=13.0 Hz, 1H), 4.93 (m, 1H), 4.88-4.84 (m, 1H), 4.66 (d, J=9.3 Hz, 1H), 4.36 (s, 1H), 3.86 (s, 1H), 3.19-3.01 (m, 2H), 2.92 (d, J=6.8 Hz, 2H), 2.55 (s, 1H), 2.44-2.30 (m, 6H), 2.27-2.22 (m, 2H), 2.19 (s, 3H), 2.05-1.96 (m, 3H), 1.95-1.86 (m, 3H), 1.82-1.58 (m, 9H), 1.45-1.36 (m, 1H), 1.27-1.20 (m, 1H), 1.19 (d, J=7.1 Hz, 3H), 1.07 (d, J=6.5 Hz, 3H), 1.01 (d, J=6.8 Hz, 3H), 0.95 (m, 3H), 0.85 (d, J=6.1 Hz, 3H) ppm. Anal. HPLC: >99%, R$_t$: 8.14 min (Method A). Chiral HPLC: >99%, R$_t$: 1.05 min (AD); >99%, 1.42 min (AS); >99%, 0.92 min (OD); >99%, 2.92 min (OJ).

(IVf) (2S,4R)-4-({2-[(1R,3R)-1-(Acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-(4-hydroxyphenyl)-2-methylpentanoic acid (IVf)

Following the general procedure for IV, IVf (8.5 mg, 43% yield) was obtained as a white solid. ESI m/z 810.3 (M+H)$^+$. $^1$H NMR (400 MHz, DMSO$_{d6}$) δ 9.19 (s, 1H), 8.18 (s, 1H), 7.71 (d, J=10.0 Hz, 1H), 6.96 (d, J=10.0 Hz, 2H), 6.63 (d, J=8.4 Hz, 2H), 5.64 (d, J=12.9 Hz, 1H), 4.46 (t, J=9.5 Hz, 1H), 4.14 (s, 1H), 3.74 (s, 1H), 3.01 (s, 1H), 2.82 (d, J=11.4 Hz, 1H), 2.75-2.70 (m, 2H), 2.68-2.62 (m, 1H), 2.47-2.45 (m, 1H), 2.39-2.15 (m, 6H), 2.13-2.08 (m, 4H), 2.06 (s, 3H), 1.95-1.72 (m, 6H), 1.62-1.60 (m, 2H), 1.54-1.32 (m, 7H), 1.20-1.08 (m, 2H), 1.05 (d, J=7.1 Hz, 3H), 0.96 (d, J=6.4 Hz, 3H), 0.85-0.80 (m, 6H), 0.68 (d, J=6.1 Hz, 3H) ppm. Anal. HPLC: >99%, R$_t$: 6.83 min (Method B).

(IVg) (2S,4R)-4-({2-[(1R,3R)-1-(Acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-(4-aminophenyl)-2-methylpentanoic acid (IVg)

Following the general procedure for IV, IVg (6.0 mg, 30% yield) was obtained as a white solid. ESI m/z 809.2 (M+H)$^+$. $^1$H NMR (500 MHz, DMSO$_{d6}$) δ 8.18 (s, 1H), 7.89 (s, 1H), 7.70 (d, J=9.3 Hz, 1H), 6.82 (d, J=8.3 Hz, 2H), 6.45 (d, J=8.3 Hz, 2H), 5.65 (d, J=13.0 Hz, 1H), 4.84 (s, 2H), 4.46 (t, J=9.5 Hz, 1H), 4.09 (s, 1H), 3.74 (s, 1H), 3.05-2.97 (m, 1H), 2.83-2.80 (m, 1H), 2.74 (t, J=8.3 Hz, 1H), 2.71-2.63 (m, 3H), 2.60-2.56 (m, 1H), 2.37-2.33 (m, 1H), 2.28-2.24 (m, 2H), 2.19-2.16 (m, 1H), 2.12 (s, 3H), 2.06 (s, 3H), 1.98-1.73 (m, 7H), 1.62-1.60 (m, 2H), 1.49-1.44 (m, 5H), 1.39-1.34 (m, 1H), 1.23 (s, 3H), 1.03 (d, J=7.5 Hz, 3H), 0.96 (d, J=6.0 Hz, 3H), 0.85-0.80 (m, 6H), 0.68 (d, J=6.0 Hz, 3H) ppm. Anal. HPLC: >99%, R$_t$: 6.87 min (Method B). Chiral HPLC: >99%, R$_t$: 0.8 min (AD); >99%, 1.24 min (AS); >99%, 3.1 min (OD); >99%, 1.47 min (OJ).

Synthesis of C-Tubulysin VII and VIII (FIG. 5A)

General Procedure for VII and VIII

To a solution of compound A-1 (1.0 equiv.) in DCM (50 mM) were added compound A-2 (1.5 equiv.) and DIPEA (4.0 equiv.), and the reaction mixture was stirred at RT for 4 hours, which was monitored by LCMS. The resulting mixture was directly purified by reversed phase flash chromatography (0-30% acetonitrile in aq. TFA (0.01%)) to give VII or VIII (7-57% yield) as an off-white solid.

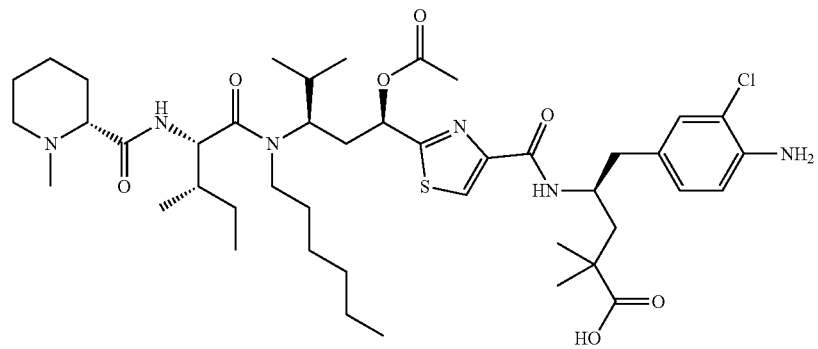 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(N)c(Cl)c2)CC(C)(C)C(=O)O)cs1)C(C)C]

(4S)-4-({2-[(1R,3R)-1-(Acetyloxy)-3-[(2S,3S)—N-hexyl-3-methyl-2-{[(2R)-1-methylpiperidin-2-yl]formamido}pentanamido]-4-methylpentyl]-1,3-thiazol-4-yl}formamido)-5-(4-amino-3-chlorophenyl)-2,2-dimethylpentanoic acid (VII)

Following the general procedure for VII and VIII from compound A-1a treated with compound A-2b, payload VII (5.0 mg, 14% yield) was obtained as a white solid. ESI m/z: 861.3 (M+H)$^+$. $^1$H NMR (400 MHz, DMSO$_{d6}$) δ 8.16 (s, 1H), 7.67 (d, J=9.6 Hz, 1H), 7.56 (br s, 1H), 7.21 (br s, 1H), 6.94 (d, J=0.8 Hz, 1H), 6.82 (d, J=8.4 Hz, 1H), 6.65 (d, J=8.4 Hz, 1H), 5.65 (d, J=13.2 Hz, 1H), 5.32 (t, J=5.2 Hz, 1H), 5.15 (s, 2H), 4.48 (t, J=9.6 Hz, 1H), 4.22-4.18 (m, 1H), 3.74-3.70 (m, 1H), 3.03-2.96 (m, 1H), 2.83 (d, J=11.2 Hz, 1H), 2.60 (d, J=6.0 Hz, 1H), 2.33-2.16 (m, 3H), 2.14 (s, 3H), 2.07 (s, 3H), 2.03-1.90 (m, 3H), 1.76-1.55 (m, 3H), 1.33-1.20 (m, 10H), 1.16-1.13 (m, 2H), 1.07-1.04 (m, 7H), 0.95 (d, J=6.4 Hz, 3H), 0.86-0.80 (m, 11H), 0.68 (d, J=5.6 Hz, 3H) ppm.

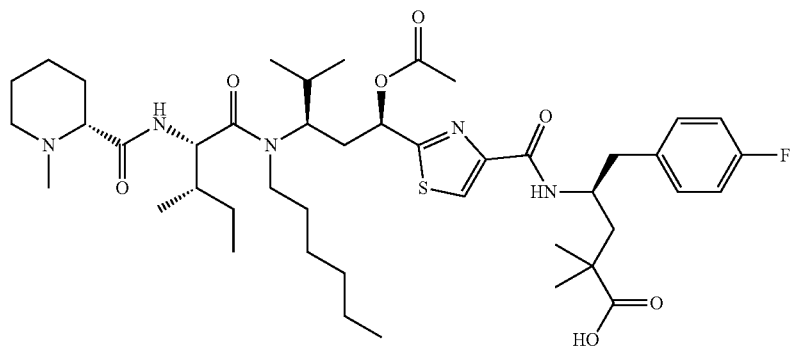 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(F)cc2)CC(C)(C)C(=O)O)cs1)C(C)C]

(4S)-4-({2-[(1R,3R)-1-(Acetyloxy)-3-[(2S,3S)—N-hexyl-3-methyl-2-{[(2R)-1-methylpiperidin-2-yl]formamido}pentanamido]-4-methylpentyl]-1,3-thiazol-4-yl}formamido)-5-(4-fluorophenyl)-2,2-dimethylpentanoic acid (VIII)

Following the general procedure for VII and VIII from compound A-1a treated with compound A-2c, payload VIII (7.0 mg, 26% yield) was obtained as a white solid. ESI m/z: 830.5 (M+H)$^+$. $^1$H NMR (400 MHz, DMSO$_{d6}$) δ 8.16 (s, 1H), 7.67 (d, J=9.6 Hz, 1H), 7.19 (dd, J=8.0 and 6.0 Hz, 2H), 7.06 (t, J=8.8 Hz, 2H), 5.64 (d, J=12.0 Hz, 1H), 4.48 (t, J=9.2 Hz, 1H), 4.27-4.23 (m, 1H), 3.73-3.65 (m, 1H), 3.02-2.93 (m, 1H), 2.84-2.75 (m, 3H), 2.33-1.83 (m, 12H), 1.90-1.40 (m, 8H), 1.28-1.23 (m, 11H), 1.17-1.13 (m, 1H), 1.06 (d, J=4.0 Hz, 6H), 0.96 (d, J=6.4 Hz, 3H), 0.87-0.79 (m, 9H), 0.68 (d, J=6.0 Hz, 3H) ppm.

Synthesis of C-triazole Tubulysin payloads IV
(FIG. 6A)

IVh

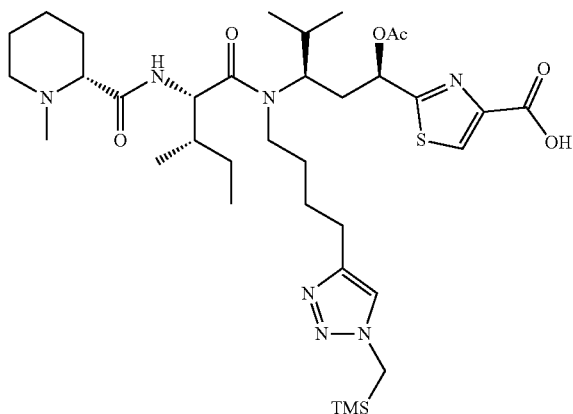 [SMILES: CC[C@H](C)[C@H](NC(=O)[C@H]1CCCCN1C)C(=O)N(CCCCc1cn(C[Si](C)(C)C)nn1)[C@H](C[C@@H](OC(C)=O)c1nc(C(=O)O)cs1)C(C)C]

2-((1R,3R)-1-acetoxy-4-methyl-3-((2S,3S)-3-
methyl-2-((R)-1-methylpiperidine-2-carboxamido)-
N-(4-(1-((trimethylsilyl)methyl)-1H-1,2,3-triazol-4-
yl)butyl)pentanamido)pentyl)thiazole-4-carboxylic
acid (IIIg1)

To a mixture of IIIe (80 mg, 132 μmol), trimethylsilylmethyl azide (34 mg, 264 μmol), and sodium ascorbate (80 mg, 132 μmol) in THF (3 mL) and water (1 mL) was added 1 drop of aqueous copper sulfate (2.1 mg, 13 μmol). The resulting mixture was stirred at rt for 1 hr, and then filtered and concentrated to afford IIIg1 (87 mg, 89.6% yield) as a white solid. ESI m/z: 734.1 (M+H)+.

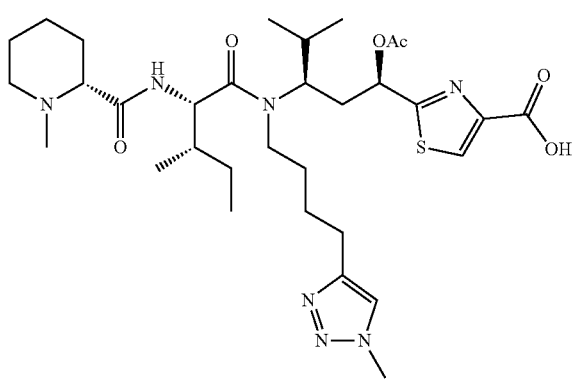 [SMILES: CC[C@H](C)[C@H](NC(=O)[C@H]1CCCCN1C)C(=O)N(CCCCc1cn(C)nn1)[C@H](C[C@@H](OC(C)=O)c1nc(C(=O)O)cs1)C(C)C]

2-((1R,3R)-1-acetoxy-4-methyl-3-((2S,3S)-3-
methyl-N-(4-(1-methyl-1H-1,2,3-triazol-4-yl)butyl)-
2-((R)-1-methylpiperidine-2-carboxamido)pentanamido)pentyl)thiazole-4-carboxylic acid (IIIg2)

A mixture of IIIg1 (87 mg, 118 μmol) and CsF (72 mg, 474 μmol) in DMF (1 mL) was stirred at 60° C. for 1 h. The reaction solution was purified by silica gel column chromatography (DCM/MeOH 15:1) to afford IIIg2 (59 mg, 75% yield) as a white solid. ESI m/z: 663.3 (M+H)+.

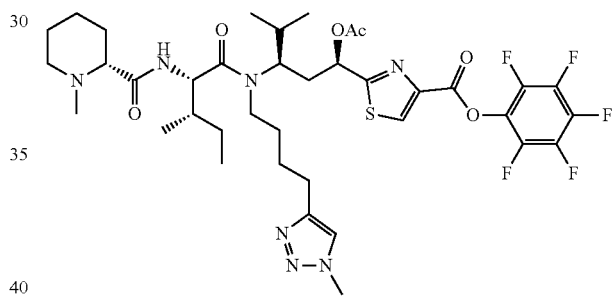

Perfluorophenyl 2-((1R,3R)-1-acetoxy-4-methyl-3-
((2S,3S)-3-methyl-N-(4-(1-methyl-1H-1,2,3-triazol-
4-yl)butyl)-2-((R)-1-methylpiperidine-2-carbox-
amido)pentanamido)pentyl)thiazole-4-carboxylate
(31)

A mixture of IIIg2 (59 mg, 89 μmol), PFP (33 mg, 178 μmol) and DIC (23 mg, 178 μmol) in THF (2 mL) was stirred at 25° C. for 18 hrs. The reaction solution was purified by silica gel column chromatography (DCM/MeOH 15:1) to afford 31 (59 mg, 75% yield) as a white solid. ESI m/z: 828.3 (M+H)+.

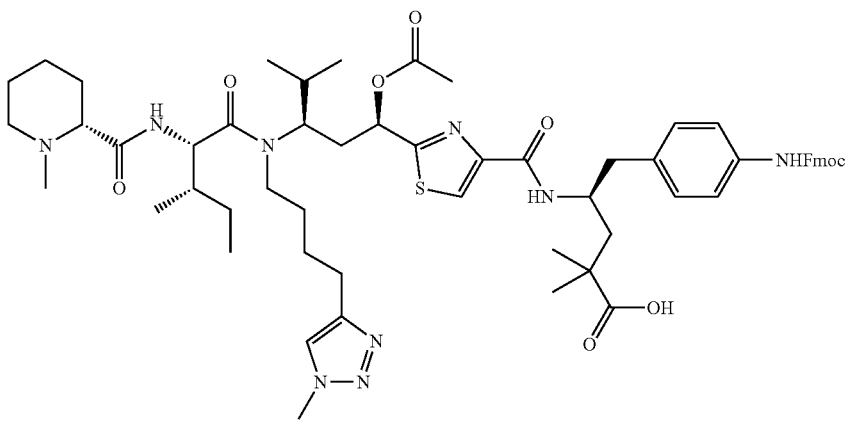

(4S)-4-({2-[(1R,3R)-1-(acetyloxy)-4-methyl-3-[(2S,3S)-3-methyl-N-[4-(1-methyl-1H-1,2,3-triazol-4-yl)butyl]-2-{[(2R)-1-methylpiperidin-2-yl]formamido}pentanamido]pentyl]-1,3-thiazol-4-yl}formamido)-5-(4-{[(9H-fluoren-9-ylmethoxy)carbonyl]amino}phenyl)-2,2-dimethylpentanoic acid (32)

A mixture of compound 31 (40 mg, 40 μmol), DIPEA (15 mg, 119 μmol), and Intermediate Ic (22 mg, 119 umol) in DMF (3 mL) was stirred at 25° C. for 16 hrs and the reaction solution was purified by RP chromatography (CH$_3$CN/H$_2$O, 0-100% CH$_3$CN) to afford 32 (23 mg, 53% yield) as a white solid. ESI m/z: 1102.1 (M+H)$^+$.

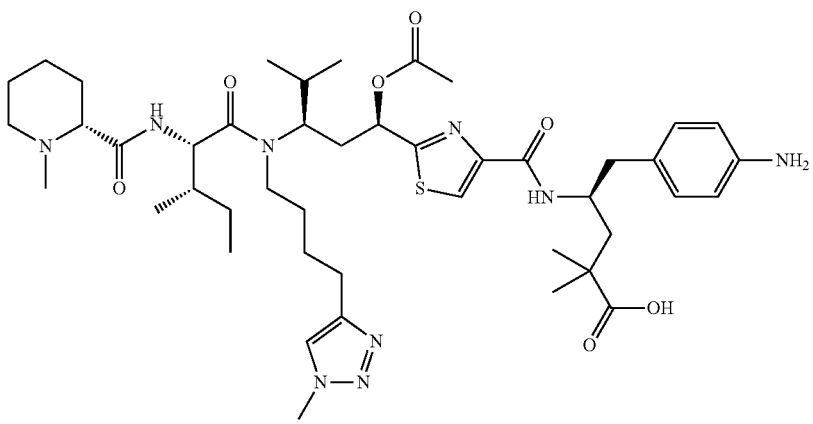 [SMILES: CC[C@H](C)[C@H](NC(=O)[C@H]1CCCCN1C)C(=O)N(CCCCc1cn(C)nn1)[C@H](C[C@@H](OC(C)=O)c1nc(C(=O)N[C@@H](Cc2ccc(N)cc2)CC(C)(C)C(=O)O)cs1)C(C)C]

(S)-4-(2-((1R,3R)-1-acetoxy-4-methyl-3-((2S,3S)-3-methyl-N-(4-(1-methyl-1H-1,2,3-triazol-4-yl)butyl)-2-((R)-1-methylpiperidine-2-carboxamido)pentanamido)pentyl)thiazole-4-carboxamido)-5-(4-aminophenyl)-2,2-dimethylpentanoic acid (IVh)

A mixture of compound 32 (23 mg, 21 umol) and piperidine (5 mg, 63 μmol) in DMF (1 mL) was stirred at 25° C. for 16 hrs and the reaction solution was directly purified by RP chromatography (0-100% $CH_3CN$ in $H_2O$) to afford IVh (5 mg, 27% yield) as a white solid. EIS m/z: 880.4 $(M+H)^+$. $^1H$ NMR (500 MHz, methanol$_{d4}$) δ 8.10 (s, 1H), 7.75 (s, 1H), 6.96 (d, J=8.2 Hz, 2H), 6.64 (d, J=8.2 Hz, 2H), 5.76 (d, J=12.5 Hz, 1H), 4.57 (d, J=9.3 Hz, 1H), 4.36-4.30 (m, 1H), 4.04 (s, 3H), 3.89-3.78 (m, 1H), 3.19-3.08 (m, 2H), 3.00-2.93 (m, 1H), 2.81-2.63 (m, 5H), 2.38-2.33 (m, 1H), 2.23 (s, 3H), 2.20-2.15 (m, 4H), 2.09-1.86 (m, 4H), 1.84-1.63 (m, 9H), 1.61-1.48 (m, 3H), 1.36-1.27 (m, 1H), 1.13 (s, 3H), 1.10 (s, 3H), 1.05 (d, J=6.4 Hz, 3H), 0.92-0.87 (m, 6H), 0.86-0.80 (m, 3H) ppm.

General Procedure for IVj-p

To a mixture of Fmoc-IVd (1 equiv.), $R^5$-azide (2 equiv.), and sodium ascorbate (2 equiv.) in THF (0.3 mL per mg of Fmoc-IVd) and water (0.1 mL per mg of Fmoc-IVd) was added aqueous copper sulfate (0.1 equiv., 1 M). The resulting mixture was stirred at rt for 16 h. The mixture was directly purified by RP chromatography to afford 32 (64%-76% yield) as a white solid. Then 32 was dissolved in DMF and piperidine (0.1-1.0 mL, excess) was added by syringe. The reaction mixture was stirred at rt for 2 hours until Fmoc was removed according to LCMS. The mixture was then directly purified by Prep-HPLC (method B) to give IVj-p as a white solid.

(IVj) (S)-4-(2-((1R,3R)-3-((2S,3S)—N-(4-(1H-1,2,3-triazol-5-yl)butyl)-3-methyl-2-((R)-1-methylpiperidine-2-carboxamido)pentanamido)-1-acetoxy-4-methylpentyl)thiazole-4-carboxamido)-5-(4-aminophenyl)-2,2-dimethylpentanoic acid (IVj)

Following the general procedure for IVj-p, IVj (2 mg, 35% yield) was obtained as a white solid. ESI m/z: 866.5 $(M+H)^+$. $^1H$ NMR (400 MHz, DMSO$_{d6}$) δ 8.15 (s, 1H), 7.70-7.62 (m, 1H), 7.48 (s, 1H), 6.82 (d, J=8.2 Hz, 2H), 6.45 (d, J=8.1 Hz, 2H), 5.61-5.55 (m, 1H), 5.32 (s, 1H), 4.85 (s, 2H), 4.38 (s, 1H), 4.12-4.03 (m, 1H), 3.77-3.63 (m, 1H), 3.11-2.96 (m, 1H), 2.87-2.79 (m, 1H), 2.74 (s, 2H), 2.69 (s, 1H), 2.67 (s, 1H), 2.33 (s, 1H), 2.25-2.19 (m, 1H), 2.11 (s, 3H), 2.06 (s, 3H), 2.00 (d, J=7.4 Hz, 2H), 1.97-1.89 (m, 3H), 1.83-1.73 (m, 3H), 1.63 (s, 3H), 1.47 (s, 4H), 1.45-1.44 (m, 1H), 1.27 (s, 2H), 1.18-1.10 (m, 2H), 0.96 (t, J=9.0 Hz, 9H), 0.85 (s, 3H), 0.79 (s, 3H), 0.66 (s, 3H) ppm.

(IVk) (S)-4-(2-((1R,3R)-1-acetoxy-3-((2S,3S)—N-(4-(1-(2-aminoethyl)-1H-1,2,3-triazol-5-yl)butyl)-3-methyl-2-((R)-1-methylpiperidine-2-carboxamido)pentanamido)-4-methylpentyl)thiazole-4-carboxamido)-5-(4-aminophenyl)-2,2-dimethylpentanoic acid (IVk)

Following the general procedure for IVj-p, IVk (2 mg, 36% yield) was obtained as a white solid. ESI m/z: 910.5 $(M+H)^+$. $^1H$ NMR (400 MHz, DMSO$_{d6}$) δ 8.17 (s, 1H), 7.83 (d, J=10.6 Hz, 1H), 7.67 (s, 1H), 6.79 (d, J=8.1 Hz, 2H), 6.44 (d, J=8.2 Hz, 2H), 5.64 (s, 1H), 5.32 (s, 1H), 4.85 (s, 2H), 4.43 (s, 1H), 4.28 (s, 2H), 4.15 (s, 1H), 3.06-3.02 (m, 1H), 2.94 (s, 2H), 2.79 (s, 4H), 2.67 (s, 3H), 2.33 (s, 1H), 2.12 (t, J=11.7 Hz, 4H), 2.06 (s, 3H), 1.99 (s, 4H), 1.86-1.77 (m, 3H), 1.59 (s, 6H), 1.50 (s, 4H), 1.45-1.35 (m, 3H), 0.97 (dd, J=14.6, 5.2 Hz, 8H), 0.85 (s, 1H), 0.78 (dd, J=16.6, 7.2 Hz, 6H), 0.66 (s, 3H) ppm.

(IVi) (S)-4-(2-((1R,3R)-1-acetoxy-3-((2S,3S)—N-(4-(1-(2-hydroxyethyl)-1H-1,2,3-triazol-5-yl)butyl)-3-methyl-2-((R)-1-methylpiperidine-2-carboxamido)pentanamido)-4-methylpentyl)thiazole-4-carboxamido)-5-(4-aminophenyl)-2,2-dimethylpentanoic acid (IVi)

Following the general procedure for IVj-p, IVi (2 mg, 36% yield) was obtained as a white solid. ESI m/z: 910.4 $(M+H)^+$. $^1H$ NMR (400 MHz, DMSO$_{d6}$) δ 8.18 (s, 1H), 7.96 (s, 1H), 7.84 (s, 1H), 7.66 (s, 1H), 6.80 (d, J=8.2 Hz, 2H), 6.43 (d, J=8.2 Hz, 2H), 5.62 (d, J=12.5 Hz, 1H), 4.84 (s, 2H), 4.44 (s, 1H), 4.31 (t, J=5.4 Hz, 2H), 4.12 (s, 1H), 3.74 (d, J=5.5 Hz, 2H), 3.04 (s, 2H), 2.82 (d, J=11.7 Hz, 1H), 2.69 (d, J=20.5 Hz, 5H), 2.29 (d, J=28.0 Hz, 2H), 2.12 (s, 3H), 2.06 (s, 3H), 2.00 (d, J=7.2 Hz, 1H), 1.92 (d, J=11.8 Hz, 2H), 1.82 (s, 4H), 1.62 (s, 4H), 1.53-1.50 (m, 1H), 1.46 (s, 3H), 1.38-1.34 (m, 1H), 1.23 (s, 3H), 1.17-1.12 (m, 1H), 0.98 (d, J=6.7 Hz, 5H), 0.95 (d, J=6.4 Hz, 3H), 0.78 (dd, J=13.5, 6.8 Hz, 6H), 0.67 (s, 3H) ppm.

(IVm) (S)-4-(2-((1R,3R)-1-acetoxy-3-((2S,3S)—N-(4-(1-(carboxymethyl)-1H-1,2,3-triazol-4-yl)butyl)-3-methyl-2-((R)-1-methylpiperidine-2-carboxamido)pentanamido)-4-methylpentyl)thiazole-4-carboxamido)-5-(4-aminophenyl)-2,2-dimethylpentanoic acid (IVm)

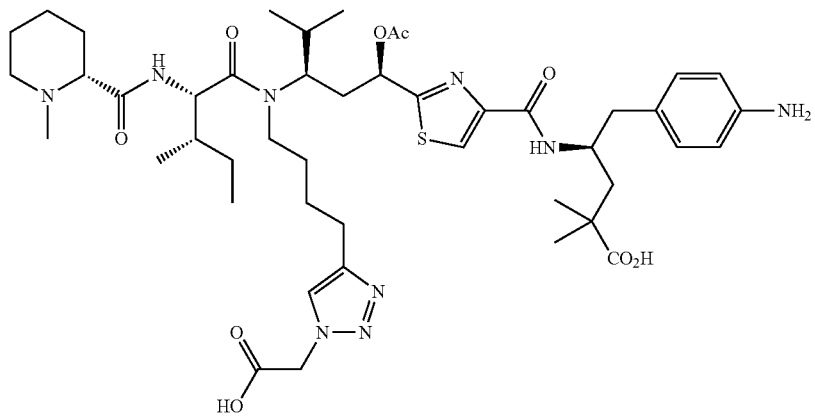 [SMILES: CC[C@H](C)[C@H](NC(=O)[C@H]1CCCCN1C)C(=O)N(CCCCc1cn(CC(=O)O)nn1)[C@H](C[C@@H](OC(C)=O)c1nc(C(=O)N[C@@H](Cc2ccc(N)cc2)CC(C)(C)C(=O)O)cs1)C(C)C]

Following the general procedure for IVj-p, IVm (2 mg, 16% yield in 2 steps) was obtained as a white solid. ESI m/z: 924.2 (M+H)+. $^1$H NMR (400 MHz, DMSO$_{d6}$) δ 9.86 (s, 1H), 8.37-8.23 (m, 1H), 8.15 (s, 1H), 8.13-7.81 (m, 1H), 7.75 (s, 1H), 7.62 (s, 1H), 6.79 (d, J=8.3 Hz, 2H), 6.42 (d, J=8.2 Hz, 2H), 5.61 (d, J=13.2 Hz, 1H), 5.31 (s, 1H), 4.93 (s, 2H), 4.48 (s, 1H), 4.17 (s, 3H), 3.66 (s, 2H), 3.00 (s, 3H), 2.66 (s, 2H), 2.32 (s, 1H), 2.22 (s, 3H), 2.12 (s, 3H), 1.99 (d, J=7.5 Hz, 2H), 1.91-1.79 (m, 4H), 1.62 (d, J=5.3 Hz, 4H), 1.54 (d, J=5.2 Hz, 4H), 1.44 (s, 4H), 1.01 (d, J=2.3 Hz, 6H), 0.95 (d, J=6.5 Hz, 3H), 0.80 (t, J=5.6 Hz, 6H), 0.69 (s, 3H) ppm.

(IVn) (S)-4-(2-((1R,3R)-1-Acetoxy-3-((2S,3S)—N-(4-(1-(3-carboxypropyl)-1H-1,2,3-triazol-4-yl)butyl)-3-methyl-2-((R)-1-methylpiperidine-2-carboxamido)pentanamido)-4-methylpentyl)thiazole-4-carboxamido)-5-(4-aminophenyl)-2,2-dimethylpentanoic acid (IVn)

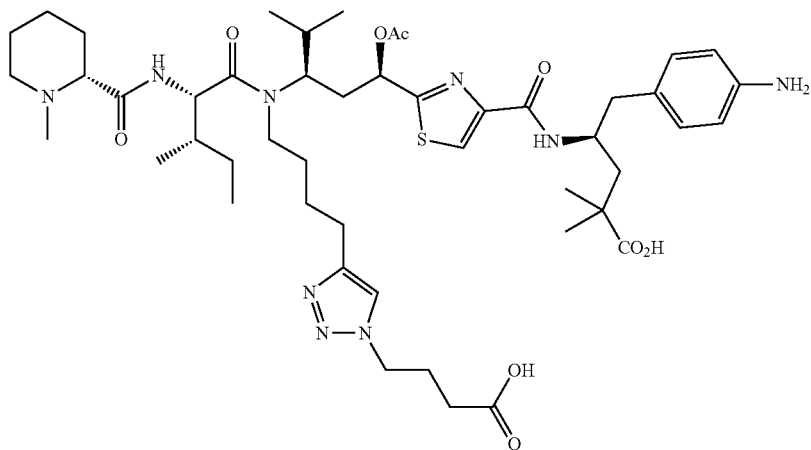 [SMILES: CC[C@H](C)[C@H](NC(=O)[C@H]1CCCCN1C)C(=O)N(CCCCc1cn(CCCC(=O)O)nn1)[C@H](C[C@@H](OC(C)=O)c1nc(C(=O)N[C@@H](Cc2ccc(N)cc2)CC(C)(C)C(=O)O)cs1)C(C)C]

Following the general procedure for IVj-p, IVn (1 mg, 11% yield in 2 steps) was obtained as a white solid. ESI m/z: 952.1 (M+H)+. $^1$H NMR (400 MHz, DMSO$_{d6}$) δ 8.17 (s, 1H), 7.81 (s, 1H), 7.80-7.72 (m, 1H), 7.67 (d, J=9.1 Hz, 1H), 6.79 (d, J=8.3 Hz, 2H), 6.44 (d, J=8.3 Hz, 2H), 5.62 (d, J=12.9 Hz, 1H), 4.42 (t, J=9.5 Hz, 1H), 4.27 (t, J=6.7 Hz, 2H), 4.14 (s, 2H), 3.76 (s, 1H), 3.03-3.00 (m, 1H), 2.82 (d, J=5.5 Hz, 5H), 2.66 (s, 3H), 2.22 (d, J=12.4 Hz, 1H), 2.12 (s, 3H), 2.06 (s, 3H), 1.93 (s, 3H), 1.81 (d, J=7.0 Hz, 2H), 1.74 (s, 1H), 1.65 (s, 2H), 1.59 (s, 2H), 1.51 (s, 6H), 1.48-1.30 (m, 4H), 1.15 (d, J=11.9 Hz, 1H), 1.07-1.00 (m, 1H), 0.96 (dd, J=11.2, 5.0 Hz, 9H), 0.81-0.72 (m, 6H), 0.66 (d, J=5.8 Hz, 3H) ppm.

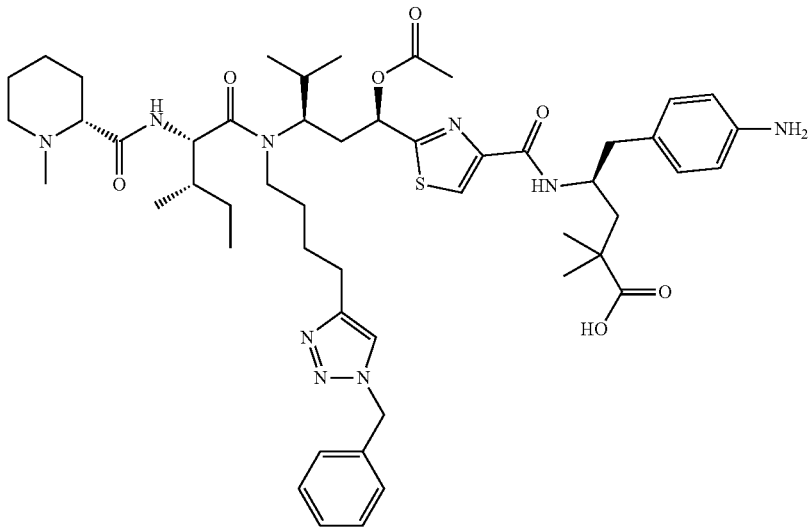

(IVo)

(S)-4-(2-((1R,3R)-1-Acetoxy-3-((2S,3S)—N-(4-(1-benzyl-1H-1,2,3-triazol-4-yl)butyl)-3-methyl-2-((R)-1-methylpiperidine-2-carboxamido)pentanamido)-4-methylpentyl)thiazole-4-carboxamido)-5-(4-aminophenyl)-2,2-dimethylpentanoic acid (IVo)

Following the general procedure for IVj-p, IVo (2.5 mg, 50% yield) was obtained as a white solid. ESI m/z: 956.5 (M+H)+. $^1$H NMR (500 MHz, DMSO$_{d6}$) δ 8.19 (s, 1H), 7.91 (s, 1H), 7.66 (s, 1H), 7.35-7.26 (m, 5H), 6.78 (d, J=8.2 Hz, 2H), 6.43 (d, J=8.1 Hz, 2H), 5.62 (d, J=13.2 Hz, 1H), 5.51 (s, 2H), 4.84 (s, 2H), 4.43 (t, J=9.1 Hz, 1H), 4.07 (s, 1H), 3.77-3.67 (m, 1H), 3.07-2.96 (s, 1H), 2.82 (d, J=11.5 Hz, 1H), 2.66 (s, 3H), 2.48-2.42 (m, 2H), 2.24 (t, J=12.7 Hz, 1H), 2.12 (s, 3H), 2.05 (s, 3H), 2.01-1.88 (m, 2H), 1.89-1.72 (m, 4H), 1.72-1.32 (m, 10H), 1.23 (s, 2H), 1.20-1.10 (m, 1H), 1.06-0.97 (m, 1H), 0.97-0.83 (m, 9H), 0.76 (dd, J=17.4, 7.0 Hz, 6H), 0.65 (s, 3H) ppm.

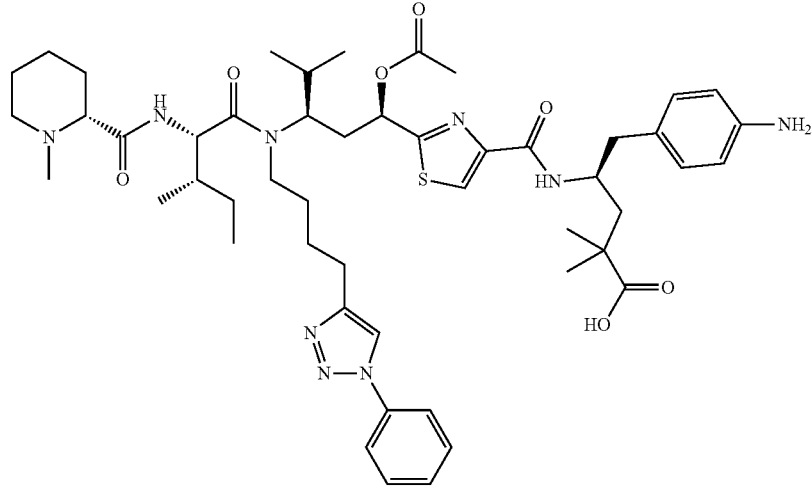

(IVp)

(S)-4-(2-((1R,3R)-1-acetoxy-4-methyl-3-((2S,3S)-3-methyl-2-((R)-1-methylpiperidine-2-carboxamido)-N-(4-(1-phenyl-1H-1,2,3-triazol-4-yl)butyl)pentanamido)pentyl)thiazole-4-carboxamido)-5-(4-aminophenyl)-2,2-dimethylpentanoic acid (IVp)

Following the general procedure for IVj-p, IVp (3.5 mg, 40% yield) was obtained as a colorless solid. ESI m/z: 942.5 (M+H)⁺. $^1$H NMR (500 MHz, DMSO$_{d6}$) δ 8.64 (s, 1H), 8.17 (s, 1H), 7.85 (d, J=7.8 Hz, 2H), 7.73-7.61 (m, 1H), 7.56 (t, J=7.9 Hz, 2H), 7.45 (t, J=7.4 Hz, 1H), 6.80 (d, J=8.2 Hz, 2H), 6.43 (d, J=8.2 Hz, 2H), 5.64 (d, J=13.0 Hz, 1H), 4.84 (s, 2H), 4.38 (t, J=9.1 Hz, 1H), 4.09 (s, 1H), 3.84-3.70 (s, 1H), 3.10-3.01 (s, 1H), 2.85-2.62 (m, 4H), 2.48-2.44 (m, 2H), 2.29-2.19 (m, 1H), 2.12 (s, 3H), 2.05 (s, 3H), 2.01-1.90 (m, 2H), 1.88-1.75 (m, 4H), 1.69-1.29 (m, 10H), 1.23 (s, 2H), 1.19-1.10 (m, 1H), 1.02-0.89 (m, 10H), 0.72-0.62 (m, 9H) ppm.

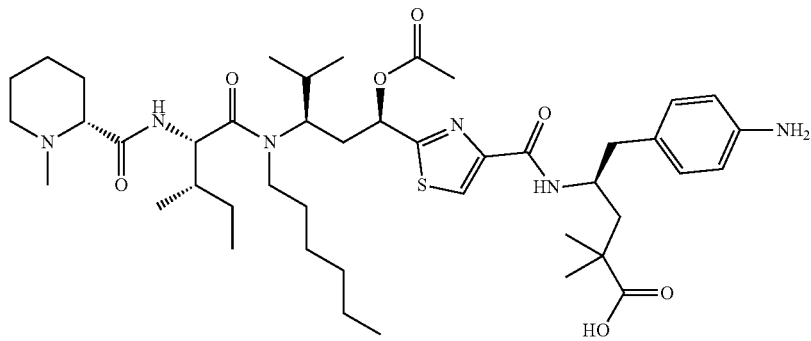

(IVq)

(S)-4-(2-((1R,3R)-1-Acetoxy-3-((2S,3S)—N-hexyl-3-methyl-2-((R)-1-methylpiperidine-2-carboxamido)pentanamido)-4-methylpentyl)thiazole-4-carboxamido)-5-(4-aminophenyl)-2,2-dimethylpentanoic acid (IVq)

Following the general procedure for IV, IVg (4.0 mg, 72% yield) was obtained as a white solid. ESI m/z 828.3 (M+H)⁺. $^1$H NMR (400 MHz, DMSO$_{d6}$) δ 8.19 (s, 1H), 8.04 (s, 1H), 7.65 (d, J=8.9 Hz, 1H), 6.81 (d, J=8.1 Hz, 2H), 6.44 (d, J=8.2 Hz, 2H), 5.64 (d, J=13.0 Hz, 1H), 4.84 (s, 2H), 4.49 (t, J=9.3 Hz, 1H), 4.43-4.20 (m, 1H), 4.11 (s, 1H), 3.67 (d, J=14.8 Hz, 2H), 3.01 (d, J=11.0 Hz, 2H), 2.83 (d, J=11.4 Hz, 1H), 2.68 (d, J=4.7 Hz, 2H), 2.28 (dd, J=24.7, 12.1 Hz, 2H), 2.13 (s, 3H), 2.07 (s, 3H), 1.98-1.88 (m, 2H), 1.87-1.81 (m, 2H), 1.73 (s, 1H), 1.59 (s, 2H), 1.54 (s, 2H), 1.45 (s, 2H), 1.29 (s, 6H), 1.19-1.06 (m, 2H), 1.00 (d, J=9.8 Hz, 6H), 0.95 (d, J=6.4 Hz, 3H), 0.83 (dd, J=16.5, 9.4 Hz, 10H), 0.68 (d, J=5.8 Hz, 3H) ppm.

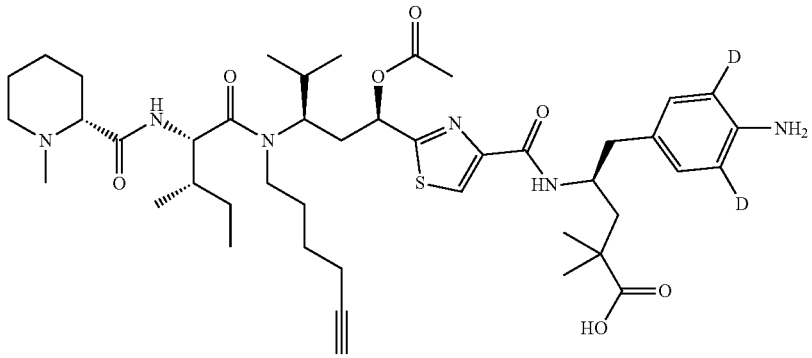

(IVr)

(S)-4-(2-((1R,3R)-1-Acetoxy-3-((2S,3S)—N-(hex-5-yn-1-yl)-3-methyl-2-((R)-1-methylpiperidine-2-carboxamido)pentanamido)-4-methylpentyl)thiazole-4-carboxamido)-5-(4-aminophenyl-3,5-d2)-2,2-dimethylpentanoic acid (IVr)

Following the general procedure for IV, IVr (2.0 mg, 34% yield) was obtained as a white solid. ESI m/z 825.5 (M+H)$^+$. $^1$H NMR (500 MHz, DMSO$_{d6}$) δ 8.15 (s, 1H), 7.71 (s, 1H), 7.59 (s, 1H), 6.81 (s, 2H), 5.65 (d, J=12.4 Hz, 1H), 4.84 (s, 2H), 4.46 (t, J=9.3 Hz, 1H), 4.18 (s, 1H), 3.73 (s, 1H), 3.01 (s, 1H), 2.83 (d, J=10.7 Hz, 1H), 2.74 (s, 1H), 2.63 (dd, J=13.2, 6.2 Hz, 1H), 2.57-2.53 (m, 1H), 2.40-2.10 (m, 7H), 2.07 (s, 3H), 2.03-1.69 (m, 7H), 1.69-1.29 (m, 10H), 1.23 (s, 2H), 1.04 (d, J=6.7 Hz, 6H), 0.95 (d, J=6.1 Hz, 3H), 0.88-0.76 (m, 6H), 0.67 (s, 3H) ppm.

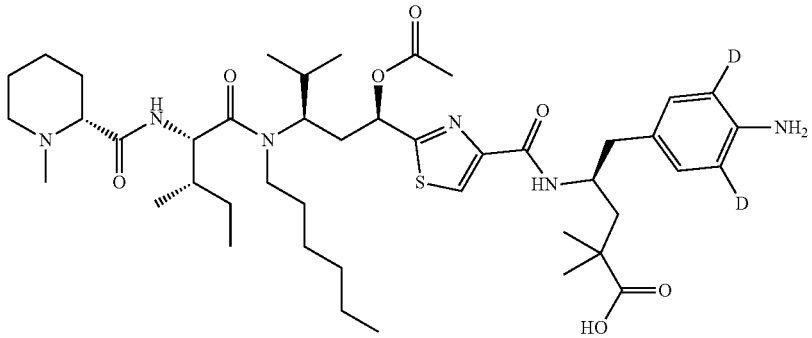

(IVs)

(S)-4-(2-((1R,3R)-1-Acetoxy-3-((2S,3S)—N-hexyl-3-methyl-2-((R)-1-methylpiperidine-2-carboxamido)pentanamido)-4-methylpentyl)thiazole-4-carboxamido)-5-(4-aminophenyl-3,5-d2)-2,2-dimethylpentanoic acid (IVs)

Following the general procedure for IV, IVs (0.80 mg, 6% yield) was obtained as a white solid. ESI m/z 829.5 (M+H)$^+$. $^1$H NMR (500 MHz, DMSO$_{d6}$) δ 8.16 (s, 1H), 7.67 (s, 1H), 7.53 (s, 1H), 6.80 (s, 2H), 5.65 (d, J=13.0 Hz, 1H), 4.80 (s, 2H), 4.48 (t, J=9.4 Hz, 1H), 4.19 (s, 1H), 3.70 (s, 1H), 2.99 (s, 1H), 2.81 (d, J=15.3 Hz, 1H), 2.68-2.52 (m, 2H), 2.43-2.10 (m, 7H), 2.07 (s, 3H), 2.02-1.73 (m, 7H), 1.73-1.33 (m, 10H), 1.33-1.28 (m, 2H), 1.23 (s, 2H), 1.05 (d, J=5.1 Hz, 6H), 0.95 (d, J=6.4 Hz, 3H), 0.89-0.78 (m, 9H), 0.68 (s, 3H) ppm.

Figure 6B:
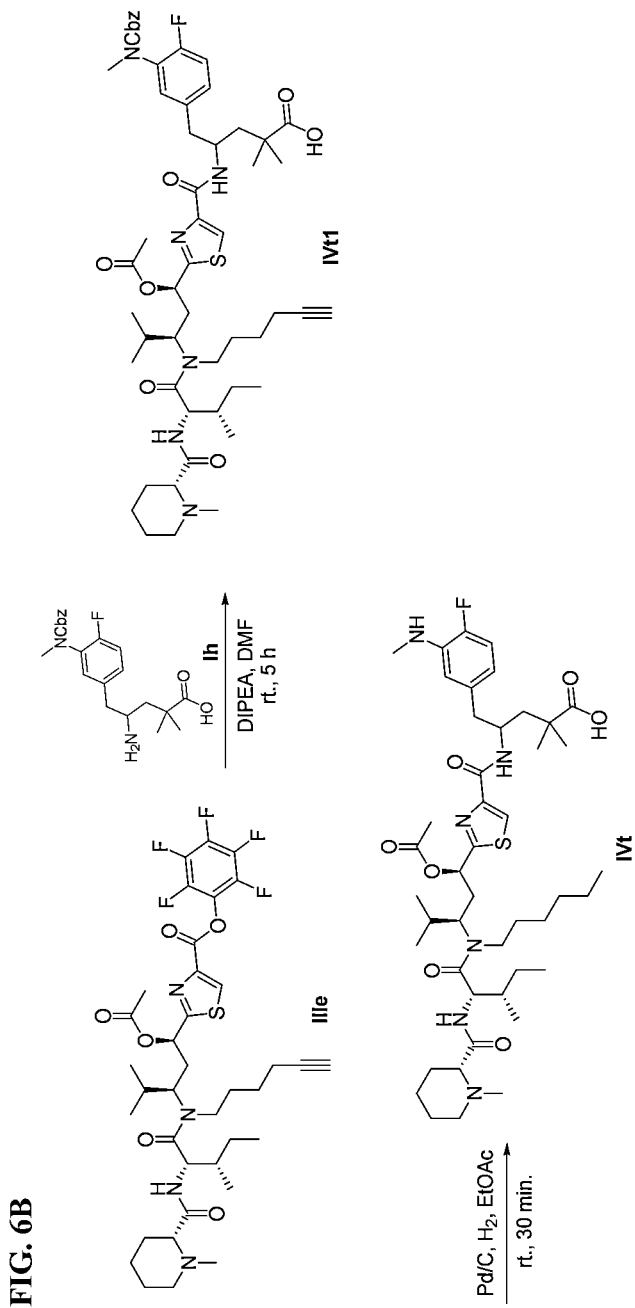

(IVt) 2-4-(2-((1R,3R)-1-acetoxy-3-((2S,3S)—N-(hex-5-ynyl)-3-methyl-2-((R)-1-methylpiperidine-2-carboxamido)pentanamido)-4-methylpentyl)thiazole-4-carboxamido)-5-(3-((benzyloxycarbonyl)(methyl)amino)-4-fluorophenyl)-2,2-dimethylpentanoic acid (IVt1) (FIG. 6B)

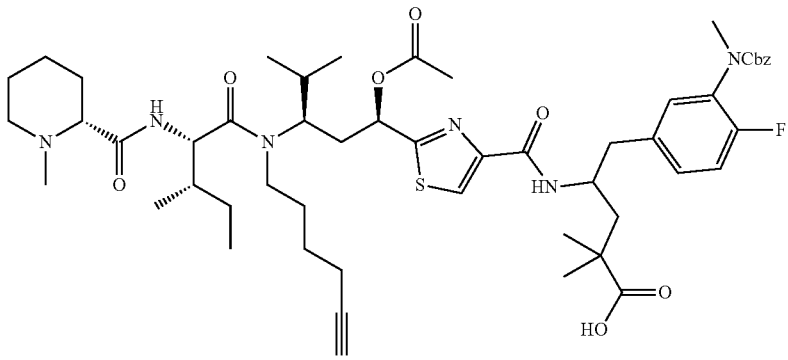

Following the general procedure for IV, IVt1 (6.0 mg, 47% yield) was obtained as a white solid. ESI m/z 989.1 (M+H)⁺.

4-(2-((1R,3R)-1-acetoxy-3-((2S,3S)—N-hexyl-3-methyl-2-((R)-1-methylpiperidine-2-carboxamido)pentanamido)-4-methylpentyl)thiazole-4-carboxamido)-5-(4-fluoro-3-(methylamino)phenyl)-2,2-dimethylpentanoic acid (IVt) (FIG. 6B)

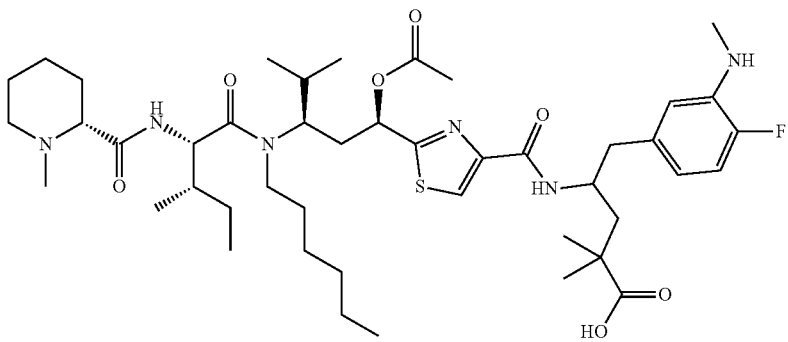 [SMILES: CCCCCCN(C(=O)[C@@H](NC(=O)[C@H]1CCCCN1C)[C@@H](C)CC)[C@H](C[C@@H](OC(C)=O)c1nc(C(=O)NC(Cc2ccc(F)c(NC)c2)CC(C)(C)C(=O)O)cs1)C(C)C]

To a solution of compound IVt1 (6 mg, 6.1 μmol) was added wet Pd/C (10% Pd, 2 mg) under nitrogen. The suspension was degassed and the atmosphere was exchanged with hydrogen 3 times and was then stirred at rt under hydrogen balloon for 30 minutes, and monitored by LCMS. The reaction mixture was filtered through Celite and the filtrate was concentrated in vacuo. The residue was purified by prep-HPLC (method B) to give compound IVt (2 mg, 38% yield) as a white solid. ESI m/z 859.1 (M+H)⁺. $^1$H NMR (400 MHz, DMSO$_{d6}$) δ 8.19 (d, J=6.2 Hz, 1H), 7.66 (d, J=9.7 Hz, 1H), 6.90-6.77 (m, 1H), 6.38 (d, J=8.3 Hz, 1H), 6.32 (s, 1H), 5.63 (d, J=12.6 Hz, 1H), 5.36 (s, 1H), 4.48 (d, J=6.9 Hz, 1H), 4.21 (s, 1H), 3.70 (s, 1H), 2.97 (s, 1H), 2.81 (s, 1H), 2.70 (d, J=21.9 Hz, 2H), 2.55 (d, J=4.9 Hz, 3H), 2.22 (s, 2H), 2.12 (d, J=3.5 Hz, 3H), 2.06 (s, 3H), 1.97-1.83 (m, 4H), 1.68-1.34 (m, 9H), 1.29 (s, 8H), 1.18-1.13 (m, 1H), 1.04 (s, 7H), 0.95 (d, J=6.4 Hz, 3H), 0.88-0.79 (m, 10H), 0.68 (d, J=5.9 Hz, 3H) ppm.

(IVuA/B) 4-({2-[(1R,3R)-1-(Acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-[3-(dibenzylamino)-4-fluorophenyl]-2,2-dimethylpentanoic acid (IVu1)

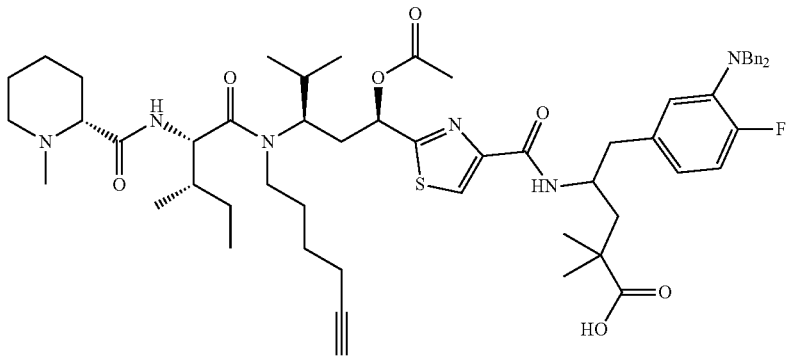

Following the general procedure for IV, IVu1 (10 mg, 40% yield) was obtained as a white solid. ESI m/z 511.3 (M/2+H)⁺.

4-({2-[(1R,3R)-1-(Acetyloxy)-3-[(2S,3S)—N-hexyl-3-methyl-2-{[(2R)-1-methylpiperidin-2-yl]formamido}pentanamido]-4-methylpentyl]-1,3-thiazol-4-yl}formamido)-5-(3-amino-4-fluorophenyl)-2,2-dimethylpentanoic acid (IVu)

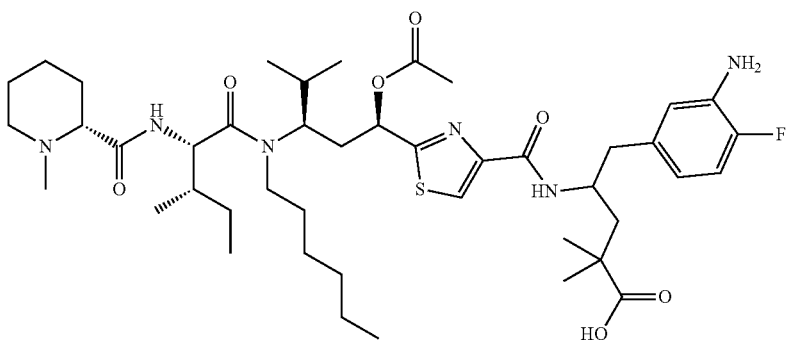 [SMILES: CCCCCCN(C(=O)[C@@H](NC(=O)[C@H]1CCCCN1C)[C@@H](C)CC)[C@H](C[C@@H](OC(C)=O)c1nc(C(=O)NC(Cc2ccc(F)c(N)c2)CC(C)(C)C(=O)O)cs1)C(C)C]

To a solution of compound IVu1 (10 mg, 9.8 μmol) was added wet Pd/C (10% Pd, 3 mg) under nitrogen. The suspension was degassed and the atmosphere was exchanged with hydrogen 3 times and was then stirred at rt under hydrogen balloon for 24 hours, and monitored by LCMS. The reaction mixture was filtered through Celite and the filtrate was concentrated in vacuo. The crude product mixture was purified by prep-HPLC (method A) to give compound IVu as a white solid.

IVuA (2 mg, 23% yield): ESI m/z 845.5 (M+H)⁺, LCMS retention time: 1.41 min; $^1$H NMR (400 MHz, DMSO$_{d6}$) δ 8.21 (d, J=8.0 Hz, 1H), 7.64 (d, J=9.2 Hz, 1H), 6.83 (dd, J=11.4, 8.2 Hz, 1H), 6.60 (t, J=10.0 Hz, 1H), 6.30 (s, 1H), 5.64 (d, J=13.2 Hz, 1H), 5.01 (s, 2H), 4.48 (t, J=9.4 Hz, 1H), 4.13 (s, 1H), 3.68 (s, 1H), 3.00 (s, 2H), 2.87-2.65 (m, 3H), 2.25 (d, J=11.9 Hz, 2H), 2.12 (d, J=4.7 Hz, 3H), 2.06 (s, 3H), 2.00-1.81 (m, 4H), 1.72 (br s, 1H), 1.65-1.25 (m, 15H), 1.18-1.04 (m, 2H), 0.98-0.59 (m, 22H) ppm.

IVuB (2 mg, 23% yield): ESI m/z 845.5 (M+H)⁺, LCMS retention time: 1.42 min; $^1$H NMR (400 MHz, DMSO$_{d6}$) δ 8.18 (s, 1H), 7.56 (s, 1H), 6.82 (dd, J=11.5, 8.2 Hz, 1H), 6.67-6.52 (m, 1H), 6.29 (s, 1H), 5.66 (s, 1H), 5.01 (s, 2H), 4.48 (t, J=9.1 Hz, 1H), 4.26 (s, 1H), 3.68 (s, 1H), 3.02 (s, 2H), 2.77-2.54 (m, 3H), 2.25 (s, 2H), 2.13 (d, J=9.8 Hz, 6H), 1.95-1.50 (m, 12H), 1.35-1.03 (m, 15H), 0.98-0.59 (m, 17H) ppm.

(IVvA/B) 4-({2-[(1R,3R)-1-(Acetyloxy)-3-[(2S,3S)—N-hexyl-3-methyl-2-{[(2R)-1-methylpiperidin-2-yl]formamido}pentanamido]-4-methylpentyl]-1,3-thiazol-4-yl}formamido)-5-(4-amino-3-fluorophenyl)-2,2-dimethylpentanoic acid (IVv, two diastereomers A and B)

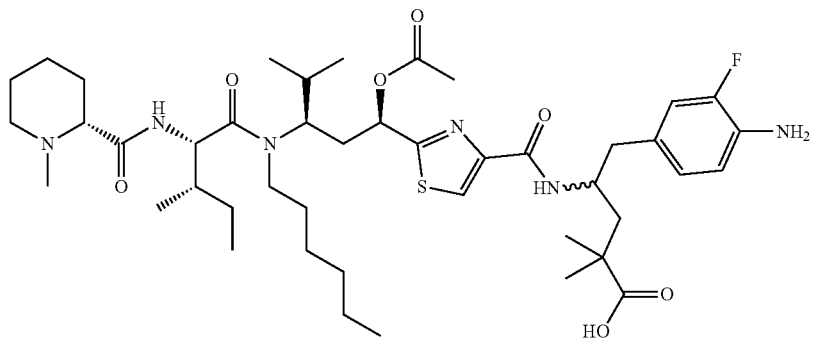 [SMILES: CCCCCCN(C(=O)[C@@H](NC(=O)[C@H]1CCCCN1C)[C@@H](C)CC)[C@H](C[C@@H](OC(C)=O)c1nc(C(=O)NC(Cc2ccc(N)c(F)c2)CC(C)(C)C(=O)O)cs1)C(C)C]

Following the similar procedure from Ii and IIIe to IVu, except substituting Ij for Ii, compound IVv as diastereomers was obtained and then separated by prep-HPLC (method A) to give diastereomer A and diastereomer B as white solids.

IVvA (5 mg, 10% yield): ESI m/z 845 (M+H)$^+$, LCMS retention time: 1.40 min.

IVvB (5 mg, 10% yield): ESI m/z 845 (M+H)$^+$, LCMS retention time: 1.41 min. Diastereomer IVvB is as shown in FIG. 5A.

(IVw) (S)-4-(2-((1R,3R)-1-Acetoxy-3-((2S,3S)—N-(hex-5-ynyl)-3-methyl-2-((R)-1-methylpiperidine-2-carboxamido)pentanamido)-4-methylpentyl)thiazole-4-carboxamido)-5-(4-(benzyloxy)-3-nitrophenyl)-2,2-dimethylpentanoic acid (IVw1)

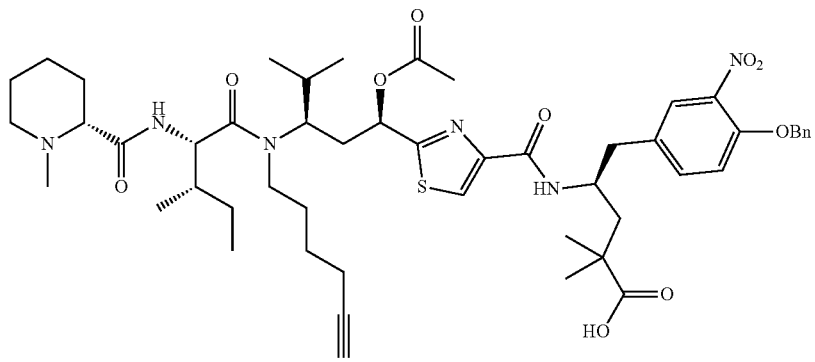 [SMILES: C#CCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(OCc3ccccc3)c([N+](=O)[O-])c2)CC(C)(C)C(=O)O)cs1)C(C)C]

Following the general procedure for Compound IV, compound IVw1 (10 mg, 40% yield) was obtained as a white solid. ESI m/z: 959.5 (M+H)$^+$.

(S)-4-(2-((1R,3R)-1-Acetoxy-3-((2S,3S)—N-hexyl-3-methyl-2-((R)-1-methylpiperidine-2-carboxamido)pentanamido)-4-methylpentyl)thiazole-4-carboxamido)-5-(3-amino-4-hydroxyphenyl)-2,2-dimethylpentanoic acid (IVw)

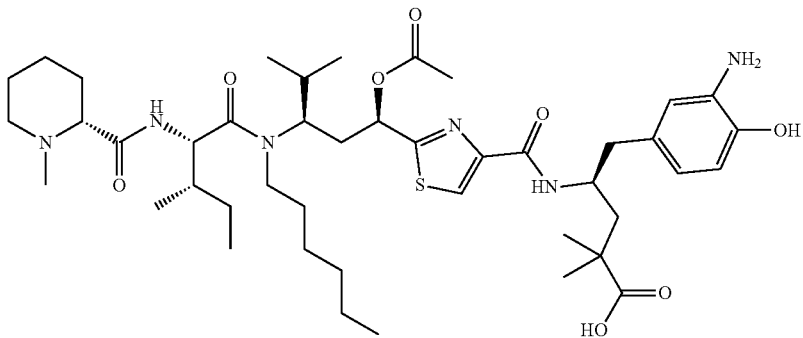 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)c(N)c2)CC(C)(C)C(=O)O)cs1)C(C)C]

To a solution of compound IVw1 (10 mg, 0.10 mmol) in ethanol (5 mL) were added conc. HCl (0.1 mL) and wet Pd/C (10% Pd, 3 mg) under nitrogen. The suspension was degassed and the atmosphere was exchanged with hydrogen 3 times and then stirred at rt under a hydrogen balloon for 30 minutes, and monitored by LCMS. The reaction mixture was filtered through Celite and the filtrate was concentrated in vacuo. The crude product was purified by prep-HPLC (method A) to give compound IVw (1 mg, 12% yield) as white solids. ESI m/z: 843.5 (M+H)$^+$.

(IVx) 4-(2-((1R,3R)-1-Acetoxy-3-((2S,3S)—N-hexyl-3-methyl-2-((R)-1-methylpiperidine-2-carboxamido)pentanamido)-4-methylpentyl)thiazole-4-carboxamido)-5-(4-amino-3-hydroxyphenyl)-2,2-dimethylpentanoic acid (IVx)

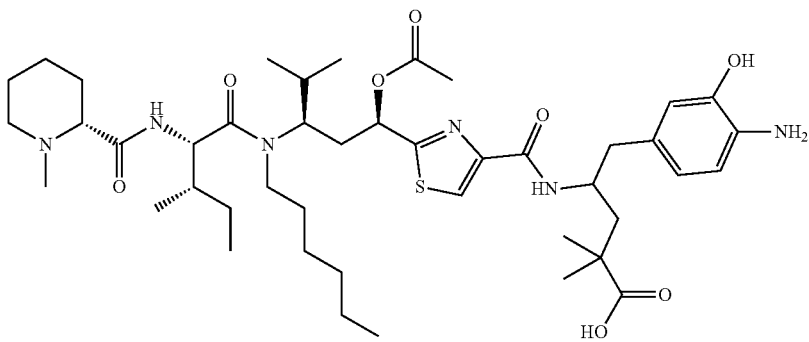 [SMILES: CCCCCCN(C(=O)[C@@H](NC(=O)[C@H]1CCCCN1C)[C@@H](C)CC)[C@H](C[C@@H](OC(C)=O)c1nc(C(=O)NC(Cc2ccc(N)c(O)c2)CC(C)(C)C(=O)O)cs1)C(C)C]

Following the similar procedure as IVw, except substituting Il for Ik, compound IVx was obtained as a white solid. ESI m/z: 843.5 (M+H)$^+$.

(IVy) (1R,3R)-1-(4-((S)-1-(4-Aminophenyl)-5-hydrazinyl-4,4-dimethyl-5-oxopentan-2-ylcarbamoyl)thiazol-2-yl)-3-((2S,3S)—N-hexyl-3-methyl-2-((R)-1-methylpiperidine-2-carboxamido)pentanamido)-4-methylpentyl acetate (IVy) 0

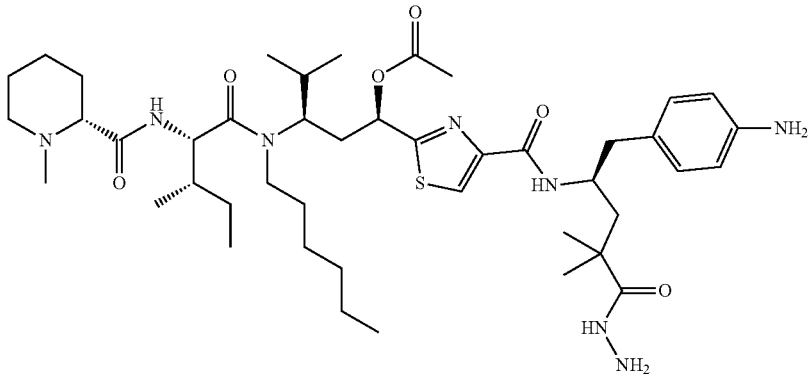 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(N)cc2)CC(C)(C)C(=O)NN)cs1)C(C)C]

To a solution of Fmoc-IVq (60 mg, 60 μmol, see the procedure of compound IVq) in dry DMF (2 mL) were added HATU (24 mg, 66 μmol) and DIPEA (24 mg, 0.18 mmol). The mixture was stirred at rt for 10 minutes followed by the addition of Boc-hydrazine (8.0 mg, 60 μmol). The resulting solution was stirred at rt for an hour, which was monitored by LCMS. The mixture was directly separated by reversed phase flash chromatography (5-95% acetonitrile in water (with 0.03% TFA)) to give the Boc-hydrazide intermediate (70 mg, ESI m/z: 1163.6 (M+H)$^+$) as a white solid. The intermediate (10 mg, 10 μmol) was dissolved in DMF (2 mL) and to the solution was added 1 drop of piperidine (ca. 0.02 mL). The solution was stirred at rt for an hour until Fmoc was removed according to LCMS. The mixture was directly separated by reversed phase flash chromatography (5-95% acetonitrile in water (with 0.03% TFA)) to give the crude de-Fmoc intermediate (5 mg, ESI m/z: 421.3 ((M−Boc)/2+H)$^+$) as a white solid, which was dissolved in DCM (2 mL). To the solution was added TFA (0.4 mL) and the mixture was stirred at rt for 2 hours until Boc was removed according to LCMS. The volatiles were removed in vacuo and the residue was purified by prep-HPLC (method B) to give compound IVy (1 mg, 11% yield from Fmoc-IVq) as a white solid. ESI m/z: 841.5 (M+H)$^+$. $^1$H NMR (500 MHz, DMSO$_{d6}$) δ 8.75 (s, 1H), 8.17 (s, 1H), 7.64 (d, J=9.1 Hz, 1H), 7.50 (d, J=8.8 Hz, 1H), 6.80 (d, J=8.2 Hz, 2H), 6.44 (d, J=8.3 Hz, 2H), 5.60 (d, J=12.7 Hz, 1H), 4.85 (s, 2H), 4.49 (t, J=9.4 Hz, 1H), 4.07 (s, 1H), 3.91 (s, 2H), 3.68 (br s, 1H), 2.99 (s, 1H), 2.82 (d, J=11.5 Hz, 1H), 2.63 (dd, J=13.0, 6.2 Hz, 1H), 2.47-2.27 (m, 4H), 2.12 (s, 3H), 2.06 (s, 3H), 2.03-1.79 (m, 5H), 1.77-1.39 (m, 8H), 1.32 (s, 7H), 1.23 (s, 2H), 1.00 (d, J=8.5 Hz, 6H), 0.96 (d, J=6.4 Hz, 3H), 0.90-0.77 (m, 9H), 0.68 (d, J=5.5 Hz, 3H) ppm.

Synthesis of O-Tubulysin Ester V (FIG. 5)

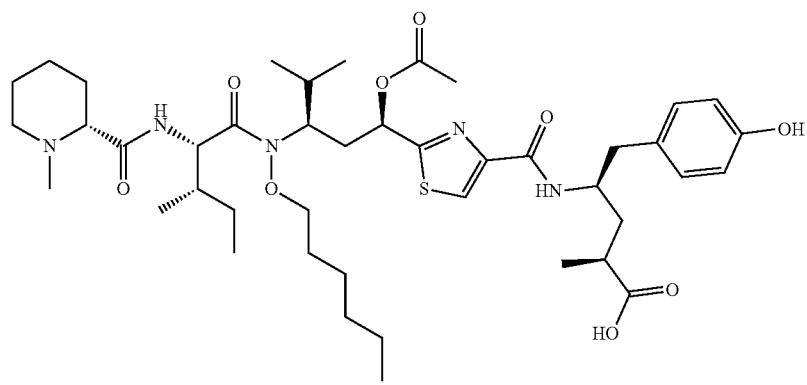

(Va)

(2S,4R)-4-(2-((1R,3R)-1-Acetoxy-3-((2S,3S)—N-(hexyloxy)-3-methyl-2-((R)-1-methylpiperidine-2-carboxamido)pentanamido)-4-methylpentyl)thiazole-4-carboxamido)-5-(4-hydroxyphenyl)-2-methylpentanoic acid (Va)

Following the general procedure for VI (infra), Va (8.5 mg, 28% yield) was obtained as a white solid. ESI m/z: 830.1 (M+H)$^+$. $^1$H NMR (500 MHz, DMSO$_{d6}$) δ 9.19 (s, 1H), 8.19 (s, 1H), 7.83 (d, J=9.0 Hz, 1H), 7.48 (d, J=9.5 Hz, 1H), 6.97 (d, J=8.5 Hz, 2H), 6.63 (d, J=8.5 Hz, 2H), 5.77 (d, J=8.5 Hz, 1H), 4.81-4.78 (m, 1H), 4.16-4.06 (m, 3H), 3.97-3.95 (m, 1H), 2.85-2.83 (m, 1H), 2.75-2.71 (m, 1H), 2.68-2.64 (m, 1H), 2.47-2.36 (m, 4H), 2.11 (s, 3H), 2.10 (s, 3H), 2.07-1.94 (m, 2H), 1.80-1.79 (m, 2H), 1.63-1.61 (m, 4H), 1.54-1.44 (m, 3H), 1.42-1.37 (m, 4H), 1.33-1.26 (m, 5H), 1.18-1.09 (m, 2H), 1.06 (d, J=7.5 Hz, 3H), 0.98 (d, J=7.0 Hz, 3H), 0.89-0.82 (m, 12H) ppm.

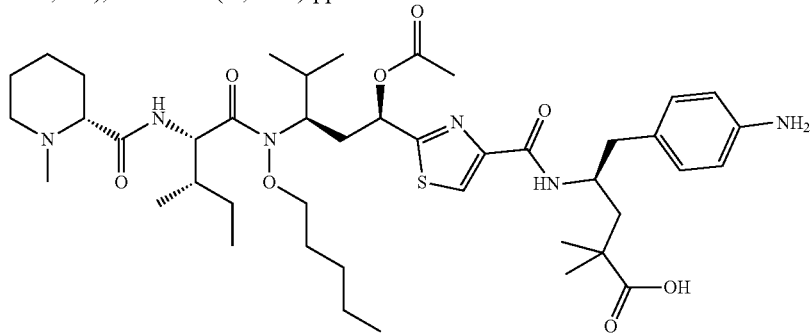

(Vb)

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-(4-aminophenyl)-2,2-dimethylpentanoic acid (Vb)

Following the general procedure for VI, Vb (6.0 mg, 30% yield) was obtained as a white solid. ESI m/z 829.4 (M+H)$^+$. $^1$H NMR (400 MHz, DMSO$_{d6}$) δ 8.17 (s, 1H), 7.74 (br s, 1H), 7.51 (d, J=9.5 Hz, 1H), 6.81 (d, J=8.0 Hz, 2H), 6.43 (d, J=8.0 Hz, 2H), 5.80 (d, J=11.5 Hz, 1H), 4.91-4.78 (m, 3H), 4.19-4.11 (m, 2H), 4.10-4.02 (m, 1H), 3.98-3.93 (m, 1H), 2.87-2.81 (m, 1H), 2.65-2.61 (m, 1H), 2.44-2.32 (m, 2H), 2.11 (d, J=14 Hz, 6H), 2.02-1.92 (m, 2H), 1.88-1.78 (m, 2H), 1.66-1.5 (m, 5H), 1.55-1.23 (m, 11H), 1.18-1.14 (m, 1H), 1.03 (d, J=11 Hz, 6H), 0.96 (d, J=7.0 Hz, 3H), 0.88-0.81 (m, 12H) ppm. Anal. HPLC: 95%, R$_t$: 8.55 min (Method B).

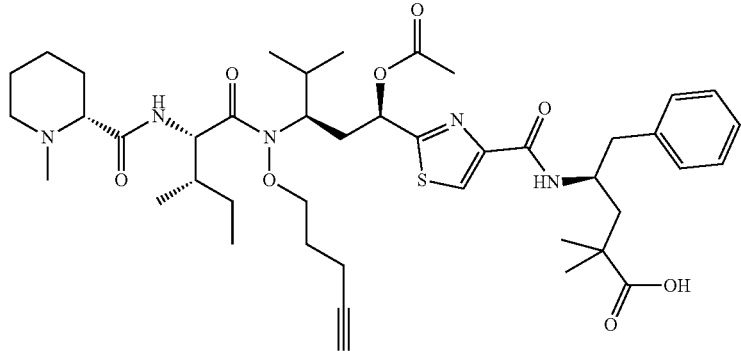

(Vc)

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-2,2-dimethyl-5-phenylpentanoic acid (Vc)

Following the general procedure for VI, Vc (7.0 mg, 35% yield) was obtained as a white solid. ESI m/z 810.0 (M+H)+. 1H NMR (500 MHz, DMSO$_{d6}$) δ 8.15 (s, 1H), 7.74 (d, J=8.5 Hz, 1H), 7.55 (d, J=10.0 Hz, 1H), 7.25-7.22 (m, 2H), 7.18-7.16 (m, 3H), 5.81 (d, J=5.0 Hz, 1H), 4.77-4.74 (m, 1H), 4.31-4.22 (m, 2H), 4.08-4.04 (m, 2H), 2.83-2.81 (m, 3H), 2.76-2.71 (m, 1H), 2.34-2.33 (m, 3H), 2.13 (s, 3H), 2.10 (s, 3H), 1.99-1.91 (m, 3H), 1.81-1.80 (m, 3H), 1.69-1.60 (m, 3H), 1.52-1.37 (m, 4H), 1.09-1.08 (m, 1H), 1.06-1.04 (m, 6H), 0.97-0.95 (m, 6H), 0.87-0.81 (m, 9H) ppm. Anal. HPLC: >99%, R$_t$: 8.63 min (Method B).

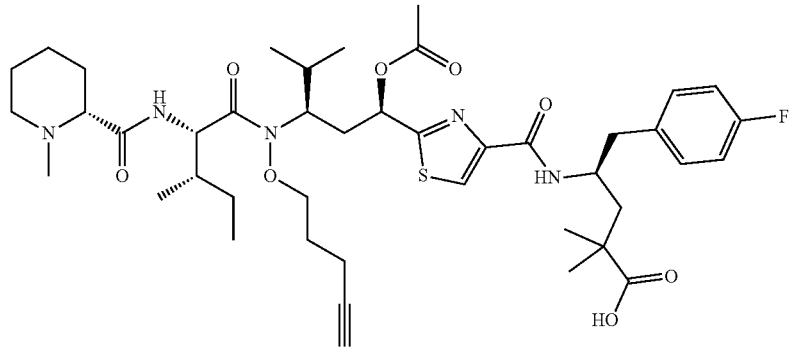

(Vd)

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-fluorophenyl)-2,2-dimethylpentanoic acid (Vd)

Following the general procedure for VI, Vd (8.0 mg, 40% yield) was obtained as a white solid. ESI m/z 828.4 (M+H)+. 1H NMR (400 MHz, DMSO$_{d6}$) δ 8.08 (s, 1H), 7.71 (d, J=9.2 Hz, 1H), 7.51 (d, J=10.0 Hz, 1H), 7.14-7.11 (m, 2H), 7.00-6.95 (m, 2H), 5.74 (d, J=10.8 Hz, 1H), 4.68 (t, J=9.6 Hz, 1H), 4.18-4.12 (m, 2H), 4.00-3.95 (m, 2H), 2.77-2.64 (m, 4H), 2.29-2.20 (m, 3H), 2.06 (s, 3H), 2.02 (s, 3H), 1.93-1.81 (m, 3H), 1.67-1.62 (m, 3H), 1.57-1.28 (m, 9H), 1.13-1.10 (m, 2H), 1.01 (s, 3H), 0.97 (s, 3H), 0.90-0.88 (m, 3H), 0.81-0.76 (m, 9H) ppm. Anal. HPLC: >99%, R$_t$: 8.40 min (Method B).

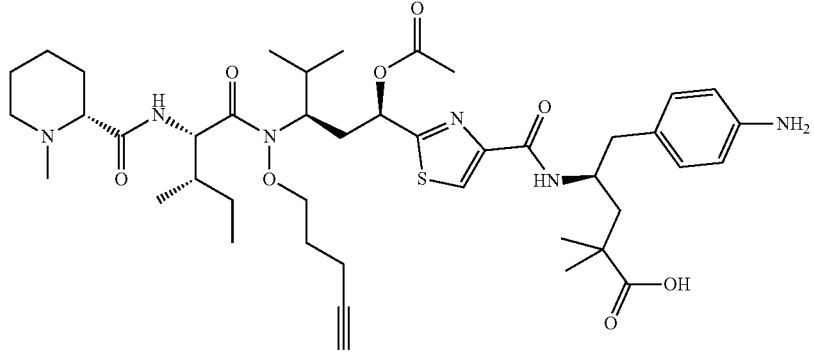

(Ve)

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-aminophenyl)-2,2-dimethylpentanoic acid (Ve)

Following the general procedure for VI, Ve (5.3 mg, 27% yield) was obtained as a white solid. ESI m/z 413.3 (M/2+H)$^+$, 825.3 (M+H)$^+$(30%). $^1$H NMR (500 MHz, DMSO$_{d6}$) δ 8.16 (s, 1H), 7.78 (d, J=8.5 Hz, 1H), 7.56 (d, J=10.0 Hz, 1H), 6.81 (d, J=8.5 Hz, 2H), 6.44 (d, J=8.0 Hz, 2H), 5.81 (d, J=11.0 Hz, 1H), 4.90-4.74 (m, 3H), 4.26-4.23 (m, 1H), 4.15-4.05 (m, 3H), 2.85-2.82 (m, 2H), 2.77 (br s, 1H), 2.68-2.64 (m, 1H), 2.36-2.31 (m, 3H), 2.13 (s, 3H), 2.09 (s, 3H), 2.03-1.96 (m, 2H), 1.89-1.78 (m, 4H), 1.62-1.35 (m, 9H), 1.19-1.05 (m, 2H), 1.04 (s, 3H), 1.00 (s, 3H), 0.96 (d, J=5.5 Hz, 3H), 0.89-0.82 (m, 9H) ppm. Anal. HPLC: 95%, R$_t$: 6.98 min (Method B).

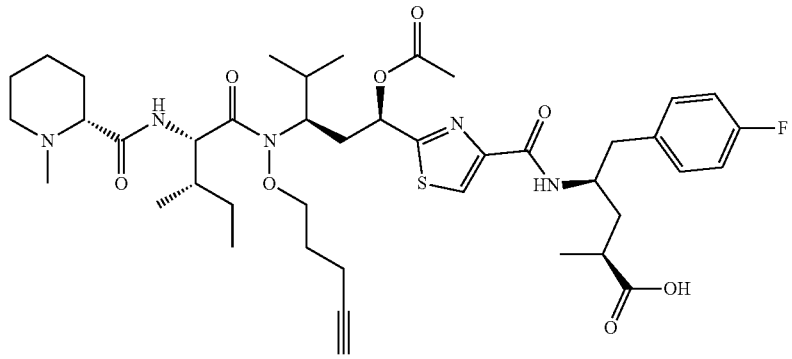

(Vf)

(2S,4R)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-fluorophenyl)-2-methylpentanoic acid (Vf)

Following the general procedure for VI, Vf (4.0 mg, 20% yield) was obtained as a white solid. ESI m/z 814.3 (M+H)$^+$. $^1$H NMR (500 MHz, methanol$_{d4}$) δ 8.11 (s, 1H), 7.25 (dd, J=8.5, 5.5 Hz, 2H), 6.96 (t, J=9.0 Hz, 2H), 5.92-5.90 (m, 1H), 4.91-4.87 (m, 1H), 4.42-4.38 (m, 1H), 4.36-4.30 (m, 1H), 4.20 (dd, J=13.9, 6.5 Hz, 1H), 4.09-4.03 (m, 1H), 3.15-3.02 (m, 2H), 2.97-2.90 (m, 2H), 2.75-2.65 (m, 1H), 2.56-2.48 (m, 1H), 2.45-2.34 (m, 8H), 2.20-2.10 (m, 4H), 2.04-1.90 (m, 5H), 1.80-1.57 (m, 6H), 1.46-1.36 (m, 1H), 1.27-1.21 (m, 1H), 1.18 (d, J=7.0 Hz, 3H), 1.07 (d, J=6.5 Hz, 3H), 1.03-1.01 (m, 6H), 0.95 (t, J=7.5 Hz, 3H) ppm. Anal. HPLC: 98%, R$_t$: 7.63 min (Method B).

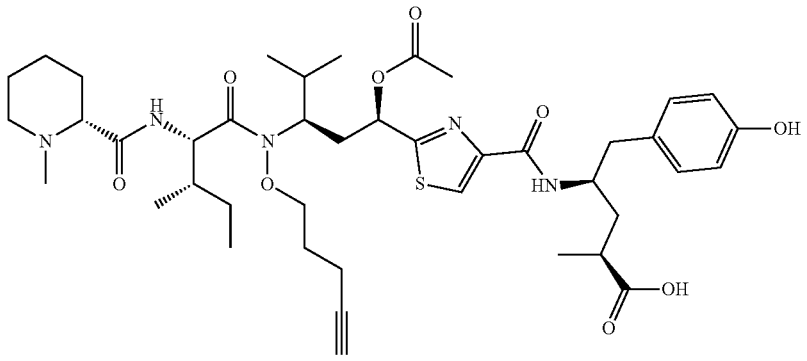

(Vg)

(2S,4R)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-hydroxyphenyl)-2-methylpentanoic acid (Vg)

Following the general procedure for VI, Vg (7.8 mg, 39% yield) was obtained as a white solid. ESI m/z 812.3 (M+H)$^+$. $^1$H NMR (500 MHz, methanol$_{d4}$) δ 8.11 (s, 1H), 7.06 (d, J=8.4 Hz, 2H), 6.69 (d, J=8.4 Hz, 2H), 5.90 (d, J=9.0 Hz, 1H), 4.89-4.85 (m, 1H), 4.64 (br s, 1H), 4.41-4.39 (m, 1H), 4.31-4.26 (m, 1H), 4.20-4.16 (m, 1H), 4.05-3.98 (s, 1H), 3.12-3.30 (m, 1H), 2.86-2.84 (m, 2H), 2.74-2.66 (m, 1H), 2.54-2.49 (m, 1H), 2.43-2.30 (m, 8H), 2.18 (s, 4H), 2.04-1.90 (m, 5H), 1.79-1.56 (m, 6H), 1.46-1.38 (m, 1H), 1.25-1.20 (m, 1H), 1.19 (d, J=7.0 Hz, 3H), 1.07 (d, J=7.0 Hz, 3H), 1.02 (d, J=7.0 Hz, 6H), 0.95 (t, J=7.0 Hz, 3H) ppm. Anal. HPLC: >99%, R$_t$: 7.68 min (Method A).

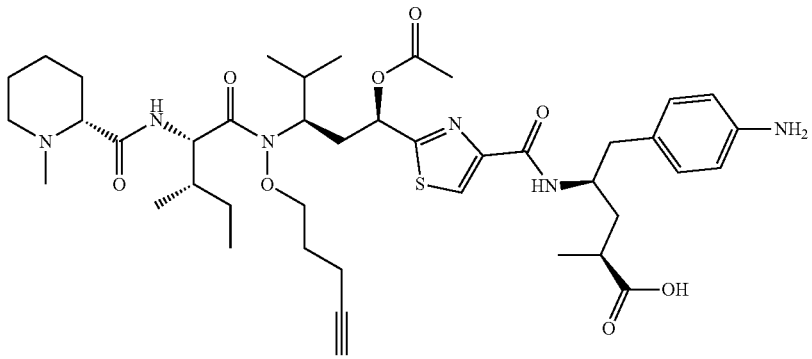

(Vh)

(2S,4R)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-aminophenyl)-2-methylpentanoic acid (Vh)

Following the general procedure for VI, Vh (12 mg, 60% yield) was obtained as a white solid. ESI m/z 406.2 (M/2+H)$^+$, 811.2 (M+H)$^+$ (10%). $^1$H NMR (500 MHz, DMSO$_{d6}$) δ 8.18 (s, 1H), 7.82 (d, J=9.0 Hz, 1H), 7.53 (d, J=9.5 Hz, 1H), 6.83 (d, J=8.5 Hz, 2H), 6.44 (d, J=8.5 Hz, 2H), 5.78 (d, J=12 Hz, 1H), 4.76 (t, J=9.6 Hz, 1H), 4.26-4.12 (m, 1H), 4.10-4.03 (m, 3H), 2.83-2.80 (m, 2H), 2.70-2.65 (m, 1H), 2.60-2.56 (m, 1H), 2.47-2.46 (m, 1H), 2.39-2.28 (m, 4H), 2.12 (s, 3H), 2.09 (s, 3H), 2.03-1.91 (m, 2H), 1.84-1.78 (m, 4H), 1.62-1.35 (m, 8H), 1.18-1.07 (m, 2H), 1.04 (d, J=10.5 Hz, 3H), 0.97 (d, J=6.5 Hz, 3H), 0.89-0.81 (m, 9H) ppm. Anal. HPLC: >99%, R$_t$: 6.84 min (Method A).

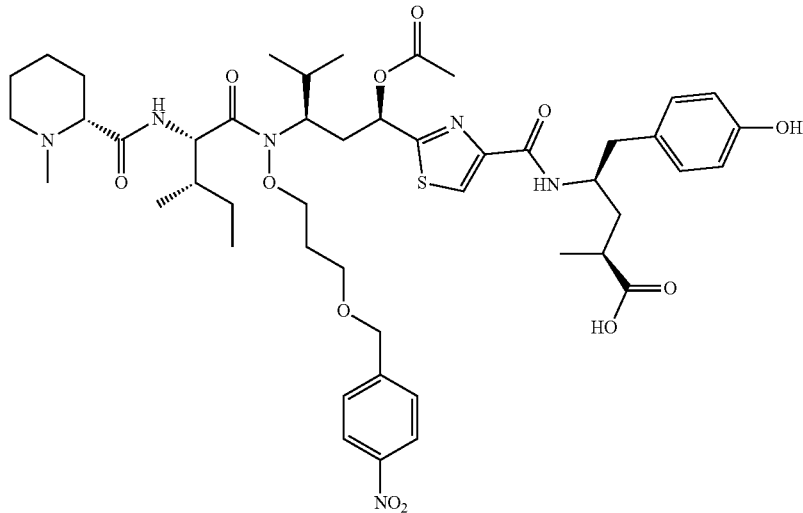

(Vi)

(2S,4R)-5-(4-Hydroxyphenyl)-4-(2-((8R,10R)-8-isopropyl-7-((2S,3S)-3-methyl-2-((R)-1-methylpiperidine-2-carboxamido)pentanoyl)-1-(4-nitrophenyl)-12-oxo-2,6,11-trioxa-7-azatridecan-10-yl)thiazole-4-carboxamido)-2-methylpentanoic acid (Vi)

Following the general procedure for VI, Vi (30 mg, 47% yield) was obtained as a white solid. ESI m/z 939.5 (M+H)$^+$. $^1$H NMR (500 MHz, DMSO$_{d6}$) δ 12.08 (s, 1H), 9.15 (s, 1H), 8.19 (s, 1H), 8.17 (d, J=8.5 Hz, 2H), 7.86 (d, J=8.5 Hz, 1H), 7.56 (d, J=8.5 Hz, 2H), 7.51 (d, J=10.0 Hz, 1H), 6.96 (d, J=8.5 Hz, 2H), 6.62 (d, J=8.5 Hz, 2H), 5.77 (d, J=12.5 Hz, 1H), 5.77 (t, J=8.5 Hz, 1H), 4.59 (s, 2H), 4.31-4.27 (m, 1H), 4.15-4.04 (m, 3H), 3.68-3.58 (m, 2H), 2.85-2.82 (m, 1H), 2.75-2.70 (m, 1H), 2.67-2.62 (m, 1H), 2.42-2.28 (m, 4H), 2.10 (s, 3H), 2.09 (s, 3H), 1.98-1.91 (m, 4H), 1.85-1.74 (m, 2H), 1.63-1.32 (m, 7H), 1.20-1.11 (m, 1H), 1.05-0.99 (m, 4H), 0.93 (d, J=6.0 Hz, 3H), 0.84 (d, J=7.0 Hz, 6H), 0.79 (t, J=7.5 Hz, 3H) ppm.

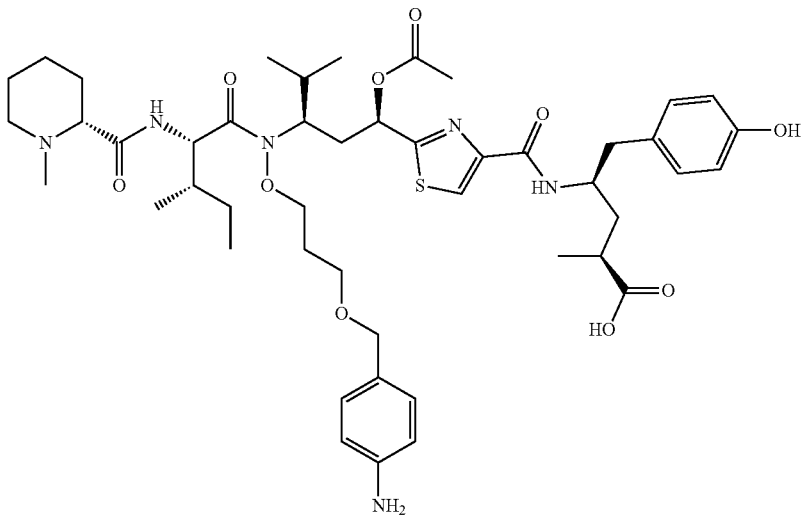

(Vj)

(2S,4R)-4-(2-(((8R,10R)-1-(4-Aminophenyl)-8-isopropyl-7-((2S,3S)-3-methyl-2-((R)-1-methylpiperidine-2-carboxamido)pentanoyl)-12-oxo-2,6,11-trioxa-7-azatridecan-10-yl)thiazole-4-carboxamido)-5-(4-hydroxyphenyl)-2-methylpentanoic acid (Vj)

To a solution of compound Vi (4.0 mg, 4.2 μmol) in ethanol (2.0 mL) was added palladium on charcoal (5% Pd, 0.6 mg) and the mixture was degassed and backfilled with hydrogen 3 times. The resulting mixture was stirred under hydrogen atmosphere at rt for 2 hours until the nitro group was totally reduced, as monitored by LCMS. The mixture was filtered through Celite and the Celite was washed with ethanol (3×). The combined filtrate was concentrated in vacuo. The residue was purified by Prep-HPLC (ammonium bicarbonate system) to give compound Vj (2.0 mg, 53% yield) as a white solid. ESI m/z: 909 (M+H)$^+$. $^1$H NMR (500 MHz, DMSO$_{d6}$) δ 9.16 (s, 1H), 8.18 (s, 1H), 7.84 (d, J=9.2 Hz, 1H), 7.48 (d, J=9.6 Hz, 1H), 6.96 (d, J=8.4 Hz, 2H), 6.90 (d, J=8.0 Hz, 2H), 6.62 (d, J=8.4 Hz, 2H), 6.46 (d, J=8.4 Hz, 2H), 5.76 (d, J=9.6 Hz, 1H), 4.75 (t, J=8.4 Hz, 1H), 4.23-4.16 (m, 3H), 4.11 (br s, 1H), 4.04-3.98 (m, 2H), 3.50-3.43 (m, 2H), 2.84-2.81 (m, 1H), 2.75-2.60 (m, 2H), 2.37-2.30 (m, 3H), 2.09-2.07 (m, 9H), 1.97-1.74 (m, 6H), 1.63-1.60 (m, 2H), 1.51-1.33 (m, 5H), 1.23-1.05 (m, 2H), 1.02 (d, J=7.6 Hz, 3H), 0.93 (d, J=6.4 Hz, 3H), 0.87-0.80 (m, 9H) ppm. Chiral SFC >99% (AD-H, AS-H, OJ-H, and OD-H), R$_t$: 1.61 min (AD-H), 2.71 min (AS-H), 4.32 min (OD-H), and 1.97 min (OJ-H).

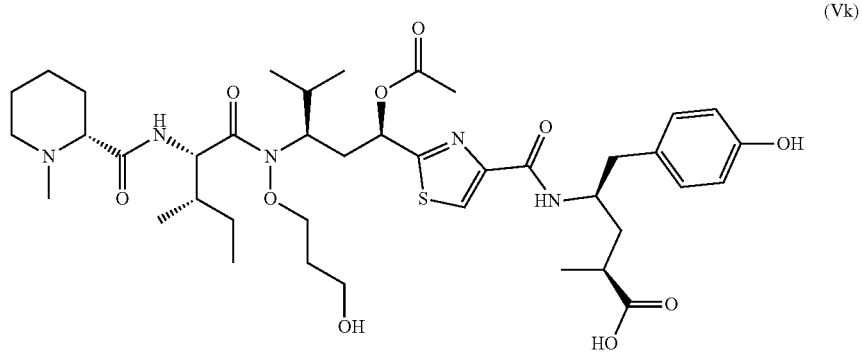 [SMILES: CC[C@H](C)[C@H](NC(=O)[C@H]1CCCCN1C)C(=O)N(OCCCO)[C@H](C[C@@H](OC(C)=O)c1nc(C(=O)N[C@@H](Cc2ccc(O)cc2)C[C@H](C)C(=O)O)cs1)C(C)C]

(Vk)

(2S,4R)-4-(2-((1R,3R)-1-Acetoxy-3-((2S,3S)—N-(3-hydroxypropoxy)-3-methyl-2-((R)-1-methylpiperidine-2-carboxamido)pentanamido)-4-methylpentyl)thiazole-4-carboxamido)-5-(4-hydroxyphenyl)-2-methylpentanoic acid (Vk)

To a solution of compound Vi (17 mg, 18 µmol) in methanol (4.0 mL) was added palladium on charcoal (5% Pd, 1.7 mg) and the mixture was degassed and backfilled with hydrogen 3 times. The resulting mixture was stirred under hydrogen atmosphere at rt overnight, and then at 50° C. for another 6 hours. LCMS showed that neither Vi nor Vj remained. The mixture was filtered through Celite and the Celite was washed with ethanol (3 times). The combined filtrate was concentrated in vacuo. The residue was purified by Prep-HPLC (ammonium bicarbonate system) to give compound Vk (6.0 mg, 41% yield) as a white solid. ESI m/z: 804.2 (M+H)$^+$. $^1$H NMR (500 MHz, DMSO$_{d6}$) δ 9.16 (s, 1H), 8.18 (s, 1H), 7.95 (br s, 1H), 7.51 (d, J=10.0 Hz, 1H), 6.98 (d, J=8.5 Hz, 2H), 6.63 (d, J=8.5 Hz, 2H), 6.80 (d, J=11.5 Hz, 1H), 4.79 (t, J=8.5 Hz, 1H), 4.26-4.22 (m, 1H), 4.14-4.06 (m, 3H), 3.58-3.56 (m, 2H), 2.85-2.82 (m, 1H), 2.77-2.72 (m, 1H), 2.67-2.63 (m, 1H), 2.48-2.46 (m, 1H), 2.40-2.30 (m, 2H), 2.13 (s, 3H), 2.10 (s, 3H), 2.04-1.91 (m, 2H), 1.85-1.79 (m, 4H), 1.64-1.62 (m, 2H), 1.55-1.32 (m, 6H), 1.20-1.09 (m, 2H), 1.05 (d, J=7.0 Hz, 3H), 0.96 (d, J=7.0 Hz, 3H), 0.89-0.82 (m, 10H) ppm.

Synthesis of O-Tubulysin (FIG. 5A)

General Procedure for IX and X

To a solution of compound A-1 (1.0 equiv.) in DCM (50 mM) were added compound A-2 (1.5 equiv.) and DIPEA (4.0 equiv.), and the reaction mixture was stirred at RT for 4 hours, which was monitored by LCMS. The resulting mixture was directly purified by reversed phase flash chromatography (0-30% acetonitrile in aq. TFA (0.01%)) to give IX or X (7-57% yield) as an off-white solid.

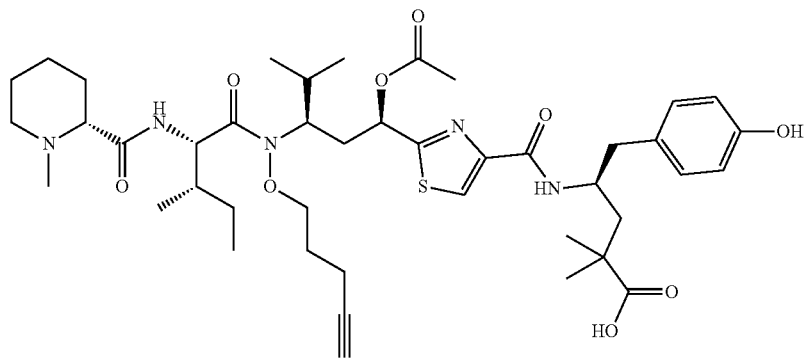 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-hydroxyphenyl)-2,2-dimethylpentanoic acid (IX)

Following the general procedure for IX and X from compound A-1b treated with compound A-2e, payload IX (15 mg, 12% yield) was obtained as a white solid. ESI m/z 826.5 (M+H)$^+$. $^1$H NMR (400 MHz, DMSO$_{d6}$) δ 9.16 (s, 1H), 8.16 (s, 1H), 7.65 (d, J=8.4 Hz, 1H), 7.59 (d, J=9.6 Hz, 1H), 6.95 (d, J=8.4 Hz, 2H), 6.62 (d, J=8.4 Hz, 2H), 5.82 (d, J=10.0 Hz, 1H), 4.76 (t, J=8.4 Hz, 1H), 4.23-4.20 (m, 2H), 4.09-4.01 (m, 2H), 2.90-2.80 (m, 2H), 2.73-2.68 (m, 1H), 2.63-2.58 (m, 1H), 2.39-2.31 (m, 3H), 2.14-2.06 (m, 6H), 2.01-1.87 (m, 3H), 1.84-1.80 (m, 3H), 1.66-1.61 (m, 3H), 1.56-1.53 (m, 1H), 1.46-1.36 (m, 3H), 1.22-1.11 (m, 2H), 1.05-1.03 (m, 7H), 0.96 (d, J=6.4 Hz, 3H), 0.88-0.81 (m, 10H) ppm.

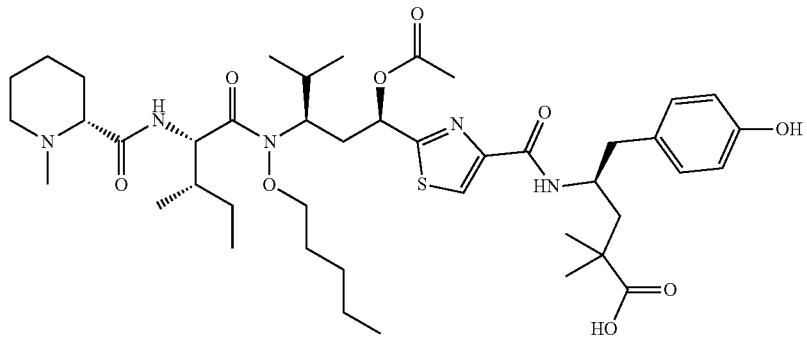 [SMILES: CCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-(4-hydroxyphenyl)-2,2-dimethylpentanoic acid (X)

Following the general procedure for IX and X from compound A-1c treated with compound A-2e, payload X (20 mg, 57% yield) was obtained as an off-white solid. ESI m/z 830.1 (M+H)$^+$. $^1$H NMR (400 MHz, DMSO$_{d6}$) δ 9.15 (s, 1H), 8.16 (s, 1H), 7.67 (br s, 1H), 7.47 (d, J=10.0 Hz, 1H), 6.94 (d, J=8.4 Hz, 2H), 6.61 (d, J=8.4 Hz, 2H), 5.80 (d, J=9.6 Hz, 1H), 4.79 (t, J=9.2 Hz, 1H), 4.19-4.04 (m, 3H), 3.95-3.93 (m, 1H), 2.85-2.81 (m, 1H), 2.71-2.62 (m, 2H), 2.43-2.30 (m, 3H), 2.11 (d, J=9.6 Hz, 6H), 2.10-1.76 (m, 4H), 1.66-1.10 (m, 15H), 1.04 (d, J=6.0 Hz, 6H), 0.96 (d, J=6.8 Hz, 3H), 0.88-0.81 (m, 12H) ppm.

Synthesis of O-Tubulysin Carbonates (VI)

General Procedure for Compound 33A,F,H (FIG. 7A)

To a mixture of compound 27a,c,f (1.0 equiv.) and bis(4-nitrophenyl) carbonate (NPC) (5.0 equiv.) in dry DMF (10 mL per gram of 27) was added DIPEA (3 equiv.) and the mixture was stirred at rt for 16 hours until compound 27a,c,f was totally consumed, as monitored by LCMS. The resulting mixture was poured into sat. aq. sodium bicarbonate and the aqueous solution was extracted with ethyl acetate (4 times). The combined organic solution was washed with brine, dried over sodium sulfate, filtered, and concentrated to dryness to give crude compound 33A,F,H as yellow oil, which was used in the next step without purification.

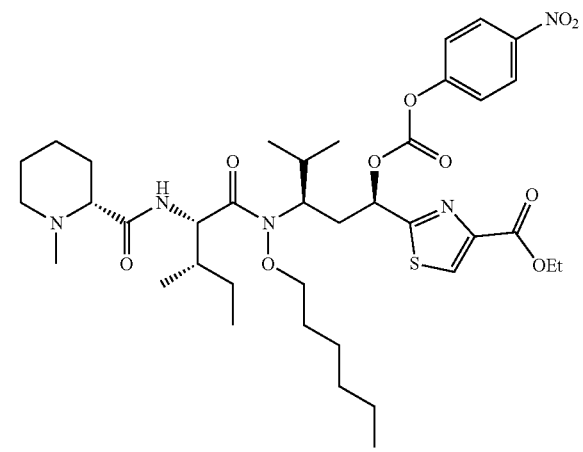 [SMILES: CCCCCCON(C(=O)[C@@H](NC(=O)[C@H]1CCCCN1C)[C@@H](C)CC)[C@H](C[C@@H](OC(=O)Oc1ccc([N+](=O)[O-])cc1)c1nc(C(=O)OCC)cs1)C(C)C]

Ethyl 2-((1R,3R)-3-((2S,3S)—N-(hexyloxy)-3-methyl-2-((R)-1-methylpiperidine-2-carboxamido)pentanamido)-4-methyl-1-((4-nitrophenoxy)carbonyloxy)pentyl)thiazole-4-carboxylate (33A)

To a mixture of compound 27a (0.10 g, 0.16 mmol) and bis(4-nitrophenyl) carbonate (NPC) (0.25 g, 0.82 mmol) in dry DMF (1 mL) was added DIPEA (63 mg, 0.49 mmol) and the mixture was stirred at rt for 16 hours until compound 27a was totally consumed, as monitored by LCMS. The resulting mixture was poured into sat. aq. sodium bicarbonate (10.0 mL) and the aqueous solution was extracted with ethyl acetate (4 times). The combined organic solution was washed with brine, dried over sodium sulfate, filtered, and concentrated to dryness to give crude compound 33A (430 mg) as a yellow oil, which was used in the next step without purification. ESI m/z: 775.8 (M+H)+.

General Procedure for Compound 34a-e,F,H (FIG. 7A)

A solution of crude 33A,F,H obtained above (1.0 equiv. calculated from compound 27a,c,f) in DCM (5.0 mL) was treated with $R^2NH_2$ (2 M solution in THF, 4.0 equiv.) by syringe. The resulting solution was stirred at rt for 16 hours. The reaction mixture was then diluted with DCM (5.0 mL) and washed with sat. aq. sodium bicarbonate (10 mL). The aqueous layer was extracted with DCM (twice). The combined organic solution was dried over sodium sulfate, filtered, and concentrated in vacuo to give a crude carbamate, which was dissolved in water and THF. To the solution was added lithium hydroxide hydrate (7-8 equiv.). The resulting mixture was stirred at rt overnight. The volatiles were removed in vacuo and the residual aqueous mixture was acidified with aq. citric acid solution (1 M) to pH 6.0. The mixture was extracted with DCM (3 times). The combined organic layers were concentrated and the residue was purified by RP chromatography (0-80% acetonitrile in water (with or without 0.01% TFA)) to give compound 34a-e,F,H as a white solid.

General Procedure for Payloads VIa-f,h (FIG. 7A)

To a mixture of compound 34 (1.0 equiv.) and PFP (1.5 equiv.) in dry DCM (10-15 mg/mL) was added a solution of DIC (1.1 equiv.) in DCM (5-10 mg/mL) dropwise at 0° C. by syringe. The resulting solution was allowed to warm to rt and stirred for 16 hours, and was monitored by LCMS. The volatiles were removed in vacuo and the residue was suspended in ethyl acetate. The solids were filtered off and the filtrate was concentrated. The residue was dissolved in dry DMF (15-20 mg/mL) and to the solution were added DIPEA (3.0 equiv.) and intermediate Ie or Ic (1.0 equiv.) in succession. The reaction mixture was stirred at rt overnight, and monitored by LCMS. The reaction mixture was directly purified by Prep-HPLC (ammonium bicarbonate system) to give VIa-e or Fmoc-VIf,h as a white solid. The compound Fmoc-VIf,h (1 equiv.) was dissolved into DMF (0.15 mL per mg of Fmoc-VIf,h). To the solution was added piperidine ($V_{pip}/V_{DMF}$=1/20, excess) and the reaction mixture was stirred at rt for an hour until Fmoc was completely removed as monitored by LCMS. The reaction mixture was directly purified by prep-HPLC (method B) to give VIf,h as a white solid.

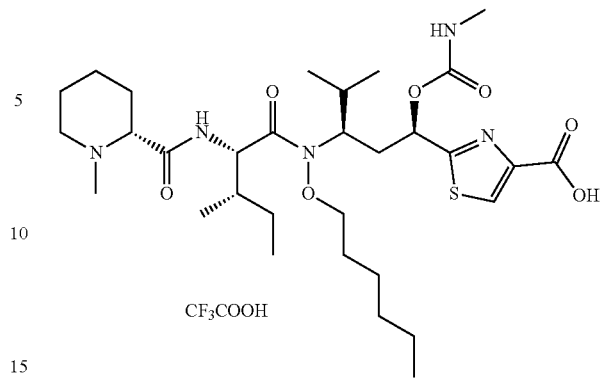

2-((5R,7R)-7-Isopropyl-8-((2S,3S)-3-methyl-2-((R)-1-methylpiperidine-2-carboxamido)pentanoyl)-3-oxo-4,9-dioxa-2,8-diazapentadecan-5-yl)thiazole-4-carboxylic acid trifluoroacetic acid salt (34a)

Following the general procedure for 34a-e,F,H, compound 34a (43 mg, 40% yield from 27a) was obtained as a trifluoroacetic acid salt. ESI m/z: 640.0 (M+H)+. $^1$H NMR (400 MHz, DMSO$_{d6}$) δ 9.70 (br s, 1H), 8.98-8.96 (m, 1H), 8.42 (s, 1H), 7.46 (d, J=4.8 Hz, 1H), 5.62 (d, J=7.6 Hz, 1H), 4.78-4.73 (m, 1H), 4.08-4.05 (m, 1H), 3.92-3.82 (m, 2H), 3.63-3.61 (m, 1H), 3.06-2.99 (m, 1H), 2.71 (s, 3H), 2.54-2.51 (m, 3H), 2.17-2.05 (m, 3H), 1.87-1.75 (m, 1H), 1.67-1.66 (m, 2H), 1.58-1.54 (m, 4H), 1.46-1.36 (m, 4H), 1.28-1.27 (m, 4H), 1.16-1.12 (m, 1H), 0.96-0.82 (m, 17H) ppm.

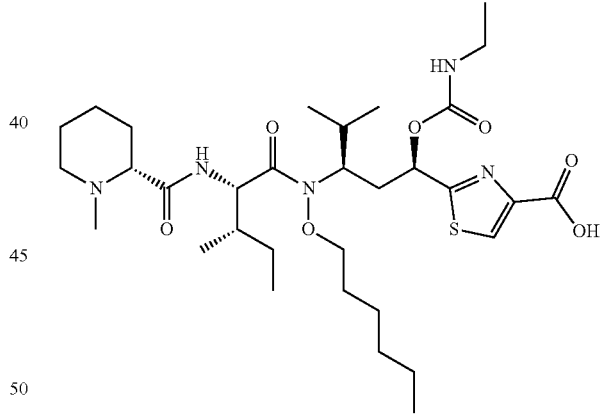

2-((6R,8R)-8-isopropyl-9-((2S,3S)-3-methyl-2-((R)-1-methylpiperidine-2-carboxamido)pentanoyl)-4-oxo-5,10-dioxa-3,9-diazahexadecan-6-yl)thiazole-4-carboxylic acid (34b)

Following the general procedure for 34a-e,F,H, compound 34b (10 mg, 10% yield from 27a) was obtained as a trifluoroacetic acid salt. ESI m/z: 654.3 (M+H)+. $^1$H NMR (500 MHz, DMSO$_{d6}$) δ 8.31 (s, 1H), 7.59 (br s, 1H), 7.51-7.48 (m, 1H), 5.60 (d, J=7.0 Hz, 1H), 4.79-4.76 (m, 1H), 4.10-4.06 (m, 1H), 3.95-3.90 (m, 1H), 3.84-3.83 (m, 1H), 3.00-2.94 (m, 2H), 2.89-2.86 (m, 1H), 2.18-2.16 (m, 4H), 2.05-2.03 (m, 2H), 1.82-1.80 (m, 1H), 1.69-1.54 (m, 6H), 1.47-1.37 (m, 6H), 1.29-1.27 (m, 5H), 1.19-1.16 (m, 1H), 1.10-1.06 (m, 1H), 0.99 (t, J=7.5 Hz, 3H), 0.94 (d, J=6.0 Hz, 3H), 0.91-0.84 (m, 12H) ppm.

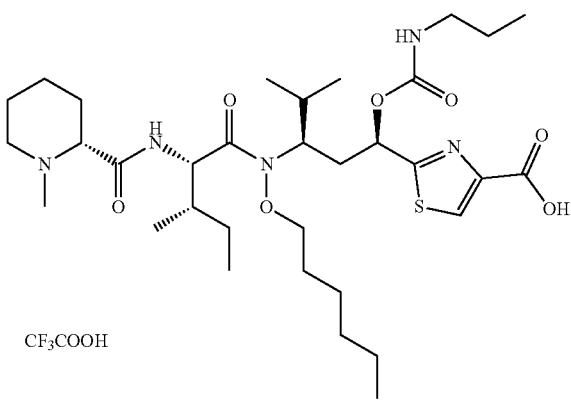 [SMILES: "CF3COOH" ; CCCCCCON(C(=O)[C@@H](NC(=O)[C@H]1CCCCN1C)[C@@H](C)CC)[C@H](C[C@@H](OC(=O)NCCC)c1nc(C(=O)O)cs1)C(C)C]

2-((7R,9R)-9-Isopropyl-10-((2S,3S)-3-methyl-2-((R)-1-methylpiperidine-2-carboxamido)pentanoyl)-5-oxo-6,11-dioxa-4,10-diazaheptadecan-7-yl)thiazole-4-carboxylic acid trifluoroacetic acid salt (34c)

Following the general procedure for 34a-e,F,H, compound 34c (45 mg, 36% yield from 27a) was obtained as a trifluoroacetic acid salt. ESI m/z: 667.9 (M+H)[+]. $^1$H NMR (400 MHz, DMSO$_{d6}$) δ 13.17 (br s, 1H), 9.67 (br s, 1H), 8.99 (s, 1H), 8.42 (s, 1H), 7.59 (t, J=5.6 Hz, 1H), 5.62 (d, J=11.8 Hz, 1H), 4.77 (t, J=8.6 Hz, 1H), 4.16-4.01 (m, 1H), 3.94-3.87 (m, 1H), 3.83 (br s, 1H), 3.63 (br s, 1H), 3.11-2.95 (m, 1H), 2.89 (q, J=6.8 Hz, 2H), 2.70 (s, 3H), 2.62-2.53 (m, 1H), 2.26-1.96 (m, 3H), 1.93-1.82 (m, 1H), 1.82-1.52 (m, 6H), 1.51-1.33 (m, 6H), 1.33-1.21 (m, 4H), 1.20-1.08 (m, 1H), 1.00-0.88 (m, 9H), 0.88-0.75 (m, 9H) ppm.

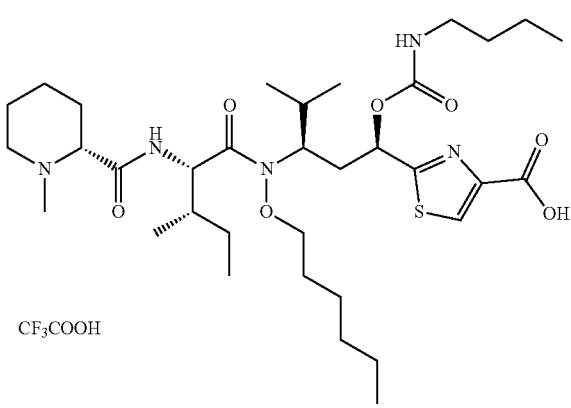 [SMILES: "CF3COOH" ; CCCCCCON(C(=O)[C@@H](NC(=O)[C@H]1CCCCN1C)[C@@H](C)CC)[C@H](C[C@@H](OC(=O)NCCCC)c1nc(C(=O)O)cs1)C(C)C]

2-((8R,10R)-10-Isopropyl-11-((2S,3S)-3-methyl-2-((R)-1-methylpiperidine-2-carboxamido)pentanoyl)-6-oxo-7,12-dioxa-5,11-diazaoctadecan-8-yl)thiazole-4-carboxylic acid trifluoroacetic acid salt (34d)

Following the general procedure for 34a-e,F,H, compound 34d (50 mg, 44% yield from 27a) was obtained as a trifluoroacetic acid salt. ESI m/z: 682.0 (M+H)[+]. $^1$H NMR (500 MHz, DMSO$_{d6}$) δ 13.16 (br s, 1H), 9.69 (s, 1H), 9.01 (d, J=9.1 Hz, 1H), 8.42 (s, 1H), 7.57 (t, J=5.6 Hz, 1H), 5.62 (d, J=11.9 Hz, 1H), 4.76 (t, J=8.7 Hz, 1H), 4.11-4.02 (m, 1H), 3.94-3.80 (m, 2H), 3.62 (s, 1H), 3.34 (d, J=12.1 Hz, 1H), 3.09-3.00 (m, 1H), 2.97-2.88 (m, 2H), 2.74-2.67 (m, 3H), 2.62-2.54 (m, 1H), 2.18-2.04 (m, 3H), 1.92-1.83 (m, 1H), 1.83-1.54 (m, 6H), 1.49-1.20 (m, 12H), 1.20-1.10 (m, 1H), 0.98-0.88 (m, 9H), 0.88-0.80 (m, 9H) ppm.

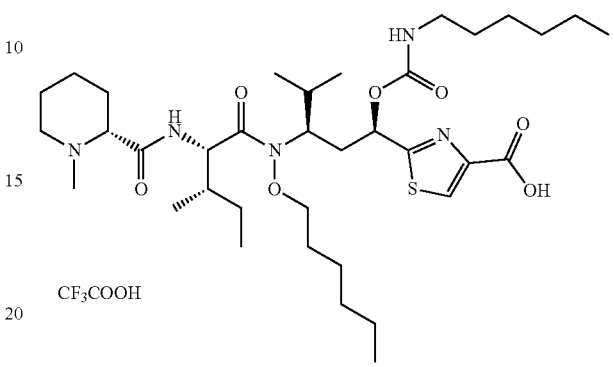

2-((9R,11R)-9-Isopropyl-8-((2S,3S)-3-methyl-2-((R)-1-methylpiperidine-2-carboxamido)pentanoyl)-13-oxo-7,12-dioxa-8,14-diazaicosan-11-yl)thiazole-4-carboxylic acid trifluoroacetic acid salt (34e)

Following the general procedure for 34a-e,F,H, compound 34e (40 mg, 46% yield from 27a) was obtained as a trifluoroacetic acid salt. ESI m/z: 709.9 (M+H)[+].

(VIa) (2S,4R)-5-(4-Hydroxyphenyl)-4-(2-((5R,7R)-7-isopropyl-8-((2S,3S)-3-methyl-2-((R)-1-methylpiperidine-2-carboxamido)pentanoyl)-3-oxo-4,9-dioxa-2,8-diazapentadecan-5-yl)thiazole-4-carboxamido)-2-methylpentanoic acid (VIa)

Following the general procedure for VIa-f,h, VIa (16 mg, 36% yield) was obtained as a white solid. ESI m/z: 845.0 (M+H)[+]. $^1$H NMR (500 MHz, DMSO$_{d6}$) δ 9.70 (s, 1H), 9.22 (br s, 1H), 8.96 (d, J=8.5 Hz, 1H), 8.17 (s, 1H), 7.82 (d, J=8.5 Hz, 1H), 7.44 (d, J=4.5 Hz, 1H), 6.98 (d, J=8.0 Hz, 2H), 6.63 (d, J=8.0 Hz, 2H), 5.65 (d, J=11.5 Hz, 1H), 4.80-4.76 (m, 1H), 4.13-4.11 (m, 2H), 3.98-3.96 (m, 1H), 3.85-3.81 (m, 2H), 3.32 (d, J=11.0 Hz, 1H), 3.08-3.01 (m, 1H), 2.74-2.66 (m, 5H), 2.55-2.53 (d, J=8.5 Hz, 3H), 2.42-2.38 (m, 1H), 2.25-2.20 (m, 1H), 2.09-2.07 (m, 2H), 1.88-1.82 (m, 4H), 1.78-1.66 (m, 4H), 1.62-1.23 (m, 10H), 1.16-1.11 (m, 1H), 1.07 (d, J=7.0 Hz, 3H), 0.98 (d, J=7.0 Hz, 3H), 0.92-0.90 (m, 6H), 0.86-0.83 (m, 6H) ppm. Chiral SFC: >99% (AD-H and AS-H).

(VIb) (2S,4R)-5-(4-hydroxyphenyl)-4-(2-((6R,8R)-8-isopropyl-9-((2S,3S)-3-methyl-2-((R)-1-methylpiperidine-2-carboxamido)pentanoyl)-4-oxo-5,10-dioxa-3,9-diazahexadecan-6-yl)thiazole-4-carboxamido)-2-methylpentanoic acid (VIb)

Following the general procedure for VIa-f,h, VIb (2.0 mg, 15% yield) was obtained as a white solid. ESI m/z: 859.5 (M+H)[+]. $^1$H NMR (500 MHz, DMSO$_{d6}$) δ 9.17 (s, 1H), 8.15 (s, 1H), 7.76 (br s, 1H), 7.49 (t, J=5.5 Hz, 1H), 7.44 (d, J=9.5 Hz, 1H), 6.97 (d, J=8.5 Hz, 2H), 6.64 (d, J=8.5 Hz, 2H), 5.65 (d, J=11.0 Hz, 1H), 4.81-4.77 (m, 1H), 4.16-4.11 (m, 2H), 3.97-3.94 (m, 2H), 3.02-2.96 (m, 1H), 2.85-2.82 (m, 1H), 2.75-2.64 (m, 4H), 2.37-2.36 (m, 1H), 2.25-2.19 (m, 1H), 2.10 (s, 3H), 2.04-1.92 (m, 3H), 1.87-1.81 (m, 2H), 1.65-1.48 (m, 7H), 1.41-1.35 (m, 4H), 1.28-1.25 (m, 5H), 1.18-1.15 (m, 2H), 1.05 (d, J=7.0 Hz, 3H), 1.02-0.97 (m, 6H), 0.89 (d, J=7.0 Hz, 6H), 0.86-0.82 (m, 6H) ppm.

(VIc) (2S,4R)-5-(4-Hydroxyphenyl)-4-(2-((7R,9R)-9-isopropyl-10-((2S,3S)-3-methyl-2-((R)-1-methylpiperidine-2-carboxamido)pentanoyl)-5-oxo-6,11-dioxa-4,10-diazaheptadecan-7-yl)thiazole-4-carboxamido)-2-methylpentanoic acid (VIc)

Following the general procedure for VIa-f,h, VIc (20 mg, 40% yield) was obtained as a white solid. ESI m/z: 873.5 (M+H)⁺. ¹H NMR (500 MHz, DMSO$_{d6}$) δ 9.16 (s, 1H), 8.15 (s, 1H), 7.70 (d, J=8.8 Hz, 1H), 7.51 (t, J=5.6 Hz, 1H), 7.45 (d, J=9.4 Hz, 1H), 6.97 (d, J=8.3 Hz, 2H), 6.63 (d, J=8.3 Hz, 2H), 5.65 (d, J=10.8 Hz, 1H), 4.79 (d, J=8.0 Hz, 1H), 4.20-4.07 (m, 2H), 4.07-3.90 (m, 2H), 2.91 (q, J=6.5 Hz, 2H), 2.87-2.79 (m, 1H), 2.76-2.61 (m, 2H), 2.47-2.34 (m, 3H), 2.27-2.17 (m, 1H), 2.10 (s, 3H), 2.07-1.90 (m, 2H), 1.88-1.76 (m, 2H), 1.67-1.56 (m, 4H), 1.56-1.44 (m, 3H), 1.44-1.31 (m, 6H), 1.29-1.22 (m, 4H), 1.21-1.08 (m, 2H), 1.05 (d, J=7.1 Hz, 3H), 0.97 (d, J=6.6 Hz, 3H), 0.91-0.78 (m, 16H) ppm. Chiral SFC: >99% (AD-H and AS-H).

(VId) (2S,4R)-5-(4-Hydroxyphenyl)-4-(2-((8R,10R)-10-isopropyl-11-((2S,3S)-3-methyl-2-((R)-1-methylpiperidine-2-carboxamido)pentanoyl)-6-oxo-7,12-dioxa-5,11-diazaoctadecan-8-yl)thiazole-4-carboxamido)-2-methylpentanoic acid (VId)

Following the general procedure for VIa-f,h, VId (33 mg, 50% yield) was obtained as a white solid. ESI m/z: 887.3 (M+H)⁺. ¹H NMR (500 MHz, DMSO$_{d6}$) δ 9.16 (s, 1H), 8.14 (s, 1H), 7.70 (d, J=8.6 Hz, 1H), 7.49 (t, J=5.7 Hz, 1H), 7.45 (d, J=9.6 Hz, 1H), 6.97 (d, J=8.3 Hz, 2H), 6.63 (d, J=8.3 Hz, 2H), 5.65 (d, J=9.6 Hz, 1H), 4.93-4.62 (m, 1H), 4.20-4.05 (m, 2H), 4.05-3.86 (m, 2H), 2.95 (q, J=6.5 Hz, 2H), 2.87-2.78 (m, 1H), 2.78-2.60 (m, 2H), 2.48-2.34 (m, 3H), 2.21 (t, J=11.5 Hz, 1H), 2.10 (s, 3H), 2.07-1.90 (m, 2H), 1.89-1.75 (m, 2H), 1.68-1.56 (m, 4H), 1.56-1.44 (m, 3H), 1.42-1.31 (m, 6H), 1.31-1.21 (m, 6H), 1.21-1.07 (m, 2H), 1.05 (d, J=7.1 Hz, 3H), 0.97 (d, J=6.5 Hz, 3H), 0.93-0.72 (m, 16H) ppm. Chiral SFC: >96% (AD-H and AS-H).

(VIe) (2S,4R)-5-(4-Hydroxyphenyl)-4-(2-((9R,11R)-9-isopropyl-8-((2S,3S)-3-methyl-2-((R)-1-methylpiperidine-2-carboxamido)pentanoyl)-13-oxo-7,12-dioxa-8,14-diazaicosan-11-yl)thiazole-4-carboxamido)-2-methylpentanoic acid (VIe)

Following the general procedure for VIa-f,h, VIe (21 mg, 40% yield) was obtained as a white solid. ESI m/z: 915.5 (M+H)⁺. ¹H NMR (400 MHz, DMSO$_{d6}$) δ 9.17 (s, 1H), 8.15 (s, 1H), 7.71 (d, J=9.0 Hz, 1H), 7.58-7.35 (m, 2H), 6.97 (d, J=8.3 Hz, 2H), 6.63 (d, J=8.3 Hz, 2H), 5.65 (d, J=10.0 Hz, 1H), 4.78 (d, J=8.4 Hz, 1H), 4.21-4.04 (m, 2H), 4.04-3.86 (m, 2H), 3.01-2.89 (m, 2H), 2.89-2.77 (m, 1H), 2.77-2.59 (m, 2H), 2.48-2.31 (m, 3H), 2.30-2.16 (m, 1H), 2.11 (s, 3H), 2.07-1.90 (m, 2H), 1.90-1.74 (m, 2H), 1.66-1.55 (m, 4H), 1.54-1.44 (m, 3H), 1.43-1.31 (m, 6H), 1.29-1.16 (m, 12H), 1.05 (d, J=7.0 Hz, 3H), 0.96 (d, J=6.5 Hz, 3H), 0.92-0.77 (m, 16H) ppm.

(VIf) Ethyl 2-[(1R,3R)-4-methyl-3-[(2S,3S)-3-methyl-2-{[(2R)-1-methylpiperidin-2-yl]formamido}-N-(pent-4-yn-1-yloxy)pentanamido]-1-[(4-nitrophenoxycarbonyl)oxy]pentyl]-1,3-thiazole-4-carboxylate (33F) (FIG. 7B)

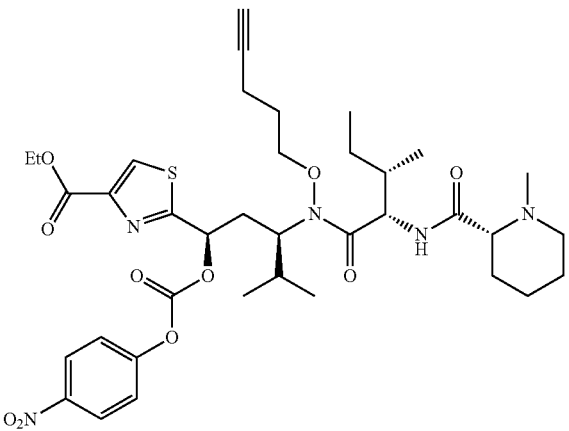 [SMILES: C#CCCCON(C(=O)[C@@H](NC(=O)[C@H]1CCCCN1C)[C@@H](C)CC)[C@H](C[C@@H](OC(=O)Oc1ccc([N+](=O)[O-])cc1)c1nc(C(=O)OCC)cs1)C(C)C]

Following the similar procedure for 33A, except substituting 27c for 27a, compound 33F (120 mg, crude) was obtained as yellow oil, which was used for the next step without further purification. ESI m/z: 758.3 (M+H)⁺.

2-[(1R,3R)-1-[(Ethylcarbamoyl)oxy]-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazole-4-carboxylic acid (34F) (FIG. 7B)

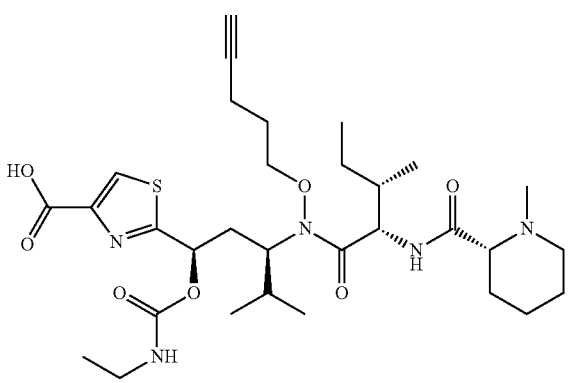 [SMILES: C#CCCCON(C(=O)[C@@H](NC(=O)[C@H]1CCCCN1C)[C@@H](C)CC)[C@H](C[C@@H](OC(=O)NCC)c1nc(C(=O)O)cs1)C(C)C]

Following the similar procedure for 34b, except substituting 33F for 33A, compound 34F (25 mg, 52% yield in 3 steps) was obtained as colorless oil after purification by reversed phase flash chromatography (45-55% acetonitrile in aq. TFA (0.01%)). ESI m/z: 636.2 (M+H)⁺.

(4S)-5-(4-Aminophenyl)-4-({2-[(1R,3R)-1-[(ethyl-carbamoyl)oxy]-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-2,2-dimethylpentanoic acid (VIf) (FIG. 7B)

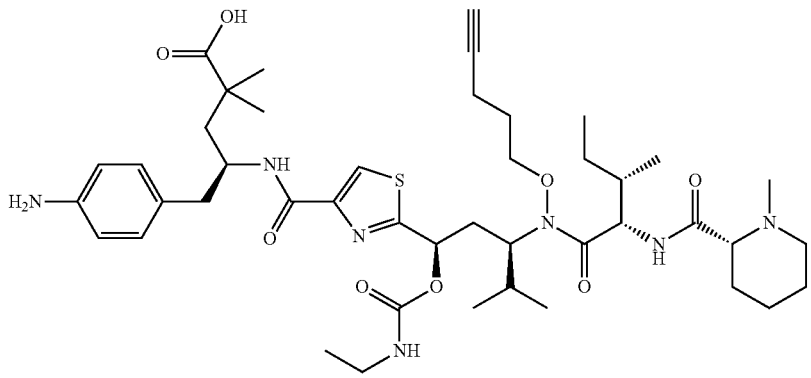 [SMILES: C#CCCCON(C(=O)[C@@H](NC(=O)[C@H]1CCCCN1C)[C@@H](C)CC)[C@H](C[C@@H](OC(=O)NCC)c1nc(C(=O)N[C@@H](Cc2ccc(N)cc2)CC(C)(C)C(=O)O)cs1)C(C)C]

Following the general procedure for VI except substituting 34F for 34 and Ic for Ie, Fmoc-VIf (15 mg) was obtained as a light brown solid. ESI m/z: 1076.3 (M+H)$^+$. The compound Fmoc-VIf (15 mg) was dissolved into DMF (2.0 mL). To the solution was added piperidine (0.10 mL) and the reaction mixture was stirred at rt for an hour until Fmoc was completely removed as monitored by LCMS. The reaction mixture was directly purified by prep-HPLC (method B) to give VIf (8 mg, 27% yield in 3 steps) as a white solid. ESI m/z: 854.5 (M+H)$^+$. $^1$H NMR (methanol$_{d4}$, 500 MHz) δ 8.07 (s, 1H), 6.99 (d, J=8.4 Hz, 2H), 6.66 (d, J=8.4 Hz, 2H), 5.78 (dd, J=11.2, 1.2 Hz, 1H), 4.90-4.88 (m, 1H), 4.38-4.27 (m, 2H), 4.20-4.15 (m, 1H), 4.00-3.91 (m, 1H), 3.16-3.09 (m, 3H), 3.04-3.01 (m, 1H), 2.94-2.91 (m, 1H), 2.85-2.66 (m, 3H), 2.49-2.12 (m, 9H), 2.06-1.55 (m, 12H), 1.43-1.31 (m, 1H), 1.24-1.00 (m, 17H), 0.94 (t, J=7.2 Hz, 3H) ppm. Anal. HPLC: >99%, Retention time: 7.85 min (method B).

(VIg) (4S)-5-(4-Acetamidophenyl)-4-({2-[(1R,3R)-1-[(ethylcarbamoyl)oxy]-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-2,2-dimethylpentanoic acid (VIg) (FIG. 7B)

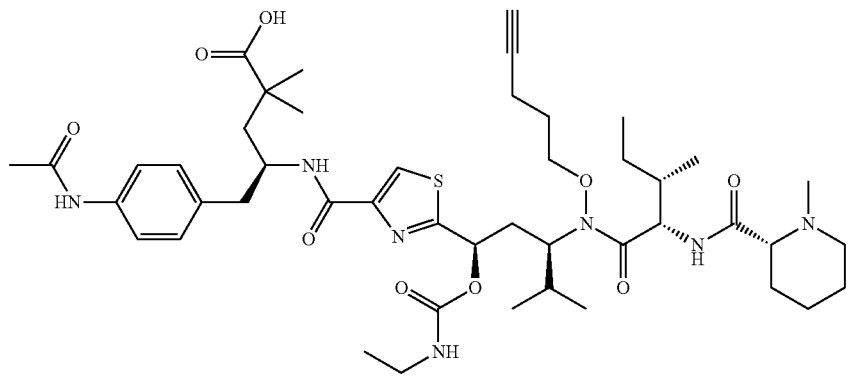 [SMILES: C#CCCCON(C(=O)[C@@H](NC(=O)[C@H]1CCCCN1C)[C@@H](C)CC)[C@H](C[C@@H](OC(=O)NCC)c1nc(C(=O)N[C@@H](Cc2ccc(NC(C)=O)cc2)CC(C)(C)C(=O)O)cs1)C(C)C]

The compound VIf (1.0 mg, 1.2 µmol) was dissolved in DCM (1.0 mL) and the solution was cooled to 0° C. in an ice-bath. To the solution were added a solution of Ac₂O (0.24 mg, 2.4 µmol) in DCM (50 µL) and a solution of DIPEA (0.30 mg, 2.4 µmol) in DCM (50 µL). The reaction mixture was stirred at rt for 2 hours. LCMS showed complete consumption of starting materials, and the desired product was detected. The volatiles were removed in vacuo and the crude product was purified directly by pre-HPLC (method B) to give VIg (0.3 mg, yield 28%) as a white solid. ESI m/z: 896.5 (M+H)⁺. Anal. HPLC: 100%, Retention time: 7.49 min (method B).

(VIh) (S)-5-(4-Aminophenyl)-4-(2-((5R,7R)-7-isopropyl-8-((2S,3S)-3-methyl-2-((R)-1-methylpiperidine-2-carboxamido)pentanoyl)-3-oxo-4,9-dioxa-2,8-diazatetradecan-5-yl)thiazole-4-carboxamido)-2,2-dimethylpentanoic acid (VIh) (FIG. 7B)

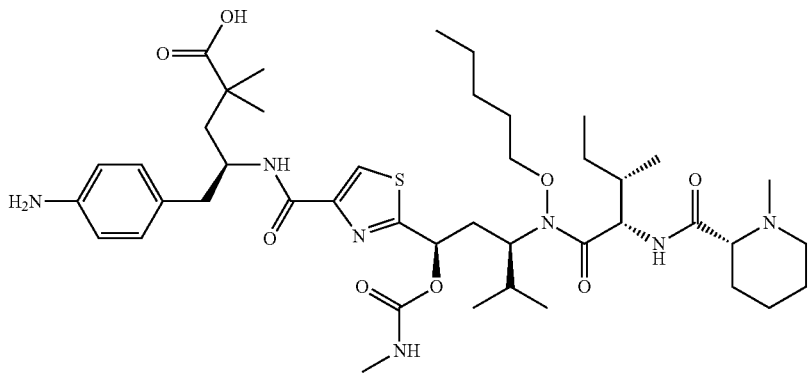 [SMILES: CCCCCON(C(=O)[C@@H](NC(=O)[C@H]1CCCCN1C)[C@@H](C)CC)[C@H](C[C@@H](OC(=O)NC)c1nc(C(=O)N[C@@H](Cc2ccc(N)cc2)CC(C)(C)C(=O)O)cs1)C(C)C]

Following the similar procedure from 27c to compound VIf, except substituting 27f for 27c, compound VIh (2 mg, 4.5% from 27f) was obtained as a white solid. ESI m/z: 844.2 (M+H)⁺. ¹H NMR (DMSO$_{d6}$, 400 MHz) δ 8.10 (d, J=21.6 Hz, 1H), 7.45 (dd, J=30.2, 7.1 Hz, 2H), 6.81 (d, J=8.2 Hz, 2H), 6.44 (d, J=8.3 Hz, 2H), 5.79-5.56 (m, 1H), 4.94-4.63 (m, 3H), 4.14 (s, 2H), 3.95 (d, J=7.1 Hz, 1H), 2.85 (d, J=11.4 Hz, 2H), 2.70-2.60 (m, 2H), 2.56 (d, J=4.6 Hz, 2H), 2.45-2.41 (m, 1H), 2.20 (d, J=11.4 Hz, 1H), 2.09 (d, J=12.0 Hz, 3H), 2.05-1.90 (m, 3H), 1.81 (s, 3H), 1.61 (s, 6H), 1.50 (d, J=20.7 Hz, 2H), 1.35 (d, J=4.8 Hz, 6H), 1.14 (d, J=28.2 Hz, 2H), 1.08 (d, J=9.2 Hz, 1H), 1.03 (d, J=7.9 Hz, 6H), 0.96 (d, J=6.6 Hz, 2H), 0.90-0.79 (m, 12H) ppm.

Exemplary Preparation Schemes E, H, J, K, M, and N

Scheme E (102 and 102a)

To a solution of Fmoc-vc-PAB-X (X=Br, Cl, or -OTf) in DMF is added piperidine and the solution is allowed to stir at rt until consumption of Fmoc-vc-PAB-X is complete by LCMS. Yields are improved in the presence of catalytic NaI. Following standard workup conditions, the crude vc-PAB-X is dissolved in DMF and 6-maleimidohexanoic acid (excess), HATU, and DIPEA are added. The reaction is stirred at rt until vc-PAB-X consumption is complete via LCMS. Following standard workup conditions, the crude material is purified by HPLC to provide 102. Following the same procedure, except substituting 6-maleimidohexanoic acid (excess) with L-3 (excess), provides 102a. Alternatively, crude vc-PAB-X is dissolved in DMF and L-4 (excess) and DIPEA are added. The reaction is stirred at rt until vc-PAB-X consumption is complete via LCMS. Following standard workup conditions, the crude material is purified by HPLC to also provide 102a.

Scheme E (104 and 104a)

To a solution of 100 in DMF is added 102 or 102a (excess). The individual reactions are stirred at rt until consumption of 100 is complete by LCMS. Following standard workup conditions, the individual crude materials are purified via HPLC to provide 104 or 104a, respectively. Alternatively, known 102aa is dissolved in THF (or another polar aprotic solvent) and reduced with DIBAL to provide 102b, after consumption of 102aa as monitored by LCMS. Following standard workup and isolation conditions, 102b is dissolved in DMF (or another polar aprotic solvent) and coupled with 102c in the presence of PyBoc and DIPEA at room temperature to provide 102dd, also after standard workup and isolation conditions (of note: known 102d is equally competent in the following steps). Fmoc-vc-PAB-X (X=Br, Cl, or -OTf) is dissolved in DMF (or another polar aprotic solvent) and treated with 102d or 102dd in the presence of cat. NaI, DMAP, and pyridine to provide crude 102f. Subsequent treatment with piperidine in DMF (or another polar aprotic solvent) provides 102f, after standard workup and isolation conditions. 102f is dissolved in DMF (or another polar aprotic solvent) and treated with L-4 and DIPEA to provide 102h, following standard workup and isolation conditions. 102h can be further manipulated as similarly described in FIGS. 4 and 5 (cf. FIG. 4, 24a-e coupling to 25) en route to 104a (cf. FIG. 5, e.g., A=Q).

Scheme H (108 and 108a)

To a solution of Fmoc-vc-PAB-Br in DMF (or another non-protonated organic solvent) is added NaN₃ and the solution is allowed to stir at rt until consumption of Fmoc-vc-PAB-Br is complete by LCMS. Then piperidine is added and allowed to stir until deprotection of Fmoc is complete by LCMS. Following standard workup conditions, the crude vc-PAB-N₃ is dissolved in DMF (or another non-protonated organic solvent) and 6-maleimidohexanoic acid (excess), HATU, and DIPEA are added. The reaction is stirred at rt until vc-PAB-Br consumption is complete via LCMS. Following standard workup conditions, the crude material is purified by HPLC to provide 108. Following the same procedure, except substituting 6-maleimidohexanoic acid (excess) with L-3 (excess), provides 108a. Alternatively, crude vc-PAB-N$_3$ is dissolved in DMF (or another non-protonated organic solvent) and L-4 (excess) and DIPEA are added. The reaction is stirred at rt until vc-PAB-N$_3$ consumption is complete via LCMS. Following standard workup conditions, the crude material is purified by HPLC to also provide 108a.

Scheme H (110 and 110a)

To a solution of 108 or 108a (excess) and sodium ascorbate in THF:water (3:1) is added 106. Then 1 drop of aq. copper sulfate is added. The individual mixtures are allowed to stir at rt until 106 is consumed by LCMS. Standard workup and purification by HPLC gives 110 and 110a, respectively.

Scheme J (116, 116a, 116b, and 116c)

To a solution of 112, L-1 (excess), and HOBt in DMF (or another non-protonated organic solvent) is added DIPEA and the reaction is allowed to stir until consumption of 112 by LCMS. Following standard workup conditions, the crude material is purified by HPLC to provide 116. Alternatively, to a solution of 112, L-2 (excess) and HOBt in DMF (or another non-protonated organic solvent) is added DIPEA and the reaction is allowed to stir until consumption of 112 by LCMS. Following standard workup conditions, the crude material is purified by HPLC to provide 116a. To a solution of 116a in DMF (or another non-protonated organic solvent) is added piperidine and the reaction is monitored by LCMS until Fmoc deprotection is complete. Following standard workup conditions, the crude material is purified by HPLC to provide 116b. To a solution of 116b in DMF (or another non-protonated organic solvent) is added L-3 (excess), HATU, and DIPEA. The reaction is stirred at rt until 116b consumption is complete via LCMS. Following standard workup conditions, the crude material is purified by HPLC to provide 116c. Or, to a solution of 116b in DMF (or another non-protonated organic solvent) is added L-4 (excess) and DIPEA, and the reaction is stirred at rt until consumption of 116b is complete by LCMS. Following standard workup conditions, the crude material is purified by HPLC to also provide 116c.

Scheme K (120, and 120a)

To a solution of Fmoc-vc-PAB-OH in DCM (or another non-protonated organic solvent) is added TBSCl and NEt$_3$. The reaction was allowed to stir until Fmoc-vc-PAB-OH is consumed by LCMS. Following standard workup conditions, the crude Fmoc-vc-PAB-OTBS is dissolved in DMF (or another non-protonated organic solvent) and piperidine is added. Following standard workup, crude vc-PAB-OTBS is dissolved in DMF (or another non-protonated organic solvent) and 6-maleimidohexanoic acid (excess), HATU, and DIPEA are added. The reaction is stirred at rt until vc-PAB-OTBS consumption via LCMS. Excess TBAF in THF is then added, and after complete deprotection by LCMS, the crude material is purified by HPLC to provide 120. Following the same procedure, except substituting 6-maleimidohexanoic acid (excess) with L-3 (excess), provides 120a. Alternatively, crude vc-PAB-OTBS is dissolved in DMF (or another non-protonated organic solvent) and L-4 (excess) and DIPEA are added. The reaction is stirred at rt until vc-PAB-OTBS consumption is complete via LCMS. Excess TBAF in THF is then added, and after complete deprotection by LCMS, the crude material is purified by HPLC to also provide 120a.

Scheme K (122 and 122a)

To a solution of 118 and PFP in DCM (or another non-protonated organic solvent) is added dropwise a solution of DIC in DCM (or another non-protonated organic solvent) at 0° C. by syringe. The resulting solution is stirred until consumption of 118 by LCMS. Then the volatiles are removed in vacuo and the residue is dissolved in ethyl acetate. The solids are filtered and the filtrate is concentrated to provide intermediate pentafluorophenyl ester. Intermediate ester is dissolved in DMF and DIPEA is added, followed by 120 or 120a. The individual solutions are stirred overnight and are purified by HPLC to give esters 122 or 122a.

Scheme M (128, 128a, 128b, and 128c)

To a solution of 124, L-1 (excess), and HOBt in DMF (or another non-protonated organic solvent) is added DIPEA and the reaction is allowed to stir until consumption of 124 by LCMS. Following standard workup conditions, the crude material is purified by HPLC to provide 128. Alternatively, to a solution of 124, L-2 (excess) and HOBt in DMF (or another non-protonated organic solvent) is added DIPEA and the reaction is allowed to stir until consumption of 124 by LCMS. Following standard workup conditions, the crude material is purified by HPLC to provide 128a. To a solution of 128a in DMF is added piperidine and the reaction is monitored by LCMS until Fmoc deprotection is complete. Following standard workup conditions, the crude material is purified by HPLC to provide 128b. To a solution of 128b in DMF (or another non-protonated organic solvent) is added L-3 (excess), HATU, and DIPEA. The reaction is stirred at rt until 128b consumption is complete via LCMS. Following standard workup conditions, the crude material is purified by HPLC to provide 128c. Or, to a solution of 128b in DMF (or another non-protonated organic solvent) is added L-4 (excess) and DIPEA, and the reaction is stirred at rt until consumption of 128b is complete by LCMS. Following standard workup conditions, the crude material is purified by HPLC to also provide 128c.

Scheme N (134, 134a, 134b, and 134c)

To a solution of 130, L-1 (excess), and HOBt in DMF (or another non-protonated organic solvent) is added DIPEA and the reaction is allowed to stir until consumption of 130 by LCMS. Following standard workup conditions, the crude material is purified by HPLC to provide 134. Alternatively, to a solution of 130, L-2 (excess) and HOBt in DMF (or another non-protonated organic solvent) is added DIPEA and the reaction is allowed to stir until consumption of 130 by LCMS. Following standard workup conditions, the crude material is purified by HPLC to provide 134a. To a solution of 134a in DMF (or another non-protonated organic solvent) is added piperidine and the reaction is monitored by LCMS until Fmoc deprotection is complete. Following standard workup conditions, the crude material is purified by HPLC to provide 134b. To a solution of 134b in DMF (or another non-protonated organic solvent) is added L-3 (excess), HATU, and DIPEA. The reaction is stirred at rt until 134b consumption is complete via LCMS. Following standard workup conditions, the crude material is purified by HPLC to provide 134c. Or, to a solution of 134b in DMF (or another non-protonated organic solvent) is added L-4 (excess) and DIPEA, and the reaction is stirred at rt until consumption of 134b is complete by LCMS. Following standard workup conditions, the crude material is purified by HPLC to also provide 134c.

Synthesis of MC-Linker-Payloads (FIG. 8)

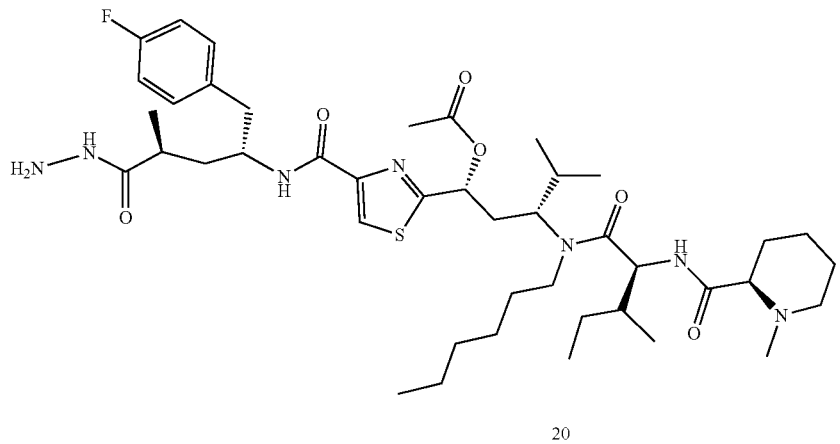

(1R,3R)-1-(4-((2R,4S)-1-(4-fluorophenyl)-5-hydrazinyl-4-methyl-5-oxopentan-2-ylcarbamoyl)thiazol-2-yl)-3-((2S,3R)—N-hexyl-3-methyl-2-((R)-1-methylpiperidine-2-carboxamido)pentanamido)-4-methylpentyl acetate (IVa')

To a solution of IVa (9 mg, 0.011 mmol) in dry ethylacetate (1 mL) under nitrogen at −15° C. were added a mixture of diisopropylethylamine (14 mg, 0.11 mmol) and isobutyl chloroformate (15 mg, 0.11 mmol). After the solution was stirred at −15° C. for an additional 2 hours under nitrogen, a solution of $NH_2NH_2 \cdot H_2O$ (8 mg, 0.17 mmol) in DMF (0.5 mL) was added thereto. The reaction mixture was stirred at −15° C. overnight and then warmed to 20° C. for another 45 min. The crude product was purified by basic prep-HPLC to give IVa' (4 mg, yield 44%) as a white solid. ESI-MS (EI+, m/z): 830 [M+H]+.

(1R,3R)-3-[(2S,3S)—N-(hexyloxy)-3-methyl-2-{[(2R)-1-methylpiperidin-2-yl]formamido}pentanamido]-1-(4-{[(2R,4S)-4-(hydrazinecarbonyl)-1-(4-hydroxyphenyl)-4-methylbutan-2-yl]carbamoyl}-1,3-thiazol-2-yl)-4-methylpentyl acetate (Va')

A mixture of compound Va (50 mg, 60.2 μmol), HATU (34 mg, 90.3 μmol), and DIPEA (16 mg, 120.4 μmol) in dry DMF (5.0 mL) was stirred at rt for 10 min, and to the mixture was then added hydrazine hydrate (95%, 9 mg, 180.7 μmol). The resulting solution was stirred for another 1 h and the reaction was deemed complete by LC-MS. The reaction mixture was directly purified by prep-HPLC (Method B) to give Va' (34 mg, yield 68%) as a white solid. ESI m/z: 844.3 (M+H)+. $^1$H NMR (500 MHz $DMSO_{d6}$) δ 9.15 (s, 1H), 8.94 (s, 1H), 8.21 (s, 1H), 7.79 (d, J=9.0 Hz, 1H), 7.46 (d, J=10.0 Hz, 1H), 6.96 (d, J=8.5 Hz, 2H), 6.62 (d, J=8.5 Hz, 2H), 5.76 (d, J=10.5 Hz, 1H), 4.81-4.78 (m, 1H), 4.18-3.94 (m, 6H), 2.85-2.82 (m, 1H), 2.73-2.62 (m, 2H), 2.47-2.28 (m, 4H), 2.12 (s, 3H), 2.10 (s, 3H), 2.03-1.93 (m, 2H), 1.84-1.77 (m, 2H), 1.64-1.61 (m, 4H), 1.56-1.53 (m, 1H), 1.47-1.45 (m, 2H), 1.39-1.35 (m, 4H), 1.27-1.26 (m, 4H), 1.18-1.05 (m, 2H), 0.97 (d, J=6.5 Hz, 6H), 0.89-0.82 (m, 12H) ppm.

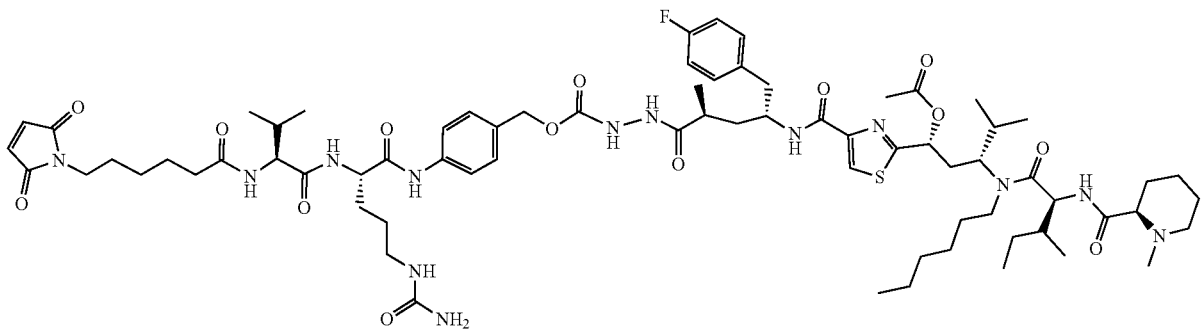 [SMILES: CCCCCCN(C(=O)[C@@H](NC(=O)[C@H]1CCCCN1C)C(C)CC)[C@H](C[C@@H](OC(C)=O)c1nc(C(=O)N[C@@H](Cc2ccc(F)cc2)C[C@H](C)C(=O)NNC(=O)OCc2ccc(NC(=O)[C@H](CCCNC(N)=O)NC(=O)[C@@H](NC(=O)CCCCCN3C(=O)C=CC3=O)C(C)C)cc2)cs1)C(C)C]

4-((S)-2-((S)-2-(6-(2,5-dioxo-2,5-dihydro-1H-pyrrol-1-yl)hexanamido)-3-methylbutanamido)-5-ureidopentanamido)benzyl-((2S,4R)-4-(2-((1R,3R)-1-acetoxy-3-((2S,3R)—N-hexyl-3-methyl-2-((R)-1-methylpiperidine-2-carboxamido)pentanamido)-4-methylpentyl)thiazole-4-carboxamido)-5-(4-fluorophenyl)-2-methylpentanoyl)hydrazinecarboxylate (LP1)

To a solution of IVa' (3.0 mg, 0.036 mmol), mc-vc-PAB-PNP (L-1) (8.1 mg, 0.108 mmol), and HOBt (9 mg, 0.07 mmol) in DMF (1 mL) was added DIPEA (0.9 mg, 0.007 mmol). The reaction mixture was stirred at rt under $N_2$ overnight. The crude product was purified by acidic prep-HPLC to obtain LP1 (3.4 mg, 66%) as a white solid. ESI-MS (EI$^+$, m/z): 1428.7 [M+H]$^+$, 715.0 [M/2+H]$^+$.

Synthesis of DIBAC-Linker-Payloads (FIG. 9)

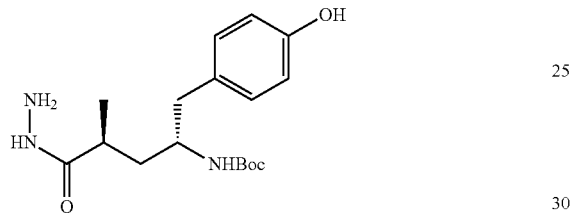

tert-butyl (2R,4S)-5-hydrazinyl-1-(4-hydroxyphenyl)-4-methyl-5-oxopentan-2-ylcarbamate (35)

A solution of intermediate Ie (500 mg, 1.5 mmol), HATU (706 mg, 1.9 mmol), and DIPEA (399 mg, 3.1 mmol) in dry DMF (7.5 mL) was stirred at rt for 30 min, and then hydrazine hydrate (95%, 712 mg, 15.5 mmol) was added. The resulting solution was stirred overnight until complete as monitored by LCMS. The reaction mixture was directly purified by RP chromatography (0-100% acetonitrile in water with 10 mM $NH_4HCO_3$) to give compound 35 (450 mg, 72%) as a white solid. ESI m/z: 338.0 (M+H)$^+$. $^1$H NMR (500 MHz, DMSO$_{d6}$) δ 9.10 (s, 1H), 8.84 (s, 1H), 6.91 (d, J=8.5 Hz, 2H), 6.64-6.60 (m, 3H), 4.11-4.07 (m, 2H), 3.40-3.37 (m, 1H), 2.49-2.46 (m, 2H), 2.29-2.25 (m, 1H), 1.68-1.62 (m, 1H), 1.34-1.21 (m, 10H), 0.96 (d, J=6.5 Hz, 3H) ppm.

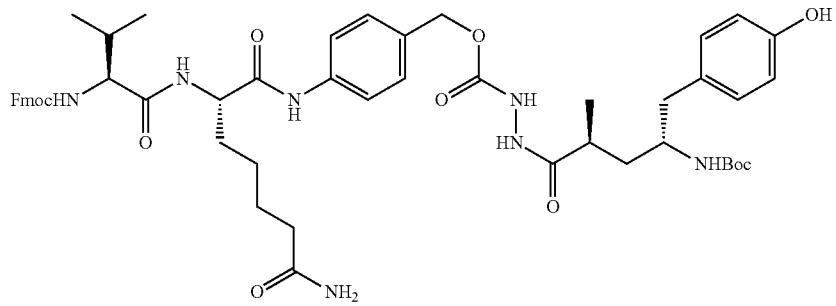

4-((S)-2-((S)-2-(((9H-fluoren-9-yl)methoxy)carbonylamino)-3-methylbutanamido)-7-amino-7-oxoheptanamido)benzyl 2-((2S,4R)-4-(tert-butoxycarbonylamino)-5-(4-hydroxyphenyl)-2-methylpentanoyl) hydrazinecarboxylate (36)

A solution of compound 35 (430 mg, 1275.9 μmol), DIPEA (317 mg, 2551.8 μmol), and HOBt (258 mg, 1913.9 μmol) in dry DMF (7.0 mL) was treated with Fmoc-vc-PAB-PNP (L-2) (1075 mg, 1403.5 μmol), and the reaction was then stirred at rt for 3 h until completion as monitored by LCMS. The completed solution was purified by RP chromatography (0-80% acetonitrile in water with 0.1% TFA) to give compound 36 (800 mg, yield 65%) as a white solid. ESI m/z: 965.4 (M+H)$^+$.

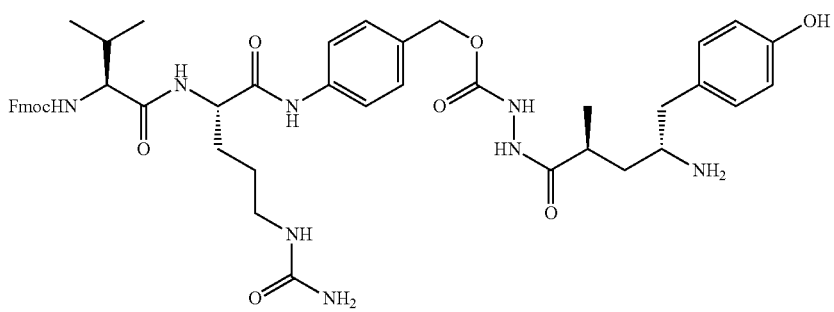

4-((S)-2-((S)-2-(((9H-fluoren-9-yl)methoxy)carbonylamino)-3-methylbutanamido)-5-ureidopentanamido)benzyl 2-((2S,4R)-4-amino-5-(4-hydroxyphenyl)-2-methylpentanoyl) hydrazinecarboxylate (37)

A solution of compound 36 (500 mg, 518.7 μmol) in DCM (9.5 mL) was treated with TFA (0.5 mL) and stirred at rt for 1 h to complete. Then the solution was cooled to 0° C. and neutralized with N-methylmorpholine (NMM) to achieve pH 7.0. Then the solution was concentrated and the residue was purified by RP chromatography (0-100% acetonitrile in deionized water) to give compound 37 (167 mg, yield 37%) as a white solid. ESI m/z: 865.4 (M+H)$^+$. $^1$H NMR (400 MHz, DMSO$_{d6}$) δ 10.09 (s, 1H), 9.72 (s, 1H), 9.34 (s, 1H), 9.24 (s, 1H), 8.13-8.10 (m, 1H), 7.90-7.86 (m, 2H), 7.75-7.71 (m, 2H), 7.68-7.67 (m, 2H), 7.61-7.58 (m, 2H), 7.44-7.38 (m, 3H), 7.33-7.29 (m, 4H), 7.04-7.69 (m, 2H), 6.71 (d, J=8.0 Hz, 2H), 5.99-5.96 (m, 1H), 5.41 (s, 2H), 5.02 (s, 2H), 4.41-4.37 (m, 1H), 4.31-4.19 (m, 3H), 3.94-3.90 (m, 1H), 3.29-3.28 (m, 1H), 3.04-2.90 (m, 2H), 2.71-2.66 (m, 2H), 2.00-1.95 (m, 1H), 1.78-1.33 (m, 6H), 1.00 (d, J=6.4 Hz, 3H), 0.88-0.83 (m, 6H) ppm. Chiral SFC: >99% (AD-H, AS-H, OJ-H, and OD-H), R$_t$: 2.14 min (AD-H), 3.89 min (AS-H), 1.99 min (OJ-H), and 4.97 min (OD-H).

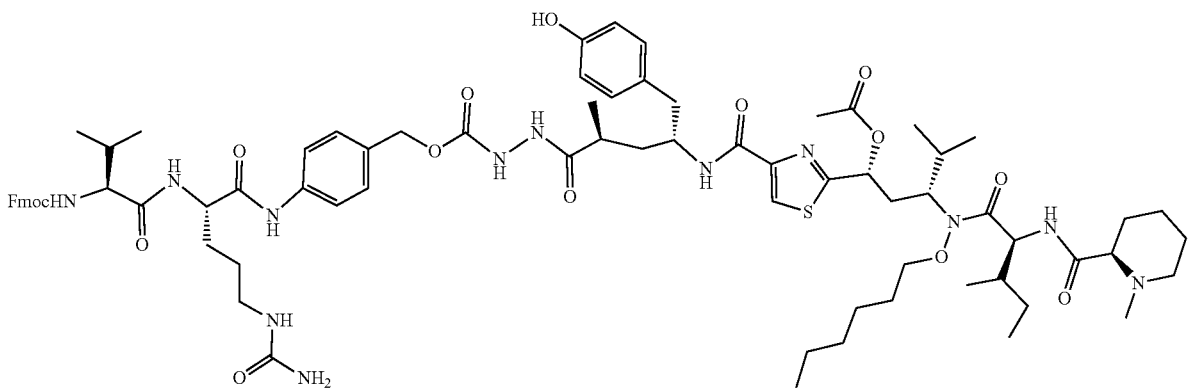

4-((S)-2-((S)-2-(((9H-fluoren-9-yl)methoxy)carbonylamino)-3-methylbutanamido)-5-ureidopentanamido)benzyl 2-((2S,4R)-4-(2-((1R,3R)-1-acetoxy-3-((2S,3S)—N-(hexyloxy)-3-methyl-2-((R)-1-methylpiperidine-2-carboxamido)pentanamido)-4-methylpentyl)thiazole-4-carboxamido)-5-(4-hydroxyphenyl)-2-methylpentanoyl) hydrazinecarboxylate (38)

A solution of compound Ia (125 mg, 200 μmol) and PFP (55 mg, 300 μmol) in dry methylene chloride (4.0 mL) was added dropwise a solution of DIC (38 mg, 300 μmol) in methylene chloride (1.0 mL) at 0° C. by syringe. The resulting solution was stirred for another 1 hour. Then the volatiles were removed in vacuo and the residue was dissolved in ethyl acetate (4.0 mL). The solids were filtered off and the filtrate was concentrated to give pentafluorophenyl ester (200 mg crude) as pale yellow oil, which was dissolved in dry DMF (3.0 mL). To the solution was then added diisopropylethylamine (DIPEA, 62 mg, 480 μmol), followed by compound 37 (138 mg, 160 μmol). The solution was stirred overnight and then purified by RP chromatography (0-100% acetonitrile in deionized water) to give compound 38 (70 mg, yield 30% over two steps) as a white solid. ESI m/z: 1471.4 (M+H)$^+$, 736.3 (M/2+H)$^+$. $^1$H NMR (500 MHz, DMSO$_{d6}$) δ 10.10 (s, 1H), 9.68 (s, 1H), 9.15 (br s, 2H), 8.22 (s, 1H), 8.14-8.13 (m, 1H), 7.91-7.88 (m, 3H), 7.77-7.73 (m, 2H), 7.62-7.57 (m, 2H), 7.46-7.40 (m, 3H), 7.35-7.23 (m, 4H), 7.00-6.90 (m, 2H), 6.61 (d, J=8.0 Hz, 2H), 5.99-5.98 (m, 1H), 5.78-5.74 (m, 1H), 5.42 (s, 2H), 5.02-5.01 (m, 2H), 4.81-4.78 (m, 1H), 4.44-4.40 (m, 1H), 4.32-4.23 (m, 3H), 4.17-4.05 (m, 3H), 3.97-3.92 (m, 2H), 3.04-2.84 (m, 3H), 2.74-2.71 (m, 2H), 2.48-2.34 (m, 3H), 2.11 (s, 6H), 2.03-1.98 (m, 3H), 1.82-1.79 (m, 2H), 1.69-1.32 (m, 16H), 1.27-1.24 (m, 5H), 1.18-1.07 (m, 2H), 1.06-1.03 (m, 2H), 1.00 (d, J=7.0 Hz, 3H), 0.90-0.82 (m, 19H) ppm. Chiral SFC: >99% (AS-H, OJ-H, and OD-H), R$_t$: 2.19 min (AD-H), 3.99 min (AS-H), 2.06 min (OJ-H), and 6.24 min (OD-H).

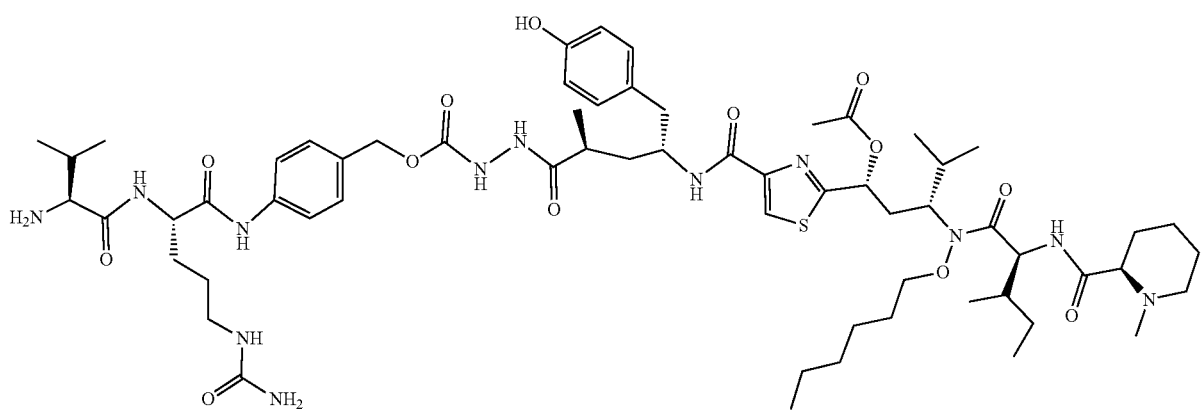 [SMILES: CCCCCCON(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCc2ccc(NC(=O)[C@H](CCCNC(N)=O)NC(=O)[C@@H](N)C(C)C)cc2)cs1)C(C)C]

4-((S)-2-((S)-2-amino-3-methylbutanamido)-5-ureidopentanamido)benzyl2-((2S,4R)-4-(2-((1R,3R)-1-acetoxy-3-((2S,3S)—N-(hexyloxy)-3-methyl-2-((R)-1-methylpiperidine-2-carboxamido)pentanamido)-4-methylpentyl)thiazole-4-carboxamido)-5-(4-hydroxyphenyl)-2-methylpentanoyl) hydrazinecarboxylate (39)

A solution of compound 38 (70.0 mg, 47.5 µmol) in dry DMF (2.0 mL) was treated with piperidine (0.5 mL) and stirred at rt for 30 min. Then the solution was concentrated to dryness and triturated with petroleum ether (3×5 mL) and purified further via Prep-HPLC (ammonium bicarbonate system) to give compound 39 (35 mg, 59%) as a white solid. ESI m/z: 1249.5 (M+H)$^+$. $^1$H NMR (500 MHz, DMSO$_{d6}$) δ 10.16 (s, 1H), 9.67 (s, 1H), 9.16 (s, 1H), 9.13 (s, 1H), 8.21 (s, 1H), 8.14-8.13 (m, 1H), 7.91-7.85 (m, 1H), 7.61 (d, J=8.0 Hz, 2H), 7.45 (d, J=10.0 Hz, 1H), 7.31 (d, J=8.0 Hz, 2H), 6.99 (d, J=8.0 Hz, 2H), 6.61 (d, J=7.5 Hz, 2H), 6.00-5.99 (m, 1H), 5.76 (dd, J=10.5, 2.5 Hz, 1H), 5.41 (s, 2H), 5.02 (s, 2H), 4.82-4.78 (m, 1H), 4.49-4.47 (m, 1H), 4.47-3.95 (m, 4H), 3.05-3.00 (m, 2H), 2.96-2.91 (m, 1H), 2.85-2.82 (m, 1H), 2.73-2.64 (m, 2H), 2.47-2.34 (m, 4H), 2.10 (s, 3H), 2.09 (s, 3H), 2.03-1.91 (m, 3H), 1.81-1.77 (m, 3H), 1.70-1.68 (m, 1H), 1.64-1.53 (m, 7H), 1.50-1.32 (m, 7H), 1.30-1.24 (m, 5H), 1.20-1.16 (m, 1H), 1.08-1.02 (m, 2H), 0.97 (d, J=6.5 Hz, 3H), 0.90-0.82 (m, 17H), 0.78 (d, J=7.0 Hz, 3H) ppm. Chiral SFC: R$_t$: 2.37 min (AD-H), 2.11 min (OJ-H), and 5.73 min (OD-H).

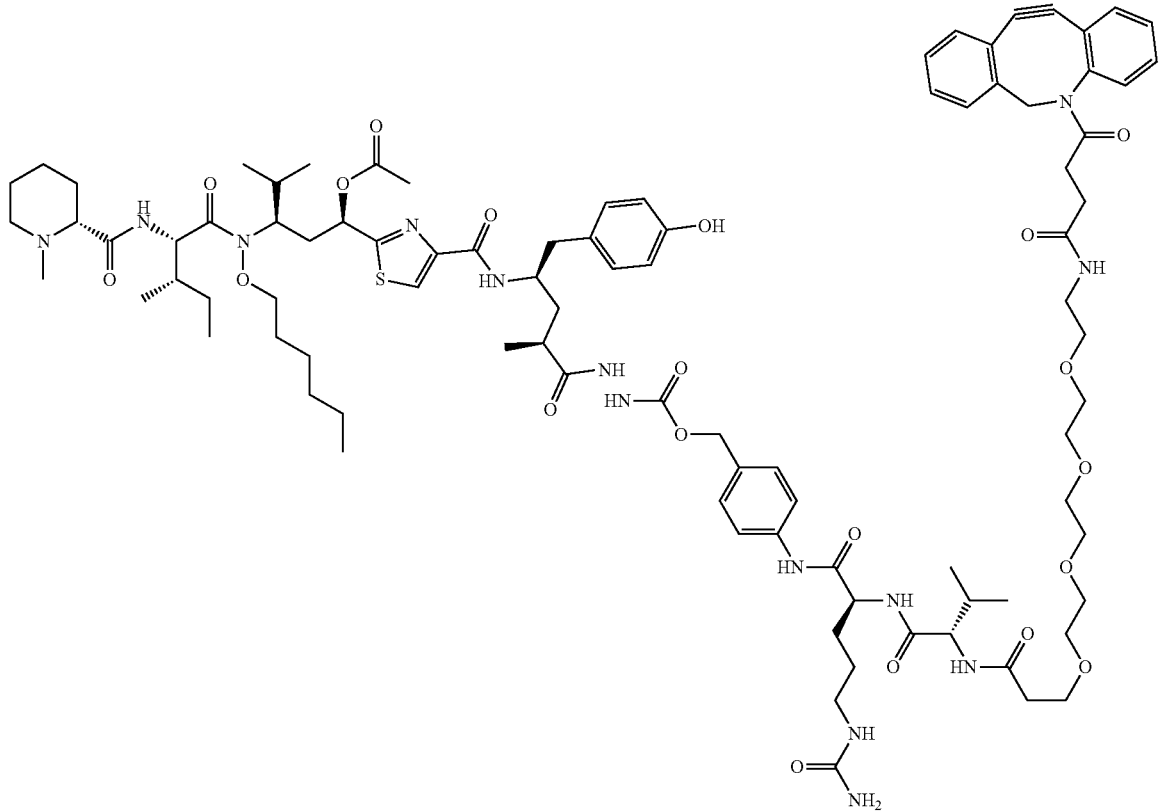

(1R,3R)-1-(4-{[(2R,4S)-4-{N'-[({4-[(2S)-2-[(2S)-2-[1-(4-{2-azatricyclo[10.4.0.0^{4,9}]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl]hydrazinecarbonyl}-1-(4-hydroxyphenyl)-4-methylbutan-2-yl]carbamoyl}-1,3-thiazol-2-yl)-3-[(2S,3S)—N-(hexyloxy)-3-methyl-2-{[(2R)-1-methylpiperidin-2-yl]formamido}pentanamido]-4-methylpentyl acetate (LP2)

A solution of DIBAC-suc-PEG4-COOH (L-3) (5.7 mg, 10.4 μmol), HATU (5.9 mg, 15.6 μmol), and DIPEA (2.7 mg, 20.8 μmol) in dry DMF (1.0 mL) was stirred at rt for 30 min, and then compound 39 (13.0 mg, 10.4 μmol) was added. The resulting solution was stirred for overnight until completion as monitored by LCMS. The reaction mixture was directly purified by prep-HPLC (Method B) to give LP2 (5 mg, 27%) as an off-white solid. ESI m/z: 892.5 (M/2+H)$^+$. $^1$H NMR (500 MHz, DMSO$_{d6}$) δ 10.02 (s, 1H), 9.67 (s, 1H), 9.13 (s, 1H), 8.24-8.18 (m, 1H), 8.13 (d, J=6.8 Hz, 1H), 7.88 (d, J=8.7 Hz, 2H), 7.77 (t, J=5.5 Hz, 1H), 7.68 (d, J=7.2 Hz, 1H), 7.64-7.41 (m, 6H), 7.40-7.20 (m, 4H), 7.02-6.84 (m, 2H), 6.70-6.29 (m, 2H), 6.04-5.95 (m, 1H), 5.76 (d, J=7.8 Hz, 1H), 5.42 (s, 2H), 5.23-4.93 (m, 3H), 4.84-4.75 (m, 1H), 4.43-4.36 (m, 1H), 4.27-4.20 (m, 1H), 4.20-4.01 (m, 3H), 3.96 (d, J=6.6 Hz, 1H), 3.65-3.42 (m, 12H), 3.31-3.24 (m, 3H), 3.15-2.99 (m, 3H), 2.97-2.91 (m, 1H), 2.87-2.81 (m, 1H), 2.77-2.54 (m, 3H), 2.48-2.33 (m, 5H), 2.29-2.19 (m, 1H), 2.15-2.05 (m, 5H), 2.04-1.91 (m, 4H), 1.89-1.68 (m, 4H), 1.67-1.49 (m, 9H), 1.45-1.22 (m, 13H), 1.12-0.92 (m, 9H), 0.92-0.77 (m, 20H) ppm.

Synthesis of DIBAC-Linker-Payloads in FIG. 10A

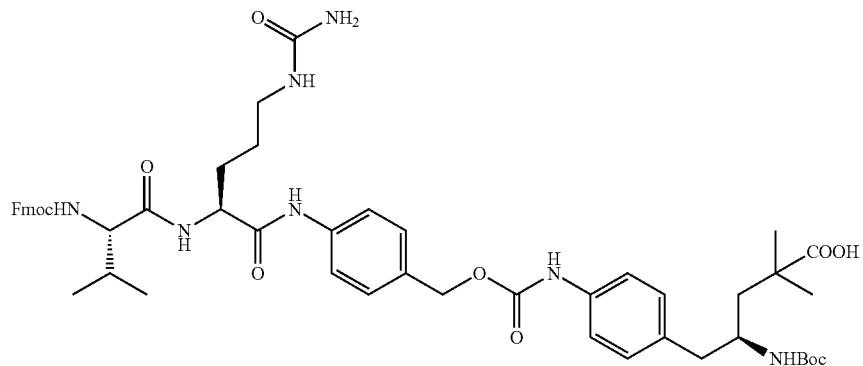

35

(S)-5-(4-((4-((S)-2-((S)-2-(((9H-fluoren-9-yl)methoxy)carbonylamino)-3-methylbutanamido)-5-ureidopentanamido)benzyloxy)carbonylamino)phenyl)-4-amino-2,2-dimethylpentanoic acid (40)

To a mixture of compound 7e (20 mg, 59 μmol) and L-2 (50 mg, 65 μmol) in DMF (2 mL) were added HOBt (8.0 mg, 59 μmol) and DIPEA (15 mg, 0.12 mmol). The reaction was stirred at rt for 16 h and monitored by LCMS. The resulting mixture was then directly purified by reversed phase chromatography (0-100% acetonitrile in aq. TFA (0.01%)) to afford 40 (31 mg, 54% yield) as a white solid. ESI m/z: 964.1 (M+H)$^+$.

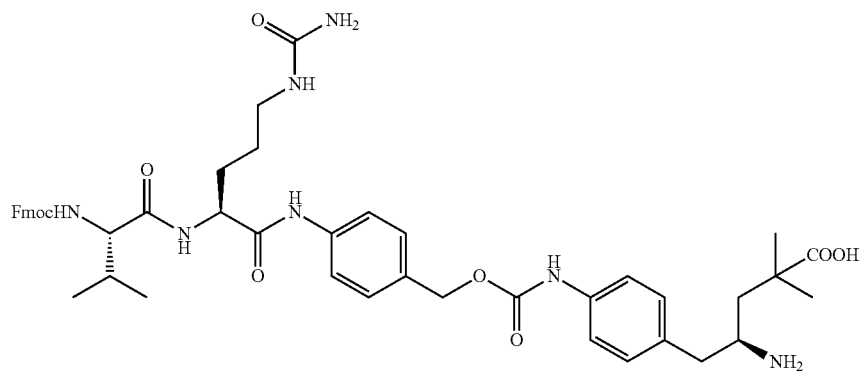

(S)-5-(4-((4-((S)-2-((S)-2-(((9H-fluoren-9-yl)
methoxy)carbonylamino)-3-methylbutanamido)-5-
ureidopentanamido)benzyloxy)carbonylamino)phe-
nyl)-4-amino-2,2-dimethylpentanoic acid (41)

A mixture of compound 40 (40 mg, 41 μmol) and TFA (0.5 mL) in DCM (5 mL) was stirred at 25° C. for 0.5 h, and then concentrated in vacuo to afford 41 (36 mg, 100% yield) as a brown oil. ESI m/z: 432.6 (M+2H)/2$^+$.

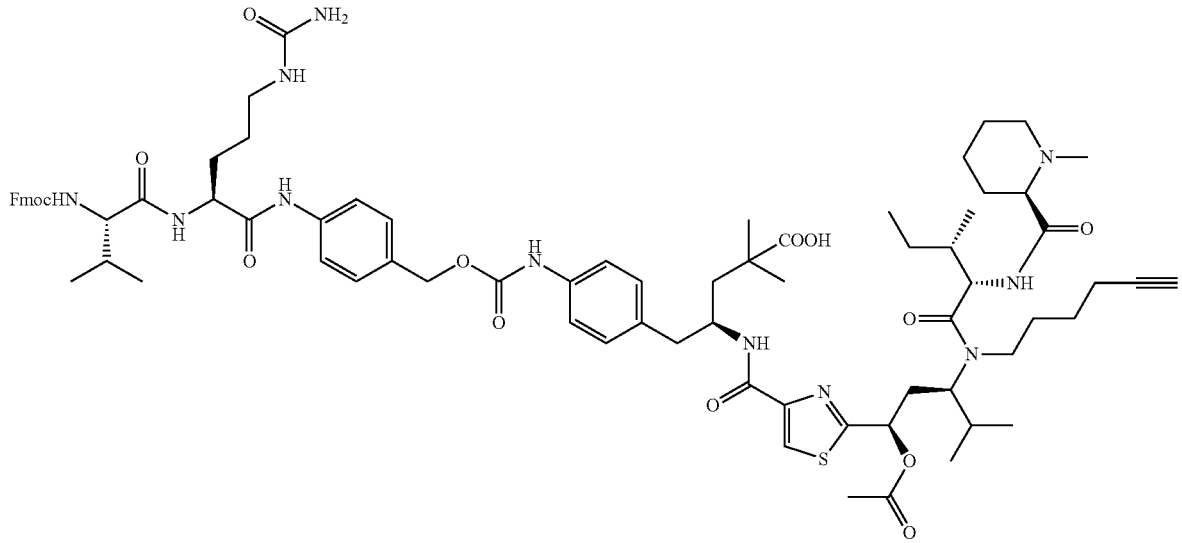

(S)-5-(4-((4-((S)-2-((S)-2-(((9H-fluoren-9-yl)
methoxy)carbonylamino)-3-methylbutanamido)-5-
ureidopentanamido)benzyloxy)carbonylamino)phe-
nyl)-4-(2-((1R,3R)-1-acetoxy-3-((2S,3S)—N-(hex-5-
ynyl)-3-methyl-2-((R)-1-methylpiperidine-2-
carboxamido) pentanamido)-4-methylpentyl)
thiazole-4-carboxamido)-2,2-dimethylpentanoic acid
(42a)

A mixture of compound 41 (36 mg, 41 μmol), DIPEA (21 mg, 167 μmol), and compound 28e (32 mg, 41 μmol) in DMF (2 mL) was stirred at 25° C. for 16 hrs and then the reaction solution was purified by RP chromatography to afford 42a (28 mg, 48% yield) as a white solid. ESI m/z: 725 (M+2H)/2$^+$.

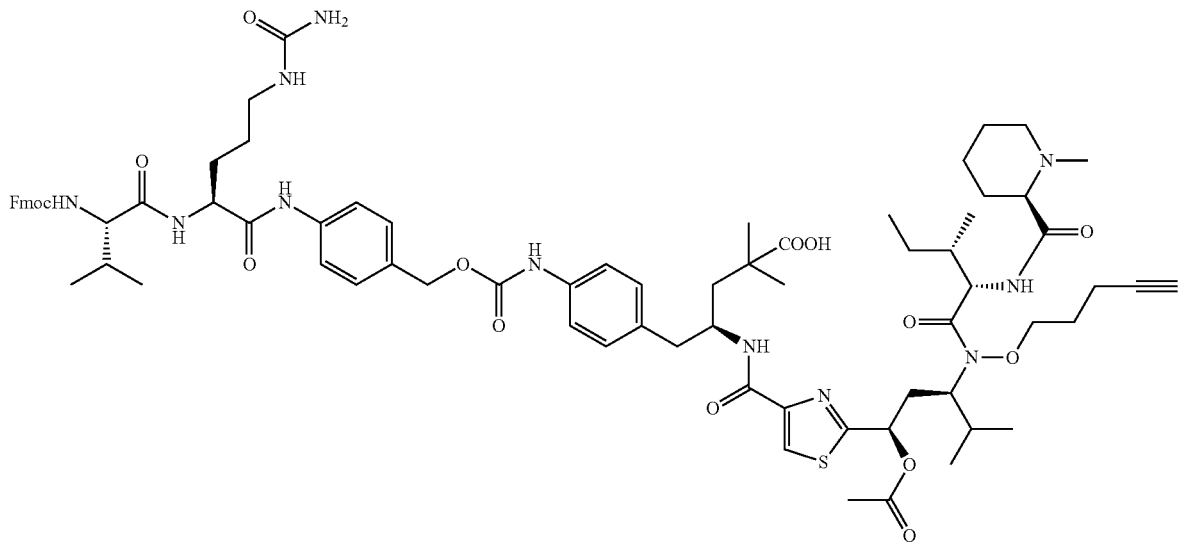

(S)-5-(4-((4-((S)-2-((S)-2-(((9H-fluoren-9-yl)methoxy)carbonylamino)-3-methylbutanamido)-5-ureidopentanamido)benzyloxy)carbonylamino)phenyl)-4-(2-((1R,3R)-1-acetoxy-4-methyl-3-((2S,3S)-3-methyl-2-((R)-1-methylpiperidine-2-carboxamido)-N-(pent-4-ynyloxy)pentanamido)pentyl)thiazole-4-carboxamido)-2,2-dimethylpentanoic acid (42b)

A mixture of compound 41 (40 mg, 46 µmol), DIPEA (18 mg, 139 µmol), and compound 28c (36 mg, 46 µmol) in DMF (3 mL) was stirred at 25° C. for 16 hrs and purified by RP chromatography to afford 42b (30 mg, 34% yield) as a white solid. ESI m/z: 727 (M+2H)/2+.

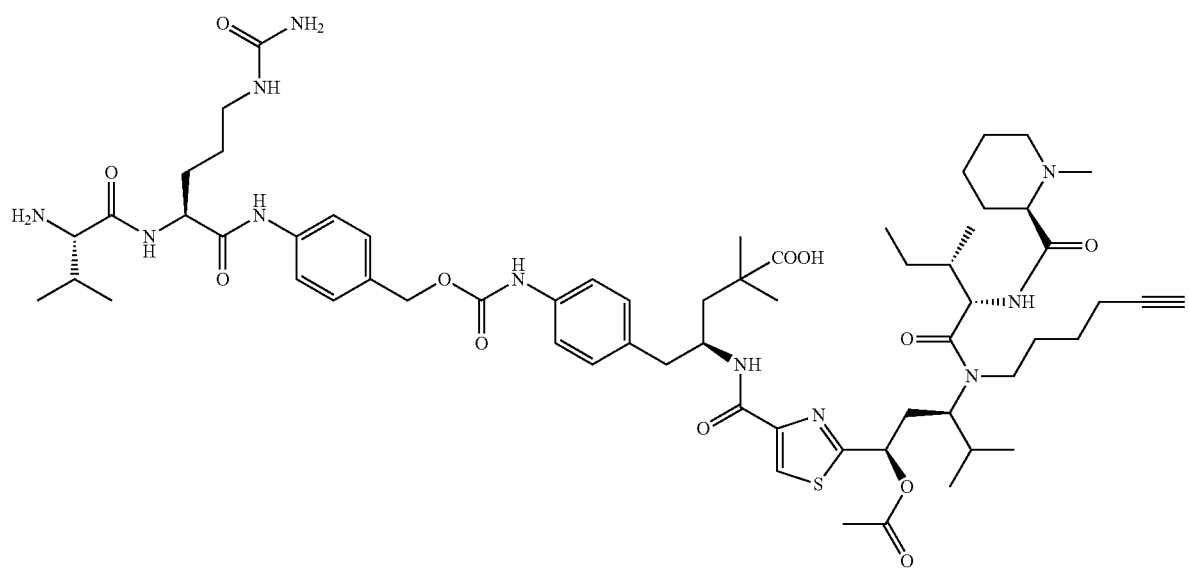 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)OCc3ccc(NC(=O)[C@H](CCCNC(N)=O)NC(=O)[C@@H](N)C(C)C)cc3)cc2)CC(C)(C)C(=O)O)cs1)C(C)C]

(S)-4-(2-((1R,3R)-1-acetoxy-3-((2S,3S)—N-(hex-5-ynyl)-3-methyl-2-((R)-1-methylpiperidine-2-carboxamido)pentanamido)-4-methylpentyl)thiazole-4-carboxamido)-5-(4-((4-((S)-2-((S)-2-amino-3-methylbutanamido)-5-ureidopentanamido)benzyloxy)carbonylamino)phenyl)-2,2-dimethylpentanoic acid (43a)

To a solution of compound 42a (40 mg, 41 µmol) in DMF (1 mL) was added piperidine (10 mg, 0.12 mmol). The reaction mixture was stirred at rt for 2 h until Fmoc was totally removed according to LCMS. The resulting mixture was subjected to reverse phase flash chromatography (0-100% acetonitrile in aq. TFA (0.01%)) to give 43a (36 mg) as a brown oil. ESI m/z: 432.6 (M+2H)/2+.

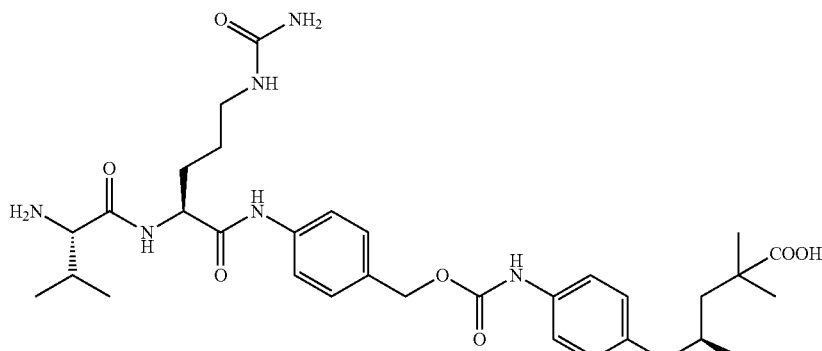
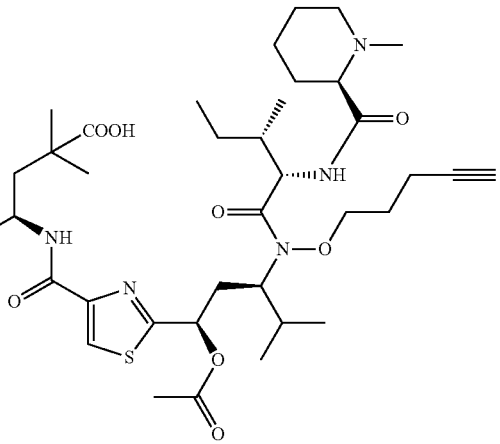

(S)-4-(2-((1R,3R)-1-acetoxy-3-((2S,3S)—N-(hex-5-ynyl)-3-methyl-2-((R)-1-methylpiperidine-2-carboxamido)pentanamido)-4-methylpentyl)thiazole-4-carboxamido)-5-(4-((4-((S)-2-((S)-2-amino-3-methylbutanamido)-5-ureidopentanamido)benzyloxy)carbonylamino)phenyl)-2,2-dimethylpentanoic acid (43b)

A mixture of compound 42b (30 mg, 20.68 µmol) and piperidine (7.98 mg, 165.43 µmol) in DMF (1 mL) was stirred at 25° C. for 16 hrs and then the reaction solution was purified by RP chromatography to afford desired product 43b (17 mg, 67% yield) as a white solid. ESI m/z: 615.8 (M+2H)/2$^+$.

Synthesis of LP3 (4S)-4-({2-[(1R,3R)-1-(acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-(4-{[({4-[(2S)-2-[(2S)-2-[1-(4-{2-azatricyclo[10.4.0.04,9]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl]amino}phenyl)-2,2-dimethylpentanoic acid (LP3)

A mixture of compound 43a (30 mg, 24.42 µmol), DIBAC-suc-PEG4-NHS (L-4) (15.86 mg, 24.42 µmol) and DIPEA (5.37 mg, 41.51 µmol) in DMF (2 mL) was stirred at 25° C. for 16 h and then the reaction solution was purified by RP chromatography (acetonitrile/water) to afford LP3 (5 mg, 35%) as a white solid. ESI m/z: 882.1 (M+2H)/2$^+$. $^1$H NMR (500 MHz, DMSO$_{d6}$) δ 12.15 (s, 1H), 10.02 (s, 1H), 9.68 (s, 1H), 8.16 (s, 2H), 7.89 (d, J=8.7 Hz, 1H), 7.78 (d, J=5.5 Hz, 2H), 7.68 (d, J=6.9 Hz, 1H), 7.62 (d, J=8.3 Hz, 4H), 7.51-7.43 (m, 3H), 7.35 (d, J=8.0 Hz, 7H), 7.07 (d, J=8.4 Hz, 2H), 6.00 (s, 1H), 5.65 (d, J=13.0 Hz, 1H), 5.43 (s, 2H), 5.03 (d, J=14.5 Hz, 1H), 4.46 (s, 1H), 4.38 (d, J=5.3 Hz, 1H), 4.24 (d, J=6.9 Hz, 2H), 3.74 (s, 1H), 3.59 (s, 3H), 3.47 (s, 14H), 3.31-3.25 (m, 4H), 3.08 (s, 2H), 3.04-2.97 (m, 2H), 2.94 (dd, J=13.1, 6.4 Hz, 1H), 2.83 (d, J=10.7 Hz, 1H), 2.75 (s, 2H), 2.67 (dd, J=15.9, 9.1 Hz, 1H), 2.59 (dd, J=16.2, 8.0 Hz, 1H), 2.48-2.45 (m, 1H), 2.36 (dd, J=14.3, 6.4 Hz, 1H), 2.23 (dd, J=15.6, 7.8 Hz, 3H), 2.14 (s, 4H), 2.07 (s, 3H), 1.98 (ddd, J=20.0, 13.8, 6.5 Hz, 4H), 1.87 (s, 3H), 1.76 (dd, J=15.2, 6.8 Hz, 2H), 1.68 (d, J=11.2 Hz, 2H), 1.61 (d, J=9.8 Hz, 3H), 1.40 (dd, J=35.4, 22.6 Hz, 7H), 1.26-1.12 (m, 2H), 1.06 (d, J=4.2 Hz, 6H), 0.95 (d, J=6.3 Hz, 3H), 0.82 (d, J=6.6 Hz, 12H), 0.67 (s, 3H) ppm.

Synthesis of LP4 (4S)-4-({2-[(1R,3R)-1-(acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-(4-{[({4-[(2S)-2-[(2S)-2-[1-(4-{2-azatricyclo[10.4.0.04,9]hexadeca-1(12),4(9),5,7,13,15-hexaen-10-yn-2-yl}-4-oxobutanamido)-3,6,9,12-tetraoxapentadecan-15-amido]-3-methylbutanamido]-2-[2-(carbamoylamino)ethoxy]acetamido]phenyl}methoxy)carbonyl]amino}phenyl)-2,2-dimethylpentanoic acid (LP4)

The mixture of compound 43b (17 mg, 14 µmol), DIBAC-suc-PEG4-NHS (L-4) (9 mg, 14 µmol) and DIPEA (5.4 mg, 42 µmol) in DMF (2 mL) was stirred at 25° C. for 16 h and then the reaction solution was purified by RP chromatography (acetonitrile and water) to afford LP4 (5 mg, 20%; 67% in a repeated synthesis) as a white solid. ESI m/z: 883.1 (M+2H)/2$^+$. $^1$H NMR (500 MHz, DMSO$_{d6}$) δ 12.01 (s, 1H), 11.16 (s, 1H), 10.00 (s, 1H), 9.68 (s, 1H), 9.63 (s, 1H), 8.95 (s, 1H), 8.18 (s, 1H), 8.10 (s, 1H), 7.87 (d, J=8.7 Hz, 1H), 7.76 (s, 2H), 7.67 (d, J=7.2 Hz, 1H), 7.62 (d, J=8.4 Hz, 3H), 7.52-7.42 (m, 3H), 7.33 (s, 7H), 7.07 (d, J=8.5 Hz, 2H), 5.99 (s, 1H), 5.82 (d, J=10.8 Hz, 1H), 5.42 (s, 2H), 5.05 (s, 3H), 4.75 (t, J=8.6 Hz, 1H), 4.42-4.34 (m, 1H), 4.23 (d, J=8.4 Hz, 3H), 4.10-3.73 (m, 2H), 3.59 (s, 3H), 3.50-3.43 (m, 12H), 3.29 (s, 4H), 3.08 (d, J=5.7 Hz, 2H), 3.02 (dd, J=13.4, 6.7 Hz, 2H), 2.96-2.91 (m, 1H), 2.83 (s, 1H), 2.77-2.73 (m, 1H), 2.67 (d, J=7.4 Hz, 1H), 2.58 (dd, J=16.2, 8.0 Hz, 1H), 2.46-2.44 (m, 1H), 2.36 (dt, J=23.7, 9.1 Hz, 5H), 2.23 (dd, J=15.5, 7.7 Hz, 1H), 2.14 (s, 3H), 2.07 (s, 1H), 2.03-1.88 (m, 4H), 1.83 (d, J=6.5 Hz, 2H), 1.75 (dd, J=14.0, 8.2 Hz, 2H), 1.68 (d, J=11.1 Hz, 2H), 1.59 (d, J=9.1 Hz, 2H), 1.47-1.34 (m, 4H), 1.24 (s, 1H), 1.13 (s, 1H), 1.06 (d, J=11.9 Hz, 6H), 0.97 (d, J=6.6 Hz, 3H), 0.89 (s, 6H), 0.87-0.80 (m, 10H) ppm.

Synthesis of DIBAC-VA-Linker-Payload (FIG. 10B)

Synthesis of LP5 (4S)-4-{[(tert-Butoxy)carbonyl]amino}-5-{4-[(2S)-2-[(2S)-2-{[(9H-fluoren-9-ylmethoxy)carbonyl]amino}-3-methylbutanamido]propanamido]phenyl}-2,2-dimethylpentanoic acid (40b)

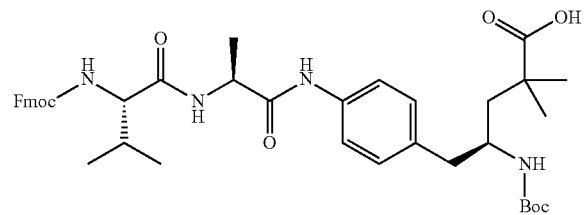

To a solution of compound L-5 (Fmoc-VA-OH, 0.21 g, 0.50 mmol) in DMF (3.0 mL) were added HATU (0.19 g, 0.50 mmol) and DIPEA (0.13 g, 1.0 mmol). The reaction mixture was stirred at rt for 10 min followed by the addition of compound 7e (0.17 g, 0.50 mmol). The mixture was stirred at rt for 2 hours, which was monitored by LCMS. The mixture was purified directly by Prep-HPLC (method B) to give compound 40b (0.15 g, 40% yield) as a white solid. ESI m/z: 746.3 (M+H$_2$O)$^+$. $^1$H NNMR (DMSO$_{d6}$, 400 MHz) (with rotamers) δ 9.88 and 9.72 (s, 1H), 8.35 and 8.17 (d, J=7.2 Hz, 1H), 7.90-7.87 (m, 2H), 7.76-7.71 (m, 2H), 7.56-7.38 (m, 5H), 7.32 (t, J=7.2 Hz, 2H), 7.05 (t, J=8.4 Hz, 2H), 6.46 (d, J=8.8 Hz, 1H), 7.46-7.39 (m, 1H), 4.33-4.18 (m, 3H), 3.93-3.85 (m, 1H), 3.70-3.60 (m, 1H), 2.60-2.50 (m, 2H), 2.02-1.93 (m, 1H), 1.72-1.65 (m, 1H), 1.57-1.53 (m, 1H), 1.29-1.17 (m, 12H), 1.06-1.02 (m, 6H), 0.89-0.84 (m, 6H) ppm. Anal. HPLC: 100%, Retention time: 7.39 min (method B).

(4S)-4-Amino-5-{4-[(2S)-2-[(2S)-2-{[(9H-fluoren-9-ylmethoxy)carbonyl]amino}-3-methylbutanamido]propanamido]phenyl}-2,2-dimethylpentanoic acid (41b)

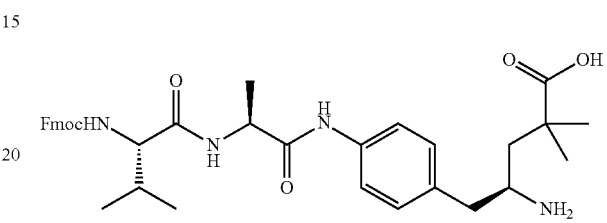

Following the similar procedure as 40 to 41, except substituting 40b for 40, compound 41b (15 mg as TFA salt, 100% crude yield) was obtained as brown oil, which was used for the next step directly. ESI m/z: 629.3 (M+H)$^+$.

(4S)-4-({2-[(1R,3R)-1-(acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-{4-[(2S)-2-[(2S)-2-{[(9H-fluoren-9-ylmethoxy)carbonyl]amino}-3-methylbutanamido]propanamido]phenyl}-2,2-dimethylpentanoic acid (42c)

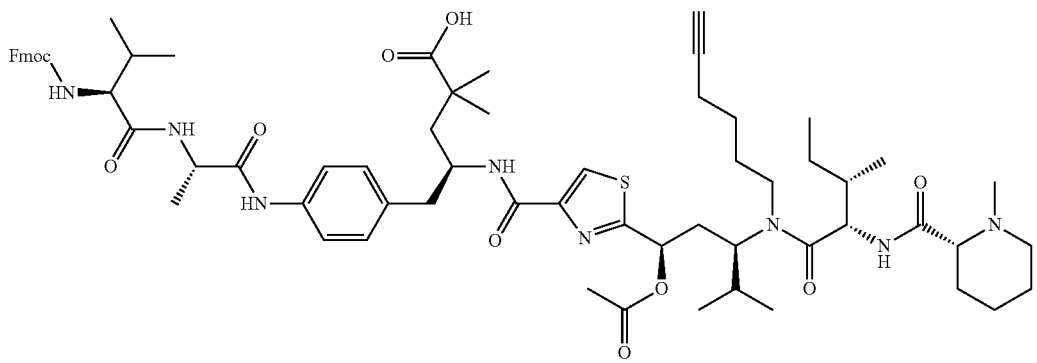

Following the similar procedure as 41 to 42a, except substituting 41b (15 mg, 18 μmol) for 41, compound 42c (10 mg, 46% yield in 2 steps) was obtained as a white solid. ESI m/z: 1215.6 (M+H)+.

(4S)-4-({2-[(1R,3R)-1-(acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-{4-[(2S)-2-[(2S)-2-amino-3-methylbutanamido]propanamido]phenyl}-2,2-dimethylpentanoic acid (43c)

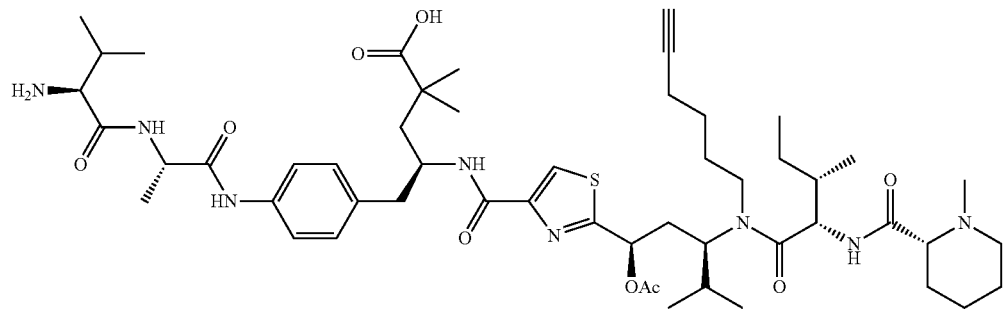 [SMILES: C#CCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](C)NC(=O)[C@@H](N)C(C)C)cc2)CC(C)(C)C(=O)O)cs1)C(C)C]

Following the similar procedure as 42a to 43a, except substituting 42c (10 mg, 8.2 μmol) for 42a, compound 43c (5 mg, 61% yield) was obtained as a white solid. ESI m/z: 497.4 (M/2+H)+.

(4S)-4-({2-[(1R,3R)-1-(acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-{4-[(2S)-2-[(2S)-2-[1-(4-{2-azatricyclo[10.4.0.04,9]hexadeca-1(12),4(9),5,7,13,15-hexaen-10-yn-2-yl}-4-oxobutanamido)-3,6,9,12-tetraoxapentadecan-15-amido]-3-methylbutanamido]propanamido]phenyl}-2,2-dimethylpentanoic acid (LP5)

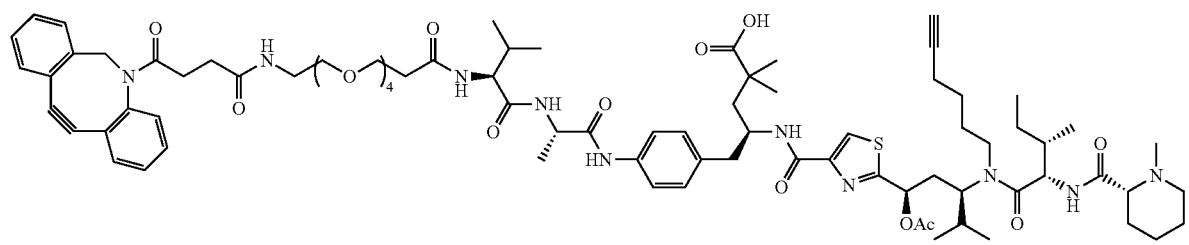

To a solution of compound L-3 (4.1 mg, 7.4 μmol) in DMF (1 mL) were added HATU (2.9 mg, 7.5 μmol) and a solution of DIPEA (1.3 mg, 0.01 mmol) in DMF (25 μL). The reaction mixture was stirred at rt for 10 min followed by the addition of compound 43c (5.0 mg, 5.0 μmol). The mixture was stirred at rt for 1 h, and monitored by LCMS. The mixture was directly purified by prep-HPLC (method B) to give compound LP5 (3 mg, 39% yield) as a white solid. ESI m/z: 764.5 (M/2+H)+. $^1$H NMR (DMSO$_{d6}$, 400 MHz) (with rotamers) δ 9.85 and 9.73 (s, 1H), 8.39-8.37 and 8.17-8.12 (m, 2H), 7.99 and 7.87 (d, J=8.4 Hz, 1H), 7.78-7.26 (m, 12H), 7.10-7.06 (m, 2H), 5.64 (d, J=11.2 Hz, 1H), 5.02 (d, J=13.6 Hz, 1H), 4.47-4.07 (m, 5H), 3.75-3.26 (m, 22H), 3.09-2.74 (m, 6H), 2.60-2.42 (m, 2H), 2.35-1.03 (m, 42H), 0.94-0.65 (m, 16H) ppm. Anal. HPLC: 100%, Retention time: 8.18 min (method B).

Figure 10C:
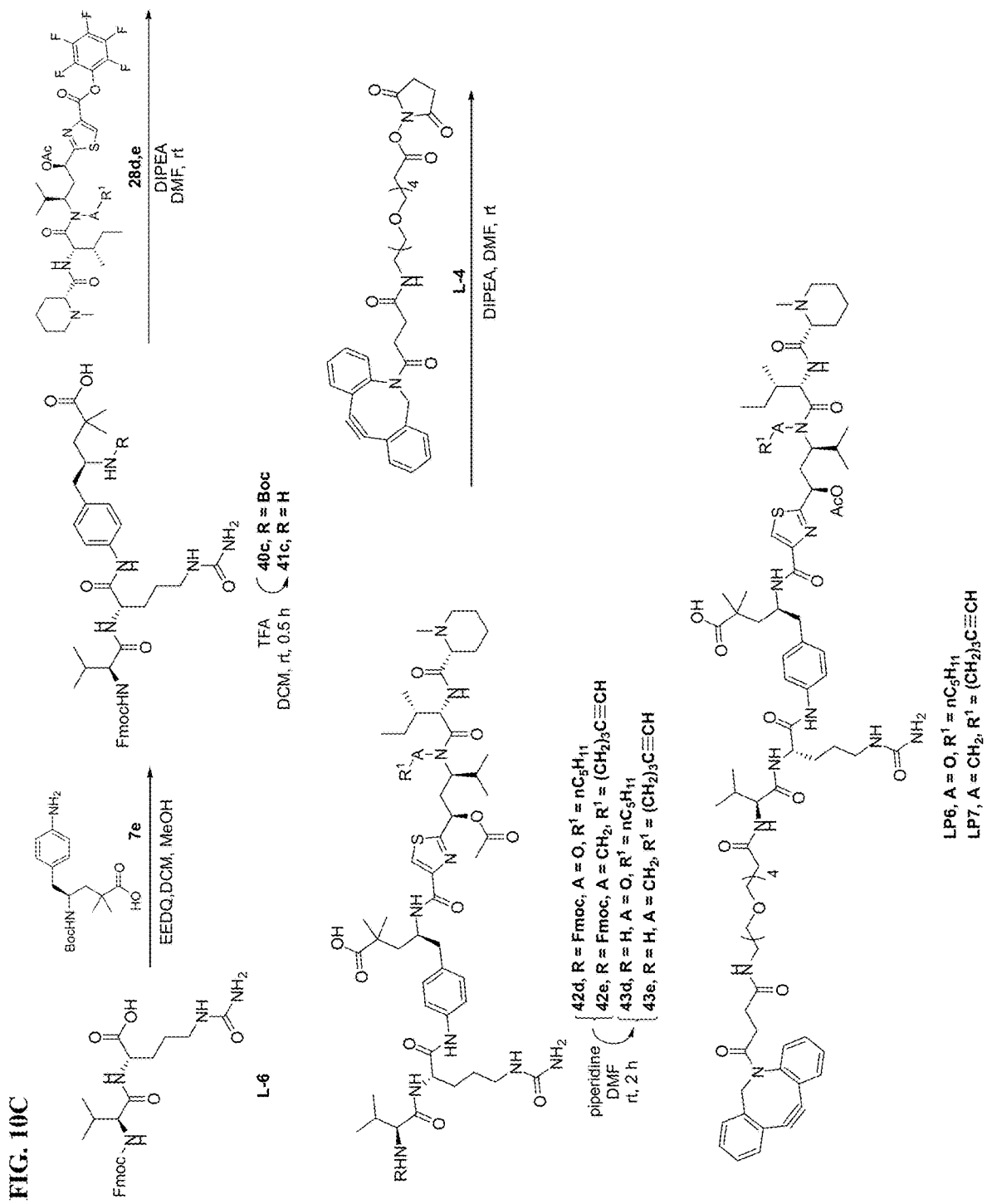

Synthesis of LP6 and LP7 (FIG. 10C)

(4S)-4-{[(tert-Butoxy)carbonyl]amino}-5-{4-[(2S)-5-(carbamoylamino)-2-[(2S)-2-{[(9H-fluoren-9-ylmethoxy)carbonyl]amino}-3-methylbutanamido]pentanamido]phenyl}-2,2-dimethylpentanoic acid (40c)

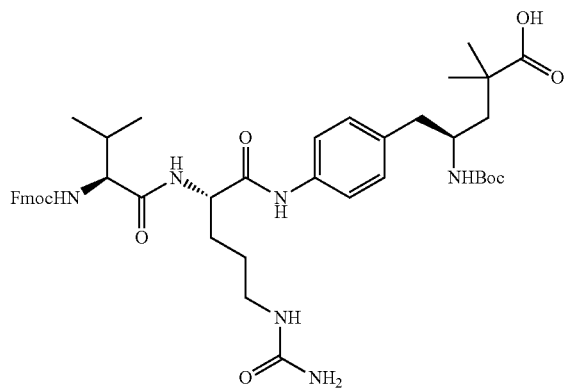

To a mixture of compound L-6 (Fmoc-Val-Cit-OH, 0.60 g, 1.2 mmol), compound 7e (0.20 g, 0.06 mmol) and EEDQ (0.22 g, 0.90 mmol) in DCM (20 mL) was added 10 mL of methanol under nitrogen atmosphere and the mixture turned clear. The solution was stirred in the dark at rt overnight, which was monitored by LCMS. The mixture was concentrated in vacuo and the residue was purified by prep-HPLC (method B) to give compound 40c (85 mg, 17% yield) as a white solid. ESI m/z: 815.3 (M+H)$^+$. $^1$H NMR (DMSO$_{d6}$, 400 MHz) δ 9.94 (s, 1H), 8.11 (d, J=7.2 Hz, 1H), 7.89 (d, J=7.6 Hz, 2H), 7.75 (t, J=7.6 Hz, 1H), 7.54-7.30 (m, 7H), 7.05 (t, J=8.0 Hz, 2H), 6.47 (d, J=8.8 Hz, 1H), 6.02-5.94 (m, 1H), 5.41 (s, 2H), 4.45-4.20 (m, 4H), 3.94-3.90 (m, 1H), 3.70-3.62 (m, 1H), 3.04-2.89 (m, 2H), 2.61-2.50 (m, 2H), 2.02-1.94 (m, 1H), 1.72-1.19 (m, 15H), 1.07-1.03 (m, 6H), 0.89-0.84 (m, 6H) ppm. Anal. HPLC: 99%, Retention time: 6.90 min (method B).

(4S)-4-Amino-5-{4-[(2S)-5-(carbamoylamino)-2-[(2S)-2-{[(9H-fluoren-9-ylmethoxy)carbonyl]amino}-3-methylbutanamido]pentanamido]phenyl}-2,2-dimethylpentanoic acid (41c)

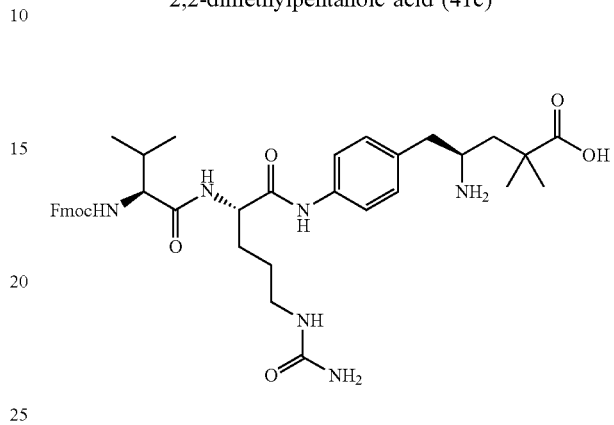

Following the similar procedures as 40 to 41, except substituting 40c for 40, compound 41c (25 mg as TFA salt, 100% crude yield) was obtained as brown oil, which was used for the next step directly. ESI m/z: 715.3 (M+H)$^+$.

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-{4-[(2S)-5-(carbamoylamino)-2-[(2S)-2-{[(9H-fluoren-9-ylmethoxy)carbonyl]amino}-3-methylbutanamido]pentanamido]phenyl}-2,2-dimethylpentanoic acid (42d)

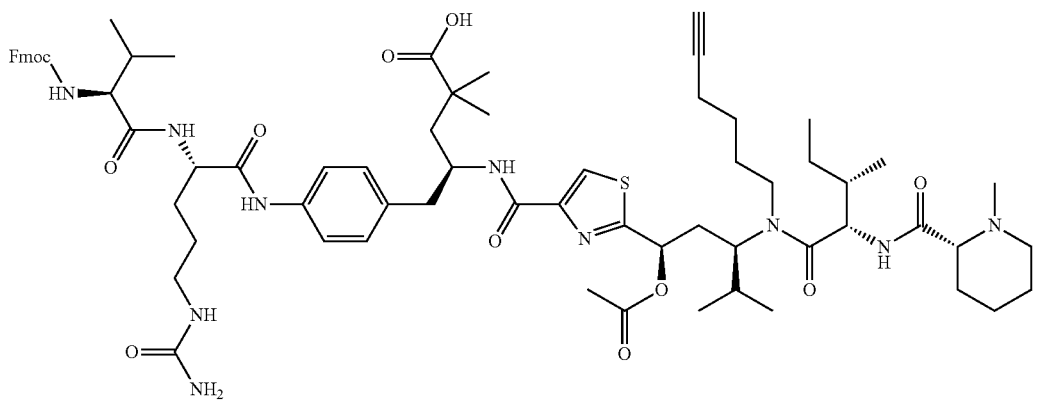

Following the similar procedure as 41 to 42a, except substituting 41c (52 mg, 60 μmol) for 41, and substituting 28d (61 mg, 78 μmol) for 28e, compound 42d (52 mg, 66% yield in 2 steps) was obtained as a white solid. ESI m/z: 654.3 (M12+H)+.

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-{4-[(2S)-2-[(2S)-2-amino-3-methylbutanamido]-5-(carbamoylamino)pentanamido]phenyl}-2,2-dimethylpentanoic acid (43d)

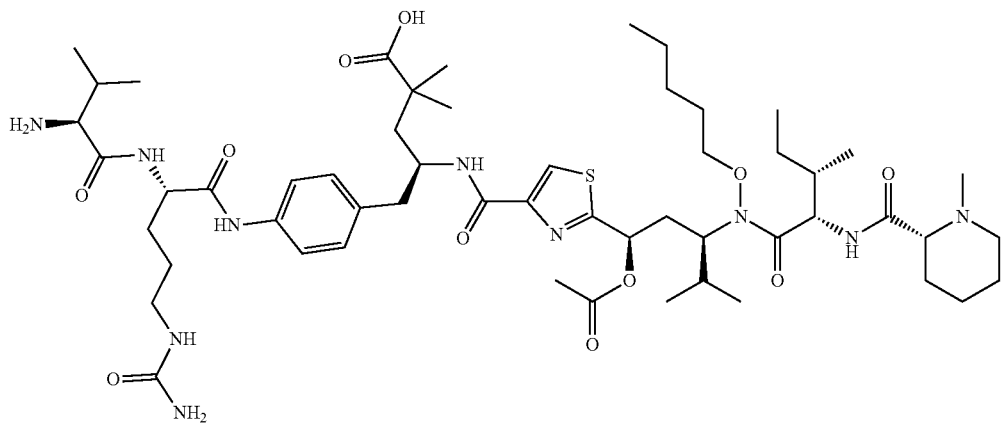 [SMILES: CCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](CCCNC(N)=O)NC(=O)[C@@H](N)C(C)C)cc2)CC(C)(C)C(=O)O)cs1)C(C)C]

Following the similar procedures as 42a to 43a, except substituting 42d (52 mg, 40 μmol) for 42a, compound 43d (37 mg, 85% yield) was obtained as a white solid. ESI m/z: 543.5 (M/2+H)+.

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-{4-[(2S)-2-[(2S)-2-[1-(4-{2-azatricyclo[10.4.0.04,9]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}-2,2-dimethylpentanoic acid (LP6)

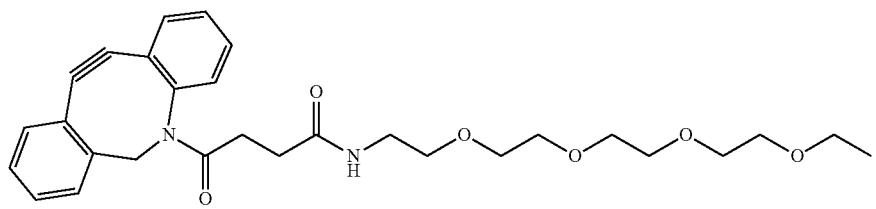

-continued

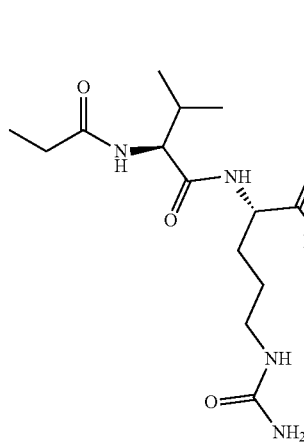 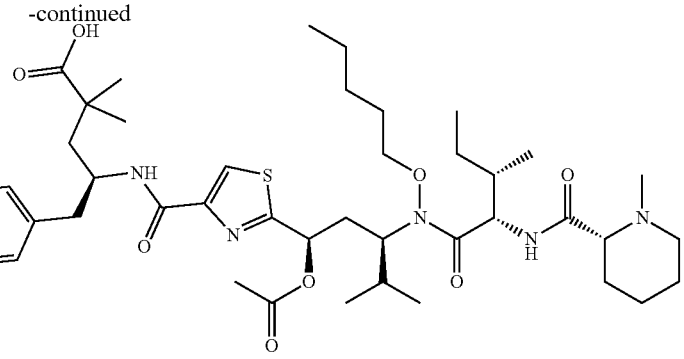

Following the similar procedure as 43a to LP3, except substituting 43d (24 mg, 22 μmol) for 43a, compound LP6 (24 mg, 67% yield) was obtained as a white solid. ESI m/z: 810.5 (M/2+H)+. ¹H NMR (DMSO$_{d6}$, 400 MHz) δ 9.87 (s, 1H), 8.17 (s, 1H), 8.08 (d, J=7.6 Hz, 1H), 7.95-7.86 (m, 1H), 7.86 (d, J=9.2 Hz, 1H), 7.76 (t, J=5.6 Hz, 1H), 7.69-7.66 (m, 1H), 7.62 (d, J=6.8 Hz, 1H), 7.55-7.43 (m, 5H), 7.40-7.28 (m, 3H), 7.09 (d, J=8.4 Hz, 2H), 6.00 (t, J=5.6 Hz, 1H), 5.80 (dd, J=6.8, 2.4 Hz, 1H), 5.41 (s, 2H), 5.03 (t, J=14.4 Hz, 1H), 4.82-4.78 (m, 1H), 4.40-4.34 (m, 1H), 4.24-4.03 (m, 4H), 3.98-3.92 (m, 1H), 3.62-3.28 (m, 23H), 3.13-2.89 (m, 4H), 2.85-2.75 (m, 2H), 2.70-2.62 (m, 1H), 2.62-2.32 (m, 5H), 2.28-2.19 (m, 1H), 2.12 (s, 3H), 2.10 (s, 3H), 2.03-1.86 (m, 5H), 1.81-1.28 (m, 17H), 1.04 (d, J=8.4 Hz, 6H), 0.97-0.94 (m, 3H), 0.89-0.80 (m, 18H) ppm. Anal. HPLC: 100%, Retention time: 8.52 min (method B).

Synthesis of LP7

(4S)-4-({2-[(1R,3R)-1-(Acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-{4-[(2S)-5-(carbamoylamino)-2-[(2S)-2-{[(9H-fluoren-9-ylmethoxy)carbonyl]amino}-3-methylbutanamido]pentanamido]phenyl}-2,2-dimethylpentanoic acid (42e)

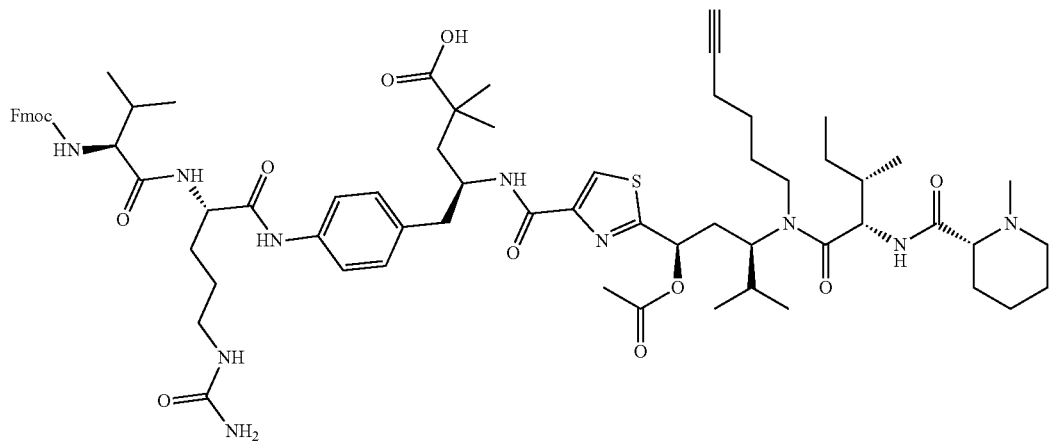

513

Following the similar procedure as 41 to 42a, except substituting 41c (25 mg, 40 μmol) for 41, compound 42e (36 mg, 70% yield in 2 steps) was obtained as a white solid. ESI m/z: 651.3 (M/2+H)+. 1H NMR (DMSO_{d6}, 400 MHz) δ 9.97 (s, 1H), 8.17 (s, 1H), 8.09 (d, J=7.2 Hz, 1H), 7.89 (d, J=7.2 Hz, 2H), 7.76-7.67 (m, 3H), 7.52-7.38 (m, 5H), 7.32 (t, J=7.2 Hz, 2H), 7.10 (d, J=8.0 Hz, 2H), 6.01 (t, J=4.8 Hz, 1H), 5.67-5.63 (m, 1H), 5.42 (s, 2H), 4.48-4.21 (m, 7H), 3.94-3.90 (m, 1H), 3.78-3.69 (m, 1H), 3.04-2.90 (m, 3H), 2.83-2.67 (m, 4H), 2.33-1.04 (m, 41H), 0.94-0.80 (m, 14H), 0.68-0.66 (m, 3H) ppm. Anal. HPLC: 99%, Retention time: 8.35 min (method B).

(4S)-4-({2-[(1R,3R)-1-(Acetyloxy)-3-[(2S,3S)—N-(hex-5-yn-1-yl)-3-methyl-2-{[(2R)-1-methylpiperidin-2-yl]formamido}pentanamido]-4-methylpentyl]-1,3-thiazol-4-yl}formamido)-5-{4-[(2S)-2-[(2S)-2-amino-3-methylbutanamido]-5-(carbamoylamino)pentanamido]phenyl}-2,2-dimethylpentanoic acid (43e)

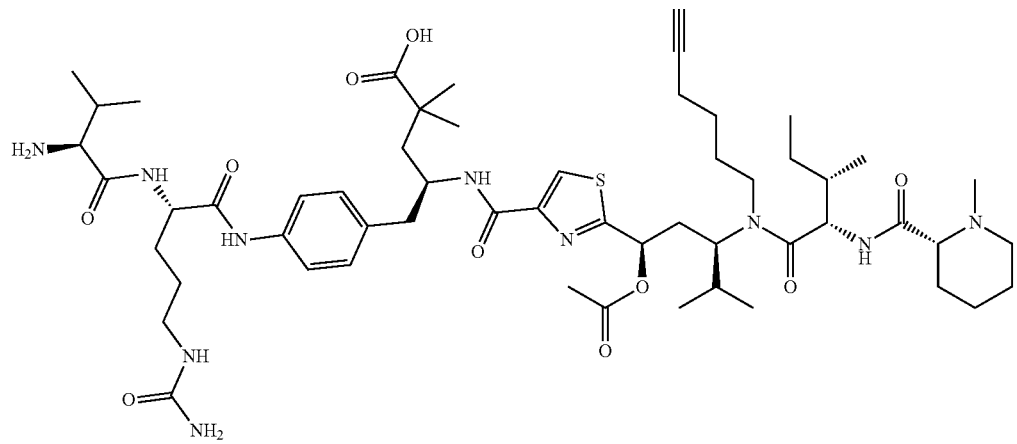 [SMILES: C#CCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](CCCNC(N)=O)NC(=O)[C@@H](N)C(C)C)cc2)CC(C)(C)C(=O)O)cs1)C(C)C]

Following the similar procedure as 42a to 43a, except substituting 42e (26 mg, 20 μmol) for 42a, compound 43e (21 mg, 97% yield) was obtained as a white solid. ESI m/z: 540.3 (M/2+H)+.

Figure 10D:
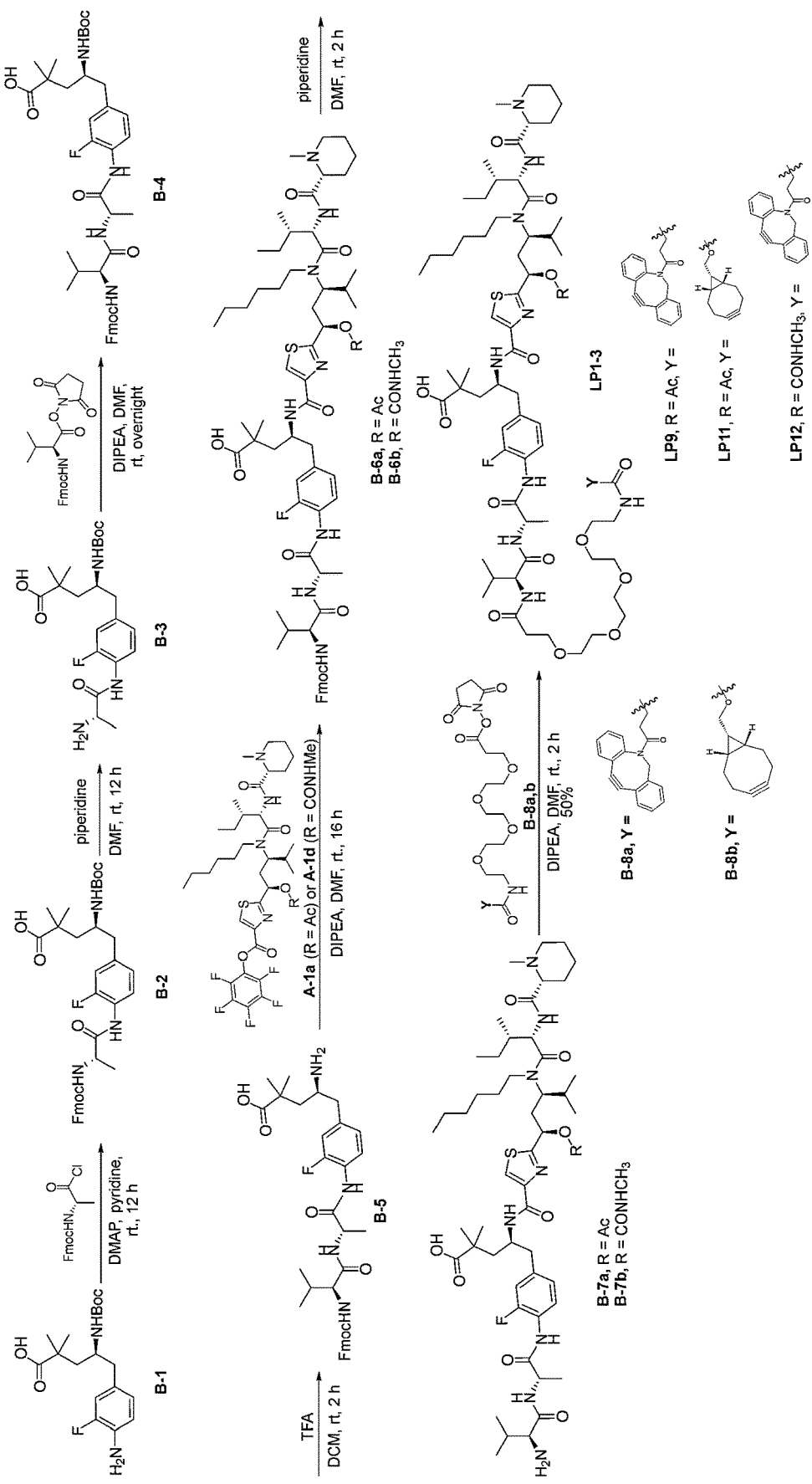

Synthesis of LP9, LP11, and LP12 (FIG. 10D)

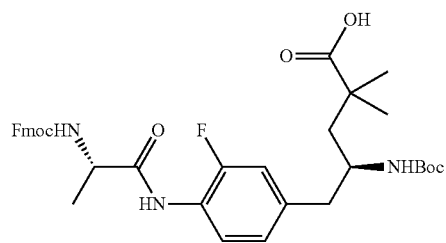

514

(4S)-4-{[(tert-Butoxy)carbonyl]amino}-5-{4-[(2S)-2-{[(9H-fluoren-9-ylmethoxy)carbonyl]amino}propanamido]-3-fluorophenyl}-2,2-dimethylpentanoic acid (B-2)

To a solution of compound B-1 (0.65 g, 1.8 mmol) in pyridine (10 mL) were added Fmoc-Ala-Cl (0.91 g, 1.5 mmol) and DMAP (10 mg, 82 μmol), and the reaction mixture was stirred at RT for 12 hours, which was monitored by LCMS. The volatiles were removed in vacuo and the residue was purified by reversed phase flash chromatography (0-100% acetonitrile in aq. TFA (0.03%)) to give crude compound B-2 (0.66 g, 80% purity, 57% yield) as a white solid. ESI m/z 548.3 (M−Boc+H)+, 670.3 (M+Na)+.

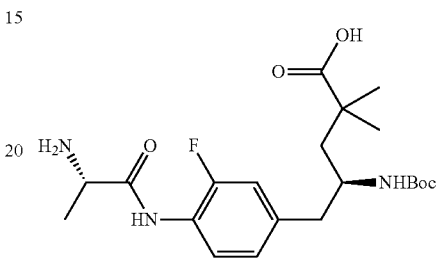

(4S)-5-{4-[(2S)-2-Aminopropanamido]-3-fluorophenyl}-4-{[(tert-butoxy)carbonyl]amino}-2,2-dimethylpentanoic acid (B-3)

Crude compound B-2 (0.66 g, 1.0 mmol) obtained above was dissolved in DMF (2 mL) and piperidine (0.26 g, 3.1 mmol) was added, and the mixture was stirred at RT for 12 hours, which was monitored by LCMS. The reaction mixture was directly purified by reversed phase flash chromatography (0-100% acetonitrile in aq. TFA (0.03%)) to give compound B-3 (0.35 g, 80% yield) as a white solid. ESI m/z 370.2 (M−tBu+H)+.

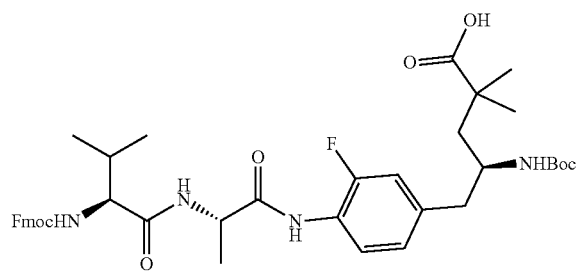
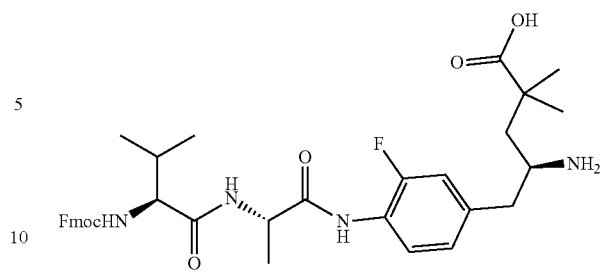

(4S)-4-{[(tert-Butoxy)carbonyl]amino}-5-{4-[(2S)-2-[(2S)-2-{[(9H-fluoren-9-ylmethoxy)carbonyl]amino}-3-methylbutanamido]propanamido]-3-fluorophenyl}-2,2-dimethylpentanoic acid (B-4)

To a solution of compound B-3 (42 mg, 0.10 mmol) in DMF (3 mL) were added Fmoc-Val-OSu (45 mg, 0.11 mmol) and DIPEA (40 mg, 0.31 mmol), and the reaction mixture was stirred at RT for 16 hours, which was monitored by LCMS. The resulting mixture was directly purified by reversed phase flash chromatography (0-100% acetonitrile in aq. TFA (0.03%)) to give compound B-4 (37 mg, 50% yield) as a white solid. ESI m/z 647.3 (M−Boc+H)$^+$, 770.3 (M+Na)$^+$.

(4S)-4-Amino-5-{4-[(2S)-2-[(2S)-2-{[(9H-fluoren-9-ylmethoxy)carbonyl]amino}-3-methylbutanamido]propanamido]-3-fluorophenyl}-2,2-dimethylpentanoic acid (B-5)

To a solution of compound B-4 (75 mg, 0.10 mmol) in DCM (5 mL) was added TFA (1 mL), and the reaction mixture was stirred at RT for 2 hours until Boc was totally removed, which was monitored by LCMS. The resulting mixture was concentrated in vacuo to give crude compound B-5 (60 mg, 92% yield) as a white solid, which was used for the next step directly without further purification. ESI m/z 647.3 (M+H)$^+$.

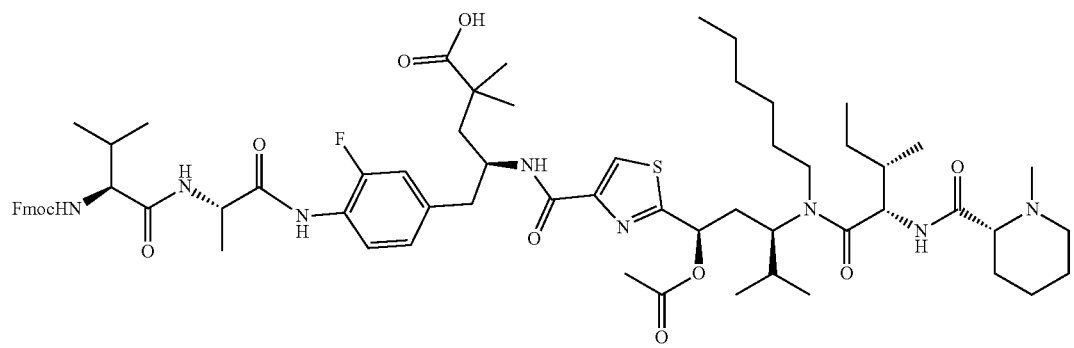

(4S)-4-({2-[(1R,3R)-1-(Acetyloxy)-3-[(2S,3S)—N-hexyl-3-methyl-2-{[(2R)-1-methylpiperidin-2-yl]formamido}pentanamido]-4-methylpentyl]-1,3-thiazol-4-yl}formamido)-5-{4-[(2S)-2-[(2S)-2-{[(9H-fluoren-9-ylmethoxy)carbonyl]amino}-3-methylbutanamido]propanamido]-3-fluorophenyl}-2,2-dimethylpentanoic acid (B-6a)

To a solution of compound B-5 (65 mg, 0.10 mmol) in DMF (5 mL) were added compound A-1a (77 mg, 0.10 mmol) and DIPEA (40 mg, 0.31 mmol), and the reaction mixture was stirred at RT overnight, which was monitored by LCMS. The resulting mixture was directly purified by reversed phase flash chromatography (0-100% acetonitrile in aq. TFA (0.03%)) to give compound B-6a (61 mg, 50% yield) as a white solid. ESI m/z 619.5 (M/2+H)$^+$, 1238.7 (M+H)$^+$.

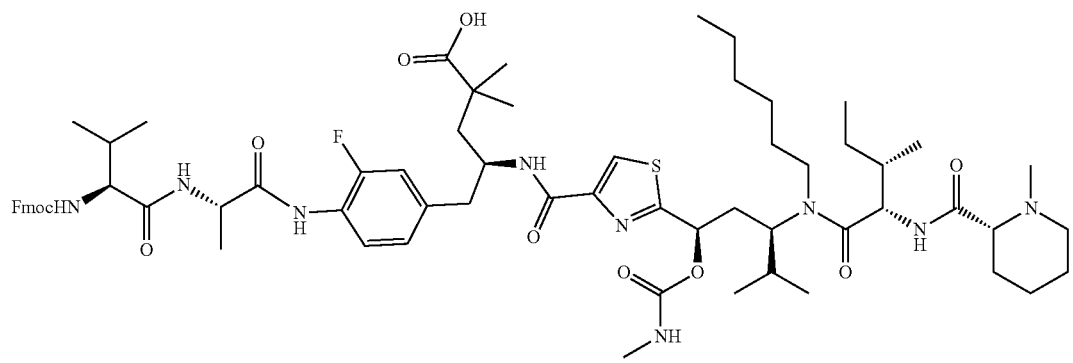

(4S)-5-{4-[(2S)-2-[(2S)-2-{[(9H-Fluoren-9-ylmethoxy)carbonyl]amino}-3-methylbutanamido]propanamido]-3-fluorophenyl}-4-({2-[(1R,3R)-3-[(2S,3S)—N-hexyl-3-methyl-2-{[(2R)-1-methylpiperidin-2-yl]formamido}pentanamido]-4-methyl-1-[(methylcarbamoyl)oxy]pentyl]-1,3-thiazol-4-yl}formamido)-2,2-dimethylpentanoic acid (B-6b)

Following a similar procedure as B-6a except substituting A-1d for A-1b, compound B-6b (0.10 g, 64% yield) was obtained as a white solid. ESI m/z 626.9 (M/2+H)$^+$.

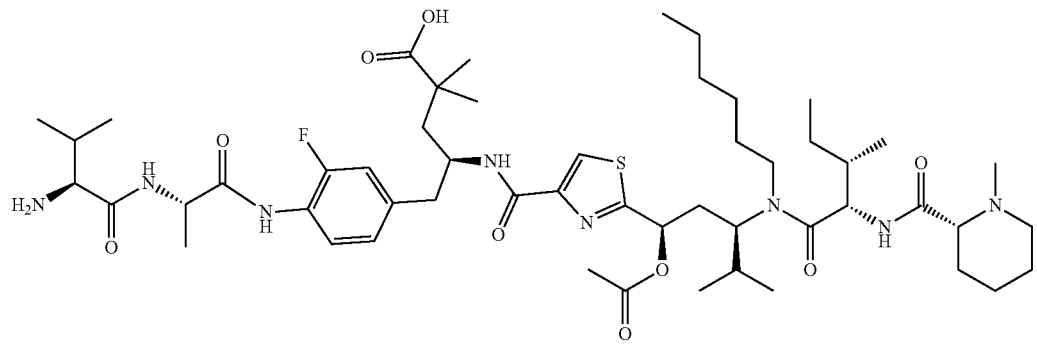 [SMILES: CCCCCCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](C)NC(=O)[C@@H](N)C(C)C)c(F)c2)CC(C)(C)C(=O)O)cs1)C(C)C]

(4S)-4-({2-[(1R,3R)-1-(Acetyloxy)-3-[(2S,3S)—N-hexyl-3-methyl-2-{[(2R)-1-methylpiperidin-2-yl]formamido}pentanamido]-4-methylpentyl]-1,3-thiazol-4-yl}formamido)-5-{4-[(2S)-2-[(2S)-2-amino-3-methylbutanamido]propanamido]-3-fluorophenyl}-2,2-dimethylpentanoic acid (B-7a)

To a solution of compound B-6a (61 mg, 49 μmol) in DMF (5 mL) was added piperidine (13 mg, 0.15 mmol), and the mixture was stirred at RT for 2 hours until Fmoc was totally removed, which was monitored by LCMS. The resulting mixture was directly purified by reversed phase flash chromatography (0-100% acetonitrile in aq. TFA (0.03%)) to give compound B-7a (41 mg, 80% yield) as a white solid. ESI m/z 508.1 (M/2+H)$^+$.

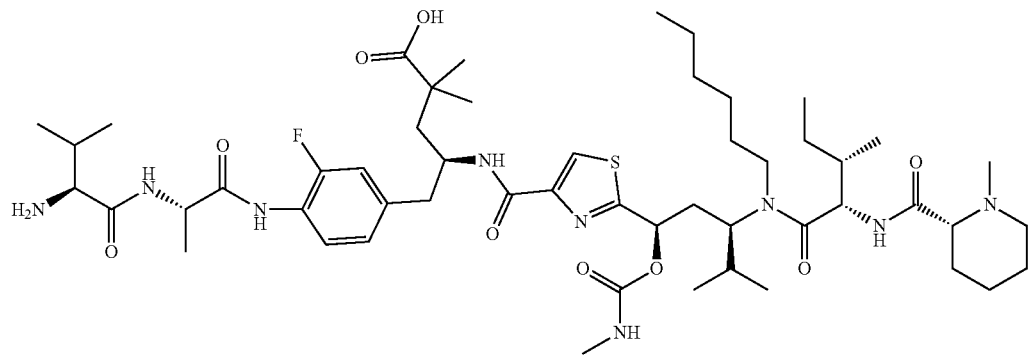 [SMILES: CCCCCCN(C(=O)[C@@H](NC(=O)[C@H]1CCCCN1C)[C@@H](C)CC)[C@H](C[C@@H](OC(=O)NC)c1nc(C(=O)N[C@@H](Cc2ccc(NC(=O)[C@H](C)NC(=O)[C@@H](N)C(C)C)c(F)c2)CC(C)(C)C(=O)O)cs1)C(C)C]

(4S)-5-{4-[(2S)-2-[(2S)-2-Amino-3-methylbutanamido]propanamido]-3-fluorophenyl}-4-({2-[(1R,3R)-3-[(2S,3S)—N-hexyl-3-methyl-2-{[(2R)-1-methylpiperidin-2-yl]formamido}pentanamido]-4-methyl-1-[(methylcarbamoyl)oxy]pentyl]-1,3-thiazol-4-yl}formamido)-2,2-dimethylpentanoic acid (B-7b)

Following a similar procedure as B-7a except substituting B-6b for B-6a, compound B-7b (60 mg, 70% yield) was obtained as a white solid. ESI m/z 516.0 (M/2+H)$^+$.

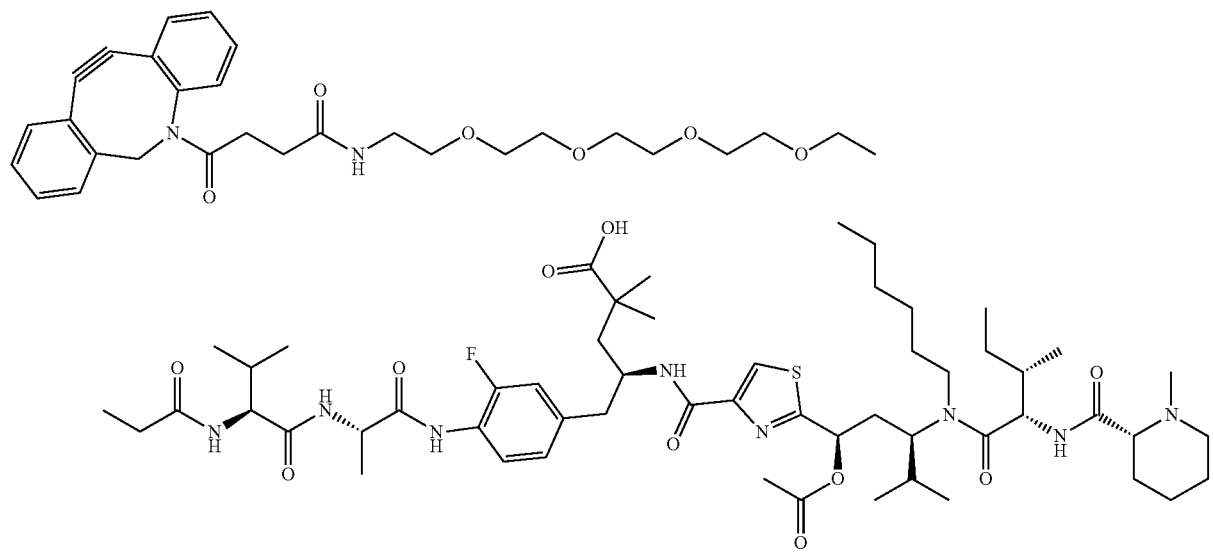

(4S)-4-({2-[(1R,3R)-1-(Acetyloxy)-3-[(2S,3S)—N-hexyl-3-methyl-2-{[(2R)-1-methylpiperidin-2-yl]formamido}pentanamido]-4-methylpentyl]-1,3-thiazol-4-yl}formamido)-5-{4-[(2S)-2-[(2S)-2-[1-(4-{2-azatricyclo[10.4.0.04,9]hexadeca-1(12),4(9),5,7,13,15-hexaen-10-yn-2-yl}-4-oxobutanamido)-3,6,9,12-tetraoxapentadecan-15-amido]-3-methylbutanamido]propanamido]-3-fluorophenyl}-2,2-dimethylpentanoic acid (LP9)

To a solution of compound B-7a (20 mg, 20 μmol) in DMF (2 mL) were added B-8a (16 mg, 25 μmol) and DIPEA (7.3 mg, 57 μmol), and the reaction solution was stirred at RT for 2 hours, which was monitored by LCMS. The resulting solution was directly purified by prep-HPLC (0-100% acetonitrile in aq. ammonium bicarbonate (10 mM)) to give linker-payload LP9 (20 mg, 65% yield) as a white solid. ESI m/z 775.2 (M/2+H)+. 1H NMR (400 MHz, DMSO$_{d6}$) δ 9.56 (s, 1H), 8.22 (d, J=6.8 Hz, 1H), 8.17 (s, 1H), 7.87 (d, J=8.8 Hz, 1H), 7.81-7.67 (m, 6H), 7.51-7.45 (m, 3H), 7.38-7.28 (m, 3H), 7.05 (d, J=11.6 Hz, 1H), 6.92 (d, J=7.6 Hz, 1H), 5.65 (d, J=12.8 Hz, 1H), 5.03 (d, J=14.0 Hz, 1H), 4.52-4.47 (m, 2H), 4.23-4.19 (m, 2H), 3.62-3.56 (m, 4H), 3.47-3.44 (m, 12H), 3.12-3.03 (m, 2H), 3.01-2.88 (m, 1H), 2.87-2.71 (m, 3H), 2.62-2.55 (m, 1H), 2.47-2.41 (m, 2H), 2.38-2.19 (m, 4H), 2.13 (s, 3H), 2.06 (m, 3H), 2.08-1.81 (m, 6H), 1.79-1.31 (m, 11H), 1.28-1.24 (m, 10H), 1.07 (s, 3H), 1.06 (s, 3H), 0.94 (d, J=6.4 Hz, 3H), 0.84-0.79 (m, 18H), 0.68 (d, J=6.0 Hz, 3H) ppm.

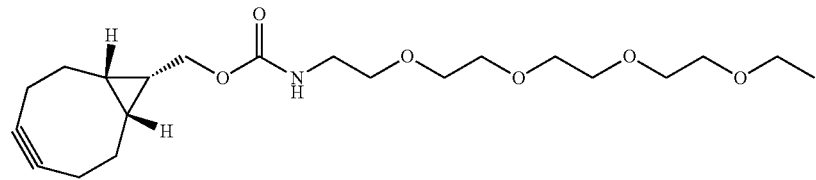

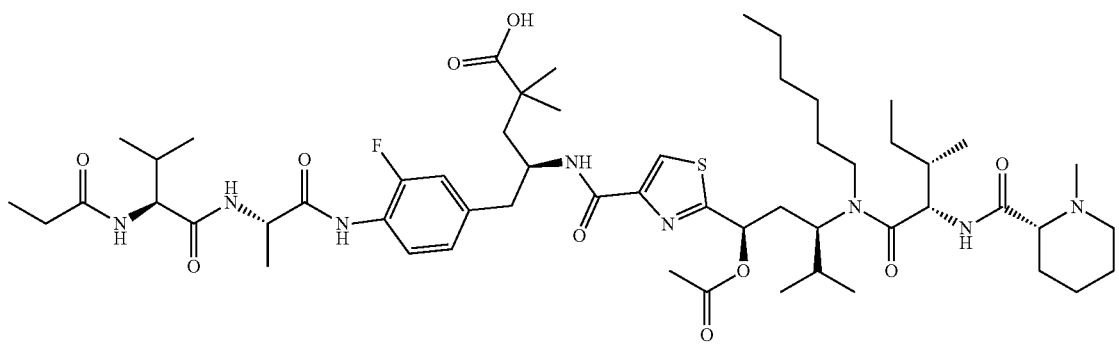

(4S)-4-({2-[(1R,3R)-1-(Acetyloxy)-3-[(2S,3S)—N-hexyl-3-methyl-2-{[(2R)-1-methylpiperidin-2-yl]formamido}pentanamido]-4-methylpentyl]-1,3-thiazol-4-yl}formamido)-5-{4-[(2S)-2-[(2S)-2-[1-({[(1R,8S,9R)-bicyclo[6.1.0]non-4-yn-9-ylmethoxy]carbonyl}amino)-3,6,9,12-tetraoxapentadecan-15-amido]-3-methylbutanamido]propanamido]-3-fluorophenyl}-2,2-dimethylpentanoic acid (LP11)

Following a similar procedure as linker-payload LP9 except substituting B-8b for B-8a, linker-payload LP11 (12 mg, 48% yield) was obtained as a white solid. ESI m/z 719.7 (M/2+H)$^+$. $^1$H NMR (400 MHz, DMSO$_{d6}$) δ 9.60 (s, 1H), 8.21 (d, J=6.8 Hz, 1H), 8.16 (s, 1H), 7.87 (d, J=7.2 Hz, 1H), 7.81-7.71 (m, 2H), 7.64 (d, J=7.2 Hz, 1H), 7.07-7.04 (m, 2H), 6.92 (d, J=8.4 Hz, 1H), 5.65 (d, J=11.6 Hz, 1H), 4.51-4.43 (m, 3H), 4.33-4.26 (m, 2H), 4.23-4.19 (m, 2H), 4.03 (d, J=8.0 Hz, 3H), 3.71-3.63 (m, 6H), 3.58-3.56 (m, 12H), 3.13-3.10 (m, 1H), 2.87-2.73 (m, 2H), 2.48-2.42 (m, 2H), 2.39-2.33 (m, 1H), 2.26-2.15 (m, 6H), 2.13 (s, 3H), 2.06 (m, 3H), 1.97-1.82 (m, 5H), 1.75-1.32 (m, 11H), 1.29-1.23 (m, 12H), 1.08 (s, 3H), 1.07 (s, 3H), 0.95 (d, J=6.4 Hz, 3H), 0.85-0.80 (m, 18H), 0.68 (d, J=6.0 Hz, 3H) ppm.

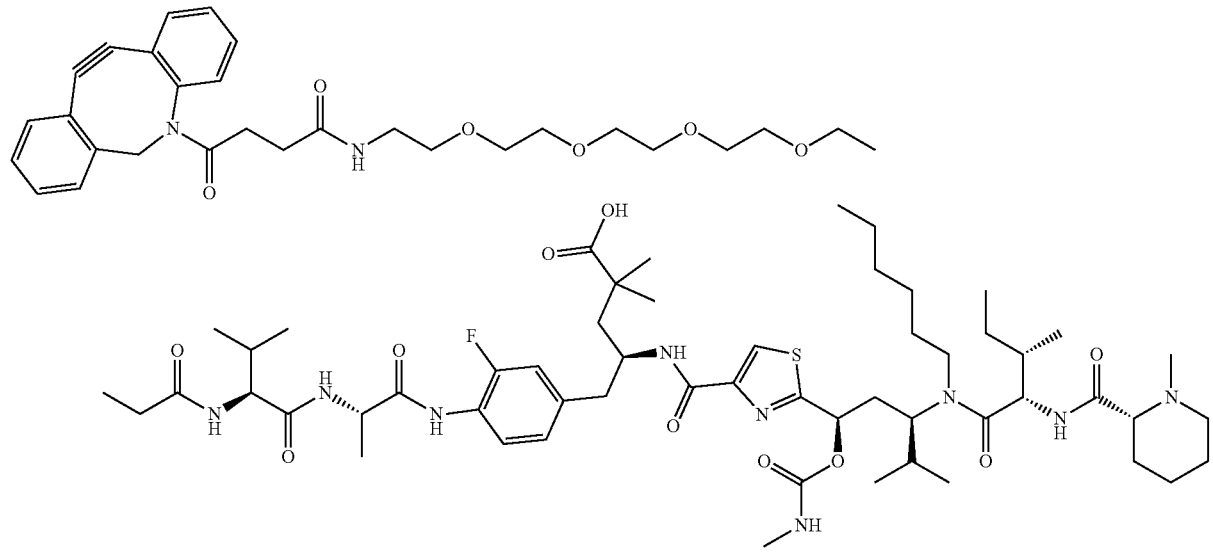

(4S)-5-{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]propanamido]-3-fluorophenyl}-4-({2-[(1R,3R)-3-[(2S,3S)—N-hexyl-3-methyl-2-{[(2R)-1-methylpiperidin-2-yl]formamido}pentanamido]-4-methyl-1-[(methylcarbamoyl)oxy]pentyl]-1,3-thiazol-4-yl}formamido)-2,2-dimethylpentanoic acid (LP12)

Following a similar procedure as linker-payload LP9 except substituting B-7b for B-7a, linker-payload LP12 (20 mg, 65% yield) was obtained as a white solid. ESI m/z 783.1 (M/2+H)$^+$. $^1$H NMR (400 MHz, DMSO$_{d6}$) δ 9.62 (s, 1H), 8.24 (d, J=6.7 Hz, 1H), 8.13 (s, 1H), 7.89 (d, J=8.8 Hz, 1H), 7.77 (s, 2H), 7.68-7.60 (m, 3H), 7.51-7.29 (m, 8H), 7.09-6.89 (m, 2H), 5.55 (s, 1H), 5.03 (d, J=14.0 Hz, 1H), 4.50-4.30 (m, 4H), 3.62 (s, 1H), 3.60-3.55 (m, 4H), 3.49-3.42 (m, 9H), 3.38-3.25 (m, 4H), 3.13-3.03 (m, 3H), 2.95 (s, 1H), 2.90-2.34 (m, 8H), 2.27-2.21 (m, 1H), 2.08-1.70 (m, 7H), 1.70-1.45 (m, 6H), 1.30-1.20 (m, 12H), 1.11-1.02 (m, 8H), 1.00-0.83 (m, 25H), 0.69 (s, 3H) ppm.

Figure 10E:
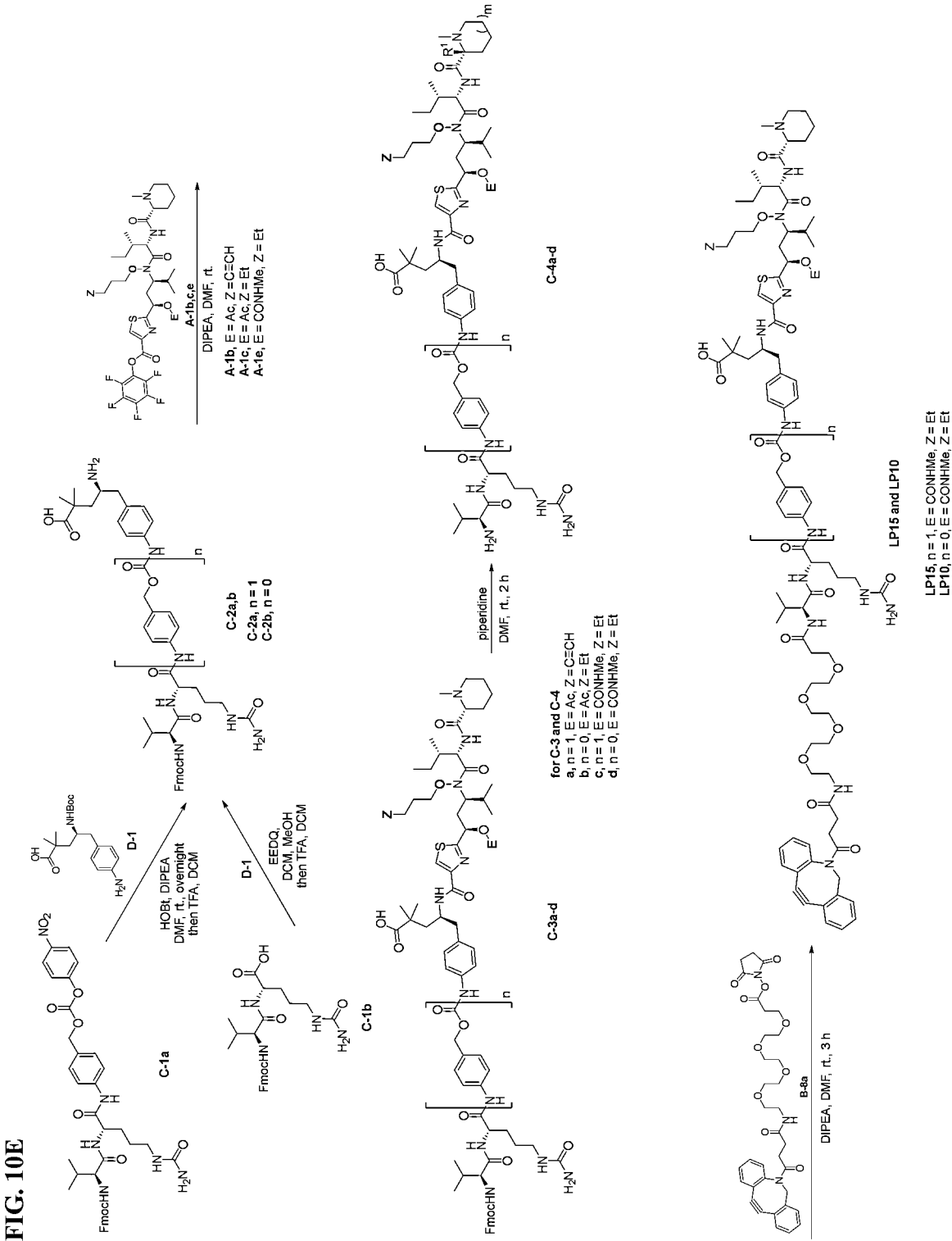

Synthesis of LP10 and LP15 (FIG. 10E)

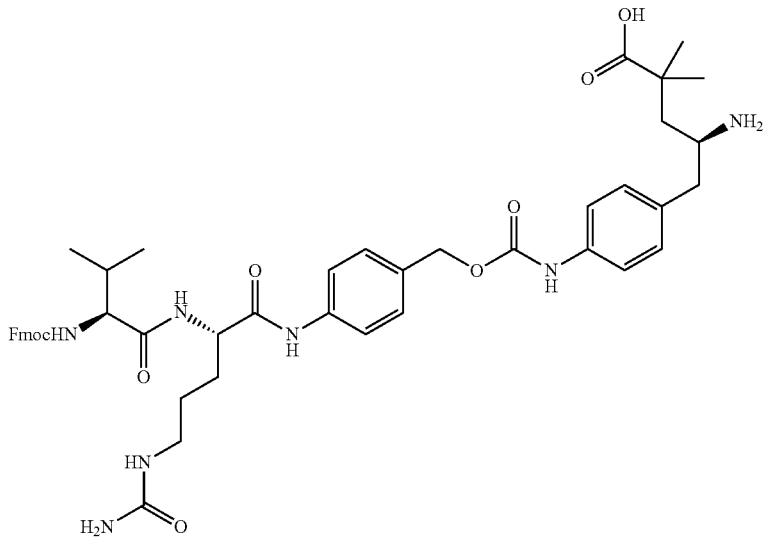

(4S)-4-Amino-5-(4-{[({4-[(2S)-5-(carbamoy-lamino)-2-[(2S)-2-{[(9H-fluoren-9-ylmethoxy)carbonyl]amino}-3-methylbutanamido]pentanamido]phenyl}methoxy)carbonyl]amino}phenyl)-2,2-dimethylpentanoic acid (C-2a)

To a mixture of compound D-1 (20 mg, 59 μmol) and Fmoc-vcPAB-PNP (C-1a) (50 mg, 65 μmol) in DMF (2 mL) were added HOBt (8.0 mg, 59 μmol) and DIPEA (15 mg, 0.12 mmol), and the reaction mixture was stirred at RT overnight, which was monitored by LCMS. The resulting mixture was then directly purified by reversed phase flash chromatography (0-100% acetonitrile in aq. TFA (0.01%)) to afford Boc-C-2a (31 mg, ESI m/z 964.1 (M+H)$^+$) as a white solid, which was dissolved in DCM (4 mL). To the solution was added TFA (0.5 mL), and the reaction mixture was stirred at RT for half an hour until Boc was totally removed, which was monitored by LCMS. The volatiles were removed in vacuo to give compound C-2a (37 mg, 54% yield, TFA salt) as brown oil. ESI m/z 432.6 (M/2+H)$^+$.

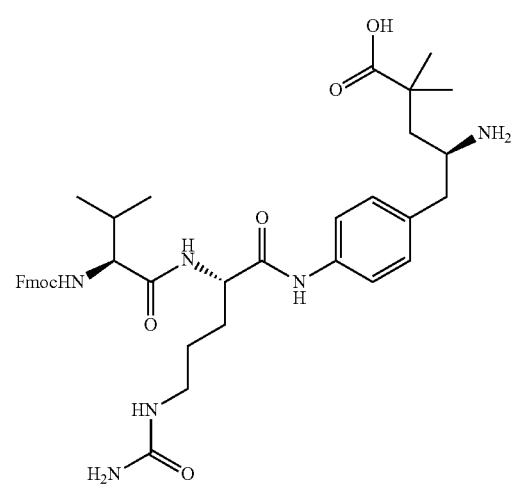

(4S)-4-Amino-5-{4-[(2S)-5-(carbamoylamino)-2-[(2S)-2-{[(9H-fluoren-9-ylmethoxy)carbonyl]amino}-3-methylbutanamido]pentanamido]phenyl}-2,2-dimethylpentanoic acid (C-2b)

To a mixture of Fmoc-Val-Cit-OH (C-1b) (0.60 g, 1.2 mmol) in DCM (20 mL) and methanol (10 mL) were added compound D-1 (0.20 g, 0.59 mmol) and EEDQ (0.22 g, 0.90 mmol) under nitrogen and the mixture turned clear. The solution was stirred in the dark at RT overnight, which was monitored by LCMS. The mixture was concentrated in vacuo and the residue was purified by reversed phase flash chromatography (0-100% acetonitrile in aq. ammonium bicarbonate (10 mM)) to give compound Boc-C-2b (85 mg, ESI m/z: 815.3 (M+H)$^+$) as a white solid; which was then dissolved in DCM (10 mL). To the solution was added TFA (1 mL), and the mixture was stirred at RT for an hour until Boc was totally removed, which was monitored by LCMS. The volatiles were removed in vacuo to give compound C-2b (84 mg, 17% yield, TFA salt) as brown oil. ESI m/z 715.3 (M+H)$^+$.

General Procedure for Compounds C-3 and C-4

To a mixture of C-2 (1.0 equiv.) in DMF (15 mM) were added DIPEA (3.0 equiv.) and pentafluorophenyl ester (A-1b,c,e), and the reaction mixture was stirred at RT overnight, which was monitored by LCMS. The resulting mixture was directly purified by reversed phase flash chromatography (0-100% acetonitrile in water) to give compound C-3 (30-67% yield) as a white solid; which was then dissolved into DMF (40 mM). To the solution was added piperidine (3.0 equiv.), and the mixture was stirred at RT for 2 hours until Fmoc was totally removed, which was monitored by LCMS. The resulting mixture was directly purified by reversed phase flash chromatography (0-100% acetonitrile in aq. TFA (0.01%)) to give compound C-4 (25-67% yield in 2 steps from activated ester).

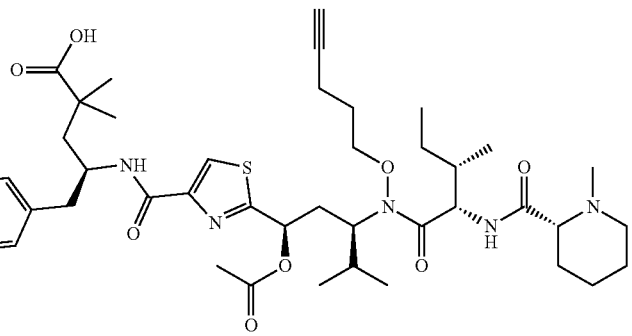
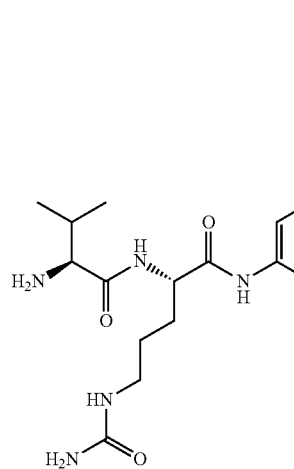

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-{[({4-[(2S)-2-[(2S)-2-amino-3-methylbutanamido]-5-(carbamoylamino)pentanamido]phenyl}methoxy)carbonyl]amino}phenyl)-2,2-dimethylpentanoic acid
(C-4a)

Following the general procedure for compounds C-3 and C-4, from C-2a treated with A-1b, compound C-4a (17 mg, 67% yield from A-1b) was obtained as a white solid. ESI m/z 615.8 (M/2+H)$^+$.

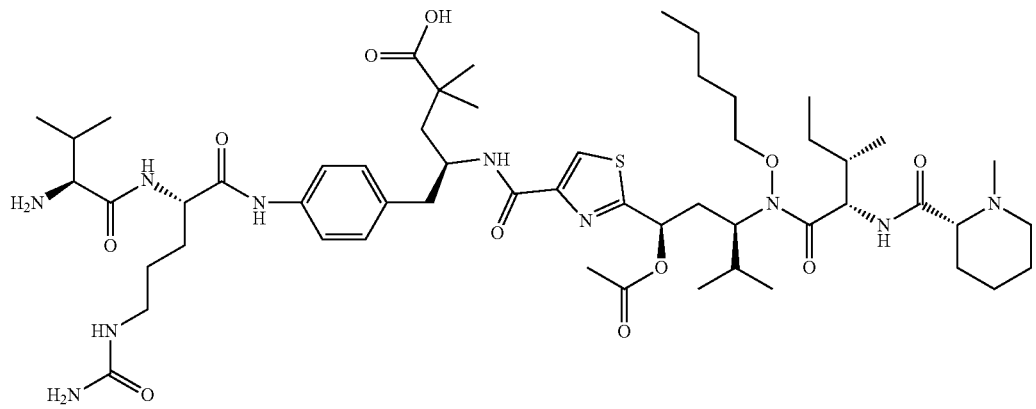 [SMILES: CCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](CCCNC(N)=O)NC(=O)[C@@H](N)C(C)C)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-{4-[(2S)-2-[(2S)-2-amino-3-methylbutanamido]-5-(carbamoylamino)pentanamido]phenyl}-2,2-dimethylpentanoic acid
(C-4b)

Following the general procedure for compounds C-3 and C-4, from C-2b treated with A-1c, compound C-4b (37 mg, 56% yield from A-1c) was obtained as a white solid. ESI m/z 543.5 (M/2+H)$^+$.

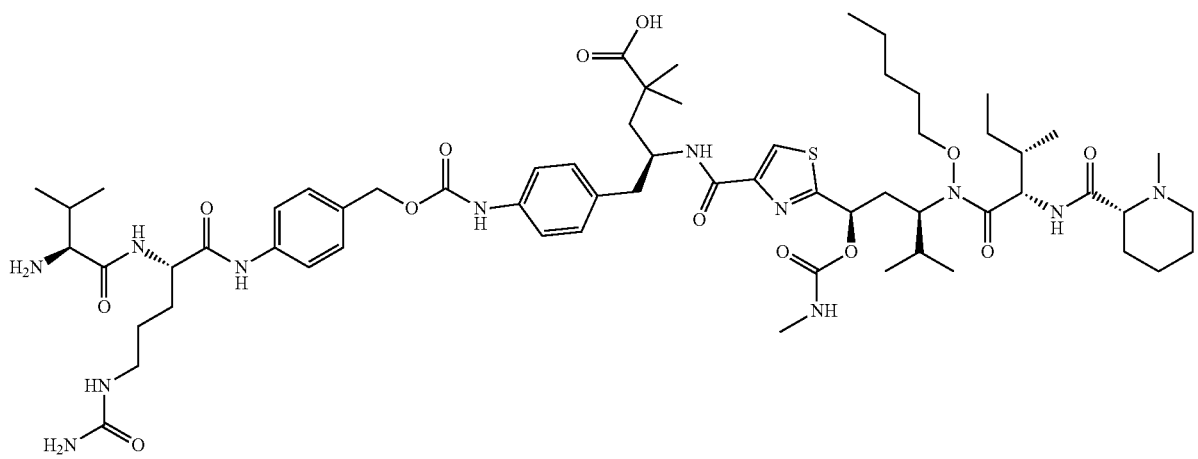 [SMILES: CCCCCON(C(=O)[C@@H](NC(=O)[C@H]1CCCCN1C)[C@@H](C)CC)[C@H](C[C@@H](OC(=O)NC)c1nc(C(=O)N[C@@H](Cc2ccc(NC(=O)OCc3ccc(NC(=O)[C@H](CCCNC(N)=O)NC(=O)[C@@H](N)C(C)C)cc3)cc2)CC(C)(C)C(=O)O)cs1)C(C)C]

(4S)-5-(4-{[({4-[(2S)-2-[(2S)-2-Amino-3-methylbutanamido]-5-(carbamoylamino)pentanamido]phenyl}methoxy)carbonyl]amino}phenyl)-2,2-dimethyl-4-({2-[(1R,3R)-4-methyl-3-[(2S,3S)-3-methyl-2-{[(2R)-1-methylpiperidin-2-yl]formamido}-N-(pentyloxy)pentanamido]-1-[(methylcarbamoyl)oxy]pentyl]-1,3-thiazol-4-yl}formamido)pentanoic acid (C-4c)

Following the general procedure for compounds C-3 and C-4, from C-2a treated with A-1e, compound C-4c (9 mg, 20% yield from A-1e) was obtained as a white solid. ESI m/z 1250.1 (M+H)⁺.

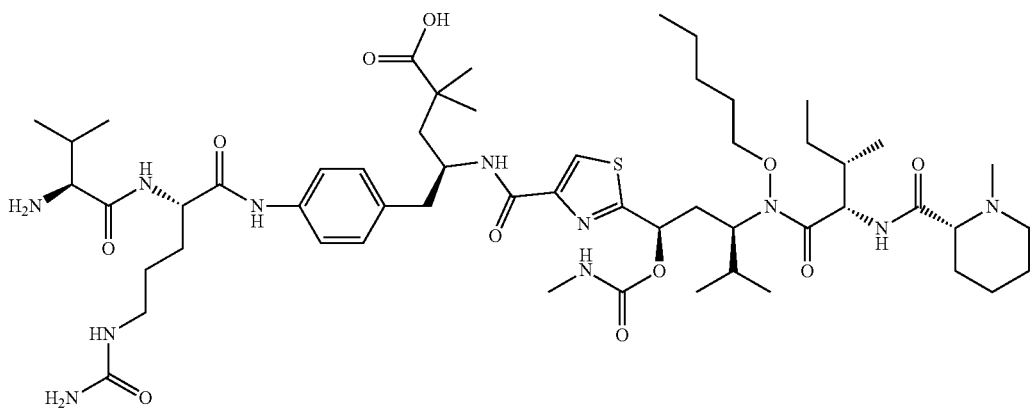 [SMILES: CCCCCON(C(=O)[C@@H](NC(=O)[C@H]1CCCCN1C)[C@@H](C)CC)[C@H](C[C@@H](OC(=O)NC)c1nc(C(=O)N[C@@H](Cc2ccc(NC(=O)[C@H](CCCNC(N)=O)NC(=O)[C@@H](N)C(C)C)cc2)CC(C)(C)C(=O)O)cs1)C(C)C]

(4S)-5-{4-[(2S)-2-[(2S)-2-Amino-3-methylbutanamido]-5-(carbamoylamino)pentanamido]phenyl}-2,2-dimethyl-4-({2-[(1R,3R)-4-methyl-3-[(2S,3S)-3-methyl-2-{[(2R)-1-methylpiperidin-2-yl]formamido}-N-(pentyloxy)pentanamido]-1-[(methylcarbamoyl)oxy]pentyl]-1,3-thiazol-4-yl}formamido)pentanoic acid (C-4d)

Following the general procedure for compounds C-3 and C-4, from C-2b treated with A-1e, compound C-4d (9 mg, 29% yield from A-1e) was obtained as a white solid. ESI m/z 1101.1 (M+H)⁺.

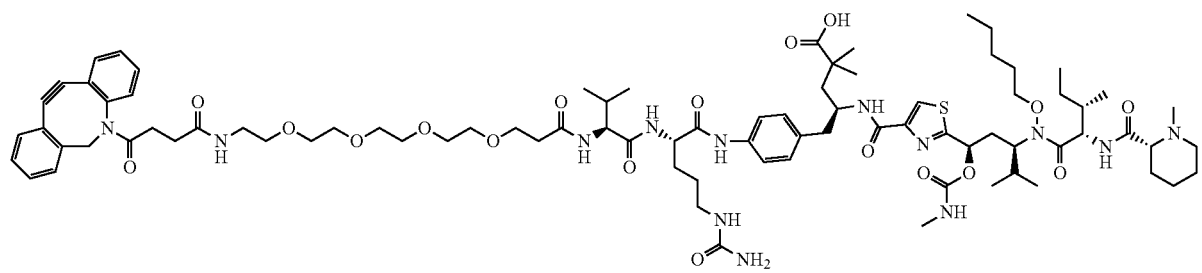 [SMILES: CCCCCON(C(=O)[C@@H](NC(=O)[C@H]1CCCCN1C)[C@@H](C)CC)[C@H](C[C@@H](OC(=O)NC)c1nc(C(=O)N[C@@H](Cc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)CC(C)(C)C(=O)O)cs1)C(C)C]

(4S)-5-{4-[(2S)-2-[(2S)-2-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}-2,2-dimethyl-4-({2-[(1R,3R)-4-methyl-3-[(2S,3S)-3-methyl-2-{[(2R)-1-methylpiperidin-2-yl]formamido}-N-(pentyloxy)pentanamido]-1-[(methylcarbamoyl)oxy]pentyl]-1,3-thiazol-4-yl}formamido)pentanoic acid (LP10)

Following the similar procedure for LP9, except substituting C-4d for B-7a, linker-payload LP10 (7 mg, 52% yield) was obtained as a white solid. ESI m/z 818.0 (M/2+H)⁺. ¹H NMR (400 MHz, DMSO$_{d6}$) δ 9.90-9.80 (m, 1H), 8.15 (s, 4H), 7.80 (s, 1H), 7.68 (d, J=7.3 Hz, 1H), 7.62 (d, J=7.2 Hz, 1H), 7.58-7.27 (m, 10H), 7.09 (d, J=8.0 Hz, 2H), 6.01 (s, 1H), 5.67 (d, J=10.9 Hz, 1H), 5.43 (s, 2H), 5.02 (d, J=13.9 Hz, 1H), 4.78 (s, 1H), 4.35 (s, 1H), 4.25-3.33 (m, 21H), 3.32-2.53 (m, 14H), 2.46-2.43 (m, 1H), 2.32-2.20 (m, 4H), 2.11 (s, 3H), 2.02-1.95 (m, 5H), 1.82-1.70 (m, 2H), 1.65-1.55 (m, 6H), 1.42-1.28 (m, 9H), 1.24 (s, 1H), 1.16-0.80 (m, 29H) ppm.

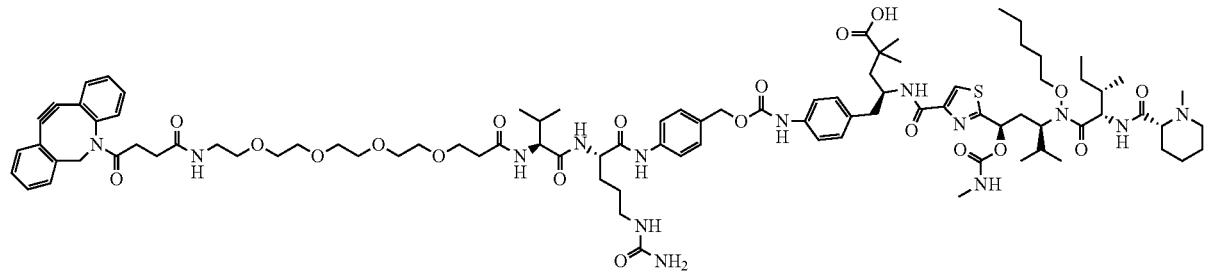 [SMILES: CCCCCON(C(=O)[C@@H](NC(=O)[C@H]1CCCCN1C)[C@@H](C)CC)[C@H](C[C@@H](OC(=O)NC)c1nc(C(=O)N[C@@H](Cc2ccc(NC(=O)OCc3ccc(NC(=O)[C@H](CCCNC(N)=O)NC(=O)[C@@H](NC(=O)CCOCCOCCOCCOCCNC(=O)CCC(=O)N4Cc5ccccc5C#Cc5ccccc54)C(C)C)cc3)cc2)CC(C)(C)C(=O)O)cs1)C(C)C]

(4S)-5-(4-{[({4-[(2S)-2-[(2S)-2-[1-(4-{2-Azatricyclo[10.4.0.04,9]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl]amino}phenyl)-2,2-dimethyl-4-({2-[(1R,3R)-4-methyl-3-[(2S,3S)-3-methyl-2-{[(2R)-1-methylpiperidin-2-yl]formamido}-N-(pentyloxy)pentanamido]-1-[(methylcarbamoyl)oxy]pentyl]-1,3-thiazol-4-yl}formamido)pentanoic acid (LP15)

Following the similar procedure as linker-payload LP9 except substituting C-4c for B-7a, linker-payload LP15 (22 mg, 80% yield) was obtained as a white solid. ESI m/z 892.5 (M/2+H)$^+$. $^1$H NMR (400 MHz, DMSO$_{d6}$) δ 9.99 (s, 1H), 9.61 (s, 1H), 8.11-8.09 (m, 2H), 7.86 (d, J=9.2 Hz, 1H), 7.75 (t, J=5.6 Hz, 1H), 7.67-7.65 (m, 1H), 7.61-7.59 (m, 3H), 7.50-7.44 (m, 4H), 7.39-7.36 (m, 2H), 7.34-7.20 (m, 7H), 7.05 (d, J=8.4 Hz, 2H), 5.97 (t, J=5.6 Hz, 1H), 5.67 (d, J=11.2 Hz, 1H), 5.40 (s, 2H), 5.04 (s, 3H), 4.78 (t, J=8.4 Hz, 1H), 4.40-4.34 (m, 1H), 4.23-4.19 (m, 2H), 4.11-4.09 (m, 1H), 4.03-3.92 (m, 3H), 3.65-3.53 (m, 6H), 3.09-2.90 (m, 8H), 2.86-2.81 (m, 1H), 2.76-2.63 (m, 3H), 2.55 (d, J=4.8 Hz, 3H), 2.46-2.43 (m, 2H), 2.39-2.31 (m, 2H), 2.26-2.16 (m, 3H), 2.10 (s, 3H), 2.01-1.92 (m, 6H), 1.88-1.70 (m, 4H), 1.68-1.48 (m, 9H), 1.46-1.27 (m, 12H), 1.04 (s, 3H), 1.02 (s, 3H), 0.94 (d, J=6.8 Hz, 3H), 0.86-0.80 (m, 18H) ppm.

Figure 10F:
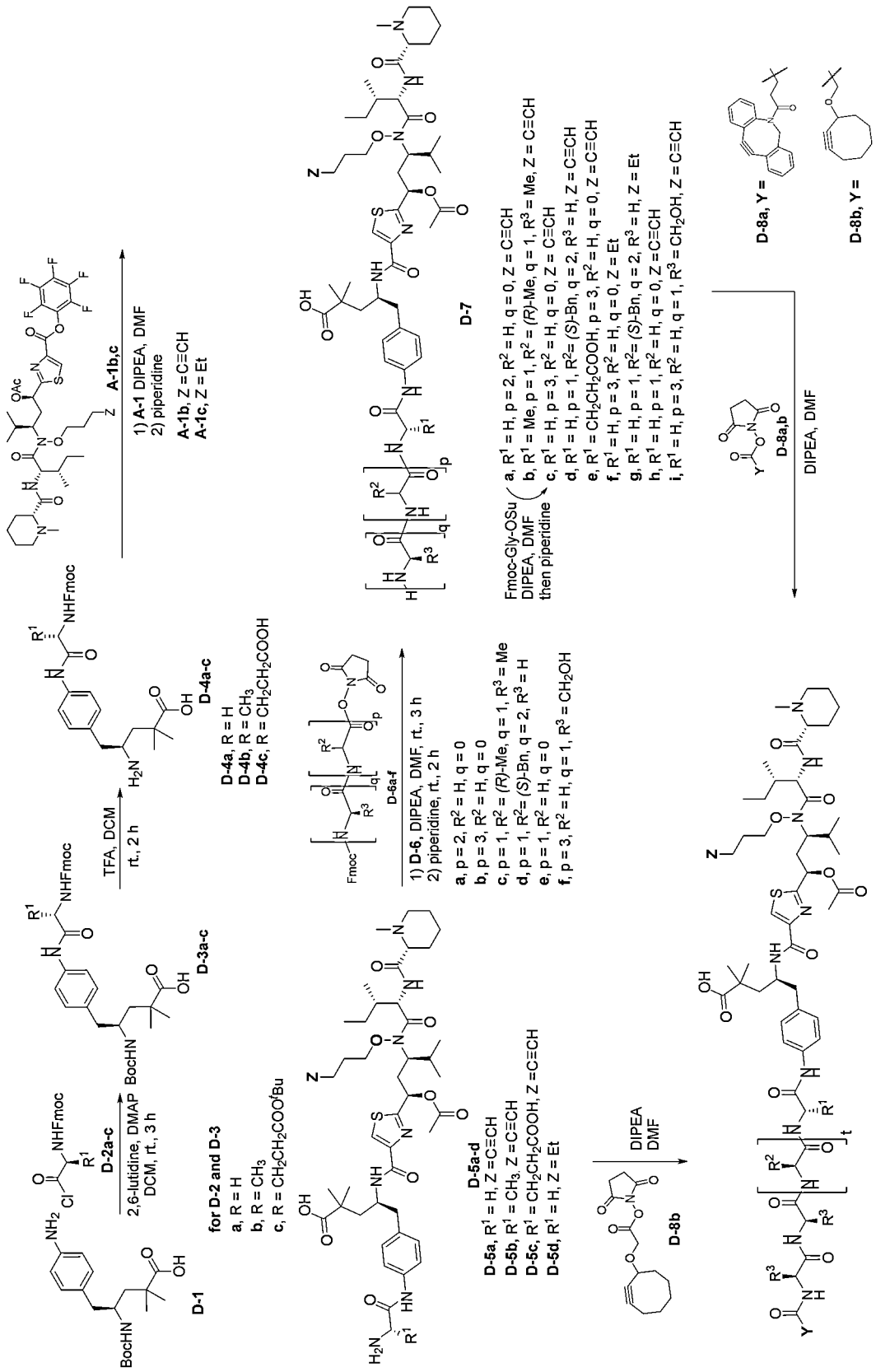

Synthesis of LP13, LP14, LP16, LP17, LP18, LP19, LP20, LP21, LP22, LP23, and LP24 (FIG. 10F)

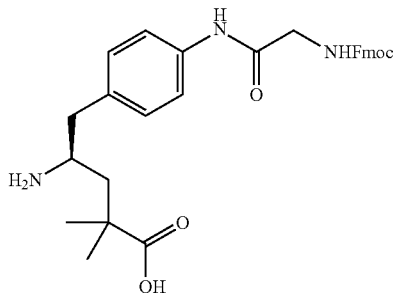

(4S)-4-Amino-5-[4-(2-{[(9H-fluoren-9-ylmethoxy)carbonyl]amino}acetamido)phenyl]-2,2-dimethylpentanoic acid (D-4a)

To a solution of D-1 (Boc-A-2d) (0.34 g, 1.0 mmol) in DCM (10 mL) were added 2,6-lutidine (0.21 g, 2.0 mmol) and Fmoc-Gly-Cl (D-2a) (0.45 g, 1.5 mmol), and the reaction mixture was stirred at RT for 3 hours, which was monitored by LCMS. The resulting mixture was diluted with ethyl acetate (50 mL), washed with water and brine, dried over anhydrous sodium sulfate and concentrated in vacuo. The residue was purified by reversed phase flash chromatography (0-100% acetonitrile in aq. TFA (0.3%)) to give compound D-3a (0.31 g, 50% yield) as a white solid. ESI m/z 516.3 (M−Boc+H)$^+$.

To a solution of D-3a (0.31 g, obtained above) in DCM (5 mL) was added TFA (1.0 mL), and the mixture was stirred at RT for 2 hours until Boc was totally removed in vacuo, which was monitored by LCMS. The volatiles were removed in vacuo to give crude compound D-4b (0.30 g, 58% yield from D-1) as a white solid. ESI m/z 516.3 (M+H)$^+$.

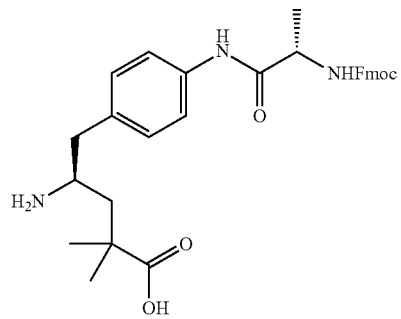

(4S)-4-Amino-5-{4-[(2S)-2-{[(9H-fluoren-9-ylmethoxy)carbonyl]amino}propanamido]phenyl}-2,2-dimethylpentanoic acid (D-4b)

Following a similar procedure for compound D-4a except substituting Fmoc-Ala-Cl (D-2b) for D-2a, compound D-4b (0.31 g, 58% yield from D-1) was obtained as a white solid. ESI m/z 530.3 (M+H)$^+$.

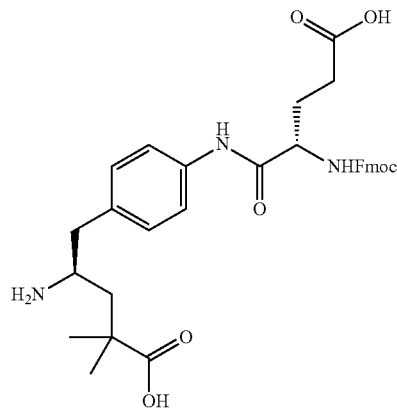

(4S)-4-Amino-5-{4-[(2S)-4-carboxy-2-{[(9H-fluoren-9-ylmethoxy)carbonyl]amino}butanamido]phenyl}-2,2-dimethylpentanoic acid (D-4c)

To a solution of Fmoc-Glu(OtBu)-OH (0.64 g, 1.5 mmol) in DCM (10 mL) was added oxalyl chloride (4.5 mmol), and the reaction mixture was stirred at RT for an hour. The resulting mixture was concentrated in vacuo to give compound Fmoc-Glu(OtBu)-Cl (D-2c), which was used for the next step directly.

Following a similar procedure for compound D-4a, except substituting compound D-2c (obtained above) for D-2a, compound D-4c (0.25 g, 43% yield from D-1) was obtained as a white solid. ESI m/z 588.3 (M+H)$^+$.

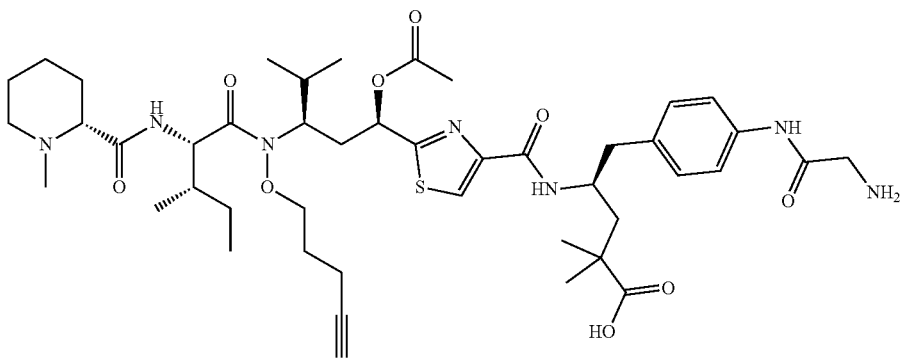 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CN)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-[4-(2-aminoacetamido)phenyl]-2,2-dimethylpentanoic acid (D-5a)

Following the general procedure for VII and VIII from compound D-4a treated with compound A-1b, compound Fmoc-D-5a (77 mg, 70% yield, ESI m/z 552.0 (M/2+H)$^+$) was obtained as a white solid, which was dissolved into DMF (1 mL). To the solution was added piperidine (26 mg, 0.31 mmol), and the reaction mixture was stirred at RT for 2 hours until Fmoc was totally removed, which was monitored by LCMS. The resulting solution was directly purified by reversed phase flash chromatography (5-75% acetonitrile in aq. ammonium bicarbonate (10 mM)) to give compound D-5a (26 mg, 50% yield) as a white solid. ESI m/z 882.4 (M+H)$^+$.

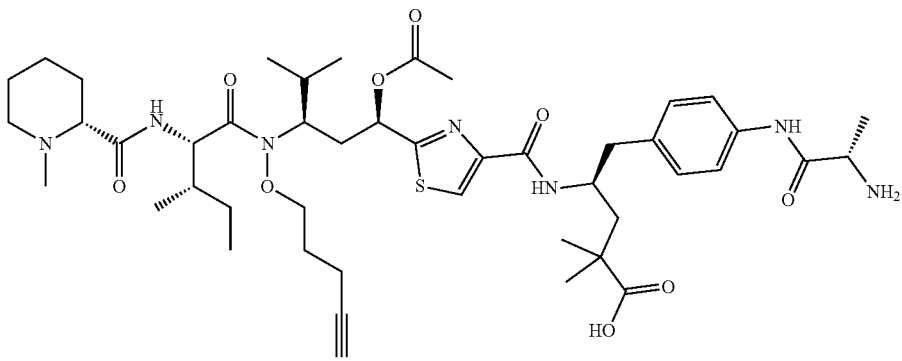 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](C)N)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-{4-[(2S)-2-aminopropanamido]phenyl}-2,2-dimethylpentanoic acid (D-5b)

Following a similar procedure for compound D-5a, except substituting compound D-4b for D-4a, compound D-5b (25 mg, 55% yield) was obtained as a white solid. ESI m/z 896.5 (M+H)$^+$.

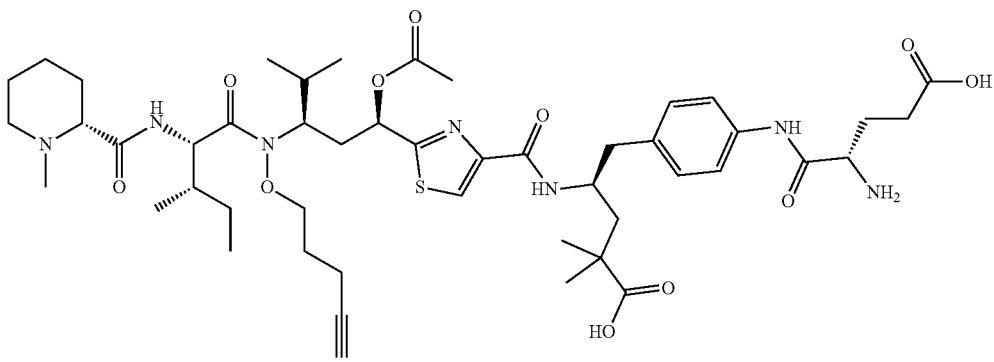 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@@H](N)CCC(=O)O)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-{4-[(2S)-2-amino-4-carboxybutanamido]phenyl}-2,2-dimethylpentanoic acid (D-5c)

Following a similar procedure for compound D-5a, except substituting compound D-4c for D-4a, compound D-5c (30 mg, 63% yield) was obtained as a white solid. ESI m/z 478.0 (M/2+H)$^+$.

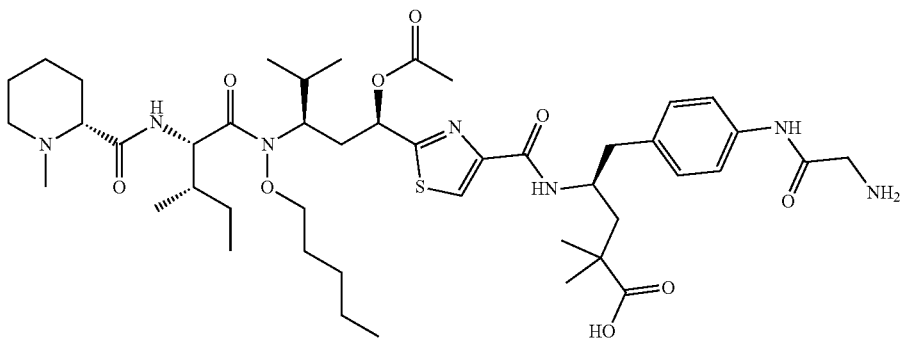 [SMILES: CCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CN)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-[4-(2-aminoacetamido)phenyl]-2,2-dimethylpentanoic acid (D-5d)

Following a similar procedure for compound D-5a, except substituting compound A-1c for A-1b, compound D-5d (15 mg, 69% yield) was obtained as a white solid. ESI m/z 886.2 (M+H)$^+$.

General Procedure for D-7 Compounds

To a solution of compound D-5 (1.0 equiv.) in DMF (6 mM) were added DIPEA (2.0 equiv.) and peptide active ester D-6 (1.0 equiv.), and the reaction mixture was stirred at RT for 3 hours, which was monitored by LCMS. To the reaction mixture was added piperidine (5.0 equiv.), and the mixture was stirred at RT for 2 hours until Fmoc was totally removed, which was monitored by LCMS. The reaction mixture was directly purified by reversed phase flash chromatography (25-75% acetonitrile in aq. ammonium bicarbonate (10 mM)) to give compound D-7 (35-48% yield) as a white solid.

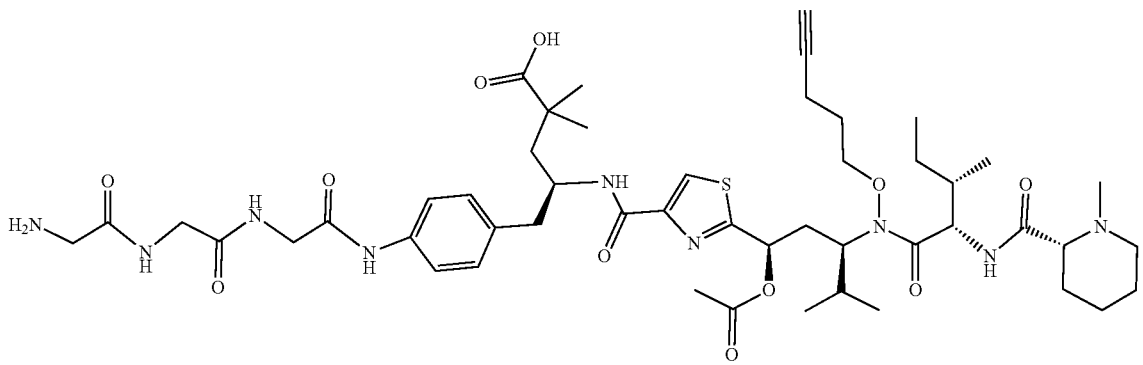 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)CNC(=O)CN)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-{2-[2-(2-aminoacetamido)acetamido]acetamido}phenyl)-2,2-dimethylpentanoic acid (D-7a)

Following the general procedure for D-7 compounds from D-5a treated with D-6a, compound D-7a (28 mg, 35% yield) was obtained as a white solid. ESI m/z: 498.7 $(M/2+H)^+$.

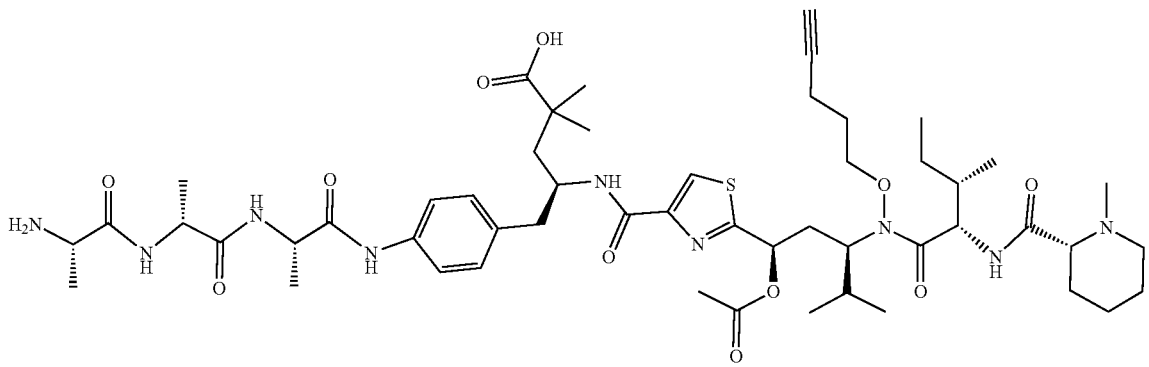 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](C)NC(=O)[C@@H](C)NC(=O)[C@H](C)N)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-{4-[(2S)-2-[(2R)-2-[(2S)-2-aminopropanamido]propanamido]propanamido]phenyl}-2,2-dimethylpentanoic acid (D-7b)

Following the general procedure for D-7 compounds from D-5b treated with D-6b, compound D-7b (30 mg, 35% yield) was obtained as a white solid. ESI m/z: 519.8 $(M/2+H)^+$. Following the general procedure for D-7 compounds, the following compound is made

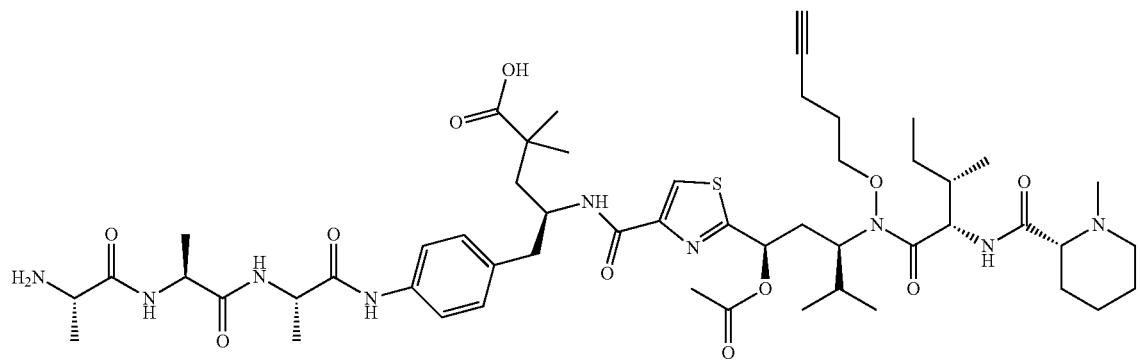

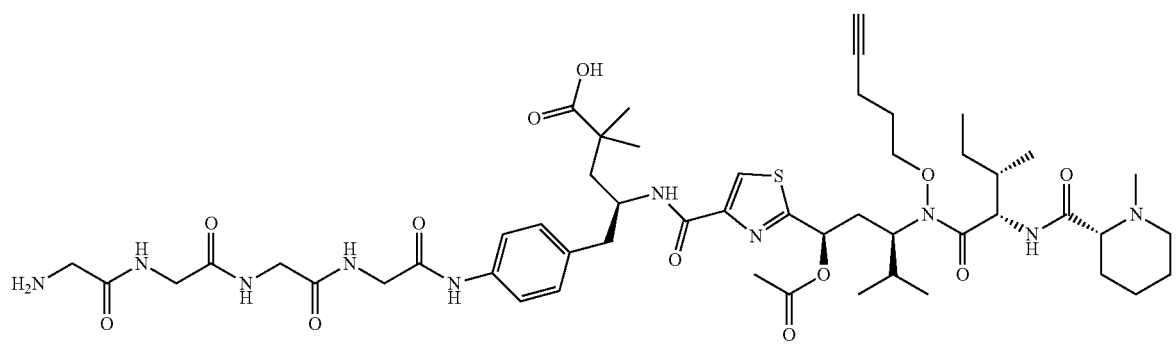

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-[4-(2-{2-[2-(2-aminoacetamido)acetamido]acetamido}acetamido)phenyl]-2,2-dimethylpentanoic acid (D-7c)

To a solution of compound D-7a (20 mg, 20 µmol) in DMF (3 mL) were added Fmoc-Gly-OSu (8 mg, 20 µmol) and DIPEA (13 mg, 0.10 mmol). The reaction mixture was stirred at RT for 3 hours before the addition of piperidine (6.0 mg, 70 µmol). The mixture was then stirred at RT for another 2 hours until Fmoc was totally removed, which was monitored by LCMS. The resulting mixture was directly purified by reversed phase flash chromatography (25-75% acetonitrile in aq. ammonium bicarbonate (10 mM)) to give compound D-7c (10 mg, 47% yield) as a white solid. ESI m/z: 527.3 (M/2+H)⁺.

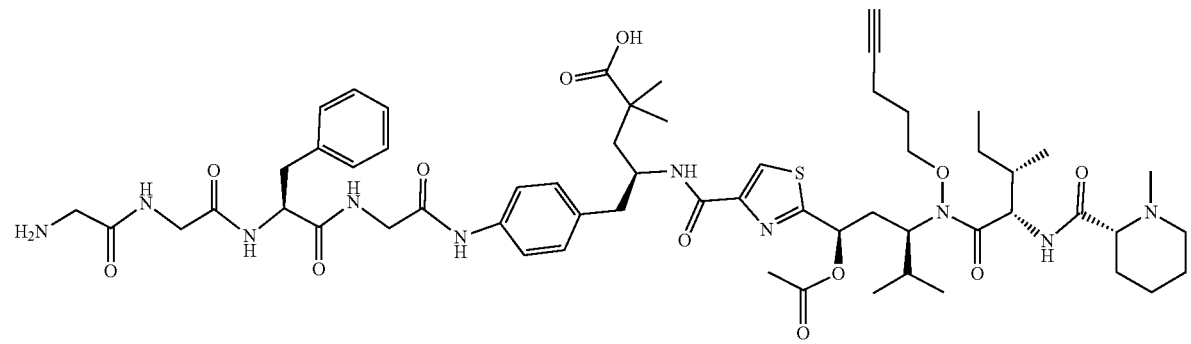 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)[C@H](Cc3ccccc3)NC(=O)CNC(=O)CN)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-{2-[(2S)-2-[2-(2-aminoacetamido)acetamido]-3-phenylpropanamido]acetamido}phenyl)-2,2-dimethylpentanoic acid (D-7d)

Following the general procedure for D-7 compounds from D-5a treated with D-6d, compound D-7d (11 mg, 43% yield) was obtained as a white solid. ESI m/z: 572.3 (M/2+H)⁺.

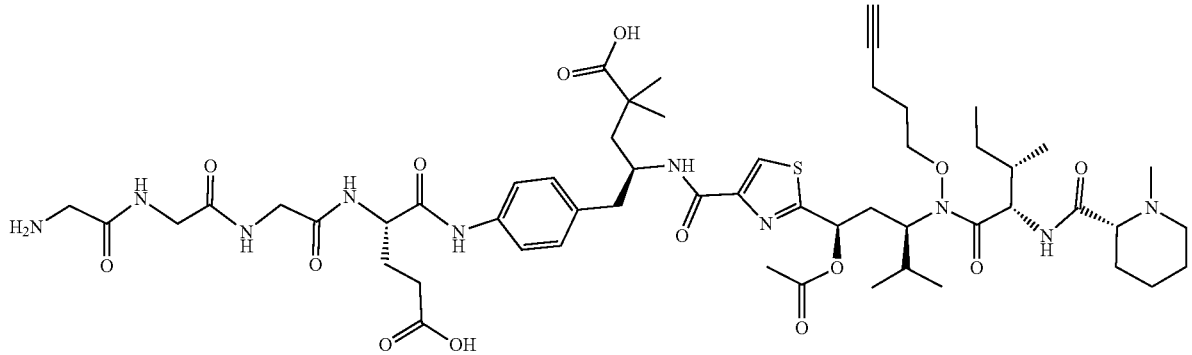 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](CCC(=O)O)NC(=O)CNC(=O)CNC(=O)CN)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-{4-[(2S)-2-{2-[2-(2-aminoacetamido)acetamido]acetamido}-4-carboxybutanamido]phenyl}-2,2-dimethylpentanoic acid (D-7e)

Following the general procedure for D-7 compounds from D-5c treated with D-6c, compound D-7e (15 mg, 34% yield) was obtained as a white solid. ESI m/z: 563.3 (M/2+H)⁺.

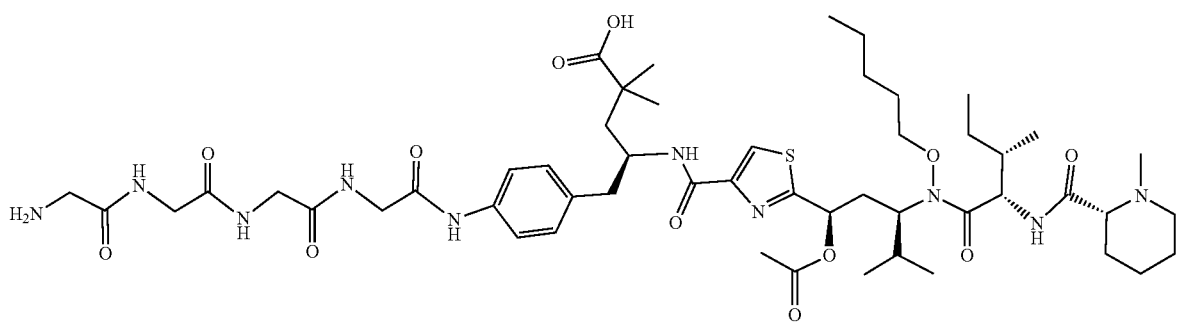 [SMILES: CCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)CNC(=O)CNC(=O)CN)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-[4-(2-{2-[2-(2-aminoacetamido)acetamido]acetamido}acetamido)phenyl]-2,2-dimethylpentanoic acid (D-7f)

Following the general procedure for D-7 compounds from D-5d treated with D-6c, compound D-7e (10 mg, 47% yield) was obtained as a white solid. ESI m/z: 529.3 (M/2+H)⁺.

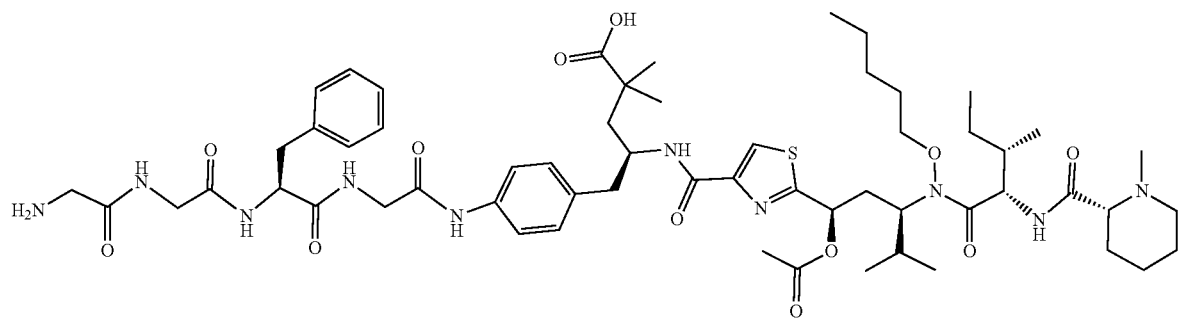 [SMILES: CCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)[C@H](Cc3ccccc3)NC(=O)CNC(=O)CN)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-(4-{2-[(2S)-2-[2-(2-aminoacetamido)acetamido]-3-phenylpropanamido]acetamido}phenyl)-2,2-dimethylpentanoic acid (D-7g)

Following the general procedure for D-7 compounds from D-5d treated with D-6d, compound D-7g (11 mg, 48% yield) was obtained as a white solid. ESI m/z: 574.3 (M/2+H)$^+$.

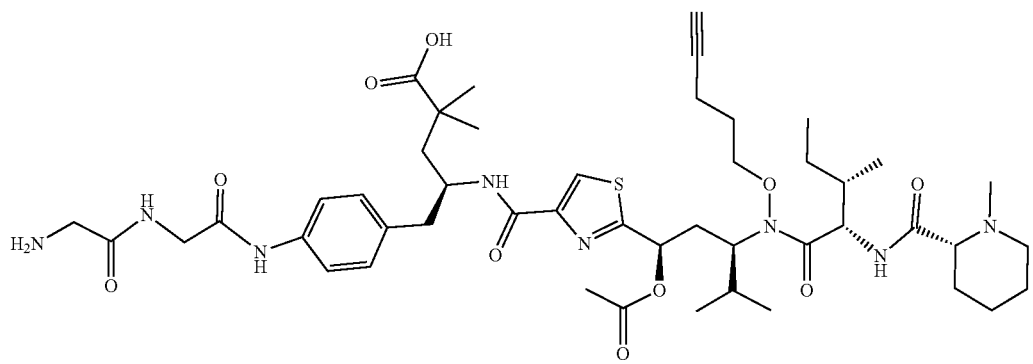 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)CN)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-{4-[2-(2-aminoacetamido)acetamido]phenyl}-2,2-dimethylpentanoic acid (D-7h)

Following the general procedure for D-7 compounds from D-5a treated with D-6e, compound D-7h (9 mg, 48% yield) was obtained as a white solid. ESI m/z: 470.3 (M/2+H)$^+$.

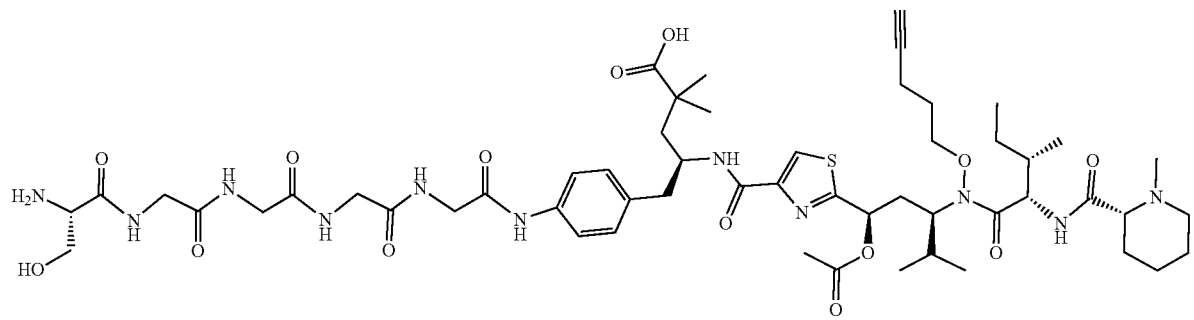 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)CNC(=O)CNC(=O)CNC(=O)[C@@H](N)CO)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-{2-[2-(2-{2-[(2S)-2-amino-3-hydroxypropanamido]acetamido}acetamido)acetamido]acetamido}phenyl)-2,2-dimethylpentanoic acid
(D-7i)

Following the general procedure for D-7 compounds from D-5a treated with D-6f, compound D-7i (8 mg, 35% yield) was obtained as a white solid. ESI m/z: 570.8 (M/2+H)$^+$.

General Procedure for Linker-Payloads LP13, LP14, LP16, LP17, LP18, LP19, LP20, LP21, LP22, LP23, and LP24

To a solution of compound D-7 (1.0 equiv.) (or compound D-5) in DMF (10 mM) were added activated ester D-8 (1.0 equiv.) and DIPEA (5.0 equiv.), and the reaction mixture was stirred at RT for 3 hours, which was monitored by LCMS. The resulting mixture was directly purified by Prep-HPLC (0-100% acetonitrile in aq. ammonium bicarbonate (10 mM)) to give linker-payload LP8-17 (33-87%) as a white solid.

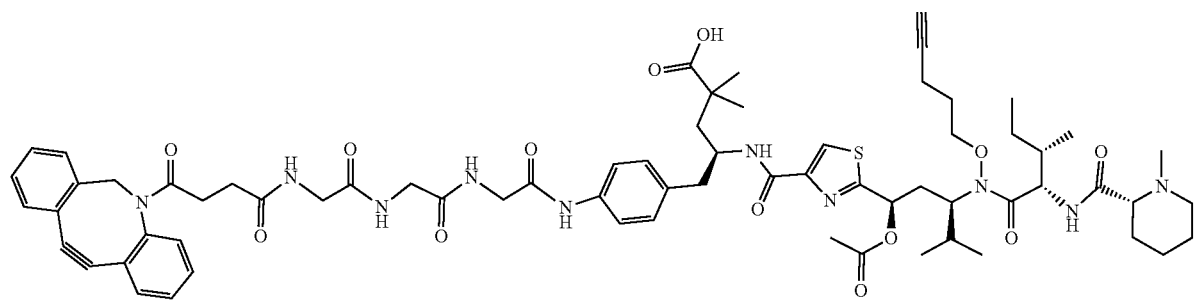 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)CNC(=O)CNC(=O)CCC(=O)N3Cc4ccccc4C#Cc4ccccc43)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-[4-(2-{2-[2-(4-{2-azatricyclo[10.4.0.04,9]hexadeca-1(12),4(9),5,7,13,15-hexaen-10-yn-2-yl}-4-oxobutanamido)acetamido]acetamido}acetamido)phenyl]-2,2-dimethylpentanoic acid (LP13)

Following the general procedure for linker-payloads LP13, LP14, and LP16-LP24 from D-7a treated with D-8a, linker-payload LP13 (10 mg, 33% yield) was obtained as a white solid. ESI m/z: 642.5 (M/2+H)$^+$. $^1$H NMR (400 MHz, DMSO$_{d6}$) δ 9.66 (s, 1H), 8.18-8.12 (m, 4H), 7.78-7.74 (m, 1H), 7.69-7.64 (m, 1H), 7.62-7.60 (m, 1H), 7.58-7.54 (m, 1H), 7.50-7.44 (m, 4H), 7.39-7.28 (m, 3H), 7.10 (d, J=8.0 Hz, 2H), 5.81 (d, J=11.2 Hz, 1H), 5.02 (d, J=14.4 Hz, 1H), 4.75 (t, J=7.2 Hz, 1H), 4.25-4.20 (m, 2H), 4.08-4.04 (m, 2H), 3.72 (t, J=4.4 Hz, 2H), 3.64-3.63 (m, 2H), 3.07-2.96 (m, 1H), 2.85-2.82 (m, 3H), 2.67-2.61 (m, 2H), 2.42-2.27 (m, 6H), 2.12 (s, 3H), 2.10 (s, 3H), 2.08-1.93 (m, 5H), 1.84-1.77 (m, 4H), 1.67-1.60 (m, 3H), 1.51-1.35 (m, 5H), 1.04 (d, J=10.8 Hz, 6H), 0.96-0.94 (m, 6H), 0.88-0.83 (m, 9H) ppm.

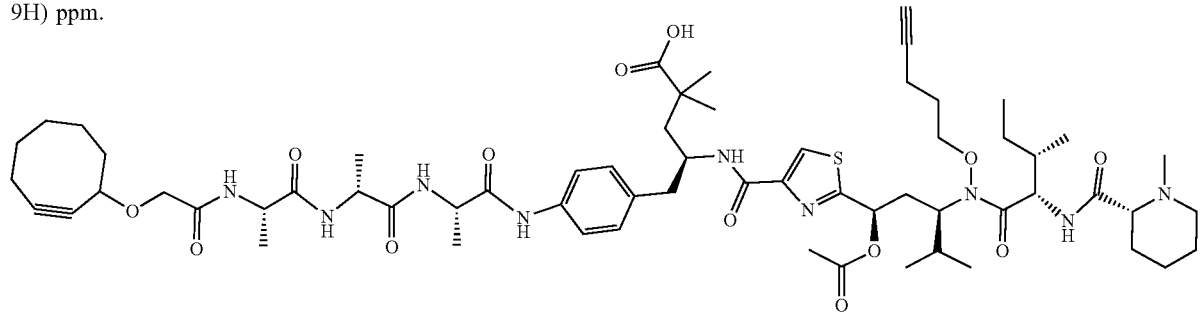

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-{4-[(2S)-2-[(2R)-2-[(2S)-2-[2-(cyclooct-2-yn-1-yloxy)acetamido]propanamido]propanamido]propanamido]phenyl}-2,2-dimethylpentanoic acid (LP18)

Following the general procedure for linker-payloads LP13, LP14, and LP16-LP24 from D-7b treated with D-8b, linker-payload LP9 (12 mg, 35% yield) was obtained as a white solid. ESI m/z: 601.8 (M/2+H)$^+$. Following the general procedure for linker-payloads LP13, LP14, and LP16-LP24, the following compound can be made (LP14)

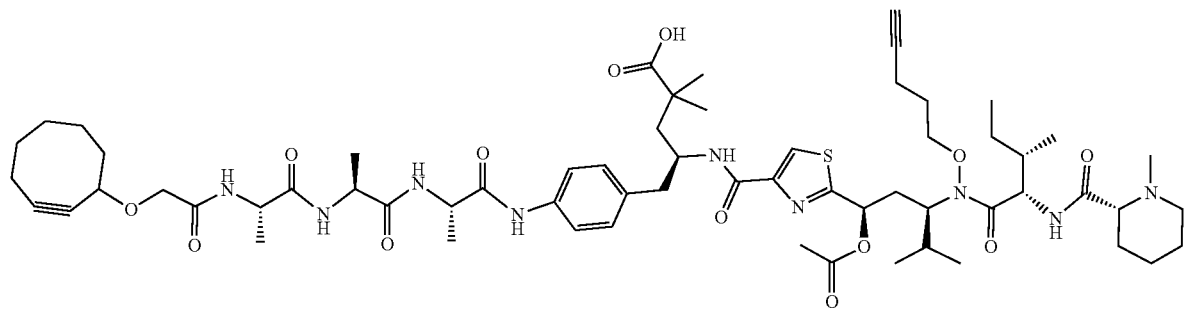 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)[C@H](C)NC(=O)[C@@H](C)NC(=O)[C@H](C)NC(=O)COC3C#CCCCCC3)cc2)CC(C)(C)C(=O)O)cs1)C(C)C]

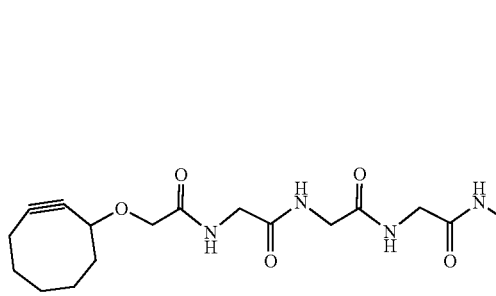
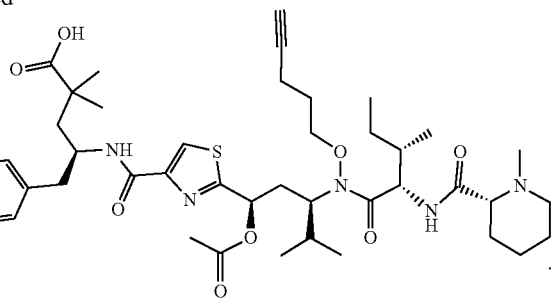

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-{2-[2-(2-{2-[2-(cyclooct-2-yn-1-yloxy)acetamido]acetamido}acetamido)acetamido]acetamido}phenyl)-2,2-dimethylpentanoic acid (LP19)

Following the general procedure for linker-payloads LP13, LP14, and LP16-LP24 from D-7c treated with D-8b, linker-payload LP19 (10 mg, 87% yield) was obtained as a white solid. ESI m/z: 609.4 (M/2+H)+. $^1$H NMR (500 MHz, DMSO$_{d6}$) δ 9.73 (s, 1H), 8.23-8.17 (m, 4H), 7.84 (t, J=5.0 Hz, 1H), 7.55 (d, J=9.5 Hz, 1H), 7.47 (d, J=8.0 Hz, 2H), 7.11 (d, J=8.0 Hz, 2H), 5.80 (d, J=10.5 Hz, 1H), 4.75 (t, J=8.5 Hz, 1H), 4.32-4.30 (m, 1H), 4.25-4.24 (m, 1H), 4.16-4.14 (m, 1H), 4.06-4.03 (m, 2H), 3.94-3.91 (m, 1H), 3.86-3.80 (m, 3H), 3.79-3.73 (m, 6H), 2.84-2.82 (m, 3H), 2.67-2.63 (m, 1H), 2.40-2.29 (m, 4H), 2.25-2.18 (m, 1H), 2.12 (s, 3H), 2.09 (s, 3H), 2.02-1.90 (m, 6H), 1.87-1.73 (m, 6H), 1.62-1.55 (m, 6H), 1.48-1.32 (m, 5H), 1.18-1.17 (m, 2H), 1.12-1.06 (m, 1H), 1.03-0.95 (m, 9H), 0.88-0.81 (m, 9H) ppm.

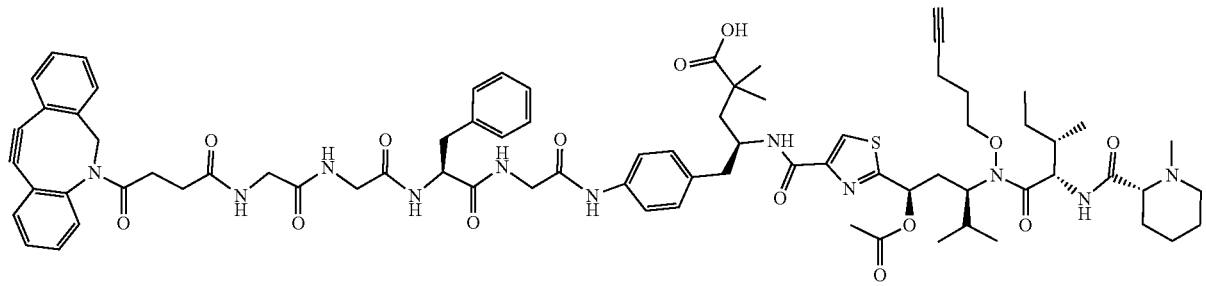 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)[C@H](Cc3ccccc3)NC(=O)CNC(=O)CNC(=O)CCC(=O)N3Cc4ccccc4C#Cc4ccccc43)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-{2-[(2S)-2-{2-[2-(4-{2-azatricyclo[10.4.0.04,9]hexadeca-1(12),4(9),5,7,13,15-hexaen-10-yn-2-yl}-4-oxobutanamido)acetamido]acetamido}-3-phenylpropanamido]acetamido}phenyl)-2,2-dimethylpentanoic acid (LP20)

Following the general procedure for linker-payloads LP13, LP14, and LP16-LP24 from D-7d treated with D-8a, linker-payload LP20 (11 mg, 80% yield) was obtained as a white solid. ESI m/z: 716.0 (M/2+H)$^+$. $^1$H NMR (500 MHz, DMSO$_{d6}$) δ 9.73 (s, 1H), 8.37-8.35 (m, 1H), 8.16 (s, 1H), 8.10-8.09 (m, 1H), 8.05-7.99 (m, 1H), 7.88-7.78 (br s, 1H), 7.69-7.63 (m, 1H), 7.59-7.52 (m, 2H), 7.50-7.42 (m, 5H), 7.37-7.27 (m, 3H), 7.26-7.24 (m, 4H), 7.21-7.16 (m, 2H), 7.11 (d, J=8.5 Hz, 2H), 5.82 (d, J=11.0 Hz, 1H), 5.23-4.98 (m, 1H), 4.76 (t, J=8.0 Hz, 1H), 4.51-4.47 (m, 1H), 4.26-4.23 (m, 2H), 4.06-4.05 (m, 2H), 3.86-3.82 (m, 2H), 3.78-3.69 (m, 1H), 3.62-3.51 (m, 4H), 3.06-3.04 (m, 2H), 2.85-2.78 (m, 4H), 2.70-2.63 (m, 2H), 2.37-2.27 (m, 4H), 2.13 (s, 3H), 2.10 (s, 3H), 2.03-1.94 (m, 5H), 1.84-1.78 (m, 4H), 1.66-1.61 (m, 3H), 1.56-1.52 (m, 1H), 1.47-1.36 (m, 4H), 1.20-1.14 (m, 1H), 1.05 (s, 3H), 1.03 (s, 3H), 0.95 (d, J=6.5 Hz, 3H), 0.89-0.82 (m, 9H) ppm.

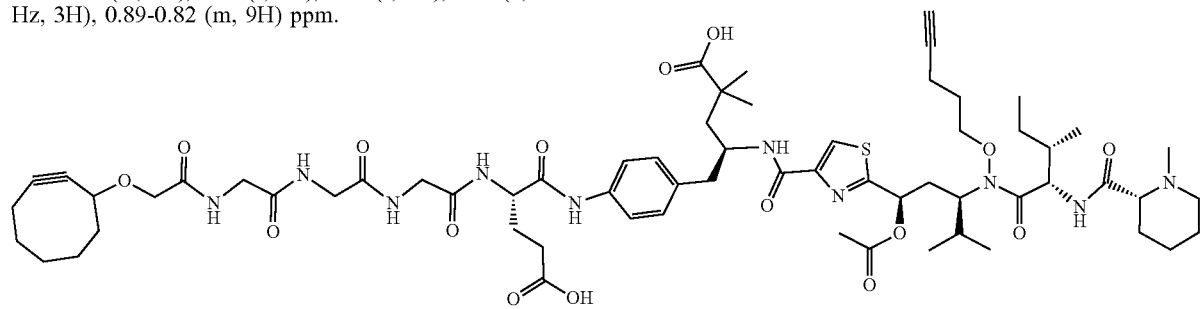

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-{4-[(2S)-4-carboxy-2-[2-(2-{2-[2-(cyclooct-2-yn-1-yloxy)acetamido]acetamido}acetamido)acetamido]butanamido]phenyl}-2,2-dimethylpentanoic acid (LP21)

Following the general procedure for linker-payloads LP13, LP14, and LP16-LP24 from D-7e treated with D-8b, linker-payload LP21 (10 mg, 58% yield) was obtained as a white solid. ESI m/z: 645.4 (M/2+H)$^+$.

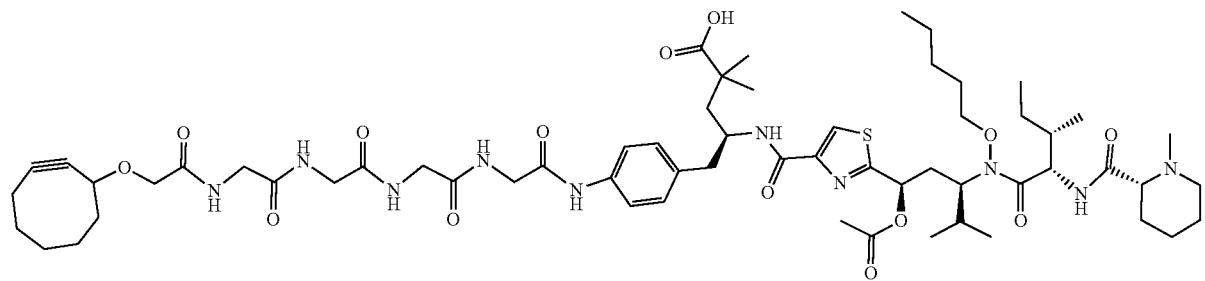 [SMILES: CCCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)CNC(=O)CNC(=O)CNC(=O)COC3C#CCCCCC3)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-(4-{2-[2-(2-{2-[2-(cyclooct-2-yn-1-yloxy)acetamido]acetamido}acetamido)acetamido]acetamido}phenyl)-2,2-dimethylpentanoic acid
(LP23)

Following the general procedure for linker-payloads LP13, LP14, and LP16-LP24 from D-7f treated with D-8b, linker-payload LP23 (8 mg, 69% yield) was obtained as a white solid. ESI m/z: 611.5 (M/2+H)⁺. ¹H NMR (500 MHz, DMSO$_{d6}$) δ 9.73 (s, 1H), 8.23-8.15 (m, 4H), 7.85-7.78 (m, 2H), 7.49-7.46 (m, 3H), 7.11-7.10 (m, 2H), 5.80 (d, J=10.5 Hz, 1H), 4.81-4.78 (m, 1H), 4.33-4.30 (m, 1H), 4.25-4.16 (m, 2H), 4.09-4.04 (m, 1H), 3.98-3.92 (m, 2H), 3.86-3.80 (m, 3H), 3.79-3.73 (m, 6H), 2.85-2.83 (m, 1H), 2.80-2.76 (m, 1H), 2.70-2.64 (m, 1H), 2.44-2.42 (m, 1H), 2.39-2.32 (m, 1H), 2.27-2.14 (m, 2H), 2.12 (s, 3H), 2.11 (s, 3H), 2.08-2.05 (m, 1H), 2.03-1.90 (m, 5H), 1.85-1.70 (m, 4H), 1.68-1.51 (m, 8H), 1.48-1.29 (m, 9H), 1.20-1.15 (m, 1H), 1.06 (s, 3H), 1.04 (s, 3H), 0.96 (d, J=6.5 Hz, 3H), 0.89-0.83 (m, 12H) ppm.

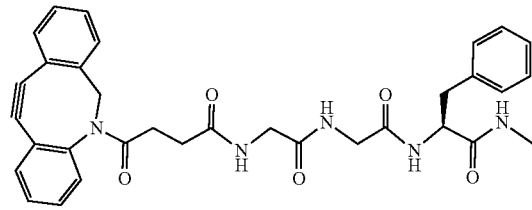
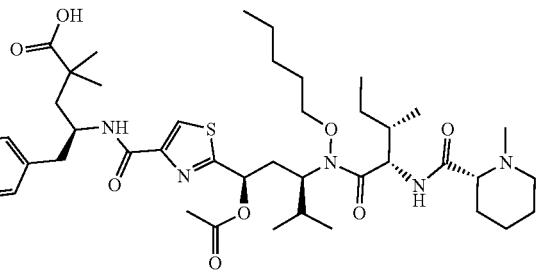

(4S)-4-({2-[(1R,3R)-1-(acetyloxy)-4-methyl-3-[(2S,3S)-3-methyl-2-{[(2R)-1-methylpiperidin-2-yl]formamido}-N-(pentyloxy)pentanamido]pentyl]-1,3-thiazol-4-yl}formamido)-5-(4-{2-[(2S)-2-{2-[2-(4-{2-azatricyclo[10.4.0.04,9]hexadeca-1(12),4(9),5,7,13,15-hexaen-10-yn-2-yl}-4-oxobutanamido)acetamido]acetamido}-3-phenylpropanamido]acetamido}phenyl)-2,2-dimethylpentanoic acid
(LP24)

Following the general procedure for linker-payloads LP13, LP14, and LP16-LP24 from D-7g treated with D-8a, linker-payload LP24 (11 mg, 80% yield) was obtained as a white solid. ESI m/z: 718.0 (M/2+H)⁺. ¹H NMR (500 MHz, DMSO$_{d6}$) δ 9.26 (s, 1H), 8.37-8.33 (m, 1H), 8.16 (s, 1H), 8.12-8.08 (m, 1H), 8.04-7.97 (m, 1H), 7.82-7.75 (br s, 1H), 7.69-7.63 (m, 1H), 7.58 (t, J=6.5 Hz, 1H), 7.48-7.43 (m, 6H), 7.35-7.29 (m, 3H), 7.24-7.23 (m, 4H), 7.21-7.16 (m, 2H), 7.11 (d, J=7.5 Hz, 2H), 6.65 (s, 1H), 5.80 (d, J=10.0 Hz, 1H), 5.32 (t, J=4.5 Hz, 1H), 5.02-4.98 (m, 1H), 4.80 (t, J=8.0 Hz, 1H), 4.52-4.47 (m, 1H), 4.24-4.22 (m, 1H), 4.16-4.15 (m, 1H), 4.08-4.04 (m, 1H), 3.97-3.95 (m, 1H), 3.87-3.81 (m, 2H), 3.77-3.69 (m, 3H), 3.64-3.58 (m, 6H), 3.07-3.04 (m, 1H), 2.85-2.76 (m, 2H), 2.70-2.63 (m, 2H), 2.44-2.42 (m, 1H), 2.37-2.36 (m, 1H), 2.35-2.27 (m, 1H), 2.11 (s, 3H), 2.10 (s, 3H), 2.02-1.96 (m, 5H), 1.94-1.91 (m, 1H), 1.80-1.78 (m, 2H), 1.68-1.61 (m, 4H), 1.56-1.53 (m, 1H), 1.47-1.44 (m, 2H), 1.39-1.30 (m, 5H), 1.06 (s, 3H), 1.04 (s, 3H), 0.95 (d, J=6.5 Hz, 3H), 0.89-0.81 (m, 9H) ppm.

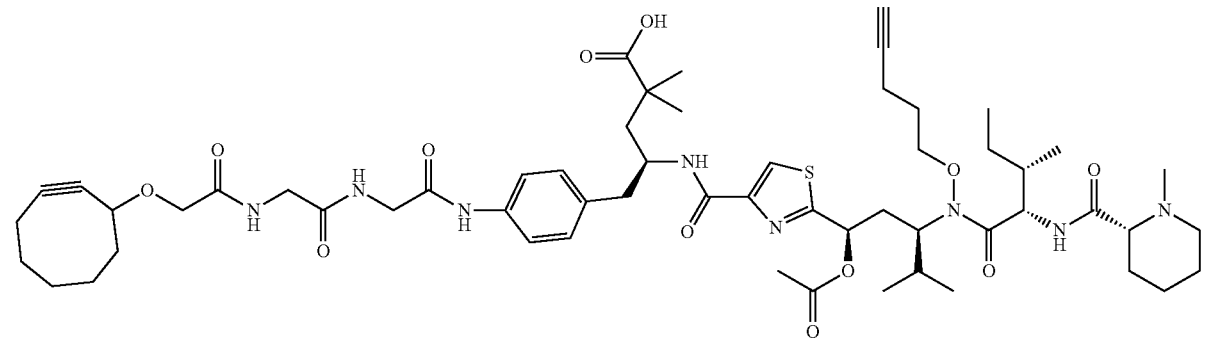 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)CNC(=O)COC3C#CCCCCC3)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-[4-(2-{2-[2-(cyclooct-2-yn-1-yloxy)acetamido]acetamido}acetamido)phenyl]-2,2-dimethylpentanoic acid (LP17)

Following the general procedure for linker-payloads LP13, LP14, and LP16-LP24 from D-7h treated with D-8b, linker-payload LP17 (5 mg, 47% yield) was obtained as a white solid. ESI m/z: 552.3 (M/2+H)⁺.

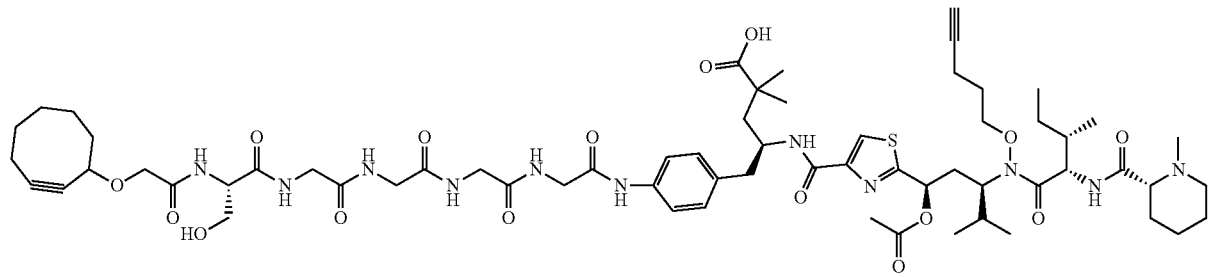 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)CNC(=O)CNC(=O)CNC(=O)[C@H](CO)NC(=O)COC3C#CCCCCC3)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-{2-[2-(2-{2-[(2S)-2-[2-(cyclooct-2-yn-1-yloxy)acetamido]-3-hydroxypropanamido]acetamido}acetamido)acetamido]acetamido}phenyl)-2,2-dimethylpentanoic acid (LP22)

Following the general procedure for linker-payloads LP13, LP14, and LP16-LP24 from D-7i treated with D-8b, linker-payload LP22 (4 mg, 44% yield) was obtained as a white solid. ESI m/z: 653.0 (M/2+H)⁺.

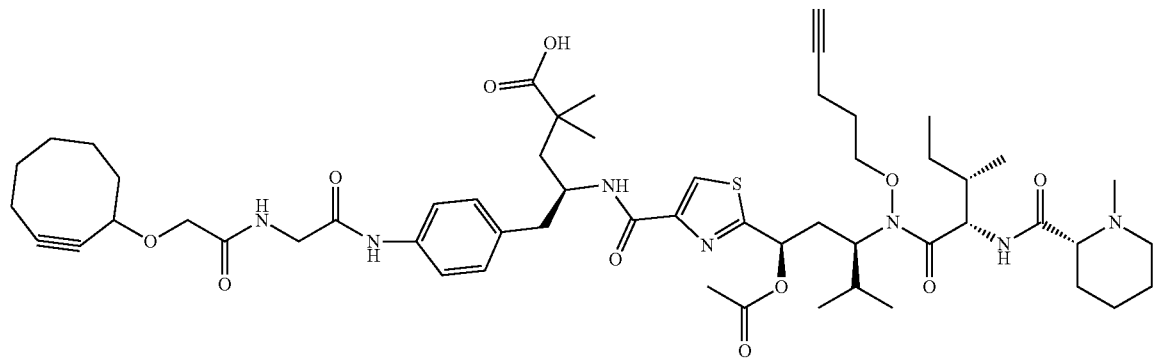 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)CNC(=O)COC3C#CCCCCC3)cc2)CC(C)(C)C(=O)O)cs1)C(C)C]

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-(4-{2-[2-(cyclooct-2-yn-1-yloxy)acetamido]acetamido}phenyl)-2,2-dimethylpentanoic acid (LP16)

Following the general procedure for linker-payloads LP13, LP14, and LP16-LP24 from D-5a treated with D-8b, linker-payload LP16 (10 mg, 48% yield) was obtained as a white solid. ESI m/z: 523.8 (M/2+H)⁺.

Figure 10G:
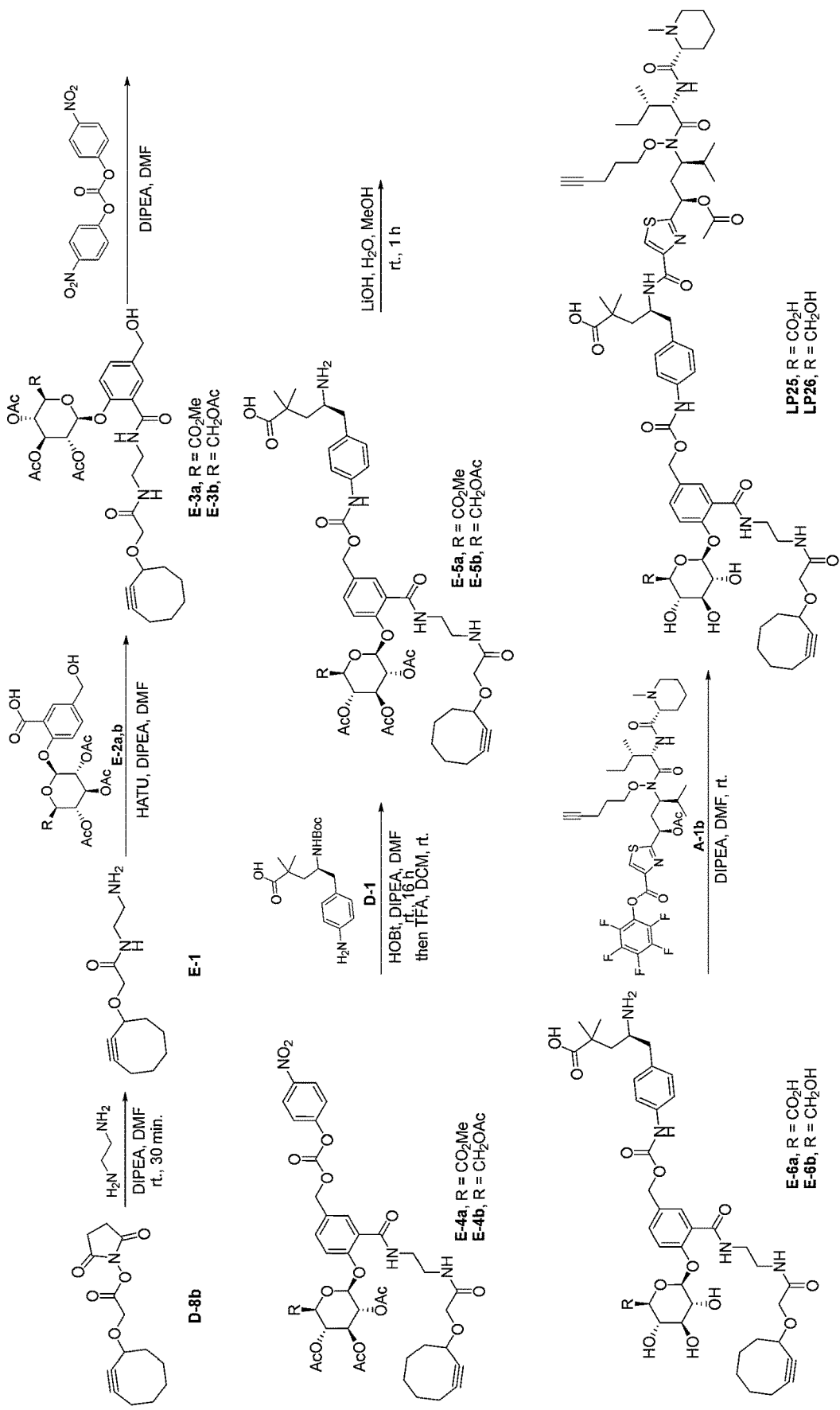

Synthesis of LP25 and LP26 (FIG. 10G)

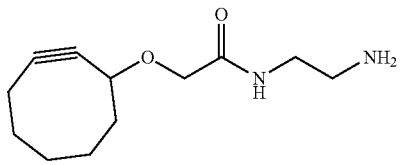 [SMILES: NCCNC(=O)COC1C#CCCCCC1]

N-(2-Aminoethyl)-2-(cyclooct-2-yn-1-yloxy)acetamide (E-1)

To a solution of ethylenediamine (0.71 g, 12 mmol) in DMF (2.0 mL) were added DIPEA (0.30 g, 2.4 mmol) and a solution of compound D-8b (0.33 g, 1.2 mmol) in DMF (3.0 mL) slowly, and the mixture was stirred at room temperature for 30 min, which was monitored by LCMS. The resulting mixture was purified by reversed phase flash chromatography (0-100% acetonitrile in aq. ammonium bicarbonate (0.8 mM)) to give compound E-1 (0.18 g, 68% yield) as colorless oil. ESI m/z: 225.2 (M+H)+. 1H NMR (400 MHz, DMSO$_{d6}$) δ 7.74-7.63 (m, 1H), 4.28 (t, J=5.8 Hz, 1H), 3.88-3.73 (m, 2H), 3.11-3.00 (m, 4H), 2.58 (t, J=6.4 Hz, 2H), 2.27-2.06 (m, 3H), 1.94-1.71 (m, 4H), 1.66-1.54 (m, 2H), 1.45-1.33 (m, 1H) ppm.

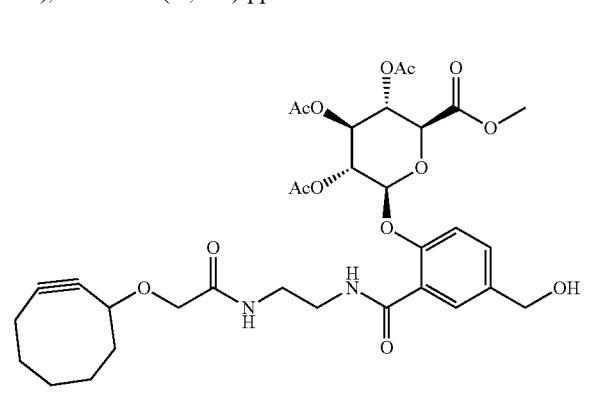

Methyl (2S,3S,4S,5R,6S)-3,4,5-tris(acetyloxy)-6-[2-({2-[2-(cyclooct-2-yn-1-yloxy)acetamido]ethyl}carbamoyl)-4-(hydroxymethyl)phenoxy]oxane-2-carboxylate (E-3a)

To a mixture of compound E-2a (synthesized according to WO2018182341A1) (0.11 g, 0.23 mmol) and HATU (96 mg, 0.25 mmol) in dry DMF (4 mL) were added compound E-1 (51 mg, 0.23 mmol) and DIPEA (89 mg, 0.69 mmol), and the reaction mixture was stirred at room temperature for 2 hours until E-2a was totally consumed, as monitored by LCMS. The resulting mixture was directly purified by reversed phase flash chromatography (0-100% acetonitrile in aq. TFA (0.01%)) to give compound E-3a (0.14 g, 90% yield) as a white solid. ESI m/z: 691.4 (M+H)+. 1H NMR (400 MHz, CDCl$_3$) δ 8.06-8.04 (m, 1H), 7.64-7.59 (m, 1H), 7.50-7.47 (m, 1H), 7.22-7.18 (m, 1H), 7.01-6.98 (m, 1H), 5.44-5.28 (m, 5H), 4.68 (s, 2H), 4.30-4.21 (m, 2H), 4.10-4.06 (m, 1H), 3.93-3.88 (m, 1H), 3.75 (s, 3H), 3.67-3.48 (m, 2H), 2.21-2.07 (m, 15H), 1.93-1.79 (m, 3H), 1.70-1.38 (m, 3H) ppm.

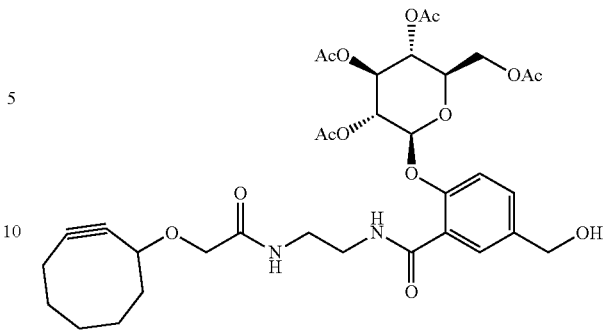

[(2R,3R,4S,5R,6S)-3,4,5-Tris(acetyloxy)-6-[2-({2-[2-(cyclooct-2-yn-1-yloxy)acetamido]ethyl}carbamoyl)-4-(hydroxymethyl)phenoxy]oxan-2-yl]methyl acetate (E-3b)

Following a similar procedure as E-3a except substituting E-2b for E-2a, compound E-3b (0.10 g, 80% yield) was obtained as a white solid. ESI m/z: 705.3 (M+H)+.

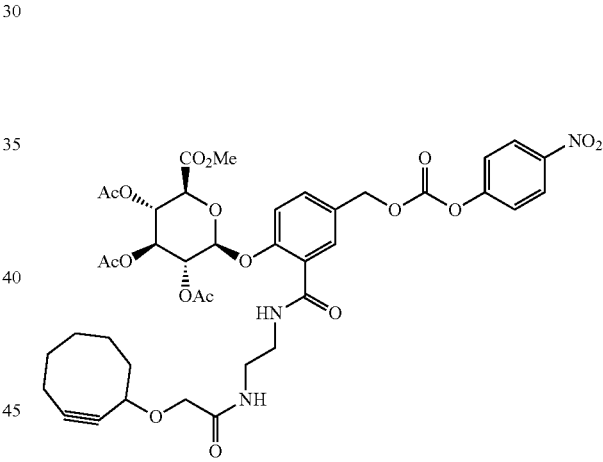

Methyl (2S,3S,4S,5R,6S)-3,4,5-tris(acetyloxy)-6-[2-({2-[2-(cyclooct-2-yn-1-yloxy)acetamido]ethyl}carbamoyl)-4-{[(4-nitrophenoxycarbonyl)oxy]methyl}phenoxy]oxane-2-carboxylate (E-4a)

To a solution of compound E-3a (0.14 g, 0.20 mmol) in DMF (2.0 mL) were added bis(4-nitrophenyl) carbonate (55 mg, 0.18 mmol) and DIPEA (26 mg, 0.20 mmol) at 0° C. under nitrogen. The reaction mixture was stirred at 0° C. for 30 min and then at room temperature for 3 hours. The reaction mixture was diluted with water (10 mL) and extracted with ethyl acetate (20 mL×3). The combined organic solution was washed with brine (10 mL), dried over anhydrous sodium sulfate, and concentration in vacuo. The residue was purified by flash chromatography (40-60% ethyl acetate in petroleum ether) to give compound E-4a (85 mg, 49% yield) as colorless oil. ESI m/z: 856.0 (M+H)+.

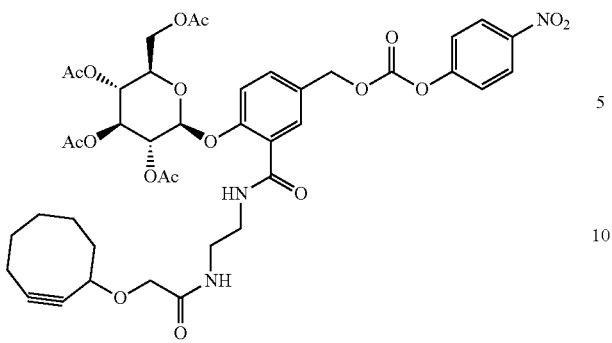

[(2R,3R,4S,5R,6S)-3,4,5-Tris(acetyloxy)-6-[2-({2-[2-(cyclooct-2-yn-1-yloxy)acetamido]ethyl}carbamoyl)-4-{[(4-nitrophenoxycarbonyl)oxy]methyl}phenoxy]oxan-2-yl]methyl acetate (E-4b)

Following a similar procedure as E-4a except substituting E-3b for E-3a, compound E-4b (62 mg, 50% yield) was obtained as a white solid. ESI m/z: 870.3 (M+H)$^+$.

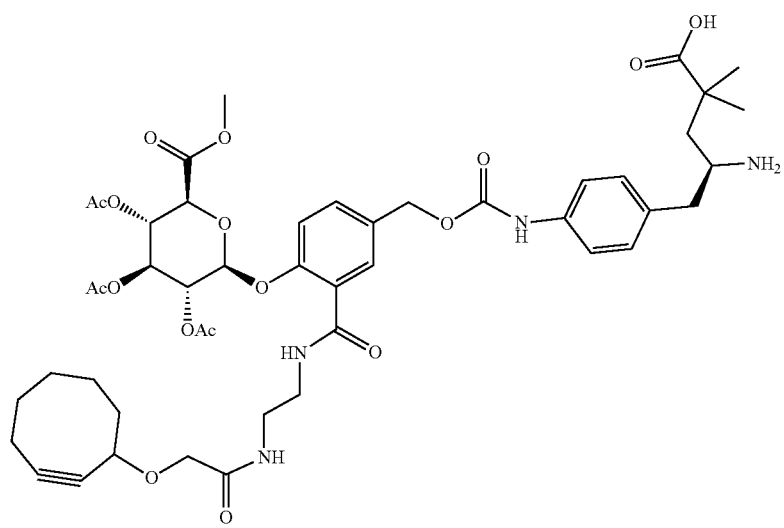 [SMILES: COC(=O)[C@H]1O[C@@H](Oc2ccc(COC(=O)Nc3ccc(C[C@H](N)CC(C)(C)C(=O)O)cc3)cc2C(=O)NCCNC(=O)COC2C#CCCCCC2)[C@H](OC(C)=O)[C@@H](OC(C)=O)[C@@H]1OC(C)=O]

(4S)-4-Amino-5-{4-[({[3-({2-[2-(cyclooct-2-yn-1-yloxy)acetamido]ethyl}carbamoyl)-4-{[(2S,3R,4S,5S,6S)-3,4,5-tris(acetyloxy)-6-(methoxycarbonyl)oxan-2-yl]oxy}phenyl]methoxy}carbonyl)amino]phenyl}-2,2-dimethylpentanoic acid (E-5a)

Following a similar procedure as C-2a except substituting E-4a for C-1a, compound E-5a (30 mg, 63% yield) was obtained as a white solid. ESI m/z: 953.3 (M+H)$^+$.

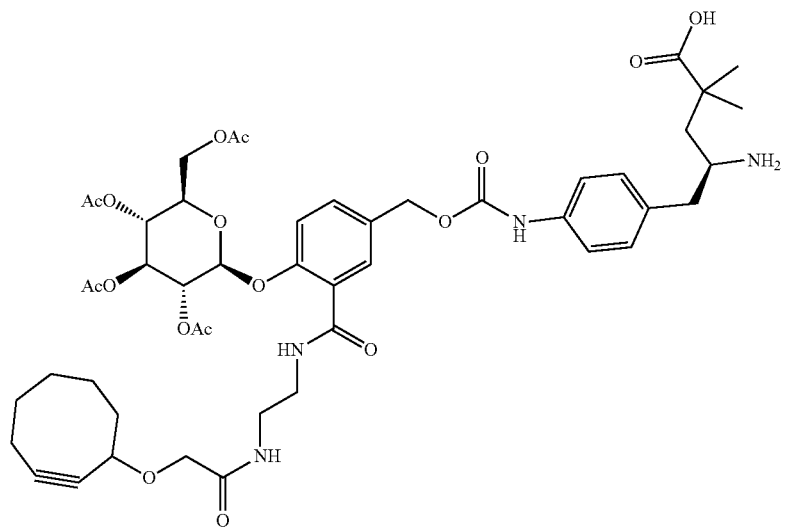 [SMILES: CC(C)(C[C@@H](N)Cc1ccc(NC(=O)OCc2ccc(O[C@@H]3O[C@H](CO)[C@@H](O)[C@H](O)[C@H]3O)c(C(=O)NCCNC(=O)COC3C#CCCCCC3)c2)cc1)C(=O)O]

(4S)-4-Amino-5-{4-[({[3-({2-[2-(cyclooct-2-yn-1-yloxy)acetamido]ethyl}carbamoyl)-4-{[(2S,3R,4S,5R,6R)-3,4,5-tris(acetyloxy)-6-[(acetyloxy)methyl]oxan-2-yl]oxy}phenyl]methoxy}carbonyl)amino]phenyl}-2,2-dimethylpentanoic acid (E-5b)

Following a similar procedure as C-2a except substituting E-4b for C-1a, compound E-5b (28 mg, 58% yield) was obtained as a white solid. ESI m/z: 967.3 (M+H)$^+$.

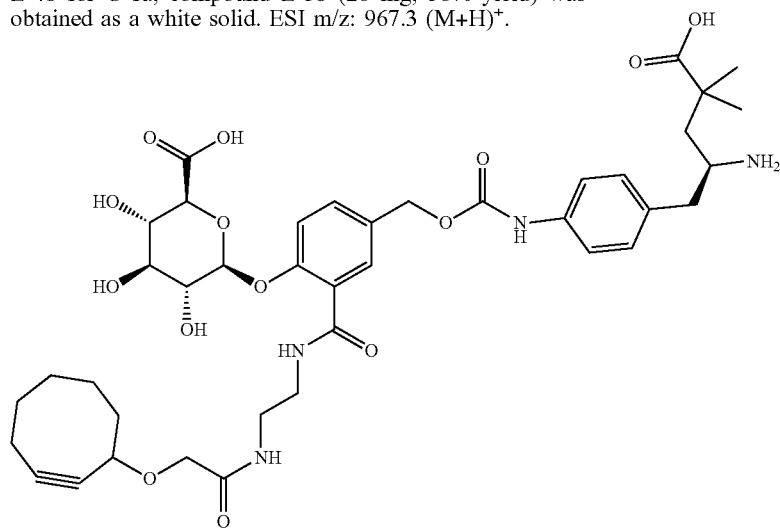

(2S,3S,4S,5R,6S)-6-(4-{[({4-[(2S)-2-Amino-4-carboxy-4,4-dimethylbutyl]phenyl}carbamoyl)oxy]methyl}-2-({2-[2-(cyclooct-2-yn-1-yloxy)acetamido]ethyl}carbamoyl)phenoxy)-3,4,5-trihydroxyoxane-2-carboxylic acid (E-6a)

To a mixture of compound E-5a (30 mg, 31 μmol) in methanol (4 mL) was added aq. lithium hydroxide (0.1 M, 4 mL), and the mixture was stirred at room temperature for an hour, which was monitored by LCMS. After quenched with aq. HCl (1 N) to pH 4, the resulting mixture was purified by reversed phase flash chromatography (5-95% acetonitrile in aq. TFA (0.01%)) to give linker-payload E-6a (18 mg, 70% yield) as a white solid. ESI m/z: 813.3 (M+H)$^+$.

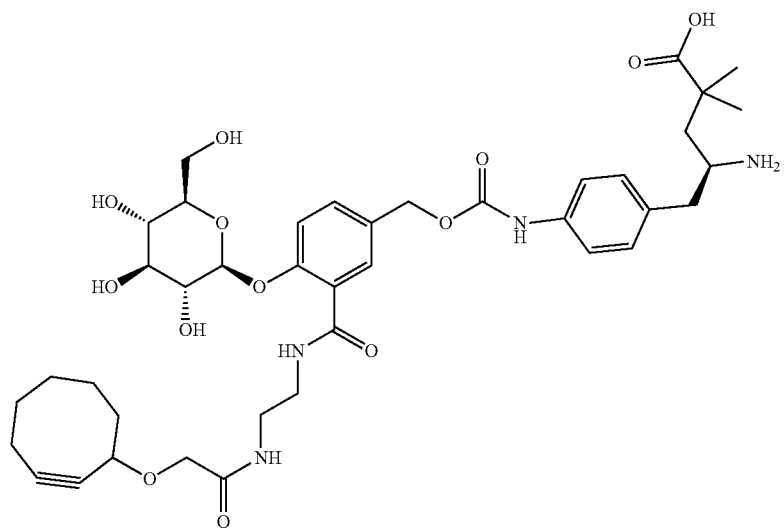

(4S)-4-Amino-5-{4-[({[3-({2-[2-(cyclooct-2-yn-1-yloxy)acetamido]ethyl}carbamoyl)-4-{[(2S,3R,4S,5S,6R)-3,4,5-trihydroxy-6-(hydroxymethyl)oxan-2-yl]oxy}phenyl]methoxy}carbonyl)amino]phenyl}-2,2-dimethylpentanoic acid (E-6b)

Following a similar procedure as E-6a except substituting E-5b for E-5a, compound E-6b (18 mg, 78% yield) was obtained as a white solid. ESI m/z: 799.3 (M+H)$^+$.

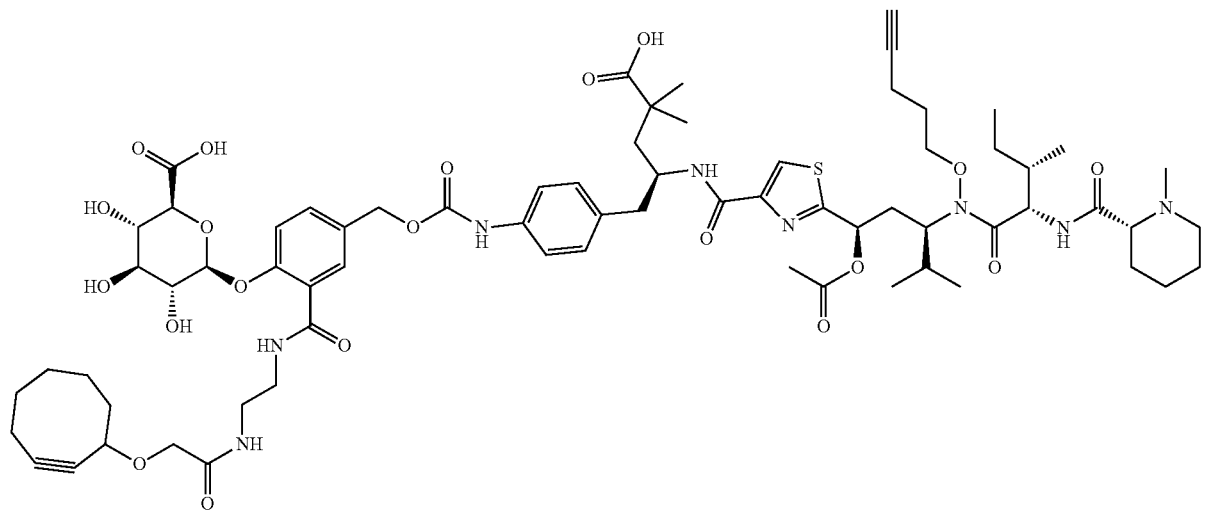 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(NC(=O)OCc3ccc(O[C@@H]4O[C@H](C(=O)O)[C@@H](O)[C@H](O)[C@H]4O)c(C(=O)NCCNC(=O)COC4C#CCCCCC4)c3)cc2)CC(C)(C)C(=O)O)cs1)C(C)C]

(2S,3S,4S,5R,6S)-6-(4-{[({4-[(2S)-2-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-4-carboxy-4,4-dimethylbutyl]phenyl}carbamoyl)oxy]methyl}-2-({2-[2-(cyclooct-2-yn-1-yloxy)acetamido]ethyl}carbamoyl)phenoxy)-3,4,5-trihydroxyoxane-2-carboxylic acid (LP25)

Following the general procedure for VII and VIII except substituting E-6a for A-2, linker-payload LP25 (10 mg, 36% yield) was obtained as a white solid. ESI m/z: 701.3 (M/2+H)$^+$.

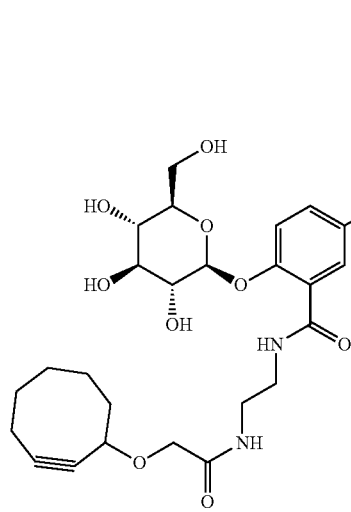
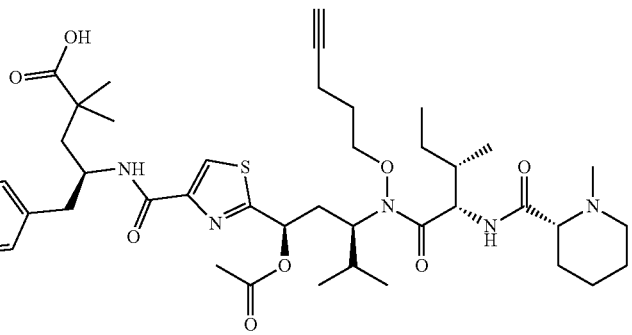

(4S)-4-({2-[(1R,3R)-1-(Acetyloxy)-4-methyl-3-[(2S,3S)-3-methyl-2-{[(2R)-1-methylpiperidin-2-yl]formamido}-N-(pent-4-yn-1-yloxy)pentanamido]pentyl]-1,3-thiazol-4-yl}formamido)-5-{4-[({[3-({2-[2-(cyclooct-2-yn-1-yloxy)acetamido]ethyl}carbamoyl)-4-[[(2S,3R,4S,5S,6R)-3,4,5-trihydroxy-6-(hydroxymethyl)oxan-2-yl]oxy}phenyl]methoxy}carbonyl)amino]phenyl}-2,2-dimethylpentanoic acid (LP26)

Following the general procedure for VII and VIII except substituting E-6b for A-2, linker-payload LP26 (8 mg, 29% yield) was obtained as a white solid. ESI m/z: 694.3 (M/2+H)+.

ADC Conjugation

Figure 13:
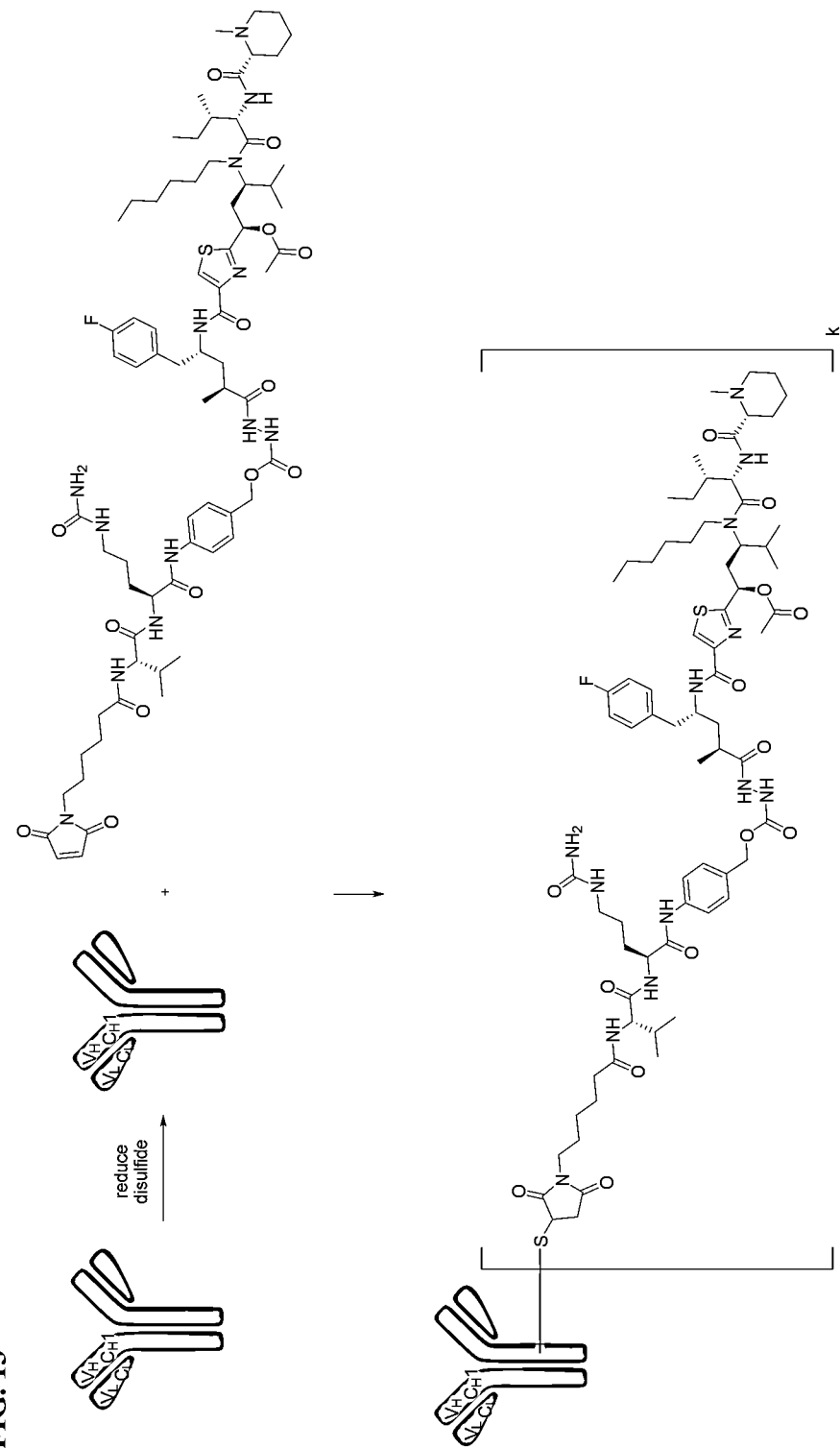
Figure 14:
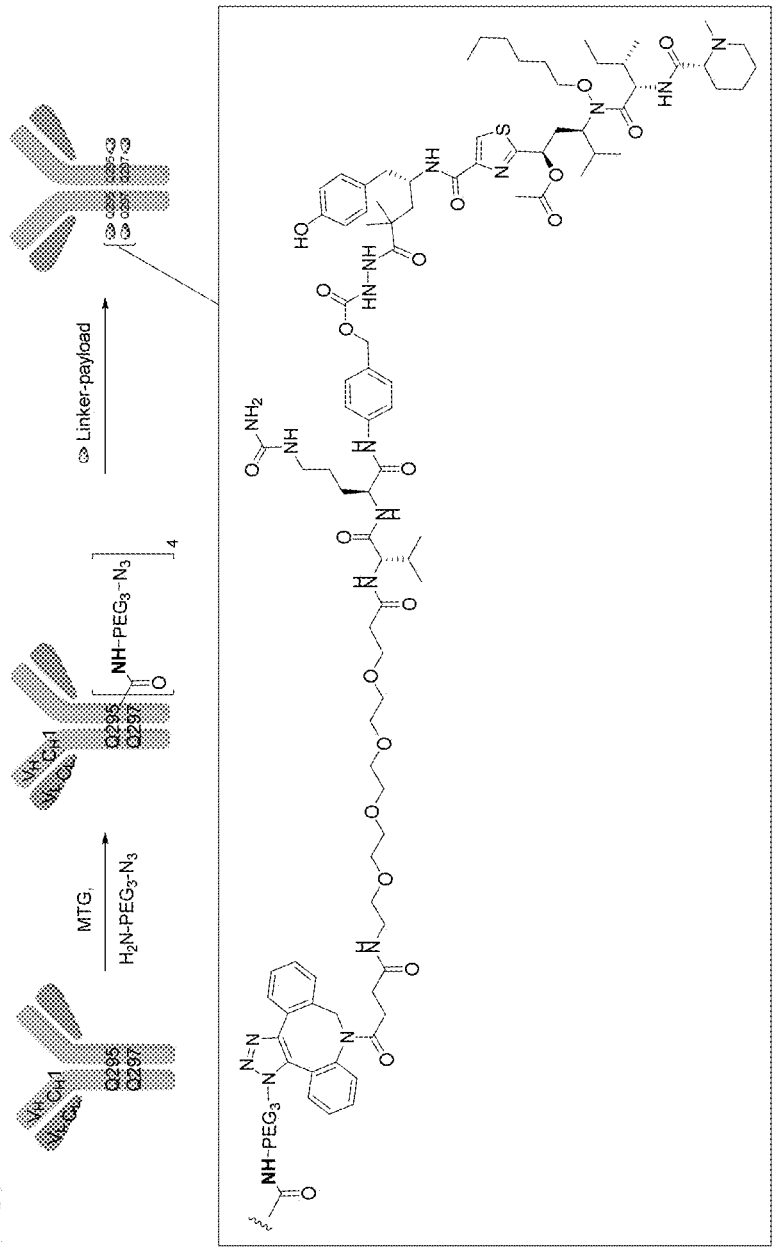

The non-site-specific conjugations of maleimide-spacer-payloads to an antibody are outlined in FIG. 13, and the site-specific conjugations of DIBAC-spacer-payloads to the azido-functionalized antibody via [3+2] click reaction are outlined in FIG. 14.

General Procedure for Non-Site-Specific Conjugation

This example demonstrates a method for conjugation of a maleimide-spacer-payload to inter-chain cysteines of an antibody or antigen-binding fragment via the formation of a thioether bond. This example refers the compounds depicted in FIG. 13.

Conjugation through antibody cysteines was performed in two steps using methods similar to those for making Adcetris®-like ADCs (See, Mol. Pharm. 2015, 12(6), 1863-71). A monoclonal antibody (mAb) (10 mg/mL in 50 mM HEPES, 150 mM NaCl) at pH 7-8 was reduced with 1 mM dithiothreitol (6 molar equiv. of antibody) or TCEP (2.5 molar equivalents to antibody) at 37° C. for 30 min. After gel filtration (G-25, pH 6.3, sodium acetate), compound LP1 at 1-10 mg/mL in DMSO was added to the reduced antibody, and the reaction was allowed to stir for 3-14 h at rt. The resulting mixture was purified by SEC to generate pure ADC.

General Procedure for Site-Specific Conjugation

This example demonstrates a method for site-specific conjugation of a cyclooctyne-linker-payload to an antibody or antigen-binding fragment thereof. This example refers to the compounds depicted in FIG. 14.

In this example, the site-specific conjugates were produced in two steps. The first step was microbial transglutaminase (MTG) based enzymatic attachment of a small molecule, such as an azido-PEG$_3$-amine, to the antibody having N297Q mutation (hereinafter "MTG-based" conjugation). The second step employed the attachment of a cyclooctyne-spacer-payload to the azido-functionalized antibody via a [2+3]cycloaddition, for example, the 1,3-dipolar cycloaddition between an azide and a cyclooctyne (aka copper-free click chemistry). See, Baskin, J. M.; Prescher, J. A.; Laughlin, S. T.; Agard, N. J.; Chang, P. V.; Miller, I. A.; Lo, A.; Codelli, J. A.; Bertozzi, C. R. PNAS 2007, 104 (43), 16793-7. Shown in FIG. 14 is an example of a linker-spacer-payload having a DIBAC moiety conjugated with an azido-functionalized antibody via a [2+3] cycloaddition. This process provided site-specific and stoichiometric conjugates in about 50-80% isolated yield.

Step 1: Preparation of an Azido-Functionalized Antibody.

Aglycosylated human antibody IgG (IgG1, IgG4, etc.) or a human IgG1 isotype with a N297Q mutation, in PBS (pH 6.5-8.0) was mixed with >200 molar equivalents of azido-PEG$_3$-amine (MW=218.26 g/mol). The resulting solution was mixed with MTG (EC 2.3.2.13 from Zedira, Darmstadt, Germany, or ACTIVA TI which contains Maltodextrin from Ajinomoto, Japan) (25 U/mL; 5U MTG per mg of antibody) resulting in a final concentration of 0.5-5 mg/mL antibody, and the solution was then incubated at 37° C. for 4-24 h while gently shaking. The reaction was monitored by ESI-MS. Upon reaction completion, the excess amine and MTG were removed by SEC or protein A column chromatography, to generate the azido-functionalized antibody. This product was characterized by SDS-PAGE and.

In a specific experiment, the N297Q antibody (24 mg) in 7 mL potassium-free PBS buffer (pH 7.3) was incubated with >200 molar equivalents of the azido-PEG$_3$-amine (MW=218.26) in the presence of MTG (0.350 mL, 35 U, mTGase, Zedira, Darmstadt, Germany). The reaction was incubated at 37° C. overnight while gently mixing. Excess azido-PEG$_3$-amine and mTGase were removed by size exclusion chromatography (SEC, Superdex 200 PG, GE Healthcare).

Step 2: Preparation of site-specific conjugates by a [2+3] click reaction between the azido-functionalized glutaminyl-modified antibodies (IgG1, IgG4, etc.) and cyclooctyne containing linker-payload (LPs) in Table 7. In general, an azido-functionalized aglycosylated antibody-LP conjugate was prepared by incubating the azido-functionalized glutaminyl-modified antibody (1 mg) in 1 mL of an aqueous medium (e.g., PBS, PBS containing 5% glycerol, HBS) with >6 molar equivalents of LP dissolved in a suitable organic solvent (e.g., DMSO, DMF or DMA; reaction mixture contains 10-20% organic solvent, v/v) at 24° C. to 32° C. for over 3 hours. The progress of the reaction was monitored by ESI-MS. Absence of azido-functionalized antibody (mAb-PEG$_3$-N$_3$) indicated completion of the conjugation. The excess linker-payload (LP) and organic solvent were removed by SEC (Waters, Superdex 200 Increase, 1.0×30 cm, GE Healthcare, flow rate 0.8 mg/mL, PBS, pH 7.2) eluting with PBS, or via protein A column chromatography via elution with acidic buffer followed by neutralization with Tris (pH 8.0). The purified conjugate was analyzed by SEC, SDS-PAGE, and ESI-MS.

In a specific example, the azido-functionalized antibody (1 mg) in 0.800 mL PBSg (PBS, 5% glycerol, pH 7.4) was treated with six equivalents of DIBAC-Suc-PEG$_4$-VC-PABC-payload (conc. 10 mg/mL in DMSO) for 6 hours at rt and the excess linker payload (LP) was removed by size exclusion chromatography (SEC, Superdex 200 HR, GE Healthcare). The final product was concentrated by ultracentrifugation and characterized by UV, SEC, SDS-PAGE and/or ESI-MS.

Summarized in Table 7 are LPs, naked antibodies (anti-PRLR Ab, Anti-Fel D1 Ab, and Anti-STEAP2 Ab), PEG$_3$-N$_3$ functionalized antibodies (Anti-PRLR N297Q Ab-PEG$_3$-N$_3$, Anti-FelD1 N297Q Ab-PEG$_3$-N$_3$, and Anti-STEAP2 N297Q Ab-PEG$_3$-N$_3$), and their corresponding ADCs. In Table 7, Ab refers to an antibody and Ab-PEG$_3$-N$_3$ refers to an azido-functionalized antibody with a PEG$_3$ spacer. The anti-PRLR antibodies had HCVR and LCVR according to SEQ TD NOS:9 and 13 (H1H6958N2 above). The anti-STEAP2 antibodies had HCVR and LCVR according to SEQ TD NOS:1 and 5 (H1H7814N, above).

TABLE 7

List of Site-specific Conjugates

| Linker-Payload (LP) | | Ab, N297Q Ab-PEG$_3$-N$_3$, or N297Q Ab-tubulysin LP conjugates | | |
|---|---|---|---|---|
| EX | MW | Name | MW (Da) | DAR |
| | | Anti-PRLR Ab | 144591 | |
| PEG$_3$-N$_3$ | 218 | Anti-PRLR N297Q Ab-PEG$_3$-N$_3$ | 145387 | 4 |
| Ex1 | 1656.9 | Anti-PRLR N297Q Ab-LP7 | 152028 | 3.9 |
| Ex2 | 1761.9 | Anti-PRLR N297Q Ab-LP3 | 152438 | 3.9 |
| Ex3 | 1763.9 | Anti-PRLR N297Q Ab-LP4 | 152454 | 3.9 |
| | | Anti-Fel D1 Ab (non-binding control) | 145439 | |
| PEG$_3$-N$_3$ | 218 | Anti-Fel D1 N297Q Ab-PEG$_3$-N$_3$ | 146235 | 4 |
| Ex4 | 1656.9 | Anti-Fel D1 N297Q Ab-LP7 | 152879 | 4 |
| Ex5 | 1761.9 | Anti-Fel D1 N297Q Ab-LP3 | 153291 | 3.8 |
| Ex6 | 1763.9 | Anti-Fel D1 N297Q Ab-LP4 | 153307 | 3.8 |
| | | Anti-STEAP2 Ab | 143986 | |
| PEG$_3$-N$_3$ | 218 | Anti-STEAP2 N297Q Ab-PEG$_3$-N$_3$ | 144785 | 4 |
| Ex7 | 1656.9 | Anti-STEAP2 N297Q Ab-LP7 | 151410 | 3.8 |
| Ex8 | 1761.9 | Anti-STEAP2 N297Q Ab-LP3 | 151833 | 3.8 |
| Ex9 | 1763.9 | Anti-STEAP2 N297Q Ab-LP4 | 151849 | 3.8 |
| Ex10 | 1782.9 | Anti-STEAP2 N297Q Ab-LP2 | 151911 | 3.8 |

General Procedure for Characterization of Antibody and ADCs

Figure 15:
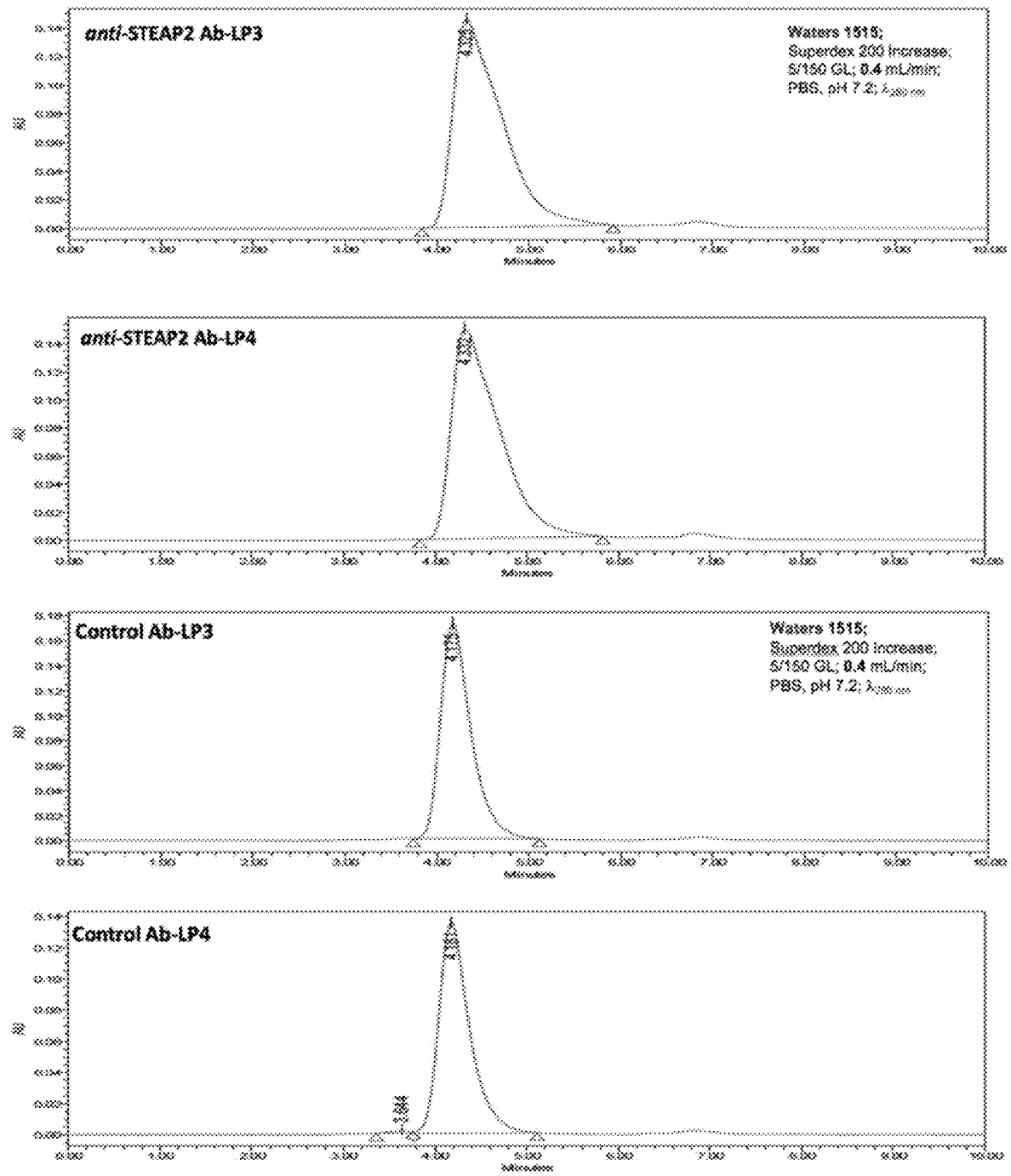
FIG. 15 shows Size Exclusion Chromatography of anti-STEAP2 Ab-LP3, anti-STEAP2 Ab-LP4, control Ab-LP3, and control Ab-LP4.

The purified conjugates were analyzed by SEC (FIG. 15), ESI-MS, and SDS-PAGE.

Characterization of ADC by SEC

Analytical SEC experiments were run using a Waters 1515 instrument, on a Superdex™ 200 Increase (1.0×30 cm) column, at flow rate of 0.80 mL/min using PBS pH 7.2, and monitored at λ=280 nm using a Waters 2998 PDA. An analytic sample was composed of 200 μL PBS (pH 7.4) with 30-100 μL of test sample. Preparative SEC purifications were performed using an AKTA Avant instrument from GE Healthcare, on Superdex 200 PG (2.6×60 cm) column, at a flow rate 2 mL/min eluting with PBS pH 7.2, and monitored at λ=280 nm. The SEC results in FIG. 15 indicate typical retention times for monomeric mAb and conjugates thereof, with minimal aggregation or degradation.

Characterization of ADC by LC-ESI-MS

Measurement of intact mass for the ADC samples by LC-ESI-MS was performed to determine drug-payload distribution profiles and to calculate the average DAR. Each testing sample (20-50 ng, 5 μL) was loaded onto an Acquity UPLC Protein BEH C$_4$ column (10K psi, 300 Å, 1.7 μm, 75 μm×100 mm; Cat No. 186003810). After desalting for 3 min, the protein was eluted and mass spectra were acquired by a Waters Synapt G2-Si mass spectrometer. As summarized in Table 7, most site-specific ADCs have near 4DAR.

Characterization of ADC by SDS-PAGE

SDS-PAGE was used to analyze the integrity and purity of the ADCs. In one method, SDS-PAGE conditions included non-reduced and reduced samples (2-4 pg) along with BenchMark Pre-Stained Protein Ladder (Invitrogen, cat #10748-010; L #1671922.) were loaded per lane in (1.0 mm×10 well) Novex 4-20% Tris-Glycine Gel and were ran at 180 V, 300 mA, for 80 min. An analytical sample was prepared using Novex Tris-Glycine SDS buffer (2×) (Invitrogen, cat #LC2676) and the reduced sample was prepared with SDS sample buffer (2×) containing 10% 2-mercaptoethanol.

In Vitro Plasma Stability

To determine the plasma stability of representative ADCs containing the tubulysin payloads, ADCs were incubated in vitro with plasma from different species, and the DAR was evaluated after incubation at physiological temperature (37° C.) for 3 days.

For the assay, each ADC sample (anti-PRLR antibody-LP3 or anti-PRLR antibody-LP4) in PBS buffer was added to fresh pooled male mouse, cynomologus monkey, rat, or human plasma, separately, at a final concentration of 50 μg/mL in a 96-well plate, and subsequently incubated at 37° C. for 72 hours. After incubation, each sample (100 μL final volume) was individually frozen at −80° C. until analysis.

Affinity capture of the ADCs from the plasma samples was carried out on a KingFisher 96 magnetic particle processor (Thermo Electron). First, biotinylated extracellular domain of human PRLR expressed with a myc-myc hexahistidine tag (hPRLR ecto-MMH; SEQ ID NO: 17;100 µg/mL) was immobilized on streptavidin paramagnetic beads (In vitrogen, Cat #60210). Each plasma sample containing tubulysin ADCs (100 µL) was mixed at 600 rpm with 100 µL of the beads (the commercial beads come in volume) at room temperature for 2 hours in a 96-well plate. The beads were then washed three times with 600 µL of HBS-EP (GE healthcare, Cat #BR100188), once with 600 µL of $H_2O$, and then once with 600 µL of 10% acetonitrile in water. Following the washes, tubulysin ADCs were eluted by incubating the beads with 70 µL of 1% formic acid in 30% acetonitrile/70% water for 15 minutes at room temperature. Each eluate sample was then transferred into a v-bottom 96-well plate and was then reduced with 5 mM TCEP (Thermo Fisher, Cat #77720) at room temperature for 20 minutes.

The reduced tubulysin ADC samples (10 µL/sample) were injected onto a 1.7 µm BEH300 $C_4$ column (Waters Corporation, Cat #186005589) coupled to a Waters Synapt G2-Si Mass Spectrometer. The flow rate was 0.1 mL/min (mobile phase A: 0.1% formic acid in water; mobile phase B: 0.1% formic acid in acetonitrile). The LC gradient started with 20% B and increased to 35% B in 16 minutes, then reached 95% B in 1 minute.

The acquired spectra were deconvoluted using MaxEnt1 software (Waters Corporation) with the following parameters: Mass range: 20-30 kDa for the light chain, and 40-60 kDa for the heavy chain; m/z range: 700 Da-3000 Da; Resolution: 1.0 Da/channel; Width at half height: 1.0 Da; Minimum intensity ratios: 33%; Iteration max: 25.

There was not any significant loss of linker-payloads observed from the tested ADCs after 72-hour incubation with human, mouse, rat, and cynomolgus monkey plasma. However, it has been reported that the acetyl group of tubulysin payloads can be hydrolyzed to a hydroxyl group (−43 Da) with significant loss of toxicity. Therefore, the hydrolyzed species observed in the LC-MS was considered as loss of drug. Drug/antibody ratio (DAR), as shown in Table 8, was calculated based on the relative abundance of different species of heavy chains as described below:

Drug/antibody Ratio $(DAR) =$ $$2 \times \frac{2 \times \text{Intensity (heavy chain with 2 drugs)} + 1 \times \text{Intensity (heavy chain with 1 drugs)}}{\text{Sum Intensity (heavy chain with 2, 1, and 0 drugs)}}$$

TABLE 8

In vitro plasma stability of Anti-PRLR N297Q antibody-LP3 and Anti-PRLR N297Q antibody-LP4

| Plasma type used for incubation | Anti-PRLR N297Q antibody-LP3 (DAR = 3.8 at 0 hr) DAR after 72 hours of incubation | Anti-PRLR N297Q antibody-LP4 (DAR = 4.0 at 0 hr) DAR after 72 hours of incubation |
|---|---|---|
| Mouse plasma | 2.7 | 2.7 |

| Plasma type used for incubation | Anti-PRLR N297Q antibody-LP3 (DAR = 3.8 at 0 hr) DAR after 72 hours of incubation | Anti-PRLR N297Q antibody-LP4 (DAR = 4.0 at 0 hr) DAR after 72 hours of incubation |
|---|---|---|
| Cynomolgus monkey plasma | 2.7 | 2.7 |
| Rat plasma | 2.7 | 2.6 |
| Human plasma | 3.0 | 3.0 |

Testing of Tubulysin Payloads in Cell-Based Killing Assays

To test the ability of the disclosed tubulysin payloads to kill human cell lines, an in vitro cytotoxicity assay was performed. In vitro cytotoxicity of the disclosed payloads, as well as reference compounds, were evaluated using the CellTiter-Glo Assay Kit (Promega, Cat #G7573), in which the quantity of ATP present is used to determine the number of viable cells in culture. For the assay, C4-2, HEK293, or T47D cells were seeded at 4000 cells/well on Nunclon white 96-well plates in complete growth medium (DME high glucose:Ham's F12 at 4:1, 10% FBS, 100 units/ml Penicillin, 100 ug/ml streptomycin, 53 ug/ml glutatmine, 10 ug/ml insulin, 220 ng/ml biotin, 12.5 pg/ml T3, 12.5 ug/ml Adenine, 4 ug/ml transferrin for C42 cells; DME high glucose, 10% FBS, 100 units/ml Penicillin, 100 ug/ml streptomycin, 53 ug/ml glutatmine for HEK293; RPMI, 10% FBS, 100 units/ml Penicillin, 100 ug/ml streptomycin, 53 ug/ml glutatmine, 10 ug/ml insulin, 10 mM HEPEs, 200 nM Sodium Pyruvate for T47D cells) and grown overnight at 37° C. in 5% $CO_2$. For cell viability curves, 1:3 serially diluted payloads were added to the cells at final concentrations ranging from 100 nM to 15 µM, including a no treatment control group, and were then incubated for 5 days. After the 5-day incubation, cells were incubated at room temperature with 100 µL of CellTiter-Glo reagents for 10 minutes. Relative luminescence units (RLU) were determined on a Victor plate reader (PerkinElmer). The $IC_{50}$ values were determined from a four-parameter logistic equation over a 10-point response curve (GraphPad Prism). All $IC_{50}$ values are expressed in molar (M) concentration. The percent cell killing (% kill) at the maximum concentration tested was estimated from the following formula (100−% viable cells). Averages±standard deviation (SD) are included where replicate experiments were performed.

As shown in Table 9, payloads herein demonstrated killing of C4-2 cells with $IC_{50}$ values between 16.4 pM and >100 nM, and maximum % cell killing between 8.9% and 96.7%. A subset of disclosed payloads that were tested demonstrated killing on HEK293 cells with $IC_{50}$ values between 57.2 pM and >100 nM, and maximum % cell killing between 4.7% and 88.5%. A subset of disclosed payloads that were tested demonstrated killing on T47D cells with $IC_{50}$ values between 35 pM and >100 nM, and maximum % cell killing between 14.6% and 84.5%. The reference compound, MMAE, demonstrated killing of C4-2 cells with $IC_{50}$ values of 283 µM, and a maximum % cell killing of 93.7%.

TABLE 9

Cytotoxicity in C4-2, HEK293, and T47D cells by Tubulysin payloads and reference compounds

| Cmpd | C4-2 IC$_{50}$ (M) | % Kill | T47D IC$_{50}$ (M) | % Kill | HEK293 IC$_{50}$ (M) | % Kill |
|---|---|---|---|---|---|---|
| TubA | 1.09E−10 | 96.4 | NT | NT | NT | NT |
| IVa | 6.53E−11 | 95.2 | NT | NT | NT | NT |
| IVa' | 1.08E−08 | 94.7 | 1.06E−08 | 81.9 | 1.44E−08 | 74.8 |
| Va | 8.03E−10 | 92.1 | NT | NT | NT | NT |
| VIa | 1.86E−09 | 94.1 | NT | NT | NT | NT |
| VId | 2.4E−09 ± 2.2E−09 | 95.5 ± 2.6 | 2.51E−09 | 68.4 | 5.26E−09 | 78.5 |
| VIc | 1.33E−09 ± 1.11E−09 | 95.5 ± 1.8 | NT | NT | NT | NT |
| VIe | 8.22E−09 ± 6.1E−09 | 94.4 ± 0.2 | 2.27E−09 | 72.7 | 4.77E−09 | 76.7 |
| VIb | 1.20E−08 | 96.5 | 1.36E−08 | 76.2 | 2.03E−08 | 75.4 |
| Va' | 1.62E−08 | 96.5 | NT | NT | NT | NT |
| Vj | 5.31E−08 ± 6.64E−08 | 68.5 ± 39.2 | >1.00E−07 | 14.6 | >1.00E−07 | 4.7 |
| Vk | ND | ND | >1.00E−07 | NT | >1.00E−07 | NT |
| Vi | 6.333E−09 ± 1.39E−09 | 96.4 ± 0.5 | 4.66E−09 | 71.3 | 6.79E−09 | 81.4 |
| Vh | 5.09E−10 | 92 | 4.58E−10 | 64.5 | 7.18E−10 | 85.6 |
| IVg | 1.36E−10 | 91.7 | 4.13E−10 | 62.9 | 5.39E−10 | 86.5 |
| IVd | 1.64E−11 ± 7.13E−12 | 93.7 ± 1.8 | 3.50E−11 | 84.5 | 5.72E−11 | 85.4 |
| Vc | 3.60E−11 | 91.7 | 6.77E−11 | 64.9 | 1.13E−10 | 86.9 |
| Ve | <4.7E−11 | 92.6 | 7.31E−11 | 69.8 | 1.03E−10 | 88.5 |
| IVc | 9.24E−11 | 92.2 | 2.05E−10 | 81.4 | 3.07E−10 | 84.8 |
| Vd | 3.84E−10 | 91.3 | 4.44E−10 | 66 | 5.90E−10 | 86.3 |
| IVh | 6.47E−10 ± 4.86E−11 | 82 ± 2.8 | 1.86E−09 | 71.6 | 1.76E−09 | 82.5 |
| Vb | 7.00E−11 ± 4.25E−11 | 92.3 ± 1.7 | 1.44E−10 | 66.5 | 2.89E−10 | 87.8 |
| IVe | 7.42E−11 | 91.8 | 1.55E−10 | 67.2 | 2.81E−10 | 86.7 |
| IVf | 2.29E−10 | 93.8 | 7.82E−10 | 67.1 | 1.64E−09 | 86.0 |
| Vf | 9.00E−10 | 90 | 3.96E−10 | 68 | 6.66E−10 | 83.8 |
| Vg | 3.69E−10 | 93.2 | 5.35E−10 | 65.2 | 7.00E−10 | 86.4 |
| IVj | 7.16E−09 | 94.5 | 1.77E−08 | 79.9 | 1.76E−08 | 75.5 |
| IVk | >4.0E−08 | 66.7 | 4.74E−08 | 68.5 | 4.30E−08 | 62.7 |
| IVl | >2.0E−08 | 86.5 | 4.25E−08 | 66.1 | 3.98E−08 | 65.2 |
| VIf | 3.12E−10 | 93.9 | 3.02E−10 | 63.2 | 3.83E−10 | 85.6 |
| IVm | >1.00E−07 | 8.9 | NT | NT | NT | NT |
| IVn | >1.00E−07 | 30.2 | NT | NT | NT | NT |
| VIg | >1.00E−07 | 10.9 | NT | NT | NT | NT |
| VIh | 1.59E−10 | 93.9 | NT | NT | NT | NT |
| IVo | 2.62E−10 | 93.4 | NT | NT | NT | NT |
| IVp | 1.77E−10 | 94.2 | NT | NT | NT | NT |
| IVs | 4.99E−11 | 93.8 | NT | NT | NT | NT |
| IVt | 1.10E−10 | 94.2 | NT | NT | NT | NT |
| IVu | 1.14E−10 | 93.9 | NT | NT | NT | NT |
| IVvA | 1.09E−08 | 96.7 | NT | NT | NT | NT |
| IVy | 1.82E−09 | 94.4 | NT | NT | NT | NT |
| IVw | >1.00E−07 | 27.9 | NT | NT | NT | NT |
| IVvB | 2.15E−11 | 94.6 | NT | NT | NT | NT |
| VII | 2.8E−11 (0.028 nM) | NT | NT | NT | NT | NT |
| IX | 5.4E−11 (0.054 nM) | NT | NT | NT | NT | NT |
| X | 6E−11 (0.060 nM) | NT | NT | NT | NT | NT |
| MMAE | 2.87E−10 ± 9.35E−11 | 93.7 ± 2.5 | NT | NT | NT | NT |

NT = not tested

Testing of Tubulysin Payloads in MDR Cell Based Killing Assays

To further test the ability of the disclosed tubulysin payloads, a cytotoxicity assay was performed using a multidrug resistant (MDR) cell line with or without Verapamil, a drug that has been shown to reverse drug resistance (Cancer Res. 1989 Sep. 15; 49(18):5002-6). In vitro cytotoxicity of the disclosed payloads as well as reference compounds were evaluated similarly as described above except using 1000 HCT15 cells, a colorectal carcinoma cell line, in growth medium (RPMI, 10% FBS, 100 units/ml Penicillin, 100 ug/ml streptomycin, 53 ug/ml glutatmine) with or without 5 ug/mL of Verapamil.

As shown in Table 10, in the absence of Verapamil, payloads of the disclosure demonstrated killing of HCT15 cells with IC$_{50}$ values between 20 μM and >100 nM, and maximum % cell killing between −3.8 and 99.7%. In the presence of Verapamil, payloads of the disclosure demonstrated killing of HCT15 cells with IC$_{50}$ values between 15 μM and >100 nM, and maximum % cell killing between −0.4% and 99.1%. For each payload, the HCT-15 IC$_{50}$ in the absence of Verapamil was divided by the HCT-15 IC$_{50}$ in the presence of Verapamil (HCT-15 IC$_{50}$/HCT-15+Verapamil IC$_{50}$). Several payloads had ratios <2.0 suggesting that these payloads are minimally impacted by multi-drug efflux pumps. The reference compound, M4 (MMAE), had a ratio of 23.7.

TABLE 10

Cytotoxicity by Tubulysin payloads and reference compounds in HCT15 cells with or without Verapamil

| Cmpd | HCT-15 IC$_{50}$ (M) | HCT-15 % Kill | HCT-15 + verapamil IC$_{50}$ (M) | HCT-15 + verapamil % Kill | HCT15 IC$_{50}$/HCT-15 + Verapamil IC$_{50}$ |
|---|---|---|---|---|---|
| TubA | 5.09E−10 | 99.1 | 1.28E−10 | 99.1 | 4.0 |
| Va | 3.63E−09 | 98 | 2.15E−10 | 99.1 | 16.9 |
| VIa | 5.80E−09 ± 7.8E−09 | 97 ± 1.9 | 2.55E−10 | 98.4 ± 0.7 | 16.6 ± 9.9 |
| VId | >3.00E−08 | 78.7 | 4.82E−10 | 99 | >62.2 |
| VIc | 1.32E−08 | 94 | 2.86E−10 | 98.8 | 46.3 |
| VIe | >1.00E−07 | 36.6 | 2.95E−10 | 98.8 | >338.6 |
| VIb | >5.00E−08 | 54.7 | 2.88E−09 | 97.8 | >17.3 |
| Va' | >1.00E−07 | 20.9 | 2.41E−09 | 98.8 | >41.5 |
| Vj | >1.00E−07 | −3.8 | 3.92E−08 | 77.4 | >2.6 |
| Vk | 1.00E−07 | 41.5 | 4.27E−08 | 83 | >2.3 |
| Vh | 1.47E−09 | 97.7 | 5.87E−10 | 98.1 | 2.5 |
| IVg | 4.60E−10 | 97.1 | 3.28E−10 | 97.5 | 1.4 |
| IVd | 5.7E−11 ± 2.01E−11 | 98.2 ± 0.5 | 4.07E−11 ± 2.2E−11 | 97.7 ± 1.8 | 1.57 ± 0.5 |
| Vc | 4.75E−10 | 97.6 | 1.46E−10 | 96.7 | 3.3 |
| Ve | 2.73E−10 ± 1.24E−10 | 98.6 ± 0.7 | 6.54E−11 ± 5.36E−11 | 98.2 ± 1.2 | 5.6 ± 2.7 |
| IVc | 3.02E−10 | 99.2 | 1.13E−10 | 98 | 2.7 |
| Vd | 1.93E−09 | 99.7 | 3.52E−10 | 98.7 | 5.5 |
| IVb | 1.51E−10 | 98 | 1.03E−10 | 98.1 | 1.5 |
| IVh | 2.5E−09 ± 3.33E−09 | 94.6 ± 3.5 | NT | NT | NT |
| Vb | 1.20E−10 ± 1.40E−10 | 98.8 ± 0.7 | 3.65E−11 ± 3.12 | 98.2 ± 0.5 | 2.8 ± 0.9 |
| IVe | 2.95E−10 | 95.8 | 1.00E−10 | 97.6 | 3.0 |
| IVf | 5.54E−10 | 96.4 | 6.86E−10 | 97.7 | 0.8 |
| Vf | 3.36E−09 | 96.5 | 3.75E−10 | 98 | 9.0 |
| Vg | 5.30E−10 | 94.9 | 2.37E−10 | 98 | 2.2 |
| IVj | 7.80E−09 | 96.4 | 5.56E−10 | 98.4 | 1.4 |
| IVk | >30E−09 | 48.3 | >30E−09 | 87.2 | 1.0 |
| IVl | 2.50E−08 | 91.6 | 1.37E−08 | 93.6 | 1.8 |
| VIf | 2.06E−09 | 99.1 | 8.54E−11 | 98.8 | 24.1 |
| IVn | >3.0E−08 | 30.9 | >3.0E−08 | 72.4 | 1.0 |
| VIh | 2.63E−10 | 99 | 7.16E−11 | 97.8 | 3.7 |
| IVo | 3.70E−10 | 98.6 | 1.09E−10 | 97.6 | 3.5 |
| IVp | 2.39E−10 | 98.7 | 8.64E−11 | 97.6 | 2.8 |
| IVr | 8.93E−11 | 99.1 | 6.24E−11 | 99 | 1.4 |
| IVq | 4.23E−11 ± 2.21 | 98.4 ± 0.8 | 2.25E−11 ± 4.5E−12 | 98.6 ± 0.7 | 1.8 ± 0.6 |
| IVs | 1.08E−10 | 99.1 | 4.59E−11 | 98.8 | 2.4 |
| IVvA | 5.27E−09 | 99.2 | 1.97E−09 | 97.1 | 2.7 |
| IVw | 9.73E−09 | 95.9 | 4.49E−09 | 98.3 | 2.2 |
| IVvB | 2.50E−11 | 97.3 | 1.50E−11 | 97.7 | 1.3 |
| VIi | (0.410 nM) | | (0.217 nM) | | |
| VII | 1.31E−10 (0.131 nM) | NT | 2.16E−10 (0.216 nM) | NT | 0.61 |
| VIII | (0.295 nM) | NT | (0.106 nM) | NT | |
| IX | (0.171 nM) | NT | (0.162 nM) | NT | |
| X | (0.097 nM) | | (0.116 nM) | | |
| MMAE | 1.77E−08 ± 1.36E−08 | 97.1 ± 3.7 | 7.82E−10 ± 4.11E−10 | 98.4 ± 0.5 | 23.7 ± 12.0 |

NT = not tested

Testing of Tubulysin Payloads in a Panel of MDR Cell Lines

To further test the ability of the disclosed tubulysin payloads, a cytotoxicity assay was performed using a panel of multidrug resistant (MDR) cell lines. In vitro cytotoxicity of the disclosed payloads as well as reference compounds were similarly evaluated as described above except using HCT-15 cells, a colorectal carcinoma cell line; H69AR, a doxorubicin resistant MDR derivative of the small cell lung cancer carcinoma cell line NCI-H69; MES-SA/MX2, a mitoxantrone resistant MDR derivative of the uterine sarcoma cell line MES-SA; and HL60/MX2, a mitoxantrone resistant MDR derivative of the acute promyelocytic leukemia cell line HL60. In these assays, cytotoxicity was evaluated in normal growth media (RPMI, 10% FBS, 100 units/ml Penicillin, 100 ug/ml streptomycin, and 53 ug/ml glutatmine for HCT-15 and HL60/MX2; RPMI, 20% FBS, 100 units/ml Penicillin, 100 ug/ml streptomycin, and 53 ug/ml glutatmine for H69-AR; Waymouths's:McCoy's (1:1), 10% FBS, 100 units/ml Penicillin, 100 ug/ml streptomycin, and 53 ug/ml glutatmine for MES-SA/MX2) with 1000 cells per well following 72 h and 144 h incubation with payloads. As shown in tables 11 and 12, several payloads killed the entire panel of MDR cell lines with sub nM IC$_{50}$, and to near baseline levels suggesting that these payloads overcome MDR in the tested lines.

TABLE 11

Cytotoxicity in HL60/MX2 and MES-SA/MX2 cells by Tubulysin payloads and reference compounds

| | HL60/MX2 | | | | MES-SA/MX2 | | | |
| | $IC_{50}$ | | % Kill | | $IC_{50}$ | | % Kill | |
| Cmpd | 72 h | 144 h | 72 h | 144 h | 72 h | 144 h | 72 h | 144 h |
|---|---|---|---|---|---|---|---|---|
| TubA | <1.5E−11 | <1.5E−11 | 98 | 100 | 5.73E−10 | 1.33E−09 | 98.6 | 99.9 |
| Va | 5.53E−10 | 1.40E−10 | 96.8 | 99.9 | >1E−07 | >1E−07 | 80.1 | 69.8 |
| Vh | 1.73E−10 | <1.5E−11 | 97.5 | 99.9 | 2.98E−09 | 8.15E−09 | 98.4 | 99.8 |
| IVg | 1.24E−10 | <1.5E−11 | 98.5 | 100 | 8.38E−10 | 9.99E−10 | 99.6 | 100 |
| IVd | <1.5E−11 | <1.5E−11 | 98.6 | 99.9 | 5.41E−11 | 1.30E−10 | 99.5 | 100 |
| Vc | <1.5E−11 | <1.5E−11 | 98.4 | 99.9 | 8.95E−11 | 2.99E−10 | 99.2 | 100 |
| Ve | <1.5E−11 | <1.5E−11 | 98.3 | 100 | 5.20E−10 | 7.34E−10 | 98.9 | 100 |
| IVc | <1.5E−11 | <1.5E−11 | 97.7 | 99.9 | 3.74E−10 | 6.04E−10 | 98.2 | 99.9 |
| IVh | 1.11E−09 | <1.5E−11 | 96.4 | 100 | 7.49E−09 | 8.80E−09 | 98.5 | 99.9 |
| Vb | <1.5E−11 | <1.5E−11 | 97.9 | 100 | 2.13E−10 | 1.04E−09 | 99.6 | 99.9 |
| IVe | <1.5E−11 | <1.5E−11 | 97.3 | 99.9 | 7.86E−10 | 2.81E−09 | 99.6 | 99.9 |
| IVf | 2.22E−10 | <1.5E−11 | 97.2 | 100 | 2.57E−09 | 3.82E−09 | 99.1 | 99.9 |
| Vg | 1.31E−10 | 6.10E−11 | 98 | 99.9 | 3.54E−09 | 5.30E−09 | 98 | 99.8 |
| VIh | 3.91E−11 | <1.5E−11 | 97.6 | 99.9 | 1.26E−09 | 2.72E−09 | 98.5 | 99.8 |
| IVo | 3.76E−11 | <1.5E−11 | 98.1 | 100 | 1.12E−09 | 2.96E−09 | 98.9 | 99.9 |
| IVp | 2.37E−10 | <1.5E−11 | 97.5 | 99.9 | 7.92E−10 | 1.66E−09 | 98.8 | 99.9 |
| IVr | <1.5E−11 | <1.5E−11 | 98.7 | 100 | 1.51E−10 | 1.76E−10 | 99.1 | 100 |
| IVx | 9.55E−10 | 7.70E−10 | 96.9 | 100 | >1E−07 | >1E−07 | 62.1 | 33.6 |
| VIi | <1.5E−11 | <1.5E−11 | 98.8 | 99.9 | 1.49E−10 | 1.98E−10 | 99.3 | 99.9 |
| Vl | 1.37E−10 | <1.5E−11 | 97 | 99.9 | 4.76E−09 | 6.91E−09 | 98.6 | 99.9 |
| IVq | <1.5E−11 | <1.5E−11 | 98.6 | 100 | 5.89E−11 | 1.05E−10 | 99.4 | 100 |
| IVs | <1.5E−11 | <1.5E−11 | 98.4 | 100 | 1.02E−10 | 2.10E−10 | 99.2 | 100 |
| IVt | <1.5E−11 | <1.5E−11 | 98.4 | 100 | 4.47E−10 | 7.40E−10 | 99.3 | 100 |
| IVu | <1.5E−11 | <1.5E−11 | 98 | 99.9 | 5.35E−10 | 1.21E−09 | 98.8 | 100 |
| IVvB | <1.5E−11 | <1.5E−11 | 98.2 | 99.8 | 4.56E−11 | 6.58E−11 | 99.1 | 99.9 |
| MMAE | 4.18E−10 | 1.64E−10 | 88.7 | 99.6 | 3.73E−08 | 6.83E−10 | 65.6 | 58.1 |

TABLE 12

Cytotoxicity in HCT-15 and H69AR cells by Tubulysin payloads and reference compounds

| | HCT-15 | | | | H69AR | | | |
| | $IC_{50}$ | | % Kill | | $IC_{50}$ | | % Kill | |
| Cmpd | 72 h | 144 h | 72 h | 144 h | 72 h | 144 h | 72 h | 144 h |
|---|---|---|---|---|---|---|---|---|
| IVa | 1.66E−10 | 3.18E−10 | 97.8 | 99.6 | 7.49E−10 | 1.38E−09 | 96.1 | 99.3 |
| VIa | 5.42E−09 | 7.17E−09 | 94 | 98.9 | 1.60E−08 | 8.01E−08 | 83.5 | 91.6 |
| Vh | 8.71E−10 | 1.27E−09 | 97 | 99.6 | 2.59E−09 | 4.21E−09 | 93.7 | 98.4 |
| IVg | 1.70E−10 | 2.23E−10 | 97.6 | 99.5 | 5.53E−10 | 5.71E−10 | 95.7 | 99.2 |
| IVd | 8.88E−12 | 2.95E−11 | 97.6 | 99.7 | 5.64E−11 | 1.33E−10 | 96.9 | 99.5 |
| Vc | 3.30E−11 | 6.75E−11 | 97.6 | 99.7 | 1.54E−10 | 2.87E−10 | 96.6 | 99.4 |
| Ve | 9.22E−11 | 1.58E−10 | 97.5 | 99.7 | 3.31E−10 | 5.59E−10 | 96.6 | 99.5 |
| IVc | 1.25E−10 | 1.65E−10 | 97.3 | 99.8 | 3.60E−10 | 7.25E−10 | 96.6 | 99.3 |
| IVh | 1.52E−09 | 1.53E−09 | 95.4 | 99.7 | 2.93E−09 | 3.30E−09 | 90.2 | 97.5 |
| Vb | 6.23E−11 | 1.27E−10 | 97.8 | 99.7 | 2.72E−10 | 6.60E−10 | 97 | 99.4 |
| IVe | 1.33E−10 | 2.30E−10 | 98.1 | 99.6 | 5.85E−10 | 1.26E−09 | 96.5 | 99 |
| IVf | 4.19E−10 | 3.96E−10 | 96.9 | 99.8 | 1.33E−09 | 1.55E−09 | 94.6 | 98.9 |
| Vg | 6.80E−10 | 9.16E−10 | 97.6 | 99.5 | 2.13E−09 | 2.72E−09 | 94.2 | 98.4 |
| VIh | 3.66E−10 | 5.15E−10 | 97.9 | 99.7 | 1.07E−09 | 1.73E−09 | 96.3 | 99.1 |
| IVo | 2.47E−10 | 3.48E−10 | 97.3 | 99.7 | 7.79E−10 | 1.27E−09 | 96.2 | 99.1 |
| IVp | 1.81E−10 | 2.31E−10 | 97.6 | 99.7 | 6.44E−10 | 1.12E−09 | 96.3 | 99.2 |
| IVr | 4.01E−11 | 6.21E−11 | 98 | 99.7 | 1.37E−10 | 2.11E−10 | 96.7 | 99 |
| IVx | 3.45E−08 | 8.48E−08 | 84.4 | 91 | >1E−07 | >1E−07 | 48.7 | 38 |
| VIi | 2.55E−11 | 5.44E−11 | 97.9 | 99.7 | 1.45E−10 | 2.31E−10 | 96.7 | 99.2 |
| Vl | 1.50E−09 | 1.72E−09 | 96.3 | 99.7 | 5.03E−09 | 6.62E−09 | 90.4 | 97.4 |
| IVq | <1.5E−11 | 2.77E−11 | 98 | 99.8 | 6.42E−11 | 1.28E−10 | 96.9 | 99.5 |
| IVs | 3.71E−11 | 5.01E−11 | 97.6 | 99.7 | 1.61E−10 | 2.81E−10 | 96.8 | 99.4 |
| IVt | 1.43E−10 | 1.80E−10 | 97.6 | 99.8 | 4.86E−10 | 8.19E−10 | 96.3 | 99.3 |
| IVu | 1.34E−10 | 2.42E−10 | 97.9 | 99.8 | 6.34E−10 | 1.04E−09 | 96.4 | 99 |
| IVvB | <1.5E−11 | 2.28E−11 | 97.7 | 99.6 | 5.99E−11 | 1.58E−10 | 96.9 | 99.1 |
| MMAE | 1.68E−08 | ND | 93.7 | ND | 9.23E−10 | 6.83E−10 | 66.8 | 92.7 |

Testing of Tubulysin Payload Containing ADCs in Cell Based Killing Assays

Bioassays were developed to assess the efficacy of an anti-PRLR antibody conjugated with the disclosed tubulysin payloads and reference payloads. It was developed to assess the activity of tubulysin payloads after internalization of an anti-PRLR-tubulysin ADC into cells, release of the payload, and subsequent cytotoxicity. For this assay, a HCT15 line was engineered to express human full length PRLR (accession #NP_000940.1). The resulting stable cell line is referred to herein as HCT15/PRLR. In vitro cytotoxicity of the disclosed payloads, reference compounds, and tested ADCs were evaluated similarly as described in this example using HCT15/PRLR cells with or without 5 pg/mL of Verapamil diluted in normal culture medium. The compounds were tested at concentrations starting at 100 nM with 3-fold serial dilution. All $IC_{50}$ values are expressed in nM concentration and the percent cell killing (% kill) at the maximum concentration tested was estimated from the following formula (100–% viable cells). These data were reported in Table 13.

As shown in Table 13, in the absence of Verapamil, anti-PRLR ADCs conjugated with disclosed linker-payloads, anti-PRLR-LP3, and anti-PRLR-LP4, demonstrated cytotoxicity in a HCT15/PRLR cell based assay at an $IC_{50}$ value of 0.525 nM, with maximum percent killing of 90%; and at an $IC_{50}$ value of 3.31 nM, with maximum percent killing of 65%, respectively. Under these conditions, one isotype control ADC, Isotype control-LP3, demonstrated some modest killing of HCT15/PRLR cells with a maximum percent killing of 51%, but the $IC_{50}$ value was >50 nM. In the absence of Verapamil, another isotype control, Isotype control-LP4 did not demonstrate any significant killing of HCT15/PRLR cells. Under these conditions, the free payloads of the invention, IVd and Ve, demonstrated killing of HCT15/PRLR cells with $IC_{50}$ values of 0.037 nM and 0.203 nM, and maximum percent killing of 99% and 99%, respectively.

In the presence of Verapamil, anti-PRLR ADCs conjugated with linker payloads of the invention, anti-PRLR-LP3 and anti-PRLR-LP4, demonstrated cytotoxicity in HCT15/PRLR cell-based assay at an $IC_{50}$ value of 0.309 nM, with maximum percent killing of 91%; and at an $IC_{50}$ value of 0.196 nM, with maximum percent killing of 91%, respectively. Under these conditions, two Isotype control ADCs, Isotype control-LP3 and Isotype control-LP4, demonstrated killing of HCT15/PRLR cells with an $IC_{50}$ value greater than 50 nM, and a maximum percent killing of 82%; and an $IC_{50}$ value greater than 50 nM, and a maximum percent killing of 76%, respectively. Under these conditions, the disclosed free payloads, IVd and Ve, demonstrated killing of HCT15/PRLR cells with $IC_{50}$ values of 0.015 nM and 0.033 nM, and maximum percent killing of 99% and 99%, respectively. The unconjugated anti-PRLR antibody did not demonstrate any killing of HCT15/PRLR cells in the presence or absence of Verapamil.

To further test the ability of the disclosed tubulysin payloads, reference compounds, and antibody drug conjugates using these payloads, a cytotoxicity assay was performed using C4-2 cells as described in this example (see above). For these studies, anti-STEAP2 antibodies were conjugated to select tubulysins payloads, and the compounds were tested at concentrations starting at 100 nM with 3-fold serial dilution. All $IC_{50}$ values are expressed in nM concentration and the percent cell killing at the maximum concentration tested was estimated from the following formula (100–% viable cells). These data were reported in Table 14.

As shown in Table 14, anti-STEAP2 ADCs conjugated with disclosed linker-payloads, anti-STEAP2-LP3, anti-STEAP2-LP4, and anti-STEAP2-LP5 demonstrated cytotoxicity in the C4-2 cell based assay at an $IC_{50}$ value of 0.097 nM, with maximum percent killing of 99%; an $IC_{50}$ value of 0.15 nM, with maximum percent killing of 99%; and an $IC_{50}$ of 0.28 nM with maximum percent killing of 96%, respectively. The reference ADC, anti-STEAP2-MMAE demonstrated cytotoxicity in the C4-2 cell-based assay with an $IC_{50}$ value of 0.53 nM, with maximum percent killing of 99%. All three isotype controls, Isotype control-LP3, Isotype control-LP4, and Isotype control-MMAE, demonstrated some modest killing of C4-2 cells at only the highest tested concentrations with a maximum percent killing of 16%-48%, but an $IC_{50}$ value >100 nM. Under these conditions, IVd (free payload of LP3) and Ve (payload of LP4), demonstrated killing of C4-2 cells with $IC_{50}$ values of 0.022 nM and 0.063 nM, and both showed maximum percent killing of 99%. Free reference payload MMAE demonstrated killing of C4-2 cells with $IC_{50}$ value of 0.22 nM, and maximum percent killing of 99%. The unconjugated anti-STEAP2 antibody did not demonstrate any killing of C4-2 cells.

TABLE 13

Cytotoxicity in HCT15/PRLR cells with or without Verapamil by Tubulysin payloads, reference compounds, and ADCs

| Test article | $IC_{50}$ (nM) on HCT15/PRLR w/o Verapamil | % kill on HCT15/PRLR w/o Verapamil | $IC_{50}$ (nM) on HCT15/PRLR w/ Verapamil | % kill on HCT15/PRLR w/ Verapamil |
|---|---|---|---|---|
| Anti-PRLR-LP3 | 0.525 | 90 | 0.309 | 91 |
| Anti-PRLR-LP4 | 3.305 | 65 | 0.196 | 91 |
| Isotype control-LP3 | >50 nM | 51 | >50 nM | 82 |
| Isotype control-LP4 | NS | NS | >50 nM | 76 |
| IVd (payload of LP3) | 0.037 | 99 | 0.015 | 99 |
| Ve (payload of LP4) | 0.203 | 99 | 0.033 | 99 |
| Anti-PRLR antibody | >50 nM | 0 | >50 nM | 0 |

NS = No significant killing at conencntrations tested

TABLE 14

Cytotoxicity in C4-2 cells by Tubulysin payloads, reference compounds, and ADCs

| Test Articles | $IC_{50}$ (nM) | % kill |
|---|---|---|
| Anti-STEAP2-LP3 | 0.097 | 99 |
| Anti-STEAP2-LP4 | 0.15 | 99 |
| Anti-STEAP2-MMAE | 0.53 | 99 |
| Isotype control-LP3 | >50 nM | 48 |
| Isotype control-LP4 | >50 nM | 34 |
| Isotype control-MMAE | >50 nM | 16 |

TABLE 14-continued

Cytotoxicity in C4-2 cells by Tubulysin payloads, reference compounds, and ADCs

| Test Articles | IC$_{50}$ (nM) | % kill |
|---|---|---|
| Anti-STEAP2 Ab | >50 nM | 0 |
| IVd (payload of LP3) | 0.022 | 99 |
| Ve (payload of LP4) | 0.063 | 99 |
| MMAE (payload of LP8) | 0.22 | 99 |

Anti-STEAP2 Antibodies

To determine the in vivo efficacy of anti-STEAP2 antibodies conjugated to tubulysins, studies were performed in immunocompromised mice bearing STEAP2 positive C4-2 prostate cancer xenografts.

For the assay, 7.5×10$^6$ C4-2 cells (ATCC, Cat #CRL-3314), which endogenously express STEAP2, were suspended in Matrigel (BD Biosciences, Cat #354234) and implanted subcutaneously into the left flank of male CB17 SCID mice (Taconic, Hudson NY). Once tumors had reached an average volume of 220 mm$^3$ (around Day 15), mice were randomized into groups of 7 and given a single dose of either anti-STEAP2 conjugated antibodies (anti-STEAP2-LP3, anti-STEAP2-LP4, anti-STEAP2-MMAE), isotype control conjugated antibody, or vehicle at 2.5 mg/kg via tail vein injection. Tumors were measured with calipers twice a week until the average size of the vehicle group reached 1500 mm$^3$. Tumor size was calculated using the formula (length×width$^2$)/2 and the average tumor size+/− SEM was then calculated. Tumor growth inhibition was calculated according to the following formula: $(1-((T_{final}-T_{initial})/(C_{final}-C_{initial})))*100$, where treated group (T) and control group (C) represent the mean tumor mass on the day the vehicle group reached 1500 mm$^3$.

In this study, anti-STEAP2 antibody conjugated to MMAE was compared to anti-STEAP2 antibody conjugated to tubulysin linker-payloads (anti-STEAP2-LP3 and anti-STEAP2-LP4) for their ability to reduce C4-2 tumor size. As summarized in Table 15, treatment with anti-STEAP2-MMAE reference ADC resulted in an average of 81% tumor growth inhibition at the completion of the study. In comparison, treatment with anti-STEAP2-LP3 and Anti-STEAP2-LP4 ADCs demonstrated an average of 108% and 97% reduction in tumor growth, respectively. Treatment with the isotype control ADCs led to an average of 31-33% reduction in tumor growth. The anti-STEAP2 antibodies comprised N297Q mutations.

TABLE 15

Inhibition of C4-2 Tumor Growth at end of study in SCID mice treated with anti-STEAP2 ADCs

| Treatment Group | Average Final Tumor size mm$^3$ (mean ± SEM) | Average Tumor Growth Inhibition (%) |
|---|---|---|
| PBS Vehicle | 1539 ± 177 | 0 |
| Isotype control-MMAE 2.5 mg/kg | 1140 ± 213 | 31 |
| Isotype control-LP3 2.5 mg/kg | 1100 ± 202 | 33 |
| Isotype control-LP4 2.5 mg/kg | 1127 ± 192 | 31 |
| Anti-STEAP2-MMAE 2.5 mg/kg | 475 ± 118 | 81 |
| Anti-STEAP2 N297Q-LP3 2.5 mg/kg | 115 ± 6 | 108 |
| Anti-STEAP2 N297Q-LP4 2.5 mg/kg | 258 ± 60 | 97 |

Efficacy of STEAP2-Tubulysin ADC in CTG-2440 and CTG-2441 PDX Prostate Cancer Models mAb Clone IDs:

| AbPID/REGN# | Common Name | N297Q mutation? |
|---|---|---|
| Isotype Control-LP4 | Control Tubulysin ADC | Yes |
| Anti-STEAP2 N297Q Ab-LP4 | STEAP2 Tubulysin ADC | Yes |

Experimental Procedure:

Prostate cancer Patient-Derived Xenograft (PDX) tumor fragments of either CTG-2440 or CTG-2441 were implanted subcutaneously into the flank of male NOG mice. Once the tumor volumes reached approximately 200 mm$^3$, mice were randomized into groups of eight and were treated according to the schedule shown in Table 16 below. Tumor growth was monitored for 60 days post-implantation.

TABLE 16

| Article | DAR | ADC Dose | Payload Dose | Dosing Schedule | Total Payload Dose |
|---|---|---|---|---|---|
| Isotype Control-LP4 | 3.9-4 | 3.64-3.72 mg/kg | 80 ug/kg | QW × 3 | 240 ug/kg |
| Anti-STEAP2 N297Q Ab-LP4 | 3.9-4 | 1.82-1.86 mg/kg | 40 ug/kg | QW × 1 | 40 ug/kg |
| Anti-STEAP2 N297Q Ab-LP4 | 3.9-4 | 1.82-1.86 mg/kg | 40 ug/kg | QW × 3 | 120 ug/kg |
| Anti-STEAP2 N297Q Ab-LP4 | 3.9-4 | 3.64-3.72 mg/kg | 80 ug/kg | QW × 3 | 240 ug/kg |

Figure 16:
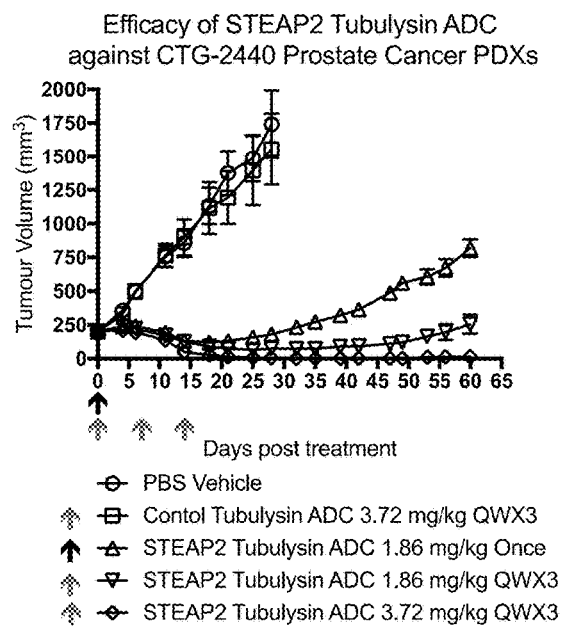
FIG. 16 shows that anti-STEAP2 Tubulysin ADCs demonstrate significant anti-tumor efficacy against CTG-2440 prostate cancer PDX bearing NOG mice.
Figure 16:
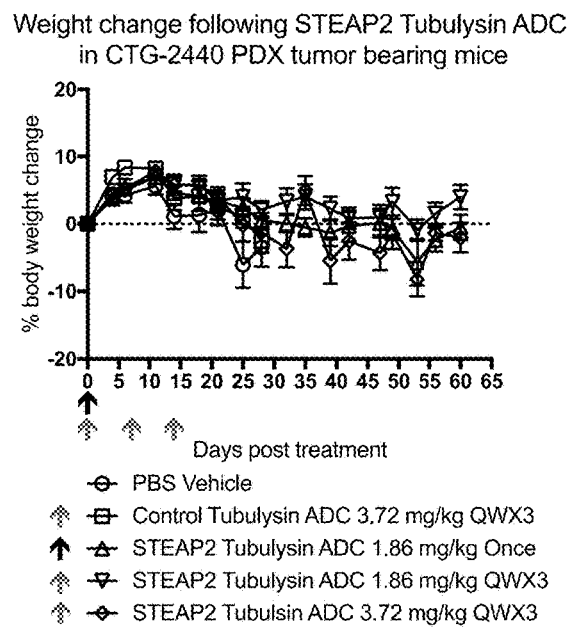

Results and Conclusions:

The anti-tumor efficacy of a STEAP2 Tubulysin ADC in a STEAP2 positive PDX model was assessed relative to control ADC. CTG-2440 tumors treated with the control ADC grew to protocol size limits within 28 days. Growth of tumors treated with STEAP2 Tubulysin ADC at 3.72 mg/kg (3 weekly doses of 80 ug/kg payload) was inhibited for 60 days with no deleterious effect on body weight change. The anti-tumor efficacy was dose dependent. Complete tumor inhibition was observed with a total payload dose of 240 ug/kg, while tumor regression was induced with 120 ug/kg and 40 ug/kg total payload doses. Tumor volume data for CTG-2440 are shown in FIG. 16.

Tabulated Data Summary for CTG-2440:

| Antibody (mg/kg) | Total Payload Dose | Final tumor volume (mm³) at termination (mean ± SD) | Tumor growth (mm³) from start of treatment (mean ± SD) |
|---|---|---|---|
| Isotype Control-LP4 (3.72 mg/kg, QW × 3) | 240 ug/kg | 1556.0 ± 747.7 | 1355.3 ± 724.0 |
| Anti-STEAP2 N297Q Ab-LP4 (1.86 mg/kg, QW × 1) | 40 ug/kg | 179.9 ± 68.5 | −20.0 ± 65.1 |
| Anti-STEAP2 N297Q Ab-LP4 (1.86 mg/kg, QW × 3) | 120 ug/kg | 73.5 ± 53.4 | −129.3 ± 67.7 |
| Anti-STEAP2 N297Q Ab-LP4 (3.72 mg/kg, QW × 3) | 240 ug/kg | 6.0 ± 11.4 | −196.5 ± 37.1 |

CTG-2441 tumors treated with the control ADC grew to protocol size limits within 30 days. Growth of tumors treated with STEAP2 Tubulysin ADC at 3.64 mg/kg (3 weekly doses of 80 ug/kg payload) was inhibited for 60 days with only moderate weight loss observed. The anti-tumor efficacy was dose dependent. Complete tumor inhibition was observed with a total payload dose of either 120 or 240 ug/kg. Tumor regression was induced following a single administration of 40 ug/kg total payload dose.

Figure 17:
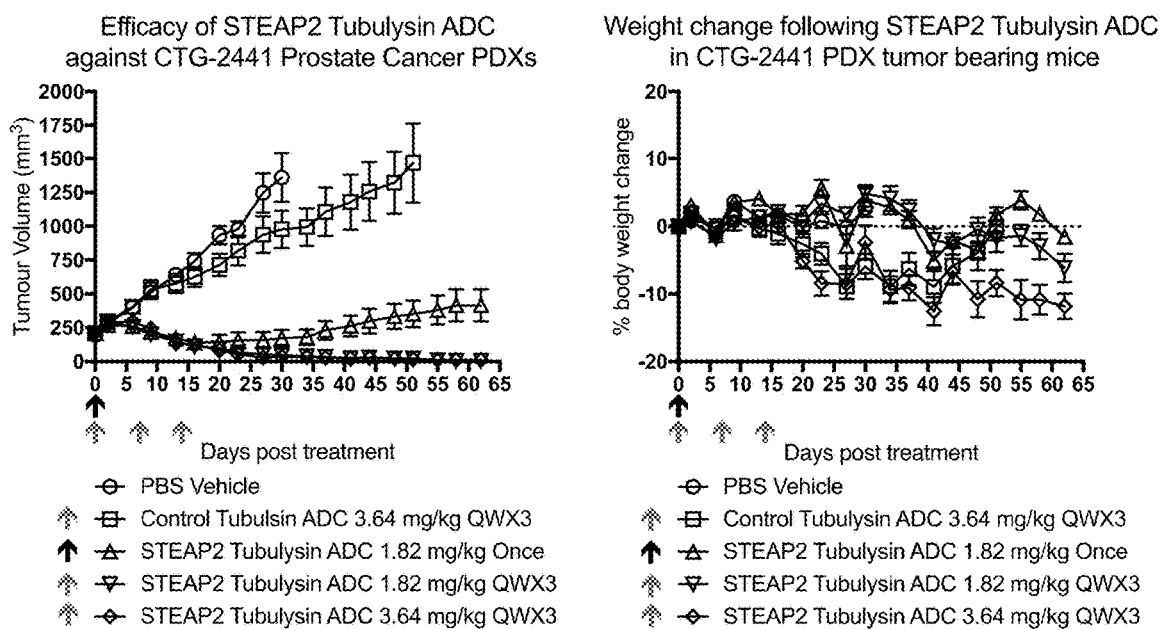
FIG. 17 shows that anti-STEAP2 Tubulysin ADCs demonstrate significant anti-tumor efficacy against CTG-2441 prostate cancer PDX bearing NOG mice.

Tumor volume data for CTG-2441 are shown in FIG. 17.

Tabulated Data Summary for CTG-2441:

| Antibody (mg/kg) | Total Payload Dose | Final tumor volume (mm³) at termination (mean ± SD) | Tumor growth (mm³) from start of treatment (mean ± SD) |
|---|---|---|---|
| Isotype Control-LP4 (3.64 mg/kg, QW × 3) | 240 ug/kg | 977.3 ± 390.0 | 770.3 ± 365.8 |
| Anti-STEAP2 N297Q Ab-LP4 (1.82 mg/kg, QW × 1) | 40 ug/kg | 171.8 ± 176.1 | −36.8 ± 167.0 |
| Anti-STEAP2 N297Q Ab-LP4 (1.82 mg/kg, QW × 3) | 120 ug/kg | 46.0 ± 15.1 | −164.0 ± 57.3 |
| Anti-STEAP2 N297Q Ab-LP4 (3.64 mg/kg, QW × 3) | 240 ug/kg | 33.5 ± 13.6 | −179.1 ± 51.3 |

PDX Model and STEAP2 Expression Information:

The prostate cancer models were derived from the bone metastases of patients with metastatic castrate resistant prostate cancer (mCRPC). STEAP2 expression was confirmed by RNA sequencing data and RNA in situ hybridization.

SEQUENCE LISTING

```
<160> NUMBER OF SEQ ID NOS: 17

<210> SEQ ID NO 1
<211> LENGTH: 115
<212> TYPE: PRT
<213> ORGANISM: Artificial Sequence
<220> FEATURE:
<223> OTHER INFORMATION: Synthetic: H1H7814N, HCVR

<400> SEQUENCE: 1

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Ile Ser Ser Tyr
            20                  25                  30

Gly Met Asn Trp Val Arg Gln Ala Pro Gly Lys Gly Leu Glu Trp Val
        35                  40                  45

Ala Val Ile Ser Tyr Asp Gly Asn Lys Tyr Ser Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Gly Arg Tyr Phe Asp Leu Trp Gly Arg Gly Thr Leu Val Thr
            100                 105                 110

Val Ser Ser
        115
```

```
<210> SEQ ID NO 2
<211> LENGTH: 8
<212> TYPE: PRT
<213> ORGANISM: Artificial Sequence
<220> FEATURE:
<223> OTHER INFORMATION: Synthetic: H1H7814N, HCDR1

<400> SEQUENCE: 2

Gly Phe Thr Ile Ser Ser Tyr Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic: H1H7814N, HCDR2

<400> SEQUENCE: 3

Ile Ser Tyr Asp Gly Gly Asn Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic: H1H7814N, HCDR3

<400> SEQUENCE: 4

Ala Arg Gly Arg Tyr Phe Asp Leu
1               5

<210> SEQ ID NO 5
<211> LENGTH: 107
<212> TYPE: PRT
<213> ORGANISM: Artificial Sequence
<220> FEATURE:
<223> OTHER INFORMATION: Synthetic: H1H7814N, LCVR

<400> SEQUENCE: 5

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Arg Ala Pro Asn Leu Leu Ile
        35                  40                  45

Ser Lys Ala Ser Ser Leu Lys Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Asp Asp Phe Ala Thr Tyr Tyr Cys Gln Gln Tyr Tyr Ser Tyr Ser Tyr
                85                  90                  95

Thr Phe Gly Gln Gly Thr Lys Leu Glu Ile Lys
            100                 105

<210> SEQ ID NO 6
<211> LENGTH: 6
<212> TYPE: PRT
<213> ORGANISM: Artificial Sequence
<220> FEATURE:
<223> OTHER INFORMATION: Synthetic: H1H7814N, LCDR1

<400> SEQUENCE: 6
```

```
Gln Ser Ile Ser Ser Trp
1               5

<210> SEQ ID NO 7
<211> LENGTH: 3
<212> TYPE: PRT
<213> ORGANISM: Artificial Sequence
<220> FEATURE:
<223> OTHER INFORMATION: Synthetic: H1H7814N, LCDR2

<400> SEQUENCE: 7

Lys Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: Synthetic: H1H7814N, LCDR3

<400> SEQUENCE: 8

Gln Gln Tyr Tyr Ser Tyr Ser Tyr Thr
1               5

<210> SEQ ID NO 9
<211> LENGTH: 115
<212> TYPE: PRT
<213> ORGANISM: Artificial Sequence
<220> FEATURE:
<223> OTHER INFORMATION: Synthetic: H1H6958N2, HCVR

<400> SEQUENCE: 9

Gln Val Gln Leu Val Glu Ser Gly Gly Gly Val Val Gln Pro Gly Arg
1               5                   10                  15

Ser Leu Arg Leu Ser Cys Gly Ala Ser Gly Phe Thr Phe Arg Asn Tyr
            20                  25                  30

Gly Met Gln Trp Val Arg Gln Gly Pro Gly Lys Gly Leu Glu Trp Val
        35                  40                  45

Thr Leu Ile Ser Phe Asp Gly Asn Asp Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Thr Glu Asp Thr Ala Val Tyr Tyr Cys
                85                  90                  95

Ala Arg Gly Gly Asp Phe Asp Tyr Trp Gly Gln Gly Thr Leu Val Thr
            100                 105                 110

Val Ser Ser
        115

<210> SEQ ID NO 10
<211> LENGTH: 8
<212> TYPE: PRT
<213> ORGANISM: Artificial Sequence
<220> FEATURE:
<223> OTHER INFORMATION: Synthetic: H1H6958N2, HCDR1

<400> SEQUENCE: 10

Gly Phe Thr Phe Arg Asn Tyr Gly
1               5

<210> SEQ ID NO 11
<211> LENGTH: 8
```

```
<212> TYPE: PRT
<213> ORGANISM: Artificial Sequence
<220> FEATURE:
<223> OTHER INFORMATION: Synthetic: H1H6958N2, HCDR2

<400> SEQUENCE: 11

Ile Ser Phe Asp Gly Asn Asp Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic: H1H6958N2, HCDR3

<400> SEQUENCE: 12

Ala Arg Gly Gly Asp Phe Asp Tyr
1               5

<210> SEQ ID NO 13
<211> LENGTH: 108
<212> TYPE: PRT
<213> ORGANISM: Artificial Sequence
<220> FEATURE:
<223> OTHER INFORMATION: Synthetic: H1H6958N2, LCVR

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Lys Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Met
                85                  90                  95

Tyr Thr Phe Gly Gln Gly Thr Lys Leu Glu Ile Lys
            100                 105

<210> SEQ ID NO 14
<211> LENGTH: 6
<212> TYPE: PRT
<213> ORGANISM: Artificial Sequence
<220> FEATURE:
<223> OTHER INFORMATION: Synthetic: H1H6958N2, LCDR1

<400> SEQUENCE: 14

Gln Asp Ile Arg Lys Asp
1               5

<210> SEQ ID NO 15
<211> LENGTH: 3
<212> TYPE: PRT
<213> ORGANISM: Artificial Sequence
<220> FEATURE:
<223> OTHER INFORMATION: Synthetic: H1H6958N2, LCDR2

<400> SEQUENCE: 15

Ala Ala Ser
1
```

```
<210> SEQ ID NO 16
<211> LENGTH: 10
<212> TYPE: PRT
<213> ORGANISM: Artificial Sequence
<220> FEATURE:
<223> OTHER INFORMATION: Synthetic: H1H6958N2, LCDR3

<400> SEQUENCE: 16

Leu Gln His Asn Ser Tyr Pro Met Tyr Thr
1               5                   10

<210> SEQ ID NO 17
<211> LENGTH: 267
<212> TYPE: PRT
<213> ORGANISM: Artificial Sequence
<220> FEATURE:
<223> OTHER INFORMATION: Synthetic: hPRLR ecto-MMH

<400> SEQUENCE: 17

Met His Arg Pro Arg Arg Gly Thr Arg Pro Pro Leu Ala Leu
1               5                   10                  15

Leu Ala Ala Leu Leu Ala Ala Arg Gly Ala Asp Ala Gln Leu Pro
                20                  25                  30

Pro Gly Lys Pro Glu Ile Phe Lys Cys Arg Ser Pro Asn Lys Glu Thr
                35                  40                  45

Phe Thr Cys Trp Trp Arg Pro Gly Thr Asp Gly Gly Leu Pro Thr Asn
    50                      55                  60

Tyr Ser Leu Thr Tyr His Arg Glu Gly Glu Thr Leu Met His Glu Cys
65                      70                  75                  80

Pro Asp Tyr Ile Thr Gly Gly Pro Asn Ser Cys His Phe Gly Lys Gln
                    85                  90                  95

Tyr Thr Ser Met Trp Arg Thr Tyr Ile Met Met Val Asn Ala Thr Asn
                100                 105                 110

Gln Met Gly Ser Ser Phe Ser Asp Glu Leu Tyr Val Asp Val Thr Tyr
                115                 120                 125

Ile Val Gln Pro Asp Pro Pro Leu Glu Leu Ala Val Glu Val Lys Gln
            130                 135                 140

Pro Glu Asp Arg Lys Pro Tyr Leu Trp Ile Lys Trp Ser Pro Pro Thr
145                 150                 155                 160

Leu Ile Asp Leu Lys Thr Gly Trp Phe Thr Leu Leu Tyr Glu Ile Arg
                165                 170                 175

Leu Lys Pro Glu Lys Ala Ala Glu Trp Glu Ile His Phe Ala Gly Gln
                180                 185                 190

Gln Thr Glu Phe Lys Ile Leu Ser Leu His Pro Gly Gln Lys Tyr Leu
                195                 200                 205

Val Gln Val Arg Cys Lys Pro Asp His Gly Tyr Trp Ser Ala Trp Ser
            210                 215                 220

Pro Ala Thr Phe Ile Gln Ile Pro Ser Asp Phe Thr Met Asn Asp Glu
225                 230                 235                 240

Gln Lys Leu Ile Ser Glu Glu Asp Leu Gly Gly Glu Gln Lys Leu Ile
                245                 250                 255

Ser Glu Glu Asp Leu His His His His His His
                260                 265
```

-continued
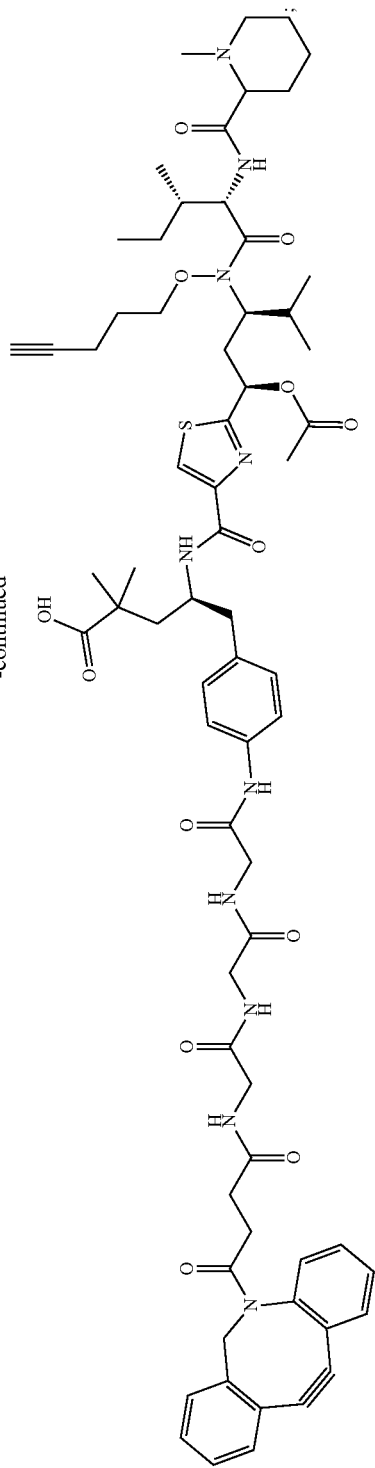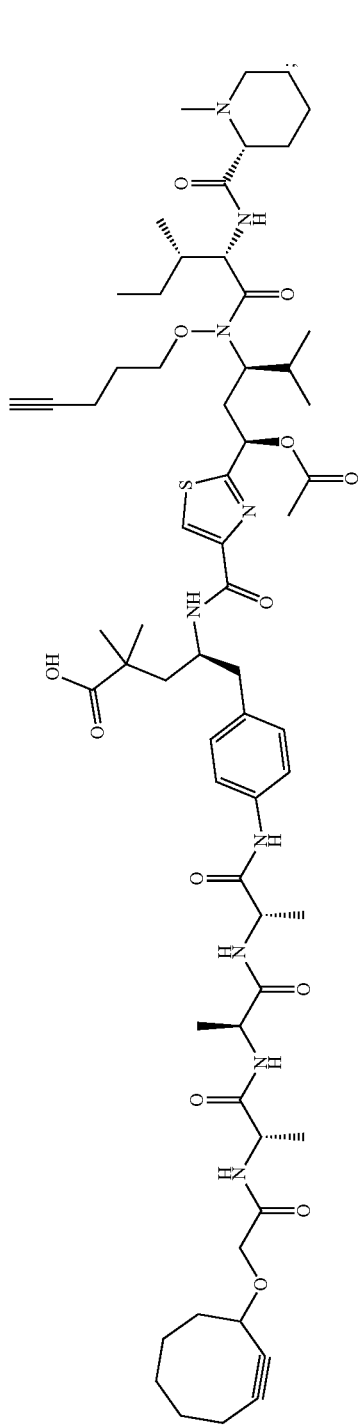

-continued
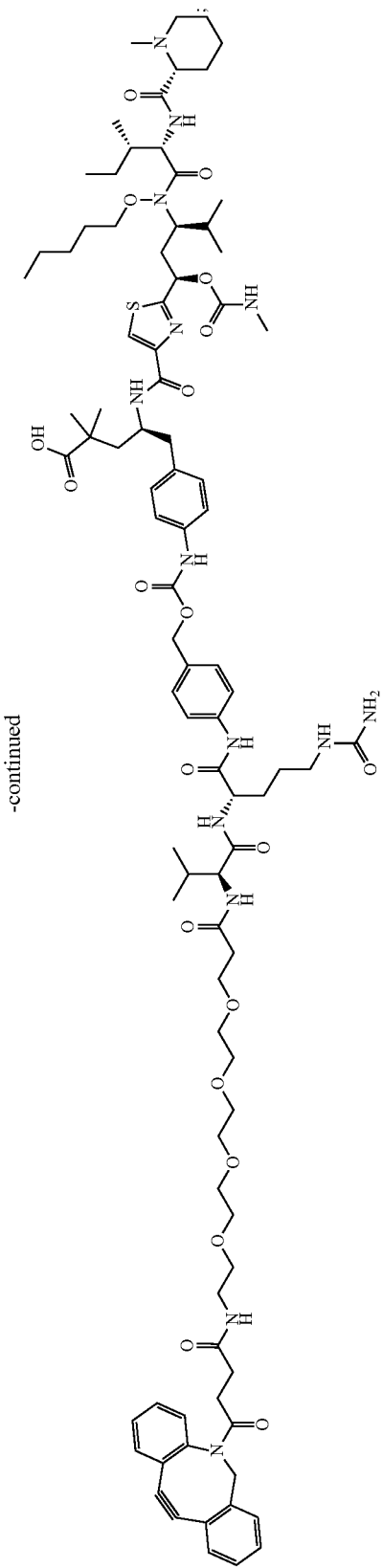
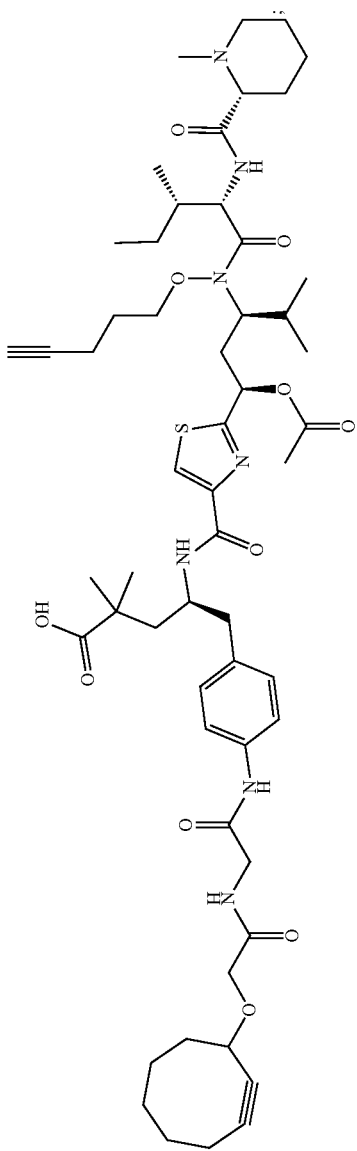

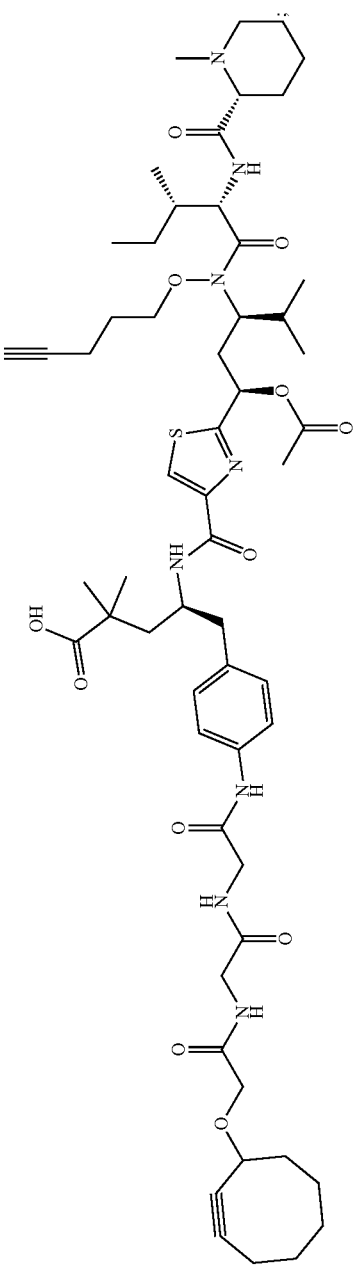
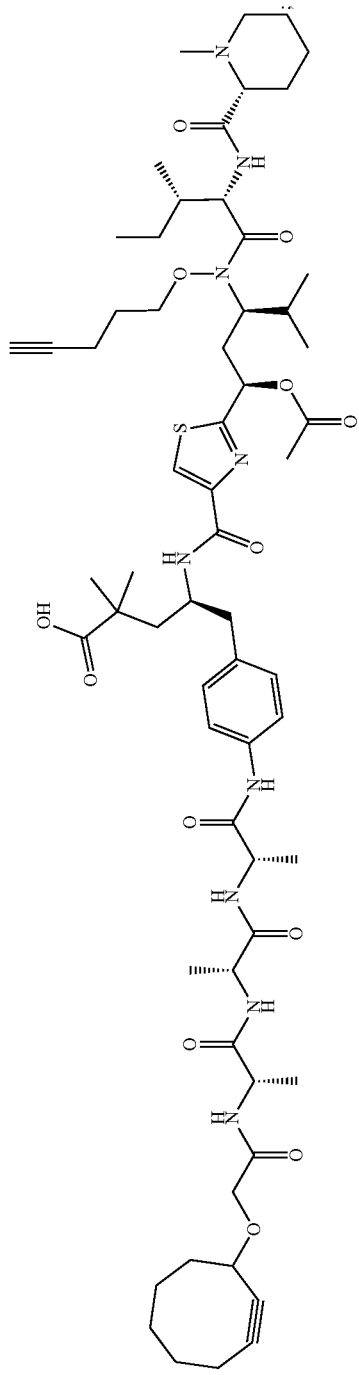

-continued
681
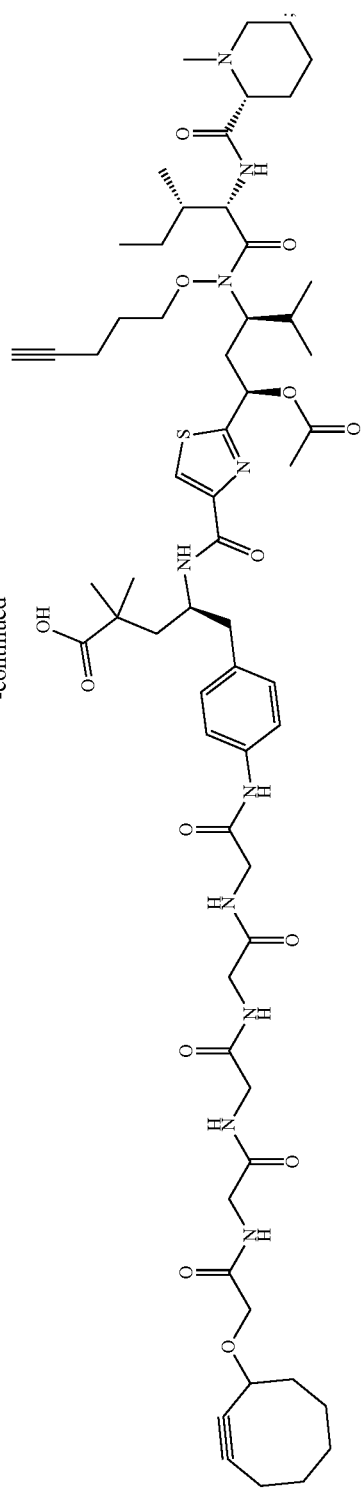
682
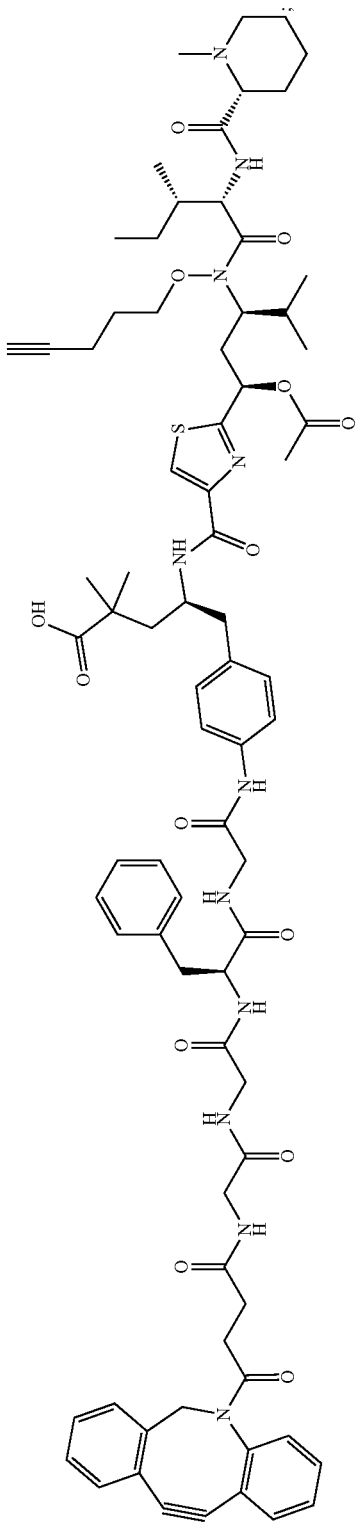

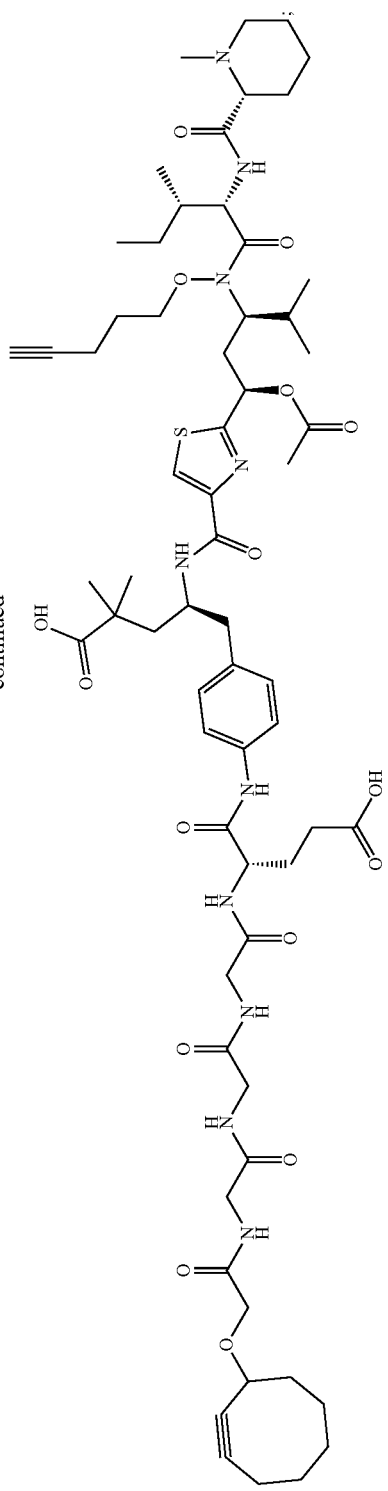
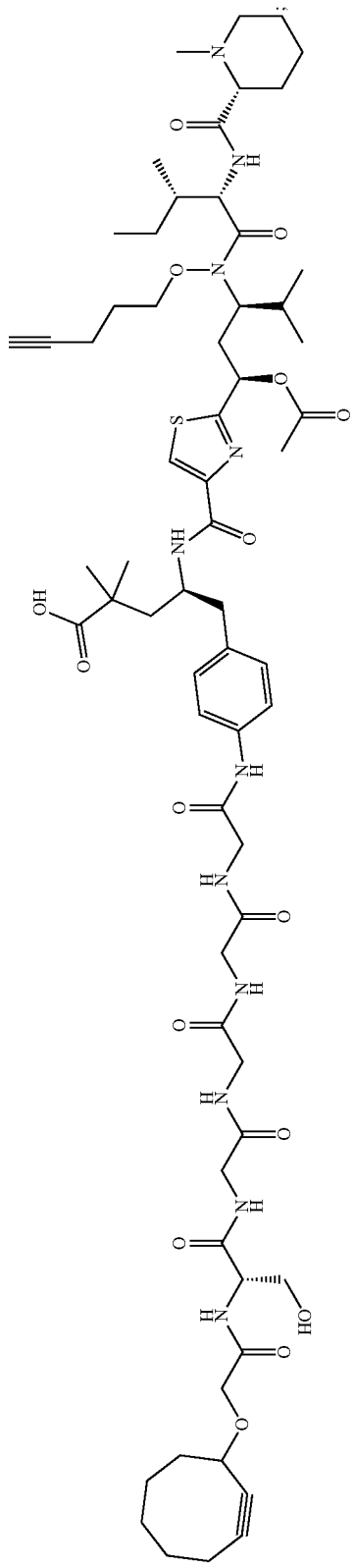

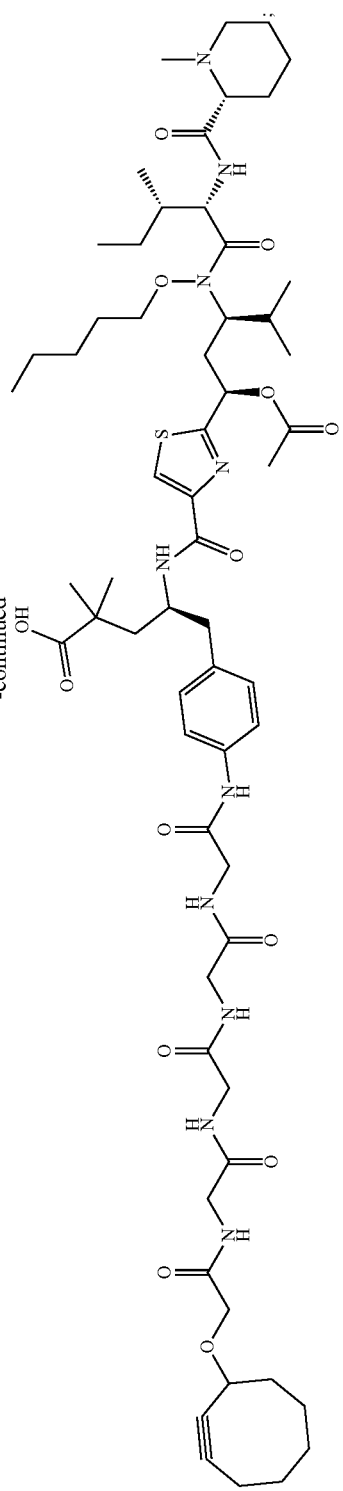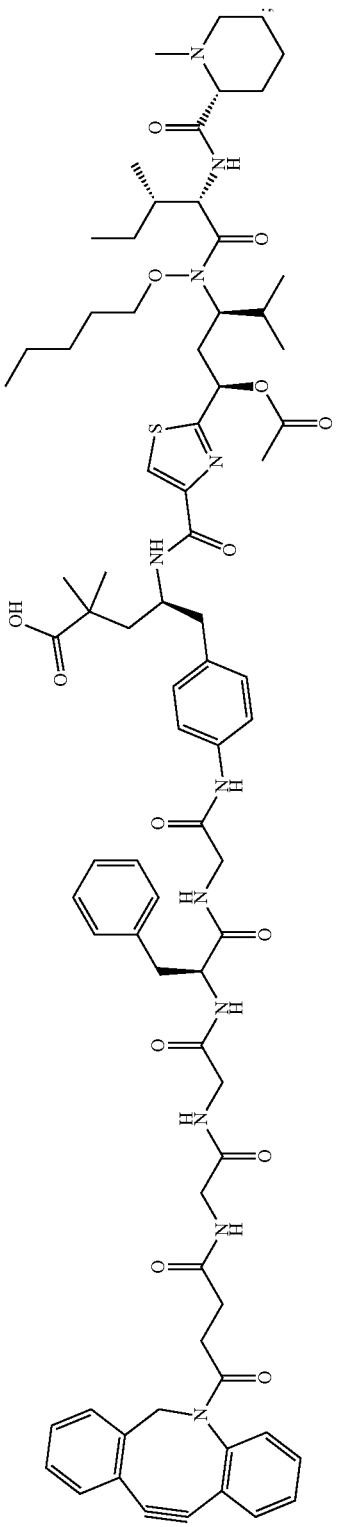

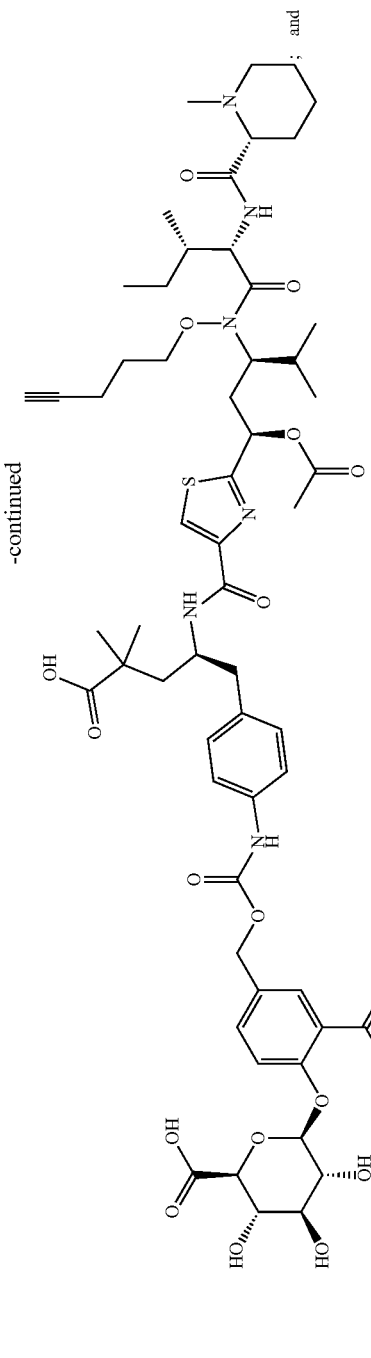
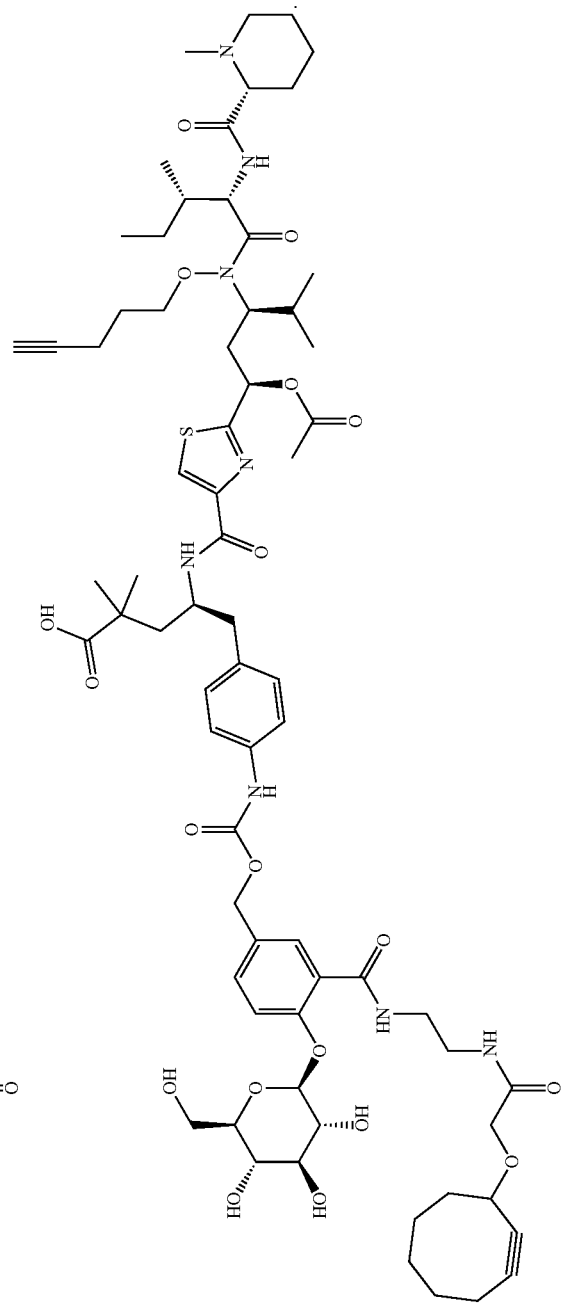

33. The linker-payload of claim 32, wherein the linker-payload is
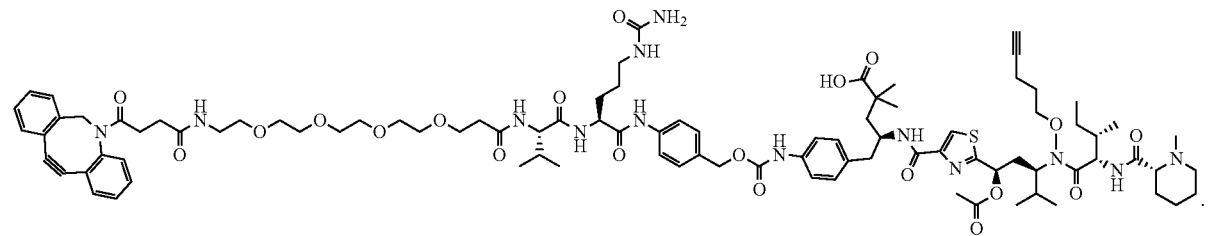

What is claimed is:
1. A compound having the following Formula B or C

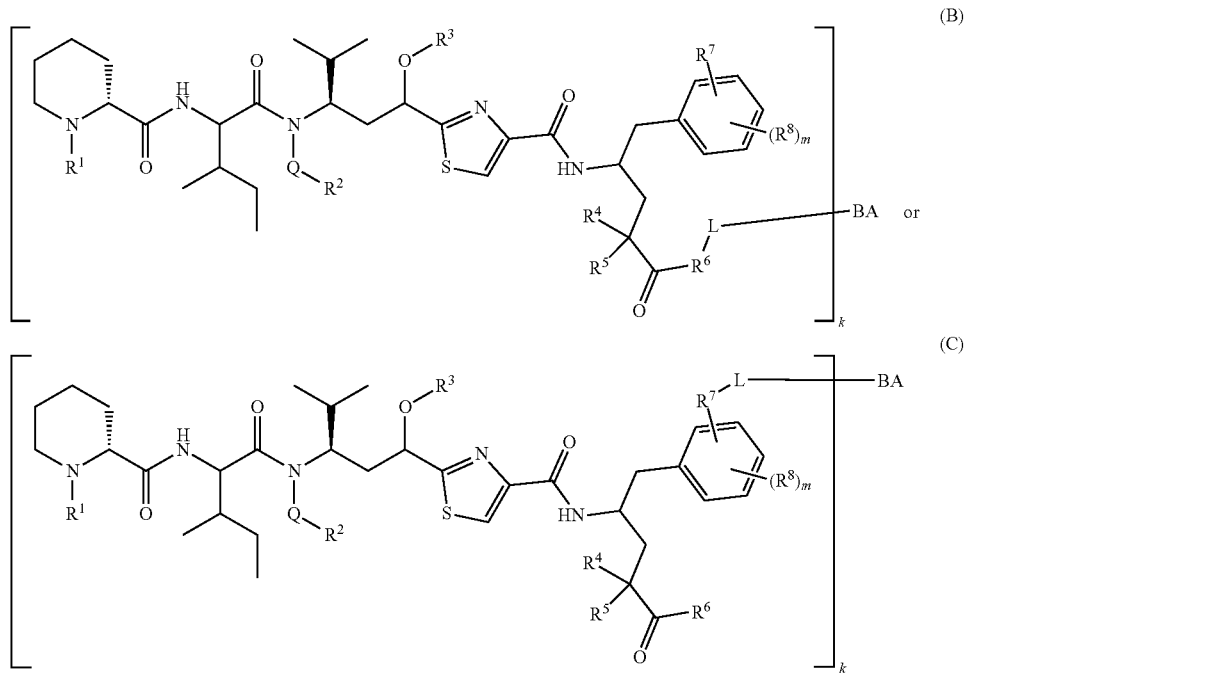

or a pharmaceutically acceptable salt thereof, wherein
BA is a binding agent;
L is a linker;
wherein
$R^1$ is $C_1$-$C_{10}$ alkyl;
$R^3$ is —C(O)$C_1$-$C_5$ alkyl, —C(O)N(H)$C_1$-$C_{10}$ alkyl, or —($C_1$-$C_{10}$ alkylene)-NR$^{3a}$R$^{3b}$,
    wherein R$^{3a}$ and R$^{3b}$ are independently in each instance, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl, wherein $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and/or $C_2$-$C_{20}$ acyl;
$R^4$ and $R^5$ are, independently in each instance, hydrogen or $C_1$-$C_5$ alkyl;
$R^6$ is —OH, —O—, —NHNH$_2$, or —NHNH—;
$R^7$ is, independently in each instance, hydrogen, —OH, —O—, halogen, or —NR$^{7a}$R$^{7b}$,
    wherein R$^{7a}$ and R$^{7b}$ are independently in each instance, a bond, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, acyl, and amino acid residue, wherein $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and/or acyl;
$R^8$ is, independently in each instance, hydrogen, deuterium, —NHR$^9$, or halogen, wherein R$^9$ is hydrogen, —$C_1$-$C_5$ alkyl, or —C(O)$C_1$-$C_5$ alkyl; and
m is one or two;
Q is oxygen;
$R^2$ is $C_1$-$C_{10}$ alkyl, $C_3$-$C_{10}$ alkynyl, —$C_1$-$C_{10}$ alkylene-(5-membered heteroaryl), —$C_1$-$C_3$ alkylene-Q$^1$-(CH$_2$)$_n$aryl, or $C_1$-$C_3$ hydroxyalkyl; and
Q$^1$ is —CH$_2$— or —O—;
    wherein said heteroaryl is unsubstituted or substituted with $C_1$-$C_{20}$ alkyl, aminoalkyl, -alkylene-NH—, hydroxylalkyl, -alkylene-O—, carboxyalkyl, -alkylene-COO—, benzyl, or phenyl;
    wherein said aryl is unsubstituted or substituted with nitro, amino, or —NH—; and
    wherein n is an integer from one to five; and
k is an integer from one to thirty.
2. The compound of claim 1, or a pharmaceutically acceptable salt thereof, wherein
L is a linker;
BA is a binding agent;
k is an integer from one to thirty;
$R^1$ is $C_1$-$C_{10}$ alkyl;
$R^3$ is —C(O)$C_1$-$C_5$ alkyl, —C(O)N(H)$C_1$-$C_{10}$ alkyl, or —($C_1$-$C_{10}$ alkylene)-NR$^{3a}$R$^{3b}$,
    wherein R$^{3a}$ and R$^{3b}$ are independently in each instance, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl, wherein $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and/or $C_2$-$C_{20}$ acyl;
$R^4$ and $R^5$ are, independently in each instance, hydrogen or $C_1$-$C_5$ alkyl;

$R^6$ is —OH, —O—, —NHNH$_2$, or —NHNH—;

$R^7$ is, independently in each instance, hydrogen, —OH, —O—, halogen, or —NR$^{7a}$R$^{7b}$, wherein R$^{7a}$ and R$^{7b}$ are independently in each instance, a bond, hydrogen, C$_1$-C$_{20}$ alkyl, C$_2$-C$_{20}$ alkenyl, C$_2$-C$_{20}$ alkynyl, C$_3$-C$_{20}$ cycloalkyl, C$_6$-C$_{20}$ aryl, 5- to 20-membered heteroaryl, and acyl, wherein C$_1$-C$_{20}$ alkyl, C$_2$-C$_{20}$ alkenyl, C$_2$-C$_{20}$ alkynyl, C$_3$-C$_{20}$ cycloalkyl, aryl, heteroaryl, and acyl are unsubstituted or substituted with C$_1$-C$_{20}$ alkyl, C$_2$-C$_{20}$ alkenyl, C$_2$-C$_{20}$ alkynyl, C$_3$-C$_{20}$ cycloalkyl, aryl, heteroaryl, and/or acyl;

$R^8$ is, independently in each instance, hydrogen, deuterium, —NHR$^9$, or halogen, wherein R$^9$ is hydrogen, —C$_1$-C$_5$ alkyl, or —C(O)C$_1$-C$_5$ alkyl; and m is one or two;

Q is oxygen;

$R^2$ is C$_1$-C$_{10}$ alkyl, C$_3$-C$_{10}$ alkynyl, —C$_1$-C$_{10}$ alkylene-(5-membered heteroaryl), —C$_1$-C$_3$ alkylene-Q$^1$-(CH$_2$)$_n$aryl, or C$_1$-C$_3$ hydroxyalkyl; and Q$^1$ is —CH$_2$— or —O—;

wherein said heteroaryl is unsubstituted or substituted with C$_1$-C$_{20}$ alkyl, aminoalkyl, -alkylene-NH—, hydroxylalkyl, -alkylene-O—, carboxyalkyl, -alkylene-COO—, benzyl, or phenyl;

wherein said aryl is unsubstituted or substituted with nitro, amino, or —NH—; and wherein n is an integer from one to two.

3. The compound of claim 1, wherein the compound is of the Formula B' or C'

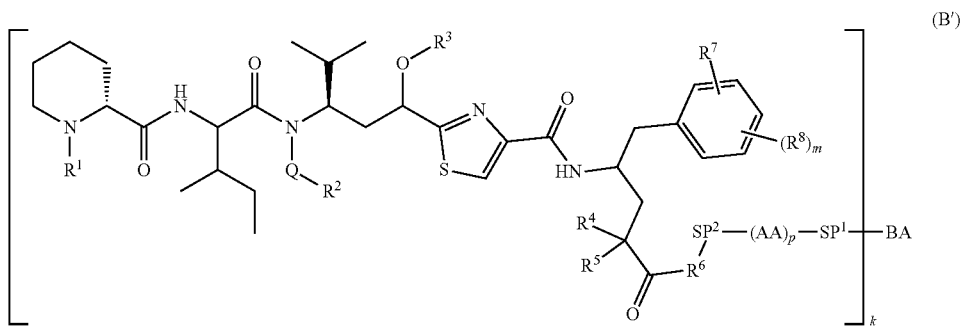

(B')

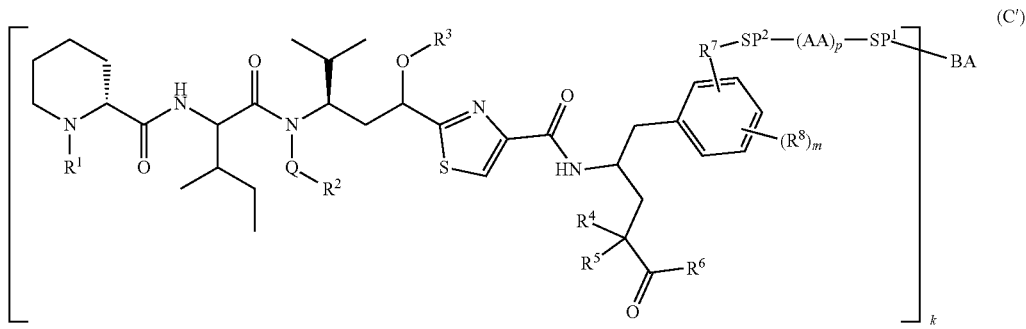

(C')

or a pharmaceutically acceptable salt thereof, wherein SP¹, when present, is

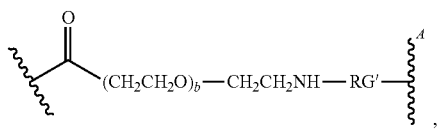

wherein
RG' is a reactive group residue following reaction of a reactive group RG with a binding agent;

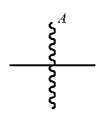

is a bond, direct or indirect, to the binding agent; and
b is an integer from one to four;
SP², when present, is

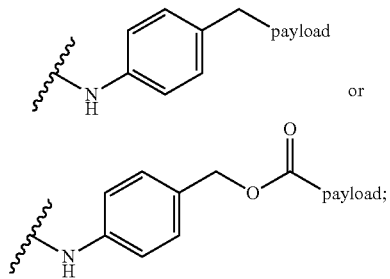

each AA is an amino acid; and
p is an integer from one to ten.

4. The compound of claim 3, wherein $(AA)_p$ is

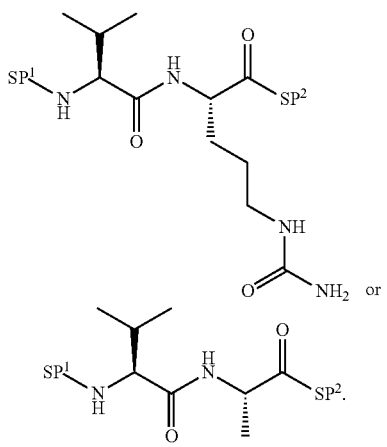

5. The compound of claim 4, wherein the binding agent is an antibody modified with a primary amine compound according to the Formula $H_2N$-LL-X, wherein LL is a divalent linker selected from the group consisting of
a divalent polyethylene glycol (PEG) group;
—$(CH_2)_n$—;
—$(CH_2CH_2O)_n$—$(CH_2)_p$—;
—$(CH_2)_n$—N(H)C(O)—$(CH_2)_m$—;
—$(CH_2CH_2O)_n$—N(H)C(O)—$(CH_2CH_2O)_m$—$(CH_2)_p$—;
—$(CH_2)_n$—C(O)N(H)—$(CH_2)_m$—;
—$(CH_2CH_2O)_n$—C(O)N(H)—$(CH_2CH_2O)_m$—$(CH_2)_p$—;
—$(CH_2)_n$—N(H)C(O)—$(CH_2CH_2O)_m$—$(CH_2)_p$—;
—$(CH_2CH_2O)_n$—N(H)C(O)—$(CH_2)_m$—;
—$(CH_2)_n$—C(O)N(H)—$(CH_2CH_2O)_m$—$(CH_2)_p$—; and
—$(CH_2CH_2O)_n$—C(O)N(H)—$(CH_2)_m$—,
wherein
n is an integer selected from one to twelve;
m is an integer selected from zero to twelve;
p is an integer selected from zero to two; and
X is selected from the group consisting of —SH, —$N_3$, —C≡CH, —C(O)H, tetrazole,

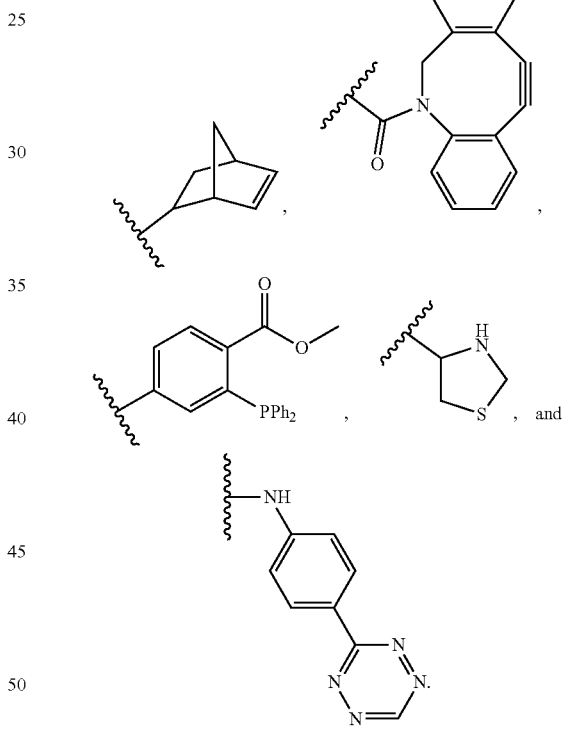

6. The compound of claim 5, wherein the binding agent is an antibody modified with a primary amine according to the following formula

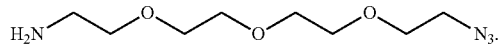 [SMILES: [N-]=[N+]=NCCOCCOCCOCCN]

7. The compound of claim 3, selected from the group consisting of

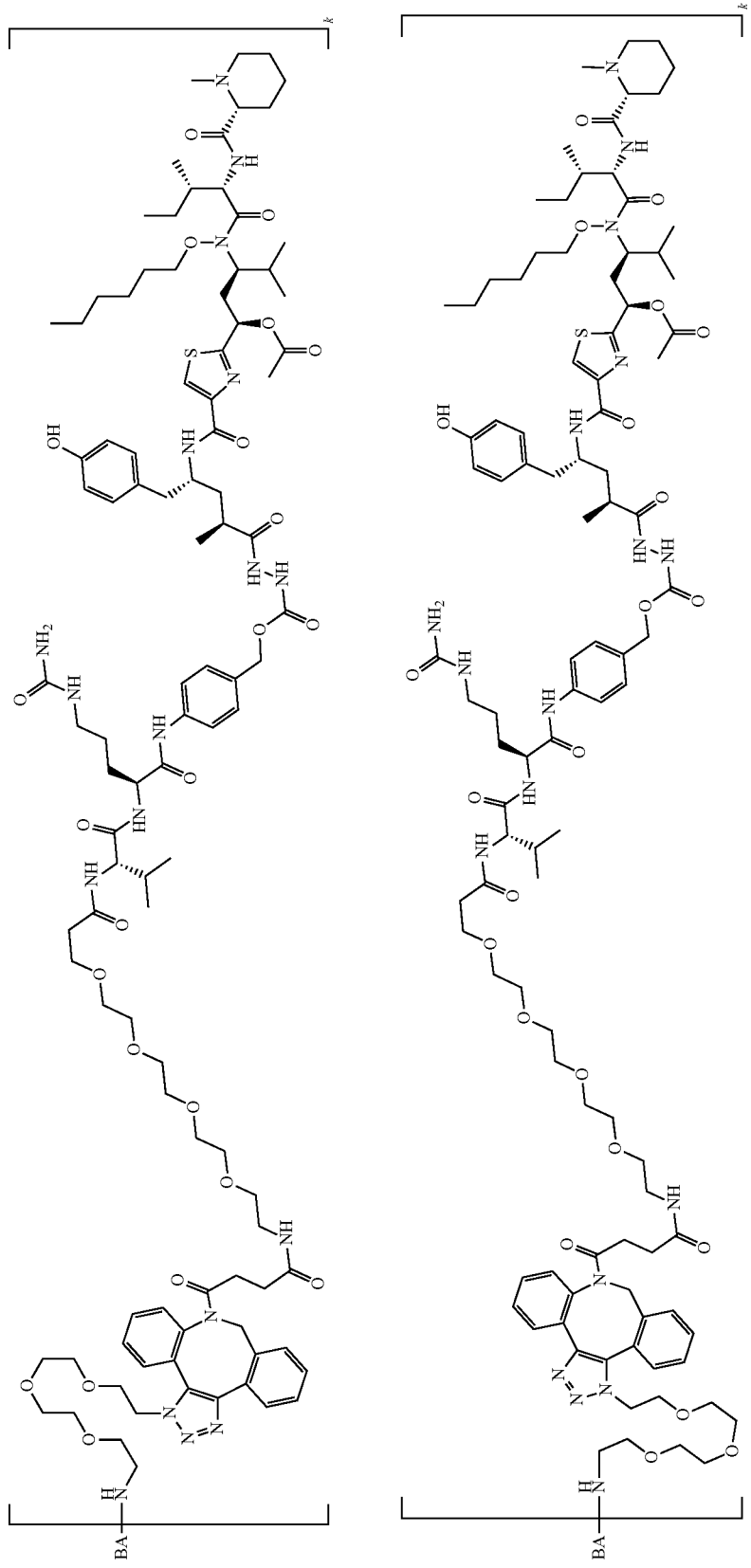

601 602
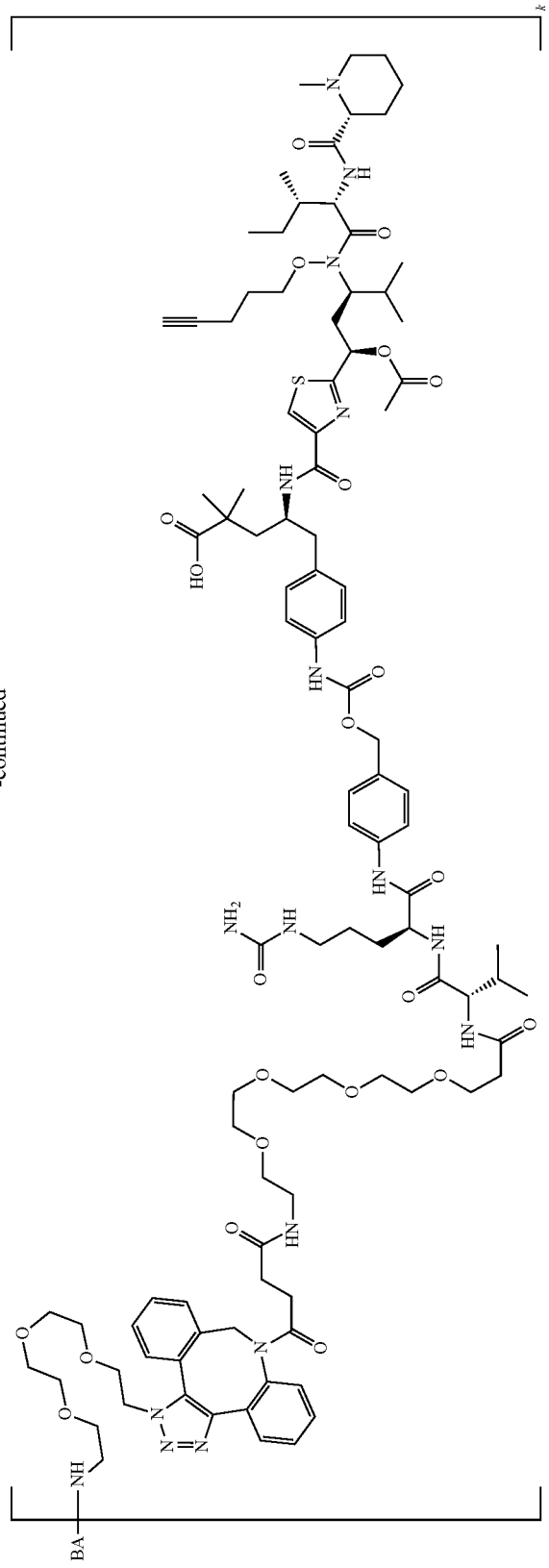
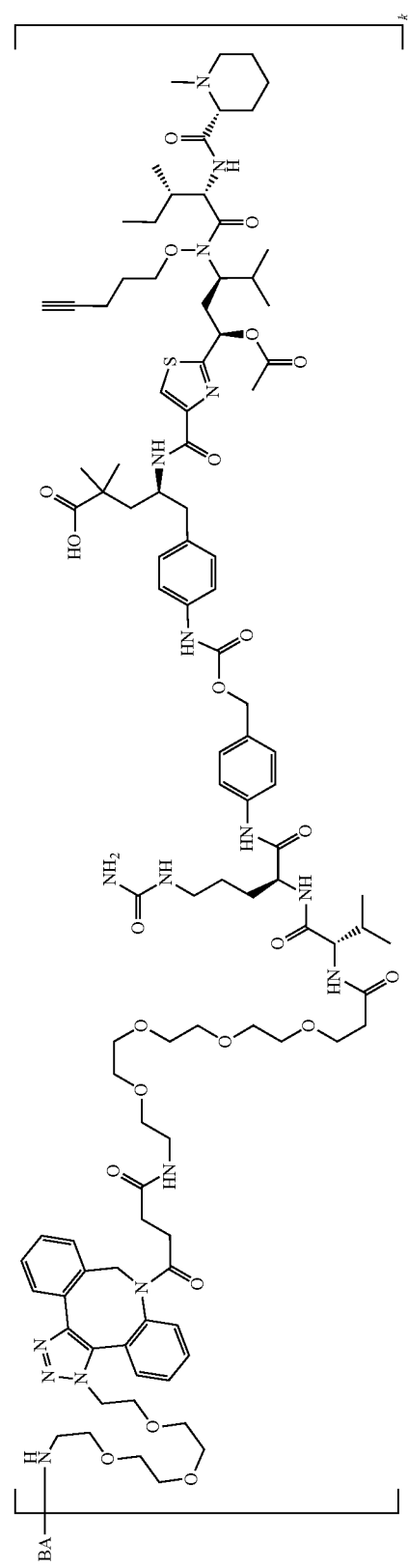

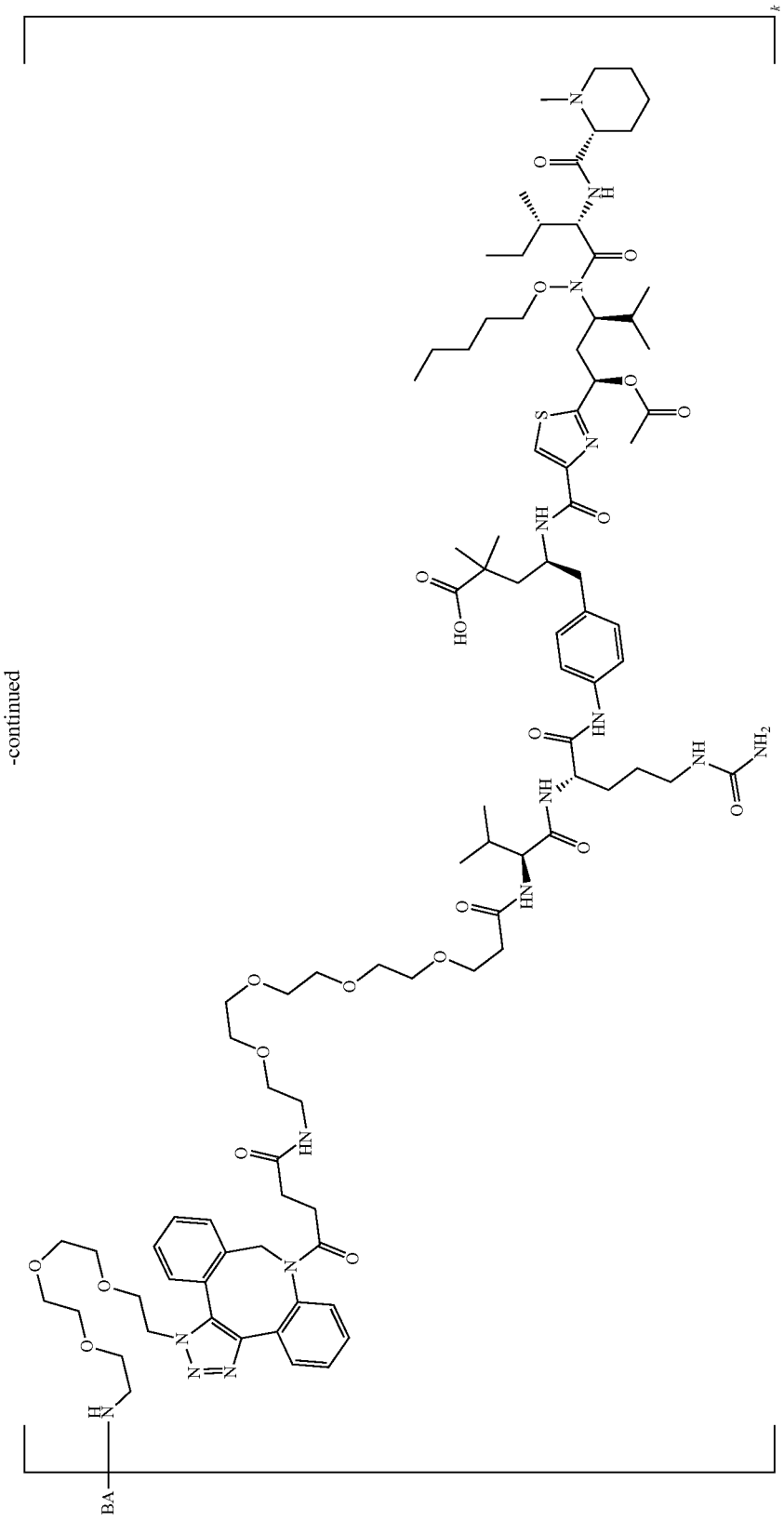

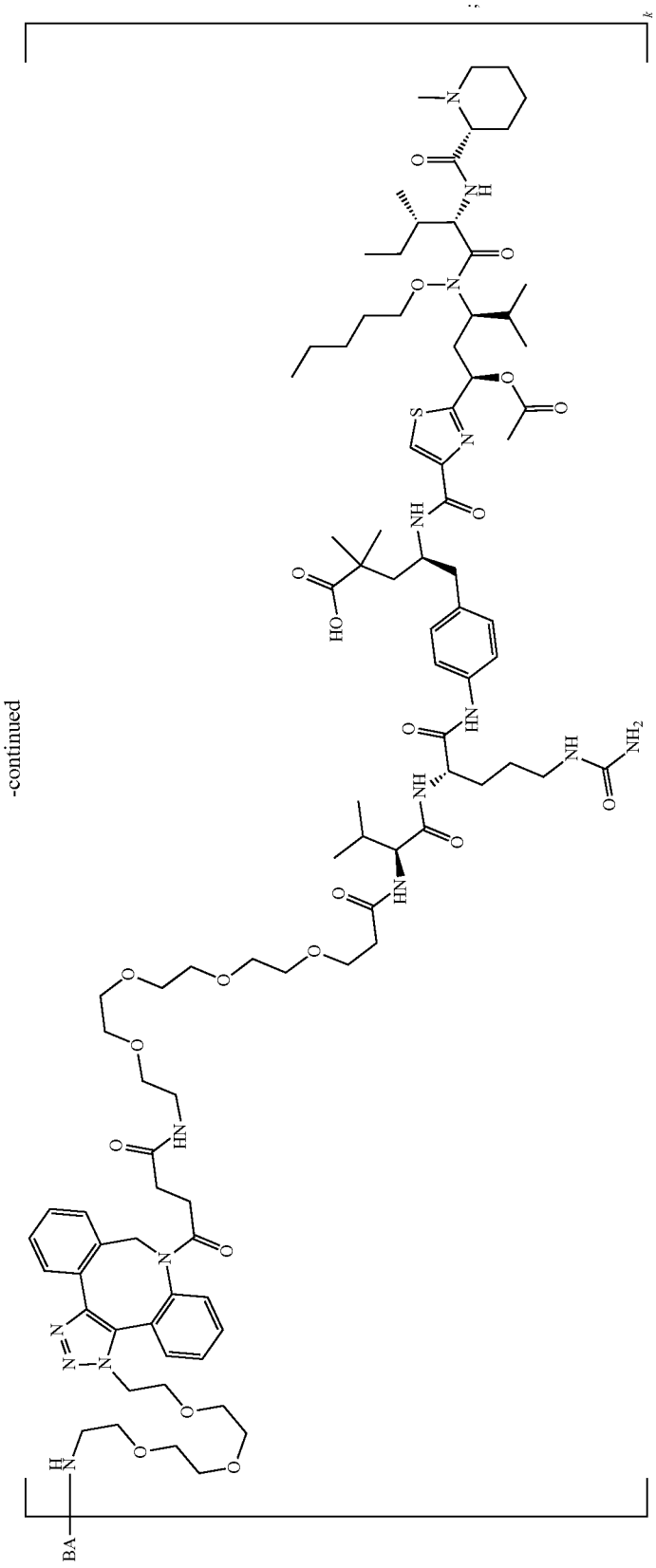

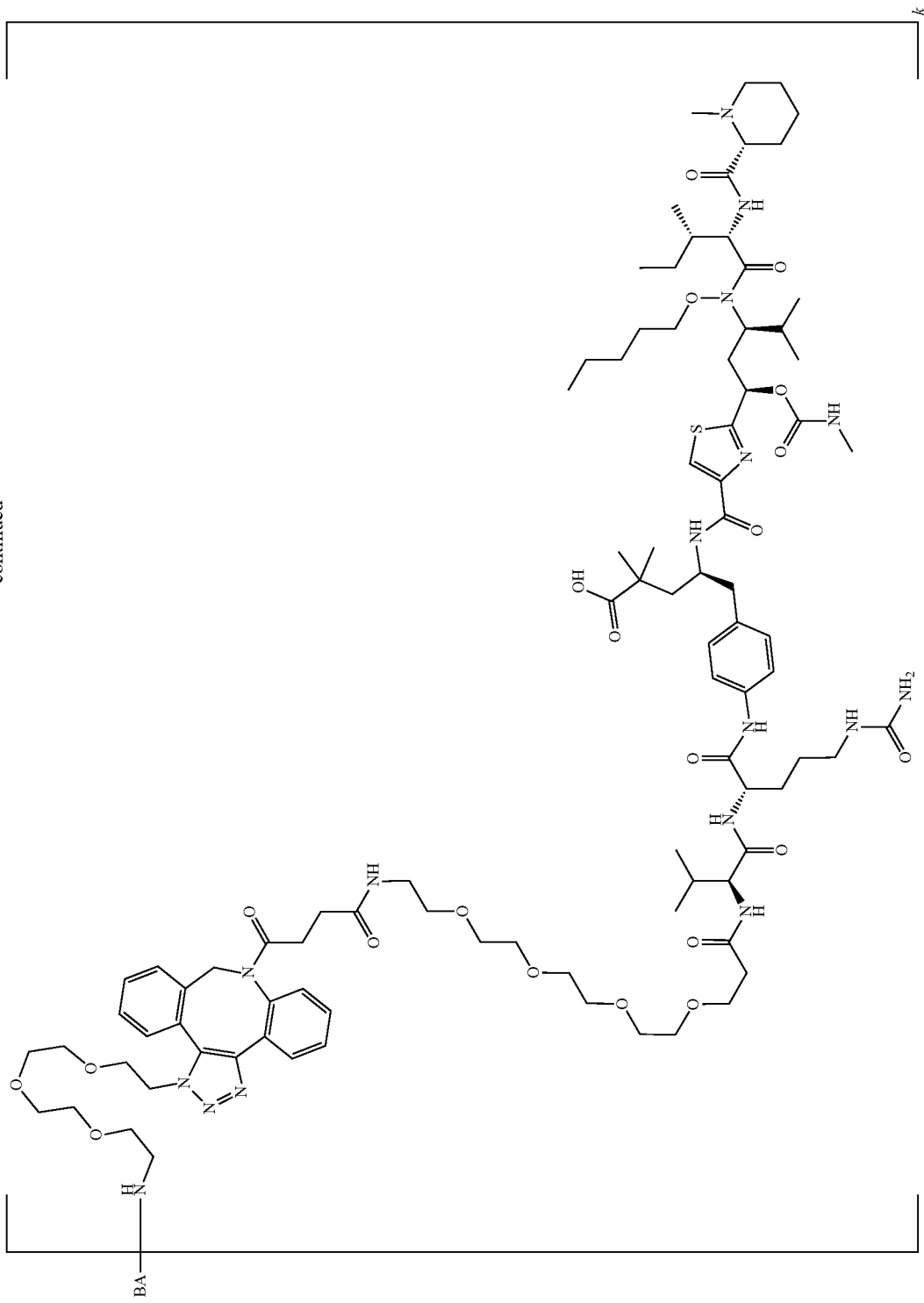

-continued
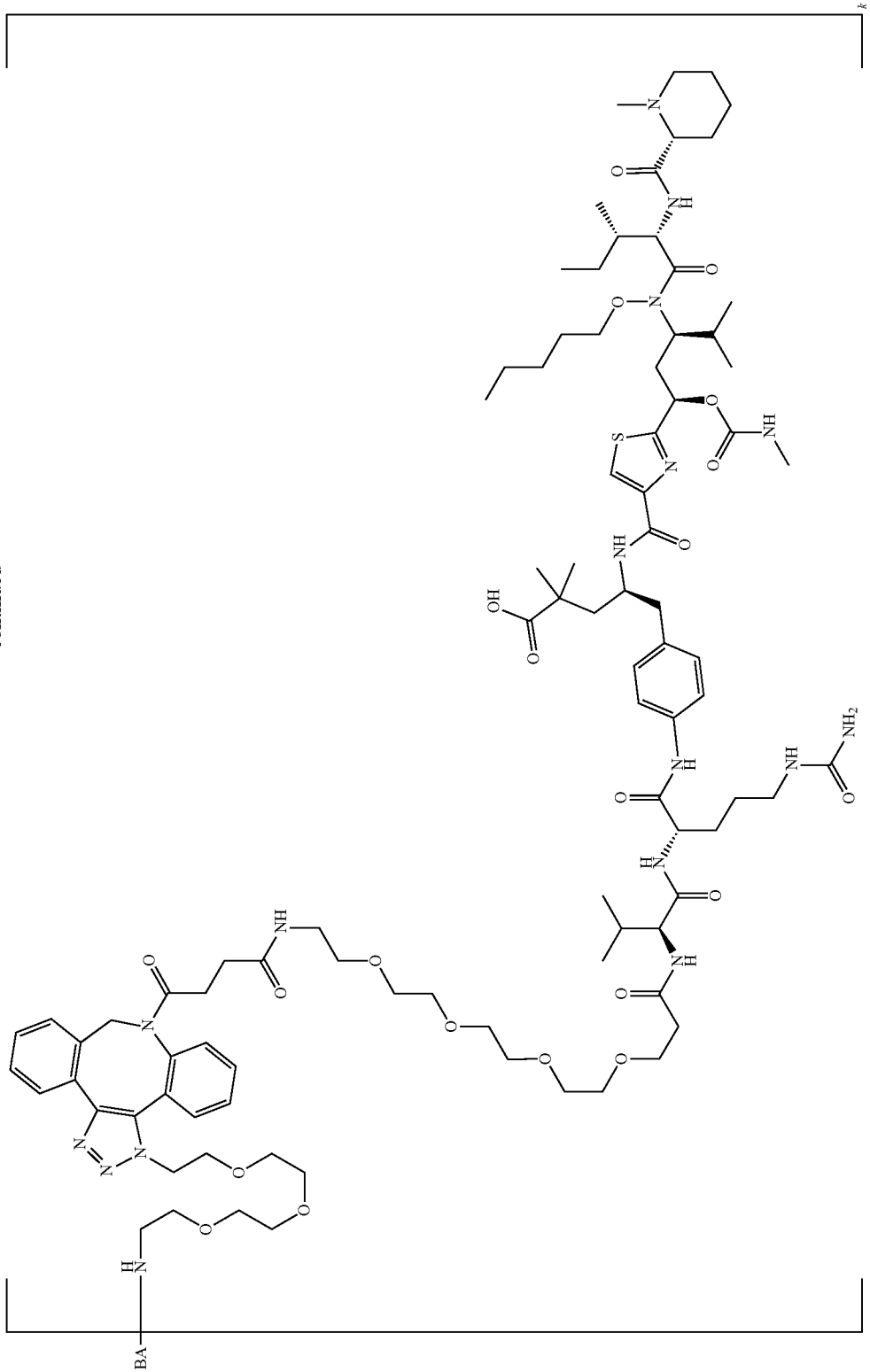

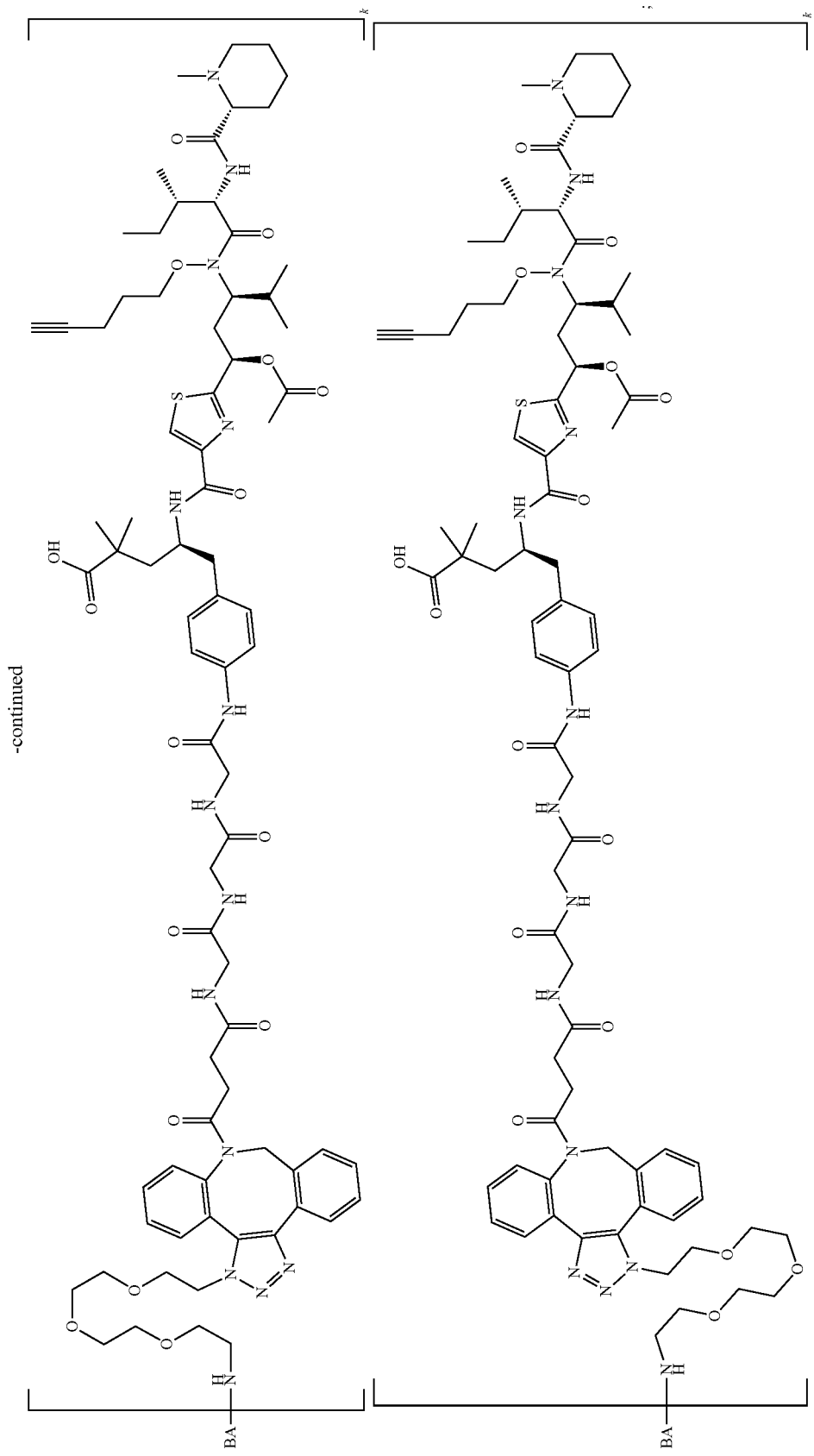

613 614
-continued
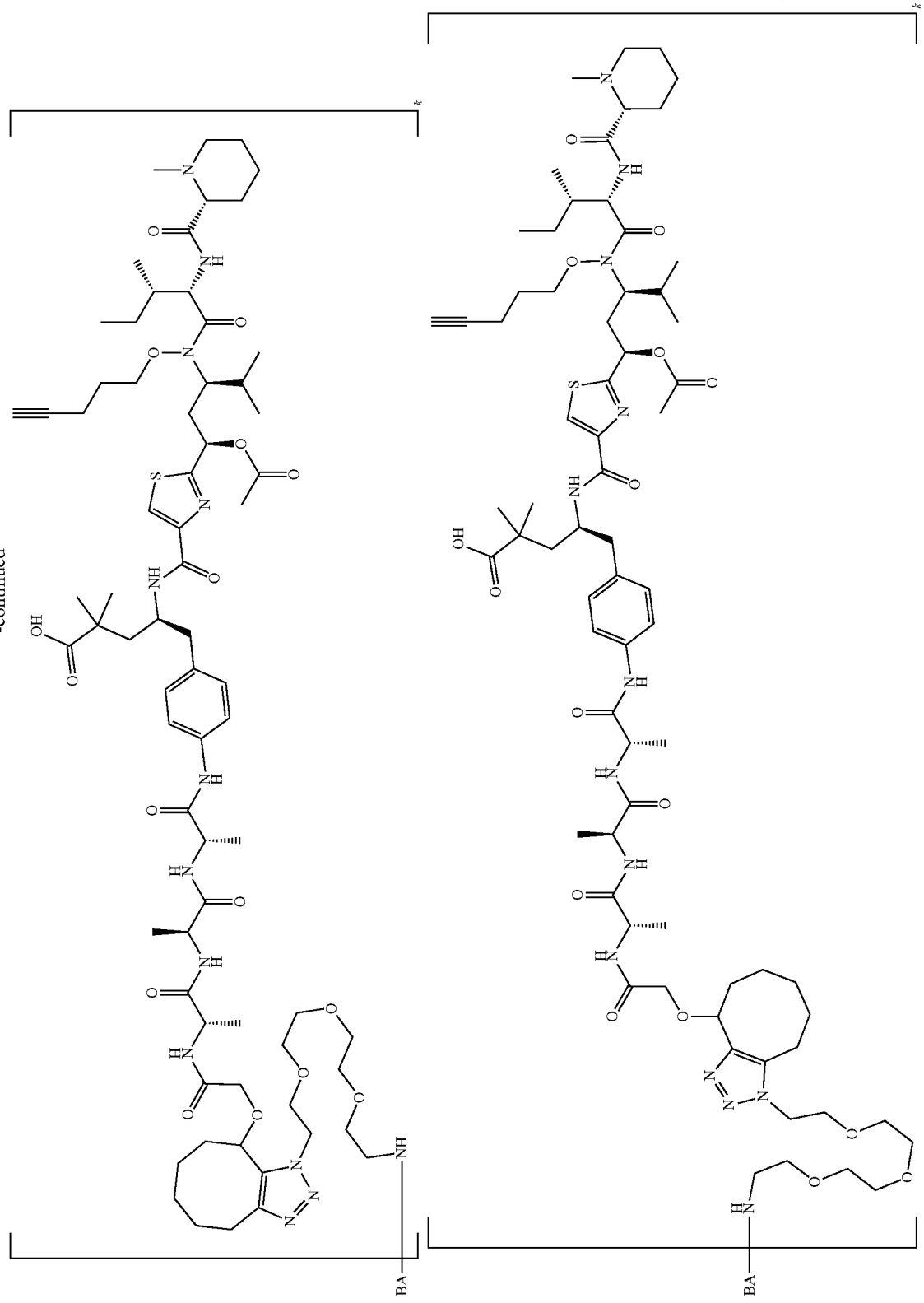

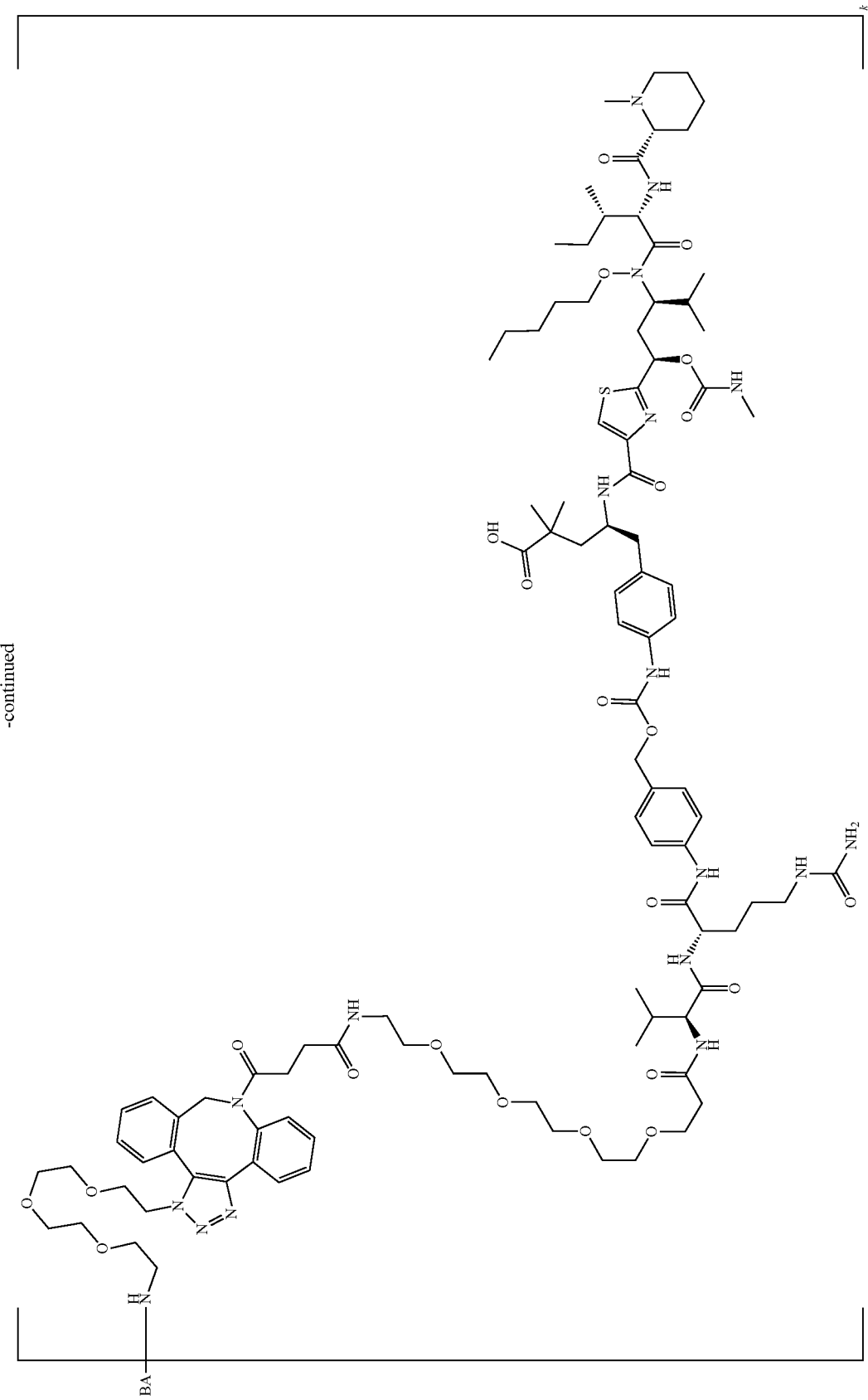

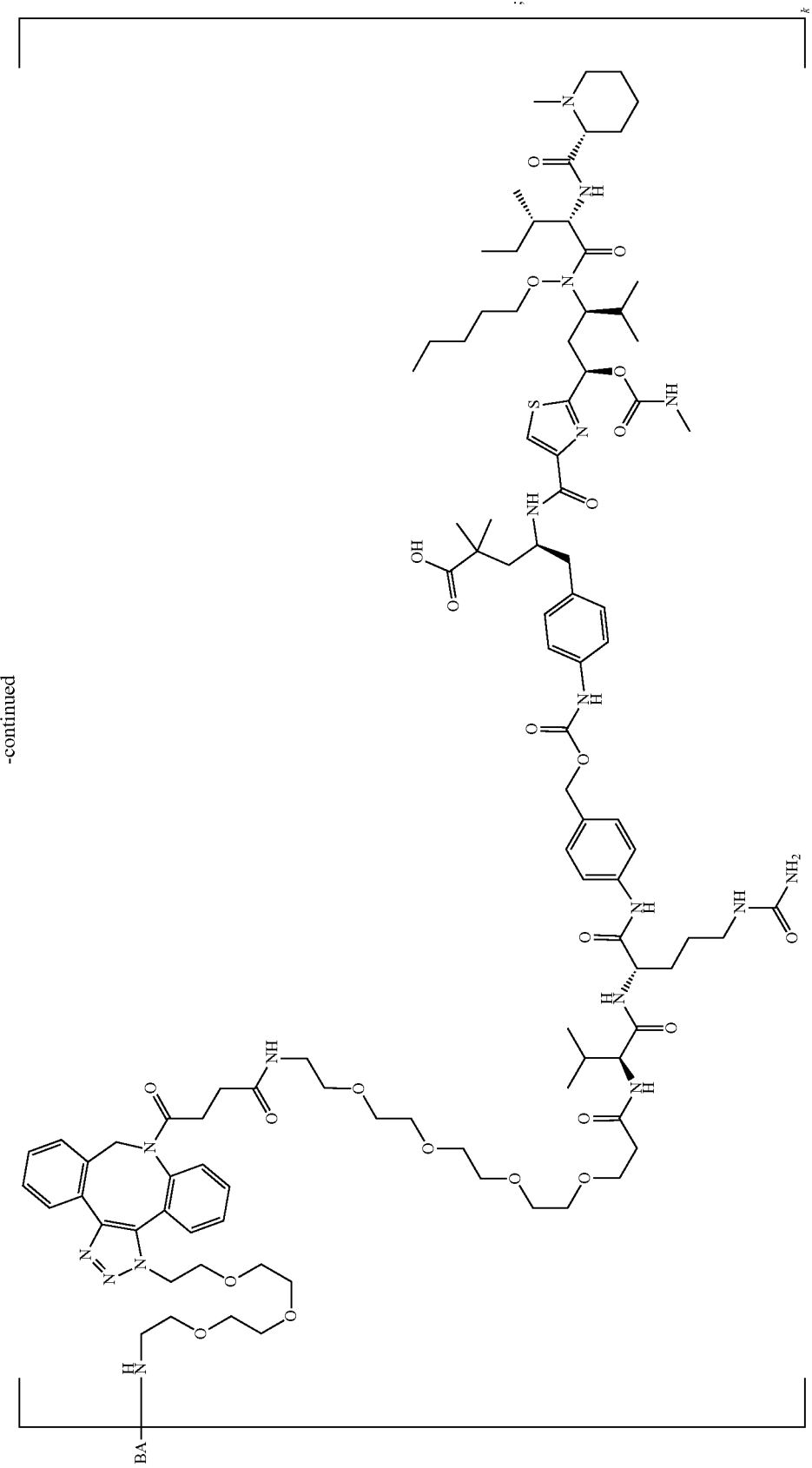

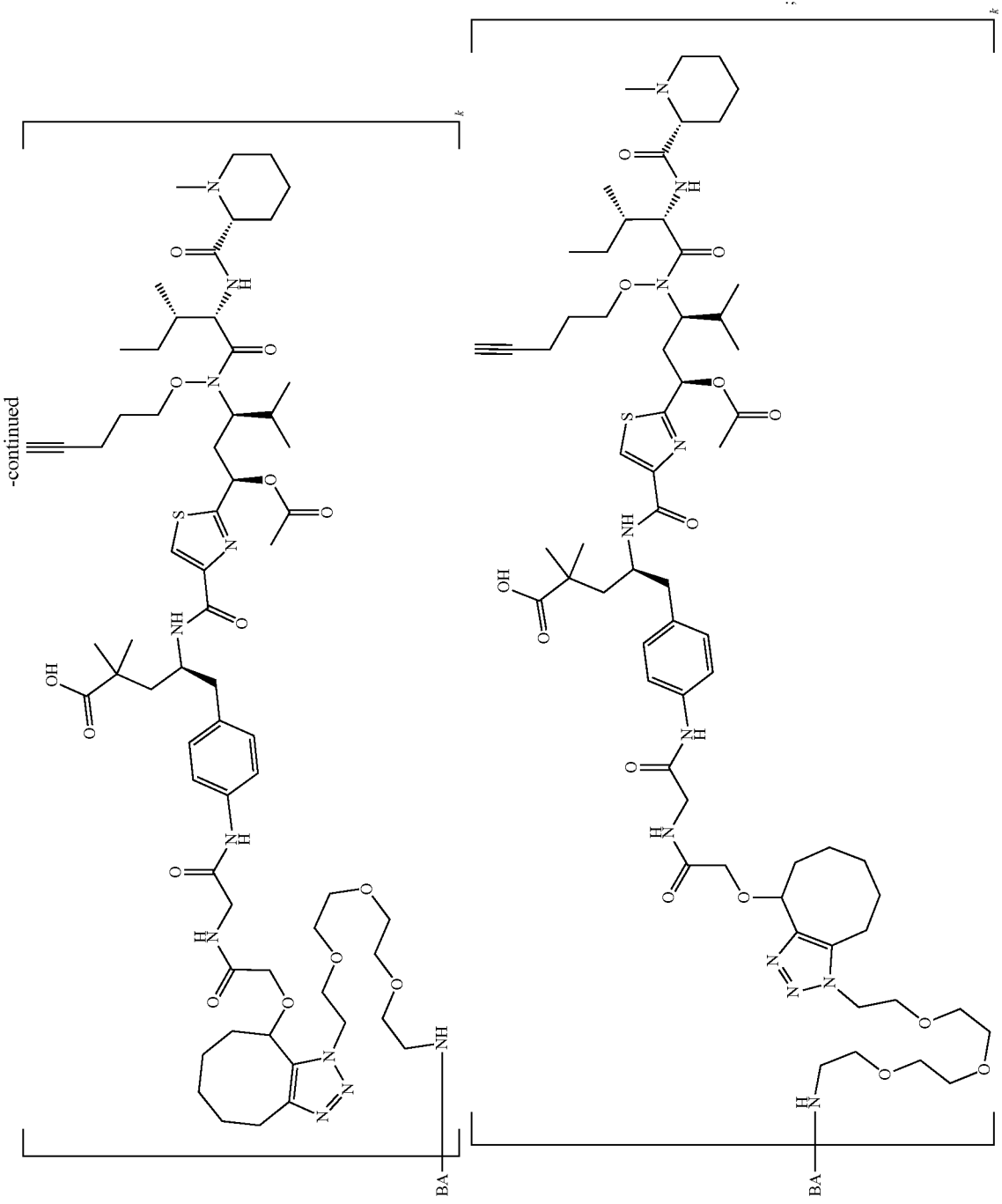

-continued
621
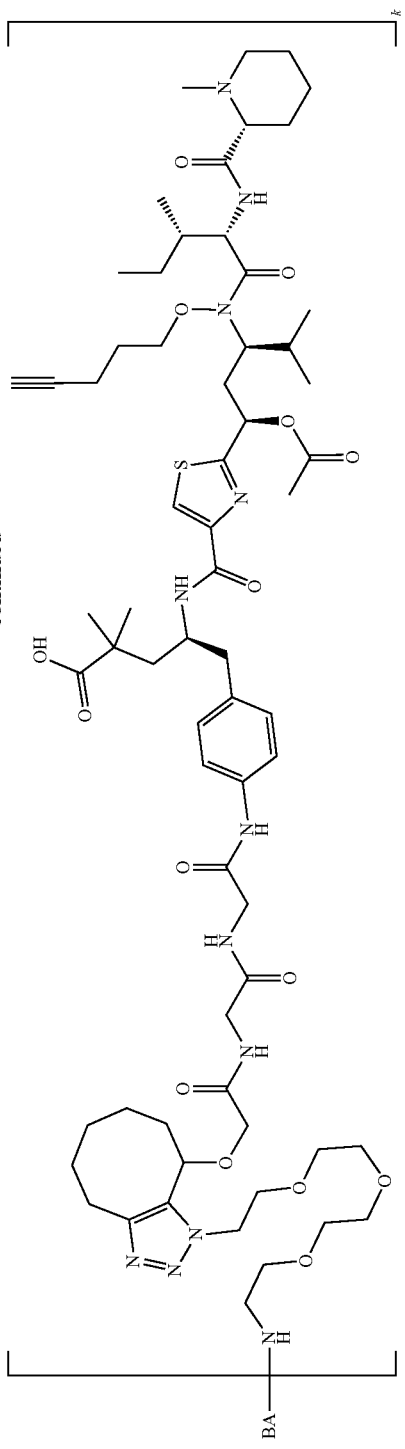
622
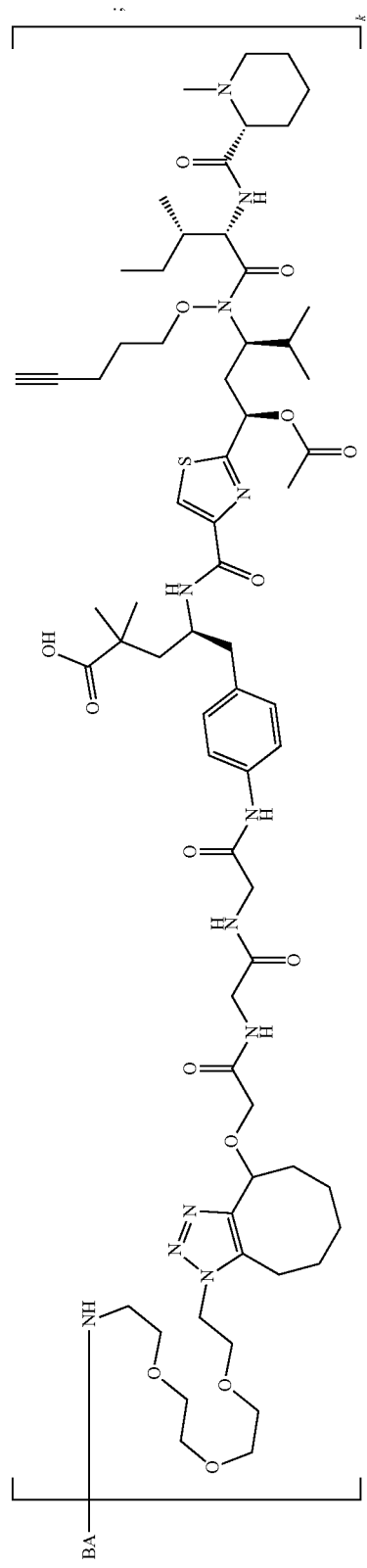

623
-continued
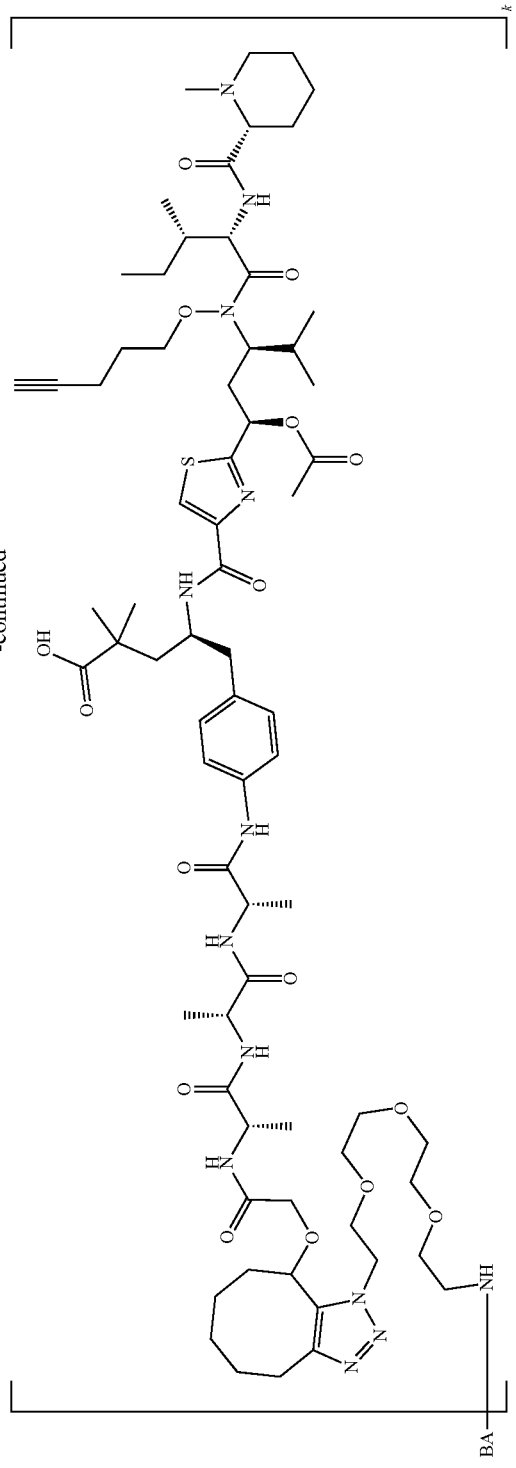
624
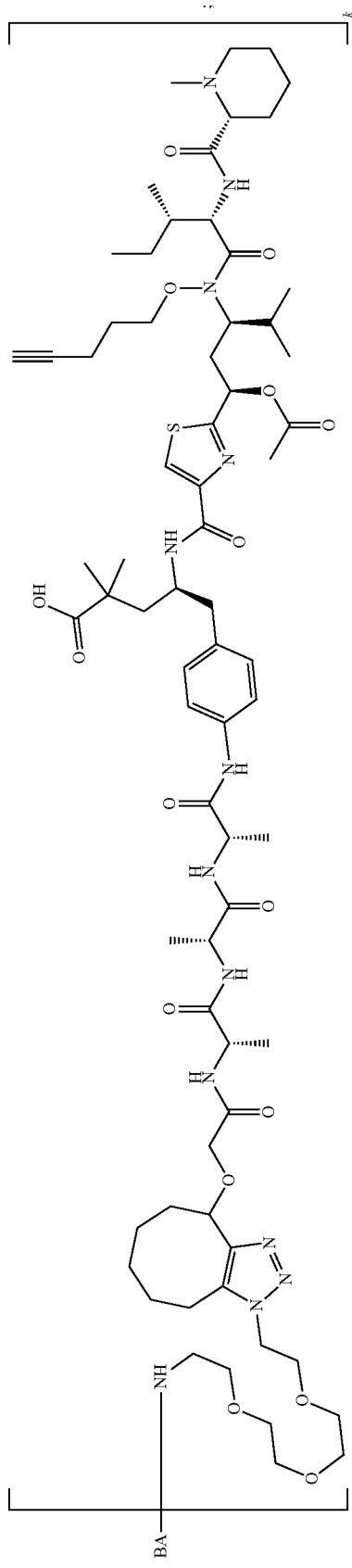

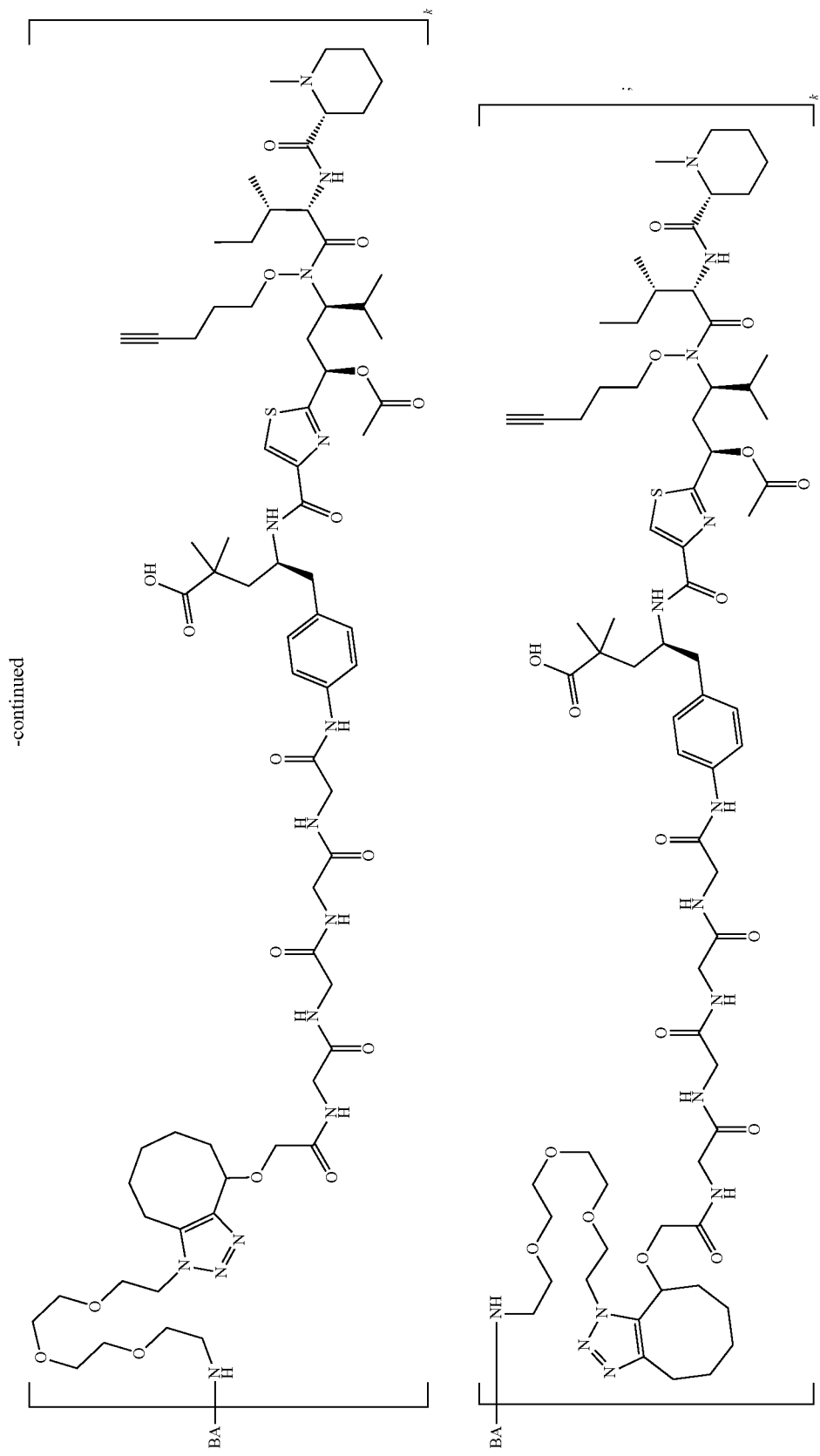

627
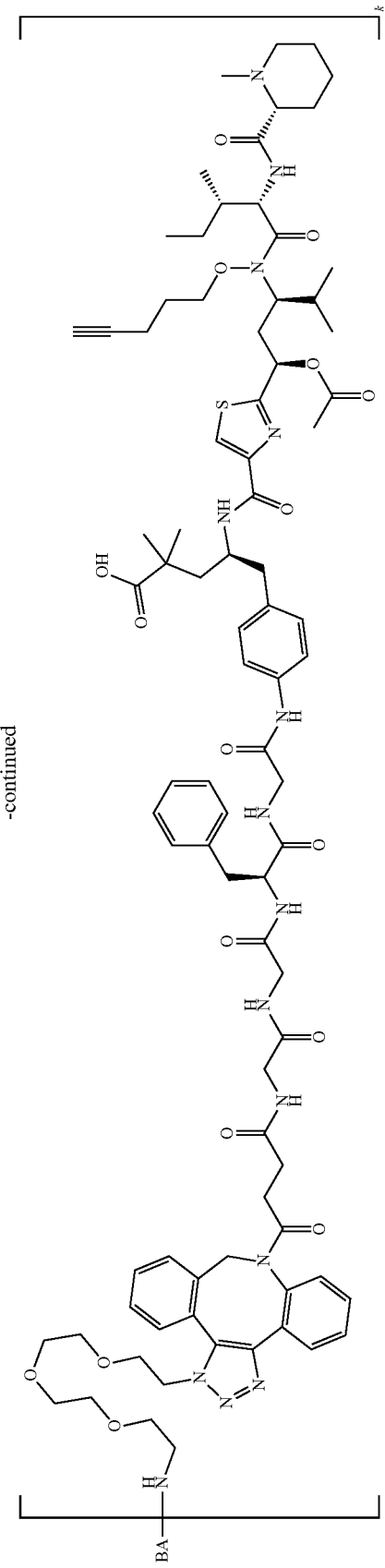
628
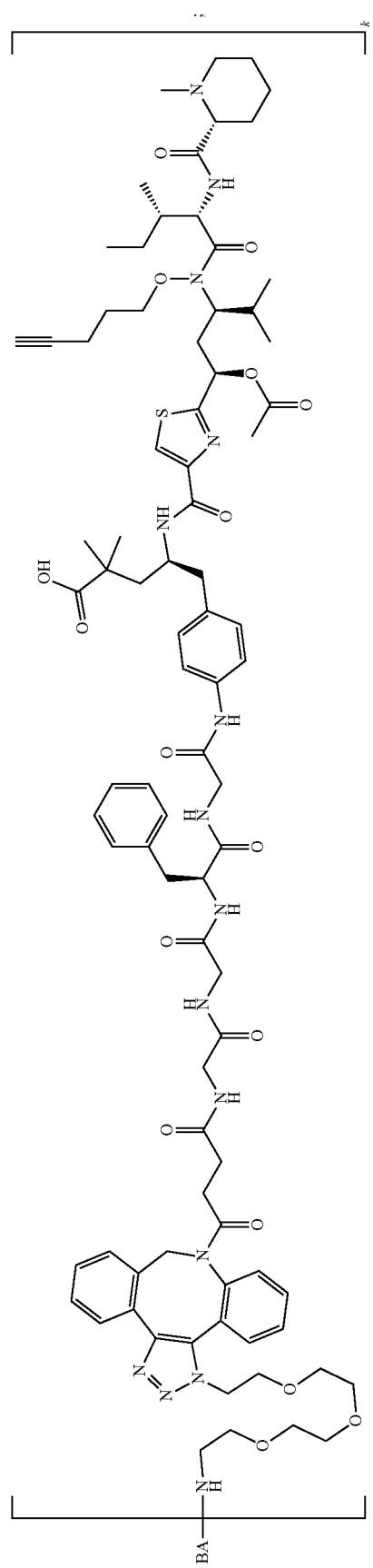

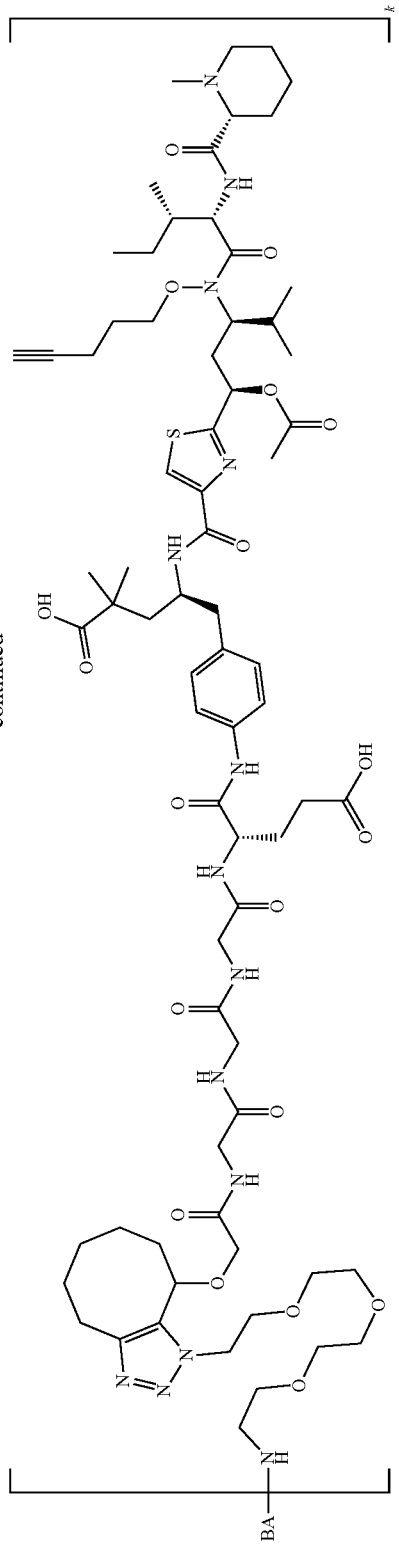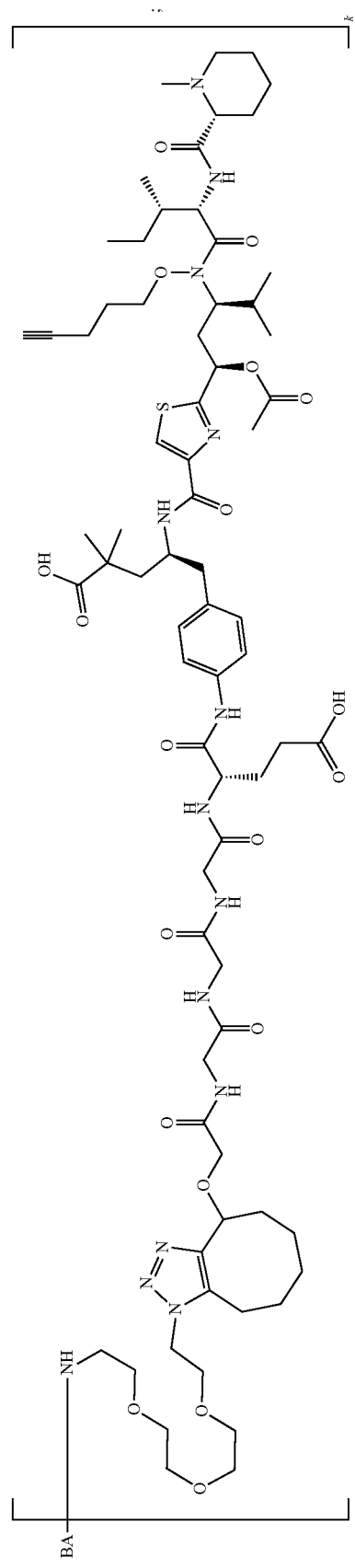

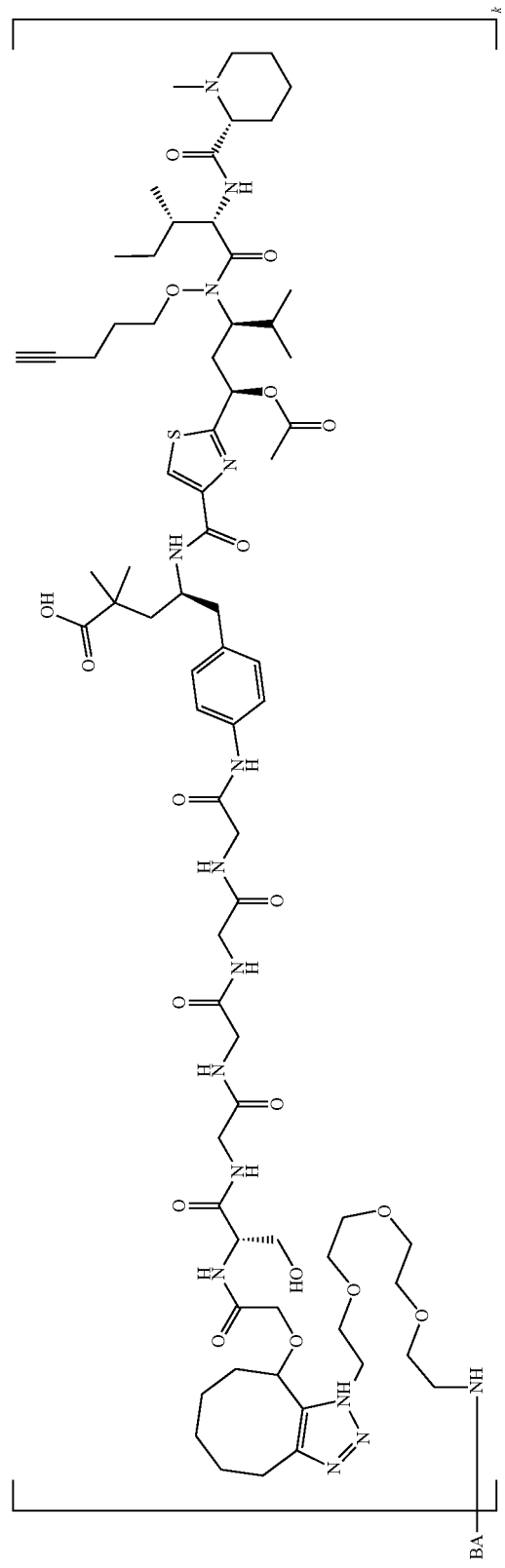

633
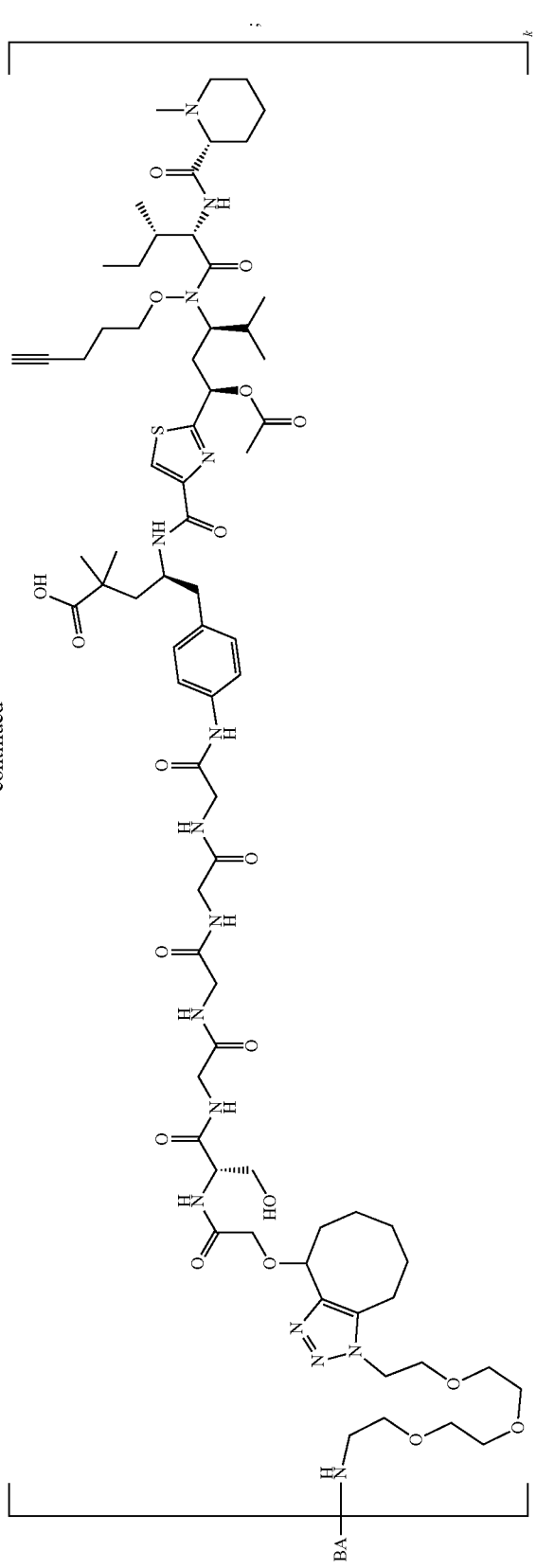
634
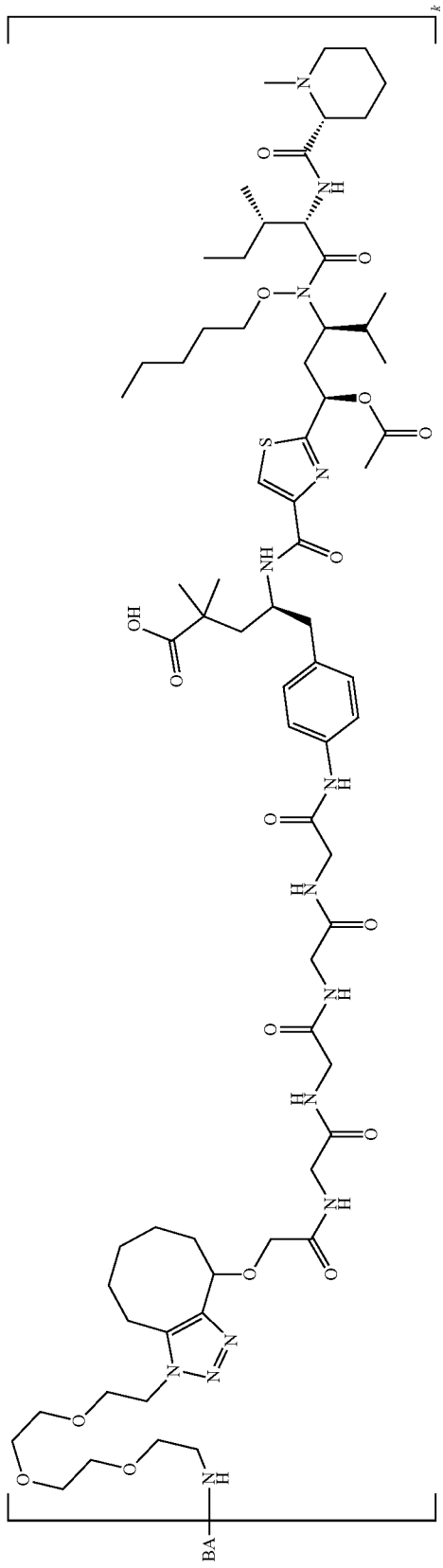

-continued
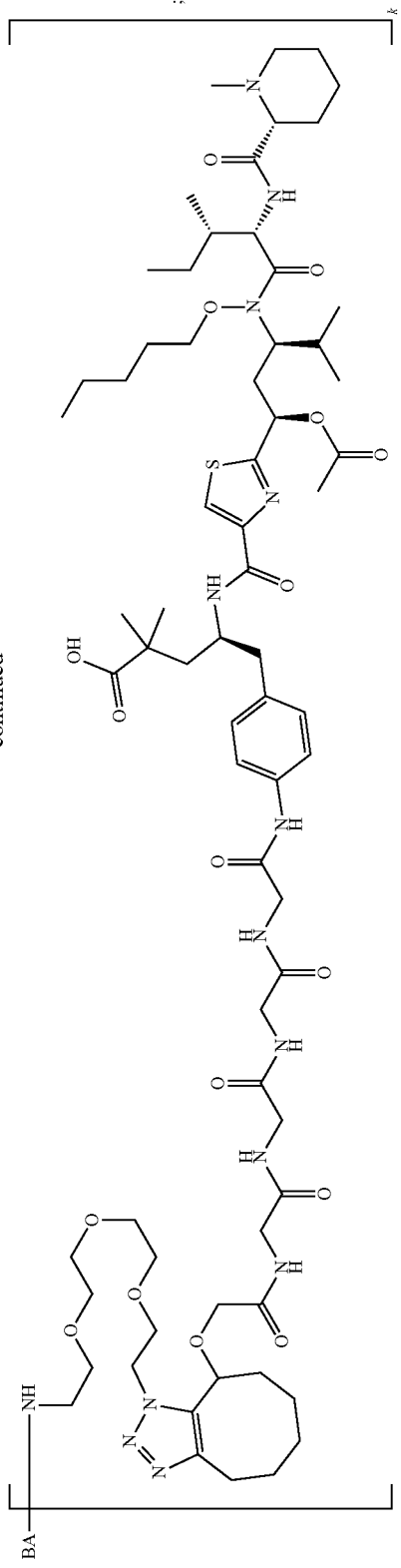
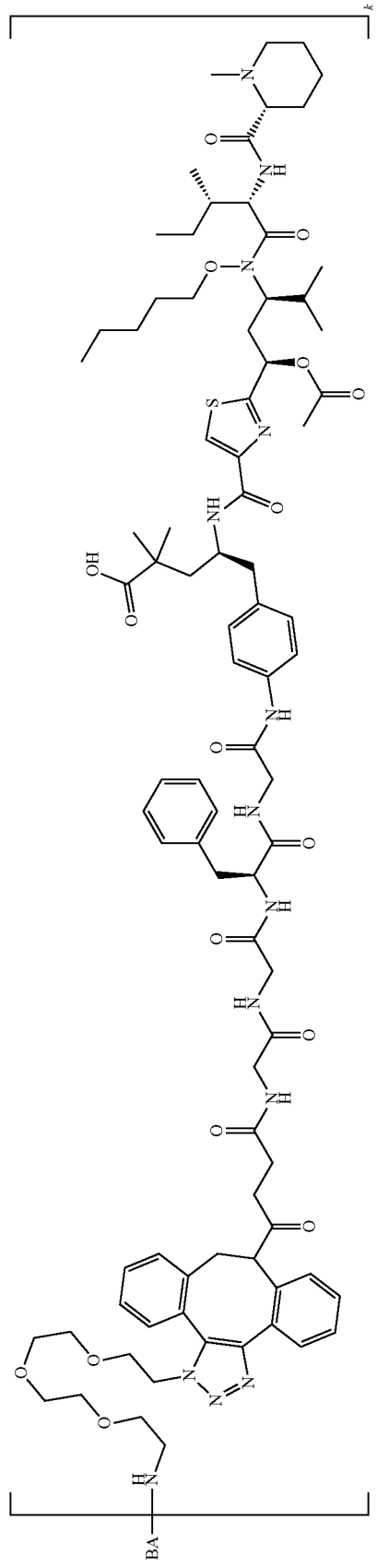

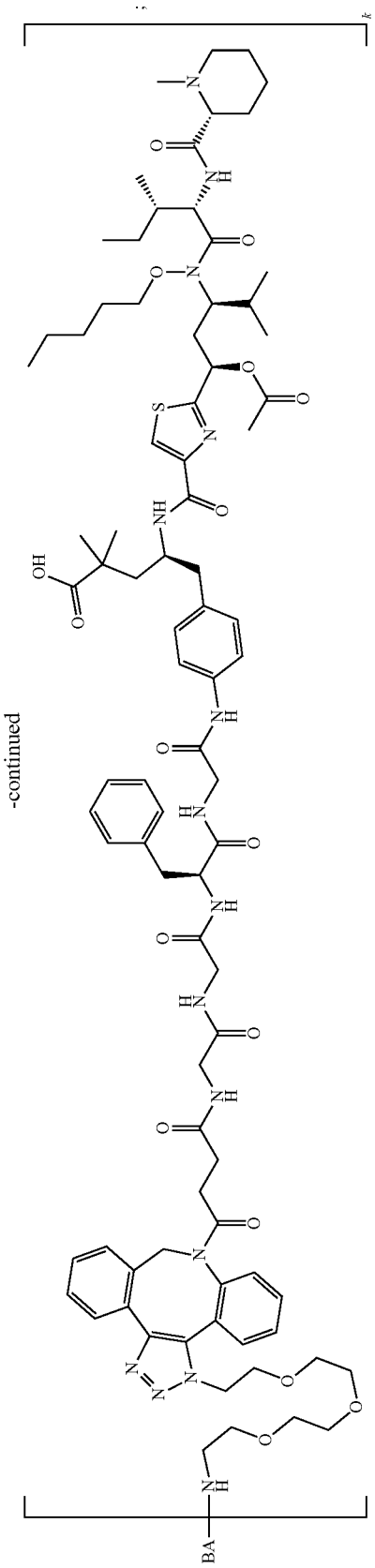
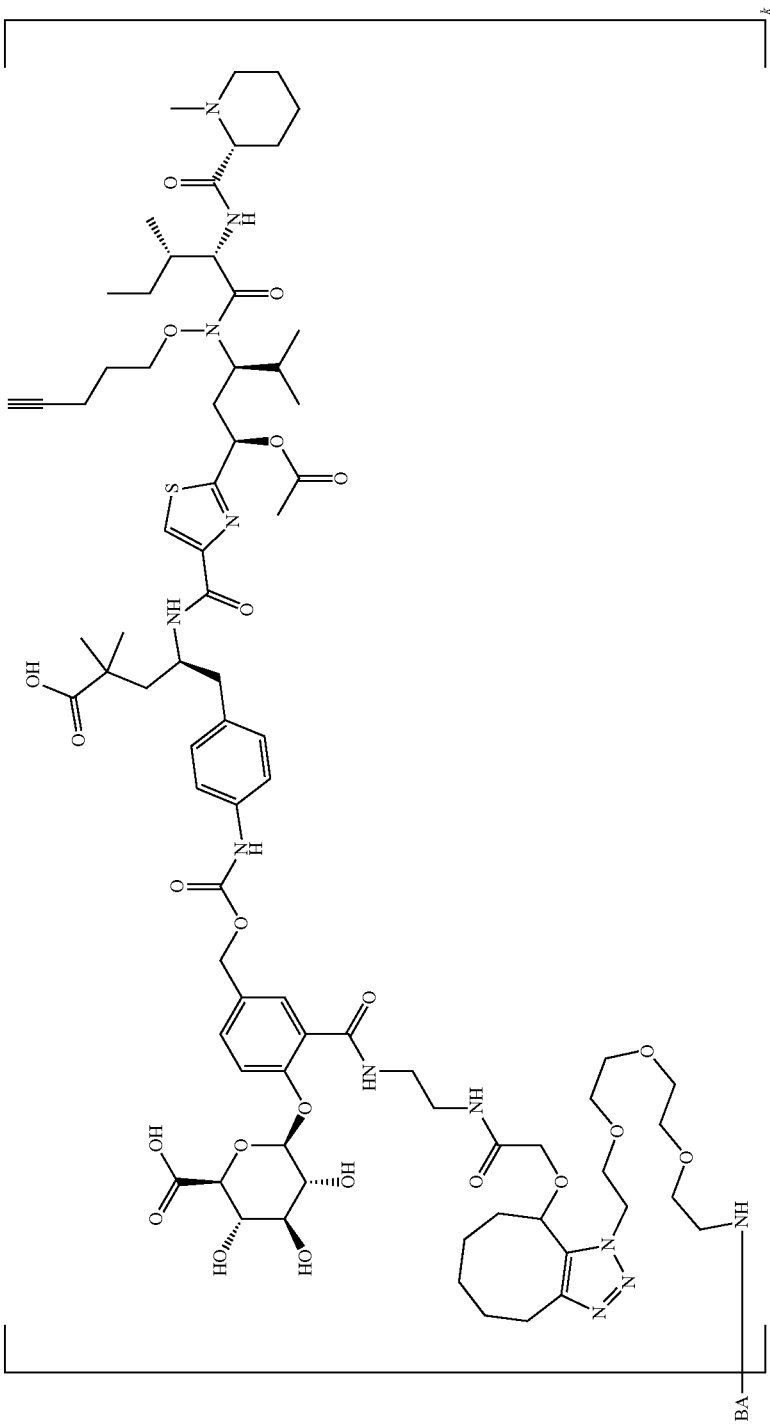

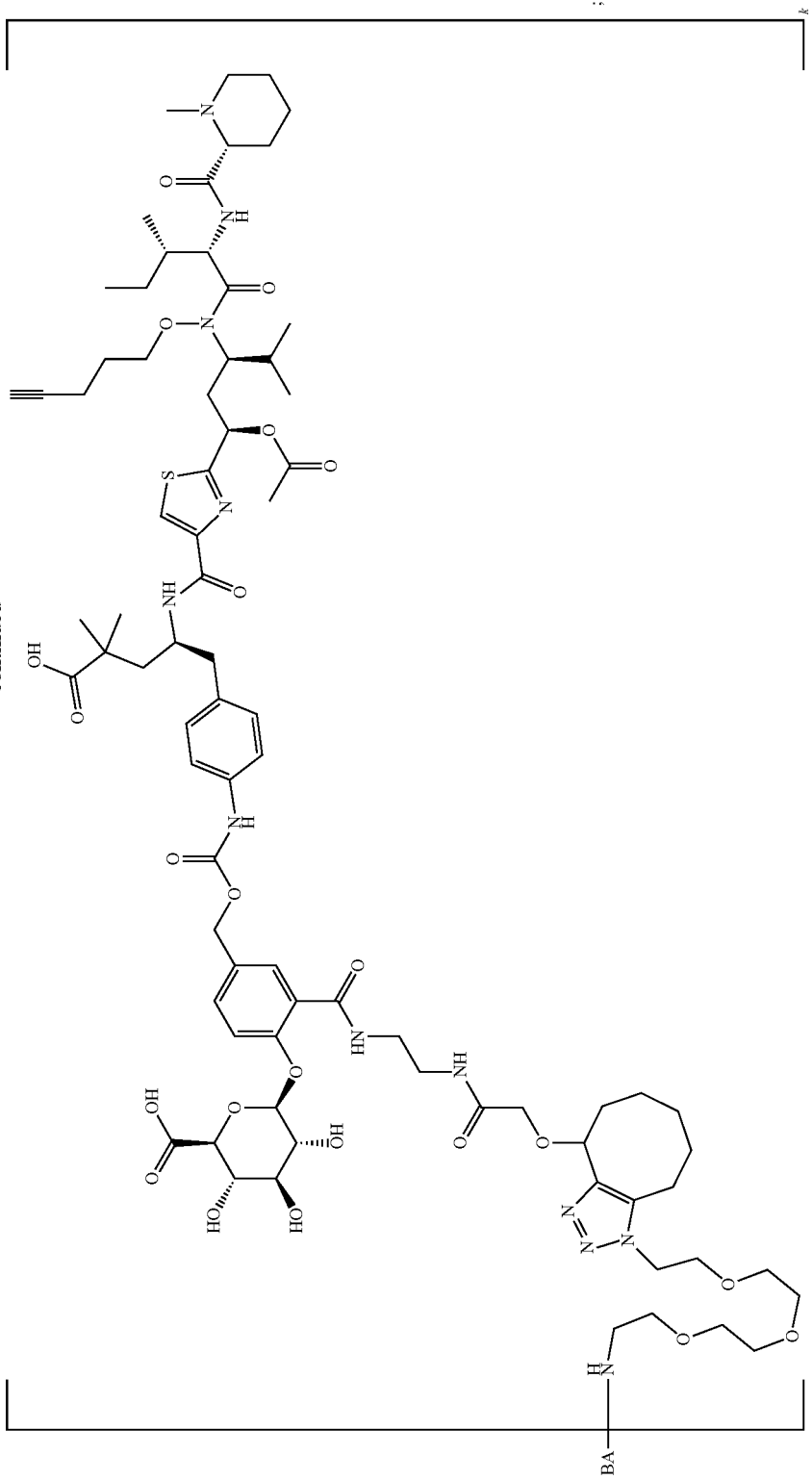

-continued
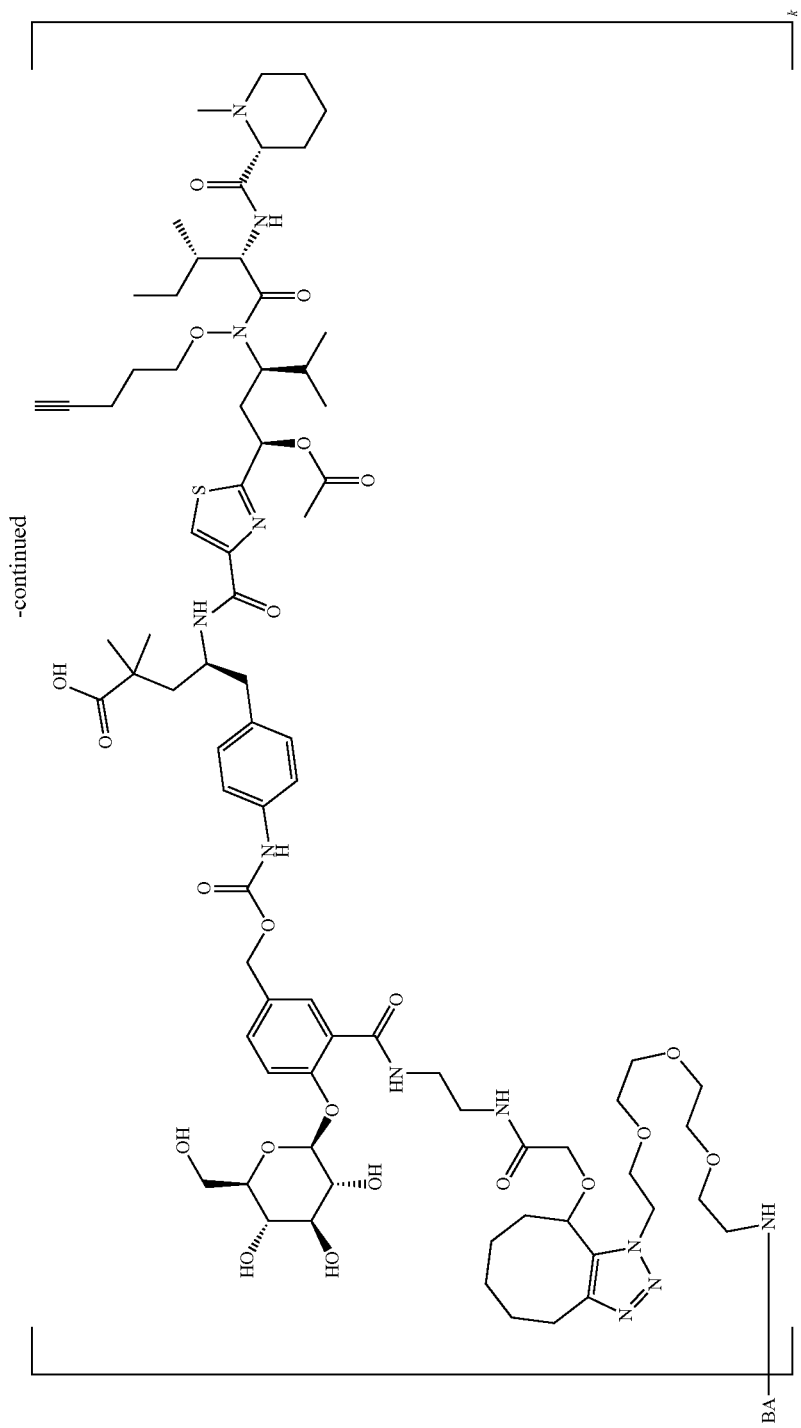

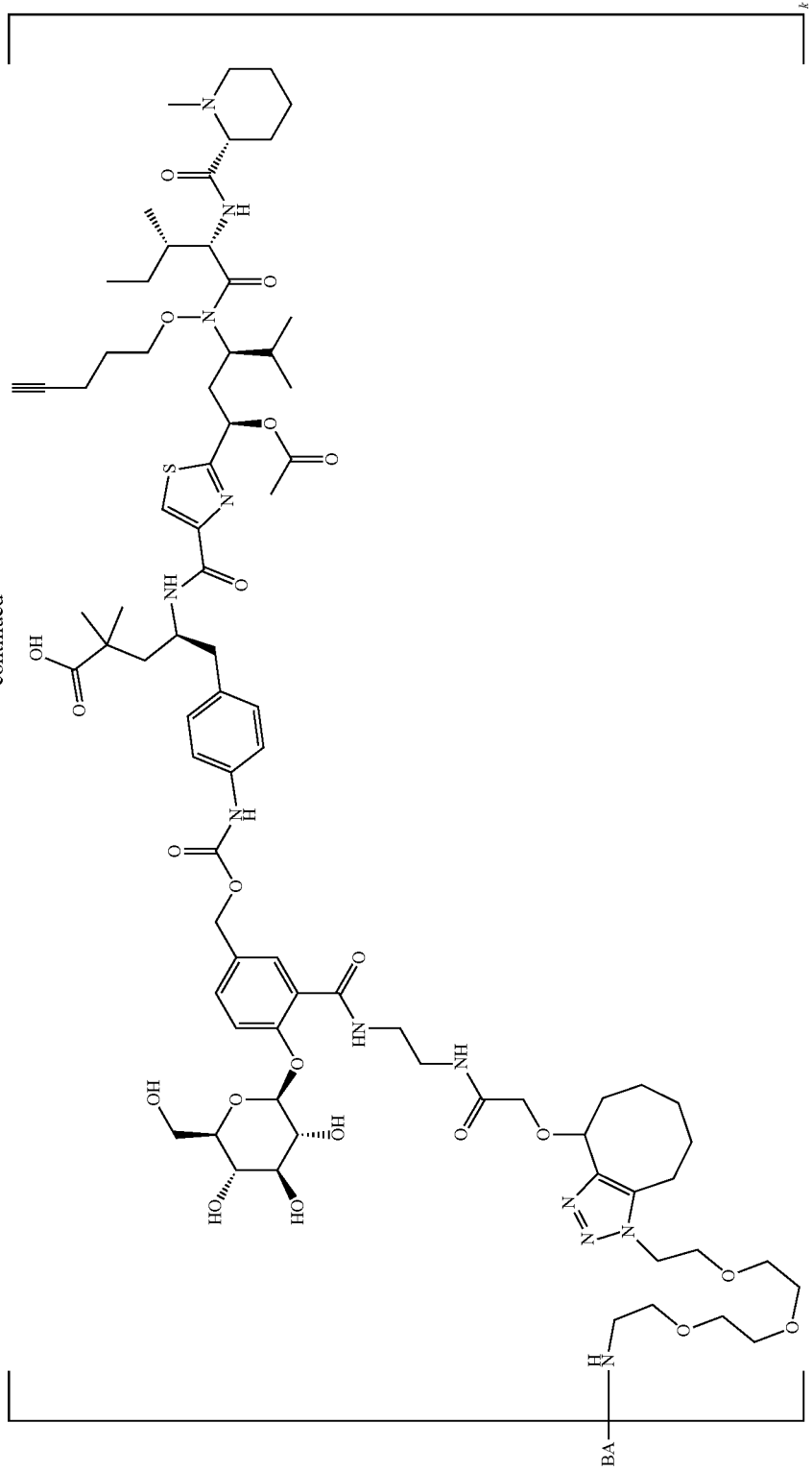

wherein BA is a binding agent; and k is one, two, three, or four.

8. The compound of claim 7, wherein the compound is

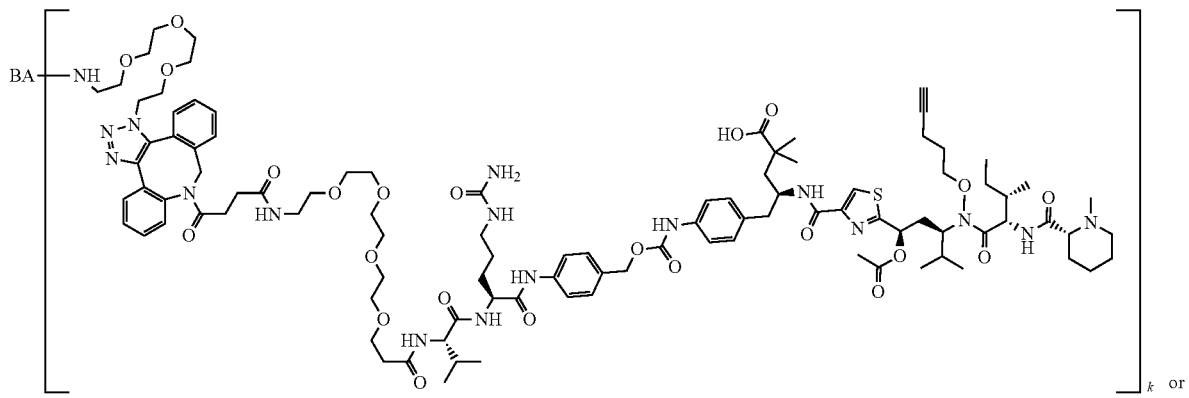

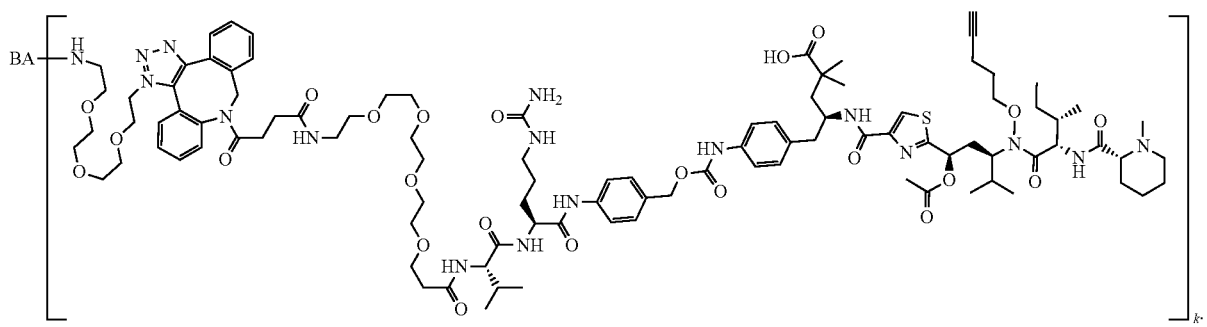

9. The compound of claim 8, wherein k is two or four.

10. The compound of claim 7, wherein BA is an antibody or antigen-binding fragment thereof.

11. The compound of claim 7, wherein BA is a transglutaminase-modified antibody or antigen-binding fragment thereof comprising at least one glutamine residue used for conjugation.

12. The compound of claim 7, wherein BA is a transglutaminase-modified antibody or antigen-binding fragment thereof comprising at least two glutamine residues used for conjugation.

13. The compound of claim 7, wherein BA is a transglutaminase-modified antibody or antigen-binding fragment thereof comprising at least four glutamine residues used for conjugation.

14. The compound of claim 13, wherein BA is a transglutaminase-modified antibody or antigen-binding fragment thereof wherein conjugation is at two Q295 residues; and k is two.

15. The compound of claim 13, wherein BA is a transglutaminase-modified antibody or antigen-binding fragment thereof wherein conjugation is at two Q295 residues and two N297Q residues; and k is four.

16. An antibody-drug conjugate comprising an antibody or antigen-binding fragment thereof conjugated to a compound selected from the group consisting of

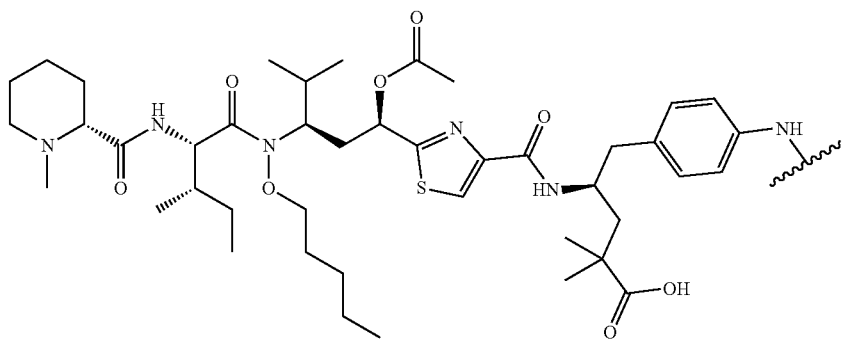

-continued
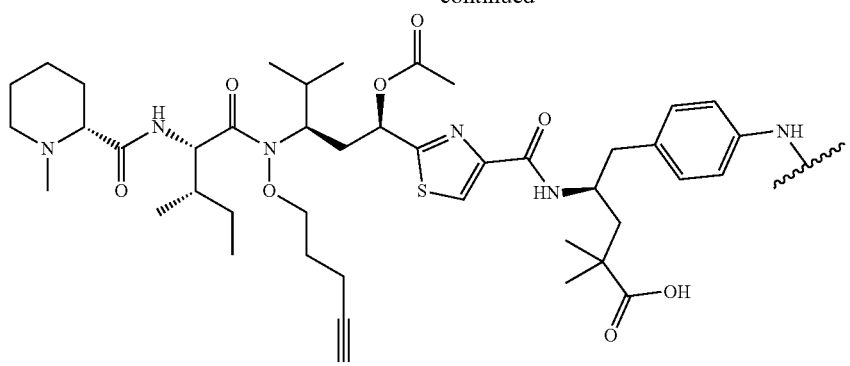
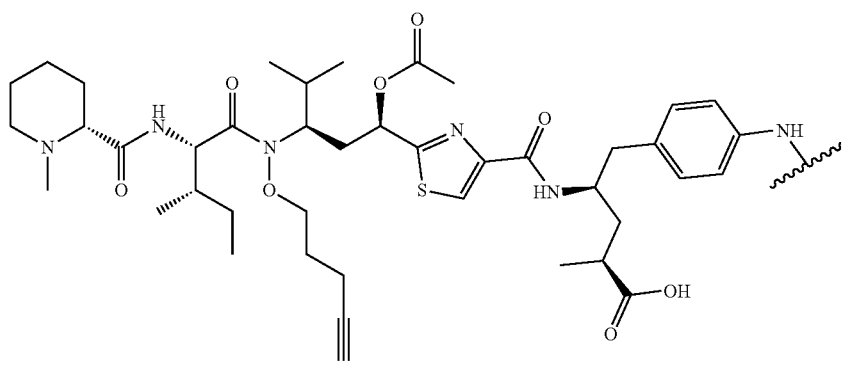
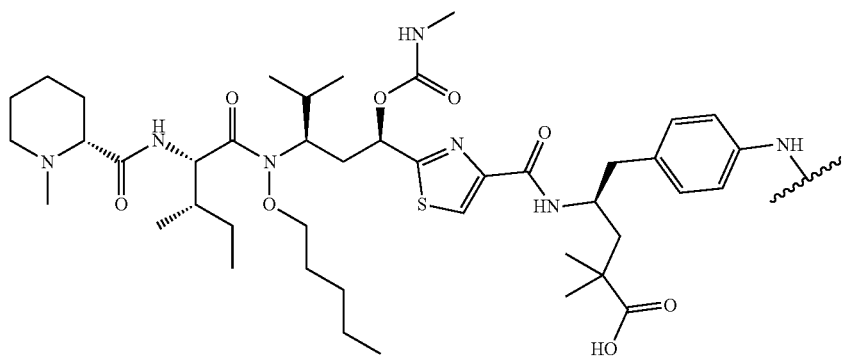
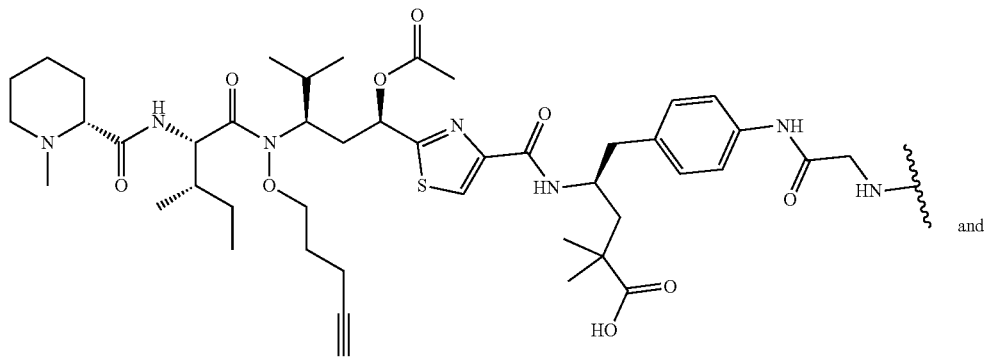
and

-continued

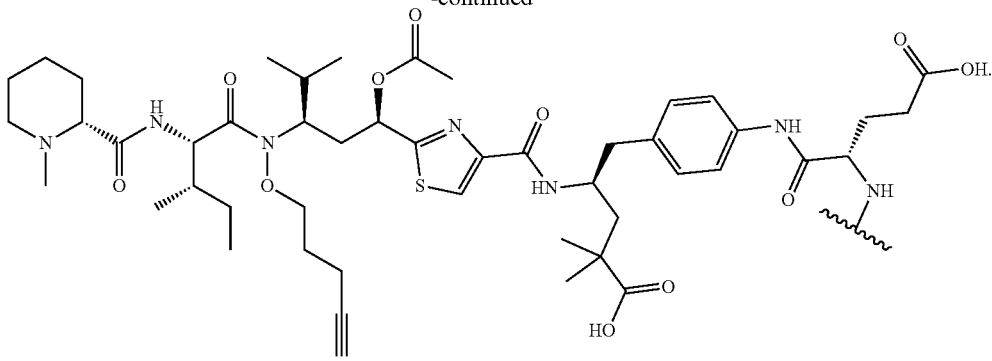

17. The compound of claim 16, wherein the compound is

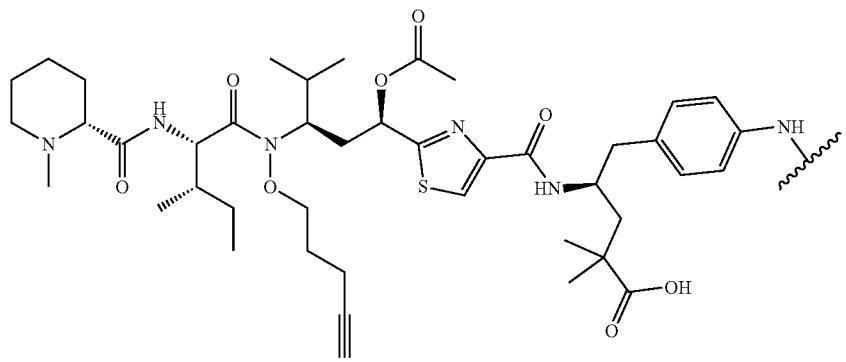

18. The compound of claim 7, wherein BA or the antibody or antigen-binding fragment thereof is selected from the group consisting of anti-MUC16, anti-PSMA, anti-EGFRvIII, anti-HER2, and anti-MET.

19. The compound of claim 7, wherein BA or the antibody or antigen-binding fragment thereof is anti-PRLR or anti-STEAP2.

20. The compound of claim 7, wherein BA or the antibody or antigen-binding fragment thereof binds to an antigen selected from the group consisting of lipoproteins; alpha1-antitrypsin; a cytotoxic T-lymphocyte associated antigen (CTLA), such as CTLA-4 or CTLA4; vascular endothelial growth factor (VEGF); receptors for hormones or growth factors; protein A or D; fibroblast growth factor receptor 2 (FGFR2), EpCAM or Epcam, GD3, FLT3, PSCA, MUC1 or Muc1, MUC16 or Muc16, STEAP, STEAP2 or Steap-2, CEA, TENB2, EphA receptors, EphB receptors, folate receptor, FOLRI, mesothelin, cripto, alphavbeta6, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80, CD81, CD103, CD105, CD134, CD137, CD138, CD152; erythropoietin; osteoinductive factors; immunotoxins; a bone morphogenetic protein (BMP); T-cell receptors; surface membrane proteins; integrins, such as CD11a, CD11b, CD11c, CD18, an ICAM, VLA-4 and VCAM; a tumor associated antigen such as AFP, ALK, B7H4, BAGE proteins, β-catenin, brc-abl, BRCA1, BORIS, CA9 (carbonic anhydrase IX), caspase-8, CD123, CDK4, CLEC12A, c-kit, cMET, c-MET, MET, cyclin-B1, CYP1B1, EGFRvIII, endoglin, EphA2, ErbB2/Her2, ErbB3/Her3, ErbB4/Her4, ETV6-AML, Fra-1, FOLR1, GAGE proteins such as GAGE-1 and GAGE-2, GD2, GloboH, glypican-3, GM3, gp100, Her2 or HER2, HLA/B-raf, HLA/EBNA1, HLA/k-ras, HLA/MAGE-A3, hTERT, IGF1R, LGR5, LMP2, MAGE proteins such as MAGE-1, -2, -3, -4, -6, and -12, MART-1, ML-IAP, CA-125, MUM1, NA17, NGEP, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSGR, PSMA (FOLH1), RAGE proteins, Ras, RGS5, Rho, SART-1, SART-3, Steap-1, STn, survivin, TAG-72, TGF-β, TMPRSS2, Tn, TNFRSF17, TRP-1, TRP-2, tyrosinase, uroplakin-3, fragments of any of the above-listed polypeptides; cell-surface expressed antigens; molecules such as class A scavenger receptors including scavenger receptor A (SR-A), and other membrane proteins such as B7 family-related member including V-set and Ig domain-containing 4 (VSIG4), Colony stimulating factor 1 receptor (CSF1R), asialoglycoprotein receptor (ASGPR), and Amyloid beta precursor-like protein 2 (APLP-2); BCMA; SLAMF7; GPNMB; and UPK3A.

21. A compound having the structure of Formula I

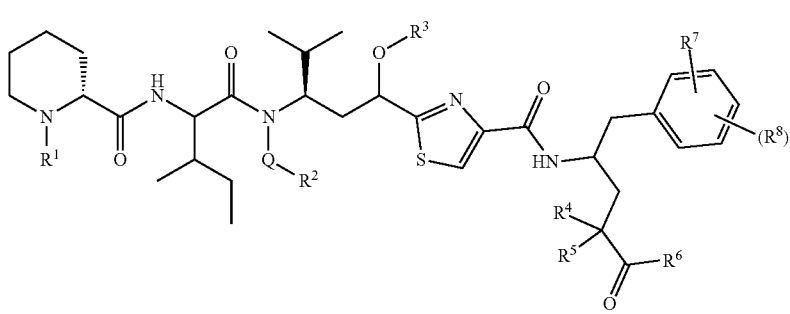

Formula I or a pharmaceutically acceptable salt thereof, wherein $R^1$ is $C_1$-$C_{10}$ alkyl;

$R^3$ is —C(O)$C_1$-$C_5$ alkyl, —C(O)N(H)$C_1$-$C_{10}$ alkyl, or —($C_1$-$C_{10}$ alkylene)-NR$^{3a}$R$^{3b}$,
  wherein R$^{3a}$ and R$^{3b}$ are independently in each instance, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl, wherein $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and/or $C_2$-$C_{20}$ acyl;

$R^4$ and $R^5$ are, independently in each instance, hydrogen or $C_1$-$C_5$ alkyl;

$R^6$ is —OH or —NHNH$_2$;

$R^7$ is, independently in each instance, hydrogen, —OH, halogen, or —NR$^{7a}$R$^{7b}$,
  wherein R$^{7a}$ and R$^{7b}$ are independently in each instance, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, acyl, and amino acid residue, wherein $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and/or acyl;

$R^8$ is, independently in each instance, hydrogen, deuterium, —NHR$^9$, or halogen,
  wherein R$^9$ is hydrogen, —$C_1$-$C_5$ alkyl, or —C(O)$C_1$-$C_5$ alkyl; and m is one or two;

Q is oxygen;

$R^2$ is $C_1$-$C_{10}$ alkyl, $C_3$-$C_{10}$ alkynyl, —$C_1$-$C_{10}$ alkylene-(5-membered heteroaryl), —$C_1$-$C_3$ alkylene-Q$^1$-(CH$_2$)$_n$aryl, or $C_1$-$C_3$ hydroxyalkyl; and Q$^1$ is —CH$_2$— or —O—;

wherein said heteroaryl is unsubstituted or substituted with $C_1$-$C_{20}$ alkyl, aminoalkyl, hydroxylalkyl, carboxyalkyl, benzyl, or phenyl;

wherein said aryl is unsubstituted or substituted with nitro or amino; and wherein n is an integer from one to five.

22. The compound of claim 21, wherein $R^1$ is $C_1$-$C_{10}$ alkyl;

$R^3$ is —C(O)$C_1$-$C_5$ alkyl, —C(O)N(H)$C_1$-$C_{10}$ alkyl, or —($C_1$-$C_{10}$ alkylene)-NR$^{3a}$R$^{3b}$,
  wherein R$^{3a}$ and R$^{3b}$ are independently in each instance, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl, wherein $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and/or $C_2$-$C_{20}$ acyl;

$R^4$ and $R^5$ are, independently in each instance, hydrogen or $C_1$-$C_5$ alkyl;

$R^6$ is —OH or —NHNH$_2$;

$R^7$ is, independently in each instance, hydrogen, —OH, halogen, or —NR$^{7a}$R$^{7b}$,
  wherein R$^{7a}$ and R$^{7b}$ are independently in each instance, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and acyl, wherein $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and/or acyl;

$R^8$ is, independently in each instance, hydrogen, deuterium, —NHR$^9$, or halogen,
  wherein R$^9$ is hydrogen, —$C_1$-$C_5$ alkyl, or —C(O)$C_1$-$C_5$ alkyl; and m is one or two;

Q is oxygen;

$R^2$ is $C_1$-$C_{10}$ alkyl, $C_3$-$C_{10}$ alkynyl, —$C_1$-$C_{10}$ alkylene-(5-membered heteroaryl), —$C_1$-$C_3$ alkylene-Q$^1$-(CH$_2$)$_n$aryl, or $C_1$-$C_3$ hydroxyalkyl; and Q$^1$ is —CH$_2$— or —O—;

wherein said heteroaryl is unsubstituted or substituted with $C_1$-$C_{20}$ alkyl, aminoalkyl, hydroxylalkyl, carboxyalkyl, benzyl, or phenyl;

wherein said aryl is unsubstituted or substituted with nitro or amino; and wherein n is an integer from one to five.

23. The compound of claim 21, wherein

Q is —O—;

$R^2$ is $C_3$-$C_{10}$ alkynyl;

$R^3$ is —C(O)$C_1$-$C_5$ alkyl; and $R^6$ is —OH.

24. The compound of claim 23, according to the structure of Formula X
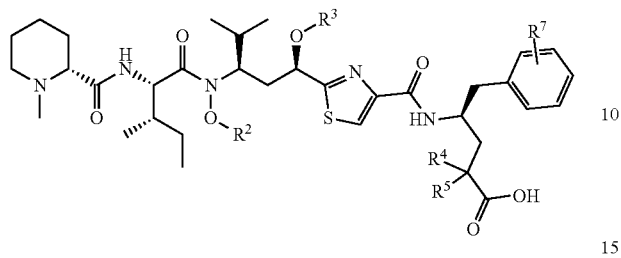
Formula X
or a pharmaceutically acceptable salt thereof.
25. The compound of claim 24, selected from the group consisting of
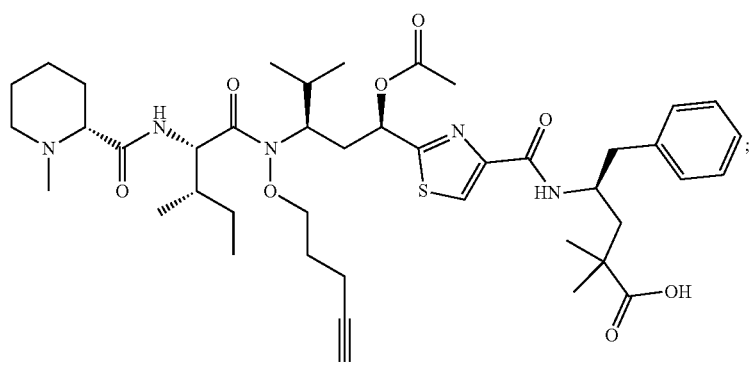
;
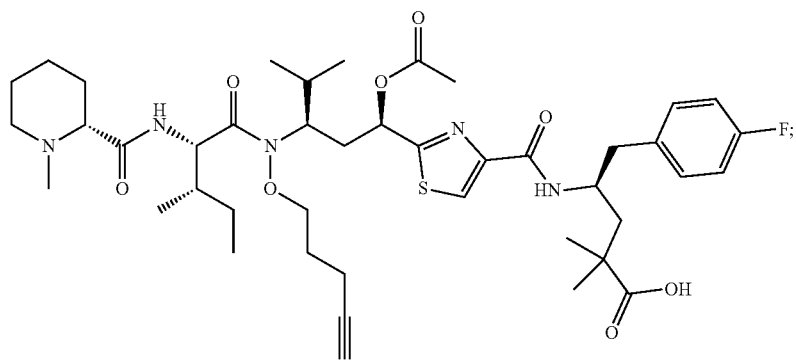
;
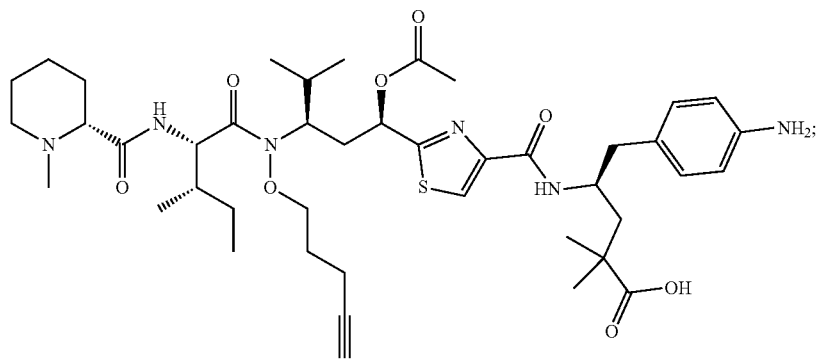
;

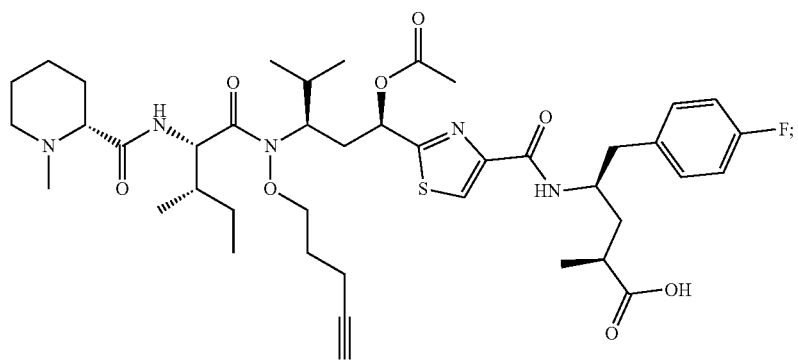
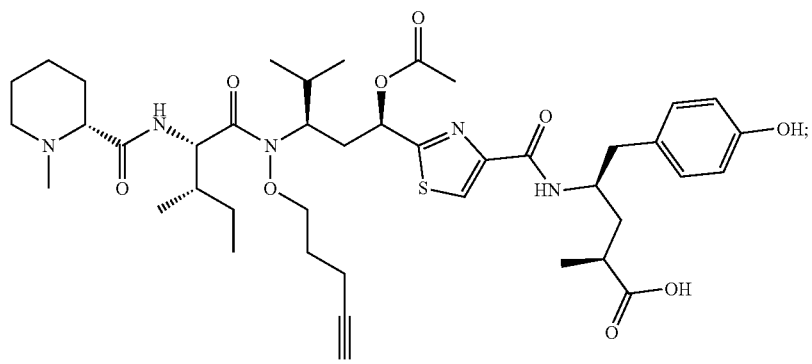
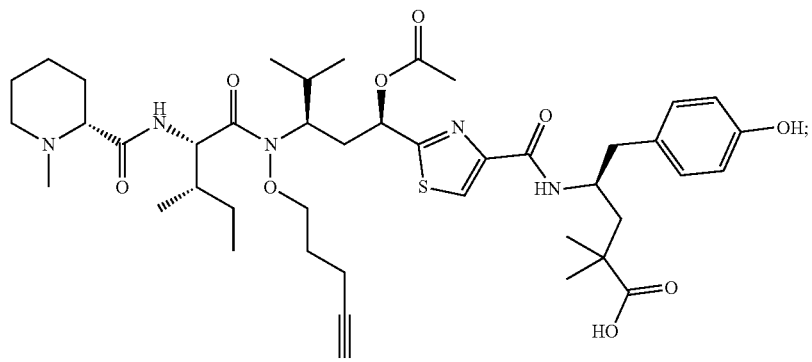
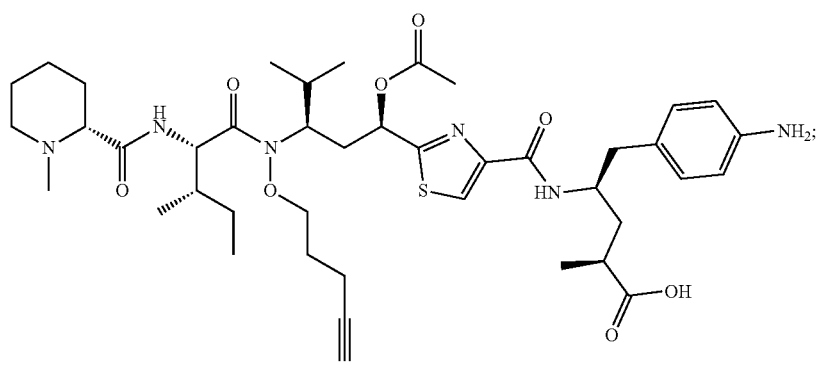

-continued
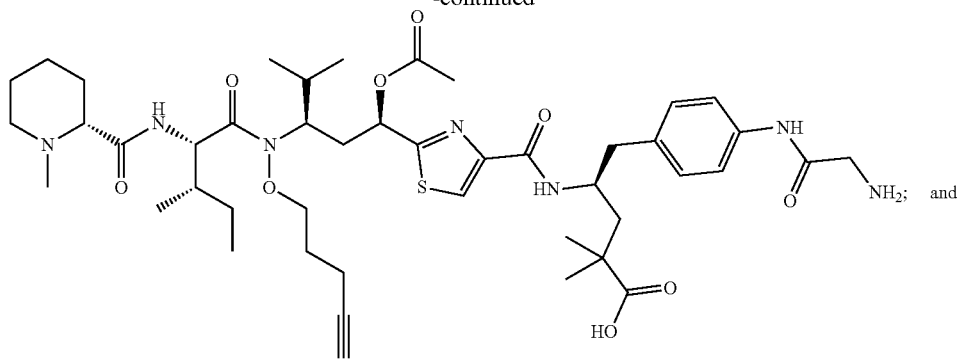
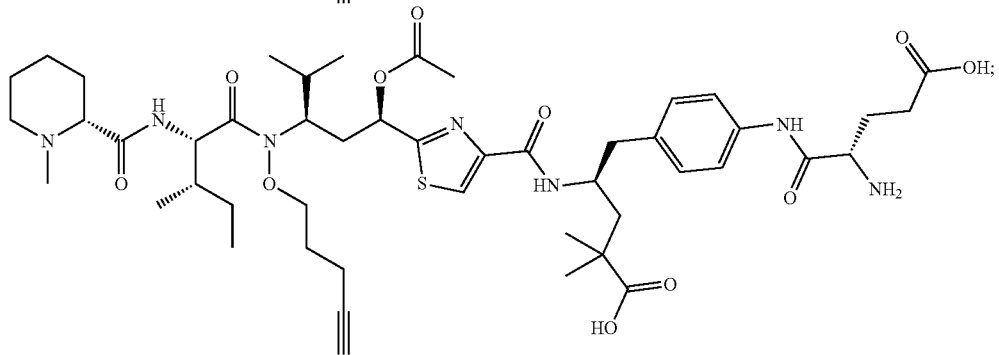
30
or
a pharmaceutically acceptable salt thereof.
26. The compound of claim 21, wherein the compound is selected from the group consisting of
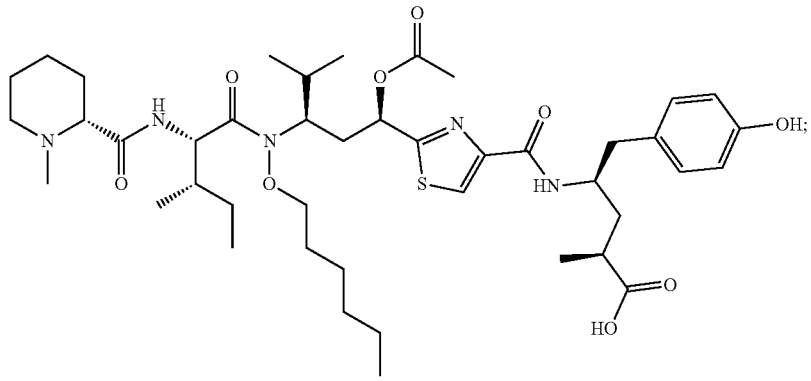
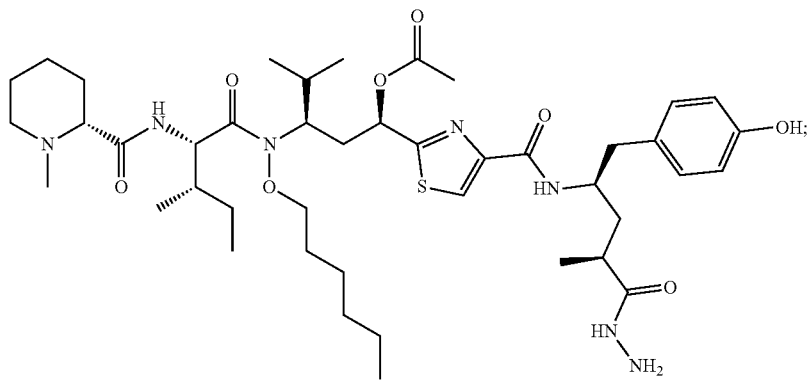

-continued
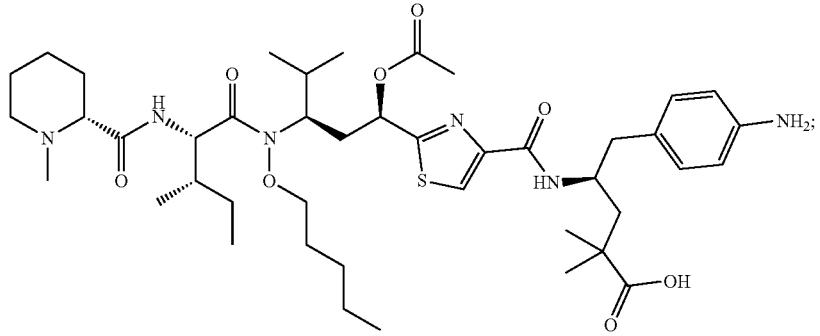
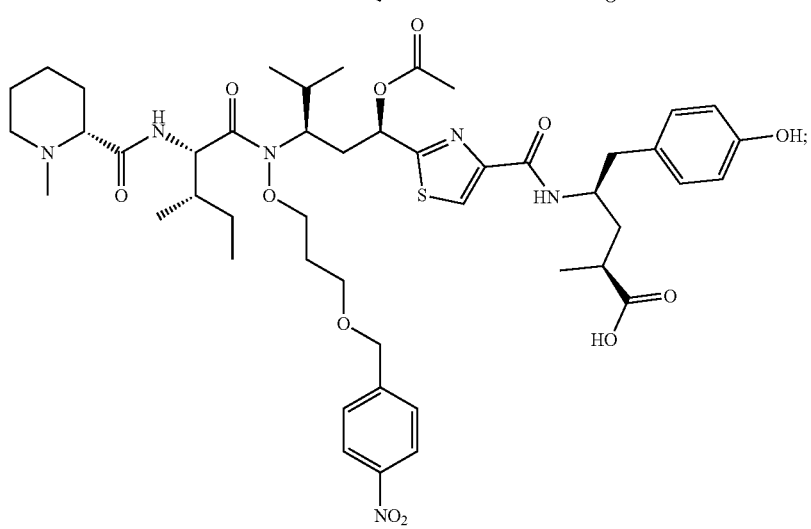
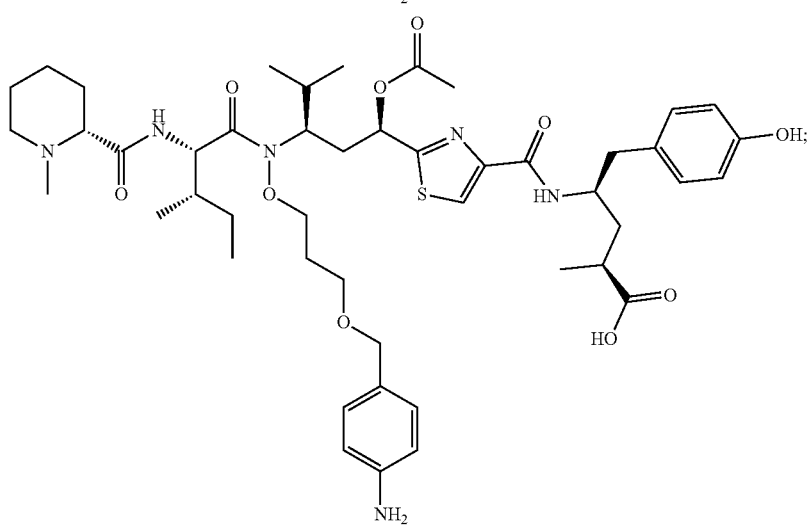
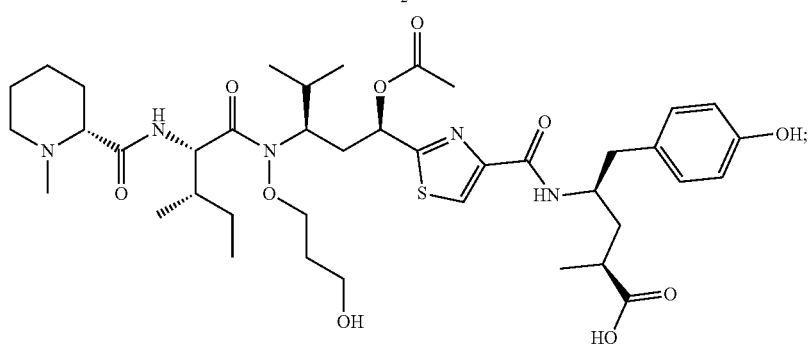

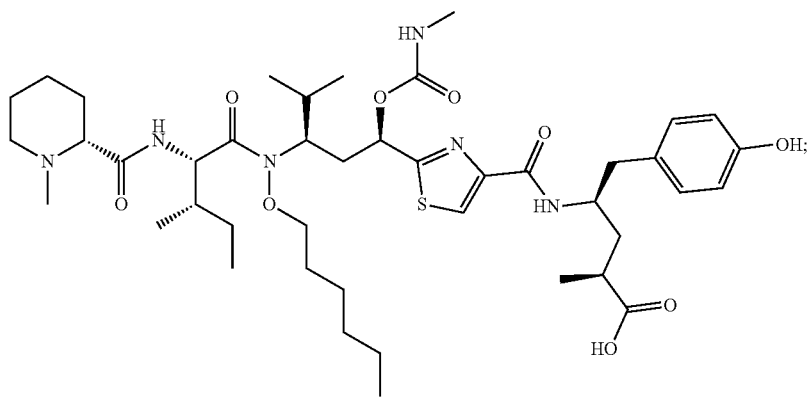
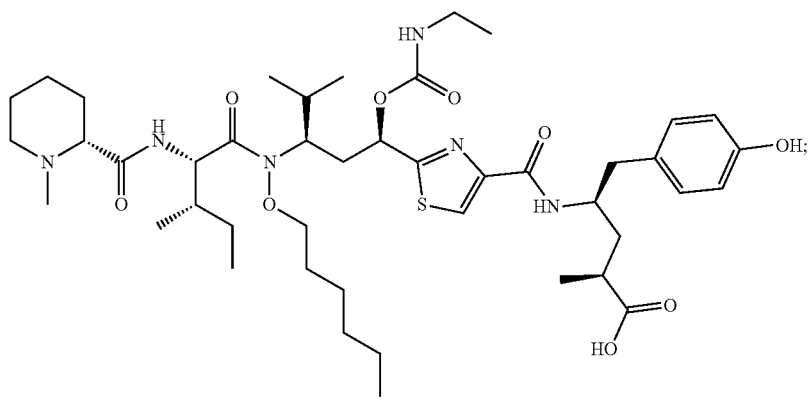
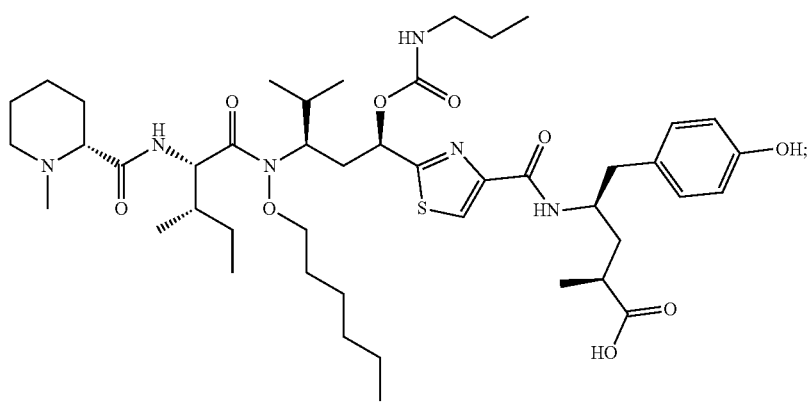
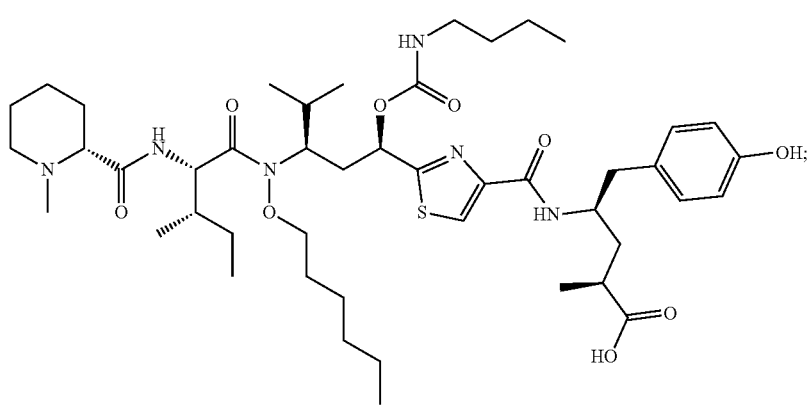

-continued
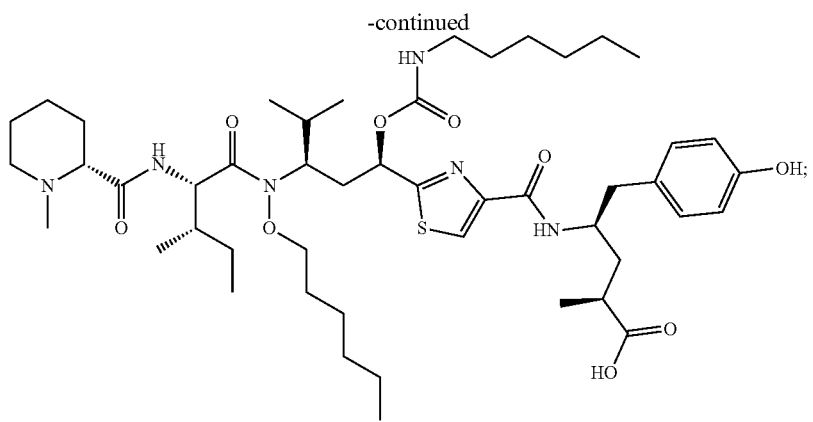
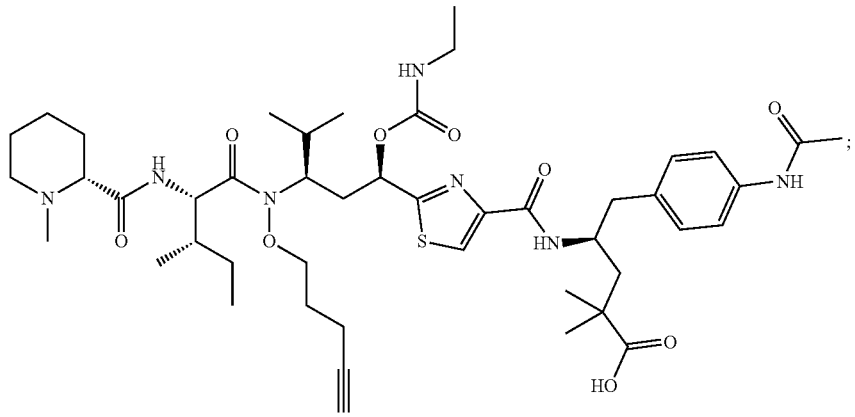
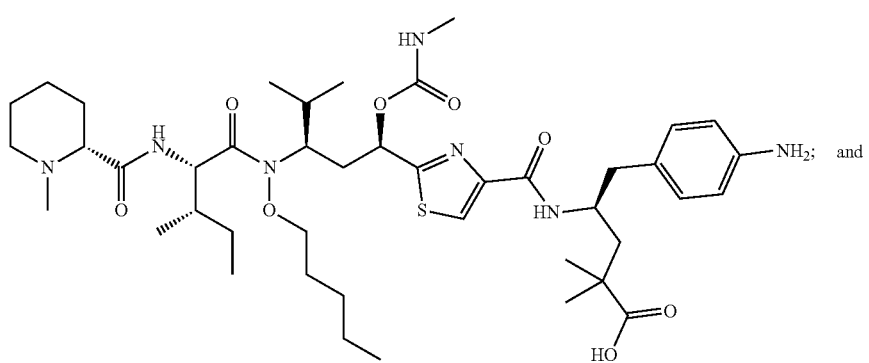
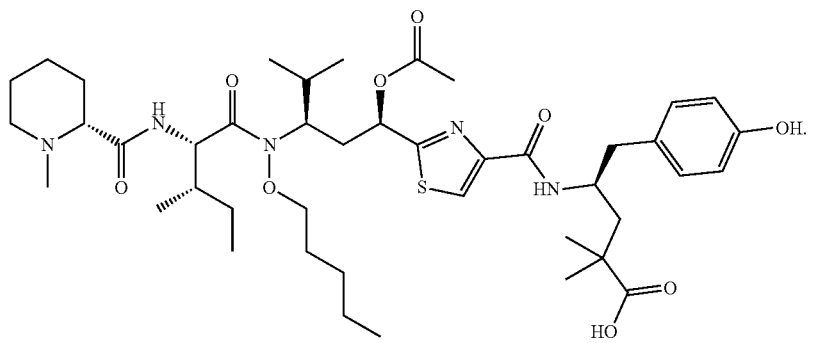

27. The compound of claim 25, wherein the compound is
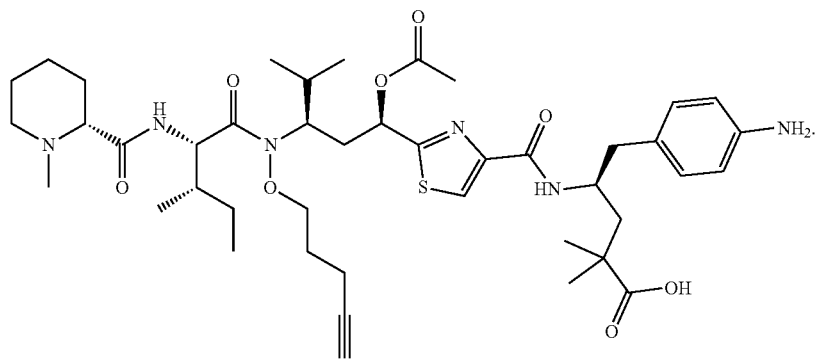 [SMILES: C#CCCCON(C(=O)[C@@H](NC(=O)[C@H]1CCCCN1C)[C@@H](C)CC)[C@H](C[C@@H](OC(C)=O)c1nc(C(=O)N[C@@H](Cc2ccc(N)cc2)CC(C)(C)C(=O)O)cs1)C(C)C]
28. A pharmaceutical composition comprising the compound of claim 1 and a pharmaceutically acceptable excipient, carrier, or diluent.
29. A linker-payload having the formula Formula LPb or LPc
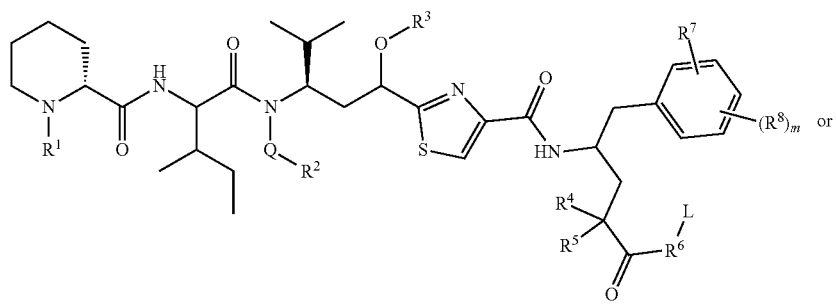
(LPb)
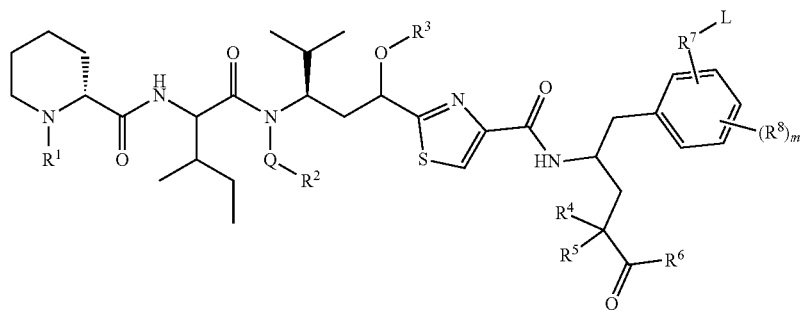
(LPc)

or a pharmaceutically acceptable salt thereof, wherein
L is a linker;
wherein
$R_1$ is $C_1$-$C_{10}$ alkyl;
$R^3$ is —C(O)$C_1$-$C_5$ alkyl, —C(O)N(H)$C_1$-$C_{10}$ alkyl, or —($C_1$-$C_{10}$ alkylene)-N$R^{3a}R^{3b}$,
  wherein $R^{3a}$ and $R^{3b}$ are independently in each instance, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl, wherein $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and/or $C_2$-$C_{20}$ acyl;
$R^4$ and $R^5$ are, independently in each instance, hydrogen or $C_1$-$C_5$ alkyl;
$R^6$ is —OH, —O—, —NHNH$_2$, or —NHNH—;
$R^7$ is, independently in each instance, hydrogen, —OH, —O—, halogen, or —N$R^{7a}R^{7b}$,
  wherein $R^{7a}$ and $R^{7b}$ are independently in each instance, a bond, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, acyl, and amino acid residue, wherein $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and/or acyl;
$R^8$ is, independently in each instance, hydrogen, deuterium, —NH$R^9$, or halogen,
  wherein $R^9$ is hydrogen, —$C_1$-$C_5$ alkyl, or —C(O)$C_1$-$C_5$ alkyl; and
m is one or two;
Q is oxygen;
$R^2$ is $C_1$-$C_{10}$ alkyl, $C_3$-$C_{10}$ alkynyl, —$C_1$-$C_{10}$ alkylene-(5-membered heteroaryl), —$C_1$-$C_3$ alkylene-$Q^1$-(CH$_2$)$_n$aryl, or $C_1$-$C_3$ hydroxyalkyl; and
$Q^1$ is —CH$_2$— or —O—;
  wherein said heteroaryl is unsubstituted or substituted with $C_1$-$C_{20}$ alkyl, aminoalkyl, -alkylene-NH—, hydroxylalkyl, -alkylene-O—, carboxylalkyl, -alkylene-COO—, benzyl, or phenyl;
  wherein said aryl is unsubstitued or substituted with nitro, amino, or —NH—; and
  wherein n is an integer from one to five.

30. The linker-payload of claim 29, or a pharmaceutically acceptable salt thereof, wherein
L is a linker;
$R^1$ is $C_1$-$C_{10}$ alkyl;
$R^3$ is —C(O)$C_1$-$C_5$ alkyl, —C(O)N(H)$C_1$-$C_{10}$ alkyl, or —($C_1$-$C_{10}$ alkylene)-N$R^{3a}R^{3b}$,
  wherein $R^{3a}$ and $R^{3b}$ are independently in each instance, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_2$-$C_{20}$ acyl, wherein $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and $C_1$-$C_{20}$ acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and/or $C_2$-$C_{20}$ acyl;
$R^4$ and $R^5$ are, independently in each instance, hydrogen or $C_1$-$C_5$ alkyl;
$R^6$ is —OH, —O—, —NHNH$_2$, or —NHNH—;
$R^7$ is, independently in each instance, hydrogen, —OH, —O—, halogen, or —N$R^{7a}R^{7b}$,
  wherein $R^{7a}$ and $R^{7b}$ are independently in each instance, a bond, hydrogen, $C_1$-$C_{20}$ alkyl, $C_2$-$C_{20}$ alkenyl, $C_2$-$C_{20}$ alkynyl, $C_3$-$C_{20}$ cycloalkyl, $C_6$-$C_{20}$ aryl, 5- to 20-membered heteroaryl, and acyl, wherein $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and acyl are unsubstituted or substituted with $C_1$-$C_{20}$ alkyl, $C_2$-$C_{20}$ alkenyl, $C_2$-$C_{20}$ alkynyl, $C_3$-$C_{20}$ cycloalkyl, aryl, heteroaryl, and/or acyl;
$R^8$ is, independently in each instance, hydrogen, deuterium, —NH$R^9$, or halogen,
  wherein $R^9$ is hydrogen, —$C_1$-$C_5$ alkyl, or —C(O)$C_1$-$C_5$ alkyl; and
m is one or two;
Q is oxygen;
$R^2$ is $C_1$-$C_{10}$ alkyl, $C_3$-$C_{10}$ alkynyl, —$C_1$-$C_{10}$ alkylene-(5-membered heteroaryl), —$C_1$-$C_3$ alkylene-$Q^1$-(CH$_2$)$_n$aryl, or $C_1$-$C_3$ hydroxyalkyl; and
$Q^1$ is —CH$_2$— or —O—;
  wherein said heteroaryl is unsubstituted or substituted with $C_1$-$C_{20}$ alkyl, aminoalkyl, -alkylene-NH—, hydroxylalkyl, -alkylene-O—, carboxylalkyl, -alkylene-COO—, benzyl, or phenyl;
  wherein said aryl is unsubstitued or substituted with nitro, amino, or —NH—; and
  wherein n is an integer from one to five.

31. The linker-payload of claim 30, having the Formula LPb' or LPc'

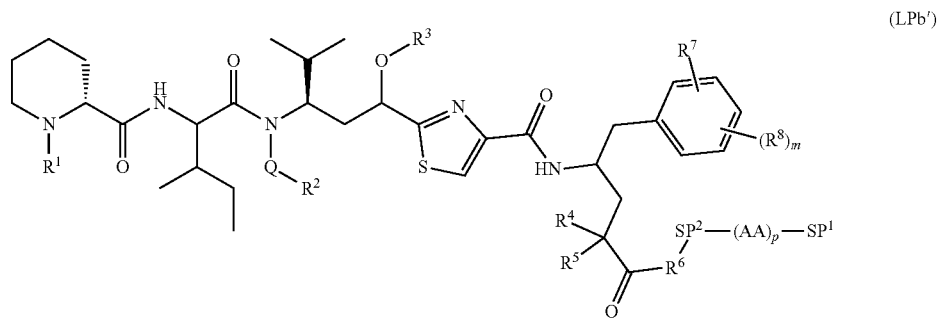

(LPb')

-continued
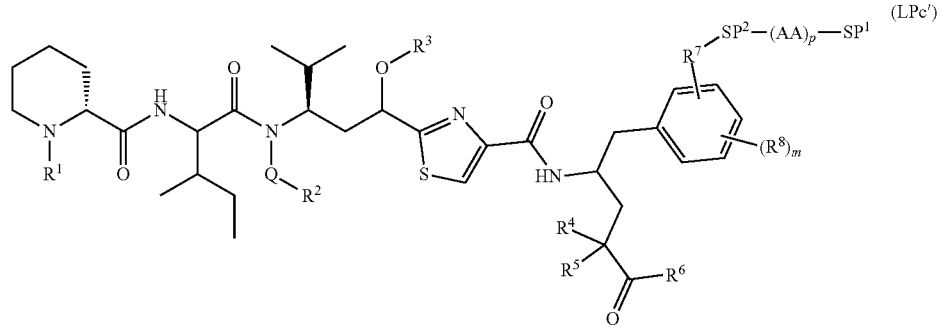
or a pharmaceutically acceptable salt thereof, wherein
SP$^1$ and SP$^2$, when present, are spacer groups;
each AA is an amino acid; and
p is an integer from one to ten.
32. The linker-payload of claim 31, wherein the linker-payload is selected from the group consisting of 671 672
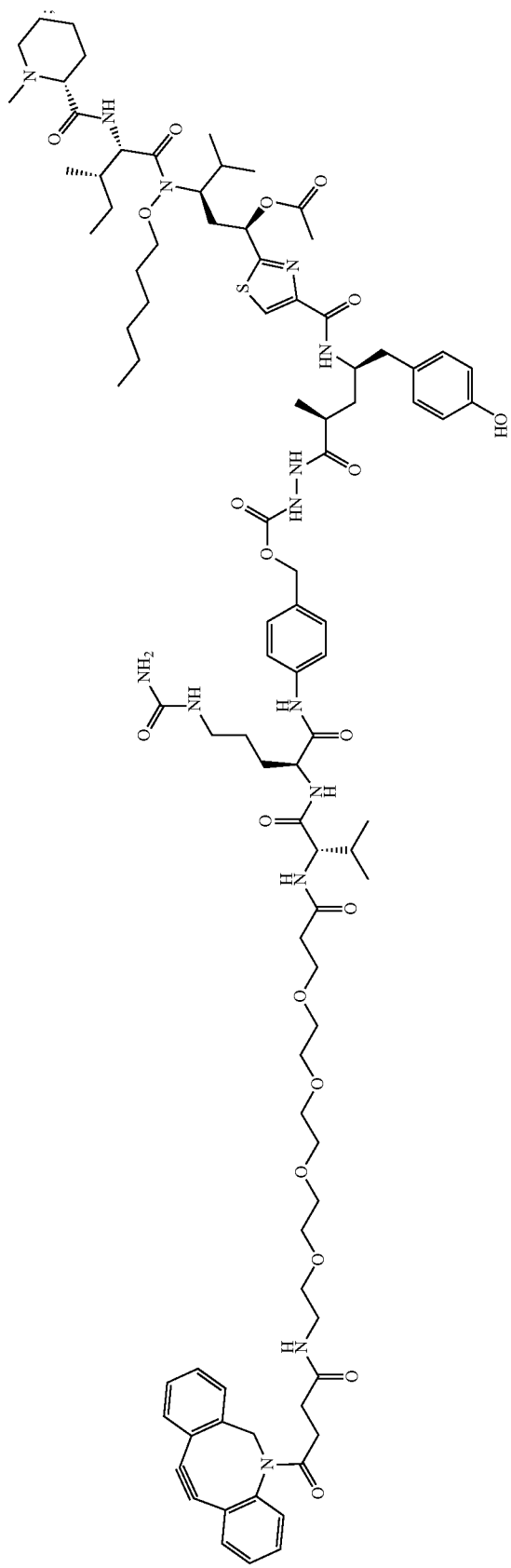
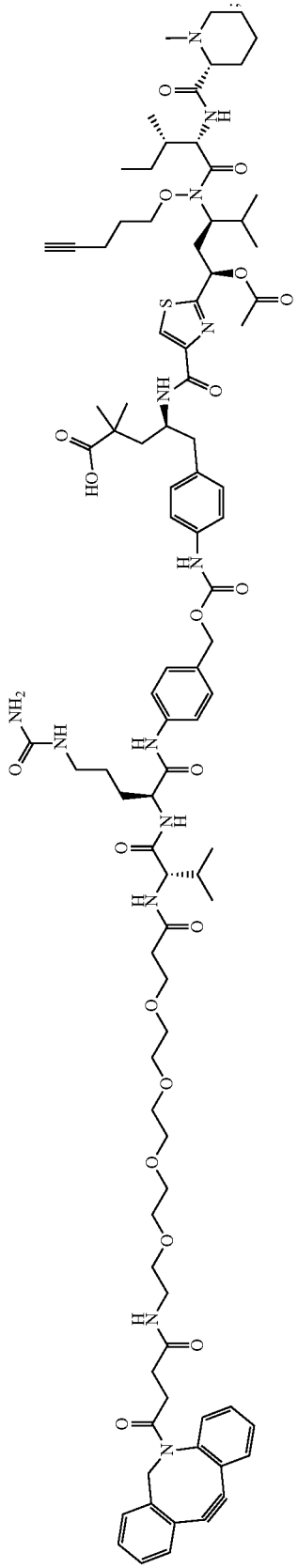

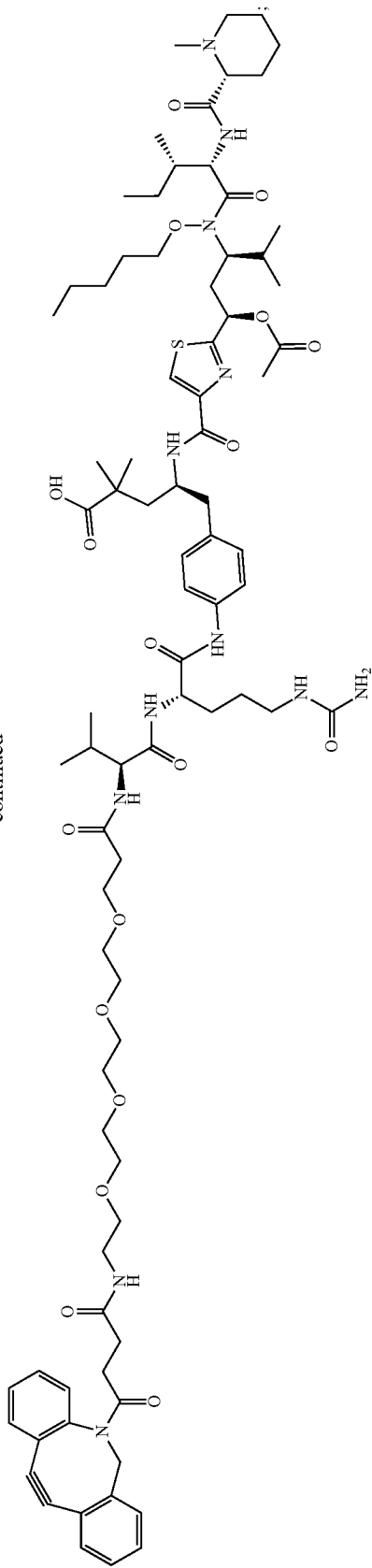
673
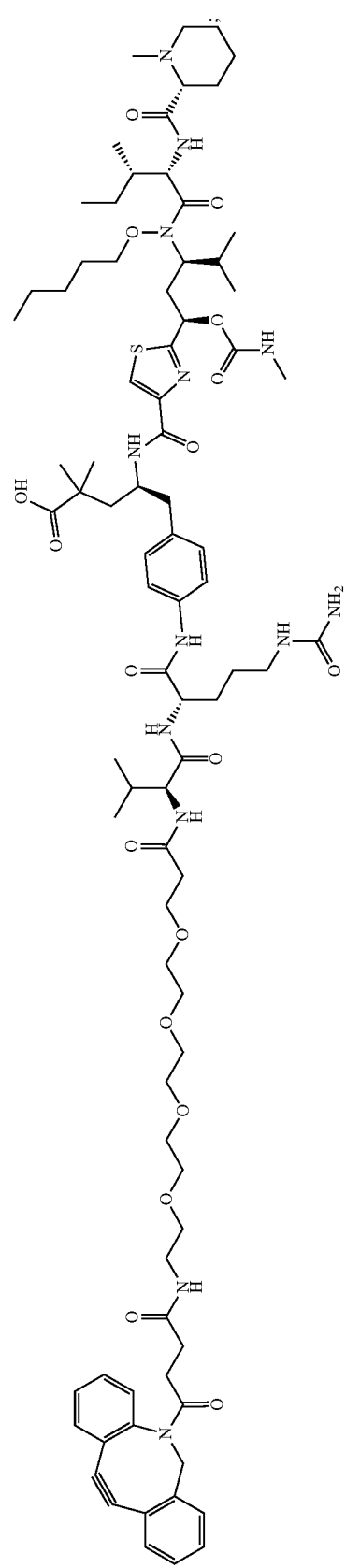
674